US010183950B2

(12) United States Patent
Dorsey et al.

(10) Patent No.: US 10,183,950 B2
(45) Date of Patent: *Jan. 22, 2019

(54) THIENOPYRIMIDINE INHIBITORS OF ATYPICAL PROTEIN KINASE C

(71) Applicant: Cancer Research Technology Limited, London (GB)

(72) Inventors: Bruce D. Dorsey, Ambler, PA (US); Keith S. Learn, Perkiomenville, PA (US); Emma L. Morris, Biggleswade (GB); Gregory R. Ott, Media, PA (US); Jonathan R. A. Roffey, Reading (GB); Christelle N. Soudy, London (GB); Jason C. Wagner, Coatesville, PA (US)

(73) Assignee: Cancer Research Technology Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/417,191

(22) Filed: Jan. 26, 2017

(65) Prior Publication Data

US 2017/0158706 A1 Jun. 8, 2017

Related U.S. Application Data

(63) Continuation of application No. 14/285,007, filed on May 22, 2014, now Pat. No. 9,604,994, which is a continuation of application No. PCT/US2012/065831, filed on Nov. 19, 2012.

(60) Provisional application No. 61/563,310, filed on Nov. 23, 2011.

(51) Int. Cl.
| | | |
|---|---|---|
| *C07D 495/04* | (2006.01) | |
| *A61K 31/519* | (2006.01) | |
| *C07D 495/14* | (2006.01) | |
| *C07D 495/20* | (2006.01) | |
| *C07D 519/00* | (2006.01) | |
| *C07F 7/08* | (2006.01) | |
| *A61P 35/02* | (2006.01) | |
| *A61P 35/04* | (2006.01) | |

(52) U.S. Cl.
CPC .......... *C07D 495/04* (2013.01); *C07D 495/14* (2013.01); *C07D 495/20* (2013.01); *C07D 519/00* (2013.01); *C07F 7/0812* (2013.01)

(58) Field of Classification Search
CPC .. C07D 495/04; C07D 495/14; C07D 495/20; A61K 31/519
USPC ....................... 544/278; 514/260.1
See application file for complete search history.

(56) References Cited

U.S. PATENT DOCUMENTS

| | | |
|---|---|---|
| 4,196,207 A | 4/1980 | Webber |
| 7,074,929 B2 | 7/2006 | Horvath et al. |
| 7,115,741 B2 | 10/2006 | Levy et al. |
| 2002/0151544 A1 | 10/2002 | Hayakawa et al. |
| 2005/0153989 A1 | 7/2005 | Grotzfeld et al. |
| 2007/0010402 A1 | 1/2007 | Ota et al. |

FOREIGN PATENT DOCUMENTS

| | | |
|---|---|---|
| CA | 2423981 | 3/2003 |
| JP | 2000-038350 | 2/2000 |
| WO | WO 99/40091 | 8/1999 |
| WO | WO 00/61586 | 4/2001 |
| WO | WO 01/83456 | 3/2003 |
| WO | WO 03/049739 | 6/2003 |
| WO | WO 2004/017950 | 3/2004 |
| WO | WO 2004/029060 | 4/2004 |
| WO | WO 2004/065391 | 8/2004 |
| WO | WO 2004/111057 | 12/2004 |
| WO | WO 2005/067546 | 7/2005 |
| WO | WO 2005/123087 | 12/2005 |
| WO | WO 2006/010568 | 2/2006 |
| WO | WO 2006/093518 | 9/2006 |

(Continued)

OTHER PUBLICATIONS

Balendran et al., A 3-Phosphoinositide-Dependent Protein Kinase-1 (PDK1) Docking Siteis Required for the Phosphorylation of Protein Kinase Czeta (PKCZETA) and PKC-Related Kinase 2 by PDKI, Journal of Biological Chemistry, American Society for Biochemistry and Molecular Biology, vol. 275, No. 27, Jul. 7, 2000 (Jul. 7, 2000) pp. 20806-20813, XP000925909, ISSN: 0021-9258, DOI: 10.1074/JBC. M000421200.

(Continued)

*Primary Examiner* — Susanna Moore
(74) *Attorney, Agent, or Firm* — Mintz Levin Cohn Ferris Glovsky & Popeo PC

(57) ABSTRACT

The present application provides a compound of formula (I)

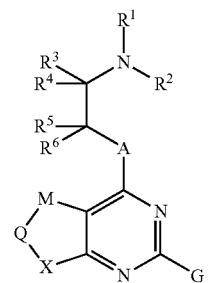

or a salt thereof, wherein $R^1$, $R^2$, $R^3$, $R^4$, $R^5$, $R^6$, A, G, M, Q and X are as defined herein. A compound of formula (I) and its salts have aPKC inhibitory activity, and may be used to treat proliferative disorders.

10 Claims, No Drawings

(56) References Cited

FOREIGN PATENT DOCUMENTS

| WO | WO 2006/100095 | 9/2006 |
|----|----------------|--------|
| WO | WO 2007/127175 | 11/2007 |
| WO | WO 2008/037607 | 4/2008 |
| WO | WO 2008/073785 | 6/2008 |
| WO | WO 2009/144584 | 12/2009 |
| WO | WO 2010/080996 | 7/2010 |
| WO | WO 2011/051452 | 5/2011 |
| WO | WO 2011/130628 | 10/2011 |

OTHER PUBLICATIONS

Berge et al., Pharmaceutical Salts, J. Pharm. Sci. (1977) 66, pp. 1-19.
Eder et al., Atypical PKG contributes to poor prognosis through loss of apical-basal polarity and Cyclin E overexpression in ovarian cancer, Proc. Natl A cad. Sci. (2005) 102, pp. 12519-12524.
Farese et al., Muscle-specific knockout of PKC-P. impairs glucose transport and induces metabolic and diabetic syndromes, J. Clin. Invest. (2007) 117, pp. 2289-2301.
Fields et al., Protein kinase Ct: Human oncogene, prognostic marker and therapeutic target, Pharmacol. Res. (2007) 55, pp. 487-497.
Filomenko et al., Atypical Protein Kinase C~ as a Target for Chemosensitization of Tumor Cells, Cancer Res. (20021 62; pp. 1815-1821.
Garcia-Cao et al., Tumour-suppression activity of the proapoptotic regulator Par4, EMBO Reports (2005) 6, pp. 577-583.
Inoue et al., Requirement of Androgen-Dependent Activation of Protein Kinase C~ for Androgen-Dependent Cell Proliferation in LNCaP Cells and Its Roles in Transition to Androgen-Independent Cells, Mol. Endocrinology (2006) 20; pp. 3053-3069.
Iorns et al., Parallel RNAi and compound screens identify the PDK1 pathway as a target for tamoxifen sensitization, Biochem. J. (2009) 417, pp. 361-370.
Joshi et al., Par-4 inhibits Ak5 and suppresses Ras-induced lung tumorigenesis, EMBO Journal (2008) 27, pp. 2181-2193.
Kojima et al., The overexpression and altered localization of the atypical protein kinase CNL in breast cancer correlates with the pathologic type of these tumors, Human Pathology (2008) 39, pp. 824-831.
Leitges et al., Targeted Disruption of the ~PKG Gene Results in the Impairment of the NF-KB Pathway, Mol. Cell (2001) 8, pp. 771-780.
Leseux et al., PKC~—mTOR pathway: a new target for rituximab therapy in follicular lymphoma, Blood (2008) 111, pp. 285-291.
Murray et al., Protein kinase Ct is required for Ras transformation and colon carcinogenesis in vivo, J. Cell Biology (2004) 164, pp. 797-802.
Ono et al., Protein Kinase C~ subspecies from rat brain: Its structure, expression, and properties, Proc. Natl. Acad. Sci. USA (1989) 86, pp. 3099-3103.
Osborne et al., Role of the Estrogen Receptor Coactivator AIBI (SRC-3) and HER-2/neu in Tamoxifen Resistance in Breast Cancer, J. Natl. Cancer Inst. (2003) 95, pp. 353-361.
Plo et al., Overexpression of the Atypical Protein Kinase C~ Reduces Topoisomerase II Catalytic Activity, Cleavable Complexes Formation and Drug-induced Cytotoxicity in Monocytic U937 Leukemia Cells, J. Biological Chem. (2002) 277, pp. 31407-31415.
Regala et al., Atypical Protein Kinase CL Expression and Aurothiomalate Sensitivity in Human Luna Cancer Cells, Cancer Res. (2008) 68, pp. 5888-5895.
Regala et al., Atypical Protein Kinase CL Plays a Critical Role in Human Lung Cancer Cell Growth and Tumorigenicity, J. Biological Chem. (2005) 280, pp. 31109-31115.
Regala et al., Atypical Protein Kinase Ct is an Oncogene in Human Non-Small Cell Lung Cancer, Cancer Res. (2005) 65; pp. 8905-8911.
Suzuki et al., The PAR-aPKC system: lessons in polarity, J. Cell Sci. (2006) 119, pp. 979-987.
Xin et al., Protein Kinase C~ Abrogates the Proapoptotic Function of Bax Through Phosphorylation, J. Biological Chem. (2007) 282, pp. 21268-21277.
Yang et al., Amplification of PRKCI, Located in 3q26, is Associated with Lymph Node Metastasis in Esophageal Squamous Cell Carcinoma, Genes, Chromosomes & Cancer(2008) 47, pp. 127-136.
Zhang et al., Integrative Genomic Analysis of Protein Kinase C (PKG) Family Identifies PKCL as a Biomarker and Potential Oncogene in Ovarian Carcinoma, Cancer Res. (2006) 66, pp. 4627-4635.
International Search Report for PCT/US2012/065831 dated Jan. 17, 2013.

THIENOPYRIMIDINE INHIBITORS OF ATYPICAL PROTEIN KINASE C

CROSS-REFERENCE TO RELATED PATENT APPLICATIONS

This application is a continuation of U.S. application Ser. No. 14/285,007, now U.S. Pat. No. 9,604,994, filed May 22, 2014, which is a U.S. National Phase application under 35 U.S.C. § 371 of International Patent Application No. PCT/US2012/065831, filed Nov. 19, 2012, which claims the benefit of U.S. Provisional Application No. 61/563,310, filed Nov. 23, 2011, the content of each of which is incorporated herein by reference in its entirety.

BACKGROUND OF THE INVENTION

PKCι and PKCζ (accession numbers NM_002740 and NM_002744 respectively) together define the atypical subclass of the protein kinase C (PKC) family (aPKCs). The aPKCs are structurally and functionally distinct from the other PKC sub-classes, classic/conventional and novel, as their catalytic activity is not dependent on diacylglycerol and calcium (Ono, Y., Fujii, T., Ogita, K., Kikkawa, U., Igarashi, K., and Nishizuka, Y. (1989). Protein kinase C zeta subspecies from rat brain: its structure, expression, and properties. Proc Natl Acad Sci USA 86, 3099-3103). Structurally, PKCι and PKCζ contain a C-terminal serine/threonine kinase domain (AGC class) and an N-terminal regulatory region containing a Phox Bem 1 (PB1) domain involved in mediating protein:protein interactions critical for aPKC function. At the amino acid level the aPKCs share 72% overall homology, however, the kinase domains share 84% identity and differ in the active site by just a single amino acid. This striking homology suggests an ATP-competitive ligand would not be expected to exhibit significant aPKC isoform selectivity.

The aPKCs have been implicated in a diverse number of signalling pathways, demonstrating both redundant and distinct signalling functions. Both isoforms have emerged as central players in the mechanisms that regulate the establishment and maintenance of cellular polarity in multiple cell types (reviewed in Suzuki, A., and Ohno, S. (2006). The PAR-aPKC system: lessons in polarity. J Cell Sci 119, 979-987). Genetic dissection of their functions using knock-out mice have also revealed preferential roles for PKC in the regulation of NF-kB signalling (Leitges, M., Sanz, L., Martin, P., Duran, A., Braun, U., Garcia, J. F., Camacho, F., Diaz-Meco, M. T., Rennert, P. D., and Moscat, J. (2001). Targeted disruption of the zetaPKC gene results in the impairment of the NF-kappaB pathway. Mol Cell 8, 771-780), and PKCι in insulin secretion and action (Farese, R. V., Sajan, M. P., Yang, H., Li, P., Mastorides, S., Gower, W. R., Jr., Nimal, S., Choi, C. S., Kim, S., Shulman, G. I., et al. (2007). Muscle-specific knockout of PKC-lambda impairs glucose transport and induces metabolic and diabetic syndromes. J Clin Invest 117, 2289-2301). In addition, both isoforms have been implicated in the pathogenesis of cancer making a strong case for the inhibition of the aPKCs as a novel therapeutic avenue.

PKCι is a known oncogene in non-small cell lung cancer (NSCLC). In one study it was shown to be overexpressed in 69% of NSCLC cases at the protein level. Consistent with this, the PKCι gene (PRKCI residing on chromosome 3q26) was shown to be amplified in 36.5% of NSCLC tumours examined, including 96% of the squamous cell carcinoma sub-type (Regala, R. P., Weems, C., Jamieson, L., Khoor, A., Edell, E. S., Lohse, C. M., and Fields, A. P. (2005b). Atypical protein kinase C iota is an oncogene in human non-small cell lung cancer. Cancer Res 65, 8905-8911). Amplification of 3q26 has also been reported in 44% of ovarian cancers, including >70% of serous epithelial ovarian cancers where 3q26 amplification is translated into increased PKCι protein expression. Moreover, increased PKCι expression is associated with poor prognosis in NSCLC and ovarian cancer where it may serve as a diagnostic biomarker of aggressive disease (Eder, A. M., Sui, X., Rosen, D. G., Nolden, L. K., Cheng, K. W., Lahad, J. P., Kango-Singh, M., Lu, K. H., Warneke, C. L., Atkinson, E. N., et al. (2005). Atypical PKCiota contributes to poor prognosis through loss of apical-basal polarity and cyclin E overexpression in ovarian cancer. Proc Natl Acad Sci USA 102, 12519-12524; Zhang, L., Huang, J., Yang, N., Liang, S., Barchetti, A., Giannakakis, A., Cadungog, M. G., O'Brien-Jenkins, A., Massobrio, M., Roby, K. F., et al. (2006). Integrative genomic analysis of protein kinase C (PKC) family identifies PKCiota as a biomarker and potential oncogene in ovarian carcinoma. Cancer Res 66, 4627-4635). 3q26 amplifications have been observed in many other cancers including oesophageal squamous cell carcinoma (Yang, Y. L., Chu, J. Y., Luo, M. L., Wu, Y. P., Zhang, Y., Feng, Y. B., Shi, Z. Z., Xu, X., Han, Y. L., Cai, Y., et al. (2008). Amplification of PRKCI, located in 3q26, is associated with lymph node metastasis in esophageal squamous cell carcinoma. Genes Chromosomes Cancer 47, 127-136) and breast cancer (Kojima, Y., Akimoto, K., Nagashima, Y., Ishiguro, H., Shirai, S., Chishima, T., Ichikawa, Y., Ishikawa, T., Sasaki, T., Kubota, Y., et al. (2008). The overexpression and altered localization of the atypical protein kinase C lambda/iota in breast cancer correlates with the pathologic type of these tumors. Hum Pathol 39, 824-831) suggesting that PKCι may also participate in the pathogenesis of these diseases.

In NSCLC the primary function of PKCι is to drive transformed growth via a Rac1/PAK/MEK/ERK signalling axis. However, PKCι also functions in NSCLC survival, resistance to chemotherapy, and invasion via distinct pathways (reviewed in Fields, A. P., and Regala, R. P. (2007). Protein kinase C iota: human oncogene, prognostic marker and therapeutic target. Pharmacol Res 55, 487-497). In ovarian cancer transformed growth is correlated with deregulated epithelial cell polarity and increased cycle E expression (Eder et al., 2005) suggesting that PKCι can influence the cancer phenotype through multiple mechanisms. Compelling evidence has emerged to suggest that inhibition of PKCι may be a useful therapeutic approach to combat tumours characterised by increased PKCι expression. In transgenic models, mice with elevated PKCι activity in the colon are more susceptible to carcinogen-induced colon carcinogenesis, and expression of a kinase-dead mutant of PKCι blocks the transformation of intestinal cells by oncogenic Ras (Murray, N. R., Jamieson, L., Yu, W., Zhang, J., Gokmen-Polar, Y., Sier, D., Anastasiadis, P., Gatalica, Z., Thompson, E. A., and Fields, A. P. (2004). Protein kinase Ciota is required for Ras transformation and colon carcinogenesis in vivo. J Cell Biol 164, 797-802). Finally, genetic or pharmacological inhibition of PKCι by a gold derivative—aurothiomalate (ATM)—blocks the growth of NSCLC cells in soft agar and significantly decreases tumour volume in xenograft models of NSCLC (Regala, R. P., Thompson, E. A., and Fields, A. P. (2008). Atypical protein kinase C iota expression and aurothiomalate sensitivity in human lung cancer cells. Cancer Res 68, 5888-5895; Regala, R. P., Weems, C., Jamieson, L., Copland, J. A., Thompson, E. A., and Fields, A. P. (2005a).

Atypical protein kinase C iota plays a critical role in human lung cancer cell growth and tumorigenicity. J Biol Chem 280, 31109-31115).

Despite the high degree of similarity between aPKC isoforms, the role of PKC in cancer is distinct from that of PKCι. PKC plays a role in NSCLC cell survival by phosphorylating and antagonising the pro-apoptotic effects of Bax in response to nicotine (Xin, M., Gao, F., May, W. S., Flagg, T., and Deng, X. (2007). Protein kinase Czeta abrogates the proapoptotic function of Bax through phosphorylation. J Biol Chem 282, 21268-21277). PKC activity has also been linked to resistance against a wide range of cytotoxic and genotoxic agents. For instance, in human leukaemia cells, overexpression of PKC confers resistance against 1-β-D-arabinofuranosylcytosine (ara-C), daunorubicin, etoposide, and mitoxantrone-induced apoptosis (Filomenko, R., Poirson-Bichat, F., Billerey, C., Belon, J. P., Garrido, C., Solary, E., and Bettaieb, A. (2002). Atypical protein kinase C zeta as a target for chemosensitization of tumor cells. Cancer Res 62, 1815-1821; Plo, I., Hernandez, H., Kohlhagen, G., Lautier, D., Pommier, Y., and Laurent, G. (2002). Overexpression of the atypical protein kinase C zeta reduces topoisomerase II catalytic activity, cleavable complexes formation, and drug-induced cytotoxicity in monocytic U937 leukemia cells. J Biol Chem 277, 31407-31415). Furthermore, inhibition of PKC activity through expression of a kinase-dead mutant sensitizes leukaemia cells to the cytotoxic effects of etoposide both in vitro and in vivo (Filomenko et al., 2002). Atypical protein kinase C regulates dual pathways for degradation of the oncogenic coactivator SRC-3/AIB1. Mol Cell 29, 465-476), and both of these proteins have been postulated to play a role in tamoxifen resistance in breast cancer (Iorns, E., Lord, C. J., and Ashworth, A. (2009). Parallel RNAi and compound screens identify the PDK1 pathway as a target for tamoxifen sensitization. Biochem J 417, 361-370; Osborne, C. K., Bardou, V., Hopp, T. A., Chamness, G. C., Hilsenbeck, S. G., Fuqua, S. A., Wong, J., Allred, D. C., Clark, G. M., and Schiff, R. (2003). Role of the estrogen receptor coactivator AIB1 (SRC-3) and HER-2/neu in tamoxifen resistance in breast cancer. J Natl Cancer Inst 95, 353-361). Together these studies suggest that inhibition of PKC activity may have beneficial therapeutic effects by acting as a chemosensitiser to a wide array of commonly used chemotoxic agents in the clinic.

Further evidence that small molecule inhibition of PKC could have important therapeutic benefits has recently emerged from tumour models that link PKC signalling to the mTOR pathway. PKC is constitutively activated in follicular lymphoma and has been identified as a novel target for the anti-CD20 therapeutic antibody rituximab (Leseux, L., Laurent, G., Laurent, C., Rigo, M., Blanc, A., Olive, D., and Bezombes, C. (2008). PKC zeta mTOR pathway: a new target for rituximab therapy in follicular lymphoma. Blood 111, 285-291). Rituximab inhibits follicular lymphoma proliferation by targeting a PKCζ-MAPK-mTOR pathway, suggesting that PKC is both a target of Rituximab, and a key regulator of its' anti-leukaemic effect. Regulation of the mTOR/p70S6K pathway by PKC has also been implicated in the transition of prostate cancer cells to an androgen-independent state (Inoue, T., Yoshida, T., Shimizu, Y., Kobayashi, T., Yamasaki, T., Toda, Y., Segawa, T., Kamoto, T., Nakamura, E., and Ogawa, O. (2006). Requirement of androgen-dependent activation of protein kinase Czeta for androgen-dependent cell proliferation in LNCaP Cells and its roles in transition to androgen-independent cells. Mol Endocrinol 20, 3053-3069). Finally, mice containing a homozygous deletion of Par4, a negative regulator of PKC, exhibit greatly enhanced PKC activity. These mice spontaneously develop tumours of the prostate and endometrium, and potentiate Ras-induced lung carcinogenesis consistent with a role for PKC in lung cancer (Garcia-Cao, I., Duran, A., Collado, M., Carrascosa, M. J., Martin-Caballero, J., Flores, J. M., Diaz-Meco, M. T., Moscat, J., and Serrano, M. (2005). Tumour-suppression activity of the proapoptotic regulator Par4. EMBO Rep 6, 577-583; Joshi, J., Fernandez-Marcos, P. J., Galvez, A., Amanchy, R., Linares, J. F., Duran, A., Pathrose, P., Leitges, M., Canamero, M., Collado, M., et al. (2008). Par-4 inhibits Akt and suppresses Ras-induced lung tumorigenesis. EMBO J 27, 2181-2193).

A need exists for aPKC inhibitors for use as pharmaceutical agents.

SUMMARY OF THE INVENTION

The invention provides a compound of formula (I)

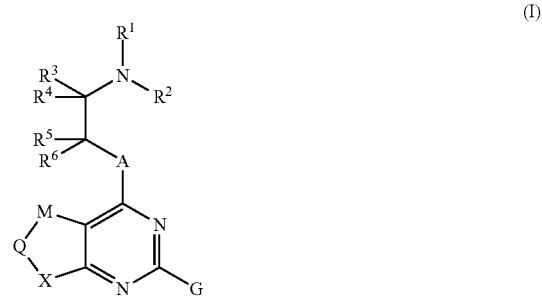

or a salt thereof, wherein $R^1$, $R^2$, $R^3$, $R^4$, $R^5$, $R^6$, A, G, M, Q and X are as defined herein.

A compound of formula (I) and its salts have aPKC inhibitory activity, and may be used to treat aPKC-dependent disorders or conditions.

The present invention further provides a pharmaceutical composition comprising a compound of formula (I) or a pharmaceutically acceptable salt thereof together with at least one pharmaceutically acceptable carrier, diluent, or excipient therefor.

In another aspect, the present invention provides a method of treating a subject suffering from an aPKC-dependent disorder or condition comprising: administering to the subject a compound of formula (I) or a pharmaceutically acceptable salt thereof.

The present invention further provides a method of treating a proliferative disorder in a subject, comprising administering to the subject a therapeutically effective amount of a compound of formula (I) or a pharmaceutically acceptable salt thereof.

DETAILED DESCRIPTION OF THE INVENTION

I. Definitions

"About" as used herein when referring to a measurable value such as an amount, a temporal duration, and the like, is meant to encompass reasonable variations of the value, such as, for example, +10% from the specified value. For example, the phrase "about 50" encompasses reasonable variations of 50, such as +10% of the numerical value 50, or from 45 to 55.

"Alkyl" or "alkyl group" refers to a monoradical of a branched or unbranched saturated hydrocarbon chain. Examples include, but are not limited to, methyl, ethyl, n-propyl, n-butyl, n-pentyl, n-hexyl, n-heptyl, n-octyl, n-nonyl, n-decyl, isopropyl, tert-butyl, isobutyl, etc. Alkyl groups typically contain 1-10 carbon atoms, such as 1-6 carbon atoms or 1-4 carbon atoms, and can be substituted or unsubstituted.

"Alkylene" or "alkylene group" refers to a diradical of a branched or unbranched saturated hydrocarbon chain. Examples include, but are not limited to, methylene (—$CH_2$—), the ethylene isomers (—$CH(CH_3)$— and —$CH_2CH_2$—), the propylene isomers (—$CH(CH_3)CH_2$—, —$CH(CH_2CH_3)$—, —$C(CH_3)_2$—, and —$CH_2CH_2CH_2$—), etc. Alkylene groups typically contain 1-10 carbon atoms, such as 1-6 carbon atoms, and can be substituted or unsubstituted.

"Alkenyl" or "alkenyl group" refers to a monoradical of a branched or unbranched hydrocarbon chain containing at least one double bond. Examples include, but are not limited to, ethenyl, 3-buten-1-yl, 2-ethenylbutyl, and 3-hexen-1-yl. Alkenyl groups typically contain 2-10 carbon atoms, such as 2-6 carbon atoms or 2-4 carbon atoms, and can be substituted or unsubstituted.

"Alkynyl" or "alkynyl group" refers to a monoradical of a branched or unbranched hydrocarbon chain containing at least one triple bond. Examples include, but are not limited to, ethynyl, 3-butyn-1-yl, propynyl, 2-butyn-1-yl, and 3-pentyn-1-yl. Alkynyl groups typically contain 2-10 carbon atoms, such as 2-6 carbon atoms or 2-4 carbon atoms, and can be substituted or unsubstituted.

"Aryl" or "aryl group" refers to phenyl and 7-15 membered monoradical bicyclic or tricyclic hydrocarbon ring systems, including bridged, spiro, and/or fused ring systems, in which at least one of the rings is aromatic. Aryl groups can be substituted or unsubstituted. Examples include, but are not limited to, naphthyl, indanyl, 1,2,3,4-tetrahydronaphthalenyl, 6,7,8,9-tetrahydro-5H-benzocycloheptenyl, and 6,7,8,9-tetrahydro-5H-benzocycloheptenyl. An aryl group may contain 6 (i.e., phenyl) or 9 to 15 ring atoms, such as 6 (i.e., phenyl) or 9-11 ring atoms, e.g., 6 (i.e., phenyl), 9 or 10 ring atoms.

"Arylene" or "arylene group" refers to a phenylene (—$C_6H_4$—) or a 7-15 membered diradical bicyclic or tricyclic hydrocarbon ring systems, including bridged, spiro, and/or fused ring systems, in which at least one of the rings is aromatic. Arylene groups can be substituted or unsubstituted. For example, an arylene group may contain 6 (i.e., phenylene) or 9 to 15 ring atoms; such as 6 (i.e., phenylene) or 9-11 ring atoms; e.g., 6 (i.e., phenylene), 9 or 10 ring atoms. An arylene group can also include ring systems substituted on ring carbons with one or more —OH functional groups (which may further tautomerize to give a ring C═O group).

"Arylalkyl" or "arylalkyl group" refers to an alkyl group in which a hydrogen atom is replaced by an aryl group, wherein alkyl group and aryl group are as previously defined (i.e., arylalkyl-). Arylalkyl groups can be substituted or unsubstituted. Examples include, but are not limited to, benzyl ($C_6H_5CH_2$—).

"Cycloalkyl" or "cycloalkyl group" refers to a monoradical non-aromatic carbocyclic ring system, which may be saturated or unsaturated, substituted or unsubstituted, and may be monocyclic, bicyclic, or tricyclic, and may be bridged, spiro, and/or fused. Examples include, but are not limited to, cyclopropyl, cyclopropenyl, cyclobutyl, cyclobutenyl, cyclopentyl, cyclopentenyl, cyclohexyl, cyclohexenyl, norbornyl, norbornenyl, bicyclo[2.2.1]hexane, bicyclo[2.2.1]heptane, bicyclo[2.2.1]heptene, bicyclo[3.1.1]heptane, bicyclo[3.2.1]octane, bicyclo[2.2.2]octane, bicyclo[3.2.2]nonane, bicyclo[3.3.1]nonane, and bicyclo[3.3.2]decane. The cycloalkyl group may contain from 3 to 10 ring atoms, such as 3 to 7 ring atoms (e.g., 3 ring atoms, 5 ring atoms, 6 ring atoms, or 7 ring atoms).

"Cycloalkylalkyl" or "cycloalkylalkyl group" refers to an alkyl group in which a hydrogen atom is replaced by a cycloalkyl group, wherein alkyl group and cycloalkyl group are as previously defined (i.e., cycloalkylalkyl-). Cycloalkylalkyl groups can be substituted or unsubstituted. Examples include, but are not limited to, cyclohexylmethyl ($C_6H_{11}CH_2$—).

"Haloalkyl" or "haloalkyl group" refers to alkyl groups in which one or more hydrogen atoms are replaced by halogen atoms. Haloalkyl includes both saturated alkyl groups and unsaturated alkenyl and alkynyl groups, such as for example —$CF_3$, —$CHF_2$, —$CH_2F$, —$CF_2CF_3$, —$CHFCF_3$, —$CH_2CF_3$, —$CF_2CH_3$, —$CHFCH_3$, —$CF_2CF_2CF_3$, —$CF_2CH_2CH_3$, —$CF═CF_2$, —$CCl═CH_2$, —$CBr═CH_2$, —$CI═CH_2$, —$C≡C≡CF_3$, —$CHFCH_2CH_3$ and —$CHFCH_2CF_3$.

"Halogen" includes fluorine, chlorine, bromine and iodine atoms.

"Heteroaryl" or "heteroaryl group" refers to (a) 5 and 6 membered monocyclic aromatic rings, which contain, in addition to carbon atom(s), at least one heteroatom, such as nitrogen, oxygen or sulfur, and (b) 7-15 membered bicyclic and tricyclic rings, which contain, in addition to carbon atom(s), at least one heteroatom, such as nitrogen, oxygen or sulfur, and in which at least one of the rings is aromatic. Heteroaryl groups can be substituted or unsubstituted, and may be bridged, spiro, and/or fused. Examples include, but are not limited to, 2,3-dihydrobenzofuranyl, 1,2-dihydroquinolinyl, 3,4-dihydroisoquinolinyl, 1,2,3,4-tetrahydroisoquinolinyl, 1,2,3,4-tetrahydroquinolinyl, benzoxazinyl, benzthiazinyl, chromanyl, furanyl, 2-furanyl, 3-furanyl, imidazolyl, isoxazolyl, isothiazolyl, oxadiazolyl, oxazolyl, pyridinyl, 2-, 3-, or 4-pyridinyl, pyrimidinyl, 2-, 4-, or 5-pyrimidinyl, pyrazolyl, pyrrolyl, 2- or 3-pyrrolyl, pyrazinyl, pyridazinyl, 3- or 4-pyridazinyl, 2-pyrazinyl, thienyl, 2-thienyl, 3-thienyl, tetrazolyl, thiazolyl, thiadiazolyl, triazinyl, triazolyl, pyridin-2-yl, pyridin-4-yl, pyrimidin-2-yl, pyridazin-4-yl, pyrazin-2-yl, naphthyridinyl, pteridinyl, phthalazinyl, purinyl, alloxazinyl, benzimidazolyl, benzofuranyl, benzofurazanyl, 2H-1-benzopyranyl, benzothiadiazine, benzothiazinyl, benzothiazolyl, benzothiophenyl, benzoxazolyl, cinnolinyl, furopyridinyl, indolinyl, indolizinyl, indolyl, or 2-, 3-, 4-, 5-, 6-, or 7-indolyl, 3H-indolyl, quinazolinyl, quinoxalinyl, isoindolyl, isoquinolinyl, 10-aza-tricyclo[6.3.1.0*2,7*]dodeca-2(7),3,5-trienyl, 12-oxa-10-aza-tricyclo[6.3.1.0*2,7*]dodeca-2(7),3,5-trienyl, 12-aza-tricyclo[7.2.1.0*2,7*]dodeca-2(7),3,5-trienyl, 10-aza-tricyclo[6.3.2.0*2,7*]trideca-2(7),3,5-trienyl, 2,3,4,5-tetrahydro-1H-benzo[d]azepinyl, 1,3,4,5-tetrahydrobenzo[d]azepin-2-onyl, 1,3,4,5-tetrahydro-benzo[b]azepin-2-onyl, 2,3,4,5-tetrahydro-benzo[c]azepin-1-onyl, 1,2,3,4-tetrahydro-benzo[e][1,4]diazepin-5-onyl, 2,3,4,5-tetrahydro-1H-benzo[e][1,4]diazepinyl, 5,6,8,9-tetrahydro-7-oxa-benzocycloheptenyl, 2,3,4,5-tetrahydro-1H-benzo[b]azepinyl, 1,2,4,5-tetrahydro-benzo[e][1,3]diazepin-3-onyl, 3,4-dihydro-2H-benzo[b][1,4]dioxepinyl, 3,4-dihydro-2H-benzo[f][1,4]oxazepin-5-onyl, 6,7,8,9-tetrahydro-5-thia-8-aza-benzocycloheptenyl, 5,5-dioxo-6,7,8,9-tetrahydro-5-thia-8-aza-benzocycloheptenyl, and 2,3,4,5-tetrahydro-benzo[f][1,4]oxazepinyl. For example, a heteroaryl group may contain 5, 6, or 8-15 ring atoms. As another example, a heteroaryl group may contain 5 to 10 ring atoms, such as 5, 6, 9, or 10 ring atoms.

"Heteroarylalkyl" or "heteroarylalkyl group" refers to an alkyl group in which a hydrogen atom is replaced by a heteroaryl group, wherein alkyl group and heteroaryl group are as previously defined (i.e., heteroarylalkyl-). Heteroarylalkyl groups can be substituted or unsubstituted. Examples include, but are not limited to, the pyridinylmethyl isomers

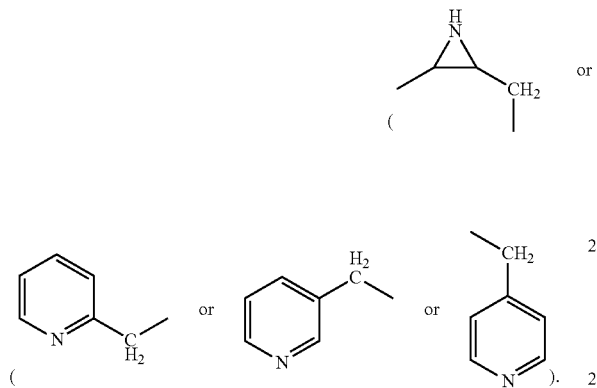

"Heterocycloalkyl" or "heterocycloalkyl group" refers to 3-15 membered monocyclic, bicyclic, and tricyclic non-aromatic rings, which may be saturated or unsaturated, can be substituted or unsubstituted, may be bridged, spiro, and/or fused, and which contain, in addition to carbon atom(s), at least one heteroatom, such as nitrogen, oxygen, sulfur or phosphorus. Examples include, but are not limited to, tetrahydrofuranyl, pyrrolidinyl, pyrrolinyl, imidazolidinyl, imidazolinyl, pyrazolidinyl, pyrazolinyl, piperidyl, piperazinyl, indolinyl, isoindolinyl, morpholinyl, thiomorpholinyl, homomorpholinyl, homopiperidyl, homopiperazinyl, thiomorpholinyl-5-oxide, thiomorpholinyl-S,S-dioxide, pyrrolidinyl, tetrahydropyranyl, piperidinyl, tetrahydrothienyl, homopiperidinyl, homothiomorpholinyl-S, S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, tetrahydrothienyl-5-oxide, tetrahydrothienyl-S,S-dioxide, homothiomorpholinyl-5-oxide, quinuclidinyl, 2-oxa-5-azabicyclo[2.2.1]heptane, 8-oxa-3-aza-bicyclo[3.2.1]octane, 3,8-diaza-bicyclo[3.2.1]octane, 2,5-diaza-bicyclo[2.2.1]heptane, 3,8-diaza-bicyclo[3.2.1]octane, 3,9-diaza-bicyclo[4.2.1]nonane, 2,6-diaza-bicyclo[3.2.2]nonane, [1,4]oxaphosphinane 4-oxide, [1,4]azaphosphinane 4-oxide, [1,2]oxaphospholane 2-oxide, phosphinane 1-oxide, [1,3]azaphospholidine 3-oxide, and [1,3]oxaphospholane 3-oxide. A heterocycloalkyl group may contain, in addition to carbon atom(s), at least one nitrogen, oxygen, or sulfur. For example, a heterocycloalkyl group may contain, in addition to carbon atom(s), at least one nitrogen or oxygen. A heterocycloalkyl group may contain, in addition to carbon atom(s), at least one nitrogen. A heterocycloalkyl group may contain from 3 to 10 ring atoms. A heterocycloalkyl group may contain from 3 to 7 ring atoms. A heterocycloalkyl group may contain from 5 to 7 ring atoms, such as 5 ring atoms, 6 ring atoms, or 7 ring atoms. Unless otherwise indicated, the foregoing heterocycloalkyl groups can be C-attached or N-attached where such is possible and results in the creation of a stable structure. For example, piperidinyl can be piperidin-1-yl (N-attached) or piperidin-4-yl (C-attached).

"Heterocycloalkylene" or "heterocycloalkylene group" refers to diradical, 3-15 membered monocyclic, bicyclic, or tricyclic non-aromatic ring systems, which may be saturated or unsaturated, can be substituted or unsubstituted, may be bridged, spiro, and/or fused, and which contain, in addition to carbon atom(s), at least one heteroatom, such as nitrogen, oxygen, sulfur or phosphorus. Examples include, but are not limited to, the azridinylene isomers

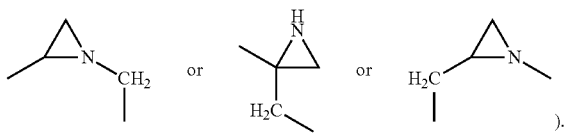

The heterocycloalkylene group may contain, in addition to carbon atom(s), at least one nitrogen, oxygen, or sulfur. The heterocycloalkylene group may contain, in addition to carbon atom(s), at least one nitrogen or oxygen. The heterocycloalkylene group may contain, in addition to carbon atom(s), at least one nitrogen. For example, a heterocycloalkylene group may contain from 3 to 10 ring atoms; such as from 3 to 7 ring atoms. A heterocycloalkylene group may contain from 5 to 7 ring atoms, such as 5 ring atoms, 6 ring atoms, or 7 ring atoms. Unless otherwise indicated, the foregoing heterocycloalkylene groups can be C-attached and/or N-attached where such is possible and results in the creation of a stable structure. A heterocycloalkylene group can also include ring systems substituted on ring carbons with one or more —OH functional groups (which may further tautomerize to give a ring C=O group) and/or substituted on a ring sulfur atom by one (1) or two (2) oxygen atoms to give S=O or $SO_2$ groups, respectively, and/or substituted on a ring phosphorus by an oxygen atom to give P=O.

"Heterocycloalkylalkyl" or "heterocycloalkylalkyl group" refers to an alkyl group in which a hydrogen atom is replaced by a heterocycloalkyl group, wherein alkyl group and heterocycloalkyl group are as previously defined (i.e., heterocycloalkylalkyl-). Heteroycloalkylalkyl groups can be substituted or unsubstituted. Examples include, but are not limited to, pyrrolidinylmethyl ($C_4H_8NCH_2$—).

"Pharmaceutically acceptable" refers to physiologically tolerable materials, which do not typically produce an allergic or other untoward reaction, such as gastric upset, dizziness and the like, when administered to a human.

"Pharmaceutical composition" refers to a composition that can be used to treat a disease, condition, or disorder in a human.

"Pseudohalogen" refers to —OCN, —SCN, —$CF_3$, and —CN.

"Stable" or "chemically stable" refers to a compound that is sufficiently robust to be isolated to a useful degree of purity from a reaction mixture. The present invention is directed solely to the preparation of stable compounds. When lists of alternative substituents include members which, owing to valency requirements, chemical stability, or other reasons, cannot be used to substitute a particular group, the list is intended to be read in context to include those members of the list that are suitable for substituting the particular group. For example, $R^1$ can be $C_{1-6}$alkyl optionally substituted by 1-13 $R^{19}$; when $R^1$ is methyl, the methyl group is optionally substituted by 1-3 $R^{19}$.

"Therapeutically effective amount" refers to an amount of a compound sufficient to inhibit, halt, or cause an improvement in a disorder or condition being treated in a particular subject or subject population. For example in a human or other mammal, a therapeutically effective amount can be determined experimentally in a laboratory or clinical setting, or may be the amount required by the guidelines of the United States Food and Drug Administration, or equivalent foreign agency, for the particular disease and subject being treated. It should be appreciated that determination of proper dosage forms, dosage amounts, and routes of administration is within the level of ordinary skill in the pharmaceutical and medical arts.

"Treatment" refers to the acute or prophylactic diminishment or alleviation of at least one symptom or characteristic associated or caused by a disorder being treated. For example, treatment can include diminishment of several symptoms of a disorder or complete eradication of a disorder.

II. Compounds

The compounds of the present invention are defined by the following numbered Embodiments. When a higher numbered Embodiment refers back to multiple previous lower numbered Embodiments in the alternative and contains a new limitation not present in the lower numbered Embodiments, the higher numbered Embodiment is intended to be an express description of each and every one of the alternatives. For example, if Embodiment 2 refers back to Embodiment 1 and contains a limitation not present in Embodiment 1, Embodiment 3 refers back Embodiments 1 or 2 and contains a limitation(s) not present in Embodiments 1 or 2, and Embodiment 4 refers back to any of Embodiments 1-3 and contains a limitation(s) not present in Embodiments 1, 2 or 3, then Embodiment 4 is intended to be an explicit description of a genus having the limitations of Embodiments 1 and 4, an explicit description of a genus having the limitations of Embodiments 1, 2 and 4, an explicit description of a genus having the limitations of Embodiments 1, 3 and 4, and an explicit description of a genus having the limitations of Embodiments 1, 2, 3 and 4. By way of example, if Embodiment 1 is a compound of formula (I) defining $R^1$, $R^2$ and $R^3$ independently as alkyl or aryl, and Embodiment 2 is a compound of Embodiment 1 defining $R^1$ as alkyl, and Embodiment 3 is a compound of Embodiments 1 or 2 defining $R^2$ as alkyl, and Embodiment 4 is a compound of any of Embodiments 1-3 defining $R^3$ as alkyl, then Embodiment 4 is an explicit description of a genus having the limitations of Embodiments 1 and 4 (i.e., a compound of formula (I) in which $R^1$ and $R^2$ are alkyl or aryl, and $R^3$ is alkyl), an explicit description of a genus having the limitations of Embodiments 1, 2 and 4 (i.e., a compound of formula (I) in which $R^2$ is alkyl or aryl, and $R^1$ and $R^3$ are alkyl), an explicit description of a genus having the limitations of Embodiments 1, 3 and 4 (i.e., a compound of formula (I) in which $R^1$ is alkyl or aryl, and $R^2$ and $R^3$ are alkyl), and an explicit description of a genus having the limitations of Embodiments 1, 2, 3 and 4 (i.e., a compound of formula (I) in which $R^1$, $R^2$ and $R^3$ are alkyl). It should be noted in this regard that when a higher numbered Embodiment refers to a lower numbered Embodiment and contains limitations for a group(s) not present in the lower numbered Embodiment, the higher numbered Embodiment should be interpreted in context to ignore the missing group(s). For example, if Embodiment 1 recites a compound of formula (I) in which A is $NR^{11}$, O, or S, Embodiment 2 recites a compound of Embodiment 1 in which A is O or S, and Embodiment 3 recites a compound of Embodiments 1 or 2 in which $R^{11}$ is alkyl, then Embodiment 3 defines a genus having the limitations of Embodiments 1 and 3 and a genus having the limitation of Embodiments 1, 2 and 3. In the genus defined by the limitations of Embodiments 1, 2 and 3, A cannot be $NR^{11}$; therefore this genus should be interpreted to ignore and omit the Embodiment 3 definition of $R^{11}$=alkyl.

Embodiment 1

A compound of formula (I)

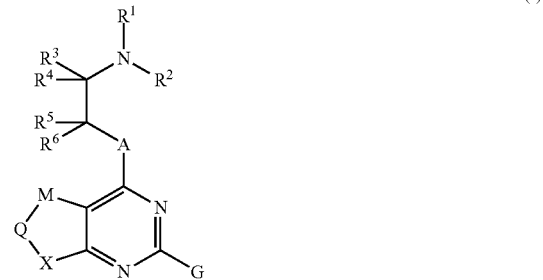

or a salt form thereof,
wherein
  A is $NR^{11}$, O, or S;
  M-Q-X is a group of formula

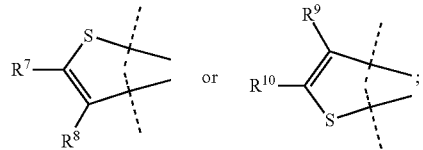

G is a group of formula

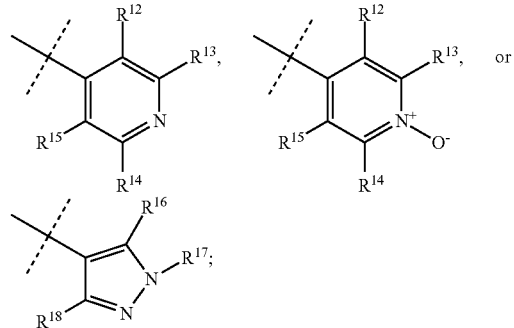

$R^1$, $R^2$, $R^{11}$, and $R^{17}$ are independently chosen from H, $C_{1-6}$alkyl optionally substituted by 1-13 $R^{19}$, $C_{2-6}$alkenyl optionally substituted by 1-11 $R^{19}$, $C_{2-6}$alkynyl optionally substituted by 1-9 $R^{19}$, $C_{6-11}$aryl optionally substituted by 1-11 $R^{19}$, $C_{7-16}$arylalkyl optionally substituted by 1-19 $R^{19}$, $C_{3-11}$cycloalkyl optionally substituted by 1-21 $R^{19}$, $C_4$-17cycloalkylalkyl optionally substituted by 1-32 $R^{19}$, 3-15 membered heterocycloalkyl optionally substituted by 1-28 $R^{19}$, 4-21 membered heterocycloalkylalkyl optionally substituted by 1-40 $R^{19}$, 5-15 membered heteroaryl optionally substituted by 1-15 $R^{19}$, 6-21 membered heteroarylalkyl optionally substituted by 1-27 $R^{19}$, and —$OR^{20}$;

$R^3$, $R^4$, $R^5$, $R^6$, $R^7$, $R^8$, $R^9$, $R^{10}$, $R^{12}$, $R^{13}$, $R^{14}$, $R^5$, $R^{16}$, and $R^{18}$ are independently chosen from H, $C_{1-6}$alkyl optionally substituted by 1-13 $R^{19}$, $C_{2-6}$alkenyl optionally substituted by 1-11 $R^{19}$, $C_{2-6}$alkynyl optionally substituted by 1-9 $R^{19}$, $C_{6-11}$aryl optionally substituted by 1-11 $R^{19}$, $C_{7-16}$arylalkyl optionally substituted by 1-19 $R^{19}$, $C_{3-11}$cycloalkyl optionally substituted by 1-21 $R^{19}$, $C_{4-17}$cycloalkylalkyl optionally substituted by 1-32 $R^{19}$, 3-15 membered heterocycloalkyl optionally substituted by 1-28 $R^{19}$, 4-21 membered heterocycloalkylalkyl optionally substituted by 1-40 $R^{19}$, 5-15 membered heteroaryl optionally substituted by 1-15 $R^{19}$, 6-21 membered heteroarylalkyl optionally substituted by 1-27 $R^{19}$, halogen, —CN, —C(=O)$R^{20}$, —C(=O)O$R^{20}$, —C(=O)N$R^{22}R^{23}$, —C(=O)C(=O)$R^{20}$, —C(=N$R^{25}$)$R^{20}$, —C(=N$R^{25}$)N$R^{22}R^{23}$, —C(=NOH)N$R^{22}R^{23}$, —C(=NO$R^{26}$)$R^{20}$, —C(=NN$R^{22}R^{23}$)$R^{20}$, —C(=NN$R^{24}$C(=O)$R^{21}$)$R^{20}$, —C(=NN$R^{22}R^{23}$)$R^{20}$, —C(=NN$R^{24}$C(=O)O$R^{21}$)$R^{20}$, —C(=S)N$R^{22}R^{23}$, —NC, —NO$_2$, —N$R^{22}R^{23}$, —N$R^{24}$N$R^{22}R^{23}$, —N=N$R^{24}$, —N$R^{24}$O$R^{26}$, —N$R^{24}$C(=O)$R^{20}$, —N$R^{24}$C(=O)C(=O)$R^{20}$, —N$R^{24}$C(=O)O$R^{21}$, —N$R^{24}$C(=O)C(=O)O$R^{21}$, —N$R^{24}$C(=O)N$R^{22}R^{23}$, —N$R^{24}$C(=O)N$R^{24}$C(=O)$R^{20}$, —N$R^{24}$C(=O)N$R^{24}$C(=O)O$R^{20}$, —N$R^{24}$C(=N$R^{25}$)N$R^{22}R^{23}$, —N$R^{24}$C(=O)C(=O)N$R^{22}R^{23}$, —N$R^{24}$C(=S)$R^{20}$, —N$R^{24}$C(=S)O$R^{20}$, —N$R^{24}$C(=S)N$R^{22}R^{23}$, —N$R^{24}$S(=O)$_2R^{21}$, —N$R^{24}$S(=O)$_2$N$R^{22}R^{23}$, —N$R^{24}$P(=O)$R^{28}R^{28}$, —N$R^{24}$P(=O)(N$R^{22}R^{23}$)(N$R^{22}R^{23}$), —N$R^{24}$P(=O)(O$R^{20}$)(O$R^{20}$), —N$R^{24}$P(=O)(S$R^{20}$)(S$R^{20}$), —O$R^{20}$, —OCN, —OC(=O)$R^{20}$, —OC(=O)N$R^{22}R^{23}$, —OC(=O)O$R^{20}$, —OC(=N$R^{25}$)N$R^{22}R^{23}$, —OS(=O)$R^{20}$, —OS(=O)$_2R^{20}$, —OS(=O)$_2$O$R^{20}$, —OS(=O)$_2$N$R^{22}R^{23}$, —OP(=O)$R^{28}R^{28}$, —OP(=O)(N$R^{22}R^{23}$)(N$R^{22}R^{23}$), —OP(=O)(O$R^{20}$)(O$R^{20}$), —OP(=O)(S$R^{20}$)(S$R^{20}$), —Si($R^{24}$)$_3$, —SCN, —S(=O)$_nR^{20}$, —S(=O)$_2R^2$, —SO$_3R^{27}$, —S(=O)$_2$N$R^{22}R^{23}$, —S(=O)N$R^{22}R^{23}$, —SP(=O)$R^{28}R^{28}$, —SP(=O)(N$R^{22}R^{23}$)(N$R^{22}R^{23}$), —SP(=O)(O$R^{20}$)(O$R^{20}$), —SP(=O)(S$R^{20}$)(S$R^{20}$), —P(=O)$R^{28}R^{28}$, —P(=O)(N$R^{22}R^{23}$)(N$R^{22}R^{23}$), —P(=O)(O$R^{20}$)(O$R^{20}$), and —P(=O)(S$R^{20}$)(S$R^{20}$);

any of $R^1$ and $R^2$, $R^1$ and $R^3$, $R^1$ and $R^5$, $R^1$ and $R^{11}$, $R^4$ and $R^{11}$, $R^6$ and $R^{11}$, and $R^{16}$ and $R^{17}$ can, together with the atoms linking them, form a 3-15 membered heterocycloalkyl optionally substituted by 1-28 $R^{19}$ or a 5-15 membered heteroaryl optionally substituted by 1-15 $R^{19}$;

any of $R^3$ and $R^6$, $R^7$ and $R^8$, $R^9$ and $R^{10}$, $R^{12}$ and $R^{13}$, and $R^{14}$ and $R^{15}$ can, together with the atoms linking them, form a $C_{6-11}$aryl optionally substituted by 1-11 $R^{19}$, $C_{3-11}$cycloalkyl optionally substituted by 1-21 $R^{19}$, 3-15 membered heterocycloalkyl optionally substituted by 1-28 $R^{19}$ or a 5-15 membered heteroaryl optionally substituted by 1-15 $R^{19}$;

$R^3$ and $R^5$ or $R^4$ and $R^6$ can together form a double bond;

any of $R^3$ and $R^4$, and $R^5$ and $R^6$ can together form =O, =N$R^{20}$, =NO$R^{20}$, or =S;

$R^{19}$ at each occurrence is independently chosen from $C_{1-6}$alkyl optionally substituted by 1-13 $R^{39}$, $C_{2-6}$alkenyl optionally substituted by 1-11 $R^{39}$, $C_{2-6}$alkynyl optionally substituted by 1-9 $R^{39}$, $C_{6-11}$aryl optionally substituted by 1-11 $R^{39}$, $C_{7-16}$arylalkyl optionally substituted by 1-19 $R^{39}$, $C_{3-11}$cycloalkyl optionally substituted by 1-21 $R^{39}$, $C_{4-17}$cycloalkylalkyl optionally substituted by 1-32 $R^{39}$, 3-15 membered heterocycloalkyl optionally substituted by 1-28 $R^{39}$, 4-21 membered heterocycloalkylalkyl optionally substituted by 1-40 $R^{39}$, 5-15 membered heteroaryl optionally substituted by 1-15 $R^{39}$, 6-21 membered heteroarylalkyl optionally substituted by 1-27 $R^{39}$, halogen, —CN, —C(=O)$R^{30}$, —C(=O)O$R^{30}$, —C(=O)N$R^{32}R^{33}$, —C(=O)C(=O)$R^{30}$, —C(=N$R^{35}$)$R^{30}$, —C(=N$R^{35}$)N$R^{32}R^{33}$, —C(=NOH)N$R^{32}R^{33}$, —C(=NO$R^{36}$)$R^{30}$, —C(=N$R^{32}R^{33}$)$R^{30}$, —C(=NN$R^{34}$C(=O)$R^{31}$)$R^{30}$, —C(=NN$R^{34}$C(=O)O$R^{31}$)$R^{30}$, —C(=S)N$R^{32}R^{33}$, —NC, —NO$_2$, —N$R^{32}R^{33}$, —N$R^{34}$N$R^{32}R^{33}$, —N=N$R^{34}$, =N$R^{30}$, =NO$R^{30}$, —N$R^{34}R^{36}$, —N$R^{34}$C(=O)$R^{30}$, —N$R^{34}$C(=O)C(=O)$R^{30}$, —N$R^{34}$C(=O)O$R^{31}$, —N$R^{34}$C(=O)C(=O)O$R^{31}$, —N$R^{34}$C(=O)N$R^{32}R^{33}$, —N$R^{34}$C(=O)N$R^{34}$C(=O)$R^{30}$, —N$R^{34}$C(=O)N$R^{34}$C(=O)O$R^{30}$, —N$R^{34}$C(=N$R^{35}$)N$R^{32}R^{33}$, —N$R^{34}$C(=O)C(=O)N$R^{32}R^{33}$, —N$R^{34}$C(=S)$R^{30}$, —N$R^{34}$C(=S)O$R^{30}$, —N$R^{34}$C(=S)N$R^{32}R^{33}$, —N$R^{34}$S(=O)$_2R^{31}$, —N$R^{34}$S(=O)$_2$N$R^{32}R^{33}$, —N$R^{34}$P(=O)$R^{38}R^{38}$, —N$R^{34}$P(=O)(N$R^{32}R^{33}$)(N$R^{32}R^{33}$), —N$R^{34}$P(=O)(O$R^{30}$)(O$R^{30}$), —N$R^{34}$P(=O)(S$R^{30}$)(S$R^{30}$), —O$R^{30}$, =O, —OCN, —OC(=O)$R^{30}$, —OC(=O)N$R^{32}R^{33}$, —OC(=O)O$R^{30}$, —OC(=N$R^{35}$)N$R^{32}R^{33}$, —OS(=O)$R^{30}$, —OS(=O)$_2R^{30}$, —OS(=O)$_2$O$R^{30}$, —OS(=O)$_2$N$R^{32}R^{33}$, —OP(=O)$R^{38}R^{38}$, —OP(=O)(N$R^{32}R^{33}$)(N$R^{32}R^{33}$), —OP(=O)(O$R^{30}$)(O$R^{30}$), —OP(=O)(S$R^{30}$)(S$R^{30}$), —Si($R^{34}$)$_3$, —SCN, =S, —S(=O)$_nR^{30}$, —S(=O)$_2$O$R^{30}$, —SO$_3R^{37}$, —S(=O)$_2$N$R^{32}R^{33}$, —S(=O)N$R^{32}R^{33}$, —SP(=O)$R^{38}R^{38}$, —SP(=O)(N$R^{32}R^{33}$)(N$R^{32}R^{33}$), —SP(=O)(O$R^{30}$)(O$R^{30}$), —SP(=O)(S$R^{30}$)(S$R^{30}$), —P(=O)$R^{38}R^{38}$, —P(=O)(N$R^{32}R^{33}$)(N$R^{32}R^{33}$), —P(=O)(O$R^{30}$)(O$R^{30}$), and —P(=O)(S$R^{30}$)(S$R^{30}$);

$R^{20}$, $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H, $C_{1-6}$alkyl optionally substituted by 1-13 $R^{49}$, $C_{2-6}$alkenyl optionally substituted by 1-11 $R^{49}$, $C_{2-6}$alkynyl optionally substituted by 1-9 $R^{49}$, $C_{6-11}$aryl optionally substituted by 1-11 $R^{49}$, $C_{7-16}$arylalkyl optionally substituted by 1-19 $R^{49}$, $C_{3-11}$cycloalkyl optionally substituted by 1-21 $R^{49}$, $C_{4}$-17cycloalkylalkyl optionally substituted by 1-32 $R^{49}$, 3-15 membered heterocycloalkyl optionally substituted by 1-28 $R^{49}$, 4-21 membered heterocycloalkylalkyl optionally substituted by 1-40 $R^{49}$, 5-15 membered heteroaryl optionally substituted by 1-15 $R^{49}$, and 6-21 membered heteroarylalkyl optionally substituted by 1-27 $R^{49}$;

$R^{28}$ and $R^{38}$ at each occurrence is independently chosen from $C_{1-6}$alkyl optionally substituted by 1-13 $R^{49}$, $C_{2-6}$alkenyl optionally substituted by 1-11 $R^{49}$, $C_{2-6}$alkynyl optionally substituted by 1-9 $R^{49}$, $C_{6-11}$aryl optionally substituted by 1-11 $R^{49}$, $C_{7-16}$arylalkyl optionally substituted by 1-19 $R^{49}$, $C_{3-11}$cycloalkyl optionally substituted by 1-21 $R^{49}$, $C_{4-17}$cycloalkylalkyl optionally substituted by 1-32 $R^{49}$, 3-15 membered heterocycloalkyl optionally substituted by 1-28 $R^{49}$, 4-21 membered heterocycloalkylalkyl optionally substituted by 1-40 $R^{49}$, 5-15 membered heteroaryl optionally substituted by 1-15 $R^{49}$, and 6-21 membered heteroarylalkyl optionally substituted by 1-27 $R^{49}$, $R^{22}$, $R^{23}$, $R^{32}$ and $R^{33}$ at each occurrence is independently chosen from H, $C_{1-6}$alkyl optionally substituted by 1-13 $R^{59}$, $C_{2-6}$alkenyl optionally substituted by 1-11 $R^{59}$, $C_{2-6}$alkynyl optionally substituted by 1-9 $R^{59}$, $C_{6-11}$aryl optionally substituted by 1-11 $R^{59}$, $C_{7-16}$arylalkyl optionally substituted by 1-19 $R^{59}$, $C_{3-11}$cycloalkyl optionally substituted by 1-21 $R^{59}$, $C_{4-17}$cycloalkylalkyl optionally substituted by 1-32 $R^{59}$, 3-15 membered heterocycloalkyl optionally substituted by 1-28 $R^{59}$, 4-21 membered heterocycloalkylalkyl optionally substituted by 1-40 $R^{59}$, 5-15 membered heteroaryl optionally substituted by 1-15 $R^{59}$, and 6-21 membered heteroarylalkyl optionally substituted by 1-27 $R^{59}$; or any $R^{22}$ and $R^{23}$ and/or $R^{32}$ and $R^{33}$ may form, together with the nitrogen atom to which they are attached, a 3-15 membered heterocycloalkyl optionally substituted by 1-28 $R^{69}$ or a 5-15 membered heteroaryl optionally substituted by 1-15 $R^{69}$;

$R^{39}$, $R^{49}$, $R^{59}$ and $R^{69}$ at each occurrence is independently chosen from $C_{1-6}$alkyl optionally substituted by 1-13 $R^{79}$, $C_{2-6}$alkenyl optionally substituted by 1-11 $R^{79}$, $C_{2-6}$alkynyl optionally substituted by 1-9 $R^{79}$, $C_{6-11}$aryl optionally substituted by 1-11 $R^{79}$, $C_{7-16}$arylalkyl optionally substituted by 1-19 $R^{79}$, $C_{3-11}$cycloalkyl optionally substituted by 1-21 $R^{79}$, $C_{4-17}$cycloalkylalkyl optionally substituted by 1-32 $R^{79}$, 3-15 membered heterocycloalkyl optionally substituted by 1-28 $R^{79}$, 4-21 membered heterocycloalkylalkyl optionally substituted by 1-40 $R^{79}$, 5-15 membered heteroaryl optionally substituted by 1-15 $R^{79}$, 6-21 membered heteroarylalkyl optionally substituted by 1-27 $R^{79}$, halogen, —CN, —C(=O)$R^{70}$, —C(=O)O$R^{70}$, —C(=O)N$R^{72}R^{73}$, —C(=O)C(=O)$R^{70}$, —C(=N$R^{75}$)$R^{70}$, —C(=N$R^{75}$)N$R^{72}R^{73}$, —C(=NOH)N$R^{72}R^{73}$, —C(=NO$R^{76}$)$R^{70}$, —C(=NN$R^{72}R^{73}$)$R^{70}$, —C(=NN$R^{74}$C(=O)$R^{71}$)$R^{70}$, —C(=NN$R^{74}$C(=O)O$R^{71}$)$R^{70}$, —C(=S)N$R^{72}R^{73}$, —NC, —NO$_2$, —N$R^{72}R^{73}$, —N$R^{74}$N$R^{72}R^{73}$, —N=N$R^{74}$, =N$R^{70}$, =NO$R^{70}$, —N$R^{74}R^{76}$, —N$R^{74}$C(=O)$R^{70}$, —N$R^{74}$C(=O)C(=O)$R^{70}$, —N$R^{74}$C(=O)O$R^{71}$, —N$R^{74}$C(=O)C(=O)O$R^{71}$, —N$R^{74}$C(=O)N$R^{72}R^{73}$, —N$R^{74}$C(=O)N$R^{74}$C(=O)$R^{70}$, —N$R^{74}$C(=O)N$R^{74}$C(=O)O$R^{70}$, —N$R^{74}$C(=N$R^{75}$)N$R^{72}R^{73}$, —N$R^{74}$C(=O)C(=O)N$R^{72}R^{73}$, —N$R^{74}$C(=S)$R^{70}$, —N$R^{74}$C(=S)O$R^{70}$, —N$R^{74}$C(=S)N$R^{72}R^{73}$, —N$R^{74}$S(=O)$_2R^{71}$, —N$R^{74}$S(=O)$_2$N$R^{72}R^{73}$, —N$R^{74}$P(=O)$R^{78}R^{78}$, —N$R^{74}$P(=O)(N$R^{72}R^{73}$)(N$R^{72}R^{73}$), —N$R^{74}$P(=O)(O$R^{70}$)(O$R^{70}$), —N$R^{74}$P(=)(S$R^{70}$)(S$R^{70}$), —O$R^{70}$, =O, —OCN, —OC(=O)$R^{70}$, —OC(=O)N$R^{72}R^{73}$, —OC(=O)O$R^{70}$, —OC(=N$R^{75}$)N$R^{72}R^{73}$, —OS(=O)$R^{70}$, —OS(=O)$_2R^{70}$, —OS(=O)$_2$O$R^{70}$, —OS(=O)$_2$N$R^{72}R^{73}$, —OP(=O)$R^{78}R^{78}$, —OP(=O)(N$R^{72}R^{73}$)(N$R^{72}R^{73}$), —OP(=O)(O$R^{70}$)(O$R^{70}$), —OP(=O)(S$R^{70}$)(S$R^{70}$), —Si($R^{74}$)$_3$, —SCN, =S, —S(=O)$_nR^{70}$, —S(=O)$_2R^{70}$, —SO$_3R^{77}$, —S(=O)$_2$N$R^{72}R^{73}$, —S(=O)N$R^{72}R^{73}$, —SP(=O)$R^{78}R^{78}$, —SP(=O)(N$R^{72}R^{73}$)(N$R^{72}R^{73}$), —SP(=O)(O$R^{70}$)(O$R^{70}$), —SP(=O)(S$R^{70}$)(S$R^{70}$), —P(=O)$R^{78}R^{78}$, —P(=O)(N$R^{72}R^{73}$)(N$R^{72}R^{73}$), —P(=O)(O$R^{70}$)(O$R^{70}$), and —P(=O)(S$R^{70}$)(S$R^{70}$);

$R^{70}$, $R^{71}$, $R^{74}$, $R^{75}$, $R^{76}$ and $R^{77}$ at each occurrence is independently chosen from H, $C_{1-6}$alkyl optionally substituted by 1-13 $R^{89}$, $C_{2-6}$alkenyl optionally substituted by 1-11 $R^{89}$, $C_{2-6}$alkynyl optionally substituted by 1-9 $R^{89}$, $C_{6-11}$aryl optionally substituted by 1-11 $R^{89}$, $C_{7-16}$arylalkyl optionally substituted by 1-19 $R^{89}$, $C_{3-11}$cycloalkyl optionally substituted by 1-21 $R^{89}$, $C_{4-17}$cycloalkylalkyl optionally substituted by 1-32 $R^{89}$, 3-15 membered heterocycloalkyl optionally substituted by 1-28 $R^{89}$, 4-21 membered heterocycloalkylalkyl optionally substituted by 1-40 $R^{89}$, 5-15 membered heteroaryl optionally substituted by 1-15 $R^{89}$, and 6-21 membered heteroarylalkyl optionally substituted by 1-27 $R^{89}$;

$R^{72}$ and $R^{73}$ at each occurrence is independently chosen from H, $C_{1-6}$alkyl optionally substituted by 1-13 $R^{99}$, $C_{2-6}$alkenyl optionally substituted by 1-11 $R^{99}$, $C_{2-6}$alkynyl optionally substituted by 1-9 $R^{99}$, $C_{6-11}$aryl optionally substituted by 1-11 $R^{99}$, $C_{7-16}$arylalkyl optionally substituted by 1-19 $R^{99}$, $C_{3-11}$cycloalkyl optionally substituted by 1-21 $R^{99}$, $C_{4-17}$cycloalkylalkyl optionally substituted by 1-32 $R^{99}$, 3-15 membered heterocycloalkyl optionally substituted by 1-28 $R^{99}$, 4-21 membered heterocycloalkylalkyl optionally substituted by 1-40 $R^{99}$, 5-15 membered heteroaryl optionally substituted by 1-15 $R^{99}$, and 6-21 membered heteroarylalkyl optionally substituted by 1-27 $R^{99}$; or any $R^{72}$ and $R^{73}$ may form, together with the nitrogen atom to which they are attached, a 3-15 membered heterocycloalkyl optionally substituted by 1-28 $R^{109}$ or a 5-15 membered heteroaryl optionally substituted by 1-15 $R^{109}$;

$R^{78}$ at each occurrence is independently chosen from $C_{1-6}$alkyl optionally substituted by 1-13 $R^{89}$, $C_{2-6}$alkenyl optionally substituted by 1-11 $R^{89}$, $C_{2-6}$alkynyl optionally substituted by 1-9 $R^{89}$, $C_{6-11}$aryl optionally substituted by 1-11 $R^{89}$, $C_{7-16}$arylalkyl optionally substituted by 1-19 $R^{89}$, $C_{3-11}$cycloalkyl optionally substituted by 1-21 $R^{89}$, $C_4$-17cycloalkylalkyl optionally substituted by 1-32 $R^{89}$, 3-15 membered heterocycloalkyl optionally substituted by 1-28 $R^{89}$, 4-21 membered heterocycloalkylalkyl optionally substituted by 1-40 $R^{89}$, 5-15 membered heteroaryl optionally substituted by 1-15 $R^{89}$, and 6-21 membered heteroarylalkyl optionally substituted by 1-27 $R^{89}$;

$R^{79}$, $R^{89}$, $R^{99}$ and $R^{109}$ at each occurrence is independently chosen from $C_{1-6}$alkyl optionally substituted by 1-13 halogen, $C_{2-6}$alkenyl, $C_{2-6}$alkynyl, $C_{6-11}$aryl, $C_{7-16}$arylalkyl, $C_{3-11}$cycloalkyl, $C_{4-17}$cycloalkylalkyl, 3-15 membered heterocycloalkyl, 4-21 membered heterocycloalkylalkyl, 5-15 membered heteroaryl, 6-21 membered heteroarylalkyl, halogen, —CN, —C(=O)$R^{110}$, —C(=O)O$R^{110}$, —C(=O)N$R^{110}R^{110}$, —C(=O)C(=O)$R^{110}$, —C(=N$R^{110}$)$R^{110}$, —C(=N$R^{110}$)N$R^{110}R^{110}$, —C(=NOH)N$R^{11}R^{110}$, —C(=NO$R^{110}$)$R^{110}$, —C(=NN$R^{110}R^{110}$)$R^{110}$, —C(=NN$R^{110}$C(=O)$R^{110}$)$R^{110}$, —C(=NN$R^{110}$C(=O)O$R^{110}$)$R^{110}$, —C(=S)N$R^{110}R^{110}$, —NC, —NO$_2$, —N$R^{11}R^{110}$, —N$R^{110}$N$R^{110}R^{110}$, —N=N$R^{110}$, =N$R^{110}$, =NO$R^{110}$, —N$R^{110}$O$R^{110}$, —N$R^{110}$C(=O)$R^{110}$, —N$R^{110}$C(=O)C(=O)$R^{110}$, —N$R^{110}$C(=O)O$R^{110}$, —N$R^{110}$C(=O)C(=O)O$R^{110}$, —N$R^{110}$C(=O)N$R^{110}R^{110}$, —N$R^{110}$C(=O)N$R^{110}$C(=O)$R^{110}$, —N$R^{110}$C(=O)N$R^{110}$C(=O)O$R^{110}$, —N$R^{110}$C(=N$R^{110}$)N$R^{110}R^{110}$, —N$R^{110}$C(=O)C(=O)N$R^{110}R^{110}$, —N$R^{110}$C(=S)$R^{110}$, —N$R^{110}$C(=S)O$R^{110}$, —N$R^{110}$C(=S)N$R^{110}R^{110}$, —N$R^{110}$S(=O)$_2R^{110}$, —N$R^{110}$S(=O)$_2$N$R^{110}R^{110}$, —N$R^{110}$P(=O)$R^{111}R^{111}$, —N$R^{110}$P(=O)(N$R^{110}R^{110}$)(N$R^{110}R^{110}$), —N$R^{110}$P(=O)(O$R^{110}$)(O$R^{110}$), —N$R^{110}$P(=O)(S$R^{110}$)(S$R^{110}$), —O$R^{110}$, =O, —OCN, —OC(=O)$R^{110}$, —OC(=O)N$R^{110}R^{110}$, —OC(=O)O$R^{110}$, —OC(=N$R^{110}$)N$R^{110}R^{110}$, —OS(=O)$R^{110}$, —OS(=O)$_2R^{110}$, —OS(=O)$_2$O$R^{110}$, —OS(=O)$_2$NR$^{110}$R$^{110}$, —OP(=O)R$^{111}$R$^{111}$, —OP(=O)(NR$^{110}$OR$^{110}$)(NR$^{110}$OR$^{110}$), —OP(=O)(OR$^{110}$)(OR$^{110}$), —OP(=O)(SR$^{110}$)(SR$^{110}$), —Si(R$^{110}$)$_3$, —SCN, =S, —S(=O)$_n$R$^{110}$, —S(=O)$_2$OR$^{110}$, —SO$_3$R$^{110}$, —S(=O)$_2$NR$^{110}$R$^{110}$, —S(=O)NR$^{110}$R$^{110}$, —SP(=O)R$^{111}$R$^{111}$, —SP(=O)(NR$^{110}$R$^{110}$)(NR$^{110}$R$^{110}$), —SP(=O)(OR$^{110}$)(OR$^{110}$), —SP(=O)(SR$^{110}$)(SR$^{110}$), —P(=O)R$^{110}$R$^{110}$, —P(=O)(NR$^{110}$R$^{110}$)(NR$^{110}$R$^{110}$), —P(=O)(OR$^{110}$)(OR$^{110}$), and —P(=O)(SR$^{110}$)(SR$^{110}$);

R$^{110}$ at each occurrence is independently chosen from H, C$_{1-6}$alkyl and C$_{1-6}$-haloalkyl;

R$^{111}$ at each occurrence is independently chosen from C$_{1-6}$alkyl and C$_{1-6}$-haloalkyl; and n at each occurrence is independently chosen from 0, 1, and 2.

Embodiment 2

The compound of Embodiment 1, wherein A is NR$^{11}$, O, or S.

Embodiment 3

The compound of Embodiment 1, wherein A is NR$^{11}$ or O.

Embodiment 4

The compound of Embodiment 1, wherein A is NR$^{11}$.

Embodiment 5

The compound of Embodiment 1, wherein A is O.

Embodiment 5

The compound of Embodiment 1, wherein A is S.

Embodiment 6

The compound of any of Embodiments 1-5, wherein M-Q-X is a group of formula

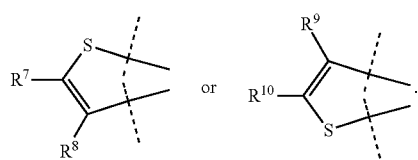

Embodiment 7

The compound of any of Embodiments 1-5, wherein M-Q-X is a group of formula

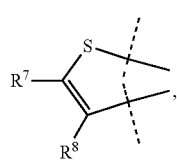

and the compound of formula (I) is a compound of formula (Ia)

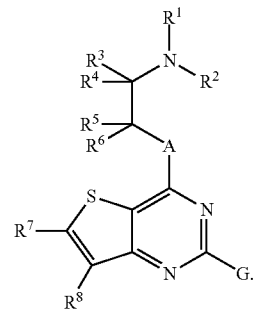

Embodiment 8

The compound of any of Embodiments 1-5, wherein M-Q-X is a group of formula

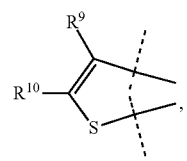

and the compound of formula (I) is a compound of formula (Ib)

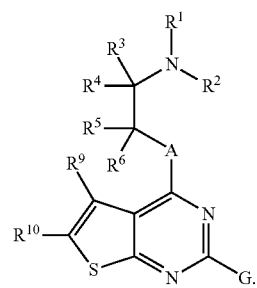

Embodiment 9

The compound of any of Embodiments 1-8, wherein G is a group of formula

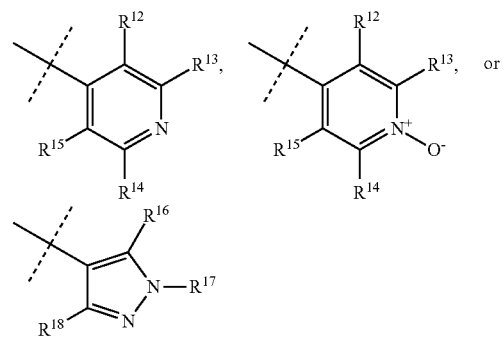

Embodiment 10

The compound of any of Embodiments 1-8, wherein G is a group of formula

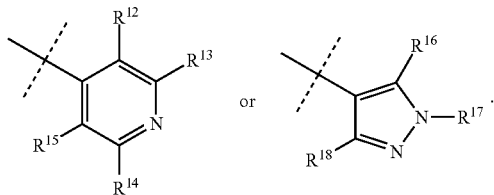

Embodiment 11

The compound of any of Embodiments 1-8, wherein G is a group of formula

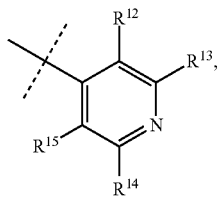

and the compound of formula (I) is a compound of formula (Ic)

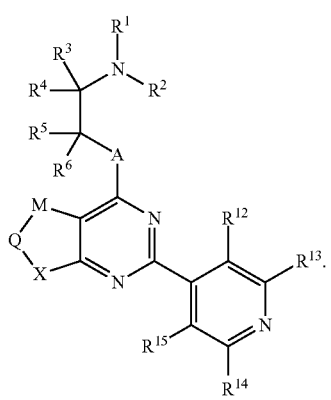

(Ic)

Embodiment 12

The compound of any of Embodiments 1-8, wherein G is a group of formula

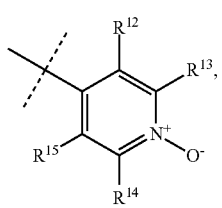

and the compound of formula (I) is a compound of formula (Id)

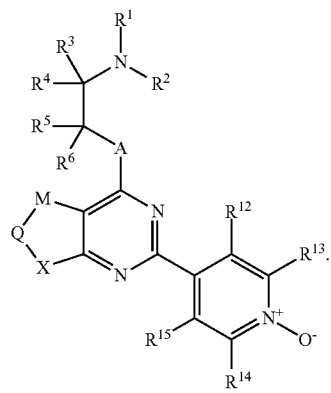

(Id)

Embodiment 13

The compound of any of Embodiments 1-8, wherein G is a group of formula

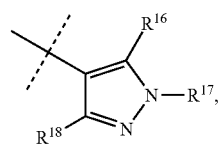

and the compound of formula (I) is a compound of formula (Ie)

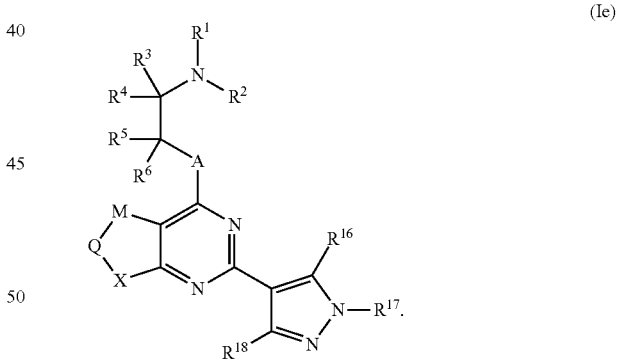

(Ie)

Embodiment 14

The compound of any of Embodiments 1-5, wherein M-Q-X is a group of formula

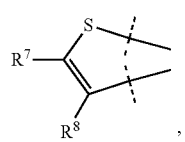

G is a group of formula

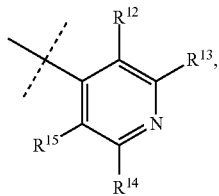

and the compound of formula (I) is a compound of formula (If)

(If)

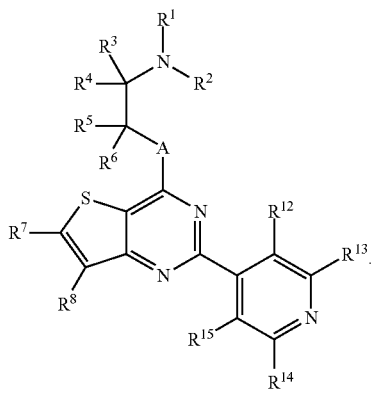

Embodiment 15

The compound of any of Embodiments 1-5, wherein M-Q-X is a group of formula

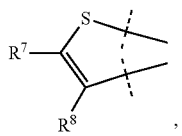

G is a group of formula

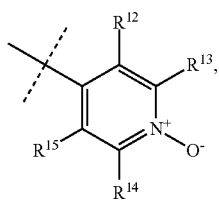

and the compound of formula (I) is a compound of formula (Ig)

(Ig)

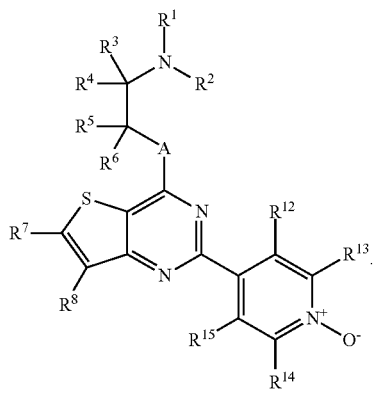

Embodiment 16

The compound of any of Embodiments 1-5, wherein M-Q-X is a group of formula

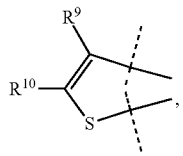

G is a group of formula

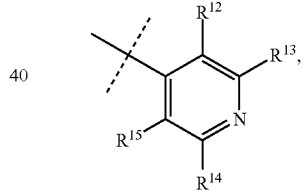

and the compound of formula (I) is a compound of formula (Ih)

(Ih)

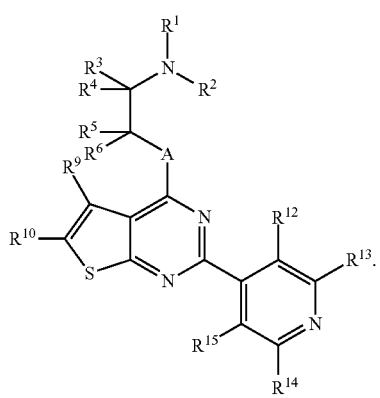

Embodiment 17

The compound of any of Embodiments 1-5, wherein M-Q-X is a group of formula

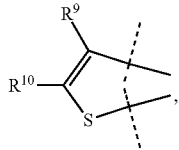

G is a group of formula

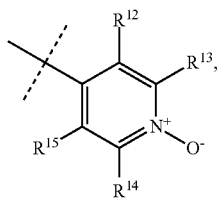

and the compound of formula (I) is a compound of formula (Ii)

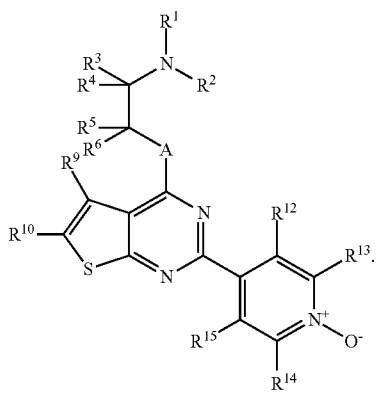
(Ii)

Embodiment 18

The compound of any of Embodiments 1-5, wherein M-Q-X is a group of formula

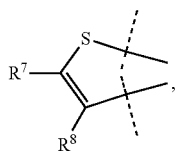

G is a group of formula

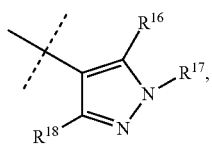

and the compound of formula (I) is a compound of formula (Ij)

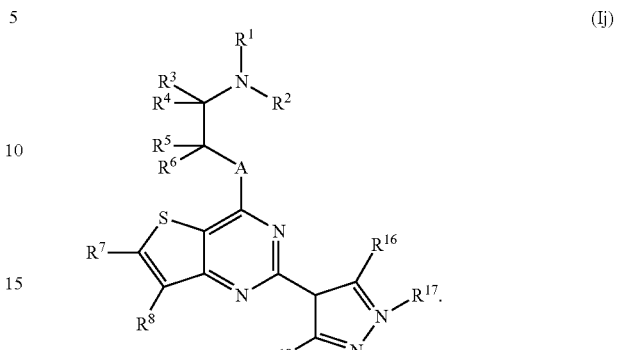
(Ij)

Embodiment 19

The compound of any of Embodiments 1-5, wherein M-Q-X is a group of formula

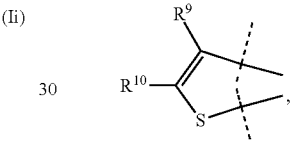

G is a group of formula

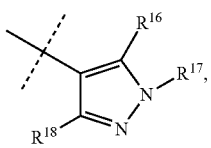

and the compound of formula (I) is a compound of formula (Ik)

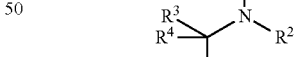
(Ik)

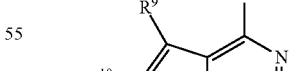

Embodiment 20

The compound of any of Embodiments 1-19, wherein $R^1$, $R^2$, and $R^{11}$ are independently chosen from H, $C_{1-6}$alkyl optionally substituted by 1-13 $R^{19}$, $C_{2-6}$alkenyl optionally substituted by 1-11 $R^{19}$, $C_{2-6}$alkynyl optionally substituted by 1-9 $R^{19}$, $C_{6-11}$-aryl optionally substituted by 1-11 $R^{19}$, $C_{7-16}$arylalkyl optionally substituted by 1-19 $R^{19}$, $C_{3-11}$cycloalkyl optionally substituted by 1-21 $R^{19}$, $C_{4-17}$cycloalkylalkyl optionally substituted by 1-32 $R^{19}$, 3-15 membered heterocycloalkyl optionally substituted by 1-28 $R^{19}$, 4-21 membered heterocycloalkylalkyl optionally substituted by 1-40 $R^{19}$, 5-15 membered heteroaryl optionally substituted by 1-15 $R^{19}$, 6-21 membered heteroarylalkyl optionally substituted by 1-27 $R^{19}$, and —$OR^{20}$; $R^3$, $R^4$, $R^5$, and $R^6$ are independently chosen from H, $C_{1-6}$alkyl optionally substituted by 1-13 $R^{19}$, $C_{2-6}$alkenyl optionally substituted by 1-11 $R^{19}$, $C_{2-6}$alkynyl optionally substituted by 1-9 $R^{19}$, $C_{6-11}$-aryl optionally substituted by 1-11 $R^{19}$, $C_{7-16}$arylalkyl optionally substituted by 1-19 $R^{19}$, $C_{3-11}$-cycloalkyl optionally substituted by 1-21 $R^{19}$, $C_{4-17}$cycloalkylalkyl optionally substituted by 1-32 $R^{19}$, 3-15 membered heterocycloalkyl optionally substituted by 1-28 $R^{19}$, 4-21 membered heterocycloalkylalkyl optionally substituted by 1-40 $R^{19}$, 5-15 membered heteroaryl optionally substituted by 1-15 $R^{19}$, 6-21 membered heteroarylalkyl optionally substituted by 1-27 $R^{19}$, halogen, —CN, —C(=O)$R^{20}$, —C(=O)$OR^{20}$, —C(=O)$NR^{22}R^{23}$, —C(=O)C(=O)$R^{20}$, —C(=$NR^{25}$)$R^{20}$, —C(=$NR^{25}$)$NR^{22}R^{23}$, —C(=NOH)$NR^{22}R^{23}$, —C(=$NOR^{26}$)$R^{20}$, —C(=$NNR^{22}R^{23}$)$R^{20}$, —C(=$NNR^{24}$C(=O)$R^{21}$)$R^{20}$, —C(=$NNR^{24}$C(=O)$OR^{21}$)$R^{20}$, —C(=S)$NR^{22}R^{23}$, —NC, —$NO_2$, —$NR^{22}R^{23}$, —$NR^{24}NR^{22}R^{23}$, —N=$NR^{24}$, —$NR^{24}OR^{26}$, —$NR^{24}$C(=O)$R^{20}$, —$NR^{24}$C(=O)C(=O)$R^{20}$, —$NR^{24}$C(=O)$OR^{21}$, —$NR^{24}$C(=O)C(=O)$OR^{21}$, —$NR^{24}$C(=O)$NR^{22}R^{23}$, —$NR^{24}$C(=O)$R^{21}$, —$NR^{24}$C(=O)$R^{20}$, —$NR^{24}$C(=O)$NR^{24}$C(=O)$OR^{20}$, —$NR^{24}$C($NR^{25}$)$NR^{22}R^{23}$, —$NR^{24}$C(=O)C(=O)$NR^{22}R^{23}$, —$NR^{24}$C(=S)$R^{20}$, —$NR^{24}$C(=S)$OR^{20}$, —$NR^{24}$C(=S)$NR^{22}R^{23}$, —$NR^{24}$S(=O)$_2R^{21}$, —$NR^{24}$S(=O)$_2NR^{22}R^{23}$, —$NR^{24}$P(=O)$R^{28}R^{28}$, —$NR^{24}$P(=O)($NR^{22}R^{23}$)($NR^{22}R^{23}$), —$NR^{24}$P(=O)($OR^{20}$)($OR^2$), —$NR^{24}$P(=O)($SR^{20}$)($SR^{20}$), —$OR^{20}$, —OCN, —OC(=O)$R^{20}$, —OC(=O)$NR^{22}R^{23}$, —OC(=O)$OR^{20}$, —OC(=$NR^{25}$)$NR^{22}R^{23}$, —OS(=O)$R^{20}$, —OS(=O)$_2R^{20}$, —OS(=O)$_2OR^{20}$, —OS(=O)$_2NR^{22}R^{23}$, —OP(=O)$R^{28}R^{28}$, —OP(=O)($NR^{22}R^{23}$)($NR^{22}R^{23}$), —OP(=O)($OR^{20}$)($OR^{20}$), —OP(=O)($SR^{20}$)($SR^{20}$), —Si($R^{24}$)$_3$, —SCN, —S(=O)$_nR^{20}$, —S(=O)$_2OR^{20}$, —$SO_3R^{27}$, —S(=O)$_2NR^{22}R^{23}$, —S(=O)$NR^{22}R^{23}$, —SP(=O)$R^{28}R^{28}$, —SP(=O)(($NR^{22}R^{23}$), —SP(=O)($OR^{20}$)($OR^{20}$), —SP(=O)($SR^{20}$)($SR^{20}$), —P(=O)$R^{28}R^{28}$, —P(=O)($NR^{22}R^{23}$)($NR^{22}R^{23}$), —P(=O)($OR^{20}$)($OR^{20}$), and —P(=O)($SR^{20}$)($SR^{20}$); alternatively, $R^3$ and $R^6$ can, together with the atoms linking them, form a $C_{6-11}$aryl optionally substituted by 1-11 $R^{19}$, $C_{3-11}$cycloalkyl optionally substituted by 1-21 $R^{19}$, 3-15 membered heterocycloalkyl optionally substituted by 1-28 $R^{19}$ or a 5-15 membered heteroaryl optionally substituted by 1-15 $R^{19}$; alternatively $R^3$ and $R^5$ or $R^4$ and $R^6$ can together form a double bond; alternatively any of $R^3$ and $R^4$, and $R^5$ and $R^6$ can together form =O, =$NR^{20}$, =$NOR^{20}$, or =S; and alternatively any of $R^1$ and $R^2$, $R^1$ and $R^3$, $R^1$ and $R^5$, $R^1$ and $R^{11}$, $R^4$ and $R^{11}$, and $R^6$ and $R^{11}$ can, together with the atoms linking them, form a 3-15 membered heterocycloalkyl optionally substituted by 1-28 $R^{19}$ or a 5-15 membered heteroaryl optionally substituted by 1-15 $R^{19}$.

Embodiment 21

The compound of any of Embodiments 1-19, wherein $R^1$, $R^2$, and $R^{11}$ are independently chosen from H, $C_{1-6}$alkyl optionally substituted by 1-13 $R^{19}$, $C_{2-6}$alkenyl optionally substituted by 1-11 $R^{19}$, $C_{2-6}$alkynyl optionally substituted by 1-9 $R^{19}$, $C_{6-11}$aryl optionally substituted by 1-11 $R^{19}$, $C_{7-16}$arylalkyl optionally substituted by 1-19 $R^{19}$, $C_{3-11}$cycloalkyl optionally substituted by 1-21 $R^{19}$, $C_{4-17}$cycloalkylalkyl optionally substituted by 1-32 $R^{19}$, 3-15 membered heterocycloalkyl optionally substituted by 1-28 $R^{19}$, 4-21 membered heterocycloalkylalkyl optionally substituted by 1-40 $R^{19}$, 5-15 membered heteroaryl optionally substituted by 1-15 $R^{19}$, 6-21 membered heteroarylalkyl optionally substituted by 1-27 $R^{19}$, and —$OR^{20}$; $R^3$, $R^4$, $R^5$, and $R^6$ are independently chosen from H, $C_{1-6}$alkyl optionally substituted by 1-13 $R^{19}$, $C_{2-6}$alkenyl optionally substituted by 1-11 $R^{19}$, $C_{2-6}$alkynyl optionally substituted by 1-9 $R^{19}$, $C_{6-11}$aryl optionally substituted by 1-11 $R^{19}$, $C_{7-16}$arylalkyl optionally substituted by 1-19 $R^{19}$, $C_{3-11}$cycloalkyl optionally substituted by 1-21 $R^{19}$, $C_{4-17}$cycloalkylalkyl optionally substituted by 1-32 $R^{19}$, 3-15 membered heterocycloalkyl optionally substituted by 1-28 $R^{19}$, 4-21 membered heterocycloalkylalkyl optionally substituted by 1-40 $R^{19}$, 5-15 membered heteroaryl optionally substituted by 1-15 $R^{19}$, 6-21 membered heteroarylalkyl optionally substituted by 1-27 $R^{19}$, halogen, —CN, —C(=O)$R^{20}$, —C(=O)$OR^{20}$, —C(=O)$NR^{22}R^{23}$, —C(=O)C(=O)$R^{20}$, —C(=$NR^{25}$)$R^{20}$, —C(=$NR^{25}$)$NR^{22}R^{23}$, —C(=NOH)$NR^{22}R^{23}$, —C(=$NOR^{26}$)$R^{20}$, —C(=$NNR^{22}R^{23}$)$R^{20}$, —C(=$NNR^{24}$C(=O)R)$R^1$)$R^{20}$, —C(=$NNR^{24}$C(=O)$OR^{21}$)$R^{20}$, —C(=S)$NR^{22}R^{23}$, —NC, —$NO_2$, —$NR^{22}R^{23}$, —$NR^{24}NR^{22}R^{23}$, —N=$NR^{24}$, —$NR^{24}OR^{26}$, —$NR^{24}$C(=O)$R^{20}$, —$NR^{24}$C(=O)C(=O)$R^{20}$, —$NR^{24}$C(=O)$OR^{21}$, —$NR^{24}$C(=O)C(=O)$OR^{21}$, —$NR^{24}$C(=O)$NR^{22}R^{23}R^{22}$, —$NR^{24}$C(=O)$R^{20}$, —$NR^{24}$C(=O)$NR^{24}$C(=O)$OR^{20}$, —$NR^{24}$C(=$NR^{25}$)$NR^{22}R^{23}$, —$NR^{24}$C(=O)C(=O)$NR^{22}R^{23}$, —$NR^{24}$C(=S)$R^{20}$, —$NR^{24}$C(=S)$OR^{20}$, —$NR^{24}$C(=S)$NR^{22}R^{23}$, —$NR^{24}$S(=O)$_2R^{21}$, —$NR^{24}$S(=O)$_2NR^{22}R^{23}$, —$NR^{24}$P(=O)$R^{28}R^{28}$, —$NR^{24}$P(=O)($NR^{22}R^{23}$)($NR^{22}R^{23}$), —$NR^{24}$P(=O)($OR^{20}$)($OR^2$), —$NR^{24}$P(=)($SR^{20}$)($SR^{20}$), —$OR^{20}$, —OCN, —OC(=O)$R^{20}$, —OC(=O)$NR^{22}R^{23}$, —OC(=O)$OR^{20}$, —OC(=$NR^{25}NR^{22}R^{23}$, —OS(=O)$R^{20}$, —OS(=O)$_2R^{20}$, —OS(=O)$_2OR^{20}$, —OS(=O)$_2NR^{22}R^{23}$, —OP(=O)$R^{28}R^{28}$, —OP(=O)($NR^{22}R^{23}$)($R^{22}R^{23}$), —OP(=O)($OR^{20}$)($OR^{20}$), —OP(=O)($SR^{20}$)($SR^{20}$), —Si($R^{24}$)$_3$, —SCN, —S(=O)$_nR^2$, —S(=O)$_2OR^{20}$, —$SO_3R^{27}$, —S(=O)$_2NR^{22}R^{23}$, —S(=O)$NR^{22}R^{23}$, —SP(=O)$R^{28}R^{28}$, —SP(=O)(($NR^{22}R^{23}$), —SP(=O)($OR^{20}$)($OR^{20}$), —SP(=O)($SR^{20}$)($SR^{20}$), —P(=O)$R^{28}R^{28}$, —P(=O)($NR^{22}R^{23}$)($NR^{22}R^{23}$), —P(=O)($OR^{20}$)($OR^{20}$), and —P(=O)($SR^{20}$)($SR^{20}$); alternatively, $R^3$ and $R^6$ can, together with the atoms linking them, form a $C_{6-10}$aryl optionally substituted by 1-6 $R^{19}$, $C_{3-10}$cycloalkyl optionally substituted by 1-6 $R^{19}$, 3-10 membered heterocycloalkyl optionally substituted by 1-6 $R^{19}$ or a 5-10 membered heteroaryl optionally substituted by 1-6 $R^{19}$; alternatively $R^3$ and $R^5$ or $R^4$ and $R^6$ can together form a double bond; alternatively any of $R^3$ and $R^4$, and $R^5$ and $R^6$ can together form =O; and alternatively any of $R^1$ and $R^2$, $R^1$ and $R^3$, $R^1$ and $R^5$, $R^1$ and $R^{11}$, $R^4$ and $R^{11}$, and $R^6$ and $R^{11}$ can, together with the atoms linking them, form a 3-15 membered heterocycloalkyl optionally substituted by 1-22 $R^{19}$ or a 5-15 membered heteroaryl optionally substituted by 1-15 $R^{19}$.

Embodiment 22

The compound of any of Embodiments 1-19, wherein $R^1$, $R^2$, and $R^{11}$ are independently chosen from H, $C_{1-6}$alkyl optionally substituted by 1-13 $R^{19}$, $C_{2-6}$alkenyl optionally substituted by 1-11 $R^{19}$, $C_{2-6}$alkynyl optionally substituted by 1-9 $R^{19}$, $C_6$-11aryl optionally substituted by 1-11 $R^{19}$, $C_{7-16}$arylalkyl optionally substituted by 1-19 $R^{19}$, $C_{3-11}$cycloalkyl optionally substituted by 1-21 $R^{19}$, $C_{4-17}$cycloalkylalkyl optionally substituted by 1-32 $R^{19}$, 3-15 membered heterocycloalkyl optionally substituted by 1-28 $R^{19}$, 4-21 membered heterocycloalkylalkyl optionally substituted by 1-40 $R^{19}$, 5-15 membered heteroaryl optionally substituted by 1-15 $R^{19}$, 6-21 membered heteroarylalkyl optionally substituted by 1-27 $R^{19}$, and —$OR^{20}$; $R^3$, $R^4$, $R^5$, and $R^6$ are independently chosen from H, $C_{1-6}$alkyl optionally substituted by 1-13 $R^{19}$, $C_{2-6}$alkenyl optionally substituted by 1-11 $R^{19}$, $C_{2-6}$alkynyl optionally substituted by 1-9 $R^{19}$, $C_{6-11}$aryl optionally substituted by 1-11 $R^{19}$, $C_{7-16}$arylalkyl optionally substituted by 1-19 $R^{19}$, $C_3$-11cycloalkyl optionally substituted by 1-21 $R^{19}$, $C_{4-17}$cycloalkylalkyl optionally substituted by 1-32 $R^{19}$, 3-15 membered heterocycloalkyl optionally substituted by 1-28 $R^{19}$, 4-21 membered heterocycloalkylalkyl optionally substituted by 1-40 $R^{19}$, 5-15 membered heteroaryl optionally substituted by 1-15 $R^{19}$, 6-21 membered heteroarylalkyl optionally substituted by 1-27 $R^{19}$, halogen, —CN, —C(=O)$R^{20}$, —C(=O)$OR^{20}$, —C(=O)$NR^{22}R^{23}$, —NC, —$NO_2$, —$NR^{22}R^{23}$, —$NR^{24}OR^{26}$, —$NR^{24}$C(=O)$R^{20}$, —$NR^{24}$C(=O)$OR^{21}$, —$NR^{24}$C(=O)$NR^{22}R^{23}$, —$NR^{24}$S(=O)$_2R^{21}$, —$NR^{24}$S(=O)$_2NR^{22}R^{23}$, —$OR^{20}$, —OCN, —OC(=O)$R^{20}$, —OC(=O)$NR^{22}R^{23}$, —OC(=O)$OR^{20}$, —OS(=O)$R^{20}$, —OS(=O)$_2R^{20}$, —OS(=O)$_2OR^{20}$, —OS(=O)$_2NR^{22}R^{23}$, —OP(=O)$R^{28}R^{28}$, —OP(=O)($OR^{20}$)($OR^{20}$), —Si($R^{24}$)$_3$, —SCN, —S(=O)$_nR^2$, —S(=O)$_2OR^{20}$, —$SO_3R^{27}$, —S(=O)$_2NR^{22}R^{23}$, —S(=O)$NR^{22}R^{23}$, —P(=O)$R^{28}R^{28}$, —P(=O)($NR^{22}R^{23}$)($NR^{22}R^{23}$), and —P(=O)($OR^{20}$)($OR^{20}$); alternatively, $R^3$ and $R^6$ can, together with the atoms linking them, form a $C_{6-10}$aryl optionally substituted by 1-6 $R^{19}$, $C_{3-10}$cycloalkyl optionally substituted by 1-6 $R^{19}$, 3-10 membered heterocycloalkyl optionally substituted by 1-6 $R^{19}$ or a 5-10 membered heteroaryl optionally substituted by 1-6 $R^{19}$; alternatively $R^3$ and $R^5$
or $R^4$ and $R^6$ can together form a double bond; alternatively any of $R^3$ and $R^4$, and $R^5$ and $R^6$ can together form =O; and alternatively any of $R^1$ and $R^2$, $R^1$ and $R^3$, $R^1$ and $R^5$, $R^1$ and $R^{11}$, $R^4$ and $R^{11}$, and $R^6$ and $R^{11}$ can, together with the atoms linking them, form a 3-15 membered heterocycloalkyl optionally substituted by 1-22 $R^{19}$ or a 5-15 membered heteroaryl optionally substituted by 1-15 $R^{19}$.

Embodiment 23

The compound of any of Embodiments 1-19, wherein $R^1$, $R^2$, and $R^{11}$ are independently chosen from H, $C_{1-6}$alkyl optionally substituted by 1-6 $R^{19}$, $C_{2-6}$alkenyl optionally substituted by 1-6 $R^{19}$, $C_{2-6}$alkynyl optionally substituted by 1-6 $R^{19}$, $C_{6-11}$aryl optionally substituted by 1-6 $R^{19}$, $C_{7-16}$arylalkyl optionally substituted by 1-6 $R^{19}$, $C_{3-11}$cycloalkyl optionally substituted by 1-6 $R^{19}$, $C_{4-17}$cycloalkylalkyl optionally substituted by 1-6 $R^{19}$, 3-15 membered heterocycloalkyl optionally substituted by 1-6 $R^{19}$, 4-21 membered heterocycloalkylalkyl optionally substituted by 1-6 $R^{19}$, 5-15 membered heteroaryl optionally substituted by 1-6 $R^{19}$, 6-21 membered heteroarylalkyl optionally substituted by 1-6 $R^{19}$, and —$OR^{20}$; $R^3$, $R^4$, $R^5$, and $R^6$ are independently chosen from H,
$C_{1-6}$alkyl optionally substituted by 1-6 $R^{19}$, $C_{2-6}$alkenyl optionally substituted by 1-6 $R^{19}$, $C_{2-6}$alkynyl optionally substituted by 1-6 $R^{19}$, $C_{6-11}$aryl optionally substituted by 1-6 $R^{19}$, $C_{7-16}$arylalkyl optionally substituted by 1-6 $R^{19}$, $C_{3-11}$cycloalkyl optionally substituted by 1-6 $R^{19}$, $C_{4-17}$cycloalkylalkyl optionally substituted by 1-6 $R^{19}$, 3-15 membered heterocycloalkyl optionally substituted by 1-6 $R^{19}$, 4-21 membered heterocycloalkylalkyl optionally substituted by 1-6 $R^{19}$, 5-15 membered heteroaryl optionally substituted by 1-6 $R^{19}$, 6-21 membered heteroarylalkyl optionally substituted by 1-6 $R^{19}$, halogen, —CN, —C(=O)$R^{20}$, —C(=O)$OR^{20}$, —C(=O)$NR^{22}R^{23}$, —NC, —$NO_2$, —$NR^{22}R^{23}$, —$NR^{24}OR^{26}$, —$NR^{24}$C(=O)$R^{20}$, —$NR^{24}$C(=O)$OR^{21}$, —$NR^{24}$C(=O)$NR^{22}R^{23}$, —$NR^{24}$S(=O)$_2R^{21}$, —$NR^{24}$S(=O)$_2NR^{22}R^{23}$, —$OR^{20}$, —OCN, —OC(=O)$R^{20}$, —OC(=O)$NR^{22}R^{23}$, —OC(=O)$OR^{20}$, —OS(=O)$R^{20}$, —OS(=O)$_2R^{20}$, —OS(=O)$_2OR^{20}$, —OS(=O)$_2NR^{22}R^{23}$, —OP(=O)$R^{28}R^{28}$, —OP(=O)($OR^{20}$)($OR^{20}$), —Si($R^{24}$)$_3$, —SCN, —S(=O)$_nR^{20}$, —S(=O)$_2OR^{20}$, —$SO_3R^{27}$, —S(=O)$_2NR^{22}R^{23}$, —S(=O)$NR^{22}R^{23}$, —P(=O)$R^{28}R^{28}$, —P(=O)($NR^{22}R^{23}$)($NR^{22}R^{23}$), and —P(=O)($OR^{20}$)($OR^{20}$); alternatively, $R^3$ and $R^6$ can, together with the atoms linking them, form a $C_{6-10}$aryl optionally substituted by 1-6 $R^{19}$, $C_{3-10}$cycloalkyl optionally substituted by 1-6 $R^{19}$, 3-10 membered heterocycloalkyl optionally substituted by 1-6 $R^{19}$ or a 5-10 membered heteroaryl optionally substituted by 1-6 $R^{19}$;
alternatively $R^3$ and $R^5$ or $R^4$ and $R^6$ can together form a double bond; alternatively any of $R^3$ and $R^4$, and $R^5$ and $R^6$ can together form =O; and alternatively any of $R^1$ and $R^2$, $R^1$ and $R^3$, $R^1$ and $R^5$, $R^1$ and $R^{11}$, $R^4$ and $R^{11}$, and $R^6$ and $R^{11}$ can, together with the atoms linking them, form a 5-15 membered heterocycloalkyl optionally substituted by 1-6 $R^{19}$ or a 5-15 membered heteroaryl optionally substituted by 1-6 $R^{19}$.

Embodiment 24

The compound of any of Embodiments 1-19, wherein $R^1$, $R^2$, and $R^{11}$ are independently chosen from H, $C_{1-6}$alkyl optionally substituted by 1-3 $R^{19}$, $C_{2-6}$alkenyl optionally substituted by 1-3 $R^{19}$, $C_{2-6}$alkynyl optionally substituted by 1-3 $R^{19}$, $C_6$-11aryl optionally substituted by 1-3 $R^{19}$, $C_7$-16arylalkyl optionally substituted by 1-3 $R^{19}$, $C_3$-11cycloalkyl optionally substituted by 1-3 $R^{19}$, $C_{4-17}$cycloalkylalkyl optionally substituted by 1-3 $R^{19}$, 3-15 membered heterocycloalkyl optionally substituted by 1-3 $R^{19}$, 4-21 membered heterocycloalkylalkyl optionally substituted by 1-3 $R^{19}$, 5-15 membered heteroaryl optionally substituted by 1-3 $R^{19}$, 6-21 membered heteroarylalkyl optionally substituted by 1-3 $R^{19}$, and —$OR^{20}$; $R^3$, $R^4$, $R^5$, and $R^6$ are independently chosen from H,
$C_{1-6}$alkyl optionally substituted by 1-3 $R^{19}$, $C_{2-6}$alkenyl optionally substituted by 1-3 $R^{19}$, $C_{2-6}$alkynyl optionally substituted by 1-3 $R^{19}$, $C_6$-11aryl optionally substituted by 1-3 $R^{19}$, $C_{7-16}$arylalkyl optionally substituted by 1-3 $R^{19}$, $C_{3-11}$cycloalkyl optionally substituted by 1-3 $R^{19}$, $C_4$-17cycloalkylalkyl optionally substituted by 1-3 $R^{19}$, 3-15 membered heterocycloalkyl optionally substituted by 1-3 $R^{19}$, 4-21 membered heterocycloalkylalkyl optionally substituted by 1-3 $R^{19}$, 5-15 membered heteroaryl optionally substituted by 1-3 $R^{19}$, 6-21 membered heteroarylalkyl optionally substituted by 1-3 $R^{19}$, halogen, —CN, —C(=O)$R^{20}$, —C(=O)$OR^{20}$, —C(=O)$NR^{22}R^{23}$, —NC, —$NO_2$, —$NR^{22}R^{23}$, —$NR^{24}OR^{26}$, —$NR^{24}$C(=O)$R^{20}$, —$NR^{24}$C(=O)$OR^{21}$, —$NR^{24}$C(=O)$NR^{22}R^{23}$, —$NR^{24}$S(=O)$_2R^{21}$, —$NR^{24}$S(=O)$_2NR^{22}R^{23}$, —$OR^{20}$, —OCN, —OC(=O)$R^{20}$, —OC(=O)$NR^{22}R^{23}$, —OC(=O)$OR^{20}$, —OS(=O)$R^{20}$, —OS(=O)$_2R^{20}$, —OS(=O)$_2OR^2$, —OS(=O)$_2NR^{22}R^{23}$, —OP(=O)$R^{28}R^{28}$, —OP(=O)($OR^{20}$)($OR^{20}$), —Si($R^{24}$)$_3$, —SCN, —S(=O)$_nR^{20}$, —S(=O)$_2OR^2$, —$SO_3R^{27}$, —S(=O)$_2NR^{22}R^{23}$, —S(=O)$NR^{22}R^{23}$, —P(=O)R$^{28}$R$^{28}$, —P(=O)(NR$^{22}$R$^{23}$)(NR$^{22}$R$^{23}$), and —P(=O)(OR$^{20}$)(OR$^{20}$); alternatively, R$^3$ and R$^6$ can, together with the atoms linking them, form a C$_{6-10}$aryl optionally substituted by 1-3 R$^{19}$, C$_{3-10}$cycloalkyl optionally substituted by 1-3 R$^{19}$, 3-10 membered heterocycloalkyl optionally substituted by 1-3 R$^{19}$ or a 5-10 membered heteroaryl optionally substituted by 1-3 R$^{19}$; alternatively R$^3$ and R$^5$ or R$^4$ and R$^6$ can together form a double bond; alternatively any of R$^3$ and R$^4$, and R$^5$ and R$^6$ can together form =O; and alternatively any of R$^1$ and R$^2$, R$^1$ and R$^3$, R$^1$ and R$^5$, R$^1$ and R$^{11}$, R$^4$ and R$^{11}$, and R$^6$ and R$^{11}$ can, together with the atoms linking them, form a 5-15 membered heterocycloalkyl optionally substituted by 1-3 R$^{19}$ or a 5-15 membered heteroaryl optionally substituted by 1-3 R$^{19}$.

Embodiment 25

The compound of any of Embodiments 1-19, wherein R$^1$, R$^2$, and R$^{11}$ are independently chosen from H, C$_{1-6}$alkyl optionally substituted by 1-3 R$^{19}$, C$_{2-6}$alkenyl optionally substituted by 1-3 R$^{19}$, C$_{2-6}$alkynyl optionally substituted by 1-3 R$^{19}$, C$_{6-11}$aryl optionally substituted by 1-3 R$^{19}$, C$_{3-11}$cycloalkyl optionally substituted by 1-3 R$^{19}$, 3-15 membered heterocycloalkyl optionally substituted by 1-3 R$^{19}$, 5-15 membered heteroaryl optionally substituted by 1-3 R$^{19}$, and —OR$^{20}$; R$^3$, R$^4$, R$^5$, and R$^6$ are independently chosen from H, C$_{1-6}$alkyl optionally substituted by 1-3 R$^{19}$, C$_{2-6}$alkenyl optionally substituted by 1-3 R$^{19}$, C$_{2-6}$ alkynyl optionally substituted by 1-3 R$^{19}$, C$_{6-11}$aryl optionally substituted by 1-3 R$^{19}$, C$_{3-11}$-cycloalkyl optionally substituted by 1-3 R$^{19}$, 3-15 membered heterocycloalkyl optionally substituted by 1-3 R$^{19}$, 5-15 membered heteroaryl optionally substituted by 1-3 R$^{19}$, halogen, —CN, —C(=O)R$^{20}$, —C(=O)OR$^{20}$, —C(=O)NR$^{22}$R$^{23}$, —NC, —NO$_2$, —NR$^{22}$R$^{23}$, —NR$^{24}$OR$^{26}$, —NR$^{24}$C(=O)R$^{20}$, —NR$^{24}$C(=O)OR$^{21}$, —NR$^{24}$C(=O)NR$^{22}$R$^{22}$R$^{23}$, —NR$^{24}$S(=O)$_2$R$^{21}$, —NR$^{24}$S(=O)$_2$NR$^{22}$R$^{23}$, —OR$^{20}$, —OCN, —OC(=O)R$^{20}$, —OC(=O)NR$^{22}$R$^{23}$, —OC(=O)OR$^{20}$, —OS(=O)R$^{20}$, —OS(=O)$_2$R$^{20}$, —OS(=O)$_2$OR$^2$, —OS(=O)$_2$NR$^{22}$R$^{23}$, —OP(=O)R$^{28}$R$^{28}$, —OP(=O)(OR$^{20}$)(OR$^{20}$), —Si(R$^{24}$)$_3$, —SCN, —S(=O)$_n$R$^{20}$, —S(=O)$_2$OR$^{20}$, —SO$_3$R$^{27}$, —S(=O)$_2$NR$^{22}$R$^{23}$, —S(=O)NR$^{22}$R$^{23}$, —P(=O)R$^{28}$R$^{28}$, —P(=O)(NR$^{22}$R$^{23}$)(NR$^{22}$R$^{23}$), and —P(=O)(OR$^{20}$)(OR$^{20}$); alternatively, R$^3$ and R$^6$ can, together with the atoms linking them, form a C$_{6-10}$aryl optionally substituted by 1-3 R$^{19}$, C$_{3-10}$cycloalkyl optionally substituted by 1-3 R$^{19}$, 3-10 membered heterocycloalkyl optionally substituted by 1-3 R$^{19}$ or a 5-10 membered heteroaryl optionally substituted by 1-3 R$^{19}$; alternatively R$^3$ and R$^5$ or R$^4$ and R$^6$ can together form a double bond; alternatively any of R$^3$ and R$^4$, and R$^5$ and R$^6$ can together form =O; and alternatively any of R$^1$ and R$^2$, R$^1$ and R$^3$, R$^1$ and R$^5$, R$^1$ and R$^{11}$, R$^4$ and R$^{11}$, and R$^6$ and R$^{11}$ can, together with the atoms linking them, form a 5-15 membered heterocycloalkyl optionally substituted by 1-3 R$^{19}$ or a 5-15 membered heteroaryl optionally substituted by 1-3 R$^{19}$.

Embodiment 26

The compound of any of Embodiments 1-19, wherein R$^1$, R$^2$, and R$^{11}$ are independently chosen from H, C$_{1-6}$alkyl optionally substituted by 1-3 R$^{19}$, C$_{2-6}$alkenyl optionally substituted by 1-3 R$^{19}$, C$_{2-6}$alkynyl optionally substituted by 1-3 R$^{19}$, C$_{6-11}$aryl optionally substituted by 1-3 R$^{19}$, C$_{3-11}$cycloalkyl optionally substituted by 1-3 R$^{19}$, 3-15 membered heterocycloalkyl optionally substituted by 1-3 R$^{19}$, 5-15 membered heteroaryl optionally substituted by 1-3 R$^{19}$, and —OR$^{20}$; R$^3$, R$^4$, R$^5$, and R$^6$ are independently chosen from H, C$_{1-6}$alkyl optionally substituted by 1-3 R$^{19}$, C$_{2-6}$alkenyl optionally substituted by 1-3 R$^{19}$, C$_{2-6}$ alkynyl optionally substituted by 1-3 R$^{19}$, C$_{6-11}$aryl optionally substituted by 1-3 R$^{19}$, C$_{3-11}$-cycloalkyl optionally substituted by 1-3 R$^{19}$, 3-15 membered heterocycloalkyl optionally substituted by 1-3 R$^{19}$, 5-15 membered heteroaryl optionally substituted by 1-3 R$^{19}$, halogen, —CN, —C(=O)R$^{20}$, —C(=O)OR$^{20}$, —C(=O)NR$^{22}$R$^{23}$, —NO$_2$, —NR$^{22}$R$^{23}$, —NR$^{24}$C(=O)R$^{20}$, —NR$^{24}$S(=O)$_2$R$^{21}$, —OR$^{20}$, —OC(=O)R$^{20}$, —S(=O)$_n$R$^{20}$, and —S(=O)$_2$NR$^{22}$R$^{23}$; alternatively, R$^3$ and R$^6$ can, together with the atoms linking them, form a C$_{6-10}$aryl optionally substituted by 1-3 R$^{19}$, C$_{3-10}$cycloalkyl optionally substituted by 1-3 R$^{19}$, 3-10 membered heterocycloalkyl optionally substituted by 1-3 R$^{19}$ or a 5-10 membered heteroaryl optionally substituted by 1-3 R$^{19}$; alternatively R$^3$ and R$^5$ or R$^4$ and R$^6$ can together form a double bond; alternatively any of R$^3$ and R$^4$, and R$^5$ and R$^6$ can together form =O; and alternatively any of R$^1$ and R$^2$, R$^1$ and R$^3$, R$^1$ and R$^5$, R$^1$ and R$^{11}$, R$^4$ and R$^{11}$, and R$^6$ and R$^{11}$ can, together with the atoms linking them, form a 5-15 membered heterocycloalkyl optionally substituted by 1-3 R$^{19}$ or a 5-15 membered heteroaryl optionally substituted by 1-3 R$^{19}$.

Embodiment 27

The compound of any of Embodiments 1-19, wherein R$^1$, R$^2$, and R$^{11}$ are independently chosen from H, C$_{1-6}$alkyl optionally substituted by 1-3 R$^{19}$, C$_{6-11}$aryl optionally substituted by 1-3 R$^{19}$, C$_{3-11}$cycloalkyl optionally substituted by 1-3 R$^{19}$, 3-15 membered heterocycloalkyl optionally substituted by 1-3 R$^{19}$, and 5-15 membered heteroaryl optionally substituted by 1-3 R$^{19}$; R$^3$, R$^4$, R$^5$, and R$^6$ are independently chosen from H, C$_{1-6}$alkyl optionally substituted by 1-3 R$^{19}$, C$_{6-11}$aryl optionally substituted by 1-3 R$^{19}$, C$_{3-11}$cycloalkyl optionally substituted by 1-3 R$^{19}$, 3-15 membered heterocycloalkyl optionally substituted by 1-3 R$^{19}$, 5-15 membered heteroaryl optionally substituted by 1-3 R$^{19}$, halogen, —CN, —C(=O)R$^{20}$, —C(=O)OR$^{20}$, —C(=O)NR$^{22}$R$^{23}$, —NO$_2$, —NR$^{22}$R$^{23}$, —NR$^{24}$C(=O)R$^{20}$, —NR$^{24}$S(=O)$_2$R$^{21}$, —OR$^{20}$, —OC(=O)R$^{20}$, —S(=O)$_n$R$^{20}$, and —S(=O)$_2$NR$^{22}$R$^{23}$; alternatively, R$^3$ and R$^6$ can, together with the atoms linking them, form a C$_{6-10}$aryl optionally substituted by 1-3 R$^{19}$, C$_{3-10}$cycloalkyl optionally substituted by 1-3 R$^{19}$, 3-10 membered heterocycloalkyl optionally substituted by 1-3 R$^{19}$ or a 5-10 membered heteroaryl optionally substituted by 1-3 R$^{19}$; alternatively R$^3$ and R$^5$ or R$^4$ and R$^6$ can together form a double bond; and alternatively any of R$^1$ and R$^2$, R$^1$ and R$^3$, R$^1$ and R$^5$, R$^1$ and R$^{11}$, R$^4$ and R$^{11}$, and R$^6$ and R$^{11}$ can, together with the atoms linking them, form a 5-15 membered heterocycloalkyl optionally substituted by 1-3 R$^{19}$ or a 5-15 membered heteroaryl optionally substituted by 1-3 R$^{19}$.

Embodiment 28

The compound of any of Embodiments 1-19, wherein R$^1$, R$^2$, and R$^{11}$ are independently chosen from H and C$_{1-6}$alkyl optionally substituted by 1-3 R$^{19}$; R$^3$, R$^4$, R$^5$, and R$^6$ are independently chosen from H, C$_{1-6}$ alkyl optionally substituted by 1-3 R$^{19}$, C$_{6-11}$aryl optionally substituted by 1-3 R$^{19}$, C$_{3-11}$cycloalkyl optionally substituted by 1-3 R$^{19}$, 3-15 membered heterocycloalkyl optionally substituted by 1-3 R$^{19}$, 5-15 membered heteroaryl optionally substituted by 1-3 R$^{19}$, halogen, —CN, —C(=O)R$^{20}$, —C(=O)OR$^{20}$, —C(=O)NR$^{22}$R$^{23}$, —NO$_2$, —NR$^{22}$R$^{23}$, —NR$^{24}$C(=O)R$^{20}$, —NR$^{24}$S(=O)$_2$R$^{21}$, —OR$^{20}$, —OC(=O)R$^{20}$, —S(=O)$_n$R$^2$, and —S(=O)$_2$NR$^{22}$R$^{23}$; alternatively, R$^3$ and R$^6$ can, together with the atoms linking them, form a C$_{6-10}$aryl optionally substituted by 1-3 R$^{19}$, C$_{3-10}$cycloalkyl optionally substituted by 1-3 R$^{19}$, 3-10 membered heterocycloalkyl optionally substituted by 1-3 R$^{19}$ or a 5-10 membered heteroaryl optionally substituted by 1-3 R$^{19}$; alternatively R$^3$ and R$^5$ or R$^4$ and R$^6$ can together form a double bond; and alternatively any of R$^1$ and R$^2$, R$^1$ and R$^3$, R$^1$ and R$^5$, R$^1$ and R$^{11}$, R$^4$ and R$^{11}$, and R$^6$ and R$^{11}$ can, together with the atoms linking them, form a 5-15 membered heterocycloalkyl optionally substituted by 1-3 R$^{19}$ or a 5-15 membered heteroaryl optionally substituted by 1-3 R$^{19}$.

Embodiment 29

The compound of any of Embodiments 1-19, wherein R$^1$, R$^2$, and R$^{11}$ are independently chosen from H and C$_{1-6}$alkyl optionally substituted by 1-3 R$^{19}$; R$^3$, R$^4$, R$^5$, and R$^6$ are independently chosen from H, C$_{1-6}$ alkyl optionally substituted by 1-3 R$^{19}$, C$_{6-11}$aryl optionally substituted by 1-3 R$^{19}$, C$_{3-11}$cycloalkyl optionally substituted by 1-3 R$^{19}$, 3-15 membered heterocycloalkyl optionally substituted by 1-3 R$^{19}$, 5-15 membered heteroaryl optionally substituted by 1-3 R$^{19}$, halogen, —CN, —C(=O)R$^{20}$, —C(=O)OR$^{20}$, —C(=O)NR$^{22}$R$^{23}$, —NO$_2$, —NR$^{22}$R$^{23}$, —NR$^{24}$C(=O)R$^{20}$, —NR$^{24}$S(=O)$_2$R$^{21}$, —OR$^{20}$, —OC(=O)R$^{20}$, —S(=O)$_n$R$^2$, and —S(=O)$_2$NR$^{22}$R$^{23}$; alternatively, any of R$^1$ and R$^2$, R$^1$ and R$^3$, R$^1$ and R$^5$, R$^1$ and R$^{11}$, R$^4$ and R$^{11}$, and R$^6$ and R$^{11}$ can, together with the atoms linking them, form a 5-15 membered heterocycloalkyl optionally substituted by 1-3 R$^{19}$.

Embodiment 30

The compound of any of Embodiments 1-19, wherein R$^1$, R$^2$, and R$^{11}$ are independently chosen from H and C$_{1-6}$alkyl optionally substituted by 1-3 R$^{19}$; R$^3$, R$^4$, R$^5$, and R$^6$ are independently chosen from H, C$_{1-6}$ alkyl optionally substituted by 1-3 R$^{19}$, C$_{6-10}$aryl optionally substituted by 1-3 R$^{19}$, C$_{3-7}$cycloalkyl optionally substituted by 1-3 R$^{19}$, 3-7 membered heterocycloalkyl optionally substituted by 1-3 R$^{19}$, 5-6 membered heteroaryl optionally substituted by 1-3 R$^{19}$, halogen, —CN, —C(=O)R$^{20}$, —C(=O)OR$^{20}$, —C(=O)NR$^{22}$R$^{23}$, —NO$_2$, —NR$^{22}$R$^{23}$, —NR$^{24}$C(=O)R$^{20}$, —NR$^{24}$S(=O)$_2$R$^{21}$, —OR$^{20}$, —OC(=O)R$^{20}$, —S(=O)$_n$R$^{20}$, and —S(=O)$_2$NR$^{22}$R$^{23}$; alternatively, any of R$^1$ and R$^2$, R$^1$ and R$^3$, R$^1$ and R$^5$, R$^1$ and R$^{11}$, R$^4$ and R$^{11}$, and R$^6$ and R$^{11}$ can, together with the atoms linking them, form a 5-7 membered heterocycloalkyl optionally substituted by 1-3 R$^{19}$.

Embodiment 31

The compound of any of Embodiments 1-19, wherein R$^1$, R$^2$, and R$^{11}$ are independently chosen from H and C$_{1-6}$alkyl optionally substituted by 1-3 R$^{19}$; R$^3$, R$^4$, R$^5$, and R$^6$ are independently chosen from H, C$_{1-6}$ alkyl optionally substituted by 1-3 R$^{19}$, halogen, —CN, —C(=O)R$^{20}$, —C(=O)OR$^{20}$, —C(=O)NR$^{22}$R$^{23}$, —NO$_2$, —NR$^{22}$R$^{23}$, —NR$^{24}$C(=O)R$^{20}$, —NR$^{24}$S(=O)$_2$R$^{21}$, —OR$^{20}$, —OC(=O)R$^{20}$, —S(=O)$_n$R$^{20}$, and —S(=O)$_2$NR$^{22}$R$^{23}$; alternatively, R$^3$ and R$^6$ can, together with the atoms linking them, form a C$_{6-10}$aryl optionally substituted by 1-3 R$^{19}$, C$_{3-10}$cycloalkyl optionally substituted by 1-3 R$^{19}$, 3-10 membered heterocycloalkyl optionally substituted by 1-3 R$^{19}$ or a 5-10 membered heteroaryl optionally substituted by 1-3 R$^{19}$; alternatively R$^3$ and R$^5$ or R$^4$ and R$^6$ can together form a double bond; and alternatively any of R$^1$ and R$^2$, R$^1$ and R$^3$, R$^1$ and R$^5$, R$^1$ and R$^{11}$, R$^4$ and R$^{11}$, and R$^6$ and R$^{11}$ can, together with the atoms linking them, form a 5-15 membered heterocycloalkyl optionally substituted by 1-3 R$^{19}$ or a 5-15 membered heteroaryl optionally substituted by 1-3 R$^{19}$.

Embodiment 32

The compound of any of Embodiments 1-19, wherein R$^1$, R$^2$, and R$^{11}$ are independently chosen from H and C$_{1-6}$alkyl optionally substituted by 1-3 R$^{19}$; R$^3$, R$^4$, R$^5$, and R$^6$ are independently chosen from H, C$_{1-6}$ alkyl optionally substituted by 1-3 R$^{19}$, halogen, —CN, —C(=O)R$^{20}$, —C(=O)OR$^{20}$, —C(=O)NR$^{22}$R$^{23}$, —NO$_2$, —NR$^{22}$R$^{23}$, —NR$^{24}$C(=O)R$^{20}$, —NR$^{24}$S(=O)$_2$R$^{21}$, —OR$^{20}$, —OC(=O)R$^{20}$, —S(=O)$_n$R$^{20}$, and —S(=O)$_2$NR$^{22}$R$^{23}$; alternatively, any of R$^1$ and R$^2$, R$^1$ and R$^3$, R$^1$ and R$^5$, R$^1$ and R$^{11}$, R$^4$ and R$^1$, and R$^6$ and R$^{11}$ can, together with the atoms linking them, form a 5-15 membered heterocycloalkyl optionally substituted by 1-3 R$^{19}$.

Embodiment 33

The compound of any of Embodiments 1-19, wherein R$^1$, R$^2$, and R$^{11}$ are independently chosen from H and C$_{1-6}$alkyl optionally substituted by 1-3 R$^{19}$; R$^3$, R$^4$, R$^5$, and R$^6$ are independently chosen from H, C$_{1-6}$ alkyl optionally substituted by 1-3 R$^{19}$, halogen, —CN, —C(=O)R$^{20}$, —C(=O)OR$^{20}$, —C(=O)NR$^{22}$R$^{23}$, —NO$_2$, —NR$^{22}$R$^{23}$, —NR$^{24}$C(=O)R$^{20}$, —NR$^{24}$S(=O)$_2$R$^{21}$, —OR$^{20}$, —OC(=O)R$^{20}$, —S(=O)$_n$R$^{20}$, and —S(=O)$_2$NR$^{22}$R$^{23}$; alternatively, any of R$^1$ and R$^2$, R$^1$ and R$^3$, R$^1$ and R$^5$, R$^1$ and R$^{11}$, R$^4$ and R$^1$, and R$^6$ and R$^{11}$ can, together with the atoms linking them, form a 5-7 membered heterocycloalkyl optionally substituted by 1-3 R$^{19}$.

Embodiment 34

The compound of any of Embodiments 1-19, wherein R$^1$, R$^2$, and R$^{11}$ are independently chosen from H and C$_{1-6}$alkyl optionally substituted by 1-3 R$^{19}$; R$^3$, R$^4$, R$^5$, and R$^6$ are independently chosen from H, C$_{1-6}$ alkyl optionally substituted by 1-3 R$^{19}$, halogen, —CN, —C(=O)R$^{20}$, —C(=O)OR$^{20}$, —C(=O)NR$^{22}$R$^{23}$, —NO$_2$, —NR$^{22}$R$^{23}$, —NR$^4$C(=O)R$^{20}$, —NR$^{24}$S(=O)$_2$R$^{21}$, —OR$^{20}$, —OC(=O)R$^{20}$, —S(=O)$_n$R$^{20}$, and —S(=O)$_2$NR$^{22}$R$^{23}$; alternatively, any of R$^1$ and R$^2$, R$^1$ and R$^3$, R$^1$ and R$^5$, R$^1$ and R$^{11}$, R$^4$ and R$^{11}$, and R$^6$ and R$^{11}$ can, together with the atoms linking them, form a 5-6 membered heterocycloalkyl optionally substituted by 1-3 R$^{19}$.

Embodiment 35

The compound of any of Embodiments 1-19, wherein R$^1$, R$^2$, and R$^{11}$ are independently chosen from H and C$_{1-6}$alkyl optionally substituted by 1-3 R$^{19}$; R$^3$, R$^4$, R$^5$, and R$^6$ are independently chosen from H, C$_{1-6}$ alkyl optionally substituted by 1-3 R$^{19}$, halogen, —CN, —C(=O)R$^{20}$, —C(=O)OR$^{20}$, —C(=O)NR$^{22}$R$^{23}$, —NO$_2$, —NR$^{22}$R$^{23}$, —NR$^4$C(=O)R$^{20}$, —NR$^{24}$S(=O)$_2$R$^{21}$, —OR$^{20}$, —OC(=O)R$^{20}$, —S(=O)$_n$R$^{20}$, and —S(=O)$_2$NR$^{22}$R$^{23}$; alternatively any of R$^1$ and R$^2$, R$^1$ and R$^3$, R$^1$ and R$^5$, R$^1$ and R$^{11}$, R$^4$ and R$^{11}$, and R$^6$ and R$^{11}$ can, together with the atoms linking them, form a 3-15 membered heterocycloalkyl optionally substituted by 1-3 $R^{19}$ or a 5-15 membered heteroaryl optionally substituted by 1-3 $R^{19}$.

Embodiment 36

The compound of any of Embodiments 1-19, wherein $R^1$, $R^2$, and $R^{11}$ are independently chosen from H and $C_{1-6}$alkyl optionally substituted by 1-3 $R^{19}$; $R^3$, $R^4$, $R^5$, and $R^6$ are independently chosen from H, $C_{1-6}$ alkyl optionally substituted by 1-3 $R^{19}$, halogen, —CN, —C(=O)$R^{20}$, —C(=O)OR$^{20}$, —C(=O)NR$^{22}$R$^{23}$, —NO$_2$, —NR$^{22}$R$^{23}$, —NR$^{24}$C(=O)R$^{20}$, —NR$^{24}$S(=O)$_2$R$^{21}$, —OR$^{20}$, —OC(=O)R$^{20}$, —S(=O)$_n$R$^{20}$, and —S(=O)$_2$NR$^{22}$R$^{23}$; alternatively any of $R^1$ and $R^2$, $R^1$ and $R^3$, $R^1$ and $R^5$, $R^1$ and $R^{11}$, $R^4$ and $R^{11}$, and $R^6$ and $R^{11}$ can, together with the atoms linking them, form a 5-15 membered heterocycloalkyl optionally substituted by 1-3 $R^{19}$ or a 5-15 membered heteroaryl optionally substituted by 1-3 $R^{19}$.

Embodiment 37

The compound of any of Embodiments 1-19, wherein $R^1$, $R^2$, and $R^{11}$ are independently chosen from H and $C_{1-6}$alkyl optionally substituted by 1-3 $R^{19}$; $R^3$, $R^4$, $R^5$, and $R^6$ are independently chosen from H, $C_{1-6}$alkyl optionally substituted by 1-3 $R^{19}$, halogen, —CN, —C(=O)$R^{20}$, —C(=O)OR$^{20}$, —C(=O)NR$^{22}$R$^{23}$, —NO$_2$, —NR$^{22}$R$^{23}$, —NR$^{24}$C(=O)R$^{20}$, —NR$^{24}$S(=O)$_2$R$^{21}$, —OR$^{20}$, —OC(=O)R$^{20}$, —S(=O)$_n$R$^{20}$, and —S(=O)$_2$NR$^{22}$R$^{23}$; alternatively any of $R^1$ and $R^2$, $R^1$ and $R^3$, $R^1$ and $R^5$, $R^1$ and $R^{11}$, $R^4$ and $R^1$, and $R^6$ and $R^{11}$ can, together with the atoms linking them, form a 5-15 membered heterocycloalkyl optionally substituted by 1-3 $R^{19}$.

Embodiment 38

The compound of any of Embodiments 1-19, wherein $R^1$, $R^2$, and $R^{11}$ are independently chosen from H and $C_{1-6}$alkyl optionally substituted by 1-3 $R^{19}$; $R^3$, $R^4$, $R^5$, and $R^6$ are independently chosen from H, $C_{1-6}$ alkyl optionally substituted by 1-3 $R^{19}$, halogen, —CN, —C(=O)$R^{20}$, —C(=O)NR$^{22}$R$^{23}$, —NR$^{22}$R$^{23}$, —NR$^{24}$C(=O)R$^{20}$, —R$^{24}$S(=O)$_2$R$^{21}$, —OR$^{20}$, —S(=O)$_n$R$^{20}$ and —S(=O)$_2$NR$^{22}$R$^{23}$; alternatively any of $R^1$ and $R^2$, $R^1$ and $R^3$, $R^1$ and $R^5$, $R^1$ and $R^{11}$, $R^4$ and $R^{11}$, and $R^6$ and $R^{11}$ can, together with the atoms linking them, form a 5-15 membered heterocycloalkyl optionally substituted by 1-3 $R^{19}$.

Embodiment 39

The compound of any of Embodiments 1-19, wherein $R^1$, $R^2$, and $R^{11}$ are independently chosen from H and $C_{1-6}$alkyl optionally substituted by 1-13 $R^{19}$, $C_{2-6}$alkenyl optionally substituted by 1-11 $R^{19}$, $C_{2-6}$alkynyl optionally substituted by 1-9 $R^{19}$, $C_{6-11}$-aryl optionally substituted by 1-11 $R^{19}$, $C_{7-16}$arylalkyl optionally substituted by 1-19 $R^{19}$, $C_{3-11}$-cycloalkyl optionally substituted by 1-21 $R^{19}$, $C_{4-17}$cycloalkylalkyl optionally substituted by 1-32 $R^{19}$, 3-15 membered heterocycloalkyl optionally substituted by 1-28 $R^{19}$, 4-21 membered heterocycloalkylalkyl optionally substituted by 1-40 $R^{19}$, 5-15 membered heteroaryl optionally substituted by 1-15 $R^{19}$, 6-21 membered heteroarylalkyl optionally substituted by 1-27 $R^{19}$, and —OR$^{20}$; $R^3$, $R^4$, $R^5$, and $R^6$ are independently chosen from H, $C_{1-6}$alkyl optionally substituted by 1-13 $R^{19}$, $C_{2-6}$alkenyl optionally substituted by 1-11 $R^{19}$, $C_{2-6}$alkynyl optionally substituted by 1-9 $R^{19}$, $C_{6-11}$aryl optionally substituted by 1-11 $R^{19}$, $C_{7-16}$arylalkyl optionally substituted by 1-19 $R^{19}$, $C_{3-11}$-cycloalkyl optionally substituted by 1-21 $R^{19}$, $C_{4-17}$cycloalkylalkyl optionally substituted by 1-32 $R^{19}$, 3-15 membered heterocycloalkyl optionally substituted by 1-28 $R^{19}$, 4-21 membered heterocycloalkylalkyl optionally substituted by 1-40 $R^{19}$, 5-15 membered heteroaryl optionally substituted by 1-15 $R^{19}$, 6-21 membered heteroarylalkyl optionally substituted by 1-27 $R^{19}$, halogen, —CN, —C(=O)$R^{20}$, —C(=O)OR$^{20}$, —C(=O)NR$^{22}$R$^{23}$, —NO$_2$, —NR$^{22}$R$^{23}$, and —OR$^{20}$ alternatively, $R^3$ and $R^6$ can, together with the atoms linking them, form a $C_{6-11}$aryl optionally substituted by 1-11 $R^{19}$, $C_{3-11}$cycloalkyl optionally substituted by 1-21 $R^{19}$, 3-15 membered heterocycloalkyl optionally substituted by 1-28 $R^{19}$ or a 5-15 membered heteroaryl optionally substituted by 1-15 $R^{19}$; alternatively $R^3$ and $R^5$ or $R^4$ and $R^6$ can together form a double bond; alternatively any of $R^3$ and $R^4$, and $R^5$ and $R^6$ can together form =O, =NR$^{20}$, =NOR$^{20}$, or =S; and alternatively any of $R^1$ and $R^2$, $R^1$ and $R^3$, $R^1$ and $R^5$, $R^1$ and $R^{11}$, $R^4$ and $R^1$, and $R^6$ and $R^{11}$ can, together with the atoms linking them, form a 3-15 membered heterocycloalkyl optionally substituted by 1-28 $R^{19}$ or a 5-15 membered heteroaryl optionally substituted by 1-15 $R^{19}$.

Embodiment 40

The compound of any of Embodiments 1-19, wherein $R^1$, $R^2$, and $R^{11}$ are independently chosen from H and $C_{1-6}$alkyl optionally substituted by 1-13 $R^{19}$, $C_{2-6}$alkenyl optionally substituted by 1-11 $R^{19}$, $C_{2-6}$alkynyl optionally substituted by 1-9 $R^{19}$, $C_{6-11}$-aryl optionally substituted by 1-11 $R^{19}$, $C_{7-16}$arylalkyl optionally substituted by 1-19 $R^{19}$, $C_{3-11}$-cycloalkyl optionally substituted by 1-21 $R^{19}$, $C_{4-17}$cycloalkylalkyl optionally substituted by 1-32 $R^{19}$, 3-15 membered heterocycloalkyl optionally substituted by 1-28 $R^{19}$, 4-21 membered heterocycloalkylalkyl optionally substituted by 1-40 $R^{19}$, 5-15 membered heteroaryl optionally substituted by 1-15 $R^{19}$, 6-21 membered heteroarylalkyl optionally substituted by 1-27 $R^{19}$, and —OR$^{20}$; $R^3$, $R^4$, $R^5$, and $R^6$ are independently chosen from H, $C_{1-6}$alkyl optionally substituted by 1-13 $R^{19}$, $C_{2-6}$alkenyl optionally substituted by 1-11 $R^{19}$, $C_{2-6}$alkynyl optionally substituted by 1-9 $R^{19}$, $C_{6-11}$aryl optionally substituted by 1-11 $R^{19}$, $C_{7-16}$arylalkyl optionally substituted by 1-19 $R^{19}$, $C_{3-11}$cycloalkyl optionally substituted by 1-21 $R^{19}$, $C_{4-17}$cycloalkylalkyl optionally substituted by 1-32 $R^{19}$, 3-15 membered heterocycloalkyl optionally substituted by 1-28 $R^{19}$, 4-21 membered heterocycloalkylalkyl optionally substituted by 1-40 $R^{19}$, 5-15 membered heteroaryl optionally substituted by 1-15 $R^{19}$, 6-21 membered heteroarylalkyl optionally substituted by 1-27 $R^{19}$, halogen, —CN, —C(=O)NR$^{22}$R$^{23}$, —NO$_2$, —NR$^{22}$R$^{23}$, and —OR$^{20}$; alternatively, $R^3$ and $R^6$ can, together with the atoms linking them, form a $C_{6-11}$aryl optionally substituted by 1-11 $R^{19}$, $C_{3-11}$cycloalkyl optionally substituted by 1-21 $R^{19}$, 3-15 membered heterocycloalkyl optionally substituted by 1-28 $R^{19}$ or a 5-15 membered heteroaryl optionally substituted by 1-15 $R^{19}$; alternatively $R^3$ and $R^5$ or $R^4$ and $R^6$ can together form a double bond; alternatively any of $R^3$ and $R^4$, and $R^5$ and $R^6$ can together form =O, =NR$^{20}$, =NOR$^{20}$, or =S; and alternatively any of $R^1$ and $R^2$, $R^1$ and $R^3$, $R^1$ and $R^5$, $R^1$ and $R^{11}$, $R^4$ and $R^{11}$, and $R^6$ and $R^1$ can, together with the atoms linking them, form a 3-15 membered heterocycloalkyl optionally substituted by 1-28 $R^{19}$ or a 5-15 membered heteroaryl optionally substituted by 1-15 $R^{19}$.

Embodiment 41. The compound of any of Embodiments 1-19, wherein $R^1$, $R^4$, $R^5$, $R^6$, and $R^{11}$ are independently chosen from H and $C_{1-6}$alkyl optionally substituted by 1-13 $R^{19}$; $R^2$ is chosen from H, $C_{1-6}$alkyl optionally substituted by 1-13 $R^{19}$, $C_{7-16}$arylalkyl optionally substituted by 1-19 $R^{19}$, and 6-21 membered heteroarylalkyl optionally substituted by 1-27 $R^{19}$; $R^3$ is chosen from H, $C_{1-6}$alkyl optionally substituted by 1-13 $R^{19}$, $C_{7-16}$arylalkyl optionally substituted by 1-19 $R^{19}$, $C_{4-17}$cycloalkylalkyl optionally substituted by 1-32 $R^{19}$, and 6-21 membered heteroarylalkyl optionally substituted by 1-27 $R^{19}$; alternatively, $R^3$ and $R^6$ can, together with the atoms linking them, form a $C_{3-10}$cycloalkyl optionally substituted by 1-6 $R^{19}$; alternatively $R^3$ and $R^4$ can together form =O; and alternatively any of R and $R^2$, R and $R^3$, R and $R^5$, R and $R^{11}$, $R^4$ and $R^{11}$, and $R^6$ and $R^{11}$ can, together with the atoms linking them, form a 3-15 membered heterocycloalkyl optionally substituted by 1-22 $R^{19}$.

Embodiment 42

The compound of any of Embodiments 1-19, wherein $R^1$, $R^4$, $R^5$, $R^6$, and $R^{11}$ are independently chosen from H and $C_{1-6}$alkyl optionally substituted by 1-13 $R^{19}$; $R^2$ is chosen from H, $C_{1-6}$alkyl optionally substituted by 1-13 $R^{19}$, $C_{7-16}$arylalkyl optionally substituted by 1-19 $R^{19}$, and 6-21 membered heteroarylalkyl optionally substituted by 1-27 $R^{19}$; $R^3$ is chosen from H, $C_{1-6}$alkyl optionally substituted by 1-13 $R^{19}$, $C_{7-16}$arylalkyl optionally substituted by 1-19 $R^{19}$, $C_{4-17}$cycloalkylalkyl optionally substituted by 1-32 $R^{19}$, and 6-21 membered heteroarylalkyl optionally substituted by 1-27 $R^{19}$; alternatively, $R^3$ and $R^6$ can, together with the atoms linking them, form a $C_{3-10}$cycloalkyl optionally substituted by 1-6 $R^{19}$; alternatively $R^3$ and $R^4$ can together form =O; and alternatively any of R and $R^2$, R and $R^3$, R and $R^5$, $R^4$ and $R^{11}$, and $R^6$ and $R^{11}$ can, together with the atoms linking them, form a 3-15 membered heterocycloalkyl optionally substituted by 1-22 $R^{19}$.

Embodiment 43

The compound of any of Embodiments 1-19, wherein $R^1$, $R^4$, $R^5$, $R^6$, and $R^{11}$ are independently chosen from H and $C_{1-6}$alkyl optionally substituted by 1-13 $R^{19}$; $R^2$ is chosen from H, $C_{1-6}$alkyl optionally substituted by 1-13 $R^{19}$, $C_{7-16}$arylalkyl optionally substituted by 1-19 $R^{19}$, and 6-21 membered heteroarylalkyl optionally substituted by 1-27 $R^{19}$; $R^3$ is chosen from H, $C_{1-6}$alkyl optionally substituted by 1-13 $R^{19}$, $C_{7-16}$arylalkyl optionally substituted by 1-19 $R^{19}$, $C_{4-17}$cycloalkylalkyl optionally substituted by 1-32 $R^{19}$, and 6-21 membered heteroarylalkyl optionally substituted by 1-27 $R^{19}$; alternatively, $R^3$ and $R^6$ can, together with the atoms linking them, form a $C_{3-6}$cycloalkyl optionally substituted by 1-6 $R^{19}$; and alternatively any of $R^1$ and $R^2$, $R^1$ and $R^3$, $R^1$ and $R^5$, $R^1$ and $R^{11}$, $R^4$ and $R^1$, and $R^6$ and $R^{11}$ can, together with the atoms linking them, form a 3-15 membered heterocycloalkyl optionally substituted by 1-22 $R^{19}$.

Embodiment 44

The compound of any of Embodiments 1-19, wherein $R^1$, $R^4$, $R^5$, $R^6$, and $R^{11}$ are independently chosen from H and $C_{1-6}$alkyl optionally substituted by 1-13 $R^{19}$; $R^2$ is chosen from H, $C_{1-6}$alkyl optionally substituted by 1-13 $R^{19}$, $C_{7-16}$arylalkyl optionally substituted by 1-19 $R^{19}$, and 6-21 membered heteroarylalkyl optionally substituted by 1-27 $R^{19}$; $R^3$ is chosen from H, $C_{1-6}$alkyl optionally substituted by 1-13 $R^{19}$, $C_{7-16}$arylalkyl optionally substituted by 1-19 $R^{19}$, $C_{4-17}$cycloalkylalkyl optionally substituted by 1-32 $R^{19}$, and 6-21 membered heteroarylalkyl optionally substituted by 1-27 $R^{19}$; alternatively, $R^3$ and $R^6$ can, together with the atoms linking them, form a $C_{3-6}$cycloalkyl optionally substituted by 1-6 $R^{19}$; and alternatively any of $R^1$ and $R^2$, $R^1$ and $R^3$, $R^1$ and $R^5$, $R^4$ and $R^{11}$, and $R^6$ and $R^{11}$ can, together with the atoms linking them, form a 3-15 membered heterocycloalkyl optionally substituted by 1-22 $R^{19}$.

Embodiment 45

The compound of any of Embodiments 1-19, wherein $R^1$, $R^4$, $R^5$, $R^6$, and $R^{11}$ are independently chosen from H and $C_{1-6}$alkyl optionally substituted by 1-13 $R^{19}$; $R^2$ is chosen from H, $C_{1-6}$alkyl optionally substituted by 1-13 $R^{19}$, $C_{7-16}$arylalkyl optionally substituted by 1-19 $R^{19}$, and 6-21 membered heteroarylalkyl optionally substituted by 1-27 $R^{19}$; $R^3$ is chosen from H, $C_{1-6}$alkyl optionally substituted by 1-13 $R^{19}$, $C_{7-16}$arylalkyl optionally substituted by 1-19 $R^{19}$, $C_{4-17}$cycloalkylalkyl optionally substituted by 1-32 $R^{19}$, and 6-21 membered heteroarylalkyl optionally substituted by 1-27 $R^{19}$; alternatively, $R^3$ and $R^6$ can, together with the atoms linking them, form a $C_{3-6}$cycloalkyl optionally substituted by 1-6 $R^{19}$.

Embodiment 46

The compound of any of Embodiments 1-19, wherein $R^1$ and $R^{11}$ are independently chosen from H and $C_{1-6}$alkyl optionally substituted by 1-13 $R^{19}$; $R^4$, $R^5$, and $R^6$ are H; $R^2$ is chosen from H, $C_{1-6}$alkyl optionally substituted by 1-13 $R^{19}$, $C_{7-16}$arylalkyl optionally substituted by 1-19 $R^{19}$, and 6-21 membered heteroarylalkyl optionally substituted by 1-27 $R^{19}$; $R^3$ is chosen from H, $C_{1-6}$alkyl optionally substituted by 1-13 $R^{19}$, $C_{7-16}$arylalkyl optionally substituted by 1-19 $R^{19}$, $C_{4-17}$cycloalkylalkyl optionally substituted by 1-32 $R^{19}$, and 6-21 membered heteroarylalkyl optionally substituted by 1-27 $R^{19}$; alternatively $R^3$ and $R^6$ can, together with the atoms linking them, form a $C_{3-6}$cycloalkyl optionally substituted by 1-6 $R^{19}$; alternatively $R^3$ and $R^4$ can together form =O; and alternatively any of $R^1$ and $R^2$, $R^1$ and $R^3$, $R^1$ and $R^5$, $R^1$ and $R^{11}$, $R^4$ and $R^{11}$, and $R^6$ and $R^{11}$ can, together with the atoms linking them, form a 3-15 membered heterocycloalkyl optionally substituted by 1-22 $R^{19}$.

Embodiment 47

The compound of any of Embodiments 1-19, wherein $R^1$ and $R^{11}$ are independently chosen from H and $C_{1-6}$alkyl optionally substituted by 1-13 $R^{19}$; $R^4$, $R^5$, and $R^6$ are H; $R^2$ is chosen from H, $C_{1-6}$alkyl optionally substituted by 1-13 $R^{19}$, $C_{7-16}$arylalkyl optionally substituted by 1-19 $R^{19}$, and 6-21 membered heteroarylalkyl optionally substituted by 1-27 $R^{19}$; $R^3$ is chosen from H, $C_{1-6}$alkyl optionally substituted by 1-13 $R^{19}$, $C_{7-16}$arylalkyl optionally substituted by 1-19 $R^{19}$, $C_{4-17}$cycloalkylalkyl optionally substituted by 1-32 $R^{19}$, and 6-21 membered heteroarylalkyl optionally substituted by 1-27 $R^{19}$; alternatively $R^3$ and $R^6$ can, together with the atoms linking them, form a $C_{3-6}$cycloalkyl optionally substituted by 1-6 $R^{19}$; alternatively $R^3$ and $R^4$ can together form =O; and alternatively any of $R^1$ and $R^2$, $R^1$ and $R^3$, $R^1$ and $R^5$, $R^4$ and $R^{11}$, and $R^6$ and $R^{11}$ can, together with the atoms linking them, form a 3-15 membered heterocycloalkyl optionally substituted by 1-22 $R^{19}$.

Embodiment 48

The compound of any of Embodiments 1-19, wherein $R^1$, $R^2$, and $R^{11}$ are independently chosen from H and $C_{1-6}$alkyl optionally substituted by 1-13 $R^{19}$; $R^4$, $R^5$, and $R^6$ are H; $R^3$ is chosen from H, $C_{1-6}$alkyl optionally substituted by 1-13 $R^{19}$, $C_{7-16}$arylalkyl optionally substituted by 1-19 $R^{19}$, $C_{4-17}$cycloalkylalkyl optionally substituted by 1-32 $R^{19}$, and 6-21 membered heteroarylalkyl optionally substituted by 1-27 $R^{19}$; alternatively $R^3$ and $R^6$ can, together with the atoms linking them, form a $C_{3-6}$cycloalkyl optionally substituted by 1-3 $R^{19}$; and alternatively any of $R^1$ and $R^2$, $R^1$ and $R^3$, $R^1$ and $R^5$, $R^1$ and $R^{11}$, $R^4$ and $R^{11}$, and $R^6$ and $R^{11}$ can, together with the atoms linking them, form a 3-15 membered heterocycloalkyl optionally substituted by 1-22 $R^{19}$.

Embodiment 49

The compound of any of Embodiments 1-19, wherein $R^1$, $R^2$, and $R^{11}$ are independently chosen from H and $C_{1-6}$alkyl optionally substituted by 1-13 $R^{19}$; $R^4$, $R^5$, and $R^6$ are H; $R^3$ is chosen from H, $C_{1-6}$alkyl optionally substituted by 1-13 $R^{19}$, $C_{7-16}$arylalkyl optionally substituted by 1-19 $R^{19}$, $C_{4-17}$cycloalkylalkyl optionally substituted by 1-32 $R^{19}$, and 6-21 membered heteroarylalkyl optionally substituted by 1-27 $R^{19}$; alternatively $R^3$ and $R^6$ can, together with the atoms linking them, form a $C_{3-6}$cycloalkyl optionally substituted by 1-3 $R^{19}$; and alternatively any of R and $R^2$, $R^1$ and $R^3$, $R^1$ and $R^5$, $R^4$ and $R^{11}$, and $R^6$ and $R^{11}$ can, together with the atoms linking them, form a 3-15 membered heterocycloalkyl optionally substituted by 1-22 $R^{19}$.

Embodiment 50

The compound of any of Embodiments 1-19, wherein $R^1$, $R^2$, and $R^{11}$ are independently chosen from H and $C_{1-6}$alkyl optionally substituted by 1-13 $R^{19}$; $R^4$, $R^5$, and $R^6$ are H; $R^3$ is chosen from H, $C_{1-6}$alkyl optionally substituted by 1-13 $R^{19}$, $C_{7-16}$arylalkyl optionally substituted by 1-19 $R^{19}$, $C_{4-17}$cycloalkylalkyl optionally substituted by 1-32 $R^{19}$, and 6-21 membered heteroarylalkyl optionally substituted by 1-27 $R^{19}$; alternatively $R^3$ and $R^6$ can, together with the atoms linking them, form a $C_{3-6}$cycloalkyl optionally substituted by 1-3 $R^{19}$.

Embodiment 51

The compound of any of Embodiments 1-19, wherein $R^1$ and $R^{11}$ are independently chosen from H and $C_{1-6}$alkyl optionally substituted by 1-13 $R^{19}$; $R^2$ is chosen from H, $C_{1-6}$alkyl optionally substituted by 1-13 $R^{19}$, $C_{7-11}$ arylalkyl optionally substituted by 1-19 $R^{19}$, and 6-21 membered heteroarylalkyl optionally substituted by 1-27 $R^{19}$; $R^3$ is chosen from H, $C_{1-6}$alkyl optionally substituted by 1-13 $R^{19}$, $C_{7-16}$arylalkyl optionally substituted by 1-19 $R^{19}$, $C_{6-10}$-cycloalkylalkyl optionally substituted by 1-10 $R^{19}$, and 6-21 membered heteroarylalkyl optionally substituted by 1-27 $R^{19}$; $R^4$, $R^5$, and $R^6$ are H; alternatively $R^3$ and $R^6$ can, together with the atoms linking them, form a $C_{3-6}$ cycloalkyl optionally substituted by 1-3 $R^{19}$; alternatively $R^3$ and $R^4$ can together form =O; and alternatively any of $R^1$ and $R^2$, $R^1$ and $R^3$, $R^1$ and $R^5$, $R^1$ and $R^{11}$, and $R^4$ and $R^{11}$ can, together with the atoms linking them, form a 3-15 membered heterocycloalkyl optionally substituted by 1-22 $R^{19}$.

Embodiment 52

The compound of any of Embodiments 1-19, wherein $R^1$ and $R^{11}$ are independently chosen from H and $C_{1-6}$alkyl optionally substituted by 1-13 $R^{19}$; $R^2$ is chosen from H, $C_{1-6}$alkyl optionally substituted by 1-13 $R^{19}$, $C_{7-11}$ arylalkyl optionally substituted by 1-19 $R^{19}$, and 6-21 membered heteroarylalkyl optionally substituted by 1-27 $R^{19}$; $R^3$ is chosen from H, $C_{1-6}$alkyl optionally substituted by 1-13 $R^{19}$, $C_{7-16}$arylalkyl optionally substituted by 1-19 $R^{19}$, $C_{6-10}$cycloalkylalkyl optionally substituted by 1-10 $R^{19}$, and 6-21 membered heteroarylalkyl optionally substituted by 1-27 $R^{19}$; $R^4$, $R^5$, and $R^6$ are H; alternatively $R^3$ and $R^6$ can, together with the atoms linking them, form a $C_{3-6}$ cycloalkyl optionally substituted by 1-3 $R^{19}$; alternatively $R^3$ and $R^4$ can together form =O; and alternatively any of $R^1$ and $R^2$, $R^1$ and $R^3$, $R^1$ and $R^5$, and $R^4$ and $R^{11}$ can, together with the atoms linking them, form a 3-15 membered heterocycloalkyl optionally substituted by 1-22 $R^{19}$.

Embodiment 53

The compound of any of Embodiments 1-19, wherein $R^1$, $R^4$, $R^5$, $R^6$, and $R^{11}$ are independently chosen from H and $C_{1-6}$alkyl optionally substituted by 1-13 $R^{19}$; $R^2$ is chosen from H, $C_{1-6}$alkyl optionally substituted by 1-13 $R^{19}$, $C_{7-12}$arylalkyl optionally substituted by 1-6 $R^{19}$, and 6-10 membered heteroarylalkyl optionally substituted by 1-6 $R^{19}$; $R^3$ is chosen from H, $C_{1-6}$alkyl optionally substituted by 1-13 $R^{19}$, $C_{7-16}$arylalkyl optionally substituted by 1-19 $R^{19}$, $C_{6-10}$cycloalkylalkyl optionally substituted by 1-10 $R^{19}$, and 6-21 membered heteroarylalkyl optionally substituted by 1-27 $R^{19}$; alternatively $R^3$ and $R^6$ can, together with the atoms linking them, form a $C_{3-6}$cycloalkyl optionally substituted by 1-3 $R^{19}$; and alternatively any of $R^1$ and $R^2$, $R^1$ and $R^3$, $R^1$ and $R^5$, $R^1$ and $R^{11}$, and $R^4$ and $R^{11}$ can, together with the atoms linking them, form a 3-15 membered heterocycloalkyl optionally substituted by 1-22 $R^{19}$.

Embodiment 54

The compound of any of Embodiments 1-19, wherein $R^1$, $R^4$, $R^5$, $R^6$, and $R^{11}$ are independently chosen from H and $C_{1-6}$alkyl optionally substituted by 1-13 $R^{19}$; $R^2$ is chosen from H, $C_{1-6}$alkyl optionally substituted by 1-13 $R^{19}$, $C_{7-12}$arylalkyl optionally substituted by 1-6 $R^{19}$, and 6-10 membered heteroarylalkyl optionally substituted by 1-6 $R^{19}$; $R^3$ is chosen from H, $C_{1-6}$alkyl optionally substituted by 1-13 $R^{19}$, $C_{7-16}$arylalkyl optionally substituted by 1-19 $R^{19}$, $C_{6-10}$cycloalkylalkyl optionally substituted by 1-10 $R^{19}$, and 6-21 membered heteroarylalkyl optionally substituted by 1-27 $R^{19}$; alternatively $R^3$ and $R^6$ can, together with the atoms linking them, form a $C_{3-6}$cycloalkyl optionally substituted by 1-3 $R^{19}$; and alternatively any of $R^1$ and $R^2$, $R^1$ and $R^3$, $R^1$ and $R^5$, and $R^4$ and $R^{11}$ can, together with the atoms linking them, form a 3-15 membered heterocycloalkyl optionally substituted by 1-22 $R^{19}$.

Embodiment 55

The compound of any of Embodiments 1-19, wherein $R^1$, $R^4$, $R^5$, $R^6$, and $R^{11}$ are independently chosen from H and $C_{1-6}$alkyl optionally substituted by 1-13 $R^{19}$; $R^2$ is chosen from H, $C_{1-6}$alkyl optionally substituted by 1-13 $R^{19}$, $C_{7-12}$arylalkyl optionally substituted by 1-6 $R^{19}$, and 6-10 membered heteroarylalkyl optionally substituted by 1-6 $R^{19}$; $R^3$ is chosen from H, $C_{1-6}$alkyl optionally substituted by 1-13 $R^{19}$, $C_{7-16}$arylalkyl optionally substituted by 1-19 $R^{19}$, $C_{6-10}$cycloalkylalkyl optionally substituted by 1-10 $R^{19}$, and 6-21 membered heteroarylalkyl optionally substituted by 1-27 $R^{19}$; alternatively $R^3$ and $R^6$ can, together with the atoms linking them, form a $C_{3-6}$cycloalkyl optionally substituted by 1-3 $R^{19}$.

Embodiment 56

The compound of any of Embodiments 1-19, wherein $R^1$ and $R^{11}$ are independently chosen from H and $C_{1-6}$alkyl optionally substituted by 1-13 $R^{19}$; $R^2$ is chosen from H, $C_{1-6}$alkyl optionally substituted by 1-13 $R^{19}$, $C_{7-12}$arylalkyl optionally substituted by 1-6 $R^{19}$, and 6-10 membered heteroarylalkyl optionally substituted by 1-6 $R^{19}$; $R^3$ is chosen from H, $C_{1-6}$alkyl optionally substituted by 1-13 $R^{19}$, $C_{7-16}$arylalkyl optionally substituted by 1-19 $R^{19}$, $C_{6-10}$-cycloalkylalkyl optionally substituted by 1-10 $R^{19}$, and 6-21 membered heteroarylalkyl optionally substituted by 1-27 $R^{19}$; $R^4$, $R^5$, and $R^6$ are H; alternatively $R^3$ and $R^6$ can, together with the atoms linking them, form a $C_{3-6}$ cycloalkyl optionally substituted by 1-3 $R^{19}$; alternatively $R^3$ and $R^4$ can together form =O; and alternatively any of $R^1$ and $R^2$, $R^1$ and $R^3$, $R^1$ and $R^5$, $R^1$ and $R^{11}$, and $R^4$ and $R^{11}$ can, together with the atoms linking them, form a 3-15 membered heterocycloalkyl optionally substituted by 1-22 $R^{19}$.

Embodiment 57

The compound of any of Embodiments 1-19, wherein $R^1$ and $R^{11}$ are independently chosen from H and $C_{1-6}$alkyl optionally substituted by 1-13 $R^{19}$; $R^2$ is chosen from H, $C_{1-6}$alkyl optionally substituted by 1-13 $R^{19}$, $C_{7-12}$arylalkyl optionally substituted by 1-6 $R^{19}$, and 6-10 membered heteroarylalkyl optionally substituted by 1-6 $R^{19}$; $R^3$ is chosen from H, $C_{1-6}$alkyl optionally substituted by 1-13 $R^{19}$, $C_{7-16}$arylalkyl optionally substituted by 1-19 $R^{19}$, $C_{6-10}$cycloalkylalkyl optionally substituted by 1-10 $R^{19}$, and 6-21 membered heteroarylalkyl optionally substituted by 1-27 $R^{19}$; $R^4$, $R^5$, and $R^6$ are H; alternatively $R^3$ and $R^6$ can, together with the atoms linking them, form a $C_{3-6}$ cycloalkyl optionally substituted by 1-3 $R^{19}$; alternatively $R^3$ and $R^4$ can together form =O; and alternatively any of $R^1$ and $R^2$, $R^1$ and $R^3$, $R^1$ and $R^5$, and $R^4$ and $R^{11}$ can, together with the atoms linking them, form a 3-15 membered heterocycloalkyl optionally substituted by 1-22 $R^{19}$.

Embodiment 58

The compound of any of Embodiments 1-19, wherein $R^1$, $R^2$, and $R^{11}$ are independently chosen from H and $C_{1-6}$alkyl optionally substituted by 1-13 $R^{19}$; $R^3$ is chosen from H, $C_{1-6}$alkyl optionally substituted by 1-13 $R^{19}$, $C_{7-16}$arylalkyl optionally substituted by 1-19 $R^{19}$, $C_{6-10}$-cycloalkylalkyl optionally substituted by 1-10 $R^{19}$, and 6-21 membered heteroarylalkyl optionally substituted by 1-27 $R^{19}$; $R^4$, $R^5$, and $R^6$ are H; alternatively $R^3$ and $R^6$ can, together with the atoms linking them, form a $C_{3-6}$cycloalkyl; and alternatively any of $R^1$ and $R^2$, $R^1$ and $R^3$, $R^1$ and $R^5$, $R^1$ and $R^{11}$, and $R^4$ and $R^{11}$ can, together with the atoms linking them, form a 3-15 membered heterocycloalkyl optionally substituted by 1-22 $R^{19}$.

Embodiment 59

The compound of any of Embodiments 1-19, wherein $R^1$, $R^2$, and $R^{11}$ are independently chosen from H and $C_{1-6}$alkyl optionally substituted by 1-13 $R^{19}$; $R^3$ is chosen from H, $C_{1-6}$alkyl optionally substituted by 1-13 $R^{19}$, $C_{7-16}$arylalkyl optionally substituted by 1-19 $R^{19}$, $C_{6-10}$-cycloalkylalkyl optionally substituted by 1-10 $R^{19}$, and 6-21 membered heteroarylalkyl optionally substituted by 1-27 $R^{19}$; $R^4$, $R^5$, and $R^6$ are H; alternatively $R^3$ and $R^6$ can, together with the atoms linking them, form a $C_{3-6}$cycloalkyl; and alternatively any of $R^1$ and $R^2$, $R^1$ and $R^3$, $R^1$ and $R^5$, and $R^4$ and $R^{11}$ can, together with the atoms linking them, form a 3-15 membered heterocycloalkyl optionally substituted by 1-22 $R^{19}$.

Embodiment 60

The compound of any of Embodiments 1-19, wherein $R^1$, $R^2$, and $R^{11}$ are independently chosen from H and $C_{1-6}$alkyl optionally substituted by 1-13 $R^{19}$; $R^3$ is chosen from H, $C_{1-6}$alkyl optionally substituted by 1-13 $R^{19}$, $C_{7-16}$arylalkyl optionally substituted by 1-19 $R^{19}$, $C_{6-10}$-cycloalkylalkyl optionally substituted by 1-10 $R^{19}$, and 6-21 membered heteroarylalkyl optionally substituted by 1-27 $R^{19}$; $R^4$, $R^5$, and $R^6$ are H; alternatively $R^3$ and $R^6$ can, together with the atoms linking them, form a $C_{3-6}$cycloalkyl.

Embodiment 61

The compound of any of Embodiments 1-19, wherein $R^1$, $R^4$, $R^5$, $R^6$, and $R^{11}$ are independently chosen from H and $C_{1-6}$alkyl optionally substituted by 1-13 $R^{19}$; $R^2$ is chosen from H, $C_{1-6}$alkyl optionally substituted by 1-13 $R^{19}$, $C_{7-11}$arylalkyl optionally substituted by 1-6 $R^{19}$, and 6-10 membered heteroarylalkyl optionally substituted by 1-6 $R^{19}$; $R^3$ is chosen from H, $C_{1-6}$alkyl optionally substituted by 1-13 $R^{19}$, $C_{7-11}$arylalkyl optionally substituted by 1-9 $R^{19}$, $C_{6-7}$cycloalkylalkyl optionally substituted by 1-6 $R^{19}$, and 6-11 membered heteroarylalkyl optionally substituted by 1-7 $R^{19}$; alternatively $R^3$ and $R^6$ can, together with the atoms linking them, form a $C_{3-6}$cycloalkyl; and alternatively any of $R^1$ and $R^2$, $R^1$ and $R^3$, $R^1$ and $R^5$, $R^1$ and $R^{11}$, and $R^4$ and $R^{11}$ can, together with the atoms linking them, form a 3-7 membered heterocycloalkyl optionally substituted by 1-11 $R^{19}$.

Embodiment 62

The compound of any of Embodiments 1-19, wherein $R^1$, $R^4$, $R^5$, $R^6$, and $R^{11}$ are independently chosen from H and $C_{1-6}$alkyl optionally substituted by 1-13 $R^{19}$; $R^2$ is chosen from H, $C_{1-6}$alkyl optionally substituted by 1-13 $R^{19}$, $C_{7-11}$arylalkyl optionally substituted by 1-6 $R^{19}$, and 6-10 membered heteroarylalkyl optionally substituted by 1-6 $R^{19}$; $R^3$ is chosen from H, $C_{1-6}$alkyl optionally substituted by 1-13 $R^{19}$, $C_{7-11}$arylalkyl optionally substituted by 1-9 $R^{19}$, $C_{6-7}$cycloalkylalkyl optionally substituted by 1-6 $R^{19}$, and 6-11 membered heteroarylalkyl optionally substituted by 1-7 $R^{19}$; alternatively $R^3$ and $R^6$ can, together with the atoms linking them, form a $C_{3-6}$cycloalkyl; and alternatively any of $R^1$ and $R^2$, $R^1$ and $R^3$, $R^1$ and $R^5$, and $R^4$ and $R^{11}$ can, together with the atoms linking them, form a 3-7 membered heterocycloalkyl optionally substituted by 1-11 $R^{19}$.

Embodiment 63

The compound of any of Embodiments 1-19, wherein $R^1$, $R^4$, $R^5$, $R^6$, and $R^{11}$ are independently chosen from H and $C_{1-6}$alkyl optionally substituted by 1-13 $R^{19}$; $R^2$ is chosen from H, $C_{1-6}$alkyl optionally substituted by 1-13 $R^{19}$, $C_{7-11}$arylalkyl optionally substituted by 1-6 $R^{19}$, and 6-10 membered heteroarylalkyl optionally substituted by 1-6 $R^{19}$; $R^3$ is chosen from H, $C_{1-6}$alkyl optionally substituted by 1-13 $R^{19}$, $C_{7-11}$arylalkyl optionally substituted by 1-9 $R^{19}$, $C_{6-7}$cycloalkylalkyl optionally substituted by 1-6 $R^{19}$, and 6-11 membered heteroarylalkyl optionally substituted by 1-7 $R^{19}$; alternatively $R^3$ and $R^6$ can, together with the atoms linking them, form a $C_{3-6}$cycloalkyl.

Embodiment 64

The compound of any of Embodiments 1-19, wherein $R^1$, $R^2$, and $R^{11}$ are independently chosen from H and $C_{1-6}$alkyl optionally substituted by 1-13 $R^{19}$; $R^3$ is chosen from H, $C_{1-6}$alkyl optionally substituted by 1-13 $R^{19}$, $C_{7-11}$arylalkyl optionally substituted by 1-9 $R^{19}$, $C_{6-7}$cycloalkylalkyl optionally substituted by 1-6 $R^{19}$,
and 6-11 membered heteroarylalkyl optionally substituted by 1-7 $R^{19}$; $R^4$, $R^5$, and $R^6$ are H; alternatively $R^3$ and $R^6$ can, together with the atoms linking them, form a $C_{3-6}$cycloalkyl; alternatively $R^3$ and $R^4$ can together form =O; and alternatively any of $R^1$ and $R^2$, $R^1$ and $R^3$, $R^1$ and $R^5$, $R^1$ and $R^{11}$, and $R^4$ and $R^{11}$ can, together with the atoms linking them, form a 3-7 membered heterocycloalkyl optionally substituted by 1-11 $R^{19}$.

Embodiment 65

The compound of any of Embodiments 1-19, wherein $R^1$, $R^2$, and $R^{11}$ are independently chosen from H and $C_{1-6}$alkyl optionally substituted by 1-13 $R^{19}$; $R^3$ is chosen from H, $C_{1-6}$alkyl optionally substituted by 1-13 $R^{19}$, $C_{7-11}$arylalkyl optionally substituted by 1-9 $R^{19}$, $C_{6-7}$cycloalkylalkyl optionally substituted by 1-6 $R^{19}$,
and 6-11 membered heteroarylalkyl optionally substituted by 1-7 $R^{19}$; $R^4$, $R^5$, and $R^6$ are H; alternatively $R^3$ and $R^6$ can, together with the atoms linking them, form a $C_{3-6}$cycloalkyl; alternatively $R^3$ and $R^4$ can together form =O; and alternatively any of $R^1$ and $R^2$, $R^1$ and $R^3$, $R^1$ and $R^5$, and $R^4$ and $R^{11}$ can, together with the atoms linking them, form a 3-7 membered heterocycloalkyl optionally substituted by 1-11 $R^{19}$.

Embodiment 66

The compound of any of Embodiments 1-19, wherein $R^1$, $R^2$, and $R^{11}$ are independently chosen from H and $C_{1-6}$alkyl optionally substituted by 1-13 $R^{19}$; $R^3$ is chosen from H, $C_{1-6}$alkyl optionally substituted by 1-13 $R^{19}$, $C_{7-11}$arylalkyl optionally substituted by 1-9 $R^{19}$, $C_{6-7}$cycloalkylalkyl optionally substituted by 1-6 $R^{19}$,
and 6-11 membered heteroarylalkyl optionally substituted by 1-7 $R^{19}$; $R^4$, $R^5$, and $R^6$ are H; alternatively $R^3$ and $R^6$ can, together with the atoms linking them, form a $C_{3-6}$cycloalkyl; alternatively $R^3$ and $R^4$ can together form =O.

Embodiment 67

The compound of any of Embodiments 1-19, wherein $R^1$, $R^4$, $R^5$, $R^6$, and $R^{11}$ are independently chosen from H and $C_{1-6}$alkyl optionally substituted by 1-13 $R^{19}$; $R^2$ is chosen from H, $C_{1-6}$alkyl optionally substituted by 1-13 $R^{19}$, $C_{7-11}$arylalkyl optionally substituted by 1-6 $R^{19}$, and 6-10 membered heteroarylalkyl optionally substituted by 1-6 $R^{19}$; $R^3$ is chosen from H, $C_{1-6}$alkyl optionally substituted by 1-13 $R^{19}$, $C_{7-11}$arylalkyl optionally substituted by 1-9 $R^{19}$, $C_{6-7}$cycloalkylalkyl optionally substituted by 1-6 $R^{19}$, and 6-11 membered heteroarylalkyl optionally substituted by 1-7 $R^{19}$; alternatively $R^3$ and $R^6$ can, together with the atoms linking them, form a cyclopropyl group optionally substituted by 1-3 $R^{19}$; and alternatively any of $R^1$ and $R^3$, $R^1$ and $R^5$, $R^1$ and $R^{11}$, and $R^4$ and $R^{11}$ can, together with the atoms linking them, form a 3-7 membered heterocycloalkyl optionally substituted by 1-11 $R^{19}$.

Embodiment 68

The compound of any of Embodiments 1-19, wherein $R^1$, $R^4$, $R^5$, $R^6$, and $R^{11}$ are independently chosen from H and $C_{1-6}$alkyl optionally substituted by 1-13 $R^{19}$; $R^2$ is chosen from H, $C_{1-6}$alkyl optionally substituted by 1-13 $R^{19}$, $C_{7-11}$arylalkyl optionally substituted by 1-6 $R^{19}$, and 6-10 membered heteroarylalkyl optionally substituted by 1-6 $R^{19}$; $R^3$ is chosen from H, $C_{1-6}$alkyl optionally substituted by 1-13 $R^{19}$, $C_{7-11}$arylalkyl optionally substituted by 1-9 $R^{19}$, $C_{6-7}$cycloalkylalkyl optionally substituted by 1-6 $R^{19}$, and 6-11 membered heteroarylalkyl optionally substituted by 1-7 $R^{19}$; alternatively $R^3$ and $R^6$ can, together with the atoms linking them, form a cyclopropyl group optionally substituted by 1-3 $R^{19}$; and alternatively any of $R^1$ and $R^3$, $R^1$ and $R^5$, and $R^4$ and $R^{11}$ can, together with the atoms linking them, form a 3-7 membered heterocycloalkyl optionally substituted by 1-11 $R^{19}$.

Embodiment 69

The compound of any of Embodiments 1-19, wherein $R^1$, $R^4$, $R^5$, $R^6$, and $R^{11}$ are independently chosen from H and $C_{1-6}$alkyl optionally substituted by 1-13 $R^{19}$; $R^2$ is chosen from H, $C_{1-6}$alkyl optionally substituted by 1-13 $R^{19}$, $C_{7-11}$arylalkyl optionally substituted by 1-6 $R^{19}$, and 6-10 membered heteroarylalkyl optionally substituted by 1-6 $R^{19}$; $R^3$ is chosen from H, $C_{1-6}$alkyl optionally substituted by 1-13 $R^{19}$, $C_{7-11}$arylalkyl optionally substituted by 1-9 $R^{19}$, $C_{6-7}$cycloalkylalkyl optionally substituted by 1-6 $R^{19}$, and 6-11 membered heteroarylalkyl optionally substituted by 1-7 $R^{19}$; alternatively $R^3$ and $R^6$ can, together with the atoms linking them, form a cyclopropyl group optionally substituted by 1-3 $R^{19}$.

Embodiment 70

The compound of any of Embodiments 1-19, wherein $R^1$, $R^2$, and $R^{11}$ are independently chosen from H and $C_{1-6}$alkyl optionally substituted by 1-13 $R^{19}$; $R^3$ is chosen from H, $C_{1-6}$alkyl optionally substituted by 1-13 $R^{19}$, $C_{7-11}$arylalkyl optionally substituted by 1-9 $R^{19}$, $C_{6-7}$cycloalkylalkyl optionally substituted by 1-6 $R^{19}$,
and 6-11 membered heteroarylalkyl optionally substituted by 1-7 $R^{19}$; $R^4$, $R^5$, and $R^6$ are H; alternatively $R^3$ and $R^6$ can, together with the atoms linking them, form a cyclopropyl group; and alternatively any of $R^1$ and $R^3$, $R^1$ and $R^5$, $R^1$ and $R^{11}$, and $R^4$ and $R^{11}$ can, together with the atoms linking them, form a 3-7 membered heterocycloalkyl optionally substituted by 1-11 $R^{19}$.

Embodiment 71

The compound of any of Embodiments 1-19, wherein $R^1$, $R^2$, and $R^{11}$ are independently chosen from H and $C_{1-6}$alkyl optionally substituted by 1-13 $R^{19}$; $R^3$ is chosen from H, $C_{1-6}$alkyl optionally substituted by 1-13 $R^{19}$, $C_{7-11}$arylalkyl optionally substituted by 1-9 $R^{19}$, $C_{6-7}$cycloalkylalkyl optionally substituted by 1-6 $R^{19}$,
and 6-11 membered heteroarylalkyl optionally substituted by 1-7 $R^{19}$; $R^4$, $R^5$, and $R^6$ are H; alternatively $R^3$ and $R^6$ can, together with the atoms linking them, form a cyclopropyl group; and alternatively any of $R^1$ and $R^3$, $R^1$ and $R^5$, and $R^4$ and $R^{11}$ can, together with the atoms linking them, form a 3-7 membered heterocycloalkyl optionally substituted by 1-11 $R^{19}$.

Embodiment 72

The compound of any of Embodiments 1-19, wherein $R^1$, $R^2$, and $R^{11}$ are independently chosen from H and $C_{1-6}$alkyl optionally substituted by 1-13 $R^{19}$; $R^3$ is chosen from H, $C_{1-6}$alkyl optionally substituted by 1-13 $R^{19}$, $C_{7-11}$arylalkyl optionally substituted by 1-9 $R^{19}$, $C_{6-7}$cycloalkylalkyl optionally substituted by 1-6 $R^{19}$,
and 6-11 membered heteroarylalkyl optionally substituted by 1-7 $R^{19}$; $R^4$, $R^5$, and $R^6$ are H; alternatively $R^3$ and $R^6$ can, together with the atoms linking them, form a cyclopropyl group.

Embodiment 73

The compound of any of Embodiments 1-19, wherein $R^1$, $R^4$, $R^5$, $R^6$, and $R^{11}$ are independently chosen from H and $C_{1-6}$alkyl optionally substituted by 1-3 $R^{19}$; $R^2$ is chosen from H, $C_{1-6}$alkyl optionally substituted by 1-3 $R^{19}$, $C_{7-11}$arylalkyl optionally substituted by 1-3 $R^{19}$, and 6-10 membered heteroarylalkyl optionally substituted by 1-3 $R^{19}$; $R^3$ is chosen from H, $C_{1-6}$alkyl optionally substituted by 1-3 $R^{19}$,
$C_{7-11}$arylalkyl optionally substituted by 1-9 $R^{19}$, $C_{6-7}$cycloalkylalkyl optionally substituted by 1-6 $R^{19}$, and 6-11 membered heteroarylalkyl optionally substituted by 1-7 $R^{19}$; and alternatively any of $R^1$ and $R^2$, $R^1$ and $R^3$, $R^1$ and $R^5$, $R^1$ and $R^{11}$, and $R^4$ and $R^{11}$ can, together with the atoms linking them, form a 3-7 membered heterocycloalkyl optionally substituted by 1-3 $R^{19}$.

Embodiment 74

The compound of any of Embodiments 1-19, wherein $R^1$, $R^4$, $R^5$, $R^6$, and $R^{11}$ are independently chosen from H and $C_{1-6}$alkyl optionally substituted by 1-3 $R^{19}$; $R^2$ is chosen from H, $C_{1-6}$alkyl optionally substituted by 1-3 $R^{19}$, $C_{7-11}$arylalkyl optionally substituted by 1-3 $R^{19}$, and 6-10 membered heteroarylalkyl optionally substituted by 1-3 $R^{19}$; $R^3$ is chosen from H, $C_{1-6}$alkyl optionally substituted by 1-3 $R^{19}$,
$C_{7-11}$arylalkyl optionally substituted by 1-9 $R^{19}$, $C_{6-7}$cycloalkylalkyl optionally substituted by 1-6 $R^{19}$, and 6-11 membered heteroarylalkyl optionally substituted by 1-7 $R^{19}$; and alternatively any of $R^1$ and $R^2$, $R^1$ and $R^3$, $R^1$ and $R^5$, and $R^4$ and $R^{11}$ can, together with the atoms linking them, form a 3-7 membered heterocycloalkyl optionally substituted by 1-3 $R^{19}$.

Embodiment 75

The compound of any of Embodiments 1-19, wherein $R^1$, $R^4$, $R^5$, $R^6$, and $R^{11}$ are independently chosen from H and $C_{1-6}$alkyl optionally substituted by 1-3 $R^{19}$; $R^2$ is chosen from H, $C_{1-6}$alkyl optionally substituted by 1-3 $R^{19}$, $C_{7-11}$arylalkyl optionally substituted by 1-3 $R^{19}$, and 6-10 membered heteroarylalkyl optionally substituted by 1-3 $R^{19}$; $R^3$ is chosen from H, $C_{1-6}$alkyl optionally substituted by 1-3 $R^{19}$,
$C_{7-11}$arylalkyl optionally substituted by 1-9 $R^{19}$, $C_{6-7}$cycloalkylalkyl optionally substituted by 1-6 $R^{19}$, and 6-11 membered heteroarylalkyl optionally substituted by 1-7 $R^{19}$; and alternatively any of $R^1$ and $R^2$, $R^1$ and $R^3$, $R^1$ and $R^5$, $R^1$ and $R^{11}$, and $R^4$ and $R^{11}$ can, together with the atoms linking them, form a 3-7 membered heterocycloalkyl optionally substituted by 1-3 $R^{19}$.

Embodiment 76

The compound of any of Embodiments 1-19, wherein $R^1$, $R^2$, and $R^{11}$ are independently chosen from H and $C_{1-6}$alkyl optionally substituted by 1-3 $R^{19}$; $R^3$ is chosen from H, $C_{1-6}$alkyl optionally substituted by 1-3 $R^{19}$, $C_{7-11}$arylalkyl optionally substituted by 1-9 $R^{19}$, $C_{6-7}$cycloalkylalkyl optionally substituted by 1-6 $R^{19}$,
and 6-11 membered heteroarylalkyl optionally substituted by 1-7 $R^{19}$; $R^4$, $R^5$, and $R^6$ are H.

Embodiment 77

The compound of any of Embodiments 1-19, wherein $R^1$, $R^2$, $R^4$, $R^5$, $R^6$, and $R^{11}$ are independently chosen from H and $C_{1-6}$alkyl optionally substituted by 1-3 $R^{19}$; $R^3$ is chosen from H, $C_{1-6}$alkyl optionally substituted by 1-3 $R^{19}$,
$C_{7-11}$arylalkyl optionally substituted by 1-3 $R^{19}$, $C_{6-7}$cycloalkylalkyl optionally substituted by 1-3 $R^{19}$, and 6-11 membered heteroarylalkyl optionally substituted by 1-3 $R^{19}$; and alternatively any of $R^1$ and $R^3$, $R^1$ and $R^5$, $R^1$ and $R^{11}$, and $R^4$ and $R^{11}$ can, together with the atoms linking them, form a 3-7 membered heterocycloalkyl optionally substituted by 1-3 $R^{19}$.

Embodiment 78

The compound of any of Embodiments 1-19, wherein $R^1$, $R^2$, $R^4$, $R^5$, $R^6$, and $R^{11}$ are independently chosen from H and $C_{1-6}$alkyl optionally substituted by 1-3 $R^{19}$; $R^3$ is chosen from H, $C_{1-6}$alkyl optionally substituted by 1-3 $R^{19}$,
$C_{7-11}$arylalkyl optionally substituted by 1-3 $R^{19}$, $C_{6-7}$cycloalkylalkyl optionally substituted by 1-3 $R^{19}$, and 6-11 membered heteroarylalkyl optionally substituted by 1-3 $R^{19}$; and alternatively any of $R^1$ and $R^3$, $R^1$ and $R^5$, and $R^4$ and $R^{11}$ can, together with the atoms linking them, form a 3-7 membered heterocycloalkyl optionally substituted by 1-3 $R^{19}$.

Embodiment 79

The compound of any of Embodiments 1-19, wherein $R^1$, $R^2$, $R^4$, $R^5$, $R^6$, and $R^{11}$ are independently chosen from H and $C_{1-6}$alkyl optionally substituted by 1-3 $R^{19}$; $R^3$ is chosen from H, $C_{1-6}$alkyl optionally substituted by 1-3 $R^{19}$,
$C_{7-11}$arylalkyl optionally substituted by 1-3 $R^{19}$, $C_{6-7}$cycloalkylalkyl optionally substituted by 1-3 $R^{19}$, and 6-11 membered heteroarylalkyl optionally substituted by 1-3 $R^{19}$.

Embodiment 80

The compound of any of Embodiments 1-19, wherein $R^1$, $R^2$, and $R^{11}$ are independently chosen from H and $C_{1-6}$alkyl optionally substituted by 1-3 $R^{19}$; $R^3$ is chosen from H, $C_{1-6}$alkyl optionally substituted by 1-3 $R^{19}$, $C_{7-11}$arylalkyl optionally substituted by 1-3 $R^{19}$, $C_{6-7}$cycloalkylalkyl optionally substituted by 1-3 $R^{19}$,
and 6-11 membered heteroarylalkyl optionally substituted by 1-3 $R^{19}$; $R^4$, $R^5$, and $R^6$ are H; and alternatively any of $R^1$ and $R^3$, $R^1$ and $R^5$, $R^1$ and $R^{11}$, and $R^4$ and $R^{11}$ can,

43 together with the atoms linking them, form a 5-7 membered heterocycloalkyl optionally substituted by 1-3 $R^{19}$.

Embodiment 81

The compound of any of Embodiments 1-19, wherein $R^1$, $R^2$, and $R^{11}$ are independently chosen from H and $C_{1-6}$alkyl optionally substituted by 1-3 $R^{19}$; $R^3$ is chosen from H, $C_{1-6}$alkyl optionally substituted by 1-3 $R^{19}$, $C_{7-11}$arylalkyl optionally substituted by 1-3 $R^{19}$, $C_{6-7}$cycloalkylalkyl optionally substituted by 1-3 $R^{19}$,
and 6-11 membered heteroarylalkyl optionally substituted by 1-3 $R^{19}$; $R^4$, $R^5$, and $R^6$ are H; and alternatively any of $R^1$ and $R^3$, $R^1$ and $R^5$, and $R^4$ and $R^{11}$ can, together with the atoms linking them, form a 5-7 membered heterocycloalkyl optionally substituted by 1-3 $R^{19}$.

Embodiment 82

The compound of any of Embodiments 1-19, wherein $R^1$, $R^2$, and $R^{11}$ are independently chosen from H and $C_{1-6}$alkyl optionally substituted by 1-3 $R^{19}$; $R^3$ is chosen from H, $C_{1-6}$alkyl optionally substituted by 1-3 $R^{19}$, $C_{7-11}$arylalkyl optionally substituted by 1-3 $R^{19}$, $C_{6-7}$cycloalkylalkyl optionally substituted by 1-3 $R^{19}$,
and 6-11 membered heteroarylalkyl optionally substituted by 1-3 $R^{19}$; $R^4$, $R^5$, and $R^6$ are H.

Embodiment 83

The compound of any of Embodiments 1-19, wherein $R^1$, $R^2$, and $R^{11}$ are independently chosen from H and $C_{1-6}$alkyl optionally substituted by 1-3 $R^{19}$; $R^3$ is chosen from H, $C_{1-6}$alkyl optionally substituted by 1-3 $R^{19}$, $C_{7-11}$arylalkyl optionally substituted by 1-3 $R^{19}$, $C_{6-7}$cycloalkylalkyl optionally substituted by 1-3 $R^{19}$,
and 6-11 membered heteroarylalkyl optionally substituted by 1-3 $R^{19}$; $R^4$, $R^5$, and $R^6$ are
H; alternatively any of $R^1$ and $R^3$, $R^1$ and $R^5$, and $R^4$ and $R^{11}$ can, together with the atoms linking them, form a 5-6 membered heterocycloalkyl optionally substituted by 1-3 $R^{19}$;
and alternatively $R^1$ and $R^{11}$ can, together with the atoms linking them, form a 5-7 membered heterocycloalkyl optionally substituted by 1-3 $R^{19}$.

Embodiment 84

The compound of any of Embodiments 1-19, wherein $R^1$, $R^2$, and $R^{11}$ are independently chosen from H and $C_{1-6}$alkyl optionally substituted by 1-3 $R^{19}$; $R^3$ is chosen from H, $C_{1-6}$alkyl optionally substituted by 1-3 $R^{19}$, $C_{7-11}$arylalkyl optionally substituted by 1-3 $R^{19}$, $C_{6-7}$cycloalkylalkyl optionally substituted by 1-3 $R^{19}$,
and 6-11 membered heteroarylalkyl optionally substituted by 1-3 $R^{19}$; $R^4$, $R^5$, and $R^6$ are H; alternatively any of $R^1$ and $R^3$, $R^1$ and $R^5$, and $R^4$ and $R^{11}$ can, together with the atoms linking them, form a 5-6 membered heterocycloalkyl optionally substituted by 1-3 $R^{19}$.

Embodiment 85

The compound of any of Embodiments 1-19, wherein $R^1$, $R^2$, and $R^{11}$ are independently chosen from H and $C_{1-6}$alkyl optionally substituted by 1-3 $R^{19}$; $R^3$ is chosen from H, $C_{1-6}$alkyl optionally substituted by 1-3 $R^{19}$, $C_{7-11}$arylalkyl optionally substituted by 1-3 $R^{19}$, $C_{6-7}$cycloalkylalkyl optionally substituted by 1-3 $R^{19}$,
and 6-11 membered heteroarylalkyl optionally substituted by 1-3 $R^{19}$; $R^4$, $R^5$, and $R^6$ are H; alternatively any of $R^1$ and $R^3$, and $R^4$ and $R^{11}$ can, together with the atoms linking them, form a 5 membered heterocycloalkyl optionally substituted by 1-3 $R^{19}$; alternatively $R^1$ and $R^5$ can, together with the atoms linking them, form a 5-6 membered heterocycloalkyl optionally substituted by 1-3 $R^{19}$; and alternatively $R^1$ and $R^{11}$ can, together with the atoms linking them, form a 6-7 membered heterocycloalkyl optionally substituted by 1-3 $R^{19}$.

Embodiment 86

The compound of any of Embodiments 1-19, wherein $R^1$, $R^2$, and $R^{11}$ are independently chosen from H and $C_{1-6}$alkyl optionally substituted by 1-3 $R^{19}$; $R^3$ is chosen from H, $C_{1-6}$alkyl optionally substituted by 1-3 $R^{19}$, $C_{7-11}$arylalkyl optionally substituted by 1-3 $R^{19}$, $C_{6-7}$cycloalkylalkyl optionally substituted by 1-3 $R^{19}$,
and 6-11 membered heteroarylalkyl optionally substituted by 1-3 $R^{19}$; $R^4$, $R^5$, and $R^6$ are H; alternatively any of $R^1$ and $R^3$, and $R^4$ and $R^{11}$ can, together with the atoms linking them, form a 5 membered heterocycloalkyl optionally substituted by 1-3 $R^{19}$; alternatively $R^1$ and $R^5$ can, together with the atoms linking them, form a 5-6 membered heterocycloalkyl optionally substituted by 1-3 $R^{19}$.

Embodiment 87

The compound of any of Embodiments 1-19, wherein $R^1$ and $R^{11}$ are independently chosen from H and $C_{1-6}$alkyl optionally substituted by 1-3 $R^{19}$; $R^2$ is chosen from H, $C_{1-6}$alkyl optionally substituted by 1-3 $R^{19}$, and $C_{7-11}$arylalkyl optionally substituted by 1-3 $R^{19}$; $R^3$ is chosen from H, $C_{1-6}$alkyl optionally substituted by 1-3 $R^{19}$, $C_{7-11}$arylalkyl optionally substituted by 1-3 $R^{19}$, $C_{6-7}$cycloalkylalkyl optionally substituted by 1-3 $R^{19}$, and 6-11 membered heteroarylalkyl optionally substituted by 1-3 $R^{19}$; $R^4$, $R^5$, and $R^6$ are H; alternatively any of $R^1$ and $R^3$, and $R^4$ and $R^{11}$ can, together with the atoms linking them, form a 5 membered heterocycloalkyl optionally substituted by 1-3 $R^{19}$; alternatively $R^1$ and $R^5$ can, together with the atoms linking them, form a 5-6 membered heterocycloalkyl optionally substituted by 1-3 $R^{19}$; and alternatively $R^1$ and $R^{11}$ can, together with the atoms linking them, form a 6-7 membered heterocycloalkyl optionally substituted by 1-3 $R^{19}$.

Embodiment 88

The compound of any of Embodiments 1-19, wherein $R^1$ and $R^{11}$ are independently chosen from H and $C_{1-6}$alkyl optionally substituted by 1-3 $R^{19}$; $R^2$ is chosen from H, $C_{1-6}$alkyl optionally substituted by 1-3 $R^{19}$, and $C_{7-11}$arylalkyl optionally substituted by 1-3 $R^{19}$; $R^3$ is chosen from H, $C_{1-6}$alkyl optionally substituted by 1-3 $R^{19}$, $C_{7-11}$arylalkyl optionally substituted by 1-3 $R^{19}$, $C_{6-7}$cycloalkylalkyl optionally substituted by 1-3 $R^{19}$, and 6-11 membered heteroarylalkyl optionally substituted by 1-3 $R^{19}$; $R^4$, $R^5$, and $R^6$ are H; alternatively any of $R^1$ and $R^3$, and $R^4$ and $R^{11}$ can, together with the atoms linking them, form a 5 membered heterocycloalkyl optionally substituted by 1-3 $R^{19}$; alternatively $R^1$ and $R^5$ can, together with the atoms linking them, form a 5-6 membered heterocycloalkyl optionally substituted by 1-3 $R^{19}$.

Embodiment 89

The compound of any of Embodiments 1-19, wherein $R^1$ and $R^{11}$ are independently chosen from H and $C_{1-6}$alkyl optionally substituted by 1-3 $R^{19}$; $R^2$ is H; $R^3$ is chosen from H, $C_{1-6}$alkyl optionally substituted by 1-3 $R^{19}$, $C_{7-11}$arylalkyl optionally substituted by 1-3 $R^{19}$, $C_{6-7}$cycloalkylalkyl optionally substituted by 1-3 $R^{19}$,
and 6-11 membered heteroarylalkyl optionally substituted by 1-3 $R^{19}$; $R^4$, $R^5$, and $R^6$ are H; alternatively $R^1$ and $R^5$ can, together with the atoms linking them, form a 5-6 membered heterocycloalkyl optionally substituted by 1-3 $R^{19}$; and alternatively $R^1$ and $R^{11}$ can, together with the atoms linking them, form a 6-7 membered heterocycloalkyl optionally substituted by 1-3 $R^{19}$.

Embodiment 90

The compound of any of Embodiments 1-19, wherein $R^1$ and $R^{11}$ are independently chosen from H and $C_{1-6}$alkyl optionally substituted by 1-3 $R^{19}$; $R^2$ is H; $R^3$ is chosen from H, $C_{1-6}$alkyl optionally substituted by 1-3 $R^{19}$, $C_{7-11}$arylalkyl optionally substituted by 1-3 $R^{19}$, $C_{6-7}$cycloalkylalkyl optionally substituted by 1-3 $R^{19}$,
and 6-11 membered heteroarylalkyl optionally substituted by 1-3 $R^{19}$; $R^4$, $R^5$, and $R^6$ are H; alternatively $R^1$ and $R^5$ can, together with the atoms linking them, form a 5-6 membered heterocycloalkyl optionally substituted by 1-3 $R^{19}$.

Embodiment 91

The compound of any of Embodiments 1-19, wherein $R^1$, $R^2$, and $R^{11}$ are independently chosen from H and $C_{1-6}$alkyl optionally substituted by 1-3 $R^{19}$; $R^3$ is chosen from H, $C_{1-6}$alkyl optionally substituted by 1-3 $R^{19}$, $C_{7-11}$arylalkyl optionally substituted by 1-3 $R^{19}$, $C_{6-7}$cycloalkylalkyl optionally substituted by 1-3 $R^{19}$,
and 6-11 membered heteroarylalkyl optionally substituted by 1-3 $R^{19}$; $R^4$, $R^5$, and $R^6$ are H; alternatively $R^1$ and $R^5$ can, together with the atoms linking them, form a 5-6 membered heterocycloalkyl optionally substituted by 1-3 $R^{19}$; and alternatively $R^1$ and $R^{11}$ can, together with the atoms linking them, form a 6-7 membered heterocycloalkyl optionally substituted by 1-3 $R^{19}$.

Embodiment 92

The compound of any of Embodiments 1-19, wherein $R^1$, $R^2$, and $R^{11}$ are independently chosen from H and $C_{1-6}$alkyl optionally substituted by 1-3 $R^{19}$; $R^3$ is chosen from H, $C_{1-6}$alkyl optionally substituted by 1-3 $R^{19}$, $C_{7-11}$arylalkyl optionally substituted by 1-3 $R^{19}$, $C_{6-7}$cycloalkylalkyl optionally substituted by 1-3 $R^{19}$,
and 6-11 membered heteroarylalkyl optionally substituted by 1-3 $R^{19}$; $R^4$, $R^5$, and $R^6$ are H; alternatively $R^1$ and $R^5$ can, together with the atoms linking them, form a 5-6 membered heterocycloalkyl optionally substituted by 1-3 $R^{19}$.

Embodiment 93

The compound of any of Embodiments 1-19, wherein $R^1$, $R^2$, and $R^{11}$ are independently chosen from H and $C_{1-6}$alkyl optionally substituted by 1-3 $R^{19}$; $R^3$ is chosen from H, $C_{1-6}$alkyl optionally substituted by 1-3 $R^{19}$, $C_{7-11}$arylalkyl optionally substituted by 1-3 $R^{19}$, $C_{6-7}$cycloalkylalkyl optionally substituted by 1-3 $R^{19}$,
and 6-11 membered heteroarylalkyl optionally substituted by 1-3 $R^{19}$; $R^4$, $R^5$, and $R^6$ are H; alternatively $R^1$ and $R^5$ can, together with the atoms linking them, form a 5-6 membered heterocycloalkyl optionally substituted by 1-3 $R^{19}$; and alternatively $R^1$ and $R^{11}$ can, together with the atoms linking them, form a 6-7 membered heterocycloalkyl optionally substituted by 1-3 $R^{19}$.

Embodiment 94

The compound of any of Embodiments 1-19, wherein $R^1$, $R^2$, and $R^{11}$ are independently chosen from H and $C_{1-6}$alkyl optionally substituted by 1-3 $R^{19}$; $R^3$ is chosen from H, $C_{1-6}$alkyl optionally substituted by 1-3 $R^{19}$, $C_{7-11}$arylalkyl optionally substituted by 1-3 $R^{19}$, $C_{6-7}$cycloalkylalkyl optionally substituted by 1-3 $R^{19}$,
and 6-11 membered heteroarylalkyl optionally substituted by 1-3 $R^{19}$; $R^4$, $R^5$, and $R^6$ are H; alternatively $R^1$ and $R^5$ can, together with the atoms linking them, form a 5-6 membered heterocycloalkyl optionally substituted by 1-3 $R^{19}$.

Embodiment 95

The compound of any of Embodiments 1-19, wherein $R^1$ and $R^{11}$ are independently chosen from H and $C_{1-6}$alkyl optionally substituted by 1-3 $R^{19}$; $R^2$ is chosen from H, $C_{1-6}$alkyl optionally substituted by 1-3 $R^{19}$, and $C_{7-11}$arylalkyl optionally substituted by 1-3 $R^{19}$; $R^3$ is chosen from H, $C_{1-6}$alkyl optionally substituted by 1-3 $R^{19}$, $C_{7-11}$arylalkyl optionally substituted by 1-3 $R^{19}$, $C_{6-7}$cycloalkylalkyl optionally substituted by 1-3 $R^{19}$, and 6-11 membered heteroarylalkyl optionally substituted by 1-3 $R^{19}$; $R^4$, $R^5$, and $R^6$ are H; alternatively $R^1$ and $R^5$ can, together with the atoms linking them, form a 5-6 membered heterocycloalkyl optionally substituted by 1-3 $R^{19}$; and alternatively $R^1$ and $R^{11}$ can, together with the atoms linking them, form a 6-7 membered heterocycloalkyl optionally substituted by 1-3 $R^{19}$.

Embodiment 96

The compound of any of Embodiments 1-19, wherein $R^1$ and $R^{11}$ are independently chosen from H and $C_{1-6}$alkyl optionally substituted by 1-3 $R^{19}$; $R^2$ is chosen from H, $C_{1-6}$alkyl optionally substituted by 1-3 $R^{19}$, and $C_{7-11}$arylalkyl optionally substituted by 1-3 $R^{19}$; $R^3$ is chosen from H, $C_{1-6}$alkyl optionally substituted by 1-3 $R^{19}$, $C_{7-11}$arylalkyl optionally substituted by 1-3 $R^{19}$, $C_{6-7}$cycloalkylalkyl optionally substituted by 1-3 $R^{19}$, and 6-11 membered heteroarylalkyl optionally substituted by 1-3 $R^{19}$; $R^4$, $R^5$, and $R^6$ are H; alternatively $R^1$ and $R^5$ can, together with the atoms linking them, form a 5-6 membered heterocycloalkyl optionally substituted by 1-3 $R^{19}$.

Embodiment 97

The compound of any of Embodiments 1-19, wherein $R^1$, $R^2$, $R^4$, $R^5$, $R^6$, and $R^{11}$ are H; $R^3$ is chosen from H, $C_{1-6}$alkyl optionally substituted by 1-3 $R^{19}$, $C_{7-11}$arylalkyl optionally substituted by 1-3 $R^{19}$, $C_{6-7}$cycloalkylalkyl optionally substituted by 1-3 $R^{19}$, and 6-11 membered heteroarylalkyl optionally substituted by 1-3 $R^{19}$; alternatively $R^1$ and $R^5$ can, together with the atoms linking them, form a 5-6 membered heterocycloalkyl optionally substituted by 1-3

$R^{19}$; and alternatively $R^1$ and $R^{11}$ can, together with the atoms linking them, form a 5-7 membered heterocycloalkyl optionally substituted by 1-3 $R^{19}$.

Embodiment 98

The compound of any of Embodiments 1-19, wherein $R^1$, $R^2$, $R^4$, $R^5$, $R^6$, and $R^{11}$ are H; $R^3$ is chosen from H, $C_{1-6}$alkyl optionally substituted by 1-3 $R^{19}$, $C_{7-11}$arylalkyl optionally substituted by 1-3 $R^{19}$, $C_{6-7}$cycloalkylalkyl optionally substituted by 1-3 $R^{19}$, and 6-11 membered heteroarylalkyl optionally substituted by 1-3 $R^{19}$; alternatively $R^1$ and $R^5$ can, together with the atoms linking them, form a 5-6 membered heterocycloalkyl optionally substituted by 1-3 $R^{19}$.

Embodiment 99

The compound of any of Embodiments 1-19, wherein $R^1$, $R^2$, $R^4$, $R^5$, $R^6$, and $R^{11}$ are H; $R^3$ is chosen from H, $C_{1-6}$alkyl optionally substituted by 1-3 $R^{19}$, $C_{7-11}$arylalkyl optionally substituted by 1-3 $R^{19}$, $C_{6-7}$cycloalkylalkyl optionally substituted by 1-3 $R^{19}$, and 6-11 membered heteroarylalkyl optionally substituted by 1-3 $R^{19}$; alternatively $R^1$ and $R^5$ can, together with the atoms linking them, form a 5 membered heterocycloalkyl optionally substituted by 1-3 $R^{19}$; and alternatively $R^1$ and $R^{11}$ can, together with the atoms linking them, form a 6 membered heterocycloalkyl optionally substituted by 1-3 $R^{19}$.

Embodiment 100

The compound of any of Embodiments 1-19, wherein $R^1$, $R^2$, $R^4$, $R^5$, $R^6$, and $R^{11}$ are H; $R^3$ is chosen from H, $C_{1-6}$alkyl optionally substituted by 1-3 $R^{19}$, $C_{7-11}$arylalkyl optionally substituted by 1-3 $R^{19}$, $C_{6-7}$cycloalkylalkyl optionally substituted by 1-3 $R^{19}$, and 6-11 membered heteroarylalkyl optionally substituted by 1-3 $R^{19}$; alternatively $R^1$ and $R^5$ can, together with the atoms linking them, form a 5 membered heterocycloalkyl optionally substituted by 1-3 $R^{19}$.

Embodiment 101

The compound of any of Embodiments 1-19, wherein $R^1$, $R^2$, $R^4$, $R^5$, $R^6$, and $R^{11}$ are H; $R^3$ is chosen from H, $C_{1-6}$alkyl optionally substituted by 1-3 $R^{19}$, benzyl optionally substituted by 1-3 $R^{19}$, $C_7$cycloalkylalkyl optionally substituted by 1-3 $R^{19}$, and 6-7 membered heteroarylalkyl optionally substituted by 1-3 $R^{19}$; alternatively $R^1$ and $R^5$ can, together with the atoms linking them, form a pyrrolidinyl group optionally substituted by 1-3 $R^{19}$; and alternatively $R^1$ and $R^{11}$ can, together with the atoms linking them, form a piperidinyl group optionally substituted by 1-3 $R^{19}$.

Embodiment 102

The compound of any of Embodiments 1-19, wherein $R^1$, $R^2$, $R^4$, $R^5$, $R^6$, and $R^{11}$ are H; $R^3$ is chosen from H, $C_{1-6}$alkyl optionally substituted by 1-3 $R^{19}$, benzyl optionally substituted by 1-3 $R^{19}$, $C_7$cycloalkylalkyl optionally substituted by 1-3 $R^{19}$, and 6-7 membered heteroarylalkyl optionally substituted by 1-3 $R^{19}$; alternatively $R^1$ and $R^5$ can, together with the atoms linking them, form a pyrrolidinyl group optionally substituted by 1-3 $R^{19}$.

Embodiment 103

The compound of any of Embodiments 1-19, wherein $R^1$, $R^2$, $R^4$, $R^5$, $R^6$, and $R^{11}$ are H; $R^3$ is chosen from H, $C_{1-6}$alkyl optionally substituted by 1-3 $R^{19}$, benzyl optionally substituted by 1-3 $R^{19}$, $C_7$cycloalkylalkyl optionally substituted by 1-3 $R^{19}$, and 6-7 membered heteroarylalkyl optionally substituted by 1-3 $R^{19}$; alternatively $R^1$ and $R^5$ can, together with the atoms linking them, form a pyrrolidinyl group; and alternatively $R^1$ and $R^{11}$ can, together with the atoms linking them, form a piperidinyl group.

Embodiment 104

The compound of any of Embodiments 1-19, wherein $R^1$, $R^2$, $R^4$, $R^5$, $R^6$, and $R^{11}$ are H; $R^3$ is chosen from H, $C_{1-6}$alkyl optionally substituted by 1-3 $R^{19}$, benzyl optionally substituted by 1-3 $R^{19}$, $C_7$cycloalkylalkyl optionally substituted by 1-3 $R^{19}$, and 6-7 membered heteroarylalkyl optionally substituted by 1-3 $R^{19}$; alternatively $R^1$ and $R^5$ can, together with the atoms linking them, form a pyrrolidinyl group.

Embodiment 105

The compound of any of Embodiments 1-19, wherein $R^1$, $R^2$, $R^4$, $R^5$, $R^6$, and $R^{11}$ are H; $R^3$ is benzyl optionally substituted by 1-3 $R^{19}$; alternatively $R^1$ and $R^5$ can, together with the atoms linking them, form a pyrrolidinyl group; and alternatively $R^1$ and $R^{11}$ can, together with the atoms linking them, form a piperidinyl group.

Embodiment 106

The compound of any of Embodiments 1-19, wherein $R^1$, $R^2$, $R^4$, $R^5$, $R^6$, and $R^{11}$ are H; $R^3$ is benzyl optionally substituted by 1-3 $R^{19}$; alternatively $R^1$ and $R^5$ can, together with the atoms linking them, form a pyrrolidinyl group.

Embodiment 107

The compound of any of Embodiments 1-19, wherein $R^1$, $R^2$, $R^4$, $R^5$, $R^6$, and $R^{11}$ are H; $R^3$ is benzyl; alternatively $R^1$ and $R^5$ can, together with the atoms linking them, form a pyrrolidinyl group; and alternatively $R^1$ and $R^{11}$ can, together with the atoms linking them, form a piperidinyl group.

Embodiment 108

The compound of any of Embodiments 1-19, wherein $R^1$, $R^2$, $R^4$, $R^5$, $R^6$, and $R^{11}$ are H; $R^3$ is benzyl; alternatively $R^1$ and $R^5$ can, together with the atoms linking them, form a pyrrolidinyl group.

Embodiment 109

The compound of any of Embodiments 1-108, wherein $R^7$, $R^8$, $R^9$, and $R^{10}$ are independently chosen from H, $C_{1-6}$alkyl optionally substituted by 1-13 $R^{19}$, $C_{2-6}$alkenyl optionally substituted by 1-11 $R^{19}$, $C_{2-6}$alkynyl optionally substituted by 1-9 $R^{19}$, $C_{6-11}$aryl optionally substituted by 1-11 $R^{19}$, $C_{7-16}$arylalkyl optionally substituted by 1-19 $R^{19}$, $C_{3-11}$cycloalkyl optionally substituted by 1-21 $R^{19}$, $C_{4-17}$cycloalkylalkyl optionally substituted by 1-32 $R^{19}$, 3-15 membered heterocycloalkyl optionally substituted by 1-28 $R^{19}$, 4-21 membered heterocycloalkylalkyl optionally substituted by 1-40 $R^{19}$, 5-15 membered heteroaryl optionally substituted by 1-15 $R^{19}$, 6-21 membered heteroarylalkyl optionally substituted by 1-27 $R^{19}$, halogen, —CN, —C(=O)$R^{20}$, —C(=O)O$R^{20}$, —C(=O)N$R^{22}R^{23}$, —C(=O)C(=O)$R^{20}$, —C(=N$R^{25}$)$R^{20}$, —C(=N$R^{25}$)N$R^{22}R^{23}$, —C(=NOH)

—NR$^{22}$R$^{23}$, —C(=NOR$^{26}$)R$^{20}$, —C(=NNR$^{22}$R$^{23}$)R$^{20}$, —C(=NNR$^{24}$C(=O)R)R$^1$)R$^2$, —C(=NNR$^{24}$C(=O)OR$^{21}$)R$^{20}$, —C(=S)NR$^{22}$R$^{23}$, —NC, —NO$_2$, —NR$^{22}$R$^{23}$, —NR$^{24}$R$^{22}$R$^{23}$, —N=NR$^{24}$, —NR$^{24}$OR$^{26}$, —NR$^{24}$C(=O)R$^{20}$, —NR$^{24}$C(=O)C(=O)R$^{20}$, —NR$^{24}$C(=O)OR$^{21}$, —NR$^{24}$C(=O)C(=O)OR$^{21}$, —NR$^{24}$C(=O)NR$^{22}$R$^{23}$, —NR$^{24}$C(=O)C(=O)R$^{24}$C(=O)R$^{20}$, —NR$^{24}$C(=O)NR$^{24}$C(=O)OR$^{20}$, —NR$^{24}$C(NR$^{25}$)NR$^{22}$R$^{23}$, —NR$^{24}$C(=O)C(=O)NR$^{22}$R$^{23}$, —NR$^{24}$C(=S)R$^{20}$, —NR$^{24}$C(=S)OR$^{20}$, —NR$^{24}$C(=S)NR$^{22}$R$^{23}$, —NR$^{24}$S(=O)$_2$R$^{21}$, —NR$^{24}$S(=O)$_2$NR$^{22}$R$^{23}$, —NR$^{24}$C(=O)R$^{28}$R$^{28}$, —NR$^{24}$P(=O)(22R$^{23}$)(NR$^{22}$R$^{23}$, —NR$^{24}$P(=)(OR$^{20}$)(OR$^{20}$), —NR$^{24}$P(=O)(SR$^{20}$)(SR$^{20}$), —OR$^{20}$, —OCN, —OC(=O)R$^{20}$, —OC(=O)NR$^{22}$R$^{23}$, —OC(=O)OR$^{20}$, —OC(=NR$^{25}$)NR$^{22}$R$^{23}$, —OS(=O)R$^{20}$, —OS(=O)$_2$R$^{20}$, —OS(=O)$_2$OR$^{20}$, —OS(=O)$_2$NR$^{22}$R$^{23}$, —OP(=O)$_2$R$^{28}$R$^{28}$, —OP(=O)(NR$^{22}$R$^{23}$)(NR$^{22}$R$^{23}$, —OP(=O)(OR$^{20}$)(OR$^{20}$), —OP(=O)(SR$^{20}$)(SR$^{20}$), —Si(R$^{24}$)$_3$, —SCN, —S(=O)$_n$R$^{20}$, —S(=O)$_2$R$^{20}$, —SO$_3$R$^{27}$, —S(=O)$_2$NR$^{22}$R$^{23}$, —S(=O)NR$^{22}$R$^{23}$, —SP(=O)R$^{28}$R$^{28}$, —SP(=O)(NR$^{22}$R$^{23}$)(NR$^{22}$R$^{23}$), —SP(=O)(OR$^{20}$)(OR$^{20}$), —SP(=O)(SR$^{20}$)(SR$^{20}$), —P(=O)R$^{28}$R$^{28}$, —P(=O)(NR$^{22}$R$^{23}$)(NR$^{22}$R$^{23}$), —P(=O)(OR$^{20}$)(OR$^{20}$), and —P(=O)(SR$^{20}$)(SR$^{20}$); alternatively, either or both of R$^7$ and R, and/or R$^9$ and R$^{10}$, can, together with the atoms linking them, form a C$_{6-11}$aryl optionally substituted by 1-11 R$^{19}$, C$_{3-11}$cycloalkyl optionally substituted by 1-21 R$^{19}$, 3-15 membered heterocycloalkyl optionally substituted by 1-28 R$^{19}$ or a 5-15 membered heteroaryl optionally substituted by 1-15 R$^{19}$.

Embodiment 110

The compound of any of Embodiments 1-108, wherein R$^7$, R$^8$, R$^9$, and R$^{10}$ are independently chosen from H, C$_{1-6}$alkyl optionally substituted by 1-13 R$^{19}$, C$_{2-6}$alkenyl optionally substituted by 1-11 R$^{19}$, C$_{2-6}$alkynyl optionally substituted by 1-9 R$^{19}$, C$_{6-11}$aryl optionally substituted by 1-11 R$^{19}$, C$_{7-16}$arylalkyl optionally substituted by 1-19 R$^{19}$, C$_{3-11}$cycloalkyl optionally substituted by 1-21 R$^{19}$, C$_{4-17}$cycloalkylalkyl optionally substituted by 1-32 R$^{19}$, 3-15 membered heterocycloalkyl optionally substituted by 1-28 R$^{19}$, 4-21 membered heterocycloalkylalkyl optionally substituted by 1-40 R$^{19}$, 5-15 membered heteroaryl optionally substituted by 1-15 R$^{19}$, 6-21 membered heteroarylalkyl optionally substituted by 1-27 R$^{19}$, halogen, —CN, —C(=O)R$^{20}$, —C(=O)OR$^{20}$, —C(=O)NR$^{22}$R$^{23}$, —NC, —NO$_2$, —NR$^{22}$R$^{23}$, —NR$^{24}$OR$^{26}$, —NR$^{24}$C(=O)R$^{20}$, —NR$^{24}$C(=O)OR$^{21}$, —NR$^{24}$C(=O)NR$^{22}$R$^{23}$, —NR$^{24}$S(=O)$_2$R$^{21}$, —NR$^{24}$S(=O)$_2$NR$^{22}$R$^{23}$, —OR$^{20}$, —OCN, —OC(=O)R$^{20}$, —OC(=O)NR$^{22}$R$^{23}$, —OC(=O)OR$^{20}$, —OS(=O)$_2$R$^{20}$, —OS(=O)$_2$OR$^{20}$, —OS(=O)$_2$NR$^{22}$R$^{23}$, —S(=O)$_n$R$^{20}$, and —S(=O)$_2$NR$^{22}$R$^{23}$; alternatively, either or both of R$^7$ and R$^8$, and/or R$^9$ and R$^{10}$, can, together with the atoms linking them, form a C$_{6-11}$aryl optionally substituted by 1-11 R$^{19}$, C$_{3-11}$cycloalkyl optionally substituted by 1-21 R$^{19}$, 3-15 membered heterocycloalkyl optionally substituted by 1-28 R$^{19}$ or a 5-15 membered heteroaryl optionally substituted by 1-15 R$^{19}$.

Embodiment 111

The compound of any of Embodiments 1-108, wherein R$^7$, R$^8$, R$^9$, and R$^{10}$ are independently chosen from H, C$_{1-6}$alkyl optionally substituted by 1-6 R$^{19}$, C$_{2-6}$alkenyl optionally substituted by 1-6 R$^{19}$, C$_{2-6}$alkynyl optionally substituted by 1-6 R$^{19}$, C$_{6-11}$aryl optionally substituted by 1-6 R$^{19}$, C$_{7-16}$arylalkyl optionally substituted by 1-6 R$^{19}$, C$_{3-11}$cycloalkyl optionally substituted by 1-6 R$^{19}$, C$_{4-17}$cycloalkylalkyl optionally substituted by 1-6 R$^{19}$, 3-15 membered heterocycloalkyl optionally substituted by 1-6 R$^{19}$, 4-21 membered heterocycloalkylalkyl optionally substituted by 1-6 R$^{19}$, 5-15 membered heteroaryl optionally substituted by 1-6 R$^{19}$, 6-21 membered heteroarylalkyl optionally substituted by 1-6 R$^{19}$, halogen, —CN, —C(=O)R$^{20}$, —C(=O)OR$^{20}$, —C(=O)NR$^{22}$R$^{23}$, —NC, —NO$_2$, —NR$^{22}$R$^{23}$, —NR$^{24}$OR$^{26}$, —NR$^{24}$C(=O)R$^{20}$, —NR$^{24}$C(=O)OR$^{21}$, —NR$^{24}$C(=O)NR$^{22}$R$^{23}$, —NR$^{24}$S(=O)$_2$R$^{21}$, —NR$^{24}$S(=O)$_2$NR$^{22}$R$^{23}$, —OR$^{20}$, —OCN, —OC(=O)R$^{20}$, —OC(=O)NR$^{22}$R$^{23}$, —OC(=O)OR$^{20}$, —OS(=O)$_2$R$^{20}$, —OS(=O)$_2$OR$^{20}$, —OS(=O)$_2$NR$^{22}$R$^{23}$, —S(=O)$_n$R$^{20}$, and —S(=O)$_2$NR$^{22}$R$^{23}$; alternatively, either or both of R$^7$ and R$^8$, and/or R$^9$ and R$^{10}$, can, together with the atoms linking them, form a C$_{6-11}$aryl optionally substituted by 1-6 R$^{19}$, C$_{3-11}$cycloalkyl optionally substituted by 1-6 R$^{19}$, 3-15 membered heterocycloalkyl optionally substituted by 1-6 R$^{19}$ or a 5-15 membered heteroaryl optionally substituted by 1-6 R$^{19}$.

Embodiment 112

The compound of any of Embodiments 1-108, wherein R$^7$, R$^8$, R$^9$, and R$^{10}$ are independently chosen from H, C$_{1-6}$alkyl optionally substituted by 1-4 R$^{19}$, C$_{2-6}$alkenyl optionally substituted by 1-4 R$^{19}$, C$_{2-6}$alkynyl optionally substituted by 1-4 R$^{19}$, C$_{6-10}$aryl optionally substituted by 1-4 R$^{19}$, C$_{7-11}$arylalkyl optionally substituted by 1-4 R$^{19}$, C$_{3-7}$cycloalkyl optionally substituted by 1-4 R$^{19}$, C$_{4-8}$cycloalkylalkyl optionally substituted by 1-4 R$^{19}$, 3-7 membered heterocycloalkyl optionally substituted by 1-4 R$^{19}$, 4-8 membered heterocycloalkylalkyl optionally substituted by 1-4 R$^{19}$, 5-6 membered heteroaryl optionally substituted by 1-4 R$^{19}$, 6-21 membered heteroarylalkyl optionally substituted by 1-4 R$^{19}$, halogen, —CN, —C(=O)R$^{20}$, —C(=O)OR$^{20}$, —C(=O)NR$^{22}$R$^{23}$, —NC, —NO$_2$, —NR$^{22}$R$^{23}$, —NR$^{24}$OR$^{26}$, —NR$^{24}$C(=O)R$^{20}$, —NR$^{24}$C(=O)OR$^{21}$, —NR$^{24}$C(=O)NR$^{22}$R$^{23}$, —NR$^{24}$S(=O)$_2$R$^{21}$, —NR$^{24}$S(=O)$_2$NR$^{22}$R$^{23}$, —OR$^{20}$, —OCN, —OC(=O)R$^{20}$, —OC(=O)NR$^{22}$R$^{23}$, —OC(=O)OR$^{20}$, —OS(=O)$_2$R$^{20}$, —OS(=O)$_2$OR$^{20}$, —OS(=O)$_2$NR$^{22}$R$^{23}$, —S(=O)$_n$R$^{20}$, and —S(=O)$_2$NR$^{22}$R$^{23}$; alternatively, either or both of R$^7$ and R$^8$, and/or R$^9$ and R$^{10}$, can, together with the atoms linking them, form a C$_{6-10}$aryl optionally substituted by 1-4 R$^{19}$, C$_{3-7}$cycloalkyl optionally substituted by 1-4 R$^{19}$, 3-7 membered heterocycloalkyl optionally substituted by 1-4 R$^{19}$ or a 5-6 membered heteroaryl optionally substituted by 1-4 R$^{19}$.

Embodiment 113

The compound of any of Embodiments 1-108, wherein R$^7$, R$^8$, R$^9$, and R$^{10}$ are independently chosen from H, C$_{1-6}$alkyl optionally substituted by 1-3 R$^{19}$, C$_{2-6}$alkenyl optionally substituted by 1-3 R$^{19}$, C$_{2-6}$alkynyl optionally substituted by 1-3 R$^{19}$, C$_{6-10}$aryl optionally substituted by 1-3 R$^{19}$, C$_{7-11}$arylalkyl optionally substituted by 1-3 R$^{19}$, C$_{3-7}$cycloalkyl optionally substituted by 1-3 R$^{19}$, C$_{4-8}$cycloalkylalkyl optionally substituted by 1-3 R$^{19}$, 3-7 membered heterocycloalkyl optionally substituted by 1-3 R$^{19}$, 4-8 membered heterocycloalkylalkyl optionally substituted by 1-3 R$^{19}$, 5-6 membered heteroaryl optionally substituted by 1-3 R$^{19}$, 6-21 membered heteroarylalkyl optionally substituted by 1-3 R$^{19}$, halogen, —CN, —C(=O)R$^{20}$, —C(=O)OR$^{20}$, —C(=O)NR$^{22}$R$^{23}$, —NC, —NO$_2$, —NR$^{22}$R$^{23}$, —NR$^{24}$OR$^{26}$, —NR$^{24}$C(=O)R$^{20}$, —NR$^{24}$C(=O)OR$^{21}$, —NR$^{24}$C(=O)NR$^{22}$R$^{23}$, —NR$^{24}$S(=O)$_2$R$^{21}$, —NR$^{24}$S(=O)$_2$NR$^{22}$R$^{23}$, —OR$^{20}$, —OCN, —OC(=O)R$^{20}$, —OC(=O)NR$^{22}$R$^{23}$, —OC(=O)OR$^{20}$, —OS(=O)$_2$R$^{20}$, —OS(=O)$_2$OR$^{20}$, —OS(=O)$_2$NR$^{22}$R$^{23}$, —S(=O)$_n$R$^{20}$, and —S(=O)$_2$NR$^{22}$R$^{23}$; alternatively, either or both of R$^7$ and R$^8$, and/or R$^9$ and R$^{10}$, can, together with the atoms linking them, form a C$_{6\text{-}10}$aryl optionally substituted by 1-3 R$^{19}$, C$_{3\text{-}7}$cycloalkyl optionally substituted by 1-3 R$^{19}$, 3-7 membered heterocycloalkyl optionally substituted by 1-3 R$^{19}$ or a 5-6 membered heteroaryl optionally substituted by 1-3 R$^{19}$.

Embodiment 114

The compound of any of Embodiments 1-108, wherein R$^7$, R$^8$, R$^9$, and R$^{10}$ are independently chosen from H, C$_{1\text{-}6}$alkyl optionally substituted by 1-3 R$^{19}$, C$_{2\text{-}6}$alkenyl optionally substituted by 1-3 R$^{19}$, C$_{2\text{-}6}$alkynyl optionally substituted by 1-3 R$^{19}$, C$_{6\text{-}10}$aryl optionally substituted by 1-3 R$^{19}$, C$_{7\text{-}11}$arylalkyl optionally substituted by 1-3 R$^{19}$, C$_{3\text{-}7}$cycloalkyl optionally substituted by 1-3 R$^{19}$, C$_{4\text{-}8}$cycloalkylalkyl optionally substituted by 1-3 R$^{19}$, 3-7 membered heterocycloalkyl optionally substituted by 1-3 R$^{19}$, 4-8 membered heterocycloalkylalkyl optionally substituted by 1-3 R$^{19}$, 5-6 membered heteroaryl optionally substituted by 1-3 R$^{19}$, 6-21 membered heteroarylalkyl optionally substituted by 1-3 R$^{19}$, halogen, —CN, —C(=O)R$^{20}$, —C(=O)OR$^{20}$, —C(=O)NR$^{22}$R$^{23}$, —NO$_2$, —NR$^{22}$R$^{23}$, —NR$^{24}$C(=O)R$^{20}$, —NR$^{24}$C(=O)OR$^{21}$, —NR$^{24}$C(=O)NR$^{22}$R$^{23}$, —NR$^{24}$S(=O)$_2$R$^{21}$, —NR$^{24}$S(=O)$_2$NR$^{22}$R$^{23}$, —OR$^{20}$, —OC(=O)R$^{20}$, —OC(=O)NR$^{22}$R$^{23}$, —OS(=O)$_2$R$^{20}$, —OS(=O)$_2$NR$^{22}$R$^{23}$, —S(=O)$_n$R$^{20}$, and —S(=O)$_2$NR$^{22}$R$^{23}$; alternatively, either or both of R$^7$ and R$^8$, and/or R$^9$ and R$^{10}$, can, together with the atoms linking them, form a C$_{6\text{-}10}$aryl optionally substituted by 1-3 R$^{19}$, C$_{3\text{-}7}$cycloalkyl optionally substituted by 1-3 R$^{19}$, 3-7 membered heterocycloalkyl optionally substituted by 1-3 R$^{19}$ or a 5-6 membered heteroaryl optionally substituted by 1-3 R$^{19}$.

Embodiment 115

The compound of any of Embodiments 1-108, wherein R$^7$, R$^8$, R$^9$, and R$^{10}$ are independently chosen from H, C$_{1\text{-}6}$alkyl optionally substituted by 1-3 R$^{19}$, C$_{2\text{-}6}$alkenyl optionally substituted by 1-3 R$^{19}$, C$_{2\text{-}6}$alkynyl optionally substituted by 1-3 R$^{19}$, C$_{6\text{-}10}$aryl optionally substituted by 1-3 R$^{19}$, C$_{7\text{-}11}$arylalkyl optionally substituted by 1-3 R$^{19}$, C$_{3\text{-}7}$cycloalkyl optionally substituted by 1-3 R$^{19}$, C$_{4\text{-}8}$cycloalkylalkyl optionally substituted by 1-3 R$^{19}$, 3-7 membered heterocycloalkyl optionally substituted by 1-3 R$^{19}$, 4-8 membered heterocycloalkylalkyl optionally substituted by 1-3 R$^{19}$, 5-6 membered heteroaryl optionally substituted by 1-3 R$^{19}$, 6-21 membered heteroarylalkyl optionally substituted by 1-3 R$^{19}$, halogen, —CN, —C(=O)R$^{20}$, —C(=O)OR$^{20}$, —C(=O)NR$^{22}$R$^{23}$, —NO$_2$, —NR$^{22}$R$^{23}$, —NR$^{24}$C(=O)R$^{20}$, —NR$^{24}$S(=O)$_2$R$^{21}$, —OR$^{20}$, —S(=O)$_n$R$^{20}$, and —S(=O)$_2$NR$^{22}$R$^{23}$; alternatively, either or both of R$^7$ and R$^8$, and/or R$^9$ and R$^{10}$, can, together with the atoms linking them, form a C$_{6\text{-}10}$aryl optionally substituted by 1-3 R$^{19}$, C$_{3\text{-}7}$cycloalkyl optionally substituted by 1-3 R$^{19}$, 3-7 membered heterocycloalkyl optionally substituted by 1-3 R$^{19}$ or a 5-6 membered heteroaryl optionally substituted by 1-3 R$^{19}$.

Embodiment 116

The compound of any of Embodiments 1-108, wherein R$^7$, R$^8$, R$^9$, and R$^{10}$ are independently chosen from H, C$_{1\text{-}6}$alkyl, C$_{2\text{-}6}$alkenyl, C$_{2\text{-}6}$alkynyl, C$_{6\text{-}10}$aryl, C$_{7\text{-}11}$arylalkyl, C$_{3\text{-}7}$cycloalkyl, C$_{4\text{-}8}$cycloalkylalkyl, 3-7 membered heterocycloalkyl, 4-8 membered heterocycloalkylalkyl, 5-6 membered heteroaryl, 6-21 membered heteroarylalkyl, halogen, —CN, —C(=O)R$^{20}$, —C(=O)OR$^{20}$, —C(=O)NR$^{22}$R$^{23}$, —NO$_2$, —NR$^{22}$R$^{23}$, —NR$^{24}$C(=O)R$^{20}$, —NR$^{24}$S(=O)$_2$R$^{21}$, —OR$^{20}$, —S(=O)$_n$R$^{20}$, and —S(=O)$_2$NR$^{22}$R$^{23}$; alternatively, either or both of R$^7$ and R$^8$, and/or R$^9$ and R$^{10}$, can, together with the atoms linking them, form a C$_{6\text{-}10}$aryl, C$_{3\text{-}7}$cycloalkyl, 3-7 membered heterocycloalkyl or a 5-6 membered heteroaryl.

Embodiment 117

The compound of any of Embodiments 1-108, wherein R$^7$, R$^8$, R$^9$, and R$^{10}$ are independently chosen from H, C$_{1\text{-}6}$alkyl optionally substituted by 1-3 R$^{19}$, C$_{2\text{-}6}$alkenyl optionally substituted by 1-3 R$^{19}$, C$_{2\text{-}6}$alkynyl optionally substituted by 1-3 R$^{19}$, C$_{6\text{-}10}$aryl optionally substituted by 1-3 R$^{19}$, C$_{7\text{-}11}$arylalkyl optionally substituted by 1-3 R$^{19}$, C$_{3\text{-}7}$cycloalkyl optionally substituted by 1-3 R$^{19}$, C$_{4\text{-}8}$cycloalkylalkyl optionally substituted by 1-3 R$^{19}$, 3-7 membered heterocycloalkyl optionally substituted by 1-3 R$^{19}$, 4-8 membered heterocycloalkylalkyl optionally substituted by 1-3 R$^{19}$, 5-6 membered heteroaryl optionally substituted by 1-3 R$^{19}$, 6-21 membered heteroarylalkyl optionally substituted by 1-3 R$^{19}$, halogen, —CN, —C(=O)R$^{20}$, —C(=O)NR$^{22}$R$^{23}$, —NO$_2$, —NR$^{22}$R$^{23}$, —NR$^{24}$S(=O)$_2$R$^{21}$, —OR$^{20}$, —S(=O)$_n$R$^{20}$, and —S(=O)$_2$NR$^{22}$R$^{23}$; alternatively, either or both of R$^7$ and R$^8$, and/or R$^9$ and R$^{10}$, can, together with the atoms linking them, form a C$_{6\text{-}10}$aryl optionally substituted by 1-3 R$^{19}$, C$_{3\text{-}7}$cycloalkyl optionally substituted by 1-3 R$^{19}$, 3-7 membered heterocycloalkyl optionally substituted by 1-3 R$^{19}$ or a 5-6 membered heteroaryl optionally substituted by 1-3 R$^{19}$.

Embodiment 118

The compound of any of Embodiments 1-108, wherein R$^7$, R$^8$, R$^9$, and R$^{10}$ are independently chosen from H, C$_{1\text{-}6}$alkyl optionally substituted by 1-3 R$^{19}$, C$_{2\text{-}6}$alkynyl optionally substituted by 1-3 R$^{19}$, C$_{6\text{-}10}$aryl optionally substituted by 1-3 R$^{19}$, C$_{3\text{-}7}$cycloalkyl optionally substituted by 1-3 R$^{19}$, 3-7 membered heterocycloalkyl optionally substituted by 1-3 R$^{19}$, 5-6 membered heteroaryl optionally substituted by 1-3 R$^{19}$, halogen, —CN, —C(=O)R$^{20}$, —C(=O)NR$^{22}$R$^{23}$, —NO$_2$, —NR$^{22}$R$^{23}$, —NR$^{24}$S(=O)$_2$R$^{21}$, —OR$^{20}$, —S(=O)$_n$R$^{20}$, and —S(=O)$_2$NR$^{22}$R$^{23}$; alternatively, either or both of R$^7$ and R$^8$, and/or R$^9$ and R$^{10}$, can, together with the atoms linking them, form a C$_{6\text{-}10}$aryl optionally substituted by 1-3 R$^{19}$, C$_{3\text{-}7}$cycloalkyl optionally substituted by 1-3 R$^{19}$, 3-7 membered heterocycloalkyl optionally substituted by 1-3 R$^{19}$ or a 5-6 membered heteroaryl optionally substituted by 1-3 R$^{19}$.

Embodiment 119

The compound of any of Embodiments 1-108, wherein R$^7$, R$^8$, R$^9$, and R$^{10}$ are independently chosen from H, C$_{1\text{-}6}$alkyl optionally substituted by 1-3 R$^{19}$, C$_{2\text{-}6}$alkynyl optionally substituted by 1-3 R$^{19}$, C$_{6\text{-}10}$aryl optionally substituted by 1-3 R$^{19}$, C$_{3\text{-}7}$cycloalkyl optionally substituted by 1-3 R$^{19}$ 3-7 membered heterocycloalkyl optionally substituted by 1-3 R$^{19}$, 5-6 membered heteroaryl optionally substituted by 1-3 R$^{19}$, halogen, —CN, —C(=O)R$^{20}$, —C(=O)NR$^{22}$R$^{23}$, —NO$_2$, —NR$^{22}$R$^{23}$, —NR$^{24}$S(=O)$_2$R$^{21}$, —OR$^{20}$, —S(=O)$_n$R$^{20}$, and —S(=O)$_2$NR$^{22}$R$^{23}$; alternatively, either or both of R$^7$ and R$^8$, and/or R$^9$ and R$^{10}$, can, together with the atoms linking them, form a C$_{3-7}$cycloalkyl optionally substituted by 1-3 R$^{19}$, or a 3-7 membered heterocycloalkyl optionally substituted by 1-3 R$^{19}$.

Embodiment 120

The compound of any of Embodiments 1-108, wherein R$^7$, R$^8$, R$^9$, and R$^{10}$ are independently chosen from H, C$_{1-6}$alkyl, C$_{2-6}$alkynyl, C$_{6-10}$aryl, C$_{3-7}$cycloalkyl, 3-7 membered heterocycloalkyl, 5-6 membered heteroaryl, halogen, —CN, —C(=O)R$^{20}$, —C(=O)NR$^{22}$R$^{23}$, —NO$_2$, —NR$^{22}$R$^{23}$, —NR$^{24}$S(=O)$_2$R$^{21}$, —OR$^{20}$, —S(=O)$_n$R$^{20}$, and —S(=O)$_2$NR$^{22}$R$^{23}$; alternatively, either or both of R$^7$ and R$^8$, and/or R$^9$ and R$^{10}$, can, together with the atoms linking them, form a C$_{3-7}$cycloalkyl, or a 3-7 membered heterocycloalkyl.

Embodiment 121

The compound of any of Embodiments 1-108, wherein R$^7$, R$^8$, R$^9$, and R$^{10}$ are independently chosen from H, C$_{1-6}$alkyl optionally substituted by 1-13 R$^{19}$, C$_{2-6}$alkenyl optionally substituted by 1-11 R$^{19}$, C$_{2-6}$alkynyl optionally substituted by 1-9 R$^{19}$, C$_{6-11}$aryl optionally substituted by 1-11 R$^{19}$, C$_{7-16}$arylalkyl optionally substituted by 1-19 R$^{19}$, C$_{3-11}$cycloalkyl optionally substituted by 1-21 R$^{19}$, C$_{4-17}$cycloalkylalkyl optionally substituted by 1-32 R$^{19}$, 3-15 membered heterocycloalkyl optionally substituted by 1-28 R$^{19}$, 4-21 membered heterocycloalkylalkyl optionally substituted by 1-40 R$^{19}$, 5-15 membered heteroaryl optionally substituted by 1-15 R$^{19}$, 6-21 membered heteroarylalkyl optionally substituted by 1-27 R$^{19}$, halogen, —CN, —C(=O)R$^{20}$, —C(=O)OR$^{20}$, —C(=O)NR$^{22}$R$^{23}$, —NO$_2$, —NR$^{22}$R$^{23}$, and —OR$^{20}$; alternatively, either or both of R$^7$ and R$^8$, and/or R$^9$ and R$^{10}$, can, together with the atoms linking them, form a C$_{6-11}$-aryl optionally substituted by 1-11 R$^{19}$, C$_{3-11}$cycloalkyl optionally substituted by 1-21 R$^{19}$, 3-15 membered heterocycloalkyl optionally substituted by 1-28 R$^{19}$ or a 5-15 membered heteroaryl optionally substituted by 1-15 R$^{19}$.

Embodiment 122

The compound of any of Embodiments 1-108, wherein R$^7$, R$^8$, R$^9$, and R$^{10}$ are independently chosen from H, C$_{1-6}$alkyl optionally substituted by 1-13 R$^{19}$, C$_{2-6}$alkenyl optionally substituted by 1-11 R$^{19}$, C$_{2-6}$alkynyl optionally substituted by 1-9 R$^{19}$, C$_{6-11}$aryl optionally substituted by 1-11 R$^{19}$, C$_{7-16}$arylalkyl optionally substituted by 1-19 R$^{19}$, C$_{3-11}$cycloalkyl optionally substituted by 1-21 R$^{19}$, C$_{4-17}$cycloalkylalkyl optionally substituted by 1-32 R$^{19}$, 3-15 membered heterocycloalkyl optionally substituted by 1-28 R$^{19}$, 4-21 membered heterocycloalkylalkyl optionally substituted by 1-40 R$^{19}$, 5-15 membered heteroaryl optionally substituted by 1-15 R$^{19}$, 6-21 membered heteroarylalkyl optionally substituted by 1-27 R$^{19}$, halogen, —CN, —C(=O)NR$^{22}$R$^{23}$, —NO$_2$, —NR$^{22}$R$^{23}$, and —OR$^{20}$; alternatively, either or both of R$^7$ and R$^8$, and/or R$^9$ and R$^{10}$, can, together with the atoms linking them, form a C$_{6-11}$aryl optionally substituted by 1-11 R$^{19}$, C$_{3-11}$cycloalkyl optionally substituted by 1-21 R$^{19}$, 3-15 membered heterocycloalkyl optionally substituted by 1-28 R$^{19}$ or a 5-15 membered heteroaryl optionally substituted by 1-15 R$^{19}$.

Embodiment 123

The compound of any of Embodiments 1-108, wherein R$^7$, R$^8$, R$^9$, and R$^{10}$ are independently chosen from H, C$_{1-6}$alkyl optionally substituted by 1-13 R$^{19}$, C$_{2-6}$alkenyl optionally substituted by 1-11 R$^{19}$, C$_{2-6}$alkynyl optionally substituted by 1-9 R$^{19}$, C$_{6-11}$aryl optionally substituted by 1-11 R$^{19}$, C$_{7-16}$arylalkyl optionally substituted by 1-19 R$^{19}$, C$_{3-11}$cycloalkyl optionally substituted by 1-21 R$^{19}$, 3-15 membered heterocycloalkyl optionally substituted by 1-28 R$^{19}$, 5-15 membered heteroaryl optionally substituted by 1-15 R$^{19}$, 6-21 membered heteroarylalkyl optionally substituted by 1-27 R$^{19}$, halogen, —CN, —C(=O)R$^{20}$, —C(=O)NR$^{22}$R$^{23}$, —NR$^{22}$R$^{23}$, —NR$^{24}$C(=O)R$^{20}$, and —OR$^{20}$; alternatively, either or both of R$^7$ and R$^8$, and/or R$^9$ and R$^{10}$, can, together with the atoms linking them, form a C$_{6-11}$aryl optionally substituted by 1-11 R$^{19}$, C$_{3-11}$cycloalkyl optionally substituted by 1-21 R$^{19}$, 3-15 membered heterocycloalkyl optionally substituted by 1-28 R$^{19}$ or a 5-15 membered heteroaryl optionally substituted by 1-15 R$^{19}$.

Embodiment 124

The compound of any of Embodiments 1-108, wherein R$^7$, R$^9$, and R$^{10}$ are independently chosen from H, C$_{1-6}$alkyl optionally substituted by 1-13 R$^{19}$, C$_{2-6}$alkenyl optionally substituted by 1-11 R$^{19}$, C$_{2-6}$alkynyl optionally substituted by 1-9 R$^{19}$, C$_{6-11}$aryl optionally substituted by 1-11 R$^{19}$, C$_{7-16}$arylalkyl optionally substituted by 1-19 R$^{19}$, C$_{3-11}$cycloalkyl optionally substituted by 1-21 R$^{19}$, 3-15 membered heterocycloalkyl optionally substituted by 1-28 R$^{19}$, 5-15 membered heteroaryl optionally substituted by 1-15 R$^{19}$, 6-21 membered heteroarylalkyl optionally substituted by 1-27 R$^{19}$, halogen, —CN, —C(=O)R$^{20}$, —C(=O)NR$^{22}$R$^{23}$, —NR$^{22}$R$^{23}$, —NR$^{24}$C(=O)R$^{20}$, and —OR$^{20}$; R$^8$ is chosen from H, C$_{1-6}$ alkyl optionally substituted by 1-13 R$^{19}$, C$_{2-6}$alkenyl optionally substituted by 1-11 R$^{19}$, C$_{2-6}$alkynyl optionally substituted by 1-9 R$^{19}$, C$_{7-16}$arylalkyl optionally substituted by 1-19 R$^{19}$, C$_{3-11}$cycloalkyl optionally substituted by 1-21 R$^{19}$, 3-15 membered heterocycloalkyl optionally substituted by 1-28 R$^{19}$, 6-21 membered heteroarylalkyl optionally substituted by 1-27 R$^{19}$, halogen, —CN, —C(=O)R$^{20}$, —C(=O)NR$^{22}$R$^{23}$, —NR$^{22}$R$^{23}$, —NR$^{24}$C(=O)R$^{20}$, and —OR$^{20}$; alternatively, either or both of R$^7$ and R$^8$, and/or R$^9$ and R$^{10}$, can, together with the atoms linking them, form a C$_{6-11}$aryl optionally substituted by 1-11 R$^{19}$, C$_{3-11}$cycloalkyl optionally substituted by 1-21 R$^{19}$, 3-15 membered heterocycloalkyl optionally substituted by 1-28 R$^{19}$ or a 5-15 membered heteroaryl optionally substituted by 1-15 R$^{19}$.

Embodiment 125

The compound of any of Embodiments 1-108, wherein R$^7$ and R$^{10}$ are independently chosen from H, C$_{1-6}$alkyl optionally substituted by 1-13 R$^{19}$, C$_{2-6}$alkenyl optionally substituted by 1-11 R$^{19}$, C$_{2-6}$alkynyl optionally substituted by 1-9 R$^{19}$, C$_{6-11}$aryl optionally substituted by 1-11 R$^{19}$, C$_{7-16}$arylalkyl optionally substituted by 1-19 R$^{19}$, C$_{3-11}$cycloalkyl optionally substituted by 1-21 R$^{19}$, 3-15 membered heterocycloalkyl optionally substituted by 1-28 R$^{19}$, 5-15 membered heteroaryl optionally substituted by 1-15 R$^{19}$, 6-21 membered heteroarylalkyl optionally substituted by 1-27 R$^{19}$, halogen, —CN, —C(=O)R$^{20}$, —C(=O)NR$^{22}$R$^{23}$, —NR$^{22}$R$^{23}$, —NR$^{24}$C(=O)R$^{20}$, and —OR$^{20}$; R$^8$ and R$^9$ are independently chosen from C$_{1-6}$alkyl optionally substituted by 1-13 R$^{19}$, C$_{2-6}$ alkenyl optionally substituted by 1-11 R$^{19}$, C$_{2-6}$alkynyl optionally substituted by 1-9 R$^{19}$, C$_{6-11}$aryl optionally substituted by 1-11 R$^{19}$, C$_{7-16}$arylalkyl optionally substituted by 1-19 R$^{19}$, C$_{3-11}$cycloalkyl optionally substituted by 1-21 R$^{19}$, 3-15 membered heterocycloalkyl optionally substituted by 1-28 $R^{19}$, 5-15 membered heteroaryl optionally substituted by 1-15 $R^{19}$, 6-21 membered heteroarylalkyl optionally substituted by 1-27 $R^{19}$, halogen, —CN, —C(=O)$R^{20}$, —C(=O)N$R^{22}R^{23}$, —N$R^{22}R^{23}$, —N$R^{24}$C(=O)$R^{20}$, and —O$R^{20}$; alternatively, either or both of $R^7$ and $R^8$, and/or $R^9$ and $R^{10}$, can, together with the atoms linking them, form a $C_{6-11}$aryl optionally substituted by 1-11 $R^{19}$, $C_{3-11}$cycloalkyl optionally substituted by 1-21 $R^{19}$, 3-15 membered heterocycloalkyl optionally substituted by 1-28 $R^{19}$ or a 5-15 membered heteroaryl optionally substituted by 1-15 $R^{19}$.

Embodiment 126

The compound of any of Embodiments 1-108, wherein $R^7$ and $R^{10}$ are independently chosen from H, $C_{1-6}$alkyl optionally substituted by 1-13 $R^{19}$, $C_{2-6}$alkenyl optionally substituted by 1-11 $R^{19}$, $C_{2-6}$alkynyl optionally substituted by 1-9 $R^{19}$, $C_{6-11}$aryl optionally substituted by 1-11 $R^{19}$, $C_{7-16}$arylalkyl optionally substituted by 1-19 $R^{19}$, $C_{3-11}$cycloalkyl optionally substituted by 1-21 $R^{19}$, 3-15 membered heterocycloalkyl optionally substituted by 1-28 $R^{19}$, 5-15 membered heteroaryl optionally substituted by 1-15 $R^{19}$, 6-21 membered heteroarylalkyl optionally substituted by 1-27 $R^{19}$, halogen, —CN, —C(=O)$R^{20}$, —C(=O)N$R^{22}R^{23}$, —N$R^{22}R^{23}$, —N$R^{24}$C(=O)$R^{20}$, and —O$R^{20}$; $R^8$ is chosen from $C_{1-6}$ alkyl optionally substituted by 1-13 $R^{19}$, $C_{2-6}$alkenyl optionally substituted by 1-11 $R^{19}$, $C_{2-6}$alkynyl optionally substituted by 1-9 $R^{19}$, $C_{7-16}$arylalkyl optionally substituted by 1-19 $R^{19}$, $C_{3-11}$cycloalkyl optionally substituted by 1-21 $R^{19}$, 3-15 membered heterocycloalkyl optionally substituted by 1-28 $R^{19}$, 6-21 membered heteroarylalkyl optionally substituted by 1-27 $R^{19}$, halogen, —CN, —C(=O)$R^{20}$, —C(=O)N$R^{22}R^{23}$, —N$R^{22}R^{23}$, —N$R^{24}$C(=O)$R^{20}$, and —O$R^{20}$; $R^9$ is chosen from $C_{1-6}$ alkyl optionally substituted by 1-13 $R^{19}$, $C_{2-6}$alkenyl optionally substituted by 1-11 $R^{19}$, $C_{2-6}$alkynyl optionally substituted by 1-9 $R^{19}$, $C_{6-11}$aryl optionally substituted by 1-11 $R^{19}$, $C_{7-16}$arylalkyl optionally substituted by 1-19 $R^{19}$, $C_{3-11}$cycloalkyl optionally substituted by 1-21 $R^{19}$, 3-15 membered heterocycloalkyl optionally substituted by 1-28 $R^{19}$, 5-15 membered heteroaryl optionally substituted by 1-15 $R^{19}$, 6-21 membered heteroarylalkyl optionally substituted by 1-27 $R^{19}$, halogen, —CN, —C(=O)$R^{20}$, —C(=O)N$R^{22}R^{23}$, —N$R^{22}R^{23}$, —N$R^{24}$C(=O)$R^{20}$, and —O$R^{20}$; alternatively, either or both of $R^7$ and $R^8$, and/or $R^9$ and $R^{10}$, can, together with the atoms linking them, form a $C_{6-11}$aryl optionally substituted by 1-11 $R^{19}$, $C_{3-11}$cycloalkyl optionally substituted by 1-21 $R^{19}$, 3-15 membered heterocycloalkyl optionally substituted by 1-28 $R^{19}$ or a 5-15 membered heteroaryl optionally substituted by 1-15 $R^{19}$.

Embodiment 127

The compound of any of Embodiments 1-108, wherein $R^8$ and $R^9$ are independently chosen from H, $C_{1-6}$alkyl optionally substituted by 1-13 $R^{19}$, $C_{2-6}$alkenyl optionally substituted by 1-11 $R^{19}$, $C_{2-6}$alkynyl optionally substituted by 1-9 $R^{19}$, $C_{6-11}$aryl optionally substituted by 1-11 $R^{19}$, $C_{7-16}$arylalkyl optionally substituted by 1-19 $R^{19}$, $C_{3-11}$cycloalkyl optionally substituted by 1-21 $R^{19}$, 3-15 membered heterocycloalkyl optionally substituted by 1-28 $R^{19}$, 5-15 membered heteroaryl optionally substituted by 1-15 $R^{19}$, 6-21 membered heteroarylalkyl optionally substituted by 1-27 $R^{19}$, halogen, —CN, —C(=O)$R^{20}$, —C(=O)N$R^{22}R^{23}$, —N$R^{22}R^{23}$, —N$R^{24}$C(=O)$R^{20}$, and —O$R^{20}$; $R^7$ and $R^{10}$ are independently chosen from $C_{1-6}$alkyl optionally substituted by 1-13 $R^{19}$, $C_{2-6}$alkenyl optionally substituted by 1-11 $R^{19}$, $C_{2-6}$alkynyl optionally substituted by 1-9 $R^{19}$, $C_{6-11}$aryl optionally substituted by 1-11 $R^{19}$, $C_{7-16}$arylalkyl optionally substituted by 1-19 $R^{19}$, $C_{3-11}$cycloalkyl optionally substituted by 1-21 $R^{19}$, 3-15 membered heterocycloalkyl optionally substituted by 1-28 $R^{19}$, 5-15 membered heteroaryl optionally substituted by 1-15 $R^{19}$, 6-21 membered heteroarylalkyl optionally substituted by 1-27 $R^{19}$, halogen, —CN, —C(=O)$R^{20}$, —C(=O)N$R^{22}R^{23}$, —N$R^{22}R^{23}$, —N$R^{24}$C(=O)$R^{20}$, and —O$R^{20}$; alternatively, either or both of $R^7$ and $R^8$, and/or $R^9$ and $R^{10}$, can, together with the atoms linking them, form a $C_{6-11}$-aryl optionally substituted by 1-11 $R^{19}$, $C_{3-11}$cycloalkyl optionally substituted by 1-21 $R^{19}$, 3-15 membered heterocycloalkyl optionally substituted by 1-28 $R^{19}$ or a 5-15 membered heteroaryl optionally substituted by 1-15 $R^{19}$.

Embodiment 128

The compound of any of Embodiments 1-108, wherein $R^8$ is chosen from H, $C_{1-6}$alkyl optionally substituted by 1-13 $R^{19}$, $C_{2-6}$alkenyl optionally substituted by 1-11 $R^{19}$, $C_{2-6}$alkynyl optionally substituted by 1-9 $R^{19}$, $C_{7-16}$arylalkyl optionally substituted by 1-19 $R^{19}$, $C_{3-11}$cycloalkyl optionally substituted by 1-21 $R^{19}$, 3-15 membered heterocycloalkyl optionally substituted by 1-28 $R^{19}$, 6-21 membered heteroarylalkyl optionally substituted by 1-27 $R^{19}$ halogen, —CN, —C(=O)$R^{20}$, —C(=O)N$R^{22}R^{23}$, —N$R^{22}R^{23}$, —N$R^{24}$C(=O)$R^{20}$, and —O$R^{20}$; $R^9$ is chosen from H, $C_{1-6}$alkyl optionally substituted by 1-13 $R^{19}$, $C_{2-6}$ alkenyl optionally substituted by 1-11 $R^{19}$, $C_{2-6}$alkynyl optionally substituted by 1-9 $R^{19}$, $C_{6-11}$aryl optionally substituted by 1-11 $R^{19}$, $C_{7-16}$arylalkyl optionally substituted by 1-19 $R^{19}$, $C_{3-11}$cycloalkyl optionally substituted by 1-21 $R^{19}$, 3-15 membered heterocycloalkyl optionally substituted by 1-28 $R^{19}$, 5-15 membered heteroaryl optionally substituted by 1-15 $R^{19}$, 6-21 membered heteroarylalkyl optionally substituted by 1-27 $R^{19}$, halogen, —CN, —C(=O)$R^{20}$, —C(=O)N$R^{22}R^{23}$, —N$R^{22}R^{23}$, —N$R^{24}$C(=O)$R^{20}$, and —O$R^{20}$; R and $R^{10}$ are independently chosen from $C_{1-6}$alkyl optionally substituted by 1-13 $R^{19}$, $C_{2-6}$alkenyl optionally substituted by 1-11 $R^{19}$, $C_{2-6}$alkynyl optionally substituted by 1-9 $R^{19}$, $C_{6-11}$aryl optionally substituted by 1-11 $R^{19}$, $C_{7-16}$arylalkyl optionally substituted by 1-19 $R^{19}$, $C_{3-11}$cycloalkyl optionally substituted by 1-21 $R^{19}$, 3-15 membered heterocycloalkyl optionally substituted by 1-28 $R^{19}$, 5-15 membered heteroaryl optionally substituted by 1-15 $R^{19}$, 6-21 membered heteroarylalkyl optionally substituted by 1-27 $R^{19}$, halogen, —CN, —C(=O)$R^{20}$, —C(=O)N$R^{22}R^{23}$, —N$R^{22}R^{23}$, —N$R^{24}$C(=O)$R^{20}$ and —O$R^{20}$; alternatively, either or both of $R^7$ and $R^8$, and/or $R^9$ and $R^{10}$, can, together with the atoms linking them, form a $C_{6-11}$aryl optionally substituted by 1-11 $R^{19}$, $C_{3-11}$cycloalkyl optionally substituted by 1-21 $R^{19}$, 3-15 membered heterocycloalkyl optionally substituted by 1-28 $R^{19}$ or a 5-15 membered heteroaryl optionally substituted by 1-15 $R^{19}$.

Embodiment 129

The compound of any of Embodiments 1-108, wherein $R^7$, $R^8$, $R^9$, and $R^{10}$ are independently chosen from H, $C_{1-6}$alkyl optionally substituted by 1-3 $R^{19}$, $C_{2-6}$alkenyl optionally substituted by 1-3 $R^{19}$, $C_{2-6}$alkynyl optionally substituted by 1-3 $R^{19}$, $C_{6-11}$aryl optionally substituted by 1-3 $R^{19}$, $C_{7-16}$arylalkyl optionally substituted by 1-3 $R^{19}$, $C_{3-11}$cycloalkyl optionally substituted by 1-3 $R^{19}$, 3-15 membered heterocycloalkyl optionally substituted by 1-3

$R^{19}$, 5-15 membered heteroaryl optionally substituted by 1-3 $R^{19}$, 6-21 membered heteroarylalkyl optionally substituted by 1-3 $R^{19}$, halogen, —CN, —C(=O)$R^{20}$, —C(=O)N$R^{22}R^{23}$, —N$R^{22}R^{23}$, —N$R^{24}$C(=O)$R^{20}$, and —O$R^{20}$; alternatively, either or both of $R^7$ and $R^8$, and/or $R^9$ and $R^{10}$, can, together with the atoms linking them, form a $C_{6-11}$aryl optionally substituted by 1-3 $R^{19}$, $C_{3-11}$cycloalkyl optionally substituted by 1-3 $R^{19}$, 3-15 membered heterocycloalkyl optionally substituted by 1-3 $R^{19}$ or a 5-15 membered heteroaryl optionally substituted by 1-3 $R^{19}$.

Embodiment 130

The compound of any of Embodiments 1-108, wherein $R^7$, $R^9$, and $R^{10}$ are independently chosen from H, $C_{1-6}$alkyl optionally substituted by 1-3 $R^{19}$, $C_{2-6}$alkenyl optionally substituted by 1-3 $R^{19}$, $C_{2-6}$alkynyl optionally substituted by 1-3 $R^{19}$, $C_{6-11}$aryl optionally substituted by 1-3 $R^{19}$, $C_{7-16}$arylalkyl optionally substituted by 1-3 $R^{19}$, $C_{3-11}$cycloalkyl optionally substituted by 1-3 $R^{19}$, 3-15 membered heterocycloalkyl optionally substituted by 1-3 $R^{19}$, 5-15 membered heteroaryl optionally substituted by 1-3 $R^{19}$, 6-21 membered heteroarylalkyl optionally substituted by 1-3 $R^{19}$, halogen, —CN, —C(=O)$R^{20}$, —C(=O)N$R^{22}R^{23}$, —N$R^{22}R^{23}$, —N$R^{24}$C(=O)$R^{20}$, and —O$R^{20}$; $R^8$ is chosen from H, $C_{1-6}$alkyl optionally substituted by 1-3 $R^{19}$, $C_{2-6}$alkenyl optionally substituted by 1-3 $R^{19}$, $C_{2-6}$alkynyl optionally substituted by 1-3 $R^{19}$, $C_{7-16}$arylalkyl optionally substituted by 1-3 $R^{19}$, $C_{3-11}$cycloalkyl optionally substituted by 1-3 $R^{19}$, 3-15 membered heterocycloalkyl optionally substituted by 1-3 $R^{19}$, 6-21 membered heteroarylalkyl optionally substituted by 1-3 $R^{19}$, halogen, —CN, —C(=O)$R^{20}$, —C(=O)N$R^{22}R^{23}$, —N$R^{22}R^{23}$, —N$R^{24}$C(=O)$R^{20}$, and —O$R^{20}$; alternatively, either or both of $R^7$ and $R^8$, and/or $R^9$ and $R^{10}$, can, together with the atoms linking them, form a $C_{6-11}$aryl optionally substituted by 1-3 $R^{19}$, $C_{3-11}$cycloalkyl optionally substituted by 1-3 $R^{19}$, 3-15 membered heterocycloalkyl optionally substituted by 1-3 $R^{19}$ or a 5-15 membered heteroaryl optionally substituted by 1-3 $R^{19}$.

Embodiment 131

The compound of any of Embodiments 1-108, wherein $R^7$ and $R^{10}$ are independently chosen from H, $C_{1-6}$alkyl optionally substituted by 1-3 $R^{19}$, $C_{2-6}$alkenyl optionally substituted by 1-3 $R^{19}$, $C_{2-6}$alkynyl optionally substituted by 1-3 $R^{19}$, $C_{6-11}$aryl optionally substituted by 1-3 $R^{19}$, $C_{7-16}$arylalkyl optionally substituted by 1-3 $R^{19}$, $C_{3-11}$cycloalkyl optionally substituted by 1-3 $R^{19}$ 3-15 membered heterocycloalkyl optionally substituted by 1-3 $R^{19}$, 5-15 membered heteroaryl optionally substituted by 1-3 $R^{19}$, 6-21 membered heteroarylalkyl optionally substituted by 1-3 $R^{19}$, halogen, —CN, —C(=O)$R^{20}$, —C(=O)N$R^{22}R^{23}$, —N$R^{22}R^{23}$, —N$R^{24}$C(=O)$R^{20}$, and —O$R^{20}$; $R^8$ and $R^9$ are independently chosen from $C_{1-6}$alkyl optionally substituted by 1-3 $R^{19}$, $C_{2-6}$alkenyl optionally substituted by 1-3 $R^{19}$, $C_{2-6}$alkynyl optionally substituted by 1-3 $R^{19}$, $C_{6-11}$aryl optionally substituted by 1-3 $R^{19}$, $C_{7-16}$arylalkyl optionally substituted by 1-3 $R^{19}$, $C_{3-11}$-cycloalkyl optionally substituted by 1-3 $R^{19}$, 3-15 membered heterocycloalkyl optionally substituted by 1-3 $R^{19}$, 5-15 membered heteroaryl optionally substituted by 1-3 $R^{19}$, 6-21 membered heteroarylalkyl optionally substituted by 1-3 $R^{19}$, halogen, —CN, —C(=O)$R^{20}$, —C(=O)N$R^{22}R^{23}$, —N$R^{22}R^{23}$, —N$R^{24}$C(=O)$R^{20}$, and —O$R^{20}$; alternatively, either or both of $R^7$ and $R^8$, and/or $R^9$ and $R^{10}$, can, together with the atoms linking them, form a $C_{6-11}$aryl optionally substituted by 1-3 $R^{19}$, $C_{3-11}$cycloalkyl optionally substituted by 1-3 $R^{19}$, 3-15 membered heterocycloalkyl optionally substituted by 1-3 $R^{19}$ or a 5-15 membered heteroaryl optionally substituted by 1-3 $R^{19}$.

Embodiment 132

The compound of any of Embodiments 1-108, wherein $R^7$ and $R^{10}$ are independently chosen from H, $C_{1-6}$alkyl optionally substituted by 1-3 $R^{19}$, $C_{2-6}$alkenyl optionally substituted by 1-3 $R^{19}$, $C_{2-6}$alkynyl optionally substituted by 1-3 $R^{19}$, $C_{6-11}$aryl optionally substituted by 1-3 $R^{19}$, $C_{7-16}$arylalkyl optionally substituted by 1-3 $R^{19}$, $C_{3-11}$cycloalkyl optionally substituted by 1-3 $R^{19}$, 3-15 membered heterocycloalkyl optionally substituted by 1-3 $R^{19}$, 5-15 membered heteroaryl optionally substituted by 1-3 $R^{19}$, 6-21 membered heteroarylalkyl optionally substituted by 1-3 $R^{19}$, halogen, —CN, —C(=O)$R^{20}$, —C(=O)N$R^{22}R^{23}$, —N$R^{22}R^{23}$, —N$R^{24}$C(=O)$R^{20}$, and —O$R^{20}$; $R^8$ is chosen from $C_{1-6}$alkyl optionally substituted by 1-3 $R^{19}$, $C_{2-6}$alkenyl optionally substituted by 1-3 $R^{19}$, $C_{2-6}$alkynyl optionally substituted by 1-3 $R^{19}$, $C_{7-16}$arylalkyl optionally substituted by 1-3 $R^{19}$, $C_{3-11}$cycloalkyl optionally substituted by 1-3 $R^{19}$, 3-15 membered heterocycloalkyl optionally substituted by 1-3 $R^{19}$, 6-21 membered heteroarylalkyl optionally substituted by 1-3 $R^{19}$, halogen, —CN, —C(=O)$R^{20}$, —C(=O)N$R^{22}R^{23}$, —N$R^{22}R^{23}$, —N$R^{24}$C(=O)$R^{20}$, and —O$R^{20}$; $R^9$ is chosen from $C_{1-6}$alkyl optionally substituted by 1-3 $R^{19}$, $C_{2-6}$alkenyl optionally substituted by 1-3 $R^{19}$, $C_{2-6}$alkynyl optionally substituted by 1-3 $R^{19}$, $C_{6-11}$aryl optionally substituted by 1-3 $R^{19}$, $C_{7-16}$arylalkyl optionally substituted by 1-3 $R^{19}$, $C_{3-11}$cycloalkyl optionally substituted by 1-3 $R^{19}$ 3-15 membered heterocycloalkyl optionally substituted by 1-3 $R^{19}$, 5-15 membered heteroaryl optionally substituted by 1-3 $R^{19}$, 6-21 membered heteroarylalkyl optionally substituted by 1-3 $R^{19}$, halogen, —CN, —C(=O)$R^{20}$, —C(=O)N$R^{22}R^{23}$, —N$R^{22}R^{23}$, —N$R^{24}$C(=O)$R^{20}$, and —O$R^{20}$; alternatively, either or both of $R^7$ and $R^8$, and/or $R^9$ and $R^{10}$, can, together with the atoms linking them, form a $C_{6-11}$-aryl optionally substituted by 1-3 $R^{19}$, $C_{3-11}$cycloalkyl optionally substituted by 1-3 $R^{19}$, 3-15 membered heterocycloalkyl optionally substituted by 1-3 $R^{19}$ or a 5-15 membered heteroaryl optionally substituted by 1-3 $R^{19}$.

Embodiment 133

The compound of any of Embodiments 1-108, wherein $R^8$ and $R^9$ are independently chosen from H, $C_{1-6}$alkyl optionally substituted by 1-3 $R^{19}$, $C_{2-6}$alkenyl optionally substituted by 1-3 $R^{19}$, $C_{2-6}$alkynyl optionally substituted by 1-3 $R^{19}$, $C_{6-11}$aryl optionally substituted by 1-3 $R^{19}$, $C_{7-16}$arylalkyl optionally substituted by 1-3 $R^{19}$, $C_{3-11}$cycloalkyl optionally substituted by 1-3 $R^{19}$, 3-15 membered heterocycloalkyl optionally substituted by 1-3 $R^{19}$, 5-15 membered heteroaryl optionally substituted by 1-3 $R^{19}$, 6-21 membered heteroarylalkyl optionally substituted by 1-3 $R^{19}$, halogen, —CN, —C(=O)$R^{20}$, —C(=O)N$R^{22}R^{23}$, —N$R^{22}R^{23}$, —N$R^{24}$C(=O)$R^{20}$, and —O$R^{20}$; $R^7$ and $R^{10}$ are independently chosen from $C_{1-6}$alkyl optionally substituted by 1-3 $R^{19}$, $C_{2-6}$alkenyl optionally substituted by 1-3 $R^{19}$, $C_{2-6}$alkynyl optionally substituted by 1-3 $R^{19}$, $C_{6-1}$aryl optionally substituted by 1-3 $R^{19}$, $C_{7-16}$arylalkyl optionally substituted by 1-3 $R^{19}$, $C_{3-11}$cycloalkyl optionally substituted by 1-3 $R^{19}$, 3-15 membered heterocycloalkyl optionally substituted by 1-3 $R^{19}$, 5-15 membered heteroaryl optionally substituted by 1-3 $R^{19}$, 6-21 membered heteroarylalkyl optionally substituted by 1-3 $R^{19}$, halogen, —CN, —C(=O)R$^{20}$, —C(=O)NR$^{22}$R$^{23}$, —NR$^{22}$R$^{23}$, —NR$^{24}$C(=O)R$^{20}$, and —OR$^{20}$; alternatively, either or both of R$^7$ and R$^8$, and/or R$^9$ and R$^{10}$, can, together with the atoms linking them, form a C$_{6-11}$aryl optionally substituted by 1-3 R$^{19}$, C$_{3-11}$cycloalkyl optionally substituted by 1-3 R$^{19}$, 3-15 membered heterocycloalkyl optionally substituted by 1-3 R$^{19}$ or a 5-15 membered heteroaryl optionally substituted by 1-3 R$^{19}$.

Embodiment 134

The compound of any of Embodiments 1-108, wherein R$^8$ is chosen from H, C$_{1-6}$alkyl optionally substituted by 1-3 R$^{19}$, C$_{2-6}$alkenyl optionally substituted by 1-3 R$^{19}$, C$_{2-6}$alkynyl optionally substituted by 1-3 R$^{19}$, C$_{7-16}$arylalkyl optionally substituted by 1-3 R$^{19}$, C$_{3-11}$cycloalkyl optionally substituted by 1-3 R$^{19}$, 3-15 membered heterocycloalkyl optionally substituted by 1-3 R$^{19}$, 6-21 membered heteroarylalkyl optionally substituted by 1-3 R$^{19}$, halogen, —CN, —C(=O)R$^{20}$, —C(=O)NR$^{22}$R$^{23}$, —NR$^{22}$R$^{23}$, —NR$^{24}$C(=O)R$^{20}$, and —OR$^{20}$; R$^9$ is chosen from H, C$_{1-6}$alkyl optionally substituted by 1-3 R$^{19}$, C$_{2-6}$alkenyl optionally substituted by 1-3 R$^{19}$, C$_{2-6}$alkynyl optionally substituted by 1-3 R$^{19}$, C$_{6-11}$aryl optionally substituted by 1-3 R$^{19}$, C$_{7-16}$arylalkyl optionally substituted by 1-3 R$^{19}$, C$_{3-11}$cycloalkyl optionally substituted by 1-3 R$^{19}$, 3-15 membered heterocycloalkyl optionally substituted by 1-3 R$^{19}$, 5-15 membered heteroaryl optionally substituted by 1-3 R$^{19}$, 6-21 membered heteroarylalkyl optionally substituted by 1-3 R$^{19}$, halogen, —CN, —C(=O)R$^{20}$, —C(=O)NR$^{22}$R$^{23}$, —NR$^{22}$R$^{23}$, —NR$^{24}$C(=O)R$^{20}$, and —OR$^{20}$; R$^7$ and R$^{10}$ are independently chosen from C$_{1-6}$alkyl optionally substituted by 1-3 R$^{19}$, C$_{2-6}$alkenyl optionally substituted by 1-3 R$^{19}$, C$_{2-6}$alkynyl optionally substituted by 1-3 R$^{19}$, C$_{6-11}$aryl optionally substituted by 1-3 R$^{19}$, C$_{7-16}$arylalkyl optionally substituted by 1-3 R$^{19}$, C$_{3-11}$cycloalkyl optionally substituted by 1-3 R$^{19}$, 3-15 membered heterocycloalkyl optionally substituted by 1-3 R$^{19}$, 5-15 membered heteroaryl optionally substituted by 1-3 R$^{19}$, 6-21 membered heteroarylalkyl optionally substituted by 1-3 R$^{19}$, halogen, —CN, —C(=O)R$^{20}$, —C(=O)NR$^{22}$R$^{23}$, —NR$^{22}$R$^{23}$, —NR$^{24}$C(=O)R$^{20}$, and —OR$^{20}$; alternatively, either or both of R$^7$ and R$^8$, and/or R$^9$ and R$^{10}$, can, together with the atoms linking them, form a C$_{6-11}$aryl optionally substituted by 1-3 R$^{19}$, C$_{3-11}$cycloalkyl optionally substituted by 1-3 R$^{19}$, 3-15 membered heterocycloalkyl optionally substituted by 1-3 R$^{19}$ or a 5-15 membered heteroaryl optionally substituted by 1-3 R$^{19}$.

Embodiment 135

The compound of any of Embodiments 1-108, wherein R$^7$, R$^8$, R$^9$, and R$^{10}$ are independently chosen from H, C$_{1-6}$alkyl optionally substituted by 1-3 R$^{19}$, C$_{2-6}$alkenyl optionally substituted by 1-3 R$^{19}$, C$_{2-6}$alkynyl optionally substituted by 1-3 R$^{19}$, C$_{6-10}$aryl optionally substituted by 1-3 R$^{19}$, C$_{7-11}$ arylalkyl optionally substituted by 1-3 R$^{19}$, C$_{3-10}$cycloalkyl optionally substituted by 1-3 R$^{19}$, 3-10 membered heterocycloalkyl optionally substituted by 1-3 R$^{19}$, 5-10 membered heteroaryl optionally substituted by 1-3 R$^{19}$, 6-11 membered heteroarylalkyl optionally substituted by 1-3 R$^{19}$, halogen, —CN, —C(=O)R$^{20}$, —C(=O)NR$^{22}$R$^{23}$, —NR$^{22}$R$^{23}$, —NR$^{24}$C(=O)R$^{20}$, and —OR$^{20}$; alternatively, either or both of R$^7$ and R$^8$, and/or R$^9$ and R$^{10}$, can, together with the atoms linking them, form a C$_{6-10}$aryl optionally substituted by 1-3 R$^{19}$, C$_{3-10}$cycloalkyl optionally substituted by 1-3 R$^{19}$, 3-10 membered heterocycloalkyl optionally substituted by 1-3 R$^{19}$ or a 5-10 membered heteroaryl optionally substituted by 1-3 R$^{19}$.

Embodiment 136

The compound of any of Embodiments 1-108, wherein R$^7$, R$^9$, and R$^{10}$ are independently chosen from H, C$_{1-6}$alkyl optionally substituted by 1-3 R$^{19}$, C$_{2-6}$alkenyl optionally substituted by 1-3 R$^{19}$, C$_{2-6}$alkynyl optionally substituted by 1-3 R$^{19}$, C$_{6-10}$aryl optionally substituted by 1-3 R$^{19}$, C$_{7-11}$arylalkyl optionally substituted by 1-3 R$^{19}$, C$_{3-10}$cycloalkyl optionally substituted by 1-3 R$^{19}$, 3-10 membered heterocycloalkyl optionally substituted by 1-3 R$^{19}$, 5-10 membered heteroaryl optionally substituted by 1-3 R$^{19}$, 6-11 membered heteroarylalkyl optionally substituted by 1-3 R$^{19}$, halogen, —CN, —C(=O)R$^{20}$, —C(=O)NR$^{22}$R$^{23}$, —NR$^{22}$R$^{23}$, —NR$^{24}$C(=O)R$^{20}$, and —OR$^{20}$; R$^8$ is chosen from H, C$_{1-6}$alkyl optionally substituted by 1-3 R$^{19}$, C$_{2-6}$alkenyl optionally substituted by 1-3 R$^{19}$, C$_{2-6}$alkynyl optionally substituted by 1-3 R$^{19}$, C$_{7-11}$arylalkyl optionally substituted by 1-3 R$^{19}$, C$_{3-10}$cycloalkyl optionally substituted by 1-3 R$^{19}$, 3-10 membered heterocycloalkyl optionally substituted by 1-3 R$^{19}$, 6-11 membered heteroarylalkyl optionally substituted by 1-3 R$^{19}$, halogen, —CN, —C(=O)R$^{20}$, —C(=O)NR$^{22}$R$^{23}$, —NR$^{22}$R$^{23}$, —NR$^{24}$C(=O)R$^{20}$, and —OR$^{20}$; alternatively, either or both of R$^7$ and R$^8$, and/or R$^9$ and R$^{10}$, can, together with the atoms linking them, form a C$_{6-10}$aryl optionally substituted by 1-3 R$^{19}$, C$_{3-10}$cycloalkyl optionally substituted by 1-3 R$^{19}$, 3-10 membered heterocycloalkyl optionally substituted by 1-3 R$^{19}$ or a 5-10 membered heteroaryl optionally substituted by 1-3 R$^{19}$.

Embodiment 137

The compound of any of Embodiments 1-108, wherein R$^7$, R$^8$, R$^9$, and R$^{10}$ are independently chosen from H, C$_{1-6}$alkyl optionally substituted by 1-3 R$^{19}$, C$_{2-6}$alkenyl optionally substituted by 1-3 R$^{19}$, C$_{2-6}$alkynyl optionally substituted by 1-3 R$^{19}$, C$_{6-10}$aryl optionally substituted by 1-3 R$^{19}$, C$_{3-10}$ cycloalkyl optionally substituted by 1-3 R$^{19}$, 3-10 membered heterocycloalkyl optionally substituted by 1-3 R$^{19}$, 5-10 membered heteroaryl optionally substituted by 1-3 R$^{19}$, halogen, —CN, —C(=O)R$^{20}$, —C(=O)NR$^{22}$R$^{23}$, —NR$^{22}$R$^{23}$, —NR$^{24}$C(=O)R$^{20}$, and —OR$^{20}$; alternatively, either or both of R$^7$ and R$^8$, and/or R$^9$ and R$^{10}$, can, together with the atoms linking them, form a C$_{6-10}$aryl optionally substituted by 1-3 R$^{19}$, C$_{3-10}$cycloalkyl optionally substituted by 1-3 R$^{19}$, 3-10 membered heterocycloalkyl optionally substituted by 1-3 R$^{19}$ or a 5-10 membered heteroaryl optionally substituted by 1-3 R$^{19}$.

Embodiment 138

The compound of any of Embodiments 1-108, wherein R$^7$, R$^9$, and R$^{10}$ are independently chosen from H, C$_{1-6}$alkyl optionally substituted by 1-3 R$^{19}$, C$_{2-6}$alkenyl optionally substituted by 1-3 R$^{19}$, C$_{2-6}$alkynyl optionally substituted by 1-3 R$^{19}$, C$_{6-10}$aryl optionally substituted by 1-3 R$^{19}$, C$_{3-10}$cycloalkyl optionally substituted by 1-3 R$^{19}$, 3-10 membered heterocycloalkyl optionally substituted by 1-3 R$^{19}$, 5-10 membered heteroaryl optionally substituted by 1-3 R$^{19}$ halogen, —CN, —C(=O)R$^{20}$, —C(=O)NR$^{22}$R$^{23}$, —NR$^{22}$R$^{23}$, —NR$^{24}$C(=O)R$^{20}$, and —OR$^{20}$; R$^8$ is chosen from H, C$_{1-6}$alkyl optionally substituted by 1-3 R$^{19}$, C$_{2-6}$alkenyl optionally substituted by 1-3 R$^{19}$, C$_{2-6}$alkynyl optionally substituted by 1-3 R$^{19}$, C$_{3-10}$cycloalkyl optionally sub-

Embodiment 139

The compound of any of Embodiments 1-108, wherein $R^7$ and $R^{10}$ are independently chosen from H, $C_{1-6}$alkyl optionally substituted by 1-3 $R^{19}$, $C_{2-6}$alkenyl optionally substituted by 1-3 $R^{19}$, $C_{2-6}$alkynyl optionally substituted by 1-3 $R^{19}$, $C_{6-10}$aryl optionally substituted by 1-3 $R^{19}$, $C_{3-10}$cycloalkyl optionally substituted by 1-3 $R^{19}$, 3-10 membered heterocycloalkyl optionally substituted by 1-3 $R^{19}$, 5-10 membered heteroaryl optionally substituted by 1-3 $R^{19}$ halogen, —CN, —C(=O)$R^{20}$, —C(=O)NR$^{22}$R$^{23}$, —NR$^{22}$R$^{23}$, —NR$^{24}$C(=O)R$^{20}$, and —OR$^{20}$; $R^8$ and $R^9$ are independently chosen from $C_{1-6}$alkyl optionally substituted by 1-3 $R^{19}$, $C_{2-6}$alkenyl optionally substituted by 1-3 $R^{19}$, $C_{2-6}$alkynyl optionally substituted by 1-3 $R^{19}$, $C_{6-10}$aryl optionally substituted by 1-3 $R^{19}$, $C_{3-10}$cycloalkyl optionally substituted by 1-3 $R^{19}$, 3-10 membered heterocycloalkyl optionally substituted by 1-3 $R^{19}$, 5-10 membered heteroaryl optionally substituted by 1-3 $R^{19}$, halogen, —CN, —C(=O)R$^{20}$, —C(=O)NR$^{22}$R$^{23}$, —NR$^{22}$R$^{23}$, —NR$^{24}$C(=O)R$^{20}$, and —OR$^{20}$; alternatively, either or both of $R^7$ and $R^8$, and/or $R^9$ and $R^{10}$, can, together with the atoms linking them, form a $C_{6-10}$aryl optionally substituted by 1-3 $R^{19}$, $C_{3-10}$cycloalkyl optionally substituted by 1-3 $R^{19}$, 3-10 membered heterocycloalkyl optionally substituted by 1-3 $R^{19}$ or a 5-10 membered heteroaryl optionally substituted by 1-3 $R^{19}$.

Embodiment 140

The compound of any of Embodiments 1-108, wherein $R^7$ and $R^{10}$ are independently chosen from H, $C_{1-6}$alkyl optionally substituted by 1-3 $R^{19}$, $C_{2-6}$alkenyl optionally substituted by 1-3 $R^{19}$, $C_{2-6}$alkynyl optionally substituted by 1-3 $R^{19}$, $C_{6-10}$aryl optionally substituted by 1-3 $R^{19}$, $C_{3-10}$cycloalkyl optionally substituted by 1-3 $R^{19}$, 3-10 membered heterocycloalkyl optionally substituted by 1-3 $R^{19}$, 5-10 membered heteroaryl optionally substituted by 1-3 $R^{19}$, halogen, —CN, —C(=O)R$^{20}$, —C(=O)NR$^{22}$R$^{23}$, —NR$^{22}$R$^{23}$, —NR$^{24}$C(=O)R$^{20}$, and —OR$^{20}$; $R^8$ is chosen from $C_{1-6}$alkyl optionally substituted by 1-3 $R^{19}$, $C_{2-6}$alkenyl optionally substituted by 1-3 $R^{19}$, $C_{2-6}$alkynyl optionally substituted by 1-3 $R^{19}$, $C_{3-10}$ cycloalkyl optionally substituted by 1-3 $R^{19}$, 3-10 membered heterocycloalkyl optionally substituted by 1-3 $R^{19}$, halogen, —CN, —C(=O)R$^{20}$, —C(=O)NR$^{22}$R$^{23}$, —NR$^{22}$R$^{23}$, —NR$^{24}$C(=O)R$^{20}$, and —OR$^{20}$; $R^9$ is chosen from $C_{1-6}$alkyl optionally substituted by 1-3 $R^{19}$, $C_{2-6}$alkenyl optionally substituted by 1-3 $R^{19}$, $C_{2-6}$alkynyl optionally substituted by 1-3 $R^{19}$, $C_{6-10}$aryl optionally substituted by 1-3 $R^{19}$, $C_{3-10}$ cycloalkyl optionally substituted by 1-3 $R^{19}$, 3-10 membered heterocycloalkyl optionally substituted by 1-3 $R^{19}$, 5-10 membered heteroaryl optionally substituted by 1-3 $R^{19}$, halogen, —CN, —C(=O) R$^{20}$, —C(=O)NR$^{22}$R$^{23}$, —NR$^{22}$R$^{23}$, —NR$^{24}$C(=O)R$^{20}$, and —OR$^{20}$; alternatively, either or both of $R^7$ and $R^8$, and/or $R^9$ and $R^{10}$, can, together with the atoms linking them, form a $C_{6-10}$aryl optionally substituted by 1-3 $R^{19}$, $C_{3-10}$cycloalkyl optionally substituted by 1-3 $R^{19}$, 3-10 membered heterocycloalkyl optionally substituted by 1-3 $R^{19}$ or a 5-10 membered heteroaryl optionally substituted by 1-3 $R^{19}$.

Embodiment 141

The compound of any of Embodiments 1-108, wherein $R^8$ and $R^9$ are independently chosen from H, $C_{1-6}$alkyl optionally substituted by 1-3 $R^{19}$, $C_{2-6}$alkenyl optionally substituted by 1-3 $R^{19}$, $C_{2-6}$alkynyl optionally substituted by 1-3 $R^{19}$, $C_{6-10}$aryl optionally substituted by 1-3 $R^{19}$, $C_{3-10}$cycloalkyl optionally substituted by 1-3 $R^{19}$, 3-10 membered heterocycloalkyl optionally substituted by 1-3 $R^{19}$, 5-10 membered heteroaryl optionally substituted by 1-3 $R^{19}$, halogen, —CN, —C(=O)R$^{20}$, —C(=O)NR$^{22}$R$^{23}$, —NR$^{22}$R$^{23}$, —NR$^{24}$C(=O)R$^{20}$, and —OR$^{20}$; $R^7$ and $R^{10}$ are independently chosen from $C_{1-6}$alkyl optionally substituted by 1-3 $R^{19}$, $C_{2-6}$alkenyl optionally substituted by 1-3 $R^{19}$, $C_{2-6}$alkynyl optionally substituted by 1-3 $R^{19}$, $C_{6-10}$aryl optionally substituted by 1-3 $R^{19}$, $C_{3-10}$cycloalkyl optionally substituted by 1-3 $R^{19}$, 3-10 membered heterocycloalkyl optionally substituted by 1-3 $R^{19}$, 5-10 membered heteroaryl optionally substituted by 1-3 $R^{19}$ halogen, —CN, —C(=O) R$^{20}$, —C(=O)NR$^{22}$R$^{23}$, —NR$^{22}$R$^{23}$, —NR$^{24}$C(=O)R$^{20}$, and —OR$^{20}$; alternatively, either or both of $R^7$ and $R^8$, and/or $R^9$ and $R^{10}$, can, together with the atoms linking them, form a $C_{6-10}$aryl optionally substituted by 1-3 $R^{19}$, $C_{3-10}$ cycloalkyl optionally substituted by 1-3 $R^{19}$, 3-10 membered heterocycloalkyl optionally substituted by 1-3 $R^{19}$ or a 5-10 membered heteroaryl optionally substituted by 1-3 $R^{19}$.

Embodiment 142

The compound of any of Embodiments 1-108, wherein $R^8$ is chosen from H, $C_{1-6}$alkyl optionally substituted by 1-3 $R^{19}$, $C_{2-6}$alkenyl optionally substituted by 1-3 $R^{19}$, $C_{2-6}$alkynyl optionally substituted by 1-3 $R^{19}$, $C_{3-10}$ cycloalkyl optionally substituted by 1-3 $R^{19}$, 3-10 membered heterocycloalkyl optionally substituted by 1-3 $R^{19}$, halogen, —CN, —C(=O)R$^{20}$, —C(=O)NR$^{22}$R$^{23}$, —NR$^{22}$R$^{23}$, —NR$^{24}$C(=O)R$^{20}$, and —OR$^{20}$; $R^9$ is chosen from H, $C_{1-6}$alkyl optionally substituted by 1-3 $R^{19}$, $C_{2-6}$alkenyl optionally substituted by 1-3 $R^{19}$, $C_{2-6}$alkynyl optionally substituted by 1-3 $R^{19}$, $C_{6-10}$aryl optionally substituted by 1-3 $R^{19}$, $C_{3-10}$cycloalkyl optionally substituted by 1-3 $R^{19}$, 3-10 membered heterocycloalkyl optionally substituted by 1-3 $R^{19}$, 5-10 membered heteroaryl optionally substituted by 1-3 $R^{19}$, halogen, —CN, —C(=O)R$^{20}$, —C(=O)NR$^{22}$R$^{23}$, —NR$^{22}$R$^{23}$, —NR$^{24}$C(=O)R$^{20}$, and —OR$^{20}$; $R^7$ and $R^{10}$ are independently chosen from $C_{1-6}$alkyl optionally substituted by 1-3 $R^{19}$, $C_{2-6}$alkenyl optionally substituted by 1-3 $R^{19}$, $C_{2-6}$ alkynyl optionally substituted by 1-3 $R^{19}$, $C_{6-10}$aryl optionally substituted by 1-3 $R^{19}$, $C_{3-10}$cycloalkyl optionally substituted by 1-3 $R^{19}$, 3-10 membered heterocycloalkyl optionally substituted by 1-3 $R^{19}$, 5-10 membered heteroaryl optionally substituted by 1-3 $R^{19}$, halogen, —CN, —C(=O)R$^{20}$, —C(=O)NR$^{22}$R$^{23}$, —NR$^{22}$R$^{23}$, —NR$^{24}$C(=O)R$^{20}$, and —OR$^{20}$; alternatively, either or both of $R^7$ and $R^8$, and/or $R^9$ and $R^{10}$, can, together with the atoms linking them, form a $C_{6-10}$aryl optionally substituted by 1-3 $R^{19}$, $C_{3-10}$cycloalkyl optionally substituted by 1-3 $R^{19}$, 3-10 membered heterocycloalkyl optionally substituted by 1-3 $R^{19}$ or a 5-10 membered heteroaryl optionally substituted by 1-3 $R^{19}$.

Embodiment 143

The compound of any of Embodiments 1-108, wherein $R^7$, $R^8$, $R^9$, and $R^{10}$ are independently chosen from H, $C_{1-6}$alkyl, $C_{2-6}$alkenyl, $C_{2-6}$ alkynyl optionally substituted by 1-3 $R^{19}$, $C_{6-10}$aryl optionally substituted by 1-3 $R^{19}$, $C_{3-10}$cycloalkyl, 3-10 membered heterocycloalkyl, 5-10 membered heteroaryl, halogen, —CN, —C(=O)$R^{20}$, —C(=O)NR$^{22}$R$^{23}$, —NR$^{22}$R$^{23}$, —NR$^{24}$C(=O)$R^{20}$, and —OR$^{20}$; alternatively, either or both of $R^7$ and $R^8$, and/or $R^9$ and $R^{10}$, can, together with the atoms linking them, form a $C_{6-10}$aryl optionally substituted by 1-3 $R^{19}$, $C_{3-10}$ cycloalkyl optionally substituted by 1-3 $R^{19}$, 3-10 membered heterocycloalkyl optionally substituted by 1-3 $R^{19}$ or a 5-10 membered heteroaryl optionally substituted by 1-3 $R^{19}$.

Embodiment 144

The compound of any of Embodiments 1-108, wherein $R^7$, $R^9$, and $R^{10}$ are independently chosen from H, $C_{1-6}$alkyl, $C_{2-6}$alkenyl, $C_{2-6}$alkynyl optionally substituted by 1-3 $R^{19}$, $C_{6-10}$aryl optionally substituted by 1-3 $R^{19}$, $C_{3-10}$ cycloalkyl, 3-10 membered heterocycloalkyl, 5-10 membered heteroaryl, halogen, —CN, —C(=O)$R^{20}$, —C(=O)NR$^{22}$R$^{23}$, —NR$^{22}$R$^{23}$, —NR$^{24}$C(=O)$R^{20}$, and —OR$^{20}$; $R^8$ is chosen from H, $C_{1-6}$alkyl, $C_{2-6}$alkenyl, $C_{2-6}$alkynyl optionally substituted by 1-3 $R^{19}$, $C_{3-10}$cycloalkyl, 3-10 membered heterocycloalkyl, halogen, —CN, —C(=O)$R^{20}$, —C(=O)NR$^{22}$R$^{23}$, —NR$^{22}$R$^{23}$, —NR$^{24}$C(=O)$R^{20}$, and —OR$^{20}$; alternatively, either or both of $R^7$ and $R^8$, and/or $R^9$ and $R^{10}$, can, together with the atoms linking them, form a $C_{6-10}$aryl optionally substituted by 1-3 $R^{19}$, $C_{3-10}$cycloalkyl optionally substituted by 1-3 $R^{19}$, 3-10 membered heterocycloalkyl optionally substituted by 1-3 $R^{19}$ or a 5-10 membered heteroaryl optionally substituted by 1-3 $R^{19}$.

Embodiment 145

The compound of any of Embodiments 1-108, wherein $R^7$, $R^8$, $R^9$, and $R^{10}$ are independently chosen from H, $C_{1-6}$alkyl, $C_{2-6}$alkenyl, $C_{2-6}$ alkynyl optionally substituted by 1-3 $R^{19}$, $C_{6-10}$aryl, $C_{3-10}$cycloalkyl, 3-10 membered heterocycloalkyl, 5-10 membered heteroaryl, halogen, —CN, —C(=O)$R^{20}$, —C(=O)NR$^{22}$R$^{23}$, —NR$^{22}$R$^{23}$, —NR$^{24}$C(=O)$R^{20}$, and —OR$^{20}$; alternatively, either or both of $R^7$ and $R^8$, and/or $R^9$ and $R^{10}$, can, together with the atoms linking them, form a $C_{6-10}$aryl, $C_{3-10}$ cycloalkyl, 3-10 membered heterocycloalkyl or a 5-10 membered heteroaryl.

Embodiment 146

The compound of any of Embodiments 1-108, wherein $R^7$, $R^9$, and $R^{10}$ are independently chosen from H, $C_{1-6}$alkyl, $C_{2-6}$alkenyl, $C_{2-6}$alkynyl optionally substituted by 1-3 $R^{19}$, $C_{6-10}$aryl, $C_{3-10}$cycloalkyl, 3-10 membered heterocycloalkyl, 5-10 membered heteroaryl, halogen, —CN, —C(=O)$R^{20}$, —C(=O)NR$^{22}$R$^{23}$, —NR$^{22}$R$^{23}$, —NR$^{24}$C(=O)$R^{20}$, and —OR$^{20}$; R is chosen from H, $C_{1-6}$ alkyl, $C_{2-6}$alkenyl, $C_{2-6}$alkynyl optionally substituted by 1-3 $R^{19}$, $C_{3-10}$cycloalkyl, 3-10 membered heterocycloalkyl, halogen, —CN, —C(=O)$R^{20}$, —C(=O)NR$^{22}$R$^{23}$, —NR$^{22}$R$^{23}$, —NR$^{24}$C(=O)$R^{20}$, and —OR$^{20}$; alternatively, either or both of $R^7$ and $R^8$, and/or $R^9$ and $R^{10}$, can, together with the atoms linking them, form a $C_{6-10}$aryl, $C_{3-10}$ cycloalkyl, 3-10 membered heterocycloalkyl or a 5-10 membered heteroaryl.

Embodiment 147

The compound of any of Embodiments 1-108, wherein $R^7$, $R^8$, $R^9$, and $R^{10}$ are independently chosen from H, $C_{1-6}$alkyl, $C_{2-6}$alkenyl, $C_{2-6}$ alkynyl, $C_{6-10}$aryl, $C_{3-10}$cycloalkyl, 3-10 membered heterocycloalkyl, 5-10 membered heteroaryl, halogen, —CN, —C(=O)$R^{20}$, —C(=O)NR$^{22}$R$^{23}$, —NR$^{22}$R$^{23}$, —NR$^{24}$C(=O)$R^{20}$, and —OR$^{20}$; alternatively, either or both of $R^7$ and $R^8$, and/or $R^9$ and $R^{10}$, can, together with the atoms linking them, form a $C_{6-10}$aryl, $C_{3-10}$ cycloalkyl, 3-10 membered heterocycloalkyl or a 5-10 membered heteroaryl.

Embodiment 148

The compound of any of Embodiments 1-108, wherein $R^7$, $R^9$, and $R^{10}$ are independently chosen from H, $C_{1-6}$alkyl, $C_{2-6}$alkenyl, $C_{2-6}$alkynyl, $C_{6-10}$aryl, $C_{3-10}$cycloalkyl, 3-10 membered heterocycloalkyl, 5-10 membered heteroaryl, halogen, —CN, —C(=O)$R^{20}$, —C(=O)NR$^{22}$R$^{23}$, —NR$^{22}$R$^{23}$, —NR$^{24}$C(=O)$R^{20}$, and —OR$^{20}$; $R^8$ is chosen from H, $C_{1-6}$alkyl, $C_{2-6}$alkenyl, $C_{2-6}$ alkynyl, $C_{3-10}$cycloalkyl, 3-10 membered heterocycloalkyl, halogen, —CN, —C(=O)$R^{20}$, —C(=O)NR$^{22}$R$^{23}$, —NR$^{22}$R$^{23}$, —NR$^{24}$C(=O)$R^{20}$, and —OR$^{20}$; alternatively, either or both of $R^7$ and $R^8$, and/or $R^9$ and $R^{10}$, can, together with the atoms linking them, form a $C_{6-10}$aryl, $C_{3-10}$cycloalkyl, 3-10 membered heterocycloalkyl or a 5-10 membered heteroaryl.

Embodiment 149

The compound of any of Embodiments 1-108, wherein $R^7$, $R^8$, $R^9$, and $R^{10}$ are independently chosen from H, $C_{1-6}$alkyl optionally substituted by 1-3 $R^{19}$, $C_{2-6}$alkenyl optionally substituted by 1-3 $R^{19}$, $C_{2-6}$alkynyl optionally substituted by 1-3 $R^{19}$, phenyl optionally substituted by 1-3 $R^{19}$, $C_{3-6}$ cycloalkyl optionally substituted by 1-3 $R^{19}$, 3-6 membered heterocycloalkyl optionally substituted by 1-3 $R^{19}$, 5-6 membered heteroaryl optionally substituted by 1-3 $R^{19}$, halogen, —CN, —C(=O)$R^{20}$, —C(=O)NR$^{22}$R$^{23}$, —NR$^{22}$R$^{23}$, —NR$^{24}$C(=O)$R^{20}$, and —OR$^{20}$; alternatively, either or both of $R^7$ and $R^8$, and/or $R^9$ and $R^{10}$, can, together with the atoms linking them, form a phenyl optionally substituted by 1-3 $R^{19}$, $C_{3-6}$cycloalkyl optionally substituted by 1-3 $R^{19}$, 3-6 membered heterocycloalkyl optionally substituted by 1-3 $R^{19}$ or a 5-6 membered heteroaryl optionally substituted by 1-3 $R^{19}$.

Embodiment 150

The compound of any of Embodiments 1-108, wherein $R^7$, $R^9$, and $R^{10}$ are independently chosen from H, $C_{1-6}$alkyl optionally substituted by 1-3 $R^{19}$, $C_{2-6}$alkenyl optionally substituted by 1-3 $R^{19}$, $C_{2-6}$alkynyl optionally substituted by 1-3 $R^{19}$, phenyl optionally substituted by 1-3 $R^{19}$, $C_{3-6}$cycloalkyl optionally substituted by 1-3 $R^{19}$, 3-6 membered heterocycloalkyl optionally substituted by 1-3 $R^{19}$, 5-6 membered heteroaryl optionally substituted by 1-3 $R^{19}$, halogen, —CN, —C(=O)$R^{20}$, —C(=O)NR$^{22}$R$^{23}$, —NR$^{22}$R$^{23}$, —NR$^{24}$C(=O)$R^{20}$, and —OR$^{20}$; $R^8$ is chosen from H, $C_{1-6}$alkyl optionally substituted by 1-3 $R^{19}$, $C_{2-6}$alkenyl optionally substituted by 1-3 $R^{19}$, $C_{2-6}$alkynyl optionally substituted by 1-3 $R^{19}$, $C_{3-6}$ cycloalkyl optionally substituted by 1-3 $R^{19}$, 3-6 membered heterocycloalkyl optionally substituted by 1-3 $R^{19}$, halogen, —CN, —C(=O)$R^{20}$, —C(=O)NR$^{22}$R$^{23}$, —NR$^{22}$R$^{23}$, —NR$^{24}$C(=O)$R^{20}$, and —OR$^{20}$; alternatively, either or both of $R^7$ and $R^8$, and/or $R^9$ and $R^{10}$, can, together with the atoms linking them, form a phenyl optionally substituted by 1-3 $R^{19}$, $C_{3-6}$cycloalkyl optionally substituted by 1-3 $R^{19}$, 3-6 membered heterocycloalkyl optionally substituted by 1-3 $R^{19}$ or a 5-6 membered heteroaryl optionally substituted by 1-3 $R^{19}$.

Embodiment 151

The compound of any of Embodiments 1-108, wherein $R^7$ and $R^{10}$ are independently chosen from H, $C_{1-6}$alkyl optionally substituted by 1-3 $R^{19}$, $C_{2-6}$alkenyl optionally substituted by 1-3 $R^{19}$, $C_{2-6}$alkynyl optionally substituted by 1-3 $R^{19}$, phenyl optionally substituted by 1-3 $R^{19}$, $C_{3-6}$cycloalkyl optionally substituted by 1-3 $R^{19}$, 3-6 membered heterocycloalkyl optionally substituted by 1-3 $R^{19}$, 5-6 membered heteroaryl optionally substituted by 1-3 $R^{19}$, halogen, —CN, —C(=O)$R^{20}$, —C(=O)NR$^{22}$R$^{23}$, —NR$^{22}$R$^{23}$, —NR$^{24}$C(=O)$R^{20}$, and —OR$^{20}$; $R^8$ and $R^9$ are independently chosen from $C_{1-6}$alkyl optionally substituted by 1-3 $R^{19}$, $C_{2-6}$alkenyl optionally substituted by 1-3 $R^{19}$, $C_{2-6}$alkynyl optionally substituted by 1-3 $R^{19}$, phenyl optionally substituted by 1-3 $R^{19}$, $C_{3-6}$cycloalkyl optionally substituted by 1-3 $R^{19}$, 3-6 membered heterocycloalkyl optionally substituted by 1-3 $R^{19}$, 5-6 membered heteroaryl optionally substituted by 1-3 $R^{19}$ halogen, —CN, —C(=O)$R^{20}$, —C(=O)NR$^{22}$R$^{23}$, —NR$^{22}$R$^{23}$, —NR$^{24}$C(=O)$R^{20}$, and —OR$^{20}$; alternatively, either or both of $R^7$ and $R^8$, and/or $R^9$ and $R^{10}$, can, together with the atoms linking them, form a phenyl optionally substituted by 1-3 $R^{19}$, $C_{3-6}$cycloalkyl optionally substituted by 1-3 $R^{19}$, 3-6 membered heterocycloalkyl optionally substituted by 1-3 $R^{19}$ or a 5-6 membered heteroaryl optionally substituted by 1-3 $R^{19}$.

Embodiment 152

The compound of any of Embodiments 1-108, wherein $R^7$ and $R^{10}$ are independently chosen from H, $C_{1-6}$alkyl optionally substituted by 1-3 $R^{19}$, $C_{2-6}$alkenyl optionally substituted by 1-3 $R^{19}$, $C_{2-6}$alkynyl optionally substituted by 1-3 $R^{19}$, phenyl optionally substituted by 1-3 $R^{19}$, $C_{3-6}$cycloalkyl optionally substituted by 1-3 $R^{19}$, 3-6 membered heterocycloalkyl optionally substituted by 1-3 $R^{19}$, 5-6 membered heteroaryl optionally substituted by 1-3 $R^{19}$, halogen, —CN, —C(=O)$R^{20}$, —C(=O)NR$^{22}$R$^{23}$, —NR$^{22}$R$^{23}$, —NR$^{24}$C(=O)$R^{20}$, and —OR$^{20}$; $R^8$ is chosen from $C_{1-6}$alkyl optionally substituted by 1-3 $R^{19}$, $C_{2-6}$alkenyl optionally substituted by 1-3 $R^{19}$, $C_{2-6}$alkynyl optionally substituted by 1-3 $R^{19}$, $C_{3-6}$ cycloalkyl optionally substituted by 1-3 $R^{19}$, 3-6 membered heterocycloalkyl optionally substituted by 1-3 $R^{19}$, halogen, —CN, —C(=O)$R^{20}$, —C(=O)NR$^{22}$R$^{23}$, —NR$^{22}$R$^{23}$, —NR$^{24}$C(=O)$R^{20}$, and —OR$^{20}$; $R^9$ is chosen from $C_{1-6}$alkyl optionally substituted by 1-3 $R^{19}$, $C_{2-6}$alkenyl optionally substituted by 1-3 $R^{19}$, $C_{2-6}$alkynyl optionally substituted by 1-3 $R^{19}$, phenyl optionally substituted by 1-3 $R^{19}$, $C_{3-6}$ cycloalkyl optionally substituted by 1-3 $R^{19}$, 3-6 membered heterocycloalkyl optionally substituted by 1-3 $R^{19}$, 5-6 membered heteroaryl optionally substituted by 1-3 $R^{19}$, halogen, —CN, —C(=O)$R^{20}$, —C(=O)NR$^{22}$R$^{23}$, —NR$^{22}$R$^{23}$, —NR$^{24}$C(=O)$R^{20}$, and —OR$^{20}$; alternatively, either or both of $R^7$ and $R^8$, and/or $R^9$ and $R^{10}$, can, together with the atoms linking them, form a phenyl optionally substituted by 1-3 $R^{19}$, $C_{3-6}$cycloalkyl optionally substituted by 1-3 $R^{19}$, 3-6 membered heterocycloalkyl optionally substituted by 1-3 $R^{19}$ or a 5-6 membered heteroaryl optionally substituted by 1-3 $R^{19}$.

Embodiment 153

The compound of any of Embodiments 1-108, wherein $R^7$, $R^8$, $R^9$, and $R^{10}$ are independently chosen from H, $C_{1-6}$alkyl, $C_{2-6}$alkenyl, $C_{2-6}$alkynyl optionally substituted by 1-3 $R^{19}$, phenyl, $C_{3-6}$cycloalkyl, 3-6 membered heterocycloalkyl, 5-6 membered heteroaryl, halogen, —CN, —C(=O)$R^{20}$, —C(=O)NR$^{22}$R$^{23}$, —NR$^{22}$R$^{23}$, —NR$^{24}$C(=O)$R^{20}$, and —OR$^{20}$; alternatively, either or both of $R^7$ and $R^8$, and/or $R^9$ and $R^{10}$, can, together with the atoms linking them, form a phenyl, $C_{3-6}$cycloalkyl, 3-6 membered heterocycloalkyl or a 5-6 membered heteroaryl.

Embodiment 154

The compound of any of Embodiments 1-108, wherein $R^7$, $R^9$, and $R^{10}$ are independently chosen from H, $C_{1-6}$alkyl, $C_{2-6}$alkenyl, $C_{2-6}$ alkynyl optionally substituted by 1-3 $R^{19}$, phenyl, $C_{3-6}$cycloalkyl, 3-6 membered heterocycloalkyl, 5-6 membered heteroaryl, halogen, —CN, —C(=O)$R^{20}$, —C(=O)NR$^{22}$R$^{23}$, —NR$^{22}$R$^{23}$, —NR$^{24}$C(=O)$R^{20}$, and —OR$^{20}$; $R^8$ is chosen from H, $C_{1-6}$ alkyl, $C_{2-6}$alkenyl, $C_{2-6}$alkynyl optionally substituted by 1-3 $R^{19}$, $C_{3-6}$cycloalkyl, 3-6 membered heterocycloalkyl, halogen, —CN, —C(=O)$R^{20}$, —C(=O)NR$^{22}$R$^{23}$, —NR$^{22}$R$^{23}$, —NR$^{24}$C(=O)$R^{20}$, and —OR$^{20}$; alternatively, either or both of $R^7$ and $R^8$, and/or $R^9$ and $R^{10}$, can, together with the atoms linking them, form a phenyl, $C_{3-6}$ cycloalkyl, 3-6 membered heterocycloalkyl or a 5-6 membered heteroaryl.

Embodiment 155

The compound of any of Embodiments 1-108, wherein $R^7$ and $R^{10}$ are independently chosen from H, $C_{1-6}$alkyl, $C_{2-6}$alkenyl, $C_{2-6}$alkynyl optionally substituted by 1-3 $R^{19}$, phenyl, $C_{3-6}$cycloalkyl, 3-6 membered heterocycloalkyl, 5-6 membered heteroaryl, halogen, —CN, —C(=O)$R^{20}$, —C(=O)NR$^{22}$R$^{23}$, —NR$^{22}$R$^{23}$, —NR$^{24}$C(=O)$R^{20}$, and —OR$^{20}$; $R^8$ and $R^9$ are independently chosen from $C_{1-6}$alkyl, $C_{2-6}$alkenyl, $C_{2-6}$alkynyl optionally substituted by 1-3 $R^{19}$, phenyl, $C_{3-6}$cycloalkyl, 3-6 membered heterocycloalkyl, 5-6 membered heteroaryl, halogen, —CN, —C(=O)$R^{20}$, —C(=O)NR$^{22}$R$^{23}$, —NR$^{22}$R$^{23}$, —NR$^{24}$C(=O)$R^{20}$, and —OR$^{20}$; alternatively, either or both of $R^7$ and $R^8$, and/or $R^9$ and $R^{10}$, can, together with the atoms linking them, form a phenyl, $C_{3-6}$cycloalkyl, 3-6 membered heterocycloalkyl or a 5-6 membered heteroaryl.

Embodiment 156

The compound of any of Embodiments 1-108, wherein $R^7$ and $R^{10}$ are independently chosen from H, $C_{1-6}$alkyl, $C_{2-6}$alkenyl, $C_{2-6}$alkynyl optionally substituted by 1-3 $R^{19}$, phenyl, $C_{3-6}$cycloalkyl, 3-6 membered heterocycloalkyl, 5-6 membered heteroaryl, halogen, —CN, —C(=O)$R^{20}$, —C(=O)NR$^{22}$R$^{23}$, —NR$^{22}$R$^{23}$, —NR$^{24}$C(=O)$R^{20}$, and —OR$^{20}$; $R^8$ is chosen from $C_{1-6}$ alkyl, $C_{2-6}$alkenyl, $C_{2-6}$alkynyl optionally substituted by 1-3 $R^{19}$, $C_{3-6}$cycloalkyl, 3-6 membered heterocycloalkyl, halogen, —CN, —C(=O)$R^{20}$, —C(=O)NR$^{22}$R$^{23}$, —NR$^{22}$R$^{23}$, —NR$^{24}$C(=O)$R^{20}$, and —OR$^{20}$; $R^9$ is chosen from $C_{1-6}$alkyl, $C_{2-6}$alkenyl, $C_{2-6}$alkynyl optionally substituted by 1-3 $R^{19}$, phenyl, $C_{3-6}$cycloalkyl, 3-6 membered heterocycloalkyl, 5-6 membered heteroaryl, halogen, —CN, —C(=O)R$^{20}$, —C(=O)NR$^{22}$R$^{23}$, —NR$^{22}$R$^{23}$, —NR$^{24}$C(=O)R$^{20}$, and —OR$^{20}$; alternatively, either
or both of R$^7$ and R$^8$, and/or R$^9$ and R$^{10}$, can, together with the atoms linking them, form a phenyl, C$_{3-6}$cycloalkyl, 3-6 membered heterocycloalkyl or a 5-6 membered heteroaryl.

Embodiment 157

The compound of any of Embodiments 1-108, wherein R$^7$, R$^8$, R$^9$, and R$^{10}$ are independently chosen from H, C$_{1-6}$alkyl, C$_{2-6}$alkenyl, C$_{2-6}$ alkynyl, phenyl, C$_{3-6}$cycloalkyl, 3-6 membered heterocycloalkyl, 5-6 membered heteroaryl, halogen, —CN, —C(=O)R$^{20}$, —C(=O)NR$^{22}$R$^{23}$, —NR$^{22}$R$^{23}$, —NR$^{24}$C(=O)R$^{20}$, and —OR$^{20}$; alternatively, either or both of R$^7$ and R$^8$, and/or R$^9$ and R$^{10}$, can, together with the atoms linking them, form a phenyl, C$_{3-6}$cycloalkyl, 3-6 membered heterocycloalkyl or a 5-6 membered heteroaryl.

Embodiment 158

The compound of any of Embodiments 1-108, wherein R$^7$, R$^9$, and R$^{10}$ are independently chosen from H, C$_{1-6}$alkyl, C$_{2-6}$alkenyl, C$_{2-6}$ alkynyl, phenyl, C$_{3-6}$cycloalkyl, 3-6 membered heterocycloalkyl, 5-6 membered heteroaryl, halogen, —CN, —C(=O)R$^{20}$, —C(=O)NR$^{22}$R$^{23}$, —NR$^{22}$R$^{23}$, —NR$^{24}$C(=O)R$^{20}$, and —OR$^{20}$; R$^8$ is chosen from H, C$_{1-6}$alkyl, C$_{2-6}$alkenyl, C$_{2-6}$alkynyl, C$_{3-6}$cycloalkyl, 3-6 membered heterocycloalkyl, halogen, —CN, —C(=O)R$^{20}$, —C(=O)NR$^{22}$R$^{23}$, —NR$^{22}$R$^{23}$, —NR$^{24}$C(=O)R$^{20}$, —OR$^{20}$; alternatively, either or both of R$^7$ and R$^8$, and/or R$^9$ and R$^{10}$, can, together with the atoms linking them, form a phenyl, C$_{3-6}$cycloalkyl, 3-6 membered heterocycloalkyl or a 5-6 membered heteroaryl.

Embodiment 159

The compound of any of Embodiments 1-108, wherein R$^7$, R$^8$, R$^9$, and R$^{10}$ are independently chosen from H, C$_{1-6}$alkyl, C$_{2-6}$alkynyl, phenyl, C$_{3-6}$cycloalkyl, 3-6 membered heterocycloalkyl, 5-6 membered heteroaryl, halogen, —CN, —C(=O)R$^{20}$, —C(=O)NR$^{22}$R$^{23}$, —NR$^{22}$R$^{23}$, —NR$^{24}$C(=O)R$^{20}$, and —OR$^{20}$; alternatively, either
or both of R$^7$ and R$^8$, and/or R$^9$ and R$^{10}$, can, together with the atoms linking them, form a C$_{3-6}$cycloalkyl or a 3-6 membered heterocycloalkyl.

Embodiment 160

The compound of any of Embodiments 1-108, wherein R$^7$, R$^9$, and R$^{10}$ are independently chosen from H, C$_{1-6}$alkyl, C$_{2-6}$alkynyl, phenyl, C$_{3-6}$cycloalkyl, 3-6 membered heterocycloalkyl, 5-6 membered heteroaryl, halogen, —CN, —C(=O)R$^{20}$, —C(=O)NR$^{22}$R$^{23}$, —NR$^{22}$R$^{23}$, —NR$^{24}$C(=O)R$^{20}$, and —OR$^{20}$; R$^8$ is chosen from H, C$_{1-6}$alkyl, C$_{2-6}$alkynyl, C$_{3-6}$cycloalkyl, 3-6 membered heterocycloalkyl, halogen, —CN, —C(=O)R$^{20}$, —C(=O)NR$^{22}$R$^{23}$, —NR$^{22}$R$^{23}$, —NR$^{24}$C(=O)R$^{20}$, and —OR$^{20}$; alternatively, either
or both of R$^7$ and R$^8$, and/or R$^9$ and R$^{10}$, can, together with the atoms linking them, form a C$_{3-6}$cycloalkyl or a 3-6 membered heterocycloalkyl.

Embodiment 161

The compound of any of Embodiments 1-108, wherein R$^7$, R$^8$, R$^9$, and R$^{10}$ are independently chosen from H, C$_{1-6}$alkyl optionally substituted by 1-13 R$^{19}$, C$_{2-6}$alkenyl optionally substituted by 1-11 R$^{19}$, C$_{2-6}$alkynyl optionally substituted by 1-9 R$^{19}$, C$_{6-11}$aryl optionally substituted by 1-11 R$^{19}$, C$_{3-11}$ cycloalkyl optionally substituted by 1-21 R$^{19}$, 3-15 membered heterocycloalkyl optionally substituted by 1-28 R$^{19}$, 5-15 membered heteroaryl optionally substituted by 1-15 R$^{19}$, halogen, —CN, —C(=O)NR$^{22}$R$^{23}$, and —NR$^{22}$R$^{23}$; alternatively, either or both of R$^7$ and R$^8$, and/or R$^9$ and R$^{10}$, can, together with the atoms linking them, form a C$_{6-11}$aryl optionally substituted by 1-11 R$^{19}$, C$_{3-11}$ cycloalkyl optionally substituted by 1-21 R$^{19}$, 3-15 membered heterocycloalkyl optionally substituted by 1-28 R$^{19}$ or a 5-15 membered heteroaryl optionally substituted by 1-15 R$^{19}$.

Embodiment 162

The compound of any of Embodiments 1-108, wherein R$^7$, R$^9$, and R$^{10}$ are independently chosen from H, C$_{1-6}$alkyl optionally substituted by 1-13 R$^{19}$, C$_{2-6}$alkenyl optionally substituted by 1-11 R$^{19}$, C$_{2-6}$alkynyl optionally substituted by 1-9 R$^{19}$, C$_{6-11}$aryl optionally substituted by 1-11 R$^{19}$, C$_{3-11}$cycloalkyl keep tagging optionally substituted by 1-21 R$^{19}$, 3-15 membered heterocycloalkyl optionally substituted by 1-28 R$^{19}$, 5-15 membered heteroaryl optionally substituted by 1-15 R$^{19}$, halogen, —CN, —C(=O)NR$^{22}$R$^{23}$, and —NR$^{22}$R$^{23}$; R$^8$ is chosen from H, C$_{1-6}$alkyl optionally substituted by 1-13 R$^{19}$, C$_{2-6}$alkenyl optionally substituted by 1-11 R$^{19}$, C$_{2-6}$alkynyl optionally substituted by 1-9 R$^{19}$, C$_{3-11}$cycloalkyl optionally substituted by 1-21 R$^{19}$, 3-15 membered heterocycloalkyl optionally substituted by 1-28 R$^{19}$, halogen, —CN, —C(=O)NR$^{22}$R$^{23}$, and —NR$^{22}$R$^{23}$; alternatively, either or both of R$^7$ and R$^8$, and/or R$^9$ and R$^{10}$, can, together with the atoms linking them, form a C$_{6-11}$ aryl optionally substituted by 1-11 R$^{19}$, C$_{3-11}$cycloalkyl optionally substituted by 1-21 R$^{19}$, 3-15 membered heterocycloalkyl optionally substituted by 1-28 R$^{19}$ or a 5-15 membered heteroaryl optionally substituted by 1-R$^{19}$.

Embodiment 163

The compound of any of Embodiments 1-108, wherein R$^7$ and R$^8$ are independently chosen from H, C$_{1-6}$alkyl optionally substituted by 1-13 R$^{19}$, C$_{2-6}$alkenyl optionally substituted by 1-11 R$^{19}$, C$_{2-6}$alkynyl optionally substituted by 1-9 R$^{19}$, C$_{6-11}$aryl optionally substituted by 1-11 R$^{19}$, C$_{3-11}$cycloalkyl optionally substituted by 1-21 R$^{19}$, 3-15 membered heterocycloalkyl optionally substituted by 1-28 R$^{19}$, 5-15 membered heteroaryl optionally substituted by 1-15 R$^{19}$, halogen, —CN, —C(=O)NR$^{22}$R$^{23}$, and —NR$^{22}$R$^{23}$; alternatively, R$^7$ and R$^8$ can, together with the atoms linking them, form a C$_{6-11}$aryl optionally substituted by 1-11 R$^{19}$, or a 5-15 membered heteroaryl optionally substituted by 1-15 R$^{19}$.

Embodiment 164

The compound of any of Embodiments 1-108, wherein R$^7$ is chosen from H, C$_{1-6}$alkyl optionally substituted by 1-13 R$^{19}$, C$_{2-6}$alkenyl optionally substituted by 1-11 R$^{19}$, C$_{2-6}$alkynyl optionally substituted by 1-9 R$^{19}$, C$_{6-11}$aryl optionally substituted by 1-11 R$^{19}$, C$_{3-11}$cycloalkyl optionally substituted by 1-21 R$^{19}$, 3-15 membered heterocycloalkyl optionally substituted by 1-28 R$^{19}$, 5-15 membered heteroaryl optionally substituted by 1-15 R$^{19}$, halogen, —CN, —C(=O)NR$^{22}$R$^{23}$, and —NR$^{22}$R$^{23}$; R$^8$ is chosen from H, C$_{1-6}$alkyl optionally substituted by 1-13 R$^{19}$, $C_{2-6}$alkenyl optionally substituted by 1-11 $R^{19}$, $C_{2-6}$alkynyl optionally substituted by 1-9 $R^{19}$, $C_{3-11}$cycloalkyl optionally substituted by 1-21 $R^{19}$, 3-15 membered heterocycloalkyl optionally substituted by 1-28 $R^{19}$, halogen, —CN, —C(=O)NR$^{22}$R$^{23}$, and —NR$^{22}$R$^{23}$; alternatively, R$^7$ and R$^8$ can, together with the atoms linking them, form a $C_{6-11}$aryl optionally substituted by 1-11 $R^{19}$, or a 5-15 membered heteroaryl optionally substituted by 1-15 $R^{19}$.

Embodiment 165

The compound of any of Embodiments 1-108, wherein R$^9$ and R$^{10}$ are independently chosen from H, $C_{1-6}$alkyl optionally substituted by 1-13 $R^{19}$, $C_{6-11}$aryl optionally substituted by 1-11 $R^{19}$, and —C(=O)NR$^{22}$R$^{23}$; alternatively, R$^9$ and R$^{10}$ can, together with the atoms linking them, form a $C_{3-11}$ cycloalkyl optionally substituted by 1-21 $R^{19}$, or a 3-15 membered heterocycloalkyl optionally substituted by 1-28 $R^{19}$.

Embodiment 166

The compound of any of Embodiments 1-108, wherein R$^7$, R$^8$, R$^9$, and R$^{10}$ are independently chosen from H, $C_{1-6}$alkyl optionally substituted by 1-13 $R^{19}$, $C_{2-6}$alkenyl optionally substituted by 1-11 $R^{19}$, $C_{2-6}$alkynyl optionally substituted by 1-9 $R^{19}$, $C_{6-11}$aryl optionally substituted by 1-11 $R^{19}$, $C_{3-11}$ cycloalkyl optionally substituted by 1-21 $R^{19}$, 5-15 membered heteroaryl optionally substituted by 1-15 $R^{19}$, halogen, —CN, —C(=O)NR$^{22}$R$^{23}$, and —NR$^{22}$R$^{23}$; alternatively, either or both of R$^7$ and R$^8$, and/or R$^9$ and R$^{10}$, can, together with the atoms linking them, form a $C_{3-11}$cycloalkyl optionally substituted by 1-21 $R^{19}$, a $C_{6-11}$aryl optionally substituted by 1-11 $R^{19}$, a 5-15 membered heteroaryl optionally substituted by 1-15 $R^{19}$, or a 3-15 membered heterocycloalkyl optionally substituted by 1-28 $R^{19}$.

Embodiment 167

The compound of any of Embodiments 1-108, wherein R$^7$, R$^9$, and R$^{10}$ are independently chosen from H, $C_{1-6}$alkyl optionally substituted by 1-13 $R^{19}$, $C_{2-6}$alkenyl optionally substituted by 1-11 $R^{19}$, $C_{2-6}$alkynyl optionally substituted by 1-9 $R^{19}$, $C_{6-11}$aryl optionally substituted by 1-11 $R^{19}$, $C_{3-11}$cycloalkyl optionally substituted by 1-21 $R^{19}$, 5-15 membered heteroaryl optionally substituted by 1-15 $R^{19}$, halogen, —CN, —C(=O)NR$^{22}$R$^{23}$, and —NR$^{22}$R$^{23}$; R$^8$ is chosen from H, $C_{1-6}$alkyl optionally substituted by 1-13 $R^{19}$, $C_{2-6}$alkenyl optionally substituted by 1-11 $R^{19}$, $C_{2-6}$alkynyl optionally substituted by 1-9 $R^{19}$, $C_{3-11}$cycloalkyl optionally substituted by 1-21 $R^{19}$, halogen, —CN, —C(=O)NR$^{22}$R$^{23}$, and —NR$^{22}$R$^{23}$; alternatively, either or both of R$^7$ and R$^8$, and/or R$^9$ and R$^{10}$, can, together with the atoms linking them, form a $C_{3-11}$-cycloalkyl optionally substituted by 1-21 $R^{19}$, a $C_{6-11}$aryl optionally substituted by 1-11 $R^{19}$, a 5-15 membered heteroaryl optionally substituted by 1-15 $R^{19}$, or a 3-15 membered heterocycloalkyl optionally substituted by 1-28 $R^{19}$.

Embodiment 168

The compound of any of Embodiments 1-108, wherein R$^7$ and R$^8$ are independently chosen from H, $C_{1-6}$alkyl optionally substituted by 1-13 $R^{19}$, $C_{2-6}$alkenyl optionally substituted by 1-11 $R^{19}$, $C_{2-6}$alkynyl optionally substituted by 1-9 $R^{19}$, $C_{6-11}$aryl optionally substituted by 1-11 $R^{19}$, $C_{3-11}$cycloalkyl optionally substituted by 1-21 $R^{19}$, 5-15 membered heteroaryl optionally substituted by 1-15 $R^{19}$, halogen, —CN, —C(=O)NR$^{22}$R$^{23}$, and —NR$^{22}$R$^{23}$; alternatively, R$^7$ and R$^8$ can, together with the atoms linking them, form a $C_{6-11}$aryl optionally substituted by 1-11 $R^{19}$, or a 5-15 membered heteroaryl optionally substituted by 1-15 $R^{19}$.

Embodiment 169

The compound of any of Embodiments 1-108, wherein R$^7$ is chosen from H, $C_{1-6}$alkyl optionally substituted by 1-13 $R^{19}$, $C_{2-6}$alkenyl optionally substituted by 1-11 $R^{19}$, $C_{2-6}$alkynyl optionally substituted by 1-9 $R^{19}$, $C_{6-11}$aryl optionally substituted by 1-11 $R^{19}$, $C_{3-11}$cycloalkyl optionally substituted by 1-21 $R^{19}$, 5-15 membered heteroaryl optionally substituted by 1-15 $R^{19}$, halogen, —CN, —C(=O)NR$^{22}$R$^{23}$, and —NR$^{22}$R$^{23}$; R$^8$ is chosen from H, $C_{1-6}$alkyl optionally substituted by 1-13 $R^{19}$, $C_{2-6}$alkenyl optionally substituted by 1-11 $R^{19}$, $C_{2-6}$alkynyl optionally substituted by 1-9 $R^{19}$, $C_{3-11}$cycloalkyl optionally substituted by 1-21 $R^{19}$, halogen, —CN, —C(=O)NR$^{22}$R$^{23}$, and —NR$^{22}$R$^{23}$; alternatively, R$^7$ and R$^8$ can, together with the atoms linking them, form a $C_{6-11}$aryl optionally substituted by 1-11 $R^{19}$, or a 5-15 membered heteroaryl optionally substituted by 1-15 $R^{19}$.

Embodiment 170

The compound of any of Embodiments 1-108, wherein R$^9$ and R$^{10}$ are independently chosen from H, $C_{1-6}$alkyl optionally substituted by 1-13 $R^{19}$, and —C(=O)NR$^{22}$R$^{23}$; alternatively, R$^9$ and R$^{10}$ can, together with the atoms linking them, form a $C_{3-11}$-cycloalkyl optionally substituted by 1-21 $R^{19}$, or a 3-15 membered heterocycloalkyl optionally substituted by 1-28 $R^{19}$.

Embodiment 171

The compound of any of Embodiments 1-108, wherein R$^7$ is chosen from H, $C_{1-6}$alkyl optionally substituted by 1-13 $R^{19}$, and halogen; R$^8$ is chosen from H, $C_{1-6}$alkyl optionally substituted by 1-13 $R^{19}$, $C_{2-6}$alkenyl optionally substituted by 1-11 $R^{19}$, $C_{2-6}$alkynyl optionally substituted by 1-9 $R^{19}$, $C_{6-11}$aryl optionally substituted by 1-11 $R^{19}$, $C_{3-11}$cycloalkyl optionally substituted by 1-21 $R^{19}$, 5-15 membered heteroaryl optionally substituted by 1-15 $R^{19}$, halogen, —CN, —C(=O)NR$^{22}$R$^{23}$, and —NR$^{22}$R$^{23}$; alternatively, R$^7$ and R$^8$ can, together with the atoms linking them, form a $C_{6-11}$aryl optionally substituted by 1-11 $R^{19}$, or a 5-15 membered heteroaryl optionally substituted by 1-15 $R^{19}$.

Embodiment 172

The compound of any of Embodiments 1-108, wherein R$^7$ is chosen from H, $C_{1-6}$alkyl optionally substituted by 1-13 $R^{19}$, and halogen; R$^8$ is chosen from H, $C_{1-6}$alkyl optionally substituted by 1-13 $R^{19}$, $C_{2-6}$alkenyl optionally substituted by 1-11 $R^{19}$, $C_{2-6}$alkynyl optionally substituted by 1-9 $R^{19}$, $C_{3-11}$cycloalkyl optionally substituted by 1-21 $R^{19}$, halogen, —CN, —C(=O)NR$^{22}$R$^{23}$, and —NR$^{22}$R$^{23}$; alternatively, R$^7$ and R$^8$ can, together with the atoms linking them, form a $C_{6-11}$-aryl optionally substituted by 1-11 $R^{19}$, or a 5-15 membered heteroaryl optionally substituted by 1-15 $R^{19}$.

Embodiment 173

The compound of any of Embodiments 1-108, wherein R$^9$ is chosen from H and $C_{1-6}$alkyl optionally substituted by

Embodiment 174

The compound of any of Embodiments 1-108, wherein $R^9$ is $C_{1-6}$alkyl optionally substituted by 1-13 $R^{19}$; $R^{10}$ is chosen from H, $C_{1-6}$alkyl optionally substituted by 1-13 $R^{19}$, and —C(=O)NR$^{22}$R$^{23}$; alternatively, $R^9$ and $R^{10}$ can, together with the atoms linking them, form a $C_{3-11}$cycloalkyl optionally substituted by 1-21 $R^{19}$, or a 3-15 membered heterocycloalkyl optionally substituted by 1-28 $R^{19}$.

Embodiment 175

The compound of any of Embodiments 1-174, wherein $R^{12}$, $R^{13}$, $R^{14}$, and $R^{15}$ are independently chosen from H, $C_{1-6}$alkyl optionally substituted by 1-13 $R^{19}$, $C_{2-6}$alkenyl optionally substituted by 1-11 $R^{19}$, $C_{2-6}$alkynyl optionally substituted by 1-9 $R^{19}$, $C_{6-11}$aryl optionally substituted by 1-11 $R^{19}$, $C_{7-16}$arylalkyl optionally substituted by 1-19 $R^{19}$, $C_{3-11}$cycloalkyl optionally substituted by 1-21 $R^{19}$, $C_4$-17cycloalkylalkyl optionally substituted by 1-32 $R^{19}$, 3-15 membered heterocycloalkyl optionally substituted by 1-28 $R^{19}$, 4-21 membered heterocycloalkylalkyl optionally substituted by 1-40 $R^{19}$, 5-15 membered heteroaryl optionally substituted by 1-15 $R^{19}$, 6-21 membered heteroarylalkyl optionally substituted by 1-27 $R^{19}$, halogen, —CN, —C(=O)R$^{20}$, —C(=O)OR$^{20}$, —C(=O)NR$^{22}$R$^{23}$, —C(=O)C(=O)R$^{20}$, —C(=NR$^{25}$)R$^{20}$, —C(=NR$^{25}$)NR$^{22}$R$^{23}$, —C(=NOH)NR$^{22}$R$^{23}$, —C(=NOR$^{26}$)R$^{20}$, —C(=NNR$^{22}$R$^{23}$)R$^{20}$, —C(=NNR$^{24}$C(=O)R$^2$)R$^{20}$, —C(=NNR$^{24}$C(=O)OR$^{21}$)R$^{20}$, —C(=S)NR$^{22}$R$^{23}$, —NC, —NO$_2$, —NR$^{22}$R$^{23}$, —NR$^{24}$R$^{22}$R$^{23}$, —N=NR$^{24}$, —NR$^{24}$OR$^{26}$, —NR$^{24}$C(=O)R$^{20}$, —NR$^{24}$C(=O)C(=O)R$^{20}$, —NR$^{24}$C(=O)OR$^{21}$, —NR$^{24}$C(=O)C(=O)OR$^{21}$, —NR$^{24}$C(=O)NR$^{22}$R$^{23}$, —NR$^{23}$NR$^{24}$C(=O)R$^{20}$, —NR$^{24}$C(=O)NR$^{24}$C(=O)OR$^{20}$, —NR$^{24}$C(NR$^{25}$)NR$^{22}$R$^{23}$, —NR$^{24}$C(=O)C(=O)NR$^{22}$R$^{23}$, —NR$^{24}$C(=S)R$^{20}$, —NR$^{24}$C(=S)OR$^{20}$, —NR$^{24}$C(=S)NR$^{22}$R$^{23}$, —NR$^{24}$S(=O)$_2$R$^{21}$, —NR$^{24}$S(=O)$_2$NR$^{22}$R$^{23}$, —NR$^{24}$P(=O)R$^{28}$R$^{28}$, —NR$^{24}$P(=O)(22R$^{23}$)(NR$^{22}$R$^{23}$), —NR$^{24}$P(=O)(OR$^{20}$)(OR$^{20}$), —NR$^{24}$P(=O)(SR$^{20}$)(SR$^{20}$), —OR$^{20}$, —OCN, —OC(=O)R$^{20}$, —OC(=O)NR$^{22}$R$^{23}$, —OC(=O)OR$^{20}$, —OC(=NNR$^{22}$R$^{23}$), —OS(=O)R$^{20}$, —OS(=O)$_2$R$^{20}$, —OS(=O)$_2$OR$^{20}$, —O(=O)$_2$NR$^{22}$R$^{23}$, —OP(=O)R$^{28}$R$^{28}$, —OP(=O)(NR$^{22}$R$^{23}$)(NR$^{22}$R$^{23}$) OP(=O)(OR$^{20}$)(OR$^{20}$), —OP(=O)(SR$^{20}$)(SR$^{20}$), —Si(R$^{24}$)$_3$, —SCN, —S(=O)$_n$R$^{20}$, —S(=O)$_2$OR$^{20}$, —SO$_3$R$^{27}$, —S(=O)$_2$NR$^{22}$R$^{23}$, —S(=O)NR$^{22}$R$^{23}$, —SP(=O)R$^{28}$R$^{28}$, —SP(=O)(NR$^{22}$R$^{23}$)(NR$^{22}$R$^{23}$), —SP(=O)(OR$^{20}$)(OR$^{20}$), —SP(=O)(SR$^{20}$)(SR$^{20}$), —P(=O)R$^{28}$R$^{28}$, —P(=O)(NR$^{22}$R$^{23}$)(NR$^{22}$R$^{23}$), —P(=O)(OR$^{20}$)(OR$^{20}$), and —P(=O)(SR$^{20}$)(SR$^{20}$); alternatively, either or both of $R^{12}$ and $R^{13}$, and/or $R^{14}$ and $R^{15}$, can, together with the atoms linking them, form a $C_{6-11}$aryl optionally substituted by 1-11 $R^{19}$, $C_{3-11}$-cycloalkyl optionally substituted by 1-21 $R^{19}$, 3-15 membered heterocycloalkyl optionally substituted by 1-28 $R^{19}$ or a 5-15 membered heteroaryl optionally substituted by 1-15 $R^{19}$.

Embodiment 176

The compound of any of Embodiments 1-174, wherein $R^{12}$, $R^{13}$, $R^{14}$, and $R^{15}$ are independently chosen from H, $C_{1-6}$alkyl optionally substituted by 1-13 $R^{19}$, $C_{2-6}$alkenyl optionally substituted by 1-11 $R^{19}$, $C_{2-6}$alkynyl optionally substituted by 1-9 $R^{19}$, $C_{6-11}$aryl optionally substituted by 1-11 $R^{19}$, $C_{7-16}$arylalkyl optionally substituted by 1-19 $R^{19}$, $C_{3-11}$-cycloalkyl optionally substituted by 1-21 $R^{19}$, $C_4$-17cycloalkylalkyl optionally substituted by 1-32 $R^{19}$, 3-15 membered heterocycloalkyl optionally substituted by 1-28 $R^{19}$, 4-21 membered heterocycloalkylalkyl optionally substituted by 1-40 $R^{19}$, 5-15 membered heteroaryl optionally substituted by 1-15 $R^{19}$, 6-21 membered heteroarylalkyl optionally substituted by 1-27 $R^{19}$, halogen, —CN, —C(=O)R$^{20}$, —C(=O)OR$^{20}$, —C(=O)NR$^{22}$R$^{23}$, —NC, —NO$_2$, —NR$^{22}$R$^{23}$, —NR$^{24}$NR$^{22}$R$^{23}$, —N=NR$^{24}$, —NR$^{24}$OR$^{26}$, —NR$^{24}$C(=O)R$^{20}$, —NR$^{24}$C(=O)OR$^{21}$, —NR$^{24}$C(=O)NR$^{22}$R$^{23}$, —NR$^{24}$S(=O)$_2$R$^{21}$, —NR$^{24}$S(=O)$_2$NR$^{22}$R$^{23}$, —NR$^{24}$P(=O)R$^{28}$R$^{28}$, —NR$^{24}$P(=O)(NR$^{22}$R$^{23}$)(NR$^{22}$R$^{23}$), —NR$^{24}$P(=O)(OR$^{20}$)(OR$^{20}$), —OR$^{20}$, —OCN, —OC(=O)R$^{20}$, —OC(=O)NR$^{22}$R$^{23}$, —OC(=O)OR$^{20}$, —OS(=O)R$^{20}$, —OS(=O)$_2$R$^{20}$, —OS(=O)$_2$OR$^{20}$, —OS(=O)$_2$NR$^{22}$R$^{23}$, —OP(=O)R$^{28}$R$^{28}$, —OP(=O)(NR$^{22}$R$^{23}$)(NR$^{22}$R$^{23}$), —OP(=O)(OR$^{20}$)(OR$^{20}$), —SCN, —S(=O)$_n$R$^{20}$, —S(=O)$_2$OR$^{20}$, —SO$_3$R$^{27}$, —S(=O)$_2$NR$^{22}$R$^{23}$, —S(=O)NR$^{22}$R$^{23}$, —P(=O)R$^{28}$R$^{28}$, —P(=O)(NR$^{22}$R$^{23}$)(NR$^{22}$R$^{23}$), and —P(=O)(OR$^{20}$)(OR$^{20}$); alternatively, either or both of $R^{12}$ and $R^{13}$, and/or $R^{14}$ and $R^{15}$, can, together with the atoms linking them, form a $C_{6-11}$aryl optionally substituted by 1-11 $R^{19}$, $C_{3-11}$-cycloalkyl optionally substituted by 1-21 $R^{19}$, 3-15 membered heterocycloalkyl optionally substituted by 1-28 $R^{19}$ or a 5-15 membered heteroaryl optionally substituted by 1-15 $R^{19}$.

Embodiment 177

The compound of any of Embodiments 1-174, wherein $R^{12}$, $R^{13}$, $R^{14}$, and $R^{15}$ are independently chosen from H, $C_{1-6}$alkyl optionally substituted by 1-6 $R^{19}$, $C_{2-6}$alkenyl optionally substituted by 1-6 $R^{19}$, $C_{2-6}$alkynyl optionally substituted by 1-6 $R^{19}$, $C_{6-11}$aryl optionally substituted by 1-6 $R^{19}$, $C_7$-16arylalkyl optionally substituted by 1-6 $R^{19}$, $C_{3-11}$cycloalkyl optionally substituted by 1-6 $R^{19}$, $C_{4-17}$cycloalkylalkyl optionally substituted by 1-6 $R^{19}$, 3-15 membered heterocycloalkyl optionally substituted by 1-6 $R^{19}$, 4-21 membered heterocycloalkylalkyl optionally substituted by 1-6 $R^{19}$, 5-15 membered heteroaryl optionally substituted by 1-6 $R^{19}$, 6-21 membered heteroarylalkyl optionally substituted by 1-6 $R^{19}$, halogen, —CN, —C(=O)R$^{20}$, —C(=O)OR$^{20}$, —C(=O)NR$^{22}$R$^{23}$, —NC, —NO$_2$, —NR$^{22}$R$^{23}$, —NR$^{24}$NR$^{22}$R$^{23}$, —N=NR$^{24}$, —NR$^{24}$OR$^{26}$, —NR$^{24}$C(=O)R$^{20}$, —NR$^{24}$C(=O)OR$^{21}$, —NR$^{24}$C(=O)NR$^{22}$R$^{22}$R$^{23}$, —NR$^{24}$S(=O)$_2$R$^{21}$, —NR$^{24}$S(=O)$_2$NR$^{22}$R$^{23}$, —NR$^{24}$P(=O)R$^{28}$R$^{28}$, —NR$^{24}$P(=O)(NR$^{22}$R$^{23}$)(NR$^{22}$R$^{23}$), —NR$^{24}$P(=O)(OR$^{20}$)(OR$^{20}$), —OR$^{20}$, —OCN, —OC(=O)R$^{20}$, —OC(=O)NR$^{22}$R$^{23}$, —OC(=O)OR$^{20}$, —OS(=O)R$^{20}$, —OS(=O)$_2$R$^{20}$, —OS(=O)$_2$OR$^{20}$, —OS(=O)$_2$NR$^{22}$R$^{23}$, —OP(=O)R$^{28}$R$^{28}$, —OP(=O)(NR$^{22}$R$^{23}$)(NR$^{2223}$), —OP(=O)(OR$^{20}$)(OR$^{20}$), —SCN, —S(=O)$_n$R$^{20}$, —S(=O)$_2$OR$^{20}$, —SO$_3$R$^{27}$, —S(=O)$_2$NR$^{22}$R$^{23}$, —S(=O)NR$^{22}$R$^{23}$, —P(=O)R$^{28}$R$^{28}$, —P(=O)(NR$^{22}$R$^{23}$)(NR$^{22}$R$^{23}$), and —P(=O)(OR$^{20}$)(OR$^{20}$); alternatively, either or both of $R^{12}$ and $R^{13}$, and/or $R^{14}$ and $R^{15}$, can, together with the atoms linking them, form a $C_{6-11}$aryl optionally substituted by 1-6 $R^{19}$, $C_{3-11}$cycloalkyl optionally substituted by 1-6 $R^{19}$, 3-15 membered heterocycloalkyl optionally substituted by 1-6 $R^{19}$ or a 5-15 membered heteroaryl optionally substituted by 1-6 $R^{19}$.

Embodiment 178

The compound of any of Embodiments 1-174, wherein $R^{12}$, $R^{13}$, $R^{14}$, and $R^{15}$ are independently chosen from H, $C_{1-6}$alkyl optionally substituted by 1-6 $R^{19}$, $C_{2-6}$alkenyl optionally substituted by 1-6 $R^{19}$, $C_{2-6}$alkynyl optionally substituted by 1-6 $R^{19}$, $C_{6-11}$aryl optionally substituted by 1-6 $R^{19}$, $C_{7-16}$arylalkyl optionally substituted by 1-6 $R^{19}$, $C_{3-11}$cycloalkyl optionally substituted by 1-6 $R^{19}$, $C_{4-17}$cycloalkylalkyl optionally substituted by 1-6 $R^{19}$, 3-15 membered heterocycloalkyl optionally substituted by 1-6 $R^{19}$, 4-21 membered heterocycloalkylalkyl optionally substituted by 1-6 $R^{19}$, 5-15 membered heteroaryl optionally substituted by 1-6 $R^{19}$, 6-21 membered heteroarylalkyl optionally substituted by 1-6 $R^{19}$, halogen, —CN, —C(=O)$R^{20}$, —C(=O)O$R^{20}$, —C(=O)N$R^{22}R^{23}$, —NO$_2$, —N$R^{22}R^{23}$, —N$R^{24}$C(=O)$R^{20}$, —N$R^{24}$C(=O)O$R^{21}$, —N$R^{24}$C(=O)N$R^{22}R^{22}R^{23}$, —N$R^{24}$S(=O)$_2R^{21}$, —N$R^{24}$S(=O)$_2$N$R^{22}R^{23}$, —O$R^{20}$, —OC(=O)$R^{20}$, —OC(=O)N$R^{22}R^{23}$, —OC(=O)O$R^{20}$, —S(=O)$_nR^{20}$, —S(=O)$_2$O$R^{20}$, —SO$_3R^{27}$, —S(=O)$_2$N$R^{22}R^{23}$, —S(=O)N$R^{22}R^{23}$, —P(=O)$R^{28}R^{28}$, —P(=O)(N$R^{22}R^{23}$)(N$R^{22}R^{23}$), and —P(=O)(O$R^{20}$)(O$R^{20}$); alternatively, either or both of $R^{12}$ and $R^{13}$, and/or $R^{14}$ and $R^{15}$, can, together with the atoms linking them, form a $C_{6-11}$aryl optionally substituted by 1-6 $R^{19}$, $C_{3-11}$cycloalkyl optionally substituted by 1-6 $R^{19}$, 3-15 membered heterocycloalkyl optionally substituted by 1-6 $R^{19}$ or a 5-15 membered heteroaryl optionally substituted by 1-6 $R^{19}$.

Embodiment 179

The compound of any of Embodiments 1-174, wherein $R^{12}$, $R^{13}$, $R^{14}$, and $R^{15}$ are independently chosen from H, $C_{1-6}$alkyl optionally substituted by 1-3 $R^{19}$, $C_{2-6}$alkenyl optionally substituted by 1-3 $R^{19}$, $C_{2-6}$alkynyl optionally substituted by 1-3 $R^{19}$, $C_{6-11}$aryl optionally substituted by 1-3 $R^{19}$, $C_{7-16}$arylalkyl optionally substituted by 1-3 $R^{19}$, $C_{3-11}$cycloalkyl optionally substituted by 1-3 $R^{19}$, $C_{4-17}$cycloalkylalkyl optionally substituted by 1-3 $R^{19}$, 3-15 membered heterocycloalkyl optionally substituted by 1-3 $R^{19}$, 4-21 membered heterocycloalkylalkyl optionally substituted by 1-3 $R^{19}$, 5-15 membered heteroaryl optionally substituted by 1-3 $R^{19}$, 6-21 membered heteroarylalkyl optionally substituted by 1-3 $R^{19}$, halogen, —CN, —C(=O)$R^{20}$, —C(=O)O$R^{20}$, —C(=O)N$R^{22}R^{23}$, —NO$_2$, —N$R^{22}R^{23}$, —N$R^{24}$C(=O)$R^{20}$, —N$R^{24}$C(=O)O$R^{21}$, —N$R^{24}$C(=O)N$R^{22}R^{23}$, —N$R^{24}$S(=O)$_2R^{21}$, —N$R^{24}$S(=O)$_2$N$R^{22}R^{23}$, —O$R^{20}$, —OC(=O)$R^{20}$, —OC(=O)N$R^{22}R^{23}$, —OC(=O)O$R^{20}$, —S(=O)$_nR^{20}$, —S(=O)$_2$O$R^{20}$, —SO$_3R^{27}$, —S(=O)$_2$N$R^{22}R^{23}$, —S(=O)N$R^{22}R^{23}$, —P(=O)$R^{28}R^{28}$, —P(=O)(N$R^{22}R^{23}$)(N$R^{22}R^{23}$), and —P(=O)(O$R^{20}$)(O$R^{20}$); alternatively, either or both of $R^{12}$ and $R^{13}$, and/or $R^{14}$ and $R^{15}$, can, together with the atoms linking them, form a $C_{6-11}$-aryl optionally substituted by 1-3 $R^{19}$, $C_{3-11}$cycloalkyl optionally substituted by 1-3 $R^{19}$, 3-15 membered heterocycloalkyl optionally substituted by 1-3 $R^{19}$ or a 5-15 membered heteroaryl optionally substituted by 1-3 $R^{19}$.

Embodiment 180

The compound of any of Embodiments 1-174, wherein $R^{12}$, $R^{13}$, $R^{14}$, and $R^{15}$ are independently chosen from H, $C_{1-6}$alkyl optionally substituted by 1-3 $R^{19}$, $C_{2-6}$alkenyl optionally substituted by 1-3 $R^{19}$, $C_{2-6}$alkynyl optionally substituted by 1-3 $R^{19}$, $C_{6-11}$aryl optionally substituted by 1-3 $R^{19}$, $C_{3-11}$cycloalkyl optionally substituted by 1-3 $R^{19}$, 3-15 membered heterocycloalkyl optionally substituted by 1-3 $R^{19}$, 5-15 membered heteroaryl optionally substituted by 1-3 $R^{19}$, halogen, —CN, —C(=O)$R^{20}$, —C(=O)O$R^{20}$, —C(=O)N$R^{22}R^{23}$, —NO$_2$, —N$R^{22}R^{23}$, —N$R^{24}$C(=O)$R^{20}$, —N$R^{24}$C(=O)O$R^{21}$, —N$R^{24}$C(=O)N$R^{22}R^{23}$, —N$R^{24}$S(=O)$_2R^{21}$, —N$R^{24}$S(=O)$_2$N$R^{22}R^{23}$, —O$R^{20}$, —OC(=O)$R^{20}$, —OC(=O)N$R^{22}R^{23}$, —OC(=O)O$R^{20}$, —S(=O)$_nR^{20}$, —S(=O)$_2$O$R^{20}$, —SO$_3R^{27}$, —S(=O)$_2$N$R^{22}R^{23}$, —S(=O)N$R^{22}R^{23}$, —P(=O)$R^{28}R^{28}$, —P(=O)(N$R^{22}R^{23}$)(N$R^{22}R^{23}$), and —P(=O)(O$R^{20}$)(O$R^{20}$); alternatively, either or both of $R^{12}$ and $R^{13}$, and/or $R^{14}$ and $R^{15}$, can, together with the atoms linking them, form a $C_{6-11}$aryl optionally substituted by 1-3 $R^{19}$, $C_{3-11}$ cycloalkyl optionally substituted by 1-3 $R^{19}$, 3-15 membered heterocycloalkyl optionally substituted by 1-3 $R^{19}$ or a 5-15 membered heteroaryl optionally substituted by 1-3 $R^{19}$.

Embodiment 181

The compound of any of Embodiments 1-174, wherein $R^{12}$, $R^{13}$, $R^{14}$, and $R^{15}$ are independently chosen from H, $C_{1-6}$alkyl optionally substituted by 1-3 $R^{19}$, $C_{2-6}$alkenyl optionally substituted by 1-3 $R^{19}$, $C_{2-6}$alkynyl optionally substituted by 1-3 $R^{19}$, $C_{6-10}$aryl optionally substituted by 1-3 $R^{19}$, $C_{3-7}$cycloalkyl optionally substituted by 1-3 $R^{19}$, 3-7 membered heterocycloalkyl optionally substituted by 1-3 $R^{19}$, 5-6 membered heteroaryl optionally substituted by 1-3 $R^{19}$, halogen, —CN, —C(=O)$R^{20}$, —C(=O)O$R^{20}$, —C(=O)N$R^{22}R^{23}$, —NO$_2$, —N$R^{22}R^{23}$, —N$R^{24}$C(=O)$R^{20}$, —N$R^{24}$C(=O)O$R^{21}$, —N$R^{24}$C(=O)N$R^{22}R^{22}R^{23}$, —N$R^{24}$S(=O)$_2R^{21}$, —N$R^{24}$S(=O)$_2$N$R^{22}R^{23}$, —O$R^{20}$, —OC(=O)$R^{20}$, —OC(=O)N$R^{22}R^{23}$, —OC(=O)O$R^{20}$, —S(=O)$_nR^{20}$, —S(=O)$_2$O$R^{20}$, —SO$_3R^{27}$, —S(=O)$_2$N$R^{22}R^{23}$, —S(=O)N$R^{22}R^{23}$, —P(=O)$R^{28}R^{28}$, —P(=O)(N$R^{22}R^{23}$)(N$R^{22}R^{23}$), and —P(=O)(O$R^{20}$)(O$R^{20}$); alternatively, either or both of $R^{12}$ and $R^{13}$, and/or $R^{14}$ and $R^{15}$, can, together with the atoms linking them, form a $C_{6-10}$aryl optionally substituted by 1-3 $R^{19}$, $C_{3-7}$cycloalkyl optionally substituted by 1-3 $R^{19}$, 3-7 membered heterocycloalkyl optionally substituted by 1-3 $R^{19}$ or a 5-6 membered heteroaryl optionally substituted by 1-3 $R^{19}$.

Embodiment 182

The compound of any of Embodiments 1-174, wherein $R^{12}$, $R^{13}$, $R^{14}$, and $R^{15}$ are independently chosen from H, $C_{1-6}$alkyl optionally substituted by 1-3 $R^{19}$, $C_{2-6}$alkenyl optionally substituted by 1-3 $R^{19}$, $C_{2-6}$alkynyl optionally substituted by 1-3 $R^{19}$, $C_{6-11}$aryl optionally substituted by 1-3 $R^{19}$, $C_{7-16}$arylalkyl optionally substituted by 1-3 $R^{19}$, $C_{3-11}$cycloalkyl optionally substituted by 1-3 $R^{19}$, $C_417$cycloalkylalkyl optionally substituted by 1-3 $R^{19}$, 3-15 membered heterocycloalkyl optionally substituted by 1-3 $R^{19}$, 4-21 membered heterocycloalkylalkyl substituted by 1-3 $R^{19}$, 5-15 membered heteroaryl optionally substituted by 1-3 $R^{19}$, 6-21 membered heteroarylalkyl optionally substituted by 1-3 $R^{19}$, halogen, —CN, —C(=O)$R^{20}$, —C(=O)N$R^{22}R^{23}$, —NO$_2$, —N$R^{22}R^{23}$, —N$R^{24}$C(=O)$R^{20}$, —N$R^{24}$S(=O)$_2R^{21}$, —O$R^{20}$, —S(=O)$_nR^{20}$, and —S(=O)$_2$N$R^{22}R^{23}$; alternatively, either or both of $R^{12}$ and $R^{13}$, and/or $R^{14}$ and $R^{15}$, can, together with the atoms linking them, form a $C_{6-11}$aryl optionally substituted by 1-3 $R^{19}$, $C_{3-11}$cycloalkyl optionally substituted by 1-3 $R^{19}$, 3-15

Embodiment 183

The compound of any of Embodiments 1-174, wherein $R^{12}$, $R^{13}$, $R^{14}$, and $R^{15}$ are independently chosen from H, $C_{1-6}$alkyl optionally substituted by 1-3 $R^{19}$, $C_{2-6}$alkenyl optionally substituted by 1-3 $R^{19}$, $C_{2-6}$alkynyl substituted by 1-3 $R^{19}$, $C_{6-11}$aryl optionally substituted by 1-3 $R^{19}$, $C_{3-11}$cycloalkyl optionally substituted by 1-3 $R^{19}$, 3-15 membered heterocycloalkyl optionally substituted by 1-3 $R^{19}$, 5-15 membered heteroaryl optionally substituted by 1-3 $R^{19}$, halogen, —CN, —C(=O)$R^{20}$, —C(=O)NR$^{22}$R$^{23}$, —NO$_2$, —NR$^{22}$R$^{23}$, —NR$^{24}$C(=O)R$^{20}$, —NR$^{24}$S(=O)$_2$R$^{21}$, —OR$^{20}$, —S(=O)$_n$R$^{2}$, and —S(=O)$_2$NR$^{22}$R$^{23}$; alternatively, either or both of $R^{12}$ and $R^{13}$, and/or $R^{14}$ and $R^{15}$, can, together with the atoms linking them, form a $C_{6-11}$aryl optionally substituted by 1-3 $R^{19}$, $C_{3-11}$cycloalkyl optionally substituted by 1-3 $R^{19}$, 3-15 membered heterocycloalkyl optionally substituted by 1-3 $R^{19}$ or a 5-15 membered heteroaryl optionally substituted by 1-3 $R^{19}$.

Embodiment 184

The compound of any of Embodiments 1-174, wherein $R^{12}$, $R^{13}$, and $R^{15}$ are H; $R^{14}$ is chosen from H, $C_{1-6}$alkyl optionally substituted by 1-3 $R^{19}$, $C_{2-6}$alkenyl optionally substituted by 1-3 $R^{19}$, $C_{2-6}$alkynyl optionally substituted by 1-3 $R^{19}$, $C_{6-11}$aryl optionally substituted by 1-3 $R^{19}$, $C_{3-11}$cycloalkyl optionally substituted by 1-3 $R^{19}$, 3-15 membered heterocycloalkyl optionally substituted by 1-3 $R^{19}$, 5-15 membered heteroaryl optionally substituted by 1-3 $R^{19}$, halogen, —CN, —C(=O)$R^{20}$, —C(=O)NR$^{22}$R$^{23}$, —NO$_2$, —NR$^{22}$R$^{23}$, —NR$^{24}$C(=O)R$^{20}$, —NR$^{24}$S(=O)$_2$R$^{21}$, —OR$^{20}$, —S(=O)$_n$R$^{20}$, and —S(=O)$_2$NR$^{22}$R$^{23}$ alternatively, either or both of $R^{12}$ and $R^{13}$, and/or $R^{14}$ and $R^{15}$, can, together with the atoms linking them, form a $C_{6-11}$aryl optionally substituted by 1-3 $R^{19}$, $C_{3-11}$cycloalkyl optionally substituted by 1-3 $R^{19}$, 3-15 membered heterocycloalkyl optionally substituted by 1-3 $R^{19}$ or a 5-15 membered heteroaryl optionally substituted by 1-3 $R^{19}$.

Embodiment 185

The compound of any of Embodiments 1-174, wherein $R^{12}$, $R^{13}$, and $R^{14}$ are H; $R^{15}$ is chosen from H, $C_{1-6}$alkyl optionally substituted by 1-3 $R^{19}$, $C_{2-6}$alkenyl optionally substituted by 1-3 $R^{19}$, $C_{2-6}$alkynyl optionally substituted by 1-3 $R^{19}$, $C_{6-11}$aryl optionally substituted by 1-3 $R^{19}$, $C_{3-11}$cycloalkyl optionally substituted by 1-3 $R^{19}$, 3-15 membered heterocycloalkyl optionally substituted by 1-3 $R^{19}$, 5-15 membered heteroaryl optionally substituted by 1-3 $R^{19}$, halogen, —CN, —C(=O)$R^{20}$, —C(=O)NR$^{22}$R$^{23}$, —NO$_2$, —NR$^{22}$R$^{23}$, —NR$^{24}$C(=O)R$^{20}$, —NR$^{24}$S(=O)$_2$R$^{21}$, —OR$^{20}$, —S(=O)$_n$R$^{20}$, and —S(=O)$_2$NR$^{22}$R$^{23}$ alternatively, either or both of $R^{12}$ and $R^{13}$, and/or $R^{14}$ and $R^{15}$, can, together with the atoms linking them, form a $C_{6-11}$aryl optionally substituted by 1-3 $R^{19}$, $C_{3-11}$cycloalkyl optionally substituted by 1-3 $R^{19}$, 3-15 membered heterocycloalkyl optionally substituted by 1-3 $R^{19}$ or a 5-15 membered heteroaryl optionally substituted by 1-3 $R^{19}$.

Embodiment 186

The compound of any of Embodiments 1-174, wherein $R^{12}$, $R^{13}$, and $R^{15}$ are H; $R^{14}$ is chosen from H, $C_{1-6}$alkyl optionally substituted by 1-3 $R^{19}$, $C_{2-6}$alkenyl optionally substituted by 1-3 $R^{19}$, $C_{2-6}$alkynyl optionally substituted by 1-3 $R^{19}$, $C_{6-11}$aryl optionally substituted by 1-3 $R^{19}$, $C_{3-11}$cycloalkyl optionally substituted by 1-3 $R^{19}$, 3-15 membered heterocycloalkyl optionally substituted by 1-3 $R^{19}$, 5-15 membered heteroaryl optionally substituted by 1-3 $R^{19}$, halogen, —CN, —C(=O)$R^{20}$, —C(=O)NR$^{22}$R$^{23}$, —NO$_2$, —NR$^{22}$R$^{23}$, —NR$^{24}$C(=O)R$^{20}$, —NR$^{24}$S(=O)$_2$R$^{21}$, —OR$^{20}$, —S(=O)$_n$R$^{20}$, and —S(=O)$_2$NR$^{22}$R$^{23}$.

Embodiment 187

The compound of any of Embodiments 1-174, wherein $R^{12}$, $R^{13}$, and $R^{14}$ are H; $R^{15}$ is chosen from H, $C_{1-6}$alkyl optionally substituted by 1-3 $R^{19}$, $C_{2-6}$alkenyl optionally substituted by 1-3 $R^{19}$, $C_{2-6}$alkynyl optionally substituted by 1-3 $R^{19}$, $C_{6-11}$aryl optionally substituted by 1-3 $R^{19}$, $C_{3-11}$cycloalkyl optionally substituted by 1-3 $R^{19}$, 3-15 membered heterocycloalkyl optionally substituted by 1-3 $R^{19}$, 5-15 membered heteroaryl optionally substituted by 1-3 $R^{19}$, halogen, —CN, —C(=O)$R^{20}$, —C(=O)NR$^{22}$R$^{23}$, —NO$_2$, —NR$^{22}$R$^{23}$, —NR$^{24}$C(=O)R$^{20}$, —NR$^{24}$S(=O)$_2$R$^{21}$, —OR$^{20}$, —S(=O)$_n$R$^{20}$, and —S(=O)$_2$NR$^{22}$R$^{23}$.

Embodiment 188

The compound of any of Embodiments 1-174, wherein $R^{12}$, $R^{13}$, $R^{14}$, and $R^{15}$ are independently chosen from H, $C_{1-6}$alkyl optionally substituted by 1-3 $R^{19}$, $C_{2-6}$alkenyl optionally substituted by 1-3 $R^{19}$, $C_{2-6}$alkynyl optionally substituted by 1-3 $R^{19}$, $C_{6-10}$aryl optionally substituted by 1-3 $R^{19}$, $C_{3-7}$cycloalkyl optionally substituted by 1-3 $R^{19}$, 3-7 membered heterocycloalkyl optionally substituted by 1-3 $R^{19}$, 5-6 membered heteroaryl optionally substituted by 1-3 $R^{19}$, halogen, —CN, —C(=O)$R^{20}$, —C(=O)NR$^{22}$R$^{23}$, —NO$_2$, —NR$^{22}$R$^{23}$, —NR$^{24}$C(=O)R$^{20}$, —NR$^{24}$S(=O)$_2$R$^{21}$, —OR$^{20}$, —S(=O)$_n$R$^{20}$, and —S(=O)$_2$NR$^{22}$R$^{23}$; alternatively, either or both of $R^{12}$ and $R^{13}$ and/or $R^{14}$ and $R^{15}$, can, together with the atoms linking them, form a $C_{6-10}$aryl optionally substituted by 1-3 $R^{19}$, $C_{3-7}$cycloalkyl optionally substituted by 1-3 $R^{19}$ 3-7 membered heterocycloalkyl optionally substituted by 1-3 $R^{19}$ or a 5-6 membered heteroaryl optionally substituted by 1-3 $R^{19}$.

Embodiment 189

The compound of any of Embodiments 1-174, wherein $R^{12}$, $R^{13}$, and $R^{15}$ are H; $R^{14}$ is chosen from H, $C_{1-6}$alkyl optionally substituted by 1-3 $R^{19}$, $C_{2-6}$alkenyl optionally substituted by 1-3 $R^{19}$, $C_{2-6}$alkynyl optionally substituted by 1-3 $R^{19}$, $C_{6-10}$aryl optionally substituted by 1-3 $R^{19}$, $C_{3-7}$cycloalkyl optionally substituted by 1-3 $R^{19}$, 3-7 membered heterocycloalkyl optionally substituted by 1-3 $R^{19}$, 5-6 membered heteroaryl optionally substituted by 1-3 $R^{19}$, halogen, —CN, —C(=O)$R^{20}$, —C(=O)NR$^{22}$R$^{23}$, —NO$_2$, —NR$^{22}$R$^{23}$, —NR$^{24}$C(=O)R$^{20}$, —NR$^{24}$S(=O)$_2$R$^{21}$, —OR$^{20}$, —S(=O)$_n$R$^{20}$, and —S(=O)$_2$NR$^{22}$R$^{23}$; alternatively, either or both of $R^{12}$ and $R^{13}$, and/or $R^{14}$ and $R^{15}$, can, together with the atoms linking them, form a $C_{6-10}$aryl optionally substituted by 1-3 $R^{19}$, $C_{3-7}$cycloalkyl optionally substituted by 1-3 $R^{19}$ 3-7 membered heterocycloalkyl optionally substituted by 1-3 $R^{19}$ or a 5-6 membered heteroaryl optionally substituted by 1-3 $R^{19}$.

Embodiment 190

The compound of any of Embodiments 1-174, wherein $R^{12}$, $R^{13}$, and $R^{14}$ are H; $R^{15}$ is chosen from H, $C_{1-6}$alkyl optionally substituted by 1-3 $R^{19}$, $C_{2-6}$alkenyl optionally substituted by 1-3 $R^{19}$, $C_{2-6}$alkynyl optionally substituted by 1-3 $R^{19}$, $C_{6-10}$aryl optionally substituted by 1-3 $R^{19}$, $C_{3-7}$cycloalkyl optionally substituted by 1-3 $R^{19}$, 3-7 membered heterocycloalkyl optionally substituted by 1-3 $R^{19}$, 5-6 membered heteroaryl optionally substituted by 1-3 $R^{19}$, halogen, —CN, —C(=O)$R^{20}$, —C(=O)NR$^{22}$R$^{23}$, —NO$_2$, —NR$^{22}$R$^{23}$, —NR$^{24}$C(=O)R$^{20}$, —NR$^{24}$S(=O)$_2$R$^{21}$, —OR$^{20}$, —S(=O)$_n$R$^{20}$, and —S(=O)$_2$NR$^{22}$R$^{23}$; alternatively, either or both of $R^{12}$ and $R^{13}$ and/or $R^{14}$ and $R^{15}$, can, together with the atoms linking them, form a $C_{6-10}$aryl optionally substituted by 1-3 $R^{19}$, $C_{3-7}$cycloalkyl optionally substituted by 1-3 $R^{19}$, 3-7 membered heterocycloalkyl optionally substituted by 1-3 $R^{19}$ or a 5-6 membered heteroaryl optionally substituted by 1-3 $R^{19}$.

Embodiment 191

The compound of any of Embodiments 1-174, wherein $R^{12}$, $R^{13}$, and $R^{15}$ are H; $R^{14}$ is chosen from H, $C_{1-6}$alkyl optionally substituted by 1-3 $R^{19}$, $C_{2-6}$alkenyl optionally substituted by 1-3 $R^{19}$, $C_{2-6}$alkynyl optionally substituted by 1-3 $R^{19}$, $C_{6-10}$aryl optionally substituted by 1-3 $R^{19}$, $C_{3-7}$cycloalkyl optionally substituted by 1-3 $R^{19}$, 3-7 membered heterocycloalkyl optionally substituted by 1-3 $R^{19}$, 5-6 membered heteroaryl optionally substituted by 1-3 $R^{19}$, halogen, —CN, —C(=O)$R^{20}$, —C(=O)NR$^{22}$R$^{23}$, —NO$_2$, —NR$^{22}$R$^{23}$, —R$^{24}$C(=O)R$^{20}$, —R$^{24}$S(=O)$_2$R$^{21}$, —OR$^{20}$, —S(=O)$_n$R$^{20}$, and —S(=O)$_2$NR$^{22}$R$^{23}$.

Embodiment 192

The compound of any of Embodiments 1-174, wherein $R^{12}$, $R^{13}$, and $R^{14}$ are H; $R^{15}$ is chosen from H, $C_{1-6}$alkyl optionally substituted by 1-3 $R^{19}$, $C_{2-6}$alkenyl optionally substituted by 1-3 $R^{19}$, $C_{2-6}$alkynyl optionally substituted by 1-3 $R^{19}$, $C_{6-10}$aryl optionally substituted by 1-3 $R^{19}$, $C_{3-7}$cycloalkyl optionally substituted by 1-3 $R^{19}$, 3-7 membered heterocycloalkyl optionally substituted by 1-3 $R^{19}$, 5-6 membered heteroaryl optionally substituted by 1-3 $R^{19}$, halogen, —CN, —C(=O)$R^{20}$, —C(=O)NR$^{22}$R$^{23}$, —NO$_2$, —NR$^{22}$R$^{23}$, —NR$^{24}$C(=O)R$^{20}$, —R$^{24}$S(=O)$_2$R$^{21}$, —OR$^{20}$, —S(=O)$_n$R$^{20}$, and —S(=O)$_2$NR$^{22}$R$^{23}$.

Embodiment 193

The compound of any of Embodiments 1-174, wherein $R^{12}$, $R^{13}$, $R^{14}$, and $R^{15}$ are independently chosen from H, $C_{1-6}$alkyl optionally substituted by 1-3 $R^{19}$, halogen, —NR$^{22}$R$^{23}$, —NR$^{24}$C(=O)R$^{20}$, —NR$^{24}$C(=O)NR$^{22}$R$^{23}$, —OR$^{20}$, and —S(=O)$_2$NR$^{22}$R$^{23}$.

Embodiment 194

The compound of any of Embodiments 1-174, wherein $R^{12}$, $R^{13}$, $R^{14}$, and $R^{15}$ are independently chosen from H, $C_{1-6}$alkyl optionally substituted by 1-3 $R^{19}$, halogen, —NR$^{22}$R$^{23}$, —NR$^{24}$C(=O)R$^{20}$, and —NR$^{24}$C(=O)NR$^{22}$R$^{23}$.

Embodiment 195

The compound of any of Embodiments 1-174, wherein $R^{12}$, $R^{13}$, and $R^{15}$ are H; $R^{14}$ is chosen from H, $C_{1-6}$alkyl optionally substituted by 1-3 $R^{19}$, halogen, —NR$^{22}$R$^{23}$, —NR$^{24}$C(=O)R$^{20}$, —NR$^{24}$C(=O)NR$^{22}$R$^{23}$, —OR$^{20}$, and —S(=O)$_2$NR$^{22}$R$^{23}$.

Embodiment 196

The compound of any of Embodiments 1-174, wherein $R^{12}$, $R^{13}$, and $R^{15}$ are H; $R^{14}$ is chosen from H, $C_{1-6}$alkyl optionally substituted by 1-3 $R^{19}$, —NR$^{22}$R$^{23}$, —NR$^{24}$C(=O)R$^{20}$, and —NR$^{24}$C(=O)NR$^{22}$R$^{23}$.

Embodiment 197

The compound of any of Embodiments 1-174, wherein $R^{12}$, $R^{13}$, and $R^{14}$ are H; $R^{15}$ is chosen from H, $C_{1-6}$alkyl optionally substituted by 1-3 $R^{19}$, halogen, —NR$^{22}$R$^{23}$, —NR$^{24}$C(=O)R$^{20}$, —NR$^{24}$C(=O)NR$^{22}$R$^{23}$, —OR$^{20}$, and —S(=O)$_2$NR$^{22}$R$^{23}$.

Embodiment 198

The compound of any of Embodiments 1-174, wherein $R^{12}$, $R^{13}$, and $R^{14}$ are H; $R^{15}$ is chosen from H, $C_{1-6}$alkyl optionally substituted by 1-3 $R^{19}$, and halogen.

Embodiment 199

The compound of any of Embodiments 1-174, wherein $R^{12}$, $R^{13}$, $R^{14}$, and $R^{15}$ are independently chosen from H and $C_{1-6}$alkyl optionally substituted by 1-3 $R^{19}$.

Embodiment 200

The compound of any of Embodiments 1-174, wherein $R^{12}$, $R^{13}$, $R^{14}$, and $R^{15}$ are independently chosen from H, $C_{1-6}$alkyl, halogen, —NR$^{22}$R$^{23}$, —NR$^{24}$C(=O)R$^{20}$, —NR$^{24}$C(=O)NR$^{22}$R$^{23}$, —OR$^{20}$, and —S(=O)$_2$NR$^{22}$R$^{23}$.

Embodiment 201

The compound of any of Embodiments 1-174, wherein $R^{12}$, $R^{13}$, $R^{14}$, and $R^{15}$ are independently chosen from H, $C_{1-6}$alkyl, halogen, —NR$^{22}$R$^{23}$, —NR$^{24}$C(=O)R$^{20}$, and —NR$^{24}$C(=O)NR$^{22}$R$^{23}$.

Embodiment 202

The compound of any of Embodiments 1-174, wherein $R^{12}$, $R^{13}$, and $R^{15}$ are H; $R^{14}$ is chosen from H, $C_{1-6}$alkyl, halogen, —NR$^{22}$R$^{23}$, —NR$^{24}$C(=O)R$^{20}$, —NR$^{24}$C(=O)NR$^{22}$R$^{23}$, —OR$^{20}$, and —S(=O)$_2$NR$^{22}$R$^{23}$.

Embodiment 203

The compound of any of Embodiments 1-174, wherein $R^{12}$, $R^{13}$, and $R^{15}$ are H; $R^{14}$ is chosen from H, $C_{1-6}$alkyl, —NR$^{22}$R$^{23}$, —NR$^{24}$C(=O)R$^{20}$, and —NR$^{24}$C(=O)NR$^{22}$R$^{23}$.

Embodiment 204

The compound of any of Embodiments 1-174, wherein $R^{12}$, $R^{13}$, and $R^{14}$ are H; $R^{15}$ is chosen from H, $C_{1-6}$alkyl, halogen, —NR$^{22}$R$^{23}$, —NR$^{24}$C(=O)R$^{20}$, —NR$^{24}$C(=O)NR$^{22}$R$^{23}$, —OR$^{20}$, and —S(=O)$_2$NR$^{22}$R$^{23}$.

Embodiment 205

The compound of any of Embodiments 1-174, wherein R$^{12}$, R$^{13}$, and R$^{14}$ are H; R$^{15}$ is chosen from H, C$_{1-6}$alkyl, and halogen.

Embodiment 206

The compound of any of Embodiments 1-174, wherein R$^{12}$, R$^{13}$, R$^{14}$, and R$^{15}$ are independently chosen from H and C$_{1-6}$alkyl.

Embodiment 207

The compound of any of Embodiments 1-174, wherein R$^{12}$, R$^{13}$, R$^{14}$, and R$^{15}$ are independently chosen from H, C$_{1-6}$alkyl optionally substituted by 1-13 R$^{19}$, C$_{2-6}$alkenyl optionally substituted by 1-11 R$^{19}$, C$_{2-6}$alkynyl optionally substituted by 1-9 R$^{19}$, C$_{6-11}$aryl optionally substituted by 1-11 R$^{19}$, C$_{7-16}$arylalkyl optionally substituted by 1-19 R$^{19}$, C$_{3-11}$-cycloalkyl optionally substituted by 1-21 R$^{19}$, C$_4$-17cycloalkylalkyl optionally substituted by 1-32 R$^{19}$, 3-15 membered heterocycloalkyl optionally substituted by 1-28 R$^{19}$, 4-21 membered heterocycloalkylalkyl optionally substituted by 1-40 R$^{19}$, 5-15 membered heteroaryl optionally substituted by 1-15 R$^{19}$, 6-21 membered heteroarylalkyl optionally substituted by 1-27 R$^{19}$, halogen, —CN, —C(=O)R$^{20}$, —C(=O)OR$^{20}$, —C(=O)NR$^{22}$R$^{23}$, —NO$_2$, —NR$^{22}$R$^{23}$, and —OR$^{20}$; alternatively, either or both of R$^{12}$ and R$^{13}$, and/or R$^{14}$ and R$^{15}$, can, together with the atoms linking them, form a C$_{6-11}$aryl optionally substituted by 1-11 R$^{19}$, C$_{3-11}$ cycloalkyl optionally substituted by 1-21 R$^{19}$, 3-15 membered heterocycloalkyl optionally substituted by 1-28 R$^{19}$ or a 5-15 membered heteroaryl optionally substituted by 1-15 R$^{19}$.

Embodiment 208

The compound of any of Embodiments 1-174, wherein R$^{12}$, R$^{13}$, R$^{14}$, and R$^{15}$ are independently chosen from H, C$_{1-6}$alkyl optionally substituted by 1-13 R$^{19}$, C$_{2-6}$alkenyl optionally substituted by 1-11 R$^{19}$, C$_{2-6}$alkynyl optionally substituted by 1-9 R$^{19}$, C$_{6-11}$-aryl optionally substituted by 1-11 R$^{19}$, C$_{7-16}$arylalkyl optionally substituted by 1-19 R$^{19}$, C$_{3-11}$cycloalkyl optionally substituted by 1-21 R$^{19}$, C$_4$-17cycloalkylalkyl optionally substituted by 1-32 R$^{19}$, 3-15 membered heterocycloalkyl optionally substituted by 1-28 R$^{19}$, 4-21 membered heterocycloalkylalkyl optionally substituted by 1-40 R$^{19}$, 5-15 membered heteroaryl optionally substituted by 1-15 R$^{19}$, 6-21 membered heteroarylalkyl optionally substituted by 1-27 R$^{19}$, halogen, —CN, —C(=O)NR$^{22}$R$^{23}$, —NO$_2$, —NR$^{22}$R$^{23}$, and —OR$^{20}$; alternatively, either or both of R$^{12}$ and R$^{13}$, and/or R$^{14}$ and R$^{15}$, can, together with the atoms linking them, form a C$_{6-11}$aryl optionally substituted by 1-11 R$^{19}$, C$_{3-11}$cycloalkyl optionally substituted by 1-21 R$^{19}$, 3-15 membered heterocycloalkyl optionally substituted by 1-28 R$^{19}$ or a 5-15 membered heteroaryl optionally substituted by 1-15 R$^{19}$.

Embodiment 209

The compound of any of Embodiments 1-174, wherein R$^{12}$, R$^{13}$, R$^{14}$, and R$^{15}$ are independently chosen from H, halogen, —NR$^{22}$R$^{23}$, —NR$^{24}$C(=O)R$^{20}$, —NR$^{24}$C(=O)NR$^{22}$R$^{23}$, —OR$^{20}$, and —S(=O)$_2$NR$^{22}$R$^{23}$.

Embodiment 210

The compound of any of Embodiments 1-174, wherein R$^{12}$, R$^{13}$, R$^{14}$, and R$^{15}$ are independently chosen from H, halogen, —NR$^{22}$R$^{23}$, —NR$^{24}$C(=O)R$^{20}$, and —NR$^{24}$C(=O)NR$^{22}$R$^{23}$.

Embodiment 211

The compound of any of Embodiments 1-174, wherein R$^{12}$, R$^{13}$, and R$^{15}$ are H; R$^{14}$ is chosen from H, halogen, —NR$^{22}$R$^{23}$, —NR$^{24}$C(=O)R$^{20}$, —NR$^{24}$C(=O)NR$^{22}$R$^{23}$, —OR$^{20}$, and —S(=O)$_2$NR$^{22}$R$^{23}$.

Embodiment 212

The compound of any of Embodiments 1-174, wherein R$^{12}$, R$^{13}$, and R$^{15}$ are H; R$^{14}$ is chosen from H, —NR$^{22}$R$^{23}$, —NR$^{24}$C(=O)R$^{20}$ and —NR$^{24}$C(=O)NR$^{22}$R$^{23}$.

Embodiment 213

The compound of any of Embodiments 1-174, wherein R$^{12}$, R$^{13}$, and R$^{14}$ are H; R$^{15}$ is chosen from H, halogen, —NR$^{22}$R$^{23}$, —NR$^{24}$C(=O)R$^{20}$, —NR$^{24}$C(=O)NR$^{22}$R$^{23}$, —OR$^{20}$, and —S(=O)$_2$NR$^{22}$R$^{23}$.

Embodiment 214

The compound of any of Embodiments 1-174, wherein R$^{12}$, R$^{13}$, and R$^{14}$ are H; R$^{15}$ is chosen from H and halogen.

Embodiment 215

The compound of any of Embodiments 1-174, wherein R$^{12}$, R$^{13}$, R$^{14}$, and R$^{15}$ are H.

Embodiment 216

The compound of any of Embodiments 1-215, wherein R$^{17}$ is chosen from H, C$_{1-6}$alkyl optionally substituted by 1-13 R$^{19}$, C$_{2-6}$ alkenyl optionally substituted by 1-11 R$^{19}$, C$_{2-6}$alkynyl optionally substituted by 1-9 R$^{19}$, C$_{6-11}$aryl optionally substituted by 1-11 R$^{19}$, C$_{7-16}$arylalkyl optionally substituted by 1-19 R$^{19}$, C$_{3-11}$cycloalkyl optionally substituted by 1-21 R$^{19}$, C$_4$-17cycloalkylalkyl optionally substituted by 1-32 R$^{19}$, 3-15 membered heterocycloalkyl optionally substituted by 1-28 R$^{19}$, 4-21 membered heterocycloalkylalkyl optionally substituted by 1-40 R$^{19}$, 5-15 membered heteroaryl optionally substituted by 1-15 R$^{19}$, 6-21 membered heteroarylalkyl optionally substituted by 1-27 R$^{19}$, and —OR$^{20}$; R$^{16}$ and R$^{18}$ are independently chosen from H, C$_{1-6}$alkyl optionally substituted by 1-13 R$^{19}$, C$_{2-6}$alkenyl optionally substituted by 1-11 R$^{19}$, C$_{2-6}$alkynyl optionally substituted by 1-9 R$^{19}$, C$_{6-11}$aryl optionally substituted by 1-11 R$^{19}$, C$_{7-16}$arylalkyl optionally substituted by 1-19 R$^{19}$, C$_{3-11}$cycloalkyl optionally substituted by 1-21 R$^{19}$, C$_{4-17}$cycloalkylalkyl optionally substituted by 1-32 R$^{19}$, 3-membered heterocycloalkyl optionally substituted by 1-28 R$^{19}$, 4-21 membered heterocycloalkylalkyl optionally substituted by 1-40 R$^{19}$, 5-15 membered heteroaryl optionally substituted by 1-15 R$^{19}$, 6-21 membered heteroarylalkyl optionally substituted by 1-27 R$^{19}$, halogen, —CN, —C(=O)R$^{20}$, —C(=O)OR²⁰, —C(=O)NR²²R²³, —C(=O)C(=O)R²⁰, —C(=NR²⁵)R²⁰, —C(=NR²⁵)NR²²R²³, —C(=NOH)NR²²R²³, —C(=NOR²⁶)R²⁰, —C(=NNR²²R²³)R²⁰, —C(=NNR²⁴C(=O)R²¹)R²⁰, —C(=NNR²⁴C(=O)OR²¹)R²⁰, —C(=S)NR²²R²³, —NC, —NO₂, —NR²²R²³, —NR²⁴R²²R²³, —N=NR²⁴, —NR²⁴OR²⁶, —NR²⁴C(=O)R²⁰, —NR²⁴C(=O)C(=O)R²⁰, —NR²⁴C(=O)OR²¹, —NR²⁴C(=O)C(=O)OR²¹, —NR²⁴C(=O)NR²²R²³, —NR²⁴C(=O)C(=O)R²⁴C(=O)R²⁰, —NR²⁴C(=O)NR²⁴C(=O)OR²⁰, —NR²⁴C(NR²⁵)NR²²R²³, —NR²⁴C(=O)C(=O)NR²²R²³, —NR²⁴C(=S)R²⁰, —NR²⁴C(=S)OR²⁰, —NR²⁴C(=S)NR²²R²³, —NR²⁴S(=O)₂R²¹, —NR²⁴S(=O)₂NR²²R²³, —NR²⁴P(=O)NR²⁸R²⁸, —NR²⁴P(=O)(R²²R²³)(NR²²R²³), —NR²⁴P(=O)(OR²⁰)(OR²), —NR²⁴P(=)(SR²⁰)(SR²⁰), —OR²⁰, —OCN, —OC(=O)R²⁰, —OC(=O)NR²²R²³, —OC(=O)OR²⁰, —OC(=NR²⁵)NR²²R²³, —OS(=O)R²⁰, —OS(=O)₂R²⁰, —OS(=O)₂OR²⁰, —OS(=O)₂NR²²R²³, —OP(=O)R²⁸R²⁸, —OP(=O)(NR²²R²³)(NR²²R²³), —OP(=O)(OR²⁰)(OR²⁰), —OP(=O)(SR²⁰)(SR²⁰), —Si(R²⁴)₃, —SCN, —S(=O)ₙR²⁰, —S(=O)₂OR²⁰, —SO₃R²⁷, —S(=O)₂NR²²R²³, —S(=O)NR²²R²³, —SP(=O)R²⁸R²⁸, —SP(=O)(NR²²R²³)(NR²²R²³), —SP(=O)(OR²⁰)(OR²⁰), —SP(=O)(SR²⁰)(SR²⁰), —P(=O)R²⁸R²⁸, —P(=O)(NR²²R²³)(NR²²R²³), —P(=O)(OR²⁰)(OR²⁰), or —P(=O)(SR²⁰)(SR²⁰); alternatively, R¹⁶ and R¹⁷ can, together with the atoms linking them, form a 3-15 membered heterocycloalkyl optionally substituted by 1-28 R¹⁹ or a 5-15 membered heteroaryl optionally substituted by 1-15 R¹⁹.

Embodiment 217

The compound of any of Embodiments 1-215, wherein R¹⁷ is chosen from H and C₁₋₆alkyl optionally substituted by 1-13 R¹⁹; R¹⁶ and R¹⁸ are independently chosen from H, C₁₋₆alkyl optionally substituted by 1-13 R¹⁹, C₂₋₆alkenyl optionally substituted by 1-11 R¹⁹, C₂₋₆alkynyl optionally substituted by 1-9 R¹⁹, C₆₋₁₁aryl optionally substituted by 1-11 R¹⁹, C₇₋₁₆arylalkyl optionally substituted by 1-19 R¹⁹, C₃₋₁₁cycloalkyl optionally substituted by 1-21 R¹⁹, C₄₋₁₇cycloalkylalkyl optionally substituted by 1-32 R¹⁹, 3-15 membered heterocycloalkyl optionally substituted by 1-28 R¹⁹, 4-21 membered heterocycloalkylalkyl optionally substituted by 1-40 R¹⁹, 5-15 membered heteroaryl optionally substituted by 1-15 R¹⁹, 6-21 membered heteroarylalkyl optionally substituted by 1-27 R¹⁹, halogen, —CN, —C(=O)R²⁰, —C(=O)OR²⁰, —C(=O)NR²²R²³, —C(=O)C(=O)R²⁰, —C(=NR²⁵)R²⁰, —C(=NR²⁵)NR²²R²³, —C(=NOH)NR²²R²³, —C(=NOR²⁶)R²⁰, —C(=NNR²²R²³)R²⁰, —C(=NNR²⁴C(=O)R²)R)R², —C(=NNR²⁴C(=O)OR²¹)R²⁰, —C(=S)NR²²R²³, —NC, —NO₂, —NR²²R²³, —NR²⁴NR²²R²³, —N=NR²⁴, —NR²⁴OR²⁶, —NR²⁴C(=O)R²⁰, —NR²⁴C(=O)C(=O)R²⁰, —NR²⁴C(=O)OR²¹, —NR²⁴C(=O)C(=O)OR²¹, —NR²⁴C(=O)NR²²R²³, —NR²⁴C(=O)C(=O)R²⁴C(=O)R²⁰, —NR²⁴C(=O)NR²⁴C(=O)OR²⁰, —NR²⁴C(=NR²⁵)NR²²R²³, —NR²⁴C(=O)C(=O)NR²²R²³, —NR²⁴C(=S)R²⁰, —NR²⁴C(=S)OR²⁰, —NR²⁴C(=S)NR²²R²³, —NR²⁴S(=O)₂R²¹, —NR²⁴S(=O)₂NR²²R²³, —NR²⁴P(=O)R²⁸R²⁸, —NR²⁴P(=O)(NR²²R²³)(NR²²R²³), —NR²⁴P(=O)(OR²⁰)(OR²), —NR²⁴P(=)(SR²⁰)(SR²⁰), —OR²⁰, —OCN, —OC(=O)R²⁰, —OC(=O)NR²²R²³, —OC(=O)OR²⁰, —OC(=NR²⁵)NR²²R²³, —OS(=O)R²⁰, —OS(=O)₂R²⁰, —OS(=O)₂OR²⁰, —OS(=O)₂NR²²R²³, —OP(=O)R²⁸R²⁸, —OP(=O)(NR²²R²³)(NR²²R²³), —OP(=O)(OR²⁰)(OR²⁰), —OP(=O)(SR²⁰)(SR²⁰), —Si(R²⁴)₃, —SCN, —S(=O)ₙR²⁰, —S(=O)₂OR²⁰, —SO₃R²⁷, —S(=O)₂NR²²R²³, —S(=O)NR²²R²³, —SP(=O)R²⁸R²⁸, —SP(=O)(NR²²R²³)(NR²²R²³), —SP(=O)(OR²⁰)(OR²⁰), —SP(=O)(SR²⁰)(SR²⁰), —P(=O)R²⁸R²⁸, —P(=O)(NR²²R²³)(NR²²R²³), —P(=O)(OR²⁰)(OR²⁰), or —P(=O)(SR²⁰)(SR²⁰); alternatively, R¹⁶ and R¹⁷ can, together with the atoms linking them, form a 3-15 membered heterocycloalkyl optionally substituted by 1-28 R¹⁹ or a 5-15 membered heteroaryl optionally substituted by 1-15 R¹⁹.

Embodiment 218

The compound of any of Embodiments 1-215, wherein R¹⁷ is chosen from H and C₁₋₆alkyl optionally substituted by 1-3 R¹⁹; R¹⁶ and R¹⁸ are independently chosen from H, C₁₋₆alkyl optionally substituted by 1-13 R¹⁹, C₂₋₆alkenyl optionally substituted by 1-11 R¹⁹, C₂₋₆alkynyl optionally substituted by 1-9 R¹⁹, C₆₋₁₁aryl optionally substituted by 1-11 R¹⁹, C₇₋₁₆arylalkyl optionally substituted by 1-19 R¹⁹, C₃₋₁₁cycloalkyl optionally substituted by 1-21 R¹⁹, C₄₋₁₇cycloalkylalkyl optionally substituted by 1-32 R¹⁹, 3-15 membered heterocycloalkyl optionally substituted by 1-28 R¹⁹, 4-21 membered heterocycloalkylalkyl optionally substituted by 1-40 R¹⁹, 5-15 membered heteroaryl optionally substituted by 1-15 R¹⁹, 6-21 membered heteroarylalkyl optionally substituted by 1-27 R¹⁹, halogen, —CN, —C(=O)R²⁰, —C(=O)OR²⁰, —C(=O)NR²²R²³, —C(=O)C(=O)R²⁰, —C(=NR²⁵)R²⁰, —C(=NR²⁵)NR²²R²³, —C(=NOH)NR²²R²³, —C(=NOR²⁶)R²⁰, —C(=NNR²²R²³)R²⁰, —C(=NNR²⁴C(=O)R²)R)R², —C(=NNR²⁴C(=O)OR²¹)R²⁰, —C(=S)NR²²R²³, —NC, —NO₂, —NR²²R²³, —NR²⁴NR²²R²³, —N=NR²⁴, —NR²⁴OR²⁶, —NR²⁴C(=O)R²⁰, —NR²⁴C(=O)C(=O)R²⁰, —NR²⁴C(=O)OR²¹, —NR²⁴C(=O)C(=O)OR²¹, —NR²⁴C(=O)NR²²R²³, —NR²⁴C(=O)C(=O)R²⁴C(=O)R²⁰, —NR²⁴C(=O)NR²⁴C(=O)OR²⁰, —NR²⁴C(=NR²⁵)NR²²R²³, —NR²⁴C(=O)C(=O)NR²²R²³, —NR²⁴C(=S)R²⁰, —NR²⁴C(=S)OR²⁰, —NR²⁴C(=S)NR²²R²³, —NR²⁴S(=O)₂R²¹, —NR²⁴S(=O)₂NR²²R²³, —NR²⁴P(=O)R²⁸R²⁸, —NR²⁴P(=O)(NR²²R²³)(NR²²R²³), —NR²⁴P(=O)(OR²⁰)(OR²), —NR²⁴P(=)(SR²⁰)(SR²⁰), —OR²⁰, —OCN, —OC(=O)R²⁰, —OC(=O)NR²²R²³, —OC(=O)OR²⁰, —OC(=NR²⁵)NR²²R²³, —OS(=O)R²⁰, —OS(=O)₂R²⁰, —OS(=O)₂OR²⁰, —OS(=O)₂NR²²R²³, —OP(=O)R²⁸R²⁸, —OP(=O)(NR²²R²³)(NR²²R²³), —OP(=O)(OR²⁰)(OR²⁰), —OP(=O)(SR²⁰)(SR²⁰), —Si(R²⁴)₃, —SCN, —S(=O)ₙR²⁰, —S(=O)₂OR²⁰, —SO₃R²⁷, —S(=O)₂NR²²R²³, —S(=O)NR²²R²³, —SP(=O)R²⁸R²⁸, —SP(=O)(NR²²R²³)(NR²²R²³), —SP(=O)(OR²⁰)(OR²⁰), —SP(=O)(SR²⁰)(SR²⁰), —P(=O)R²⁸R²⁸, —P(=O)(NR²²R²³)(NR²²R²³), —P(=O)(OR²⁰)(OR²⁰), or —P(=O)(SR²⁰)(SR²⁰); alternatively, R¹⁶ and R¹⁷ can, together with the atoms linking them, form a 3-15 membered heterocycloalkyl optionally substituted by 1-28 R¹⁹ or a 5-15 membered heteroaryl optionally substituted by 1-15 R¹⁹.

Embodiment 219

The compound of any of Embodiments 1-215, wherein R¹⁷ is chosen from H and C₁₋₆alkyl; R¹⁶ and R¹⁸ are independently chosen from H, C₁₋₆alkyl optionally substituted by 1-13 R¹⁹, C₂₋₆alkenyl optionally substituted by 1-11 R¹⁹, C₂₋₆alkynyl optionally substituted by 1-9 R¹⁹, C₆₋₁₁aryl optionally substituted by 1-11 R¹⁹, C₇₋₁₆arylalkyl optionally substituted by 1-19 R¹⁹, C₃₋₁₁cycloalkyl optionally substituted by 1-21 R¹⁹, C₄₋₁₇cycloalkylalkyl optionally substituted by 1-32 R¹⁹, 3-15 membered heterocycloalkyl optionally substituted by 1-28 R¹⁹, 4-21 membered heterocycloalkylalkyl optionally substituted by 1-40 $R^{19}$, 5-15 membered heteroaryl optionally substituted by 1-15 $R^{19}$, 6-21 membered heteroarylalkyl optionally substituted by 1-27 $R^{19}$, halogen, —CN, —C(=O)$R^{20}$, —C(=O)O$R^{20}$, —C(=O)N$R^{22}R^{23}$, —C(=O)C(=O)$R^{20}$, —C(=N$R^{25}$)$R^{20}$, —C(=N$R^{25}$)N$R^{22}R^{23}$, —C(=NOH)N$R^{22}R^{23}$, —C(=NO$R^{26}$)$R^{20}$, —C(=N$R^{22}R^{23}$)$R^{20}$, —C(=NN$R^{24}$C(=O)$R^{21}$)$R^{20}$, —C(=NN$R^{24}$C(=O)$R^{21}$)$R^{20}$, —C(=S)N$R^{22}R^{23}$, —NC, —NO$_2$, —N$R^{22}R^{23}$, —N$R^{24}$N$R^{22}R^{23}$, —N=N$R^{24}$, —N$R^{24}$O$R^{26}$, —N$R^{24}$C(=O)$R^{20}$, —N$R^{24}$C(=O)C(=O)$R^{20}$, —N$R^{24}$C(=O)O$R^{21}$, —N$R^{24}$C(=O)C(=O)O$R^{21}$, —N$R^{24}$C(=O)N$R^{22}R^{23}$, —N$R^{24}$C(=O)$R^{24}$C(=O)$R^{20}$, —N$R^{24}$C(=O)N$R^{24}$C(=O)O$R^{20}$, —N$R^{24}$C(=N$R^{25}$)N$R^{22}R^{23}$, —N$R^{24}$C(=O)C(=O)N$R^{22}R^{23}$, —N$R^{24}$C(=S)$R^{20}$, —N$R^{24}$C(=S)O$R^{20}$, —N$R^{24}$C(=S)N$R^{22}R^{23}$, —N$R^{24}$S(=O)$_2R^{21}$, —N$R^{24}$S(=O)$_2$N$R^{22}R^{23}$, —N$R^{24}$P(=O)$R^{28}R^{28}$, —N$R^{24}$P(=O)(N$R^{22}R^{23}$)(N$R^{22}R^{23}$), —N$R^{24}$P(=O)(O$R^{20}$)(O$R^2$), —N$R^{24}$P(=)(S$R^{20}$)(S$R^{20}$), —O$R^{20}$, —OCN, —OC(=O)$R^{20}$, —OC(=O)N$R^{22}R^{23}$, —OC(=O)O$R^{20}$, —OC(=N$R^{25}$N$R^{22}R^{23}$, —OS(=O)$R^{20}$, —OS(=O)$_2R^{20}$, —OS(=O)$_2$O$R^{20}$, —OS(=O)$_2$N$R^{22}R^{23}$, —OP(=O)$R^{28}R^{28}$, —OP(=O)(N$R^{22}R^{23}$)(N$R^{22}R^{23}$), —OP(=O)(O$R^{20}$)(O$R^{20}$), —OP(=O)(S$R^{20}$)(S$R^{20}$), —Si($R^{24}$)$_3$, —SCN, —S(=O)$_nR^{20}$, —S(=O)$_2R^{20}$, —SO$_3R^{27}$, —S(=O)$_2$N$R^{22}R^{23}$, —S(=O)N$R^{22}R^{23}$, —SP(=O)$R^{28}R^{28}$, —SP(=O)(N$R^{22}R^{23}$)(N$R^{22}R^{23}$), —SP(=O)(O$R^{20}$)(O$R^{20}$), —SP(=O)(S$R^{20}$)(S$R^{20}$), —P(=O)$R^{28}R^{28}$, —P(=O)(N$R^{22}R^{23}$)(N$R^{22}R^{23}$), —P(=O)(O$R^{20}$)(O$R^{20}$), or —P(=O)(S$R^{20}$)(S$R^{20}$); alternatively, $R^{16}$ and $R^{17}$ can, together with the atoms linking them, form a 3-15 membered heterocycloalkyl optionally substituted by 1-28 $R^{19}$ or a 5-15 membered heteroaryl optionally substituted by 1-15 $R^{19}$.

Embodiment 220

The compound of any of Embodiments 1-215, wherein $R^{17}$ is chosen from H and $C_{1-6}$alkyl; $R^{16}$ and $R^{18}$ are independently chosen from H, $C_{1-6}$alkyl optionally substituted by 1-6 $R^{19}$, $C_{2-6}$alkenyl optionally substituted by 1-6 $R^{19}$, $C_{2-6}$alkynyl optionally substituted by 1-6 $R^{19}$, $C_{6-10}$aryl optionally substituted by 1-6 $R^{19}$, $C_{7-11}$arylalkyl optionally substituted by 1-6 $R^{19}$, $C_{3-10}$cycloalkyl optionally substituted by 1-6 $R^{19}$, 3-10 membered heterocycloalkyl optionally substituted by 1-6 $R^{19}$, 5-10 membered heteroaryl optionally substituted by 1-6 $R^{19}$, halogen, —CN, —C(=O)$R^{20}$, —C(=O)O$R^{20}$, —C(=O)N$R^{22}R^{23}$, —C(=O)C(=O)$R^{20}$, —NC, —NO$_2$, —N$R^{22}R^{23}$, —N$R^{24}$N$R^{22}R^{23}$, —N=N$R^{24}$, —N$R^{24}$O$R^{26}$, —N$R^{24}$C(=O)$R^{20}$, —N$R^{24}$C(=O)C(=O)$R^{20}$, —N$R^{24}$C(=O)O$R^{21}$, —N$R^{24}$C(=O)C(=O)O$R^{21}$, —N$R^{24}$C(=O)N$R^{22}R^{23}$, $R^{24}$C(=O)N$R^{24}$C(=O)$R^{20}$, —N$R^{24}$C(=O)N$R^{24}$C(=O)O$R^{20}$, —N$R^{24}$C(=O)C(=O)N$R^{22}R^{23}$, —N$R^{24}$S(=O)$_2R^{21}$, —N$R^{24}$S(=O)$_2$N$R^{22}R^{23}$, —O$R^{20}$, —OCN, —OC(=O)$R^{20}$, —OC(=O)N$R^{22}R^{23}$, —OC(=O)O$R^{20}$, —OS(=O)$R^{20}$, —OS(=O)$_2R^{20}$, —OS(=O)$_2$O$R^{20}$, —OS(=O)$_2$N$R^{22}R^{23}$, —SCN, —S(=O)$_nR^{20}$, —S(=O)$_2R^2$, —SO$_3R^{27}$, —S(=O)$_2$N$R^{22}R^{23}$, and —S(=O)N$R^{22}R^{23}$; alternatively, $R^{16}$ and $R^{17}$ can, together with the atoms linking them, form a 3-10 membered heterocycloalkyl optionally substituted by 1-6 $R^{19}$ or a 5-10 membered heteroaryl optionally substituted by 1-6 $R^{19}$.

Embodiment 221

The compound of any of Embodiments 1-215, wherein $R^{17}$ is chosen from H and $C_{1-6}$alkyl; $R^{16}$ and $R^{18}$ are independently chosen from H, $C_{1-6}$alkyl optionally substituted by 1-3 $R^{19}$, $C_{2-6}$alkenyl optionally substituted by 1-1 $R^{19}$, $C_{2-6}$alkynyl optionally substituted by 1-3 $R^{19}$, $C_{6-10}$aryl optionally substituted by 1-3 $R^{19}$, $C_7$11arylalkyl optionally substituted by 1-3 $R^{19}$, $C_{3-10}$cycloalkyl optionally substituted by 1-3 $R^{19}$, 3-10 membered heterocycloalkyl optionally substituted by 1-3 $R^{19}$, 5-10 membered heteroaryl optionally substituted by 1-3 $R^{19}$, halogen, —CN, —C(=O)$R^{20}$, —C(=O)O$R^{20}$, —C(=O)N$R^{22}R^{23}$, —C(=O)C(=O)$R^{20}$, —NC, —NO$_2$, —N$R^{22}R^{23}$, —N$R^{24}$N$R^{22}R^{23}$, —N=N$R^{24}$, —N$R^{24}R^{26}$, —N$R^{24}$C(=O)$R^{20}$, —N$R^{24}$C(=O)C(=O)$R^{20}$, —N$R^{24}$C(=O)O$R^{21}$, —N$R^{24}$C(=O)C(=O)O$R^{21}$, —N$R^{24}$C(=O)N$R^{22}R^{23}$, —N$R^{24}$C(=O)N$R^{24}$C(=O)$R^{20}$, —N$R^{24}$C(=O)N$R^{24}$C(=O)O$R^{20}$, —N$R^{24}$C(=O)C(=O)N$R^{22}R^{23}$, —N$R^{24}$S(=O)$_2R^{21}$, —N$R^{24}$S(=O)$_2$N$R^{22}R^{23}$, —O$R^{20}$, —OCN, —OC(=O)$R^{20}$, —OC(=O)N$R^{22}R^{23}$, —OC(=O)O$R^{20}$, —OS(=O)$R^{20}$, —OS(=O)$_2R^{20}$, —OS(=O)$_2$O$R^{20}$, —OS(=O)$_2$N$R^{22}R^{23}$, —SCN, —S(=O)$_nR^{20}$, —S(=O)$_2$O$R^{20}$, —SO$_3R^{27}$, —S(=O)$_2$N$R^{22}R^{23}$, and —S(=O)N$R^{22}R^{23}$; alternatively, $R^{16}$ and $R^{17}$ can, together with the atoms linking them, form a 3-10 membered heterocycloalkyl optionally substituted by 1-3 $R^{19}$ or a 5-10 membered heteroaryl optionally substituted by 1-3 $R^{19}$.

Embodiment 222

The compound of any of Embodiments 1-215, wherein $R^{17}$ is chosen from H and $C_{1-6}$alkyl; $R^{16}$ and $R^{18}$ are independently chosen from H, $C_{1-6}$alkyl optionally substituted by 1-3 $R^{19}$, $C_{6-10}$aryl optionally substituted by 1-3 $R^{19}$, $C_{7-11}$arylalkyl optionally substituted by 1-3 $R^{19}$, $C_{3-10}$cycloalkyl optionally substituted by 1-3 $R^{19}$, 3-10 membered heterocycloalkyl optionally substituted by 1-3 $R^{19}$, 5-10 membered heteroaryl optionally substituted by 1-3 $R^{19}$, halogen, —CN, —C(=O)$R^{20}$, —C(=O)O$R^{20}$, —C(=O)N$R^{22}R^{23}$, —NC, —NO$_2$, —N$R^{22}R^{23}$, —N$R^{24}$N$R^{22}R^{23}$, —N$R^{24}$C(=O)$R^{20}$, —N$R^{24}$C(=O)O$R^{21}$, —N$R^{24}$C(=O)N$R^{22}R^{23}$, —N$R^{24}$S(=O)$_2R^{21}$, —N$R^{24}$S(=O)$_2$N$R^{22}R^{23}$, —O$R^{20}$, —OCN, —OC(=O)$R^{20}$, —OC(=O)N$R^{22}R^{23}$, —OC(=O)O$R^{20}$, —OS(=O)$R^{20}$, —SCN, —S(=O)$_nR^{20}$, —S(=O)$_2$O$R^{20}$, —SO$_3R^{27}$, —S(=O)$_2$N$R^{22}R^{23}$, and —S(=O)N$R^{22}R^{23}$; alternatively, $R^{16}$ and $R^{17}$ can, together with the atoms linking them, form a 3-10 membered heterocycloalkyl optionally substituted by 1-3 $R^{19}$ or a 5-10 membered heteroaryl optionally substituted by 1-3 $R^{19}$.

Embodiment 223

The compound of any of Embodiments 1-215, wherein $R^{17}$ is chosen from H and $C_{1-6}$alkyl; $R^{16}$ and $R^{18}$ are independently chosen from H, $C_{1-6}$alkyl optionally substituted by 1-3 $R^{19}$, $C_{6-10}$aryl optionally substituted by 1-3 $R^{19}$, $C_{7-11}$arylalkyl optionally substituted by 1-3 $R^{19}$, $C_{3-10}$cycloalkyl optionally substituted by 1-3 $R^{19}$, 3-10 membered heterocycloalkyl optionally substituted by 1-3 $R^{19}$, 5-10 membered heteroaryl optionally substituted by 1-3 $R^{19}$ halogen, —CN, —C(=O)$R^{20}$, —C(=O)O$R^{20}$, —C(=O)N$R^{22}R^{23}$, —NC, —NO$_2$, —N$R^{22}R^{23}$, —N$R^{24}$C(=O)$R^{20}$, —N$R^{24}$C(=O)O$R^{21}$, —N$R^{24}$C(=O)N$R^{22}R^{22}R^{23}$, —N$R^{24}$S(=O)$_2R^{21}$, —O$R^{20}$, —OCN, —OC(=O)$R^{20}$, —OC(=O)N$R^{22}R^{23}$, —SCN, —S(=O)$_nR^{20}$, —S(=O)$_2$O$R^{20}$, —SO$_3R^{27}$, —S(=O)$_2$N$R^{22}R^{23}$, and —S(=O)N$R^{22}R^{23}$; alternatively, $R^{16}$ and $R^{17}$ can, together with the atoms linking them, form a 3-10 membered heterocycloalkyl Embodiment 224

The compound of any of Embodiments 1-215, wherein $R^{17}$ is chosen from H and $C_{1-6}$alkyl; $R^{16}$ and $R^{18}$ are independently chosen from H, $C_{1-6}$alkyl optionally substituted by 1-3 $R^{19}$, $C_{6-10}$aryl optionally substituted by 1-3 $R^{19}$, $C_{7-11}$arylalkyl optionally substituted by 1-3 $R^{19}$, $C_{3-10}$cycloalkyl optionally substituted by 1-3 $R^{19}$, 3-10 membered heterocycloalkyl optionally substituted by 1-3 $R^{19}$, 5-10 membered heteroaryl optionally substituted by 1-3 $R^{19}$ halogen, —CN, —C(=O)$R^{20}$, —C(=O)NR$^{22}$R$^{23}$, —NC, —NO$_2$, —NR$^{22}$R$^{23}$, —NR$^{24}$C(=O)$R^{20}$, —NR$^{24}$C(=O)OR$^{21}$, —NR$^{24}$S(=O)$_2$R$^{21}$, —OR$^{20}$, —S(=O)$_n$R$^{20}$, and —S(=O)$_2$NR$^{22}$R$^{23}$; alternatively, $R^{16}$ and $R^{17}$ can, together with the atoms linking them, form a 3-10 membered heterocycloalkyl optionally substituted by 1-3 $R^{19}$ or a 5-10 membered heteroaryl optionally substituted by 1-3 $R^{19}$.

Embodiment 225

The compound of any of Embodiments 1-215, wherein $R^{17}$ is chosen from H and $C_{1-6}$alkyl; $R^{16}$ and $R^{18}$ are independently chosen from H, $C_{1-6}$alkyl optionally substituted by 1-3 $R^{19}$, $C_{6-10}$aryl optionally substituted by 1-3 $R^{19}$, $C_{7-11}$arylalkyl optionally substituted by 1-3 $R^{19}$, $C_{3-10}$cycloalkyl optionally substituted by 1-3 $R^{19}$, 3-10 membered heterocycloalkyl optionally substituted by 1-3 $R^{19}$, 5-10 membered heteroaryl optionally substituted by 1-3 $R^{19}$ halogen, —CN, —C(=O)$R^{20}$, —C(=O)NR$^{22}$R$^{23}$, —NO$_2$, —NR$^{22}$R$^{23}$, —NR$^{24}$C(=O)$R^{20}$, —NR$^{24}$S(=O)$_2$R$^{21}$, —OR$^{20}$, —S(=O)$_n$R$^{20}$, and —S(=O)$_2$NR$^{22}$R$^{23}$; alternatively, $R^{16}$ and $R^{17}$ can, together with the atoms linking them, form a 3-10 membered heterocycloalkyl optionally substituted by 1-3 $R^{19}$ or a 5-10 membered heteroaryl optionally substituted by 1-3 $R^{19}$.

Embodiment 226

The compound of any of Embodiments 1-215, wherein $R^{17}$ is H; $R^{16}$ and $R^{18}$ are independently chosen from H, $C_{1-6}$alkyl optionally substituted by 1-3 $R^{19}$, $C_{6-10}$aryl optionally substituted by 1-3 $R^{19}$, $C_{7-11}$arylalkyl optionally substituted by 1-3 $R^{19}$, $C_{3-10}$cycloalkyl optionally substituted by 1-3 $R^{19}$, 3-10 membered heterocycloalkyl optionally substituted by 1-3 $R^{19}$, 5-10 membered heteroaryl optionally substituted by 1-3 $R^{19}$, halogen, —CN, —C(=O)$R^{20}$, —C(=O)NR$^{22}$R$^{23}$, —NO$_2$, —NR$^{22}$R$^{23}$, —NR$^{24}$C(=O)$R^{20}$, —NR$^{24}$S(=O)$_2$R$^{21}$, —OR$^{20}$, —S(=O)$_n$R$^{20}$, and —S(=O)$_2$NR$^{22}$R$^{23}$; alternatively, $R^{16}$ and $R^{17}$ can, together with the atoms linking them, form a 3-10 membered heterocycloalkyl optionally substituted by 1-3 $R^{19}$ or a 5-10 membered heteroaryl optionally substituted by 1-3 $R^{19}$.

Embodiment 227

The compound of any of Embodiments 1-215, wherein $R^{17}$ is chosen from H and $C_{1-6}$alkyl; $R^{16}$ and $R^{18}$ are independently chosen from H, $C_{1-6}$alkyl optionally substituted by 1-3 $R^{19}$, $C_{6-10}$aryl, $C_{7-11}$arylalkyl, $C_{3-10}$cycloalkyl, 3-10 membered heterocycloalkyl, 5-10 membered heteroaryl, halogen, —CN, —C(=O)$R^{20}$, —C(=O)NR$^{22}$R$^{23}$, —NO$_2$, —NR$^{22}$R$^{23}$, —NR$^{24}$C(=O)$R^{20}$, —NR$^{24}$S(=O)$_2$R$^{21}$, —OR$^{20}$, —S(=O)$_n$R$^{20}$, and —S(=O)$_2$NR$^{22}$R$^{23}$; alternatively, $R^{16}$ and $R^{17}$ can, together with the atoms linking them, form a 3-10 membered heterocycloalkyl or a 5-10 membered heteroaryl.

Embodiment 228

The compound of any of Embodiments 1-215, wherein $R^{17}$ is H; $R^{16}$ and $R^{18}$ are independently chosen from H, $C_{1-6}$alkyl optionally substituted by 1-3 $R^{19}$, $C_{6-10}$aryl, $C_{7-11}$arylalkyl, $C_{3-10}$cycloalkyl, 3-10 membered heterocycloalkyl, 5-10 membered heteroaryl, halogen, —CN, —C(=O)$R^{20}$, —C(=O)NR$^{22}$R$^{23}$, —NO$_2$, —NR$^{22}$R$^{23}$, —NR$^{24}$C(=O)$R^{20}$, —NR$^{24}$S(=O)$_2$R$^{21}$, —OR$^{20}$, —S(=O)$_n$R$^{20}$, and —S(=O)$_2$NR$^{22}$R$^{23}$; alternatively, $R^{16}$ and $R^{17}$ can, together with the atoms linking them, form a 3-10 membered heterocycloalkyl or a 5-10 membered heteroaryl.

Embodiment 229

The compound of any of Embodiments 1-215, wherein $R^{17}$ is chosen from H and $C_{1-6}$alkyl; $R^{16}$ and $R^{18}$ are independently chosen from H, $C_{1-6}$alkyl optionally substituted by 1-3 $R^{19}$, halogen, —CN, —C(=O)$R^{20}$, —C(=O)NR$^{22}$R$^{23}$, —NO$_2$, —NR$^{22}$R$^{23}$, —NR$^{24}$C(=O)$R^{20}$, —NR$^{24}$S(=O)$_2$R$^{21}$, —OR$^{20}$, —S(=O)$_n$R$^{20}$, and —S(=O)$_2$NR$^{22}$R$^{23}$; alternatively, $R^{16}$ and $R^{17}$ can, together with the atoms linking them, form a 3-10 membered heterocycloalkyl or a 5-10 membered heteroaryl.

Embodiment 230

The compound of any of Embodiments 1-215, wherein $R^{17}$ is H; $R^{16}$ and $R^{18}$ are independently chosen from H, $C_{1-6}$alkyl optionally substituted by 1-3 $R^{19}$, halogen, —CN, —C(=O)$R^{20}$, —C(=O)NR$^{22}$R$^{23}$, —NO$_2$, —NR$^{22}$R$^{23}$, —NR$^{24}$C(=O)$R^{20}$, —NR$^{24}$S(=O)$_2$R$^{21}$, —OR$^{20}$, —S(=O)$_n$R$^2$, and —S(=O)$_2$NR$^{22}$R$^{23}$; alternatively, $R^{16}$ and $R^{17}$ can, together with the atoms linking them, form a 3-10 membered heterocycloalkyl or a 5-10 membered heteroaryl.

Embodiment 231

The compound of any of Embodiments 1-215, wherein $R^{17}$ is chosen from H and $C_{1-6}$alkyl; $R^{16}$ and $R^{18}$ are independently chosen from H, $C_{1-6}$alkyl optionally substituted by 1-3 $R^{19}$, halogen, —CN, —C(=O)$R^{20}$, —C(=O)NR$^{22}$R$^{23}$, —NO$_2$, —NR$^{22}$R$^{23}$, —NR$^{24}$C(=O)$R^{20}$, —NR$^{24}$S(=O)$_2$R$^{21}$, —OR$^{20}$, —S(=O)$_n$R$^{20}$, and —S(=O)$_2$NR$^{22}$R$^{23}$.

Embodiment 232

The compound of any of Embodiments 1-215, wherein $R^{17}$ is H; $R^{16}$ and $R^{18}$ are independently chosen from H, $C_{1-6}$alkyl optionally substituted by 1-3 $R^{19}$, halogen, —CN, —C(=O)$R^{20}$, —C(=O)NR$^{22}$R$^{23}$, —NO$_2$, —NR$^{22}$R$^{23}$, —NR$^{24}$C(=O)$R^{20}$, —NR$^{24}$S(=O)$_2$R$^{21}$, —OR$^{20}$, —S(=O)$_n$R$^{20}$, and —S(=O)$_2$NR$^{22}$R$^{23}$.

Embodiment 233

The compound of any of Embodiments 1-215, wherein $R^{17}$ is chosen from H and $C_{1-6}$alkyl; $R^{16}$ and $R^{18}$ are independently chosen from H, $C_{1-6}$alkyl optionally substituted by 1-3 $R^{19}$, halogen, and —$OR^{20}$.

Embodiment 234

The compound of any of Embodiments 1-215, wherein $R^7$ is H; $R^{16}$ and $R^{18}$ are independently chosen from H, $C_{1-6}$alkyl optionally substituted by 1-3 $R^{19}$, halogen, and —$OR^{20}$.

Embodiment 235

The compound of any of Embodiments 1-215, wherein $R^{17}$ is H; $R^{16}$ and $R^{18}$ are independently chosen from H, $C_{1-6}$alkyl optionally substituted by 1-3 $R^{19}$, and halogen.

Embodiment 236

The compound of any of Embodiments 1-215, wherein $R^{17}$ is H; $R^{16}$ and $R^{18}$ are independently chosen from H, $C_{1-6}$alkyl, and halogen.

Embodiment 237

The compound of any of Embodiments 1-215, wherein $R^{16}$, $R^{17}$, and $R^{18}$ are independently chosen from H and $C_{1-6}$alkyl.

Embodiment 238

The compound of any of Embodiments 1-215, wherein $R^{17}$ is chosen from H, $C_{1-6}$alkyl optionally substituted by 1-13 $R^{19}$, $C_{2-6}$ alkenyl optionally substituted by 1-11 $R^{19}$, $C_{2-6}$alkynyl optionally substituted by 1-9 $R^{19}$, $C_{6-11}$aryl optionally substituted by 1-11 $R^{19}$, $C_{7-16}$arylalkyl optionally substituted by 1-19 $R^{19}$, $C_{3-11}$cycloalkyl optionally substituted by 1-21 $R^{19}$, $C_{4-17}$cycloalkylalkyl optionally substituted by 1-32 $R^{19}$, 3-15 membered heterocycloalkyl optionally substituted by 1-28 $R^{19}$, 4-21 membered heterocycloalkylalkyl optionally substituted by 1-40 $R^{19}$, 5-15 membered heteroaryl optionally substituted by 1-15 $R^{19}$, 6-21 membered heteroarylalkyl optionally substituted by 1-27 $R^{19}$, and —$OR^{20}$; $R^{16}$ and $R^{18}$ are independently chosen from H, $C_{1-6}$alkyl optionally substituted by 1-13 $R^{19}$, $C_{2-6}$alkenyl optionally substituted by 1-11 $R^{19}$, $C_{2-6}$alkynyl optionally substituted by 1-9 $R^{19}$, $C_{6-11}$aryl optionally substituted by 1-11 $R^{19}$, $C_{7-16}$arylalkyl optionally substituted by 1-19 $R^{19}$, $C_{3-11}$cycloalkyl optionally substituted by 1-21 $R^{19}$, $C_{4-17}$cycloalkylalkyl optionally substituted by 1-32 $R^{19}$, 3-15 membered heterocycloalkyl optionally substituted by 1-28 $R^{19}$, 4-21 membered heterocycloalkylalkyl optionally substituted by 1-40 $R^{19}$, 5-15 membered heteroaryl optionally substituted by 1-15 $R^{19}$, 6-21 membered heteroarylalkyl optionally substituted by 1-27 $R^{19}$, halogen, —CN, —C(=O)$R^{20}$, —C(=O)$OR^{20}$, —C(=O)$NR^{22}R^{23}$, —$NO_2$, —$NR^{22}R^{23}$, and —$OR^{20}$; alternatively, $R^{16}$ and $R^{17}$ can, together with the atoms linking them, form a 3-15 membered heterocycloalkyl optionally substituted by 1-28 $R^{19}$ or a 5-15 membered heteroaryl optionally substituted by 1-15 $R^{19}$.

Embodiment 239

The compound of any of Embodiments 1-215, wherein $R^{17}$ is chosen from H, $C_{1-6}$alkyl optionally substituted by 1-13 $R^{19}$, $C_{2-6}$alkenyl optionally substituted by 1-11 $R^{19}$, $C_{2-6}$alkynyl optionally substituted by 1-9 $R^{19}$, $C_{6-11}$aryl optionally substituted by 1-11 $R^{19}$, $C_{7-16}$arylalkyl optionally substituted by 1-19 $R^{19}$, $C_{3-11}$cycloalkyl optionally substituted by 1-21 $R^{19}$, $C_{4-17}$cycloalkylalkyl optionally substituted by 1-32 $R^{19}$, 3-15 membered heterocycloalkyl optionally substituted by 1-28 $R^{19}$, 4-21 membered heterocycloalkylalkyl optionally substituted by 1-40 $R^{19}$, 5-15 membered heteroaryl optionally substituted by 1-15 $R^{19}$, 6-21 membered heteroarylalkyl optionally substituted by 1-27 $R^{19}$, and —$OR^{20}$; $R^{16}$ and $R^{18}$ are independently chosen from H, $C_{1-6}$alkyl optionally substituted by 1-13 $R^{19}$, $C_{2-6}$alkenyl optionally substituted by 1-11 $R^{19}$, $C_{2-6}$alkynyl optionally substituted by 1-9 $R^{19}$, $C_{6-11}$aryl optionally substituted by 1-11 $R^{19}$, $C_{7-16}$arylalkyl optionally substituted by 1-19 $R^{19}$, $C_{3-11}$cycloalkyl optionally substituted by 1-21 $R^{19}$, $C_{4-17}$cycloalkylalkyl optionally substituted by 1-32 $R^{19}$, 3-15 membered heterocycloalkyl optionally substituted by 1-28 $R^{19}$, 4-21 membered heterocycloalkylalkyl optionally substituted by 1-40 $R^{19}$, 5-15 membered heteroaryl optionally substituted by 1-15 $R^{19}$, 6-21 membered heteroarylalkyl optionally substituted by 1-27 $R^{19}$, halogen, —CN, —C(=O)$NR^{22}R^{23}$, —$NO_2$, —$NR^{22}R^{23}$, and —$OR^{20}$; alternatively, $R^{16}$ and $R^{17}$ can, together with the atoms linking them, form a 3-15 membered heterocycloalkyl optionally substituted by 1-28 $R^{19}$ or a 5-15 membered heteroaryl optionally substituted by 1-15 $R^{19}$.

Embodiment 240

The compound of any of Embodiments 1-215, wherein $R^{17}$ is H; $R^{16}$ and $R^{18}$ are independently chosen from H and $C_{1-6}$alkyl optionally substituted by 1-3 $R^{19}$.

Embodiment 241

The compound of any of Embodiments 1-215, wherein $R^7$ is H; $R^{16}$ and $R^{18}$ are independently chosen from H and $C_{1-6}$alkyl.

Embodiment 242

The compound of any of Embodiments 1-215, wherein $R^{17}$ is H; $R^{16}$ and $R^{18}$ are independently chosen from H and $C_{1-4}$alkyl.

Embodiment 243

The compound of any of Embodiments 1-215, wherein $R^{17}$ is H; $R^{16}$ and $R^{18}$ are independently chosen from H and $C_{1-3}$alkyl.

Embodiment 244

The compound of any of Embodiments 1-215, wherein $R^{17}$ is H; $R^{16}$ and $R^{18}$ are independently chosen from H and methyl.

Embodiment 245

The compound of any of Embodiments 1-215, wherein $R^{16}$, $R^{17}$, and $R^{18}$ are H.

Embodiment 246

The compound of any of Embodiments 1-240, wherein $R^{19}$ at each occurrence is independently chosen from $C_{1-6}$alkyl optionally substituted by 1-13 $R^{39}$, $C_{2-6}$alkenyl optionally substituted by 1-11 $R^{39}$, $C_{2-6}$alkynyl optionally substituted by 1-9 $R^{39}$, $C_{6-11}$aryl optionally substituted by 1-11 $R^{39}$, $C_{7-16}$arylalkyl optionally substituted by 1-19 $R^{39}$, $C_{3-11}$cycloalkyl optionally substituted by 1-21 $R^{39}$, $C_{4-17}$cycloalkylalkyl optionally substituted by 1-32 $R^{39}$, 3-15 membered heterocycloalkyl optionally substituted by 1-28 $R^{39}$, 4-21 membered heterocycloalkylalkyl optionally substituted by 1-40 $R^{39}$, 5-15 membered heteroaryl optionally substituted by 1-15 $R^{39}$, 6-21 membered heteroarylalkyl optionally substituted by 1-27 $R^{39}$, halogen, —CN, —C(=O)$R^{30}$, —C(=O)O$R^{30}$, —C(=O)N$R^{32}R^{33}$, —C(=O)C(=O)$R^{30}$, —C(=N$R^{35}$)$R^{30}$, —C(=N$R^{35}$)N$R^{32}R^{33}$, —C(=NOH)N$R^{32}R^{33}$, —C(=NO$R^{36}$)$R^{30}$, —C(=NN$R^{32}R^{33}$)$R^{30}$, —C(=NN$R^{34}$C(=O)$R^{31}$)$R^{30}$, —C(=NN$R^{34}$C(=O)O$R^{31}$)$R^{30}$, —C(=S)N$R^{32}R^{33}$, —NC, —NO$_2$, —N$R^{32}R^{33}$, —N$R^{34}$N$R^{32}R^{33}$, —N=N$R^{34}$, =N$R^{30}$, =NO$R^{30}$, —N$R^{34}R^{36}$, —N$R^{34}$C(=O)$R^{30}$, —N$R^{34}$C(=O)C(=O)$R^{30}$, —N$R^{34}$C(=O)O$R^{31}$, —N$R^{34}$C(=O)C(=O)O$R^{31}$, —N$R^{34}$C(=O)N$R^{32}R^{33}$, —N$R^{34}$C(=O)N$R^{34}$C(=O)$R^{30}$, —N$R^{34}$C(=O)N$R^{34}$C(=O)O$R^{30}$, —N$R^{34}$C(=N$R^{35}$)N$R^{32}R^{33}$, —N$R^{34}$C(=O)C(=O)N$R^{32}R^{33}$, —N$R^{34}$C(=S)$R^{30}$, —N$R^{34}$C(=S)O$R^{30}$, —N$R^{34}$C(=S)N$R^{32}R^{33}$, —N$R^{34}$S(=O)$_2R^{31}$, —N$R^{34}$S(=O)$_2$N$R^{32}R^{33}$, —N$R^{34}$P(=O)$R^{38}R^{38}$, —N$R^{34}$P(=O)(N$R^{32}R^{33}$)(N$R^{32}R^{33}$), —N$R^{34}$P(=)(O$R^{30}$)(O$R^{30}$), —N$R^{34}$P(=O)(S$R^{30}$)(S$R^{30}$), —O$R^{30}$, =O, —OCN, —OC(=O)$R^{30}$, —OC(=O)N$R^{32}R^{33}$, —OC(=O)O$R^{30}$, —OC(=N$R^{35}$)N$R^{32}R^{33}$, —OS(=O)$R^{30}$, —OS(=O)$_2R^{30}$, —OS(=O)$_2R^{30}$, —OS(=O)$_2$N$R^{32}R^{33}$, —OP(=O)$R^{38}R^{38}$, —OP(=O)(N$R^{32}R^{33}$)(N$R^{32}R^{33}$), —OP(=O)(O$R^{30}$)(O$R^{30}$), —OP(=O)(S$R^{30}$)(S$R^{30}$), —Si($R^{34}$)$_3$, —SCN, =S, —S(=O)$_nR^{30}$, —S(=O)$_2$O$R^{30}$, —SO$_3R^{37}$, —S(=O)$_2$N$R^{32}R^{33}$, —S(=O)N$R^{32}R^{33}$, —SP(=O)$R^{38}R^{38}$, —SP(=O)(N$R^{32}R^{33}$)(N$R^{32}R^{33}$), —SP(=O)(O$R^{30}$)(O$R^{30}$), —SP(=O)(S$R^{30}$)(S$R^{30}$), —P(=O)$R^{38}R^{38}$, —P(=O)(N$R^{22}R^{23}$)(N$R^{32}R^{33}$), —P(=O)(O$R^{30}$)(O$R^{30}$), and —P(=O)(S$R^{30}$)(S$R^{30}$).

Embodiment 247

The compound of any of Embodiments 1-240, wherein $R^{19}$ at each occurrence is independently chosen from $C_{1-6}$alkyl optionally substituted by 1-6 $R^{39}$, $C_{2-6}$alkenyl optionally substituted by 1-6 $R^{39}$, $C_{2-6}$alkynyl optionally substituted by 1-6 $R^{39}$, $C_{6-11}$aryl optionally substituted by 1-6 $R^{39}$, $C_{7-16}$arylalkyl optionally substituted by 1-6 $R^{39}$, $C_{3-11}$cycloalkyl optionally substituted by 1-6 $R^{39}$, $C_{4-17}$cycloalkylalkyl optionally substituted by 1-6 $R^{39}$, 3-15 membered heterocycloalkyl optionally substituted by 1-6 $R^{39}$, 4-21 membered heterocycloalkylalkyl optionally substituted by 1-6 $R^{39}$, 5-15 membered heteroaryl optionally substituted by 1-6 $R^{39}$, 6-21 membered heteroarylalkyl optionally substituted by 1-6 $R^{39}$, halogen, —CN, —C(=O)$R^{30}$, —C(=O)O$R^{30}$, —C(=O)N$R^{32}R^{33}$, —C(=O)C(=O)$R^{30}$, —C(=N$R^{35}$)$R^{30}$, —C(=N$R^{35}$)N$R^{32}R^{33}$, —C(=NOH)N$R^{32}R^{33}$, —C(=NO$R^{36}$)$R^{30}$, —C(=N$R^{32}R^{33}$)$R^{30}$, —C(=NN$R^{34}$C(=O)$R^{31}$)$R^{30}$, —C(=NN$R^{34}$C(=O)O$R^{31}$)$R^{30}$, —C(=S)N$R^{32}R^{33}$, —NC, —NO$_2$, —N$R^{32}R^{33}$, —N$R^{34}$N$R^{32}R^{33}$, —N=N$R^{34}$, =N$R^{30}$, =NO$R^{30}$, —N$R^{34}$O$R^{36}$, —N$R^{34}$C(=O)$R^{30}$, —N$R^{34}$C(=O)C(=O)$R^{30}$, —N$R^{34}$C(=O)O$R^{31}$, —N$R^{34}$C(=O)C(=O)O$R^{31}$, —N$R^{34}$C(=O)N$R^{32}R^{33}$, —$R^{34}$C(=O)N$R^{34}$C(=O)$R^{30}$, —N$R^{34}$C(=O)N$R^{34}$C(=O)O$R^{30}$, —N$R^{34}$C(=N$R^{35}$)N$R^{32}R^{33}$, —N$R^{34}$C(=O)C(=O)N$R^{32}R^{33}$, —N$R^{34}$C(=S)$R^{30}$, —N$R^{34}$C(=S)O$R^{30}$, —N$R^{34}$C(=S)N$R^{32}R^{33}$, —N$R^{34}$S(=O)$_2R^{31}$, —N$R^{34}$S(=O)$_2$N$R^{32}R^{33}$, —N$R^{34}$P(=O)$R^{38}R^{38}$, —N$R^{34}$P(=O)(N$R^{32}R^{33}$)(N$R^{32}R^{33}$), —N$R^{34}$P(=O)(O$R^{30}$)(O$R^{30}$), —N$R^{34}$P(=O)(S$R^{30}$)(S$R^{30}$), —O$R^{30}$, =O, —OCN, —OC(=O)$R^{30}$, —OC(=O)N$R^{32}R^{33}$, —OC(=O)O$R^{30}$, —OC(=N$R^{35}$)N$R^{32}R^{33}$, —OS(=O)$R^{30}$, —OS(=O)$_2R^{30}$, —OS(=O)$_2R^{30}$, —OS(=O)$_2$N$R^{32}R^{33}$, —OP(=O)$R^{38}R^{38}$, —OP(=O)(N$R^{32}R^{33}$)($R^{32}R^{33}$), —OP(=O)(O$R^{30}$)(O$R^{30}$), —OP(=O)(S$R^{30}$)(S$R^{30}$), —Si($R^{34}$)$_3$, —SCN, =S, —S(=O)$_nR^{30}$, —S(=O)$_2$O$R^{30}$, —SO$_3R^{37}$, —S(=O)$_2$N$R^{32}R^{33}$, —S(=O)N$R^{32}R^{33}$, —S(=O)N$R^{32}R^{33}$, —SP(=O)$R^{38}R^{38}$, —SP(=O)(N$R^{32}R^{33}$)(N$R^{32}R^{33}$), —SP(=O)(O$R^{30}$)(O$R^{30}$), —SP(=O)(S$R^{30}$)(S$R^{30}$), —P(=O)$R^{38}R^{38}$, —P(=O)(N$R^{32}R^{33}$)(N$R^{32}R^{33}$), —P(=O)(O$R^{30}$)(O$R^{30}$), and —P(=O)(S$R^{30}$)(S$R^{30}$).

Embodiment 248

The compound of any of Embodiments 1-240, wherein $R^{19}$ at each occurrence is independently chosen from $C_{1-6}$alkyl optionally substituted by 1-6 $R^{39}$, $C_{2-6}$alkenyl optionally substituted by 1-6 $R^{39}$, $C_{2-6}$alkynyl optionally substituted by 1-6 $R^{39}$, $C_{6-11}$aryl optionally substituted by 1-6 $R^{39}$, $C_{7-16}$arylalkyl optionally substituted by 1-6 $R^{39}$, $C_{3-11}$cycloalkyl optionally substituted by 1-6 $R^{39}$, $C_{4-17}$cycloalkylalkyl optionally substituted by 1-6 $R^{39}$, 3-15 membered heterocycloalkyl optionally substituted by 1-6 $R^{39}$, 4-21 membered heterocycloalkylalkyl optionally substituted by 1-6 $R^{39}$, 5-15 membered heteroaryl optionally substituted by 1-6 $R^{39}$, 6-21 membered heteroarylalkyl optionally substituted by 1-6 $R^{39}$, halogen, —CN, —C(=O)$R^{30}$, —C(=O)O$R^{30}$, —C(=O)N$R^{32}R^{33}$, —C(=O)C(=O)$R^{30}$, —NC, —NO$_2$, —N$R^{32}R^{33}$, —N$R^{34}$N$R^{32}R^{33}$, —N$R^{34}$O$R^{36}$, —N$R^{34}$C(=O)$R^{30}$, —N$R^{34}$C(=O)C(=O)$R^{30}$, —N$R^{34}$C(=O)O$R^{31}$, —N$R^{34}$C(=O)C(=O)O$R^{31}$, —N$R^{34}$C(=O)N$R^{32}R^{33}$, —N$R^{34}$C(=O)N$R^{34}$C(=O)$R^{30}$, —N$R^{34}$C(=O)N$R^{34}$C(=O)O$R^{30}$, —N$R^{34}$C(=O)O$R^{30}$, —N$R^{34}$C(=N$R^{35}$)N$R^{32}R^{33}$, —N$R^{34}$C(=O)C(=O)N$R^{32}R^{33}$, —N$R^{34}$S(=O)$_2R^{31}$, —N$R^{34}$S(=O)$_2$N$R^{32}R^{33}$, —O$R^{30}$, =O, —OCN, —OC(=O)$R^{30}$, —OC(=O)N$R^{32}R^{33}$, —OC(=O)O$R^{30}$, —OC(=N$R^{35}$)N$R^{32}R^{33}$, —Si($R^{34}$)$_3$, —SCN, =S, —S(=O)$_nR^{30}$, —S(=O)$_2$O$R^{30}$, —SO$_3R^{37}$, —S(=O)$_2$N$R^{32}R^{33}$, —S(=O)N$R^{32}R^{33}$, —P(=O)$R^{38}R^{38}$, —P(=O)(N$R^{323}$)(N$R^{32}R^{33}$), —P(=O)(O$R^{30}$)(O$R^{30}$), and —P(=O)(S$R^{30}$)(S$R^{30}$).

Embodiment 249

The compound of any of Embodiments 1-240, wherein $R^{19}$ at each occurrence is independently chosen from $C_{1-6}$alkyl optionally substituted by 1-3 $R^{39}$, $C_{2-6}$alkenyl optionally substituted by 1-3 $R^{39}$, $C_{2-6}$alkynyl optionally substituted by 1-3 $R^{39}$, $C_{6-11}$aryl optionally substituted by 1-3 $R^{39}$, $C_{7-16}$arylalkyl optionally substituted by 1-3 $R^{39}$, $C_{3-11}$cycloalkyl optionally substituted by 1-3 $R^{39}$, $C_{4-17}$cycloalkylalkyl optionally substituted by 1-3 $R^{39}$, 3-15 membered heterocycloalkyl optionally substituted by 1-3 $R^{39}$, 4-21 membered heterocycloalkylalkyl optionally substituted by 1-3 $R^{39}$, 5-15 membered heteroaryl optionally substituted by 1-3 $R^{39}$, 6-21 membered heteroarylalkyl optionally substituted by 1-3 $R^{39}$, halogen, —CN, —C(=O)$R^{30}$, —C(=O)O$R^{30}$, —C(=O)N$R^{32}R^{33}$, —C(=O)C(=O)$R^{30}$, —NC, —NO$_2$, —N$R^{32}R^{33}$, —N$R^{34}$N$R^{32}R^{33}$, —N$R^{340}R^{36}$, —N$R^{34}$C(=O)$R^{30}$, —N$R^{34}$C(=O)C(=O)$R^{30}$, —N$R^{34}$C(=O)O$R^{31}$, —N$R^{34}$C(=O)C(=O)O$R^{31}$, —N$R^{34}$C(=O)N$R^{32}R^{33}$, —N$R^{34}$C(=O)N$R^{34}$C(=O)$R^{30}$, —N$R^{34}$C(=O)N$R^{34}$C(=O)O$R^{30}$, —N$R^{34}$C(=N$R^{35}$)N$R^{32}R^{33}$, —N$R^{34}$C(=O)C(=O)N$R^{32}R^{33}$, —N$R^{34}$S(=O)$_2R^{31}$, —N$R^{34}$S(=O)$_2$N$R^{32}R^{33}$, —O$R^{30}$, =O, —OCN, —OC(=O)$R^{30}$, —OC(=O)N$R^{32}R^{33}$, —OC(=O)O$R^{30}$, —OC(=N$R^{35}$)N$R^{32}R^{33}$, —Si($R^{34}$)$_3$, —SCN, =S, —S(=O)$_nR^{30}$, —S(=O)$_2$O$R^{30}$, —SO$_3R^{37}$, —S(=O)$_2$N$R^{32}R^{33}$, —S(=O)

$NR^{32}R^{33}$, $-P(=O)R^{38}R^{38}$, $-P(=O)(NR^{323})(NR^{32}R^{33})$, $-P(=O)(OR^{30})(OR^{30})$, and $-P(=O)(SR^{30})(SR^{30})$.

Embodiment 250

The compound of any of Embodiments 1-240, wherein $R^{19}$ at each occurrence is independently chosen from $C_{1-6}$alkyl optionally substituted by 1-3 $R^{39}$, $C_{2-6}$alkenyl optionally substituted by 1-3 $R^{39}$, $C_{2-6}$alkynyl optionally substituted by 1-3 $R^{39}$, $C_{6-10}$aryl optionally substituted by 1-3 $R^{39}$, $C_{7-11}$arylalkyl optionally substituted by 1-3 $R^{39}$, $C_{3-10}$cycloalkyl optionally substituted by 1-3 $R^{39}$, 3-10 membered heterocycloalkyl optionally substituted by 1-3 $R^{39}$, 5-10 membered heteroaryl optionally substituted by 1-3 $R^{39}$, halogen, $-CN$, $-C(=O)R^{30}$, $-C(=O)OR^{30}$, $-C(=O)NR^{32}R^{33}$, $-C(=O)C(=O)R^{30}$, $-NC$, $-NO_2$, $-NR^{32}R^{33}$, $-NR^{34}NR^{32}R^{33}$, $-NR^{340}R^{36}$, $-NR^{34}C(=O)R^{30}$, $-NR^{34}C(=O)C(=O)R^{30}$, $-NR^{34}C(=O)OR^{31}$, $-NR^{34}C(=O)C(=O)OR^{31}$, $-NR^{34}C(=O)NR^{32}R^{33}$, $-NR^{34}C(=O)NR^{34}C(=O)R^{30}$, $-NR^{34}C(=O)NR^{34}C(=O)OR^{30}$, $-NR^{34}C(=NR^{35})NR^{32}R^{33}$, $-NR^{34}C(=O)C(=O)NR^{32}R^{33}$, $-NR^{34}S(=O)_2R^{31}$, $-NR^{34}S(=O)_2NR^{32}R^{33}$, $-OR^{30}$, $=O$, $-OCN$, $-OC(=O)R^{30}$, $-OC(=O)NR^{32}R^{33}$, $-OC(=O)OR^{30}$, $-OC(=NR^{35})NR^{32}R^{33}$, $-Si(R^{34})_3$, $-SCN$, $=S$, $-S(=O)_nR^{30}$, $-S(=O)_2OR^{30}$, $-SO_3R^{37}$, $-S(=O)_2NR^{32}R^{33}$, $-S(=O)NR^{32}R^{33}$, $-P(=O)R^{38}R^{38}$, $-P(=O)(NR^{32}R^{33})(NR^{32}R^{33})$, $-P(=O)(OR^{30})(OR^{30})$, and $-P(=O)(SR^{30})(SR^{30})$.

Embodiment 251

The compound of any of Embodiments 1-240, wherein $R^{19}$ at each occurrence is independently chosen from $C_{1-6}$alkyl optionally substituted by 1-3 $R^{39}$, $C_{2-6}$alkenyl optionally substituted by 1-3 $R^{39}$, $C_{2-6}$alkynyl optionally substituted by 1-3 $R^{39}$, $C_{6-10}$aryl optionally substituted by 1-3 $R^{39}$, $C_{7-11}$arylalkyl optionally substituted by 1-3 $R^{39}$, $C_{3-10}$cycloalkyl optionally substituted by 1-3 $R^{39}$, 3-10 membered heterocycloalkyl optionally substituted by 1-3 $R^{39}$, 5-10 membered heteroaryl optionally substituted by 1-3 $R^{39}$, halogen, $-CN$, $-C(=O)R^{30}$, $-C(=O)OR^{30}$, $-C(=O)NR^{32}R^{33}$, $-NO_2$, $-NR^{32}R^{33}$, $-NR^{34}C(=O)R^{30}$, $-NR^{34}C(=O)OR^{31}$, $-NR^{34}C(=O)NR^{32}R^{32}R^{33}$, $-NR^{34}S(=O)_2R^{31}$, $-NR^{34}S(=O)_2NR^{32}R^{33}$, $-OR^{30}$, $=O$, $-OC(=O)R^{30}$, $-OC(=O)NR^{32}R^{33}$, $-Si(R^{34})_3$, $=S$, $-S(=O)_nR^{30}$, $-S(=O)_2OR^3$, $-SO_3R^{37}$, $-S(=O)_2NR^{32}R^{33}$, $-S(=O)NR^{32}R^{33}$, $-P(=O)R^{38}R^{38}$, $-P(=O)(NR^{32}R^{33})(NR^{32}R^{33})$, $-P(=O)(OR^{30})(OR^{30})$, and $-P(=O)(SR^{30})(SR^{30})$.

Embodiment 252

The compound of any of Embodiments 1-240, wherein $R^{19}$ at each occurrence is independently chosen from $C_{1-6}$alkyl optionally substituted by 1-3 $R^{39}$, $C_{2-6}$alkenyl optionally substituted by 1-3 $R^{39}$, $C_{2-6}$alkynyl optionally substituted by 1-3 $R^{39}$, $C_{6-10}$aryl optionally substituted by 1-3 $R^{39}$, $C_{7-11}$arylalkyl optionally substituted by 1-3 $R^{39}$, $C_{3-10}$cycloalkyl optionally substituted by 1-3 $R^{39}$, 3-10 membered heterocycloalkyl optionally substituted by 1-3 $R^{39}$, 5-10 membered heteroaryl optionally substituted by 1-3 $R^{39}$, halogen, $-CN$, $-C(=O)R^{30}$, $-C(=O)OR^{30}$, $-C(=O)NR^{32}R^{33}$, $-NO_2$, $-NR^{32}R^{33}$, $-NR^{34}C(=O)R^{30}$, $-NR^{34}C(=O)OR^{31}$, $-NR^{34}C(=O)NR^{32}R^{33}$, $-NR^{34}S(=O)_2R^{31}$, $-NR^{34}S(=O)_2NR^{32}R^{33}$, $-OR^{30}$, $=O$, $-OC(=O)R^{30}$, $-OC(=O)NR^{32}R^{33}$, $-Si(R^{34})_3$, $=S$, $-S(=O)_nR^3$, $-S(=O)_2NR^{32}R^{33}$, and $-S(=O)NR^{32}R^{33}$.

Embodiment 253

The compound of any of Embodiments 1-240, wherein $R^{19}$ at each occurrence is independently chosen from $C_{1-6}$alkyl optionally substituted by 1-3 $R^{39}$, $C_{2-6}$alkenyl optionally substituted by 1-3 $R^{39}$, $C_{2-6}$alkynyl optionally substituted by 1-3 $R^{39}$, $C_{6-10}$aryl optionally substituted by 1-3 $R^{39}$, $C_{7-11}$arylalkyl optionally substituted by 1-3 $R^{39}$, $C_{3-10}$cycloalkyl optionally substituted by 1-3 $R^{39}$, 3-10 membered heterocycloalkyl optionally substituted by 1-3 $R^{39}$, 5-10 membered heteroaryl optionally substituted by 1-3 $R^{39}$, halogen, $-CN$, $-C(=O)R^{30}$, $-C(=O)OR^{30}$, $-C(=O)NR^{32}R^{33}$, $-NO_2$, $-NR^{32}R^{33}$, $-NR^{34}C(=O)R^{30}$, $-NR^{34}C(=O)NR^{32}R^{33}$, $-NR^{34}S(=O)_2R^{31}$, $-NR^{34}S(=O)_2NR^{32}R^{33}$, $-OR^{30}$, $=O$, $-OC(=O)R^{30}$, $-OC(=O)NR^{32}R^{33}$, $-Si(R^{34})_3$, $=S$, $-S(=O)_nR^{30}$, and $-S(=O)_2NR^{32}R^{33}$.

Embodiment 254

The compound of any of Embodiments 1-240, wherein $R^{19}$ at each occurrence is independently chosen from $C_{1-6}$alkyl optionally substituted by 1-3 $R^{39}$, $C_{2-6}$alkenyl optionally substituted by 1-3 $R^{39}$, $C_{2-6}$alkynyl optionally substituted by 1-3 $R^{39}$, $C_{6-10}$aryl optionally substituted by 1-3 $R^{39}$, $C_{7-11}$arylalkyl optionally substituted by 1-3 $R^{39}$, $C_{3-6}$cycloalkyl optionally substituted by 1-3 $R^{39}$, 3-6 membered heterocycloalkyl optionally substituted by 1-3 $R^{39}$, 5-6 membered heteroaryl optionally substituted by 1-3 $R^{39}$, halogen, $-CN$, $-C(=O)R^{30}$, $-C(=O)OR^{30}$, $-C(=O)NR^{32}R^{33}$, $-NO_2$, $-NR^{32}R^{33}$, $-NR^{34}C(=O)R^{30}$, $-NR^{34}C(=O)NR^{32}R^{33}$, $-NR^{34}S(=O)_2R^{31}$, $-NR^{34}S(=O)_2NR^{32}R^{33}$, $-OR^{30}$, $=O$, $-OC(=O)R^{30}$, $-OC(=O)NR^{32}R^{33}$, $-Si(R^{34})_3$, $=S$, $-S(=O)_nR^{30}$, and $-S(=O)_2NR^{32}R^{33}$.

Embodiment 255

The compound of any of Embodiments 1-240, wherein $R^{19}$ at each occurrence is independently chosen from $C_{1-6}$alkyl optionally substituted by 1-3 $R^{39}$, $C_{6-10}$aryl optionally substituted by 1-3 $R^{39}$, $C_{7-11}$arylalkyl optionally substituted by 1-3 $R^{39}$, $C_{3-6}$cycloalkyl optionally substituted by 1-3 $R^{39}$ 3-6 membered heterocycloalkyl optionally substituted by 1-3 $R^{39}$, 5-6 membered heteroaryl optionally substituted by 1-3 $R^{39}$, halogen, $-CN$, $-C(=O)R^{30}$, $-C(=O)OR^{30}$, $-C(=O)NR^{32}R^{33}$, $-NO_2$, $-NR^{32}R^{33}$, $-NR^{34}C(=O)R^{30}$, $-NR^{34}S(=O)_2R^{31}$, $-OR^{30}$, $=O$, $-OC(=O)R^{30}$, $-OC(=O)NR^{32}R^{33}$, $-Si(R^{34})_3$, $-S(=O)_nR^{30}$, and $-S(=O)_2NR^{32}R^{33}$.

Embodiment 256

The compound of any of Embodiments 1-240, wherein $R^{19}$ at each occurrence is independently chosen from $C_{1-6}$alkyl optionally substituted by 1-3 $R^{39}$, $C_{6-10}$aryl optionally substituted by 1-3 $R^{39}$, $C_{7-11}$arylalkyl optionally substituted by 1-3 $R^{39}$, $C_{3-6}$cycloalkyl optionally substituted by 1-3 $R^{39}$, 3-6 membered heterocycloalkyl optionally substituted by 1-3 $R^{39}$, 5-6 membered heteroaryl optionally substituted by 1-3 $R^{39}$, halogen, $-CN$, $-C(=O)R^{30}$,

Embodiment 257

The compound of any of Embodiments 1-240, wherein $R^{19}$ at each occurrence is independently chosen from $C_{1-6}$alkyl optionally substituted by 1-3 $R^{39}$, $C_{6-10}$aryl optionally substituted by 1-3 $R^{39}$, $C_{7-11}$arylalkyl optionally substituted by 1-3 $R^{39}$, $C_{3-6}$cycloalkyl optionally substituted by 1-3 $R^{39}$ 3-6 membered heterocycloalkyl optionally substituted by 1-3 $R^{39}$, 5-6 membered heteroaryl optionally substituted by 1-3 $R^{39}$, halogen, —CN, —C(=O)$R^{30}$, —C(=O)NR$^{32}$R$^{33}$, —NR$^{32}$R$^{33}$, —NR$^{34}$C(=O)R$^{30}$, —OR$^{30}$, and =O.

Embodiment 258

The compound of any of Embodiments 1-240, wherein $R^{19}$ at each occurrence is independently chosen from $C_{1-6}$alkyl, $C_{6-10}$aryl, $C_{7-11}$arylalkyl, $C_{3-6}$cycloalkyl, 3-6 membered heterocycloalkyl, 5-6 membered heteroaryl, halogen, —CN, —C(=O)R$^{30}$, —C(=O)NR$^{33}$, —NR$^{32}$R$^{33}$, —NR$^{34}$C(=O)R$^{30}$, —OR$^{30}$, and =O.

Embodiment 259

The compound of any of Embodiments 1-240, wherein $R^{19}$ at each occurrence is independently chosen from $C_{1-6}$alkyl, $C_{6-10}$aryl, $C_{7-11}$arylalkyl, $C_{3-6}$cycloalkyl, 3-6 membered heterocycloalkyl, 5-6 membered heteroaryl, halogen, —C(=O)R$^{30}$, —C(=O)OR$^{30}$, —C(=O)NR$^{32}$R$^{33}$, —NR$^{32}$R$^{33}$, and —OR$^{30}$.

Embodiment 260

The compound of any of Embodiments 1-240, wherein $R^{19}$ at each occurrence is independently chosen from $C_{1-6}$alkyl optionally substituted by 1-13 $R^{39}$, $C_{2-6}$alkenyl optionally substituted by 1-11 $R^{39}$, $C_{2-6}$alkynyl optionally substituted by 1-9 $R^{39}$, $C_{6-11}$aryl optionally substituted by 1-11 $R^{39}$, $C_{7-16}$arylalkyl optionally substituted by 1-19 $R^{39}$, $C_{3-11}$cycloalkyl optionally substituted by 1-21 $R^{39}$, $C_{4-17}$cycloalkylalkyl optionally substituted by 1-32 $R^{39}$, 3-15 membered heterocycloalkyl optionally substituted by 1-28 $R^{39}$, 4-21 membered heterocycloalkylalkyl optionally substituted by 1-40 $R^{39}$, 5-15 membered heteroaryl optionally substituted by 1-15 $R^{39}$, 6-21 membered heteroarylalkyl optionally substituted by 1-27 $R^{39}$, halogen, —CN, —C(=O)NR$^{32}$R$^{33}$, —NO$_2$, —NR$^{32}$R$^{33}$, and —OR$^{30}$.

Embodiment 261

The compound of any of Embodiments 1-240, wherein $R^{19}$ at each occurrence is independently chosen from $C_{1-6}$alkyl optionally substituted by 1-13 $R^{39}$.

Embodiment 262

The compound of any of Embodiments 1-240, wherein $R^{19}$ at each occurrence is independently chosen from $C_{1-6}$alkyl optionally substituted by 1-3 $R^{39}$, $C_{6-10}$aryl optionally substituted by 1-3 $R^{39}$, $C_{3-6}$cycloalkyl optionally substituted by 1-3 $R^{39}$, 3-6 membered heterocycloalkyl optionally substituted by 1-3 $R^{39}$, 5-6 membered heteroaryl optionally substituted by 1-3 $R^{39}$, halogen, —C(=O)OR$^{30}$, —NR$^{32}$R$^{33}$, and —OR$^{30}$.

Embodiment 263

The compound of any of Embodiments 1-240, wherein $R^{19}$ at each occurrence is independently chosen from $C_{1-6}$alkyl optionally substituted by 1-3 $R^{39}$, phenyl optionally substituted by 1-3 $R^{39}$, $C_{3-6}$cycloalkyl optionally substituted by 1-3 $R^{39}$, 3-6 membered heterocycloalkyl optionally substituted by 1-3 $R^{39}$, 5-6 membered heteroaryl optionally substituted by 1-3 $R^{39}$ halogen, —C(=O)OR$^{30}$, —NR$^{32}$R$^{33}$, and —OR$^{30}$.

Embodiment 264

The compound of any of Embodiments 1-240, wherein $R^{19}$ at each occurrence is independently chosen from $C_{1-6}$alkyl, phenyl optionally substituted by 1-3 $R^{39}$, $C_{3-6}$cycloalkyl, 3-6 membered heterocycloalkyl optionally substituted by 1-3 $R^{39}$, 5-6 membered heteroaryl, halogen, —C(=O)OR$^{30}$, —NR$^{32}$R$^{33}$, and —OR$^{30}$.

Embodiment 265

The compound of any of Embodiments 1-240, wherein $R^{19}$ at each occurrence is independently chosen from $C_{1-6}$alkyl, phenyl optionally substituted by 1 $R^{39}$, $C_{3-6}$cycloalkyl, 3-6 membered heterocycloalkyl optionally substituted by 1 $R^{39}$, 5-6 membered heteroaryl, halogen, —C(=O)OR$^{3}$, —NR$^{32}$R$^{33}$, and —OR$^{30}$.

Embodiment 266

The compound of any of Embodiments 1-240, wherein $R^{19}$ at each occurrence is independently chosen from $C_{1-6}$alkyl, phenyl, $C_{3-6}$ cycloalkyl, 3-6 membered heterocycloalkyl, 5-6 membered heteroaryl, halogen, —C(=O)OR$^{30}$, —NR$^{32}$R$^{33}$, and —OR$^{30}$.

Embodiment 267

The compound of any of Embodiments 1-266, wherein $R^{20}$, $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H, $C_{1-6}$alkyl optionally substituted by 1-6 $R^{49}$, $C_{2-6}$alkenyl optionally substituted by 1-6 $R^{49}$, $C_{2-6}$alkynyl optionally substituted by 1-6 $R^{49}$, $C_{6-11}$aryl optionally substituted by 1-6 $R^{49}$, $C_{7-16}$arylalkyl optionally substituted by 1-6 $R^{49}$, $C_{3-11}$cycloalkyl optionally substituted by 1-6 $R^{49}$, $C_{4-17}$cycloalkylalkyl optionally substituted by 1-6 $R^{49}$, 3-15 membered heterocycloalkyl optionally substituted by 1-6 $R^{49}$, 4-21 membered heterocycloalkylalkyl optionally substituted by 1-6 $R^{49}$, 5-15 membered heteroaryl optionally substituted by 1-6 $R^{49}$, and 6-21 membered heteroarylalkyl optionally substituted by 1-6 $R^{49}$.

Embodiment 268

The compound of any of Embodiments 1-266, wherein $R^{20}$, $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H, $C_{1-6}$alkyl optionally substituted by 1-6 $R^{49}$, $C_{2-6}$alkenyl optionally substituted by 1-6 $R^{49}$, $C_{2-6}$alkynyl optionally substituted by 1-6 $R^{49}$, $C_{6-10}$aryl optionally substituted by 1-6 $R^{49}$, $C_{7-11}$arylalkyl optionally substituted by 1-6 $R^{49}$, $C_{3-10}$cycloalkyl optionally substituted by 1-6 $R^{49}$, 3-10 membered heterocycloalkyl optionally substituted by 1-6 $R^{49}$, and 5-10 membered heteroaryl optionally substituted by 1-6 $R^{49}$.

Embodiment 269

The compound of any of Embodiments 1-266, wherein $R^{20}$, $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H, $C_{1-6}$alkyl optionally substituted by 1-3 $R^{49}$, $C_{2-6}$ alkenyl optionally substituted by 1-3 $R^{49}$, $C_{2-6}$alkynyl optionally substituted by 1-3 $R^{49}$, $C_{6-10}$aryl optionally substituted by 1-3 $R^{49}$, $C_{7-11}$arylalkyl optionally substituted by 1-3 $R^{49}$, $C_{3-10}$cycloalkyl optionally substituted by 1-3 $R^{49}$, 3-10 membered heterocycloalkyl optionally substituted by 1-3 $R^{49}$, and 5-10 membered heteroaryl optionally substituted by 1-3 $R^{49}$.

Embodiment 270

The compound of any of Embodiments 1-266, wherein $R^{20}$, $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H, $C_{1-6}$alkyl optionally substituted by 1-3 $R^{49}$, $C_{6-10}$aryl optionally substituted by 1-3 $R^{49}$, $C_{7-11}$arylalkyl optionally substituted by 1-3 $R^{49}$, $C_{3-10}$cycloalkyl optionally substituted by 1-3 $R^{49}$, 3-10 membered heterocycloalkyl optionally substituted by 1-3 $R^{49}$, and 5-10 membered heteroaryl optionally substituted by 1-3 $R^{49}$.

Embodiment 271

The compound of any of Embodiments 1-266, wherein $R^{20}$, $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H, $C_{1-6}$alkyl optionally substituted by 1-3 $R^{49}$, $C_{6-10}$aryl optionally substituted by 1-3 $R^{49}$, $C_{7-11}$arylalkyl optionally substituted by 1-3 $R^{49}$, $C_{3-6}$cycloalkyl optionally substituted by 1-3 $R^{49}$, 3-6 membered heterocycloalkyl optionally substituted by 1-3 $R^{49}$, and 5-6 membered heteroaryl optionally substituted by 1-3 $R^{49}$.

Embodiment 272

The compound of any of Embodiments 1-266, wherein $R^{20}$, $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H, $C_{1-6}$alkyl optionally substituted by 1-3 $R^{49}$, phenyl optionally substituted by 1-3 $R^{49}$, benzyl optionally substituted by 1-3 $R^{49}$, $C_{3-6}$ cycloalkyl optionally substituted by 1-3 $R^{49}$, 3-6 membered heterocycloalkyl optionally substituted by 1-3 $R^{49}$, and 5-6 membered heteroaryl optionally substituted by 1-3 $R^{49}$.

Embodiment 273

The compound of any of Embodiments 1-266, wherein $R^{20}$, $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H, $C_{1-6}$alkyl optionally substituted by 1-3 $R^{49}$, phenyl optionally substituted by 1-3 $R^{49}$, benzyl optionally substituted by 1-3 $R^{49}$, $C_{3-6}$ cycloalkyl, 3-6 membered heterocycloalkyl, and 5-6 membered heteroaryl.

Embodiment 274

The compound of any of Embodiments 1-266, wherein $R^{20}$ at each occurrence is independently chosen from H, $C_{1-6}$alkyl optionally substituted by 1-3 $R^{49}$, phenyl optionally substituted by 1-3 $R^{49}$, benzyl optionally substituted by 1-3 $R^{49}$, $C_{3-6}$cycloalkyl, 3-6 membered heterocycloalkyl, and 5-6 membered heteroaryl; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H and $C_{1-6}$alkyl optionally substituted by 1-3 $R^{49}$.

Embodiment 275

The compound of any of Embodiments 1-266, wherein $R^{20}$ at each occurrence is independently chosen from H, $C_{1-6}$alkyl optionally substituted by 1-3 $R^{49}$, phenyl optionally substituted by 1-3 $R^{49}$, benzyl optionally substituted by 1-3 $R^{49}$, $C_{3-6}$cycloalkyl, 3-6 membered heterocycloalkyl, and 5-6 membered heteroaryl; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H and $C_{1-6}$alkyl.

Embodiment 276

The compound of any of Embodiments 1-266, wherein $R^{20}$ at each occurrence is independently chosen from H, $C_{1-6}$alkyl optionally substituted by 1-3 $R^{49}$, phenyl optionally substituted by 1-3 $R^{49}$, benzyl optionally substituted by 1-3 $R^{49}$, $C_{3-6}$cycloalkyl, 3-6 membered heterocycloalkyl, and 5-6 membered heteroaryl; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is H.

Embodiment 277

The compound of any of Embodiments 1-266, wherein $R^{20}$, $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H and $C_{1-6}$alkyl optionally substituted by 1-6 $R^{49}$.

Embodiment 278

The compound of any of Embodiments 1-266, wherein $R^{20}$, $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H and $C_{1-6}$alkyl.

Embodiment 279

The compound of any of Embodiments 1-266, wherein $R^{20}$, $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H, $C_{1-6}$alkyl optionally substituted by 1-3 $R^{49}$, $C_{6-10}$aryl optionally substituted by 1-3 $R^{49}$, $C_{3-6}$cycloalkyl optionally substituted by 1-3 $R^{49}$, 3-6 membered heterocycloalkyl optionally substituted by 1-3 $R^{49}$, and 5-6 membered heteroaryl optionally substituted by 1-3 $R^{49}$.

Embodiment 280

The compound of any of Embodiments 1-266, wherein $R^{20}$, $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H, $C_{6-11}$aryl optionally substituted by 1-3 $R^{49}$, $C_{3-6}$ cycloalkyl optionally substituted by 1-3 $R^{49}$, 3-6 membered heterocycloalkyl optionally substituted by 1-3 $R^{49}$, and 5-6 membered heteroaryl optionally substituted by 1-3 $R^{49}$.

Embodiment 281

The compound of any of Embodiments 1-266, wherein $R^{20}$, $R^{21}$, $R^{24}$, $R^{25}$, $R^{26}$, $R^{27}$, $R^{30}$, $R^{31}$, $R^{34}$, $R^{35}$, $R^{36}$ and $R^{37}$

97 at each occurrence is independently chosen from H, $C_{1-6}$alkyl optionally substituted by 1-3 $R^{49}$, phenyl optionally substituted by 1-3 $R^{49}$, $C_{3-6}$cycloalkyl optionally substituted by 1-3 $R^{49}$ 5-6 membered heterocycloalkyl optionally substituted by 1-3 $R^{49}$, and 5-6 membered heteroaryl optionally substituted by 1-3 $R^{49}$.

Embodiment 282

The compound of any of Embodiments 1-266, wherein $R^{20}$, $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H, phenyl optionally substituted by 1-3 $R^{49}$, $C_{3-6}$cycloalkyl optionally substituted by 1-3 $R^{49}$, 5-6 membered heterocycloalkyl optionally substituted by 1-3 $R^{49}$, and 5-6 membered heteroaryl optionally substituted by 1-3 $R^{49}$.

Embodiment 283

The compound of any of Embodiments 1-266, wherein $R^{20}$, $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H, $C_{1-6}$alkyl, phenyl optionally substituted by 1-3 $R^{49}$, $C_{3-6}$cycloalkyl, 5-6 membered heterocycloalkyl, and 5-6 membered heteroaryl.

Embodiment 284

The compound of any of Embodiments 1-266, wherein $R^{20}$, $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H, phenyl optionally substituted by 1-3 $R^{49}$, $C_{3-6}$ cycloalkyl, 5-6 membered heterocycloalkyl, and 5-6 membered heteroaryl.

Embodiment 285

The compound of any of Embodiments 1-266, wherein $R^{20}$, $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H, $C_{1-6}$alkyl, phenyl optionally substituted by 1-3 $R^{49}$ cyclopropyl, 5 membered heterocycloalkyl, and 5 membered heteroaryl.

Embodiment 286

The compound of any of Embodiments 1-266, wherein $R^{20}$, $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H, phenyl optionally substituted by 1-3 $R^{49}$ cyclopropyl, 5 membered heterocycloalkyl, and 5 membered heteroaryl.

Embodiment 287

The compound of any of Embodiments 1-266, wherein $R^{20}$, $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H, $C_{1-6}$alkyl, phenyl optionally substituted by 1 $R^{49}$, $C_{3-6}$ cycloalkyl, 5-6 membered heterocycloalkyl, and 5-6 membered heteroaryl.

Embodiment 288

The compound of any of Embodiments 1-266, wherein $R^{20}$, $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H, phenyl

98 optionally substituted by 1 $R^{49}$, $C_{3-6}$ cycloalkyl, 5-6 membered heterocycloalkyl, and 5-6 membered heteroaryl.

Embodiment 289

The compound of any of Embodiments 1-266, wherein $R^{20}$, $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H, $C_{1-6}$alkyl, phenyl, $C_{3-6}$cycloalkyl, 5-6 membered heterocycloalkyl, and 5-6 membered heteroaryl.

Embodiment 290

The compound of any of Embodiments 1-266, wherein $R^{20}$, $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H, phenyl, $C_{3-6}$cycloalkyl, 5-6 membered heterocycloalkyl, and 5-6 membered heteroaryl.

Embodiment 291

The compound of any of Embodiments 1-266, wherein $R^{20}$, $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H, $C_{1-6}$alkyl, phenyl, cyclopropyl, 5 membered heterocycloalkyl, and 5 membered heteroaryl.

Embodiment 292

The compound of any of Embodiments 1-266, wherein $R^{20}$, $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H, phenyl, cyclopropyl, 5 membered heterocycloalkyl, and 5 membered heteroaryl.

Embodiment 293

The compound of any of Embodiments 1-266, wherein $R^{20}$ at each occurrence is independently chosen from H, $C_{1-6}$alkyl optionally substituted by 1-3 $R^{49}$, $C_{6-10}$aryl optionally substituted by 1-3 $R^{49}$, $C_{3-6}$cycloalkyl optionally substituted by 1-3 $R^{49}$, 3-6 membered heterocycloalkyl optionally substituted by 1-3 $R^{49}$, and 5-6 membered heteroaryl optionally substituted by 1-3 $R^{49}$; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H and $C_{1-6}$alkyl optionally substituted by 1-3 $R^{49}$.

Embodiment 294

The compound of any of Embodiments 1-266, wherein $R^{20}$ at each occurrence is independently chosen from H, $C_{6-10}$aryl optionally substituted by 1-3 $R^{49}$, $C_{3-6}$cycloalkyl optionally substituted by 1-3 $R^{49}$, 3-6 membered heterocycloalkyl optionally substituted by 1-3 $R^{49}$, and 5-6 membered heteroaryl optionally substituted by 1-3 $R^{49}$; $R^{21}$, $R^{24}$, $R^{25}$, $R^{26}$, $R^{27}$, $R^{3}$, $R^{31}$, $R^{34}$, $R^{35}$, $R^{36}$ and $R^{37}$ at each occurrence is independently chosen from H and $C_{1-6}$alkyl optionally substituted by 1-3 $R^{49}$.

Embodiment 295

The compound of any of Embodiments 1-266, wherein $R^{20}$ at each occurrence is independently chosen from H, $C_{1-6}$alkyl optionally substituted by 1-3 $R^{49}$, phenyl optionally substituted by 1-3 $R^{49}$, $C_{3-6}$cycloalkyl optionally substituted by 1-3 $R^{49}$, 5-6 membered heterocycloalkyl optionally substituted by 1-3 $R^{49}$, and 5-6 membered heteroaryl optionally substituted by 1-3 $R^{49}$; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H and $C_{1-6}$alkyl optionally substituted by 1-3 $R^{49}$.

Embodiment 296

The compound of any of Embodiments 1-266, wherein $R^{20}$ at each occurrence is independently chosen from H, phenyl optionally substituted by 1-3 $R^{49}$, $C_{3-6}$cycloalkyl optionally substituted by 1-3 $R^{49}$, 5-6 membered heterocycloalkyl optionally substituted by 1-3 $R^{49}$, and 5-6 membered heteroaryl optionally substituted by 1-3 $R^{49}$; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H and $C_{1-6}$alkyl optionally substituted by 1-3 $R^{49}$.

Embodiment 297

The compound of any of Embodiments 1-266, wherein $R^{20}$ at each occurrence is independently chosen from H, $C_{1-6}$alkyl, phenyl optionally substituted by 1-3 $R^{49}$, $C_{3-6}$cycloalkyl, 5-6 membered heterocycloalkyl, and 5-6 membered heteroaryl; $R^{21}$, $R^{24}$, $R^{25}$, $R^{26}$, $R^{27}$, $R^3$, $R^{31}$, $R^{34}$, $R^{35}$, $R^{36}$ and $R^{37}$ at each occurrence is independently chosen from H and $C_{1-6}$alkyl optionally substituted by 1-3 $R^{49}$.

Embodiment 298

The compound of any of Embodiments 1-266, wherein $R^{20}$ at each occurrence is independently chosen from H, phenyl optionally substituted by 1-3 $R^{49}$, $C_{3-6}$cycloalkyl, 5-6 membered heterocycloalkyl, and 5-6 membered heteroaryl; $R^{21}$, $R^{24}$, $R^{25}$, $R^{26}$, $R^{27}$, $R^3$, $R^{31}$, $R^{34}$, $R^{35}$, $R^{36}$ and $R^{37}$ at each occurrence is independently chosen from H and $C_{1-6}$alkyl optionally substituted by 1-3 $R^{49}$.

Embodiment 299

The compound of any of Embodiments 1-266, wherein $R^{20}$ at each occurrence is independently chosen from H, $C_{1-6}$alkyl, phenyl optionally substituted by 1-3 $R^{49}$, cyclopropyl, 5 membered heterocycloalkyl, and 5 membered heteroaryl; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H and $C_{1-6}$alkyl optionally substituted by 1-3 $R^{49}$.

Embodiment 300

The compound of any of Embodiments 1-266, wherein $R^{20}$ at each occurrence is independently chosen from H, phenyl optionally substituted by 1-3 $R^{49}$, cyclopropyl, 5 membered heterocycloalkyl, and 5 membered heteroaryl; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H and $C_{1-6}$alkyl optionally substituted by 1-3 $R^{49}$.

Embodiment 301

The compound of any of Embodiments 1-266, wherein $R^{20}$ at each occurrence is independently chosen from H, $C_{1-6}$alkyl, phenyl optionally substituted by 1 $R^{49}$, $C_{3-6}$cycloalkyl, 5-6 membered heterocycloalkyl, and 5-6 membered heteroaryl; $R^{21}$, $R^{24}$, $R^{25}$, $R^{26}$, $R^{27}$, $R^{30}$, $R^{31}$, $R^{34}$, $R^3$, $R^{36}$ and $R^{37}$ at each occurrence is independently chosen from H and $C_{1-6}$alkyl optionally substituted by 1-3 $R^{49}$.

Embodiment 302

The compound of any of Embodiments 1-266, wherein $R^{20}$ at each occurrence is independently chosen from H, phenyl optionally substituted by 1 $R^{49}$, $C_{3-6}$cycloalkyl, 5-6 membered heterocycloalkyl, and 5-6 membered heteroaryl; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H and $C_{1-6}$alkyl optionally substituted by 1-3 $R^{49}$.

Embodiment 303

The compound of any of Embodiments 1-266, wherein $R^{20}$ at each occurrence is independently chosen from H, $C_{1-6}$alkyl, phenyl, $C_{3-6}$cycloalkyl, 5-6 membered heterocycloalkyl, and 5-6 membered heteroaryl; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H and $C_{1-6}$alkyl optionally substituted by 1-3 $R^{49}$.

Embodiment 304

The compound of any of Embodiments 1-266, wherein $R^{20}$ at each occurrence is independently chosen from H, phenyl, $C_{3-6}$cycloalkyl, 5-6 membered heterocycloalkyl, and 5-6 membered heteroaryl; $R^{21}$, $R^{24}$, $R^{25}$, $R^{26}$, $R^{27}$, $R^3$, $R^{31}$, $R^{34}$, $R^{35}$, $R^{36}$ and $R^{37}$ at each occurrence is independently chosen from H and $C_{1-6}$alkyl optionally substituted by 1-3 $R^{49}$.

Embodiment 305

The compound of any of Embodiments 1-266, wherein $R^{20}$ at each occurrence is independently chosen from H, $C_{1-6}$alkyl, phenyl, cyclopropyl, 5 membered heterocycloalkyl, and 5 membered heteroaryl; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H and $C_{1-6}$alkyl optionally substituted by 1-3 $R^{49}$.

Embodiment 306

The compound of any of Embodiments 1-266, wherein $R^{20}$ at each occurrence is independently chosen from H, phenyl, cyclopropyl, 5 membered heterocycloalkyl, and 5 membered heteroaryl; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H and $C_{1-6}$alkyl optionally substituted by 1-3 $R^{49}$.

Embodiment 307

The compound of any of Embodiments 1-266, wherein $R^{20}$ at each occurrence is independently chosen from H, $C_{1-6}$alkyl optionally substituted by 1-3 $R^{49}$, $C_{6-10}$aryl optionally substituted by 1-3 $R^{49}$, $C_{3-6}$cycloalkyl optionally substituted by 1-3 $R^{49}$, 3-6 membered heterocycloalkyl optionally substituted by 1-3 $R^{49}$, and 5-6 membered heteroaryl optionally substituted by 1-3 $R^{49}$; $R^{21}$, $R^{24}$, $R^{25}$, $R^{26}$, $R^{27}$, $R^3$, $R^{31}$, $R^{34}$, $R^{35}$, $R^{36}$ and $R^{37}$ at each occurrence is independently chosen from H and $C_{1-6}$alkyl.

Embodiment 308

The compound of any of Embodiments 1-266, wherein $R^{20}$ at each occurrence is independently chosen from H,

Embodiment 308 (continued)

$C_{6-10}$aryl optionally substituted by 1-3 $R^{49}$, $C_{3-6}$cycloalkyl optionally substituted by 1-3 $R^{49}$, 3-6 membered heterocycloalkyl optionally substituted by 1-3 $R^{49}$, and 5-6 membered heteroaryl optionally substituted by 1-3 $R^{49}$; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H and $C_{1-6}$alkyl.

Embodiment 309

The compound of any of Embodiments 1-266, wherein $R^{20}$ at each occurrence is independently chosen from H, $C_{1-6}$alkyl optionally substituted by 1-3 $R^{49}$, phenyl optionally substituted by 1-3 $R^{49}$, $C_{3-6}$cycloalkyl optionally substituted by 1-3 $R^{49}$, 5-6 membered heterocycloalkyl optionally substituted by 1-3 $R^{49}$, and 5-6 membered heteroaryl optionally substituted by 1-3 $R^{49}$; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H and $C_{1-6}$alkyl.

Embodiment 310

The compound of any of Embodiments 1-266, wherein $R^{20}$ at each occurrence is independently chosen from H, phenyl optionally substituted by 1-3 $R^{49}$, $C_{3-6}$cycloalkyl optionally substituted by 1-3 $R^{49}$, 5-6 membered heterocycloalkyl optionally substituted by 1-3 $R^{49}$, and 5-6 membered heteroaryl optionally substituted by 1-3 $R^{49}$; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H and $C_{1-6}$alkyl.

Embodiment 311

The compound of any of Embodiments 1-266, wherein $R^{20}$ at each occurrence is independently chosen from H, $C_{1-6}$alkyl, phenyl optionally substituted by 1-3 $R^{49}$, $C_{3-6}$cycloalkyl, 5-6 membered heterocycloalkyl, and 5-6 membered heteroaryl; $R^{21}$, $R^{24}$, $R^{25}$, $R^{26}$, $R^{27}$, $R^{3}$, $R^{31}$, $R^{34}$, $R^{35}$, $R^{36}$ and $R^{37}$ at each occurrence is independently chosen from H and $C_{1-6}$alkyl.

Embodiment 312

The compound of any of Embodiments 1-266, wherein $R^{20}$ at each occurrence is independently chosen from H, phenyl optionally substituted by 1-3 $R^{49}$, $C_{3-6}$cycloalkyl, 5-6 membered heterocycloalkyl, and 5-6 membered heteroaryl; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H and $C_{1-6}$alkyl.

Embodiment 313

The compound of any of Embodiments 1-266, wherein $R^{20}$ at each occurrence is independently chosen from H, $C_{1-6}$alkyl, phenyl optionally substituted by 1-3 $R^{49}$, cyclopropyl, 5 membered heterocycloalkyl, and 5 membered heteroaryl; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H and $C_{1-6}$alkyl.

Embodiment 314

The compound of any of Embodiments 1-266, wherein $R^{20}$ at each occurrence is independently chosen from H, phenyl optionally substituted by 1-3 $R^{49}$, cyclopropyl, 5 membered heterocycloalkyl, and 5 membered heteroaryl; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H and $C_{1-6}$alkyl.

Embodiment 315

The compound of any of Embodiments 1-266, wherein $R^{20}$ at each occurrence is independently chosen from H, $C_{1-6}$alkyl, phenyl optionally substituted by 1 $R^{49}$, $C_{3-6}$cycloalkyl, 5-6 membered heterocycloalkyl, and 5-6 membered heteroaryl; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H and $C_{1-6}$alkyl.

Embodiment 316

The compound of any of Embodiments 1-266, wherein $R^{20}$ at each occurrence is independently chosen from H, phenyl optionally substituted by 1 $R^{49}$, $C_{3-6}$cycloalkyl, 5-6 membered heterocycloalkyl, and 5-6 membered heteroaryl; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H and $C_{1-6}$alkyl.

Embodiment 317

The compound of any of Embodiments 1-266, wherein $R^{20}$ at each occurrence is independently chosen from H, $C_{1-6}$alkyl, phenyl, $C_{3-6}$ cycloalkyl, 5-6 membered heterocycloalkyl, and 5-6 membered heteroaryl; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H and $C_{1-6}$alkyl.

Embodiment 318

The compound of any of Embodiments 1-266, wherein $R^{20}$ at each occurrence is independently chosen from H, phenyl, $C_{3-6}$cycloalkyl, 5-6 membered heterocycloalkyl, and 5-6 membered heteroaryl; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H and $C_{1-6}$alkyl.

Embodiment 319

The compound of any of Embodiments 1-266, wherein $R^{20}$ at each occurrence is independently chosen from H, $C_{1-6}$alkyl, phenyl, cyclopropyl, 5 membered heterocycloalkyl, and 5 membered heteroaryl; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H and $C_{1-6}$alkyl.

Embodiment 320

The compound of any of Embodiments 1-266, wherein $R^{20}$ at each occurrence is independently chosen from H, phenyl, cyclopropyl, 5 membered heterocycloalkyl, and 5 membered heteroaryl; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H and $C_{1-6}$alkyl.

Embodiment 321

The compound of any of Embodiments 1-266, wherein $R^{20}$ at each occurrence is independently chosen from H, $C_{1-6}$alkyl optionally substituted by 1-3 $R^{49}$, $C_{6-10}$aryl optionally substituted by 1-3 $R^{49}$, $C_{3-6}$cycloalkyl optionally substituted by 1-3 $R^{49}$, 3-6 membered heterocycloalkyl optionally substituted by 1-3 $R^{49}$, and 5-6 membered heteroaryl optionally substituted by 1-3 $R^{49}$; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is H.

Embodiment 322

The compound of any of Embodiments 1-266, wherein $R^{20}$ at each occurrence is independently chosen from H, $C_{6-10}$aryl optionally substituted by 1-3 $R^{49}$, $C_{3-6}$cycloalkyl optionally substituted by 1-3 $R^{49}$, 3-6 membered heterocycloalkyl optionally substituted by 1-3 $R^{49}$, and 5-6 membered heteroaryl optionally substituted by 1-3 $R^{49}$; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is H.

Embodiment 323

The compound of any of Embodiments 1-266, wherein $R^{20}$ at each occurrence is independently chosen from H, $C_{1-6}$alkyl optionally substituted by 1-3 $R^{49}$, phenyl optionally substituted by 1-3 $R^{49}$, $C_{3-6}$cycloalkyl optionally substituted by 1-3 $R^{49}$, 5-6 membered heterocycloalkyl optionally substituted by 1-3 $R^{49}$, and 5-6 membered heteroaryl optionally substituted by 1-3 $R^{49}$; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is H.

Embodiment 324

The compound of any of Embodiments 1-266, wherein $R^{20}$ at each occurrence is independently chosen from H, phenyl optionally substituted by 1-3 $R^{49}$, $C_{3-6}$cycloalkyl optionally substituted by 1-3 $R^{49}$, 5-6 membered heterocycloalkyl optionally substituted by 1-3 $R^{49}$, and 5-6 membered heteroaryl optionally substituted by 1-3 $R^{49}$; $R^{21}$, $R^{24}$, $R^{25}$, $R^{26}$, $R^{27}$, $R^{3}$, $R^{31}$, $R^{34}$, $R^{35}$, $R^{36}$ and $R^{37}$ at each occurrence is H.

Embodiment 325

The compound of any of Embodiments 1-266, wherein $R^{20}$ at each occurrence is independently chosen from H, $C_{1-6}$alkyl, phenyl optionally substituted by 1-3 $R^{49}$, $C_{3-6}$cycloalkyl, 5-6 membered heterocycloalkyl, and 5-6 membered heteroaryl; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is H.

Embodiment 326

The compound of any of Embodiments 1-266, wherein $R^{20}$ at each occurrence is independently chosen from H, phenyl optionally substituted by 1-3 $R^{49}$, $C_{3-6}$cycloalkyl, 5-6 membered heterocycloalkyl, and 5-6 membered heteroaryl; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is H.

Embodiment 327

The compound of any of Embodiments 1-266, wherein $R^{20}$ at each occurrence is independently chosen from H, $C_{1-6}$alkyl, phenyl optionally substituted by 1-3 $R^{49}$, cyclopropyl, 5 membered heterocycloalkyl, and 5 membered heteroaryl; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is H.

Embodiment 328

The compound of any of Embodiments 1-266, wherein $R^{20}$ at each occurrence is independently chosen from H, phenyl optionally substituted by 1-3 $R^{49}$, cyclopropyl, 5 membered heterocycloalkyl, and 5 membered heteroaryl; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is H.

Embodiment 329

The compound of any of Embodiments 1-266, wherein $R^{20}$ at each occurrence is independently chosen from H, $C_{1-6}$alkyl, phenyl optionally substituted by 1 $R^{49}$, $C_{3-6}$cycloalkyl, 5-6 membered heterocycloalkyl, and 5-6 membered heteroaryl; $R^{21}$, $R^{24}$, $R^{25}$, $R^{26}$, $R^{27}$, $R^{3}$, $R^{31}$, $R^{34}$, $R^{35}$, $R^{36}$ and $R^{37}$ at each occurrence is H.

Embodiment 330

The compound of any of Embodiments 1-266, wherein $R^{20}$ at each occurrence is independently chosen from H, phenyl optionally substituted by 1 $R^{49}$, $C_{3-6}$cycloalkyl, 5-6 membered heterocycloalkyl, and 5-6 membered heteroaryl; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is H.

Embodiment 331

The compound of any of Embodiments 1-266, wherein $R^{20}$ at each occurrence is independently chosen from H, $C_{1-6}$alkyl, phenyl, $C_{3-6}$ cycloalkyl, 5-6 membered heterocycloalkyl, and 5-6 membered heteroaryl; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is H.

Embodiment 332

The compound of any of Embodiments 1-266, wherein $R^{20}$ at each occurrence is independently chosen from H, phenyl, $C_{3-6}$cycloalkyl, 5-6 membered heterocycloalkyl, and 5-6 membered heteroaryl; $R^{21}$, $R^{24}$, $R^{25}$, $R^{26}$, $R^{27}$, $R^{3}$, $R^{31}$, $R^{34}$, $R^{35}$, $R^{36}$ and $R^{37}$ at each occurrence is H.

Embodiment 333

The compound of any of Embodiments 1-266, wherein $R^{20}$ at each occurrence is independently chosen from H, $C_{1-6}$alkyl, phenyl, cyclopropyl, 5 membered heterocycloalkyl, and 5 membered heteroaryl; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is H.

Embodiment 334

The compound of any of Embodiments 1-266, wherein $R^{20}$ at each occurrence is independently chosen from H, phenyl, cyclopropyl, 5 membered heterocycloalkyl, and 5 membered heteroaryl; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is H.

Embodiment 335

The compound of any of Embodiments 1-266, wherein $R^{20}$, $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is H.

Embodiment 336

The compound of any of Embodiments 1-335, wherein $R^{28}$ and $R^{38}$ at each occurrence is independently chosen from $C_{1-6}$alkyl optionally substituted by 1-13 $R^{49}$, $C_{2-6}$alkenyl optionally substituted by 1-11 $R^{49}$, $C_{2-6}$alkynyl optionally substituted by 1-9 $R^{49}$, $C_{6-11}$aryl optionally substituted by 1-11 $R^{49}$, $C_{7-16}$arylalkyl optionally substituted by 1-19 $R^{49}$, $C_{3-11}$-cycloalkyl optionally substituted by 1-21 $R^{49}$, $C_{4-17}$cycloalkylalkyl optionally substituted by 1-32 $R^{49}$, 3-15 membered heterocycloalkyl optionally substituted by 1-28 $R^{49}$, 4-21 membered heterocycloalkylalkyl optionally substituted by 1-40 $R^{49}$, 5-15 membered heteroaryl optionally substituted by 1-15 $R^{49}$, and 6-21 membered heteroarylalkyl optionally substituted by 1-27 $R^{49}$.

Embodiment 337

The compound of any of Embodiments 1-335, wherein $R^{28}$ and $R^{38}$ at each occurrence is independently chosen from $C_{1-6}$alkyl optionally substituted by 1-3 $R^{49}$, $C_{2-6}$alkenyl optionally substituted by 1-3 $R^{49}$, $C_{2-6}$alkynyl optionally substituted by 1-3 $R^{49}$, $C_{6-11}$aryl optionally substituted by 1-3 $R^{49}$, $C_{7-11}$ arylalkyl optionally substituted by 1-3 $R^{49}$, $C_{3-11}$-cycloalkyl optionally substituted by 1-3 $R^{49}$, $C_{4-17}$cycloalkylalkyl optionally substituted by 1-3 $R^{49}$, 3-15 membered heterocycloalkyl optionally substituted by 1-3 $R^{49}$, 4-21 membered heterocycloalkylalkyl optionally substituted by 1-3 $R^{49}$, 5-15 membered heteroaryl optionally substituted by 1-3 $R^{49}$, and 6-21 membered heteroarylalkyl optionally substituted by 1-3 $R^{49}$.

Embodiment 338

The compound of any of Embodiments 1-335, wherein $R^{28}$ and $R^{38}$ at each occurrence is independently chosen from $C_{1-6}$alkyl optionally substituted by 1-3 $R^{49}$, $C_{2-6}$alkenyl optionally substituted by 1-3 $R^{49}$, $C_{2-6}$alkynyl optionally substituted by 1-3 $R^{49}$, $C_{6-10}$aryl optionally substituted by 1-3 $R^{49}$, $C_{7-11}$ arylalkyl optionally substituted by 1-3 $R^{49}$, $C_{3-10}$cycloalkyl optionally substituted by 1-3 $R^{49}$, 3-10 membered heterocycloalkyl optionally substituted by 1-3 $R^{49}$, and 5-10 membered heteroaryl optionally substituted by 1-3 $R^{49}$.

Embodiment 339

The compound of any of Embodiments 1-335, wherein $R^{28}$ and $R^{38}$ at each occurrence is independently chosen from $C_{1-6}$alkyl optionally substituted by 1-3 $R^{49}$, $C_{6-10}$aryl optionally substituted by 1-3 $R^{49}$, $C_{7-11}$arylalkyl optionally substituted by 1-3 $R^{49}$, $C_{3-10}$cycloalkyl optionally substituted by 1-3 $R^{49}$, 3-10 membered heterocycloalkyl optionally substituted by 1-3 $R^{49}$, and 5-10 membered heteroaryl optionally substituted by 1-3 $R^{49}$.

Embodiment 340

The compound of any of Embodiments 1-335, wherein $R^{28}$ and $R^{38}$ at each occurrence is independently chosen from $C_{1-6}$alkyl, $C_{6-10}$aryl, $C_{7-11}$arylalkyl, $C_{3-10}$cycloalkyl, 3-10 membered heterocycloalkyl, and 5-10 membered heteroaryl.

Embodiment 341

The compound of any of Embodiments 1-335, wherein $R^{28}$ and $R^{38}$ at each occurrence is independently chosen from $C_{1-6}$alkyl, $C_{6-10}$aryl, and $C_{7-11}$arylalkyl.

Embodiment 342

The compound of any of Embodiments 1-335, wherein $R^{28}$ and $R^{38}$ at each occurrence is independently chosen from $C_{1-6}$alkyl, phenyl, and benzyl.

Embodiment 343

The compound of any of Embodiments 1-335, wherein $R^{28}$ and $R^{38}$ at each occurrence is independently chosen from $C_{1-6}$alkyl and $C_{6-10}$ aryl.

Embodiment 344

The compound of any of Embodiments 1-335, wherein $R^{28}$ and $R^{38}$ at each occurrence is independently chosen from $C_{1-6}$alkyl and phenyl.

Embodiment 345

The compound of any of Embodiments 1-335, wherein $R^{28}$ and $R^{38}$ at each occurrence is $C_{1-6}$alkyl optionally substituted by 1-3 $R^{49}$.

Embodiment 346

The compound of any of Embodiments 1-335, wherein $R^{28}$ and $R^{38}$ at each occurrence is $C_{1-6}$alkyl.

Embodiment 347

The compound of any of Embodiments 1-346, wherein $R^{22}$, $R^{23}$, $R^{32}$ and $R^{33}$ at each occurrence is independently chosen from H, $C_{1-6}$alkyl optionally substituted by 1-13 $R^{59}$, $C_{2-6}$alkenyl optionally substituted by 1-11 $R^{59}$, $C_{2-6}$alkynyl optionally substituted by 1-9 $R^{59}$, $C_{6-11}$aryl optionally substituted by 1-11 $R^{59}$, $C_{7-16}$arylalkyl optionally substituted by 1-19 $R^{59}$, $C_{3-11}$cycloalkyl optionally substituted by 1-21 $R^{59}$, $C_{4-17}$cycloalkylalkyl optionally substituted by 1-32 $R^{59}$, 3-15 membered heterocycloalkyl optionally substituted by 1-28 $R^{59}$, 4-21 membered heterocycloalkylalkyl optionally substituted by 1-40 $R^{59}$, 5-15 membered heteroaryl optionally substituted by 1-15 $R^{59}$, and 6-21 membered heteroarylalkyl optionally substituted by 1-27 $R^{59}$; alternatively, any $R^{22}$ and $R^{23}$ and/or $R^{32}$ and $R^{33}$ may form, together with the nitrogen atom to which they are attached, a 3-15 membered heterocycloalkyl optionally substituted by 1-28 $R^{69}$ or a 5-15 membered heteroaryl optionally substituted by 1-15 $R^{69}$.

Embodiment 348

The compound of any of Embodiments 1-346, wherein $R^{22}$, $R^{23}$, $R^{32}$ and $R^{33}$ at each occurrence is independently chosen from H, $C_{1-6}$alkyl optionally substituted by 1-3 $R^{59}$, $C_{2-6}$alkenyl optionally substituted by 1-3 $R^{59}$, $C_{2-6}$ alkynyl optionally substituted by 1-3 $R^{59}$, $C_{6-11}$aryl optionally substituted by 1-3 $R^{59}$, $C_{7-16}$arylalkyl optionally substituted by 1-3 $R^{59}$, $C_{3-11}$-cycloalkyl optionally substituted by 1-3 $R^{59}$, $C_{4-17}$cycloalkylalkyl optionally substituted by 1-3 $R^{59}$, 3-15 membered heterocycloalkyl optionally substituted by 1-3 $R^{59}$, 4-21 membered heterocycloalkylalkyl optionally substituted by 1-3 $R^{59}$, 5-15 membered heteroaryl optionally substituted by 1-3 $R^{59}$, and 6-21 membered heteroarylalkyl optionally substituted by 1-3 $R^{59}$; alternatively, any $R^{22}$ and $R^{23}$ and/or $R^{32}$ and $R^{33}$ may form, together with the nitrogen atom to which they are attached, a 3-15 membered heterocycloalkyl optionally substituted by 1-3 $R^{69}$ or a 5-15 membered heteroaryl optionally substituted by 1-3 $R^{69}$.

Embodiment 349

The compound of any of Embodiments 1-346, wherein $R^{22}$, $R^{23}$, $R^{32}$ and $R^{33}$ at each occurrence is independently chosen from H, $C_{1-6}$alkyl optionally substituted by 1-3 $R^{59}$, $C_{2-6}$alkenyl optionally substituted by 1-3 $R^{59}$, $C_{2-6}$ alkynyl optionally substituted by 1-3 $R^{59}$, $C_{6-10}$aryl optionally substituted by 1-3 $R^{59}$, $C_{7-11}$arylalkyl optionally substituted by 1-3 $R^{59}$, $C_{3-10}$cycloalkyl optionally substituted by 1-3 $R^{59}$, 3-10 membered heterocycloalkyl optionally substituted by 1-3 $R^{59}$, and 5-10 membered heteroaryl optionally substituted by 1-3 $R^{59}$; alternatively, any $R^{22}$ and $R^{23}$ and/or $R^{32}$ and $R^{33}$ may form, together with the nitrogen atom to which they are attached, a 3-10 membered heterocycloalkyl optionally substituted by 1-3 $R^{69}$ or a 5-10 membered heteroaryl optionally substituted by 1-3 $R^{69}$.

Embodiment 350

The compound of any of Embodiments 1-346, wherein $R^{22}$, $R^{23}$, $R^{32}$ and $R^{33}$ at each occurrence is independently chosen from H, $C_{1-6}$alkyl optionally substituted by 1-3 $R^{59}$, $C_{2-6}$alkenyl optionally substituted by 1-3 $R^{59}$, $C_{2-6}$ alkynyl optionally substituted by 1-3 $R^{59}$, $C_{6-10}$aryl optionally substituted by 1-3 $R^{59}$, $C_{7-11}$arylalkyl optionally substituted by 1-3 $R^{59}$, $C_{3-10}$cycloalkyl optionally substituted by 1-3 $R^{59}$, 3-10 membered heterocycloalkyl optionally substituted by 1-3 $R^{59}$, and 5-10 membered heteroaryl optionally substituted by 1-3 $R^{59}$.

Embodiment 351

The compound of any of Embodiments 1-346, wherein $R^{22}$, $R^{23}$, $R^{32}$ and $R^{33}$ at each occurrence is independently chosen from H, $C_{1-6}$alkyl optionally substituted by 1-3 $R^{59}$, $C_{6-10}$aryl optionally substituted by 1-3 $R^{59}$, $C_{7-11}$arylalkyl optionally substituted by 1-3 $R^{59}$, $C_{3-10}$cycloalkyl optionally substituted by 1-3 $R^{59}$, 3-10 membered heterocycloalkyl optionally substituted by 1-3 $R^{59}$, and 5-10 membered heteroaryl optionally substituted by 1-3 $R^{59}$; alternatively, any $R^{22}$ and $R^{23}$ and/or $R^{32}$ and $R^{33}$ may form, together with the nitrogen atom to which they are attached, a 3-10 membered heterocycloalkyl optionally substituted by 1-3 $R^{69}$ or a 5-10 membered heteroaryl optionally substituted by 1-3 $R^{69}$.

Embodiment 352

The compound of any of Embodiments 1-346, wherein $R^{22}$, $R^{23}$, $R^{32}$ and $R^{33}$ at each occurrence is independently chosen from H, $C_{1-6}$alkyl optionally substituted by 1-3 $R^{59}$, $C_{6-10}$aryl optionally substituted by 1-3 $R^{59}$, $C_{7-11}$arylalkyl optionally substituted by 1-3 $R^{59}$, $C_{3-10}$cycloalkyl optionally substituted by 1-3 $R^{59}$, 3-10 membered heterocycloalkyl optionally substituted by 1-3 $R^{59}$, and 5-10 membered heteroaryl optionally substituted by 1-3 $R^{59}$.

Embodiment 353

The compound of any of Embodiments 1-346, wherein $R^{22}$, $R^{23}$, $R^{32}$ and $R^{33}$ at each occurrence is independently chosen from H, $C_{1-6}$alkyl, $C_{6-10}$aryl, $C_{7-11}$arylalkyl, $C_{3-10}$cycloalkyl, 3-10 membered heterocycloalkyl, and 5-10 membered heteroaryl; alternatively, any $R^{22}$ and $R^{23}$ and/or $R^{32}$ and $R^{33}$ may form, together with the nitrogen atom to which they are attached, a 3-10 membered heterocycloalkyl or a 5-10 membered heteroaryl.

Embodiment 354

The compound of any of Embodiments 1-346, wherein $R^{22}$, $R^{23}$, $R^{32}$ and $R^{33}$ at each occurrence is independently chosen from H, $C_{1-6}$alkyl, $C_{6-10}$aryl, $C_{7-11}$arylalkyl, $C_{3-10}$cycloalkyl, 3-10 membered heterocycloalkyl, and 5-10 membered heteroaryl.

Embodiment 355

The compound of any of Embodiments 1-346, wherein $R^{22}$, $R^{23}$, $R^{32}$ and $R^{33}$ at each occurrence is independently chosen from H, $C_{1-6}$alkyl optionally substituted by 1-3 $R^{59}$, $C_{6-10}$aryl optionally substituted by 1-3 $R^{59}$, and 5-10 membered heteroaryl optionally substituted by 1-3 $R^{59}$.

Embodiment 356

The compound of any of Embodiments 1-346, wherein $R^{22}$, $R^{23}$, $R^{32}$ and $R^{33}$ at each occurrence is independently chosen from H, $C_{6-10}$aryl optionally substituted by 1-3 $R^{59}$, and 5-10 membered heteroaryl optionally substituted by 1-3 $R^{59}$.

Embodiment 357

The compound of any of Embodiments 1-346, wherein $R^{22}$, $R^{23}$, $R^{32}$ and $R^{33}$ at each occurrence is independently chosen from H, phenyl optionally substituted by 1-3 $R^{59}$, and 5-6 membered heteroaryl optionally substituted by 1-3 $R^{59}$.

Embodiment 358

The compound of any of Embodiments 1-346, wherein $R^{22}$, $R^{23}$, $R^{32}$ and $R^{33}$ at each occurrence is independently chosen from H, phenyl optionally substituted by 1-3 $R^{59}$, and 6 membered heteroaryl optionally substituted by 1-3 $R^{59}$.

Embodiment 359

The compound of any of Embodiments 1-346, wherein $R^{22}$, $R^{23}$, $R^{32}$ and $R^{33}$ at each occurrence is independently chosen from H, phenyl optionally substituted by 1 $R^{59}$, and 6 membered heteroaryl optionally substituted by 1 $R^{59}$.

Embodiment 360

The compound of any of Embodiments 1-346, wherein $R^{22}$ at each occurrence is independently chosen from H, $C_{1-6}$alkyl optionally substituted by 1-13 $R^{59}$, $C_{2-6}$alkenyl optionally substituted by 1-11 $R^{59}$, $C_{2-6}$alkynyl optionally substituted by 1-9 $R^{59}$, $C_{6-11}$aryl optionally substituted by 1-11 $R^{59}$, $C_{7-16}$arylalkyl optionally substituted by 1-19 $R^{59}$, $C_{3-11}$cycloalkyl optionally substituted by 1-21 $R^{59}$, $C_4$-17cycloalkylalkyl optionally substituted by 1-32 $R^{59}$, 3-15 membered heterocycloalkyl optionally substituted by 1-28 $R^{59}$, 4-21 membered heterocycloalkylalkyl optionally substituted by 1-40 $R^{59}$, 5-15 membered heteroaryl optionally substituted by 1-15 $R^{59}$, and 6-21 membered heteroarylalkyl optionally substituted by 1-27 $R^{59}$; $R^{23}$, $R^{32}$ and $R^{33}$ at each occurrence is independently chosen from H and $C_{1-6}$alkyl; alternatively, any $R^{22}$ and $R^{23}$ and/or $R^{32}$ and $R^{33}$ may form, together with the nitrogen atom to which they are attached, a 3-15 membered heterocycloalkyl optionally substituted by 1-28 $R^{69}$ or a 5-15 membered heteroaryl optionally substituted by 1-15 $R^{69}$.

Embodiment 361

The compound of any of Embodiments 1-346, wherein $R^{22}$ at each occurrence is independently chosen from H, $C_{1-6}$alkyl optionally substituted by 1-3 $R^{59}$, $C_{2-6}$alkenyl optionally substituted by 1-3 $R^{59}$, $C_{2-6}$alkynyl optionally substituted by 1-3 $R^{59}$, $C_{6-11}$-aryl optionally substituted by 1-3 $R^{59}$, $C_{7-16}$arylalkyl optionally substituted by 1-3 $R^{59}$, $C_{3-11}$-cycloalkyl optionally substituted by 1-3 $R^{59}$, $C_{4-17}$cycloalkylalkyl optionally substituted by 1-3 $R^{59}$, 3-15 membered heterocycloalkyl optionally substituted by 1-3 $R^{59}$, 4-21 membered heterocycloalkylalkyl optionally substituted by 1-3 $R^{59}$, 5-15 membered heteroaryl optionally substituted by 1-3 $R^{59}$, and 6-21 membered heteroarylalkyl optionally substituted by 1-3 $R^{59}$; $R^{23}$, $R^{32}$ and $R^{33}$ at each occurrence is independently chosen from H and $C_{1-6}$alkyl; alternatively, any $R^{22}$ and $R^{23}$ and/or $R^{32}$ and $R^{33}$ may form, together with the nitrogen atom to which they are attached, a 3-15 membered heterocycloalkyl optionally substituted by 1-3 $R^{69}$ or a 5-15 membered heteroaryl optionally substituted by 1-3 $R^{69}$.

Embodiment 362

The compound of any of Embodiments 1-346, wherein $R^{22}$ at each occurrence is independently chosen from H, $C_{1-6}$alkyl optionally substituted by 1-3 $R^{59}$, $C_{2-6}$alkenyl optionally substituted by 1-3 $R^{59}$, $C_{2-6}$alkynyl optionally substituted by 1-3 $R^{59}$, $C_{6-10}$aryl optionally substituted by 1-3 $R^{59}$, $C_{7-11}$arylalkyl optionally substituted by 1-3 $R^{59}$, $C_{3-10}$cycloalkyl optionally substituted by 1-3 $R^{59}$, 3-10 membered heterocycloalkyl optionally substituted by 1-3 $R^{59}$, and 5-10 membered heteroaryl optionally substituted by 1-3 $R^{59}$; $R^{23}$, $R^{32}$ and $R^{33}$ at each occurrence is independently chosen from H and $C_{1-6}$alkyl; alternatively, any $R^{22}$ and $R^{23}$ and/or $R^{32}$ and $R^{33}$ may form, together with the nitrogen atom to which they are attached, a 3-10 membered heterocycloalkyl optionally substituted by 1-3 $R^{69}$ or a 5-10 membered heteroaryl optionally substituted by 1-3 $R^{69}$.

Embodiment 363

The compound of any of Embodiments 1-346, wherein $R^{22}$ at each occurrence is independently chosen from H, $C_{1-6}$alkyl optionally substituted by 1-3 $R^{59}$, $C_{2-6}$alkenyl optionally substituted by 1-3 $R^{59}$, $C_{2-6}$alkynyl optionally substituted by 1-3 $R^{59}$, $C_{6-10}$aryl optionally substituted by 1-3 $R^{59}$, $C_{7-11}$arylalkyl optionally substituted by 1-3 $R^{59}$, $C_{3-10}$cycloalkyl optionally substituted by 1-3 $R^{59}$, 3-10 membered heterocycloalkyl optionally substituted by 1-3 $R^{59}$, and 5-10 membered heteroaryl optionally substituted by 1-3 $R^{59}$; $R^{23}$, $R^{32}$ and $R^{33}$ at each occurrence is independently chosen from H and $C_{1-6}$alkyl.

Embodiment 364

The compound of any of Embodiments 1-346, wherein $R^{22}$ at each occurrence is independently chosen from H, $C_{1-6}$alkyl optionally substituted by 1-3 $R^{59}$, $C_{6-10}$aryl optionally substituted by 1-3 $R^{59}$, $C_{7-11}$arylalkyl optionally substituted by 1-3 $R^{59}$, $C_{3-10}$cycloalkyl optionally substituted by 1-3 $R^{59}$ 3-10 membered heterocycloalkyl optionally substituted by 1-3 $R^{59}$, and 5-10 membered heteroaryl optionally substituted by 1-3 $R^{59}$; $R^{23}$, $R^{32}$ and $R^{33}$ at each occurrence is independently chosen from H and $C_{1-6}$alkyl; alternatively, any $R^{22}$ and $R^{23}$ and/or $R^{32}$ and $R^{33}$ may form, together with the nitrogen atom to which they are attached, a 3-10 membered heterocycloalkyl optionally substituted by 1-3 $R^{69}$ or a 5-10 membered heteroaryl optionally substituted by 1-3 $R^{69}$.

Embodiment 365

The compound of any of Embodiments 1-346, wherein $R^{22}$ at each occurrence is independently chosen from H, $C_{1-6}$alkyl optionally substituted by 1-3 $R^{59}$, $C_{6-10}$aryl optionally substituted by 1-3 $R^{59}$, $C_{7-11}$arylalkyl optionally substituted by 1-3 $R^{59}$, $C_{3-10}$cycloalkyl optionally substituted by 1-3 $R^{59}$, 3-10 membered heterocycloalkyl optionally substituted by 1-3 $R^{59}$, and 5-10 membered heteroaryl optionally substituted by 1-3 $R^{59}$; $R^{23}$, $R^{32}$ and $R^{33}$ at each occurrence is independently chosen from H and $C_{1-6}$alkyl.

Embodiment 366

The compound of any of Embodiments 1-346, wherein $R^{22}$ at each occurrence is independently chosen from H, $C_{1-6}$alkyl, $C_{6-10}$aryl, $C_{7-11}$arylalkyl, $C_{3-10}$cycloalkyl, 3-10 membered heterocycloalkyl, and 5-10 membered heteroaryl; $R^{23}$, $R^{32}$ and $R^{33}$ at each occurrence is independently chosen from H and $C_{1-6}$alkyl; alternatively, any $R^{22}$ and $R^{23}$ and/or $R^{32}$ and $R^{33}$ may form, together with the nitrogen atom to which they are attached, a 3-10 membered heterocycloalkyl or a 5-10 membered heteroaryl.

Embodiment 367

The compound of any of Embodiments 1-346, wherein $R^{22}$ at each occurrence is independently chosen from H, $C_{1-6}$alkyl, $C_{6-10}$aryl, $C_{7-11}$ arylalkyl, $C_{3-10}$cycloalkyl, 3-10 membered heterocycloalkyl, and 5-10 membered heteroaryl; $R^{23}$, $R^{32}$ and $R^{33}$ at each occurrence is independently chosen from H and $C_{1-6}$alkyl.

Embodiment 368

The compound of any of Embodiments 1-346, wherein $R^{22}$ at each occurrence is independently chosen from H, $C_{1-6}$alkyl optionally substituted by 1-3 $R^{59}$, $C_{6-10}$aryl optionally substituted by 1-3 $R^{59}$, and 5-10 membered heteroaryl optionally substituted by 1-3 $R^{59}$; $R^{23}$, $R^{32}$ and $R^{33}$ at each occurrence is independently chosen from H and $C_{1-6}$alkyl.

Embodiment 369

The compound of any of Embodiments 1-346, wherein $R^{22}$ at each occurrence is independently chosen from H, $C_{6-10}$aryl optionally substituted by 1-3 $R^{59}$, and 5-10 membered heteroaryl optionally substituted by 1-3 $R^{59}$; $R^{23}$, $R^{32}$ and $R^{33}$ at each occurrence is independently chosen from H and $C_{1-6}$ alkyl.

Embodiment 370

The compound of any of Embodiments 1-346, wherein $R^{22}$ at each occurrence is independently chosen from H,

111 phenyl optionally substituted by 1-3 $R^{59}$, and 5-6 membered heteroaryl optionally substituted by 1-3 $R^{59}$; $R^{23}$, $R^{32}$ and $R^{33}$ at each occurrence is independently chosen from H and $C_{1-6}$ alkyl.

Embodiment 371

The compound of any of Embodiments 1-346, wherein $R^{22}$ at each occurrence is independently chosen from H, phenyl optionally substituted by 1-3 $R^{59}$, and 6 membered heteroaryl optionally substituted by 1-3 $R^{59}$; $R^{23}$, $R^{32}$ and $R^{33}$ at each occurrence is independently chosen from H and $C_{1-6}$ alkyl.

Embodiment 372

The compound of any of Embodiments 1-346, wherein $R^{22}$ at each occurrence is independently chosen from H, phenyl optionally substituted by 1 $R^{59}$, and 6 membered heteroaryl optionally substituted by 1 $R^{59}$; $R^{23}$, $R^{32}$ and $R^{33}$ at each occurrence is independently chosen from H and $C_{1-6}$alkyl.

Embodiment 373

The compound of any of Embodiments 1-346, wherein $R^{22}$ at each occurrence is independently chosen from H, $C_{1-6}$alkyl optionally substituted by 1-13 $R^{59}$, $C_{2-6}$alkenyl optionally substituted by 1-11 $R^{59}$, $C_{2-6}$alkynyl optionally substituted by 1-9 $R^{59}$, $C_{6-11}$aryl optionally substituted by 1-11 $R^{59}$, $C_7$16arylalkyl optionally substituted by 1-19 $R^{59}$, $C_{3-11}$cycloalkyl optionally substituted by 1-21 $R^{59}$, $C_{4-17}$cycloalkylalkyl optionally substituted by 1-32 $R^{59}$, 3-15 membered heterocycloalkyl optionally substituted by 1-28 $R^{59}$, 4-21 membered heterocycloalkylalkyl optionally substituted by 1-40 $R^{59}$, 5-15 membered heteroaryl optionally substituted by 1-15 $R^{59}$, and 6-21 membered heteroarylalkyl optionally substituted by 1-27 $R^{59}$; $R^{23}$, $R^{32}$ and $R^{33}$ at each occurrence is H; alternatively, any $R^{22}$ and $R^{23}$ and/or $R^{32}$ and $R^{33}$ may form, together with the nitrogen atom to which they are attached, a 3-15 membered heterocycloalkyl optionally substituted by 1-28 $R^{69}$ or a 5-15 membered heteroaryl optionally substituted by 1-15 $R^{69}$.

Embodiment 374

The compound of any of Embodiments 1-346, wherein $R^{22}$ at each occurrence is independently chosen from H, $C_{1-6}$alkyl optionally substituted by 1-3 $R^{59}$, $C_{2-6}$alkenyl optionally substituted by 1-3 $R^{59}$, $C_{2-6}$alkynyl optionally substituted by 1-3 $R^{59}$, $C_{6-11}$aryl optionally substituted by 1-3 $R^{59}$, $C_7$-16arylalkyl optionally substituted by 1-3 $R^{59}$, $C_{3-11}$cycloalkyl optionally substituted by 1-3 $R^{59}$, $C_{4-17}$cycloalkylalkyl optionally substituted by 1-3 $R^{59}$, 3-15 membered heterocycloalkyl optionally substituted by 1-3 $R^{59}$, 4-21 membered heterocycloalkylalkyl optionally substituted by 1-3 $R^{59}$, 5-15 membered heteroaryl optionally substituted by 1-3 $R^{59}$, and 6-21 membered heteroarylalkyl optionally substituted by 1-3 $R^{59}$; $R^{23}$, $R^{32}$ and $R^{33}$ at each occurrence is H; alternatively,
any $R^{22}$ and $R^{23}$ and/or $R^{32}$ and $R^{33}$ may form, together with the nitrogen atom to which they are attached, a 3-15 membered heterocycloalkyl optionally substituted by 1-3 $R^{69}$ or a 5-15 membered heteroaryl optionally substituted by 1-3 $R^{69}$.

112

Embodiment 375

The compound of any of Embodiments 1-346, wherein $R^{22}$ at each occurrence is independently chosen from H, $C_{1-6}$alkyl optionally substituted by 1-3 $R^{59}$, $C_{2-6}$alkenyl optionally substituted by 1-3 $R^{59}$, $C_{2-6}$alkynyl optionally substituted by 1-3 $R^{59}$, $C_{6-10}$aryl optionally substituted by 1-3 $R^{59}$, $C_{7-11}$arylalkyl optionally substituted by 1-3 $R^{59}$, $C_{3-10}$cycloalkyl optionally substituted by 1-3 $R^{59}$, 3-10 membered heterocycloalkyl optionally substituted by 1-3 $R^{59}$, and 5-10 membered heteroaryl optionally substituted by 1-3 $R^{59}$; $R^{23}$, $R^{32}$ and $R^{33}$ at each occurrence is H; alternatively, any $R^{22}$ and $R^{23}$ and/or $R^{32}$ and $R^{33}$ may form, together with the nitrogen atom to which they are attached, a 3-10 membered heterocycloalkyl optionally substituted by 1-3 $R^{69}$ or a 5-10 membered heteroaryl optionally substituted by 1-3 $R^{69}$.

Embodiment 376

The compound of any of Embodiments 1-346, wherein $R^{22}$ at each occurrence is independently chosen from H, $C_{1-6}$alkyl optionally substituted by 1-3 $R^{59}$, $C_{2-6}$alkenyl optionally substituted by 1-3 $R^{59}$, $C_{2-6}$alkynyl optionally substituted by 1-3 $R^{59}$, $C_{6-10}$aryl optionally substituted by 1-3 $R^{59}$, $C_{7-11}$arylalkyl optionally substituted by 1-3 $R^{59}$, $C_{3-10}$cycloalkyl optionally substituted by 1-3 $R^{59}$, 3-10 membered heterocycloalkyl optionally substituted by 1-3 $R^{59}$, and 5-10 membered heteroaryl optionally substituted by 1-3 $R^{59}$; $R^{23}$, $R^{32}$ and $R^{33}$ at each occurrence is H.

Embodiment 377

The compound of any of Embodiments 1-346, wherein $R^{22}$ at each occurrence is independently chosen from H, $C_{1-6}$alkyl optionally substituted by 1-3 $R^{59}$, $C_{6-10}$aryl optionally substituted by 1-3 $R^{59}$, $C_7$11arylalkyl optionally substituted by 1-3 $R^{59}$, $C_{3-10}$cycloalkyl optionally substituted by 1-3 $R^{59}$, 3-10 membered heterocycloalkyl optionally substituted by 1-3 $R^{59}$, and 5-10 membered heteroaryl optionally substituted by 1-3 $R^{59}$; $R^{23}$, $R^{32}$ and $R^{33}$ at each occurrence is H; alternatively, any $R^{22}$ and $R^{23}$ and/or $R^{32}$ and $R^{33}$ may form, together with the nitrogen atom to which they are attached, a 3-10 membered heterocycloalkyl optionally substituted by 1-3 $R^{69}$ or a 5-10 membered heteroaryl optionally substituted by 1-3 $R^{69}$.

Embodiment 378

The compound of any of Embodiments 1-346, wherein $R^{22}$ at each occurrence is independently chosen from H, $C_{1-6}$alkyl optionally substituted by 1-3 $R^{59}$, $C_{6-10}$aryl optionally substituted by 1-3 $R^{59}$, $C_{7-11}$arylalkyl optionally substituted by 1-3 $R^{59}$, $C_{3-10}$cycloalkyl optionally substituted by 1-3 $R^{59}$, 3-10 membered heterocycloalkyl optionally substituted by 1-3 $R^{59}$, and 5-10 membered heteroaryl optionally substituted by 1-3 $R^{59}$; $R^{23}$, $R^{32}$ and $R^{33}$ at each occurrence is H.

Embodiment 379

The compound of any of Embodiments 1-346, wherein $R^{22}$ at each occurrence is independently chosen from H, $C_{1-6}$alkyl, $C_{6-10}$aryl, $C_{7-11}$arylalkyl, $C_{3-10}$cycloalkyl, 3-10 membered heterocycloalkyl, and 5-10 membered heteroaryl; $R^{23}$, $R^{32}$ and $R^{33}$ at each occurrence is H; alternatively, any $R^{22}$ and $R^{23}$ and/or $R^{32}$ and $R^{33}$ may form, together with the nitrogen atom to which they are attached, a 3-10 membered heterocycloalkyl or a 5-10 membered heteroaryl.

Embodiment 380

The compound of any of Embodiments 1-346, wherein $R^{22}$ at each occurrence is independently chosen from H, $C_{1-6}$alkyl, $C_{6-10}$aryl, $C_{7-11}$arylalkyl, $C_{3-10}$cycloalkyl, 3-10 membered heterocycloalkyl, and 5-10 membered heteroaryl; $R^{23}$, $R^{32}$ and $R^{33}$ at each occurrence is H.

Embodiment 381

The compound of any of Embodiments 1-346, wherein $R^{22}$ at each occurrence is independently chosen from H, $C_{1-6}$alkyl optionally substituted by 1-3 $R^{59}$, $C_{6-10}$aryl optionally substituted by 1-3 $R^{59}$, and 5-10 membered heteroaryl optionally substituted by 1-3 $R^{59}$; $R^{23}$, $R^{32}$ and $R^{33}$ at each occurrence is H.

Embodiment 382

The compound of any of Embodiments 1-346, wherein $R^{22}$ at each occurrence is independently chosen from H, $C_{6-10}$aryl optionally substituted by 1-3 $R^{59}$, and 5-10 membered heteroaryl optionally substituted by 1-3 $R^{59}$; $R^{23}$, $R^{32}$ and $R^{33}$ at each occurrence is H.

Embodiment 383

The compound of any of Embodiments 1-346, wherein $R^{22}$ at each occurrence is independently chosen from H, phenyl optionally substituted by 1-3 $R^{59}$, and 5-6 membered heteroaryl optionally substituted by 1-3 $R^{59}$; $R^{23}$, $R^{32}$ and $R^{33}$ at each occurrence is H.

Embodiment 384

The compound of any of Embodiments 1-346, wherein $R^{22}$ at each occurrence is independently chosen from H, phenyl optionally substituted by 1-3 $R^{59}$, and 6 membered heteroaryl optionally substituted by 1-3 $R^{59}$; $R^{23}$, $R^{32}$ and $R^{33}$ at each occurrence is H.

Embodiment 385

The compound of any of Embodiments 1-346, wherein $R^{22}$ at each occurrence is independently chosen from H, phenyl optionally substituted by 1 $R^{59}$, and 6 membered heteroaryl optionally substituted by 1 $R^{59}$; $R^{23}$, $R^{32}$ and $R^{33}$ at each occurrence is H.

Embodiment 386

The compound of any of Embodiments 1-346, wherein $R^{22}$, $R^{23}$, $R^{32}$ and $R^{33}$ at each occurrence is independently chosen from H and $C_{1-6}$ alkyl.

Embodiment 387

The compound of any of Embodiments 1-346, wherein $R^{22}$, $R^{23}$, $R^{32}$ and $R^{33}$ at each occurrence is H.

Embodiment 388

The compound of any of Embodiments 1-346, wherein $R^{22}$, $R^{23}$, $R^{32}$ and $R^{33}$ at each occurrence is independently chosen from H and $C_{1-6}$ alkyl optionally substituted by 1-13 $R^{59}$; alternatively, any $R^{22}$ and $R^{23}$ and/or $R^{32}$ and $R^{33}$ may form, together with the nitrogen atom to which they are attached, a 3-15 membered heterocycloalkyl optionally substituted by 1-28 $R^{69}$ or a 5-15 membered heteroaryl optionally substituted by 1-15 $R^{69}$.

Embodiment 389

The compound of any of Embodiments 1-346, wherein $R^{22}$, $R^{23}$, $R^{32}$ and $R^{33}$ at each occurrence is independently chosen from H and $C_{1-6}$ alkyl optionally substituted by 1-6 $R^{59}$; alternatively, any $R^{22}$ and $R^{23}$ and/or $R^{32}$ and $R^{33}$ may form, together with the nitrogen atom to which they are attached, a 3-15 membered heterocycloalkyl optionally substituted by 1-6 $R^{69}$ or a 5-15 membered heteroaryl optionally substituted by 1-6 $R^{69}$.

Embodiment 390

The compound of any of Embodiments 1-346, wherein $R^{22}$, $R^{23}$, $R^{32}$ and $R^{33}$ at each occurrence is independently chosen from H and $C_{1-6}$ alkyl optionally substituted by 1-6 $R^{59}$; alternatively, any $R^{22}$ and $R^{23}$ and/or $R^{32}$, and $R^{33}$ may form, together with the nitrogen atom to which they are attached, a 3-10 membered heterocycloalkyl optionally substituted by 1-6 $R^{69}$ or a 5-10 membered heteroaryl optionally substituted by 1-6 $R^{69}$.

Embodiment 391

The compound of any of Embodiments 1-346, wherein $R^{22}$, $R^{23}$, $R^{32}$ and $R^{33}$ at each occurrence is independently chosen from H and $C_{1-6}$ alkyl optionally substituted by 1-6 $R^{59}$; alternatively, any $R^{22}$ and $R^{23}$ and/or $R^{32}$ and $R^{33}$ may form, together with the nitrogen atom to which they are attached, a 3-6 membered heterocycloalkyl optionally substituted by 1-6 $R^{69}$ or a 5-6 membered heteroaryl optionally substituted by 1-6 $R^{69}$.

Embodiment 392

The compound of any of Embodiments 1-346, wherein $R^{22}$, $R^{23}$, $R^{32}$ and $R^{33}$ at each occurrence is independently chosen from H and $C_{1-6}$ alkyl optionally; alternatively, any $R^{22}$ and $R^{23}$ and/or $R^{32}$ and $R^{33}$ may form, together with the nitrogen atom to which they are attached, a 3-6 membered heterocycloalkyl or a 5-6 membered heteroaryl.

Embodiment 393

The compound of any of Embodiments 1-392, wherein $R^{39}$, $R^{49}$, $R^{59}$ and $R^{69}$ at each occurrence is independently chosen from $C_{1-6}$alkyl optionally substituted by 1-13 $R^{79}$, $C_{2-6}$alkenyl optionally substituted by 1-11 $R^{79}$, $C_{2-6}$alkynyl optionally substituted by 1-9 $R^{79}$, $C_{6-11}$aryl optionally substituted by 1-11 $R^{79}$, $C_{7-16}$arylalkyl optionally substituted by 1-19 $R^{79}$, $C_{3-11}$cycloalkyl optionally substituted by 1-21 $R^{79}$, $C_{4-17}$cycloalkylalkyl optionally substituted by 1-32 $R^{79}$, 3-15 membered heterocycloalkyl optionally substituted by 1-28 $R^{79}$, 4-21 membered heterocycloalkylalkyl optionally substituted by 1-40 $R^{79}$, 5-15 membered heteroaryl optionally substituted by 1-15 $R^{79}$, 6-21 membered heteroarylalkyl optionally substituted by 1-27 $R^{79}$, halogen, —CN, —C(=O)$R^{70}$, —C(=O)O$R^{70}$, —C(=O)N$R^{72}R^{73}$, —C(=O)C(=O)$R^{70}$, —C(=N$R^{75}$)$R^{70}$, —C(=N$R^{75}$)N$R^{72}R^{73}$, —C(=NOH)N$R^{72}R^{73}$, —C(=NO$R^{76}$)$R^{70}$, —C(=NNR$^{72}$R$^{73}$)R$^{70}$, —C(=NNR$^{74}$C(=O)R$^{71}$)R$^{70}$, —C(=NNR$^{74}$C(=O)OR$^{71}$)R$^{70}$, —C(=S)NR$^{72}$R$^{73}$, —NC, —NO$_2$, —NR$^{72}$R$^{73}$, —NR$^{74}$NR$^{72}$R$^{73}$, —N=NR$^{74}$, =NR$^{70}$, =NOR$^{70}$, —NR$^{74}$OR$^{76}$, —NR$^{74}$C(=O)R$^{70}$, —NR$^{74}$C(=O)C(=O)R$^{70}$, —NR$^{74}$C(=O)OR$^{71}$, —NR$^{74}$C(=O)C(=O)OR$^{71}$, —NR$^{74}$C(=O)NR$^{72}$R$^{73}$, —NR$^{74}$C(=O)NR$^{74}$C(=O)R$^{70}$, —NR$^{74}$C(=O)NR$^{74}$C(=O)OR$^{70}$, —NR$^{74}$C(=NR$^{75}$)NR$^{72}$R$^{73}$, —NR$^{74}$C(=O)C(=O)NR$^{72}$R$^{73}$, —NR$^{74}$C(=S)R$^{70}$, —NR$^{74}$C(=S)OR$^{70}$, —NR$^{74}$C(=S)NR$^{72}$R$^{73}$, —NR$^{74}$S(=O)$_2$R$^{71}$, —NR$^{74}$S(=O)$_2$NR$^{72}$R$^{73}$, —NR$^{74}$P(=O)R$^{78}$R$^{78}$, —NR$^{74}$P(=O)(NR$^{72}$R$^{73}$)(NR$^{72}$R$^{73}$), —NR$^{74}$P(=)(OR$^{70}$)(OR$^{70}$), —NR$^{74}$P(=O)(SR$^{70}$)(SR$^{70}$), —OR$^{70}$, =O, —OCN, —OC(=O)R$^{70}$, —OC(=O)NR$^{72}$R$^{73}$, —OC(=O)OR$^{70}$, —OC(=NR$^{75}$)NR$^{72}$R$^{73}$, —OS(=O)R$^{70}$, —OS(=O)$_2$R$^{7}$, —OS(=O)$_2$OR$^{70}$, —OS(=O)$_2$NR$^{72}$R$^{73}$, —OP(=O)R$^{78}$R$^{78}$, —OP(=O)(NR$^{72}$R$^{73}$ (NR$^{72}$R$^{73}$), —OP(=O)(OR$^{70}$)(OR$^{70}$), —OP(=O)(SR$^{70}$)(SR$^{70}$), —Si(R$^{74}$)$_3$, —SCN, =S, —S(=O)$_n$R$^{70}$, —S(=O)$_2$OR$^{7}$, —SO$_3$R$^{77}$, —S(=O)$_2$NR$^{72}$R$^{73}$, —S(=O)NR$^{72}$R$^{73}$, —SP(=O)R$^{78}$R$^{78}$, —SP(=O)(NR$^{72}$R$^{73}$)(NR$^{72}$R$^{73}$), —SP(=O)(OR$^{70}$)(OR$^{70}$), —SP(=O)(SR$^{70}$)(SR$^{70}$), —P(=O)R$^{78}$R$^{78}$, —P(=O)(NR$^{72}$R$^{73}$)(NR$^{72}$R$^{73}$), —P(=O)(OR$^{70}$)(OR$^{70}$), and —P(=O)(SR$^{70}$)(SR$^{70}$).

Embodiment 394

The compound of any of Embodiments 1-392, wherein R$^{39}$, R$^{49}$, R$^{59}$ and R$^{69}$ at each occurrence is independently chosen from C$_{1-6}$alkyl optionally substituted by 1-6 R$^{79}$, C$_{2-6}$alkenyl optionally substituted by 1-6 R$^{79}$, C$_{2-6}$ alkynyl optionally substituted by 1-6 R$^{79}$, C$_{6-11}$aryl optionally substituted by 1-6 R$^{79}$, C$_{7-16}$arylalkyl optionally substituted by 1-6 R$^{79}$, C$_3$11cycloalkyl optionally substituted by 1-6 R$^{79}$, C$_{4-17}$cycloalkylalkyl optionally substituted by 1-6 R$^{79}$, 3-15 membered heterocycloalkyl optionally substituted by 1-6 R$^{79}$, 4-21 membered heterocycloalkylalkyl optionally substituted by 1-6 R$^{79}$, 5-15 membered heteroaryl optionally substituted by 1-6 R$^{79}$, 6-21 membered heteroarylalkyl optionally substituted by 1-6 R$^{79}$, halogen, —CN, —C(=O)R$^{70}$, —C(=O)OR$^{70}$, —C(=O)NR$^{72}$R$^{73}$, —C(=O)C(=O)R$^{70}$, —C(=NR$^{75}$)R$^{70}$, —C(=NR$^{75}$)NR$^{72}$R$^{73}$, —C(=NOH)NR$^{72}$R$^{73}$, —C(=NOR$^{76}$)R$^{70}$, —C(=NNR$^{72}$R$^{73}$)R$^{70}$, —C(=NNR$^{74}$C(=O)R$^{71}$)R$^{70}$, —C(=NNR$^{74}$C(=O)OR$^{70}$, —C(=S)NR$^{72}$R$^{73}$, —NC, —NO$_2$, —NR$^{72}$R$^{73}$, —NR$^{74}$NR$^{72}$R$^{73}$, —N=NR$^{74}$, =NR$^{70}$, =NOR$^{70}$, —NR$^{74}$OR$^{76}$, —NR$^{74}$C(=O)R$^{70}$, —NR$^{74}$C(=O)C(=O)R$^{70}$, —R$^{74}$C(=O)OR, —NR$^{74}$C(=O)C(=O)OR$^{71}$, —NR$^{74}$C(=O)NR$^{72}$R$^{73}$, —NR$^{74}$C(=O)NR$^{74}$C(=O)R$^{70}$, —NR$^{74}$C(=O)NR$^{74}$C(=O)OR$^{70}$, —NR$^{74}$C(=NR$^{75}$)NR$^{72}$R$^{73}$, —NR$^{74}$C(=O)C(=O)NR$^{72}$R$^{73}$, —NR$^{74}$C(=S)R$^{70}$, —NR$^{74}$C(=S)OR$^{70}$, —NR$^{74}$C(=S)NR$^{72}$R$^{73}$, —NR$^{74}$S(=O)$_2$R, —NR$^{74}$S(=O)$_2$NR$^{72}$R$^{73}$, —NR$^{74}$P(=O)R$^{78}$R$^{78}$, —NR$^{74}$P(=O)(NR$^{72}$R$^{73}$)(NR$^{72}$R$^{73}$)—NR$^{74}$P(=)(OR$^{70}$)(OR$^{70}$), —NR$^{74}$P(=)(SR$^{70}$)(SR$^{70}$), —OR$^{70}$, =O, —OCN, —OC(=O)R$^{70}$, —OC(=O)NR$^{72}$R$^{73}$, —OC(=O)OR$^{70}$, —OC(=NR$^{75}$)NR$^{72}$R$^{73}$, —OS(=O)R$^{70}$, —OS(=O)$_2$R$^{70}$, —OS(=O)$_2$OR$^{70}$, —OS(=O)$_2$NR$^{72}$R$^{73}$, —OP(=O)R$^{78}$R$^{78}$, —OP(=O)(NR$^{72}$R$^{73}$)(NR$^{72}$R$^{73}$), —OP(=O)(OR$^{70}$)(OR$^{70}$), —OP(=O)(SR$^{70}$)(SR$^{70}$), —Si(R$^{74}$)$_3$, —SCN, =S, —S(=O)$_n$R$^{70}$, —S(=O)$_2$OR$^{70}$, —SO$_3$R$^{77}$, —S(=O)$_2$NR$^{72}$R$^{73}$, —S(=O)NR$^{72}$R$^{73}$, —SP(=O)R$^{78}$R$^{78}$, —SP(=O)(NR$^{72}$R$^{73}$)(NR$^{72}$R$^{73}$), —SP(=O)(OR$^{70}$)(OR$^{70}$), —SP(=O)(SR$^{70}$)(SR$^{70}$), —P(=O)R$^{78}$R$^{78}$, —P(=O)(NR$^{72}$R$^{73}$)(R$^{72}$R$^{73}$72R$^{73}$), —P(=O)(OR$^{70}$)(OR$^{70}$), and —P(=O)(SR$^{70}$)(SR$^{70}$).

Embodiment 395

The compound of any of Embodiments 1-392, wherein R$^{39}$, R$^{49}$, R$^{59}$ and R$^{69}$ at each occurrence is independently chosen from C$_{1-6}$alkyl optionally substituted by 1-6 R$^{79}$, C$_{2-6}$alkenyl optionally substituted by 1-6 R$^{79}$, C$_{2-6}$ alkynyl optionally substituted by 1-6 R$^{79}$, C$_{6-11}$aryl optionally substituted by 1-6 R$^{79}$, C$_{7-16}$arylalkyl optionally substituted by 1-6 R$^{79}$, C$_{3-11}$cycloalkyl optionally substituted by 1-6 R$^{79}$, 3-15 membered heterocycloalkyl optionally substituted by 1-6 R$^{79}$, 5-15 membered heteroaryl optionally substituted by 1-6 R$^{79}$, halogen, —CN, —C(=O)R$^{70}$, —C(=O)OR$^{70}$, —C(=O)NR$^{72}$R$^{73}$, —C(=O)C(=O)R$^{70}$, —NC, —NO$_2$, —NR$^{72}$R$^{73}$, —NR$^{74}$NR$^{72}$R$^{73}$, —N=NR$^{74}$, =NR$^{70}$, =NOR$^{70}$, —NR$^{740}$R$^{76}$, —NR$^{74}$C(=O)R$^{70}$, —NR$^{74}$C(=O)C(=O)R$^{70}$, —NR$^{74}$C(=O)OR$^{71}$, —NR$^{74}$C(=O)OR, —NR$^{74}$C(=O)NR$^{72}$R$^{73}$, —NR$^{74}$C(=O)NR$^{74}$C(=O)R$^{70}$, —NR$^{74}$C(=O)NR$^{74}$C(=O)OR$^{70}$, —NR$^{74}$C(=NR$^{75}$)NR$^{72}$R$^{73}$, —NR$^{74}$C(=O)C(=O)NR$^{72}$R$^{73}$, —NR$^{74}$S(=O)$_2$R$^{71}$, —NR$^{74}$S(=O)$_2$NR$^{72}$R$^{73}$, —NR$^{74}$P(=O)R$^{78}$R$^{78}$, —NR$^{74}$P(=O)(NR$^{72}$R$^{73}$)(NR$^{72}$R$^{73}$)—NR$^{74}$P(=O)(OR$^{70}$)(OR$^{7}$), —OR$^{70}$, =O, —OCN, —OC(=O)R$^{70}$, —OC(=O)NR$^{72}$R$^{73}$, —OC(=O)OR$^{70}$, —OC(=NR$^{75}$)NR$^{72}$R$^{73}$, —OS(=O)R$^{70}$, —OS(=O)$_2$R$^{70}$, —OS(=O)$_2$OR$^{70}$, —OS(=O)$_2$NR$^{72}$R$^{73}$, —OP(=O)R$^{78}$R$^{78}$, —OP(=O)(NR$^{72}$R$^{73}$)(NR$^{72}$R$^{73}$), —OP(=O)(OR$^{70}$)(OR$^{70}$), —Si(R$^{74}$)$_3$, —SCN, =S, —S(=O)$_n$R$^{70}$, —S(=O)$_2$OR$^{7}$, —SO$_3$R$^{77}$, —S(=O)$_2$NR$^{72}$R$^{73}$, —S(=O)NR$^{72}$R$^{73}$, —SP(=O)R$^{78}$R$^{78}$, —SP(=O)(NR$^{72}$R$^{73}$)(NR$^{72}$R$^{73}$), —SP(=O)(OR$^{70}$)(OR$^{70}$), —SP(=O)(SR$^{70}$)(SR$^{70}$), —P(=O)R$^{78}$R$^{78}$, —P(=O)(NR$^{72}$R$^{73}$)(NR$^{72}$R$^{73}$), and —P(=O)(OR$^{70}$)(OR$^{70}$).

Embodiment 396

The compound of any of Embodiments 1-392, wherein R$^{39}$, R$^{49}$, R$^{59}$ and R$^{69}$ at each occurrence is independently chosen from C$_{1-6}$alkyl optionally substituted by 1-6 R$^{79}$, C$_{2-6}$alkenyl optionally substituted by 1-6 R$^{79}$, C$_{2-6}$ alkynyl optionally substituted by 1-6 R$^{79}$, C$_{6-10}$aryl optionally substituted by 1-6 R$^{79}$, C$_{7-11}$arylalkyl optionally substituted by 1-6 R$^{79}$, C$_{3-10}$cycloalkyl optionally substituted by 1-6 R$^{79}$, 3-10 membered heterocycloalkyl optionally substituted by 1-6 R$^{79}$, 5-10 membered heteroaryl optionally substituted by 1-6 R$^{79}$, halogen, —CN, —C(=O)R$^{70}$, —C(=O)OR$^{70}$, —C(=O)NR$^{72}$R$^{73}$, —C(=O)C(=O)R$^{70}$, —NC, —NO$_2$, —NR$^{72}$R$^{73}$, —NR$^{74}$NR$^{72}$R$^{73}$, —N=NR$^{74}$, =NR$^{70}$, =NOR$^{70}$, —NR$^{74}$R$^{76}$, —NR$^{74}$C(=O)R$^{70}$, —NR$^{74}$C(=O)OR, —NR$^{74}$C(=O)NR$^{72}$R$^{73}$, —NR$^{74}$S(=O)$_2$R, —NR$^{74}$S(=O)$_2$NR$^{72}$R$^{73}$, —NR$^{74}$P(=O)R$^{78}$R$^{78}$, —NR$^{74}$P(=O)(NR$^{72}$R$^{73}$)(NR$^{72}$R$^{73}$), —NR$^{74}$P(=)(OR$^{70}$)(OR$^{70}$), —OR$^{70}$, =O, —OCN, —OC(=O)R$^{70}$, —OC(=O)NR$^{72}$R$^{73}$, —OC(=O)OR$^{70}$, —OC(=NR$^{75}$)NR$^{72}$R$^{73}$, —OS(=O)R$^{70}$, —OS(=O)$_2$R$^{70}$, —OS(=O)$_2$OR$^{70}$, —OS(=O)$_2$NR$^{72}$R$^{73}$, —OP(=O)R$^{78}$R$^{78}$, —OP(=O)(NR$^{72}$R$^{73}$ (NR$^{72}$R$^{73}$), —OP(=O)(OR$^{70}$)(OR$^{70}$), —Si(R$^{74}$)$_3$, —SCN, =S, —S(=O)$_n$R$^{70}$, —S(=O)$_2$OR$^{7}$, —SO$_3$R$^{77}$, —S(=O)$_2$NR$^{72}$R$^{73}$, —S(=O)NR$^{72}$R$^{73}$, —P(=O)R$^{78}$R$^{78}$, —P(=O)(NR$^{72}$R$^{73}$)(R$^{72}$R$^{73}$), and —P(=O)(OR$^{70}$)(OR$^{70}$).

Embodiment 397

The compound of any of Embodiments 1-392, wherein R$^{39}$, R$^{49}$, R$^{59}$ and R$^{69}$ at each occurrence is independently chosen from $C_{1-6}$alkyl optionally substituted by 1-3 $R^{79}$, $C_{2-6}$alkenyl optionally substituted by 1-3 $R^{79}$, $C_{2-6}$ alkynyl optionally substituted by 1-3 $R^{79}$, $C_{6-10}$aryl optionally substituted by 1-3 $R^{79}$, $C_{7-11}$arylalkyl optionally substituted by 1-3 $R^{79}$, $C_{3-10}$cycloalkyl optionally substituted by 1-3 $R^{79}$, 3-10 membered heterocycloalkyl optionally substituted by 1-3 $R^{79}$, 5-10 membered heteroaryl optionally substituted by 1-3 $R^{79}$, halogen, —CN, —C(=O)$R^{70}$, —C(=O)O$R^{70}$, —C(=O)N$R^{72}R^{73}$, —NC, —NO$_2$, —N$R^{72}R^{73}$, —N$R^{74}$N$R^{72}R^{73}$, —N$R^{74}$O$R^{76}$, —N$R^{74}$C(=O)$R^{70}$, —N$R^{74}$C(=O)O$R^1$, —N$R^{74}$C(=O)N$R^{72}R^{73}$, —N$R^{74}$S(=O)$_2R^{71}$, —N$R^{74}$S(=O)$_2$N$R^{72}R^{73}$, —O$R^{70}$, =O, —OCN, —OC(=O)$R^{70}$, —OC(=O)N$R^{72}R^{72}R^{73}$, —OC(=O)O$R^{70}$, —OS(=O)$_2$N$R^{72}R^{73}$, —Si($R^{74}$)$_3$, —SCN, —S(=O)$R^{70}$, —S(=O)$_2$N$R^{72}R^{73}$, —S(=O)N$R^{72}R^{73}$2R, —P(=O)$R^{78}R^{78}$, —P(=O)(N$R^{72}R^{73}$)(N$R^{72}R^{73}$), and —P(=O)(O$R^{70}$)(O$R^{70}$).

Embodiment 398

The compound of any of Embodiments 1-392, wherein $R^{39}$, $R^{49}$, $R^{59}$ and $R^{69}$ at each occurrence is independently chosen from $C_{1-6}$alkyl optionally substituted by 1-3 $R^{79}$, $C_{2-6}$alkenyl optionally substituted by 1-3 $R^{79}$, $C_{2-6}$ alkynyl optionally substituted by 1-3 $R^{79}$, $C_{6-10}$aryl optionally substituted by 1-3 $R^{79}$, $C_{7-11}$arylalkyl optionally substituted by 1-3 $R^{79}$, $C_{3-10}$cycloalkyl optionally substituted by 1-3 $R^{79}$, 3-10 membered heterocycloalkyl optionally substituted by 1-3 $R^{79}$, 5-10 membered heteroaryl optionally substituted by 1-3 $R^{79}$, halogen, —CN, —C(=O)$R^{70}$, —C(=O)O$R^{70}$, —C(=O)N$R^{72}R^{73}$, —NO$_2$, —N$R^{72}R^{73}$, —N$R^{74}$O$R^{76}$, —N$R^{74}$C(=O)$R^{70}$, —N$R^{74}$C(=O)OR, —N$R^{74}$C(=O)N$R^{72}R^{73}$, —N$R^{74}$S(=O)$_2$R, —N$R^{74}$S(=O)$_2$N$R^{72}R^{73}$, —O$R^{70}$, =O, —OC(=O)$R^{70}$, —OC(=O)N$R^{72}R^{73}$, —OS(=O)$_2$N$R^{72}R^{73}$, —S(=O)$_n R^{70}$, and —S(=O)$_2$N$R^{72}R^{73}$.

Embodiment 399

The compound of any of Embodiments 1-392, wherein $R^{39}$, $R^{49}$, $R^{59}$ and $R^{69}$ at each occurrence is independently chosen from $C_{1-6}$alkyl optionally substituted by 1-3 $R^{79}$, $C_{2-6}$alkenyl optionally substituted by 1-3 $R^{79}$, $C_{2-6}$ alkynyl optionally substituted by 1-3 $R^{79}$, $C_{6-10}$aryl optionally substituted by 1-3 $R^{79}$, $C_{7-11}$arylalkyl optionally substituted by 1-3 $R^{79}$, $C_{3-10}$cycloalkyl optionally substituted by 1-3 $R^{79}$, 3-10 membered heterocycloalkyl optionally substituted by 1-3 $R^{79}$, 5-10 membered heteroaryl optionally substituted by 1-3 $R^{79}$, halogen, —CN, —C(=O)$R^{70}$, —C(=O)O$R^{70}$, —C(=O)N$R^{72}R^{73}$, —NO$_2$, —N$R^{72}R^{73}$, —N$R^{74}$C(=O)$R^{70}$, —N$R^{74}$C(=O)N$R^{72}R^{73}$, —N$R^{74}$S(=O)$_2R^{70}$, —O$R^{70}$, =O, —S(=O)$_n R^{70}$ and —S(=O)$_2$N$R^{72}R^{73}$.

Embodiment 400

The compound of any of Embodiments 1-392, wherein $R^{39}$, $R^{49}$, $R^{59}$ and $R^{69}$ at each occurrence is independently chosen from $C_{1-6}$alkyl optionally substituted by 1-3 $R^{79}$, $C_{6-10}$aryl optionally substituted by 1-3 $R^{79}$, $C_{7-11}$ arylalkyl optionally substituted by 1-3 $R^{79}$, $C_{3-10}$cycloalkyl optionally substituted by 1-3 $R^{79}$, 3-10 membered heterocycloalkyl optionally substituted by 1-3 $R^{79}$, 5-10 membered heteroaryl optionally substituted by 1-3 $R^{79}$, halogen, —CN, —C(=O)$R^{70}$, —C(=O)O$R^{70}$, —C(=O)N$R^{72}R^{73}$, —NO$_2$, —N$R^{72}R^{73}$, —N$R^{74}$C(=O)$R^{70}$, —N$R^{74}$C(=O)N$R^{72}R^{73}$, —N$R^{74}$S(=O)$_2R^7$, —O$R^{70}$, =O, —S(=O)$_n R^{70}$, and —S(=O)$_2$N$R^{72}R^{73}$.

Embodiment 401

The compound of any of Embodiments 1-392, wherein $R^{39}$, $R^{49}$, $R^{59}$ and $R^{69}$ at each occurrence is independently chosen from $C_{1-6}$alkyl optionally substituted by 1-3 $R^{79}$, $C_{6-10}$aryl optionally substituted by 1-3 $R^{79}$, 3-10 membered heterocycloalkyl optionally substituted by 1-3 $R^{79}$, 5-10 membered heteroaryl optionally substituted by 1-3 $R^{79}$, —CN, and —C(=O)$R^{70}$.

Embodiment 402

The compound of any of Embodiments 1-392, wherein $R^{39}$, $R^{49}$, $R^{59}$ and $R^{69}$ at each occurrence is independently chosen from $C_{1-6}$alkyl optionally substituted by 1-3 $R^{79}$, phenyl optionally substituted by 1-3 $R^{79}$, 5-6 membered heterocycloalkyl optionally substituted by 1-3 $R^{79}$, 5-9 membered heteroaryl optionally substituted by 1-3 $R^{79}$, —CN, and —C(=O)$R^{70}$.

Embodiment 403

The compound of any of Embodiments 1-392, wherein $R^{39}$, $R^{49}$, $R^{59}$ and $R^{69}$ at each occurrence is independently chosen from $C_{1-6}$alkyl optionally substituted by 1 $R^{79}$, phenyl, 6 membered heterocycloalkyl optionally substituted by 1 $R^{79}$, 5-9 membered heteroaryl optionally substituted by 1-3 $R^{79}$, —CN, and —C(=O)$R^{70}$.

Embodiment 404

The compound of any of Embodiments 1-392, wherein $R^{39}$ at each occurrence is independently chosen from $C_{1-6}$alkyl and 5-9 membered heteroaryl optionally substituted by 1-3 $R^{79}$; $R^{59}$ and $R^{69}$ at each occurrence is independently $C_{1-6}$alkyl; $R^{49}$ at each occurrence is independently chosen from $C_{1-6}$ alkyl optionally substituted by 1 $R^{79}$, phenyl, 6 membered heterocycloalkyl optionally substituted by 1 $R^{79}$, 5 membered heteroaryl optionally substituted by 1-3 $R^{79}$, —CN, and —C(=O)$R^{70}$.

Embodiment 405

The compound of any of Embodiments 1-392, wherein $R^{39}$, $R^{49}$, $R^{59}$ and $R^{69}$ at each occurrence is independently chosen from $C_{1-6}$alkyl, phenyl, 5-6 membered heterocycloalkyl, 5-9 membered heteroaryl, —CN, and —C(=O)$R^{70}$.

Embodiment 406

The compound of any of Embodiments 1-392, wherein $R^{39}$, $R^{49}$, $R^{59}$ and $R^{69}$ at each occurrence is independently chosen from $C_{1-6}$alkyl, phenyl, 5-6 membered heterocycloalkyl, and 5-9 membered heteroaryl.

Embodiment 407

The compound of any of Embodiments 1-392, wherein $R^{39}$, $R^{49}$, $R^{59}$ and $R^{69}$ at each occurrence is independently chosen from $C_{1-6}$alkyl optionally substituted by 1-13 $R^{79}$.

Embodiment 408

The compound of any of Embodiments 1-392, wherein $R^{39}$, $R^{49}$, $R^{59}$ and $R^{69}$ at each occurrence is independently chosen from $C_{1-6}$alkyl optionally substituted by 1-6 $R^{79}$.

Embodiment 409

The compound of any of Embodiments 1-392, wherein $R^{39}$, $R^{49}$, $R^{59}$ and $R^{69}$ at each occurrence is independently chosen from $C_{1-6}$alkyl optionally substituted by 1-3 $R^{79}$.

Embodiment 410

The compound of any of Embodiments 1-392, wherein $R^{39}$, $R^{49}$, $R^{59}$ and $R^{69}$ at each occurrence is independently $C_{1-6}$alkyl.

Embodiment 411

The compound of any of Embodiments 1-410, wherein $R^{70}$, $R^{71}$, $R^{74}$, $R^{75}$, $R^{76}$ and $R^{77}$ at each occurrence is independently chosen from H, $C_{1-6}$alkyl optionally substituted by 1-13 $R^{89}$, $C_{2-6}$alkenyl optionally substituted by 1-11 $R^{89}$, $C_{2-6}$alkynyl optionally substituted by 1-9 $R^{89}$, $C_{6-11}$aryl optionally substituted by 1-11 $R^{89}$, $C_{7-16}$arylalkyl optionally substituted by 1-19 $R^{89}$, $C_{3-11}$ cycloalkyl optionally substituted by 1-21 $R^{89}$, $C_{4-17}$cycloalkylalkyl optionally substituted by 1-32 $R^{89}$, 3-15 membered heterocycloalkyl optionally substituted by 1-28 $R^{89}$, 4-21 membered heterocycloalkylalkyl optionally substituted by 1-40 $R^{89}$, 5-15 membered heteroaryl optionally substituted by 1-15 $R^{89}$, and 6-21 membered heteroarylalkyl optionally substituted by 1-27 $R^{89}$.

Embodiment 412

The compound of any of Embodiments 1-410, wherein $R^{70}$, $R^{71}$, $R^{74}$, $R^{75}$, $R^{76}$ and $R^{77}$ at each occurrence is independently chosen from H, $C_{1-6}$alkyl optionally substituted by 1-6 $R^{89}$, $C_{2-6}$alkenyl optionally substituted by 1-6 $R^{89}$, $C_{2-6}$alkynyl optionally substituted by 1-6 $R^{89}$, $C_{6-10}$aryl optionally substituted by 1-6 $R^{89}$, $C_{7-11}$arylalkyl optionally substituted by 1-6 $R^{89}$, $C_{3-10}$cycloalkyl optionally substituted by 1-6 $R^{89}$, 3-10 membered heterocycloalkyl optionally substituted by 1-6 $R^{89}$, and 5-10 membered heteroaryl optionally substituted by 1-6 $R^{89}$.

Embodiment 413

The compound of any of Embodiments 1-410, wherein $R^{70}$, $R^{71}$, $R^{74}$, $R^{75}$, $R^{76}$ and $R^{77}$ at each occurrence is independently chosen from H, $C_{1-6}$alkyl optionally substituted by 1-3 $R^{89}$, $C_{2-6}$alkenyl optionally substituted by 1-3 $R^{89}$, $C_{2-6}$alkynyl optionally substituted by 1-3 $R^{89}$, $C_{6-10}$aryl optionally substituted by 1-3 $R^{89}$, $C_{7-11}$arylalkyl optionally substituted by 1-3 $R^{89}$, $C_{3-10}$cycloalkyl optionally substituted by 1-3 $R^{89}$, 3-10 membered heterocycloalkyl optionally substituted by 1-3 $R^{89}$, and 5-10 membered heteroaryl optionally substituted by 1-3 $R^{89}$.

Embodiment 414

The compound of any of Embodiments 1-410, wherein $R^{70}$, $R^{71}$, $R^{74}$, $R^{75}$, $R^{76}$ and $R^{77}$ at each occurrence is independently chosen from H, $C_{1-6}$alkyl optionally substituted by 1-3 $R^{89}$, $C_{6-10}$aryl optionally substituted by 1-3 $R^{89}$, $C_{7-11}$arylalkyl optionally substituted by 1-3 $R^{89}$, $C_{3-10}$cycloalkyl optionally substituted by 1-3 $R^{89}$, 3-10 membered heterocycloalkyl optionally substituted by 1-3 $R^{89}$, and 5-10 membered heteroaryl optionally substituted by 1-3 $R^{89}$.

Embodiment 415

The compound of any of Embodiments 1-410, wherein $R^{70}$, $R^{71}$, $R^{74}$, $R^{75}$, $R^{76}$ and $R^{77}$ at each occurrence is independently chosen from H, $C_{1-6}$alkyl, $C_{6-10}$aryl, $C_{7-11}$arylalkyl, $C_{3-10}$cycloalkyl, 3-10 membered heterocloalkyl, and 5-10 membered heteroaryl.

Embodiment 416

The compound of any of Embodiments 1-410, wherein $R^{70}$, $R^{71}$, $R^{74}$, $R^{75}$, $R^{76}$ and $R^{77}$ at each occurrence is independently chosen from H, $C_{1-6}$alkyl optionally substituted by 1-3 $R^{89}$, phenyl optionally substituted by 1-3 $R^{89}$, benzyl optionally substituted by 1-3 $R^{89}$, $C_{5-6}$cycloalkyl optionally substituted by 1-3 $R^{89}$, 5-6 membered heterocycloalkyl optionally substituted by 1-3 $R^{89}$, and 5-6 membered heteroaryl optionally substituted by 1-3 $R^{89}$.

Embodiment 417

The compound of any of Embodiments 1-410, wherein $R^{70}$, $R^{71}$, $R^{74}$, $R^{75}$, $R^{76}$ and $R^{77}$ at each occurrence is independently chosen from H, $C_{1-6}$alkyl, phenyl, benzyl, $C_{5-6}$cycloalkyl, 5-6 membered heterocycloalkyl, and 5-6 membered heteroaryl.

Embodiment 418

The compound of any of Embodiments 1-410, wherein $R^{70}$, $R^{71}$, $R^{74}$, $R^{75}$, $R^{76}$ and $R^{77}$ at each occurrence is independently chosen from H, $C_{1-6}$alkyl, phenyl, benzyl, $C_{5-6}$cycloalkyl, 5-6 membered heterocycloalkyl optionally substituted by 1-3 $R^{89}$, and 5-6 membered heteroaryl.

Embodiment 419

The compound of any of Embodiments 1-410, wherein $R^{70}$, $R^{71}$, $R^{74}$, $R^{75}$, $R^{76}$ and $R^{77}$ at each occurrence is independently chosen from H, $C_{1-6}$alkyl, phenyl, benzyl, $C_{5-6}$cycloalkyl, 5-6 membered heterocycloalkyl optionally substituted by 1 $R^{89}$, and 5-6 membered heteroaryl.

Embodiment 420

The compound of any of Embodiments 1-410, wherein $R^{70}$, $R^{71}$, $R^{74}$, $R^{75}$, $R^{76}$ and $R^{77}$ at each occurrence is independently chosen from H, $C_{1-6}$alkyl, and 5-6 membered heterocycloalkyl optionally substituted by 1-3 $R^{89}$.

Embodiment 421

The compound of any of Embodiments 1-410, wherein $R^{70}$, $R^{71}$, $R^{74}$, $R^{75}$, $R^{76}$ and $R^{77}$ at each occurrence is independently chosen from H, $C_{1-6}$alkyl, and 5-6 membered heterocycloalkyl optionally substituted by $C_{1-6}$alkyl.

Embodiment 422

The compound of any of Embodiments 1-410, wherein $R^{70}$, $R^{71}$, $R^{74}$, $R^{75}$, $R^{76}$ and $R^{77}$ at each occurrence is independently chosen from H, $C_{1-6}$alkyl, and 5-6 membered heterocycloalkyl.

Embodiment 423

The compound of any of Embodiments 1-410, wherein $R^{70}$ at each occurrence is independently chosen from H, $C_{1-6}$alkyl, and 5-6 membered heterocycloalkyl optionally substituted by 1-3 $R^{89}$; $R^{71}$, $R^{74}$, $R^{75}$, $R^{76}$ and $R^{77}$ at each occurrence is H.

Embodiment 424

The compound of any of Embodiments 1-410, wherein $R^{70}$ at each occurrence is independently chosen from H, $C_{1-6}$alkyl, and 5-6 membered heterocycloalkyl optionally substituted by $C_{1-6}$alkyl; $R^{71}$, $R^{74}$, $R^{75}$, $R^{76}$ and $R^{77}$ at each occurrence is H.

Embodiment 425

The compound of any of Embodiments 1-410, wherein $R^{70}$ at each occurrence is independently chosen from H, $C_{1-6}$alkyl, and 5-6 membered heterocycloalkyl; $R^{71}$, $R^{74}$, $R^{75}$, $R^{76}$ and $R^{77}$ at each occurrence is H.

Embodiment 426

The compound of any of Embodiments 1-410, wherein $R^{70}$, $R^{71}$, $R^{74}$, $R^{75}$, $R^{76}$ and $R^{77}$ at each occurrence is independently chosen from H and $C_{1-6}$alkyl.

Embodiment 427

The compound of any of Embodiments 1-410, wherein $R^{70}$, $R^{71}$, $R^{74}$, $R^{75}$, $R^{76}$ and $R^{77}$ at each occurrence is H.

Embodiment 428

The compound of any of Embodiments 1-427, wherein $R^{72}$ and $R^{73}$ at each occurrence is independently chosen from H, $C_{1-6}$alkyl optionally substituted by 1-13 $R^{99}$, $C_{2-6}$alkenyl optionally substituted by 1-11 $R^{99}$, $C_{2-6}$alkynyl optionally substituted by 1-9 $R^{99}$, $C_{6-11}$aryl optionally substituted by 1-11 $R^{99}$, $C_{7-16}$arylalkyl optionally substituted by 1-19 $R^{99}$, $C_{3-11}$cycloalkyl optionally substituted by 1-21 $R^{99}$, $C_{4-17}$cycloalkylalkyl optionally substituted by 1-32 $R^{99}$, 3-15 membered heterocycloalkyl optionally substituted by 1-28 $R^{99}$, 4-21 membered heterocycloalkylalkyl optionally substituted by 1-40 $R^{99}$, 5-15 membered heteroaryl optionally substituted by 1-15 $R^{99}$, and 6-21 membered heteroarylalkyl optionally substituted by 1-27 $R^{99}$; alternatively, any $R^{72}$ and $R^{73}$ may form, together with the nitrogen atom to which they are attached, a 3-15 membered heterocycloalkyl optionally substituted by 1-28 $R^{109}$ or a 5-15 membered heteroaryl optionally substituted by 1-15 $R^{109}$.

Embodiment 429

The compound of any of Embodiments 1-427, wherein $R^{72}$ and $R^{73}$ at each occurrence is independently chosen from H, $C_{1-6}$alkyl optionally substituted by 1-6 $R^{99}$, $C_{2-6}$alkenyl optionally substituted by 1-6 $R^{99}$, $C_{2-6}$ alkynyl optionally substituted by 1-6 $R^{99}$, $C_{6-11}$aryl optionally substituted by 1-6 $R^{99}$, $C_{7-16}$arylalkyl optionally substituted by 1-6 $R^{99}$, $C_{3-11}$cycloalkyl optionally substituted by 1-6 $R^{99}$, $C_{4-17}$cycloalkylalkyl optionally substituted by 1-6 $R^{99}$, 3-15 membered heterocycloalkyl optionally substituted by 1-6 $R^{99}$, 4-21 membered heterocycloalkylalkyl optionally substituted by 1-6 $R^{99}$, 5-15 membered heteroaryl optionally substituted by 1-6 $R^{99}$, and 6-21 membered heteroarylalkyl optionally substituted by 1-6 $R^{99}$; alternatively, any $R^{72}$ and $R^{73}$ may form, together with the nitrogen atom to which they are attached, a 3-15 membered heterocycloalkyl optionally substituted by 1-6 $R^{109}$ or a 5-15 membered heteroaryl optionally substituted by 1-6 $R^{109}$.

Embodiment 430

The compound of any of Embodiments 1-427, wherein $R^{72}$ and $R^{73}$ at each occurrence is independently chosen from H, $C_{1-6}$alkyl optionally substituted by 1-3 $R^{99}$, $C_{2-6}$alkenyl optionally substituted by 1-3 $R^{99}$, $C_{2-6}$ alkynyl optionally substituted by 1-3 $R^{99}$, $C_{6-11}$aryl optionally substituted by 1-3 $R^{99}$, $C_{7-16}$arylalkyl optionally substituted by 1-3 $R^{99}$, $C_{3-11}$cycloalkyl optionally substituted by 1-3 $R^{99}$, $C_{4-17}$cycloalkylalkyl optionally substituted by 1-3 $R^{99}$, 3-15 membered heterocycloalkyl optionally substituted by 1-3 $R^{99}$, 4-21 membered heterocycloalkylalkyl optionally substituted by 1-3 $R^{99}$, 5-15 membered heteroaryl optionally substituted by 1-3 $R^{99}$, and 6-21 membered heteroarylalkyl optionally substituted by 1-3 $R^{99}$; alternatively, any $R^{72}$ and $R^{73}$ may form, together with the nitrogen atom to which they are attached, a 3-15 membered heterocycloalkyl optionally substituted by 1-3 $R^{109}$ or a 5-15 membered heteroaryl optionally substituted by 1-3 $R^{109}$.

Embodiment 431

The compound of any of Embodiments 1-427, wherein $R^{72}$ and $R^{73}$ at each occurrence is independently chosen from H, $C_{1-6}$alkyl optionally substituted by 1-3 $R^{99}$, $C_{2-6}$alkenyl optionally substituted by 1-3 $R^{99}$, $C_{2-6}$ alkynyl optionally substituted by 1-3 $R^{99}$, $C_{6-10}$aryl optionally substituted by 1-3 $R^{99}$, $C_{7-11}$arylalkyl optionally substituted by 1-3 $R^{99}$, $C_{3-10}$cycloalkyl optionally substituted by 1-3 $R^{99}$, 3-10 membered heterocycloalkyl optionally substituted by 1-3 $R^{99}$, and 5-10 membered heteroaryl optionally substituted by 1-3 $R^{99}$; alternatively, any $R^{72}$ and $R^{73}$ may form, together with the nitrogen atom to which they are attached, a 3-10 membered heterocycloalkyl optionally substituted by 1-3 $R^{109}$ or a 5-10 membered heteroaryl optionally substituted by 1-3 $R^{109}$.

Embodiment 432

The compound of any of Embodiments 1-427, wherein $R^{72}$ and $R^{73}$ at each occurrence is independently chosen from H, $C_{1-6}$alkyl optionally substituted by 1-3 $R^{99}$, $C_{6-10}$aryl optionally substituted by 1-3 $R^{99}$, $C_{7-11}$arylalkyl optionally substituted by 1-3 $R^{99}$, $C_{3-10}$cycloalkyl optionally substituted by 1-3 $R^{99}$, 3-10 membered heterocycloalkyl optionally substituted by 1-3 $R^{99}$, and 5-10 membered heteroaryl optionally substituted by 1-3 $R^{99}$; alternatively, any $R^{72}$ and $R^{73}$ may form, together with the nitrogen atom to which they are attached, a 3-10 membered heterocycloalkyl optionally substituted by 1-3 $R^{109}$ or a 5-10 membered heteroaryl optionally substituted by 1-3 $R^{109}$.

Embodiment 433

The compound of any of Embodiments 1-427, wherein $R^{72}$ and $R^{73}$ at each occurrence is independently chosen from H, $C_{1-6}$alkyl optionally substituted by 1-3 $R^{99}$, phenyl optionally substituted by 1-3 $R^{99}$, benzyl optionally substituted by 1-3 $R^{99}$, $C_{5-6}$cycloalkyl optionally substituted by 1-3 $R^{99}$, 5-6 membered heterocycloalkyl optionally substituted by 1-3 $R^{99}$, and 5-6 membered heteroaryl optionally substituted by 1-3 $R^{99}$; alternatively, any $R^{72}$ and $R^{73}$ may form, together with the nitrogen atom to which they are attached, a 5-6 membered heterocycloalkyl optionally substituted by 1-3 $R^{109}$ or a 5-6 membered heteroaryl optionally substituted by 1-3 $R^{109}$.

Embodiment 434

The compound of any of Embodiments 1-427, wherein $R^{72}$ and $R^{73}$ at each occurrence is independently chosen from H, $C_{1-6}$alkyl optionally substituted by 1-3 $R^{99}$, phenyl optionally substituted by 1-3 $R^{99}$, benzyl optionally substituted by 1-3 $R^{99}$, $C_{5-6}$cycloalkyl optionally substituted by 1-3 $R^{99}$, 5-6 membered heterocycloalkyl optionally substituted by 1-3 $R^{99}$, and 5-6 membered heteroaryl optionally substituted by 1-3 $R^{99}$.

Embodiment 435

The compound of any of Embodiments 1-427, wherein $R^{72}$ and $R^{73}$ at each occurrence is independently chosen from H, $C_{1-6}$alkyl, phenyl, benzyl, $C_{5-6}$cycloalkyl, 5-6 membered heterocycloalkyl, and 5-6 membered heteroaryl; alternatively, any $R^{72}$ and $R^{73}$ may form, together with the nitrogen atom to which they are attached, a 5-6 membered heterocycloalkyl or a 5-6 membered heteroaryl.

Embodiment 436

The compound of any of Embodiments 1-427, wherein $R^{72}$ and $R^{73}$ at each occurrence is independently chosen from H, $C_{1-6}$alkyl, phenyl, benzyl, $C_{5-6}$cycloalkyl, 5-6 membered heterocycloalkyl, and 5-6 membered heteroaryl.

Embodiment 437

The compound of any of Embodiments 1-427, wherein $R^{72}$ and $R^{73}$ at each occurrence is independently chosen from H, $C_{1-6}$alkyl optionally substituted by 1-3 $R^{99}$, phenyl optionally substituted by 1-3 $R^{99}$, and benzyl optionally substituted by 1-3 $R^{99}$.

Embodiment 438

The compound of any of Embodiments 1-427, wherein $R^{72}$ and $R^{73}$ at each occurrence is independently chosen from H and $C_{1-6}$alkyl optionally substituted by 1-3 $R^{99}$.

Embodiment 439

The compound of any of Embodiments 1-427, wherein $R^{72}$ and $R^{73}$ at each occurrence is independently chosen from H, $C_{1-6}$alkyl, phenyl, and benzyl.

Embodiment 440

The compound of any of Embodiments 1-427, wherein $R^{72}$ and $R^{73}$ at each occurrence is independently chosen from H and $C_{1-6}$alkyl.

Embodiment 441

The compound of any of Embodiments 1-427, wherein $R^{72}$ and $R^{73}$ at each occurrence is H.

Embodiment 442

The compound of any of Embodiments 1-441, wherein $R^{78}$ at each occurrence is independently chosen from $C_{1-6}$alkyl optionally substituted by 1-13 $R^{89}$, $C_{2-6}$alkenyl optionally substituted by 1-11 $R^{89}$, $C_{2-6}$alkynyl optionally substituted by 1-9 $R^{89}$, $C_{6-11}$aryl optionally substituted by 1-11 $R^{89}$, $C_{7-16}$arylalkyl optionally substituted by 1-19 $R^{89}$, $C_{3-11}$cycloalkyl optionally substituted by 1-21 $R^{89}$, $C_{4-17}$cycloalkylalkyl optionally substituted by 1-32 $R^{89}$, 3-15 membered heterocycloalkyl optionally substituted by 1-28 $R^{89}$, 4-21 membered heterocycloalkylalkyl optionally substituted by 1-40 $R^{89}$, 5-15 membered heteroaryl optionally substituted by 1-15 $R^{89}$, and 6-21 membered heteroarylalkyl optionally substituted by 1-27 $R^{89}$.

Embodiment 443

The compound of any of Embodiments 1-441, wherein $R^{78}$ at each occurrence is independently chosen from $C_{1-6}$alkyl optionally substituted by 1-3 $R^{89}$, $C_{2-6}$alkenyl optionally substituted by 1-3 $R^{89}$, $C_{2-6}$alkynyl optionally substituted by 1-3 $R^{89}$, $C_{6-11}$aryl optionally substituted by 1-3 $R^{89}$, $C_{7-16}$arylalkyl optionally substituted by 1-3 $R^{89}$, $C_{3-11}$cycloalkyl optionally substituted by 1-3 $R^{89}$, $C_{4-17}$cycloalkylalkyl optionally substituted by 1-3 $R^{89}$, 3-15 membered heterocycloalkyl optionally substituted by 1-3 $R^{89}$, 4-21 membered heterocycloalkylalkyl optionally substituted by 1-3 $R^{89}$, 5-15 membered heteroaryl optionally substituted by 1-3 $R^{89}$, and 6-21 membered heteroarylalkyl optionally substituted by 1-3 $R^{89}$.

Embodiment 444

The compound of any of Embodiments 1-441, wherein $R^{78}$ at each occurrence is independently chosen from $C_{1-6}$alkyl optionally substituted by 1-3 $R^{89}$, $C_{2-6}$alkenyl optionally substituted by 1-3 $R^{89}$, $C_{2-6}$alkynyl optionally substituted by 1-3 $R^{89}$, $C_{6-10}$aryl optionally substituted by 1-3 $R^{89}$, $C_{7-11}$arylalkyl optionally substituted by 1-3 $R^{89}$, $C_{3-10}$cycloalkyl optionally substituted by 1-3 $R^{89}$, 3-10 membered heterocycloalkyl optionally substituted by 1-3 $R^{89}$, and 5-10 membered heteroaryl optionally substituted by 1-3 $R^{89}$.

Embodiment 445

The compound of any of Embodiments 1-441, wherein $R^{78}$ at each occurrence is independently chosen from $C_{1-6}$alkyl optionally substituted by 1-3 $R^{89}$, $C_{6-10}$aryl optionally substituted by 1-3 $R^{89}$, $C_{7-11}$arylalkyl optionally substituted by 1-3 $R^{89}$, $C_{3-10}$cycloalkyl optionally substituted by 1-3 $R^{89}$, 3-10 membered heterocycloalkyl optionally substituted by 1-3 $R^{89}$, and 5-10 membered heteroaryl optionally substituted by 1-3 $R^{89}$.

Embodiment 446

The compound of any of Embodiments 1-441, wherein $R^{78}$ at each occurrence is independently chosen from $C_{1-6}$alkyl optionally substituted by 1-3 $R^{89}$, phenyl optionally substituted by 1-3 $R^{89}$, benzyl optionally substituted by 1-3 $R^{89}$, $C_{3-6}$cycloalkyl optionally substituted by 1-3 $R^{89}$, 3-6 membered heterocycloalkyl optionally substituted by 1-3 $R^{89}$, and 5-6 membered heteroaryl optionally substituted by 1-3 $R^{89}$.

Embodiment 447

The compound of any of Embodiments 1-441, wherein $R^{78}$ at each occurrence is independently chosen from $C_{1-6}$alkyl, phenyl, benzyl, $C_{3-6}$ cycloalkyl, 3-6 membered heterocycloalkyl, and 5-6 membered heteroaryl.

Embodiment 448

The compound of any of Embodiments 1-441, wherein $R^{78}$ at each occurrence is independently chosen from $C_{1-6}$alkyl optionally substituted by 1-3 $R^{89}$, phenyl optionally substituted by 1-3 $R^{89}$, and benzyl optionally substituted by 1-3 $R^{89}$.

Embodiment 449

The compound of any of Embodiments 1-441, wherein $R^{78}$ at each occurrence is independently chosen from $C_{1-6}$alkyl, phenyl, and benzyl.

Embodiment 450

The compound of any of Embodiments 1-441, wherein $R^{78}$ at each occurrence is $C_{1-6}$alkyl optionally substituted by 1-3 $R^{89}$.

Embodiment 451

The compound of any of Embodiments 1-441, wherein $R^{78}$ at each occurrence is $C_{1-6}$alkyl.

Embodiment 452

The compound of any of Embodiments 1-451, wherein $R^{79}$, $R^{89}$, $R^{99}$ and $R^{109}$ at each occurrence is independently chosen from $C_{1-6}$alkyl optionally substituted by 1-13 halogen, $C_{2-6}$alkenyl, $C_{2-6}$alkynyl, $C_{6-11}$-aryl, $C_{7-11}$ arylalkyl, $C_{3-11}$cycloalkyl, $C_{4-17}$cycloalkylalkyl, 3-15 membered heterocycloalkyl, 4-21 membered heterocycloalkylalkyl, 5-15 membered heteroaryl, 6-21 membered heteroarylalkyl, halogen, —CN, —C(=O)$R^{110}$, —C(=O)O$R^{110}$, —C(=O)N$R^{110}R^{110}$, —C(=O)C(=O)$R^{110}$, —C(=N$R^{110}$)$R^{110}$, —C(=N$R^{110}$)N$R^{110}R^{110}$, —C(=NOH)N$R^{110}R^{110}$, —C(=NO$R^{110}$)$R^{110}$, —C(=NN$R^{110}R^{110}$)$R^{110}$, —C(=NN$R^{110}$C(=O)$R^{110}$)$R^{110}$, —C(=NN$R^{110}$C(=O)O$R^{110}$)$R^{110}$, —C(=S)N$R^{110}R^{110}$, —NC, —NO$_2$, —N$R^{110}R^{110}$, —N$R^{110}$N$R^{110}R^{110}$, —N=N$R^{110}$, =N$R^{110}$, =NO$R^{110}$, —N$R^{110}$O$R^{110}$, —N$R^{110}$C(=O)$R^{110}$, —N$R^{110}$C(=O)C(=O)R, —N$R^{110}$C(=O)O$R^{110}$, —N$R^{110}$C(=O)C(=O)O$R^{110}$, —N$R^{110}$C(=O)N$R^{110}R^{110}$, —N$R^{110}$C(=O)N$R^{110}$C(=O)$R^{110}$, —N$R^{110}$C(=O)N$R^{110}$C(=O)O$R^{110}$, —N$R^{110}$C(=N$R^{110}$)N$R^{110}R^{110}$, —N$R^{110}$C(=O)C(=O)N$R^{110}R^{110}$, —N$R^{110}$C(=S)$R^{110}$, —N$R^{110}$C(=S)O$R^{110}$, —N$R^{110}$C(=S)N$R^{110}R^{110}$, —N$R^{110}$S(=O)$_2R^{110}$, —N$R^{110}$S(=O)$_2$N$R^{110}R^{110}$, —N$R^{110}$P(=O)$R^{111}R^{111}$, —N$R^{110}$P(=O)(N$R^{110}R^{110}$)(N$R^{110}R^{110}$), —N$R^{110}$P(=O)(O$R^{110}$)(O$R^{110}$), —N$R^{110}$P(=O)(S$R^{110}$)(SR), —O$R^{110}$, =O, —OCN, —OC(=O)$R^{110}$, —OC(=O)N$R^{110}R^{110}$, —OC(=O)O$R^{110}$, —OC(=N$R^{110}$)N$R^{110}R^{110}$, —OS(=O)$R^{110}$, —OS(=O)$_2R^{110}$, —OS(=O)$_2$O$R^{110}$, —OS(=O)$_2$N$R^{110}R^{110}$, —OP(=O)$R^{111}R^{111}$, —OP(=O)(N$R^{110}R^{110}$)(N$R^{110}R^{110}$), —OP(=O)(O$R^{110}$)(O$R^{110}$), —OP(=O)(S$R^{110}$)(S$R^{110}$), —Si($R^{110}$)$_3$, —SCN, =S, —S(=O)$_nR^{110}$, —S(=O)$_2$O$R^{110}$, —SO$_3R^{110}$, —S(=O)$_2$N$R^{110}$O$R^{110}$, —S(=O)N$R^{110}R^{110}$, —SP(=O)$R^{111}R^{111}$, —SP(=O)(N$R^{110}R^{110}$)(N$R^{110}R^{110}$), —SP(=O)(O$R^{110}$)(O$R^{110}$), —SP(=O)(S$R^{110}$)(S$R^{110}$), —P(=O)$R^{111}R^{111}$, —P(=O)(N$R^{110}R^{110}$)(N$R^{110}R^{110}$), —P(=O)(O$R^{110}$)(O$R^{110}$), and —P(=O)(S$R^{110}$)(S$R^{110}$).

Embodiment 453

The compound of any of Embodiments 1-451, wherein $R^{79}$, $R^{89}$, $R^{99}$ and $R^{109}$ at each occurrence is independently chosen from $C_{1-6}$alkyl optionally substituted by 1-6 halogen, $C_{2-6}$alkenyl, $C_{2-6}$alkynyl, $C_{6-11}$aryl, $C_{7-16}$arylalkyl, $C_{3-11}$cycloalkyl, $C_{4-17}$cycloalkylalkyl, 3-15 membered heterocycloalkyl, 4-15 membered heterocycloalkylalkyl, 5-15 membered heteroaryl, 6-15 membered heteroarylalkyl, halogen, —CN, —C(=O)$R^{110}$, —C(=O)O$R^{110}$, —C(=O)N$R^{110}R^{110}$, —C(=O)C(=O)$R^{110}$, —NC, —NO$_2$, —N$R^{110}R^{110}$, —N$R^{110}$N$R^{110}$, —N$R^{110}$O$R^{110}$, —N$R^{110}$C(=O)$R^{110}$, —N$R^{110}$C(=O)C(=O)$R^{110}$, —N$R^{110}$C(=O)O$R^{110}$, —N$R^{110}$C(=O)C(=O)O$R^{110}$, —N$R^{110}$C(=O)N$R^{110}R^{110}$, —N$R^{110}$C(=O)N$R^{110}$C(=O)$R^{110}$, —N$R^{110}$C(=O)N$R^{110}$C(=O)O$R^{110}$, —N$R^{110}$S(=O)$_2R^{110}$, —N$R^{110}$S(=O)$_2$N$R^{110}R^{110}$, —N$R^{110}$P(=O)$R^{111}R^{111}$, —N$R^{110}$P(=O)(N$R^{110}R^{110}$)(N$R^{110}R^{110}$), —N$R^{110}$P(=O)(O$R^{110}$)(O$R^{110}$), —O$R^{110}$, =O, —OCN, —OC(=O)$R^{110}$, —OC(=O)N$R^{110}R^{110}$, —OC(=O)O$R^{110}$, —OS(=O)$R^{110}$, —OS(=O)$_2R^{110}$, —OS(=O)$_2$O$R^{110}$, —OS(=O)$_2$N$R^{110}R^{110}$, —OP(=O)$R^{111}R^{111}$, —OP(=O)(N$R^{110}R^{110}$)(N$R^{110}R^{110}$), —OP(=O)(O$R^{110}$)(O$R^{110}$), —Si($R^{110}$)$_3$, —SCN, =S, —S(=O)$_nR^{110}$, —S(=O)$_2R^{110}$, —SO$_3R^{110}$, —S(=O)$_2$N$R^{110}R^{110}$, —S(=O)N$R^{110}R^{110}$, —P(=O)$R^{111}R^{111}$, —P(=O)(N$R^{110}R^{110}$)(N$R^{110}R^{110}$), and —P(=O)(O$R^{110}$)(O$R^{110}$).

Embodiment 454

The compound of any of Embodiments 1-451, wherein $R^{79}$, $R^{89}$, $R^{99}$ and $R^{109}$ at each occurrence is independently chosen from $C_{1-6}$alkyl optionally substituted by 1-3 halogen, $C_{2-6}$alkenyl, $C_{2-6}$alkynyl, $C_{6-10}$aryl, $C_{7-11}$arylalkyl, $C_{3-10}$cycloalkyl, $C_{4-17}$cycloalkylalkyl, 3-10 membered heterocycloalkyl, 4-10 membered heterocycloalkylalkyl, 5-10 membered heteroaryl, 6-10 membered heteroarylalkyl, halogen, —CN, —C(=O)$R^{110}$, —C(=O)O$R^{110}$, —C(=O)N$R^{110}R^{110}$, —NC, —NO$_2$, —N$R^{110}R^{110}$, —N$R^{110}$O$R^{110}$, —N$R^{110}$C(=O)$R^{110}$, —N$R^{110}$C(=O)O$R^{110}$, —N$R^{110}$C(=O)N$R^{110}R^{110}$, —N$R^{110}$C(=O)N$R^{110}$C(=O)$R^{110}$, —N$R^{110}$S(=O)$_2R^{110}$, —N$R^{110}$S(=O)$_2$N$R^{110}R^{110}$, —N$R^{110}$P(=O)$R^{111}R^{111}$, —N$R^{110}$P(=O)(N$R^{110}R^{110}$)(N$R^{110}R^{110}$), —N$R^{110}$P(=O)(O$R^{110}$)(O$R^{110}$), —O$R^{110}$, =O, —OCN, —OC(=O)$R^{110}$, —OC(=O)N$R^{110}R^{110}$, —OS(=O)$_2$N$R^{110}R^{110}$, —OP(=O)$R^{111}R^{111}$, —OP(=O)(N$R^{110}R^{110}$)(N$R^{110}R^{110}$), —SCN, =S, —S(=O)$_nR^{110}$, —S(=O)$_2$N$R^{110}R^{110}$, —S(=O)N$R^{110}R^{110}$, —P(=O)$R^{111}R^{111}$, and —P(=O)(N$R^{110}R^{110}$)(N$R^{110}R^{110}$).

Embodiment 455

The compound of any of Embodiments 1-451, wherein $R^{79}$, $R^{89}$, $R^{99}$ and $R^{109}$ at each occurrence is independently chosen from $C_{1-6}$alkyl optionally substituted by 1-3 halogen, $C_{2-6}$alkenyl, $C_{2-6}$alkynyl, $C_{6-10}$aryl, $C_{7-11}$arylalkyl, $C_{3-10}$cycloalkyl, 3-10 membered heterocycloalkyl, 5-10 membered heteroaryl, halogen, —CN, —C(=O)$R^{110}$, —C(=O)O$R^{110}$, —C(=O)N$R^{110}R^{110}$, —NO$_2$, —N$R^{110}R^{110}$, —N$R^{110}R^{110}$, —N$R^{110}$C(=O)$R^{110}$, —N$R^{110}$C(=O)N$R^{110}R^{110}$, —N$R^{110}$S(=O)$_2R^{110}$, —N$R^{110}$S(=O)$_2$N$R^{110}R^{110}$, —O$R^{110}$, =O, —OCN, —OC(=O)$R^{110}$, —S(=O)$_nR^{110}$, —S(=O)$_2$N$R^{110}R^{110}$, and —S(=O)N$R^{110}R^{110}$.

Embodiment 456

The compound of any of Embodiments 1-451, wherein $R^{79}$, $R^{89}$, $R^{99}$ and $R^{109}$ at each occurrence is independently chosen from $C_{1-6}$alkyl optionally substituted by 1-3 halogen, $C_{2-6}$alkenyl, $C_{2-6}$alkynyl, phenyl, benzyl, $C_{3-6}$ cycloalkyl, 3-6 membered heterocycloalkyl, 5-6 membered heteroaryl, halogen, —CN, —C(=O)$R^{110}$, —C(=O)O$R^{110}$, —C(=O)

$NR^{110}R^{110}$, $-NO_2$, $-NR^{110}R^{110}$, $-NR^{110}C(=O)R^{110}$, $-NR^{110}C(=O)NR^{110}R^{110}$, $-NR^{110}S(=O)_2R^{110}$, $-NR^{110}S(=O)_2NR^{110}R^{110}$, $-OR^{110}$, $=O$, $-S(=O)_nR^{110}$, and $-S(=O)_2NR^{110}R^{110}$.

Embodiment 457

The compound of any of Embodiments 1-451, wherein $R^{79}$, $R^{89}$, $R^{99}$ and $R^{109}$ at each occurrence is independently chosen from $C_{1-6}$alkyl optionally substituted by 1-3 halogen, $C_{2-6}$alkenyl, $C_{2-6}$alkynyl, phenyl, benzyl, $C_{3-6}$cycloalkyl, 3-6 membered heterocycloalkyl, 5-6 membered heteroaryl, halogen, $-CN$, $-C(=O)R^{110}$, $-C(=O)OR^{110}$, $-C(=O)NR^{110}R^{110}$, $-NR^{110}R^{110}$, $-NR^{110}C(=O)R^{110}$, $-NR^{110}S(=O)_2R^{110}$, $-OR^{110}$, $=O$, $-S(=O)_nR^{110}$, and $-S(=O)_2NR^{110}R^{110}$.

Embodiment 458

The compound of any of Embodiments 1-451, wherein $R^{79}$, $R^{89}$, $R^{99}$ and $R^{109}$ at each occurrence is independently chosen from $C_{1-6}$alkyl optionally substituted by 1-3 halogen, phenyl, benzyl, $C_{3-6}$cycloalkyl, 3-6 membered heterocycloalkyl, 5-6 membered heteroaryl, halogen, $-CN$, $-C(=O)R^{110}$, $-C(=O)OR^{110}$, $-C(=O)NR^{110}R^{110}$, $-NR^{110}R^{110}$, $-OR^{110}$, $=O$, $-S(=O)_nR^{110}$, and $-S(=O)_2NR^{110}R^{110}$.

Embodiment 459

The compound of any of Embodiments 1-451, wherein $R^{79}$, $R^{89}$, $R^{99}$ and $R^{109}$ at each occurrence is independently chosen from $C_{1-6}$alkyl optionally substituted by 1-3 halogen, halogen, and $-NR^{110}R^{110}$.

Embodiment 460

The compound of any of Embodiments 1-451, wherein $R^{79}$, $R^{89}$, $R^{99}$ and $R^{109}$ at each occurrence is independently chosen from $C_{1-6}$alkyl, halogen, and $-NR^{111}R^{110}$.

Embodiment 461

The compound of any of Embodiments 1-451, wherein $R^{79}$, $R^{89}$, $R^{99}$ and $R^{109}$ at each occurrence is independently chosen from $C_{1-6}$alkyl and $-NR^{110}R^{110}$.

Embodiment 462

The compound of any of Embodiments 1-451, wherein $R^{79}$, $R^{89}$, $R^{99}$ and $R^{109}$ at each occurrence is $-NR^{110}R^{110}$.

Embodiment 463

The compound of any of Embodiments 1-451, wherein $R^{79}$, $R^{89}$, $R^{99}$ and $R^{109}$ at each occurrence is $C_{1-6}$alkyl.

Embodiment 464

The compound of any of Embodiments 1-451, wherein $R^{79}$ at each occurrence is independently chosen from $C_{1-6}$alkyl and $-NR^{110}R^{110}$; $R^{89}$, $R^{99}$ and $R^{109}$ at each occurrence is $C_{1-6}$alkyl.

Embodiment 465

The compound of any of Embodiments 1-451, wherein $R^{79}$ at each occurrence is independently chosen from $C_{1-6}$alkyl and $-NR^{110}R^{110}$; $R^{89}$, $R^{99}$ and $R^{109}$ at each occurrence is $-NR^{110}R^{110}$.

Embodiment 466

The compound of any of Embodiments 1-451, wherein $R^{79}$ at each occurrence is $-NR^{110}R^{110}$; $R^{89}$, $R^{99}$ and $R^{109}$ at each occurrence is $C_{1-6}$alkyl.

Embodiment 467

The compound of any of Embodiments 1-466, wherein $R^{110}$ at each occurrence is independently chosen from H, $C_{1-6}$alkyl and $C_{1-6}$-haloalkyl.

Embodiment 468

The compound of any of Embodiments 1-466, wherein $R^{110}$ at each occurrence is independently chosen from H and $C_{1-6}$alkyl.

Embodiment 469

The compound of any of Embodiments 1-466, wherein $R^{110}$ at each occurrence is $C_{1-6}$alkyl.

Embodiment 470

The compound of any of Embodiments 1-466, wherein $R^{110}$ at each occurrence is H.

Embodiment 471

The compound of any of Embodiments 1-470, wherein $R^{110}$ at each occurrence is independently chosen from $C_{1-6}$alkyl and $C_{1-6}$-haloalkyl.

Embodiment 472

The compound of any of Embodiments 1-470, wherein $R^{110}$ at each occurrence is $C_{1-6}$alkyl.

Embodiment 473

The compound of any of Embodiments 1-470, wherein $R^{111}$ at each occurrence is $C_{1-6}$-haloalkyl.

Embodiment 474

The compound of any of Embodiments 1-473, wherein n at each occurrence is independently chosen from 0, 1, and 2.

Embodiment 475

The compound of any of Embodiments 1-473, wherein n at each occurrence is independently chosen from 0 and 2.

Embodiment 476

The compound of any of Embodiments 1-473, wherein n at each occurrence is independently chosen from 1 and 2.

Embodiment 477

The compound of any of Embodiments 1-473, wherein n at each occurrence is independently chosen from 0 and 1.

Embodiment 478

The compound of any of Embodiments 1-473, wherein n at each occurrence is 0.

Embodiment 479

The compound of any of Embodiments 1-473, wherein n at each occurrence is 1.

Embodiment 480

The compound of any of Embodiments 1-473, wherein n at each occurrence is 2.

Embodiment 481

The compound of any of Embodiments 1-480, wherein neither $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, nor $R^{28}$ contain either of the following chemical moieties

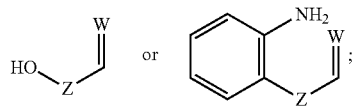

wherein W is O or S, and Z is N or C.

Embodiment 482

The compound of any of Embodiments 1-481, wherein neither $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, nor $R^{28}$ is.

(a)

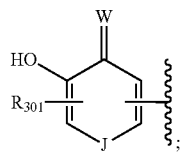

where W is O or S; J is O, NH or $NCH_3$; and $R_{301}$ is hydrogen or alkyl;

(b)

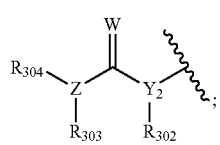

where W is O or S; $Y_2$ is absent, N, or CH; Z is N or CH; $R_{302}$ and $R_{304}$ are independently hydrogen, hydroxyl, or an aliphatic group; provided that if $R_{302}$ and $R_{304}$ are both present, one of $R_{302}$ or $R_{304}$ must be hydroxyl and if $Y_2$ is absent, $R_{304}$ must be hydroxyl; and $R_{303}$ is hydrogen or aliphatic group;

(c)

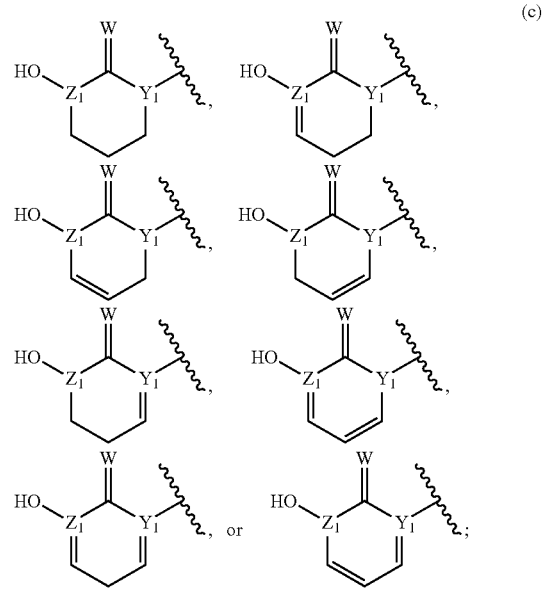

where W is O or S; $Y_1$ and $Z_1$ are independently N, C or CH; or (d)

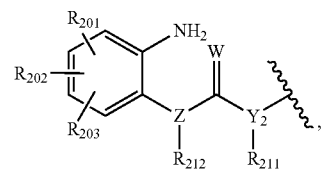

where Z is N or CH; $Y_2$ is absent, N, or CH; W is O or S; $R_{211}$ and $R_{212}$ are independently selected from hydrogen or aliphatic group; $R_{201}$, $R_{202}$ and $R_{203}$ are independently selected from hydrogen, hydroxyl, amino, halogen, alkoxy, alkylamino, dialkylamino, $CF_3$, CN, $NO_2$, sulfonyl, acyl, aliphatic group, substituted aliphatic group, aryl, substituted aryl, heteroaryl, substituted heteroaryl, heterocyclic, and substituted heterocyclic;

wherein for the purpose of this Embodiment, the following definitions apply:

an aliphatic group is a non-aromatic moiety that may be saturated (e.g. single bond) or contain one or more units of unsaturation, e.g., double and/or triple bonds; an aliphatic group may be straight chained, branched or cyclic, contain carbon, hydrogen or, optionally, one or more heteroatoms and may be substituted or unsubstituted;

"acyl" refers to hydrogen, alkyl, partially saturated or fully saturated cycloalkyl, partially saturated or fully saturated heterocycle, aryl, and heteroaryl substituted carbonyl groups;

"alkoxy" embraces linear or branched oxy-containing radicals each having alkyl portions of one to about twenty carbon atoms or, preferably, one to about twelve carbon atoms; and "heterocyclic" refers to saturated, partially unsaturated and unsaturated heteroatom-containing ringshaped radicals, where the heteroatoms may be selected from nitrogen, sulfur and oxygen;

Embodiment 483

The compound of any of Embodiments 1-482, wherein A is not S.

Embodiment 484

The compound of any of Embodiments 1-483, wherein $R^1$ is not —$OR^{20}$.

Embodiment 485

The compound of any of Embodiments 1-484, wherein $R^8$ is not tetrahydrofuranyl substituted by 4 or 5 $R^{19}$.

Embodiment 486

The compound of any of Embodiments 1-484, wherein $R^8$ is not

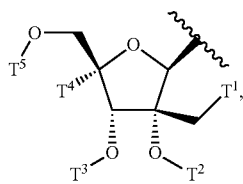

wherein $T^1$ is $R^{39}$; $T^2$, $T^3$, and $T^5$ are independently chosen from $R^{30}$, —C(=O)$R^{30}$, —C(=O)$NR^{32}R^{33}$, —C(=O)$OR^{30}$, —C(=$NR^{35}$)$NR^{32}R^{33}$, —S(=O)$R^{30}$, —S(=O)$_2R^{30}$, —S(=O)$_2OR^{30}$, —S(=O)$_2NR^{32}R^{33}$, —P(=O)$R^{38}R^{38}$, —P(=O)($NR^{32}R^{33}$)($NR^{32}R^{33}$), —P(=O)($OR^{30}$)($OR^{30}$), and —P(=O)($SR^{30}$)($SR^{30}$); and $T^4$ is $R^{19}$.

Embodiment 487

The compound of any of Embodiments 1-484, wherein $R^8$ is not

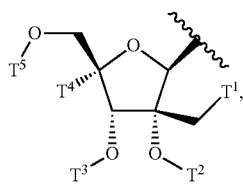

wherein $T^1$ is hydrogen, fluoro, azido, amino, hydroxyl, $C_{1-3}$alkoxy, mercapto, or $C_{1-3}$alkylthio; $T^2$, $T^3$, and $T^5$ are independently chosen from $R^{30}$, —C(=O)$R^{30}$, —C(=O)$NR^{33}$, —C(=O)$OR^{30}$, —C(=$NR^{35}$)$NR^{32}R^{33}$, —S(=O)$R^{30}$, —S(=O)$_2R^{30}$, —S(=O)$_2OR^{30}$, —S(=O)$_2NR^{32}R^{33}$, —P(=O)$R^3R^3$, —P(=O)($NR^{32}R^{33}$)($NR^{32}R^{33}$), —P(=O)($OR^{30}$)($OR^{30}$), and —P(=O)($SR^{30}$)($SR^{30}$); and $T^4$ is hydrogen, azido, methyl, hydroxymethyl, or fluoromethyl.

Embodiment 488

The compound of any of Embodiments 1-487, wherein $R^{10}$ is not —CN.

Embodiment 489

The compound of any of Embodiments 1-488, wherein none of $R^1$ and $R^2$, $R^1$ and $R^3$, $R^1$ and $R^5$, or $R^1$ and $R^{11}$, together with the atoms linking them, form a heterocycloalkyl optionally substituted by one or more $R^{19}$ or a heteroaryl optionally substituted by one ore more $R^{19}$.

Embodiment 490

The compound of any of Embodiments 1-488, wherein $R^1$ and $R^{11}$ do not, together with the atoms linking them, form a heterocycloalkyl optionally substituted by one or more $R^{19}$ or a heteroaryl optionally substituted by one or more $R^{19}$.

Embodiment 491

The compound of any of Embodiments 1-490, wherein neither $R^7$ nor $R^{10}$ is H, or neither $R^8$ nor $R^9$ is H.

Embodiment 492

The compound of Embodiment 491, wherein neither $R^7$ nor $R^{10}$ is H.

Embodiment 493

The compound of Embodiment 491, wherein neither $R^8$ nor $R^9$ is H.

Embodiment 494

The compound of any of Embodiments 1-493, wherein neither $R^3$ and $R^4$ nor $R^5$ and $R^6$ together form =O, =$NR^{20}$, =$NOR^{20}$, or =S.

Embodiment 495

The compound of any of Embodiments 1-494, wherein neither $R^3$ and $R^4$ nor $R^5$ and $R^6$ together form =O.

Embodiment 496

The compound of any of Embodiments 1-495, wherein
(a) when $R^1$ is H, $R^2$ is neither aryl optionally substituted by one or more $R^{19}$ nor heteroaryl optionally substituted by one or more $R^{19}$,
(b) when $R^2$ is H, $R^1$ is neither optionally substituted by one or more $R^{19}$ nor heteroaryl optionally substituted by one or more $R^{19}$,
(c) $R^3$, $R^4$, $R^5$, and $R^6$ are not —$NHR^{22}$, $NHR^{23}$, —$SO_2NHR^{22}$, —$SO_2NHR^{23}$, —C(=O)$NHR^{22}$, or —C(=O)$NHR^{23}$, wherein $R^{22}$ and $R^{23}$ are either aryl optionally substituted by one or more $R^{59}$ or heteroaryl optionally substituted by one or more $R^{59}$, and
(d) $R^3$, $R^4$, $R^5$, and $R^6$ do not contain a group of formula —NHR, —$SO_2$NHR, or —C(=O)NHR, wherein R is optionally substituted aryl, or optionally substituted heteroaryl.

Embodiment 497

The compound of any of Embodiments 1-496, wherein the group of formula

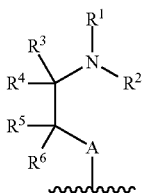

does not together form a group of formula

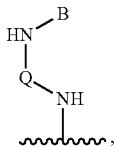

wherein
- B is an optionally substituted aryl, or optionally substituted heteroaryl;
- Q is a $C_{1-4}$alkylidene chain in which each methylene unit of said Q is substituted by $R^2$ and $R^{2'}$, and up to two non-adjacent methylene units of said Q are optionally and independently replaced by —$SO_2$ or —C(=O);
- each $R^2$ is independently selected from H, —OH, $C_{1-10}$alkyl, $C_{1-10}$ aliphatic, ($C_{1-10}$ aliphatic)-NH—($C_{1-10}$ aliphatic); —O—($C_{1-10}$ aliphatic); —$NH_2$, —NH($C_{1-10}$aliphatic), —N($C_{1-10}$ aliphatic)$_2$, —C(=O)R, aryl, or heteroaryl, wherein said aliphatic, aryl, or heteroaryl is optionally substituted;
- each $R^{2'}$ is independently selected from H and an optionally substituted $C_{1-10}$ aliphatic group; and
- R is selected from an optionally substituted group selected from $C_{1-10}$ aliphatic, aryl, aralkyl, heteroaryl, and heteroaralkyl;
- wherein for the purpose of this Embodiment, the following definitions apply:
  - "alkylidene chain" refers to a straight or branched carbon chain that may be fully saturated or have one or more units of un saturation and has two points of attachment to the rest of the molecule;
  - "aliphatic" or "aliphatic group" means a straight-chain or branched, substituted or unsubstituted $C_1$-$C_8$ hydrocarbon chain that is completely saturated or that contains one or more units of unsaturation, or a monocyclic $C_3$-$C_5$ hydrocarbon or bicyclic $C_8$-$C_{12}$ hydrocarbon that is completely saturated or that contains one or more units of unsaturation, but which is not aromatic, that has a single point of attachment to the rest of the molecule wherein any individual ring in said bicyclic ring system has 3-7 members.

Embodiment 498

The compound of any of Embodiments 1-497, wherein $R^8$ is neither aryl optionally substituted by one or more $R^{19}$ nor heteroaryl optionally substituted by one or more $R^{19}$.

Embodiment 499

The compound of any of Embodiments 1-498, wherein:
(a) when $R^9$ is —$NH_2$, $R^{10}$ is not —C(=O)$NH_2$;
(b) when $R^9$ is —NHC(=S)NHCOPh, $R^{10}$ is not —C(=O)O$R^{20}$, wherein $R^{20}$ is alkyl optionally substituted by $R^{49}$; and (c) $R^9$ and $R^{10}$ do not, together with the atoms linking them, form a group of formula

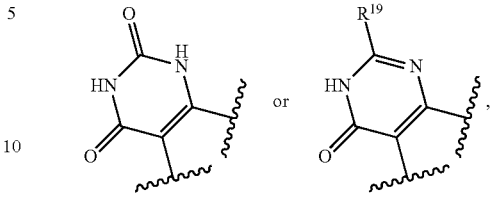

wherein $R^{19}$ is as defined herein.

Embodiment 500

The compound of any of Embodiments 1-499, wherein:
(a) when $R^9$ is —$NH_2$, $R^{10}$ is not —C(=O)$NH_2$; and
(b) $R^9$ and $R^{10}$ do not, together with the atoms linking them, form a group of formula

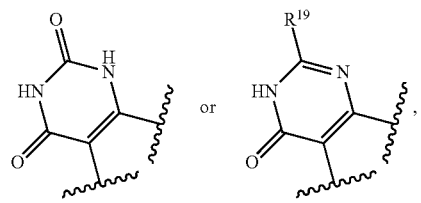

or wherein $R^{19}$ is as defined herein.

Embodiment 501

The compound of any of Embodiments 1-500, wherein $R^9$ and $R^{10}$ do not, together with the atoms linking them, form a group of formula

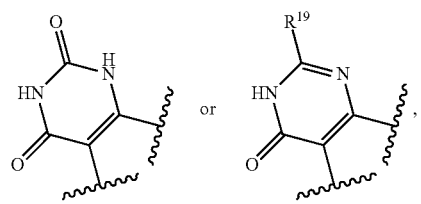

wherein $R^{19}$ is as defined herein.

Embodiment 502

The compound of any of Embodiments 1-501, wherein neither $R^1$ and $R^2$ nor $R^1$ and $R^3$, together with the atoms linking them, form a heterocycloalkyl optionally substituted by one or more $R^{19}$ or a heteroaryl optionally substituted by one or more $R^{19}$, wherein $R^{19}$ is as defined herein.

Embodiment 503

The compound of any of Embodiments 1-502, wherein $R^{10}$ is not —CN, aryl optionally substituted by one or more $R^{19}$, heterocycloalkyl optionally substituted by one or more $R^{19}$, or heteroaryl optionally substituted by one or more $R^{19}$, wherein $R^{19}$ is as defined herein.

Embodiment 504

The compound of any of Embodiments 1-503, wherein $R^9$ is neither —$NH_2$ nor —OH when $R^{10}$ is —C(=O)$R^{20}$, —C(=O)O$R^{20}$, or —C(=O)N$R^{22}R^{23}$, wherein $R^{20}$, $R^{22}$, and $R^{23}$ are as defined herein.

Embodiment 505

The compound of any of Embodiments 1-504, wherein when
(a) $R^9$ is chosen from H, $C_1$-$C_6$alkyl, $C_3$-$C_7$cycloalkyl and —(CH$_2$)$_{n1}$—$R^{411}$ wherein the subscript n1 is an integer of from 0 to 3 and $R^{411}$ is selected from $C_1$-$C_6$alkoxy, $C_1$-$C_6$alkylthio, mono- or di-($C_1$-$C_6$alkyl)amino, amino, phenyl, pyridyl, furanyl, pyrrolyl, imidazolyl, oxazolyl, isoxazolyl, triazolyl, tetrazolyl, thiazolyl, pyrazolyl, and thienyl, wherein each of the rings is optionally substituted with from 1 to 3 substituents selected from halogen, $N_3$, $NO_2$, CN, $C_1$-$C_6$alkyl, $OR^{412}$, N($R^{412}$)$_2$, $CO_2R^{412}$ and CON($R^{412}$)$_2$, wherein each $R^{412}$ is independently H or $C_1$-$C_6$alkyl; and
(b) $R^{10}$ is chosen from —$R^{401}$, —$OR^{401}$, —$SR^{401}$, —N($R^{410}$)$R^{401}$, —C(=O)$R^{401}$ and —CH(OH)$R^{401}$, wherein $R^{410}$ is selected from H, $C_1$-$C_6$alkyl and C(=O)$C_1$-$C_6$alkyl; and $R^{401}$ is chosen from H, halo, CN, $NO_2$, —$N_3$, $C_1$-$C_6$alkyl, $C_3$-$C_7$cycloalkyl, —C($R^{413}$)=C($R^{413}$)$_2$, —C≡C$R^{413}$ or —(CH$_2$)$_{n2}$—$R^{414}$; wherein each $R^{413}$ is independently selected from H, F, Cl, Br, CN, $C_1$-$C_6$alkyl, $C_3$-$C_7$cycloalkyl, (CH$_2$)$_{n2}$—$R^{414}$ and C(O)—(CH$_2$)$_{n2}$—$R^{414}$; and wherein each subscript n2 is independently an integer of from 0 to 3 and each $R^{414}$ is independently selected from $C_1$-$C_6$alkoxy, $C_1$-$C_6$alkylthio, mono- or di-($C_1$-$C_6$)alkylamino, amino, phenyl, pyridyl, furanyl, pyrrolyl, imidazolyl, oxazolyl, isoxazolyl, triazolyl, tetrazolyl, thiazolyl, pyrazolyl, and thienyl, wherein each of the rings is optionally substituted with from 1 to 3 substituents selected from halogen, $NO_2$, —$N_3$, CN, ($C_1$-$C_6$)alkyl, $OR^{415}$, N($R^{415}$)$_2$, $CO_2R^{415}$ and CON($R^{415}$)$_2$, wherein each $R^{415}$ is independently H or $C_1$-$C_6$alkyl; and wherein any alkyl or cycloalkyl portions of $R^{401}$ are optionally substituted with from one to five F substituents;
$R^1$ and $R^{11}$ do not, together with the atoms linking them, form a 6-7 membered heterocycloalkyl optionally substituted by one or more $R^{19}$, wherein $R^{19}$ is as defined herein.

Embodiment 506

The compound of any of Embodiments 1-504, wherein when
(a) $R^9$ is chosen from H, $C_1$-$C_6$alkyl, $C_3$-$C_7$cycloalkyl and —(CH$_2$)$_{n1}$—$R^{411}$ wherein the subscript n1 is an integer of from 0 to 3 and $R^{411}$ is selected from $C_1$-$C_6$alkoxy, $C_1$-$C_6$alkylthio, mono- or di-($C_1$-$C_6$alkyl)amino, amino, phenyl, pyridyl, furanyl, pyrrolyl, imidazolyl, oxazolyl, isoxazolyl, triazolyl, tetrazolyl, thiazolyl, pyrazolyl, and thienyl, wherein each of the rings is optionally substituted with from 1 to 3 substituents selected from halogen, $N_3$, $NO_2$, CN, $C_1$-$C_6$alkyl, $OR^{412}$, N($R^{412}$)$_2$, $CO_2R^{412}$ and CON($R^{412}$)$_2$, wherein each $R^{412}$ is independently H or $C_1$-$C_6$alkyl; and
(b) $R^{10}$ is chosen from —$R^{401}$, —$OR^{401}$, —$SR^{401}$, —N($R^{410}$)$R^{401}$, —C(=O)$R^{401}$ and —CH(OH)$R^{401}$, wherein $R^{410}$ is selected from H, $C_1$-$C_6$alkyl and C(=O)$C_1$-$C_6$alkyl; and $R^{401}$ is chosen from H, halo, CN, $NO_2$, —$N_3$, $C_1$-$C_6$alkyl, $C_3$-$C_7$cycloalkyl, —C($R^{413}$)=C($R^{413}$)$_2$, —C≡C$R^{413}$ or —(CH$_2$)$_{n2}$—$R^{414}$; wherein each $R^{413}$ is independently selected from H, F, Cl, Br, CN, $C_1$-$C_6$alkyl, $C_3$-$C_7$cycloalkyl, (CH$_2$)$_{n2}$—$R^{414}$ and C(O)—(CH$_2$)$_{n2}$—$R^{414}$; and wherein each subscript n2 is independently an integer of from 0 to 3 and each $R^{414}$ is independently selected from $C_1$-$C_6$alkoxy, $C_1$-$C_6$alkylthio, mono- or di-($C_1$-$C_6$)alkylamino, amino, phenyl, pyridyl, furanyl, pyrrolyl, imidazolyl, oxazolyl, isoxazolyl, triazolyl, tetrazolyl, thiazolyl, pyrazolyl, and thienyl, wherein each of the rings is optionally substituted with from 1 to 3 substituents selected from halogen, $NO_2$, —$N_3$, CN, ($C_1$-$C_6$)alkyl, $OR^{415}$, N($R^{415}$)$_2$, $CO_2R^{415}$ and CON($R^{415}$)$_2$, wherein each $R^{415}$ is independently H or $C_1$-$C_6$alkyl; and wherein any alkyl or cycloalkyl portions of $R^{401}$ are optionally substituted with from one to five F substituents;
$R^1$ and $R^{11}$ do not, together with the atoms linking them, form a 6-7 membered heterocycloalkyl optionally substituted by 1-4 $R^{403}$, wherein each $R^{403}$ is independently chosen from $C_1$-$C_6$alkyl, $C_3$-$C_7$cycloalkyl, —(CH$_2$)$_{n4}$—$R^{419}$ and —C(O)—(CH$_2$)$_{n4}$—$R^{419}$; wherein the subscript n4 is an integer of from 0 to 4 and each $R^{419}$ is independently selected from $C_1$-$C_6$alkoxy, $C_1$-$C_6$alkylthio, mono- or di-($C_1$-$C_6$)alkylamino, amino, phenyl, pyridyl, furanyl, pyrrolyl, imidazolyl, oxazolyl, isoxazolyl, triazolyl, tetrazolyl, thiazolyl, pyrazolyl, and thienyl, wherein each of the rings is optionally substituted with from 1 to 3 substituents selected from halogen, $N_3$, $NO_2$, CN, $C_1$-$C_6$alkyl, —$OR^{420}$, —N($R^{420}$)$_2$, $CO_2R^{420}$ and CON($R^{420}$)$_2$, wherein each $R^{420}$ is independently H or $C_1$-$C_6$alkyl; and wherein any alkyl or cycloalkyl portions of $R^{403}$ are optionally substituted with from one to five F substituents.

Embodiment 507

The compound of any of Embodiments 1-504, wherein $R^1$ and $R^{11}$ do not, together with the atoms linking them, form a 6-7 membered heterocycloalkyl optionally substituted by 1-4 $R^{403}$, wherein each $R^{403}$ is independently chosen from $C_1$-$C_6$alkyl, $C_3$-$C_7$cycloalkyl, —(CH$_2$)$_{n4}$—$R^{419}$ and —C(O)—(CH$_2$)$_{n4}$—$R^{419}$; wherein the subscript n4 is an integer of from 0 to 4 and each $R^{419}$ is independently selected from $C_1$-$C_6$alkoxy, $C_1$-$C_6$alkylthio, mono- or di-($C_1$-$C_6$)alkylamino, amino, phenyl, pyridyl, furanyl, pyrrolyl, imidazolyl, oxazolyl, isoxazolyl, triazolyl, tetrazolyl, thiazolyl, pyrazolyl, and thienyl, wherein each of the rings is optionally substituted with from 1 to 3 substituents selected from halogen, $N_3$, $NO_2$, CN, $C_1$-$C_6$alkyl, —$OR^{420}$, —N($R^{420}$)$_2$, $CO_2R^{420}$ and CON($R^{420}$)$_2$, wherein each $R^{420}$ is independently H or $C_1$-$C_6$alkyl; and wherein any alkyl or cycloalkyl portions of $R^{403}$ are optionally substituted with from one to five F substituents.

Embodiment 508

The compound of any of Embodiments 1-504, wherein $R^1$ and $R^{11}$ do not, together with the atoms linking them, form a 6-7 membered heterocycloalkyl optionally substituted by one or more $R^{19}$, wherein $R^{19}$ is as defined herein.

The above Embodiments include salts of acidic and basic compounds of formula (I). Preferably, the salts are pharmaceutically acceptable. Pharmaceutically acceptable acid addition salts of basic compounds of formula (I) include, but are not limited to, salts derived from inorganic acids such as hydrochloric, nitric, phosphoric, sulfuric, hydrobromic, hydriodic, and phosphorus, as well as the salts derived from organic acids, such as aliphatic mono- and dicarboxylic acids, phenyl-substituted alkanoic acids, hydroxy alkanoic acids, alkanedioic acids, aromatic acids, and aliphatic and aromatic sulfonic acids. Such salts thus include, but are not limited to, sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, and methanesulfonate. See, for example, Berge et al., "Pharmaceutical Salts," J. of Pharmaceutical Science, 1977; 66:1-19.

Acid addition salts may be prepared by contacting a compound of formula (I) with a sufficient amount of the desired acid to produce the salt in the conventional manner. The free base form of the compound of formula (I) may be regenerated by contacting the salt form with a base and isolating the free base in the conventional manner.

Pharmaceutically acceptable base salts of acidic compounds of formula (I) are formed with metals or amines, such as alkali and alkaline earth metal hydroxides, or of organic amines. Examples of metals used as cations include, but are not limited to, sodium, potassium, magnesium, and calcium. Examples of suitable amines include, but are not limited to, N,N'-dibenzylethylenediamine, chloroprocaine, choline, diethanolamine, ethylenediamine (ethane-1,2-diamine), N-methylglucamine, and procaine. See, for example, Berge et al., "Pharmaceutical Salts," J. of Pharmaceutical Science, 1977; 66:1-19.

Base salts may be prepared by contacting a compound of formula (I) with a sufficient amount of the desired base to produce the salt in the conventional manner. The acid form of the compound of formula (I) may be regenerated by contacting the salt form with an acid and isolating the acid in a conventional manner.

Some compounds of the present invention may exist as stereoisomers, including enantiomers, diastereomers, and geometric isomers. Geometric isomers include compounds of the present invention that have alkenyl groups, which may exist as entgegen or zusammen conformations, in which case all geometric forms thereof, both entgegen and zusammen, cis and trans, and mixtures thereof, are within the scope of the present invention. Some compounds of the present invention have cycloalkyl groups, which may be substituted at more than one carbon atom, in which case all geometric forms thereof, both cis and trans, and mixtures thereof, are within the scope of the present invention. All of these forms, including (R), (S), epimers, diastereomers, cis, trans, syn, anti, (E), (Z), tautomers, and mixtures thereof, are included in the compounds of the present invention.

The compounds of the present invention may be in any physical form, including amorphous or crystalline solids in any polymorphic form, in any state of purity. Crystalline polymorphic forms include unsolvated forms as well as solvated forms, such as hydrated forms.

III. Pharmaceutical Compositions

The present invention further provides pharmaceutical compositions comprising a compound of any of the above Embodiments (e.g., a compound of formula (I) or a pharmaceutically acceptable salt thereof), together with a pharmaceutically acceptable excipient therefor. For preparing a pharmaceutical composition from a compound of the present invention, pharmaceutically acceptable excipients can be either solid or liquid. An excipient can be one or more substances which may act as, e.g., a carrier, diluent, flavoring agent, binder, preservative, tablet disintegrating agent, or an encapsulating material. The pharmaceutical composition may contain two or more compounds of the present invention (e.g., two different salt forms of a compound of formula (I), may be used together in the same pharmaceutical composition). Preferably, the pharmaceutical composition contains a therapeutically effective amount of a compound of formula (I) or a pharmaceutically acceptable salt form thereof. In one embodiment, the composition contains an amount of a compound of formula (I) or a pharmaceutically acceptable salt form thereof effective to treat an atypical protein kinase C (aPKC)-dependent disorder or condition. Preferably, a compound of the present invention will cause a decrease in symptoms or disease indicia associated with an aPKC-dependent disorder as measured quantitatively or qualitatively. The composition may also contain, in addition to a compound of formula (I) or a pharmaceutically acceptable salt form thereof and a pharmaceutically acceptable excipient, another therapeutic compound, such as a compound useful in the treatment of cancer.

A compound of the present invention can be formulated as a pharmaceutical composition in any delivery form, such as a syrup, an elixir, a suspension, a powder, a granule, a tablet, a capsule, a lozenge, a troche, an aqueous solution, a cream, an ointment, a lotion, a gel, an emulsion, etc. Solid form preparations include powders, tablets, pills, capsules, cachets, suppositories, and dispersible granules. Preferably, the pharmaceutical composition is a tablet or capsule. In one embodiment, the pharmaceutical composition is a tablet. In another embodiment, the pharmaceutical composition is a capsule.

In powders, the excipient may be a finely divided solid in a mixture with a finely divided active component (i.e., compound of the present invention). In tablets, the active component may be mixed with an excipient having the necessary binding properties in suitable proportions and compacted in the shape and size desired. Suitable excipients include magnesium carbonate, magnesium stearate, talc, sugar, lactose, pectin, dextrin, starch, gelatin, tragacanth, methylcellulose, sodium carboxymethylcellulose, low melting wax, cocoa butter, and the like.

The pharmaceutical composition preferably contains from 1% to 95% (w/w) of the active compound (i.e., compound of the present invention). More preferably, the pharmaceutical composition contains from 5% to 70% (w/w) of the active compound.

For preparing suppositories, a low melting wax, such as a mixture of fatty acid glycerides or cocoa butter, may be melted and the active component dispersed homogeneously therein, as by stirring. The molten homogeneous mixture may then be poured into convenient sized molds, allowed to cool, and thereby to solidify.

Liquid form preparations include solutions, suspensions, and emulsions. Formulations suitable for parenteral administration, such as, for example, by intravenous, intramuscular, intradermal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and nonaqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. The formulations of compounds can be presented in unit-dose or multi-dose sealed containers, such as ampoules and vials. Injection solutions and suspensions can be prepared from sterile powders, granules, and tablets of the kind previously described.

A compound of the present invention, alone or in combination with other suitable components, can be made into aerosol formulations (e.g., they can be "nebulized") to be administered via inhalation. Aerosol formulations can be placed into pressurized acceptable propellants, such as dichlorodifluoromethane, propane, nitrogen, and the like.

Pharmaceutically acceptable excipients are determined in part by the particular composition being administered, as well as by the particular method used to administer the composition. Accordingly, there is a wide variety of suitable formulations of pharmaceutical compositions of the present invention (see, e.g., *Remington: The Science and Practice of Pharmacy*, 20th ed., Gennaro et al. Eds., Lippincott Williams and Wilkins, 2000).

The quantity of active component in a pharmaceutical composition may be varied or adjusted from, e.g., 1 mg to 1,000 mg, 5 mg to 500 mg, 10 mg to 300 mg, or 25 mg to 250 mg, according to the particular application and the desired size of the dosage form.

The dose administered to a subject is preferably sufficient to induce a beneficial therapeutic response in the subject over time. The beneficial dose can vary from subject to subject depending upon, e.g., the subject's condition, body weight, surface area, and side effect susceptibility. Administration can be accomplished via single or divided doses.

IV. Method of Treatment

In another aspect, the present invention provides a method of treating an aPKC-dependent disorder or condition in a subject comprising: administering to the subject a compound of formula (I) as defined in any of the above Embodiments or a pharmaceutically acceptable salt form thereof. In another aspect, the present invention provides a compound of formula (I) as defined in any of the above Embodiments or a pharmaceutically acceptable salt form thereof for use in treating an aPKC-dependent disorder or condition in a subject. In another aspect, the present invention provides a compound of formula (I) as defined in any of the above Embodiments or a pharmaceutically acceptable salt form thereof for use in the preparation of a medicament for treating an aPKC-dependent disorder or condition in a subject. Preferably, the compound is administered to the subject as a pharmaceutical composition comprising a pharmaceutically acceptable excipient. Preferably, the compound is administered to the subject in a pharmaceutically acceptable amount. In one embodiment, the aPKC-dependent condition or disorder is cancer. In another embodiment, the aPKC-dependent condition is selected from non-small cell lung cancer (NSCLC), squamous cell carcinoma (e.g., oesophageal squamous cell carcinoma), leukaemia, prostate cancer, non-Hodgkin's lymphoma (e.g., follicular lymphoma), endometrial cancer, lung cancer and breast cancer.

The aPKC-dependent disorder or condition can be treated prophylactically, acutely, or chronically using compounds of the present invention, depending on the nature of the disorder or condition. Typically, the subject in each of these methods is human, although other mammals can also benefit from the administration of a compound of the present invention.

In another embodiment, the present invention provides a method of treating a proliferative disorder in a subject, comprising administering to the subject a compound of formula (I) as defined in any of the above Embodiments or a pharmaceutically acceptable salt form thereof. In another aspect, the present invention provides a compound of formula (I) as defined in any of the above Embodiments or a pharmaceutically acceptable salt form thereof for use in treating a proliferative disorder in a subject. In another aspect, the present invention provides a compound of formula (I) as defined in any of the above Embodiments or a pharmaceutically acceptable salt form thereof for use in the preparation of a medicament for treating a proliferative disorder in a subject. Preferably, the compound is administered to the subject in a pharmaceutical composition comprising a pharmaceutically acceptable excipient. Preferably, the compound is administered to the subject in a pharmaceutically acceptable amount. In certain embodiments, the proliferative disorder is aPKC-dependent. In certain embodiments, the proliferative disorder is cancer. In certain embodiments, the proliferative disorder is selected from non-small cell lung cancer (NSCLC), squamous cell carcinoma (e.g., oesophageal squamous cell carcinoma), leukaemia, prostate cancer, non-Hodgkin's lymphoma (e.g., follicular lymphoma), endometrial cancer, lung cancer and breast cancer.

The proliferative disorder can be treated prophylactically, acutely, or chronically using a compound of the present invention, depending on the nature of the disorder or condition. Typically, the subject in each of these methods is human, although other mammals can also benefit from the administration of a compound of the present invention.

In therapeutic applications, the compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present invention can be administered transdermally. In another embodiment, the compounds of the present invention are delivered orally. The compounds can also be delivered rectally, bucally or by insufflation.

Determination of the proper dosage for a particular situation is within the skill of the practitioner. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired. A typical dose is about 1 mg to about 1,000 mg per day, such as about 5 mg to about 500 mg per day. In certain embodiments, the dose is about 10 mg to about 300 mg per day, such as about 25 mg to about 250 mg per day.

V. Chemistry

Abbreviations

For convenience, the following common abbreviations are used herein:
LCMS for Liquid Chromatography-Mass Spectrometry.
HPLC for High Pressure Liquid Chromatography.
NMR for Nuclear Magnetic Resonance.
RT for Retention Time.
MI for Molecular Ion
h for hours
min for minutes
$AlCl_3$ for aluminium chloride
$BBr_3$ for boron tribromide Boc for tert-butoxycarbonyl
cataCXium C for trans-Bis(acetato)bis[o-(di-o-tolylphosphino)benzyl]dipalladium(II).
$Cs_2CO_3$ for cesium carbonate
CuI for copper(I)iodide
DAST for diethylaminosulfur trifluoride
DBU for 1,8-diazabicyclo(5.4.0)undec-7-ene
DMAP for 4-(dimethylamino) pyridine
DCE for 1,1-dichloroethane or ethylidene chloride
DCM for dichloromethane or methylene chloride
DEA for diethanolamine
DIPEA for N,N,-di-isopropyethylamine, Hunig's base
DMA for N,N-dimethylacetamide
DMF for N,N-dimethylformamide
DMSO for dimethylsulfoxide.
$Et_3N$ for triethylamine
EtOH for ethyl alcohol, ethanol
HCl for hydrochloric acid
$H_2SO_4$ for sulfuric acid
KOH for potassium hydroxide
MW for microwave
mCPBA for meta-Chloroperoxybenzoic acid
MeOH for methyl alcohol, methanol
$Mo(CO)_6$ for Molybdenum hexacarbonyl
$MP-BH_4$ for macroporous triethylammonium methyl polystyrene borohydride
NaOH for sodium hydroxide
$Na_2CO_3$ for sodium carbonate
$Na_2SO_4$ for sodium sulphate
NaOAc for sodium acetate
NaOtBu for sodium t-butoxide
NMP for 1-methyl-2-pyrrolidinone
NMM for N-methylmorpholine
$Pd(dba)_2$ for Bis(dibenzylideneacetone)palladium
$Pd(OAc)_2$ for Palladium diacetate
$Pd(Ph_3)_4$ for tetrakis(triphenylphosphine)palladium
$Pd(PPh_3)_2Cl_2$ for Bis(triphenylphosphine)palladium(II) dichloride
$POCl_3$ for phosphorus oxychloride
$PPh_3$ for triphenylphosphine
PS-TsCl for polystyrene sulfonyl chloride
$PS-PPh_3-Pd$ for polystyrene triphenylphosphine-Pd(0)
SCX-2 for a silica-based sorbent with a chemically bonded propylsulfonic acid functional group
TBAF for Tetra-n-butylammonium fluoride
TBDMS for tert-butyldimethylsilyl
TCA for trichloroacetic acid
TFA for trifluoroacetic acid
THF for tetrahydrofuran
TMS azide for trimethylsilyl azide
Xantphos for 4,5-Bis(diphenylphosphino)-9,9-dimethylxanthene
XPhos for 2-Dicyclohexylphosphino-2',4',6'-triisopropylbiphenyl

NMR

Proton NMR spectra are recorded using a Bruker AMX-300 NMR machine at 300 MHz or a Bruker Avance NMR machine at 400 MHz. Shifts are reported in ppm values relative to an internal standard of tetramethylsilane (TMS) or residual protic solvent. The following abbreviations are used to describe the splitting patterns: s (singlet), d (doublet), t (triplet), q (quartet), m (multiplet), dd (double-doublet), dt (double-triplet), br (broad).

LCMS Methods

Samples analysed by High Performance Liquid Chromatography-Mass Spectrometry employed the following conditions.

Method 1

Method 1 employed Gilson 306 pumps, Gilson 811C mixer, Gilson 806 manometric module, and Gilson UV/VIS 152 detector at 254 nm wavelength. The mass spectrometer was a Finnigan AQA and the column used was a Waters SunFire, 5 μm pore size, C18 of dimensions 50×4.60 mm. The injection volume was 10 μl.

The mobile phase consisted of a mixture of water and acetonitrile containing 0.1% formic acid. The eluent flow rate was 1.5 mL/min, using 95% water: 5% acetonitrile, changed linearly to 5% water: 95% acetonitrile over 5.5 minutes and then maintained at this mixture for 2 minutes.

Method 2

Method 2 employed Waters 515 pumps, a Waters 2525 mixer and a Waters 2996 diode array detector. The detection was performed between 210 nm and 650 nm. The mass spectrometer was a Waters micromass ZQ and the column used was a Waters SunFire, 5 μm pore size, C18 of dimensions 50×4.60 mm. The injection volume was 10 μl.

The mobile phase consisted of a mixture of water and acetonitrile containing 0.1% formic acid. The eluent flow rate was 1.5 mL/min, using 95% water: 5% acetonitrile, changed linearly to 5% water: 95% acetonitrile over 5.5 minutes and then maintained at this mixture for 2 minutes.

Method 3

Method 3 employed Waters 515 pumps, a Waters 2525 mixer and a Waters 2487 UV detector (single wavelength 254 nm). The mass spectrometer was a Waters micromass ZQ and the column used was a Waters SunFire, 5 μm pore size, C18 of dimensions 50×4.60 mm. The injection volume was 10 μl. The mobile phase consisted of a mixture of water and acetonitrile containing 0.1% formic acid. The eluent flow rate was 1.5 mL/min, using 95% water: 5% acetonitrile, changed linearly to 5% water: 95% acetonitrile over 5.5 minutes and then maintained at this mixture for 2 minutes.

Method 4

Method 4 employed Waters 515 pumps, a Waters 2545 mixer with valves directing to the different columns and a Waters 2996 diode array detector. The detection was performed between 210 nm and 650 nm. The mass spectrometer used was a Waters 3100 which detected masses between 100 and 700 g/mol. The column used was a XBridge, 5 micron pore size, C18, 50×4.60 mm. The injection volume was 10 μl of a solution (around 1 mg/ml). The flow rate was 1.5 mL/min and the mobile phases of water pH 10 0.03% ammonium hydroxide) (3 ml/10l) and acetonitrile 0.03% ammonium hydroxide (3 ml/10l). The elution was started at 95% water: 5% acetonitrile ramping up to 5% water:95% acetonitrile over 5.50 minutes. The eluent level was returned to the starting conditions of 95% water: 5% acetonitrile over 6 seconds. These conditions were held for 1.4 minutes to allow equilibration of the column before the next sample was injected. The run lasted 7 minutes in total.

Method 5

Method 5 employed Waters 515 pumps, a Waters 2525 mixer with valves directing to the different columns and a Waters 2487 UV detector. The detection was done between at 254 nm. The mass spectrometer used was a Waters micromass ZQ which detected masses between 100 and 700 g/mol. The column used was a SunFire, 5 micron pore size, C18 column of dimensions 50×4.60 mm was used. The injection volume was 10 μL of a solution (around 1 mg/mL). The flow rate was 1.5 mL/min and the mobile phases of water and methanol contained 0.1% formic acid. The elution was started at 85% water: 15% methanol ramping up to 15% water:85% methanol over 4.5 minutes, these conditions were held for 1 minute before the eluent level was returned to the starting conditions of 85% water: 15% methanol over 6 seconds. These conditions were held for 1.4 minutes to allow equilibration of the column before the next sample was injected. The run lasted 7 minutes in total.

Method 6

Method 6 employed Waters 515 pumps, a Waters 2545 mixer with valves directing to the different columns and a Waters 2996 diode array detector. The detection was done between 210 nm and 650 nm. The mass spectrometer used was a Waters 3100 which detected masses between 100 and 700 g/mol. The column used was a XBridge, 5 micron pore size, C18, 50×4.60 mm. The injection volume was 10 µL of a solution (around 1 mg/mL). The flow rate was 1.5 mL/min and the mobile phases of water pH 10 0.03% ammonium hydroxide) (3 ml/10l) and methanol 0.03% ammonium hydroxide (3 ml/10 l). The elution was started at 85% water: 15% methanol ramping up to 15% water: 85% methanol over 4.5 minutes. These conditions were held for 1 minute before the eluent level was returned to the starting conditions of 85% water: 15% methanol over 6 seconds. These conditions were held for 1.4 minutes to allow equilibration of the column before the next sample was injected. The run lasted 7 minutes in total.

Method 7

Method 7 employed Waters 515 pumps, a Waters 2545 mixer with valves directing to the different columns and a Waters 2487 UV detector. The detection was done between at 254 nm. The mass spectrometer used was a Waters micromass ZQ which detected masses between 100 and 700 g/mol. The column used was a SunFire, 5 micron pore size, C18 column of dimensions 50×4.60 mm was used. The injection volume was 10 µL of a solution (around 1 mg/mL). The flow rate was 1.5 mL/min and the mobile phases of water and methanol contained 0.1% formic acid. The elution was started at 85% water: 15% methanol ramping up to 15% water:85% methanol over 4.5 minutes, these conditions were held for 1 minute before the eluent level was returned to the starting conditions of 85% water: 15% methanol over 6 seconds. These conditions were held for 1.4 minutes to allow equilibration of the column before the next sample was injected. The run lasted 7 minutes in total.

Method 8

Method 8 employed Waters 515 pumps, a Waters 2525 mixer with valves directing to the different columns and a Waters 2487 UV detector. The detection was done between at 254 nm. The mass spectrometer used was a Waters micromass ZQ which detected masses between 100 and 700 g/mol. The column used was a SunFire, 5 micron pore size, C18 column of dimensions 50×4.60 mm was used. The injection volume was 10 µL of a solution (around 1 mg/mL). The flow rate was 1.5 mL/min and the mobile phases of water and methanol contained 0.1% formic acid. The elution was started at 85% water: 15% methanol ramping up to 15% water:85% methanol over 3 minutes, these conditions were held for 2.5 minute before the eluent level was returned to the starting conditions of 85% water: 15% methanol over 6 seconds. These conditions were held for 1.4 minutes to allow equilibration of the column before the next sample was injected. The run lasted 7 minutes in total.

Method 9

Method 9 employed Waters 515 pumps, a Waters 2545 mixer with valves directing to the different columns and a Waters 2487 UV detector. The detection was done between at 254 nm. The mass spectrometer used was a Waters micromass ZQ which detected masses between 100 and 700 g/mol. The column used was a XBridge, 5 micron pore size, C18, 50×4.60 mm. The injection volume was 10 µL of a solution (around 1 mg/mL). The flow rate was 1.5 mL/min and the mobile phases of water pH 10 0.03% ammonium hydroxide) (3 ml/101) and methanol 0.03% ammonium hydroxide (3 ml/10 l). The elution was started at 85% water: 15% methanol ramping up to 15% water: 85% methanol over 4.5 minutes. These conditions were held for 1 minute before the eluent level was returned to the starting conditions of 85% water: 15% methanol over 6 seconds. These conditions were held for 1.4 minutes to allow equilibration of the column before the next sample was injected. The run lasted 7 minutes in total.

Method 10

LCMS results were obtained on either of two instruments. LCMS analysis was performed on a Waters Aquity Ultra Performance LC with a 2.1 mm×50 mm Waters Aquity UPLC BEH C18 1.7 µm column. The target column temperature was 45° C., with a run time of two (2) minutes, a flow rate of 0.600 mL/min, and a solvent mixture of 5% (0.1% formic acid/water):95% (acetonitrile/0.1% formic acid). The mass spectrometry data was acquired on a Micromass LC-ZQ 2000 quadrupole mass spectrometer. Alternatively, LCMS analysis was performed on a Bruker Esquire 200 ion trap.

Preparative HPLC Methods

Samples purified by Mass Spectrometry directed High Performance Liquid Chromatography employed the following conditions.

Method A

Method A employed Waters 515 pumps, a Waters 2525 mixer and a Waters 2487 UV detector (single wavelength 254 nm). The mass spectrometer was a Waters micromass ZQ and the column used was a Waters SunFire, 5 µm pore size, C18 of dimensions 50×19 mm. The injection volume was up to 500 µL of solution at a maximum concentration of 50 mg/mL. The mobile phase consisted of a mixture of water and acetonitrile containing 0.1% formic acid. The eluent flow rate was 25 mL/min using 95% water, 5% acetonitrile, changing linearly over 5.3 minutes to 95% acetonitrile, 5% water, and maintaining for 0.5 minutes.

Method B

Method B employed Waters 515 pumps a Waters 2545 mixer with valves directing to the different columns and a Waters 2996 diode array detector. The detection was performed between 210 nm and 650 nm. The mass spectrometer used was a Waters 3100 which detected masses between 100 and 700 g/mol. The column used was a XBridge, 5 micron pore size, C18, 50×19 mm. The injection volume was chosen by the user and can be up to 500 µL of the solution (max 50 mg/mL). The flow rate was 25 mL/min and the mobile phases of water pH 10 0.03% ammonium hydroxide (3 ml/101) and acetonitrile 0.03% ammonium hydroxide (3 ml/101). The elution was started at 95% water:5% acetonitrile ramping up to 5% water:95% acetonitrile over 5.30 minutes. The eluent level was returned to the starting conditions of 95% water: 5% acetonitrile over 0.6 minutes. These conditions were held for 1.4 minutes to allow equilibration of the column before the next sample was injected. The run lasted 7 minutes in total.

Analytical HPLC Methods

Method X

Method X employs gradient elution (0 to 100%) acetonitrile (containing 0.1% trifluoroacetic acid):water (containing 0.1% trifluoroacetic acid) over five minutes on a 4.6×75 mm (2.5 micron) Zorbax XDB-C8 column at 2.5 ml/min on an Agilent 1100 series HPLC.

Synthesis

Several methods for the chemical synthesis of 4-substituted-2-(pyridin-4-yl)-thieno[2,3-d]pyrimidine compounds ("4PT23P compounds") and 4-substituted-2-(pyridin-4-yl)-thieno[3,2-d]pyrimidine compounds ("4PT32P compounds") of the present invention are described herein. These and/or other well known methods may be modified and/or adapted in known ways in order to facilitate the synthesis of additional compounds within the scope of the present invention. Unless otherwise stated, compounds are of commercial origin or readily synthesized by standard methods well known to one skilled in the art of organic synthesis.

It is understood that the examples and embodiments described herein are for illustrative purposes only and that various modifications or changes in light thereof will be suggested to persons skilled in the art and are to be included within the spirit and purview of this invention. Specific chemical transformations are listed in the ensuing schemes and one skilled in the art appreciates that a variety of different reagents may be used in place of those listed. Common replacements for such reagents can be found in texts such as "Encyclopedia of Reagents for Organic Synthesis" Leo A. Paquette, John Wiley & Son Ltd (1995) or "Comprehensive Organic Transformations: A Guide to Functional Group Preparations" Richard C. Larock. Wiley-VCH and "Strategic Applications of Named Reactions in Organic Synthesis" Kurti and Czako, Elsevier, 2005 and references cited therein.

4PT23P Compounds

In one approach, compounds of formula [F-1] (where A=NH or N alkyl) are prepared by reacting a compound of formula [F-2] (where X is a halogen such as chlorine or sulfonate) with a compound of formula [F-3] (where A is NH or $NH_2$ and Z on the terminal nitrogen is H, alkyl or a suitable nitrogen protecting group, such as Boc, Alloc, Cbz or Fmoc) in a suitable solvent such as DMF in the presence of a suitable base such as triethylamine.

The reaction is suitably conducted at an elevated temperature for example 40° C. Where Z is a suitable nitrogen protecting group, such as Boc, Alloc, Cbz or Fmoc, compounds of formula [F-1] are prepared by a suitable deprotection reaction. For example: where Z is a Boc protecting group reaction with an acid such as TFA in a suitable solvent such as DCM. The reaction is suitably conducted at ambient temperature. In one approach, compounds of formula [F-1] (where A is O) are prepared by reacting a compound of formula [F-2] (where X is a halogen such as chlorine or sulfonate) with a compound of formula [F-2] (where A=OH and Z on the terminal nitrogen is H, alkyl or a suitable nitrogen protecting group, such as Boc, Alloc, Cbz or Fmoc) in a suitable solvent such as DMA in the presence of a suitable base such as sodium hydride. The reaction is suitably conducted at ambient temperature. Where Z is a suitable nitrogen protecting group, such as Boc, Alloc, Cbz or Fmoc, compounds of formula [F-1] are prepared by a suitable deprotection reaction. For example: where Z is a Boc protecting group reaction with an acid such as TFA in a suitable solvent such as DCM. The reaction is suitably conducted at ambient temperature.

In one approach, compounds of formula [F-2] (where X is a halogen such as chlorine) are prepared by reacting a compound of formula [F-4] with a suitable halogenating agent such as phosphorous oxychloride. The reaction is suitably conducted at elevated temperature such as 125° C. Compounds of formula [F-2](where X is a sulfonate) are prepared by reacting a compound of formula [F-4] with a suitably substituted sulfonyl chloride such as 2,4,6-triisopropylbenzenesulfonyl chloride in a suitable solvent such as DMA in the presence of a suitable base such as triethylamine and a catalytic amount of DMAP. The reaction is suitably conducted at ambient temperature.

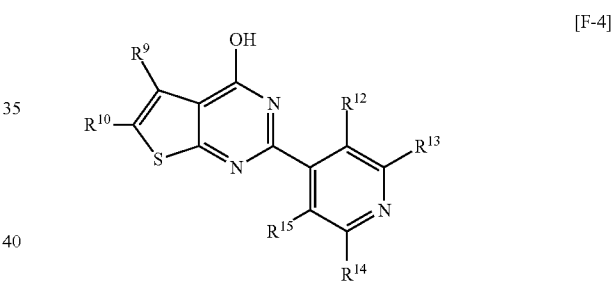

[F-4]

In one approach, compounds of formula [F-4] are prepared by reacting a compound of formula [F-5] (where Rx is an alkyl group such as methyl or ethyl) with a compound of formula [F-6] in a suitable solvent such as dioxane with a suitable base such as potassium-tert-pentylate. The reaction is suitably conducted at ambient temperature.

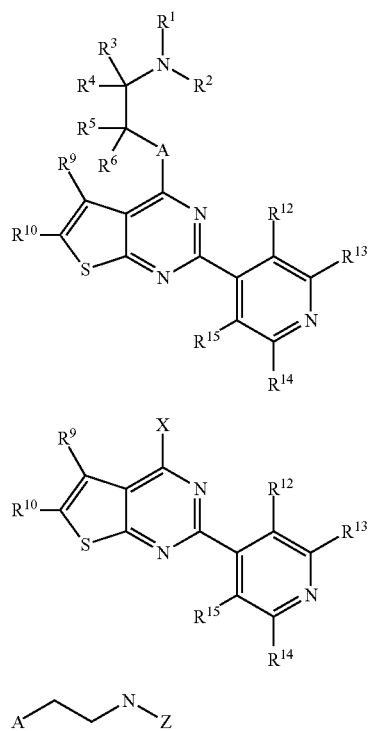

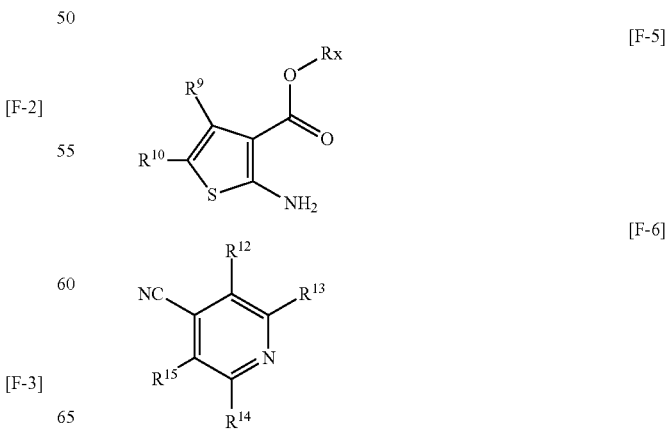

In one approach, compounds of formula [F-5] are prepared by reacting a ketone derivative of formula [F-7] (where R$^{x1}$ and R$^{x2}$ are H, alkyl, aryl or form a cyclic saturated ring) with a cyanoacetic acid derivative of formula [F-8] (where Rx is an alkyl group such as methyl or ethyl) with elemental sulphur in the presence of a base such as morpholine in a suitable solvent such as ethanol. The reaction is suitably conducted at an elevated temperature for example 80-90° C.

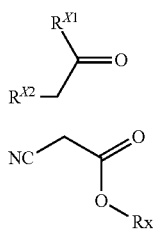

In one approach, compounds of formula [F-3] (where A is OH) are prepared by reacting a compound of formula [F-9] (where Z on the terminal nitrogen is H, alkyl or a suitable nitrogen protecting group, such as Boc, Alloc, Cbz or Fmoc) with a reducing agent such as borane-THF complex in a suitable solvent such as THF. The reaction is suitably conducted at low temperature for example 0° C. In one approach, compounds of formula [F-3] (where A is NH$_2$) are prepared by reacting a compound of formula [F-10] (where Z on the terminal nitrogen is H, alkyl or a suitable nitrogen protecting group, such as Boc, Alloc, Cbz or Fmoc) with a reducing agent such as borane-THF complex in a suitable solvent such as THF. The reaction is suitably conducted at low temperature for example 0° C. In one approach, compounds of formula [F-10] are prepared by reacting compounds of formula [F-9] with Boc anhydride in the presence of a suitable base such as pyridine, ammonium carbonate in a suitable solvent such as dioxane. The reaction is suitably conducted at ambient temperature.

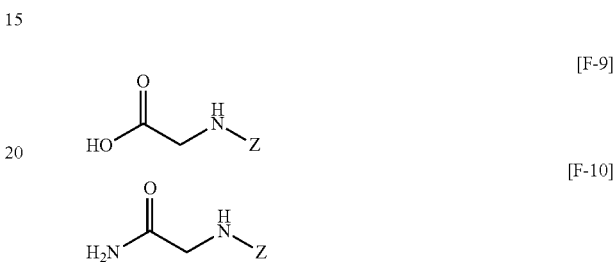

An example of a method as described above is illustrated in the following scheme.

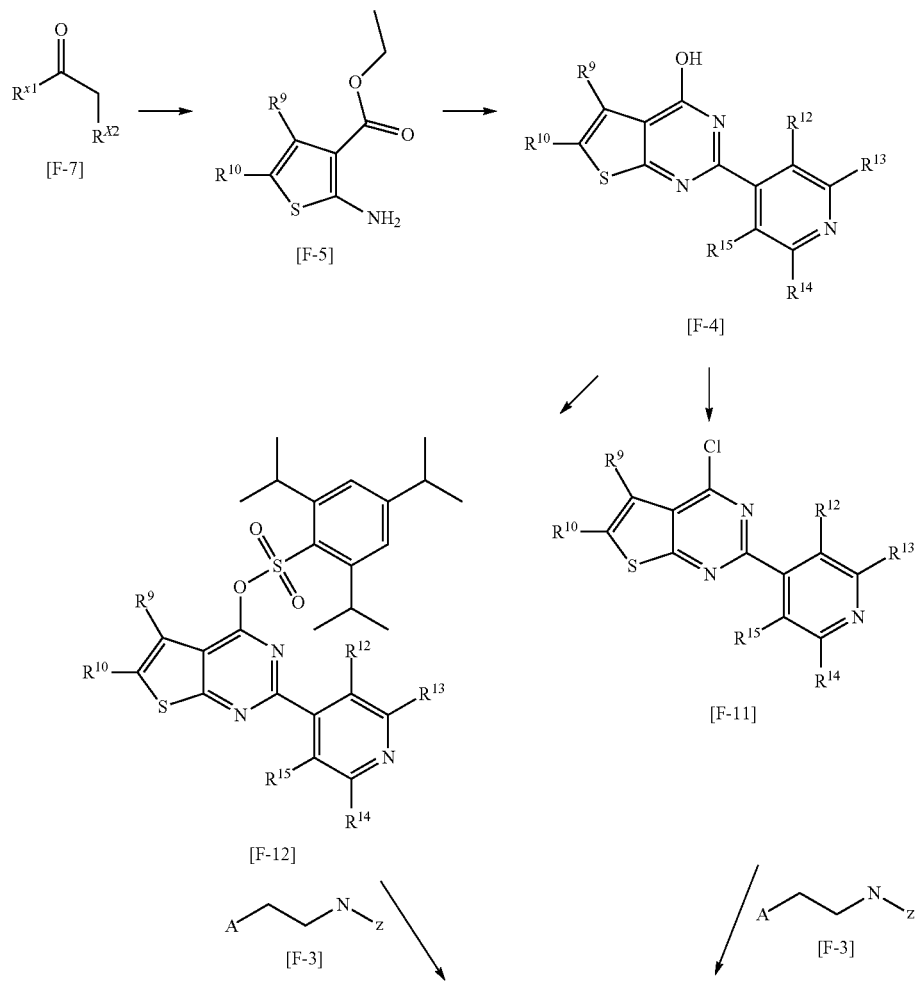

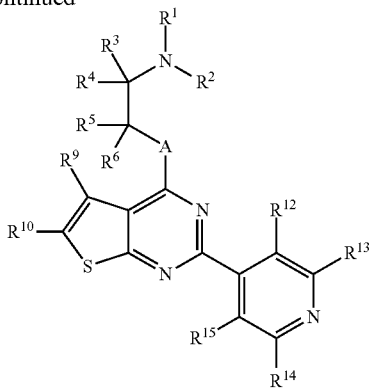

[F-1]

General Synthesis of 2-amino-4,5-substituted-thiophene-3-carboxylic acid ethyl esters of general formula [F-5] (Scheme A1)

2-amino-4,5-substituted-thiophene-3-carboxylic acid ethyl esters of general formula [F-5] were synthesised by a cyclisation reaction with cyano-acetic acid ethyl ester of general formula [F-8], a substituted ketone of general formula [F-7] and elemental sulphur in the presence of morpholine in a polar protic solvent such as ethanol at reflux (scheme A1).

Scheme A1

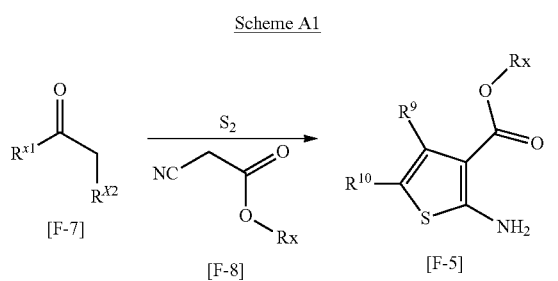

Synthesis of 2-Amino-1,4-Dioxa-spiro[6.6]4,5,6,7-tetrahydro-benzo[b]thiophene-3-carboxylic acid ethyl ester [AA-1]

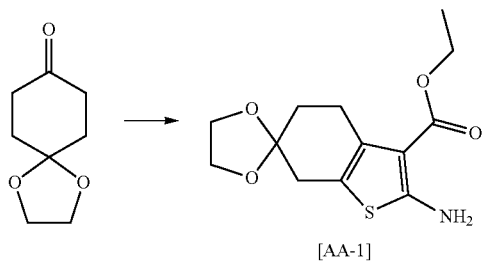

To a mixture of 1,4-Dioxa-spiro[4.5]decan-8-one (1.56 g, 10 mmol), cyano-acetic acid ethyl ester (1.13 g, 10 mmol) and elemental sulphur (320 mg, 10 mmol) in ethanol (20 ml) was added morpholine (870 mg, 10 mmol). The reaction was heated at reflux overnight. The mixture was left to cool down and a precipitate formed which was recovered by filtration and washed with cold ethanol (40 ml), then dried under reduced pressure to give the title compound (2.1 g, 76%) which was used without further purification. LCMS method: 3, RT: 5.24 min, MI: 284 [M+1]. 1H NMR (300 MHz, DMSO): 4.21 (m, 1H), 4.17 (q, 2H), 4.01 (m, 1H), 3.82 (m, 2H), 3.08 (m, 1H), 2.68 (m, 1H), 1.91 (m, 4H), 1.21 (t, 3H).

Synthesis of 2-amino-6,6-dimethyl-4,5,6,7-tetrahydro-benzo[b]thiophene-3-carboxylic acid ethyl ester [AA-2]

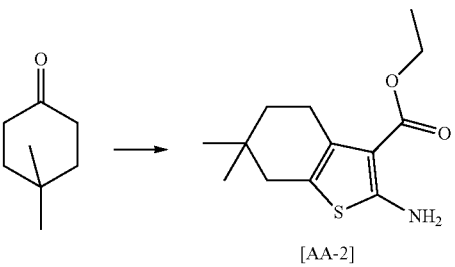

To a mixture of 4,4-Dimethyl-cyclohexanone, cyanoacetic acid ethyl ester and elemental sulphur in ethanol was added morpholine. The reaction was reflux overnight. The mixture was left to cool down and a precipitate appeared. The solid was recovered by filtration and to give the title compound as a yellow solid. LCMS method: 3, RT: 5.64 min, MI: 254 [M+1].

Synthesis of 2-amino-4,7-dihydro-5H-thieno[2,3-c]thiopyran-3-carboxylic acid ethyl ester [AA-3]

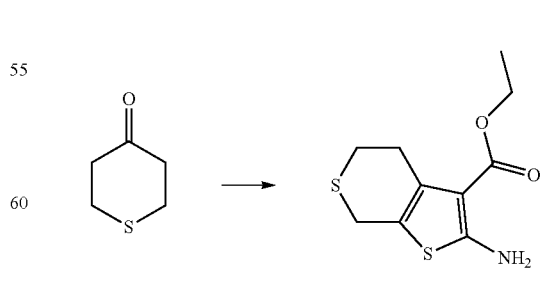

To a mixture of tetrahydro-thiopyran-4-one, cyano-acetic acid ethyl ester and elemental sulphur in ethanol was added morpholine. The reaction was reflux overnight. The mixture was left to cool down and a precipitate appeared. The solid was recovered by filtration and to give the title compound as a yellow solid. LCMS method: 3, RT: 5.78 min, MI: 244 [M+1].

Synthesis of 2-amino-4,7-dihydro-5H-thieno[2,3-c]pyran-3-carboxylic acid ethyl ester [AA-4]

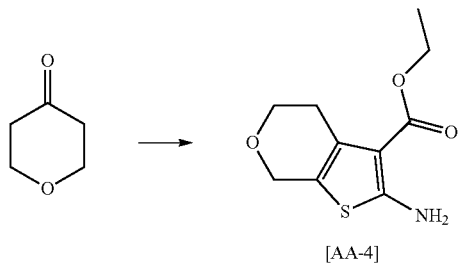

[AA-4]

To a mixture of tetrahydro-pyran-4-one, cyano-acetic acid ethyl ester and elemental sulphur in ethanol was added morpholine. The reaction was reflux overnight. The mixture was left to cool down and a precipitate appeared. The solid was recovered by filtration and to give the title compound as a yellow solid. LCMS method: 3, RT: 5.86 min, MI: 228 [M+1].

General Synthesis of 5,6-substituted 2-pyridin-4-yl-thieno [2,3-d]pyrimidin-4-ols of General Formula [F-4] (Scheme A2)

4,5-substituted-2-amino-thiophene-3-carboxylic acid alkyl esters of general formula [F-5] were subjected to a cyclisation reaction with 4-cyanopyridine of general formula [F-6] in the presence of a hindered alkoxide base such as potassium-tert-pentylate 1.7M in toluene or potassium-tert-butoxide in a dry non-aprotic solvent such as dioxane or THF at ambient temperature.

Scheme A2

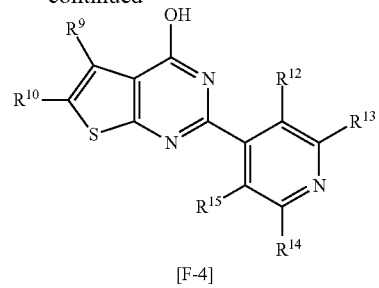

[F-4]

Synthesis of 2-pyridin-4-yl-5,6,7,8-tetrahydro-benzo[4,5]thieno[2,3-d]pyrimidin-4-ol [AA-5]

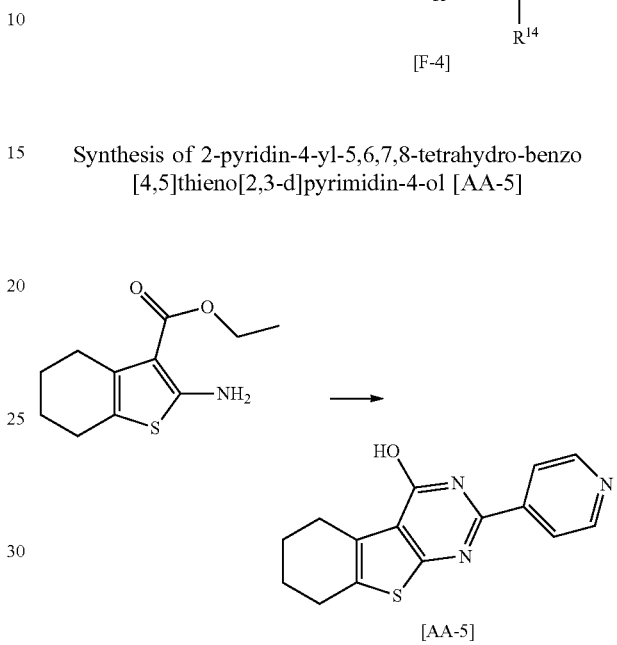

[AA-5]

To a solution of 4-cyanopyridine (1.25 g, 12 mmol) in dry dioxane (10 ml) was added 2-amino-4,5,6,7-tetrahydro-benzo[b]thiophene-3-carboxylic acid ethyl ester (2.25 g, 10 mmol) followed by potassium-tert-pentylate 1.7M in toluene (12 ml, 20 mmol). The reaction mixture was stirred at room temperature overnight. After completion the precipitate formed was filtered and washed with diethyl ether. The residue was used without any further purification in the next step. LCMS method: 1, RT: 3.54 min, MI: 284 [M+1]. 1H 1H NMR (300 MHz, DMSO): 8.56 (d, 2H), 8.12 (d, 2H), 2.90 (m, 2H), 2.67 (m, 2H), 1.76 (m, 4H). The following compounds were prepared according to the general synthesis shown in scheme A2:

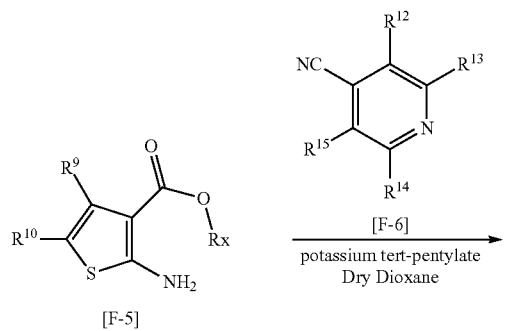

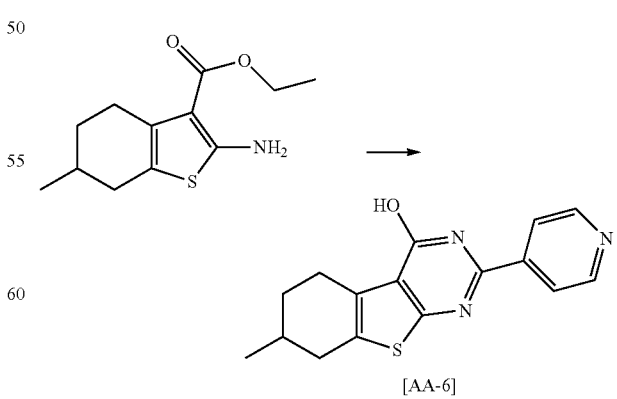

[AA-6]

7-methyl-2-pyridin-4-yl-5,6,7,8-tetrahydro-benzo[4,5]thieno[2,3-d]pyrimidin-4-ol [AA-6] was prepared by reaction of 2-amino-6-methyl-4,5,6,7-tetrahydro-benzo[b]thiophene-3-carboxylic acid ethyl ester, 4-cyanopyridine, potassium-tert-pentylate 1.7M in toluene and dioxane at room temperature to give the title compound as an off-white solid. LCMS method: 1, RT: 3.68 min, MI: 298 [M+1].

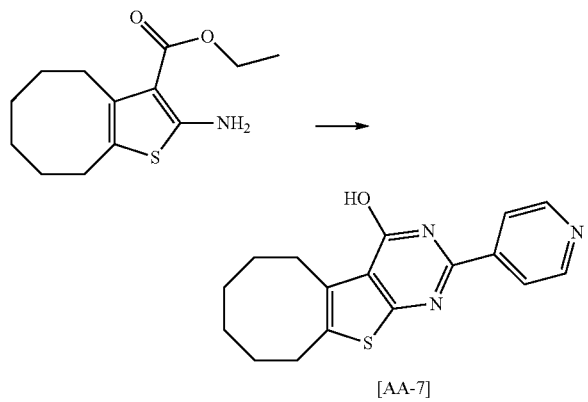

[AA-7]

2-pyridin-4-yl-5,6,7,8,9,10-hexahydro-11-thia-1,3-diaza-cyclooctа[a]inden-4-ol [AA-7] was prepared by reaction of 2-amino-4,5,6,7,8,9-hexahydro-cycloocta[b]thiophene-3-carboxylic acid ethyl ester, 4-cyanopyridine, potassium-tert-pentylate 1.7M in toluene and dioxane at room temperature to give the title compound as an off-white solid. LCMS method: 1, RT: 3.72 min, MI: 312 [M+1].

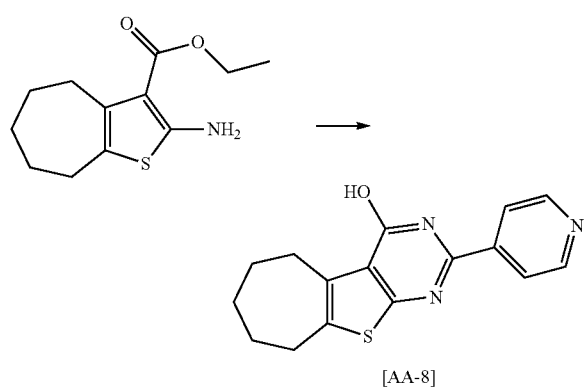

[AA-8]

2-pyridin-4-yl-6,7,8,9-tetrahydro-5H-10-thia-1,3-diaza-benzo[a]azulen-4-ol [AA-8] was prepared by reaction of 2-amino-5,6,7,8-tetrahydro-4H-cyclohepta[b]thiophene-3-carboxylic acid ethyl ester, 4-cyanopyridine, potassium-tert-pentylate 1.7M in toluene and dioxane at room temperature to give the title compound as a yellow solid. LCMS method: 2, RT: 3.87 min, MI: 298 [M+1].

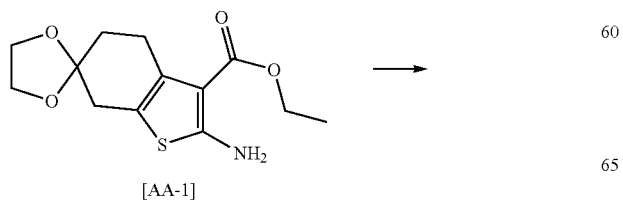

[AA-1]

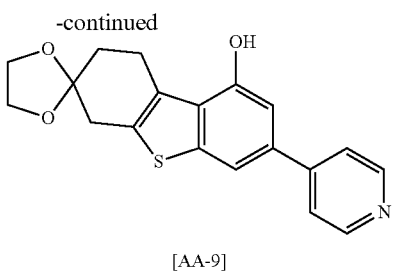

[AA-9]

1,4-Dioxa-spiro[7.7]-2-pyridin-4-yl-5,6,7,8-tetrahydro-benzo[4,5]thieno[2,3-d]pyrimidin-4-ol [AA-9] was prepared by reaction of 2-Amino-1,4-Dioxa-spiro[6.6]4,5,6,7-tetrahydro-benzo[b]thiophene-3-carboxylic acid ethyl ester [AA-1], 4-cyanopyridine, potassium-tert-pentylate 1.7M in toluene and dioxane at room temperature to give the title compound as a yellow solid. LCMS method: 3, RT: 2.80 min, MI: 342 [M+1].

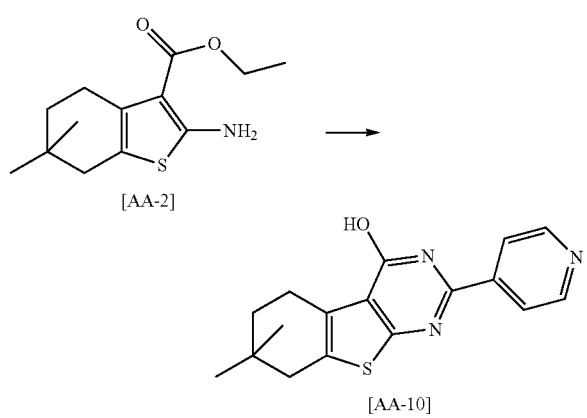

[AA-2]

[AA-10]

7,7-dimethyl-2-pyridin-4-yl-5,6,7,8-tetrahydro-benzo[4,5]thieno[2,3-d]pyrimidin-4-ol [AA-10] was prepared by reaction of 2-amino-6,6-dimethyl-4,5,6,7-tetrahydro-benzo[b]thiophene-3-carboxylic acid ethyl ester [AA-2], 4-cyanopyridine, potassium-tert-pentylate 1.7M in toluene and dioxane at room temperature to give the title compound as an off-white solid. LCMS method: 3, RT: 4.24 min, MI: 312 [M+1].

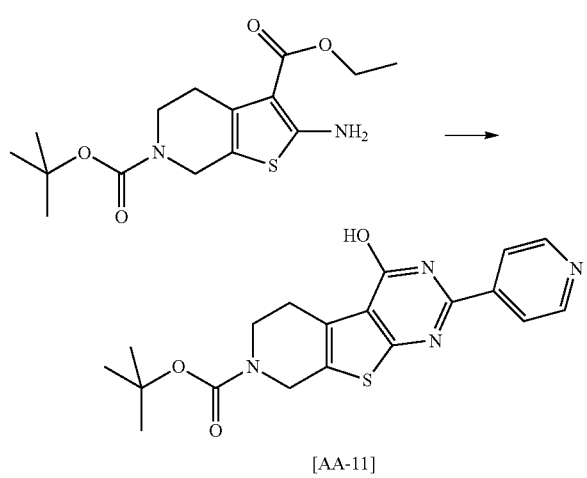

[AA-11]

4-hydroxy-2-pyridin-4-yl-5,8-dihydro-6H-pyrido[4',3':4,5]thieno[2,3-d]pyrimidine-7-carboxylic acid tert-butyl ester [AA-11] was prepared by reaction of 2-amino-4,7-dihydro-5H-thieno[2,3-c]pyridine-3,6-dicarboxylic acid 6-tert-butyl ester 3-ethyl ester, 4-cyanopyridine, potassium-tert-pentylate 1.7M in toluene and dioxane at room temperature to give the title compound as an off-white solid. LCMS method: 1, RT: 3.50 min, MI: 384 [M+1].

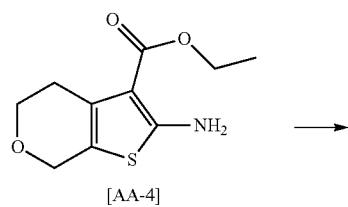

[AA-4]

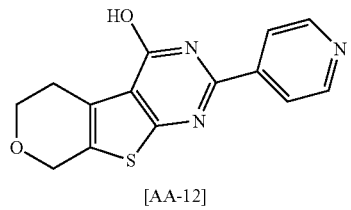

[AA-12]

2-pyridin-4-yl-5,8-dihydro-6H-pyrano[4',3':4,5]thieno[2,3-d]pyrimidin-4-ol [AA-12] was prepared by reaction of 2-amino-4,7-dihydro-5H-thieno[2,3-c]pyran-3-carboxylic acid ethyl ester [AA-4], 4-cyanopyridine, potassium-tert-pentylate 1.7M in toluene and dioxane at room temperature to give the title compound as a yellow solid. LCMS method: 3, RT: 3.50 min MI: 286 [M+1].

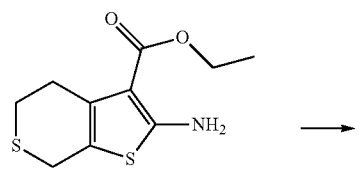

[AA-3]

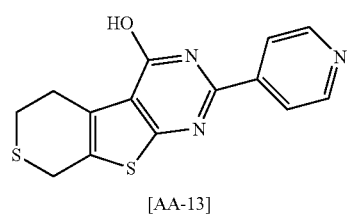

[AA-13]

2-pyridin-4-yl-5,8-dihydro-6H-thiopyrano[4',3':4,5]thieno[2,3-d]pyrimidin-4-ol [AA-13] was prepared by reaction of 2-amino-4,7-dihydro-5H-thieno[2,3-c]thiopyran-3-carboxylic acid ethyl ester [AA-3], 4-cyanopyridine, potassium-tert-pentylate 1.7M in toluene and dioxane at room temperature to give the title compound as a yellow solid. LCMS method: 2, RT: 3.14 min, MI: 302 [M+1].

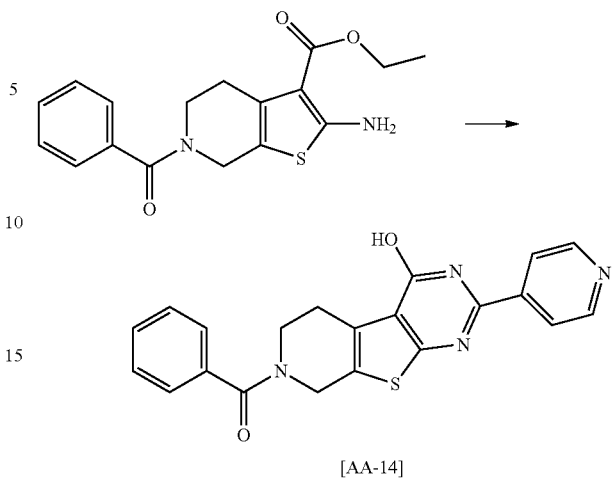

[AA-14]

(4-Hydroxy-2-pyridin-4-yl-5,8-dihydro-6H-pyrido[4',3':4,5]thieno[2,3-d]pyrimidin-7-yl)-phenyl-methanone [AA-14] was prepared by reaction of 2-Amino-6-benzoyl-4,5,6,7-tetrahydro-thieno[2,3-c]pyridine-3-carboxylic acid ethyl ester, 4-cyanopyridine, potassium-tert-pentylate 1.7M in toluene and THF at room temperature to give the title compound as a yellow solid. LCMS method: 3, RT: 3.02 min, MI: 389[M+1].

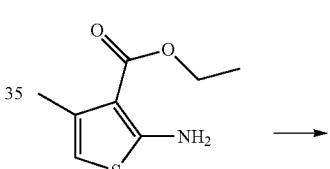

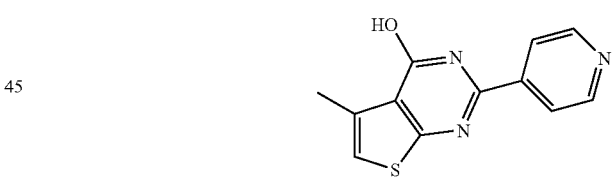

[AA-15]

5-Methyl-2-pyridin-4-yl-thieno[2,3-d]pyrimidin-4-ol [AA-15] was prepared by reaction of ethyl 2-amino-4-methylthiophene-3-carboxylate, 4-cyanopyridine, potassium-tert-pentylate 1.7M in toluene and THF at room temperature to give the title compound as a yellow solid. LCMS method: 3, RT: 2.56 min, MI: 244[M+1].

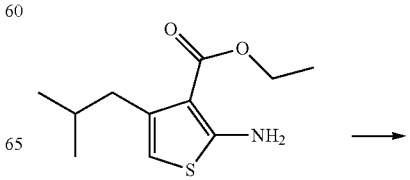

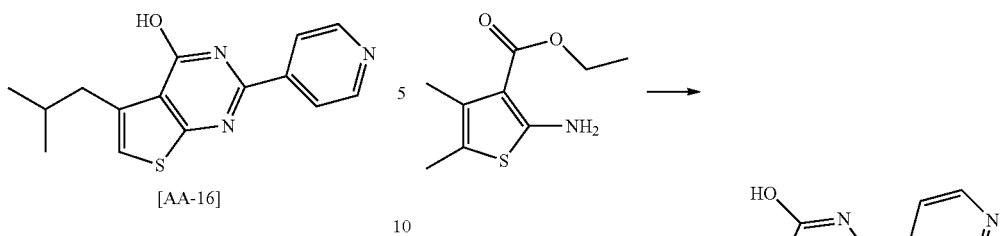

[AA-16]

5-isobutyl-2-pyridin-4-yl-thieno[2,3-d]pyrimidin-4-ol [AA-16] was prepared by reaction of 2-amino-4-isobutyl-thiophene-3-carboxylic acid ethyl ester, 4-cyanopyridine, potassium-tert-pentylate 1.7M in toluene and dioxane at room temperature to give the title compound as a brown solid. LCMS method: 2, RT: 3.14 min, MI: 286 [M+1].

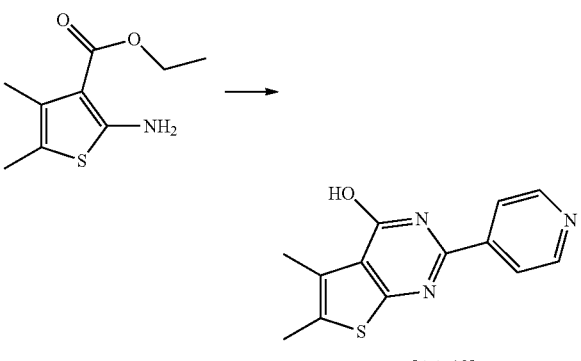

[AA-19]

5,6-dimethyl-2-pyridin-4-yl-thieno[2,3-d]pyrimidin-4-ol [AA-19] was prepared by reaction of 2-amino-4,5-dimethyl-thiophene-3-carboxylic acid ethyl ester, 4-cyanopyridine, potassium-tert-pentylate 1.7M in toluene and dioxane at room temperature to give the title compound as a yellow solid. LCMS method: 3, RT: 3.05 min, MI: 258 [M+1].

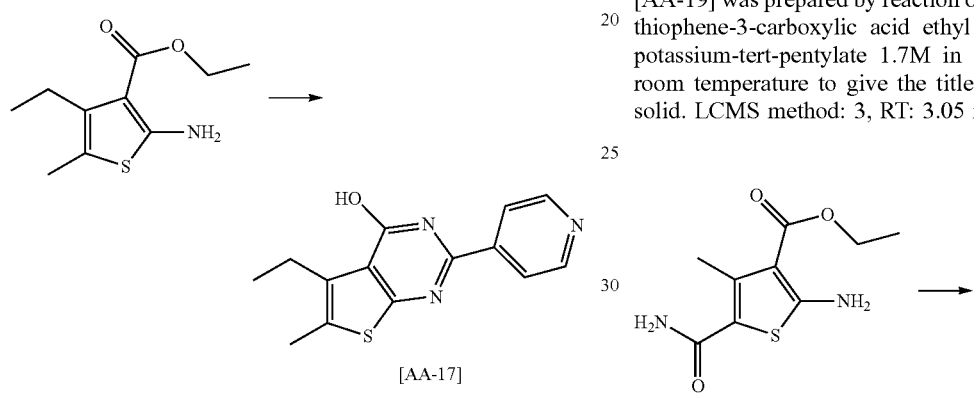

[AA-17]

5-ethyl-6-methyl-2-pyridin-4-yl-thieno[2,3-d]pyrimidin-4-ol [AA-17] was prepared by reaction of 2-amino-4-ethyl-5-methyl-thiophene-3-carboxylic acid ethyl ester, 4-cyano-pyridine, potassium-tert-pentylate 1.7M in toluene and dioxane at room temperature to give the title compound as a brown solid. LCMS method: 2, RT: 3.26 min, MI: 272 [M+1].

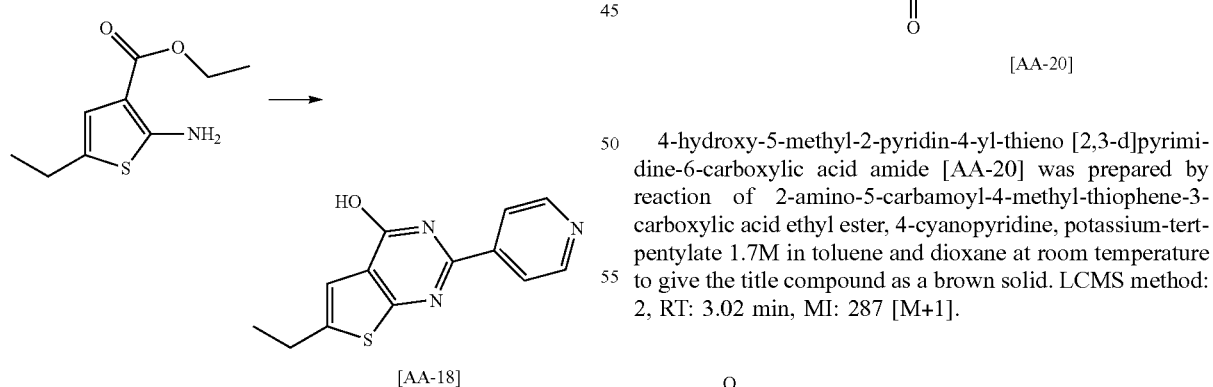

[AA-20]

4-hydroxy-5-methyl-2-pyridin-4-yl-thieno [2,3-d]pyrimidine-6-carboxylic acid amide [AA-20] was prepared by reaction of 2-amino-5-carbamoyl-4-methyl-thiophene-3-carboxylic acid ethyl ester, 4-cyanopyridine, potassium-tert-pentylate 1.7M in toluene and dioxane at room temperature to give the title compound as a brown solid. LCMS method: 2, RT: 3.02 min, MI: 287 [M+1].

[AA-18]

6-ethyl-2-pyridin-4-yl-thieno [2,3-d]pyrimidin-4-ol [AA-18] was prepared by reaction of 2-amino-5-ethyl-thiophene-3-carboxylic acid ethyl ester, 4-cyanopyridine, potassium-tert-pentylate 1.7M in toluene and dioxane at room temperature to give the title compound as a brown solid. LCMS method: 2, RT: 3.15 min, MI: 258 [M+1].

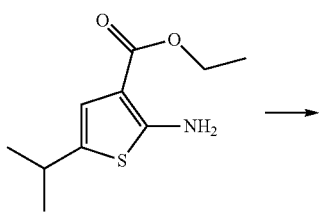

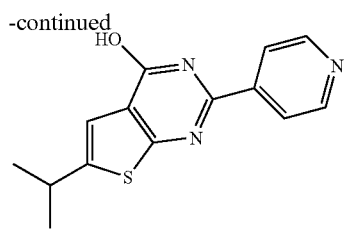

[AA-21]

6-isopropyl-2-pyridin-4-yl-thieno[2,3-d]pyrimidin-4-ol [AA-21] was prepared by reaction of 2-amino-5-isopropyl-thiophene-3-carboxylic acid ethyl ester, 4-cyanopyridine, potassium-tert-pentylate 1.7M in toluene and dioxane at room temperature to give the title compound as a brown solid. LCMS method: 2, RT: 3.29 min, MI: 272 [M+1].

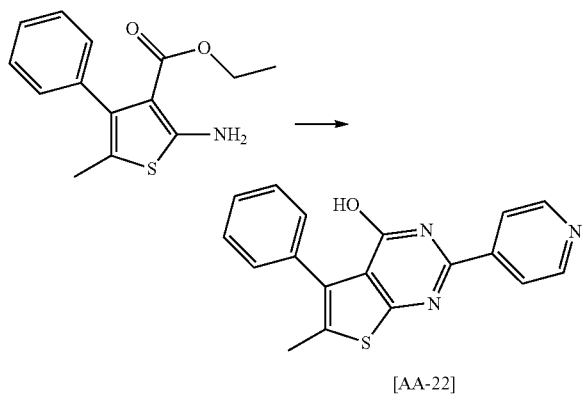

[AA-22]

6-methyl-5-phenyl-2-pyridin-4-yl-thieno[2,3-d]pyrimidin-4-ol [AA-22] was prepared by reaction of 2-amino-5-methyl-4-phenyl-thiophene-3-carboxylic acid ethyl ester, 4-cyanopyridine, potassium-tert-pentylate 1.7M in toluene and dioxane at room temperature to give the title compound as a yellow solid. LCMS method: 2, RT: 3.79 min, MI: 320 [M+1].

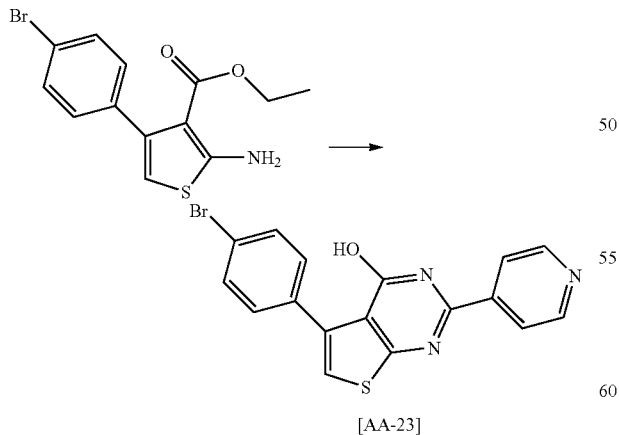

[AA-23]

5-(4-bromo-phenyl)-2-pyridin-4-yl-thieno [2,3-d]pyrimidin-4-ol [AA-23] was prepared by reaction of 2-amino-4-(4-bromo-phenyl)-thiophene-3-carboxylic acid ethyl ester, 4-cyanopyridine, potassium-tert-pentylate 1.7M in toluene and dioxane at room temperature to give the title compound as a brown solid. LCMS method: 2, RT: 4.16 min, MI: 384-386 [M+1].

General Synthesis of 5,6 Substituted 4-amino-2-pyridin-4-yl-thieno[2,3-d]pyrimidines of General Formula [F-1] (Scheme A3)

5,6-substituted 2-pyridin-4-yl-thieno[2,3-d]pyrimidin-4-ol derivatives of general formula [F-4] were reacted in an activation step using a chlorinating reagent such as phosphorus oxychloride or phosphorous pentachloride to yield the 5,6-substituted 4-chloro-2-pyridin-4-yl-thieno[2,3-d]pyrimidine derivatives of general formula [F-11], which were reacted with primary or secondary amine derivative of general formula [F-13] at ambient temperature. After reaction work up, typically by a liquid-liquid extraction or purification by acidic ion exchange catch-release, the crude reaction product was purified by reverse phase preparative HPLC.

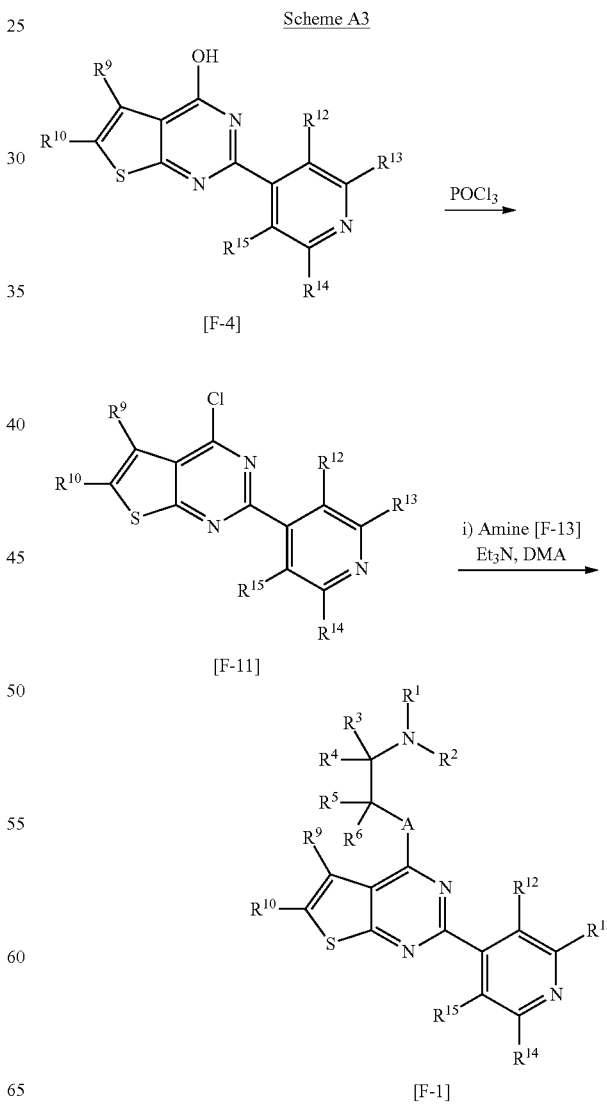

Synthesis of 4-chloro-2-pyridin-4-yl-5,6,7,8-tetra-hydro-benzo[4,5]thieno[2,3-d]pyrimidine [AA-24]

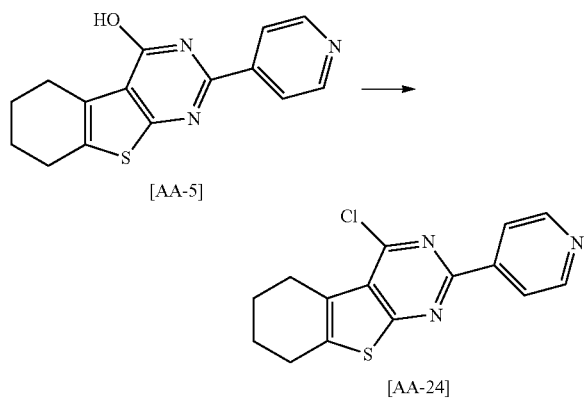

2-pyridin-4-yl-5,6,7,8-tetrahydro-benzo[4,5]thieno[2,3-d]pyrimidin-4-ol [AA-5] (1 g, 3.6 mmol) was stirred in POCl$_3$ (10 ml, 109 mmol) at reflux at 125° C. overnight. The mixture was allowed to cool down to room temperature and the excess of POCl$_3$ was removed under reduced pressure. The residue was carefully poured into ice-water and the solution was basified with a saturated solution of sodium hydrogen carbonate (50 ml) and the product was extracted into DCM (2×25 ml). The combined extracts were dried with magnesium sulfate, filtered and evaporated under reduced pressure to yield the title compound as a yellow-orange solid, which was used without further purification. LCMS method: 2, RT: 5.46 min, MI: 302 [M+1].

Synthesis of N,N-dimethyl-N'-(2-pyridin-4-yl-5,6,7,8-tetrahydro-benzo[4,5]thieno[2,3-d]pyrimidin-4-yl)-ethane-1,2-diamine[1]

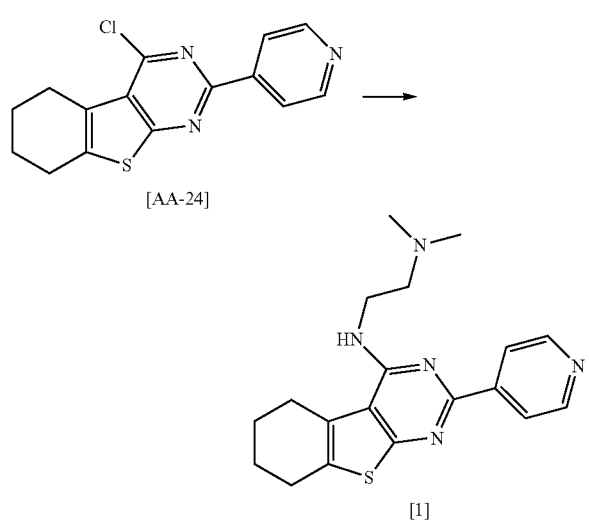

To a solution of 4-chloro-2-pyridin-4-yl-5,6,7,8-tetrahydro-benzo[4,5]thieno[2,3-d]pyrimidine (50 mg, 0.166 mmol) [AA-24] in DMA (1 ml) was added N,N-dimethyl-ethylenediamine (20 µl, 0.166 mmol) followed by Et$_3$N (32 µl, 0.232 mmol) and the mixture was stirred at room temperature for 2 hours. The reaction mixture was loaded onto a SCX-2 cartridge, and washed with methanol. The product was released from the cartridge using a solution of 2M ammonia/methanol. The ammonia/methanol eluent was concentrated under reduced pressure and the crude product was purified by preparative HPLC (method A) to yield to the title compound. LCMS method: 2: RT: 2.1 min, MI: 354 [M+1]. 1H NMR (300 MHz, DMSO): 8.70 (d, 2H) 8.20 (d, 2H), 3.7 (m, 2H), 2.9 (m, 2H), 2.8 (m, 2H), 2.6 (m, 2H), 2.3 (s, 6H), 1.8 (m, 4H).

The following compounds were prepared according to the general synthesis shown in scheme A3:

| Ex | SM | Amine [F-13] | Characterisation |
|---|---|---|---|
| 2 | [AA-24] | H$_2$N-CH$_2$-C(R)(NH$_2$)- | method: 2, RT: 2.05 min, MI: 340 [M + 1] |
| 3 | [AA-24] | piperazine (HN-NH) | method: 2, RT: 2.13 min, MI: 352 [M + 1] |
| 4 | [AA-24] | HN-(CH$_2$)-N-CH$_3$ (homopiperazine, N-methyl) | method: 2, RT: 2.15 min, MI: 380 [M + 1]; 1H NMR (300 MHz, DMSO): 8.70 (d, 2H) 8.20 (d, 2H), 4 (m, 2H), 3.8 (m, 2H), 3.2 (m, 2H), 3 (m, 2H), 2.9 (m, 4H), 2.1 (m, 2H), 1.9 (m, 2H), 1.7 (m, 2H), 0.8 (s, 3H) |
| 5 | [AA-24] | H$_2$N-CH$_2$-C(S)(NH$_2$)- | method: 2, RT: 2.10 min, MI: 340 [M + 1] |
| 6 | [AA-24] | H$_2$N-CH$_2$-C(R)(NH$_2$)-CH$_2$-S-CH$_3$ | method: 2, RT: 2.33 min, MI: 400 [M + 1] |
| 7 | [AA-24] | H$_2$N-CH$_2$-C(R)(NH$_2$)-CH$_2$-(indolyl) | method: 2, RT: 2.46 min, MI: 455 [M + 1] |
| 8 | [AA-24] | A-N(piperazine, (S)-methyl)-NH | method: 2, RT: 2.20 min, MI: 366 [M + 1] |
| 9 | [AA-24] | HN-piperazine-(S,R)-dimethyl-NH | method: 2, RT: 2.23 min, MI: 380 [M + 1] |

-continued

| Ex | SM | Amine [F-13] | Characterisation |
|---|---|---|---|
| 10 | [AA-24] | 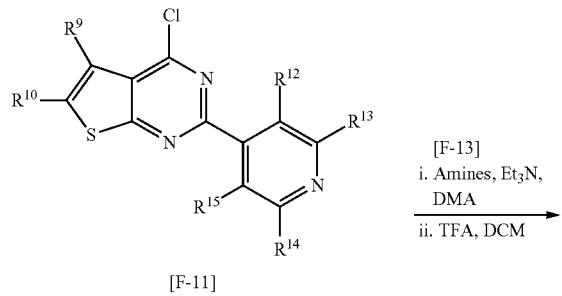 | method: 2, RT: 2.30 min, MI: 380 [M + 1]  1H NMR (300 MHz, DMSO): 8.8 (d, 2H), 8.2 (d, 2H), 3.4 (m, 2H), 3.2 (m, 2H), 3.1 (m, 2H), 2.90 (m, 2H), 2.68 (m, 2H), 1.9 (m, 4H), 1.13 (d, 6H) |
| 11 | [AA-24] |  | method: 2, RT: 2.10 min, MI: 338 [M + 1] |

General Synthesis of 5,6 Substituted 4-amino-2-pyridin-4-yl-thieno[2,3-d]pyrimidine Derivatives of General Formula [F-1] (Scheme A4)

5,6 substituted 4-chloro-2-pyridin-4-yl-thieno[2,3-d]pyrimidine derivatives of general formula [F-11] were reacted with N-Boc protected primary or secondary diamine derivatives of general formula [F-13] at ambient temperature. After reaction work up, typically by a liquid-liquid extraction or purification by acidic ion exchange catch-release, the N-Boc derivatives were deprotected under acidic conditions with a strong acid such as TFA, TCA, methanesulfonic acid, HCl or $H_2SO_4$ in a solvent such as DCM, DCE, THF, EtOH or MeOH and, the crude reaction product was purified by reverse phase preparative HPLC Scheme A4

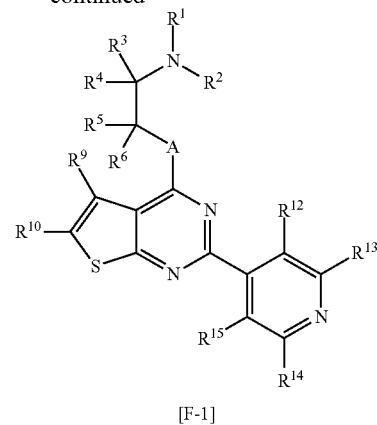

[F-1]

Synthesis of N*1*-(2-pyridin-4-yl-5,6,7,8-tetrahydro-benzo[4,5]thieno[2,3-d]pyrimidin-4-yl)-ethane-1,2-diamine[12]

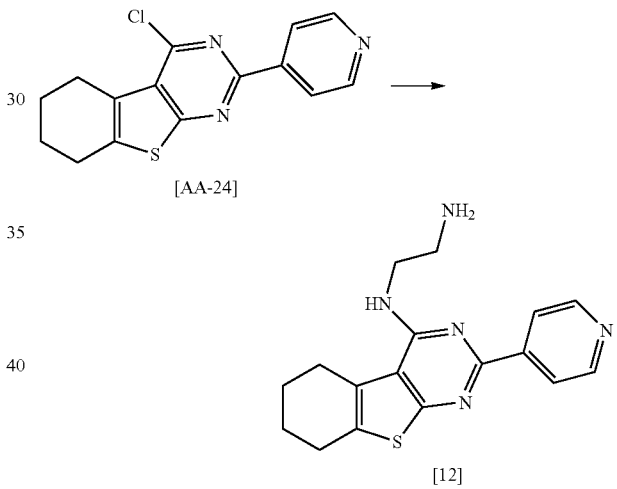

To a solution of 4-chloro-2-pyridin-4-yl-5,6,7,8-tetrahydro-benzo[4,5]thieno[2,3-d]pyrimidine (50 mg, 0.166 mmol) [AA-24] in DMA (1 ml) was added (2-amino-ethyl)-carbamic acid tert-butyl ester (28 μl, 0.182 mmol) followed by $Et_3N$ (32 μl, 0.232 mmol), the mixture was stirred at room temperature for 2 hours. The product was extracted with DCM (1 ml) and washed with brine (2 ml). To the organic phase was added TFA (1 ml) and the mixture was stirred at room temperature for 1 hour. After completion the mixture was loaded onto a SCX-2 cartridge and washed with methanol. The product was released from the cartridge using a solution of 2M ammonia/methanol. The ammonia/methanol eluent was concentrated under reduced pressure and the crude product was purified by preparative HPLC (method A) to yield to the title compound. LCMS method: 2, RT: 2.07 min, MI: 326 [M+1]. 1H NMR (300 MHz, DMSO): 8.70 (d, 2H), 8.28 (d, 2H), 3.88 (m, 2H), 3.14 (m, 2H), 2.94 (m, 2H), 2.78 (m, 2H), 1.84 (m, 4H).

The following compounds were prepared according to the general synthesis shown in Scheme A4:

| Ex | SM | Amine [F-13] | Characterisation |
|---|---|---|---|
| 13 | [AA-5] | boc-NH-CH2CH2-NH2 | method: 2, RT: 2.05 min, MI: 340 [M + 1] | 1H NMR (300 MHz, DMSO): 8.7 (d, 2H), 8.2 (d, 2H), 3.9 (m, 2H), 3.1 (m, 2H), 3 (m, 2H), 2.8 (m, 2H), 2.45 (s, 3H), 1.8 (m, 4H) |
| 14 | [AA-5] | boc-N(homopiperazine)NH | method 2, RT: 2.10 min, MI: 366 [M + 1] |
| 15 | [AA-5] | HN-CH2CH2-N(Me)-boc | method: 2, RT: 2.17 min, MI: 340 [M + 1] |
| 16 | [AA-5] | H2N-CH(R)(iBu)-NH-boc | method: 2, RT: 2.35 min, MI: 382 [M + 1] |
| 17 | [AA-5] | H2N-CH2-CH(R)(Et)-NH-boc | method: 2, RT: 2 18 min, MI: 354 [M + 1] |
| 18 | [AA-5] | HN-(bicyclic (S,S))-N-boc | method: 2, RT: 2.13 min, MI: 364 [M + 1] |

General Synthesis of 5,6-substituted-(2,4,6-triisopropyl-benzenesulfonic acid)-2-pyridin-4-yl-thieno[2,3-d]pyrimidin-4-yl ester Derivatives of General Formula [F-12] (Scheme A5)

Compounds were prepared by the reaction of 5,6-substituted 2-pyridin-4-yl-thieno[2,3-d]pyrimidin-4-ol derivatives of general formula [F-4] (described in scheme A2) with 2,4,6-triisopropylbenzenesulfonyl chloride in halogenated solvent such as DCM or a polar aprotic solvent such as DMA, DMF, NMP with a tertiary alkylamine base such as Et₃N, DIPEA or NMM and a catalytic amount of DMAP.

Scheme A5

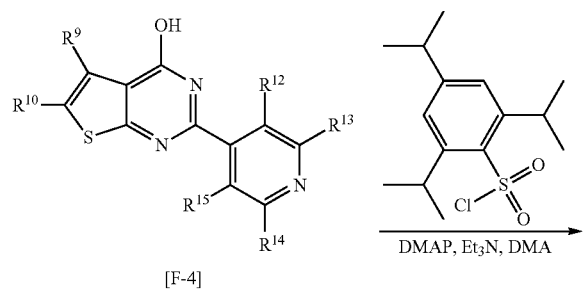

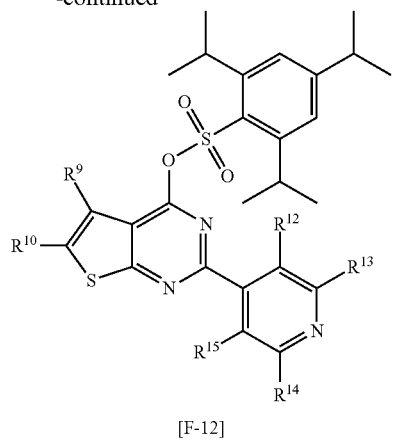

[F-12]

Synthesis of 2,4,6-triisopropyl-benzenesulfonic acid 2-pyridin-4-yl-5,6,7,8-tetrahydro-benzo[4,5]thieno[2,3-d]pyrimidin-4-yl ester [AA-25]

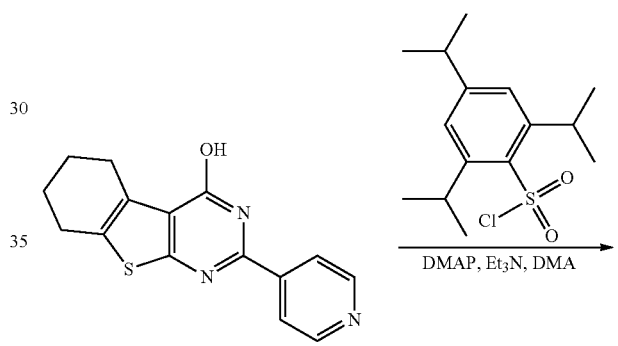

[AA-5]

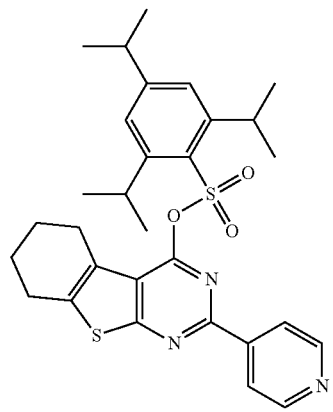

[AA-25]

To a solution of 2-pyridin-4-yl-5,6,7,8-tetrahydro-benzo[4,5]thieno[2,3-d]pyrimidin-4-ol (1 g, 3.5 mmol) [AA-5] in DCM (10 ml) was added 2,4,6-triisopropylbenzenesulfonyl chloride (1.3 g, 4.2 mmol), Et₃N (1.5 ml, 10.5 mmol) and DMAP (6 mg, 0.05 mmol). The mixture was stirred for at room temperature for one hour. After completion the mixture was diluted with water and the product was extracted into DCM (2×2 ml). The combined extracts were dried with magnesium sulfate, filtered and evaporated under reduced pressure to yield the title compound as a brown solid, which was used without further purification in the next step. LCMS method: 3, RT: 6.23 min, MI: 550 [M+1].

The following compounds were prepared according to the general synthesis shown in scheme A5:

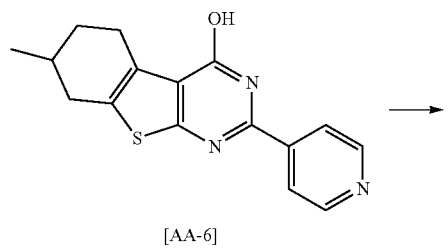

[AA-6]

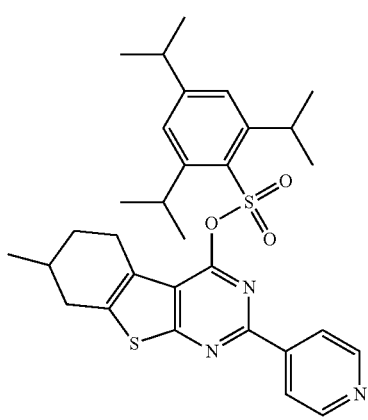

[AA-26]

2,4,6-triisopropyl-benzenesulfonic acid 7-methyl-2-pyridin-4-yl-5,6,7,8-tetrahydro-benzo[4,5]thieno[2,3-d]pyrimidin-4-yl ester [AA-26] was prepared by reaction of 7-methyl-2-pyridin-4-yl-5,6,7,8-tetrahydro-benzo[4,5]thieno[2,3-d]pyrimidin-4-ol [AA-6], 2,4,6-triisopropyl benzene sulfonyl chloride, Et₃N, DMAP and DCM at room temperature to give the desired compound as a brown solid. LCMS method: 3, RT: 6.34 min, MI: 564 [M+1].

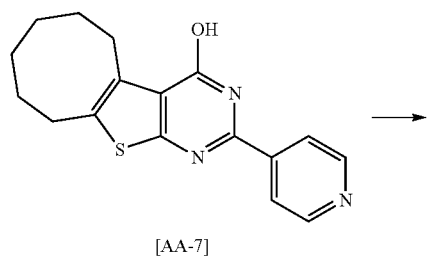

[AA-7]

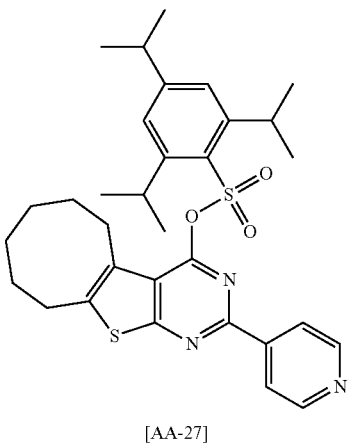

[AA-27]

2,4,6-triisopropyl-benzenesulfonic acid 2-pyridin-4-yl-5,6,7,8,9,10-hexahydro-1-thia-1,3-diaza-cycloocta[a]inden-4-yl ester [AA-27] was prepared by reaction of 2-pyridin-4-yl-5,6,7,8,9,10-hexahydro-11-thia-1,3-diaza-cycloocta[a]inden-4-ol [AA-7], 2,4,6-triisopropylbenzenesulfonyl chloride, Et₃N, DMAP and DCM at room temperature to give the desired compound as a brown solid. LCMS method: 3, RT: 6.47 min, MI: 578 [M+1].

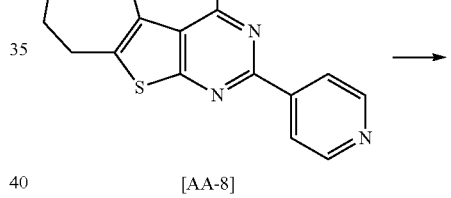

[AA-8]

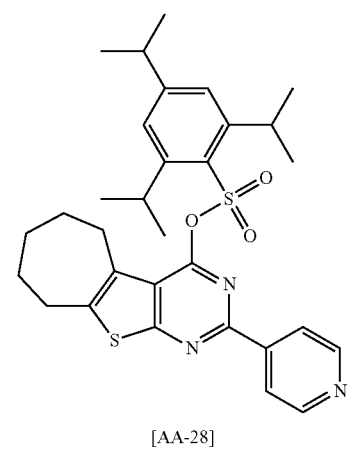

[AA-28]

2,4,6-triisopropyl-benzenesulfonic acid 2-pyridin-4-yl-6,7,8,9-tetrahydro-5H-10-thia-1,3-diaza-benzo[a]azulen-4-yl ester [AA-28] was prepared by reaction of 2-pyridin-4-yl-6,7,8,9-tetrahydro-5H-10-thia-1,3-diaza-benzo[a]azulen-4-ol [AA-8], 2,4,6-triisopropylbenzenesulfonyl chloride, Et₃N, DMAP and DCM at room temperature to give the title compound as a brown solid. LCMS method: 3, RT: 6.39 min, MI: 564 [M+1].

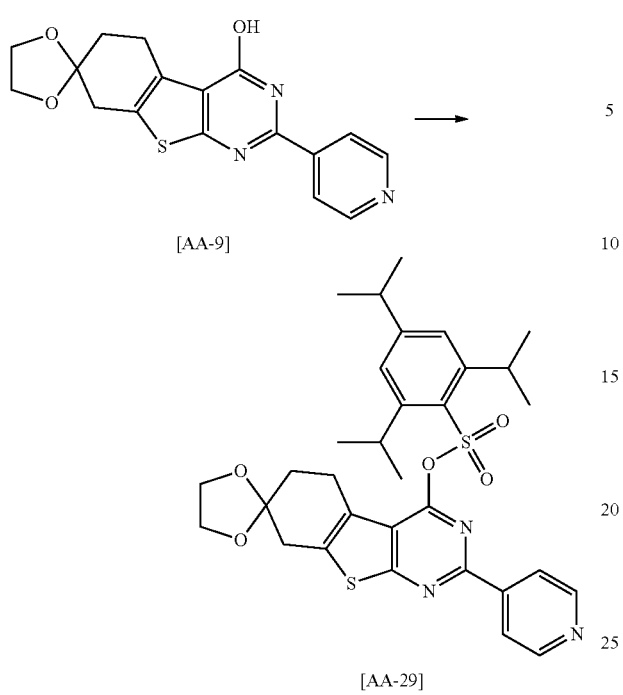

2,4,6-triisopropyl-benzenesulfonic acid 1,4-Dioxa-spiro [7.7]-2-pyridin-4-yl-5,6,7,8-tetrahydro-benzo[4,5]thieno[2, 3-d]pyrimidin-4-ol ester [AA-29] was prepared by reaction of 1,4-Dioxa-spiro[7.7]-2-pyridin-4-yl-5,6,7,8-tetrahydro-benzo[4,5]thieno[2,3-d]pyrimidin-4-ol [AA-9], 2,4,6-triisopropylbenzenesulfonyl chloride, Et$_3$N, DMAP and DCM at room temperature to give the desired compound as a brown solid. LCMS method: 3, RT: 6.56 min, MI: 608 [M+1].

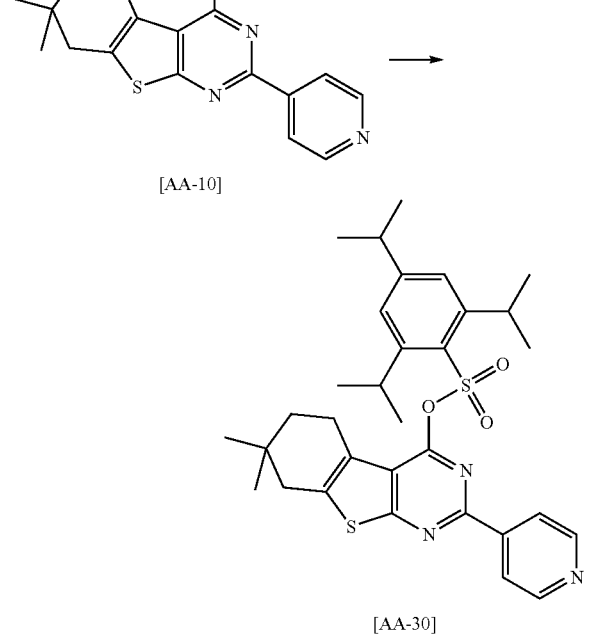

2,4,6-triisopropyl-benzenesulfonic acid 7,7-dimethyl-2-pyridin-4-yl-5,6,7,8-tetrahydro-benzo[4,5]thieno[2,3-d]pyrimidin-4-yl ester [AA-30] was prepared by reaction of 7,7-dimethyl-2-pyridin-4-yl-5,6,7,8-tetrahydro-benzo[4,5]thieno[2,3-d]pyrimidin-4-ol [AA-10], 2,4,6-triisopropyl benzenesulfonyl chloride, Et$_3$N, DMAP and DCM at room temperature to give the desired compound as a brown solid. LCMS method: 3, RT: 6.37 min, MI: 578 [M+1].

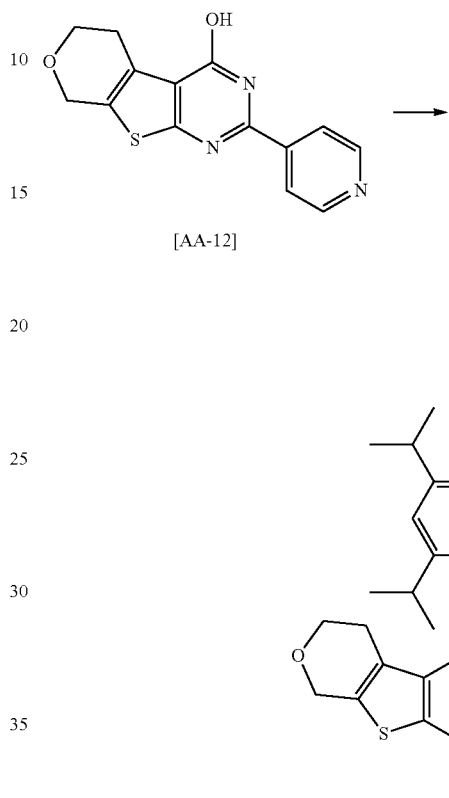

2,4,6-triisopropyl-benzenesulfonic acid 2-pyridin-4-yl-5, 8-dihydro-6H-pyrano[4',3':4,5]thieno [2,3-d]pyrimidin-4-yl ester [AA-31] was prepared by reaction of 2-pyridin-4-yl-5,8-dihydro-6H-pyrano[4',3':4,5]thieno[2,3-d]pyrimidin-4-ol [AA-12], 2,4,6-triisopropylbenzenesulfonyl chloride, Et$_3$N, DMAP and DCM at room temperature to give the desired compound as a brown solid. LCMS method: 3, RT: 6.29 min, MI: 552 [M+1].

-continued

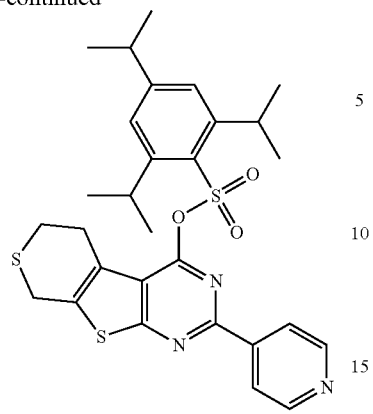

[AA-32]

2,4,6-Triisopropyl-benzenesulfonic acid 2-pyridin-4-yl-5,8-dihydro-6H-thiopyrano[4',3':4,5]thieno[2,3-d]pyrimidin-4-yl ester [AA-32] was prepared by reaction of 2-pyridin-4-yl-5,8-dihydro-6H-thiopyrano[4',3':4,5]thieno[2,3-d]pyrimidin-4-ol [AA-13], 2,4,6-triisopropyl benzene sulfonyl chloride, Et$_3$N, DMAP and DCM at room temperature to give the desired compound as a brown solid. LCMS method: 3, RT: 6.58 min, MI: 568 [M+1].

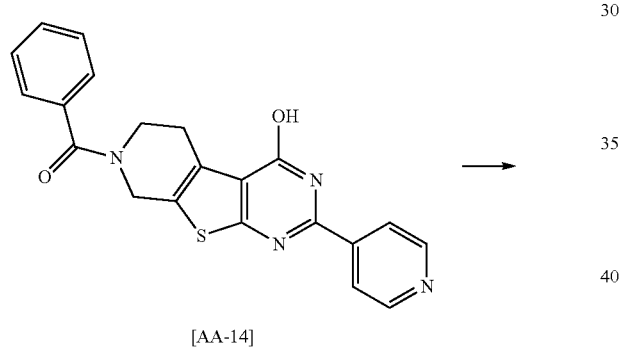

[AA-14]

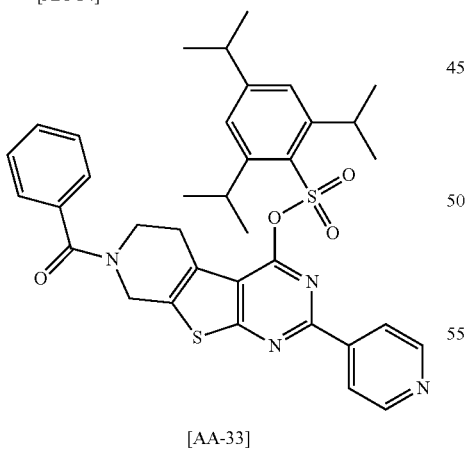

[AA-33]

2,4,6-Triisopropyl-benzenesulfonic acid 7-benzoyl-2-pyridin-4-yl-5,6,7,8-tetrahydro-pyrido[4',3':4,5]thieno[2,3-d]pyrimidin-4-yl ester [AA-33] was prepared by reaction of (4-Hydroxy-2-pyridin-4-yl-5,8-dihydro-6H-pyrido[4',3':4,5]thieno[2,3-d]pyrimidin-7-yl)-phenyl-methanone [AA-14], 2,4,6-triisopropyl benzene sulfonyl chloride, Et$_3$N, DMAP and DCM at room temperature to give the desired compound as a brown solid. LCMS method: 3, RT: 6.67 min, MI: 655 [M+1].

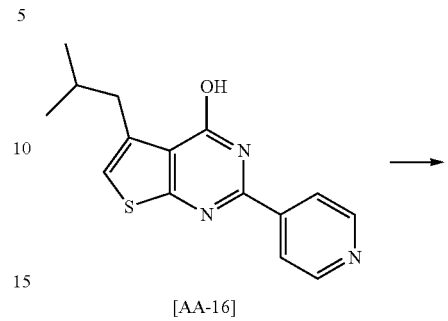

[AA-16]

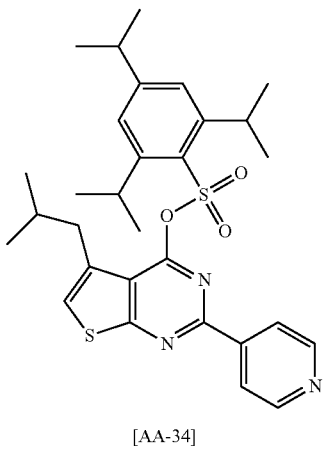

[AA-34]

2,4,6-triisopropyl-benzenesulfonic acid 5-isobutyl-2-pyridin-4-yl-thieno[2,3-d]pyrimidin-4-yl ester [AA-34] was prepared by reaction of 5-Isobutyl-2-pyridin-4-yl-thieno[2,3-d]pyrimidin-4-ol [AA-16], 2,4,6-triisopropylbenzenesulfonyl chloride, Et$_3$N, DMAP and DCM at room temperature to give the desired compound as a brown solid. LCMS method: 3, RT: 6.36 min, MI: 552 [M+1].

[AA-17]

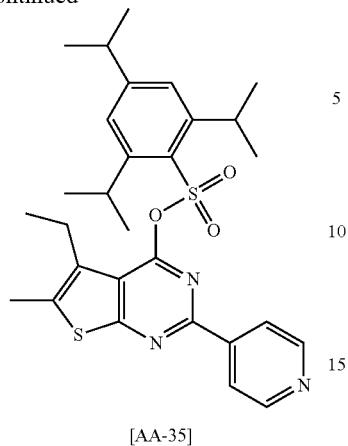

[AA-35]

2,4,6-triisopropyl-benzenesulfonic acid 5-ethyl-6-methyl-2-pyridin-4-yl-thieno[2,3-d]pyrimidin-4-yl ester [AA-35] was prepared by reaction of 5-ethyl-6-methyl-2-pyridin-4-yl-thieno[2,3-d]pyrimidin-4-ol [AA-17], 2,4,6-triisopropyl-benzenesulfonyl chloride, Et₃N, DMAP and DCM at room temperature to give the desired compound as a brown solid. LCMS method: 3, RT: 6.29 min, MI: 538 [M+1].

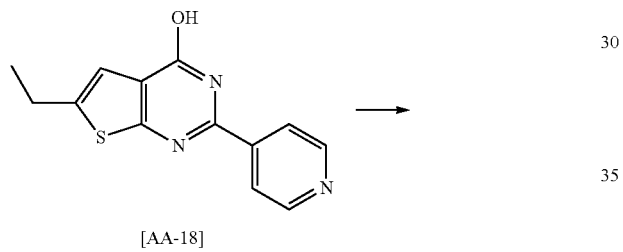

[AA-18]

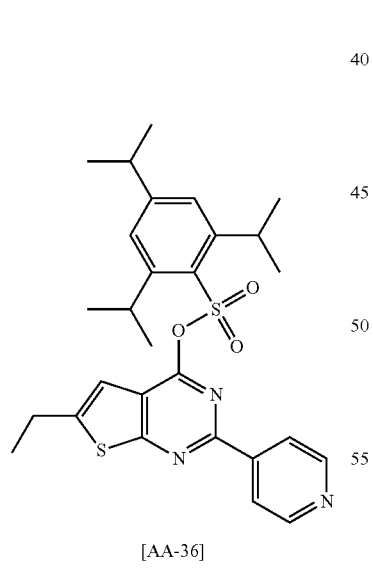

[AA-36]

2,4,6-triisopropyl-benzenesulfonic acid 6-ethyl-2-pyridin-4-yl-thieno [2,3-d]pyrimidin-4-yl ester [AA-36] was prepared by reaction of 6-ethyl-2-pyridin-4-yl-thieno[2,3-d]pyrimidin-4-ol [AA-18], 2,4,6-triisopropylbenzenesulfonyl chloride, Et₃N, DMAP and DCM at room temperature to give the desired compound as a brown solid. LCMS method: 3, RT: 6.22 min, MI: 524 [M+1].

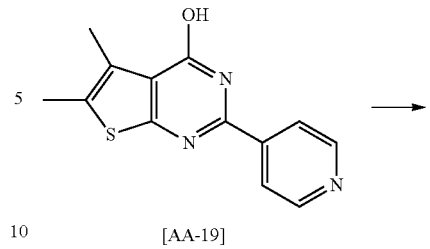

[AA-19]

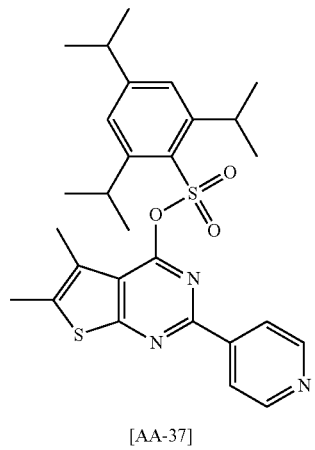

[AA-37]

2,4,6-triisopropyl-benzenesulfonic acid 5,6-dimethyl-2-pyridin-4-yl-thieno [2,3-d]pyrimidin-4-yl ester [AA-37] was prepared by reaction of 5,6-dimethyl-2-pyridin-4-yl-thieno [2,3-d]pyrimidin-4-ol [AA-19], 2,4,6-triisopropylbenzenesulfonyl chloride, Et₃N, DMAP and DCM at room temperature to give the desired compound as a brown solid. LCMS method: 3, RT: 6.18 min, MI: 524 [M+1].

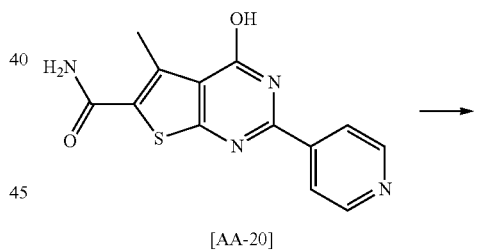

[AA-20]

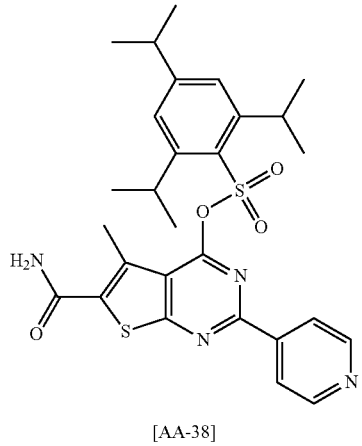

[AA-38]

2,4,6-triisopropyl-benzenesulfonic acid 6-carbamoyl-5-methyl-2-pyridin-4-yl-thieno[2,3-d]pyrimidin-4-yl ester

[AA-38] was prepared by reaction of 4-hydroxy-5-methyl-2-pyridin-4-yl-thieno[2,3-d]pyrimidine-6-carboxylic acid amide [AA-20], 2,4,6-triisopropylbenzenesulfonyl chloride, Et₃N, DMAP and DCM at room temperature to give the desired compound as a brown solid. LCMS method: 3, RT: 6.12 min, MI: 553 [M+1].

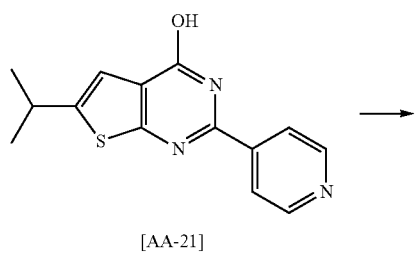

[AA-21]

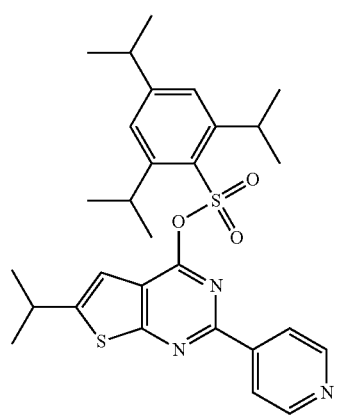

[AA-39]

2,4,6-triisopropyl-benzenesulfonic acid 6-isopropyl-2-pyridin-4-yl-thieno[2,3-d]pyrimidin-4-yl ester [AA-39] was prepared by reaction of 6-isopropyl-2-pyridin-4-yl-thieno[2,3-d]pyrimidin-4-ol [AA-21], 2,4,6-triisopropylbenzenesulfonyl chloride, Et₃N, DMAP and DCM at room temperature to give the desired compound as a brown solid. LCMS method: 3, RT: 6.24 min, MI: 538 [M+1].

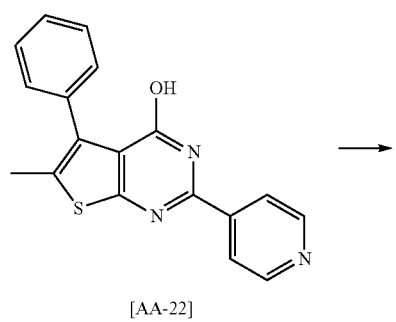

[AA-22]

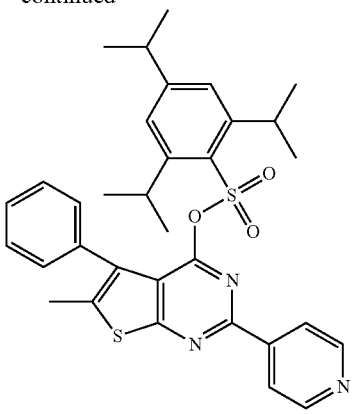

[AA-40]

2,4,6-triisopropyl-benzenesulfonic acid 6-methyl-5-phenyl-2-pyridin-4-yl-thieno[2,3-d]pyrimidin-4-yl ester [AA-40] was prepared by reaction of 6-methyl-5-phenyl-2-pyridin-4-yl-thieno[2,3-d]pyrimidin-4-ol [AA-22], 2,4,6-triisopropylbenzenesulfonyl chloride, Et₃N, DMAP and DCM at room temperature to give the desired compound as a brown solid. LCMS method: 3, RT: 6.55 min, MI: 586 [M+1].

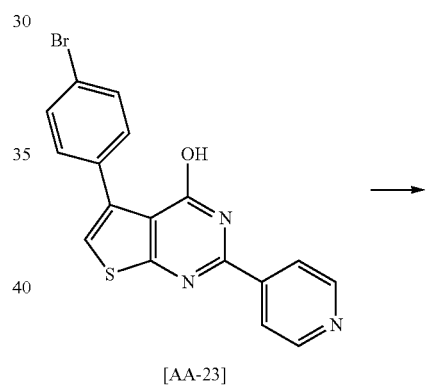

[AA-23]

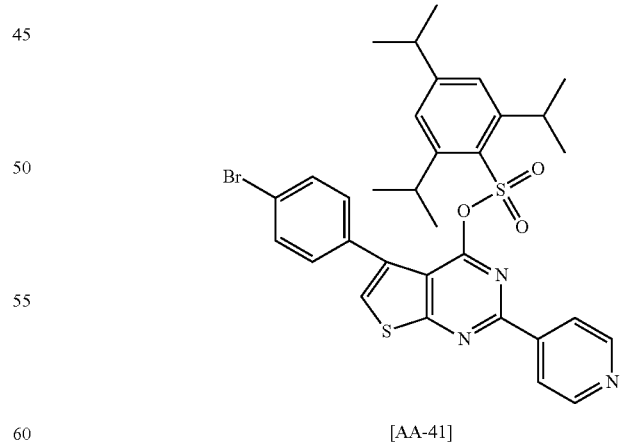

[AA-41]

2,4,6-triisopropyl-benzenesulfonic acid 5-(4-bromo-phenyl)-2-pyridin-4-yl-thieno[2,3-d]pyrimidin-4-yl ester [AA-41] was prepared by reaction of 5-(4-bromo-phenyl)-2-pyridin-4-yl-thieno[2,3-d]pyrimidin-4-ol [AA-23], 2,4,6-triisopropylbenzenesulfonyl chloride, Et₃N, DMAP and DCM at room temperature to give the desired compound as a brown solid. LCMS method: 3, RT: 6.66 min, MI: 651 [M+1].

General Synthesis of 5,6 Substituted 4-amino-2-pyridin-4-yl-thieno[2,3-d]pyrimidine Derivatives of General Formula [F-1] (Scheme A6)

5,6-substituted-(2,4,6-triisopropyl-benzenesulfonic acid)-2-pyridin-4-yl-thieno[2,3-d]pyrimidin-4-yl ester derivatives of general formula [F-12] [prepared in scheme A5] were reacted with a primary or secondary amino derivative of general formula [F-13] in a polar aprotic solvent such as DMA, DMF, NMP in the presence of a tertiary amine base such as Et$_3$N, DIPEA or NMM at ambient temperature. After reaction work up, typically by a liquid-liquid extraction or purification by acidic ion exchange catch-release, the N-Boc derivatives were deprotected under acidic conditions with a strong acid such as TFA, TCA, methanesulfonic acid, HCl or H$_2$SO$_4$ in a solvent such as DCM, DCE, THF, EtOH or MeOH and the crude reaction product was purified by reverse phase preparative HPLC Scheme A6

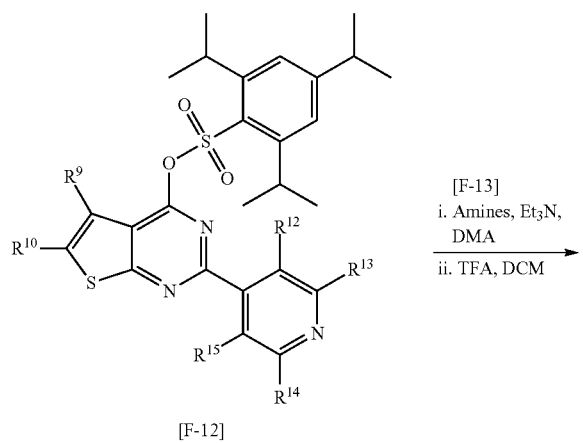

[F-12]

i. Amines, Et$_3$N, DMA
ii. TFA, DCM

[F-13]

[F-1]

(2-pyridin-4-yl-5,6,7,8-tetrahydro-benzo[4,5]thieno[2,3-d]pyrimidin-4-yl)-(R)-pyrrolidin-3-yl-amine
[19]

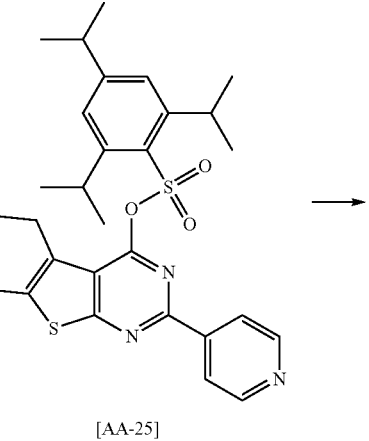

[AA-25]

[19]

To a solution of 2,4,6-triisopropyl-benzenesulfonic acid 2-pyridin-4-yl-5,6,7,8-tetrahydro-benzo[4,5]thieno[2,3-d]pyrimidin-4-yl ester (60 mg, 0.110 mmol) [AA-25] in DMA (1 ml) was added (R)-(+)-1-Boc-3-aminopyrrolidine (23 mg, 0.121 mmol) followed by Et$_3$N (30 µl, 0.220 mmol) and the mixture was stirred at room temperature for 2 hours. Water (1 ml) was added and the mixture was extracted with DCM (2×ml), the extracts were combined and washed with brine (2 ml). To the organic phase was added TFA (1 ml) and the mixture was stirred at room temperature for 1 hour. After completion the mixture was loaded onto a SCX-2 cartridge and washed with methanol. The product was released from the cartridge using a solution of 2M ammonia/methanol. The ammonia/methanol eluent was concentrated under reduced pressure and the crude product was purified by preparative HPLC (method B) to yield to the desired compound. LCMS method: 4, RT: 4.43 min, MI: 352 [M+1]. 1H NMR (300 MHz, DMSO): 8.70 (d, 2H), 8.24 (d, 2H), 3.53 (m, 2H), 3.33 (m, 1H), 3.22 (m, 2H), 3.03 (m, 2H), 2.81 (m, 2H), 2.34 (m, 1H), 2.10 (m, 1H), 1.83 (m, 4H).

The following compounds were prepared according to the general synthesis shown in scheme A6:

| Ex | SM | Amine | Characterisation |
|---|---|---|---|
| 20 | [AA-25] | 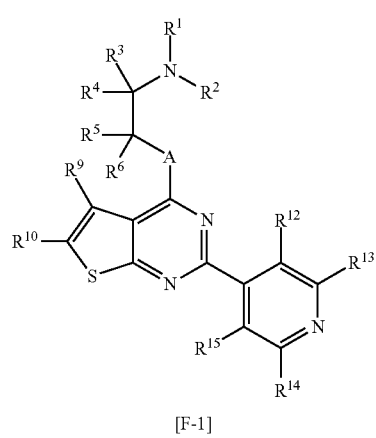 | method: 4, RT: 4.14 min, MI: 352 [M + 1] |

| Ex | SM | Amine | Characterisation |
|---|---|---|---|
| 21 | [AA-26] | H₂N–CH₂–CH₂–NH–boc | method: 2, RT: 2.32 min, MI: 340 [M + 1] |
| 22 | [AA-26] | H₂N–CH₂–CH(R)(CH₃)–NH–boc | method: 2, RT: 2.73 min, MI: 354 [M + 1] |
| 23 | [AA-26] | H₂N–CH₂–CH(S)(CH₃)–NH–boc | method: 2, RT: 2.66 min, MI: 354 [M + 1] |
| 24 | [AA-27] | H₂N–CH₂–CH₂–NH–boc | method: 2, RT: 2.36 min, MI: 354 [M + 1] |
| 25 | [AA-27] | H₂N–CH₂–CH(S)(CH₃)–NH–boc | method: 2, RT: 2.68 min, MI 368 [M + 1] |
| 26 | [AA-27] | H₂N–CH₂–CH(R)(CH₃)–NH–boc | method: 2, RT: 2.57 min, MI: 368 [M + 1] |
| 27 | [AA-33] | H₂N–CH₂–CH₂–NH–boc | method: 3, RT: 2.16 min, MI: 431 [M + 1] |
| 28 | [AA-34] | H₂N–CH₂–CH₂–NH–boc | method: 2, RT: 2.37 min, MI: 328 [M + 1] |
| 29 | [AA-34] | H₂N–CH₂–CH(S)(CH₃)–NH–boc | method: 2, RT: 2.41 min, MI: 342 [M + 1] |
| 30 | [AA-34] | H₂N–CH₂–CH(R)(CH₃)–NH–boc | method 2, RT: 2.51 min, MI: 342 [M + 1] |
| 31 | [AA-35] | H₂N–CH₂–CH(S)(CH₃)–NH–boc | method: 2, RT: 2.30 min, MI: 328 [M + 1] |
| 32 | [AA-35] | H₂N–CH₂–CH(R)(CH₃)–NH–boc | method 2, RT: 2.32 min, MI: 328 [M + 1] |
| 33 | [AA-36] | H₂N–CH₂–CH₂–NH–boc | method: 2, RT: 2.01 min, MI: 300 [M + 1] |
| 34 | [AA-36] | H₂N–CH₂–CH(S)(CH₃)–NH–boc | method: 2, RT: 2.12 min, MI: 314 [M + 1] |
| 35 | [AA-36] | H₂N–CH₂–CH(R)(CH₃)–NH–boc | method: 2, RT: 2.12 min, MI: 314 [M + 1] |
| 36 | [AA-37] | H₂N–CH₂–CH₂–NH–boc | method 2, RT: 1.92 min, MI: 300 [M + 1] |
| 37 | [AA-37] | H₂N–CH₂–CH(S)(CH₃)–NH–boc | method: 2, RT: 2.08 min, MI: 314 [M + 1] |
| 38 | [AA-37] | H₂N–CH₂–CH(R)(CH₃)–NH–boc | method: 2, RT: 2.52 min, MI: 314 [M + 1] |
| 39 | [AA-38] | H₂N–CH₂–CH₂–NH–boc | method: 2, RT: 1.60 min, MI: 329 [M + 1] |
| 40 | [AA-39] | H₂N–CH₂–CH₂–NH–boc | method: 2, RT: 2.07 min, MI: 314 [M + 1] |
| 41 | [AA-39] | H₂N–CH₂–CH(R)(CH₃)–NH–boc | method 2, RT 2.16 min, MI: 328 [M + 1] |
| 42 | [AA-29] | H₂N–CH₂–CH₂–NH–boc | method: 3, RT: 1.48 min, MI: 384 [M + 1]; 1H NMR (300 MHz, DMSO): 8.7 (d, 2H) 8.42 (s, HCOOH, 1H) 8.26 (d, 2H), 3.94 (bs, 2H), 3.86 (bm, 4H), 3.86 (bm, 2H), 3.30 (m, 2H), 3.22 (m, 4H), |
| 43 | [AA-30] | H₂N–CH₂–CH₂–NH–boc | method: 3, RT: 2.33 min, MI: 354 [M + 1] |
| 44 | [AA-32] | H₂N–CH₂–CH₂–NH–boc | method: 3, RT: 2.07 min, MI: 344 [M + 1] |
| 45 | [AA-31] | H₂N–CH₂–CH₂–NH–boc | method: 3, RT: 1.81 min, MI: 328 [M + 1] |

General Synthesis of 5,6 Substituted 4-amino-2-pyridin-4-yl-thieno[2,3-d]pyrimidine Derivatives of General Formula [F-1] (Scheme A7)

Compounds were synthesised starting from an N-Boc protected amino acid derivative of general formula [F-14] which was converted to a primary carboxamide derivative of general formula [F-15] by reaction with di-tert-butyl dicarbonate in the presence of a base such as pyridine or 2,6-lutidine and ammonium carbonate in an anhydrous solvent such as dioxane, THF or diethylether. The resultant primary carboxamide derivative was reduced to the amino derivative of general formula [F-16] with a borane reducing agent such as $BH_3 \cdot THF$ or $BH_3 \cdot SMe_2$ in an anhydrous solvent such as THF, dioxane or diethylether. The resultant amino derivative was then reacted with a 5,6-substituted-(2,4,6-triisopropyl-benzenesulfonic acid)-2-pyridin-4-yl-thieno[2,3-d]pyrimidin-4-yl ester [F-12] [prepared in scheme A5] in a polar aprotic solvent such as DMA, DMF, NMP in the presence of a tertiary amine base such as Et₃N, DIPEA or NMM at ambient temperature. After reaction work up, typically by a liquid-liquid extraction or purification by acidic ion exchange catch-release, the N-Boc derivatives were deprotected under acidic conditions with a strong acid such as TFA, TCA, methanesulfonic acid, HCl or $H_2SO_4$ in a solvent such as DCM, DCE, THF, EtOH or MeOH and the crude reaction product was purified by reverse phase preparative HPLC.

((S)-1-carbamoyl-2-p-tolyl-ethyl)-carbamic acid tert-butyl ester [AA-42]

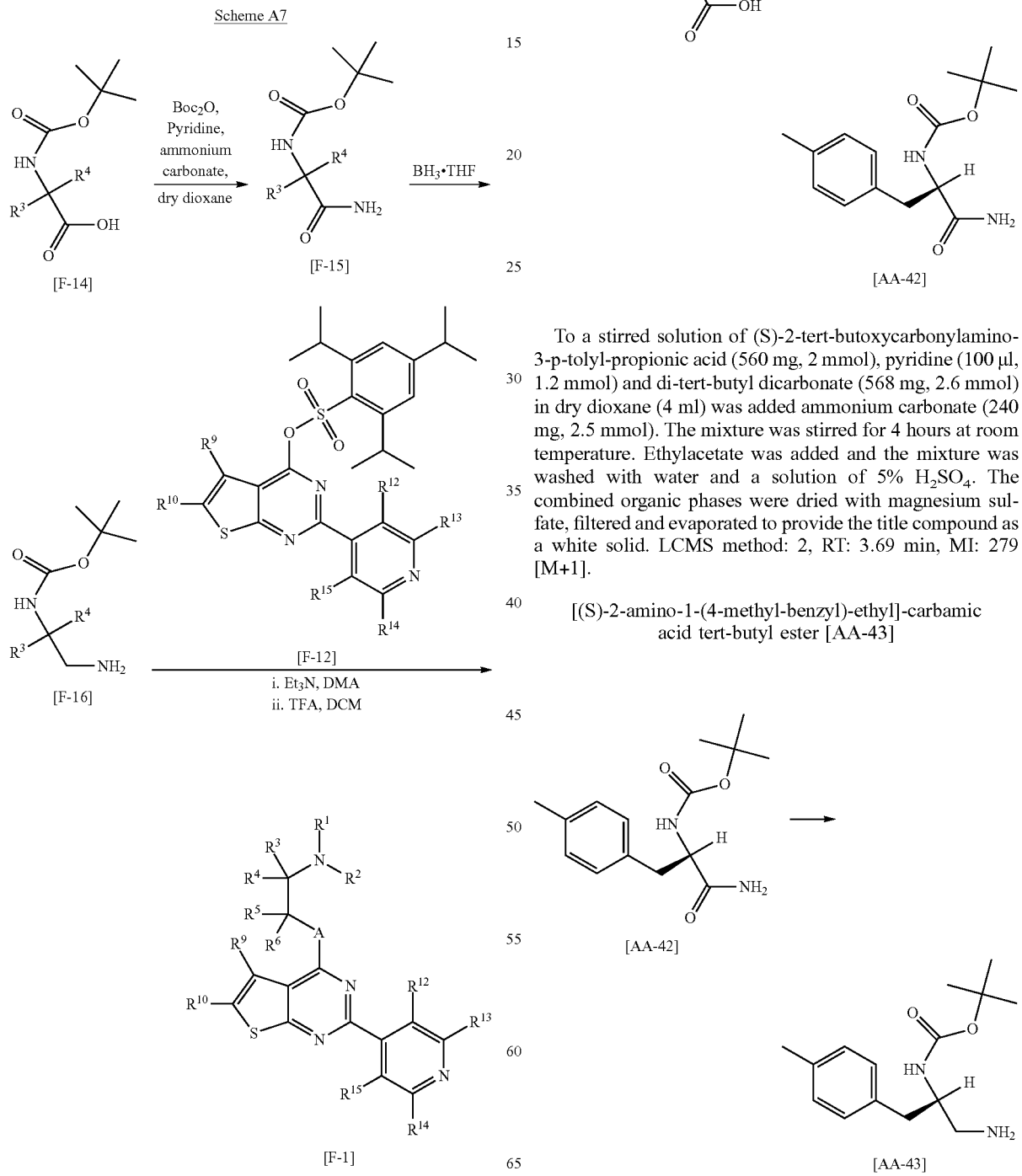

To a stirred solution of (S)-2-tert-butoxycarbonylamino-3-p-tolyl-propionic acid (560 mg, 2 mmol), pyridine (100 µl, 1.2 mmol) and di-tert-butyl dicarbonate (568 mg, 2.6 mmol) in dry dioxane (4 ml) was added ammonium carbonate (240 mg, 2.5 mmol). The mixture was stirred for 4 hours at room temperature. Ethylacetate was added and the mixture was washed with water and a solution of 5% $H_2SO_4$. The combined organic phases were dried with magnesium sulfate, filtered and evaporated to provide the title compound as a white solid. LCMS method: 2, RT: 3.69 min, MI: 279 [M+1].

[(S)-2-amino-1-(4-methyl-benzyl)-ethyl]-carbamic acid tert-butyl ester [AA-43]

A 1M solution of BH₃ in THF (15 ml, 15 mmol) was added dropwise to ((S)-1-carbamoyl-2-p-tolyl-ethyl)-carbamic acid tert-butyl ester [AA-42] (560 mg, 2 mmol), the solution was stirred overnight at room temperature then subsequently hydrolysed by slow addition of excess of 10% acetic acid/MeOH (30 ml) and stirred at room temperature for a further 2 hours. The solvent was removed under reduced pressure the residue dissolved in methanol and passed through a SCX-2 cartridge and washed with methanol. The product was released from the cartridge using a solution of 2M ammonia/methanol. The solvent was evaporated to provide the title compound as a white solid. LCMS method: 2, RT: 2.42 min, MI: 265 [M+1].

[(S)-1-carbamoyl-2-(2-methoxy-phenyl)-ethyl]-carbamic acid tert-butyl ester [AA-44]

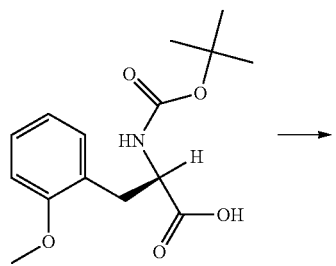

To a stirred solution of (S)-2-tert-butoxycarbonylamino-3-(2-methoxy-phenyl)-propionic acid (998 mg, 3.3 mmol), pyridine (300 μl, 3.6 mmol) and di-tert-butyl dicarbonate (1.16 g, 5.32 mmol) in dry dioxane (10 ml) was added ammonium carbonate (512 mg, 5.32 mmol). The mixture was stirred for 4 hours at room temperature. Ethylacetate was added and after washings with water and a solution of 5% H₂SO₄. The combined organic phases were dried with magnesium sulfate, filtered and evaporated to provide the title compound as a white solid. LCMS method: 4, RT: 3.09 min, MI: 295 [M+1].

[(S)-2-amino-1-(2-methoxy-benzyl)-ethyl]-carbamic acid tert-butyl ester [AA-45]

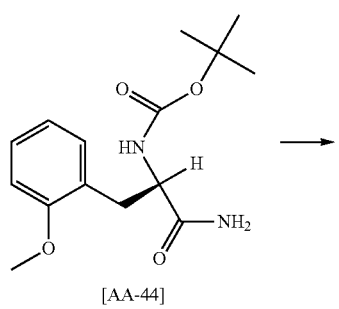

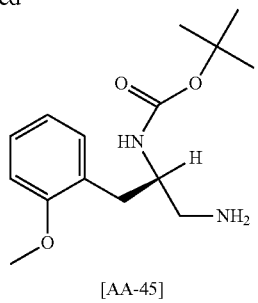

A 1M solution of BH₃ in THF (15 ml, 15 mmol) was added dropwise to [(S)-1-carbamoyl-2-(2-methoxy-phenyl)-ethyl]-carbamic acid tert-butyl ester [AA-44] (980 mg, 3.32 mmol), the solution was stirred overnight at room temperature then subsequently hydrolysed by slow addition of excess of 10% acetic acid/MeOH (30 ml) and stirred at room temperature for a further 2 hours. The solvent was removed under reduced pressure the residue dissolved in methanol and passed through a SCX-2 cartridge and washed with methanol. The product was released from the cartridge using a solution of 2M ammonia/methanol. The solvent was evaporated to provide the title compound as a white solid. LCMS method: 2, RT: 2.40 min, MI: 281 [M+1].

(S)-1-(4-methyl-benzyl)-3-(2-pyridin-4-yl-5,6,7,8-tetrahydro-benzo[4,5]thieno[2,3-d]pyrimidin-4-yl)-propylamine [46]

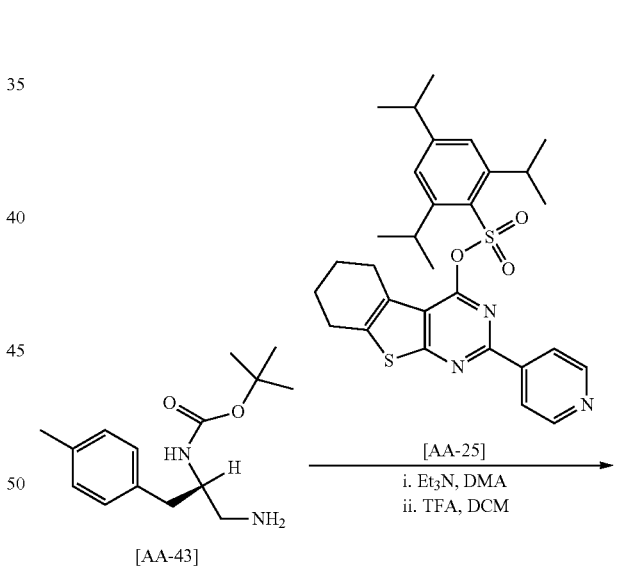

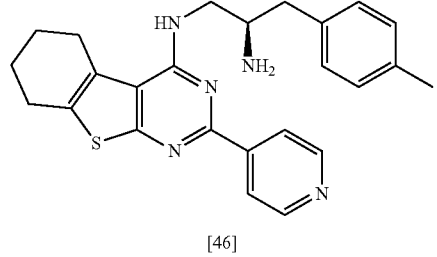

To a solution of 2,4,6-triisopropyl-benzenesulfonic acid 2-pyridin-4-yl-5,6,7,8-tetrahydro-benzo[4,5]thieno[2,3-d]pyrimidin-4-yl ester (100 mg, 0.182 mmol) [AA-25] in DMA (2 ml) was added [(S)-2-amino-1-(4-methyl-benzyl)-ethyl]-carbamic acid tert-butyl ester [AA-43] (58 mg, 0.218 mmol) followed by Et₃N (76 µl, 0.546 mmol), the mixture was stirred at room temperature for 2 hours. Then the product was extracted with DCM (2 ml) and washed with brine (3 ml). To the organic phase was added TFA (2 ml) and the mixture was stirred at room temperature for 1 hour. After completion the mixture was loaded onto a SCX-2 cartridge and washed with methanol. The product was released from the cartridge using a solution of 2M ammonia/methanol. The ammonia/methanol eluent was concentrated under reduced pressure and the crude product was purified by preparative HPLC (method B) to yield to the title compound. LCMS method: 4, RT: 4.85 min, MI: 430 [M+1]. 1H NMR (300 MHz, DMSO): 8.64 (d, 2H), 7.99 (d, 2H), 7.18 (m, 4H), 3.89 (m, 2H), 3.49 (m, 2H), 2.98 (m, 1H), 2.94 (m, 2H), 2.78 (m, 2H), 2.31 (s, 3H), 1.83 (m, 4H).

The following compounds were prepared according to the general synthesis shown in Scheme A7:

| Ex | SM | Amino acid [F-14] | Characterisation |
|---|---|---|---|
| 47 | [AA-25] | | method 3, RT: 2.47 min, MI: 446 [M + 1] |
| 48 | [AA-25] | | method; 3, RT: 2.64 min, MI: 430 [M + 1] |
| 49 | [AA-25] | | method: 3, RT: 2.66 min, MI: 446 [M + 1] |
| 50 | [AA-25] | | method: 3, RT: 2.76 min, MI: 434 [M + 1] |
| 51 | [AA-25] | | method 3, RT: 2.56 min, MI: 434 [M + 1] |
| 52 | [AA-25] | | method: 3, RT: 2.87 min, MI: 466 [M + 1] |
| 53 | [AA-25] | | method: 3, RT: 2.65 min, MI: 430 [M + 1] |
| 54 | [AA-25] | | method: 3, RT: 2.53 min, MI: 446 [M + 1] |
| 55 | [AA-25] | | method 3, RT: 2.23 min, MI: 432 [M + 1] |
| 56 | [AA-25] | | method: 3, RT: 1.87 min, MI: 417 [M + 1] |
| 57 | [AA-25] | | method: 3, RT: 1.98 min, MI: 417 [M + 1] |
| 58 | [AA-25] | | method: 3, RT: 2.18 min, MI: 417 [M + 1] |
| 59 | [AA-25] | | method: 3, RT: 2.26 min, MI: 423 [M + 1] |
| 60 | [AA-25] | | method: 3, RT: 2.44 min, MI: 396 [M + 1] |
| 61 | [AA-25] | | method: 3, RT: 2.59 min, MI: 472 [M + 1] |

| Ex | SM | Amino acid [F-14] | Characterisation |
|---|---|---|---|
| 62 | [AA-25] | (structure: piperidine with N-boc, (R)-carboxylic acid) | method: 3, RT: 2.21 min, MI: 380 [M + 1] |
| 63 | [AA-25] | (structure: (R)-tryptophan N-boc) | method: 4, RT: 4.60 min, MI: 455 [M + 1] |
| 64 | [AA-32] | (structure: (S)-2-methoxyphenylalanine N-boc) | method: 4, RT: 4.55 min, MI: 464 [M + 1] |

General Synthesis of (S)-3-(2 or 3-hydroxy-phenyl)-N*1*-(2-pyridin-4-yl-5,6,7,8-tetra hydro-benzo[4,5]thieno[2,3-d]pyrimidin-4-yl)-propane-1,2-diamine Derivatives of General Formula [F-18] (Scheme A8)

Compounds were synthesised starting from (S)-3-(2 or 3-methoxy-phenyl)-N*1*-(2-pyridin-4-yl-5,6,7,8-tetrahydro-benzo[4,5]thieno[2,3-d]pyrimidin-4-yl)-propane-1,2-diamine derivatives of general formula [F-17] (described in scheme A7) by a de-methylation reaction with a Lewis acid such as BBr₃ or AlCl₃ in a chlorinated solvent such as DCM or DCE at low reaction temperature. After reaction work up, typically by a liquid-liquid extraction or purification by acidic ion exchange catch-release, the crude reaction product was purified by reverse phase preparative HPLC.

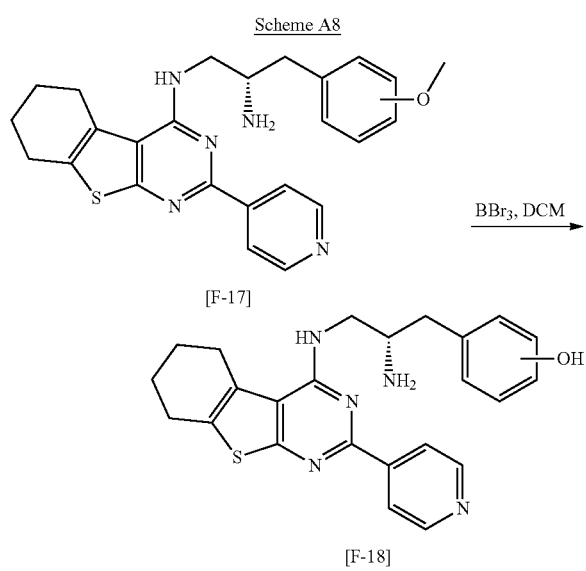

Scheme A8

Synthesis of 2-[(S)-2-amino-3-(2-pyridin-4-yl-5,6,7,8-tetrahydro-benzo[4,5]thieno[2,3-d]pyrimidin-4-ylamino)-propyl]-phenol [65]

To a solution of (S)-3-(2-methoxy-phenyl)-N*1*-(2-pyridin-4-yl-5,6,7,8-tetrahydro-benzo[4,5]thieno[2,3-d]pyrimidin-4-yl)-propane-1,2-diamine [49] (30 mg, 0.06 mmol) in DCM (1 ml) at −30° C. was added dropwise a solution of 1 M BBr₃ in DCM (180 µl, 0.180 mmol) under a nitrogen atmosphere. The reaction mixture was stirred at −30° C. for 1 hour and then stirred overnight at room temperature. The crude reaction mixture was concentrated under reduced pressure and then purified by preparative HPLC (method A) to yield to the title compound. LCMS method: 3, RT: 2.28 min, MI: 432 [M+1].

The following compounds were prepared according to the general synthesis shown in Scheme A8:

| Example | SM | Characterisation |
|---|---|---|
| 66 | [54] | method: 3, RT: 2.34 min, MI: 432 [M + 1] |

General Synthesis of 5,6 Substituted 4-amino-2-pyridin-4-yl-thieno[2,3-d]pyrimidine Derivatives of General Formula [F-1] (Scheme A9)

Compounds were synthesised starting from the hydrochloride or hydrobromide salt of an α-amino acid carboxamide derivative of general formula [F-19] which was converted to the free base by reaction with a base such as Et₃N or DIPEA in a chlorinated solvent such as DCM or DCE. The resultant free base was then reduced to a diamino derivative of general formula [F-20] by reaction with a borane reducing agent such as BH₃.THF or BH₃.SMe₂ in an anhydrous solvent such as THF, dioxane or diethylether. The resultant diamino derivative [F-20] was then reacted with a 5,6-substituted-(2,4,6-triisopropyl-benzenesulfonic acid)-2- pyridin-4-yl-thieno[2,3-d]pyrimidin-4-yl ester of general formula [F-12] [prepared in scheme A5] in a polar aprotic solvent such as DMA, DMF, NMP in the presence of a tertiary amine base such as Et₃N, DIPEA or NMM at ambient temperature. After reaction work up, typically by a liquid-liquid extraction or purification by acidic ion exchange catch-release the crude reaction product was purified by reverse phase preparative HPLC.

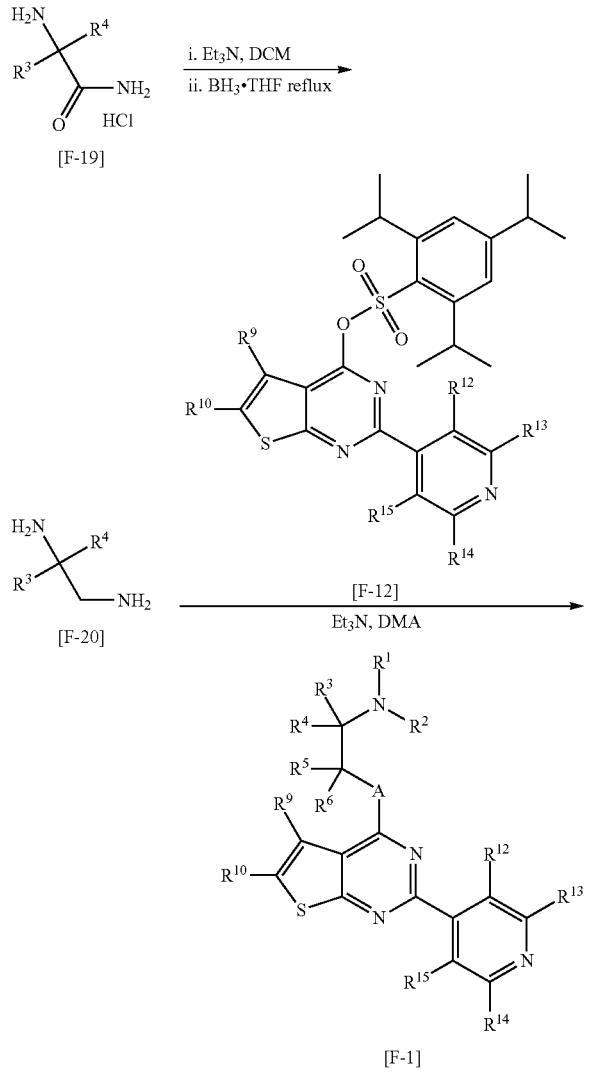

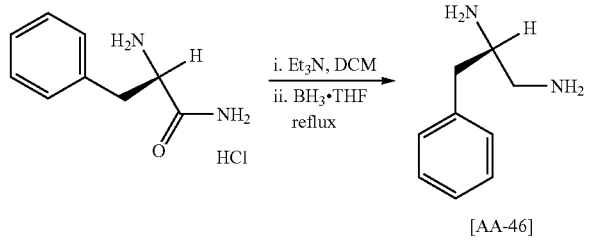

To a suspension of (S)-2-amino-3-phenyl-propionamide hydrochloride (540 mg, 2.7 mmol) in DCM (5 ml) was added Et₃N (3801, 2.7 mmol). The suspension was stirred for 2 h at room temperature, the resulting solid was filtered and the filtrate was concentrated under reduced pressure to yield to a white solid to which was added dropwise a 1M solution of BH₃ in THF (20 ml, 20 mmol) the solution was stirred overnight at reflux. After cooling the solution was hydrolysed by slow addition of excess of 10% acetic acid/MeOH (30 ml) and refluxed for a further 2 hours. The solvent was removed under reduced pressure, the residue dissolved in methanol and passed through a SCX-2 cartridge and washed with methanol. The product was released from the cartridge using a solution of 2M ammonia/methanol. The solvent was evaporated to provide the title compound as a white solid. LCMS method: 1, RT: 0.36 min, MI: 151 [M+1].

Synthesis of (S)—N*1*-(2-pyridin-4-yl-5,6,7,8-tetrahydro-benzo[4,5]thieno[2,3-d]pyrimidin-4-yl)-butane-1,2-diamine [67]

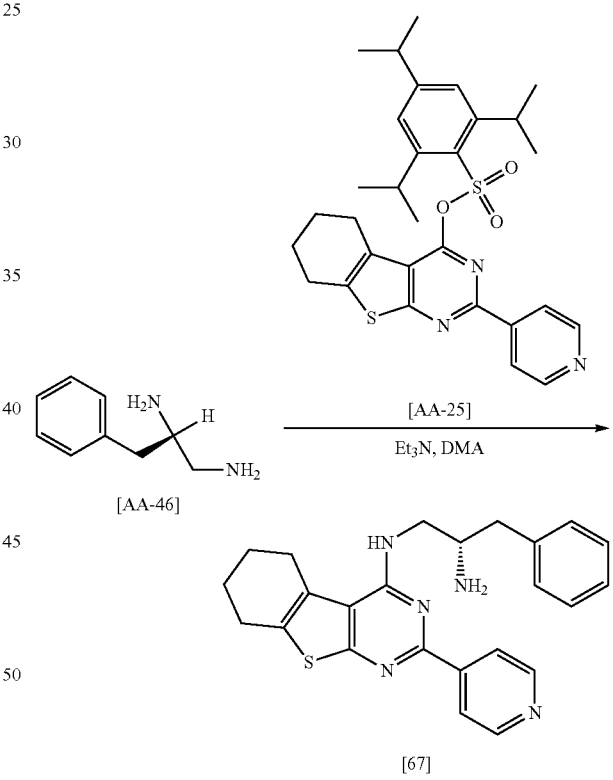

To a solution of 2,4,6-triisopropyl-benzenesulfonic acid 2-pyridin-4-yl-5,6,7,8-tetrahydro-benzo[4,5]thieno[2,3-d]pyrimidin-4-yl ester [AA-25] (100 mg, 0.180 mmol) in DMA (2 ml) was added (S)-3-phenyl-propane-1,2-diamine [AA-46] (30 mg, 0.180 mmol) followed by Et₃N (50 µl, 0.36 mmol), the mixture was stirred at room temperature for 2 hours. After completion the mixture was loaded onto a SCX-2 cartridge and washed with methanol. The product was released from the cartridge using a solution of 2M ammonia/methanol. The ammonia/methanol eluent was concentrated under reduced pressure and the crude product was purified by preparative HPLC (method A) to yield to the title compound. LCMS method: 4, RT: 2.51 min, MI: 416 [M+1]. 1H NMR (300 MHz, DMSO): 8.64 (d, 2H), 7.95 (d, 2H), 7.36 (m, 5H), 3.92 (m, 2H), 3.46 (m, 2H), 2.92 (m, 1H), 2.91 (m, 2H), 2.79 (m, 2H), 1.83 (m, 4H).

The following compounds were prepared according to the general synthesis shown in Scheme A9:

| Ex | SM [F-12] | Carboxamide [F-19] | Characterisation |
|---|---|---|---|
| 68 | [AA-25] | H₂N-C(=O)-CH(S)(NH₂)-CH₂CH₃ | method: 2, RT: 2.16 min, MI: 354 [M + 1]; 1H NMR (300 MHz, DMSO): 8.7(d, 2H), 8.2 (d, 2H), 3.9 (m, 1H), 3.6 (m, 1H), 3.3 (m, 1H), 1.8 (m, 4H), 1.6 (m, 2H), 1 (t, 3H) |
| 69 | [AA-26] | H₂N-C(=O)-CH(S)(NH₂)-CH₂-Ph | method: 2, RT: 2.94 min, MI: 430 [M + 1] |
| 70 | [AA-28] | H₂N-C(=O)-CH(R)(NH₂)-CH₂-Ph | method: 2, RT: 2.72 min, MI: 430 [M + 1] |
| 71 | [AA-25] | H₂N-C(=O)-CH(R)(NH₂)-CH₂-Ph | method: 3, RT: 2.54 min, MI: 416 [M + 1]; 1H NMR (300 MHz, DMSO): 8.67 (d, 2H), 7.9 (d, 2H), 7.3 (m, 5H), 3.9 (m, 2H), 3.53 (m, 2H), 2.92 (m, 1H), 2.91 (m, 2H), 2.79 (m, 2H), 1.83 (m, 4H) |
| 72 | [AA-33] | H₂N-C(=O)-CH(S)(NH₂)-CH₂-Ph | method: 3, RT: 2.52 min, MI: 521 [M + 1] |
| 73 | [AA-33] | H₂N-C(=O)-CH(R)(NH₂)-CH₂-Ph | method: 3, RT: 2.53 min, MI: 521 [M + 1] |
| 74 | [AA-38] | H₂N-C(=O)-CH(S)(NH₂)-CH₂-Ph | method: 2, RT: 2.31 min, MI: 419 [M + 1] |
| 75 | [AA-39] | H₂N-C(=O)-CH(S)(NH₂)-CH₂-Ph | method: 2, RT: 2.56 min, MI: 404 [M + 1] |
| 76 | [AA-27] | H₂N-C(=O)-CH(S)(NH₂)-CH₂-Ph | method: 2, RT: 2.95 min, MI: 444 [M + 1] |
| 77 | [AA-30] | H₂N-C(=O)-CH(S)(NH₂)-CH₂-Ph | method: 3, RT: 2.77 min, MI: 444 [M + 1] |
| 78 | [AA-29] | H₂N-C(=O)-CH(S)(NH₂)-CH₂-Ph | method: 3, RT: 2.37 min, MI: 474 [M + 1] |
| 79 | [AA-29] | H₂N-C(=O)-CH(S)(NH₂)-CH₂-Ph | method: 3, RT: 2.37 min, MI: 474 [M + 1] |
| 80 | [AA-32] | H₂N-C(=O)-CH(S)(NH₂)-CH₂-Ph | method: 3, RT: 2.59 min, MI: 434 [M + 1] |
| 81 | [AA-32] | H₂N-C(=O)-CH(S)(NH₂)-CH₂-Ph | method: 3, RT: 2.60 min, MI: 434 [M + 1] |
| 82 | [AA-31] | H₂N-C(=O)-CH(S)(NH₂)-CH₂-Ph | method: 3, RT: 2.23 min, MI: 418 [M + 1] |
| 83 | [AA-31] | H₂N-C(=O)-CH(S)(NH₂)-CH₂-Ph | method: 3, RT: 2.27 min, MI: 418 [M + 1] |

General Synthesis of 5,6 Substituted 4-amino-2-pyridin-4-yl-thieno[2,3-d]pyrimidine Derivatives of General Formula [F-1] (Scheme A10)

5,6-substituted 2-pyridin-4-yl-thieno [2,3-d]pyrimidin-4-ol derivatives of general formula [F-4] [prepared in scheme A2] were subjected to a activation reaction by reaction with a solid supported sulfonyl chloride derivative such as benzenesulfonyl chloride on polystyrene resin in a polar aprotic solvent such as DMA, DMF, NMP in the presence of a tertiary amine base such as Et₃N, DIPEA or NMM with a catalytic amount of DMAP at ambient temperature. Excess reagents and reactants were removed by filtration and washing the polystyrene resin with solvents such as DCM, DMF, THF. The polymer supported reagent of general formula [F-21] was then reacted with an N-Boc protected diamino derivative of general formula [F-13] in a polar aprotic solvent such as DMA, DMF, NMP in the presence of a tertiary amine base such as Et₃N, DIPEA or NMM at ambient temperature. The resin was filtered through a PTFE frit and washed with a solvent such as DCM or ethylacetate, the filtrate was combined and after reaction work up, typically by a liquid-liquid extraction or purification by acidic ion exchange catch-release, the N-Boc derivatives were deprotected under acidic conditions with a strong acid such as TFA, TCA, methanesulfonic acid, HCl or H₂SO₄ in a solvent such as DCM, DCE, THF, EtOH or MeOH and the crude reaction product was purified by reverse phase preparative HPLC.

Scheme A10

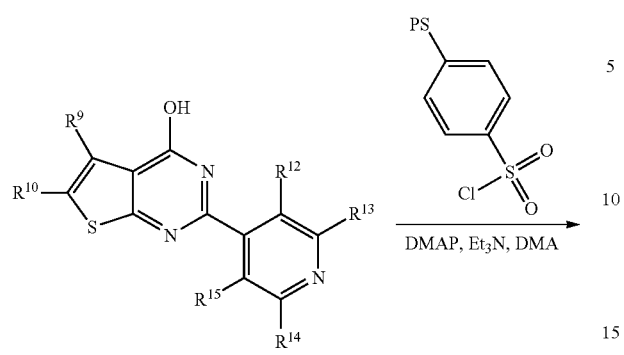

[F-4]

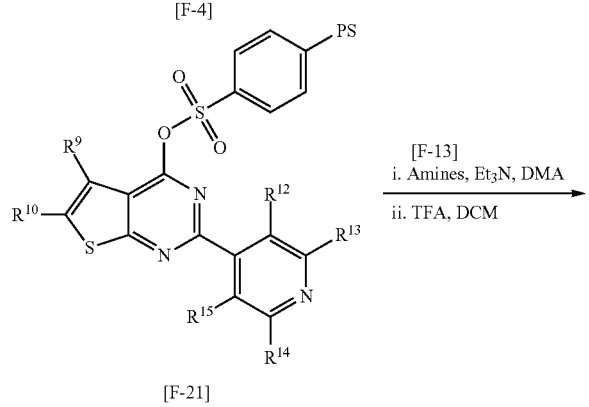

[F-21]

[F-13]
i. Amines, Et₃N, DMA
ii. TFA, DCM

[F-1]

Synthesis of polystyrene supported benzenesulfonic acid 2-pyridin-4-yl-6,7,8,9-tetrahydro-5H-10-thia-1,3-diaza-benzo[a]azulen-4-yl ester [AA-47]

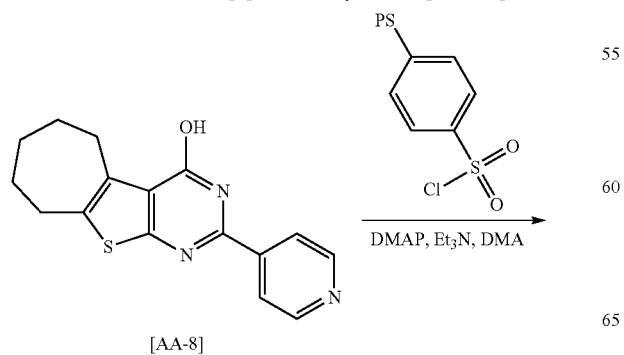

[AA-8]

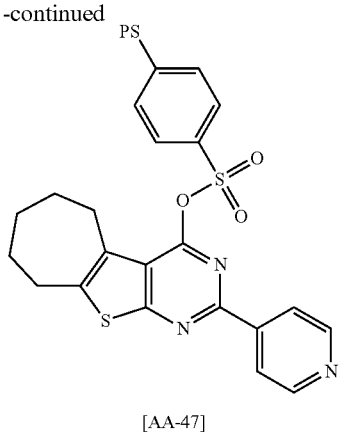

[AA-47]

2-pyridin-4-yl-6,7,8,9-tetrahydro-5H-10-thia-1,3-diaza-benzo[a]azulen-4-ol [AA-8] (70 mg, 0.241 mmol) and PS-TSCl (70 mg, 0.241 mmol) were placed into sealed filter cartridge. DMA was added (2 ml) followed by Et₃N (100 µl, 0.723 mmol) and DMAP (1.5 mg, 0.001 mmol). The reaction mixture was shaken for 3 hours at room temperature and then the resin was filtered, through a PTFE frit. The resin was washed with DCM to yield to the polystyrene supported benzenesulfonic acid 2-pyridin-4-yl-6,7,8,9-tetrahydro-5H-10-thia-1,3-diaza-benzo[a]azulen-4-yl ester [AA-77] which was used in the next step without further purification.

Synthesis of N*1*-(2-pyridin-4-yl-6,7,8,9-tetrahydro-5H-10-thia-1,3-diaza-benzo[a]azulen-4-yl)-ethane-1,2-diamine [84]

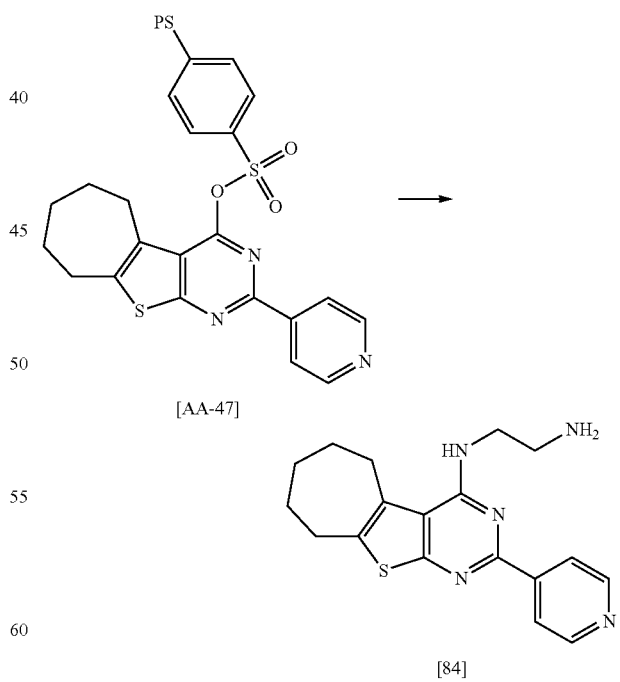

[AA-47]

[84]

The polystyrene supported benzenesulfonic acid 2-pyridin-4-yl-6,7,8,9-tetrahydro-5H-10-thia-1,3-diaza-benzo[a]azulen-4-yl ester [AA-47] (70 mg, 0.24 mmol) was placed in a filter cartridge and DMA (2 ml) was added followed by Boc-ethylenediamine (39 mg, 0.241 mmol) and Et₃N (67 μl, 0.482 mmol). The reaction was shaken overnight at room temperature. The resin was filtered through a PTFE frit and washed with ethylacetate. The filtrate was concentrated under reduced pressure and the crude product was dissolved in DCM (2 ml) and TFA (2 ml) was added and the mixture was stirred at room temperature for 1 hour. After completion the mixture was loaded onto a SCX-2 cartridge and washed with methanol. The product was released from the cartridge using a solution of 2M ammonia/methanol. The ammonia/methanol eluent was concentrated under reduced pressure and the crude product was purified by preparative HPLC (method A) to yield to the title compound. LCMS method: 2, RT: 3.22 min, MI: 340 [M+1].

The following compounds were prepared according to the general synthesis shown in Scheme A10:

| Ex | SM | Amine [F-13] | Characterisation | |
|---|---|---|---|---|
| 85 | [AA-8] | | method: 2, RT: 2.26 min, MI: 366 [M + 1] | 1H NMR (300 MHz, DMSO): 8.72 (d, 2H), 8.25 (d, 2H), 3.62 (m, 2H), 3.44 (m, 4H), 3.06 (m, 2H), 3.03 (m, 4H), 1.88 (m, 2H), 1.64 (m, 4H) |
| 86 | [AA-8] | | method: 2, RT: 2.27 min, MI: 380 [M + 1] | |
| 87 | [AA-8] | | method: 2, RT: 2.77 min, MI: 430 [M + 1] | |
| 88 | [AA-8] | | method: 2, RT: 2.25 min, MI: 354 [M + 1] | |
| 89 | [AA-8] | | method: 2, RT: 2.26 min, MI: 354 [M + 1] | 1H NMR (300 MHz, DMSO): 8.71 (d, 2H), 8.26 (d, 2H), 3.83 (m, 1H), 3.75 (m, 1H), 3.62 (m, 1H), 3.09 (m, 2H), 2.98 (m, 2H), 1.89 (m, 2H), 1.66 (m, 4H), 1.21 (d, 3H) |
| 90 | [AA-11] | | method: 2, RT: 2.63 min, MI: 517 [M + 1] | |
| 91 | [AA-22] | | method: 2, RT: 2.41 min, MI: 362 [M + 1] | |
| 92 | [AA-22] | | method: 2, RT: 2.41 min, MI: 402 [M + 1] | |
| 93 | [AA-23] | | method: 2, RT: 2.48 min, MI: 467 [M + 1] | |
| 94 | [AA-15] | | method: 2, RT: 1.90 min, MI: 312 [M + 1] | |
| 95 | [AA-15] | | method: 2, RT: 1.91 min, MI: 326 [M + 1] | |
| 96 | [AA-11] | | method: 2, RT: 2.32 min, MI: 441 [M + 1] | |

General Synthesis of pyridyl Substituted 4-amino-2-pyridin-4-yl-thieno[2,3-d]pyrimidine Derivatives of General Formula [F-1] (Scheme A11)

A 2,4-dichloro-5,6,7,8-tetrahydro-enzo[4,5]thieno [2,3-d] pyrimidine derivative of general formula [F-21] was reacted with primary and secondary amino derivative of general formula [F-13] in a polar aprotic solvent such as DMA, DMF, NMP in the presence of a tertiary amine base such as Et₃N, DIPEA or NMM at ambient temperature. Following reaction work up, typically by a liquid-liquid extraction or purification by acidic ion exchange catch-release, the amino derivative of general formula [F-23] was reacted with pyridyl boronic acids or boronate esters of general formula [F-24] in the presence of a palladium catalyst such as Pd(PPh₃)₄ or Pd(PPh₃)₂Cl₂ a base such as Et₃N, KOH, Na₂CO₃ or NaOH in a polar solvent such as EtOH, THF, DMA or dioxane at high temperature either by heating thermally or using a microwave reactor. Following reaction work up, typically by a liquid-liquid extraction or purification by acidic ion exchange catch-release the crude reaction product was purified by reverse phase preparative HPLC.

Scheme A11

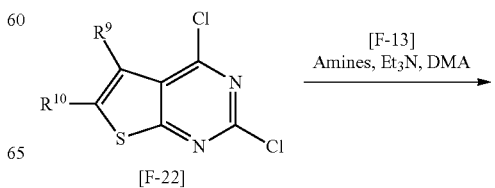

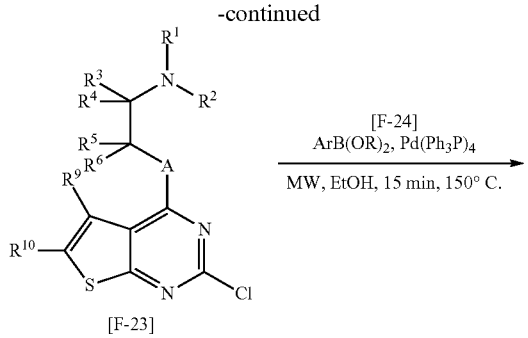

[F-23]

ArB(OR)$_2$, Pd(Ph$_3$P)$_4$ [F-24]

MW, EtOH, 15 min, 150° C.

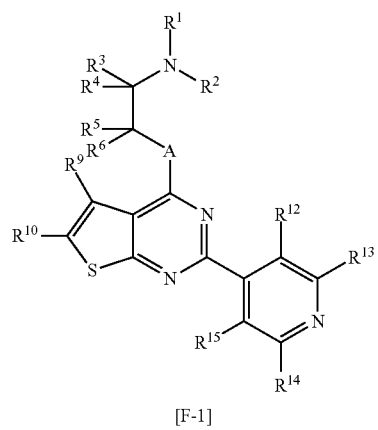

[F-1]

Synthesis of [2-(2-chloro-5,6,7,8-tetrahydro-benzo[4,5]thieno[2,3-d]pyrimidin-4-ylamino)-ethyl]-carbamic acid tert-butyl ester [AA-49]

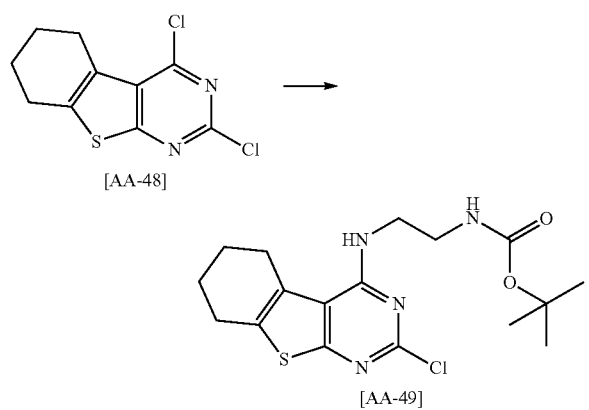

To a solution of 2,4-dichloro-5,6,7,8-tetrahydro-benzo[4,5]thieno[2,3-d]pyrimidine [AA-48] (100 mg, 0.387 mmol) in DMA (5 ml) was added Boc-ethylenediamine (62 mg, 0.387 mmol) followed by Et$_3$N (110 µl, 0.774 mmol), the mixture was stirred at room temperature for 2 hours. Then the product was extracted with DCM (2×10 ml) and washed with brine (2×10 ml). The combined organic phases were dried with magnesium sulfate, filtered and evaporated to provide a brown solid. The residue was used without further purification in the next step. LCMS method: 1, RT: 6.26 min, MI: 383 [M+1].

Synthesis of N*1*-[2-(3-fluoro-pyridin-4-yl)-5,6,7,8-tetrahydro-benzo[4,5]thieno [2,3-d]pyrimidin-4-yl]-ethane-1,2-diamine [97]

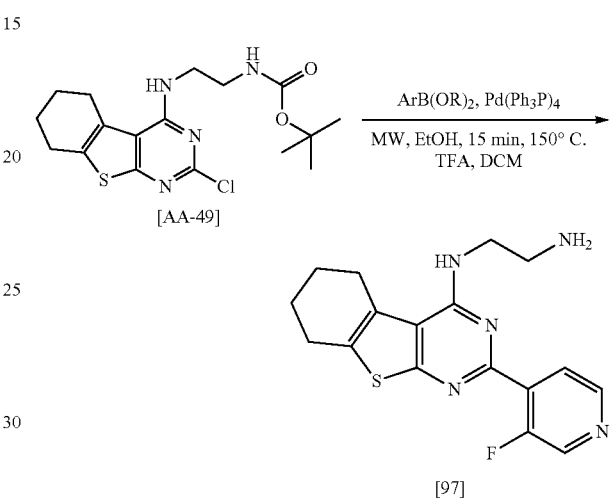

A microwave vial was charged with [2-(2-chloro-5,6,7,8-tetrahydro-benzo[4,5]thieno[2,3-d]pyrimidin-4-ylamino)-ethyl]-carbamic acid tert-butyl ester [AA-49] (80 mg, 0.210 mmol), 3-fluoropyridine-4-boronic acid hydrate (38 mg, 0.24 mmol), tetrakis (triphenyl phosphine) palladium (12 mg, 0.01 mmol), Na$_2$CO$_3$ (2M in water, 300 µl, 0.6 mmol) and EtOH (1 ml). The reaction was heated to 150° C. for 15 minutes under microwave irradiation. The mixture was then filtered through a plug of silica, washed with methanol and the filtrate was concentrated under reduced pressure. To a solution of the crude product in DCM (2 ml) was added TFA (2 ml) and the mixture was stirred at room temperature for 1 hour. After completion the mixture was loaded onto a SCX-2 cartridge and washed with methanol. The product was released from the cartridge using a solution of 2M ammonia/methanol. The ammonia/methanol eluent was concentrated under reduced pressure and the crude product was purified by preparative HPLC (method A) to yield to the title compound. LCMS method: 2, RT: 2.41 min, MI: 344 [M+1]. The following compounds were prepared according to the general synthesis shown in Scheme A11:

| Ex | SM | Boronic acid [F24] | Amine [F-13] | Characterisation |
|---|---|---|---|---|
| 98 | [AA-49] | 3-fluoro-pyridine-4-boronic acid | H$_2$N-CH$_2$CH$_2$-NH-boc | method: 2, RT: 2.64 min, MI: 344 [M + 1] |

| Ex | SM | Boronic acid [F24] | Amine [F-13] | Characterisation | |
|---|---|---|---|---|---|
| 99 | [AA-49] | 3-fluoro-4-pyridyl boronic acid | (R)-N-boc-1,2-diaminopropane | method: 2, RT: 2.56 min, MI: 358 [M + 1] | 1H NMR (300 MHz, DMSO): 8.677 (d, 1H), 8.26 (d, 1H), 8.34 (s, 1H), 3.83 (m, 1H), 3.75 (m, 1H), 3.62 (m, 1H), 2.91 (m, 2H), 2.79 (m, 2H), 1.66 (m, 4H), 1.21 (d, 3H) |
| 100 | [AA-49] | 3-fluoro-4-pyridyl boronic acid | (S)-N-boc-1,2-diaminopropane | method: 2, RT: 2.52 min, MI: 358 [M + 1] | |
| 101 | [AA-49] | 3-fluoro-4-pyridyl boronic acid | (S)-N-boc-phenylalaninamine | method: 2, RT: 2.79 min, MI: 434 [M + 1] | 1H NMR (300 MHz, DMSO): 8.64 (d, 1H), 8.53 (d, 1H), 7.83 (m, 1H), 7.26 (m, 5H), 3.92 (m, 2H), 3.46 (m, 2H), 2.92 (m, 1H), 2.91 (m, 2H), 2.79 (m, 2H), 1.83 (m, 4H) |
| 102 | [AA-49] | 3-methoxy-4-pyridyl boronic acid | (S)-N-boc-phenylalaninamine | method: 4, RT: 4.22 min, MI: 446 [M + 1] | |

Synthesis of 4-[4-((S)-2-Amino-3-phenyl-propylamino)-5,6,7,8-tetrahydro-benzo[4,5]thieno[2,3-d]pyrimidin-2-yl]-pyridin-3-ol [103] (Scheme A12)

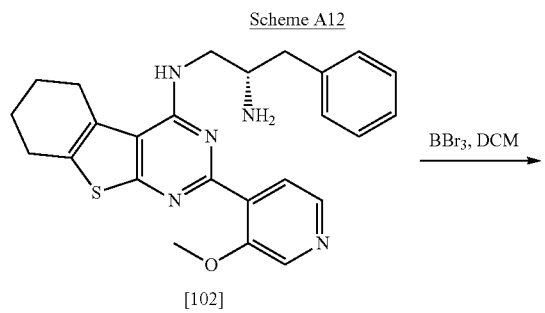

Scheme A12

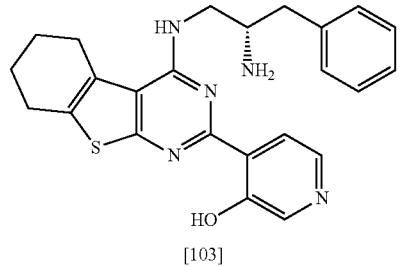

[103]

To a solution of (S)—N*1*-[2-(3-methoxy-pyridin-4-yl)-5,6,7,8-tetrahydro-benzo[2,3-d]pyrimidin-4-yl]-3-phenyl-propane-1,2-diamine (prepared according to the general synthesis shown in scheme A11) [102] (30 mg, 0.06 mmol) in DCM (1 ml) cooled to −30° C. was added dropwise a solution of 1 M BBr$_3$ in DCM (180 μl, 0.180 mmol) under nitrogen. The reaction mixture was stirred at −30° C. for 1 hour and stirred overnight at room temperature. The residue was concentrated under reduced pressure and then dissolved in DMSO and purified by preparative HPLC (method B) to yield to the title compound. LCMS method: 4, RT: 4.43 min, MI: 432 [M+1]. 1H NMR (300

MHz, DMSO): 8.30 (d, 1H), 8.10 (d, 1H), 7.81 d, 1H), 7.28 (m, 5H), 3.46 (m, 2H), 3.40 (m, 1H), 2.96 (m, 2H), 2.79 (m, 4H), 1.83 (m, 4H).

General Synthesis of 1-[4-(2-amino-ethylamino)-2-pyridin-4-yl-5,8-dihydro-6H-pyrido[4',3':4,5]thieno[2,3-d]pyrimidin-7-yl]-alkylanone Derivatives of General Formula [[F-26] (Scheme A13)

4-benzenesulfonyloxy-2-pyridin-4-yl-5,8-dihydro-6H-pyrido[4',3':4,5]thieno[2,3-d]pyrimidine-7-carboxylic acid tert-butyl ester [AA-11] (described in scheme A2) was subjected to an activation by reaction with a solid supported sulfonyl chloride derivative such as benzenesulfonyl chloride on polystyrene in a polar aprotic solvent such as DMA, DMF, NMP in the presence of a tertiary amine base such as Et$_3$N, DIPEA or NMM with a catalytic amount of DMAP at ambient temperature. Excess reagents and reactants were removed by filtration and washing the polystyrene resin with a solvent such as DCM, DMF, THF. The polymer supported reagent was then reacted with (2-amino-ethyl)-carbamic acid allyl ester in a polar aprotic solvent such as DMA, DMF, NMP in the presence of a tertiary amine base such as Et$_3$N, DIPEA or NMM at ambient temperature. The resin was fitted through a PTFE frit and washed with a solvent such as DCM or ethylacetate, the extracts were combined and after reaction work up, typically by a liquid-liquid extraction or purification by acidic ion exchange catch-release, the N-Boc derivative was deprotected under acidic conditions with a strong acid such as TFA, TCA, methanesulfonic acid, HCl or H$_2$SO$_4$ in a solvent such as DCM, DCE, THF, EtOH or MeOH to give [2-(2-pyridin-4-yl-5,6,7,8-tetrahydro-pyrido[4',3':4,5]thieno[2,3-d]pyrimidin-4-ylamino)-ethyl]-carbamic acid allyl ester [AA-50]. Reaction of pyridin-4-yl-5,6,7,8-tetrahydro-pyrido[4',3':4,5]thieno[2,3-d]pyrimidin-4-ylamino)-ethyl]-carbamic acid allyl ester [AA-50] with an acyl chloride derivative of general formula [F-27] in a polar aprotic solvent such as DMA, DMF, NMP in the presence of a tertiary amine base such as Et$_3$N, DIPEA or NMM gave the N-acylated [F-25] derivative which was subjected to an N-allyl deprotection reaction with polymer supported palladium, polymer supported borohydride in DCM, MeOH and water to give the corresponding amino derivates [F-26]. Following reaction work up, typically by a liquid-liquid extraction or purification by acidic ion exchange catch-release the crude reaction product was purified by reverse phase preparative HPLC.

Scheme A13

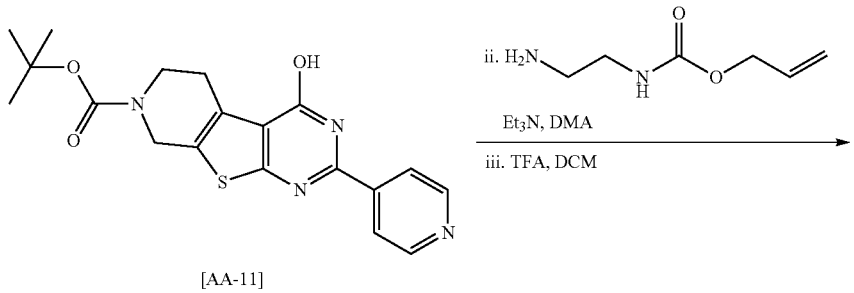

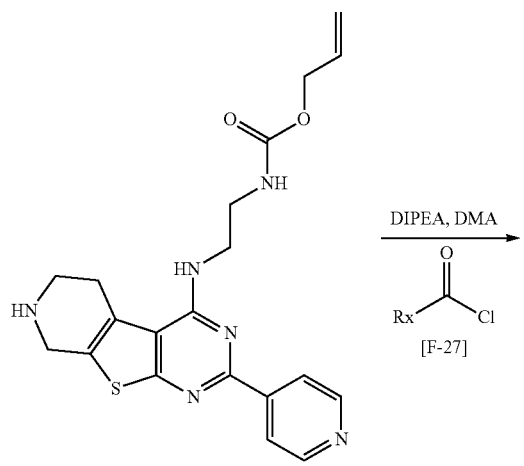

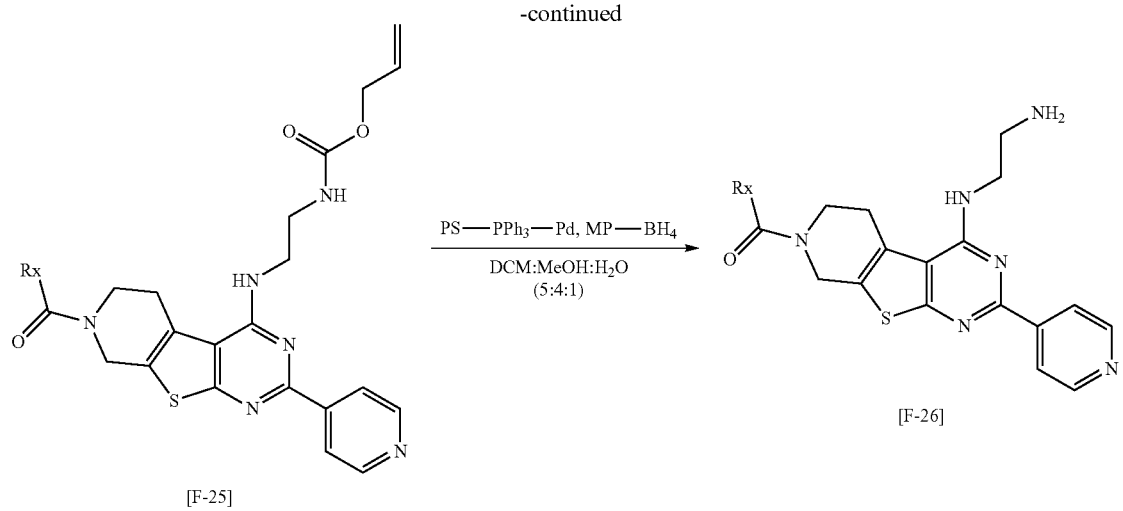

[F-25] → [F-26]

Synthesis of Polystyrene Supported 4-benzenesulfonyloxy-2-pyridin-4-yl-5,8-dihydro-6H-pyrido[4',3':4,5]thieno[2,3-d]pyrimidine-7-carboxylic acid tert-butyl ester [AA-51]

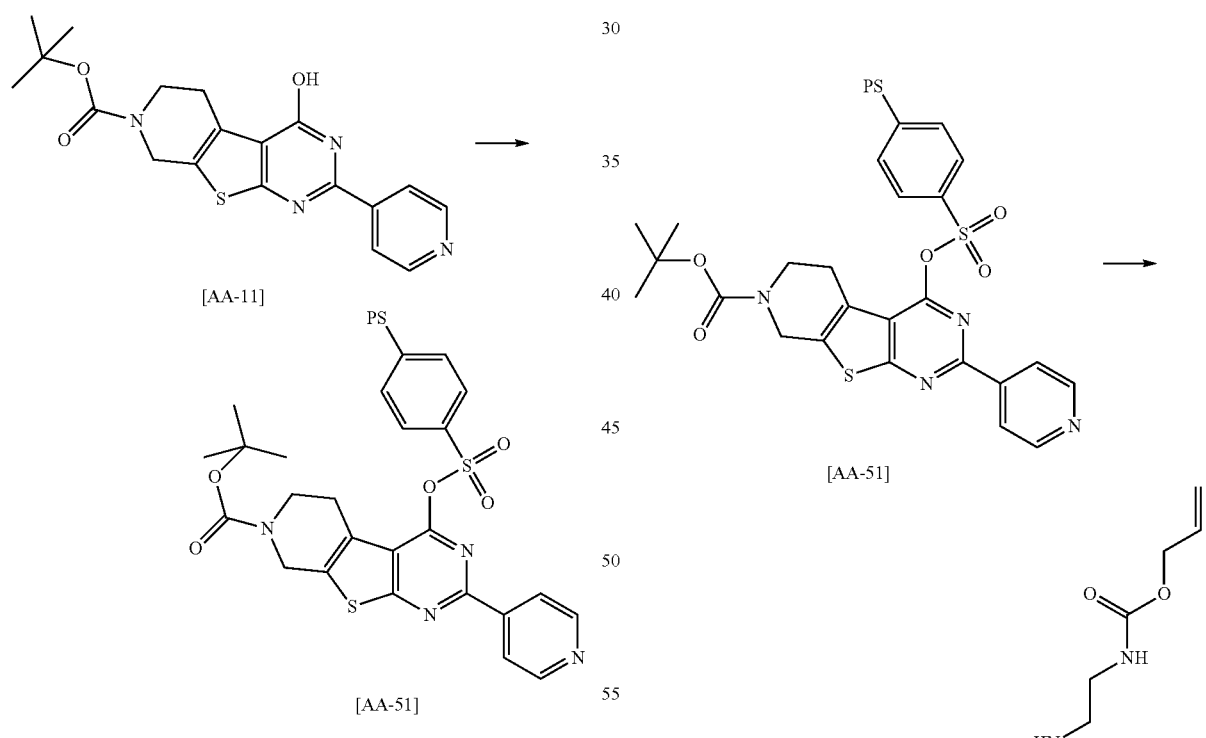

2-pyridin-4-yl-6,7,8,9-tetrahydro-5H-10-thia-1,3-diazabenzo[a]azulen-4-ol [AA-11] (700 mg, 1.83 mmol) and PS-TSCl (1.2 g, 2.92 mmol) were placed into filter cartridge closed with a stopper. DMA (10 ml) was added followed by Et₃N (510 μl, 3.66 mmol) and DMAP (11 mg, 0.09 mmol). The reaction was shaken for 3 hours at room temperature and then the resin was filtered through a PTFE frit. The resin was washed with DCM (6 ml) to yield to the polystyrene supported 4-benzenesulfonyloxy-2-pyridin-4-yl-5,8-dihydro-6H-pyrido[4',3':4,5]thieno [2,3-d]pyrimidine-7-carboxylic acid tert-butyl ester [AA-51], which was used in the next step without further purification.

Synthesis of [2-(2-pyridin-4-yl-5,6,7,8-tetrahydropyrido[4',3':4,5]thieno[2,3-d]pyrimidin-4-ylamino)-ethyl]-carbamic acid allyl ester [AA-50]

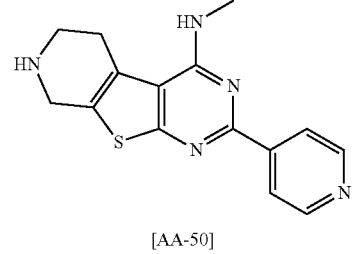

[AA-50]

205

To the polystyrene supported 4-benzenesulfonyloxy-2-pyridin-4-yl-5,8-dihydro-6H-pyrido[4',3':4,5]thieno [2,3-d]pyrimidine-7-carboxylic acid tert-butyl ester [AA-51] placed into a filter cartridge was added DMA (2 ml) followed by allyl-N-(2-aminoethyl)carbamate hydrochloride (397 mg, 2.2 mmol) and Et₃N (510 µl, 3.66 mmol). The reaction was shaken overnight at room temperature. The resin was filtered through a PTFE frit and washed with ethylacetate (6 ml) followed by DCM (6 ml). The extracts were combined and evaporated under reduced pressure. The crude reaction product was dissolved in DCM (25 ml) and washed with sodium hydrogen carbonate (20 ml) then brine (20 ml), dried with magnesium sulfate, filtered and evaporated under reduced pressure to provide an orange solid. To a solution of the crude product in DCM (5 ml) was added TFA (5 ml) and the mixture was stirred at room temperature for 1 hour. After completion the mixture was loaded onto a SCX-2 cartridge and washed with methanol. The product was released from the cartridge using a solution of 2M ammonia/methanol. The ammonia/methanol eluent was concentrated under reduced pressure and the crude product was used without further purification in the next step. LCMS method: 1, RT: 4.23 min, MI: 411 [M+1].

Synthesis of {2-[7-(2,2-dimethyl-propionyl)-2-pyridin-4-yl-5,6,7,8-tetrahydro-pyrido[4',3':4,5]thieno[2,3-d]pyrimidin-4-ylamino]-ethyl}-carbamic acid allyl ester [AA-52]

206

To a solution of [2-(2-pyridin-4-yl-5,6,7,8-tetrahydro-pyrido[4',3':4,5]thieno[2,3-d]pyrimidin-4-ylamino)-ethyl]-carbamic acid allyl ester [AA-50] (50 mg, 0.121 mmol) in DMA (1 ml) at −10° C. were added trimethylacetyl chloride (16 µl, 0.133 mmol) and N,N,-di-isopropyethylamine (60 µl, 0.363 mmol). The mixture was stirred overnight. After completion the reaction mixture was treated with water (2 ml) and brine (2 ml) and extracted with DCM (3 ml). The organics were evaporated under vacuum and the crude product was used without further purification in the next step.

Synthesis of 1-[4-(2-amino-ethylamino)-2-pyridin-4-yl-5,8-dihydro-6H-pyrido[4',3':4,5]thieno[2,3-d]pyrimidin-7-yl]-2,2-dimethyl-propan-1-one [104]

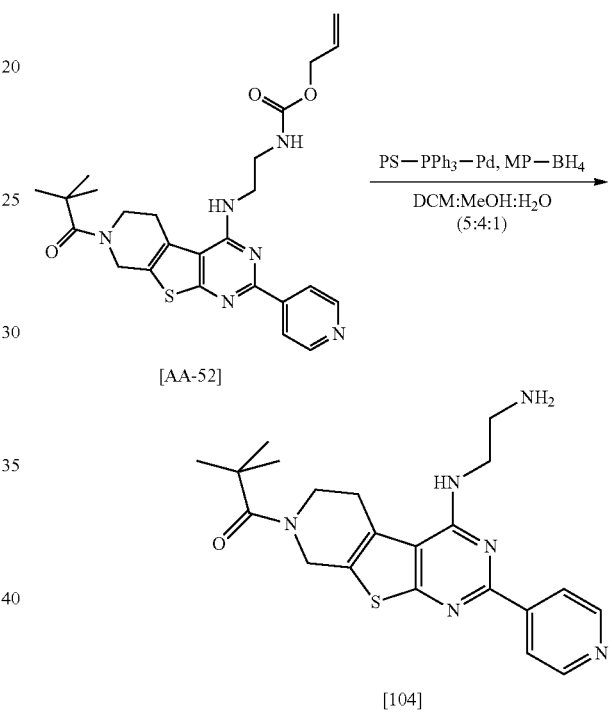

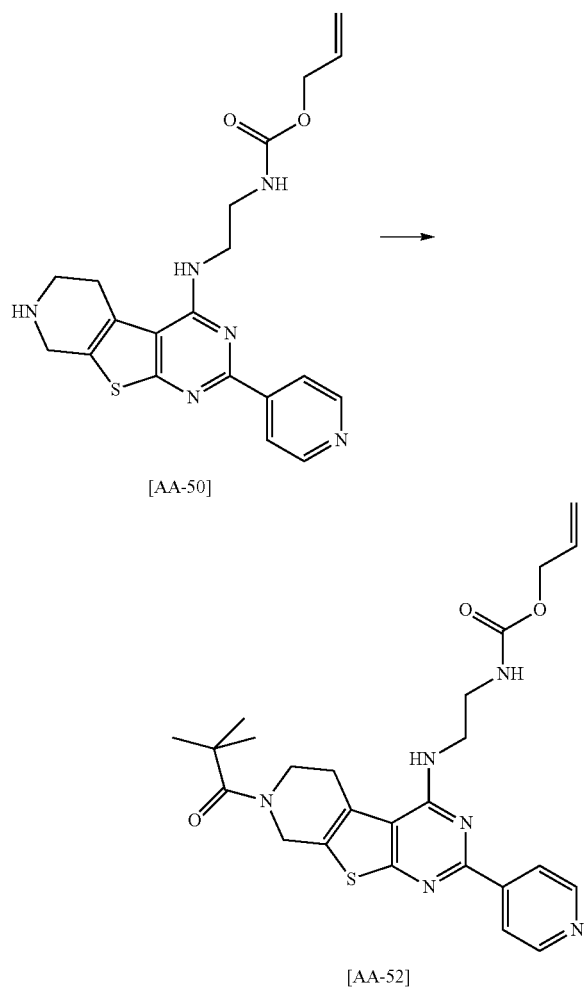

To a solution of {2-[7-(2,2-dimethyl-propionyl)-2-pyridin-4-yl-5,6,7,8-tetrahydro-pyrido[4',3':4,5]thieno[2,3-d]pyrimidin-4-ylamino]-ethyl}-carbamic acid allyl ester [AA-52] (50 mg, 0.121 mmol) in DCM:MeOH:H₂O (5:4:1) (2 ml) in a filter cartridge were added PS—PPh₃-Pd (18 mg, 0.002 mmol) and MP-BH₄ (116 mg, 0.363 mmol). The reaction was shaken for 2 h after then the solution was filtered through Na₂SO₄ plug. The filtrate was concentrated under reduced pressure and the crude residue was purified by preparative HPLC (method A) to yield to the title compound. LCMS method: 2, RT: 2.26 min, MI: 411 [M+1]. The following compounds were prepared according to the general synthesis shown in Scheme A13:

| Ex | SM | Acid chloride [F-27] | Characterisation |
|---|---|---|---|
| 105 | [AA-52] | ![acetyl chloride structure] | method: 2, RT: 1.83 min, MI: 369 [M + 1] |

207 -continued

| Ex | SM | Acid chloride [F-27] | Characterisation |
|---|---|---|---|
| 106 | [AA-52] | propionyl chloride | method: 2, RT: 1.97 min, MI: 383 [M + 1] |
| 107 | [AA-52] | isobutyryl chloride | method: 2, RT: 2.02 min, MI: 397 [M + 1] |
| 108 | [AA-52] | cyclopropanecarbonyl chloride | method: 2, RT: 2.01 min, MI: 395 [M + 1] |
| 109 | [AA-52] | cyclobutanecarbonyl chloride | method: 2, RT: 2.13 min, MI: 409 [M + 1] |
| 110 | [AA-52] | valeryl chloride | method: 2, RT: 2.32 min, MI: 411 [M + 1] |
| 111 | [AA-52] | N,N-dimethylglycyl chloride | method: 2, RT: 1.66 min, MI: 412 [M + 1] |

General Synthesis of N*1*-(7-alkyl-2-pyridin-4-yl-5,6,7,8-tetrahydro-pyrido[4',3':4,5]thieno [2,3-d]pyrimidin-4-yl)-ethane-1,2-diamine Derivatives of General Formula [F-28] (Scheme A14)

[2-(2-pyridin-4-yl-5,6,7,8-tetrahydro-pyrido[4',3':4,5]thieno[2,3-d]pyrimidin-4-ylamino)-ethyl]-carbamic acid allyl ester [AA-50] was reacted in reductive amination reaction with aldehyde derivative of general formula [F-30] and a solid supported borohydride reagent in acetic acid and a polar protic solvent such as MeOH or EtOH. The N-alkylated derivative of general formula [F-29] was subjected to an N-allyl deprotection reaction with polymer supported palladium, polymer supported borohydride in DCM, MeOH and water to provide the amino derivative [F-28]. Following reaction work up, typically filtration through a PTFE frit followed by a liquid-liquid extraction or purification by acidic ion exchange catch-release the crude reaction product was purified by reverse phase preparative HPLC.

Scheme A14

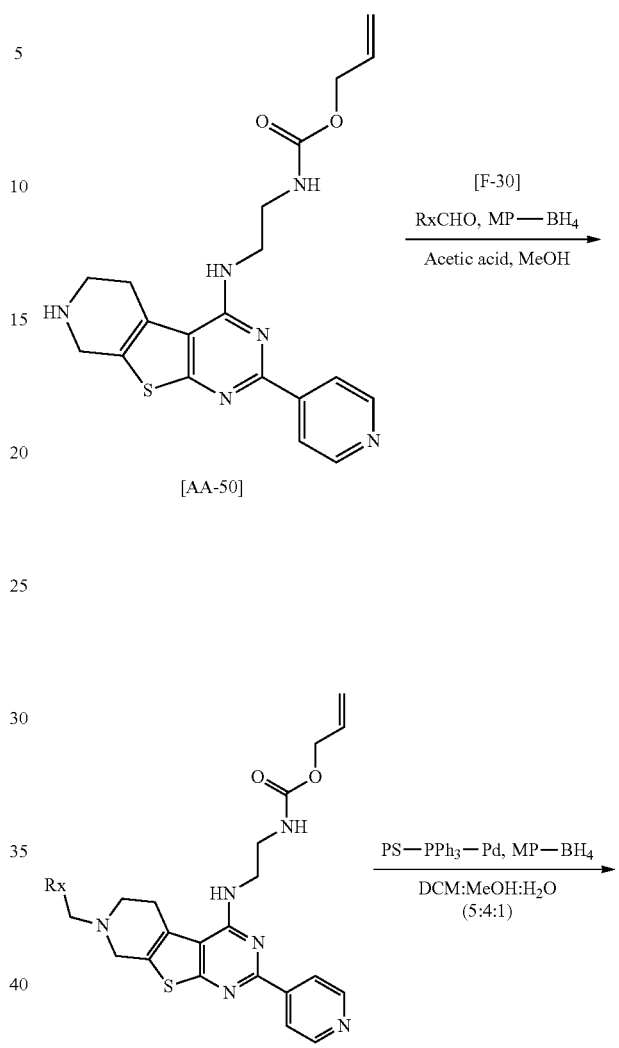

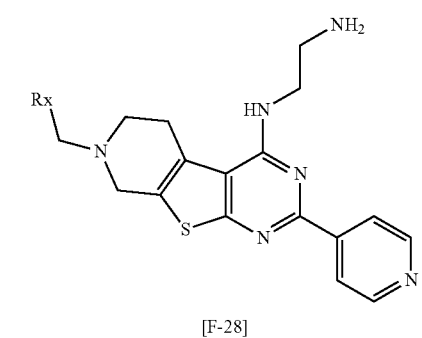

209
Synthesis of [2-(7-ethyl-2-pyridin-4-yl-5,6,7,8-tetra-hydro-pyrido[4',3':4,5]thieno[2,3-d]pyrimidin-4-ylamino)-ethyl]-carbamic acid allyl ester [AA-53]

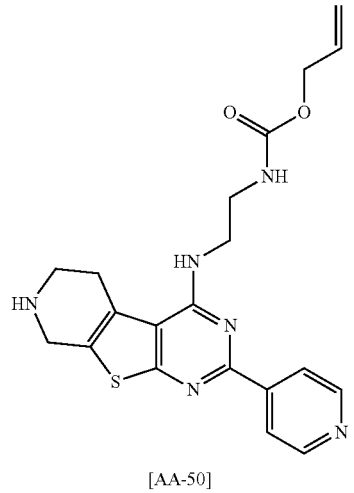

[AA-50]

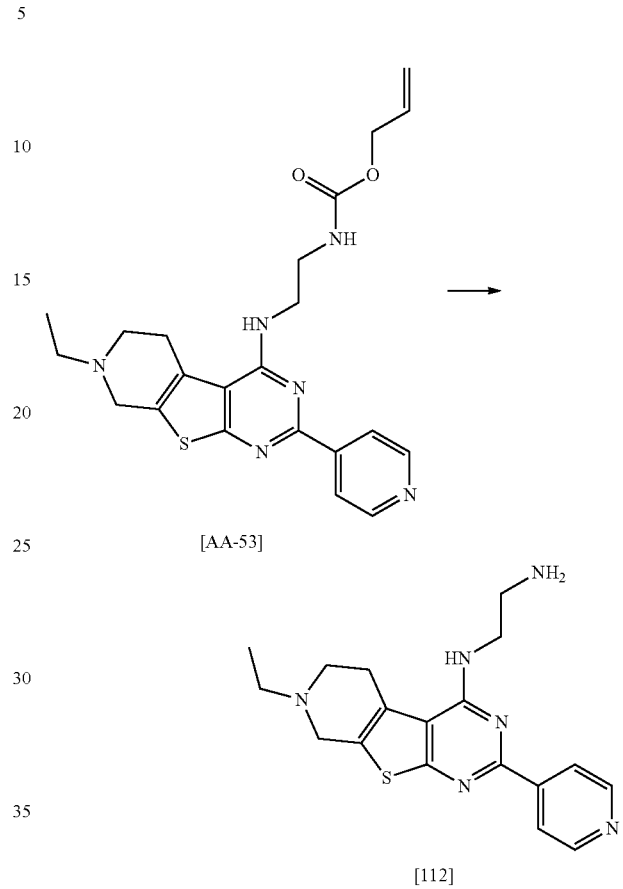

[AA-53]

To a solution of [2-(2-pyridin-4-yl-5,6,7,8-tetrahydro-pyrido[4',3':4,5]thieno[2,3-d]pyrimidin-4-ylamino)-ethyl]-carbamic acid allyl ester [AA-50] (50 mg, 0.121 mmol) in MeOH (1 ml) in a filter cartridge were added MP-BH$_4$ (144 mg, 0.290 mmol) followed by acetaldehyde (4 µl, 0.075 mmol) and acetic acid (7 µl, 0.121 mmol). The reaction was shaken overnight at room temperature and then filtered through a PTFE frit. The filtrate was evaporated under reduced pressure and the resulting residue was dissolved in methanol and the mixture was loaded onto a SCX-2 cartridge and washed with methanol. The product was released from the cartridge using a solution of 2M ammonia/methanol. The ammonia/methanol eluent was concentrated under reduced pressure to yield the title compound which was used without further purification in the next step.

210
Synthesis of N*1*-(7-ethyl-2-pyridin-4-yl-5,6,7,8-tetrahydro-pyrido[4',3':4,5]thieno[2,3-d]pyrimidin-4-yl)-ethane-1,2-diamine [112]

To a solution of [2-(7-ethyl-2-pyridin-4-yl-5,6,7,8-tetra-hydropyrido[4',3':4,5]-thieno[2,3-d]pyrimidin-4-ylamino)-ethyl]-carbamic acid allyl ester [AA-53] (50 mg, 0.121 mmol) in DCM:MeOH:H$_2$O (5:4:1) (2 ml) in a filter cartridge were added PS—PPh$_3$-Pd (18 mg, 0.002 mmol) and MP-BH$_4$ (116 mg, 0.363 mmol). The reaction was shaken for 2 h after completion the solution was filtered through Na$_2$SO$_4$ plug. The filtrate was concentrated under reduced pressure and the residue purified by preparative HPLC (method A) to yield to the title compound. LCMS method: 2, RT: 1.89 min, MI: 355 [M+1].

The following compounds were prepared according to the general synthesis shown in Scheme A14:

| Ex | SM | Aldehyde [F-30] | Characterisation |
|---|---|---|---|
| 113 | [AA-50] | O=CH-CH$_3$ | method: 2, RT: 1.96 min, MI: 341 [M + 1] |
| 114 | [AA-50] | (CH$_3$)$_2$CHCH$_2$CHO | method: 2, RT: 1.61 min, MI: 383 [M + 1] |

General Synthesis of 4-(4-alkyl-piperazin-1-yl)-2-pyridin-4-yl-5,6,7,8-tetrahydro-benzo[4,5]thieno[2,3-d]pyrimidine Derivatives of General Formula [F-31] (Scheme A15)

4-piperazin-1-yl-2-pyridin-4-yl-5,6,7,8-tetrahydro-benzo[4,5]thieno[2,3-d]pyrimidine [3] was subjected to a reductive amination reaction with aldehyde derivatives of general formula [F-30] and a solid supported borohydride reagent in acetic acid and a polar protic solvent such as MeOH or EtOH to yield the alkylated derivative [F-27]. Following reaction work up, typically by a liquid-liquid extraction or purification by acidic ion exchange catch-release the crude reaction product was purified by reverse phase preparative HPLC.

Scheme A15

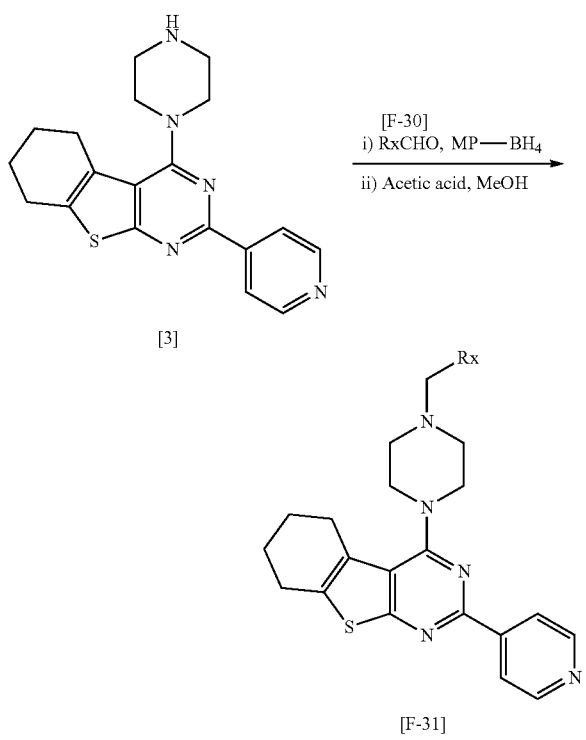

Synthesis of 4-(4-benzyl-piperazin-1-yl)-2-pyridin-4-yl-5,6,7,8-tetrahydro-benzo[4,5]thieno[2,3-d]pyrimidine [115]

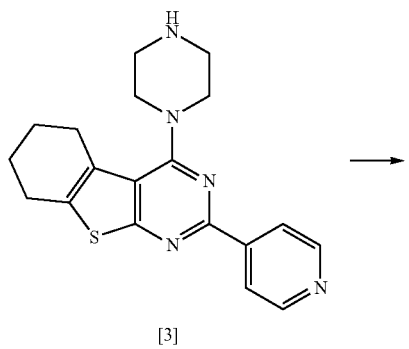

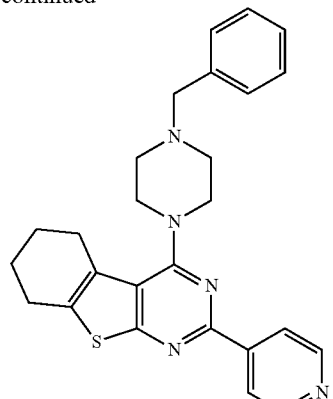

To a solution of 4-piperazin-1-yl-2-pyridin-4-yl-5,6,7,8-tetrahydro-benzo[4,5]thieno[2,3-d]pyrimidine [3] (50 mg, 0.142 mmol) in MeOH (2 ml) in a filter cartridge were added MP-BH$_4$ (170 mg, 0.341 mmol), p-anisaldehyde (11 μl, 0.09 mmol) and acetic acid (8 μl, 0.142 mmol). The reaction was shaken overnight at room temperature and then filtered through a PTFE frit. The filtrate was evaporated under reduced pressure and the resulting residue was dissolved in methanol and the mixture was loaded onto a SCX-2 cartridge and washed with methanol. The product was released from the cartridge using a solution of 2M ammonia/methanol. The ammonia/methanol eluent was concentrated under reduced pressure and purified by preparative HPLC (method A) to yield to the title compound. LCMS method: 2, RT: 2.61 min, MI: 456 [M+1]. 1H NMR (300 MHz, DMSO): 8.70 (d, 2H), 8.22 (d, 2H), 7.21 (d, 2H), 7.15 (d, 2H), 3.47 (m, 7H), 2.90 (m, 5H), 2.54 (s, 2H), 2.28 (s, 3H), 1.87 (br s, 2H), 1.73 (br s, 2H).

The following compounds were prepared according to the general synthesis shown in Scheme A15:

| Ex | SM | Aldehyde [F-30] | Characterisation |
|---|---|---|---|
| 116 | [3] | benzaldehyde | method: 2, RT: 2.56 min, MI: 442 [M + 1] |
| 117 | [3] | 4-bromobenzaldehyde | method: 2, RT: 2.77 min, MI: 520 [M + 1] |
| 118 | [3] | isonicotinaldehyde | method: 2, RT: 2.3 min, MI: 443 [M + 1] |
| 119 | [3] | acetaldehyde | method: 2, RT: 2.22 min, MI: 380 [M + 1] |

213 -continued

| Ex | SM | Aldehyde [F-30] | Characterisation |
|---|---|---|---|
| 120 | | pyridine-2-carbaldehyde | method: 2, RT: 2.32 min, MI: 443 [M + 1] |
| 121 | [3] | 4-(trifluoromethyl)benzaldehyde | method: 2, RT 2.97 min, MI: 510 [M + 1]  1H NMR (300 MHz, DMSO): 8.72 (d, 2H), 8.24 (d, 2H), 8.17 (s, 1H), 7,73 (d, 2H), 7.58 (d, 2H), 3,66 (s, 2H), 3.51 (m, 4H), 2.9 (m, 4H), 2.61 (m, 2H), 2.53 (m, 2H), 1.87 (m, 2H), 1.74 (m, 2H) |
| 122 | [3] | 4-chlorobenzaldehyde | method: 2, RT: 2.72 min, MI: 476 [M + 1] |
| 123 | [3] | 2-chlorobenzaldehyde | method: 2, RT 2.78 min, MI: 476 [M + 1] |
| 124 | [3] | 3-chlorobenzaldehyde | method: 2, RT: 2.76 min, MI: 476 [M + 1]  1H NMR (300 MHz, DMSO): 8.68 (d, 2H), 8.22 (d, 2H), 8.16 (s, 1H), 7.34 (m, 4H), 3.45 (s, 2H), 3.48 (m, 4H), 2.87 (m, 4H), 2.57 (m, 2H), 2.53 (m, 2H), 1.87 (m, 2H), 1.73 (m, 2H) |
| 125 | [3] | formaldehyde | method: 2, RT: 2.19 min, MI: 366 [M + 1]  1H NMR (300 MHz, DMSO): 8.68 (d, 2H), 8.22 (d, 2H), 3.48 (m, 4H), 2.87 (m, 4H), 2.57 (m, 2H), 2.53 (m, 2H), 2.28 (s, 3H), 1.87 (d, 2H), 1.72 (d, 2H) |
| 126 | [3] | 3-hydroxybenzaldehyde | method: 2, RT: 2.41 min, MI: 458 [M + 1] |
| 127 | [3] | 3-bromobenzaldehyde | method: 2, RT 2.83 min, MI: 520 [M + 1] |
| 128 | [3] | 6-bromopyridine-3-carbaldehyde | method: 2, RT: 2.57 min, MI: 520 [M + 1] |
| 129 | [3] | butyraldehyde | method: 2, RT: 2.32 min, MI: 408 [M + 1] |

214 -continued

| Ex | SM | Aldehyde [F-30] | Characterisation |
|---|---|---|---|
| 130 | [3] | pyridine-3-carbaldehyde | method: 2, RT: 2.23 min, MI: 443 [M + 1]  1H NMR (300 MHz, DMSO): 8.69 (d, 2H), 8.53 (s, 1H), 8.48 (m, 1H), 8.23 (d, 2H), 7.75 (m, 1H), 7.35 (m, 1H), 3.58 (m, 2H), 3.48 (m, 4H), 2.88 (m, 4H), 2.59 (m, 2H), 2.53 (m, 4H), 1.87 (m, 2H), 1.73 (m, 2H) |
| 131 | [3] | 3-bromopyridine-4-carbaldehyde | method: 2, RT: 3.28 min, MI: 520 [M + 1] |
| 132 | [3] | phenylacetaldehyde | method: 2, RT: 2.57 min, MI: 456 [M + 1] |
| 133 | [3] | propanal | method: 2, RT: 2.30 min, MI: 394 [M + 1] |
| 134 | [3] | isobutyraldehyde | method: 2, RT: 2.32 min, MI: 408 [M + 1] |

General Synthesis of 5,6 Substituted 4-alkoxy-2-pyridin-4-yl-thieno[2,3-d]pyrimidine Derivatives of General Formula [F-32] (Scheme A16)

4-chloro-2-pyridin-4-yl-5,6,7,8-tetrahydro-benzo[4,5]thieno[2,3-d]pyrimidine [AA-24] was subjected to a nucleophilic substitution reaction with an amino alcohol or N-Boc protected amino alcohol of general formula [F-33] in the presence of a strong base such as NaH, KH or LDA in the presence of an anhydrous polar aprotic solvent such as DMA, DMF or NNP. After reaction work up, typically by a liquid-liquid extraction or purification by acidic ion exchange catch-release, the N-Boc derivative was deprotected under acidic conditions with a strong acid such as TFA, TCA, methanesulfonic acid, HCl or $H_2SO_4$ in a solvent such as DCM, DCE, THF, EtOH or MeOH and the crude reaction product was purified by reverse phase preparative HPLC.

Scheme A16

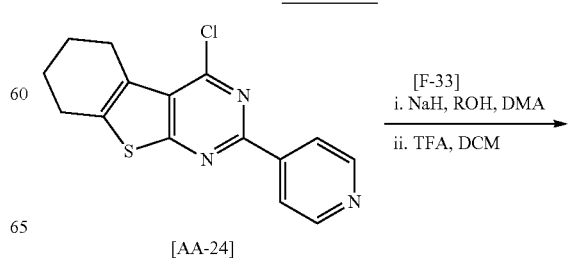

[AA-24]  →  [F-33]
i. NaH, ROH, DMA
ii. TFA, DCM

215
-continued

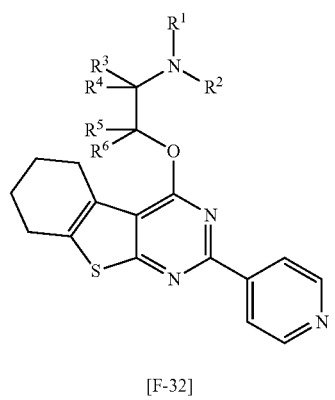

[F-32]

Synthesis of dimethyl-[2-(2-pyridin-4-yl-5,6,7,8-tetrahydro-benzo[4,5]thieno[2,3-d]pyrimidin-4-yloxy)-ethyl]-amine [135]

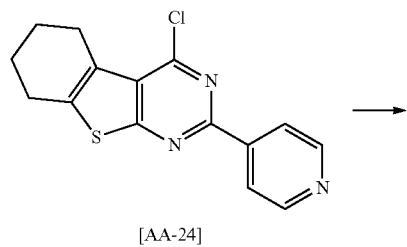

[AA-24]

↓

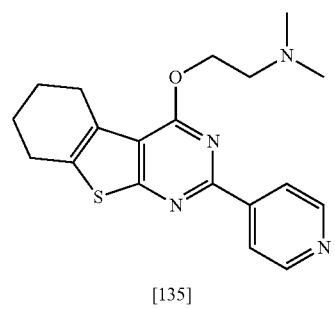

[135]

To a mixture of 4-chloro-2-pyridin-4-yl-5,6,7,8-tetrahydro-benzo[4,5]thieno[2,3-d]pyrimidine [AA-24] (80 mg, 0.280 mmol) and 2-dimethylaminoethanol (34 μl, 0.340 mmol) in DMA (1 ml) was added NaH (13 mg, 0.560 mmol). The reaction mixture was allowed to stir at room temperature for 2 hours and after completion the mixture was diluted with water and the product was extracted into DCM (2×2 ml). The combined organic phases were dried with magnesium sulfate, filtered and evaporated under reduced pressure and the crude product was purified by preparative HPLC (method A) to yield to the title compound. LCMS method: 2, RT: 2.20 min, MI: 355 [M+1]. 1H NMR (300 MHz, DMSO): 8.70 (d, 2H), 8.22 (d, 2H), 3.1 (m, 2H), 2.9 (m, 2H), 2.75 (m, 2H), 2.65 (m, 2H), 2.34 (s, 6H), 1.83 (m, 4H).

216

Synthesis of methyl-[2-(2-pyridin-4-yl-5,6,7,8-tetrahydro-benzo[4,5]thieno[2,3-d]pyrimidin-4-yloxy)-ethyl]-amine [136]

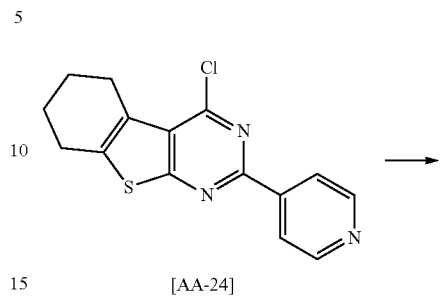

[AA-24]

→

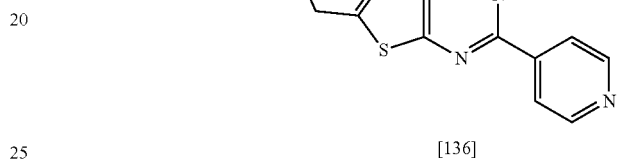

[136]

To a mixture of 4-chloro-2-pyridin-4-yl-5,6,7,8-tetrahydro-benzo[4,5]thieno[2,3-d]pyrimidine [AA-24] (80 mg, 0.280 mmol) and tert-butyl-N-2-hydroxyethylcarbamate (53 μl, 0.340 mmol) in DMA (1 ml) was added NaH (13 mg, 0.560 mmol). The reaction mixture was allowed to stir at room temperature for 2 hours and after completion the mixture was diluted with water and the product was extracted into DCM (2×2 ml). The combined organic phases were dried with magnesium sulfate, filtered and evaporated under vacuum. To a solution of the crude product in DCM (1 ml) was added TFA (1 ml) and the mixture was stirred at room temperature for 1 hour. After completion the mixture was loaded onto a SCX-2 cartridge and washed with methanol. The product was released from the cartridge using a solution of 2M ammonia/methanol. The ammonia/methanol eluent was concentrated under reduced pressure and the product was purified by preparative HPLC (method A) to yield to the title compound. LCMS method: 2, RT: 2.16 min, MI: 327 [M+1]. 1H NMR (300 MHz, DMSO): 8.70 (d, 2H), 8.3 (d, 2H), 2.96 (m, 2H), 2.8 (m, 2H), 2.56 m, 2H), 2.45 (m, 2H), 1.81 (m, 4H).

The following compounds were prepared according to the general synthesis shown in Scheme A16:

| Ex | SM | Alcohol [F-33] | Characterisation |
|---|---|---|---|
| 137 | [AA-24] | HO∼∼N(boc)(Me) | method: 2, RT: 2.83 min, MI: 341 [M + 1] |
| 138 | [AA-24] | HO-CH2-CH(NHboc)-CH2-CH(Me)2 (S) | method: 2, RT: 2.45 min, MI: 383 [M + 1] |
| 139 | [AA-24] | HO-(S)-pyrrolidine-N-boc | method: 2, RT: 2.20 min, MI: 353 [M + 1] |

-continued

| Ex | SM | Alcohol [F-33] | Characterisation |
|---|---|---|---|
| 140 | [AA-24] | (R)-1-Boc-3-hydroxypyrrolidine | method: 2, RT: 2.20 min, MI: 353 [M + 1] |
| 141 | [AA-24] | 1-Boc-3-hydroxypiperidine | method: 2, RT: 2.29 min, MI: 367 [M + 1] |
| 142 | [AA-24] | (R)-N-Boc-phenylalaninol | method: 2, RT: 2.60 min, MI: 417 [M + 1] |
| 143 | [AA-24] | (S)-N-Boc-phenylalaninol | method: 2, RT: 2.56 min, MI: 417 [M + 1] |
| 144 | [AA-24] | (S)-N-Boc-alaninol | method: 2, RT: 2.22 min, MI: 341 [M + 1] |
| 145 | [AA-24] | (R)-N-Boc-alaninol | method: 2, RT: 2.88 min, MI: 341 [M + 1] |
| 146 | [AA-24] | (R)-N-Boc-leucinol | method: 2, RT: 2.52 min, MI: 383 [M + 1] |
| 147 | [AA-24] | (R)-N-Boc-phenylglycinol | method: 2, RT: 3.47 min, MI: 403 [M + 1] |
| 148 | [AA-24] | (R)-N-Boc-valinol | method: 2, RT: 2.37 min, MI: 369 [M + 1] |

-continued

| Ex | SM | Alcohol [F-33] | Characterisation |
|---|---|---|---|
| 149 | [AA-24] | (R)-N-Boc-2-amino-1-butanol | method: 2, RT: 2.31 min, MI: 355 [M + 1] |
| 150 | [AA-24] | (S)-N-Boc-2-amino-1-butanol | method: 2, RT: 2.32 min, MI: 355 [M + 1] |
| 151 | [AA-24] | (S)-N-Boc-valinol | method: 2, RT: 2.40 min, MI: 369 [M + 1] |
| 152 | [AA-24] | 1-Boc-3-hydroxyazetidine | method: 2, RT: 2.21 min, MI: 339 [M + 1] |
| 153 | [AA-24] | (R)-1-Boc-2-(hydroxymethyl)pyrrolidine | method: 2, RT: 2.27 min, MI: 367 [M + 1] |
| 154 | [AA-24] | (S)-1-Boc-2-(hydroxymethyl)pyrrolidine | method: 2, RT: 2.27 min, MI: 367 [M + 1] |
| 155 | [AA-24] | (S)-N-Boc-phenylglycinol | method: 2, RT: 2.49 min, MI: 403 [M + 1] |

219

General Synthesis of 5,6 substituted 4-alkoxy-2-pyridin-4-yl-thieno[2,3-d]pyrimidines [F-32] (Scheme A17)

2,4,6-triisopropyl-benzenesulfonic acid 2-pyridin-4-yl-5,6,7,8-tetrahydro-benzo[4,5]thieno[2,3-d]pyrimidin-4-yl ester [AA-25] was subjected to a nucleophilic substitution reaction with a N-Boc protected amino alcohol of general formula F-33] in the presence of a strong base such as NaH, KH or LDA in the presence of an anhydrous polar aprotic solvent such as DMA, DMF or NNP. After reaction work up, typically by a liquid-liquid extraction or purification by acidic ion exchange catch-release, the N-Boc derivative was deprotected under acidic conditions with a strong acid such as TFA, TCA, methanesulfonic acid, HCl or $H_2SO_4$ in a solvent such as DCM, DCE, THF, EtOH or and the crude reaction product was purified by reverse phase preparative HPLC.

Scheme A17

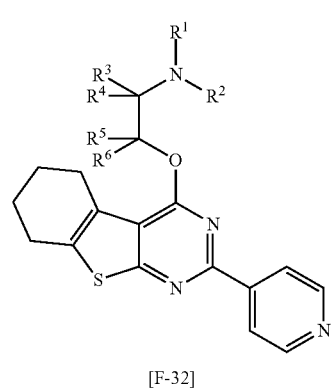

220

Synthesis of(S)-1-cyclohexyl-2-(2-pyridin-4-yl-5,6,7,8-tetrahydro-benzo[4,5]thieno[2,3-d]pyrimidin-4-yloxy)-ethylamine [156]

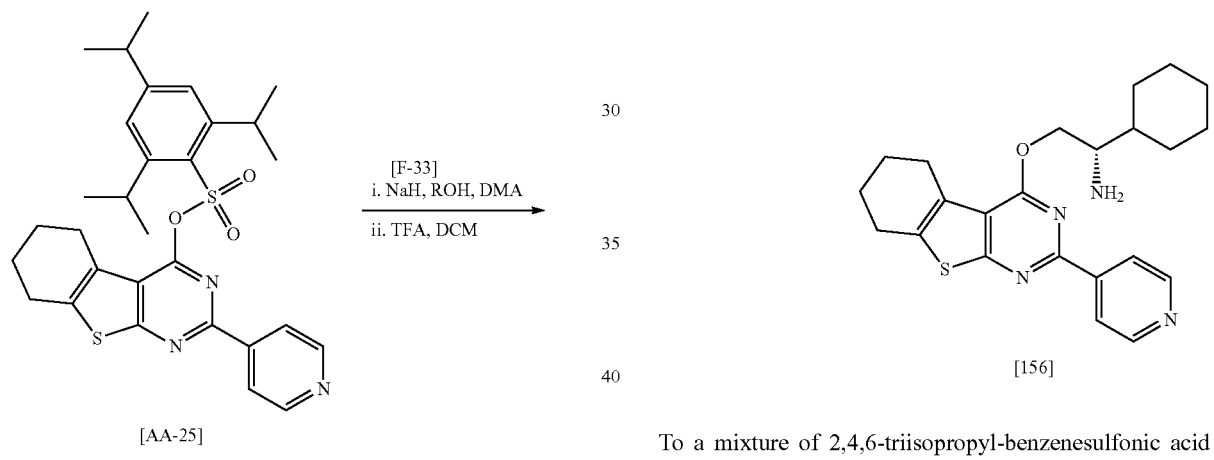

To a mixture of 2,4,6-triisopropyl-benzenesulfonic acid 2-pyridin-4-yl-5,6,7,8-tetrahydro-benzo[4,5]thieno[2,3-d]pyrimidin-4-yl ester [AA-25] (100 mg, 0.185 mmol) and N-Boc-L-cyclohexylglycinol (67 mg, 0.278 mmol) in DMA (1 ml) was added NaH (13 mg, 0.560 mmol). The reaction mixture was allowed to stir at room temperature for 2 hours and after completion the mixture was diluted with water and the product was extracted into DCM (2×2 ml). The combined organic phases were dried with magnesium sulfate, filtered and evaporated under reduced pressure. The crude product was dissolved in DCM (1 ml) and TFA (1 ml) was added and the mixture was stirred at room temperature for 1 hour. After completion the mixture was loaded onto a SCX-2 cartridge and washed with methanol. The product was released from the cartridge using a solution of 2M ammonia/methanol. The ammonia/methanol eluent was concentrated under reduced pressure and the product was purified by preparative HPLC (method A) to yield to the title compound. LCMS method: 2, RT: 2.62 min, MI: 409 [M+1]. 1H NMR (300 MHz, DMSO): 8.7 (d, 2H), 8.3 (d, 2H), 4.7 (m, 2H), 4.5 (m, 2H), 3 (m, 2H), 2.9 (m, 2H), 1.81 (m, 4H), 1.7 (m, 3H), 1.6 (m, 3H), 1.2 (m, 4H).

The following compounds were prepared according to the general synthesis shown in Scheme A17:

| Ex | SM | Alcohol [F-33] | Characterisation |
|---|---|---|---|
| 157 | [AA-25] | 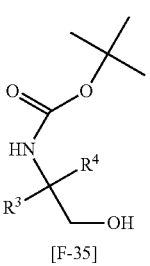 | method: 2, RT: 2.82 min, MI: 423 [M + 1]  1H NMR (300 MHz, DMSO): 8.7 (d, 2H), 8.3 (d, 2H), 4.7 (m, 2H), 4.5 (m, 2H), 3.2 (m, 2H), 2.8 (m, 2H), 1.81 (m, 4H), 1.7 (m, 4H), 1.6 (m, 2H), 1.4 (m, 2H), 1.2 (m, 2H), 0.9 (m, 2H) |
| 158 | [AA-25] |  | method: 2, RT: 2.82 min, MI: 456 [M + 1] |

General Synthesis of 5,6 substituted 4-alkoxy-2-pyridin-4-yl-thieno[2,3-d]pyrimidine Derivatives of General Formula [F-32] (Scheme A18)

Compounds were synthesised starting from an N-Boc protected amino acid of general formula [F-34] which was converted to a primary alcohol derivative of general formula [F-35] by reduction with a borane reducing agent such as $BH_3.THF$ or $BH_3.SMe_2$ in an anhydrous solvent such as THF, dioxane or diethylether. The resultant aminoalcohol derivative [F-35] was then reacted with a 5,6-substituted-(2,4,6-triisopropyl-benzenesulfonic acid)-2-pyridin-4-yl-thieno[2,3-d]pyrimidin-4-yl ester [AA-25] [prepared in scheme A5] in the presence of a strong base such as NaH, KH or LDA in the presence of an anhydrous polar aprotic solvent such as DMA, DMF or NNP. After reaction work up, typically by a liquid-liquid extraction or purification by acidic ion exchange catch-release, the N-Boc derivative was deprotected under acidic conditions with a strong acid such as TFA, TCA, methanesulfonic acid, HCl or $H_2SO_4$ in a solvent such as DCM, DCE, THF, EtOH or MeOH the crude reaction product was purified by reverse phase preparative HPLC.

Scheme A18

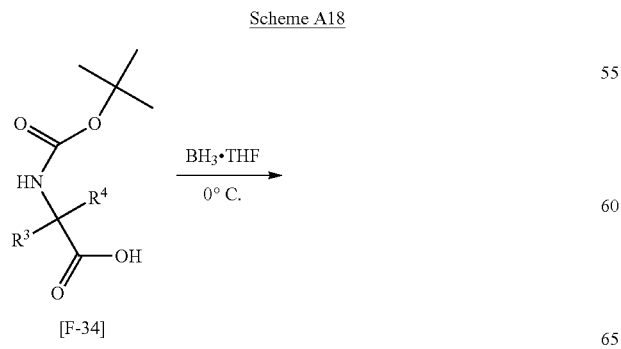

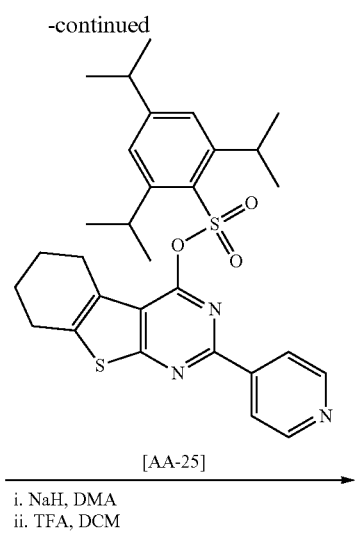

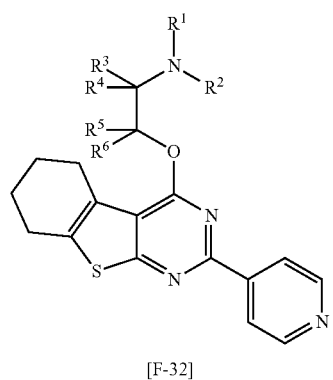

Synthesis of [(S)-2-hydroxy-1-(4-methoxy-benzyl)-ethyl]-carbamic acid tert-butyl ester [AA-54]

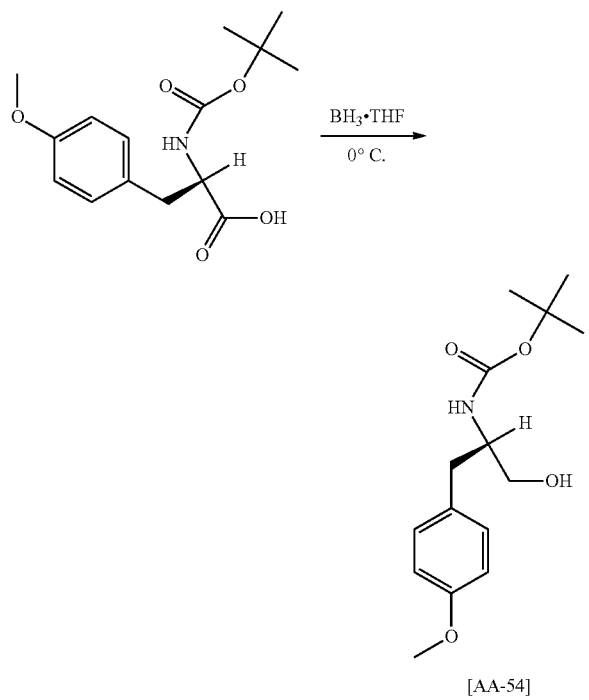

A 1M solution of BH$_3$ in THF (1.7 ml, 1.7 mmol) was added dropwise to a stirred solution of (S)-2-tert-butoxycarbonylamino-3-(4-methoxy-phenyl)-propionic acid (200 mg, 0.678 mmol) in dry THF (2.5 ml) at 0° C. The mixture was stirred for 2 hours at O° C. then hydrolysed by slow addition of excess of 10% acetic acid/MeOH (5 ml) and stirred at room temperature for a further 2 hours. The solvent was removed under reduced pressure the residue was dissolved in ethylacetate (5 ml) and washed with saturated sodium bicarbonate (2×5 ml) and brine (2×5 ml). The combined organic phases were dried with magnesium sulfate, filtered and evaporated under reduced pressure to provide the title compound as a white solid which was used without further purification in the next step. LCMS method: 1, RT: 2.82 min, MI: 441 [M+1].

Synthesis of (S)-1-(4-methoxy-benzyl)-2-(2-pyridin-4-yl-5,6,7,8-tetrahydro-benzo[4,5]thieno [2,3-d] pyrimidin-4-yloxy)-ethylamine [159]

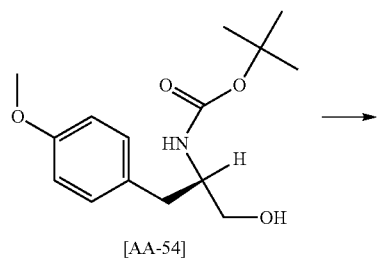

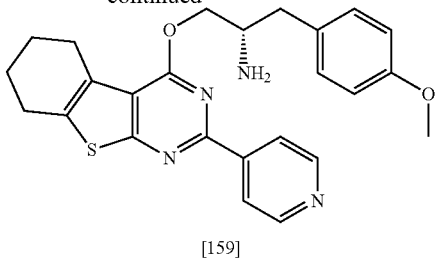

To a solution of 2,4,6-triisopropyl-benzenesulfonic acid 2-pyridin-4-yl-5,6,7,8-tetrahydro-benzo[4,5]thieno[2,3-d]pyrimidin-4-yl ester [AA-25] (50 mg, 0.091 mmol) in DMA (1 ml) was added [(S)-2-amino-1-(4-methyl-benzyl)-ethyl]-carbamic acid tert-butyl ester [AA-54] (31 mg, 0.110 mmol) followed by NaH (4 mg, 0.110 mmol), the mixture was stirred at room temperature for 2 hours. After completion the product was extracted with DCM (2 ml) and washed with brine (3 ml). To the organic phase was added TFA (2 ml) and the mixture was stirred at room temperature for 1 hour. After completion the mixture was loaded onto a SCX-2 cartridge and washed with methanol. The product was released from the cartridge using a solution of 2M ammonia/methanol. The ammonia/methanol eluent was concentrated under reduced pressure and the crude product was purified by preparative HPLC (method A) to yield to the title compound. LCMS method: 2, RT: 2.61 min, MI: 447 [M+1]. 1H NMR (300 MHz, DMSO): 8.7 (d, 2H), 8.1 (d, 2H), 7.2 (d, 2H), 6.9 (d, 2H), 4.7 (m, 1H), 4.5 (m, 1H), 3.8 (s, 3H), 3.6 (m, 2H), 2.9 (m, 1H), 2.8 (m, 2H), 2.7 (m, 2H), 1.81 (m, 4H).

The following compounds were prepared according to the general synthesis shown in Scheme A18:

| Ex | SM | Amino acid [F-34] | Characterisation |
|---|---|---|---|
| 160 | [AA-25] | 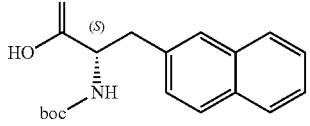 | method: 2, RT: 2.77 min, MI: 467 [M + 1] |
| 161 | [AA-25] | 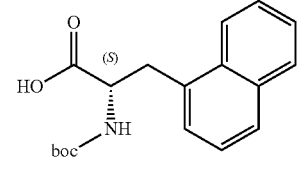 | method: 2, RT: 2.81 min, MI: 467 [M + 1] |
| 162 | [AA-25] | 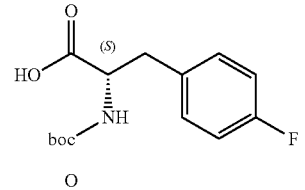 | method: 2, RT: 2.62 min, MI: 435 [M + 1] |
| 163 | [AA-25] | 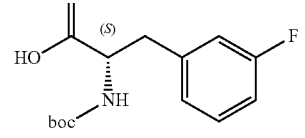 | method: 2, RT: 2.69 min, MI: 435 [M + 1] |

| Ex | SM | Amino acid [F-34] | Characterisation |
|---|---|---|---|
| 164 | [AA-25] | (S)-2-(boc-amino)-3-(2-fluorophenyl)propanoic acid | method: 2, RT: 2.70 min, MI: 435 [M + 1] |
| 165 | [AA-25] | (S)-2-(boc-amino)-3-(3-methylphenyl)propanoic acid | method: 2, RT: 2.70 min, MI: 435 [M + 1] |
| 166 | [AA-25] | (S)-2-(boc-amino)-3-(4-methylphenyl)propanoic acid | method: 2, RT: 2.71 min, MI: 431 [M + 1] |
| 167 | [AA-25] | (R)-2-(boc-amino)-4-phenylbutanoic acid | method: 2, RT: 2.74 min, MI: 431 [M + 1] |
| 168 | [AA-25] | (S)-2-(boc-amino)-3-(thiophen-2-yl)propanoic acid | method: 2, RT: 2.71 min, MI: 423 [M + 1] |
| 169 | [AA-25] | (R)-2-(boc-amino)-3-(4-methoxyphenyl)propanoic acid | method: 2, RT: 2.71 min, MI: 447 [M + 1] |
| 170 | [AA-25] | (R)-2-(boc-amino)-3-(thiophen-2-yl)propanoic acid | method: 2, RT: 2.58 min, MI: 423 [M + 1] |
| 171 | [AA-25] | (S)-2-(boc-amino)-3-(4-bromophenyl)propanoic acid | method: 2, RT: 2.76 min, MI: 495 [M + 1] |
| 172 | [AA-25] | (R)-2-(boc-amino)-3-(naphthalen-2-yl)propanoic acid | method: 2, RT: 3.04 min, MI: 467 [M + 1] |
| 173 | [AA-25] | (R)-2-(boc-amino)-3-(naphthalen-1-yl)propanoic acid | method: 2, RT: 2.81 min, MI: 467 [M + 1] |
| 174 | [AA-25] | (R)-2-(boc-amino)-3-(2-methylphenyl)propanoic acid | method: 2, RT: 2.76 min, MI: 431 [M + 1] |
| 175 | [AA-25] | (R)-2-(boc-amino)-3-(1H-imidazol-4-yl)propanoic acid | method: 2, RT: 2.19 min, MI: 407 [M + 1] |
| 176 | [AA-25] | (R)-2-(boc-amino)-3-(benzo[b]thiophen-3-yl)propanoic acid | method: 2, RT: 2.87 min, MI: 473 [M + 1] |
| 177 | [AA-25] | (S)-2-(boc-amino)-3-(benzo[b]thiophen-3-yl)propanoic acid | method: 2, RT: 2.82 min, MI: 473 [M + 1] |
| 178 | [AA-25] | (R)-1-boc-piperidine-2-carboxylic acid | method: 2, RT: 2.37 min, MI: 381 [M + 1] |
| 179 | [AA-25] | (S)-1-boc-piperidine-2-carboxylic acid | method: 2, RT: 2.38 min, MI: 381 [M + 1] |
| 180 | [AA-25] | (S)-2-(boc-amino)-3-(3-methoxyphenyl)propanoic acid | method: 2, RT: 2.59 min, MI: 447 [M + 1] |

General Synthesis of Substituted 4-amino-2-pyrazolyl-4-yl-thieno[2,3-d]pyrimidine Derivatives of General Formula [F-35] (Scheme A19)

A 2,4-dichloro-5,6,7,8-tetrahydro-enzo[4,5]thieno [2,3-d]pyrimidine of general formula [F-21] was reacted with primary and secondary amino derivative of general formula [F-13] in a polar aprotic solvent such as DMA, DMF, NMP in the presence of a tertiary amine base such as Et₃N, DIPEA or NMM at ambient temperature. Following reaction work up, typically by a liquid-liquid extraction or purification by acidic ion exchange catch-release, the amino derivative of general formula [F-23] were reacted with pyrazolyl boronic acids or boronate esters of general formula [F-36] in the presence of a palladium catalyst such as Pd(PPh$_3$)$_4$ or Pd(PPh$_3$)$_2$Cl$_2$ a base such as Et$_3$N, KOH, Na$_2$CO$_3$ or NaOH in a polar solvent such as EtOH, THF, DMA or dioxane at high temperature either by heating thermally or using a microwave reactor. After reaction work up, typically by a liquid-liquid extraction or purification by acidic ion exchange catch-release, the N-Boc derivative was deprotected under acidic conditions with a strong acid such as TFA, TCA, methanesulfonic acid, HCl or H$_2$SO$_4$ in a solvent such as DCM, DCE, THF, EtOH or MeOH the crude reaction product was purified by reverse phase preparative HPLC.

Scheme A19

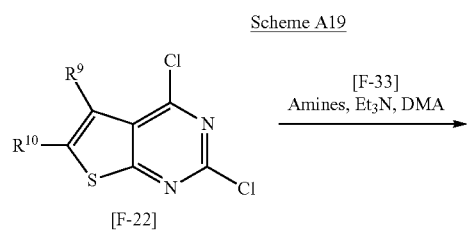

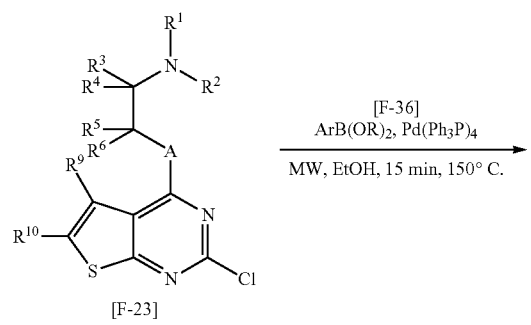

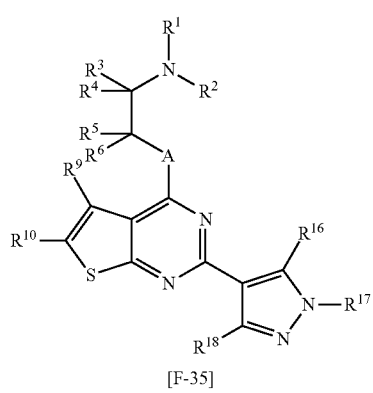

Synthesis of [2-(2-chloro-5,6,7,8-tetrahydro-benzo[4,5]thieno[2,3-d]pyrimidin-4-ylamino)-ethyl]-carbamic acid tert-butyl ester [AA-49]

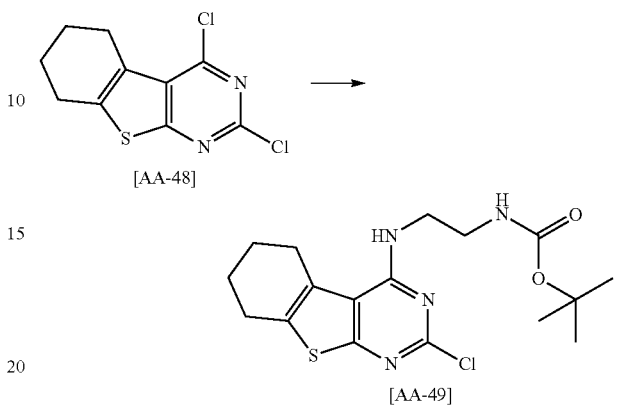

To a solution of 2,4-dichloro-5,6,7,8-tetrahydro-benzo[4,5]thieno[2,3-d]pyrimidine [AA-48] (100 mg, 0.387 mmol) in DMA (5 ml) was added Boc-ethylenediamine (62 mg, 0.387 mmol) followed by Et$_3$N (110 µl, 0.774 mmol), the mixture was stirred at room temperature for 2 hours. Then the product was extracted with DCM (2×10 ml) and washed with brine (2×10 ml). The combined organic phases were dried with magnesium sulfate, filtered and evaporated under reduced pressure to provide a brown solid. The residue was used without further purification in the next step. LCMS method: 1, RT: 6.26 min, MI: 383 [M+1].

Synthesis of N*1*-[2-(1H-Pyrazol-4-yl)-5,6,7,8-tetrahydro-benzo[4,5]thieno[2,3-d]pyrimidin-4-yl]-ethane-1,2-diamine [181]

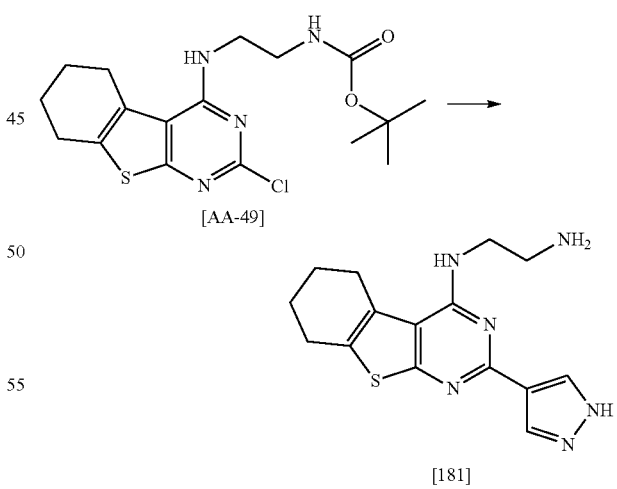

A microwave vial was charged with [2-(2-chloro-5,6,7,8-tetrahydro-benzo[4,5]thieno[2,3-d]pyrimidin-4-ylamino)-ethyl]-carbamic acid tert-butyl ester [AA-49] (40 mg, 0.17 mmol), 1H-pyrazole-4-boronic acid (23 mg, 0.20 mmol), tetrakis (triphenyl phosphine) palladium (10 mg, 0.008 mmol), Na$_2$CO$_3$ (2M in water, 180 µl, 0.6 mmol) and EtOH (1 ml). The reaction was heated to 150° C. for 15 minutes under microwave irradiation. The mixture was then filtered through a plug of silica, washed with methanol and the filtrate was concentrated under reduced pressure. To a solution of the crude product in DCM (2 ml) was added TFA (2 ml) and the mixture was stirred at room temperature for 1 hour. After completion the mixture was loaded onto a SCX-2 cartridge and washed with methanol. The product was released from the cartridge using a solution of 2M ammonia/methanol. The ammonia/methanol eluent was concentrated under reduced pressure and the crude product was purified by preparative HPLC (method A) to yield to the title compound. LCMS method: 2, RT: 2.20 min, MI: 315 [M+1], 1H NMR (300 MHz, DMSO): 8.41 (s, 1H), 8.20 (s, 2H), 6.80 (t, 1H), 3.74 (m, 2H), 3.06 (m, 2H), 2.94 (m, 2H), 2.74 (s, 2H), 2.53 (s, 2H), 1.81 (s, 4H).

The following compounds were prepared according to the general synthesis shown in Scheme A19:

| Ex | SM | Boronic acid [F36] | Amine [F-13] | Characterisation | |
|---|---|---|---|---|---|
| 182 | [AA-48] | (3,5-dimethyl-1H-pyrazol-4-yl)boronic acid | H2N-CH2CH2-NHboc | method: 2, RT: 2.32 min, MI: 343 [M + 1] | 1H NMR (300 MHz, DMSO): 8.37 (s, 1H), 6.87 (t, 1H), 3.73 (m, 2H), 3.15 (m, 2H), 3.03 (m, 2H), 2.97 (s, 2H), 2.74 (s, 2H), 2.49 (s, 6H), 1.84 (s, 4H) |
| 183 | [AA-48] | (1H-pyrazol-4-yl)boronic acid | (S)-H2N-CH2-CH(NHboc)-CH2-Ph | method: 2, RT: 2.52 min, MI: 405 [M + 1] | |
| 184 | [AA-48] | (3,5-dimethyl-1H-pyrazol-4-yl)boronic acid | (S)-H2N-CH2-CH(NHboc)-CH2-Ph | method: 2, RT: 2.65 min, MI: 433 [M + 1] | |
| 185 | [AA-48] | (1H-pyrazol-4-yl)boronic acid | 1-boc-piperazine | method: 2, RT: 2.30 min, MI: 341 [M + 1] | 1H NMR (300 MHz, DMSO): 8.20 (s, 2H), 3.51 (m, 4H), 3.19 (m, 4H), 2.88 (m, 4H), 1.87 (m, 2H), 1.78 (m, 2H) |
| 186 | [AA-48] | (1H-pyrazol-4-yl)boronic acid | 1-boc-1,4-diazepane | method: 2, RT: 2.31 min, MI: 355 [M + 1] | 1H NMR (300 MHz, DMSO): 8.17 (s, 2H), 3.87 (m, 2H), 3.74 (m, 2H), 3.38 (m, 2H), 3.11 (m, 2H), 2.84 (m, 2H), 1.88 (m, 2H), 1.77 (m, 2H) |
| 187 | [AA-48] | (1H-pyrazol-4-yl)boronic acid | (S)-H2N-CH2-CH(NHboc)-CH3 | method: 2, RT: 2.21 min, MI: 329 [M + 1] | |

-continued

| Ex | SM | Boronic acid [F36] | Amine [F-13] | Characterisation | |
|---|---|---|---|---|---|
| 188 | [AA-49] | 4-pyrazolyl boronic acid | H₂N-CH₂-C*(R)*H(CH₃)-NHboc | method: 2, RT: 2.26 min, MI: 329 [M + 1] | |
| 189 | [AA-48] | 4-pyrazolyl boronic acid | (R)-3-amino-1-boc-pyrrolidine | method: 2, RT: 2.27 min, MI: 341 [M + 1] | |
| 190 | [AA-48] | 3,5-dimethyl-4-pyrazolyl boronic acid | 1-boc-piperazine | method: 2, RT: 2.49 min, MI: 369[M + 1] | 1H NMR (300 MHz, DMSO): 8.97 (s, 1H), 3.51 (m, 6H), 2.84 (m, 6H), 1.88 (m, 2H), 1.77 (m, 2H) |
| 191 | [AA-48] | 3,5-dimethyl-4-pyrazolyl boronic acid | 1-boc-1,4-diazepane | method: 2, RT: 2.48 min, MI: 383[M + 1] | |
| 192 | [AA-49] | 3,5-dimethyl-4-pyrazolyl boronic acid | (S)-H₂N-CH₂-CH(CH₃)-NHboc | method: 2, RT: 2.38 min, MI: 357[M + 1] | |
| 193 | [AA-48] | 3,5-dimethyl-4-pyrazolyl boronic acid | (R)-H₂N-CH₂-CH(CH₃)-NHboc | method: 2, RT: 2.37 min, MI: 357[M + 1] | |
| 194 | [AA-48] | 3,5-dimethyl-4-pyrazolyl boronic acid | (R)-3-amino-1-boc-pyrrolidine | method: 2, RT: 2.41 min, MI: 369[M + 1] | |

| Ex | SM | Boronic acid [F36] | Amine [F-13] | Characterisation |
|---|---|---|---|---|
| 195 | [AA-48] | 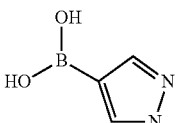 | 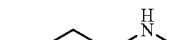 | method: 2, RT: 2.27 min, MI: 329[M + 1] |
| 196 | [AA-48] | 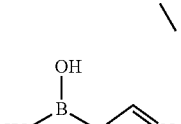 | 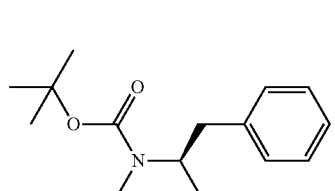 | method: 7, RT: 3.76 min, MI: 431[M + 1] |

4PT32P Compounds

In one approach, compounds of formula [G-100] (where A=NH or N alkyl) are prepared by reacting a compound of formula [G-102] (where X is a halogen such as chlorine or a sulfonate) with a compound of formula [G-103](where A is NH or $NH_2$ and Z on the terminal nitrogen is H, alkyl or a suitable nitrogen protecting group, such as Boc, Alloc, Cbz or Fmoc) in a suitable solvent such as DMF in the presence of a suitable base such as triethylamine.

The reaction is suitably conducted at an elevated temperature for example 40° C. Where Z is a suitable nitrogen protecting group, such as Boc, Alloc, Cbz or Fmoc, compounds of formula [G-100] are prepared by a suitable deprotection reaction. For example: where Z is a Boc protecting group reaction with an acid such as TFA in a suitable solvent such as DCM. The reaction is suitably conducted at ambient temperature. In one approach, compounds of formula [G-100] (where A=O) are prepared by reacting a compound of formula [G-102] (where X is a halogen such as chlorine or sulfonate) with a compound of formula [G-103] (where A is OH and Z on the terminal nitrogen is H, alkyl or a suitable nitrogen protecting group, such as Boc, Alloc, Cbz or Fmoc) in a suitable solvent such as DMA in the presence of a suitable base such as sodium hydride. The reaction is suitably conducted at ambient temperature. Where Z is a suitable nitrogen protecting group, such as Boc, Alloc, Cbz or Fmoc, compounds of formula [G-100] are prepared by a suitable deprotection reaction. For example: where Z is a Boc protecting group reaction with an acid such as TFA in a suitable solvent such as DCM. The reaction is suitably conducted at ambient temperature.

In one approach, compounds of formula [G-102] (where X is a halogen such as chlorine) are prepared by reacting a compound of formula [G-104] with a suitable halogenating agent such as phosphorous oxychloride. The reaction is suitably conducted at elevated temperature such as 125° C. Compounds of formula [G-102] (where X is a sulfonate) are prepared by reacting a compound of formula [G-104] with a suitably substituted sulfonyl chloride in a suitable solvent such as DMA in the presence of a suitable base such as triethylamine and a catalytic amount of DMAP. The reaction is suitably conducted at ambient temperature.

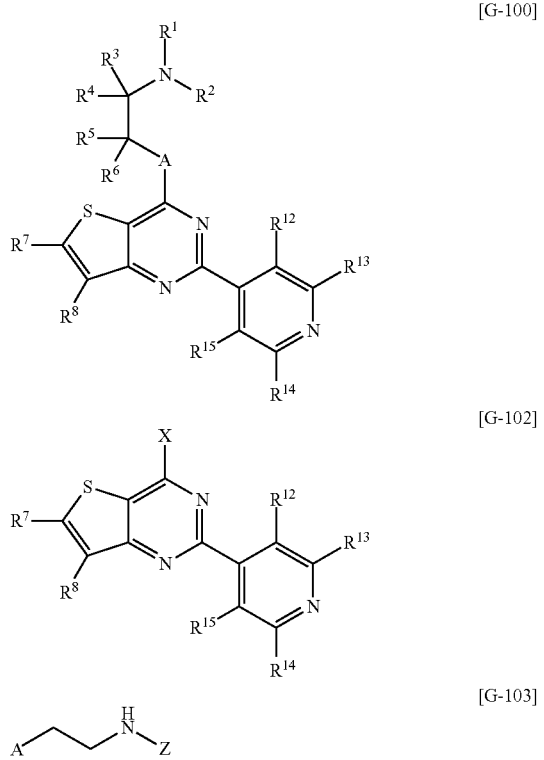

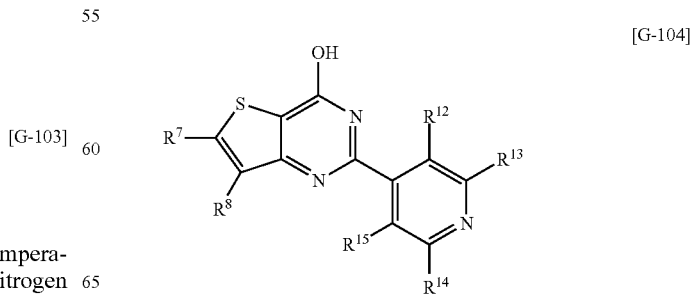

In one approach, compounds of formula [G-104] are prepared by reacting a compound of formula [G-105] (where $R_{x1}$ is an alkyl group such as methyl or ethyl) with a compound of formula [G-106] in a suitable solvent such as dioxane with a suitable base such as potassium-tert-pentylate. The reaction is suitably conducted at ambient temperature.

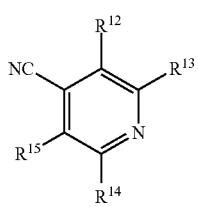

[G-105]

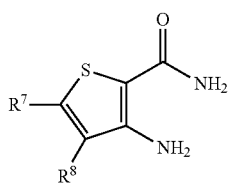

[G-106]

In another approach compounds of formula [G-104] are prepared by reacting a compound of [G-107] with a compound of formula [G-108] in a suitable solvent such as methanol with a suitable protic acid such as hydrogen chloride. The reaction is suitably conducted at elevated temperature. Full aromatisation to yield compounds of formula [G-104] is achieved by reaction with an oxidising agent such as 2,3-dichloro-5,6-dicyanobenzoquinone in a suitable solvent such as dichloromethane. The reaction is suitably conducted at ambient temperature.

[G-107]

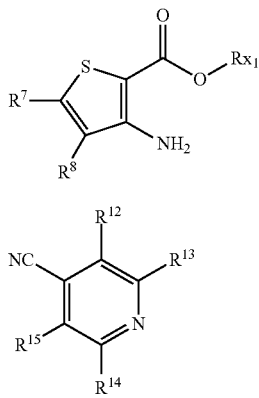

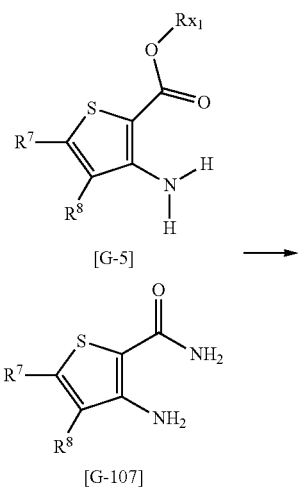

[G-5]

→

[G-107]

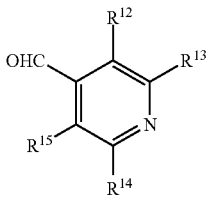

[G-108]

In one approach, compounds of formula [G-103] (where A is OH) are prepared by reacting a compound of formula [G-109] (where Z on the terminal nitrogen is H, alkyl or a suitable nitrogen protecting group, such as Boc, Alloc, Cbz or Fmoc) with a reducing agent such as borane-THF complex in a suitable solvent such as THF. The reaction is suitably conducted at low temperature for example 0° C. In one approach, compounds of formula [G-103] (where A is $NH_2$) are prepared by reacting a compound of formula [G-110] (where Z on the terminal nitrogen is H, alkyl or a suitable nitrogen protecting group, such as Boc, Alloc, Cbz or Fmoc) with a reducing agent such as borane-THF complex in a suitable solvent such as THF. The reaction is suitably conducted at low temperature for example 0° C. In one approach, compounds of formula [G-110] are prepared by reacting compounds of formula [G-109] with Boc anhydride in the presence of a suitable base such as pyridine, ammonium carbonate in a suitable solvent such as dioxane. The reaction is suitably conducted at ambient temperature.

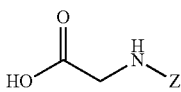

[G-109]

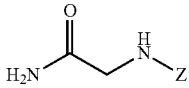

[G-110]

An example of a method as described above is illustrated in the following scheme.

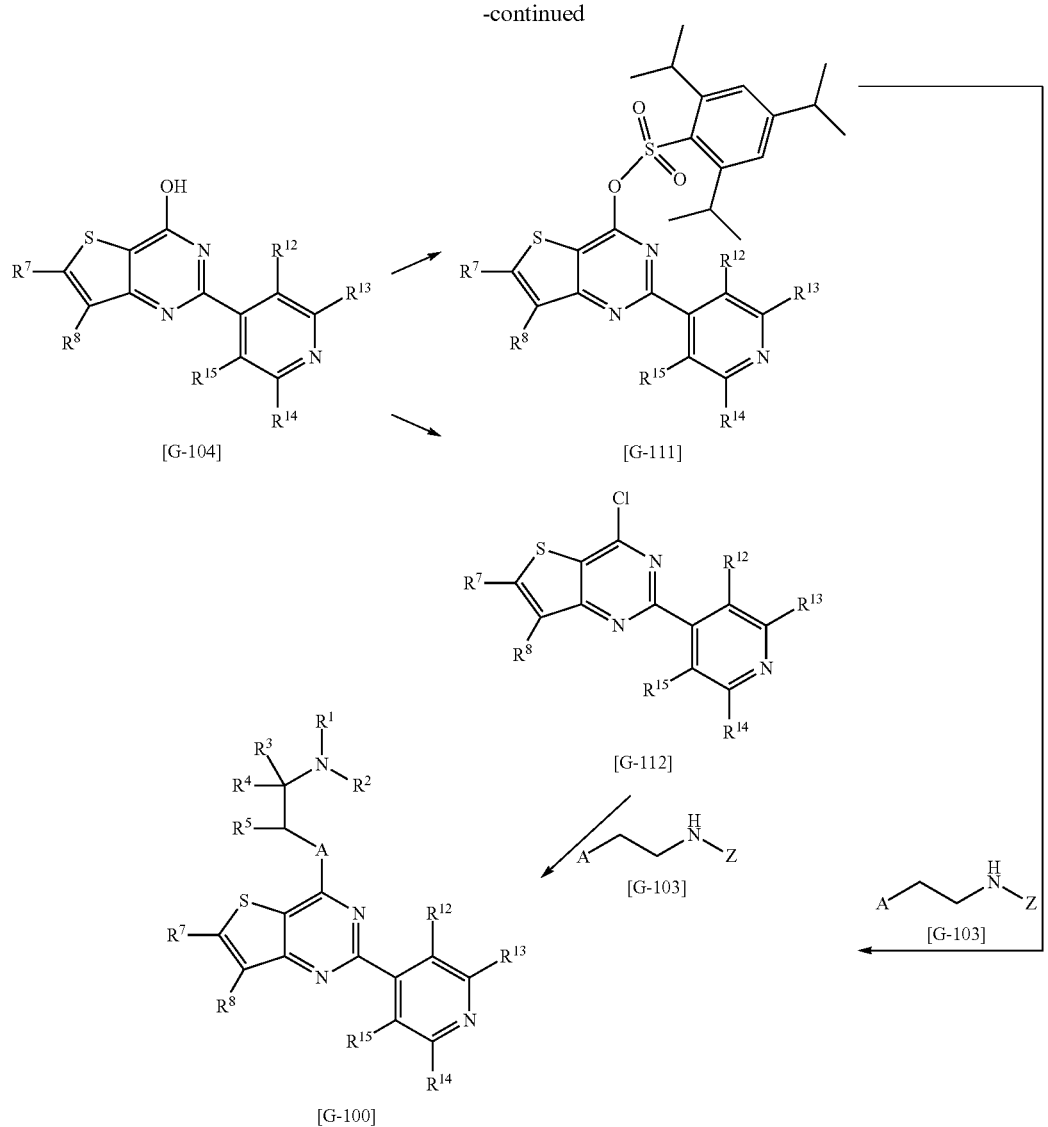

General Synthesis of 6,7-substituted 2-pyridin-4-yl-thieno [3,2-d]pyrimidin-4-ol, of General Formula [G-104] (Scheme B1)

A 4,5-substituted-3-Amino-thiophene-2-carboxylic acid alkyl ester derivative, of general formula [G-105] (where Rx=alkyl such as methyl or ethyl) was subjected to a cyclisation reaction with a 4-cyanopyridine derivative of general formula [G-106] in the presence of a hindered alkoxide base such as potassium-tert-pentylate 1.7M in toluene or potassium-tert-butoxide in a dry non-aprotic solvent such as dioxane or THF at ambient temperature, to yield the 6,7-substituted 2-pyridin-4-yl-thieno [3,2-d]pyrimidin-4-ol derivative of formula [G-104].

Scheme B1

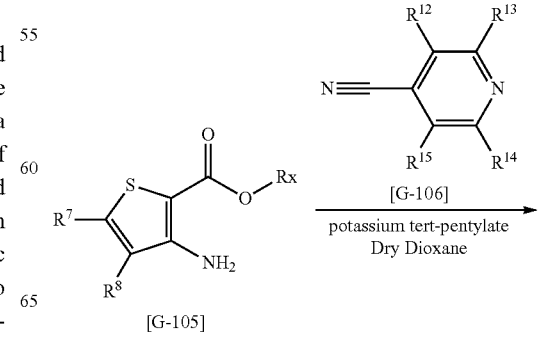

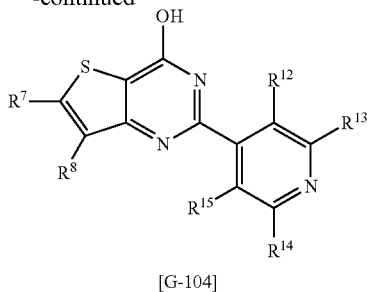

[G-104]

Synthesis of 6-methyl-2-pyridin-4-yl-thieno [3,2-d] pyrimidin-4-ol [BB-01]

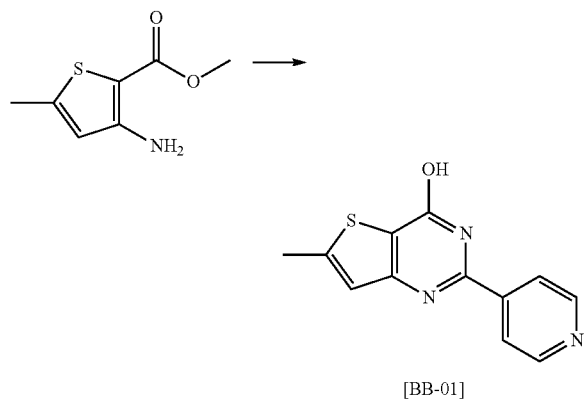

[BB-01]

To a solution of 4-cyanopyridine (552 mg, 5.3 mmol) in dry dioxane (10 ml) was added 3-amino-5-methyl-thiophene-2-carboxylic acid methyl ester (1 g, 5.84 mmol) followed by potassium-tert-pentylate 1.7M in toluene (6.9 ml, 11.7 mmol). The reaction mixture was stirred at room temperature overnight. After completion the precipitate formed was filtered and washed with diethyl ether. The residue was used without any further purification in the next step. LCMS method: 3, RT: 2.44 min, MI: 244 [M+1]. 1H NMR (300 MHz, DMSO): 2.60 (s, 3H), 7.23 (d, 1H), 8.05 (m, 2H), 8.76 (m, 2H).

The following compounds were prepared according to the general synthesis shown in scheme B1:

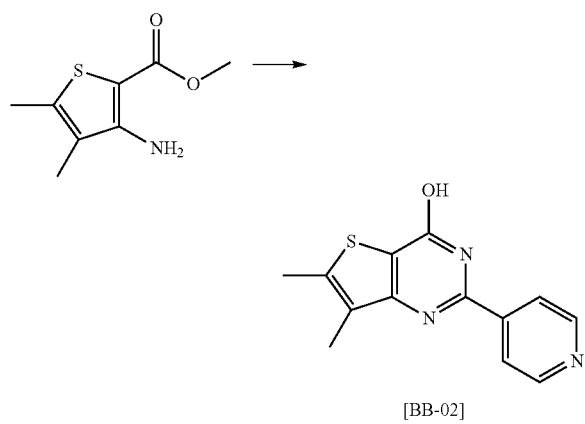

[BB-02]

6,7-Dimethyl-2-pyridin-4-yl-thieno[3,2-d]pyrimidin-4-ol [BB-02] was prepared by reaction of 3-amino-4,5-dimethyl-thiophene-2-carboxylic acid methyl ester, 4-cyanopyridine, potassium-tert-pentylate 1.7M in toluene and dioxane at room temperature to give the title compound as a yellow solid. LCMS method: 3, RT: 3.05 min, MI: 258 [M+1].

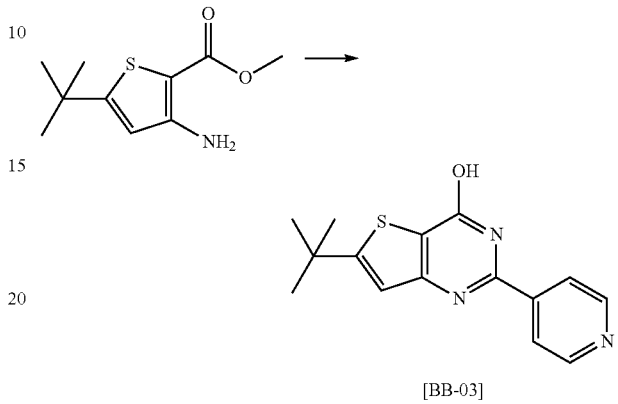

[BB-03]

6-tert-butyl-2-pyridin-4-yl-thieno[3,2-d]pyrimidin-4-ol [BB-03] was prepared by reaction of 3-amino-5-tert-butyl-thiophene-2-carboxylic acid methyl ester, 4-cyanopyridine, potassium-tert-pentylate 1.7M in toluene and dioxane at room temperature to give the title compound as an off-white solid. LCMS method: 3, RT: 3.02 min, MI: 286 [M+1].

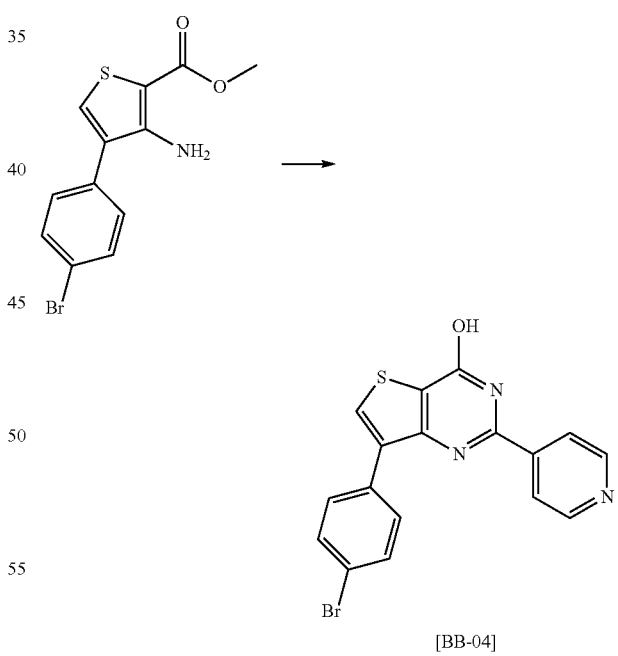

[BB-04]

7-(4-bromo-phenyl)-2-pyridin-4-yl-thieno[3,2-d]pyrimidin-4-ol [BB-04] was prepared by reaction of 3-amino-4-(4-bromo-phenyl)-thiophene-2-carboxylic acid methyl ester, 4-cyanopyridine, potassium-tert-pentylate 1.7M in toluene and dioxane at room temperature to give the title compound as a yellow solid. LCMS method: 3, RT: 4.11 min, MI: 384-386 [M+1].

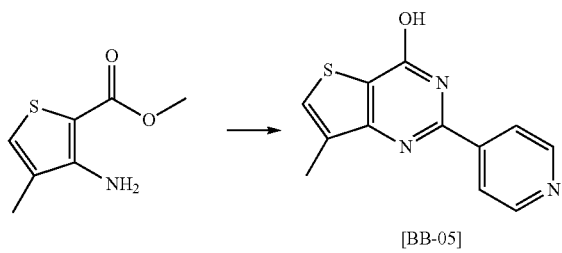 [SMILES: COC(=O)c1scc(C)c1N ; Cc1csc2c(O)nc(-c3ccncc3)nc12]

[BB-05]

7-methyl-2-pyridin-4-yl-thieno[3,2-d]pyrimidin-4-ol [BB-05] was prepared by reaction of 3-amino-4-methyl-thiophene-2-carboxylic acid methyl ester, 4-cyanopyridine, potassium-tert-pentylate 1.7M in toluene and dioxane at room temperature to give the title compound as a yellow solid. LCMS method: 1, RT: 3.09 min, MI: 243 [M+1].

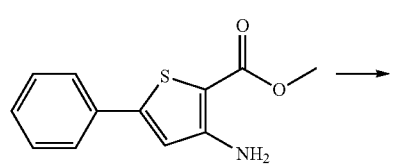

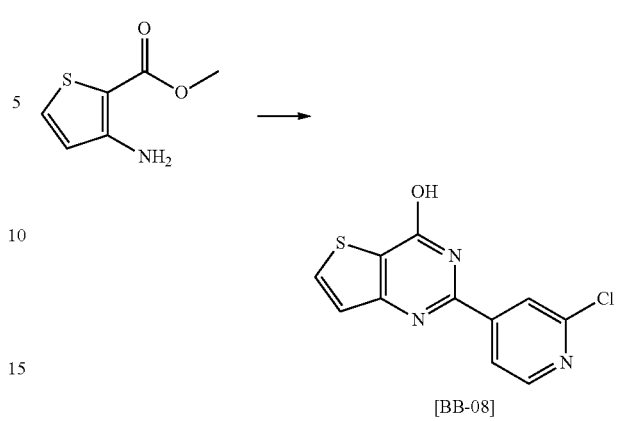

[BB-08]

2-(2-Chloro-pyridin-4-yl)-thieno[3,2-d]pyrimidin-4-ol [BB-08] was prepared by reaction of methyl 3-amino-2-thiophene-carboxylate, 2-Chloro-4-pyridinecarbonitrile, potassium-tert-pentylate 1.7M in toluene and THF at room temperature to give the title compound as a pale yellow solid. LCMS method: 8, RT: 3.32 min, MI: 264 [M+1].

[BB-06]

6-phenyl-2-pyridin-4-yl-thieno[3,2-d]pyrimidin-4-ol [BB-06] was prepared by reaction of 3-amino-5-phenyl-thiophene-2-carboxylic acid methyl ester, 4-cyanopyridine, potassium-tert-pentylate 1.7M in toluene and dioxane at room temperature to give the title compound as an off-white solid. LCMS method: 1, RT: 3.46 min, MI: 306 [M+1].

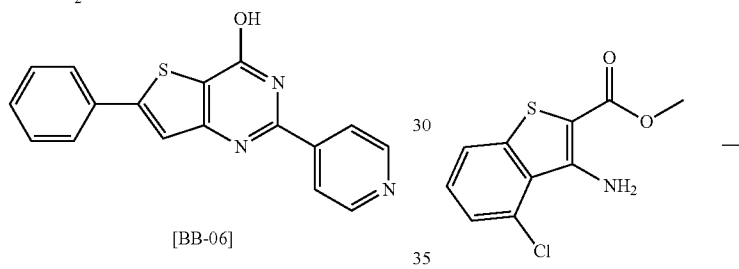

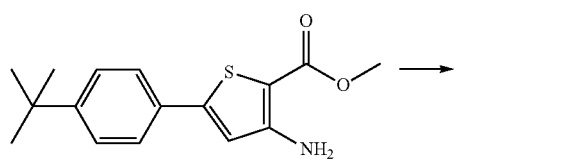

[BB-07]

6-(4-tert-butyl-phenyl)-2-pyridin-4-yl-thieno[3,2-d]pyrimidin-4-ol [BB-07] was prepared by reaction of 3-amino-5-(4-tert-butyl-phenyl)-thiophene-2-carboxylic acid methyl ester, 4-cyanopyridine, potassium-tert-pentylate 1.7M in toluene and dioxane at room temperature to give the title compound as an off-white solid. LCMS method: 1, RT: 4.78 min, MI: 362 [M+1].

[BB-09]

9-Chloro-2-(2-chloro-pyridin-4-yl)-benzo[4,5]thieno[3,2-d]pyrimidin-4-ol [BB-09] was prepared by reaction of 3-Amino-4-chloro-benzo[b]thiophene-2-carboxylic acid methyl ester 4-cyanopyridine, potassium-tert-pentylate 1.7M in toluene and THF at room temperature to give the title compound as an off-white solid. LCMS method: 2, RT: 3.6 min, MI: 314 [M+1].

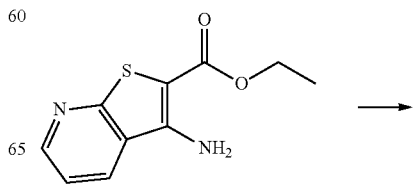

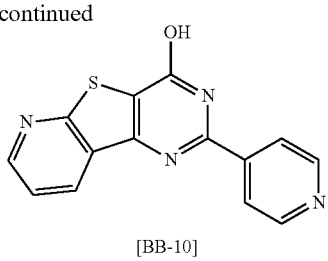

[BB-10]

2-Pyridin-4-yl-pyrido[3',2':4,5]thieno[3,2-d]pyrimidin-4-ol [BB-10] was prepared by reaction of ethyl 3-aminothieno[2,3-b]pyridine-2-carboxylate, 4-cyanopyridine, potassium-tert-pentylate 1.7M in toluene and THF at room temperature to give the title compound as an of-white solid. LCMS method: 2, RT: 2.57 min, MI: 281 [M+1].

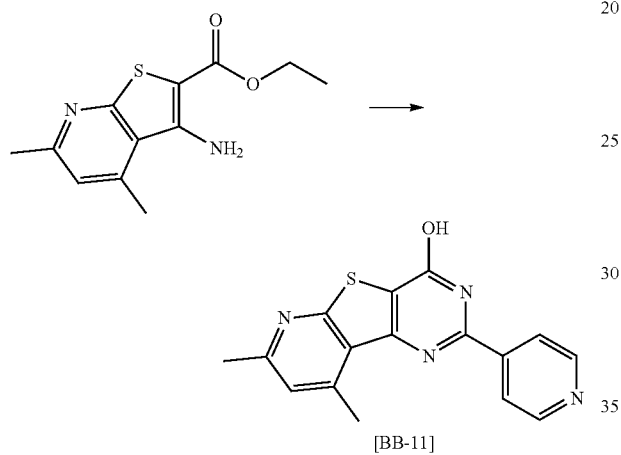

[BB-11]

7,9-Dimethyl-2-pyridin-4-yl-pyrido[3',2':4,5]thieno[3,2-d]pyrimidin-4-ol [BB-11] was prepared by reaction of ethyl 3-amino-4,6-dimethylthieno[2,3-b]pyridine-2-carboxylate, 4-cyanopyridine, potassium-tert-pentylate 1.7M in toluene and THF at room temperature to give the title compound as an off-white solid. LCMS method: 2, RT: 3.07 min, MI: 309[M+1].

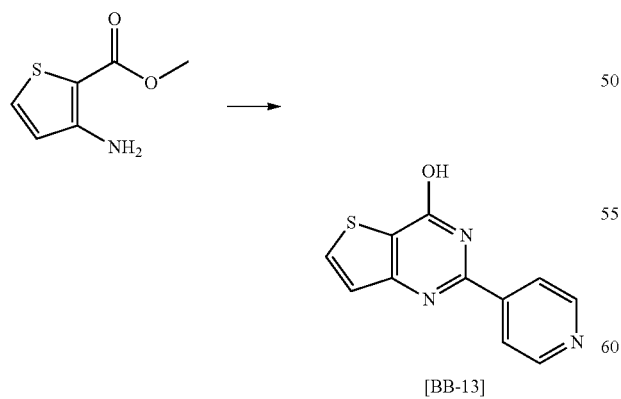

[BB-13]

2-Pyridin-4-yl-thieno[3,2-d]pyrimidin-4-ol [BB-13] was prepared by reaction of methyl 3-amino-2-thiophene-carboxylate, 4-pyridinecarbonitrile, potassium-tert-pentylate 1.7M in toluene and THF at room temperature to give the title compound as a pale yellow solid: LCMS method B: 1.98 min, 100%, 230.00 [M+H]

General Synthesis of 6,7-substituted 2-pyridin-4-yl-thieno [3,2-d]pyrimidin-4-ol, of General Formula [G-104] (Scheme B2)

An 4,5-substituted-3-amino-thiophene-2-carboxylic acid amide derivative of general formula [G-107] was subjected to a cyclisation reaction with an isonicotinaldehyde derivative of general formula [G-108] in the presence of 4M hydrogen chloride in dioxane in a suitable solvent such as methanol. The reaction is suitably conducted at an elevated temperature for example 140° C. in a microwave reactor for 20 minutes. Full aromatisation is subsequently achieved with 2,3-dichloro-5,6-dicyanobenzoquinone in a suitable solvent such as dichloromethane at ambient temperature, to yield the 6,7-substituted 2-pyridin-4-yl-thieno [3,2-d]pyrimidin-4-ol, of general formula [G-104].

Scheme B2

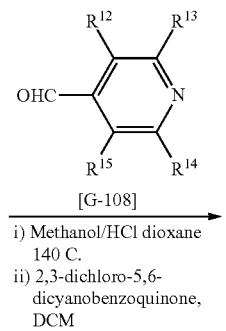

[G-107]

[G-108]

i) Methanol/HCl dioxane 140 C.
ii) 2,3-dichloro-5,6-dicyanobenzoquinone, DCM

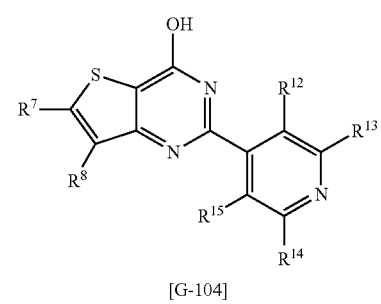

[G-104]

Synthesis of 2-(3-Fluoro-pyridin-4-yl)-thieno[3,2-d]pyrimidin-4-ol [BB-14]

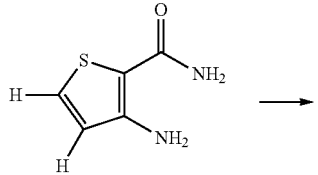

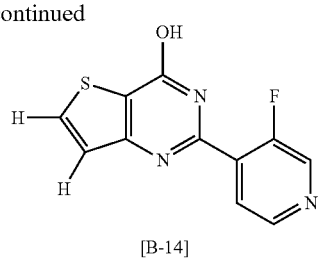

[B-14]

A microwave vial was charged with 3-amino-thiophene-2-carboxylic acid amide (2 g, 14.07 mmol), 3-fluoroisonicotinaldehyde (0.85 ml, 8.52 mmol), hydrogen chloride 4M in dioxane (0.7 ml, 2.81 mmol) and methanol (20 ml). The reaction mixture was heated to 140° C. for 20 minutes under microwave irradiation. After completion, the mixture was concentrated under reduced pressure. To a solution of the crude product in dichloromethane (20 ml) was added 2,3-dichloro-5,6-dicyanobenzoquinone (3.2 g, 14.07). The mixture was stirred at room temperature for 18 hours. After completion, the precipitate formed was filtered and washed with methanol. The residue was used without any further purification in the next step. LCMS method: 5, RT: 3.39 min, MI: 248 [M+1]. NMR 1H (DMSO, 300 MHz): 13.03 (s, 1H), 8.80 (d, 1H), 8.62 (dd, 1H), 8.27 (d, 1H), 7.80 (t, 1H), 7.52 (d, 1H).

The following compounds were prepared according to the general synthesis shown in scheme B2:

2-(2-Chloro-5-fluoro-pyridin-4-yl)-thieno[3,2-d]pyrimidin-4-ol [BB-15]

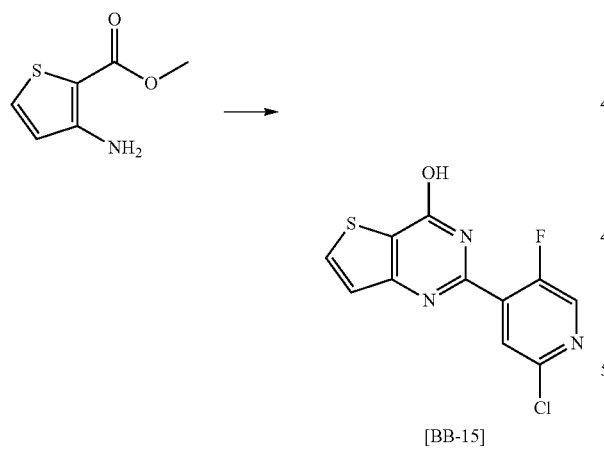

[BB-15]

A microwave vial was charged with 3-amino-thiophene-2-carboxylic acid amide (1.3 g, 9.3 mmol), 2-Chloro-5-fluoro-4-formylpyridine (1g, 5.6 mmol), concentrated hydrogen chloride (1 drop) and methanol (10 ml). The reaction mixture was heated to 120° C. for 20 minutes under microwave irradiation. After completion, the mixture was concentrated under reduced pressure. To a solution of the crude product in dichloromethane (20 ml) was added 2,3-dichloro-5,6-dicyanobenzoquinone (2.3 g, 9.3 mmol). The mixture was stirred at room temperature for 18 hours. After completion, the precipitate formed was filtered and washed with methanol. The residue was used without any further purification in the next step. LCMS method: 8, RT: 3.20 min, MI: 281-283 [M+1]. 1H NMR (DMSO, 300 MHz): 8.68 (1H, d), 8.27 (1H, d), 7.96 (1H, d), 7.51 (1H, d).

2-(2-Chloro-3-fluoro-pyridin-4-yl)-thieno[3,2-d]pyrimidin-4-ol [BB-15a]

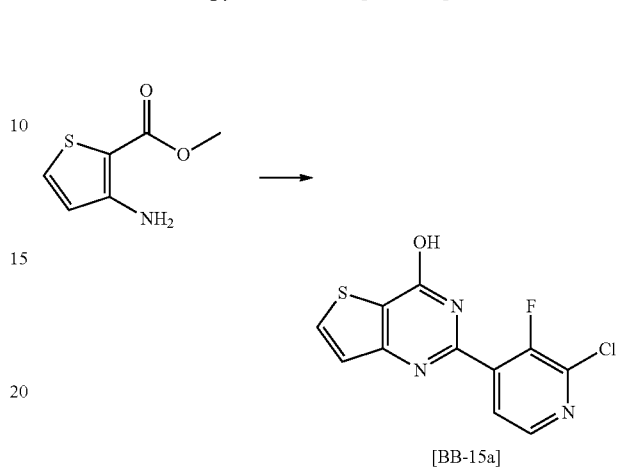

[BB-15a]

A microwave vial was charged with 3-amino-thiophene-2-carboxylic acid amide (0.5 g, 3.5 mmol), 2-Chloro-3-fluoro-4-formylpyridine (0.75 g, 2.12 mmol), 1.25 N hydrogen chloride (1 drop) and methanol (4 ml). The reaction mixture was heated to 120° C. for 20 minutes under microwave irradiation. After completion, the mixture was concentrated under reduced pressure. To a solution of the crude product in dichloromethane (5 ml) was added 2,3-dichloro-5,6-dicyanobenzoquinone (800 mg, 3.5 mmol). The mixture was stirred at room temperature for 18 hours. After completion, the precipitate formed was filtered and washed with methanol. The residue was used without any further purification in the next step. LCMS method: 8, RT: 3.21 min, MI: 281-283 [M+1]. 1H NMR (DMSO) 13.09 (1H, s, br), 8.46 (1H, d), 8.29 (1H, d), 7.83 (1H, t), 7.51 (1H, d).

2-(3-Chloro-pyridin-4-yl)-thieno[3,2-d]pyrimidin-4-ol [BB-15b]

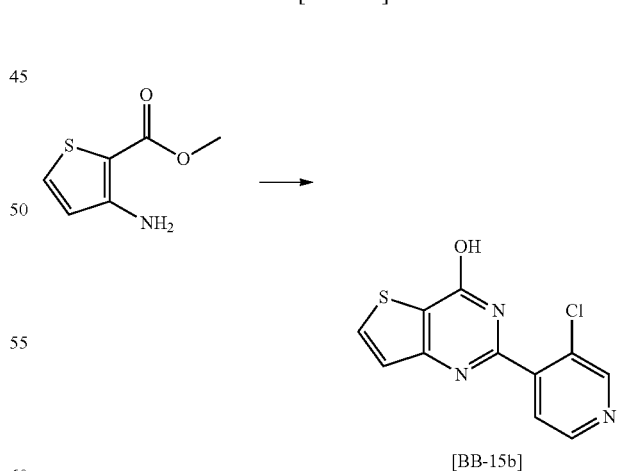

[BB-15b]

A microwave vial was charged with 3-amino-thiophene-2-carboxylic acid amide (1 g, 7.03 mmol), 3-Chloro-pyridine-4-carbaldehyde (0.6 g, 4.24 mmol), 2.5 N hydrogen chloride in ethanol (0.56 mL, 1.4 mmol) and ethanol (10 ml). The reaction mixture was heated to 140° C. for 20 minutes under microwave irradiation. After completion, the precipitate formed was filtered and washed with DCM then methanol. The residue was purified by flash column chromatography (SiO2, MeOH:DCM elution) to five the title compound (0.52 g, 47% yield). LCMS method: 10, MI: 264 [M+1].

General Synthesis of 7-halo substituted-2-pyridin-4-yl-thieno[3,2-d]pyrimidin-4-ol of General Formula [G-113] (Scheme B3a)

A 6-substituted 2-pyridin-4-yl-thieno [3,2-d]pyrimidin-4-ol derivative of general formula [G-112] was brominated at the C7 position in the presence of a halogenating agent such as $Br_2$, N-Bromosuccinimide, Phosphorus(V) oxybromide, and an acidic reagent such as acetic acid. Or chlorinated at the C7 position in the presence of a halogenating agent such as N-chlorosuccinimide and an acidic reagent such as acetic acid to give the corresponding 7-halo substituted-2-pyridin-4-yl-thieno[3,2-d]pyrimidin-4-ol derivative of general formula [G-113], Scheme B3a.

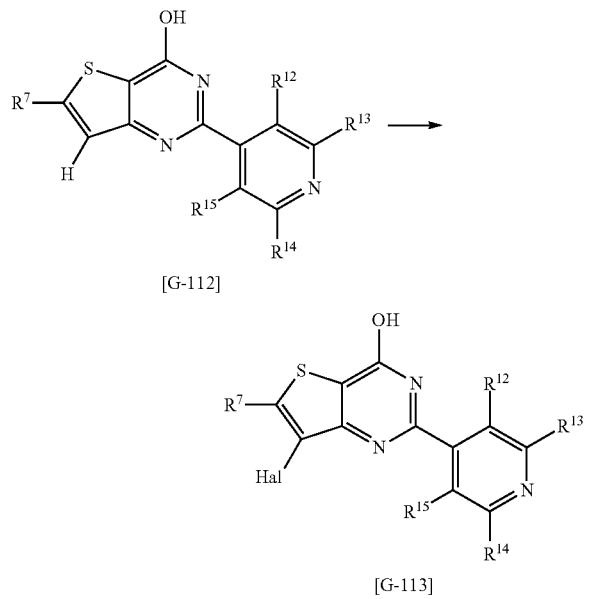

Synthesis of 7-bromo-6-methyl-2-pyridin-4-yl-thieno[3,2-d]pyrimidin-4-ol [BB-16]

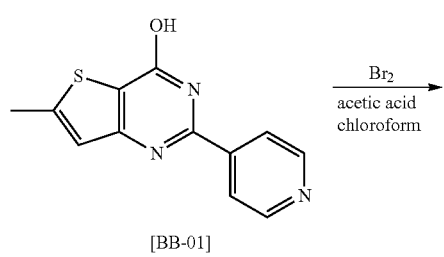

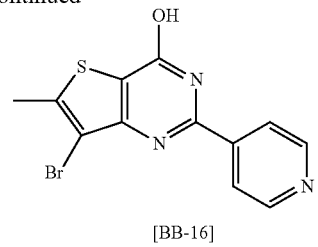

[BB-16]

A solution of bromine (1.2 ml, 23.2 mmol) in chloroform (10 ml) was added to a stirring solution of 6-tert-butyl-2-pyridin-4-yl-thieno[3,2-d]pyrimidin-4-ol [BB-01] (2.84 g, 11.6 mmol) in chloroform (15 ml) acetic acid (15 ml) at 0° C. The mixture was allowed to warm to room temperature and stirred over night. After completion the resulting solid was filtered and washed with chloroform and diethylether to yield the title compound as a yellow solid. LCMS method: 4, RT: 2.14 min, MI: 322-324 [M+1]. 1H NMR (300 MHz, DMSO): 8.76 (m, 2H), 8.05 (m, 2H), 2.60 (s, 3H).

The following compounds were prepared according to the general synthesis shown in scheme B3a:

Synthesis of 7-Bromo-2-(3-fluoro-pyridin-4-yl)-thieno[3,2-d]pyrimidin-4-ol [BB-17]

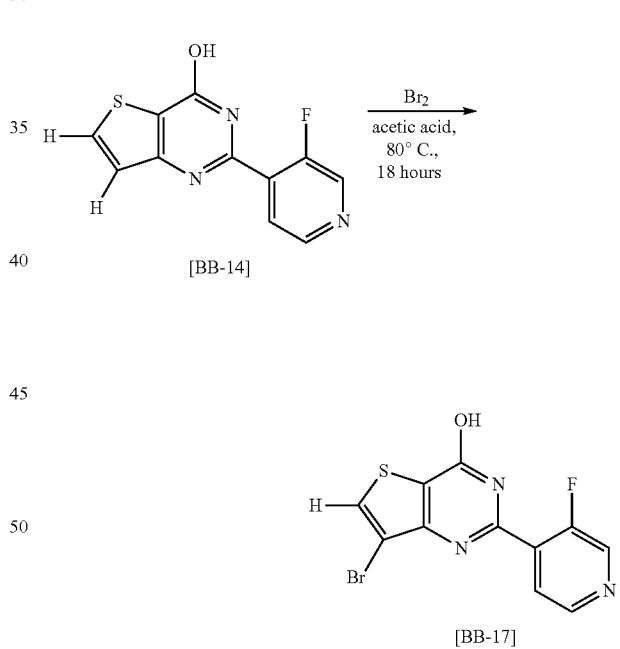

Bromine (1.2 ml, 24.27 mmol) was added to a stirring solution of 2-(3-Fluoro-pyridin-4-yl)-thieno[3,2-d]pyrimidin-4-ol [BB-14] (2.00 g, 8.09 mmol) in acetic acid (20 ml) at ambient temperature. The mixture was heated to 80° C. and stirred over night under reflux conditions. After completion, 10% sodium thiosulphate solution (5 ml) was added and the resulting solid was filtered and washed with water and ethyl acetate to yield the title compound as a colourless solid. LCMS method: 6, RT: 4.33 min, MI: 326-238 [M+1]. NMR 1H (DMSO, 300 MHz): 7.82 (dd, 1H), 8.47 (s, 1H), 8.63 (d, 1H), 8.81 (s, 1H), 13.28 (bs, 1H).

Synthesis of 7-Chloro-2-pyridin-4-yl-thieno[3,2-d]pyrimidin-4-ol [BB-18]

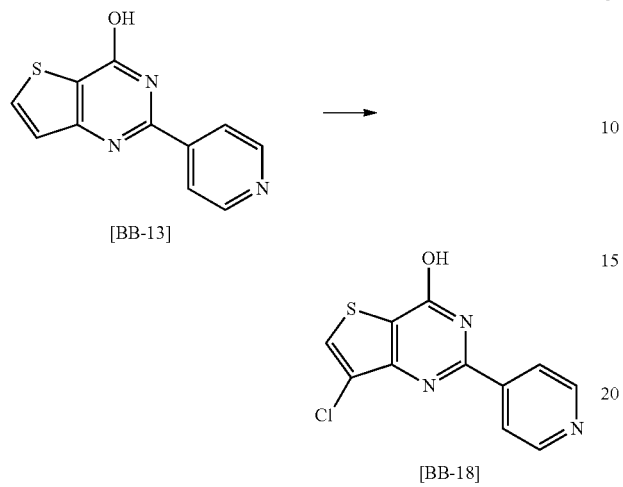

To a stirred suspension of 2-Pyridin-4-yl-thieno[3,2-d]pyrimidin-4-ol [BB-13] (0.5 g, 2.18 mmol) in AcOH (10 ml) was added NCS (1.46 g, 10.9 mmol) and the reaction heated to 80° C. After 18 hr further NCS (0.58 g, 4.36 mmol) was added and the mixture was left to stir at 80° C. for a further another 24 hr. The reaction mixture was cooled and evaporated under reduced pressure and the resulting residue suspended in $H_2O$ and the solid formed was collected by filtration, to give the title compound (0.4 g, 70% yield) which was used without further purification: LCMS method B: 4.16 min, 64%, 263.95 [M+H]

Synthesis of 7-Bromo-6-tert-butyl-2-pyridin-4-yl-thieno[3,2-d]pyrimidin-4-ol [BB-19]

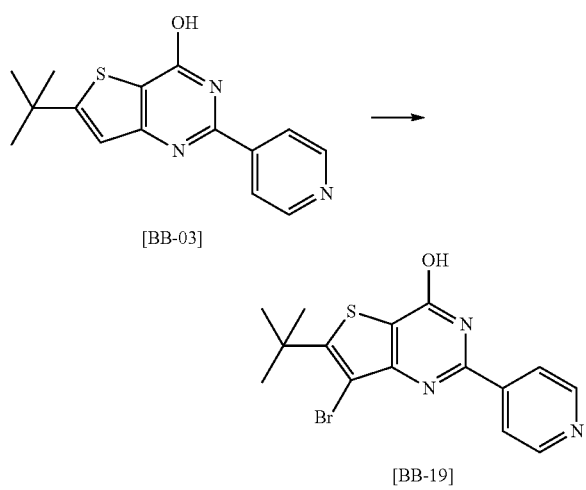

A solution of bromine (60 μL, 1.17 mmol) in chloroform (1 ml) was added to a stirring solution of 6-tert-Butyl-2-pyridin-4-yl-thieno[3,2-d]pyrimidin-4-ol [BB-03] (0.33 g, 1.17 mmol) in chloroform (4 ml) and acetic acid (5 ml) at 0° C. The mixture was allowed to warm to room temperature and stirred over night. After completion the resulting solid was filtered and washed with chloroform and diethylether to yield the title compound as a yellow solid. LCMS method: 3, RT: 4.22 min, MI: 364-366 [M+1].

Synthesis of 7-Bromo-2-pyridin-4-yl-thieno[3,2-d]pyrimidin-4-ol [BB-20]

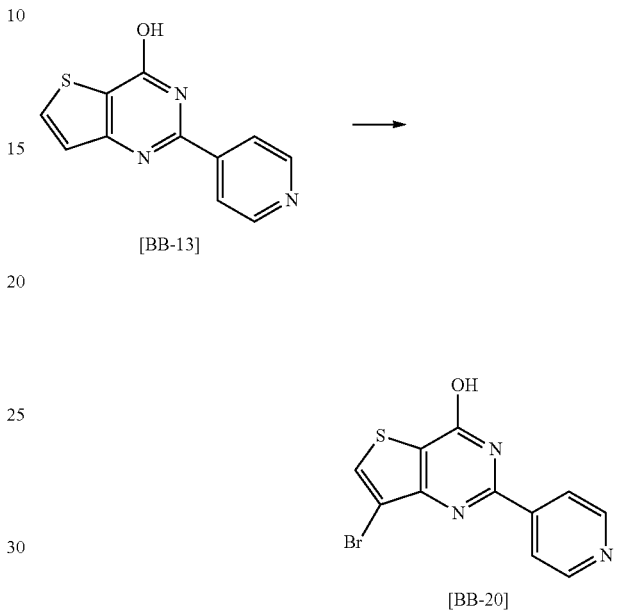

To a stirred suspension of 2-Pyridin-4-yl-thieno[3,2-d]pyrimidin-4-ol [BB-13] (20 g, 87.2 mmol) in AcOH (400 ml) was added $Br_2$ (20 ml). The mixture was left to stir 80° C. for 24 hr then an additional $Br_2$ (10 ml) was added and the mixture was left to stir 80° C. for a further 24 hours. The reaction mixture was cooled and poured into $H_2O$-ice mixture, and the yellow precipitate was collected by filtration and washed with saturated sodium metabisulfite, then $H_2O$ followed by $Et_2O$, to give the title compound as a pale yellow solid (24.1 g, 90% yield). LCMS method: 8, RT: 3.28 min, MI: 307-309 [M+1]. 1H NMR (DMSO) 8.99 (2H, d), 8.49 (1H, s), 8.42 (2H, d).

General Synthesis of 6-halo substituted-2-pyridin-4-yl-thieno[3,2-d]pyrimidin-4-ol Derivative of General Formula [G-116] (Scheme B3b)

A 7-substituted 2-pyridin-4-yl-thieno [3,2-d]pyrimidin-4-ol derivative of general formula [G-115] was brominated at the C6 position in the presence of a halogenating agent such as $Br_2$, N-Bromosuccinimide, Phosphorus(V) oxybromide, and an acidic reagent such as acetic acid. Or chlorinated at the C6 position in the presence of a halogenating agent such as N-chlorosuccinimide and an acidic reagent such as acetic acid to give the corresponding 6-halo substituted-2-pyridin-4-yl-thieno[3,2-d]pyrimidin-4-ol derivative of general formula [G-116], Scheme B3b.

Scheme B3b

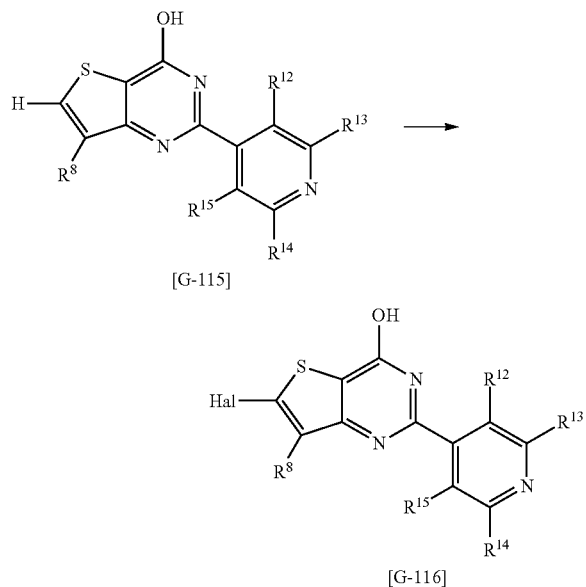

Synthesis of 6-Bromo-7-methyl-2-pyridin-4-yl-thieno[3,2-d]pyrimidin-4-ol [BB-21]

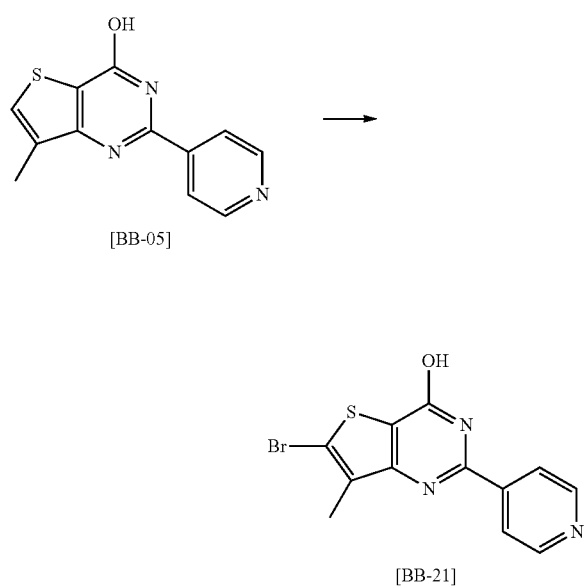

A solution of bromine (600 μL, 4.1 mmol) in chloroform (30 ml) was added to a stirring solution of 7-methyl-2-pyridin-4-yl-thieno[3,2-d]pyrimidin-4-ol [BB-05] (1 g, 10.030 mmol) in chloroform (20 ml) acetic acid (15 ml) at 0° C. The mixture was allowed to warm to room temperature and stirred over night. After completion the resulting solid was filtered and washed with chloroform and diethylether to yield the title compound as a yellow solid, which was used without further purification in the next step: LCMS method B, Purity: 98%, RT: 3.85 min, MI: 321-323.

General Synthesis of 4PT32P Derivatives of General Formula [G-100] (Scheme B4)

4PT32P derivatives of general formula [G-100] were prepared by the reaction of a 6,7-substituted 2-pyridin-4-yl-thieno [3,2-d]pyrimidin-4-ol, of general formula [G-104] (described in scheme B1 & B2) with 2,4,6-triisopropylbenzenesulfonyl chloride in a polar aprotic solvent such as DMA, DMF, NMP with a tertiary alkylamine base such as $Et_3N$, DIPEA or NMM and a catalytic amount of DMAP. The intermediate 6,7-substituted-(2,4,6-triisopropyl-benzenesulfonic acid)-2-pyridin-4-yl-thieno[3,2-d]pyrimidin-4-yl ester, of general formula [G-111] was isolated and then reacted with a primary or secondary amino derivative, of general formula [G-117], in a polar aprotic solvent such as DMA, DMF, NMP in the presence of a tertiary amine base such as $Et_3N$, DIPEA or NMM at ambient temperature [Method A]. After reaction work up, typically by a liquid-liquid extraction or purification by acidic ion exchange catch-release, the N-Boc derivatives were deprotected under acidic conditions with a strong acid such as TFA, TCA, methanesulfonic acid, HCl or $H_2SO_4$ in a solvent such as DCM, DCE, THF, EtOH or MeOH and the crude reaction product was purified by reverse phase preparative HPLC. 4PT32P derivatives of general formula [G-100] were prepared by the reaction of a 6,7-substituted 2-pyridin-4-yl-thieno [3,2-d]pyrimidin-4-ol, of general formula [G-104] (described in scheme B1, B2 & B3) with 2,4,6-triisopropylbenzenesulfonyl chloride in a polar aprotic solvent such as DMA, DMF, NMP with a tertiary alkylamine base such as $Et_3N$, DIPEA or NMM and a catalytic amount of DMAP then used crude and reacted further with a primary or secondary amino derivative, of general formula [G-117], in a polar aprotic solvent such as DMA, DMF, NMP in the presence of a tertiary amine base such as $Et_3N$, DIPEA or NMM at ambient temperature [Method B] without further purification. After reaction work up, typically by a liquid-liquid extraction or purification by acidic ion exchange catch-release, the N-Boc derivatives were deprotected under acidic conditions with a strong acid such as TFA, TCA, methanesulfonic acid, HCl or $H_2SO_4$ in a solvent such as DCM, DCE, THF, EtOH or MeOH and the crude reaction product was purified by reverse phase preparative HPLC. 4PT32P derivatives of general formula [G-100] were prepared by the reaction of a 6,7-substituted 2-pyridin-4-yl-thieno [3,2-d]pyrimidin-4-ol of general formula [G-104] with a chlorination reagent such as phosphorus oxychloride to give compounds of general formula [G-112] and then reacted with a primary or secondary amino derivative, of general formula [G-117], in a polar aprotic solvent such as DMA, DMF, NMP in the presence of a tertiary amine base such as $Et_3N$, DIPEA or NMM at ambient temperature [Method C]. After reaction work up, typically by a liquid-liquid extraction or purification by acidic ion exchange catch-release, the N-Boc derivatives were deprotected under acidic conditions with a strong acid such as TFA, TCA, methanesulfonic acid, HCl or $H_2SO_4$ in a solvent such as DCM, DCE, THF, EtOH or MeOH and the crude reaction product was purified by reverse phase preparative HPLC.

Scheme B4
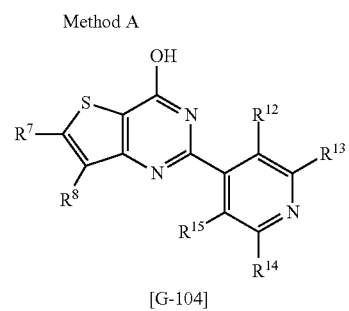
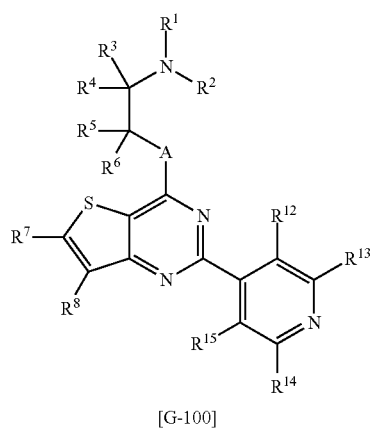
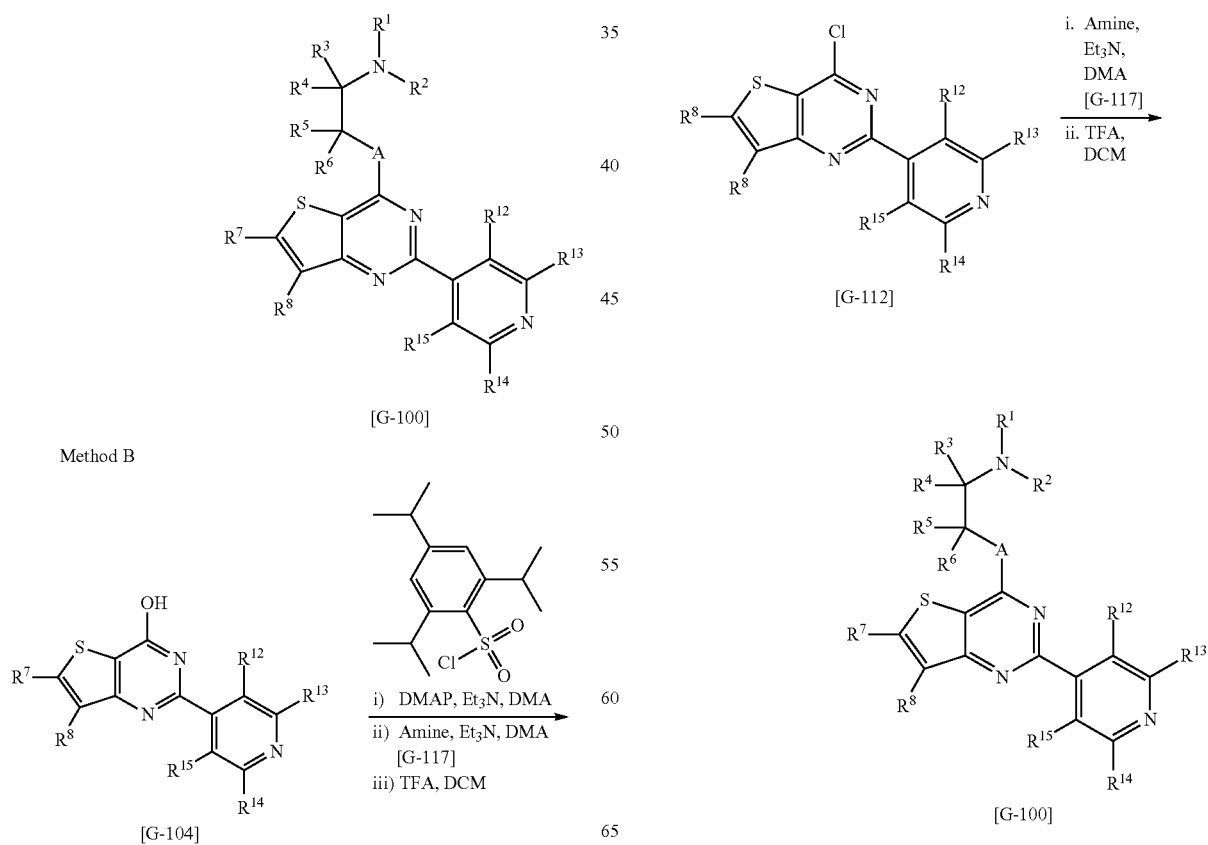

Method A

Synthesis of 2,4,6-triisopropyl-benzenesulfonic acid 7-bromo-6-methyl-2-pyridin-4-yl-thieno [3,2-d]pyrimidin-4-yl ester [BB-22]

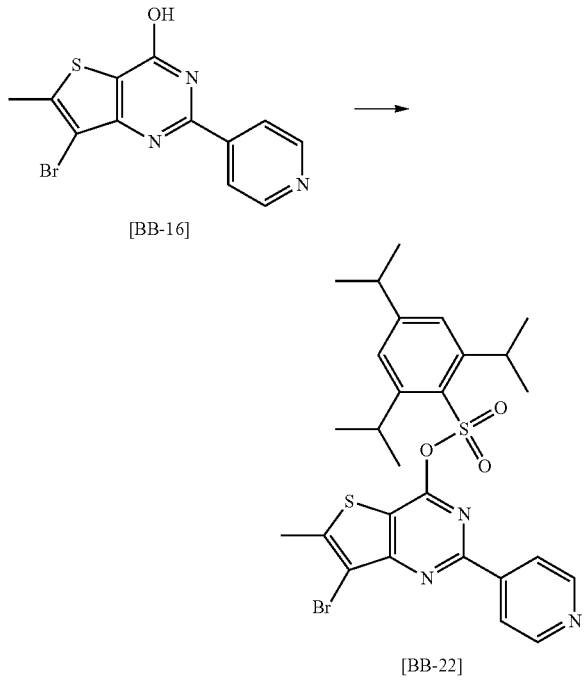

To a solution of 7-bromo-6-methyl-2-pyridin-4-yl-thieno [3,2-d]pyrimidin-4-ol [BB-16] (3.76 g, 11.6 mmol) in DCM (15 ml) was added 2,4,6-triisopropylbenzenesulfonyl chloride (4.25 g, 23.2 mmol), Et$_3$N (2.2 ml, 23.2 mmol) and DMAP (27 mg, 0.22 mmol). The mixture was stirred for one hour. After completion the mixture was diluted with water and the product was extracted into DCM (2×10 ml). The combined organic phases were dried (MgSO$_4$), filtered and evaporated under reduced pressure to provide the title compound as a brown solid. The crude was used without further purification in the next step. LCMS method: 3, RT: 6.36 min, MI: 588-590 [M+1].

Synthesis of (S)—N*1*-(7-bromo-6-methyl-2-pyridin-4-yl-thieno[3,2-d]pyrimidin-4-yl)-3-phenyl-propane-1,2-diamine [300]

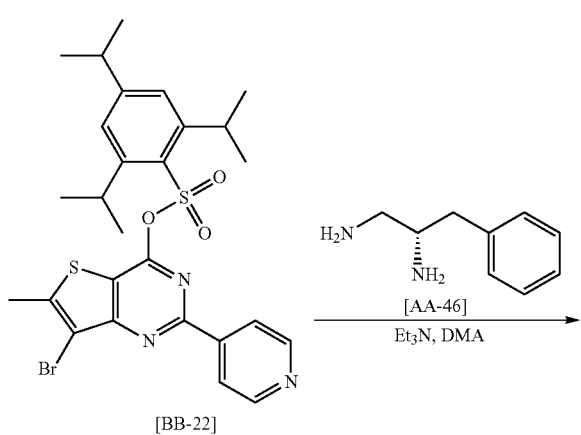

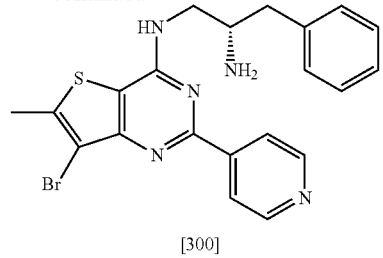

To a solution of 2,4,6-triisopropyl-benzenesulfonic acid 7-bromo-6-methyl-2-pyridin-4-yl-thieno[3,2-d]pyrimidin-4-yl ester [BB-22] (2.5 g, 4.24 mmol) in DMA (5 ml) was added (S)-3-phenyl-propane-1,2-diamine [AA-46] (700 μl, 4.66 mmol) followed by Et$_3$N (1.1 ml, 8.48 mmol), the mixture was stirred at room temperature for 2 hours. After completion the mixture was loaded onto a SCX-2 cartridge and washed with methanol. The product was released from the cartridge using a solution of 2M ammonia/methanol. The ammonia/methanol eluent was concentrated under reduced pressure and the crude product was purified by preparative HPLC (method A) to yield to the title compound. LCMS method: 4, RT: 4.07 min, MI: 454-456 [M+1]. $^1$H NMR (300 MHz, DMSO): 8.69 (d, 2H), 8.06 (d, 2H), 7.32 (m, 5H), 3.86 (m, 1H), 3.37 (m, 2H), 2.77 (m, 2H), 2.59 (s, 3H)

Synthesis of 2,4,6-Triisopropyl-benzenesulfonic acid 6-phenyl-2-pyridin-4-yl-thieno[3,2-d]pyrimidin-4-yl ester [BB-23]

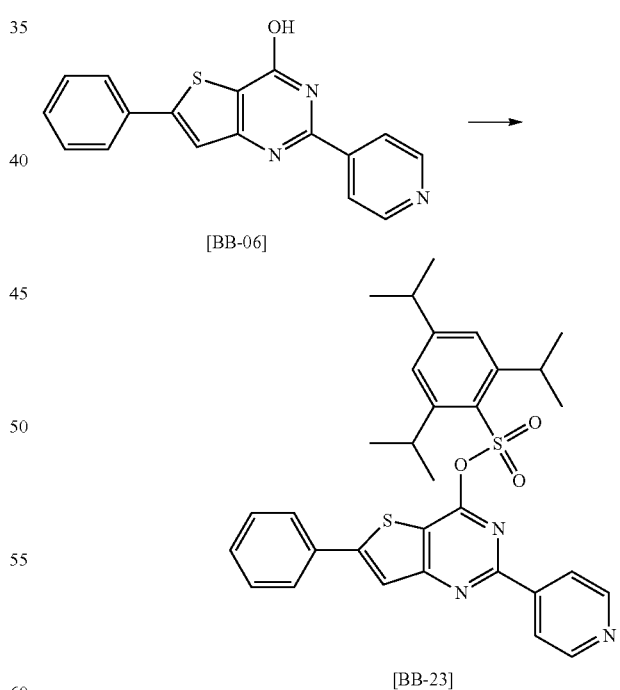

To a solution of 6-Phenyl-2-pyridin-4-yl-thieno[3,2-d]pyrimidin-4-ol [BB-06] (671 mg, 2.2 mmol) in DCM (5 ml) was added 2,4,6-triisopropylbenzenesulfonyl chloride (710 mg, 2.64 mmol) were added Et$_3$N (920 μl, 6.6 mmol) and DMAP (14 mg, 0.11 mmol). The mixture was stirred for one hour. After completion the mixture was diluted with water and the product was extracted into DCM (2×2 ml). The combined organic phases were dried with magnesium sulfate, filtered and evaporated to provide 2,4,6-Triisopropyl-benzenesulfonic acid 6-phenyl-2-pyridin-4-yl-thieno[3,2-d]pyrimidin-4-yl ester [BB-16] as a brown solid. The crude was used without further purification in the next step. LCMS method: 3, RT: 6.12 min, MI: 572 [M+1].

Synthesis of 6-phenyl-4-piperazin-1-yl-2-pyridin-4-yl-thieno[3,2-d]pyrimidine

Synthesis of 2,4,6-triisopropylbenzenesulfonic acid 6-tert-butyl-2-pyridin-4-yl-thieno[3,2-d]pyrimidin-4-yl ester [BB-24]

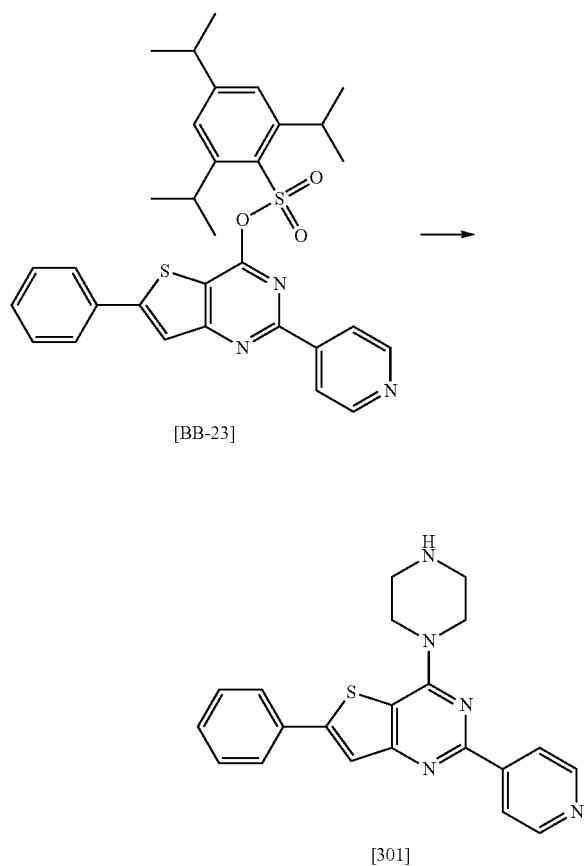

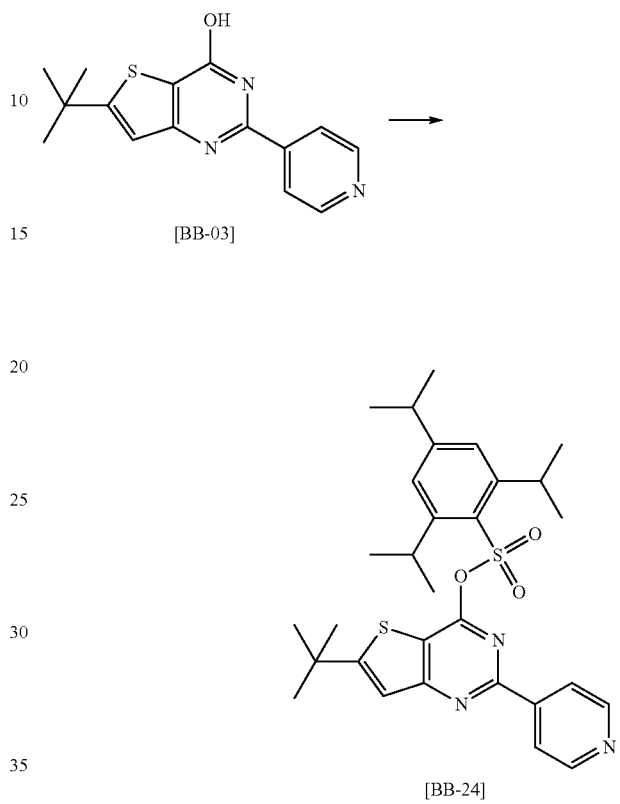

To a solution of 2,4,6-triisopropylbenzenesulfonic acid 6-phenyl-2-pyridin-4-yl-thieno[3,2-d]pyrimidin-4-yl ester [BB-23] (60 mg, 0.105 mmol) in DMA (1 ml) was added piperazine (10 mg, 0.115 mmol) followed by Et₃N (30 µl, 0.210 mmol), the mixture was stirred at room temperature for 2 hours. The crude reaction mixture was extracted with DCM (1 ml) and washed with brine (2 ml) and the extracts were loaded onto a SCX-2 cartridge and washed with methanol. The product was released from the cartridge using a solution of 2M ammonia/methanol. The ammonia/methanol eluent was concentrated under reduced pressure and the crude product was purified by preparative HPLC (method A) to yield to the desired compound. LCMS method: 2, RT: 2.20 min, MI: 374 [M+1]. 1H NMR (300 MHz, DMSO): 8.73 (dd, 2H), 8.27 (dd, 2H), 8 (s, 1H), 7.91 (d, 2H), 7.51 (m, 3H), 4.06 (m, 4H), 3.04 (m, 4H).

The following 6,7-substituted-(2,4,6-triisopropyl-benzenesulfonic acid)-2-pyridin-4-yl-thieno[3,2-d]pyrimidin-4-yl esters of general formula [G-111] were prepared:

To a solution of 6-tert-butyl-2-pyridin-4-yl-thieno[3,2-d]pyrimidin-4-ol [BB-03] (630 mg, 2.2 mmol) in DCM (5 ml) was added 2,4,6-triisopropylbenzenesulfonyl chloride (710 mg, 2.64 mmol), Et₃N (920 µl, 6.6 mmol) and DMAP (14 mg, 0.110 mmol). The mixture was stirred for one hour. After completion the mixture was diluted with water and the product was extracted into DCM (2×2 ml). The combined organic phases were dried (MgSO₄), filtered and evaporated under reduced pressure to provide the title compound as a brown solid. The crude was used without further purification in the next step. LCMS method: 3, RT: 6.25 min, MI: 551 [M+1].

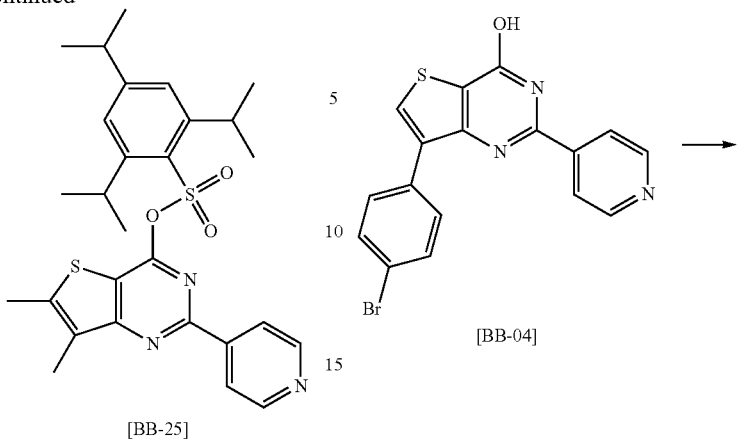

2,4,6-triisopropyl-benzenesulfonic acid 6,7-dimethyl-2-pyridin-4-yl-thieno[3,2-d]pyrimidin-4-yl ester [BB-25] was prepared by reaction of 6,7-dimethyl-2-pyridin-4-yl-thieno[3,2-d]pyrimidin-4-ol [BB-02], 2,4,6-triisopropylbenzenesulfonyl chloride, Et₃N, DMAP and DCM at room temperature to give the desired compound as a brown solid. LCMS method: 3, RT: 6.33 min, MI: 524 [M+1].

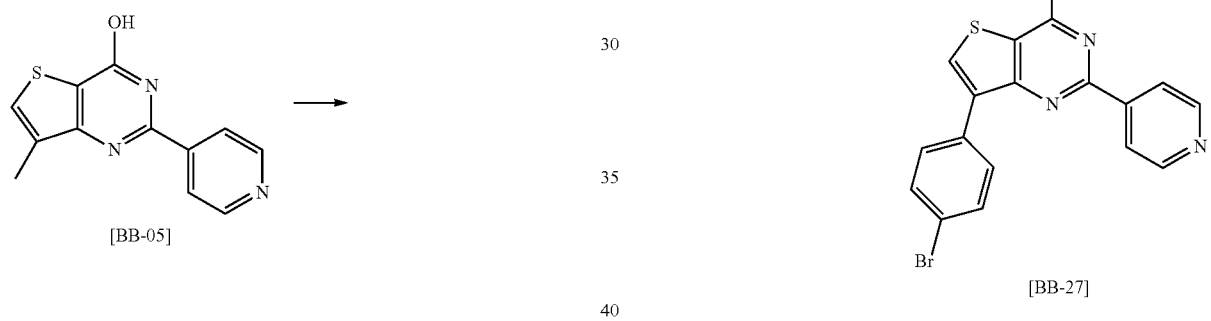

2,4,6-triisopropyl-benzenesulfonic acid 7-methyl-2-pyridin-4-yl-thieno[3,2-d]pyrimidin-4-yl ester [BB-26] was prepared by reaction of 7-methyl-2-pyridin-4-yl-thieno[3,2-d]pyrimidin-4-ol [BB-05], 2,4,6-triisopropylbenzenesulfonyl chloride, Et₃N, DMAP and DCM at room temperature to give the desired compound as a brown solid. LCMS method: 3, RT: 6.15 min, MI: 510 [M+1].

2,4,6-triisopropyl-benzenesulfonic acid 7-(4-bromo-phenyl)-2-pyridin-4-yl-thieno[3,2-d]pyrimidin-4-yl ester [BB-27] was prepared by reaction of 7-(4-bromo-phenyl)-2-pyridin-4-yl-thieno[3,2-d]pyrimidin-4-ol [BB-04], 2,4,6-triisopropylbenzenesulfonyl chloride, Et₃N, DMAP and DCM at room temperature to give the desired compound as a brown solid. LCMS method: 3, RT: 6.69 min, MI: 650 [M+1].

Synthesis of 2,4,6-Triisopropyl-benzenesulfonic acid 7-bromo-6-tert-butyl-2-pyridin-4-yl-thieno[3,2-d]pyrimidin-4-yl ester [BB-29]

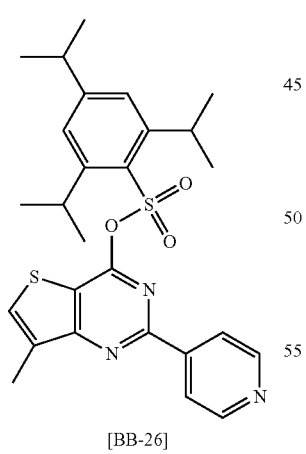

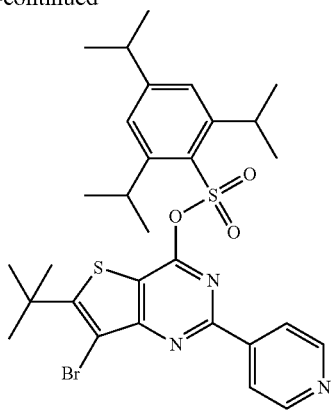

[BB-29]

2,4,6-Triisopropyl-benzenesulfonic acid 7-bromo-6-tert-butyl-2-pyridin-4-yl-thieno[3,2-d]pyrimidin-4-yl ester [BB-28] was prepared by reaction of 7-Bromo-6-tert-butyl-2-pyridin-4-yl-thieno[3,2-d]pyrimidin-4-ol [BB-19], 2,4,6-triisopropyl benzene sulfonyl chloride, Et$_3$N, DMAP and DCM at room temperature to give the desired compound as a brown solid. LCMS method: 3, RT: 6.56 min, MI: 630-632 [M+1].

Synthesis of (S)—N*1*-(2-pyridin-4-yl-5,6,7,8-tetrahydro-benzo[4,5]thieno[2,3-d]pyrimidin-4-yl)-butane-1,2-diamine [302]

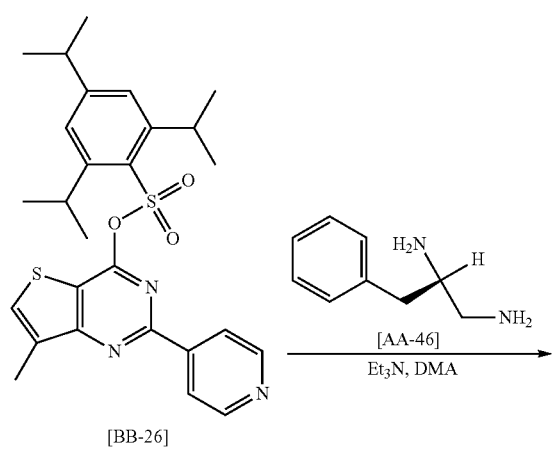

To a solution of 2,4,6-triisopropyl-benzenesulfonic acid 7-methyl-2-pyridin-4-yl-thieno[3,2-d]pyrimidin-4-yl ester [BB-26] (100 mg, 0.196 mmol) in DMA (2 ml) was added (S)-3-phenyl-propane-1,2-diamine [AA-46] (32 mg, 0.216 mmol) followed by Et$_3$N (55 µl, 0.392 mmol), the mixture was stirred at room temperature for 2 hours. After completion the mixture was loaded onto a SCX-2 cartridge and washed with methanol. The product was released from the cartridge using a solution of 2M ammonia/methanol. The ammonia/methanol eluent was concentrated under reduced pressure and the crude product was purified by preparative HPLC (method B) to yield to the title compound. LCMS method: 4, RT: 3.70 min, MI: 376 [M+1]. 1H NMR (300 MHz, DMSO): 8.68 (dd, 2H), 8.10 (dd, 2H), 7.80 (s, 1H), 7.34 (m, 5H), 3.87 (m, 1H), 3.39 (m, 2H), 2.79 (m, 2H), 2.41 (s, 3H).

(S)—N*1*-(7-bromo-6-tert-butyl-2-pyridin-4-yl-thieno[3,2-d]pyrimidin-4-yl)-3-(2-methoxy-phenyl)-propane-1,2-diamine [303]

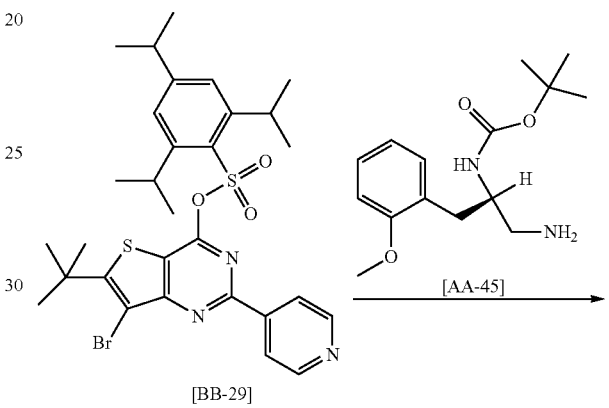

To a solution of 2,4,6-triisopropyl-benzenesulfonic acid 7-bromo-6-tert-butyl-2-pyridin-4-yl-thieno[3,2-d]pyrimidin-4-yl ester [BB-29] (173 mg, 0.275 mmol) in DMA (2 ml) was added [(S)-2-amino-1-(2-methoxy-benzyl)-ethyl]-carbamic acid tert-butyl ester [AA-45] (85 mg, 0.302 mmol) followed by Et$_3$N (120 µl, 0.825 mmol), the mixture was stirred at room temperature for 2 hours. The crude reaction mixture was extracted with DCM (2 ml) and washed with brine (3 ml). To the organic phase was added TFA (2 ml) and the mixture was stirred at room temperature for 1 hour. After completion the mixture was loaded onto a SCX-2 cartridge and washed with methanol. The product was released from the cartridge using a solution of 2M ammonia/methanol. The ammonia/methanol eluent was concentrated under reduced pressure and the crude product was purified by preparative HPLC (method A) to yield to the title compound. LCMS method: 4, RT: 3.79 min, MI: 526-528 [M+1].

Method B

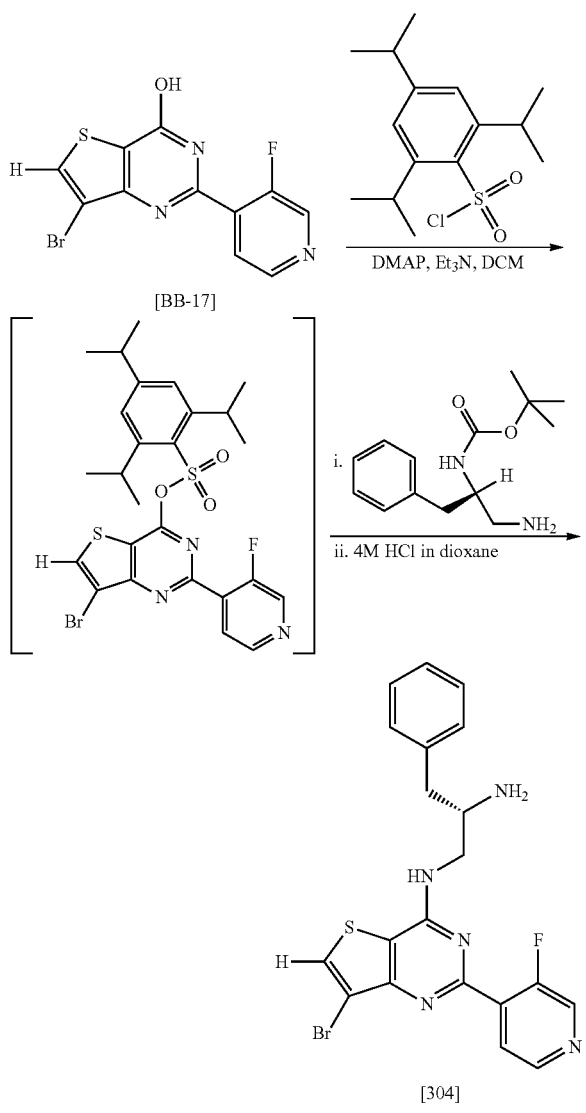

Synthesis of (S)—N*1*-[7-Bromo-2-(3-fluoro-pyridin-4-yl)-thieno[3,2-d]pyrimidin-4-yl]-3-phenyl-propane-1,2-diamine [304]

To a solution of 7-Bromo-2-(3-fluoro-pyridin-4-yl)-thieno[3,2-d]pyrimidin-4-ol [BB-17] (2.0 g, 6.13 mmol) in DCM (40 ml) was added 2,4,6-triisopropylbenzenesulfonyl chloride (2.2 g, 7.36 mmol), triethylamine (2.6 ml, 18.40 mmol) and DMAP (75 mg, 0.613 mmol). The solution was stirred at room temperature for 4 hours. ((S)-2-Amino-1-benzyl-ethyl)-carbamic acid tert-butyl ester (1.84 g, 7.36 mmol) was added and the mixture was stirred at room temperature for 18 hours. The crude reaction mixture was extracted with DCM (150 ml), washed with brine (100 ml) the combined organic phases were dried (MgSO₄), filtered and evaporated under reduced pressure to provide a crude gum which was titrutated with ether to provide the N-Boc protected intermediated as a pale white solid. The N-Boc protected intermediate was taken up in a 4M solution of HCl/dioxane (10 ml) and the mixture was stirred at room temperature overnight. After completion the mixture was loaded onto a SCX-2 cartridge and washed with methanol. The product was released from the cartridge using a solution of 2M ammonia/methanol. The ammonia/methanol eluent was concentrated under reduced pressure followed by trituration in ether to yield the desired compound. LCMS method: 9, RT: 5.34 min, MI: 458-460 [M+1]. 1H NMR (MeOD, 300 MHz): 8.61 (d, 1H), 8.52 (dd, 1H), 8.18 (s, 1H), 8.02 (m, 1H), 7.32 (m, 5H), 3.99 (m, 2H), 3.77 (m, 1H), 3.06 (d, 2H).

Synthesis of (R)-3-[2-(2-Chloro-5-fluoro-pyridin-4-yl)-thieno[3,2-d]pyrimidin-4-ylamino]-pyrrolidine-1-carboxylic acid tert-butyl ester [BB-31]

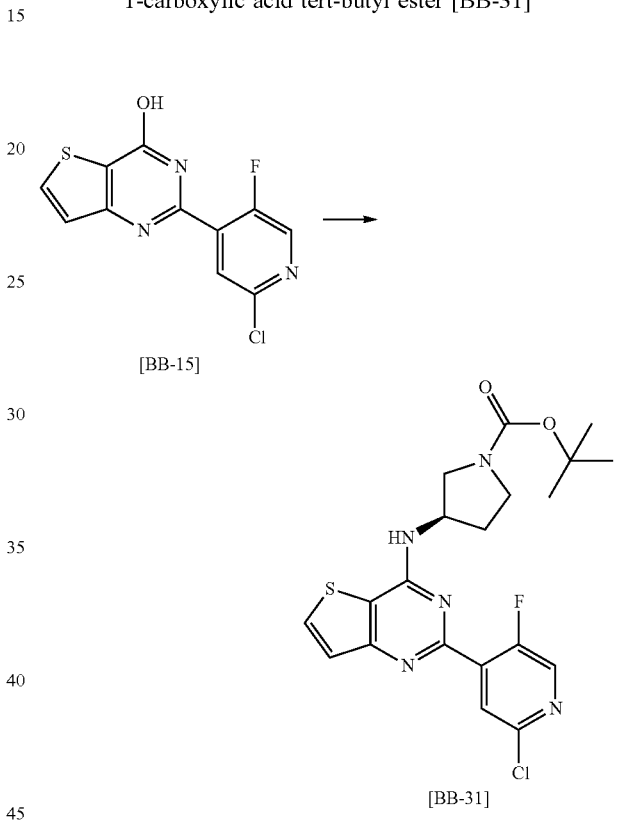

To a stirred suspension of 2-(2-Chloro-5-fluoro-pyridin-4-yl)-thieno[3,2-d]pyrimidin-4-ol [BB-15] (1.46 g, 5.18 mmol) and DMAP (63 mg, 0.518 mmol) in DCM (10 ml) was added triethylamine (1.6 ml, 11.4 mmol) followed by 2,4,6-Triisopropylbenzenesulfonyl chloride (2.35 g, 7.77 mmol). The reaction mixture was stirred at room temperature for 1 hr, during which time the solution became clear. The crude reaction mixture was evaporated under reduced pressure, then the residue was dissolved in DMA (10 ml) and triethylamine (1.6 ml, 11.4 mmol) followed by (R)-(+)-1-Boc-3-aminopyrrolidine (450 μL, 7.77 mmol) added and the mixture was left to stir at room temperature for 18 hr. The mixture was partitioned between (DCM:H₂O) and organic phase separated and evaporated under reduced pressure to give a pale brown oil, which was purified by normal phase chromatography (SiO2, ethyl acetate: cyclohexane elution) to give the title compound (1.71 g, 73% yield: LCMS method 3: 4.70 min, 95%, 450.06 [M+H]; 1H NMR (MeOD) 8.40 (1H, d), 8.05 (1H, d), 8.03 (1H, d), 7.44 (1H, d), 4.80 (1H, m), 3.87-3.77 (1H, m), 3.59-3.42 (2H, m), 3.40 (1H, dd), 3.36-3.26 (1H, m), 2.18-2.09 (1H, m), 1.46 (9H, s).

265

Synthesis of (R)-3-[2-(2-Chloro-pyridin-4-yl)-thieno[3,2-d]pyrimidin-4-ylamino]-pyrrolidine-1-carboxylic acid tert-butyl ester[BB-32]

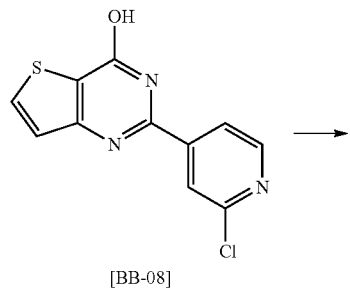

[BB-08]

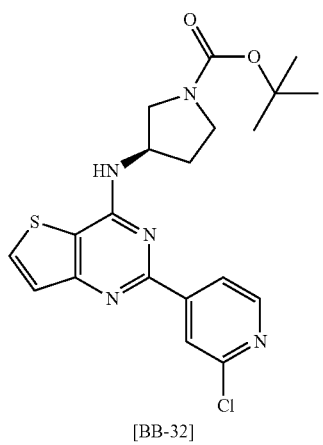

[BB-32]

To a stirred suspension of 2-(2-Chloro-pyridin-4-yl)-thieno[3,2-d]pyrimidin-4-ol [BB-08] (2.69 g, 10.2 mmol) and DMAP (125 mg, 1 mmol) in DCM (30 ml) was added triethylamine (3.1 ml, 22.4 mmol) followed by 2,4,6-Triisopropylbenzenesulfonyl chloride (4.6 g, 15.3 mmol). The reaction mixture was stirred at room temperature for 1 hr. The crude reaction mixture was evaporated under reduced pressure, then the residue was dissolved in DMA (30 ml) and triethylamine (3.1 ml, 22.4 mmol) followed by (R)-(+)-1-Boc-3-aminopyrrolidine (2.6 ml, 15.3 mmol) added and the mixture was left to stir at room temperature for 18 hr. The crude reaction mixture was partitioned between (DCM: H₂O) and organic phase separated, dried (MgSO₄), filtered and evaporated under reduced pressure to give a pale brown oil, which was purified by normal phase chromatography (SiO₂, ethyl acetate: cyclohexane elution) to give the title compound (2.2 g, 50% yield: LCMS method 3: 4.81 min, 85%, 432.07 [M+H]; ¹H NMR (DMSO) 8.54 (1H, dd), 8.29 (1H, d), 8.28 (1H, s), 8.21 (1H, d), 7.51 (1H, d), 4.89-4.80 (1H, m), 3.79-3.67 (1H, m), 3.51-3.25 (3H, m), 2.30-2.19 (1H, m), 2.07-2.01 (1H, m), 1.40 (9H, s).

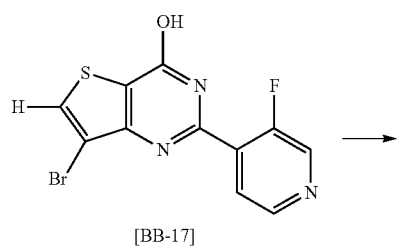

[BB-17]

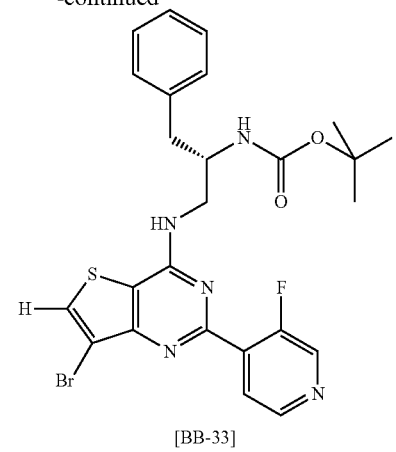

[BB-33]

{1-Benzyl-2-[7-bromo-2-(3-fluoro-pyridin-4-yl)-thieno[3,2-d]pyrimidin-4-ylamino]-ethyl})-carbamic acid tert-butyl ester [BB-33] was prepared by reaction of 7-Bromo-2-(3-fluoro-pyridin-4-yl)-thieno[3,2-d]pyrimidin-4-ol [BB-17], DMAP, triethylamine, 2,4,6-Triisopropylbenzenesulfonyl chloride in DCM, followed by reaction with ((S)-1-Aminomethyl-2-phenyl-ethyl)-carbamic acid tert-butyl ester to give the title compound: LCMS method B, RT: 4.78 min, MI: 558-560

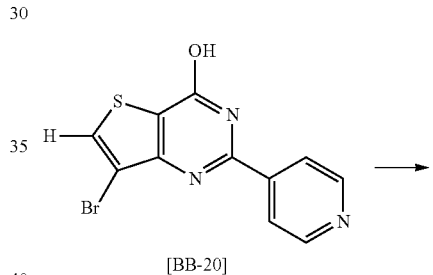

[BB-20]

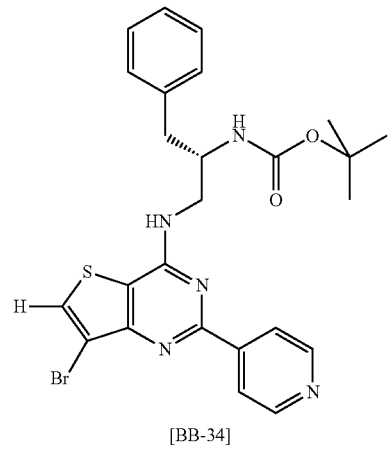

[BB-34]

[1-Benzyl-2-(7-bromo-2-pyridin-4-yl-thieno[3,2-d]pyrimidin-4-ylamino)-ethyl]-carbamic acid tert-butyl ester [BB-34] was prepared by reaction of 7-Bromo-2-pyridin-4-yl-thieno[3,2-d]pyrimidin-4-ol [BB-20], DMAP, triethylamine, 2,4,6-Triisopropylbenzenesulfonyl chloride in DCM, followed by reaction with ((S)-1-Aminomethyl-2-phenyl-ethyl)-carbamic acid tert-butyl ester to give the title compound: LCMS method 3: 4.39 min, 95%, 542.04 [M+H]; ¹H NMR (DMSO) 8.70 (2H, d), 8.39 (1H, s), 8.20 (2H, d), 7.29-7.22 (5H, m), 6.83 (1H, d), 4.09-4.06 (1H, m), 3.78-3.71 (1H, m), 3.51 (1H, m), 2.82-2.78 (2H, m), 1.23 (7H, s), 0.88 (2H, s).

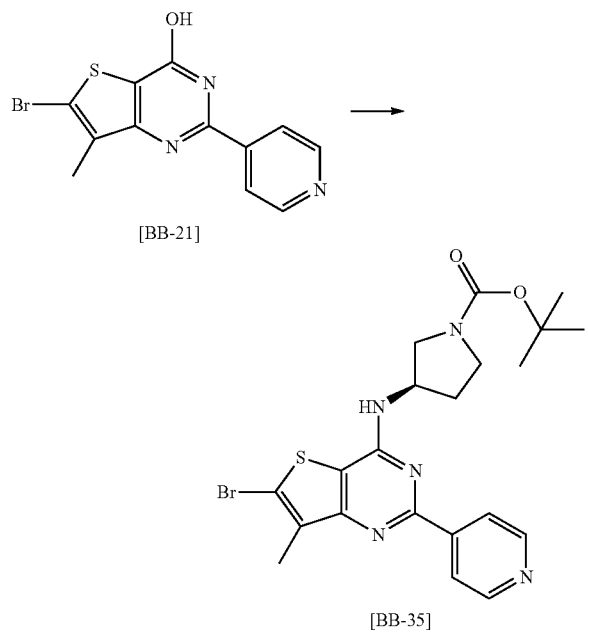

(R)-3-(6-Bromo-7-methyl-2-pyridin-4-yl-thieno[3,2-d]pyrimidin-4-ylamino)-pyrrolidine-1-carboxylic acid tert-butyl ester [BB-35] was prepared by reaction of 6-Bromo-7-methyl-2-pyridin-4-yl-thieno[3,2-d]pyrimidin-4-ol [BB-21], DMAP, triethylamine, 2,4,6-Triisopropylbenzenesulfonyl chloride in DCM, followed by reaction with (R)-(+)-1-Boc-3-aminopyrrolidine to give the title compound: LCMS method 3 RT: 4.77 min, MI: 490-492

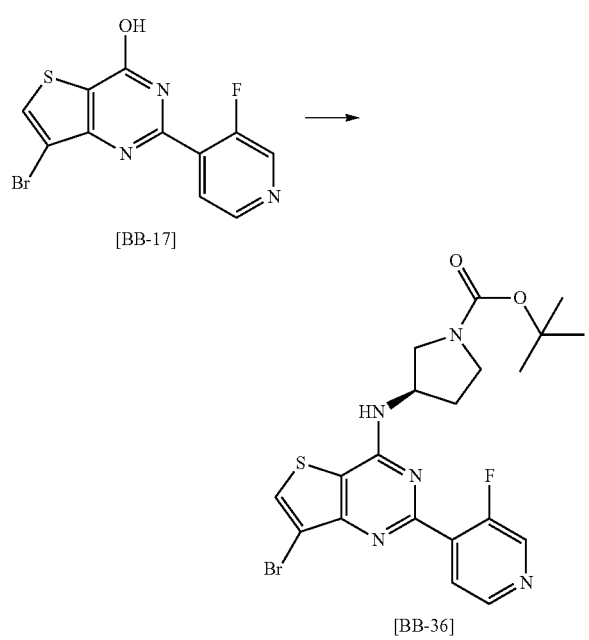

(R)-3-[7-Bromo-2-(3-fluoro-pyridin-4-yl)-thieno[3,2-d]pyrimidin-4-ylamino]-pyrrolidine-1-carboxylic acid tert-butyl ester [BB-36] was prepared by reaction of 67-Bromo-2-(3-fluoro-pyridin-4-yl)-thieno[3,2-d]pyrimidin-4-ol [BB-17], DMAP, triethylamine, 2,4,6-Triisopropylbenzenesulfonyl chloride in DCM, followed by reaction with (R)-(+)-1-Boc-3-aminopyrrolidine to give the title compound: LCMS method 3 RT: 4.49 min, MI: 494-496
Method C

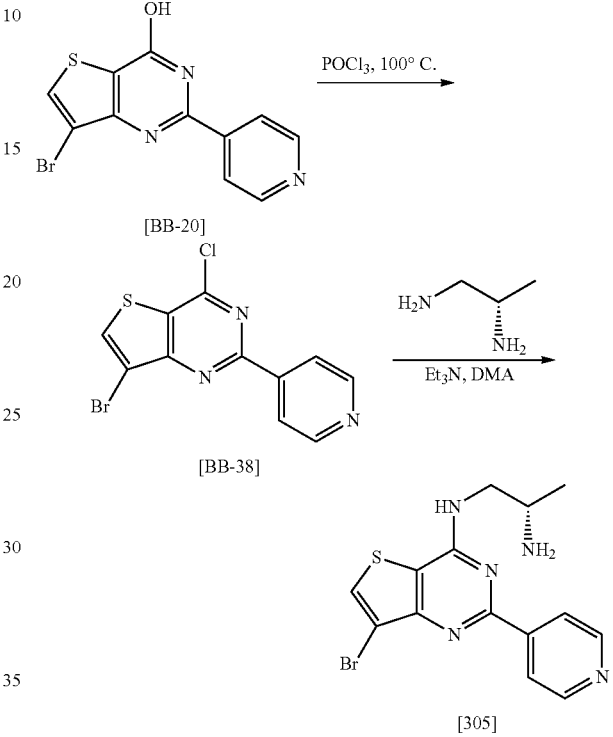

Synthesis of 7-Bromo-4-chloro-2-pyridin-4-yl-thieno[3,2-d]pyrimidine (BB-38) 7-Bromo-2-pyridin-4-yl-thieno[3,2-d]pyrimidin-4-ol [BB-20]

(12 g, 38.9 mmol) was suspended in phosphorus oxychloride (120 ml) and the suspension heated to 110° C. After 1 hour the reaction mixture was allowed to cool then phosphorus oxychloride removed under reduced pressure and the residue azeotroped with toluene. The pH was adjusted to pH 8 by the cautious addition of 2M NaOH and the mixture was left to stir at room temperature for 18 hours and the pale brown solid was collected by filtration, washed with water and dried under reduced pressure to give the title compound which was used in the next step without further purification. LCMS method: 5, RT: 5.68 min, MI: 327 [M+1]. 1H NMR (300 MHz, DMSO) 8.92 (2H, dd), 8.88 (1H, s), 8.50 (2H, dd).

Synthesis of (S)—N*1*-(7-Bromo-2-pyridin-4-yl-thieno[3,2-d]pyrimidin-4-yl)-propane-1,2-diamine [305]

To a solution of Bromo-4-chloro-2-pyridin-4-yl-thieno[3,2-d]pyrimidine [BB-38] (100 mg, 0.307 mmol) in DMA (2 ml) was added S-(−)-1,2-diaminopropane dihydrochloride (50 mg, 0.308 mmol) followed by Et₃N (128 µl, 0.921 mmol), and the mixture stirred at room temperature for 18 hours. After completion the mixture was loaded onto a SCX-2 cartridge and washed with methanol. The product was released from the cartridge using a solution of 2M ammonia/methanol. The ammonia/methanol eluent was concentrated under reduced pressure and the crude product was purified by preparative HPLC (method A) to yield the title compound. LCMS method: 3, RT: 2.25 min, MI: 364-366 [M+1]. 1H NMR (300 MHz, DMSO): 8.74 (2H, dd), 8.41 (1H, s), 8.38 (1H, s), 8.34 (dd, 2H), 3.72 (m, 2H), 3.46 (m, 1H), 1.21 (s, 3H).

Synthesis of 7-chloro-4-chloro-2-pyridin-4-yl-thieno[3,2-d]pyrimidine (BB-39)

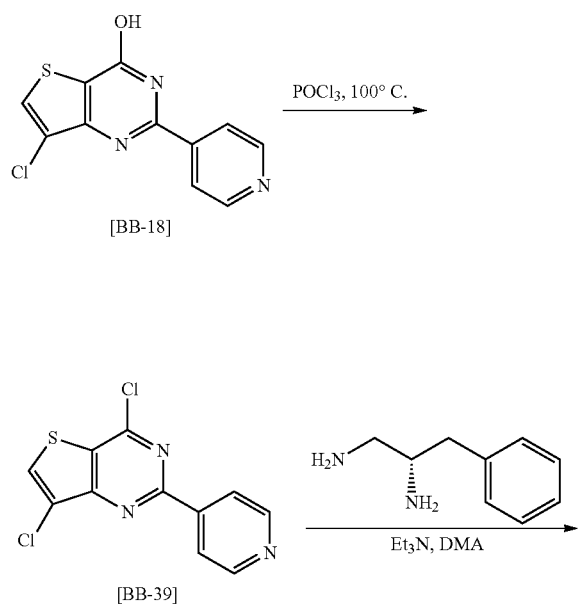

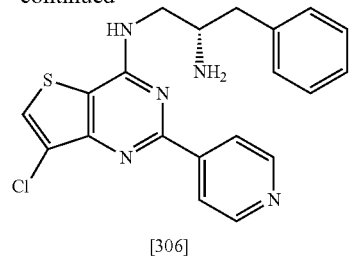

[306]

To a stirred solution of 7-Chloro-2-pyridin-4-yl-thieno[3,2-d]pyrimidin-4-ol [BB-18] (0.2 g, 0.78 mmol) in DMF (2 ml) was added POCl$_3$ (40 µL) and the RM stirred at 80° C. for 48 hours. The reaction mixture was cooled and poured into ice-water and the dark brown solid was collected by filtration to give the title compound which was used without further purification: LCMS method B 5.29 min, 281.89 [M+H].

Synthesis of (S)—N*1*-(7-Chloro-2-pyridin-4-yl-thieno[3,2-d]pyrimidin-4-yl)-3-phenyl-propane-1,2-diamine [306]

To a stirred suspension of 7-chloro-4-chloro-2-pyridin-4-yl-thieno[3,2-d]pyrimidine [BB-39] (0.5 g, 0.18 mmol) in DMA (1 ml) was added ((S)-1-aminomethyl-2-phenyl-ethyl)-carbamic acid tert-butyl ester (30 mg, 0.19 mmol) and triethylamine (50 µL, 0.36 mmol). The mixture was left to stir at room temperature for 18 hr then the crude reaction mixture was loaded onto an SCX cartridge and washed with methanol. The product was released from the cartridge using a solution of 2M ammonia/methanol. The filtrate was evaporated under reduced pressure and the crude reaction product was purified by preparative HPLC (method B) to give the title compound. LCMS method 5: 33.06 min, 85%, 396.04 [M+H]; $^1$H NMR (DMSO, 300 MHz): 9.00 (1H, s), 8.67 (2H, d), 8.33 (2H, s), 7.99 (2H, d), 7.36 (5H, m), 3.96 (1H, d), 3.60 (1H, m), 3.53 (1H, m), 3.01 (1H, dd), 2.84 (1H, dd), 2.49 (2H, m).

The following compounds were prepared according to the general synthesis shown in Scheme B3:

| Ex | SM | Method | Amine [G-117] | Characterisation |
|---|---|---|---|---|
| 307 | [BB-24] | A | 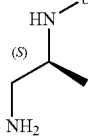 (S) HN-boc, NH$_2$ | method: 2, RT: 2.11 min, MI: 342 [M + 1] |
| 308 | [BB-24] | A | 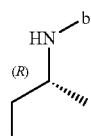 (R) HN-boc, NH$_2$ | method: 2, RT: 2.15 min, MI: 342 [M + 1] |
| 309 | [BB-25] | A |  HN-boc, NH$_2$ | method: 3, RT: 1.91 min, MI: 300 [M + 1] |

-continued

| Ex | SM | Method | Amine [G-117] | Characterisation |
|---|---|---|---|---|
| 310 | [BB-27] | A | HN(boc)-CH2CH2-NH2 | method: 3, RT: 2.41 min, MI: 426 [M + 1] |
| 311 | [BB-24] | A | HN(boc)-CH2CH2-NH2 | method: 2, RT: 2.03 min, MI: 328 [M + 1] |
| 312 | [BB-26] | A | (R)-1-boc-3-aminopyrrolidine | method: 2, RT: 1.88 min, MI: 312 [M + 1] |
| 313 | [BB-23] | A | HN(boc)-CH2CH2-NH2 | method: 2, RT: 2.15 min, MI: 348 [M + 1] |
| 314 | [BB-13] | B | (S)-2-(boc-amino)-3-phenylpropylamine | method: 4, RT: 3.18 min, MI: 362 [M + 1] |
| 315 | [BB-13] | B | (3R,4R)-1-benzyl-4-fluoropyrrolidin-3-amine | method: 10, RT: 1.57 min, MI: 406 [M + 1], |
| 316 | [BB-13] | B | (R)-1-boc-3-aminopiperidine | method: 10, RT: 1.23 min, MI: 312 [M + 1], |
| 317 | [BB-13] | B | (R)-1-boc-3-aminopyrrolidine | method: 10, RT: 1.10 min, MI: 298 [M + 1], |

-continued
| Ex | SM | Method | Amine [G-117] | Characterisation |
|---|---|---|---|---|
| 318 | [BB-13] | B | 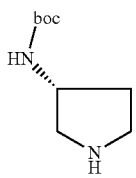 | method: 10, RT: 1.07 min, MI: 298 [M + 1], |
| 319 | [BB-13] | B | 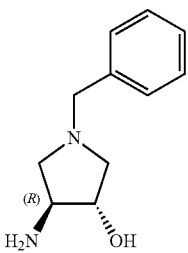 | method: 10, RT: 0.99 min, MI: 314 [M + 1], |
| 320 | [BB-13] | B | 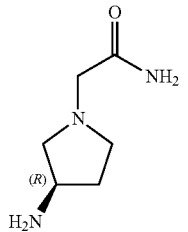 | method: 10, RT: 1.11 min, MI: 355 [M + 1], |
| 321 | [BB-13] | B | 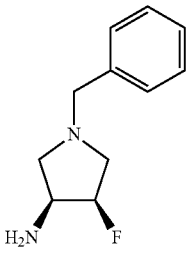 | method: 10, RT: 1.16 min, MI: 316 [M + 1], |
| 322 | [BB-15b] | B | 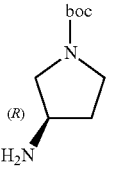 | method: 10, RT: 1.31 min, MI: 332 [M + 1], |
| 323 | [BB-15b] | B | 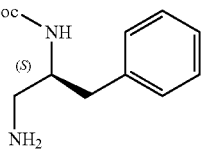 | method: 10, RT: 1.87 min, MI: 396 [M + 1], |
| 324 | [BB-24] | A | 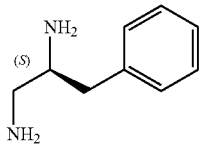  [BB-22] | method: 4, RT: 3.32 min, MI: 418 [M + 1] |

-continued

| Ex | SM | Method | Amine [G-117] | Characterisation | |
|---|---|---|---|---|---|
| 325 | [BB-25] | A | (S)-2-amino-3-phenylpropan-1-amine [BB-22] | method: 3, RT: 2.30 min, MI: 390 [M + 1] | |
| 326 | [BB-27] | A | (S)-2-amino-3-phenylpropan-1-amine [BB-22] | method: 3, RT: 2.73 min, MI: 513 [M + 1] | |
| 327 | [BB-27] | A | (S)-2-amino-3-phenylpropan-1-amine [BB-22] | method: 3, RT: 2.72 min, MI: 513 [M + 1] | |
| 328 | [BB-22] | A | (R)-1-boc-3-aminopyrrolidine | method: 4, RT: 4.11 min, MI: 390-392 [M + 1] | 1H NMR (300 MHz, DMSO): 8.73 (d, 2H), 8.30 (d, 2H), 4.88 (m, 1H), 3.41 (m, 2H), 3.15 (m, 1H), 3.06 (m, 2H), 2.6 (s, 3H), 2.24 (m, 1H), 1.97 (m, 1H) |
| 329 | [BB-22] | A | (S)-N-boc-2-amino-3-phenylpropan-1-amine | method: 4, RT: 4.43 min, MI: 454-456 [M + 1] | |
| 330 | [BB-22] | A | (R)-N-boc-1,2-diaminopropane | method: 4, RT: 3.79 min, MI: 378-380 [M + 1] | |
| 331 | [BB-22] | A | (S)-N-boc-1,2-diaminopropane | method: 4, RT: 3.78 min, MI: 378-380 [M + 1] | |
| 332 | [BB-22] | A | (S)-1-boc-3-aminopyrrolidine | method: 4, RT: 4.26 min, MI: 390-392 [M + 1] | |

-continued

| Ex | SM | Method | Amine [G-117] | Characterisation | |
|---|---|---|---|---|---|
| 333 | [BB-29] | A | HN-boc, NH₂ (2-aminoethyl carbamate) | method: 3, RT: 4.18 min, MI: 406-408 [M + 1] | |
| 334 | [BB-29] | A | boc-NH, (S), NH₂, benzyl | method: 4, RT: 4.42 min, MI: 496-498 [M + 1] | |
| 335 | [BB-29] | A | boc-NH, (R), NH₂, benzyl | method: 4, RT: 4.94 min, MI: 496-498 [M + 1] | |
| 336 | [BB-20] | B | boc-NH, (S), NH₂, benzyl | method: 4, RT: 3.82 min, MI: 440-442 [M + 1] | 1H NMR (DMSO, 300 MHz): 8.70 (2H, dd), 8.36(1H, s), 8.11 (2H, dd), 7.25 (m, 5H), 3.79 (dd, 1H), 3.30 (m, 1H), 2.70 (m, 2H), 2.50 (m, 2H) |
| 337 | [BB-21] | B | boc-NH, (S), NH₂, benzyl | method: 4, RT: 4.49 min, MI: 454 [M + 1] | |
| 338 | [BB-20] | C | NH₂-CH₂-C(=O)-NH₂ | method: 3, RT: 2.49 min, MI: 365.9 [M + 1] | |
| 339 | [BB-20] | C | (CH₃)₂N-CH₂-CH₂-NH₂ | method: 4, RT: 4.87 min, MI: 379.98 [M + 1] | |
| 340 | [BB-21] | B | N-boc pyrrolidine, (R), H₂N | method: 3, RT: 2.49 min, MI: 391.92 [M + 1] | |
| 341 | [BB-20] | C | boc-N pyrrolidine, (S), CH₂NH₂ | method: 4, RT: 4.99 min, MI: 392.01 [M + 1] | |

-continued

| Ex | SM | Method | Amine [G-117] | Characterisation |
|---|---|---|---|---|
| 342 | [BB-20] | C | (R)-1-boc-pyrrolidin-2-yl-methanamine | method: 3, RT: 1.97 min, MI: 391.92 [M + 1] |
| 343 | [BB-20] | C | (S)-1-boc-3-(aminomethyl)piperidine | method: 3, RT: 2.16 min, MI: 392 [M + 1] |
| 344 | [BB-20] | C | (S)-1-boc-3-aminopyrrolidine | method: 3, RT: 2.34 min, MI: 364-366 [M + 1] |
| 345 | [BB-20] | C | N-methyl-N-boc-ethylenediamine | method: 3, RT: 2.28 min, MI: 364-366 [M + 1] |
| 346 | [BB-20] | C | (S)-2-amino-4-methylpentan-1-amine | method: 3, RT: 2.57 min, MI: 406-408 [M + 1] |
| 347 | [BB-20] | C | (S)-2-amino-3-methylbutan-1-amine | method: 3, RT: 2.39 min, MI: 392-394 [M + 1] |
| 348 | [BB-20] | C | (S)-2-amino-3-cyclohexylpropan-1-amine | method: 3, RT: 2.64 min, MI: 446-448 [M + 1] |
| 349 | [BB-20] | C | N-boc-ethylenediamine | method: 3, RT: 1.78 min, MI: 350-352 [M + 1] |
| 350 | [BB-20] | C | 1-boc-piperazine | method: 3, RT: 1.89 min, MI: 376-378 [M + 1] |

-continued

| Ex | SM | Method | Amine [G-117] | Characterisation | |
|---|---|---|---|---|---|
| 351 | [BB-20] | C | (R)-1-boc-3-aminopyrrolidine | method: 8, RT: 1.88 min, MI: 376-378 [M + 1] | 1H NMR (DMSO, 300 MHz): 8.96 (2H, s, br), 8.83 (2H, d), 8.54 (1H, d), 8.48 (2H, dd), 8.45 (1H, s), 4.95 (1H, m), 3.70 (1H, m), 3.28 (3H, m), 2.35 (1H, m), 2.15 (1H, m) |
| 352 | [BB-17] | B | (R)-1-Boc-3-aminopyrrolidine | method: 6, RT: 4.95 min, MI: 394-396 [M + 1] | 1H NMR (DMSO, 300 MHz): 8.69(1H, d), 8.57 (1H, dd), 8.50 (1H, s), 8.06 (1H, m), 4.80 (1H, m), 3.87-3.77 (1H, m), 3.59-3.42 (2H, m), 3.40 (1H, dd), 3.36-3.26 (1H, m), 2.18-2.09 (1H, m) |
| 353 | [BB-14] | B | (S)-N-Boc-1,2-diaminopropane | method: 5, RT: 2.02 min, MI: 304 [M + 1] | |
| 354 | [BB-14] | B | (R)-1-Boc-3-aminopyrrolidine | method: 5, RT: 2.06 min, MI: 316 [M + 1] | 1H NMR (DMSO, 300 MHz): 8.70(1H, d), 8.56 (1H, dd), 8.40 (1H, s), 8.07 (1H, m), 7.52 (1H, d), 4.78 (1H, m), 3.49 (1H, m), 3.32 (1H, m), 3.23 (2H, m), 2.26 (1H, m), 2.09 (1H, m) |
| 355 | [BB-14] | B | (S)-2-amino-3-phenylpropan-1-amine | method: 5, RT: 3.02 min, MI: 380 [M + 1] | |
| [BB-39a] | [BB-20] | C | (R)-N-boc-2-amino-3-phenylpropan-1-amine | method: 5, RT: 3.13 min, MI: 440-442 [M + 1] | |

| Ex | SM | Method | Amine [G-117] | | Characterisation |
|---|---|---|---|---|---|
| [BB-39b] | [BB-15a] | C | 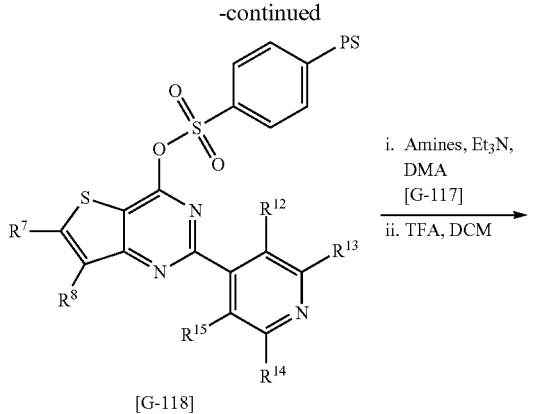 | method: 8, RT: 4.70 min, MI: 448-450 [M + 1] | 1H NMR (DMSO) 8.37 (1H, d), 8.32 (1H, d), 8.23 (1H, d), 8.06 (1H, t), 7.50 (1H, d), 4.74-4.69 (1H, m), 3.78-3.61 (1H, m), 3.49-3.41 (1H, m), 3.35-3.25 (2H, m), 2.26-2.15 (1H, m), 2.08-2.01 (1H, m). |

General Synthesis of 6,7-substituted-4 amino-2-pyridin-4-yl-thieno[3,2-d]pyrimidines (Scheme B4)

6,7-substituted 2-pyridin-4-yl-thieno [3,2-d]pyrimidin-4-ol, of general formula [G-104] (prepared in scheme B1) were subjected to a activation reaction by reaction with a solid supported sulfonyl chloride derivative such as benzene sulfonyl chloride on polystyrene in a polar aprotic solvent such as DMA, DMF, NMP in the presence of a tertiary amine base such as Et$_3$N, DIPEA or NMM with a catalytic amount of DMAP at ambient temperature. Excess reagents and reactants were removed by filtration and washing the polystyrene resin with solvents such as DCM, DMF, THF. The polymer supported reagent, of general formula [G-118], was then reacted with a primary or secondary amino derivative, of general formula [G-117], in a polar aprotic solvent such as DMA, DMF or NMP in the presence of a tertiary amine base such as Et$_3$N, DIPEA or NMM at ambient temperature. The resin was filtered through a PTFE frit, washed with a solvent such as DCM and the filtrate and combined washings were loaded onto an acidic ion exchange catch release cartridge, which was washed with an organic solvent such as methanol and then the product was released with methanolic ammonia solution and the crude product was purified by reverse phase preparative HPLC. The N-Boc derivatives were deprotected under acidic conditions with a strong acid such as TFA, TCA, methanesulfonic acid, HCl or H$_2$SO$_4$ in a solvent such as DCM, DCE, THF, EtOH or MeOH and the crude reaction mixture was purified by acidic ion exchange catch-release or reverse phase preparative HPLC.

Scheme B4

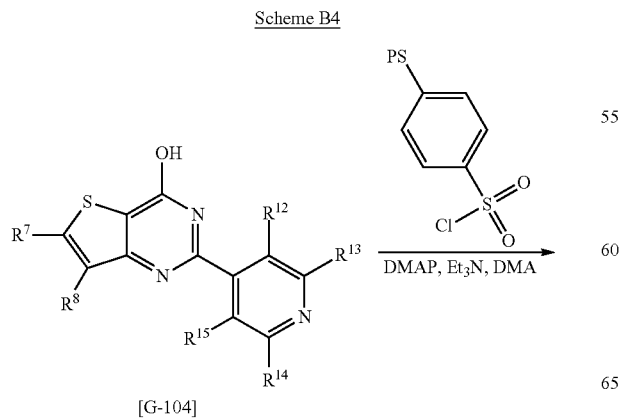

[G-104]

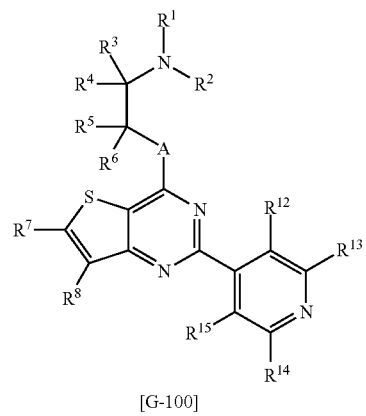

[G-118]

i. Amines, Et$_3$N, DMA [G-117]
ii. TFA, DCM

[G-100]

285
Synthesis of Polystyrene Supported benzenesulfonic acid 6-(4-tert-butyl-phenyl)-2-pyridin-4-yl-thieno[3,2-d]pyrimidin-4-yl ester [BB-40]

286
Synthesis of 6-(4-tert-butyl-phenyl)-4-[1,4]diazepan-1-yl-2-pyridin-4-yl-thieno[3,2-d]pyrimidine [356]

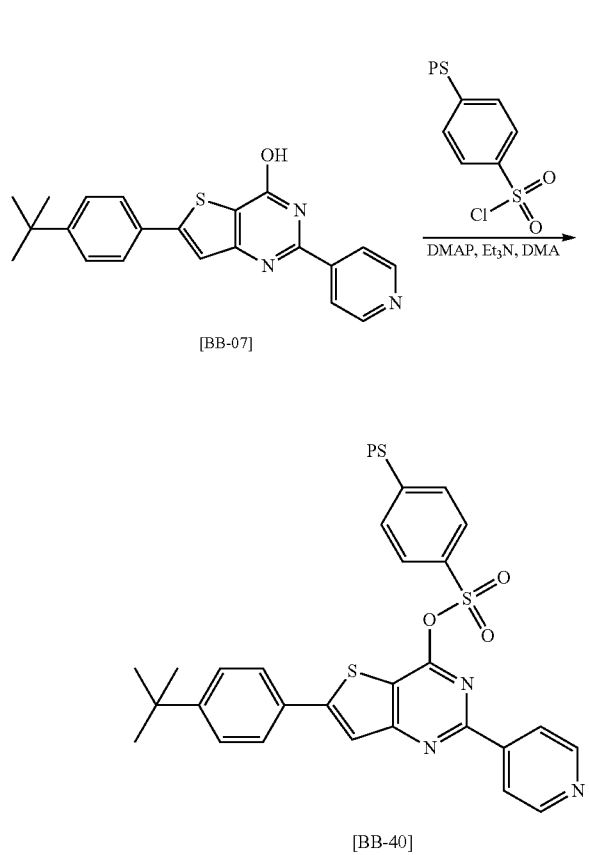

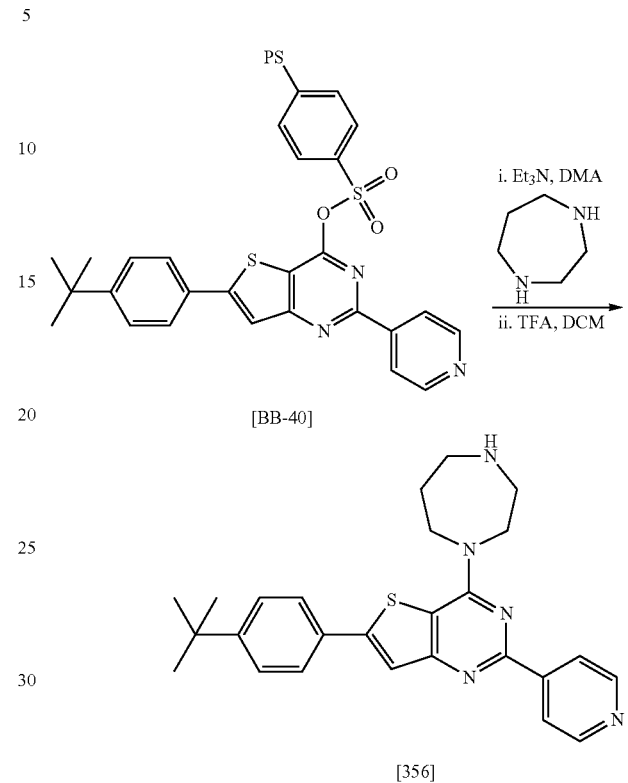

6-(4-tert-butyl-phenyl)-2-pyridin-4-yl-thieno [3,2-d]pyrimidin-4-ol [BB-07] (60 mg, 0.167 mmol) and PS-TSCl (120 mg, 0.250 mmol) were placed into filter cartridge closed with a stopper. DMA was added (2 ml) followed by Et$_3$N (70 µl, 0.5 mmol) and DMAP (1.1 mg, 0.009 mmol). The reaction was shaken for 3 hours at room temperature and then the polymer was filtered (after removing the stopper). The resin was washed with DCM to yield to the polystyrene supported benzenesulfonic acid 6-(4-tert-butyl-phenyl)-2-pyridin-4-yl-thieno[3,2-d]pyrimidin-4-yl ester.

To the polystyrene supported benzenesulfonic acid 6-(4-tert-butyl-phenyl)-2-pyridin-4-yl-thieno[3,2-d]pyrimidin-4-yl ester [BB-40] placed into a filter cartridge was added DMA (2 ml) followed by homopiperazine (20 mg, 0.2 mmol) and Et$_3$N (70 µl, 0.5 mmol). The reaction was shaken overnight at room temperature. The resin was filtered and washed with ethylacetate and the mixture was loaded onto a SCX-2 cartridge and washed with methanol. The product was released from the cartridge using a solution of 2M ammonia/methanol. The ammonia/methanol eluent was concentrated under reduced pressure and the crude product was purified by preparative HPLC (method A) to yield to the title compound. LCMS method: 2, RT: 2.66 min, MI: 444 [M+1]. 1H NMR (300 MHz, DMSO): 8.68 (d, 2H), 8.22 (d, 2H), 7.82 (s, 1H), 7.8 (d, 2H), 7.52 (d, 2H), 4.22 (m, 2H), 4.15 (m, 2H), 3.28 (m, 2H), 3.06 (m, 2H), 2.13 (m, 2H), 1.32 (s, 9H). The following compounds were prepared according to the general synthesis shown in Scheme B4:

| Ex | SM | Amine [G-117] | Characterisation |
|---|---|---|---|
| 357 | BB-07 | (piperazine-N-boc) | method: 2, RT: 2.67 min, MI: 430 [M + 1] |

-continued

| Ex | SM | Amine [G-117] | Characterisation | |
|---|---|---|---|---|
| 358 | BB-07 | (R)-CH(CH₃)(NHBoc)CH₂NH₂ | method: 2, RT: 2.73 min, MI: 418 [M + 1] | |
| 359 | BB-07 | (S)-CH(CH₃)(NHBoc)CH₂NH₂ | method: 2, RT: 2.67 min, MI: 418 [M + 1] | |
| 360 | BB-07 | BocNH-CH₂CH₂-NH₂ | method: 2, RT: 2.65 min, MI: 404 [M + 1] | |
| 361 | BB-05 | CH(CH₃)(NHBoc)CH₂NH₂ | method: 2, RT: 1.81 min, MI: 300 [M + 1] | |
| 362 | BB-05 | 1-Boc-homopiperazine | method: 2, RT: 1.88 min, MI: 326 [M + 1] | 1H NMR (300 MHz, DMSO): 8.76 (m, 2H), 8.33 (m, 2H), 7.94 (s, 1H), 4.22 (m, 1H), 4.09 (m, 3H), 3.74 (m, 2H), 3.41 (m, 2H), 2.43 (s, 3H), 1.95 (m, 2H) |
| 363 | BB-05 | 1-Boc-piperazine | method: 2, RT: 1.82 min, MI: 312 [M + 1] | 1H NMR (300 MHz, DMSO): 8.72 (m, 2H), 8.35 (m, 2H), 8.16 (m, 1H), 7.93 (s, 1H), 4.02 (m, 4H), 2.96 (m, 4H), 2.44 (s, 3H) |
| 364 | BB-05 | (S)-1-Boc-3-aminopyrrolidine | method: 2, RT: 1.79 min, MI: 312 [M + 1] | |
| 365 | BB-05 | N-Me-N-Boc-ethylenediamine | method: 2, RT: 1.89 min, MI: 300 [M + 1] | |
| 366 | BB-06 | (R)-CH(CH₃)(NHBoc)CH₂NH₂ | method: 2, RT: 2.22 min, MI: 362 [M + 1] | |

-continued

| Ex | SM | Amine [G-117] | | Characterisation | |
|---|---|---|---|---|---|
| 367 | BB-06 | HN(boc)-CH(CH3)-CH2-NH2 | method: 2, RT: 2.21 min, MI: 362 [M + 1] | | |
| 368 | BB-06 | HN-(1,4-diazepane)-N-boc | method: 2, RT: 2.23 min, MI: 388 [M + 1] | 1H NMR (300 MHz, DMSO): 8.72 (d, 2H), 8.27 (d, 2H), 7.97 (s, 1H), 7.90 (d, 2H), 7.49 (m, 3H), 4.21 (m, 2H), 4.11 (m, 2H), 3.33 (m, 2H), 3.08 (m, 2H), 2.1 (m, 2H) | |
| 369 | BB-05 | (R)-HN(boc)-CH(CH3)-CH2-NH2 | method: 2, RT: 1.82 min, MI: 300 [M + 1] | | |
| 370 | BB-05 | HN(boc)-CH2-CH2-NH2 | method: 2, RT: 1.76 min, MI: 286 [M + 1] | | |
| 371 | BB-09 | HN-(1,4-diazepane)-N-boc | method: 2, RT: 2.24 min, MI: 387 [M + 1] | | |
| 372 | BB-09 | (S)-boc-NH-CH(CH2Ph)-CH2-NH2 | method: 2, RT: 2.57 min, MI: 446 [M + 1] | | |
| 373 | BB-09 | HN(boc)-CH(CH3)-CH2-NH2 | method: 2, RT: 2.22 min, MI: 370 [M + 1] | | |
| 374 | BB-09 | (R)-HN(boc)-CH(CH3)-CH2-NH2 | method: 2, RT: 2.26 min, MI: 370 [M + 1] | | |
| 375 | BB-10 | HN(boc)-CH2-CH2-NH2 | method: 2, RT: 1.82 min, MI: 323 [M + 1] | 1H NMR (300 MHz, DMSO): 8.86 (dd, 1H), 8.77 (m, 3H), 8.41 (m, 2H), 7.69 (dd, 1H), 3.86 (m, 2), 3.10 (m, 2H) | |
| 376 | BB-10 | HN-piperazine-N-boc | method: 2, RT: 1.86 min, MI: 349 [M + 1] | | |

-continued

| Ex | SM | Amine [G-117] | | Characterisation |
|---|---|---|---|---|
| 377 | BB-10 | [1-boc-1,4-diazepane] | method: 2, RT: 1.92 min, MI: 362 [M + 1] | 1H NMR (300 MHz, DMSO): 8.97 (dd, 1H), 8.76 (m, 3H), 8.34 (m, 2H), 7.65 (dd, 1H), 4.07 (m, 4), 3.18 (m, 2H), 2.93 (m, 2H) |
| 378 | BB-10 | [N-boc-1,2-propanediamine] | method: 2, RT: 1.9 min, MI: 337 [M + 1] | |
| 379 | BB-10 | [(R)-N-boc-1,2-propanediamine] | method: 2, RT: 1.89 min, MI: 337 | 1H NMR (300 MHz, DMSO): 8.87 (dd, 1H), 8.79 (m, 3H), 8.44 (m, 2H), 7.69 (dd, 1H), 3.80 (m, 2), 3.48(m, 1H), 1.26(d, 3H) |
| 380 | BB-11 | [1-boc-piperazine] | method: 2, RT: 2.15 min, MI: 377 | |
| 381 | BB-11 | [1-boc-1,4-diazepane] | method: 2, RT: 2.17 min, MI: 391 | |
| 382 | BB-11 | [N-boc-1,2-propanediamine] | method: 2, RT: 2.19 min, MI: 365 | |
| 383 | BB-11 | [(R)-N-boc-1,2-propanediamine] | method: 2, RT: 2.16 min, MI: 365 | |
| 384 | BB-09 | [(R)-1-boc-3-aminopyrrolidine] | method: 2, RT: 2.32 min, MI: 382 | |
| 385 | BB-09 | [N-boc-N'-methyl-ethylenediamine] | method: 2, RT: 2.32 min, MI: 370 | |

| Ex | SM | Amine [G-117] | Characterisation | |
|---|---|---|---|---|
| 386 | BB-09 | HN-boc, NH2 (ethylenediamine mono-Boc) | method: 2, RT: 2.16 min, MI: 356 | |
| 387 | BB-09 | HN-piperazine-N-boc | method: 2, RT: 2.20 min, MI: 382 | 1H NMR (300 MHz, DMSO): 8.78 (dd, 2H), 8.40 (dd, 2H), 8.18 (m, 1H), 7.69 (dd, 2H), 4.04 (m, 4), 2.98 (m, 4H) |

General Synthesis of 6 or 7 aryl substituted-4PT32P Derivatives, of General Formula [G-120] and [G-122] (Scheme B5)

The 7-bromo-6-substituted-2-pyridin-4-yl-thieno[3,2-d]pyrimidine derivative, of general formula [G-119] or the 6-bromo-7-substituted-2-pyridin-4-yl-thieno[3,2-d]pyrimidine derivative, of general formula [G-121] were reacted in a Suzuki type reaction utilising a suitable boronic acid or boronic ester, of general formula [G-123], a palladium catalyst such as $Pd(PPh_3)_4$ or $Pd(PPh_3)_2Cl_2$ a base such as $Et_3N$, KOH, $Na_2CO_3$ or NaOH in a polar solvent such as EtOH, THF, DMA or dioxane at high temperature either by heating thermally or using a microwave reactor. After reaction work up, typically by a liquid-liquid extraction or purification by acidic ion exchange catch-release, the N-Boc derivatives were deprotected under acidic conditions with a strong acid such as TFA, TCA, methanesulfonic acid, HCl or $H_2SO_4$ in a solvent such as DCM, DCE, THF, EtOH or MeOH and the crude reaction product was purified by reverse phase preparative HPLC.

Scheme B5

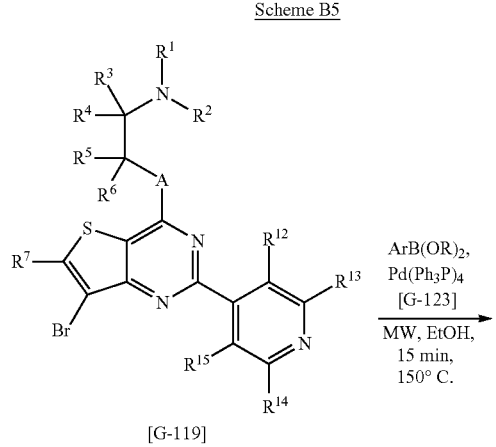

[G-119]

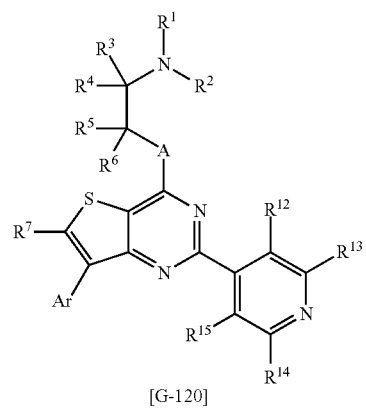

[G-120]

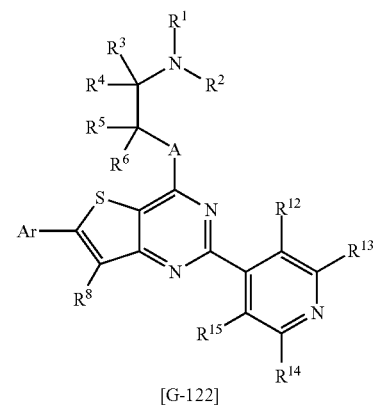

[G-121]

[G-122]

Synthesis of (S)—N*1*-[6-methyl-7-(2H-pyrazol-3-yl)-2-pyridin-4-yl-thieno[3,2-d]pyrimidin-4-yl]-3-phenyl-propane-1,2-diamine [388]

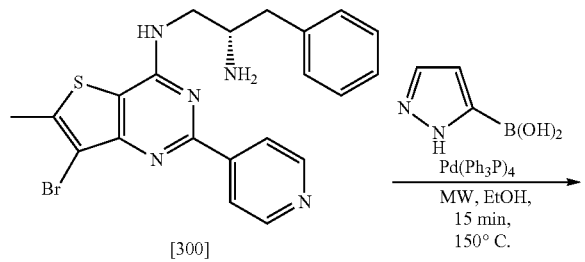

Synthesis of [7-Methyl-6-(2H-pyrazol-3-yl)-2-pyridin-4-yl-thieno[3,2-d]pyrimidin-4-yl]-(R)-pyrrolidin-3-yl-amine [389]

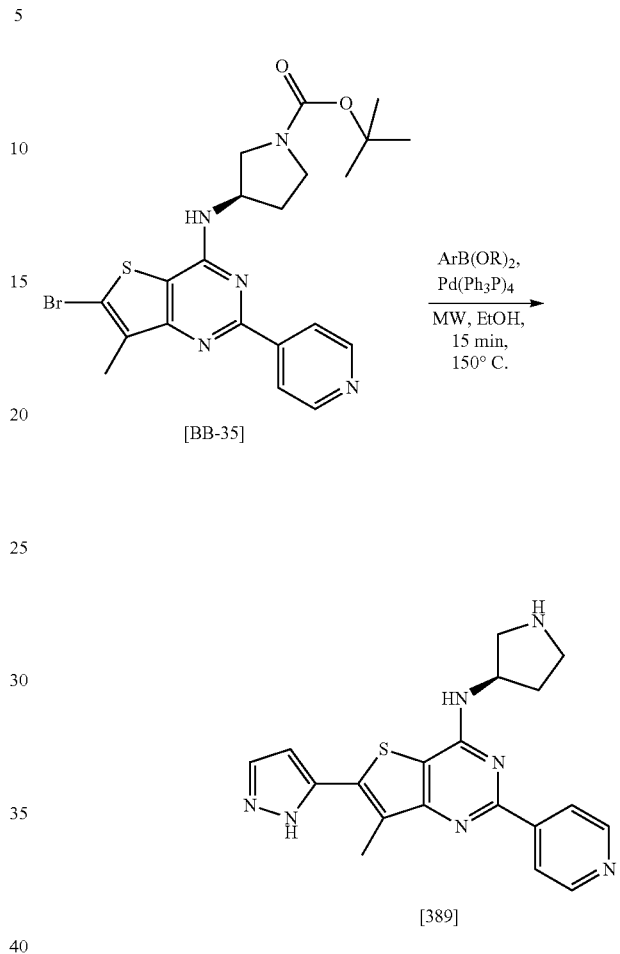

A microwave vial was charged with (S)—N*1*-(7-bromo-6-methyl-2-pyridin-4-yl-thieno[3,2-d]pyrimidin-4-yl)-3-phenyl-propane-1,2-diamine [300](50 mg, 0.100 mmol), 1H-pyrazole-5-boronic acid (13 mg, 0.115 mmol), tetrakis (triphenyl phosphine) palladium (11 mg, 0.009 mmol), Na₂CO₃ (2M in water, 100 µl, 0.2 mmol) and EtOH (2 ml). The reaction was heated to 150° C. for 15 minutes under microwave irradiation. The mixture was then filtered through a plug of silica, washed with methanol and the filtrate was concentrated under reduced pressure. The crude reaction product was dissolved in DCM (2 ml) and TFA (2 ml) was added and the mixture was stirred at room temperature for 1 hour. After completion the mixture was loaded onto a SCX-2 cartridge and washed with methanol. The product was released from the cartridge using a solution of 2M ammonia/methanol. The ammonia/methanol eluent was concentrated under reduced pressure and the crude product was purified by preparative HPLC (method B) to yield to the title compound. LCMS method: 4, RT: 3.71 min, MI: 442 [M+1]. 1H NMR (DMSO, 300 MHz): 8.67 (d, 2H), 8.06 (d, 2H), 8.30 (d, 1H), 7.88 (d, 1H), 7.33 (m, 5H), 3.88 (m, 1H), 3.41 (m, 2H), 2.93 (m, 2H), 2.83 (s, 3H).

A microwave vial was charged with (R)-3-(6-Bromo-7-methyl-2-pyridin-4-yl-thieno[3,2-d]pyrimidin-4-ylamino)-pyrrolidine-1-carboxylic acid tert-butyl ester [BB-35] (100 mg, 0.200 mmol), 1H-pyrazole-5-boronic acid (26 mg, 0.23 mmol), tetrakis (triphenyl phosphine) palladium (31 mg, 0.02 mmol), Na₂CO₃ (2M in water, 200 µl, 0.4 mmol) and EtOH (2 ml). The reaction was heated to 150° C. for 15 minutes under microwave irradiation. The mixture was then filtered through a plug of silica, washed with methanol and the filtrate was concentrated under reduced pressure. The crude reaction product was dissolved in DCM (2 ml) and TFA (2 ml) was added and the mixture was stirred at room temperature for 1 hour. After completion the mixture was loaded onto a SCX-2 cartridge and washed with methanol. The product was released from the cartridge using a solution of 2M ammonia/methanol. The ammonia/methanol eluent was concentrated under reduced pressure and the crude product was purified by preparative HPLC (method B) to yield to the title compound. LCMS method: 2, RT: 2.43 min, MI: 378. 1H NMR (DMSO, 300 MHz): 8.28 (dd, 1H), 8.73 (dd, 2H), 8.35 (dd, 2H), 7.95 (d, 1H), 4.93 (m, 1H), 3.48 (m, 1H), 3.25 (m, 1H), 3.17 m, 1H), 3.14 (m, 1H), 2.61 (s, 3H), 2.28 (M, 1H), 2.05 (m, 1H).

The following compounds were prepared according to the general synthesis shown in Scheme B5:

| Example | SM | Boronic acid[a] [G-123] | Characterisation | |
|---|---|---|---|---|
| 390 | [336] | 3-pyrazolyl-B(OH)₂ (1H-pyrazol-3-yl boronic acid) | method: 4, RT: 3.26 min, MI: 428 [M + 1] | 1H NMR (DMSO, 300 MHz) 8.72 (2H, d), 8.56 (1H, s, br), 8.43 (3H, m, br), 8.12 (2H, dd), 7.78 (1H, d, br), 7.34 (5H, m), 3.91 (1H, m), 3.45 (2H, m), 2.82 (2H, m) |
| 391 | [336] | 1-methyl-1H-pyrazol-5-yl-B(OH)₂ | method: 4, RT: 3.30 min, MI 442 [M + 1] | |
| 392 | [336] | 3,5-dimethylisoxazol-4-yl-B(OH)₂ | method: 4, RT: 3.65 min, MI 457 [M + 1] | 1H NMR (DMSO, 300 MHz): 8.66 (2H, d), 8.38 (1H, s, br), 8.22 (1H, s), 8.00 (2H, d), 7.30 (6H, m), 3.85 (1H, m, br), 3.34 (2H, m), 2.73 (2H, t), 2.43 (3H, s), 2.25 (3H, s). |
| 393 | [336] | 1H-pyrazol-4-yl-B(OH)₂ | method: 3, RT: 2.25 min, MI: 428 [M + 1] | |
| 394 | [336] | 1-isobutyl-1H-pyrazol-5-yl-B(OH)₂ | method: 3, RT: 2.81 min, MI: 484 [M + 1] | |
| 395 | [336] | 4-methylthiophen-2-yl-B(OH)₂ | method: 3, RT: 2.92 min, MI: 458 [M + 1] | 1H NMR (DMSO, 300 MHz): 8.72 (2H, dd), 8.50 (1H, s, br), 8.39 (1H, s), 8.29 (1H, s), 8.12 (2H, dd), 7.72 (1H, s), 7.35 (4H, m), 7.20 (1H, s), 3.91 (1H, d), 3.48 (1H, d), 2.84 (1H, m), 2.49 (2H, m), 2.29 (3H, s) |

-continued
| Example | SM | Boronic acid[a] [G-123] | Characterisation | |
|---|---|---|---|---|
| 396 | [336] | 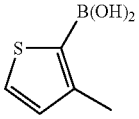 | method: 3, RT: 2.89 min, MI: 458 [M + 1] | 1H NMR (DMSO, 300 MHz): 8.68 (2H, dd), 8.61 (1H, s, br), 8.30 (1H, s), 8.25 (1H, s), 8.06 (2H, dd), 7.57 (1H, d), 7.35 (4H, m), 7.06 (1H, d), 3.95 (1H, d), 3.52 (1H, m), 2.93 (1H, m), 2.49 (2H, m), 2.40 (3H, s) |
| 397 | [336] | 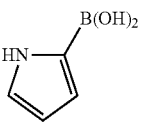 | method: 3, RT: 2.53 min, MI: 427 [M + 1] | |
| 398 | [336] | 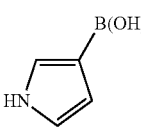 | method: 3, RT: 2.47 min, MI: 427 [M + 1] | |
| 399 | [336] | 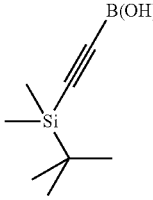 | method: 5, RT: 4.82 min, MI: 500 [M + 1] | |
| 400 | [336] | 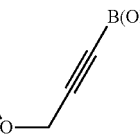 | method: 5, RT: 2.95 min, MI: 430 [M + 1] | |
| 401 | [336] | 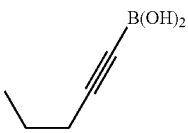 | method: 5, RT: 3.68 min, MI: 428 [M + 1] | |
| 402 | [336] | 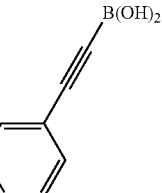 | method: 5, RT: 3.98 min, MI: 462 [M + 1] | 1H NMR (DMSO, 300 MHz): 8.80 (1H, s, br), 8.68 (2H, d), 8.48 (1H, s), 8.38 (1H, s), 8.05 (2H, d), 7.63 (2H, d), 7.47 (2H, m), 7.35 (4H, m), 3.94 (1H, d), 3.50 (2H, m), 2.94 (1H, dd), 2.82 (1H, dd) |

-continued

| Example | SM | Boronic acid[a] [G-123] | Characterisation | |
|---|---|---|---|---|
| 403 | [351] | 3-pyrazolyl-B(OH)2 | method: 5, RT: 1.97 min, MI: 364 [M + 1] | 1H NMR (DMSO, 300 MHz): 8.76 (2H, dd), 8.68 (1H, d), 8.44 (1H, s), 8.38 (2H, dd), 8.31 (1H, s), 7.79 (1H, d), 7.37 (1H, d), 5.01 (1H, m), 3.60 (1H, dd), 3.29 (2H, m), 2.49 (2H, m), 2.32 (1H, m), 2.15 (1H, m) |
| 404 | [336] | MeOCH2-CH=CH-B(OH)2 | method: 5, RT: 3.13 min, MI: 432 [M + 1] | |
| 405 | [336] | cyclopropyl-CH=CH-B(OH)2 | method: 6, RT: 5.99 min, MI: 428 [M + 1] | 1H NMR (DMSO, 300 MHz): 8.66 (2H, dd), 8.46 (1H, s, br), 8.34 (1H, s), 8.01 (2H, dd), 7.95 (1H, s), 7.35 (5H, m), 6.81 (1H, d), 6.47 (1H, dd), 3.91 (2H, d, br), 3.51 (2H, m), 2.91 (1H, dd), 2.81 (1H, dd), 1.64 (1H, m), 0.85 (2H, m), 0.56 (2H, m). |
| 406 | [336] | tBu-CH=CH-B(OH)2 | method: 5, RT: 4.28 min, MI: 444 [M + 1] | |
| 407 | [336] | Et-CH=CH-B(OH)2 (cis) | method: 6, RT: 5.95 min, MI: 402 [M + 1] | 1H NMR (DMSO, 300 MHz): 8.66 (2H, dd), 8.32 (1H, s), 8.10 (1H, s), 8.04 (2H, dd), 7.36 (5H, m), 6.88 (1H, dd), 6.00 (1H, m), 3.91 (2H, d, br), 3.49 (3H, m), 2.88 (1H, dd), 2.81 (1H, dd), 1.97 (2H, dd), 1.92 (1H, dd). |
| 408 | [336] | CH2=CH-B(OH)2 | method: 5, RT: 3.26 min, MI: 388 [M + 1] | |

-continued
| Example | SM | Boronic acid[a] [G-123] | | Characterisation | |
|---|---|---|---|---|---|
| 409 | [336] | 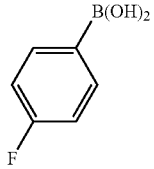 | method: 5, RT: 4.01 min, MI: 456 [M + 1] | 1H NMR (DMSO, 300 MHz): 8.83 (1H, s), 8.67 (2H, d), 8.41 (1H, s), 8.36 (1H, s), 8.17 (2H, t), 7.97 (2H, d), 7.38 (5H, m), 4.00 (1H, m), 3.64 (2H, m), 3.08 (1H, dd), 2.89 (1H, dd). | |
| 410 | [336] | 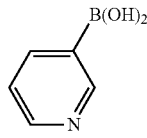 | method: 5, RT: 2.24 min, MI: 439 [M + 1] | | |
| 411 | [336] | 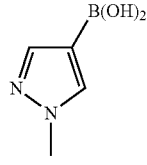 | method: 5, RT: 3.02 min, MI: 442 [M + 1] | | |
| 412 | [336] | 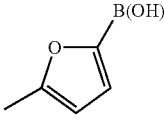 | method: 5, RT: 4.01 min, MI: 442 [M + 1] | | |
| 413 | [336] | 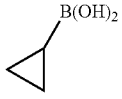 | method: 5, RT: 3.36 min, MI: 402 [M + 1] | 1H NMR (DMSO, 300 MHz): 8.66 (2H, d), 8.37 (1H, s), 8.02 (2H, d), 7.59 (1H, s), 7.35 (5H, m), 3.93 (1H, m), 3.52 (2H, m), 2.93 (1H, dd), 2.82 (1H, dd), 2.38 (2H, m), 1.00 (3H, m) | |
| 414 | [BB-39a] | 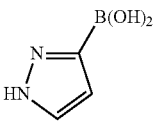 | method: 5, RT: 2.96 min, MI: 428 [M + 1] | | |
| 415 | [336] | 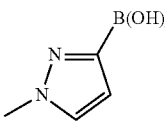 | method: 5, RT: 3.07 min, MI: 442 [M + 1] | 1H NMR (DMSO, 300 MHz): 8.72 (1H, s), 8.70 (2H, d), 8.39 (1H, s), 8.34 (1H, s), 8.03 (2H, d), 7.81 (1H, d), 7.37 (5H, m), 3.92 (3H, s), 3.56 (3H, m), 2.93 (1H, dd), 2.77 (1H, m) | |

-continued

| Example | SM | Boronic acid[a] [G-123] | | Characterisation | |
|---|---|---|---|---|---|
| 416 | [BB-33] | pyrazol-3-yl B(OH)₂ (HN-) | method: 5, RT: 3.42 min, MI: 446 [M + 1] | 1H NMR (DMSO, 300 MHz): 8.73 (d, 1H), 8.57 (d, 1H), 8.43 (s, 1H), 8.24 (s, 1H), 8.03 (m, 1H), 7.74 (s, 1H), 7.27 (m, 5H), 3.70 (m, 1H), 2.75 (m, 1H), 2.64 (m, 1H). | |
| 417 | [336] | phenyl-B(OH)₂ | method: 6, RT: 6.53 min, MI: 438 [M + 1] | 1H NMR (DMSO, 300 MHz): 8.67 (3H, d, br), 8.42 (1H, s), 8.30 (2H, s), 8.12 (2H, d), 8.00 (2H, d), 7.53 (2H, t), 7.40-7.37 (5H, m), 4.00 (1H, m), 3.58 (2H, m), 3.00 (1H, dd), 2.86-2.81 (1H, m). | |
| 418 | [336] | 5-cyclopropyl-1H-pyrazol-3-yl B(OH)₂ (b) | method: 5, RT: 3.48 min, MI: 468 [M + 1] | 1H NMR (DMSO, 300 MHz): 8.69 (2H, d), 8.64 (1H, s, br), 8.35 (1H, s), 8.27 (2H, s, br), 8.03 (2H, d), 7.42-7.36 (5H, m), 6.95 (1H, s), 4.00 (1H, d, br), 3.71-3.58 (2H, m), 3.13 (1H, dd), 2.84 (1H, dd), 2.03-1.98 (1H, m), 0.98-0.92 (2H, m), 0.78-0.73 (2H, m) | |
| 419 | [BB-33] | 1H-pyrrol-2-yl B(OH)₂ | method: 6, RT: 5.23 min, MI: 445 [M + 1] | | |
| 420 | [BB-33] | 1H-pyrrol-3-yl B(OH)₂ | method: 5, RT: 5.61 min, MI: 445 [M + 1] | 1H NMR (DMSO, 300 MHz): 8.26 (s, 1H), 8.70 (d, 1H), 8.53 (d, 1H), 7.96 (s, 1H), 7.91 (m, 1H), 7.30 (m, 5H), 6.83 (d, 1H), 6.68 (d, 1H), 3.66 (m, 1H), 2.74 (m, 2H), 2.62 (m, 2H) | |
| 421 | [BB-33] | 5-(trifluoromethyl)-1H-pyrazol-3-yl B(OH)₂ (b) | method: 5, RT: 4.32 min, MI: 514 [M + 1] | | |

-continued
| Example | SM | Boronic acid[a] [G-123] | Characterisation | |
|---|---|---|---|---|
| 422 | [BB-33] | 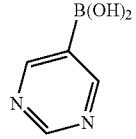 | method: 5, RT: 3.4 min, MI: 458 [M + 1] | |
| 423 | [BB-33] Or [304] | 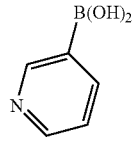 | method: 5, RT: 3.03 min, MI: 457 [M + 1] | |
| 424 | [BB-33] | 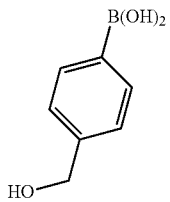 | method: 5, RT: 3.61 min, MI: 486 [M + 1] | |
| 425 | [BB-33] | 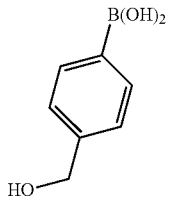 [SMILES: OCc1ccc(B(O)O)cc1] | method: 5, RT: 3.7 min, MI: 486 [M + 1] | |
| 426 | [BB-33] | 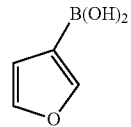 | method: 5, RT: 4.02 min, MI: 446 [M + 1] | |
| 427 | [BB-33] | 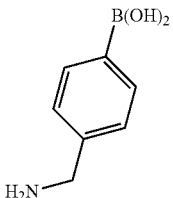 | method: 5, RT: 2.51 min, MI: 485 [M + 1] | |
| 428 | [BB-33] | 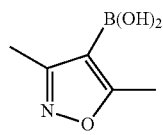 | method: 5, RT: 3.44 min, MI: 475 [M + 1] | 1H NMR (MeOD, 300 MHz): 8.58 (d, 1H), 8.52 (s, 1H), 8.49 (d, 1H), 7.93 (m, 1H), 7.32 (m, 5H), 3.95 (m, 2H), 3.77 (m, 1H), 3.03 (m, 2H), 2.43 (s, 3H), 2.27 (s, 3H). |
| 429 | [BB-33] | 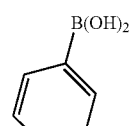 | method: 5, RT: 2.64 min, MI: 457 [M + 1] | |

| Example | SM | Boronic acid[a] [G-123] | Characterisation | |
|---|---|---|---|---|
| 430 | [BB-33] | 4-fluorophenylboronic acid | method: 5, RT: 4.21 min, MI: 474 [M + 1] | |
| 431 | [BB-33] | thiophen-3-ylboronic acid | method: 5, RT: 4.12 min, MI: 462 [M + 1] | 1H NMR (DMSO, 300 MHz): 8.62(m, 2H), 8.52 (m, 2H), 8.08(dd, 1H), 7.8 (dd, 1H), 7.48(dd, 1H), 7.35 (m, 5H), 4.03 (m, 2H), 3.93 (m, 2H), 3.76 (m, 1H) |
| 432 | [BB-33] | furan-2-ylboronic acid | method: 5, RT: 4.07 min, MI: 446 [M + 1] | |
| 433 | [BB-33] | 2-methylphenylboronic acid | method: 5, RT: 4.02 min, MI: 470 [M + 1] | |
| 434 | [BB-33] | phenylboronic acid | method: 5, RT: 4.11 min, MI: 456 [M + 1] | |
| 435 | [BB-33] | 5-(aminomethyl)furan-2-ylboronic acid | method: 5, RT: 2.51 min, MI: 475 [M + 1] | |
| 436 | [334] | 3-fluorophenylboronic acid | method: 4, RT: 5.49 min, MI: 512 [M + 1] | |
| 437 | [334] | 1H-pyrazol-4-ylboronic acid | method: 4, RT: 3.82 min, MI: 484 [M + 1] | |

-continued
| Example | SM | Boronic acid[a] [G-123] | Characterisation | |
|---|---|---|---|---|
| 438 | [300] | 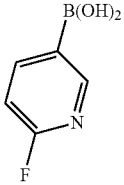 | method: 4, RT: 4.24 min, MI: 471 [M + 1] | |
| 439 | [300] | 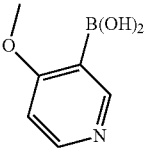 | method: 4, RT: 3.37 min, MI: 483 [M + 1] | 1H NMR (DMSO, 300 MHz): 8.59(dd, 2H), 8.53 (d, 1H), 8.36(d, 2H), 7.86(d, 2H), 7.33(m, 5H), 7.25 (d, 1H), 3.81 (s, 3H), 3.45 (m, 2H), 2.81 (m, 3H), 2.44 (s, 3H) |
| 440 | [300] | 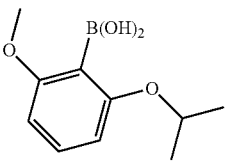 | method: 4, RT: 4.49 min, MI: 540 [M + 1] | |
| 441 | [334] | 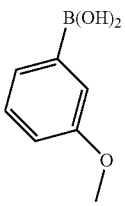 | method: 4, RT: 5.35 min, MI: 524 [M + 1] | |
| 442 | [334] | 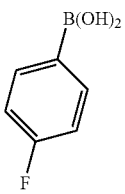 | method: 4, RT: 5.51 min, MI: 512 [M + 1] | |
| 443 | [334] | 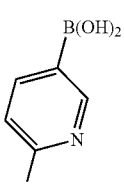 | method: 4, RT: 4.79 min, MI: 513 [M + 1] | |
| 444 | [334] | 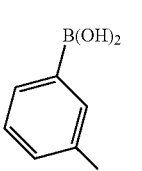 | method: 4, RT: 4.57 min, MI: 509 [M + 1] | |

-continued
| Example | SM | Boronic acid[a] [G-123] | Characterisation | |
|---|---|---|---|---|
| 445 | [334] | 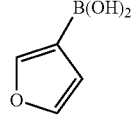 | method: 4, RT: 5.07 min, MI: 484 [M + 1] | |
| 446 | [300] | 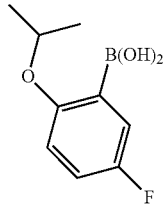 | method: 4, RT: 4.80 min, MI: 528 [M + 1] | 1H NMR (DMSO, 300 MHz): 8.62 (dd, 2H), 7.90 (dd, 2H), 7.46 (m, 1H), 7.29 (m, 5H), 7.27 (m, 1H), 7.16 (m, 1H), 3.84 (m, 2H), 3.16 (d, 6H), 2.92 (m, 2H), 2.81 (m, 1H), 2.65 (m, 1H), 2.53 (s, 3H) |
| 447 | [334] | 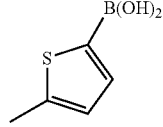 | method: 4, RT: 5.72 min, MI: 514 [M + 1] | |
| 448 | [334] | 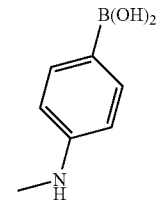 | method: 4, RT: 4.45 min, MI: 523 [M + 1] | |
| 449 | [300] | 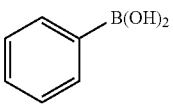 | method: 4, RT: 4.51 min, MI: 452 [M + 1] | 1H NMR (DMSO, 300 MHz): 8.62 (dd, 2H), 7.90 (dd, 2H), 7.57 (m, 5H), 7.34 (m, 5H), 3.5 (m, 1H), 2.92 (m, 2H), 2.81 (m, 1H), 2.65 (m, 1H), 2.6 (s, 3H) |
| 450 | [300] | 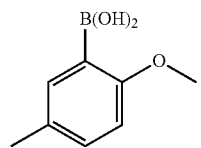 | method: 4, RT: 4.59 min, MI: 496 [M + 1] | |
| 451 | [334] | 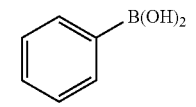 | method: 4, RT: 5.51 min, MI: 494 [M + 1] | |
| 452 | [300] | 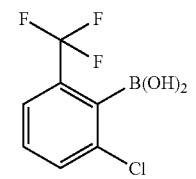 | method: 4, RT: 5.02 min, MI: 554 [M + 1] | |

-continued
| Example | SM | Boronic acid [G-123] | Characterisation | |
|---|---|---|---|---|
| 453 | [300] | 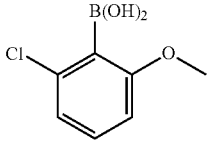 | method: 4, RT: 4.41 min, MI: 516 [M + 1] | |
| 454 | [300] | 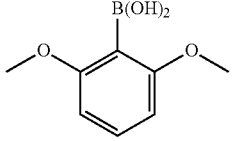 | method: 4, RT: 4.12 min, MI: 512 [M + 1] | |
| 455 | [330] | 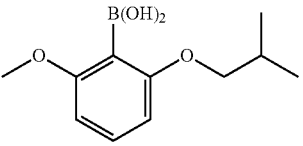 | method: 4, RT: 4.74 min, MI: 554 [M + 1] | |
| 456 | [300] | 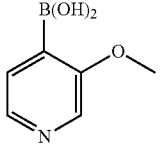 | method: 4, RT: 3.45 min, MI: 483 [M + 1] | |
| 457 | [300] | 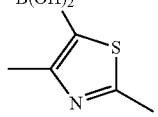 | method: 4, RT: 3.73 min, MI: 487 [M + 1] | |
| 458 | [300] | 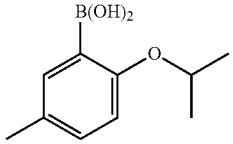 | method: 4, RT: 5.03 min, MI: 524 [M + 1] | 1H NMR (DMSO, 300 MHz): 8.6 (dd, 2H), 7.85 (dd, 2H), 7.34 (m, 5H), 7.17 (m, 1H), 7.03 (m, 2H), 3.5 (m, 1H), 2.92 (m, 2H), 2.81 (m, 2H), 2.53 (d, 6H), 2.65 (m, 1H), 2.41 (s, 3H), 2.3 (s, 3H) |
| 459 | [300] | 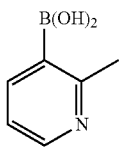 | method: 4, RT: 3.49 min, MI: 467 [M + 1] | |

| Example | SM | Boronic acid<sup>a</sup> [G-123] | Characterisation | |
|---|---|---|---|---|
| 460 | [300] | 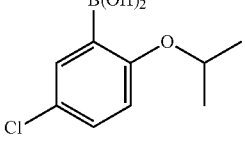 | method: 4, RT: 5.13 min, MI: 544 [M + 1] | 1H NMR (DMSO, 300 MHz): 8.62 (dd, 2H), 7.92 (dd, 2H), 7.44 (m, 5H), 7.32 (m, 1H), 7.28 (m, 2H), 7.19 (m, 2H), 3.5 (m, 1H), 2.92 (m, 2H), 2.81 (m, 2H), 2.65 (m, 1H), 2.53 (d, 6H), 2.42 (s, 3H) |
| 461 | [300] | 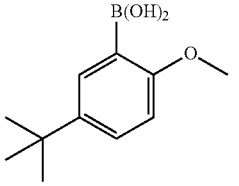 | | |
| 462 | [300] | 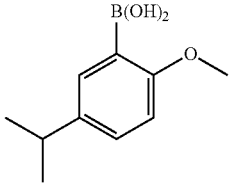 | method: 4, RT: 5.14 min, MI: 524 [M + 1] | |
| 463 | [300] | 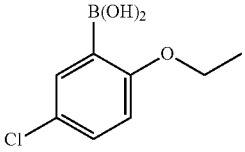 | method: 4, RT: 4.91 min, MI: 530 [M + 1] | |
| 464 | [300] | 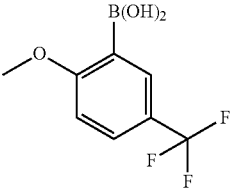 | method: 4, RT: 4.73 min, MI: 550 [M + 1] | |
| 465 | [300] | 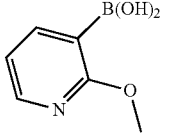 | method: 4, RT: 3.96 min, MI: 483 [M + 1] | 1H NMR (DMSO, 300 MHz): 8.6 (dd, 2H), 8.28 (dd, 1H), 7.82 (dd, 2H), 7.72 (m, 1H), 7.34 (m, 5H), 7.15 (m, 1H), 3.82 (s, 3H), 3.5 (m, 3H), 2.93 (m, 1H), 2.82 (m, 1H), 2.43 (s, 3H) |
| 466 | [300] | 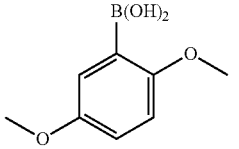 | method: 4, RT: 4.24 min, MI: 512 [M + 1] | |

| Example | SM | Boronic acid[a] [G-123] | Characterisation |
|---|---|---|---|
| 467 | [300] | 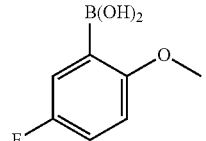 | method: 4, RT: 4.35 min, MI: 500 [M + 1] |
| 468 | [334] | 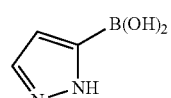 | method: 4, RT: 3.83 min, MI: 484 [M + 1] |
| 469 | [BB-41] | 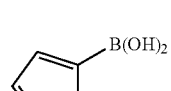 | method: 3, RT: 2.26 min, MI: 392 [M + 1] |

[a]site of attachment to thieno pyrimidine core.
b Clapham, Kate M.; Batsanov, Andrei S.; Bryce, Martin R.; Tarbit, Brian, *Organic and Biomolecular Chemistry*, 2009, vol. 7, p. 2155-216

General Synthesis of 7-amido-4PT32P Derivatives of General Formula [G-128](Scheme B6)

A 7-unsubstituted 2-pyridin-4-yl-thieno[3,2-d]pyrimidin-4-ol of general formula [G-124] was nitrated at the C-7 position by reaction with a nitrating agent such as fuming nitric acid in concentrated sulphuric acid to yield the corresponding 7-nitro-substituted 4PT32P derivative of general formula [G-125]. The 7-nitro-4PT32P derivative was then reduced to the corresponding 7-amino PT32P derivative of general formula [G-126] by hydrogenation reaction under an atmosphere of hydrogen in the presence of a catalyst such as palladium on activated charcoal. Amide formation was performed by reaction with an acyl chloride, of general formula [G-129] with the 7-amino-4PT32P derivative [G-126] to yield the corresponding 7-amidosubstituted 4PT32P derivative of general formula [G-127]. The intermediate 7-amidosubstituted 4PT32P derivative of general formula [G-127] was then reacted with 2,4,6-triisopropylbenzenesulfonyl chloride in a polar aprotic solvent such as DMA, DMF, NMP with a tertiary alkylamine base such as $Et_3N$, DIPEA or NMM and a catalytic amount of DMAP, and the intermediate 7-amidosubstituted-(2,4,6-triisopropyl-benzenesulfonic acid)-2-pyridin-4-yl-thieno[3,2-d]pyrimidin-4-yl ester was used crude and reacted further with a primary or secondary amino derivative, of general formula [G-117], in a polar aprotic solvent such as DMA, DMF, NMP in the presence of a tertiary amine base such as $Et_3N$, DIPEA or NMM at ambient temperature. After reaction work up, typically by a liquid-liquid extraction or purification by acidic ion exchange catch-release, the N-Boc derivatives were deprotected under acidic conditions with a strong acid such as TFA, TCA, methanesulfonic acid, HCl or $H_2SO_4$ in a solvent such as DCM, DCE, THF, EtOH or MeOH and the crude reaction product was purified by reverse phase preparative HPLC.

Scheme B6

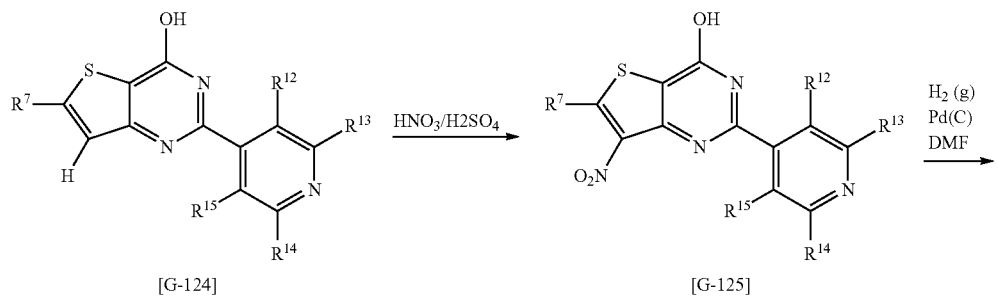

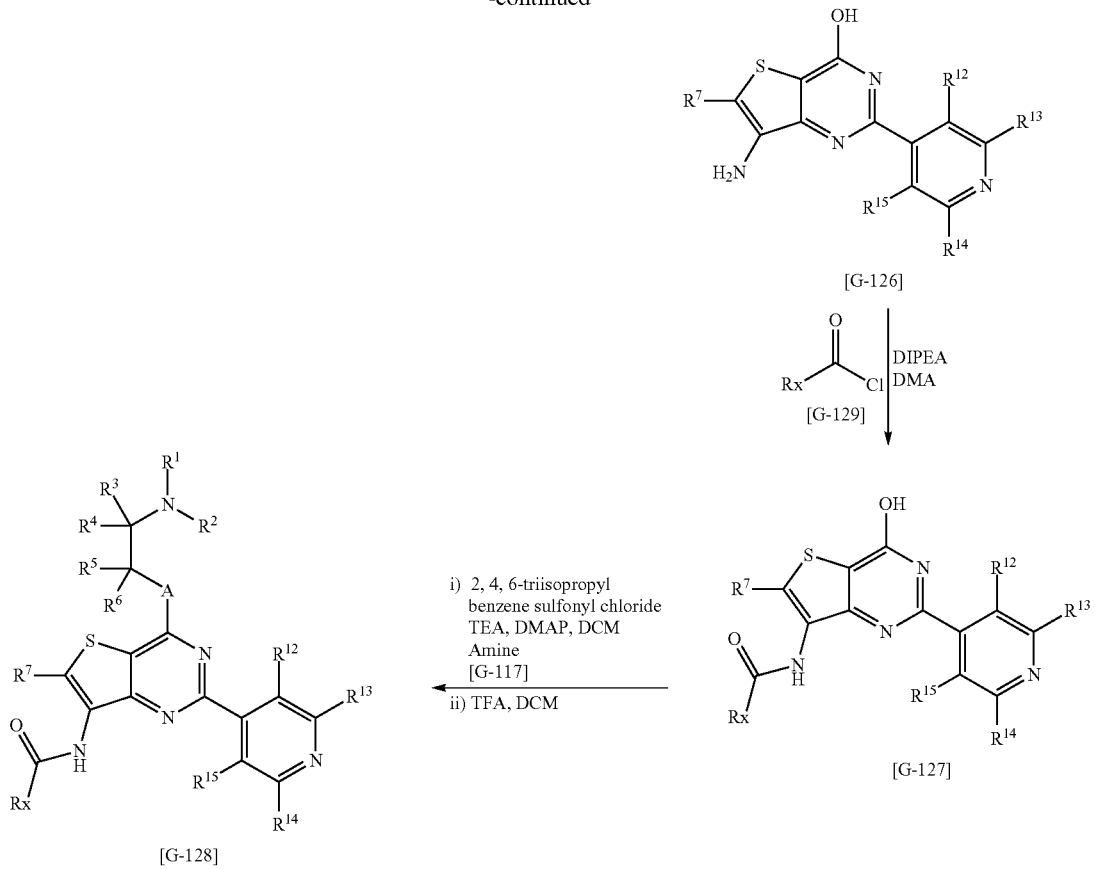

Synthesis of 7-nitro-2-Pyridin-4-yl-thieno[3,2-d]pyrimidin-4-ol [BB-40]

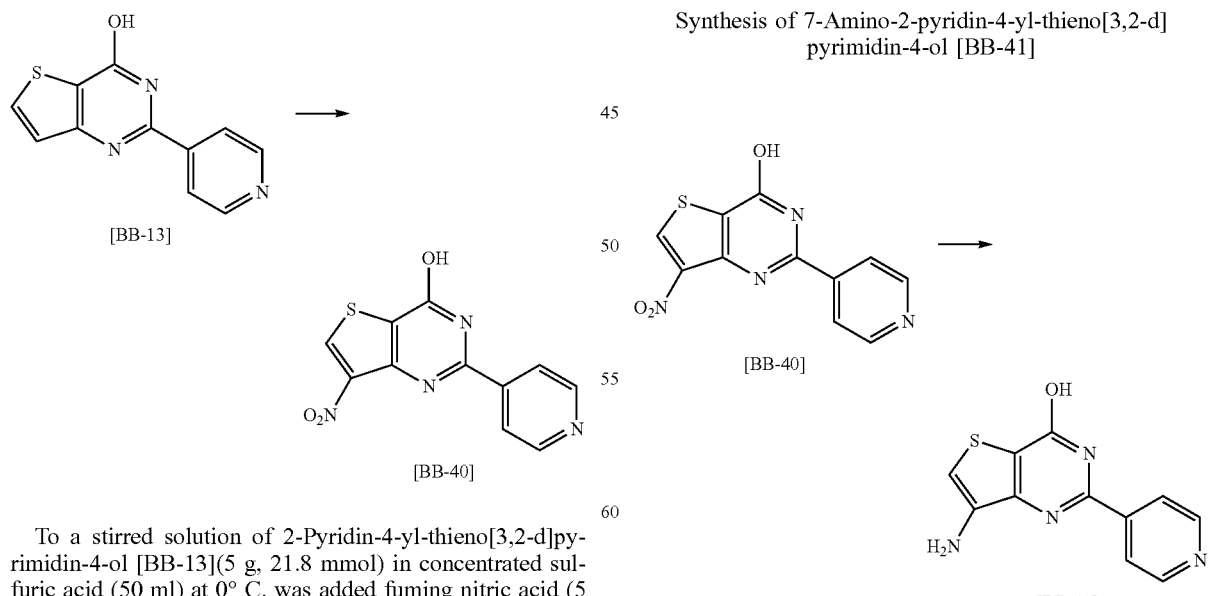

To a stirred solution of 2-Pyridin-4-yl-thieno[3,2-d]pyrimidin-4-ol [BB-13] (5 g, 21.8 mmol) in concentrated sulfuric acid (50 ml) at 0° C. was added fuming nitric acid (5 ml) dropwise. The reaction mixture was left to stir at 0° C. for 1 hr then the mixture was poured onto ice and left to stir at room temperature overnight. The pale yellow precipitate was collected by filtration, and washed with $H_2O$ followed by THF, to yield the title compound as a pale yellow solid (1.84 g, 31% yield) which was used in the next step without further purification: LCMS method 3, 2.94 min, 100%, 274.97 [M+H]

Synthesis of 7-Amino-2-pyridin-4-yl-thieno[3,2-d]pyrimidin-4-ol [BB-41]

7-Nitro-2-pyridin-4-yl-thieno[3,2-d]pyrimidin-4-ol [BB-40] (4.25 g, 15.5 mmol) was dissolved in 2:3 mixture of MeOH-DMF (500 ml) and filtered through a PTFE phase separation frit to remove any undissolved solids. The filtrate was then loaded onto an H-cube with a flow rate of 1 ml/min [using a paladium on activated charcoal cartridge at room temperature and an atmospheric pressure of $H_2$]. The crude reaction mixture was evaporated under reduced pressure to remove the MeOH and the resulting DMF solution was poured onto an SCX cartridge, which was washed with MeOH followed by $NH_3$:MeOH. The methanolic ammonia flush was concentrated in vacuo to provide the title compound as a brown solid (1.5 g, 40% yield) which was used in the next step without further purification: LCMS method 3, 2.35 min, 100%, 244.99 [M+H]

Synthesis of Cyclopentanecarboxylic acid [2-pyridin-4-yl-4-((R)-pyrrolidin-3-ylamino)-thieno[3,2-d]pyrimidin-7-yl]-amide [470]

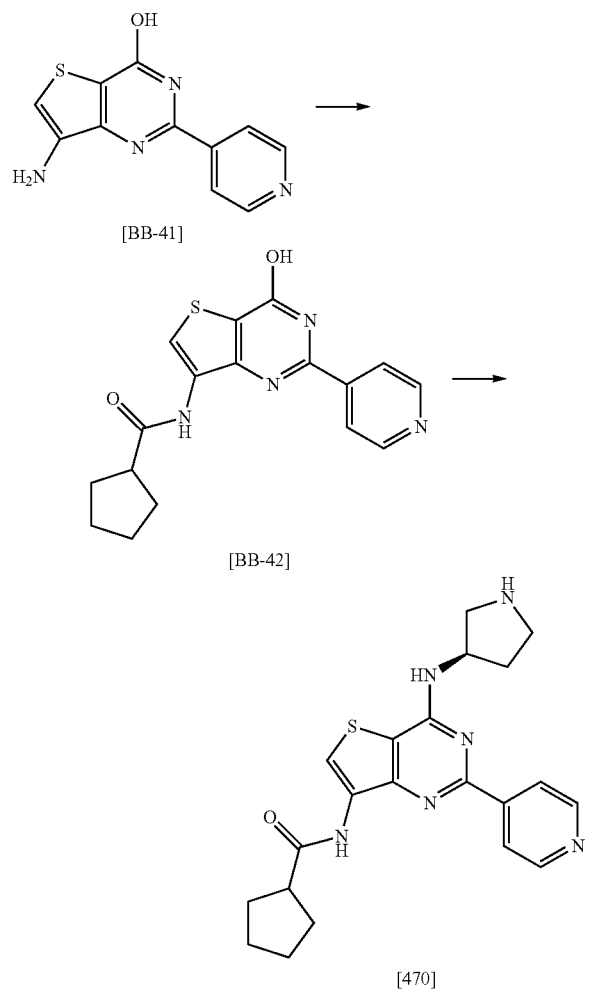

7-Amino-2-pyridin-4-yl-thieno[3,2-d]pyrimidin-4-ol [BB-41] (100 mg, 0.42 mmol) was dissolved in DMA (2 ml) and DIPEA (150 μL). The reaction mixture was cooled to 0° C. and a mixture of cyclopentane carbonyl chloride (100 μL, 0.84 mmol) in DMA (1 ml) was added and the reaction was left to stir at 0° C. for 2 hours. The mixture was treated with water (1 ml) and left to stir for 2 hours at room temperature. The crude reaction mixture was extracted with DCM (2 ml) and washed with brine (3 ml) and the organic extract was then loaded on a SCX-2 cartridge, which was washed with MeOH followed by $NH_3$:MeOH. The methanolic ammonia flush was concentrated under reduced pressure to provide cyclopentanecarboxylic acid (4-hydroxy-2-pyridin-4-yl-thieno[3,2-d]pyrimidin-7-yl)-amide [BB-42], which was used crude in the next step. To a solution of crude cyclopentanecarboxylic acid (4-hydroxy-2-pyridin-4-yl-thieno[3,2-d]pyrimidin-7-yl)-amide [BB-42] (70 mg, 0.21 mmol), DMAP (3 mg), TEA (60 ml, 0.42 mmol) in DMA (5 ml) was added 2,4,6-triisopropylbenzenesulfonyl chloride (77 mg, 0.25 mmol). The mixture was left to stir at room temperature overnight. A mixture of (R)-(+)-1-Boc-3-aminopyrrolidine (40 ml, 0.21 mmol) in DMA (1 ml) was added and the mixture was left to stir at room temperature for 24 hours. Water was added and the reaction mixture was extracted with DCM and the extract was dried ($MgSO_4$), filtered and evaporated under reduced pressure. The crude product was dissolved in DCM (2 ml) and TFA (1 ml) was added, the mixture was left to stir at room temperature for 1 hour then the crude reaction mixture was loaded on to a SCX-2 cartridge, which was washed with MeOH followed by $NH_3$:MeOH. The methanolic ammonia flush was concentrated in vacuo and the residue was purified by preparative LC-MS to provide the title compound. LCMS method 5, 2.71 min, 409 [M+H].

The following compounds were prepared according to the general synthesis shown in Scheme B6:

| Example | SM | Amine [F117] | [F-129] | Characterisation |
|---|---|---|---|---|
| 471 | [BB-41] | boc-N-pyrrolidine (R), $H_2N$ | isobutyryl Cl | LCMS method 5, 3.00 min, 411 [M + H] |
| 472 | [BB-41] | boc-NH, (S), benzyl, $NH_2$ | isobutyryl Cl | LCMS method 5, 4.01 min, 475 [M + H] |
| 473 | [BB-41] | boc-N-pyrrolidine (R), $H_2N$ | cyclohexanecarbonyl Cl | LCMS method 5, 3.09 min, 423 [M + H] |
| 474 | [BB-41] | boc-NH, (S), benzyl, $NH_2$ | cyclohexanecarbonyl Cl | LCMS method 5, 4.39 min, 487 [M + H] |

325
-continued

| Example | SM | Amine [F117] | Rx—C(=O)—Cl [F-129] | Characterisation |
|---|---|---|---|---|
| 475 | [BB-41] | boc-NH-(S)-CH(CH$_2$Ph)-CH$_2$-NH$_2$ | cyclohexanecarbonyl chloride | LCMS method 5, 3.91 min, 473 [M + H] |

General Synthesis of 4-alkoxy-substituted 4PT32P Derivative of General Formula [G-130] (Scheme B7)

The Polystyrene supported benzenesulfonic acid 6,7 substituted-2-pyridin-4-yl-thieno[3,2-d]pyrimidin-4-yl ester of general formula [G-118] [prepared in scheme B5] was subjected to a nucleophilic substitution reaction with an amino alcohol, of general formula [G-131], in the presence of a strong base such as NaH, KH or LDA in an anhydrous polar aprotic solvent such as DMA, DMF or NMP. After reaction work up, typically filtration of the resin through a PTFE frit followed by a liquid-liquid extraction or purification by acidic ion exchange catch-release, the N-Boc derivatives were deprotected under acidic conditions with a strong acid such as TFA, TCA, methanesulfonic acid, HCl or H$_2$SO$_4$ in a solvent such as DCM, DCE, THF, EtOH or MeOH and the crude reaction product was purified by reverse phase preparative HPLC.

Scheme B7

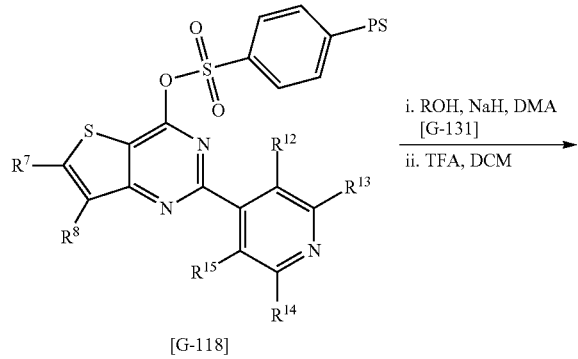

326
-continued

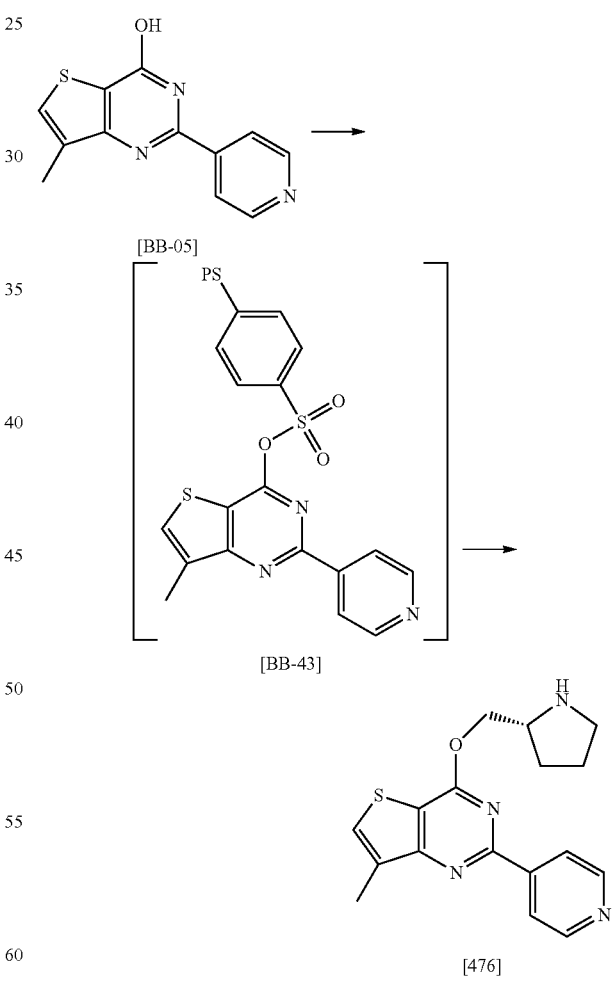

Synthesis of 7-methyl-2-pyridin-4-yl-4-((R)-1-pyrrolidin-2-ylmethoxy)-thieno[3,2-d]pyrimidine [476]

7-methyl-2-pyridin-4-yl-thieno[3,2-d]pyrimidin-4-ol [BB-05] (70 mg, 0.28 mmol) and PS-TSCl (210 mg, 0.45 mmol) were placed into filter cartridge closed with a stopper. DMA (2 ml) was added followed by Et$_3$N (70 μl, 0.5 mmol) and DMAP (1.1 mg, 0.009 mmol). The reaction was shaken for 3 hours at room temperature and then the polymer was filtered through a PTFE frit. The resin was washed with DCM, DMA, DCM to yield to the intermediate polystyrene supported benzenesulfonic acid 7-methyl-2-pyridin-4-yl-thieno[3,2-d]pyrimidin-4-yl ester [BB-43], which was used in the next step without further purification.

Polymer supported benzenesulfonic acid 7-methyl-2-pyridin-4-yl-thieno[3,2-d]pyrimidin-4-yl ester [BB-43] (0.280 mmol) was placed in a filter cartridge and DMA (2 ml) was added, followed by (R)-(+)-1-boc-2-pyrrolidinemethanol (68 µl, 0.340 mmol) and NaH (14 mg, 0.340 mmol). The reaction was shaken overnight at room temperature. The resin was filtered through a PTFE frit and washed with ethylacetate. The filtrates were combined and concentrated under reduced pressure. The crude product was dissolved in DCM (2 ml) and TFA (2 ml) was added and the mixture was stirred at room temperature for 1 hour. After completion the mixture was loaded onto a SCX-2 cartridge and washed with methanol. The product was released from the cartridge using a solution of 2M ammonia/methanol. The ammonia/methanol eluent was concentrated under reduced pressure and the crude product was purified by preparative HPLC (method A) to yield to the title compound. LCMS method: 2, RT: 1.91 min, MI: 313 [M+1].

The following compounds were prepared according to the general synthesis shown in scheme B7:

| Example | SM | ROH [G-131] | Characterisation |
|---|---|---|---|
| 477 | [BB-09] | | method: 2, RT: 3.47 min, MI: 447 [M + 1] |
| 478 | [BB-09] | | method: 2, RT: 3.29 min, MI: 397 [M + 1] |
| 479 | [BB-09] | | method: 2, RT: 2.28 min, MI: 397 [M + 1] |
| 480 | [BB-05] | | method: 2, RT: 1.95 min, MI: 327 [M + 1] |
| 481 | [BB-05] | | method: 2, RT: 2.80 min, MI: 377 [M + 1] |
| 482 | [BB-05] | 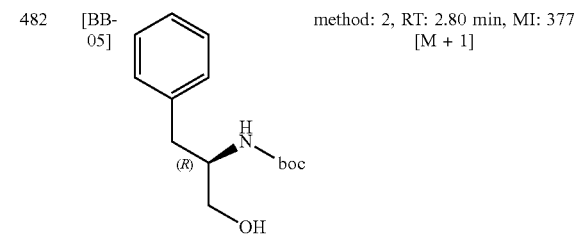 | method: 2, RT: 2.80 min, MI: 377 [M + 1] |
| 483 | [BB-05] | | method: 2, RT: 1.92 min, MI: 313 [M + 1] |
| 484 | [BB-05] | 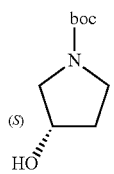 | method: 2, RT: 1.91 min, MI: 313 [M + 1] |

General Synthesis of 7-arylaminosubstituted-4PT32P Derivatives of General Formula [F-132] (Scheme B8)

The 7-bromo-6-substituted-2-pyridin-4-yl-thieno[3,2-d]pyrimidine derivative of general formula [G-119] was involved in a Buchwald type reaction utilising a suitable amine, of general formula [G-133], a palladium catalyst such as Pd(dba)$_2$ or Pd(OAc)$_2$, a ligand such as Xantphos and a base such as NaOtBu or Cs$_2$CO$_3$ in a polar solvent such as dioxane or a combination of dioxane and DMA at high temperature either by heating thermally or using a microwave reactor. After reaction work up, typically by a liquid-liquid extraction or purification by acidic ion exchange catch-release, the N-Boc derivatives were deprotected under acidic conditions with a strong acid such as TFA, TCA, methanesulfonic acid, HCl or H$_2$SO$_4$ in a solvent such as DCM, DCE, THF, EtOH or MeOH and the crude reaction product was purified by preparative reverse phase HPLC.

Scheme B8

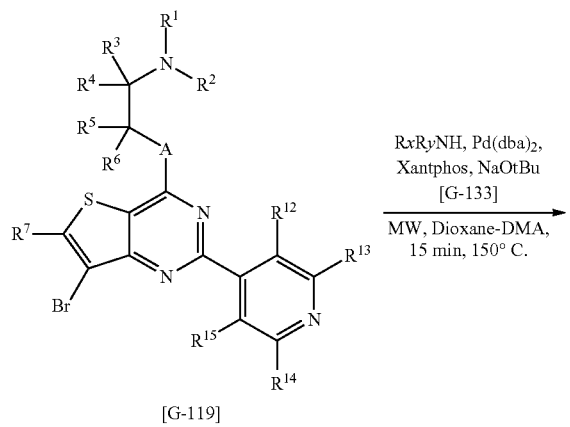

[G-119]

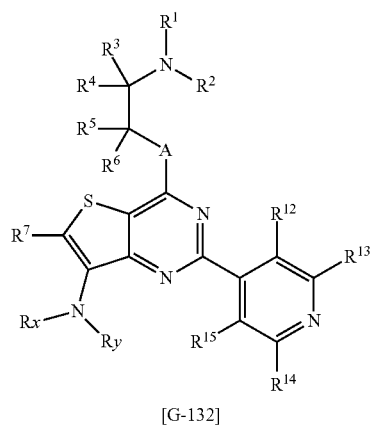

[G-132]

Synthesis of N*4*-((S)-2-Amino-3-phenyl-propyl)-N*7*-phenyl-2-pyridin-4-yl-thieno[3,2-d]pyrimidine-4,7-diamine [485]

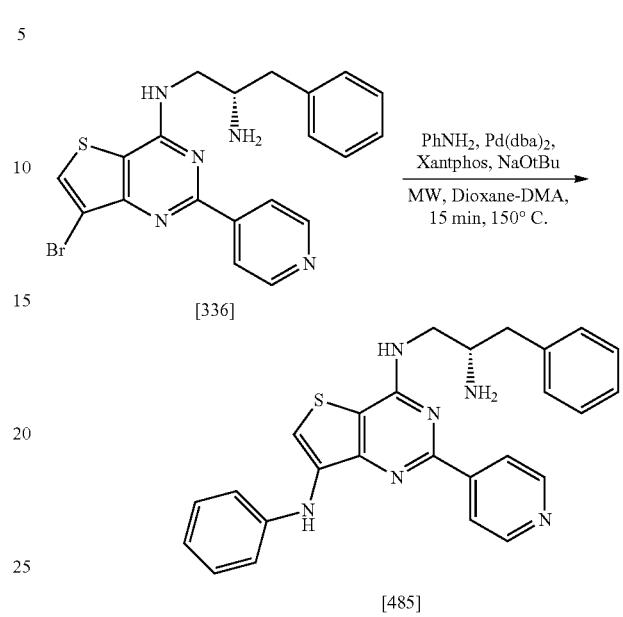

A microwave vial was charged with (S)—N*1*-(7-bromo-6-methyl-2-pyridin-4-yl-thieno[3,2-d]pyrimidin-4-yl)-3-phenyl-propane-1,2-diamine [336] (100 mg, 0.227 mmol), aniline (27 μl, 0.295 mmol), Pd(dba)$_2$ (7 mg, 0.011 mmol), Xantphos (13 mg, 0.023 mmol), NaOtBu (45 mg, 0.454 mmol), DMA (few drops) and dioxane (1 ml). The reaction was heated to 150° C. for 15 minutes under microwave irradiation. The mixture was then loaded onto a SCX-2 cartridge and washed with methanol. The product was released from the cartridge using a solution of 2M ammonia/methanol. The ammonia/methanol eluent was concentrated under reduced pressure and the crude product was purified by preparative HPLC (method B) to yield the title compound. LCMS method: 4, RT: 4.38 min, MI: 453 [M+1]. $^1$H NMR (300 MHz, DMSO): 8.68 (2H, d), 8.41 (1H, s, br), 8.24 (2H, d), 8.17 (1H, s), 7.34 (9H, m), 6.87 (1H, t), 3.89 (1H, m, br), 3.40 (2H, t), 2.78 (2H, d).

The following compounds were prepared according to the general synthesis shown in Scheme B8:

| Example | SM | RxRyNH [G-133] | | Characterisation |
|---|---|---|---|---|
| 486 | [336] | pyridin-2-amine | method: 5, RT: 3.06 min, MI: 454 [M + 1] | |
| 487 | [351] | pyridin-2-amine | method: 5, RT: 1.60 min, MI: 390 [M + 1] | 1H NMR (300, MHz, DMSO): 9.07 (1H, s), 8.76 (2H, d), 8.54 (2H, d), 8.39 (2H, t), 8.26 (1H, d), 7.66 (1H, t), 7.35 (1H, d), 6.84 (1H, t), 4.90 (1H, m), 3.44 (2H, m), 3.09 (2H, m) 2.25 (1H, m), 1.88 (1H, m) |
| 488 | [336] | pyrimidin-2-amine | method: 5, RT: 3.33 min, MI: 455 [M + 1] | 1H NMR (300, MHz, DMSO): 9.02 (1H, s), 8.67 (2H, s, br), 8.61 (2H, d), 8.25 (1H, s), 8.18 (2H, d), 7.35 (5H, m), 6.98 (2H, t), 3.95 (1H, m), 3.49 (2H, m), 2.93 (1H, m), 2.81 (1H, m) |

| Example | SM | RxRyNH [G-133] | | Characterisation | |
|---|---|---|---|---|---|
| 489 | [336] | pyrimidin-4-amine | method: 5, RT: 3.22 min, MI: 455 [M + 1] | |
| 490 | [336] | 5-methylisoxazol-3-amine | method: 5, RT: 3.29 min, MI: 458 [M + 1] | |
| 491 | [BB-33] | aniline | method: 5, RT: 4.15 min, MI: 471 [M + 1] | 1H NMR (300, MHz, MeOD): 8.62 (d, 1H), 8.53 (s, 1H), 8.51 (d, 1H), 8.12 (m, 10H), 3.95 (m, 2H), 3.76 (m, 1H), 3.04 (m, 2H). |
| 492 | [352] | 3-methylaniline | method: 5, RT: 3.89 min, MI: 421 [M + 1] | |
| 493 | [352] | 4-fluoroaniline | method: 5, RT: 3.64 min, MI: 425 [M + 1] | |
| 494 | [352] | pyridin-3-amine | method: 5, RT: 1.19 min, MI: 408 [M + 1] | |
| 495 | [352] | pyridin-2-amine | method: 5, RT: 2.08 min, MI: 408 [M + 1] | |
| 496 | [352] | 5-methylisoxazol-3-amine | method: 5, RT: 3.07 min, MI: 412 [M + 1] | |
| 497 | [352] | isoxazol-3-amine | method: 5, RT: 2.82 min, MI: 398 [M + 1] | |
| 498 | [352] | 2-methylaniline | method: 5, RT: 3.95 min, MI: 421 [M + 1] | 1H NMR (300, MHz, MeOD): 8.6 (1H, d), 8.52 (1H, d), 8.48 (1H, s), 8.27 (1H, m), 7.23 (2H, d), 7.35 (1H, d), 6.92 (1H, m), 4.9 (1H, m), 3.44 (2H, m), 3.09 (2H, m), 2.25 (1H, m), 1.88 (1H, m) |
| 499 | [352] | 3-fluoroaniline | method: 5, RT: 3.69 min, MI: 425 [M + 1] | |
| 500 | [352] | 2-fluoroaniline | method: 5, RT: 3.8 min, MI: 425 [M + 1] | 1H NMR (300, MHz, MeOD): 8.61 (1H, d), 8.53 (1H, d), 8.49 (1H, s), 8.28 (1H, m), 7.24 (2H, d), 7.34 (1H, d), 6.91 (1H, m), 4.91 (1H, m), 3.44 (2H, m), 3.08 (2H, m), 2.27 (1H, m), 1.88 (1H, m) |

333

General Synthesis of 7-alkynyl-substituted-4PT32P and 6-alkynyl substituted-4PT32P Derivatives of General Formula [F134] & [G-135] (Scheme B9)

The 7-Bromo-6-substituted-4-amino-2-(3-substituted-pyridin-4-yl)-thieno[3,2-d]pyrimidine derivative of general formula [G-119] or 6-Bromo-6-substituted-4-amino-2-(3-substituted-pyridin-4-yl)-thieno[3,2-d]pyrimidine derivative of general formula [G-121] was involved in a Sonogashira coupling reaction utilising a suitable terminal alkyne, of general formula [G-136], in the presence of copper(I)iodide with $Pd(PPh_3)_2Cl_2$ as catalyst, triphenylphosphine as ligand, and a base such as $Et_3N$, or DEA in a polar solvent such as DMA or DMF at a high temperature either by heating thermally or using a microwave reactor. After reaction work up, typically by a liquid-liquid extraction or purification by acidic ion exchange catch-release, the N-Boc derivatives were deprotected under acidic conditions with a strong acid such as TFA, HCl in a solvent such as DCM, DCE or 1,4-dioxane or by catch and release sulfonic acidic resins such as polymer supported toluene sulfonic acid. In the case of silyl protected acetylenes, a further deprotection using 1M TBAF in THF was used prior to the acid mediated cleavage of the Boc group and the crude reaction mixtures were purified by preparative reverse phase HPLC.

Scheme B9

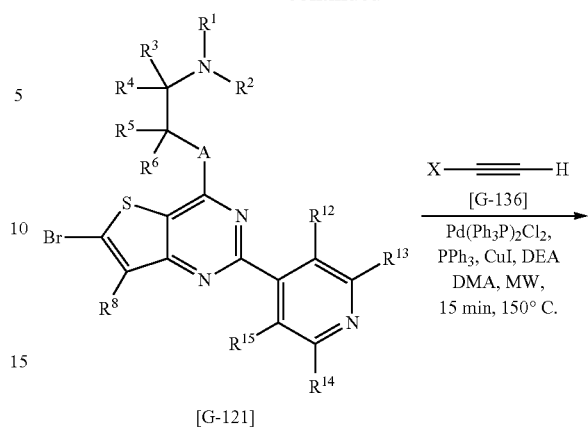

[G-121]

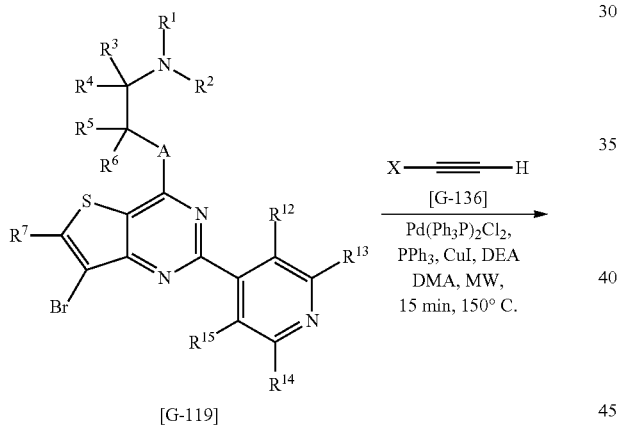

[G-119]

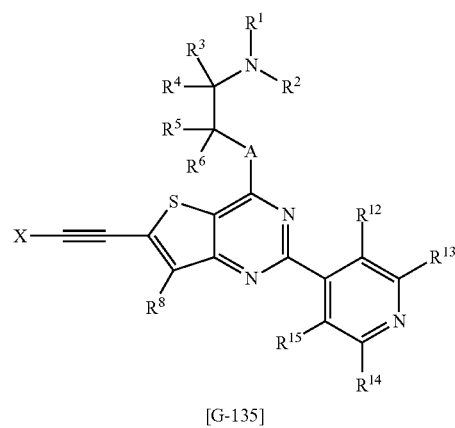

[G-135]

Synthesis of 4-[4-((S)-2-Amino-3-phenyl-propylamino)-2-(3-fluoro-pyridin-4-yl)-thieno[3,2-d]pyrimidin-7-yl]-but-3-yn-1-ol [501]

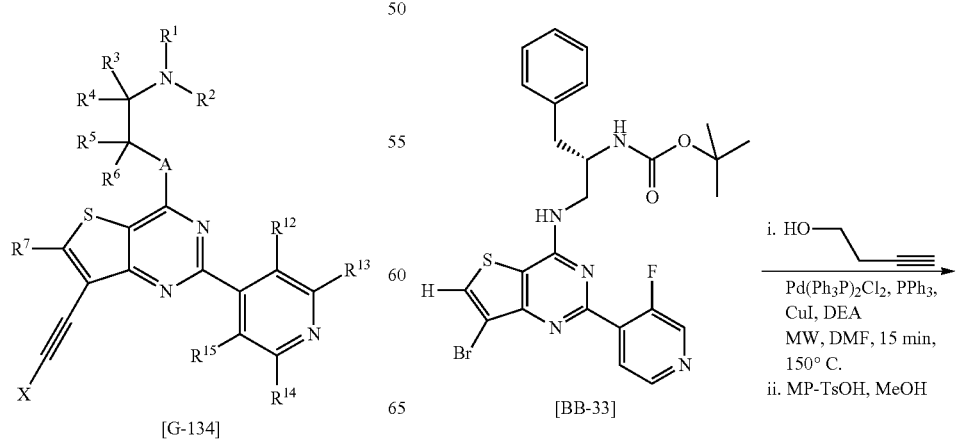

[G-134]     [BB-33]

336
Synthesis of 2-Methyl-4-[7-methyl-2-pyridin-4-yl-4-((R)-pyrrolidin-3-ylamino)-thieno[3,2-d]pyrimidin-6-yl]-but-3-yn-2-ol [502]

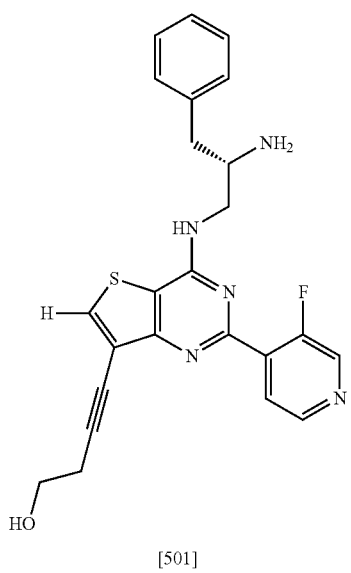

[501]

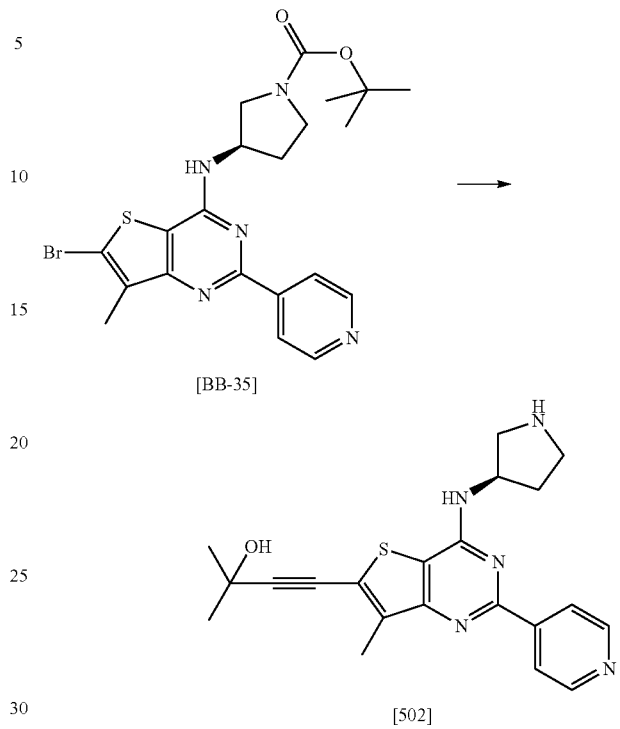

A microwave vial was charged with {(S)-1-Benzyl-2-[7-bromo-2-(3-fluoro-pyridin-4-yl)-thieno[3,2-d]pyrimidin-4-ylamino]-ethyl}-carbamic acid tert-butyl ester [BB-33] (100 mg, 0.179 mmol), 3-butyn-1-ol (15 µL, 0.197 mmol), bis(triphenylphosphine)palladiumchloride (13 mg, 0.018 mmol), copper(I)Iodide (3.4 mg, 0.018 mmol), triphenylphosphine (9.4 mg, 0.036 mmol), diethylamine (0.28 ml, 2.686 mmol) and DMF (1 ml). The reaction mixture was heated to 150° C. for 15 minutes under microwave irradiation. After completion, the product was extracted with ethyl acetate (2×2 ml), washed with brine (2 ml) and the combined organic phases were dried (MgSO$_4$), filtered and evaporated under reduced pressure. The crude product was dissolved in DCM (2 ml) and TFA (1 ml) was added, the mixture was stirred at room temperature for 1 hour then the crude product was loaded onto an SCX cartridge and the cartridge was washed with methanol then the product was eluted with 2M ammonia/methanol. The eluent was concentrated under reduced pressure and the crude mixture purified by preparative HPLC (method A) to yield the title compound: LCMS method: 7, RT: 3.15 min, MI: 448 [M+1]. $^1$H NMR (300, MHz, DMSO): 8.69 (d, 1H), 8.55 (d, 1H), 8.28 (s, 1H), 7.90 (m, 1H), 7.24 (m, 5H), 4.92 (bs, 1H), 3.62 (m, 2H), 2.78 (m, 1H), 2.62 (m, 2H).

A microwave vial was charged with (R)-3-(6-Bromo-7-methyl-2-pyridin-4-yl-thieno[3,2-d]pyrimidin-4-ylamino)-pyrrolidine-1-carboxylic acid tert-butyl ester [BB-35] (60 mg, 0.13 mmol), 2-methyl-3-butyn-1-ol (51 µL, 0.53 mmol), bis(triphenylphosphine)palladiumchloride (93 mg, 0.13 mmol), copper(I)Iodide (25 mg, 0.13 mmol), triphenylphosphine (70 mg, 0.26 mmol), diethylamine (0.2 ml, 1.9 mmol) and DMF (1 ml). The reaction mixture was heated to 150° C. for 10 minutes under microwave irradiation. After completion, the product was extracted with ethyl acetate (2×2 ml), washed with brine (2 ml) and the combined organic phases were dried (MgSO$_4$), filtered and evaporated under reduced pressure. The crude product was dissolved in DCM (2 ml) and TFA (1 ml) was added, the mixture was stirred at room temperature for 1 hour then the crude product was loaded onto an SCX cartridge and the cartridge was washed with methanol then the product was eluted with 2M ammonia/methanol. The eluent was concentrated under reduced pressure and the crude mixture purified by preparative HPLC (method A) to yield the title compound. LCMS method 5, 2.83 min, 394 [M+H].

The following compounds were prepared according to the general synthesis shown in Scheme B9:

| Ex | SM | Terminal alkyne [G-136] | Characterisation |
|---|---|---|---|
| 503 | [328] | ![HO-C(CH3)2-C≡C-H] | method: 5, RT: 2.41 min, MI: 394 [M + 1] |

-continued

| Ex | SM | Terminal alkyne [G-136] | | Characterisation | |
|---|---|---|---|---|---|
| 504 | [300] | HO-C(CH3)2-C≡C-H | method: 5, RT: 3.28 min, MI: 458 [M + 1] | |
| 505 | [334] | HO-C(CH3)2-C≡C-H | method: LC-MS15QC, RT: 5.93 min, MI: 500 [M + 1] | |
| 506 | [BB-33] | tetrahydropyran-O-CH2-C≡C-H | method: 5, RT: 3.02 min, MI: 434 [M + 1] | 1H NMR (300 MHz, DMSO): 8.68 (1H, d), 8.56 (1H, dd), 8.38 (1H, s), 7.89 (1H, m), 7.24 (5H, m), 4.35 (2H, s), 3.67 (2H, m), 3.25 (2H, m), 2.77 (1H, m), 2.58 (1H, m) |
| 507 | [BB-33] | 1-hydroxycyclobutyl-C≡C-H (c) | method: 5, RT: 3.55 min, MI: 474 [M + 1] | 1H NMR (300 MHz, MeOD): 8.62 (d, 1H), 8.53 (d, 1H), 8.47 (s, 1H), 8.20 (s, 1H), 7.98 (m, 1H), 7.31 (m, 5H), 4.62 (s, 2H), 3.95 (m, 2H), 3.74 (m, 1H), 3.02 (d, 2H), 2.55 (m, 2H), 2.35 (m, 2H), 1.89 (m, 2H) |
| 508 | [BB-33] | (R)-CH3-CH(OH)-C≡C-H | method: 5, RT: 3.32 min, MI: 448 [M + 1] | 1H NMR (300 MHz, DMSO): 8.68 (d, 1H), 8.53 (d, 1H), 8.35 (s, 1H), 7.84 (dd, 1H), 7.25 (m, 5H), 4.62 (q, 1H), 3.71 (m, 1H), 3.45 (m, 2H), 2.80 (m, 2H), 1.39 (d, 3H) |
| 509 | [BB-33] | HO-C(CH3)2-C≡C-H | method: LC-MS15QC, RT: 5.58 min, MI: 462 [M + 1] | 1H NMR (300 MHz, DMSO): 8.68 (d, 1H), 8.53 (d, 1H), 8.31 (s, 1H), 7.91 (t, 1H), 7.25 (m, 5H), 3.68 (m, 1H), 2.75 (m, 2H), 2.60 (m, 2H), 1.49 (s, 6H) |
| 510 | [BB-34] | HO-C(CH3)2-C≡C-H | method: 6, RT: 4.87 min, MI: 444 [M + 1] | 1H NMR (DMSO, 300 MHz): 8.77 (1H, s, br), 8.68 (2H, d), 8.37 (1H, s, br), 8.29 (1H, s), 8.00 (2H, d), 7.36 (5H, m), 3.93 (1H, d, br), 3.50 (2H, m), 2.93 (1H, dd), 2.82 (1H, m), 1.53 (6H, s) |
| 511 | [BB-34] | (CH3)3C-C≡C-H | method: 5, RT: 4.01 min, MI: 442 [M + 1] | |
| 512 | [336] | cyclopropyl-C≡C-H | method: 5, RT: 3.41 min, MI: 426 [M + 1] | |
| 513 | [336] | CH3-CH(OH)-C≡C-H | method: 5, RT: 2.84 min, MI: 430 [M + 1] | 1H NMR (DMSO, 300 MHz) 8.75 (2H, s, br), 8.37 (1H, t), 8.30 (1H, s), 8.13 (2H, s, br), 7.39 (5H, m), 4.70 (1H, q), 3.93 (1H, dd), 3.65 (2H, m), 3.13 (1H, dd), 1.45 (3H, d) |
| 514 | [351] | HO-C(CH3)2-C≡C-H | method: 5, RT: 2.10 min, MI: 380 [M + 1] | 1H NMR (DMSO, 300 MHz) 8.75 (2H, d), 8.66 (2H, d), 8.35 (2H, d), 4.98 (1H, m), 3.60 (1H, m), 3.31 (2H, m), 2.35 (2H, m), 2.12 (2H, m), 1.56 (6H, s) |

| Ex | SM | Terminal alkyne [G-136] | | Characterisation |
|---|---|---|---|---|
| 515 | [BB-34] | 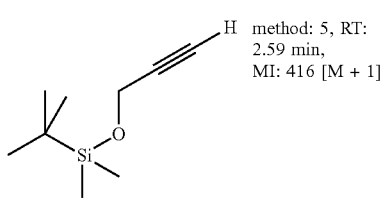 | method: 5, RT: 2.59 min, MI: 416 [M + 1] | 1H NMR (DMSO, 300 MHz) 8.68 (2H, d), 8.37 (1H, s), 8.01 (2H, d), 7.36 (5H, m), 4.40 (2H, s), 3.95 (2H, m), 3.49 (2H, m), 2.95 (1H, m), 2.77 (1H, m) |
| 516 | [336] | 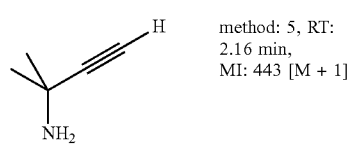 | method: 5, RT: 2.16 min, MI: 443 [M + 1] | 1H NMR (DMSO, 300 MHz) 8.69 (2H, d), 8.27 (1H, s, br), 8.21 (1H, s), 8.11 (2H, d), 7.33-7.26 (5H, m), 3.82 (1H, m), 3.30 (2H, m), 2.71 (2H, m), 1.44 (6H, s) |
| 517 | [351] | 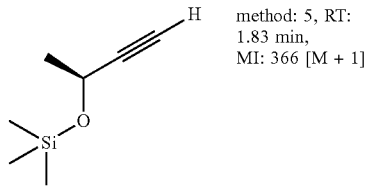 | method: 5, RT: 1.83 min, MI: 366 [M + 1] | 1H NMR (DMSO, 300 MHz): 8.75 (2H, d), 8.59 (1H, s), 8.34 (2H, d), 4.91 (1H, m), 4.70 (1H, m), 3.46 (1H, m), 3.23 (1H, m), 3.16 (1H, m), 2.27 (1H, m), 2.07 (2H, m), 1.46 (3H, d) |
| 518 | [336] | 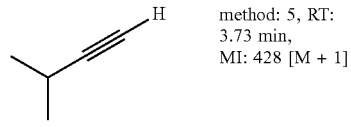 | method: 5, RT: 3.73 min, MI: 428 [M + 1] | 1H NMR (DMSO, 300 MHz): 8.68 (2H, d), 8.46 (1H, s), 8.24 (1H, s), 8.05 (2H, d), 7.33 (5H, m), 3.89 (1H, m), 2.91 (1H, m), 2.81 (1H, m), 1.29 (3H, s), 1.27 (3H, s) |
| 519 | [352] | 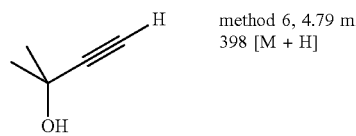 | method 6, 4.79 min, 398 [M + H] | |
| 520 | [336] | 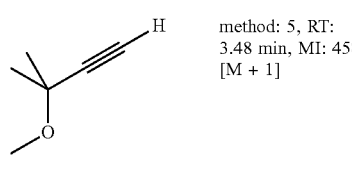 | method: 5, RT: 3.48 min, MI: 458 [M + 1] | 1H NMR (DMSO, 300 MHz): 8.69 (2H, d), 8.36 (1H, s), 8.05 (2H, d), 7.35-7.29 (5H, m), 3.87 (1H, m), 3.45 (3H, s), 2.79-2.71 (2H, m), 1.53 (6H, s) |
| 521 | [336] | 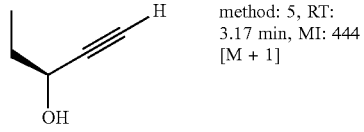 | method: 5, RT: 3.17 min, MI: 444 [M + 1] | 1H NMR (DMSO, 300 MHz): 8.68 (2H, d), 8.47 (1H, s), 8.32 (1H, s), 8.27 (1H, s), 8.05 (2H, d), 7.35-7.29 (5H, m), 4.48 (1H, t), 3.88 (1H, d, br), 3.41 (2H, m), 2.89-2.77 (2H, m), 1.77-1.67 (2H, m), 1.08 (3H, t) |
| 522 | [336] | 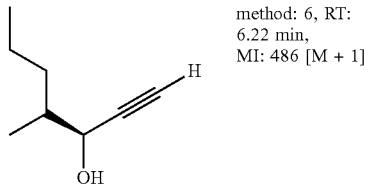 | method: 6, RT: 6.22 min, MI: 486 [M + 1] | 1H NMR (DMSO, 300 MHz): 8.67 (2H, d), 8.51 (1H, s, br), 8.31 (1H, s), 8.05 (2H, d), 7.36-7.28 (5H, m), 4.40 (1H, dd), 3.89 (1H, m), 3.42 (2H, m), 2.81 (2H, m), 1.72 (2H, m), 1.43 (1H, m), 1.31 (2H, m), 1.04 (3H, m), 0.89 (3H, t) |
| 523 | [336] | 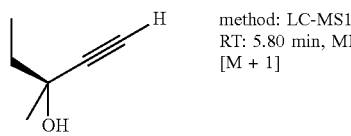 | method: LC-MS15QC, RT: 5.80 min, MI: 458 [M + 1] | |

-continued

| Ex | SM | Terminal alkyne [G-136] | Characterisation |
|---|---|---|---|
| 524 | [336] | (isopropyl-C(OH)(Me)-C≡C-H) | method: 5, RT: 3.60 min, MI: 472 [M + 1] |
| 525 | [336] | (Et-C(OH)(Et)-C≡C-H) | method: 5, RT: 3.70 min, MI: 472 [M + 1] |
| 526 | [336] | (n-Pr-CH(OH)-C≡C-H) | method: 5, RT: 3.46 min, MI: 458 [M + 1]; 1H NMR (DMSO, 300 MHz): 8.67 (2H, d), 8.52 (1H, s, br), 8.30 (1H, s), 8.26 (1H, s), 8.03 (2H, d), 7.38-7.31 (5H, m), 4.54 (1H, t), 3.90 (1H, m), 3.49 (2H, m), 2.90-2.81 (2H, m), 1.71-1.56 (4H, m), 0.97 (3H, s) |
| 527 | [352] | (Me-CH(OH)-C≡C-H) | method: 5, RT: 2.44 min, MI: 384 [M + 1]; 1H NMR (DMSO, 300 MHz): 8.02 (dd, 1H), 8.21 (bs, 1H), 8.70 (d, 1H), 8.55 (d, 1H), 8.47 (s, 1H), 4.64 (q, 1H), 3.88 (m, 1H), 3.66 (m, 2H), 3.12 (m, 2H), 2.24 (m, 1H), 2.19 (m, 1H), 1.43 (d, 3H) |
| 528 | [BB-34] | (1-ethynylcyclopentan-1-ol) | method: 5, RT: 3.48 min, MI: 470 [M + 1]; 1H NMR (DMSO, 300 MHz): 8.70 (1H, s, br), 8.68 (2H, d), 8.35 (1H, s), 8.29 (1H, s), 8.00 (2H, d), 7.36-7.33 (5H, m), 3.93 (1H, d, br), 3.46-3.41 (2H, m), 2.92 (1H, dd), 2.79-2.75 (1H, m), 2.00-1.90 (4H, m), 1.75 (4H, d, br) |
| 529 | [336] | (2-ethynylpyridine) | method: 5, RT: 3.27 min, MI: 463 [M + 1]; 1H NMR (DMSO, 300 MHz): 9.06 (1H, s, br), 8.67 (2H, d), 8.64 (1H, m), 8.60 (1H, s), 8.38 (1H, s), 8.01 (2H, d), 7.89 (1H, t), 7.72 (1H, d), 7.47-7.34 (6H, m), 4.02-3.97 (1H, m), 3.59-3.50 (2H, m), 3.03 (1H, dd), 2.86-2.77 (1H, m) |
| 530 | [336] | (2-fluorophenylacetylene) | method: 5, RT: 4.00 min, MI: 480 [M + 1]; 1H NMR (DMSO, 300 MHz): 8.83 (1H, s, br), 8.67 (2H, d), 8.54 (1H, s), 8.37 (1H, s), 8.04 (2H, d), 7.71 (1H, t), 7.53-7.48 (1H, m), 7.41-7.28 (6H, m), 3.97-3.94 (1H, m), 3.50-3.46 (2H, m), 2.95 (1H, dd), 2.84-2.77 (1H, m) |
| 531 | [336] | (HO-CH2-CH2-CH2-C≡C-H) | method: 5, RT: 2.67 min, MI: 430 [M + 1]; 1H NMR (DMSO, 300 MHz): 8.79 (1H, s, br), 8.67 (2H, d), 8.28 (3H, d), 7.98 (2H, d), 7.40-7.34 (5H, m), 3.97 (1H, d, br), 3.64 (2H, t), 3.54-3.48 (2H, m), 3.01 (1H, dd), 2.84 (1H, m), 2.63 (2H, t) |
| 532 | [336] | *d* (1-ethynylcyclopropan-1-ol) | method: 5, RT: 2.89 min, MI: 442 [M + 1]; 1H NMR (DMSO, 300 MHz): 8.69 (2H, d), 8.39 (1H, s), 8.28 (2H, d), 8.06 (2H, d), 7.35-7.28 (5H, m), 6.41 (1H, s, br), 3.86 (1H, m), 2.86 (2H, m), 2.78-2.72 (2H, m), 1.13 (2H, t), 1.04 (2H, m) |
| 533 | [336] | *A* ((S)-Me-C(OH)-C≡C-H) | method: 5, RT: 2.74 min, MI: 430 [M + 1]; 1H NMR (DMSO, 300 MHz): 8.85 (1H, s, br), 8.67 (2H, d), 8.33 (1H, s), 8.29 (2H, s, br), 7.98 (2H, d), 7.41-7.36 (5H, m), 4.68 (1H, q), 3.97 (1H, d, br), 3.62-3.51 (2H, m), 2.93 (1H, dd), 2.84 (1H, dd), 1.45 (3H, s) |

| Ex | SM | Terminal alkyne [G-136] | | Characterisation |
|---|---|---|---|---|
| 534 | [336] | (S)-but-3-yn-2-ol structure | method: 5, RT: 2.76 min, MI: 430 [M + 1] | 1H NMR (DMSO, 300 MHz): 8.87 (1H, s, br), 8.67 (2H, d), 8.33 (1H, s), 8.29 (2H, s, br), 7.97 (2H, d), 7.41-7.36 (5H, m), 4.68 (1H, q), 3.97 (1H, d, br), 3.64-3.52 (2H, m), 2.93 (1H, dd), 2.84 (1H, dd), 1.45 (3H, s) |
| 535 | [336] | hex-5-yn-1-ol structure | method: 5, RT: 2.84 min, MI: 444 [M + 1] | 1H NMR (DMSO, 300 MHz): 8.76 (1H, s, br), 8.67 (2H, d), 8.35 (2H, s), 8.25 (1H, s), 7.99 (2H, d), 7.39-7.32 (5H, m), 3.96 (1H, d, br), 3.61 (2H, t), 3.51-3.46 (2H, m), 2.97 (1H, dd), 2.82 (1H, dd), 2.55 (2H, m), 1.74 (2H, q) |
| 536 | [336] | pent-4-yn-2-ol structure | method: 5, RT: 2.93 min, MI: 444 [M + 1] | 1H NMR (DMSO, 300 MHz): 8.77 (1H, s, br), 8.66 (2H, d), 8.30 (2H, s, br), 8.26 (1H, s), 7.98 (2H, d), 7.40-7.34 (5H, m), 3.96-3.90 (2H, m), 3.60-3.49 (2H, m), 3.00 (1H, dd), 2.86-2.82 (1H, m), 2.63 (1H, dd), 1.29 (3H, d) |
| 537 | [336] | e, 2-methylpent-4-yn-2-ol structure | method: 5, RT: 3.08 min, MI: 458 [M + 1] | 1H NMR (DMSO, 300 MHz): 8.68 (2H, d), 8.24 (2H, s, br), 8.09 (2H, d), 7.32-7.25 (5H, m), 4.67 (1H, s), 3.80 (1H, d, br), 3.28 (2H, m), 2.72-2.67 (2H, m), 2.58 (2H, s), 1.34 (6H, s). |
| 538 | [336] | f, N-Boc-N-methyl-propargylamine structure | method: 5, RT: 1.44 min, MI: 429 [M + 1] | 1H NMR (DMSO, 300 MHz): 8.67 (2H, d), 8.31 (2H, s), 8.01 (2H, d), 7.38-7.31 (5H, m), 3.93 (1H, d, br), 3.63 (2H, s), 3.48-3.40 (2H, m), 2.93 (1H, dd), 2.80 (1H, dd), 2.45 (3H, s) |
| 539 | [BB-34] | c, 1-ethynylcyclobutan-1-ol structure | method: 5, RT: 3.18 min, MI: 456 [M + 1] | 1H NMR (MeOD, 300 MHz): 8.61 (2H, d), 8.25 (2H, d), 8.10 (1H, s), 7.37-7.27 (5H, m), 4.01-3.98 (1H, m), 3.58-3.52 (2H, m), 2.86 (2H, dd), 2.65-2.55 (2H, m), 2.42-2.32 (2H, m), 1.99-1.92 (2H, m) |
| 540 | [BB-34] | A, (R)-pent-4-yn-2-ol structure | method: 5, RT: 6.43 min, MI: 444 [M + 1] | 1H NMR (MeOD, 300 MHz): 8.58 (2H, d), 8.35 (2H, s), 8.13 (2H, d), 8.03 (1H, s), 7.41-7.35 (5H, m), 4.13 (1H, dd), 4.05 (1H, q), 3.92-3.89 (1H, m), 3.70 (1H, dd), 3.11 (1H, dd), 3.00 (1H, dd), 2.66 (2H, d), 1.41 (3H, d) |
| 541 | [336] | g, trimethylsilylacetylene structure | method: 5, RT: 2.82 min, MI: 386 [M + 1] | 1H NMR (MeOD, 300 MHz): 8.65 (2H, dd), 8.29 (1H, s), 8.25 (2H, dd), 7.41-7.35 (5H, m), 4.09 (1H, dd), 3.86 (1H, s), 3.76-3.63 (2H, m), 3.00-2.97 (2H, d) |

-continued

| Ex | SM | Terminal alkyne [G-136] | | Characterisation |
|---|---|---|---|---|
| 542 | [336] | h | method: 5, RT: 2.98 min, MI: 400 [M + 1] | 1H NMR (DMSO, 300 MHz): 8.66 (2H, d), 8.54 (1H, s, br), 8.31 (2H, s), 8.04 (2H, d), 7.93 (1H, s), 7.34 (5H, m), 6.73 (1H, t), 5.35 (2H, d), 3.80 (2H, m), 3.50 (2H, m), 2.99 (1H, dd), 2.65 (1H, dd) |
| 543 | [BB-35] | g | method: 5, RT: 2.77 min, MI: 452 [M + 1] | |

[c]Li-Mei Wei, Li-Lan Wei, Wen-Bin Pan and Ming-Jung Wu Tetrahedron Letters, 2003, vol. 44, p. 595-597
[d]Emme, Ingo; Bruneau, Christian; Dixneuf, Pierre H.; Militzer, Hans-Christian; Meijere, Armin de; Synthesis, 2007, vol. 22 p. 3574-358
[e]Dinges, Juergen; Albert, Daniel H.; Arnold, Lee D.; Ashworth, Kimba L.; Akritopoulou-Zanze, Irini; Bousquet, Peter F.; Bouska, Jennifer J.; Cunha, George A.; Davidsen, Steven K.; Diaz, Gilbert J.; Djuric, Stevan W.; et al. Journal of Medicinal Chemistry, 2007, vol. 50, No. 9 p. 2011-2029
[f]Bradbury, Barton J.; Baumgold, Jesse; Jacobson, Kenneth A. Journal of Medicinal Chemistry, 1990, vol. 33, No. 2 p. 741-748
[g]Derived from TBDMS protected acetylene.
[h]Derived from TMS protected acetylene.

General Synthesis of fluoro-alkynyl-7-4PT32P Derivatives of General Formula [G-134], (Scheme B10)

The 7-Bromo-6-substituted-4-amino-2-(3-substituted-pyridin-4-yl)-thieno[3,2-d]pyrimidine derivative of general formula [G-119] was involved in a Sonogashira coupling reaction utilising a suitable terminal propargylic or homopropargylic alcohol, of general formula [G-136], in the presence of copper(I)iodide with Pd(PPh$_3$)$_2$Cl$_2$ as catalyst, triphenylphosphine as ligand, and a base such as Et$_3$N, or DEA in a polar solvent such as DMA or DMF at a high temperature either by heating thermally or using a microwave reactor. After reaction work up, typically by a liquid-liquid extraction or purification by acidic ion exchange catch-release, the intermediate was purified by column chromatography to give the acetylenic intermediate. This was involved in a fluorination reaction utilising (diethylamino)sulfur trifluoride in a chlorinated solvent such as chloroform or DCM at low temperature. After reaction work up, typically by a liquid-liquid extraction, the N-Boc derivatives were deprotected under acidic conditions with a strong acid such as TFA, HCl in a solvent such as DCM, DCE or 1,4-dioxane or by catch and release sulfonic acidic resins such as polymer supported toluene sulfonic acid and the crude reaction product was purified by reverse phase preparative HPLC.

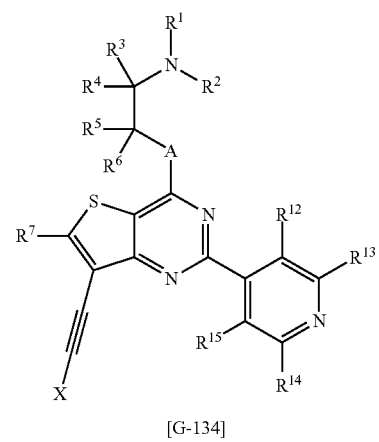

[G-134]

Synthesis of (S)—N*1*-[7-(3-Fluoro-but-1-ynyl)-2-pyridin-4-yl-thieno[3,2-d]pyrimidin-4-yl]-3-phenyl-propane-1,2-diamine [544]

Scheme B10

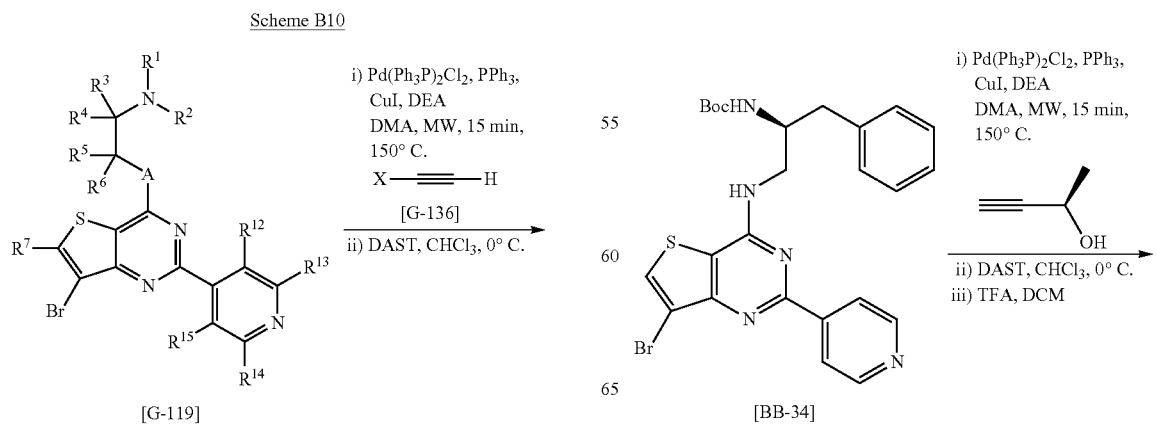

-continued

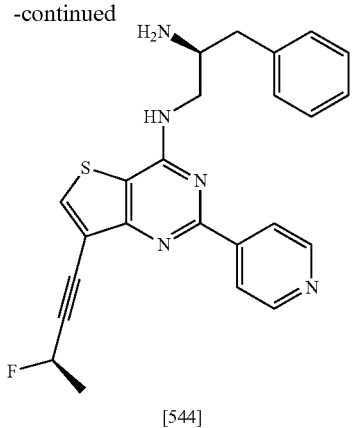

[544]

A microwave vial was charged with [(S)-1-Benzyl-2-(7-bromo-2-pyridin-4-yl-thieno[3,2-d]pyrimidin-4-ylamino)-ethyl]-carbamic acid tert-butyl ester [BB-34](100 mg, 0.185 mmol), (S)-(−)-3-Butyn-2-ol (59 μL, 0.740 mmol), Bis(triphenylphosphine)palladiumchloride (13 mg, 0.018 mmol), Copper(I)Iodide (4 mg, 0.019 mmol), triphenylphosphine (10 mg, 0.036 mmol), diethylamine (0.28 ml, 2.686 mmol) and DMF (0.8 ml). The reaction mixture was heated under microwave irradiation then the crude product isolated by liquid-liquid extraction and purified by column chromatography (0-5% MeOH:DCM) to provide the desired propargylic alcohol which was dissolved in $CHCl_3$ (2 ml) and cooled to 0° C. DAST (100 μl, 0.82 mmol) was added and the mixture stirred for 2 hours at 0° C. The reaction mixture was quenched with ice, basified with $NaHCO_3$ and the crude product extracted into DCM, then loaded onto a phase separation cartridge. The DCM solution was cooled to 0° C. and TFA added. After 2 hours the reaction mixture was loaded onto an SCX cartridge and washed with MeOH then the product eluted with 2M ammonia/methanol. The ammonia/methanol eluent was concentrated under reduced pressure and the crude product was purified by preparative HPLC (method A) to yield the title compound. LCMS method: 5, RT: 3.32 min, MI: 432 [M+1]. 1H NMR (DMSO, 300 MHz): 8.87 (1H, s, br), 8.67 (2H, d), 8.50 (1H, s), 8.28 (2H, s), 7.99 (2H, d), 7.39-7.33 (5H, m), 5.75 (1H, dq), 3.97-3.92 (1H, m), 3.54-3.45 (2H, m), 2.93-2.77 (2H, m), 1.68 (3H, dd).

The following compounds were prepared according to the general synthesis shown in scheme B10:

Synthesis of 7 (S)-3-Phenyl-N*1*-[2-pyridin-4-yl-7-(3H-[1,2,3]triazol-4-yl)-thieno[3,2-d]pyrimidin-4-yl]-propane-1,2-diamine [547] (Scheme B11)

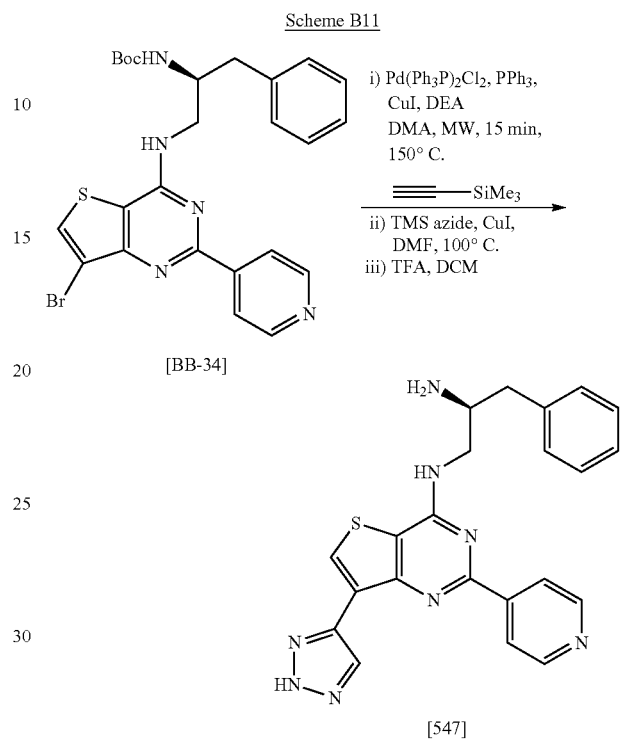

Synthesis of (S)-3-Phenyl-N*1*-[2-pyridin-4-yl-7-(3H-[1,2,3]triazol-4-yl)-thieno[3,2-d]pyrimidin-4-yl]-propane-1,2-diamine [547]

A microwave vial was charged with [(S)-1-Benzyl-2-(7-bromo-2-pyridin-4-yl-thieno[3,2-d]pyrimidin-4-ylamino)-ethyl]-carbamic acid tert-butyl ester [BB-34](60 mg, 0.114 mmol), (TMS)-acetylene (65 μL, 0.456 mmol), Bis(triphenylphosphine)palladiumchloride (9 mg, 0.012 mmol), copper (I) iodide (3 mg, 0.012 mmol), triphenylphosphine (7 mg, 0.024 mmol), diethylamine (0.2 ml) and DMF (0.8 ml). The reaction mixture was heated under microwave irradia-

| Ex | SM | Alkyne [G-136] | Characterisation |
|---|---|---|---|
| 545 | [BB-34] |  | method: 5, RT: 2.97 min, MI: 418 [M + 1] | 1H NMR (DMSO, 300 MHz): 8.68 (2H, d), 8.60 (1H, s, br), 8.53 (1H, s), 8.28 (1H, s), 8.03 (2H, d), 7.37-7.30 (5H, m), 5.52 (1H, s), 5.37 (1H, s), 3.47-3.39 (2H, m), 2.91-2.75 (2H, m) |
| 546 | [BB-34] | 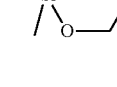 | method: 5, RT: 2.93 min, MI: 432 [M + 1] | 1H NMR (DMSO, 300 MHz): 8.68 (2H, d), 8.32 (1H, s), 8.27 (1H, s), 8.03 (2H, d), 7.37-7.30 (5H, m), 4.71 (1H, t), 4.56 (1H, t), 3.88 (1H, d, br), 3.46 (2H, m), 3.01 (1H, t), 2.93 (1H, t), 2.84-2.78 (2H, m) | tion then the crude product isolated by liquid-liquid extraction. To a stirred solution of the crude acetylene and copper (I) iodide (2 mg, 0.006 mmol) in DMF (2 ml) was added TMS azide (30 μL, 0.226 mmol) and the reaction mixture heated to 100° C. After 18 hours the reaction mixture was loaded onto an SCX cartridge and washed with MeOH then the product eluted with 2M ammonia/methanol and evaporated. The crude product was dissolved in DCM (2 ml) and TFA added (2 ml), and after 5 hours the reaction mixture again loaded onto an SCX cartridge and washed with MeOH then the product eluted with 2M ammonia/methanol. The ammonia/methanol eluent was concentrated under reduced pressure and the crude product was purified by preparative HPLC (method A) to yield the title compound. LCMS method: 5, RT: 2.80 min, MI: 429 [M+1]. 1H NMR (DMSO, 300 MHz): 8.78 (1H, s), 8.69 (2H, d), 8.53 (1H, s), 8.36 (1H, s, br), 8.10 (2H, d), 7.39-7.33 (5H, m), 3.95 (1H, m), 3.51 (2H, m), 2.95-2.93 (1H, m), 2.74 (1H, m).

General Synthesis of aryl-ethynyl-7-substituted-4PT32P Derivatives of General Formula [G-138] (Scheme B12)

The 7-Bromo-4PT32P derivative, of general formula [G-119], was involved in a Sonogashira coupling reaction utilising a protected acetylene, in the presence of copper(I) iodide with Pd(PPh₃)₂Cl₂ as catalyst, triphenylphosphine as a ligand, and a base such as Et₃N, or DEA in a polar solvent such as DMA or DMF at a high temperature either by heating thermally or using a microwave reactor. After reaction work up, typically by a liquid-liquid extraction or purification by acidic ion exchange catch-release, the protected acetylene was deprotected using a suitable source of fluoride such as TBAF, and then subjected to a second Sonogashira with the appropriate bromide, of general formula [G-137]. After reaction work up, typically by a liquid-liquid extraction, the N-Boc derivatives were deprotected under acidic conditions with a strong acid such as TFA, HCl in a solvent such as DCM, DCE or 1,4-dioxane or by catch and release sulfonic acidic resins such as polymer supported toluene sulfonic acid and the crude reaction product was purified by reverse phase preparative HPLC.

Scheme B12

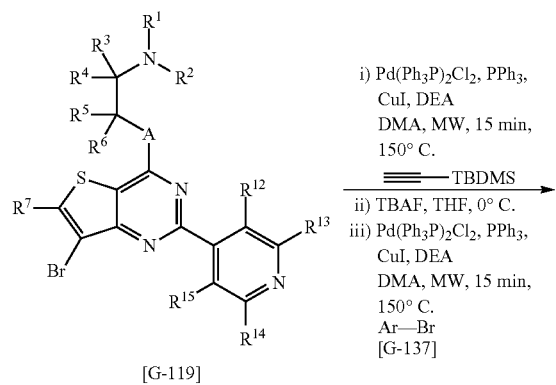

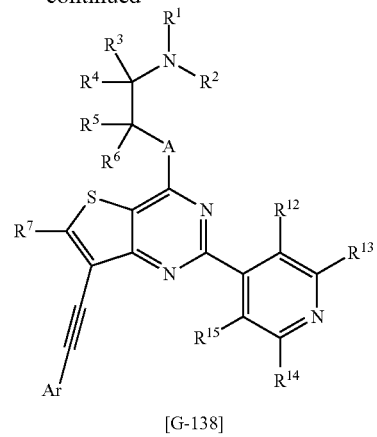

[G-138]

Synthesis of (S)-3-Phenyl-N*1*-(2-pyridin-4-yl-7-thiazol-4-ylethynyl-thieno[3,2-d]pyrimidin-4-yl)-propane-1,2-diamine [548]

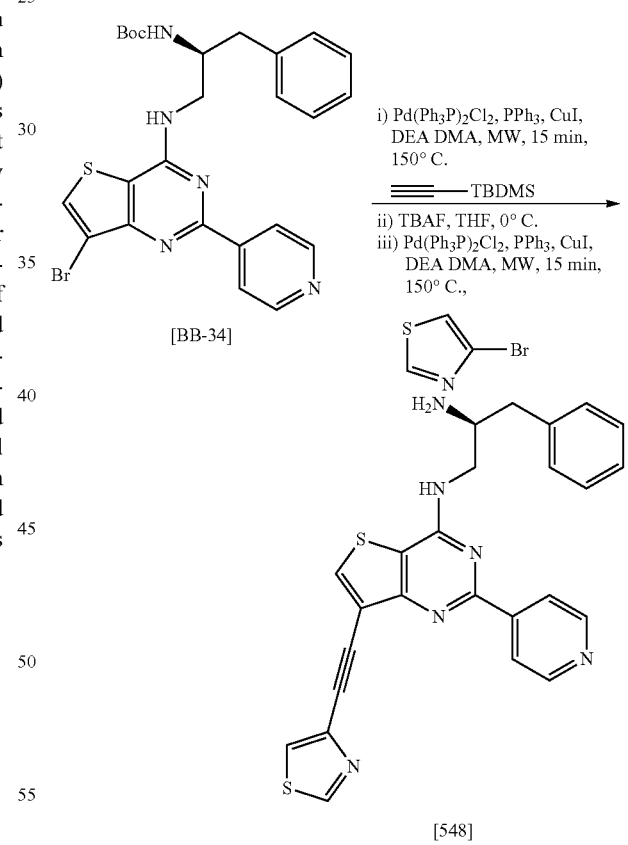

A microwave vial was charged with [(S)-1-benzyl-2-(7-bromo-2-pyridin-4-yl-thieno[3,2-d]pyrimidin-4-ylamino)-ethyl]-carbamic acid tert-butyl ester [BB-34](500 mg, 0.925 mmol), tert-butyldimethylsilylacetylene (700 μL, 3.7 mmol), bis(triphenylphosphine)palladiumchloride (65 mg, 0.093 mmol), copper (I) iodide (18 mg, 0.093 mmol), triphenylphosphine (50 mg, 0.186 mmol), diethylamine (0.2 ml) and DMF (0.8 ml). The reaction mixture was heated under microwave irradiation at 150° C. for 10 min then the crude reaction mixture was partitioned between (DCM:H$_2$O) and organic phase separated, dried (MgSO$_4$), filtered and evaporated under reduced pressure. The crude reaction product was dissolved in THF (15 ml), cooled to 0° C. and TBAF (1M in THF, 1.1 ml, 1.06 mmol) added. After 3 hours the crude reaction mixture was partitioned between (DCM:H$_2$O) and organic phase separated, dried (MgSO$_4$), filtered and evaporated under reduced pressure and used crude in the second Sonogashira coupling. To the crude reaction product (100 mg, 0.2 mmol) was added 4-bromothiazole (74 µl, 0.84 mmol), dichlorobis(triphenylphosphine)-palladium(II) (15 mg, 0.021 mmol), PPh$_3$ (11 mg, 0.042 mmol), CuI (4 mg, 0.021 mmol) and diethylamine-DMF (1:4, 1 ml) and then mixture was heated under microwave irradiation at 150° C. for 10 min. The crude reaction mixture was partitioned between (DCM:H$_2$O) and organic phase separated, dried (MgSO$_4$), filtered and evaporated under reduced pressure. The crude reaction product was dissolved in DCM (2 ml) and TFA (1 ml) was added and the mixture was stirred at room temperature for 2 hours then the reaction mixture was loaded onto an SCX cartridge and washed with MeOH then the product eluted with 2M ammonia/methanol. The ammonia/methanol eluent was concentrated under reduced pressure and the crude product was purified by preparative HPLC (method A) to yield the title compound. LCMS method: 5, RT: 3.05 min, MI: 469 [M+1]. 1H NMR (MeOD, 300 MHz) 9.08 (1H, d), 8.58 (2H, d), 8.28 (2H, d), 8.27 (1H, s), 8.00 (1H, d), 7.36-7.24 (5H, m), 3.97 (1H, dd), 3.54-3.47 (2H, m), 2.84-2.81 (2H, m).

The following compounds were prepared according to the general synthesis shown in Scheme B12:

Scheme B13

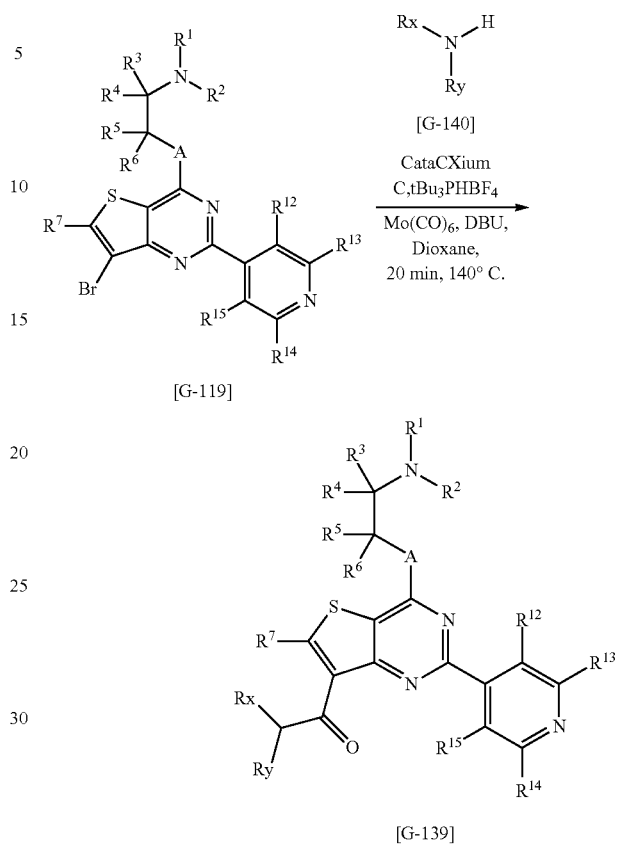

[G-119]

[G-139]

| Ex | SM | Arylhalide [G-137] | Characterisation |
|---|---|---|---|
| 539 | [BB-34] |  Br | method: 5, RT: 3.03 min, MI: 452 [M + 1]    1H NMR (MeOD, 300 MHz): 8.61 (2H, d), 8.44 (1H, s), 8.28 (1H, s), 8.23 (2H, d), 7.71 (1H, s), 7.42-7.38 (5H, m), 6.63 (1H, s), 4.15 (1H, dd), 3.96-3.89 (1H,m), 3.73 (1H, dd), 3.14-3.03 (2H, m). |

General Synthesis of 7-amido substituted-4PT32P Derivatives of General Formula [G-139] (Scheme B13)

The 7-bromo-4PT32P derivative, of general formula [G-119], was involved in a carbonylation type reaction utilising a suitable amine, of general formula [G-140], a carbonyl source such as molybdenum hexacarbonyl, a palladium catalyst such as cataCXium C, a ligand such as tri-tert-butylphosphonium tetrafluoroborate and a base such as DBU in a polar solvent such as dioxane at high temperature either by heating thermally or using a microwave reactor. After reaction work up, typically by a liquid-liquid extraction or purification by acidic ion exchange catch-release the crude reaction product was purified by reverse phase preparative HPLC Synthesis of 4-((S)-2-Amino-3-phenyl-propylamino)-2-pyridin-4-yl-thieno[3,2-d]pyrimidine-7-carboxylic acid dimethylamide [550]

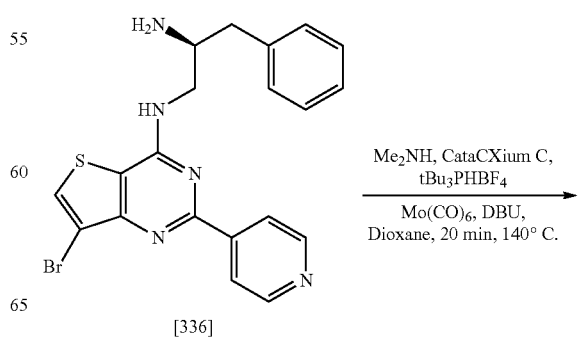

[336]

353
-continued

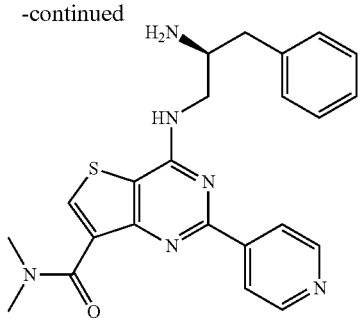

[550]

A microwave vial was charged with (S)—N*1*-(7-bromo-6-methyl-2-pyridin-4-yl-thieno [3,2-d]pyrimidin-4-yl)-3-phenyl-propane-1,2-diamine [336](50 mg, 0.114 mmol), dimethylamine (2M in THF, 570 µl, 1.14 mmol), CataCXium C (10 mg, 0.010 mmol), tri-tert-butylphosphonium tetrafluoroborate (6 mg, 0.020 mmol), DBU (51 µl, 0.342 mmol), molybdenum hexacarbonyl (30 mg, 0.114 mmol) and dioxane (0.5 ml). The reaction was heated to 140° C. for 15 minutes under microwave irradiation. The mixture was then loaded onto a SCX-2 cartridge and washed with methanol. The product was released from the cartridge using a solution of 2M ammonia/methanol. The ammonia/methanol eluent was concentrated under reduced pressure and the crude product was purified by preparative HPLC (method B) to yield the title compound. LCMS method: 5, RT: 2.28 min, MI: 433 [M+1]. 1H NMR (300 MHz, DMSO): 8.68 (2H, d), 8.26 (2H, s), 8.04 (2H, d), 7.31 (5H, m), 3.81 (1H, d, br), 3.33 (1H, m), 2.67 (3H, m), 1.29 (3H, s), 1.25 (3H, s).

The following compounds were prepared according to the general synthesis shown in Scheme B13:

| Ex | SM | Amine [G-140] | Characterisation |
|---|---|---|---|
| 551 | [336] | NH₂ (propyl) | method: 8, RT: 3.59 min, MI: 447 [M + 1] |
| 552 | [336] | H-N (diethylamine) | method: 8, RT: 2.80 min, MI: 461 [M + 1] |
| 553 | [336] | NH₂ (isopropyl) | method: 6, RT: 5.12 min, MI: 419 [M + 1] |
| 554 | [336] | NH₂ (propyl) | method: 5, RT: 3.32 min, MI: 433 [M + 1] | 8 (d, 2H), 8.77 (s, 1H). 8.72 (d, 2H), 8.2 (s, 1H), 7.33 (m, 5H), 3.91 (m, 2H), 3.48 (m, 2H), 3.42 (m, 1H), 2.88 (m, 2H), 1.27 (t, 3H) |
| 555 | [336] | NH₂ (isobutyl) | method: 5, RT: 3.64 min, MI: 447 [M + 1] | 1H NMR (300 MHz, DMSO): 8.76 (s, 1H)., 8.73 (d, 2H), 8.26 (s, 1H), 7.97 (d, 2H), 7.34 (m, 5H), 4.11 (sep, 1H), 3.91 (m, 2H), 3.48 (m, 2H), 3.42 (m, 1H), 1.32 (d, 6H) |
| 556 | [336] | NH₂ (cyclopropyl) | method: 5, RT: 3.43 min, MI: 445 [M + 1] | 1H NMR (300 MHz, DMSO): 8.72 (d, 2H), 8.29 (s, 1H), 7.89 (d, 2H), 7.33 (m, 5H), 3.90 (m, 1H), 3.47 (m, 2H), |

354
-continued

| Ex | SM | Amine [G-140] | Characterisation |
|---|---|---|---|
| | | | 2.95 (m, 2H), 2.76 (m, 1H), 0.85 (m, 2H), 0.65 (m, 2H) |
| 557 | [336] | tBu-NH₂ | method: 5, RT: 3.95 min, MI: 461 [M + 1] | 1H NMR (300 MHz, DMSO): 8.73 (s, 1H). 8.70 (d, 2H), 8.27 (s, 1H), 7.99 (d, 2H), 7.31 (m, 5H), 3.86 (m, 1H), 3.42 (m, 2H), 2.81 (m, 2H), 1.49 (s, 9H) |

Synthesis of (E)-3-[4-((S)-2-Amino-3-phenyl-propylamino)-2-pyridin-4-yl-thieno[3,2-d]pyrimidin-7-yl]-acrylic acid tert-butyl ester [558] (Scheme B14)

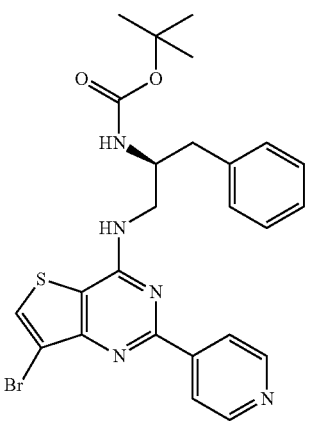

[BB-34]

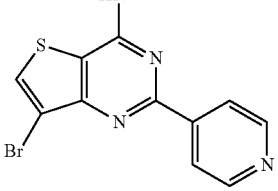

[558]

A microwave vial was charged with [(S)-1-Benzyl-2-(7-bromo-2-pyridin-4-yl-thieno[3,2-d]pyrimidin-4-ylamino)-ethyl]-carbamic acid tert-butyl ester [BB-34](50 mg, 0.091 mmol), tert-butyl acrylate (271, 0.182 mmol), palladium acetate (2 mg, 0.009 mmol), tri-tert-butylphosphonium tetrafluoroborate (3 mg, 0.010 mmol), sodium acetate (15 mg, 0.182 mmol) and DMF (1 ml). The reaction was heated to 150° C. for 30 minutes under microwave irradiation. The mixture was then loaded onto a SCX-2 cartridge and washed with methanol. The product was released from the cartridge using a solution of 2M ammonia/methanol. The ammonia/methanol eluent was concentrated under reduced pressure and the crude product was dissolved in DCM (2 ml) and TFA (1 ml) was added and the mixture was stirred at room temperature for 1 hour. After completion the mixture was loaded onto a SCX-2 cartridge and washed with methanol. The product was released from the cartridge using a solution of 2M ammonia/methanol. The ammonia/methanol eluent was concentrated under reduced pressure and the crude product was purified by preparative HPLC (method B) to yield the title compound. LCMS method: 5, RT: 2.98 min, MI: 432 [M+1]. 1H NMR (300 MHz, DMSO): 8.84 (1H, s, br), 8.65 (2H, d), 8.53 (1H, s), 7.94 (2H, d), 7.78 (1H, d, J=15 Hz), 7.34 (5H, m), 7.25 (1H, d, J=15 Hz), 3.94 (1H, d, br), 3.62 (2H, m), 3.01 (1H, dd), 2.85 (1H, m).

Synthesis of (7-Ethynyl-2-pyridin-4-yl-thieno[3,2-d]pyrimidin-4-yl)-(R)-pyrrolidin-3-yl-amine (559) (Scheme B15)

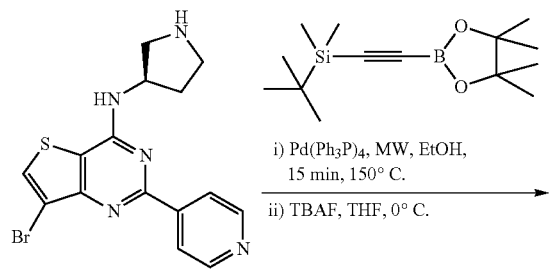

[351]

the title compound. LCMS method: 5, RT: 1.87 min, MI: 322 [M+1]. ¹H NMR (DMSO, 300 MHz): 8.59 (2H, d), 8.52 (1H, s), 8.45 (2H, d), 4.93 (1H, dd), 4.48 (1H, s), 3.68 (1H, m), 3.09 (1H, m), 2.49 (2H, m), 2.35 (1H, m), 2.16 (1H, m).

Synthesis of 4-((S)-2-Amino-3-phenyl-propylamino)-2-pyridin-4-yl-thieno[3,2-d]pyrimidine-7-carbonitrile (560) (Scheme B16)

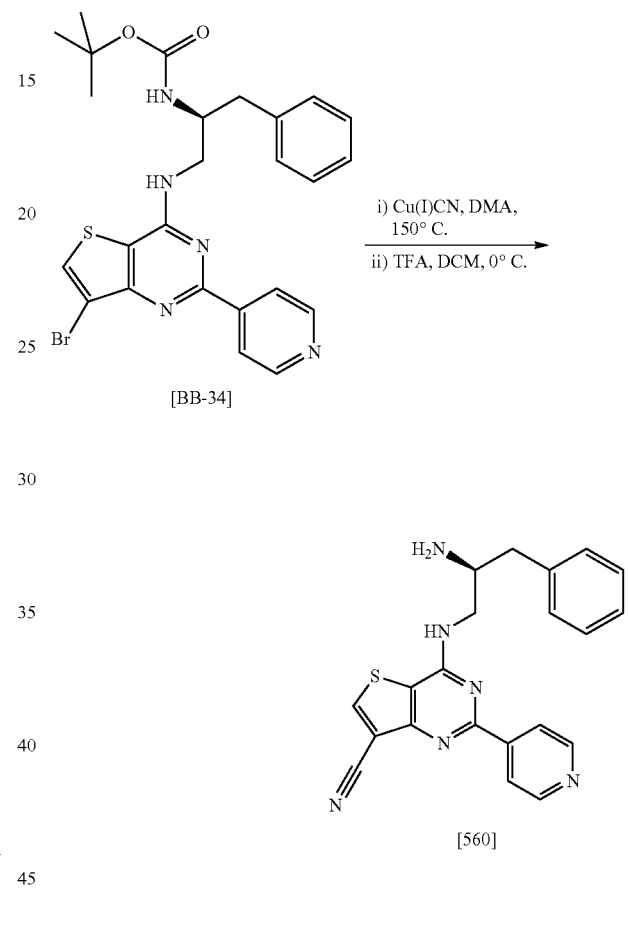

[BB-34]

[560]

A microwave vial was charged with (7-Bromo-2-pyridin-4-yl-thieno[3,2-d]pyrimidin-4-yl)-(R)-pyrrolidin-3-yl-amine [351] (70 mg, 0.186 mmol), 2-[(tert-Butyl-dimethyl-silanyl)-ethynyl]boronic acid pinacol ester (100 mg, 0.372 mmol), tetrakis (triphenyl phosphine) palladium (22 mg, 0.019 mmol), Na₂CO₃ (2M in water, 200 μl, 0.4 mmol) and EtOH (1 ml). The reaction was heated to 150° C. for 15 minutes under microwave irradiation. The mixture was then loaded onto a SCX-2 cartridge and washed with methanol. The product was released from the cartridge using a solution of 2M ammonia/methanol. The ammonia/methanol eluent was concentrated under reduced pressure and the crude product dissolved in THF (2 ml), cooled to 0° C. and TBAF (190 μl, 1M in THF, 0.372 mmol) added. After 18 hours the reaction mixture was concentrated under reduced pressure and the crude reaction mixture was partitioned between (DCM:H₂O) and organic phase separated, dried (MgSO₄), filtered and evaporated under reduced pressure and the residue purified by preparative HPLC (method B) to yield to A round bottomed flask was charged with [(S)-1-Benzyl-2-(7-bromo-2-pyridin-4-yl-thieno[3,2-d]pyrimidin-4-ylamino)-ethyl]-carbamic acid tert-butyl ester [BB-34] (50 mg, 0.093 mmol), copper cyanide (25 mg, 0.279 mmol) and DMA (2 ml). The reaction was heated to 150° C. for 18 hours. The crude reaction mixture was partitioned between (DCM:H₂O) and organic phase separated, dried (MgSO₄), filtered and evaporated under reduced pressure to a volume of 2 ml. The mixture was cooled to 0° C. and TFA (2 ml) was added. After 18 hours the solution was loaded onto a SCX-2 cartridge and washed with methanol. The product was released from the cartridge using a solution of 2M ammonia/methanol. The ammonia/methanol eluent was concentrated under reduced pressure and the crude product was purified by preparative HPLC (method B) to yield to the title compound. LCMS method: 5, RT: 2.75 min, MI: 387 [M+1].

Synthesis of (S)-3-Phenyl-N*1*-(7-pyrazol-1-yl-2-pyridin-4-yl-thieno [3,2-d]pyrimidin-4-yl)-propane-1,2-diamine (561) (Scheme B17)

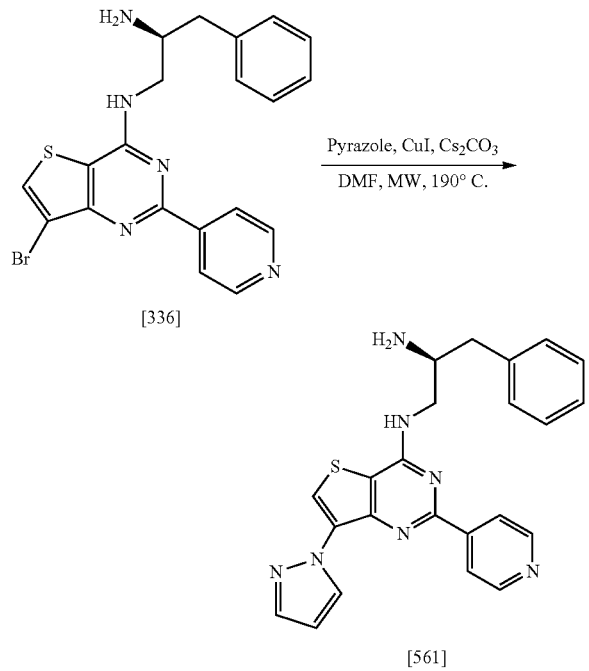

A microwave vial was charged with (S)—N*1*-(7-Bromo-2-pyridin-4-yl-thieno[3,2-d]pyrimidin-4-yl)-3-phenyl-propane-1,2-diamine [336] (50 mg, 0.111 mmol), pyrazole (12 mg, 0.555 mmol), copper iodide (5 mg, 0.022 mmol), caesium carbonate (73 mg, 0.222 mmol) and DMF (1 ml). The reaction was heated to 190° C. under microwave irradiation for 5 minutes. The solution was then loaded onto a SCX-2 cartridge and washed with methanol. The product was released from the cartridge using a solution of 2M ammonia/methanol. The ammonia/methanol eluent was concentrated under reduced pressure and the crude product was purified by preparative HPLC (method B) to yield to the title compound. LCMS method: 5, RT: 3.11 min, MI: 428 [M+1]. 1H NMR (DMSO) 8.71 (1H, d), 8.65 (2H, d), 7.95 (2H, d), 7.84 (1H, s), 7.76 (1H, s), 7.38 (5H, m), 6.68 (1H, t), 3.94 (1H, m), 3.57 (2H, m), 2.97 (1H, dd), 2.84 (1H, m).

Synthesis of (S)-3-Phenyl-N*1*-(2-pyridin-4-yl-7-[1,2,3]triazol-1-yl-thieno[3,2-d]pyrimidin-4-yl)-propane-1,2-diamine (562) (Scheme B18)

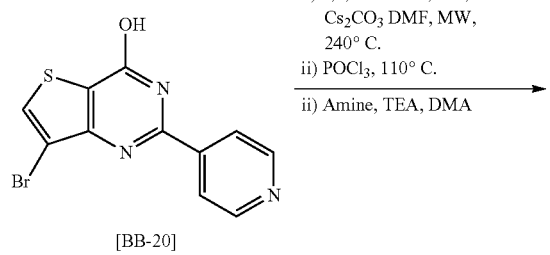

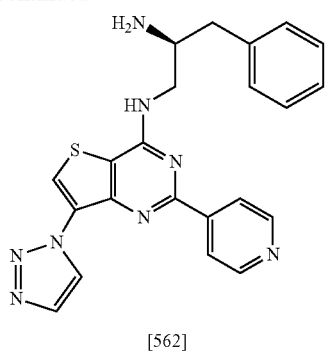

A microwave vial was charged with 7-bromo-2-pyridin-4-yl-thieno[3,2-d]pyrimidin-4-ol [BB-20] (0.13 g, 0.42 mmol), 1,2,3-triazole (56 mg, 0.811 mmol), copper iodide (6 mg, 0.033 mmol), caesium carbonate (106 mg, 0.324 mmol) and DMF (1 ml). The reaction was heated to 240° C. under microwave irradiation for 2 hours. The solution was then loaded onto a SCX-2 cartridge and washed with methanol. The product was released from the cartridge using a solution of 2M ammonia/methanol. The ammonia/methanol eluent was concentrated under reduced pressure and the crude product suspended in POCl₃ and heated to reflux. After 1 hour the reaction mixture was cooled, concentrated and azeotroped with toluene twice. The residue was basified with a 2M solution of NaOH and the product extracted into DCM (×2). The combined organics were dried (MgSO₄), filtered and evaporated under reduced pressure. The crude product was dissolved in DMA (2 ml) and triethylamine (174 μl, 1.257 mmol) and (S)-3-Phenyl-propane-1,2-diamine (75 mg, 0.503 mmol) was added. After 18 hours the solution was loaded onto a SCX-2 cartridge and washed with methanol. The product was released from the cartridge using a solution of 2M ammonia/methanol. The ammonia/methanol eluent was concentrated under reduced pressure and the crude product purified by preparative HPLC (method B) to yield to the title compound. LCMS method: 17, RT: 2.91 min, MI: 429 [M+1]. ¹H NMR (300 MHz, DMSO) 9.23 (1H, s), 8.70 (2H, d), 8.69 (1H, s), 8.07 (2H, d), 8.04 (1H, s), 7.33 (5H, m), 3.92 (1H, m), 3.45 (2H, m), 2.82 (2H, m).

Synthesis of (S)—N*1*-[7-(2-Cyclopropyl-ethyl)-2-pyridin-4-yl-thieno[3,2-d]pyrimidin-4-yl]-3-phenyl-propane-1,2-diamine (563) (Scheme B19)

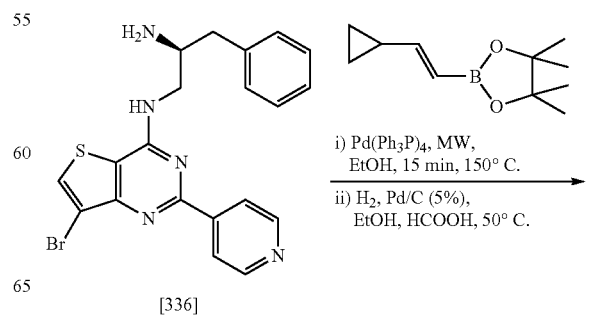

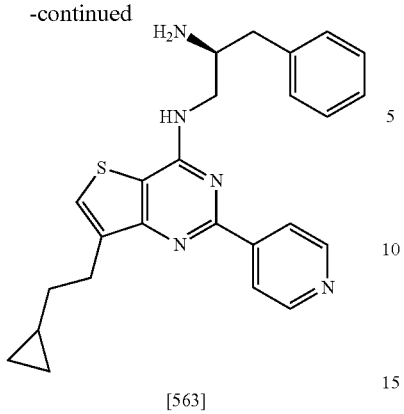

[563]

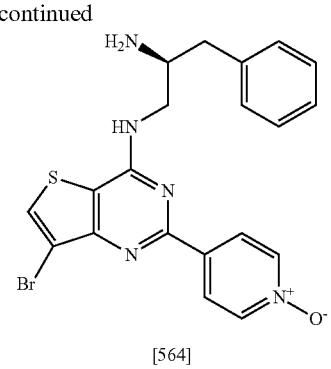

[564]

A microwave vial was charged with (S)—N*1*-(7-Bromo-2-pyridin-4-yl-thieno[3,2-d]pyrimidin-4-yl)-3-phenyl-propane-1,2-diamine [336] (50 mg, 0.114 mmol), trans-2-cyclopropylvinylboronic acid pinacol ester (44 mg, 0.228 mmol), tetrakis (triphenyl phosphine) palladium (13 mg, 0.011 mmol), Na$_2$CO$_3$ (2M in water, 200 µl, 0.4 mmol) and EtOH (1 ml). The reaction was heated to 150° C. for 15 minutes under microwave irradiation. The mixture was then loaded onto a SCX-2 cartridge and washed with methanol. The product was released from the cartridge using a solution of 2M ammonia/methanol. The ammonia/methanol eluent was concentrated under reduced pressure and the crude product taken up in EtOH, Pd/C (5%, 10 mg) added followed by a few drops of formic acid and the reaction mixture stirred under an atmosphere of hydrogen at 50° C. for 18 hours. The suspension was filtered through celite, concentrated under reduced pressure and purified by preparative HPLC (method B) to yield to the title compound. LCMS method: 5, RT: 4.23 min, MI: 430 [M+1]. $^1$H NMR (DMSO, 300 MHz) 8.66 (2H, d), 8.41 (1H, s), 8.34 (1H, s), 8.02 (2H, s), 7.79 (1H, d), 7.35 (5H, m), 3.92 (1H, m), 3.49 (2H, m), 2.91 (4H, m), 1.63 (2H, m), 0.76 (1H, m), 0.40 (2H, m), 0.06 (2H, m).

To a stirred suspension of [(S)-1-benzyl-2-(7-bromo-2-pyridin-4-yl-thieno[3,2-d]pyrimidin-4-ylamino)-ethyl]-carbamic acid tert-butyl ester [BB-34](100 mg, 0.185 mmol), in DCM (2 ml) at 0° C. was added mCPBA (35 mg, 0.204 mmol). After 18 hours the reaction diluted with DCM (10 ml) and the mixture washed with saturated solution of Na$_2$SO$_3$ (2×10 ml) then H$_2$O (10 ml) and finally brine (10 ml), dried (MgSO$_4$), filtered and evaporated under reduced pressure and the crude product was purified by column chromatography (0-5% MeOH:DCM) to provide the desired reaction intermediate. This was taken up in 4N HCl in dioxane (2 ml) and stirred at room temperature for 2 hours. The crude reaction mixture was loaded onto a SCX-2 cartridge and washed with methanol. The product was released from the cartridge using a solution of 2M ammonia/methanol. The ammonia/methanol eluent was concentrated under reduced pressure and the crude product was purified by preparative HPLC (method B) to yield to the title compound. LCMS method: 5, RT: 2.81 min, MI: 456-458 [M+1]. H NMR (MeOD, 300 MHz) 8.53 (1H, s), 8.31 (q, 4H), 8.10 (1H, s), 7.38-7.31 (5H, m), 4.06-4.03 (1H, m), 3.64-3.60 (1H, m), 3.31-3.29 (1H, m), 2.93 (2H, m).

Synthesis of (S)—N*1*-[7-Bromo-2-(1-oxy-pyridin-4-yl)-thieno[3,2-d]pyrimidin-4-yl]-3-phenyl-propane-1,2-diamine (564) (Scheme B20)

Synthesis of (S)—N*1*-[2-(1-Oxy-pyridin-4-yl)-7-(2H-pyrazol-3-yl)-thieno[3,2-d]pyrimidin-4-yl]-3-phenyl-propane-1,2-diamine (565) (Scheme B21)

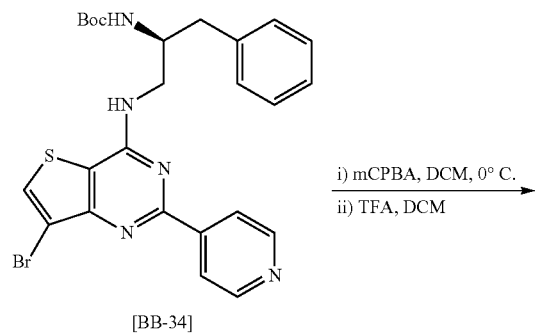

[BB-34]

i) mCPBA, DCM, 0° C.
ii) TFA, DCM

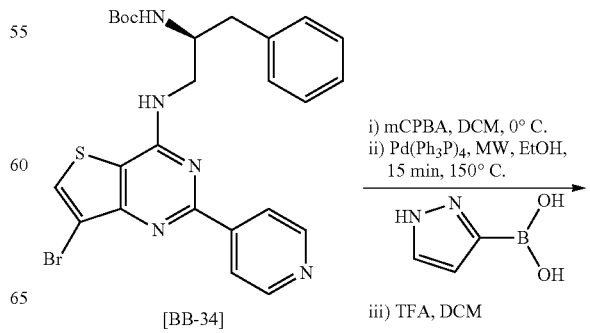

[BB-34]

i) mCPBA, DCM, 0° C.
ii) Pd(Ph$_3$P)$_4$, MW, EtOH, 15 min, 150° C.

iii) TFA, DCM

-continued

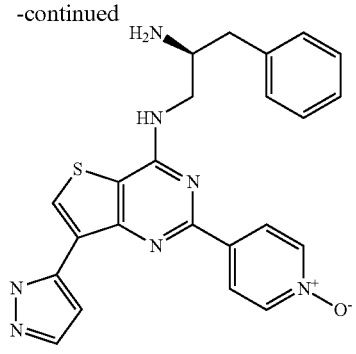

[565]

To a stirred suspension of [(S)-1-benzyl-2-(7-bromo-2-pyridin-4-yl-thieno[3,2-d]pyrimidin-4-ylamino)-ethyl]-carbamic acid tert-butyl ester [BB-34](200 mg, 0.37 mmol), in DCM (2 ml) at 0° C. was added mCPBA (70 mg, 0.408 mmol). After 18 hours the reaction was diluted with DCM (10 ml) and the mixture washed with saturated solution of $Na_2SO_3$ (2×10 ml) then $H_2O$ (10 ml) and finally brine (10 ml), dried ($MgSO_4$), filtered and evaporated under reduced pressure. To the crude reaction product was added 1H-Pyrazole-5-boronic acid (50 mg, 0.444 mmol), $Pd(PPh_3)_4$ (43 mg, 0.037 mmol), $Na_2CO_3$ (2M in water, 200 μl, 0.4 mmol) and EtOH (2 ml) and the mixture was heated to 150° C. for 15 minutes under microwave irradiation. The mixture was then loaded onto a SCX-2 cartridge and washed with methanol. The product was released from the cartridge using a solution of 2M ammonia/methanol. The ammonia/methanol eluent was concentrated under reduced pressure. This was suspended in 4N HCl:dioxine (2 ml) and stirred at room temperature for 18 hours. The reaction mixture was evaporated under reduced pressure and the residue dissolved in MeOH, loaded onto a SCX-2 cartridge and washed with methanol. The product was released from the cartridge using a solution of 2M ammonia/methanol. The ammonia/methanol eluent was concentrated under reduced pressure and the crude product was purified by preparative HPLC (method B) to yield to the title compound. LCMS method: 5, RT: 3.08 min, MI: 444 [M+1]. $^1$H NMR (DMSO, 300 MHz) 8.38 (1H, s, br), 8.23 (2H, d), 8.07 (2H, d), 7.83 (1H, s), 7.35-7.29 (6H, m), 3.87 (1H, m), 3.48-3.45 (2H, m), 2.90-2.83 (2H, m).

General Synthesis of 7-amino-substituted 4PT32P derivatives of General Formula [G-143] (Scheme B22)

2-Pyridin-4-yl-thieno[3,2-d]pyrimidin-4-ol, of general formula [G-141], was involved in a chlorination reaction using phosphorus oxychloride, then nitrated at the 7-position using a combination of fuming nitric acid and concentrated sulphuric acid, to give compounds of general formula [G-142]. The nitro group was subsequently reduced under a dissolving metal reduction using iron and hydrochloric acid, and finally reacted with an N-Boc protected primary or secondary amine derivative, of general formula [G-117], in a polar aprotic solvent such as DMA, DMF, NMP in the presence of a tertiary amine base such as $Et_3N$, DIPEA or NMM at ambient temperature. After reaction work up, typically by a liquid-liquid extraction, the N-Boc derivatives were deprotected under acidic conditions with a strong acid such as TFA, HCl in a solvent such as DCM, DCE or 1,4-dioxane or by catch and release sulfonic acidic resins such as polymer supported toluene sulfonic acid and the crude reaction product was purified by reverse phase preparative HPLC.

Scheme B22

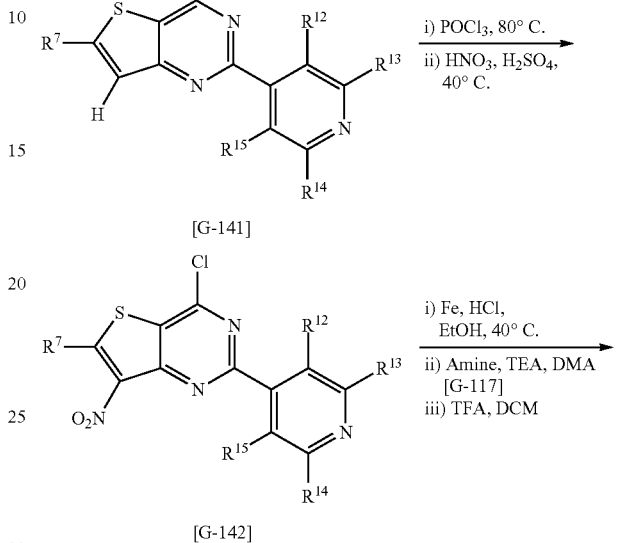

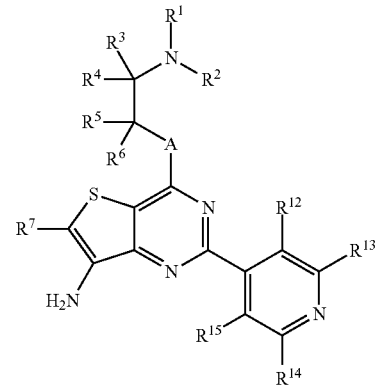

Synthesis of 4-Chloro-7-nitro-2-pyridin-4-yl-thieno [3,2-d]pyrimidine [BB-44]

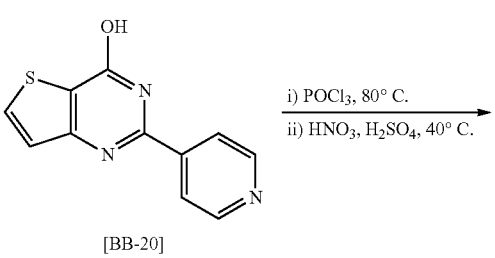

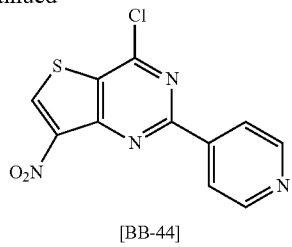

[BB-44]

2-Pyridin-4-yl-thieno[3,2-d]pyrimidin-4-ol [BB-20] (5 g, 21.8 mmol) was heated to 80° C. in phosphorus oxychloride (50 ml) for 30 minutes. The reaction mixture was allowed to cool to room temperature then evaporated under reduced pressure and the crude product was zeotroped with toluene. The residue was trituration with a mixture of diethyl ether and 2N NaOH and the solid formed was was collected by filtration and washed with water followed by ether to yield the title compound as a beige solid which was used in the next step without further purification: LCMS method: 17, RT: 4.91 min, MI: 248 [M+1].

To a solution of 4-Chloro-2-pyridin-4-yl-thieno[3,2-d]pyrimidine (4 g, 15.9 mmol) in sulphuric acid (10 ml) was added nitric acid (1 ml) and the reaction mixture heated to 40° C. After 2 hours the solution was cooled to 0° C. then added to vigorously stirred ice-water, and the resulting precipitate was collected by filtration and washed with water to yield the title compound as a yellow solid which was used in the next step without further purification: LCMS method: 5, RT: 4.54 min, MI: 293 [M+1]. 1H NMR (DMSO, 300 MHz) 9.83 (1H, s), 9.01 (2H, d), 8.65 (2H, d).

Synthesis of N*4*-((S)-2-Amino-3-phenyl-propyl)-2-pyridin-4-yl-thieno[3,2-d]pyrimidine-4,7-diamine [566]

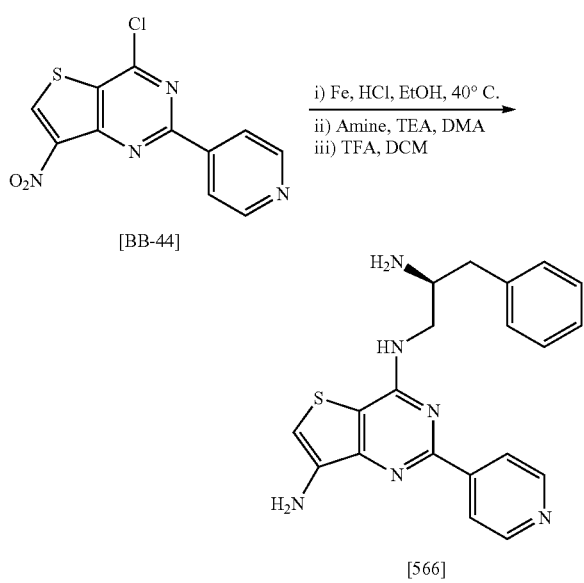

To a stirred suspension of 4-chloro-7-nitro-2-pyridin-4-yl-thieno[3,2-d]pyrimidine [BB-44] (1 g, 3.42 mmol) and iron powder (770 mg, 13.7 mmol) in EtOH (20 ml) at 40° C. was added concentrated HCl (20 ml) dropwise. After 20 minutes the reaction mixture was loaded onto a SCX-2 cartridge and washed with methanol. The product was released from the cartridge using a solution of 2M ammonia/methanol. The ammonia/methanol eluent was concentrated under reduced pressure to give a brown solid. LCMS method: 18, RT: 3.38 min, MI: 263 [M+1].

To a solution of 4-Chloro-7-amino-2-pyridin-4-yl-thieno[3,2-d]pyrimidine (130 mg, 0.476 mmol) in DMA (1 ml) was added ((S)-2-Amino-1-benzyl-ethyl)-carbamic acid tert-butyl ester (143 mg, 0.571 mmol) followed by triethylamine (200 μl, 1.43 mmol), and the mixture stirred at room temperature for 18 hours. The crude reaction mixture was partitioned between (DCM:H₂O) and organic phase separated, dried (MgSO₄), filtered and evaporated under reduced pressure and the crude product was loaded onto a phase separation cartridge and washed with methanol. The product was released from the cartridge using a solution of 2M ammonia/methanol. The ammonia/methanol eluent was concentrated under reduced pressure to give a brown solid. The crude reaction product was dissolved in DCM (2 ml) and TFA (2 ml) was added and the mixture was stirred at room temperature for 1 hour then the mixture was loaded onto a SCX-2 cartridge and washed with methanol. The product was released from the cartridge using a solution of 2M ammonia/methanol. The ammonia/methanol eluent was concentrated under reduced pressure and the crude product was purified by preparative HPLC (method A) to yield the title compound. LCMS method: 6, RT: 4.62 min, MI: 377 [M+1]. ¹H NMR (DMSO) 8.67 (2H, d), 8.16 (2H, d), 7.92 (1H, s), 7.28 (5H, m), 6.49 (1H, s), 5.29 (2H, s, br), 3.79 (1H, m), 3.28 (2H, m), 2.69 (2H, m).

The following compounds were prepared according to the general synthesis shown in Scheme B22:

| Example | SM | Amine [G-117] | Characterisation |
|---|---|---|---|
| 567 | [BB-44] | (R) A—NH— (pyrrolidine) | method: 6, RT: 3.90 min, MI: 313 [M + 1] |

General Synthesis of 7-heteroaryl-substituted 4PT32P Derivatives of General Formula [G-145] (Scheme B23)

The 7-bromo-substituted 4PT32P derivative, of general formula [G-119], was involved in a Heck type reaction utilising a suitable olefin, of general formula [G-146], a palladium catalyst such as palladium acetate, a ligand such as tri-t-butyl phosphonium tetrafluoroborate and a base such as sodium acetate in a polar solvent such as DMF at high temperature either by heating thermally or using a microwave reactor. The generated olefin derivative, of general formula [G-144], was then cyclised using either para-toluenesulfonylhydrazide or N-hydroxyl-4-toluenesulfonamide to provide either the corresponding pyrazole or isoxazole respectively. After reaction work up, typically by a liquid-liquid extraction, the N-Boc derivatives were deprotected under acidic conditions with a strong acid such as TFA, HCl in a solvent such as DCM, DCE or 1,4-dioxane or by catch and release sulfonic acidic resins such as polymer supported toluene sulfonic acid and the crude reaction product was purified by reverse phase preparative HPLC Scheme B23

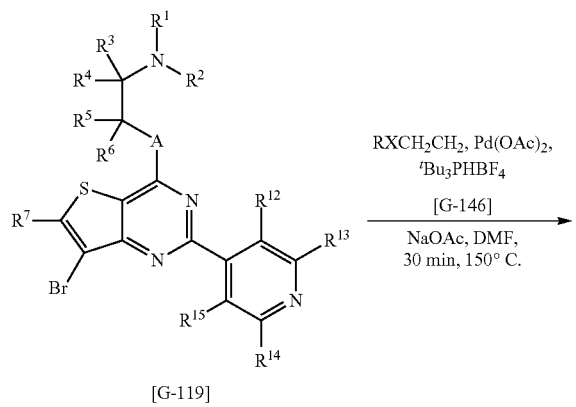

[G-119]

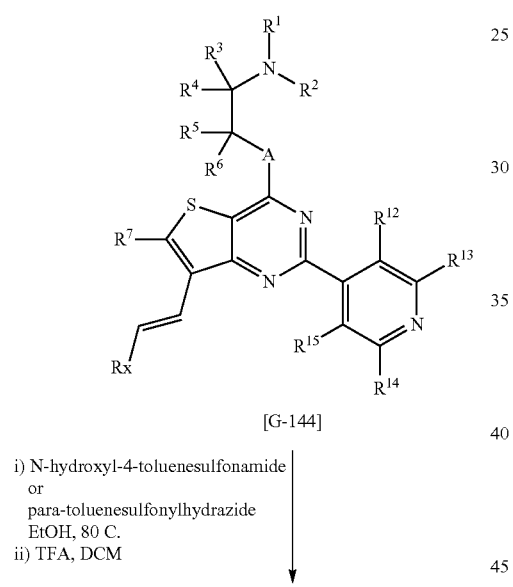

[G-144]

i) N-hydroxyl-4-toluenesulfonamide or para-toluenesulfonylhydrazide EtOH, 80 C.
ii) TFA, DCM

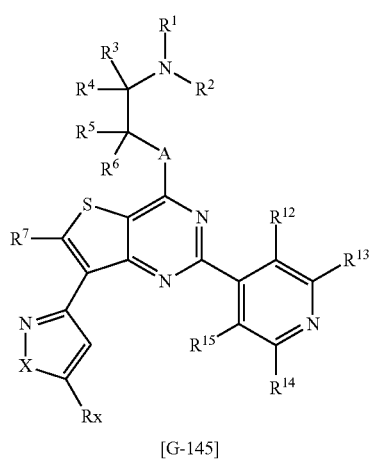

[G-145]

Synthesis of (E)-3-[4-((S)-2-Amino-3-phenyl-propylamino)-2-pyridin-4-yl-thieno[3,2-d]pyrimidin-7-yl]-acrylic acid tert-butyl ester [BB-45]

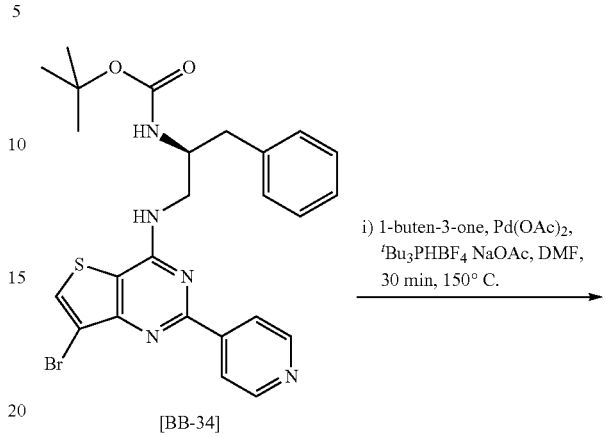

[BB-34]

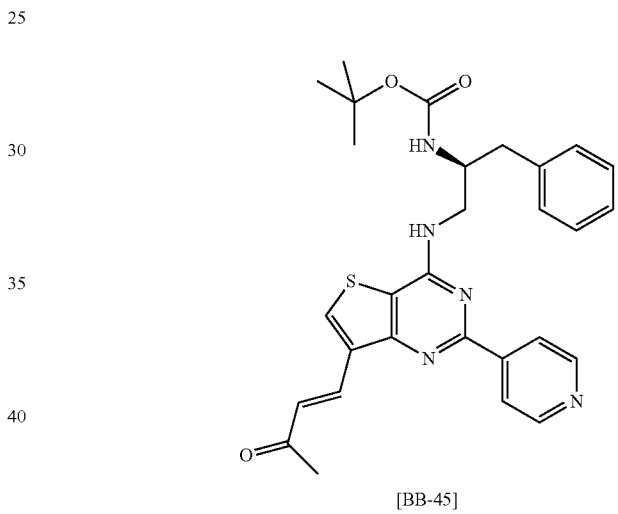

[BB-45]

A microwave vial was charged with [(S)-1-Benzyl-2-(7-bromo-2-pyridin-4-yl-thieno[3,2-d]pyrimidin-4-ylamino)-ethyl]-carbamic acid tert-butyl ester [BB-34](50 mg, 0.091 mmol), tert-butyl acrylate (27 μl, 0.182 mmol), palladium acetate (2 mg, 0.009 mmol), tri-tert-butylphosphonium tetrafluoroborate (3 mg, 0.010 mmol), sodium acetate (15 mg, 0.182 mmol) and DMF (1 ml). The reaction was heated to 150° C. for 30 minutes under microwave irradiation. The mixture was then loaded onto a SCX-2 cartridge and washed with methanol. The product was released from the cartridge using a solution of 2M ammonia/methanol. The ammonia/methanol eluent was concentrated under reduced pressure and the crude product was purified by preparative HPLC (method B) to yield the title compound. LCMS method: 5, RT: 2.98 min, MI: 432 [M+1]. $^1$H NMR (300 MHz, DMSO): 8.84 (1H, s, br), 8.65 (2H, d), 8.53 (1H, s), 7.94 (2H, d), 7.78 (1H, d, J=15 Hz), 7.34 (5H, m), 7.25 (1H, d, J=15 Hz), 3.94 (1H, d, br), 3.62 (2H, m), 3.01 (1H, dd), 2.85 (1H, m).

Synthesis of (S)—N*1*-[7-(5-Methyl-isoxazol-3-yl)-2-pyridin-4-yl-thieno[3,2-d]pyrimidin-4-yl]-3-phenyl-propane-1,2-diamine [568]

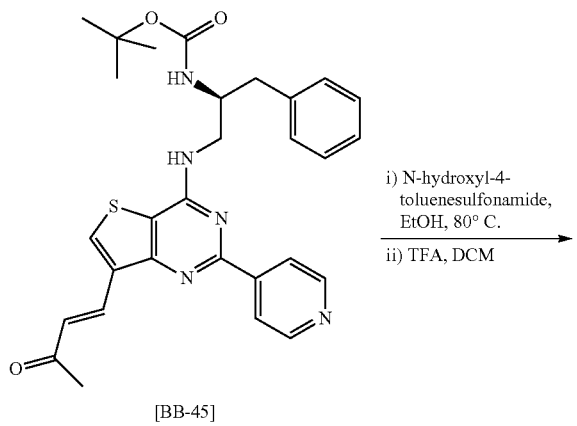

[BB-45]

i) N-hydroxyl-4-toluenesulfonamide, EtOH, 80° C.
ii) TFA, DCM

N-hydroxyl-4-toluenesulfonamide (128 mg, 0.74 mmol) was added to a stirred suspension of (E)-3-[4-((S)-2-Amino-3-phenyl-propylamino)-2-pyridin-4-yl-thieno[3,2-d]pyrimidin-7-yl]-acrylic acid tert-butyl ester [BB-45] (90 mg, 0.166 mmol) in ethanol (2 ml) and the reaction mixture heated to 90° C. After 2 hours the mixture was loaded onto a SCX-2 cartridge and washed with methanol. The product was released from the cartridge using a solution of 2M ammonia/methanol. The ammonia/methanol eluent was concentrated under reduced pressure and the crude product was dissolved in DCM (2 ml) and TFA (2 ml) was added and the mixture stirred at room temperature for 1 hour. After completion the mixture was loaded onto a SCX-2 cartridge and washed with methanol. The product was released from the cartridge using a solution of 2M ammonia/methanol. The ammonia/methanol eluent was concentrated under reduced pressure and the crude product was purified by preparative HPLC (method B) to yield the title compound. LCMS method: 5, RT: 3.36 min, MI: 443 [M+1]. $^1$H NMR (300 MHz, DMSO): 8.70 (2H, d), 8.66 (1H, s), 8.50 (1H, s, br), 8.11 (2H, d), 7.33 (5H, m), 7.24 (1H, s), 3.89 (1H, m), 3.39 (2H, m), 2.77 (2H, m), 2.55 (3H, s).

The following compounds were prepared according to the general synthesis shown in Scheme B23:

| Ex | SM | Olefin [G-146] | Reactant | Characterisation | |
|---|---|---|---|---|---|
| 569 | [BB-34] | | para-toluenesulfonylhydrazide | method: 5, RT: 3.33 min, MI: 442 [M + 1] | |
| 570 | [BB-34] | | N-hydroxyl-4-toluenesulfonamide | method: 5, RT: 3.65 min, MI: 457 [M + 1] | |
| 571 | [BB-34] | | para-toluenesulfonylhydrazide | method: 6, RT: 6.00 min, MI: 456 [M + 1] | 1H NMR (300 MHz, DMSO): 8.71 (2H, d), 8.35 (1H, s), 8.26 (1H, s, br), 8.11 (2H, d), 7.38-7.29 (5H, m), 7.09 (1H, s), 3.89 (1H, m), 2.82 (2H, m), 2.69 (2H, q), 1.27 (3H, t). |
| 572 | [BB-34] | H-C(=O)-C=C | N-hydroxyl-4-toluenesulfonamide | method: 5, RT: 3.02 min, MI: 429 [M + 1] | |

-continued

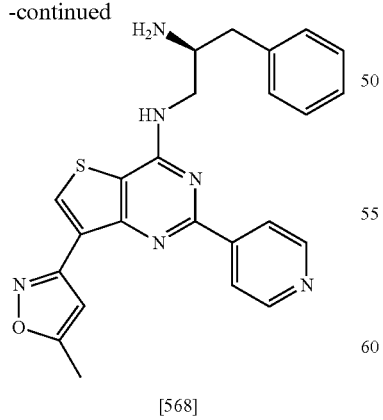

[568]

General Synthesis of 2-Amino-pyridyl-substituted-4PT32P Derivatives of General Formula [G-148], [G-149], [G-150] & [G-151] (Scheme B24)

The 2-chloropyridyl 4PT32P derivative of general formula [G-147] was involved in a Buchwald type reaction utilising a suitable amine, of general formula [G-133], a palladium catalyst such as Pd(dba)$_2$ or Pd(OAc)$_2$, a ligand such as Xantphos and a base such as NaOtBu or Cs$_2$CO$_3$ in a polar solvent such as dioxane or a combination of dioxane and DMA at high temperature either by heating thermally or using a microwave reactor, to yield aminopyridyl 4PT32P derivative of general formula [G-148], method A. After reaction work up, typically by a liquid-liquid extraction or purification by acidic ion exchange catch-release, the intermediate was purified by column chromatography and the N-Boc derivatives were deprotected under acidic conditions with a strong acid such as TFA, HCl in a solvent such as DCM, DCE or 1,4-dioxane or by catch and release sulfonic acidic resins such as polymer supported toluene sulfonic acid and the crude reaction product was purified by reverse phase preparative HPLC. The 2-chloropyridyl 4PT32P derivative of general formula [G-147] was involved in a Buchwald type reaction utilising a suitable amide, of general formula [G-152], a palladium catalyst such as Pd(dba)$_2$ or Pd(OAc)$_2$, a ligand such as Xantphos and a base such as NaOtBu or Cs$_2$CO$_3$ in a polar solvent such as dioxane or a combination of dioxane and DMA at high temperature either by heating thermally or using a microwave reactor, to yield aminopyridyl 4PT32P derivative of general formula [G-149], method B. After reaction work up, typically by a liquid-liquid extraction or purification by acidic ion exchange catch-release, the intermediate was purified by column chromatography and the N-Boc derivatives were deprotected under acidic conditions with a strong acid such as TFA, HCl in a solvent such as DCM, DCE or 1,4-dioxane or by catch and release sulfonic acidic resins such as polymer supported toluene sulfonic acid and the crude reaction product was purified by reverse phase preparative HPLC. The 2-chloropyridyl 4PT32P derivative of general formula [G-147] was involved in a Buchwald type reaction utilising a suitable urea, of general formula [G-153], a palladium catalyst such as Pd(dba)$_2$ or Pd(OAc)$_2$, a ligand such as 2-Dicyclohexylphosphino-2'-(N,N-dimethylamino)biphenyl and a base such as NaOtBu or Cs$_2$CO$_3$ in a polar solvent such as dioxane or a combination of dioxane and DMA at high temperature either by heating thermally or using a microwave reactor, to yield aminopyridyl 4PT32P derivative of general formula [G-150], method C. After reaction work up, typically by a liquid-liquid extraction or purification by acidic ion exchange catch-release, the intermediate was purified by column chromatography and the N-Boc derivatives were deprotected under acidic conditions with a strong acid such as TFA, HCl in a solvent such as DCM, DCE or 1,4-dioxane or by catch and release sulfonic acidic resins such as polymer supported toluene sulfonic acid and the crude reaction product was purified by reverse phase preparative HPLC. The 2-chloropyridyl 4PT32P derivative of general formula [G-147] was involved in a Buchwald type reaction utilising a suitable sulfonamide, of general formula [G-154], a palladium catalyst such as Pd(dba)$_2$ or Pd(OAc)$_2$, a ligand such as 2-Dicyclohexylphosphino-2'-(N,N-dimethylamino)biphenyl and a base such as NaOtBu or Cs$_2$CO$_3$ in a polar solvent such as dioxane or a combination of dioxane and DMA at high temperature either by heating thermally or using a microwave reactor, to yield aminopyridyl 4PT32P derivative of general formula [G-151], method D. After reaction work up, typically by a liquid-liquid extraction or purification by acidic ion exchange catch-release, the intermediate was purified by column chromatography and the N-Boc derivatives were deprotected under acidic conditions with a strong acid such as TFA, HCl in a solvent such as DCM, DCE or 1,4-dioxane or by catch and release sulfonic acidic resins such as polymer supported toluene sulfonic acid and the crude reaction product was purified by reverse phase preparative HPLC.

Scheme B24

Method A

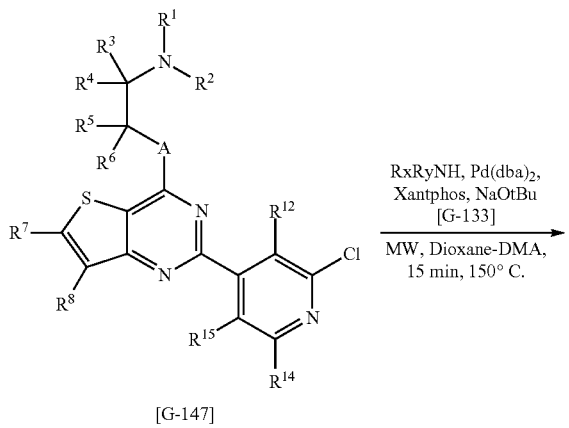

[G-147]

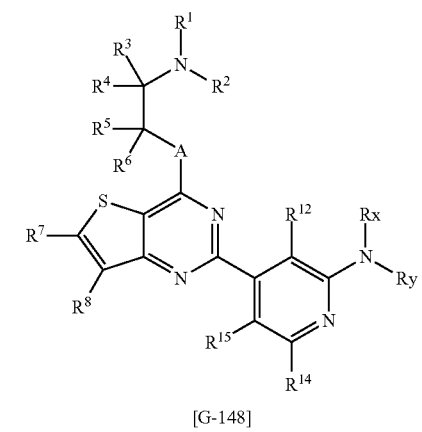

[G-148]

Method B

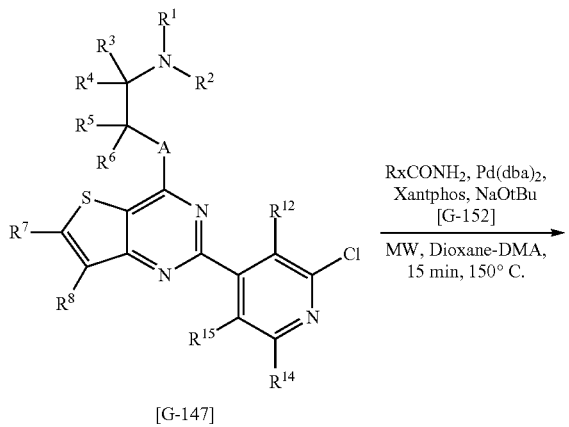

[G-147]

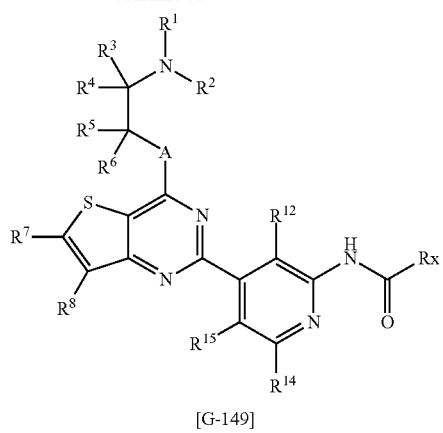
[G-149]
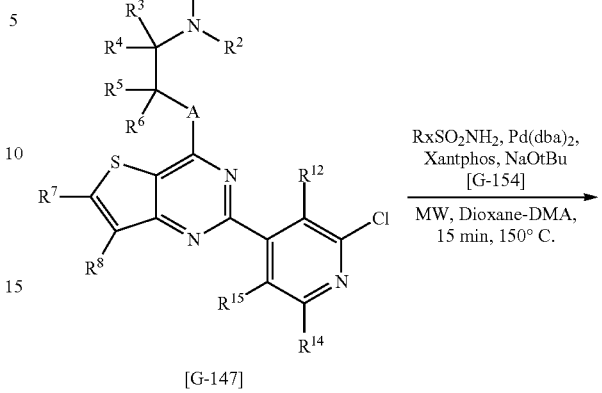
[G-147]
Method C
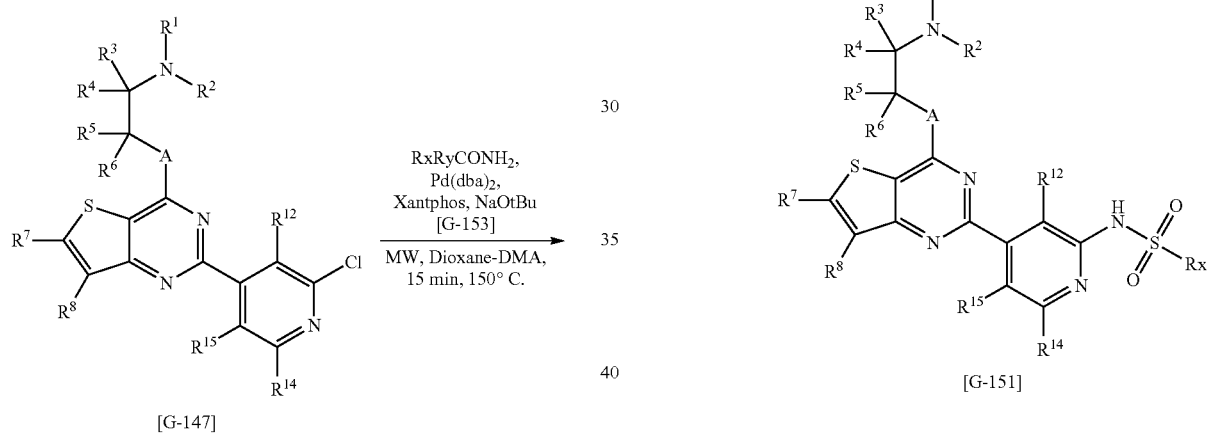
[G-147]
[G-151]
Method D
Method A
Synthesis of [2-(2-Phenylamino-pyridin-4-yl)-thieno[3,2-d]pyrimidin-4-yl]-(R)-pyrrolidin-3-yl-amine [573]
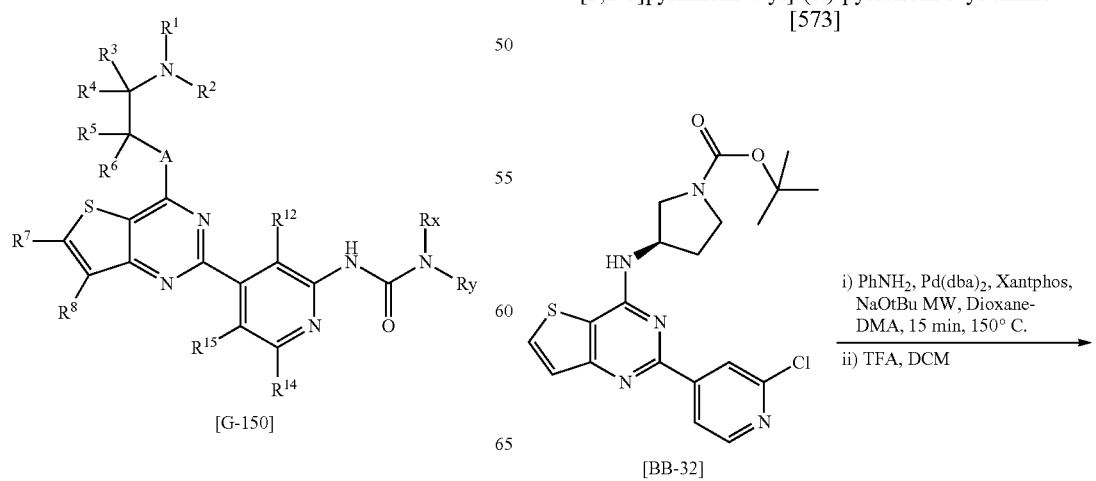
[BB-32]
i) PhNH₂, Pd(dba)₂, Xantphos, NaOtBu MW, Dioxane-DMA, 15 min, 150° C.
ii) TFA, DCM
[G-150]

373

-continued

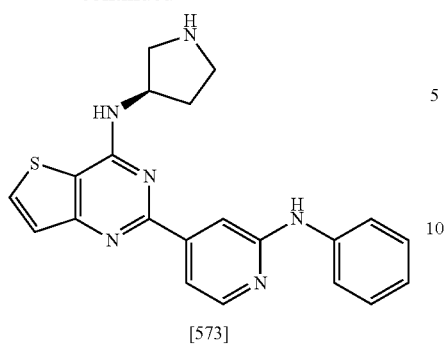

[573]

A microwave vial was charged with (R)-3-[2-(2-Chloro-pyridin-4-yl)-thieno[3,2-d]pyrimidin-4-ylamino]-pyrrolidine-1-carboxylic acid tert-butyl ester [BB-32] (50 mg, 0.116 mmol), Aniline (22 μl, 0.232 mmol), Pd(dba)$_2$ (4 mg, 0.006 mmol), Xantphos (7 mg, 0.012 mmol), NaOtBu (23 mg, 0.232 mmol), DMA (few drops) and dioxane (1 ml). The reaction was heated to 150° C. for 15 minutes under microwave irradiation. The reaction mixture was partitioned between DCM and saturated NH$_4$Cl (50%) and the organic phase separated, dried (MgSO$_4$), filtered and evaporated under reduced pressure. The crude reaction product was dissolved in DCM (2 ml) and TFA (2 ml) was added and the mixture stirred at room temperature for 2 hours. The reaction mixture was loaded onto a SCX-2 cartridge and washed with methanol. The product was released from the cartridge using a solution of 2M ammonia/methanol. The ammonia/methanol eluent was concentrated under reduced pressure and the crude product was purified by preparative HPLC (method B) to yield the title compound. LCMS method: 5, RT: 2.16 min, MI: 389 [M+1]. $^1$H NMR (300 MHz, DMSO): 9.40 (1H, s), 8.40 (1H, d), 8.36 (1H, s), 8.27 (1H, d), 8.20 (1H, d), 7.94 (1H, s), 7.74 (2H, d), 7.67 (1H, d), 7.48 (1H, d), 7.27 (2H, t), 6.88 (1H, t), 4.94-4.85 (1H, m), 3.66 (1H, dd), 3.39-3.19 (3H, m), 2.34-2.30 (1H, m), 2.17-2.10 (1H, m).

Method B

Synthesis of Furan-2-carboxylic acid {4-[4-((R)-pyrrolidin-3-ylamino)-thieno[3,2-d]pyrimidin-2-yl]-pyridin-2-yl)}-amide [574]

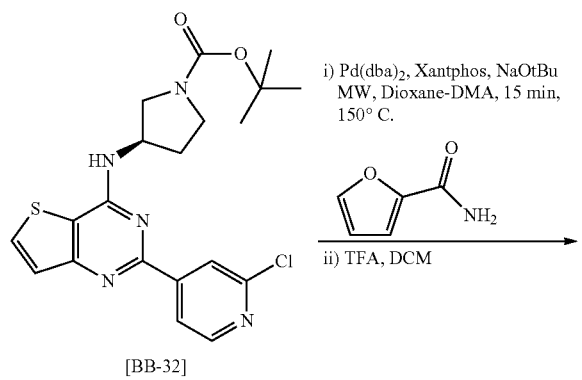

374

-continued

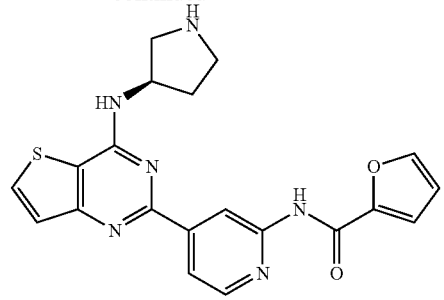

[574]

A microwave vial was charged with (R)-3-[2-(2-Chloro-pyridin-4-yl)-thieno[3,2-d]pyrimidin-4-ylamino]-pyrrolidine-1-carboxylic acid tert-butyl ester [BB-32] (50 mg, 0.11 mmol), furan-2-carboxamide (mg, 0.23 mmol), Pd(dba)$_2$ (4 mg, 0.006 mmol), Xantphos (7 mg, 0.012 mmol), NaOtBu (23 mg, 0.23 mmol), DMA (few drops) and dioxane (1 ml). The reaction was heated to 150° C. for 15 minutes under microwave irradiation. The reaction mixture was partitioned between DCM and saturated NH$_4$Cl (50%) and the organic phase separated, dried (MgSO$_4$), filtered and evaporated under reduced pressure. The crude reaction product was dissolved in DCM (2 ml) and TFA (2 ml) was added and the mixture stirred at 0° C. for 2 hours. The reaction mixture was concentrated under reduced pressure and the resulting residue was dissolved in 10% HCOOH:MeOH and loaded onto an SCX cartridge which was washed with MeOH and the product was released from the cartridge using a solution of 2M ammonia/methanol. The ammonia/methanol eluent was concentrated under reduced pressure. The crude product was purified by preparative HPLC (method B) to yield the title compound. LCMS method: 5, RT: 3.04 min, MI: 407 [M+1]. $^1$H NMR (DMSO) 9.86 (1H, s), 9.09 (1H, s), 8.44 (1H, d), 8.29 (1H, s), 8.21 (1H, d), 8.06 (1H, dd), 7.53 (1H, d), 4.88 (1H, m), 4.52 (1H, dd), 4.04-3.97 (1H, m), 3.88-3.82 (1H, m), 3.52 (1H, dd), 3.29-3.15 (3H, m), 2.34-1.89 (4H, m).

Method C

Synthesis of 1-Phenyl-3-{4-[4-((R)-pyrrolidin-3-ylamino)-thieno[3,2-d]pyrimidin-2-yl]-pyridin-2-yl}-urea [575]

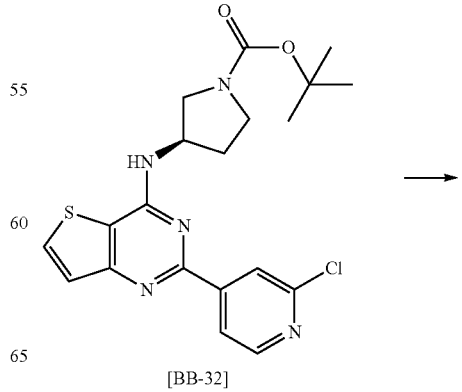

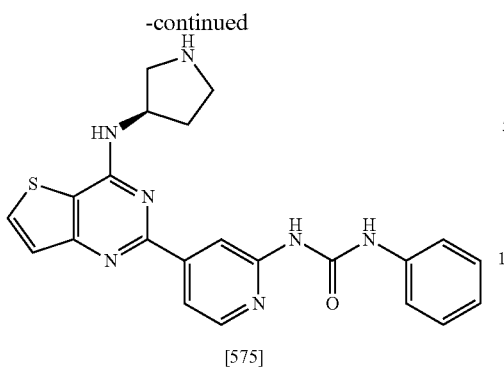

[575]

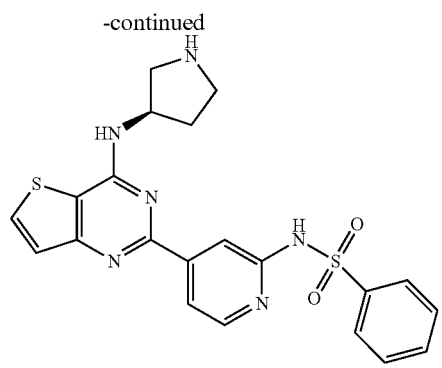

[576]

A microwave vial was charged with (R)-3-[2-(2-chloro-pyridin-4-yl)-thieno[3,2-d]pyrimidin-4-ylamino]-pyrrolidine-1-carboxylic acid tert-butyl ester [BB-32] (100 mg, 0.23 mmol), N-phenylurea (38 mg, 0.278 mmol), Pd(dba)$_2$ (11 mg, 0.012 mmol), 2-dicyclohexylphosphino-2'-(N,N-dimethylamino)biphenyl (9 mg, 0.023 mmol), Cs$_2$CO$_3$ (106 mg, 0.32 mmol), DMA (few drops) and dioxane (0.5 ml). The reaction was heated to 180° C. for 10 minutes under microwave irradiation. The reaction mixture was partitioned between DCM and NH$_4$Cl (50%) and the organic phase collected then loaded onto a SCX-2 cartridge and washed with methanol. The product was released from the cartridge using a solution of 2M ammonia/methanol. The ammonia/methanol eluent was concentrated under reduced pressure and the crude product dissolved 4N HCl:dioxane (2 ml) and stirred at room temperature for 4 hr. The reaction mixture was concentrated under reduced pressure and the resulting residue was dissolved in 10% HCOOH:MeOH and loaded onto an SCX cartridge which was washed with MeOH and the product was released from the cartridge using a solution of 2M ammonia/methanol. The ammonia/methanol eluent was concentrated under reduced pressure. The crude product was purified by preparative HPLC (method B) to yield the title compound. LCMS method: 5, RT: 3.05 min, MI: 432 [M+1]. $^1$H NMR (MeOD) 8.46 (1H, s), 8.39 (1H, d), 8.36 (1H, s), 8.07 (1H, d), 7.96 (1H, dd), 7.53 (2H, dd), 7.49 (1H, d), 7.33 (2H, t), 7.08 (1H, t), 5.04 (1H, m), 3.87 (1H, d), 3.63-3.45 (3H, m), 2.58-2.49 (1H, m), 2.40-2.29 (1H, m).

Method D

Synthesis of N-({4-[4-((R)-Pyrrolidin-3-ylamino)-thieno[3,2-d]pyrimidin-2-yl]-pyridin-2-yl}-benzenesulfonamide [576]

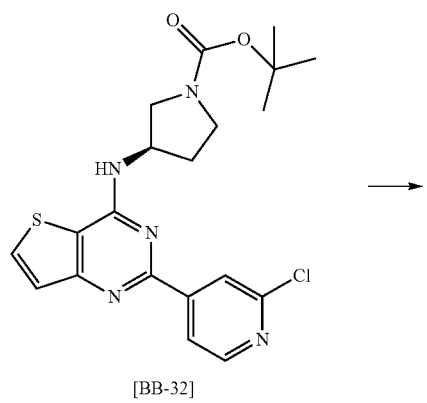

[BB-32]

A microwave vial was charged with (R)-3-[2-(2-Chloro-pyridin-4-yl)-thieno[3,2-d]pyrimidin-4-ylamino]-pyrrolidine-1-carboxylic acid tert-butyl ester [BB-32] (100 mg, 0.23 mmol), benzenesulfonamide (44 mg, 0.278 mmol), Pd(dba)$_2$ (11 mg, 0.012 mmol), 2-Dicyclohexylphosphino-2'-(N,N-dimethylamino)biphenyl (9 mg, 0.023 mmol), Cs$_2$CO$_3$ (106 mg, 0.32 mmol), DMA (few drops) and dioxane (0.5 ml). The reaction was heated to 180° C. for 10 minutes under microwave irradiation. The reaction mixture was partitioned between DCM and NH$_4$Cl (50%) and the organic phase collected then loaded onto a SCX-2 cartridge and washed with methanol. The product was released from the cartridge using a solution of 2M ammonia/methanol. The ammonia/methanol eluent was concentrated under reduced pressure and the crude product dissolved 4N HCl:dioxane (2 ml) and stirred at room temperature for 4 hr. The reaction mixture was concentrated under reduced pressure and the resulting residue was dissolved in 10% HCOOH:MeOH and loaded onto an SCX cartridge which was washed with MeOH and the product was released from the cartridge using a solution of 2M ammonia/methanol. The ammonia/methanol eluent was concentrated under reduced pressure. The crude product was purified by preparative HPLC (method B) to yield the title compound. LCMS method: 5, RT: 2.74 min, MI: 453 [M+1]. 1H NMR (DMSO) 8.41 (1H, d), 8.21 (1H, s), 8.10 (1H, d), 7.92-7.89 (2H, m), 7.75 (1H, dd), 7.55-7.50 (5H, m), 4.85-4.80 (1H, m), 3.60 (1H, dd), 3.43-3.25 (3H, m), 2.38-2.31 (1H, m), 2.19-2.11 (1H, m).

The following compounds were prepared according to the general synthesis shown in Scheme B24:

| Example | Method | SM | Amine | Characterisation | |
|---|---|---|---|---|---|
| 577 | A | [BB-32] | pyrazin-2-amine | method: 5, RT: 1.85 min, MI: 391 [M + 1] | |
| 578 | B | [BB-32] | tetrahydrofuran-2-carboxamide | method: 5, RT: 2.78 min, MI: 411 [M + 1] | 1H NMR (DMSO, 300 MHz): 9.15 (1H, s), 8.49 (2H, d), 8.30 (1H, s), 8.20 (1H, d), 8.07 (1H, d), 7.97 (1H, s), 7.64 (1H, d), 7.54 (1H, d), 6.71 (1H, dd), 4.90-4.88 (1H, m), 3.55 (1H, dd), 3.31-3.15 (3H, m), 2.37-2.30 (1H, m), 2.15 (1H, m) |
| 579 | A | [BB-31] | aniline | method: 5, RT: 2.81 min, MI: 407 [M + 1] | 1H NMR (MeOD, 300 MHz): 8.32 (2H, s), 8.11 (1H, d), 8.08 (1H, d), 7.53 (2H, dd), 7.45 (1H, d), 7.40 (1H, d), 7.27 (2H, t), 6.95 (1H, t), 4.90 (1H, m), 3.73 (1H, dd), 3.56-3.29 (3H, m), 2.51-2.44 (1H, m), 2.32-2.30 (1H, m). |
| 580 | A | [BB-31] | pyrazin-2-amine | method: 5, RT: 4.37 min, MI: 409 [M + 1] | 1H NMR (MeOD, 300 MHz): 8.85 (1H, d), 8.40 (1H, d), 8.29 (1H, d), 8.23 (1H, dd), 8.11 (1H, d), 8.02 (1H, d), 7.91-7.88 (3H, m), 7.68 (1H, d), 7.50 (1H, d), 4.93-4.87 (1H, m), 3.78 (1H, dd), 3.62-3.43 (3H, m), 2.56-2.45 (1H, m), 2.40-2.30 (1H, m) |
| 581 | C | [BB-32] | N,N-dimethylurea | method: 7, RT: 1.90 min, MI: 384 [M + 1] | 1H NMR (MeOD, 300 MHz): 8.84 (1H, s), 8.31 (1H, d), 7.99 (1H, d), 7.95 (1H, dd), 7.43 (1H, d), 4.92-4.89 (1H, m), 3.54 (1H, dd), 3.23-3.20 (1H, m), 3.15-3.10 (2H, m), 3.08 (6H, s), 2.41-2.37 (1H, m), 2.09-2.02 (1H, m). |
| 582 | C | [BB-32] | N-tert-butylurea | method: 7, RT: 3.40 min, MI: 412 [M + 1] | 1H NMR (MeOD, 300 MHz): 8.25 (1H, d), 8.06 (1H, s), 8.00 (1H, d), 7.84 (1H, dd), 7.42 (1H, d), 4.93-4.89 (1H, m), 3.51 (1H, Cdd), 3.18-3.09 (2H, m), 2.41-2.37 (1H, m), 2.07-2.05 (1H, m), 1.43 (9H, s). |
| 583 | C | [BB-32] | N-methylurea | method: 7, RT: 2.26 min, MI: 370 [M + 1] | 1H NMR (MeOD, 300 MHz): 8.27 (1H, d), 8.04 (1H, s), 7.99 (1H, d), 7.85 (1H, dd), 7.43 (1H, d), 4.93-4.89 (1H, m), 3.48 (1H, dd), 3.26-3.22 (1H, m), 3.12-3.08 (1H, m), 3.04 (1H, dd), 2.90 (3H, s), 2.41-2.34 (1H, m), 2.06-1.99 (1H, m). |
| 584 | C | [BB-32] | piperidine-1-carboxamide | method: 7, RT: 2.48 min, MI: 424 [M + 1] | 1H NMR (DMSO, 300 MHz): 9.15 (1H, s), 8.75 (1H, s), 8.32 (1H, d), 8.19 (1H, d), 7.89 (1H, d), 7.51 (1H, d), 4.79-4.75 (1H, m), 3.45-3.44 (2H, m), 3.21 (1H, dd), 3.07-3.02 (4H, m), 2.31-2.21 (1H, m), 2.02-1.97 (1H, m), 1.60-1.50 (2H, m), 1.49-1.41 (4H, m), 1.40-1.35 (2H, m). |

-continued

| Example | Method | SM | Amine | Characterisation | |
|---|---|---|---|---|---|
| 585 | A | [BB-39b] | pyrazin-2-amine | method: 5, RT: 2.41 min, MI: 409 [M + 1] | 1H NMR (MeOD, 300 MHz): 9.52 (1H, d), 8.49 (1H, s), 8.30 (1H, dd), 8.20 (1H, d), 8.16 (1H, d), 8.10 (1H, d), 7.54 (1H, t), 7.47 (1H, d), 4.95-4.88 (1H, m), 3.76 (1H, dd), 3.61-3.50 (3H, m), 2.53-2.46 (1H, m), 2.36-2.31 (1H, m). |
| 586 | A | [BB-32] | (S)-1-phenylethan-1-amine | method: 6, RT: 5.68 min, MI: 417 [M + 1] | 1H NMR (DMSO, 300 MHz): 8,39 (d, 1H), 8.14 (d, 1H), 8 (d, 1H), 7.56 (s, 1H), 7.45 (m, 1H), 7.43 (m, 1H), 7.31 (m, 2H), 7.16 (m, 1H), 5.07 (m, 1H), 4.82 (m, 1H), 3.24 (m, 1H), 3.12 (m, 2H), 2.24 (m, 1H), 2.03 (m, 1H), 1.43 (d, 3H) |
| 587 | | H | 1-phenylethan-1-amine | method: 6, RT: 5.7 min, MI: 417 [M + 1] | |
| 588 | A | [BB-32] | 6-methylpyridazin-3-amine | method: 6, RT: 5.22 min, MI: 405 [M + 1] | 1H NMR (DMSO, 300 MHz): 8.46 (m, 1H), 8.33 (m, 1H), 8.03 (s, 1H), 7.81 (m, 1H), 7.53 (m, 1H), 7.47 (m, 1H), 7.44 (m, 1H), 4.85 (m, 1H), 3.66 (m, 1H), 3.18 (m, 1H), 3.15 (m, 2H), 2.31 (m, 1H), 2.09 (m, 1H) |
| 589 | A | [BB-32] | (S)-1-phenylpropan-1-amine | method: 6, RT: 5.93 min, MI: 431 [M + 1] | 1H NMR (DMSO, 300 MHz): 8.31 (d, 1H), 8.15 (d, 1H)., 7.98 (d, 1H), 7.57 (s, 1H), 7.44 (M, 1H), 7.36 (m, 2H), 7.28 (m, 2H), 7.16 (m, 1H), 4.83 (m, 1H), 3.51 (m, 1H), 3.25 (m, 2H), 3.10 (m, 2H), 2.26 (m, 1H), 2.04 (m, 1H), 1.76 (q, 2H), 0.90 (t, 3H) |
| 590 | A | [BB-32] | (R)-1-phenylpropan-1-amine | method: 6, RT: 5.95 min, MI: 431 [M + 1] | |
| 591 | A | [BB-32] | (S)-1-amino-2-hydroxypropane | | |
| 592 | A | [BB-32] | (R)-1-amino-2-hydroxypropane | | |

-continued

| Example | Method | SM | Amine | Characterisation |
|---|---|---|---|---|
| 593 | A | [BB-32] | (S)-2-amino-1-phenylethanol (HO, NH₂, phenyl) | method: 6, RT: 5.49 min, MI: 433 [M + 1] |
| 594 | A | [BB-32] | cyclopropylamine | method: 5, RT: 1.8 min, MI: 353 [M + 1] |
| 595 | B | [BB-32] | thiophene-2-carboxamide | method: 5, RT: 5.41 min, MI: 423 [M + 1] |
| 596 | B | [BB-32] | 3-methoxybenzamide | method: 5, RT: 5.61 min, MI: 447 [M + 1] |
| 597 | A | [BB-32] | cyclopropylmethanamine | method: 10, RT: 1.61 min, MI: 367 [M + 1], |
| 598 | A | [BB-32] | benzylamine | method: 10, RT: 1.82 min, MI: 403 [M + 1], |
| 599 | B | [BB-32] | cyclopropanecarboxamide | method: 10, RT: 1.52 min, MI: 381 [M + 1], |
| 600 | A | [BB-32] | pyridin-2-amine | method: 10, RT: 1.53 min, MI: 390 [M + 1], |
| 601 | A | [BB-32] | 4-phenylpyridin-2-amine | method: 10, RT: 2.26 min, MI: 466 [M + 1], |

-continued

| Example | Method | SM | Amine | Characterisation |
|---|---|---|---|---|
| 602 | A | [BB-32] | 4-(2-aminopyridin-4-yl)morpholine | method: 10, RT: 1.39 min, MI: 475 [M + 1], |
| 603 | A | [BB-32] | 4-(4-methylpiperazin-1-yl)pyridin-2-amine | method: 10, RT: 1.28 min, MI: 488 [M + 1], |
| 604 | A | [BB-32] | 2-aminoisonicotinonitrile | method: 10, RT: 1.71 min, MI: 415 [M + 1], |
| 605 | A | [BB-32] | 3-(4-methylpiperazin-1-yl)aniline | method: 10, RT: 1.44 min, MI: 487 [M + 1], |
| 606 | A | [BB-32] | 3-aminobenzonitrile | method: 10, RT: 1.76 min, MI: 414 [M + 1], |
| 607 | A | [BB-32] | 4-aminobenzonitrile | method: 10, RT: 1.86 min, MI: 414 [M + 1], |
| 608 | A | [BB-32] | 4-(piperidin-1-yl)aniline | method: 10, RT: 1.45 min, MI: 472 [M + 1], |

-continued

| Example | Method | SM | Amine | Characterisation |
|---|---|---|---|---|
| 609 | A | [BB-32] | 6-aminopyridine-3-carbonitrile | method: 10, RT: 1.71 min, MI: 415 [M + 1], |
| 610 | A | [BB-32] | 4-amino-N,N-dimethylbenzenesulfonamide | method: 10, RT: 1.89 min, MI: 496 [M + 1], |
| 611 | A | [BB-32] | 4-(pyrrolidin-1-ylmethyl)aniline | method: 10, RT: 1.39 min, MI: 472 [M + 1], |
| 612 | A | [BB-32] | 4-(isopropylsulfonyl)aniline | method: 10, RT: 1.85 min, MI: 496 [M + 1], |
| 613 | A | [BB-32] | (4-aminophenyl)(4-methylpiperazin-1-yl)methanone | method: 10, RT: 1.35 min, MI: 529 [M + 1], |

-continued

| Example | Method | SM | Amine | Characterisation | |
|---|---|---|---|---|---|
| 614 | A | [BB-32] | 1-(4-aminobenzyl)imidazole | method: 10, RT: 1.35 min, MI: 469 [M + 1], | |
| 615 | B | [BB-32] | pyrazine-2-carboxamide (amino) | method: 10, RT: 1.60 min, MI: 419 [M + 1], | |
| 616 | A | [BB-32] | 4-(thiophen-2-yl)aniline | method: 10, RT: 2.28 min, MI: 471 [M + 1], | |
| 617 | A | [BB-32] | 4-(thiophen-3-yl)aniline | method: 10, RT: 2.33 min, MI: 471 [M + 1], | |
| 618 | A | [BB-32] | 4-fluoro-benzamide (amino) | method: 10, RT: 1.90 min, MI: 435 [M + 1], | |
| 619 | A | [BB-39b] | aniline | method: 5, RT: 3.05 min, MI: 407 [M + 1] | 1H NMR (MeOD) 8.10 (1H, d), 7.99 (1H, d), 7.67 (2H, dd), 7.47 (1H, d), 7.33-7.24 (3H, m), 7.01 (1H, t), 4.95-4.89 (1H, m), 3.76 (1H, dd), 3.64-3.55 (1H, m), 3.50-3.40 (1H, m), 2.53-2.44 (1H, m), 2.37-2.31 (1H, m). |
| 620 | B | [BB-32] | 4-(4-methylpiperazin-1-yl)benzamide | method: 10, RT: 1.49 min, MI: 515 [M + 1], | |

-continued

| Example | Method | SM | Amine | Characterisation | |
|---|---|---|---|---|---|
| 621 | B | [BB-32] | 4-morpholinobenzamide | method: 10, RT: 1.93 min, MI: 502 [M + 1], | |
| 622 | D | [BB-32] | cyclopropanesulfonamide | method: 7, RT: 2.28 min, MI: 417 [M + 1] | 1H NMR (MeOD) 8.38 (1H, s), 8.17 (1H, d), 8.07 (1H, d), 7.90 (1H, dd), 7.48 (1H, d), 4.99-4.97 (1H, m), 3.86 (1H, dd), 3.62-3.56 (1H, m), 3.50-3.46 (2H, m), 2.89-2.86 (1H, m), 2.58-2.51 (1H, m), 2.37-2.32 (1H, m), 1.19-1.16 (2H, m), 1.03-0.99 (2H, m). |
| 623 | A | [BB-32] | cyclohexylamine | method: 7, RT: 2.21 min, MI: 395 [M + 1] | 1H NMR (MeOD) 7.99 (2H, d), 7.48 (1H, s), 7.41 (2H, d), 4.92-4.89 (1H, m), 3.70-3.65 (1H, m), 3.52 (1H, dd), 3.31-3.29 (1H, m), 3.20-3.13 (2H, m), 2.40-2.36 (1H, m), 2.09-2.04 (3H, m), 1.81-1.78 (2H, m), 1.68-1.66 (1H, m), 1.48-1.41 (2H, m), 1.30-1.26 (3H, m). |
| 624 | D | [BB-32] | methanesulfonamide | method: 7, RT: 2.07 min, MI: 391 [M + 1] | 1H NMR (MeOD) 8.29 (1H, s), 8.19 (1H, d), 8.07 (1H, d), 7.90 (1H, d), 7.49 (1H, d), 5.01-4.95 (1H, m), 3.86 (1H, dd), 3.63-3.57 (1H, m), 3.52-3.47 (2H, m), 3.20 (3H, s), 2.59-2.51 (1H, m), 2.38-2.32 (1H, m). |
| 625 | A | [BB-32] | tetrahydropyran-4-amine | method: 7, RT: 1.60 min, MI: 397 [M + 1] | 1H NMR (MeOD) 8.03 (1H, d), 8.00 (1H, d), 7.52 (1H, s), 7.45 (1H, dd), 7.42 (1H, d), 4.96-4.94 (1H, m), 4.00-3.94 (3H, m), 3.65-3.55 (3H, m), 3.40-3.34 (2H, m), 3.29-3.19 (1H, m), 2.45-2.38 (1H, m), 2.16-2.13 (1H, m), 2.03-2.00 (2H, m), 1.61-1.54 (2H, m). |
| 626 | A | [BB-32] | isopropylamine | method: 5, RT: 1.87 min, MI: 355 [M + 1] | |
| 627 | (R)-3-hydroxypyrrolidine | H | thiophene-2-carboxamide | method: 10, RT: 1.67 min, MI: 440 [M + 1], | |
| 628 | (R)-1-methylpyrrolidin-3-amine | H | thiophene-2-carboxamide | Method: 10, RT: 1.84 min, MI: 437 [M + 1], | |

| Example | Method | SM | Amine | Characterisation |
|---|---|---|---|---|
| 629 | (structure with pyrrolidine, OH, NH, acetamide) | H | thiophene-2-carboxamide | Method: 10, RT: 1.62 min, MI: 496 [M + 1], |
| 630 | (S)-configured structure with NH₂, NH, CF₃-phenyl | | thiophene-2-carboxamide | Method: 10, RT: 2.56 min, MI: 555 [M + 1], |

Synthesis of 2-{(R)-3-[2-(2-Phenylamino-pyridin-4-yl)-thieno[3,2-d]pyrimidin-4ylamino]pyrrolidin-1-yl}-acetamide [631]

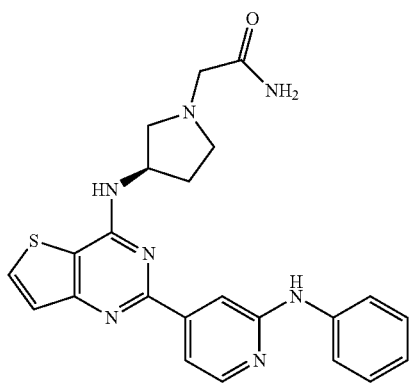

[631]

A sealed tube containing [2-(2-Phenylamino-pyridin-4-yl)-thieno[3,2-d]pyrimidin-4-yl]-(R)-pyrrolidin-3-yl-amine [573] (261 mg, 0.67 mmol) was charged with iodoacetamide (150 mg, 0.81 mmol), cesium carbonate (0.88 g, 2.7 mmol) and acetonitrile (7.0 mL) was heated at 70° C. until complete. Partitioning between dichloromethane and sat aq. NaHCO3, separation of the organic layer, drying (MgSO4), filtration, concentration and purification by RP-HPLC, acetonitrile/water gradient provided the title compound as a yellowish solid (106 mg, 35% yield). HPLC: method: 10, RT: 1.61 min, MI: 446 [M+1].

General Synthesis of Substituted 4-amino-2-pyrazolyl-4-yl-thieno[3,2-d]pyrimidine Derivatives of General Formula [F-156] (Scheme B25)

An 4,5-substituted-3-amino-thiophene-2-carboxylic acid amide derivative of general formula [G-107] was subjected to a cyclisation reaction with an pyrazole aldehyde derivative of general formula [G-157] in the presence of 4M hydrogen chloride in dioxane in a suitable solvent such as methanol. The reaction is suitably conducted at an elevated temperature for example 140° C. in a microwave reactor for 20 minutes. Full aromatisation is subsequently achieved with 2,3-dichloro-5,6-dicyanobenzoquinone in a suitable solvent such as dichloromethane at ambient temperature, to yield the 6,7-substituted 2-pyrazolyl-4-yl-thieno [3,2-d]pyrimidin-4-ol, of general formula [G-155]. The corresponding 6,7-substituted 2-pyrazolyl-4-yl-thieno [3,2-d]pyrimidin-4-ol, of general formula [G-155] was reacted with 2,4,6-triisopropylbenzenesulfonyl chloride in a polar aprotic solvent such as DMA, DMF, NMP with a tertiary alkylamine base such as Et₃N, DIPEA or NMM and a catalytic amount of DMAP and used crude and reacted further with a primary or secondary amino derivative, of general formula [G-117]. After reaction work up, typically by a liquid-liquid extraction or purification by acidic ion exchange catch-release, the N-Boc derivatives were deprotected under acidic conditions with a strong acid such as TFA, TCA, methanesulfonic acid, HCl or H₂SO₄ in a solvent such as DCM, DCE, THF, EtOH or MeOH and the crude reaction product was purified by reverse phase preparative HPLC.

Scheme B25

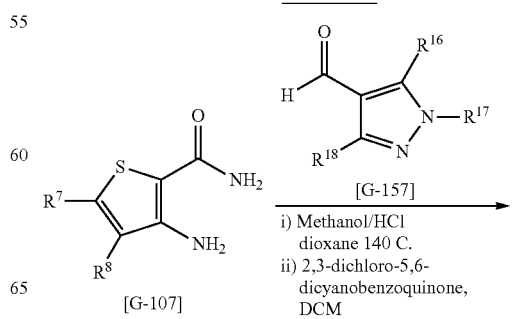

i) Methanol/HCl dioxane 140 C.
ii) 2,3-dichloro-5,6-dicyanobenzoquinone, DCM

-continued

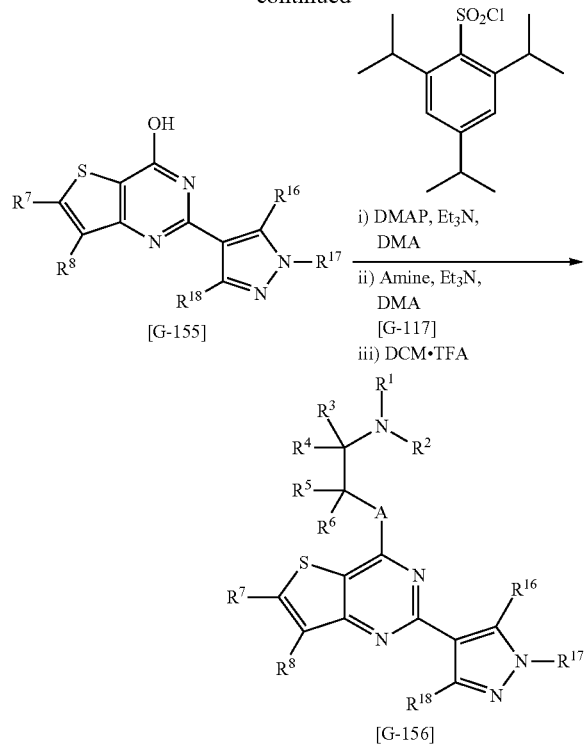

[G-155] i) DMAP, Et₃N, DMA
ii) Amine, Et₃N, DMA [G-117]
iii) DCM·TFA

[G-156]

Synthesis of 2-(5-Methyl-1H-pyrazol-4-yl)-thieno[3,2-d]pyrimidin-4-ol [BB-46]

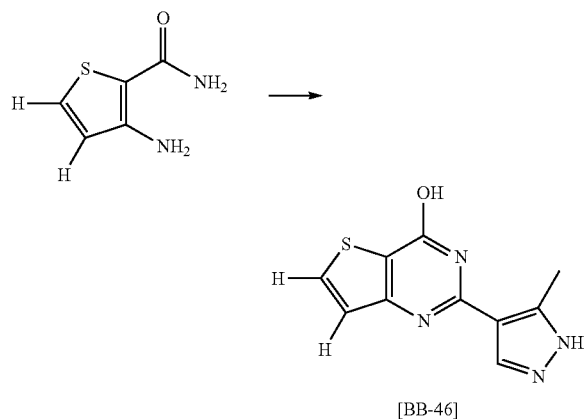

[BB-46]

A microwave vial was charged with 3-amino-thiophene-2-carboxylic acid amide (0.25 g, 1.76 mmol), 3-methyl-1H-pyrazole-4-carbaldehyde (165 mg, 1.5 mmol), hydrogen chloride 4M in dioxane (7 l, 0.03 mmol) and methanol (2 ml). The reaction mixture was heated to 140° C. for 20 minutes under microwave irradiation. After completion, the mixture was concentrated under reduced pressure. To a solution of the crude product in dichloromethane (3 ml) was added 2,3-dichloro-5,6-dicyanobenzoquinone (440 mg, 1.93 mmol). The mixture was stirred at room temperature for 18 hours. After completion, the precipitate formed was filtered and washed with methanol. The residue was used without any further purification in the next step. LCMS method: 8, RT: 2.48 min, MI: 233 [M+1]. 1H NMR (DMSO) 12.38 (1H, br s), 8.36 (1H, s), 8.16 (1H, d), 7.35 (1H, d), 2.56 (3H, s).

Synthesis of [2-(5-Methyl-1H-pyrazol-4-yl)-thieno[3,2-d]pyrimidin-4-yl]-(R)-pyrrolidin-3-yl-amine [633]

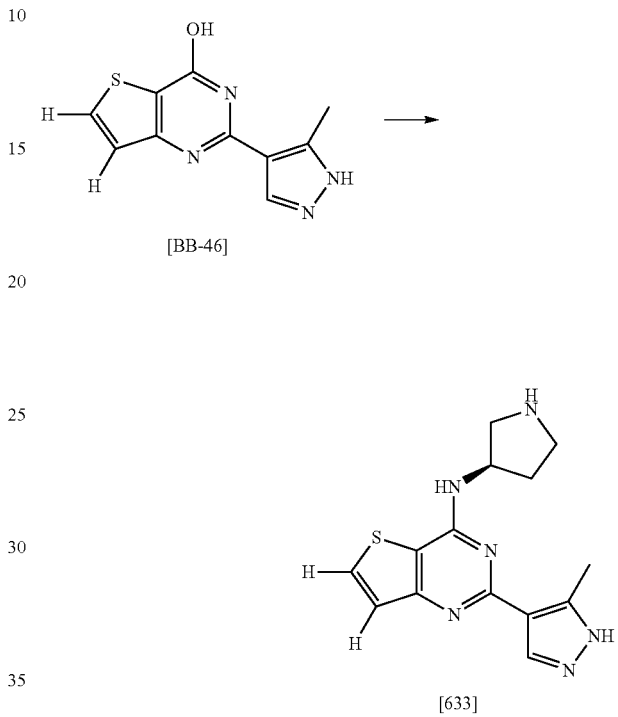

[BB-46]

[633]

To a solution of 2-(5-Methyl-1H-pyrazol-4-yl)-thieno[3,2-d]pyrimidin-4-ol [BB-46] (0.28 mg, 1.2 mmol) in DMA (10 ml) was added 2,4,6-triisopropylbenzenesulfonyl chloride (438 mg, 1.45 mmol), triethylamine (0.34 ml, 2.4 mmol) and DMAP (16 mg, 0.12 mmol). The solution was stirred at room temperature for 4 hours then (R)-(+)-1-Boc-3-aminopyrrolidine (220 mg, 1.2 mmol) was added and the mixture was stirred at room temperature for 18 hours. Water was added and the mixture was extracted with DCM (50 ml), washed with brine (50 ml) and dried (MgSO₄), filtered and evaporated under reduced pressure. The crude reaction product was dissolved in DCM (5 ml) and TFA (2 ml) was added and the mixture stirred at room temperature for 2 hours. After completion the mixture was loaded onto a SCX-2 cartridge and washed with methanol. The product was released from the cartridge using a solution of 2M ammonia/methanol. The ammonia/methanol eluent was concentrated under reduced pressure followed by trituration in ether and the crude product was purified by preparative HPLC (method B) to yield the title compound. LCMS method: 6, RT: 3.80 min, MI: 301 [M+1].

N*1*-[2-(5-Methyl-1H-pyrazol-4-yl)-thieno[3,2-d]pyrimidin-4-yl]-3-(S)-phenyl-propane-1,2-diamine [634] was prepared according to the above procedure from 2-(5-Methyl-1H-pyrazol-4-yl)-thieno[3,2-d]pyrimidin-4-ol [BB-46] and ((S)-1-Aminomethyl-2-phenyl-ethyl)-carbamic acid tert-butyl ester to give the title compound: LCMS method: 6, RT: 3.65 min, MI: 365 [M+1].

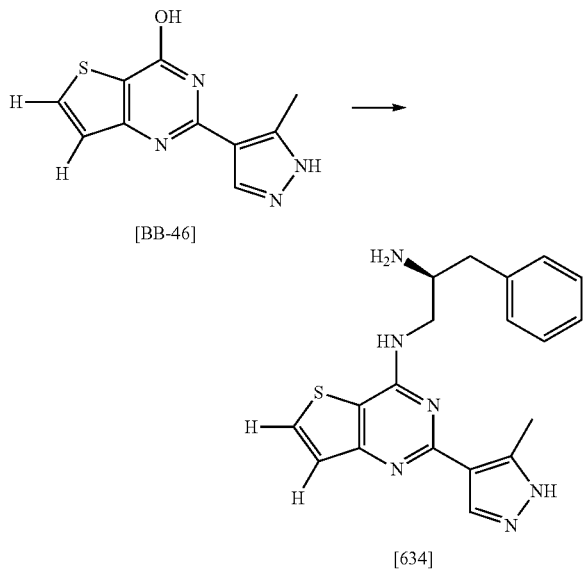

[BB-46]

[634]

VI. Biology

PKCι IC$_{50}$ Assay

Assays are based on the ability of PKCι to phosphorylate a commercially available peptide substrate in vitro. The peptide substrate is FAM-PKCε pseudopeptide derived peptide, and comprises the amino acid sequence 5FAM-ERM-RPRKRQGSVRRRV-NH$_2$. Recombinant, full-length human PKCι expressed in Sf21 insect cells is also commercially available. Recombinant, kinase-domain human PKCι is expressed and purified in-house.

The procedure below explains how dose response curves for inhibitors of PKCι are obtained. The screen described is for a 384 well format but the assay can be adapted to 1536 or other formats as required.

Compounds to be tested are dissolved in 100% DMSO. Compounds are diluted as required to give a final concentration of 4% DMSO (v/v) in the assay. 1 μl is plated into 384 well black low-binding flat bottomed assay plates which are used immediately. Dilutions and additions of compound to assay plates are carried out using Matrix WellMate® and Matrix PlateMate® Plus liquid handling systems.

On the day of the screen PKCι/substrate working solution, and ATP working solution, are prepared in buffer containing 20 mM tris-HCl pH7.5, 10 mM MgCl$_2$, 0.01% Triton X100, 250 μM EGTA and 1 mM DTT. The final concentration of PKCι used varies depending on the batch of protein but is typically 15 pM. The final concentration of peptide substrate in the assay is 100 nM. ATP is used at a final concentration of 150 μM or 2 μM in the assays containing full-length or kinase-domain PKCι respectively, which corresponds to five times or equal to the $K_M^{APP}$ for ATP for each enzyme, respectively. The final buffer concentration in the assay is 18 mM tris-HCl pH7.5, 9 mM MgCl$_2$, 0.009% Triton X100, 225 μM EGTA and 0.9 mM DTT. Relevant controls are included, namely no compound and no enzyme. 5 μl PKCι/substrate working solution at 30 pM and 200 nM, respectively, is added to the wells, followed by 4 μl ATP working solution at 375 μM or 62.5 μM for full-length or kinase-domain PKCι respectively, using a 16 channel Matrix pipette. The reaction is allowed to incubate for 60 minutes at room temperature, before the reaction is stopped and developed by the addition of 20 μl IMAP™ development reagent (Molecular Devices). IMAP development reagent consists of 0.25% (v/v) IMAP progressive binding reagent, 17% (v/v) IMAP progressive binding buffer A and 3% (v/v) IMAP progressive binding buffer B. The plates are then incubated for 2 hours at room temperature before being read using an appropriate plate reader, for example a Molecular Devices HT Analyst or a BMG Pherastar. Plates are read using a fluorescence polarisation protocol with excitation at 485 nm and emission at 530 nm, and dichroic mirror at 505 nm.

Percentage inhibition values are calculated from fluorescence polarisation values, using the no compound and no enzyme control values as 0% and 100% inhibition, respectively. IC50 determination is performed with ExcelFit software (IDBS) using curve fit 205. Z' factors are determined for each plate tested and are all above 0.5.

Results

Biological data for the Example compounds is presented in the following table. Activities are set forth as follows:

IC50 in IMAP assay against full length PKCi at 15 μM ATP:
A=<100 nM
B=100 nM to 1,000 nM
C=1,000 nM to 10,000 nM
D=10,000 nM to 40,000 nM IC50 in IMAP assay against kinase domain PKCi at 2 μM ATP:
A*=<100 nM
B*=100 nM to 1,000 nM
C*=1,000 nM to 10,000 nM
D*=10,000 nM to 40,000 nM

| Ex | Activity | Structure | Name |
|---|---|---|---|
| 1 | C* | 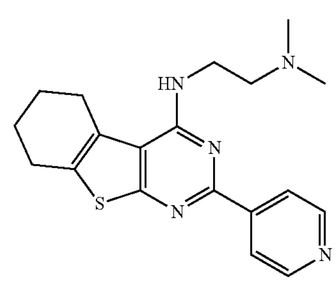 [SMILES: CN(C)CCNc1nc(-c2ccncc2)nc2sc3c(c12)CCCC3] | N,N-Dimethyl-N'-(2-pyridin-4-yl-5,6,7,8-tetrahydro-benzo[4,5]thieno[2,3-d]pyrimidin-4-yl)-ethane-1,2-diamine |

| Ex | Activity | Structure | Name |
|---|---|---|---|
| 2 | B* | 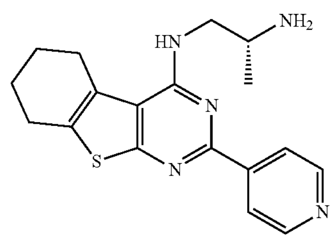 [SMILES: C[C@@H](N)CNc1nc(-c2ccncc2)nc2sc3c(c12)CCCC3] | (R)-N*1*-(2-Pyridin-4-yl-5,6,7,8-tetrahydro-benzo[4,5]thieno[2,3-d]pyrimidin-4-yl)-propane-1,2-diamine |
| 3 | B* | 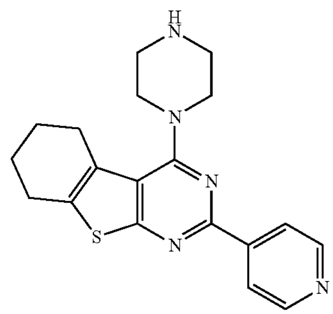 [SMILES: c1cc(-c2nc(N3CCNCC3)c3c4c(sc3n2)CCCC4)ccn1] | 4-Piperazin-1-yl-2-pyridin-4-yl-5,6,7,8-tetrahydro-benzo[4,5]thieno[2,3-d]pyrimidine |
| 4 | B* | 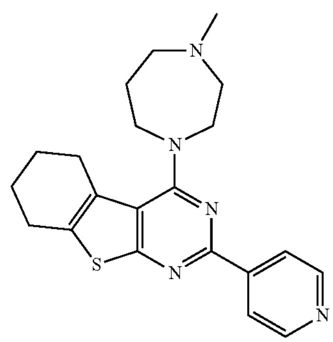 [SMILES: CN1CCCN(c2nc(-c3ccncc3)nc3sc4c(c23)CCCC4)CC1] | 4-(4-Methyl-[1,4]diazepan-1-yl)-2-pyridin-4-yl-5,6,7,8-tetrahydro-benzo[4,5]thieno[2,3-d]pyrimidine |
| 5 | A* | 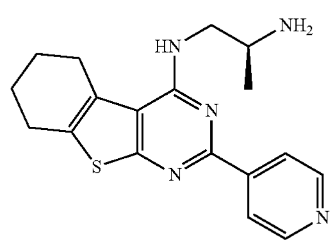 [SMILES: C[C@H](N)CNc1nc(-c2ccncc2)nc2sc3c(c12)CCCC3] | (S)-N*1*-(2-Pyridin-4-yl-5,6,7,8-tetrahydro-benzo[4,5]thieno[2,3-d]pyrimidin-4-yl)-propane-1,2-diamine |
| 6 | C* | 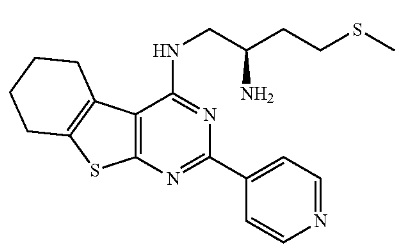 [SMILES: CSCC[C@@H](N)CNc1nc(-c2ccncc2)nc2sc3c(c12)CCCC3] | (R)-4-Methylsulfanyl-N*1*-(2-pyridin-4-yl-5,6,7,8-tetrahydro-benzo[4,5]thieno[2,3-d]pyrimidin-4-yl)-butane-1,2-diamine |

| Ex | Activity | Structure | Name |
|---|---|---|---|
| 7 | C* | 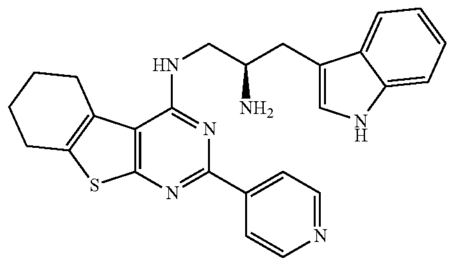 [SMILES: N[C@@H](CNc1nc(-c2ccncc2)nc2sc3c(c12)CCCC3)Cc1c[nH]c2ccccc12] | (R)-3-(1H-Indol-3-yl)-N*1*-(2-pyridin-4-yl-5,6,7,8-tetrahydro-benzo[4,5]thieno[2,3-d]pyrimidin-4-yl)-propane-1,2-diamine |
| 8 | B* | 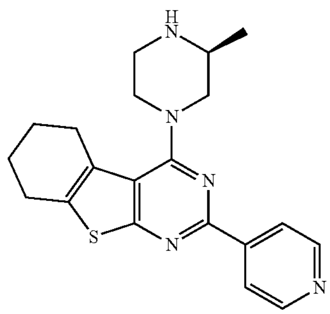 [SMILES: C[C@H]1CN(c2nc(-c3ccncc3)nc3sc4c(c23)CCCC4)CCN1] | 4-((S)-3-Methyl-piperazin-1-yl)-2-pyridin-4-yl-5,6,7,8-tetrahydro-benzo[4,5]thieno[2,3-d]pyrimidine |
| 9 | C* | 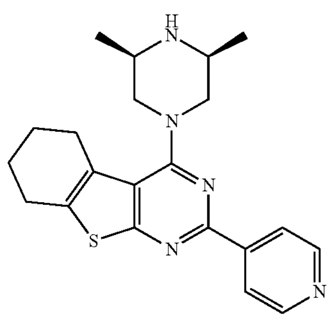 [SMILES: C[C@@H]1CN(c2nc(-c3ccncc3)nc3sc4c(c23)CCCC4)C[C@H](C)N1] | 4-((3R,5S)-3,5-Dimethyl-piperazin-1-yl)-2-pyridin-4-yl-5,6,7,8-tetrahydro-benzo[4,5]thieno[2,3-d]pyrimidine |
| 10 | C* | 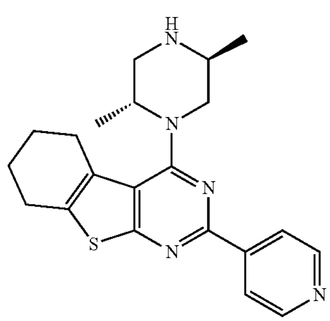 [SMILES: C[C@@H]1CN[C@@H](C)CN1c1nc(-c2ccncc2)nc2sc3c(c12)CCCC3] | 4-((2R,5S)-2,5-Dimethyl-piperazin-1-yl)-2-pyridin-4-yl-5,6,7,8-tetrahydro-benzo[4,5]thieno[2,3-d]pyrimidine |
| 11 | D* | 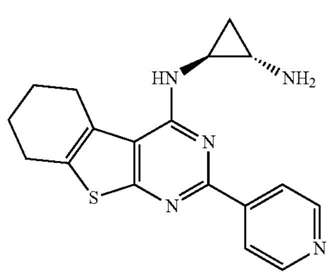 [SMILES: N[C@H]1C[C@@H]1Nc1nc(-c2ccncc2)nc2sc3c(c12)CCCC3] | (1S,2S)-N-(2-Pyridin-4-yl-5,6,7,8-tetrahydro-benzo[4,5]thieno[2,3-d]pyrimidin-4-yl)-cyclopropane-1,2-diamine |

-continued

| Ex | Activity | Structure | Name |
|---|---|---|---|
| 12 | B | 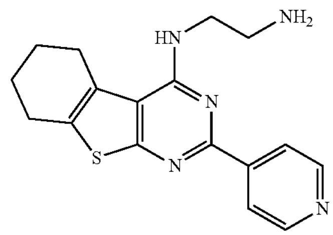 [SMILES: NCCNc1nc(-c2ccncc2)nc2sc3c(c12)CCCC3] | N*1*-(2-Pyridin-4-yl-5,6,7,8-tetrahydro-benzo[4,5]thieno[2,3-d]pyrimidin-4-yl)-ethane-1,2-diamine |
| 13 | B* | 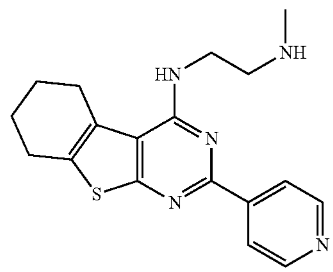 [SMILES: CNCCNc1nc(-c2ccncc2)nc2sc3c(c12)CCCC3] | N-Methyl-N'-(2-pyridin-4-yl-5,6,7,8-tetrahydro-benzo[4,5]thieno[2,3-d]pyrimidin-4-yl)-ethane-1,2-diamine |
| 14 | B* | 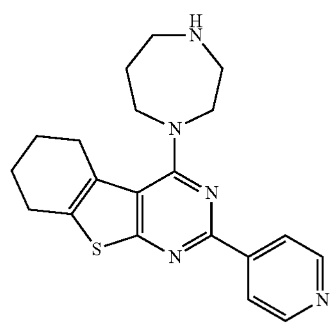 [SMILES: c1cc(-c2nc(N3CCCNCC3)c3c4c(sc3n2)CCCC4)ccn1] | 4-[1,4]Diazepan-1-yl-2-pyridin-4-yl-5,6,7,8-tetrahydro-benzo[4,5]thieno[2,3-d]pyrimidine |
| 15 | B* | 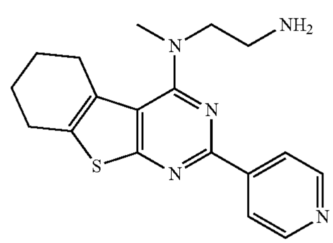 [SMILES: CN(CCN)c1nc(-c2ccncc2)nc2sc3c(c12)CCCC3] | N*1*-Methyl-N*1*-(2-pyridin-4-yl-5,6,7,8-tetrahydro-benzo[4,5]thieno[2,3-d]pyrimidin-4-yl)-ethane-1,2-diamine |
| 16 | C* | 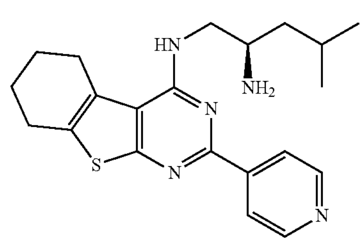 [SMILES: CC(C)C[C@@H](N)CNc1nc(-c2ccncc2)nc2sc3c(c12)CCCC3] | (R)-4-Methyl-N*1*-(2-pyridin-4-yl-5,6,7,8-tetrahydro-benzo[4,5]thieno[2,3-d]pyrimidin-4-yl)-pentane-1,2-diamine |
| 17 | C* | 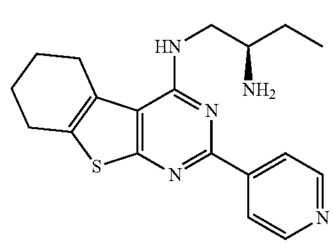 [SMILES: CC[C@@H](N)CNc1nc(-c2ccncc2)nc2sc3c(c12)CCCC3] | (R)-N*1*-(2-Pyridin-4-yl-5,6,7,8-tetrahydro-benzo[4,5]thieno[2,3-d]pyrimidin-4-yl)-butane-1,2-diamine |

-continued

| Ex | Activity | Structure | Name |
|---|---|---|---|
| 18 | B* | 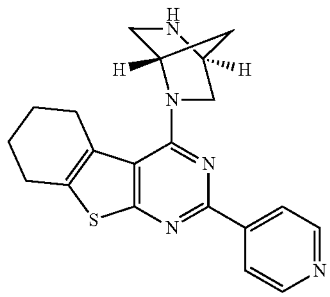 [SMILES: c1cc(-c2nc(N3C[C@@H]4C[C@H]3CN4)c3c4c(sc3n2)CCCC4)ccn1] | 4-(1S,4S)-2,5-Diaza-bicyclo[2.2.1]hept-2-yl-2-pyridin-4-yl-5,6,7,8-tetrahydro-benzo[4,5]thieno[2,3-d]pyrimidine |
| 19 | B* | 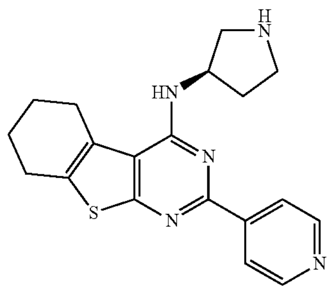 [SMILES: c1cc(-c2nc(N[C@@H]3CCNC3)c3c4c(sc3n2)CCCC4)ccn1] | (2-Pyridin-4-yl-5,6,7,8-tetrahydro-benzo[4,5]thieno[2,3-d]pyrimidin-4-yl)-(R)-pyrrolidin-3-yl-amine |
| 20 | C* | 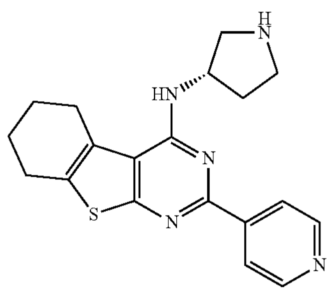 [SMILES: c1cc(-c2nc(N[C@H]3CCNC3)c3c4c(sc3n2)CCCC4)ccn1] | (2-Pyridin-4-yl-5,6,7,8-tetrahydro-benzo[4,5]thieno[2,3-d]pyrimidin-4-yl)-(S)-pyrrolidin-3-yl-amine |
| 21 | B* | 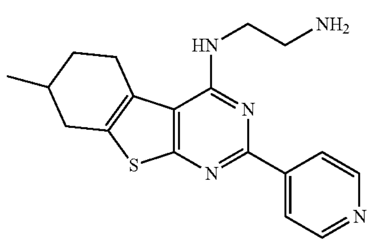 [SMILES: CC1CCc2c(sc3nc(-c4ccncc4)nc(NCCN)c23)C1] | N*1*-(7-Methyl-2-pyridin-4-yl-5,6,7,8-tetrahydro-benzo[4,5]thieno[2,3-d]pyrimidin-4-yl)-ethane-1,2-diamine |
| 22 | C* | 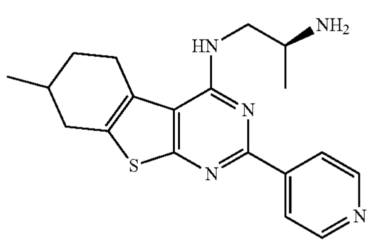 [SMILES: CC1CCc2c(sc3nc(-c4ccncc4)nc(NC[C@H](C)N)c23)C1] | (S)-N*1*-(7-Methyl-2-pyridin-4-yl-5,6,7,8-tetrahydro-benzo[4,5]thieno[2,3-d]pyrimidin-4-yl)-propane-1,2-diamine |
| 23 | C* | 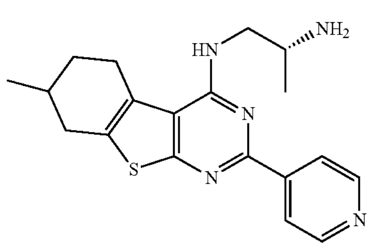 [SMILES: CC1CCc2c(sc3nc(-c4ccncc4)nc(NC[C@@H](C)N)c23)C1] | (R)-N*1*-(7-Methyl-2-pyridin-4-yl-5,6,7,8-tetrahydro-benzo[4,5]thieno[2,3-d]pyrimidin-4-yl)-propane-1,2-diamine |

-continued

| Ex | Activity | Structure | Name |
|---|---|---|---|
| 24 | B* | 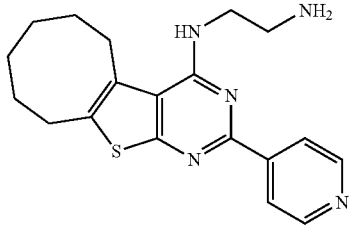 [SMILES: NCCNc1nc(-c2ccncc2)nc2sc3c(c12)CCCCCC3] | N*1*-(2-Pyridin-4-yl-5,6,7,8,9,10-hexahydro-11-thia-1,3-diaza-cycloocta[a]inden-4-yl)-ethane-1,2-diamine |
| 25 | C* | 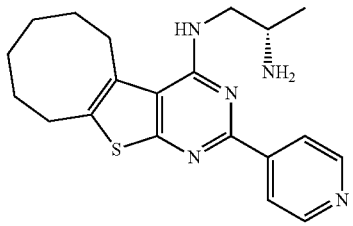 [SMILES: C[C@H](N)CNc1nc(-c2ccncc2)nc2sc3c(c12)CCCCCC3] | (S)-N*1*-(2-Pyridin-4-yl-5,6,7,8,9,10-hexahydro-11-thia-1,3-diaza-cycloocta[a]inden-4-yl)-propane-1,2-diamine |
| 26 | C* | 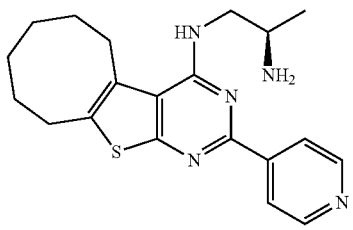 [SMILES: C[C@@H](N)CNc1nc(-c2ccncc2)nc2sc3c(c12)CCCCCC3] | (R)-N*1*-(2-Pyridin-4-yl-5,6,7,8,9,10-hexahydro-11-thia-1,3-diaza-cycloocta[a]inden-4-yl)-propane-1,2-diamine |
| 27 | D | 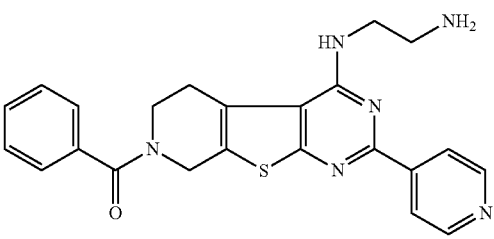 [SMILES: NCCNc1nc(-c2ccncc2)nc2sc3c(c12)CCN(C(=O)c1ccccc1)C3] | [4-(2-Amino-ethylamino)-2-pyridin-4-yl-5,8-dihydro-6H-pyrido[4',3':4,5]thieno[2,3-d]pyrimidin-7-yl]-phenyl-methanone |
| 28 | B* | 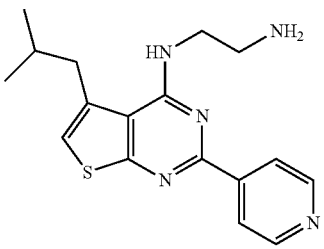 [SMILES: CC(C)Cc1csc2nc(-c3ccncc3)nc(NCCN)c12] | N*1*-(5-Isobutyl-2-pyridin-4-yl-thieno[2,3-d]pyrimidin-4-yl)-ethane-1,2-diamine |
| 29 | B* | 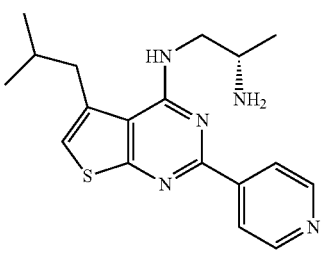 [SMILES: CC(C)Cc1csc2nc(-c3ccncc3)nc(NC[C@H](C)N)c12] | (S)-N*1*-(5-Isobutyl-2-pyridin-4-yl-thieno[2,3-d]pyrimidin-4-yl)-propane-1,2-diamine |

| Ex | Activity | Structure | Name |
|----|----------|-----------|------|
| 30 | C* | 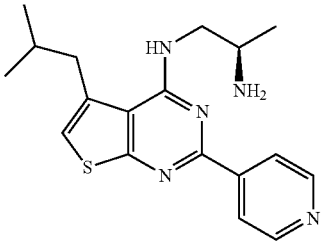 [SMILES: CC(C)Cc1csc2nc(-c3ccncc3)nc(NC[C@@H](C)N)c12] | (R)-N*1*-(5-Isobutyl-2-pyridin-4-yl-thieno[2,3-d]pyrimidin-4-yl)-propane-1,2-diamine |
| 31 | C* | 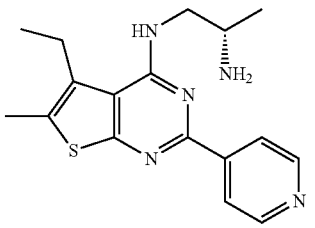 [SMILES: CCc1c(C)sc2nc(-c3ccncc3)nc(NC[C@H](C)N)c12] | (S)-N*1*-(5-Ethyl-6-methyl-2-pyridin-4-yl-thieno[2,3-d]pyrimidin-4-yl)-propane-1,2-diamine |
| 32 | D* | 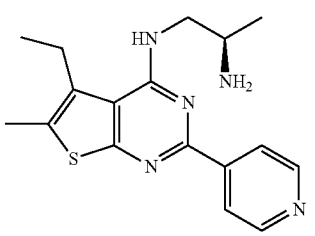 [SMILES: CCc1c(C)sc2nc(-c3ccncc3)nc(NC[C@@H](C)N)c12] | (R)-N*1*-(5-Ethyl-6-methyl-2-pyridin-4-yl-thieno[2,3-d]pyrimidin-4-yl)-propane-1,2-diamine |
| 33 | C* | 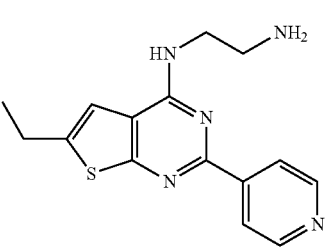 [SMILES: CCc1cc2c(NCCN)nc(-c3ccncc3)nc2s1] | N*1*-(6-Ethyl-2-pyridin-4-yl-thieno[2,3-d]pyrimidin-4-yl)-ethane-1,2-diamine |
| 34 | C* | 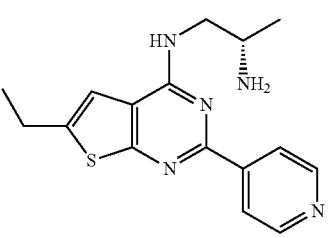 [SMILES: CCc1cc2c(NC[C@H](C)N)nc(-c3ccncc3)nc2s1] | (S)-N*1*-(6-Ethyl-2-pyridin-4-yl-thieno[2,3-d]pyrimidin-4-yl)-propane-1,2-diamine |
| 35 | C* | 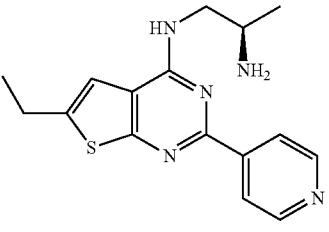 [SMILES: CCc1cc2c(NC[C@@H](C)N)nc(-c3ccncc3)nc2s1] | (R)-N*1*-(6-Ethyl-2-pyridin-4-yl-thieno[2,3-d]pyrimidin-4-yl)-propane-1,2-diamine |

-continued

| Ex | Activity | Structure | Name |
|---|---|---|---|
| 36 | B* | 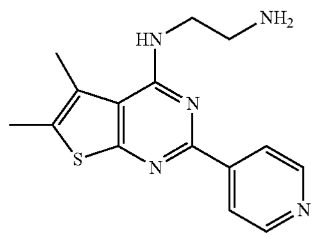 [SMILES: Cc1sc2nc(-c3ccncc3)nc(NCCN)c2c1C] | N*1*-(5,6-Dimethyl-2-pyridin-4-yl-thieno[2,3-d]pyrimidin-4-yl)-ethane-1,2-diamine |
| 37 | C* | 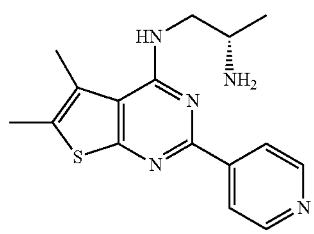 [SMILES: Cc1sc2nc(-c3ccncc3)nc(NC[C@H](C)N)c2c1C] | (S)-N*1*-(5,6-Dimethyl-2-pyridin-4-yl-thieno[2,3-d]pyrimidin-4-yl)-propane-1,2-diamine |
| 38 | C* | 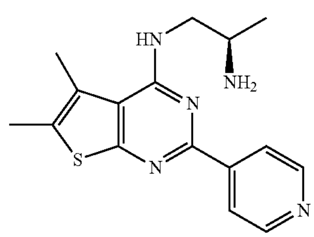 [SMILES: Cc1sc2nc(-c3ccncc3)nc(NC[C@@H](C)N)c2c1C] | (R)-N*1*-(5,6-Dimethyl-2-pyridin-4-yl-thieno[2,3-d]pyrimidin-4-yl)-propane-1,2-diamine |
| 39 | B* | 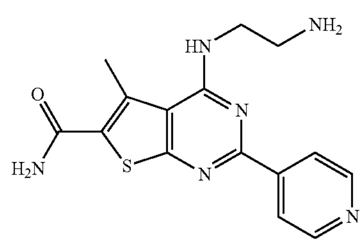 [SMILES: Cc1c(C(N)=O)sc2nc(-c3ccncc3)nc(NCCN)c12] | 4-(2-Amino-ethylamino)-5-methyl-2-pyridin-4-yl-thieno[2,3-d]pyrimidine-6-carboxylic acid amide |
| 40 | C* | 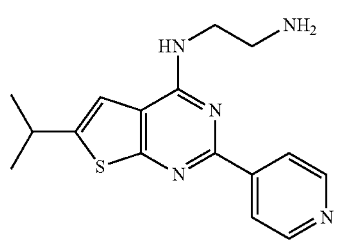 [SMILES: CC(C)c1cc2c(NCCN)nc(-c3ccncc3)nc2s1] | N*1*-(6-Isopropyl-2-pyridin-4-yl-thieno[2,3-d]pyrimidin-4-yl)-ethane-1,2-diamine |
| 41 | D* | 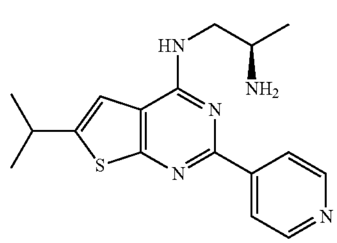 [SMILES: CC(C)c1cc2c(NC[C@@H](C)N)nc(-c3ccncc3)nc2s1] | (R)-N*1*-(6-Isopropyl-2-pyridin-4-yl-thieno[2,3-d]pyrimidin-4-yl)-propane-1,2-diamine |

| Ex | Activity | Structure | Name |
|----|----------|-----------|------|
| 42 | C | 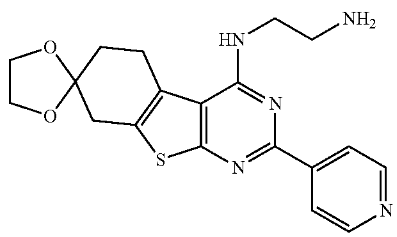 [SMILES: NCCNc1nc(-c2ccncc2)nc2sc3c(c12)CCC1(C3)OCCO1] | N*1*-1,4-Dioxa-spiro[7.7]-(2-pyridin-4-yl-5,6,7,8-tetrahydro-benzo[4,5]thieno[2,3-d]pyrimidin-4-yl)-propane-1,2-diamine |
| 43 | C | 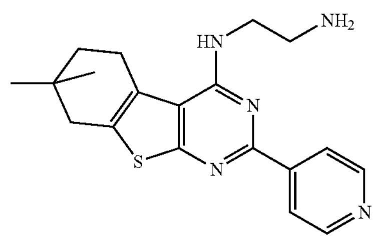 | N*1*-(7,7-Dimethyl-2-pyridin-4-yl-5,6,7,8-tetrahydro-benzo[4,5]thieno[2,3-d]pyrimidin-4-yl)-ethane-1,2-diamine |
| 44 | C | 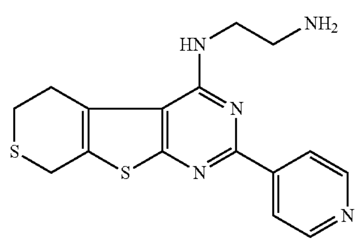 [SMILES: NCCNc1nc(-c2ccncc2)nc2sc3c(c12)CCSC3] | N*1*-(2-Pyridin-4-yl-5,8-dihydro-6H-thio-pyrano[4',3':4,5]thieno[2,3-d]pyrimidin-4-yl)-ethane-1,2-diamine |
| 45 | D | 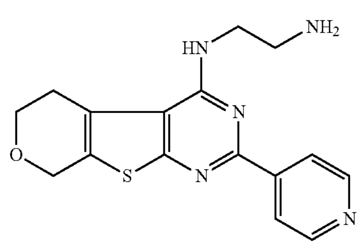 [SMILES: NCCNc1nc(-c2ccncc2)nc2sc3c(c12)CCOC3] | N*1*-(2-Pyridin-4-yl-5,8-dihydro-6H-pyrano[4'3':4,5]thieno[2,3-d]pyrimidin-4-yl)-ethane-1,2-diamine |
| 46 | C | 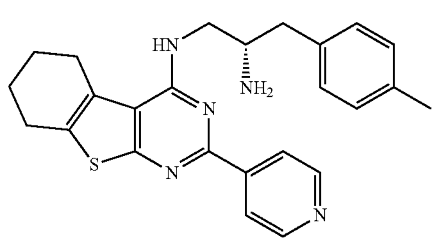 [SMILES: Cc1ccc(C[C@H](N)CNc2nc(-c3ccncc3)nc3sc4c(c23)CCCC4)cc1] | (S)-N*1*-(2-Pyridin-4-yl-5,6,7,8-tetrahydro-benzo[4,5]thieno[2,3-d]pyrimidin-4-yl)-3-p-tolyl-propane-1,2-diamine |
| 47 | B | 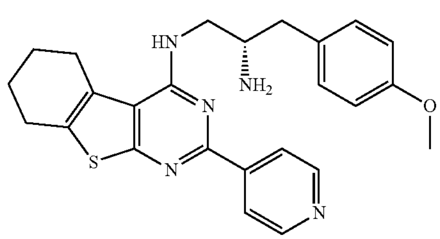 [SMILES: COc1ccc(C[C@H](N)CNc2nc(-c3ccncc3)nc3sc4c(c23)CCCC4)cc1] | (S)-3-(4-Methoxy-phenyl)-N*1*-(2-pyridin-4-yl-5,6,7,8-tetrahydro-benzo[4,5]thieno[2,3-d]pyrimidin-4-yl)-propane-1,2-diamine |

-continued

| Ex | Activity | Structure | Name |
|---|---|---|---|
| 48 | B | 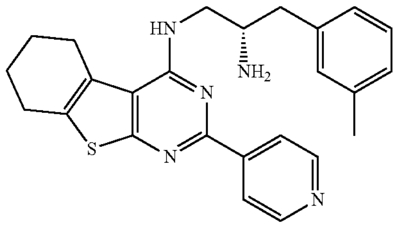 | (S)-N*1*-(2-Pyridin-4-yl-5,6,7,8-tetrahydro-benzo[4,5]thieno[2,3-d]pyrimidin-4-yl)-3-m-tolyl-propane-1,2-diamine |
| 49 | C | 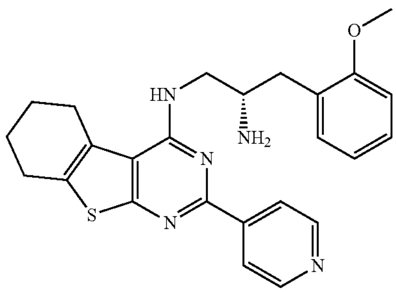 [SMILES: COc1ccccc1C[C@H](N)CNc1nc(-c2ccncc2)nc2sc3c(c12)CCCC3] | (S)-3-(2-Methoxy-phenyl)-N*1*-(2-pyridin-4-yl-5,6,7,8-tetrahydro-benzo[4,5]thieno[2,3-d]pyrimidin-4-yl)-propane-1,2-diamine |
| 50 | C | 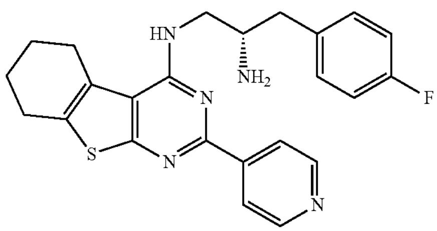 [SMILES: N[C@H](CNc1nc(-c2ccncc2)nc2sc3c(c12)CCCC3)Cc1ccc(F)cc1] | (S)-3-(4-Fluoro-phenyl)-N*1*-(2-pyridin-4-yl-5,6,7,8-tetrahydro-benzo[4,5]thieno[2,3-d]pyrimidin-4-yl)-propane-1,2-diamine |
| 51 | B | 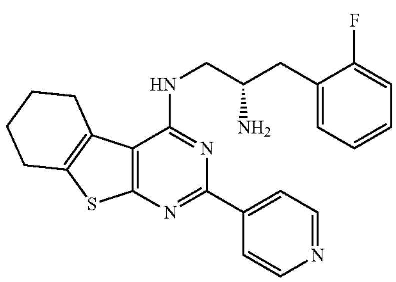 [SMILES: N[C@H](CNc1nc(-c2ccncc2)nc2sc3c(c12)CCCC3)Cc1ccccc1F] | (S)-3-(2-Fluoro-phenyl)-N*1*-(2-pyridin-4-yl-5,6,7,8-tetrahydro-benzo[4,5]thieno[2,3-d]pyrimidin-4-yl)-propane-1,2-diamine |
| 52 | C | 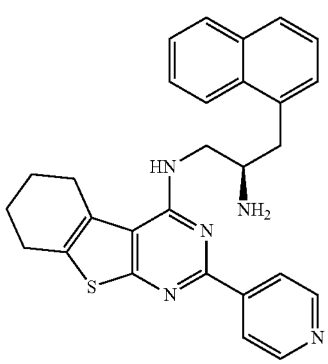 [SMILES: N[C@@H](CNc1nc(-c2ccncc2)nc2sc3c(c12)CCCC3)Cc1cccc2ccccc12] | (R)-3-Naphthalen-1-yl-N*1*-(2-pyridin-4-yl-5,6,7,8-tetrahydro-benzo[4,5]thieno[2,3-d]pyrimidin-4-yl)-propane-1,2-diamine |

| Ex | Activity | Structure | Name |
|---|---|---|---|
| 53 | B | 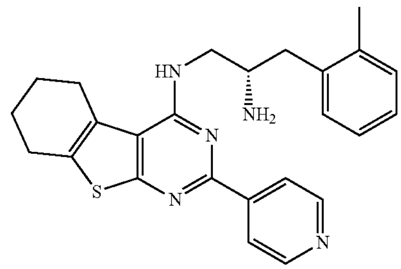 | (S)-N*1*-(2-Pyridin-4-yl-5,6,7,8-tetrahydro-benzo[4,5]thieno[2,3-d]pyrimidin-4-yl)-3-o-tolyl-propane-1,2-diamine |
| 54 | C | 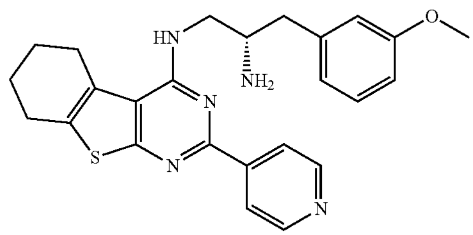 [SMILES: COc1cccc(C[C@H](N)CNc2nc(-c3ccncc3)nc3sc4c(c23)CCCC4)c1] | (S)-3-(3-Methoxy-phenyl)-N*1*-(2-pyridin-4-yl-5,6,7,8-tetrahydro-benzo[4,5]thieno[2,3-d]pyrimidin-4-yl)-propane-1,2-diamine |
| 55 | C | 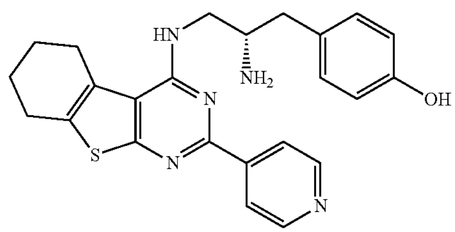 [SMILES: N[C@H](CNc1nc(-c2ccncc2)nc2sc3c(c12)CCCC3)Cc1ccc(O)cc1] | 4-[(S)-2-Amino-3-(2-pyridin-4-yl-5,6,7,8-tetrahydro-benzo[4,5]thieno[2,3-d]pyrimidin-4-ylamino)-propyl]-phenol |
| 56 | C | 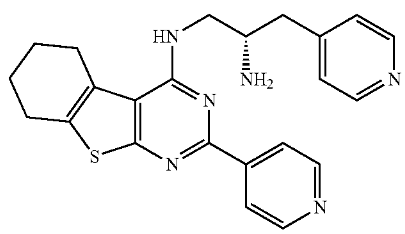 [SMILES: N[C@H](CNc1nc(-c2ccncc2)nc2sc3c(c12)CCCC3)Cc1ccncc1] | (S)-3-Pyridin-4-yl-N*1*-(2-pyridin-4-yl-5,6,7,8-tetrahydro-benzo[4,5]thieno[2,3-d]pyrimidin-4-yl)-propane-1,2-diamine |
| 57 | B | 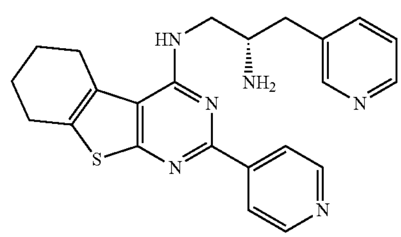 [SMILES: N[C@H](CNc1nc(-c2ccncc2)nc2sc3c(c12)CCCC3)Cc1cccnc1] | (S)-3-Pyridin-3-yl-N*1*-(2-pyridin-4-yl-5,6,7,8-tetrahydro-benzo[4,5]thieno[2,3-d]pyrimidin-4-yl)-propane-1,2-diamine |
| 58 | C | 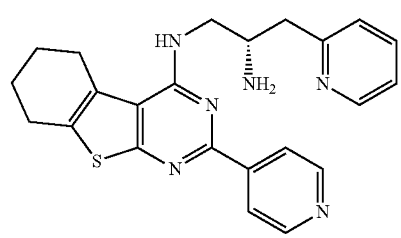 | (S)-3-Pyridin-2-yl-N*1*-(2-pyridin-4-yl-5,6,7,8-tetrahydro-benzo[4,5]thieno[2,3-d]pyrimidin-4-yl)-propane-1,2-diamine |

-continued

| Ex | Activity | Structure | Name |
|---|---|---|---|
| 59 | B | 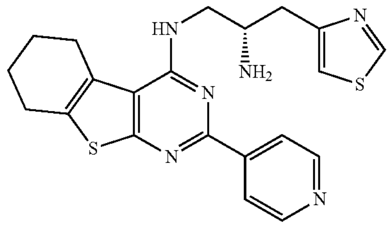 [SMILES: N[C@H](CNc1nc(-c2ccncc2)nc2sc3c(c12)CCCC3)Cc1cscn1] | (S)-N*1*-(2-Pyridin-4-yl-5,6,7,8-tetrahydro-benzo[4,5]thieno[2,3-d]pyrimidin-4-yl)-3-thiazol-4-yl-propane-1,2-diamine |
| 60 | C | 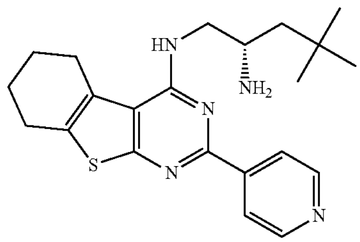 [SMILES: CC(C)(C)C[C@H](N)CNc1nc(-c2ccncc2)nc2sc3c(c12)CCCC3] | (S)-4,4-Dimethyl-N*1*-(2-pyridin-4-yl-5,6,7,8-tetrahydro-benzo[4,5]thieno[2,3-d]pyrimidin-4-yl)-pentane-1,2-diamine |
| 61 | C | 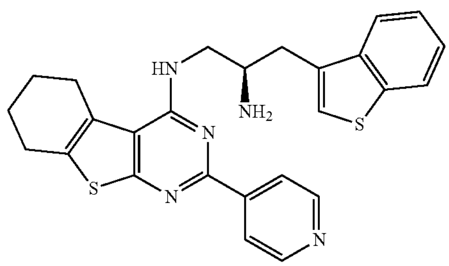 [SMILES: N[C@@H](CNc1nc(-c2ccncc2)nc2sc3c(c12)CCCC3)Cc1csc2ccccc12] | (R)-3-Benzo[b]thiophen-3-yl-N*1*-(2-pyridin-4-yl-5,6,7,8-tetrahydro-benzo[4,5]thieno[2,3-d]pyrimidin-4-yl)-propane-1,2-diamine |
| 62 | C | 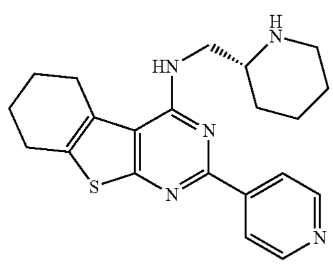 [SMILES: c1cc(-c2nc(NC[C@H]3CCCCN3)c3c4c(sc3n2)CCCC4)ccn1] | (R)-1-Piperidin-2-ylmethyl-(2-pyridin-4-yl-5,6,7,8-tetrahydro-benzo[4,5]thieno[2,3-d]pyrimidin-4-yl)-amine |
| 63 | C | 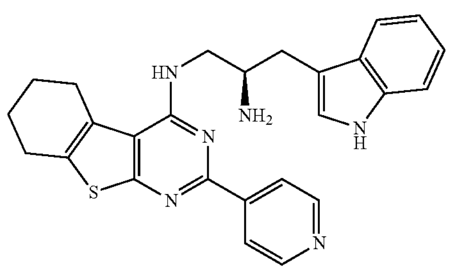 [SMILES: N[C@@H](CNc1nc(-c2ccncc2)nc2sc3c(c12)CCCC3)Cc1c[nH]c2ccccc12] | (S)-3-(1H-Indol-3-yl)-N*1*-(2-pyridin-4-yl-5,6,7,8-tetrahydro-benzo[4,5]thieno[2,3-d]pyrimidin-4-yl)-propane-1,2-diamine |
| 64 | D | 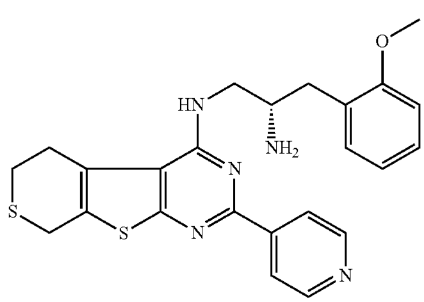 [SMILES: COc1ccccc1C[C@H](N)CNc1nc(-c2ccncc2)nc2sc3c(c12)CCSC3] | (S)-3-(2-Methoxy-phenyl)-N*1*-(2-pyridin-4-yl-5,8-dihydro-6H-thio-pyrano[4',3':4,5]thieno[2,3-d]pyrimidin-4-yl)-propane-1,2-diamine |

| Ex | Activity | Structure | Name |
|---|---|---|---|
| 65 | A | 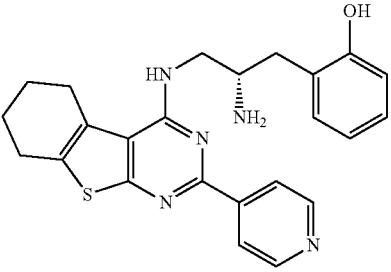 [SMILES: N[C@H](CNc1nc(-c2ccncc2)nc2sc3c(c12)CCCC3)Cc1ccccc1O] | 2-[(S)-2-Amino-3-(2-pyridin-4-yl-5,6,7,8-tetrahydro-benzo[4,5]thieno[2,3-d]pyrimidin-4-ylamino)-propyl]-phenol |
| 66 | B | 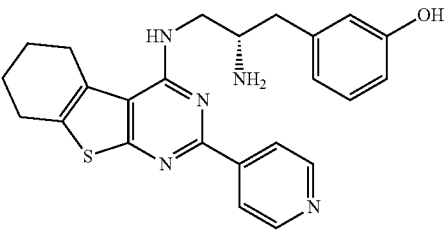 [SMILES: N[C@H](CNc1nc(-c2ccncc2)nc2sc3c(c12)CCCC3)Cc1cccc(O)c1] | 3-[(S)-2-Amino-3-(2-pyridin-4-yl-5,6,7,8-tetrahydro-benzo[4,5]thieno[2,3-d]pyrimidin-4-ylamino)-propyl]-phenol |
| 67 | A* | 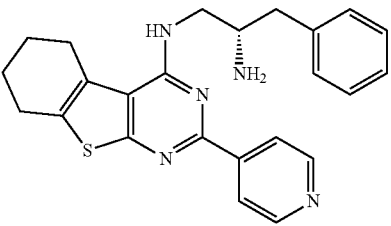 [SMILES: N[C@H](CNc1nc(-c2ccncc2)nc2sc3c(c12)CCCC3)Cc1ccccc1] | (S)-3-Phenyl-N*1*-(2-pyridin-4-yl-5,6,7,8-tetrahydro-benzo[4,5]thieno[2,3-d]pyrimidin-4-yl)-propane-1,2-diamine |
| 68 | C* | 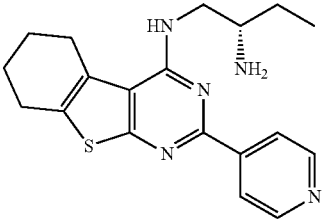 | (S)-N*1*-(2-Pyridin-4-yl-5,6,7,8-tetrahydro-benzo[4,5]thieno[2,3-d]pyrimidin-4-yl)-butane-1,2-diamine |
| 69 | B* | 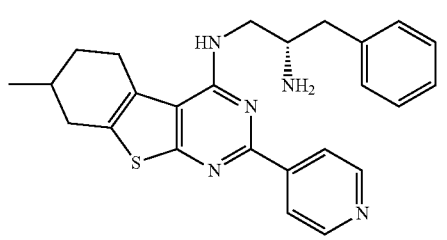 [SMILES: CC1CCc2c(sc3nc(-c4ccncc4)nc(NC[C@@H](N)Cc4ccccc4)c23)C1] | (S)-N*1*-(7-Methyl-2-pyridin-4-yl-5,6,7,8-tetrahydro-benzo[4,5]thieno[2,3-d]pyrimidin-4-yl)-3-phenyl-propane-1,2-diamine |
| 70 | C | 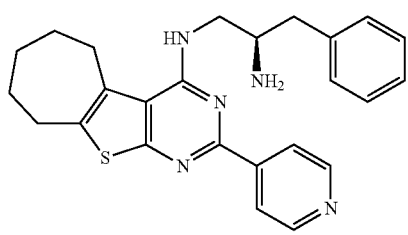 [SMILES: N[C@@H](CNc1nc(-c2ccncc2)nc2sc3c(c12)CCCCC3)Cc1ccccc1] | (R)-3-Phenyl-N*1*-(2-pyridin-4-yl-6,7,8,9-tetrahydro-5H-10-thia-1,3-diaza-benzo[a]azulen-4-yl)-propane-1,2-diamine |

| Ex | Activity | Structure | Name |
|---|---|---|---|
| 71 | C* | 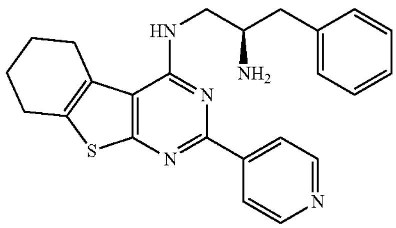 | (R)-3-Phenyl-N*1*-(2-pyridin-4-yl-5,6,7,8-tetrahydro-benzo[4,5]thieno[2,3-d]pyrimidin-4-yl)-propane-1,2-diamine |
| 72 | C | 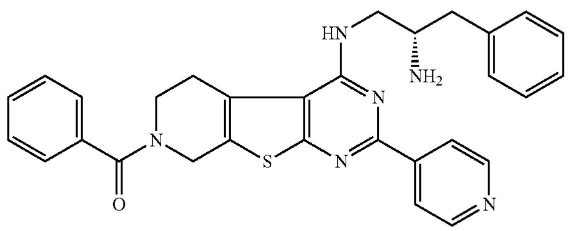 [SMILES: N[C@H](CNc1nc(-c2ccncc2)nc2sc3c(c12)CCN(C(=O)c1ccccc1)C3)Cc1ccccc1] | [4-((S)-2-Amino-3-phenyl-propylamino)-2-pyridin-4-yl-5,8-dihydro-6H-pyrido[4',3':4,5]thieno[2,3-d]pyrimidin-7-yl]-phenyl-methanone |
| 73 | C | 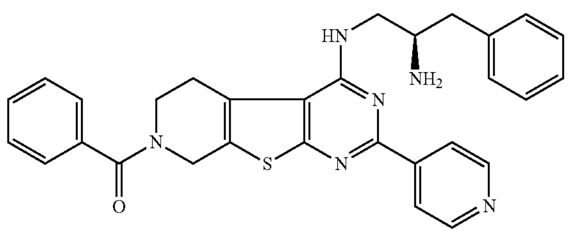 [SMILES: N[C@@H](CNc1nc(-c2ccncc2)nc2sc3c(c12)CCN(C(=O)c1ccccc1)C3)Cc1ccccc1] | [4-((R)-2-Amino-3-phenyl-propylamino)-2-pyridin-4-yl-5,8-dihydro-6H-pyrido[4',3':4,5]thieno[2,3-d]pyrimidin-7-yl]-phenyl-methanone |
| 74 | B* | 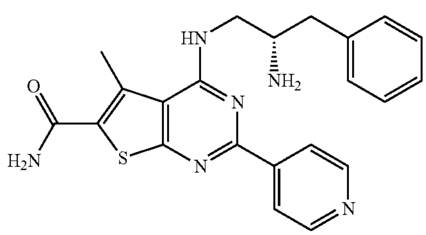 [SMILES: Cc1c(C(N)=O)sc2nc(-c3ccncc3)nc(NC[C@@H](N)Cc3ccccc3)c12] | 4-((S)-2-Amino-3-phenyl-propylamino)-5-methyl-2-pyridin-4-yl-thieno[2,3-d]pyrimidine-6-carboxylic acid amide |
| 75 | C* | 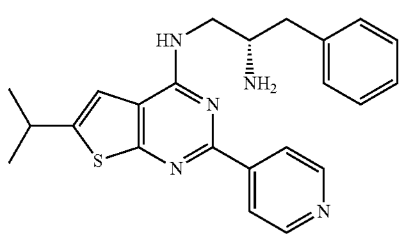 [SMILES: CC(C)c1cc2c(NC[C@@H](N)Cc3ccccc3)nc(-c3ccncc3)nc2s1] | (S)-N*1*-(6-Isopropyl-2-pyridin-4-yl-thieno[2,3-d]pyrimidin-4-yl)-3-phenyl-propane-1,2-diamine |
| 76 | B* | 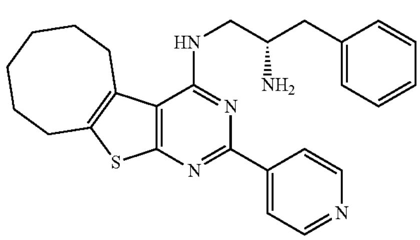 [SMILES: N[C@H](CNc1nc(-c2ccncc2)nc2sc3c(c12)CCCCCC3)Cc1ccccc1] | (S)-3-Phenyl-N*1*-(2-pyridin-4-yl-5,6,7,8,9,10-hexahydro-11-thia-1,3-diaza-cycloocta[a]inden-4-yl)-propane-1,2-diamine |

-continued

| Ex | Activity | Structure | Name |
|---|---|---|---|
| 77 | D | 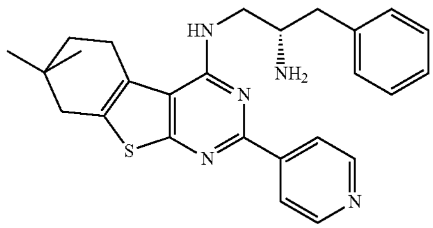 | (S)-N*1*-(7,7-Dimethyl-2-pyridin-4-yl-5,6,7,8-tetrahydro-benzo[4,5]thieno[2,3-d]pyrimidin-4-yl)-3-phenyl-propane-1,2-diamine |
| 78 | C | 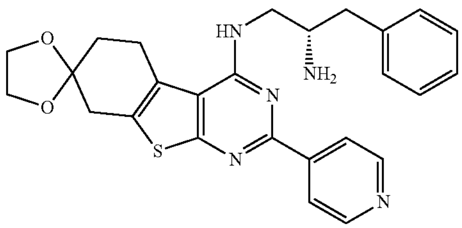 [SMILES: N[C@H](CNc1nc(-c2ccncc2)nc2sc3c(c12)CCC1(C3)OCCO1)Cc1ccccc1] | (S)-3-Phenyl-N*1*-*-1,4-Dioxa-spiro[7.7]- (2-pyridin-4-yl-5,6,7,8-tetrahydro-benzo[4,5]thieno[2,3-d]pyrimidin-4-yl)-propane-1,2-diamine |
| 79 | B | 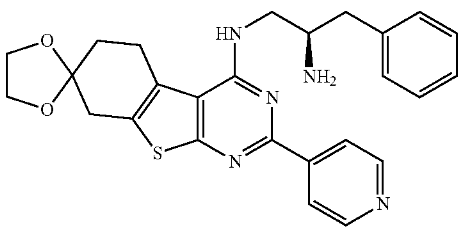 [SMILES: N[C@@H](CNc1nc(-c2ccncc2)nc2sc3c(c12)CCC1(C3)OCCO1)Cc1ccccc1] | (R)-3-Phenyl-N*1*-*-1,4-Dioxa-spiro[7.7]-(2-pyridin-4-yl-5,6,7,8-tetrahydro-benzo[4,5]thieno[2,3-d]pyrimidin-4-yl)-propane-1,2-diamine |
| 80 | B | 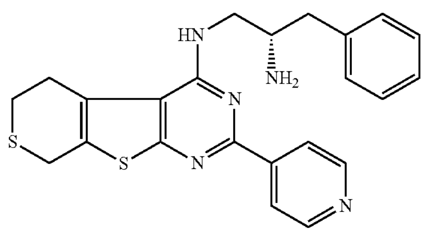 [SMILES: N[C@H](CNc1nc(-c2ccncc2)nc2sc3c(c12)CCSC3)Cc1ccccc1] | (S)-3-Phenyl-N*1*-(2-pyridin-4-yl-5,8-dihydro-6H-thiopyrano[4',3':4,5]thieno[2,3-d]pyrimidin-4-yl)-propane-1,2-diamine |
| 81 | C | 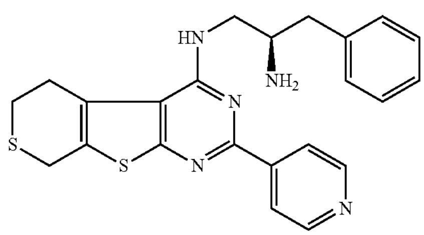 [SMILES: N[C@@H](CNc1nc(-c2ccncc2)nc2sc3c(c12)CCSC3)Cc1ccccc1] | (R)-3-Phenyl-N*1*-(2-pyridin-4-yl-5,8-dihydro-6H-thiopyrano[4',3':4,5]thieno[2,3-d]pyrimidin-4-yl)-propane-1,2-diamine |
| 82 | C | 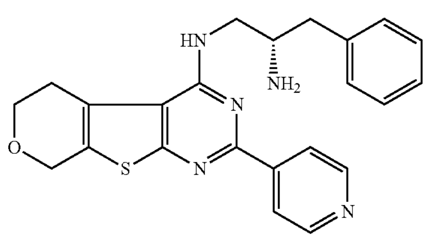 [SMILES: N[C@H](CNc1nc(-c2ccncc2)nc2sc3c(c12)CCOC3)Cc1ccccc1] | (S)-3-Phenyl-N*1*-(2-pyridin-4-yl-5,8-dihydro-6H-pyrano[4',3':4,5]thieno[2,3-d]pyrimidin-4-yl)-propane-1,2-diamine |

-continued

| Ex | Activity | Structure | Name |
|---|---|---|---|
| 83 | D | 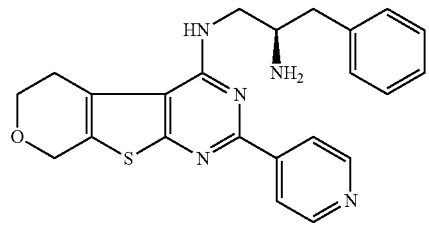 [SMILES: N[C@@H](CNc1nc(-c2ccncc2)nc2sc3c(c12)CCOC3)Cc1ccccc1] | (R)-3-Phenyl-N*1*-(2-pyridin-4-yl-5,8-dihydro-6H-pyrano[4',3':4,5]thieno[2,3-d]pyrimidin-4-yl)-propane-1,2-diamine |
| 84 | B* | 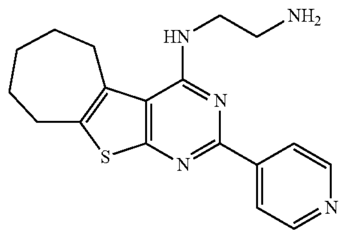 [SMILES: NCCNc1nc(-c2ccncc2)nc2sc3c(c12)CCCCC3] | N*1*-(2-Pyridin-4-yl-6,7,8,9-tetrahydro-5H-10-thia-1,3-diaza-benzo[a]azulen-4-yl)-ethane-1,2-diamine |
| 85 | B* | 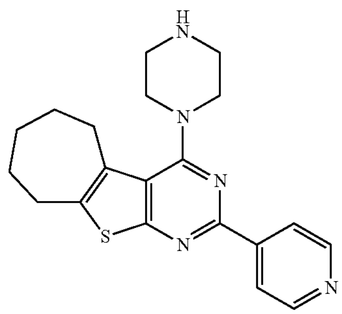 [SMILES: c1cc(-c2nc(N3CCNCC3)c3c4c(sc3n2)CCCCC4)ccn1] | 4-Piperazin-1-yl-2-pyridin-4-yl-6,7,8,9-tetrahydro-5H-10-thia-1,3-diaza-benzo[a]azulene |
| 86 | B* | 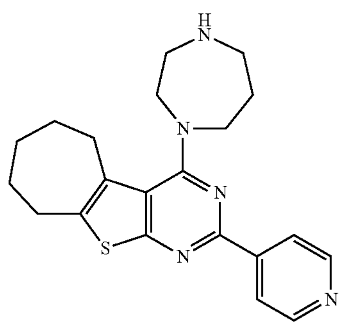 [SMILES: c1cc(-c2nc(N3CCCNCC3)c3c4c(sc3n2)CCCCC4)ccn1] | 4-[1,4]Diazepan-1-yl-2-pyridin-4-yl-6,7,8,9-tetrahydro-5H-10-thia-1,3-diaza-benzo[a]azulene |
| 87 | B* | 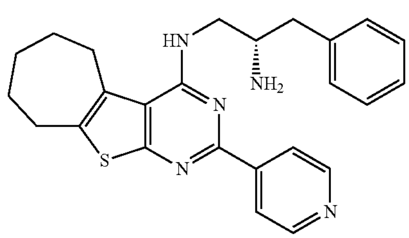 [SMILES: N[C@H](CNc1nc(-c2ccncc2)nc2sc3c(c12)CCCCC3)Cc1ccccc1] | (S)-3-Phenyl-N*1*-(2-pyridin-4-yl-6,7,8,9-tetrahydro-5H-10-thia-1,3-diaza-benzo[a]azulen-4-yl)-propane-1,2-diamine |
| 88 | B* | 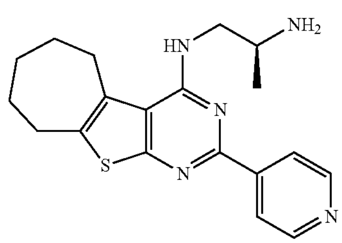 [SMILES: C[C@H](N)CNc1nc(-c2ccncc2)nc2sc3c(c12)CCCCC3] | (S)-N*1*-(2-Pyridin-4-yl-6,7,8,9-tetrahydro-5H-10-thia-1,3-diaza-benzo[a]azulen-4-yl)-propane-1,2-diamine |

-continued

| Ex | Activity | Structure | Name |
|---|---|---|---|
| 89 | B* | 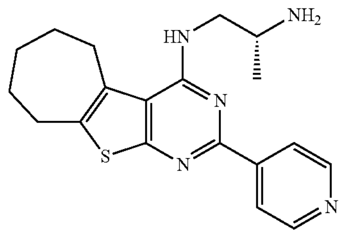 [SMILES: C[C@@H](N)CNc1nc(-c2ccncc2)nc2sc3c(c12)CCCCC3] | (R)-N*1*-(2-Pyridin-4-yl-6,7,8,9-tetrahydro-5H-10-thia-1,3-diaza-benzo[a]azulen-4-yl)-propane-1,2-diamine |
| 90 | C | 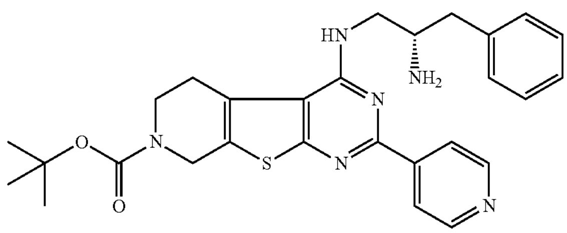 [SMILES: CC(C)(C)OC(=O)N1CCc2c(sc3nc(-c4ccncc4)nc(NC[C@@H](N)Cc4ccccc4)c23)C1] | 4-((S)-2-Amino-3-phenyl-propylamino)-2-pyridin-4-yl-5,8-dihydro-6H-pyrido[4',3':4,5]thieno[2,3-d]pyrimidine-7-carboxylic acid tert-butyl ester |
| 91 | C* | 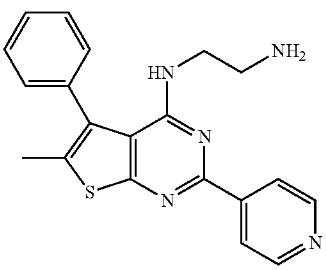 [SMILES: Cc1sc2nc(-c3ccncc3)nc(NCCN)c2c1-c1ccccc1] | N*1*-(6-Methyl-5-phenyl-2-pyridin-4-yl-thieno[2,3-d]pyrimidin-4-yl)-ethane-1,2-diamine |
| 92 | C* | 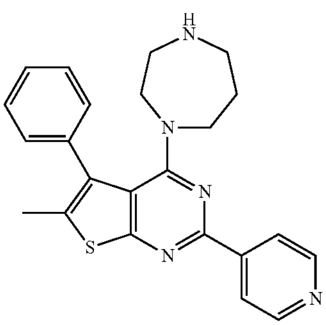 [SMILES: Cc1sc2nc(-c3ccncc3)nc(N3CCCNCC3)c2c1-c1ccccc1] | 4-[1,4]Diazepan-1-yl-6-methyl-5-phenyl-2-pyridin-4-yl-thieno[2,3-d]pyrimidine |
| 93 | C* | 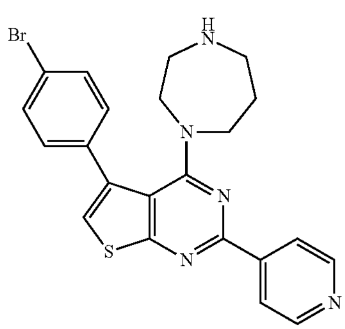 [SMILES: Brc1ccc(-c2csc3nc(-c4ccncc4)nc(N4CCCNCC4)c23)cc1] | 5-(4-Bromo-phenyl)-4-[1,4]diazepan-1-yl-2-pyridin-4-yl-thieno[2,3-d]pyrimidine |

-continued

| Ex | Activity | Structure | Name |
|---|---|---|---|
| 94 | A* | 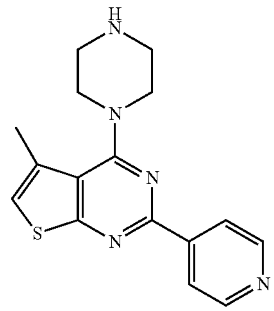 [SMILES: Cc1csc2nc(-c3ccncc3)nc(N3CCNCC3)c12] | 5-Methyl-4-piperazin-1-yl-2-pyridin-4-yl-thieno[2,3-d]pyrimidine |
| 95 | B* | 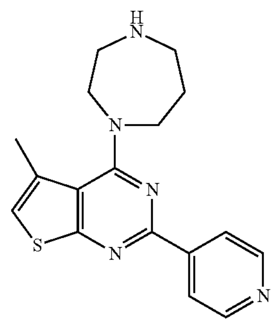 [SMILES: Cc1csc2nc(-c3ccncc3)nc(N3CCCNCC3)c12] | 4-[1,4]Diazepan-1-yl-5-methyl-2-pyridin-4-yl-thieno[2,3-d]pyrimidine |
| 96 | D | 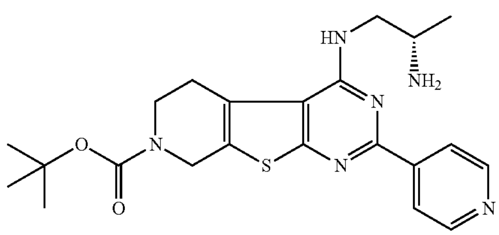 [SMILES: C[C@H](N)CNc1nc(-c2ccncc2)nc2sc3c(c12)CCN(C(=O)OC(C)(C)C)C3] | 4-((S)-2-Amino-propylamino)-2-pyridin-4-yl-5,8-dihydro-6H-pyrido[4',3':4,5]thieno[2,3-d]pyrimidine-7-carboxylic acid tert-butyl ester |
| 97 | C* | 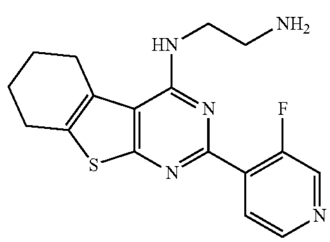 [SMILES: NCCNc1nc(-c2ccncc2F)nc2sc3c(c12)CCCC3] | N*1*-[2-(3-Fluoro-pyridin-4-yl)-5,6,7,8-tetrahydro-benzo[4,5]thieno[2,3-d]pyrimidin-4-yl]-ethane-1,2-diamine |
| 98 | D* | 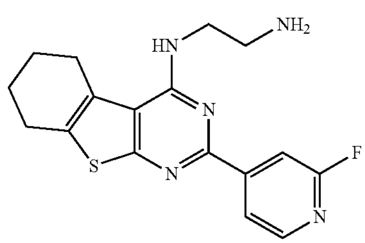 [SMILES: NCCNc1nc(-c2ccnc(F)c2)nc2sc3c(c12)CCCC3] | N*1*-[2-(2-Fluoro-pyridin-4-yl)-5,6,7,8-tetrahydro-benzo[4,5]thieno[2,3-d]pyrimidin-4-yl]-ethane-1,2-diamine |
| 99 | C* | 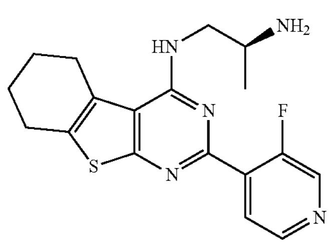 [SMILES: C[C@H](N)CNc1nc(-c2ccncc2F)nc2sc3c(c12)CCCC3] | (S)-N*1*-[2-(3-Fluoro-pyridin-4-yl)-5,6,7,8-tetrahydro-benzo[4,5]thieno[2,3-d]pyrimidin-4-yl]-propane-1,2-diamine |

| Ex | Activity | Name |
|---|---|---|
| 100 | C* | (R)-N*1*-[2-(3-Fluoro-pyridin-4-yl)-5,6,7,8-tetrahydro-benzo[4,5]thieno[2,3-d]pyrimidin-4-yl]-propane-1,2-diamine |
| 101 | C | (S)-N*1*-[2-(3-Fluoro-pyridin-4-yl)-5,6,7,8-tetrahydro-benzo[4,5]thieno[2,3-d]pyrimidin-4-yl]-3-phenyl-propane-1,2-diamine |
| 102 | D | (S)-N*1*-[2-(3-Methoxy-pyridin-4-yl)-5,6,7,8-tetrahydro-benzo[4,5]thieno[2,3-d]pyrimidin-4-yl]-3-phenyl-propane-1,2-diamine |
| 103 | C | 4-[4-((S)-2-Amino-3-phenyl-propylamino)-5,6,7,8-tetrahydro-benzo[4,5]thieno[2,3-d]pyrimidin-2-yl]-pyridin-3-ol |
| 104 | D | 1-[4-(2-Amino-ethylamino)-2-pyridin-4-yl-5,8-dihydro-6H-pyrido[4',3':4,5]thieno[2,3-d]pyrimidin-7-yl]-2,2-dimethyl-propan-1-one |
| 105 | C | 1-[4-(2-Amino-ethylamino)-2-pyridin-4-yl-5,8-dihydro-6H-pyrido[4',3':4,5]thieno[2,3-d]pyrimidin-7-yl]-ethanone |

-continued

| Ex | Activity | Structure | Name |
|---|---|---|---|
| 106 | D | 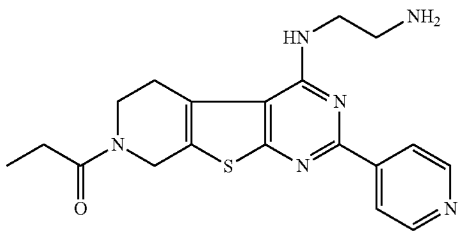 [SMILES: CCC(=O)N1CCc2c(sc3nc(-c4ccncc4)nc(NCCN)c23)C1] | 1-[4-(2-Amino-ethylamino)-2-pyridin-4-yl-5,8-dihydro-6H-pyrido[4',3':4,5]thieno[2,3-d]pyrimidin-7-yl]-propan-1-one |
| 107 | D | 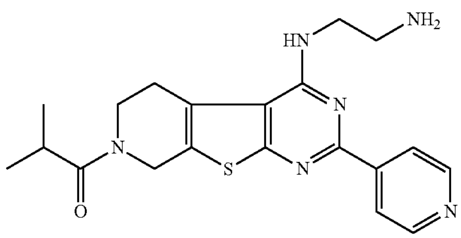 [SMILES: CC(C)C(=O)N1CCc2c(sc3nc(-c4ccncc4)nc(NCCN)c23)C1] | 1-[4-(2-Amino-ethylamino)-2-pyridin-4-yl-5,8-dihydro-6H-pyrido[4',3':4,5]thieno[2,3-d]pyrimidin-7-yl]-2-methyl-propan-1-one |
| 108 | D | 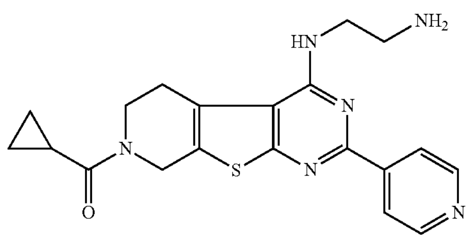 [SMILES: NCCNc1nc(-c2ccncc2)nc2sc3c(c12)CCN(C(=O)C1CC1)C3] | [4-(2-Amino-ethylamino)-2-pyridin-4-yl-5,8-dihydro-6H-pyrido[4',3':4,5]thieno[2,3-d]pyrimidin-7-yl]-cyclopropyl-methanone |
| 109 | D | 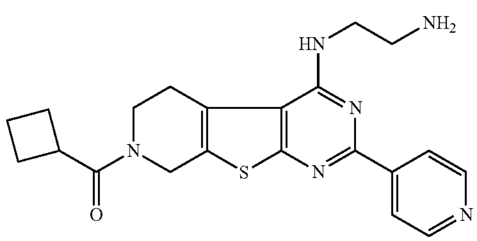 [SMILES: NCCNc1nc(-c2ccncc2)nc2sc3c(c12)CCN(C(=O)C1CCC1)C3] | [4-(2-Amino-ethylamino)-2-pyridin-4-yl-5,8-dihydro-6H-pyrido[4',3':4,5]thieno[2,3-d]pyrimidin-7-yl]-cyclobutyl-methanone |
| 110 | D | 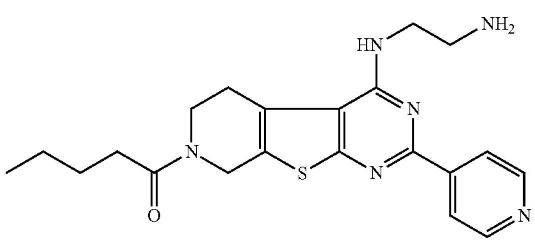 [SMILES: CCCCC(=O)N1CCc2c(sc3nc(-c4ccncc4)nc(NCCN)c23)C1] | 1-[4-(2-Amino-ethylamino)-2-pyridin-4-yl-5,8-dihydro-6H-pyrido[4',3':4,5]thieno[2,3-d]pyrimidin-7-yl]-pentan-1-one |
| 111 | D | 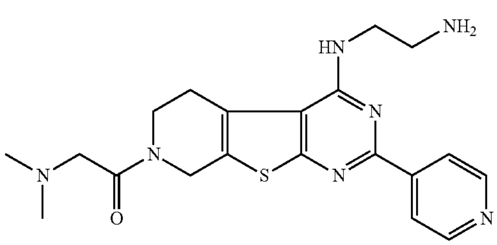 [SMILES: CN(C)CC(=O)N1CCc2c(sc3nc(-c4ccncc4)nc(NCCN)c23)C1] | 1-[4-(2-Amino-ethylamino)-2-pyridin-4-yl-5,8-dihydro-6H-pyrido[4',3':4,5]thieno[2,3-d]pyrimidin-7-yl]-2-dimethylamino-ethanone |

| Ex | Activity | Structure | Name |
|---|---|---|---|
| 112 | D | 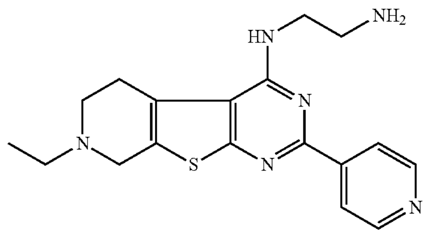 [SMILES: CCN1CCc2c(sc3nc(-c4ccncc4)nc(NCCN)c23)C1] | N*1*-(7-Ethyl-2-pyridin-4-yl-5,6,7,8-tetrahydro-pyrido[4',3':4,5]thieno[2,3-d]pyrimidin-4-yl)-ethane-1,2-Diamine |
| 113 | D | 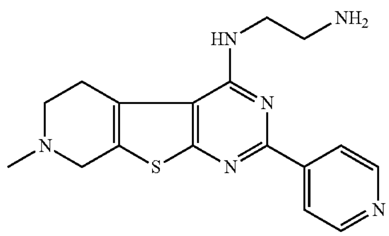 [SMILES: CN1CCc2c(sc3nc(-c4ccncc4)nc(NCCN)c23)C1] | N*1*-(7-Methyl-2-pyridin-4-yl-5,6,7,8-tetrahydro-pyrido[4',3':4,5]thieno[2,3-d]pyrimidin-4-yl)-ethane-1,2-diamine |
| 114 | D | 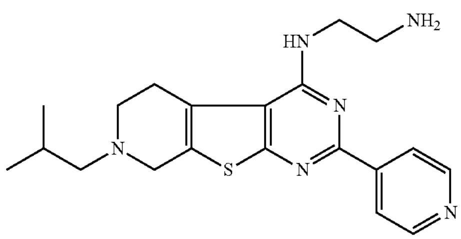 [SMILES: CC(C)CN1CCc2c(sc3nc(-c4ccncc4)nc(NCCN)c23)C1] | N*1*-(7-Isobutyl-2-pyridin-4-yl-5,6,7,8-tetrahydro-pyrido[4',3':4,5]thieno[2,3-d]pyrimidin-4-yl)-ethane-1,2-diamine |
| 115 | D* | 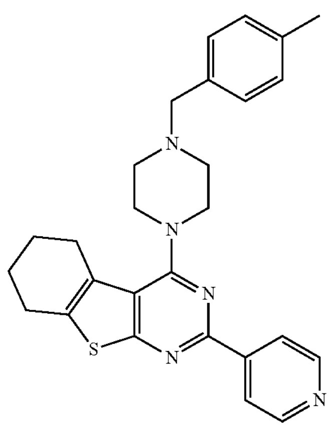 [SMILES: Cc1ccc(CN2CCN(c3nc(-c4ccncc4)nc4sc5c(c34)CCCC5)CC2)cc1] | 4-[4-(4-Methyl-benzyl)-piperazin-1-yl]-2-pyridin-4-yl-5,6,7,8-tetrahydro-benzo[4,5]thieno[2,3-d]pyrimidine |
| 116 | D* | 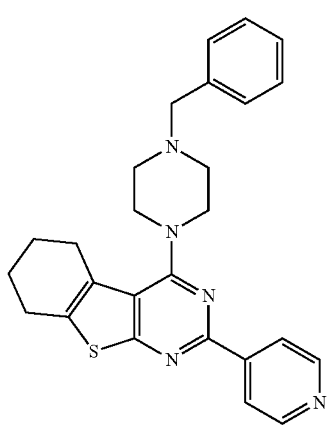 [SMILES: c1ccc(CN2CCN(c3nc(-c4ccncc4)nc4sc5c(c34)CCCC5)CC2)cc1] | 4-(4-Benzyl-piperazin-1-yl)-2-pyridin-4-yl-5,6,7,8-tetrahydro-benzo[4,5]thieno[2,3-d]pyrimidine |

-continued

| Ex | Activity | Structure | Name |
|---|---|---|---|
| 117 | D* | 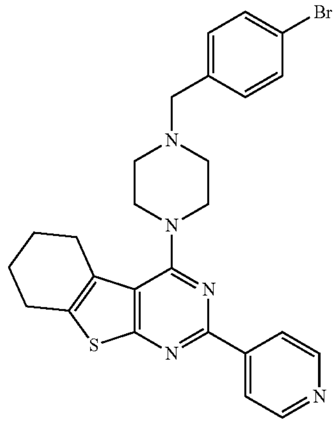 [SMILES: Brc1ccc(CN2CCN(c3nc(-c4ccncc4)nc4sc5c(c34)CCCC5)CC2)cc1] | 4-[4-(4-Bromo-benzyl)-piperazin-1-yl]-2-pyridin-4-yl-5,6,7,8-tetrahydro-benzo[4,5]thieno[2,3-d]pyrimidine |
| 118 | C* | 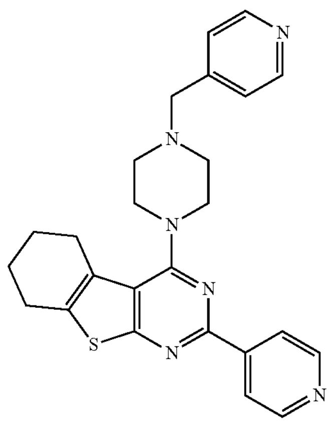 [SMILES: c1cc(CN2CCN(c3nc(-c4ccncc4)nc4sc5c(c34)CCCC5)CC2)ccn1] | 2-Pyridin-4-yl-4-(4-pyridin-4-ylmethyl-piperazin-1-yl)-5,6,7,8-tetrahydro-benzo[4,5]thieno[2,3-d]pyrimidine |
| 119 | C* | 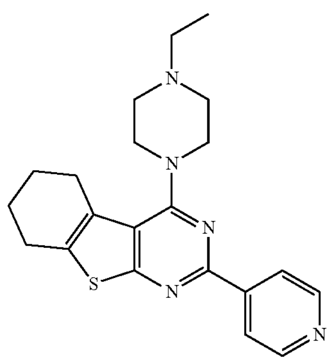 [SMILES: CCN1CCN(c2nc(-c3ccncc3)nc3sc4c(c23)CCCC4)CC1] | 4-(4-Ethyl-piperazin-1-yl)-2-pyridin-4-yl-5,6,7,8-tetrahydro-benzo[4,5]thieno[2,3-d]pyrimidine |
| 120 | D* | 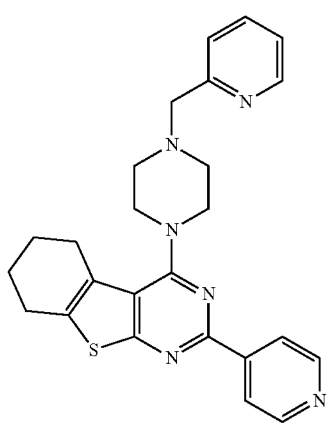 [SMILES: c1ccc(CN2CCN(c3nc(-c4ccncc4)nc4sc5c(c34)CCCC5)CC2)nc1] | 2-Pyridin-4-yl-4-(4-pyridin-2-ylmethyl-piperazin-1-yl)-5,6,7,8-tetrahydro-benzo[4,5]thieno[2,3-d]pyrimidine |

| Ex | Activity | Name |
|---|---|---|
| 121 | D* | 2-Pyridin-4-yl-4-[4-(4-trifluoromethyl-benzyl)-piperazin-1-yl]-5,6,7,8-tetrahydro-benzo[4,5]thieno[2,3-d]pyrimidine |
| 122 | D* | 4-[4-(4-Chloro-benzyl)-piperazin-1-yl]-2-pyridin-4-yl-5,6,7,8-tetrahydro-benzo[4,5]thieno[2,3-d]pyrimidine |
| 123 | D* | 4-[4-(2-Chloro-benzyl)-piperazin-1-yl]-2-pyridin-4-yl-5,6,7,8-tetrahydro-benzo[4,5]thieno[2,3-d]pyrimidine |

| Ex | Activity | Structure | Name |
|---|---|---|---|
| 124 | D* | 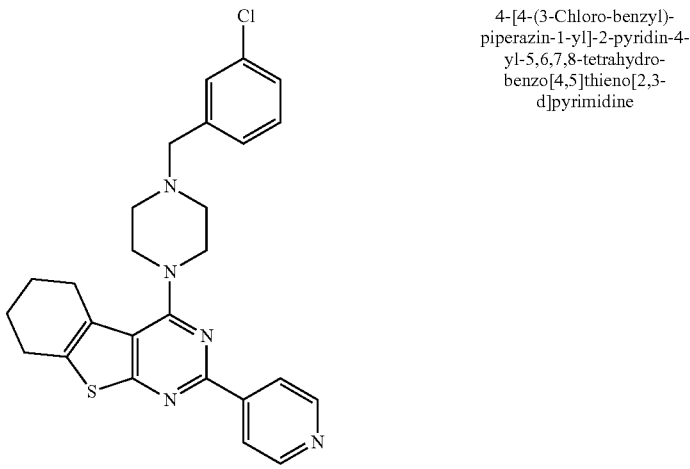 | 4-[4-(3-Chloro-benzyl)-piperazin-1-yl]-2-pyridin-4-yl-5,6,7,8-tetrahydro-benzo[4,5]thieno[2,3-d]pyrimidine |
| 125 | C* | 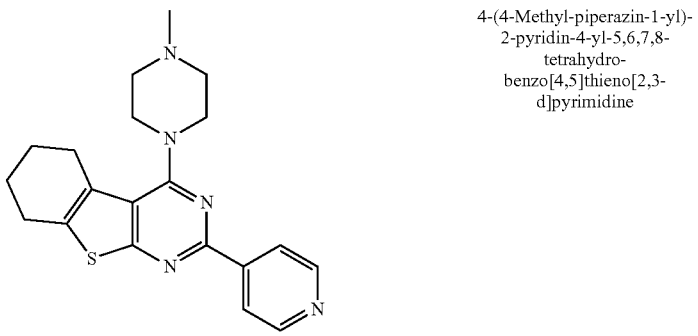 | 4-(4-Methyl-piperazin-1-yl)-2-pyridin-4-yl-5,6,7,8-tetrahydro-benzo[4,5]thieno[2,3-d]pyrimidine |
| 126 | D* | 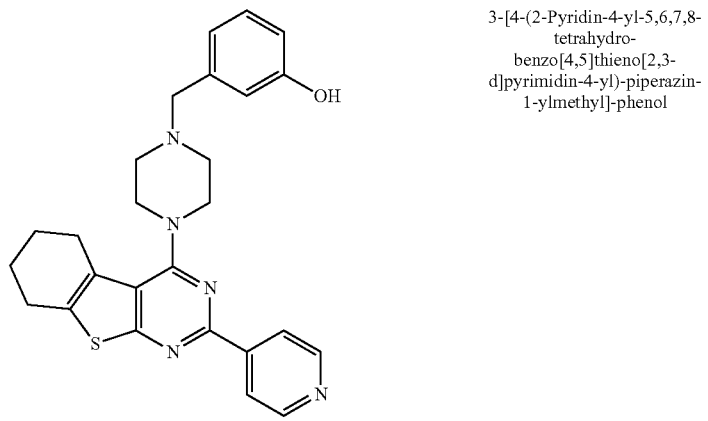 | 3-[4-(2-Pyridin-4-yl-5,6,7,8-tetrahydro-benzo[4,5]thieno[2,3-d]pyrimidin-4-yl)-piperazin-1-ylmethyl]-phenol |

-continued

| Ex | Activity | Structure | Name |
|---|---|---|---|
| 127 | D* | 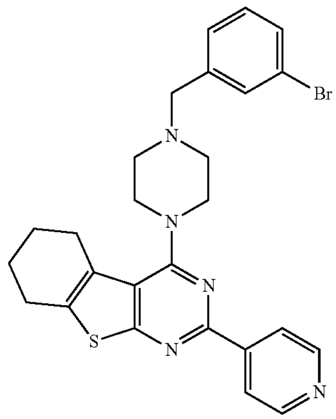 [SMILES: Brc1cccc(CN2CCN(c3nc(-c4ccncc4)nc4sc5c(c34)CCCC5)CC2)c1] | 4-[4-(3-Bromo-benzyl)-piperazin-1-yl]-2-pyridin-4-yl-5,6,7,8-tetrahydro-benzo[4,5]thieno[2,3-d]pyrimidine |
| 128 | D* | 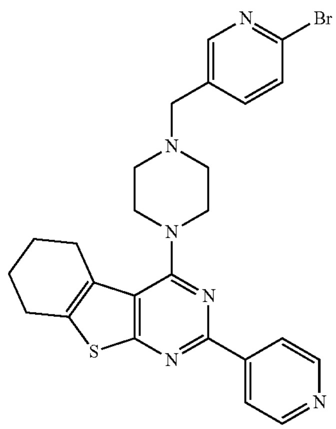 [SMILES: Brc1ccc(CN2CCN(c3nc(-c4ccncc4)nc4sc5c(c34)CCCC5)CC2)cn1] | 4-[4-(6-Bromo-pyridin-3-ylmethyl)-piperazin-1-yl]-2-pyridin-4-yl-5,6,7,8-tetrahydro-benzo[4,5]thieno[2,3-d]pyrimidine |
| 129 | D* | 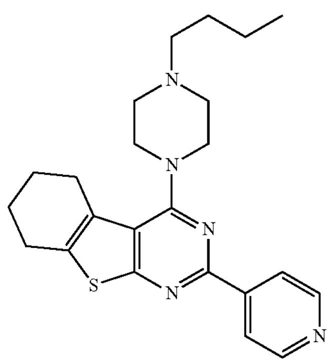 [SMILES: CCCCN1CCN(c2nc(-c3ccncc3)nc3sc4c(c23)CCCC4)CC1] | 4-(4-Butyl-piperazin-1-yl)-2-pyridin-4-yl-5,6,7,8-tetrahydro-benzo[4,5]thieno[2,3-d]pyrimidine |
| 130 | D* | 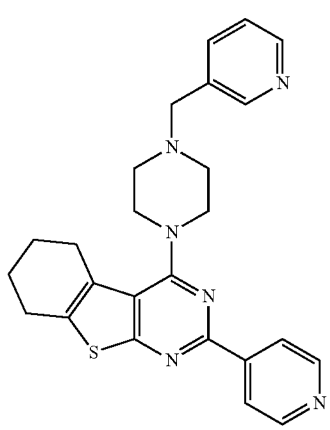 [SMILES: c1cncc(CN2CCN(c3nc(-c4ccncc4)nc4sc5c(c34)CCCC5)CC2)c1] | 2-Pyridin-4-yl-4-(4-pyridin-3-ylmethyl-piperazin-1-yl)-5,6,7,8-tetrahydro-benzo[4,5]thieno[2,3-d]pyrimidine |

| Ex | Activity | Structure | Name |
|---|---|---|---|
| 131 | D* | 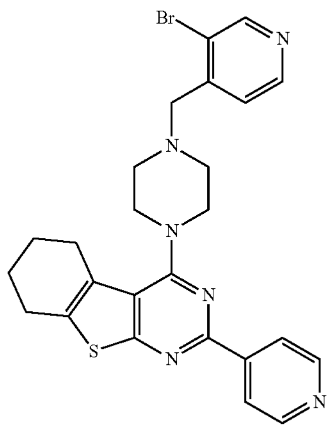 [SMILES: Brc1cnccc1CN1CCN(c2nc(-c3ccncc3)nc3sc4c(c23)CCCC4)CC1] | 4-[4-(3-Bromo-pyridin-4-ylmethyl)-piperazin-1-yl]-2-pyridin-4-yl-5,6,7,8-tetrahydro-benzo[4,5]thieno[2,3-d]pyrimidine |
| 132 | D* | 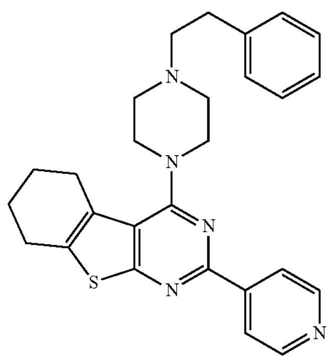 [SMILES: c1ccc(CCN2CCN(c3nc(-c4ccncc4)nc4sc5c(c34)CCCC5)CC2)cc1] | 4-(4-Phenethyl-piperazin-1-yl)-2-pyridin-4-yl-5,6,7,8-tetrahydro-benzo[4,5]thieno[2,3-d]pyrimidine |
| 133 | D* | 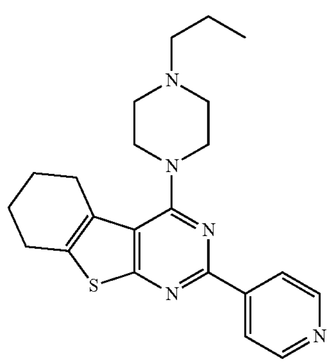 [SMILES: CCCN1CCN(c2nc(-c3ccncc3)nc3sc4c(c23)CCCC4)CC1] | 4-(4-Propyl-piperazin-1-yl)-2-pyridin-4-yl-5,6,7,8-tetrahydro-benzo[4,5]thieno[2,3-d]pyrimidine |
| 134 | D* | 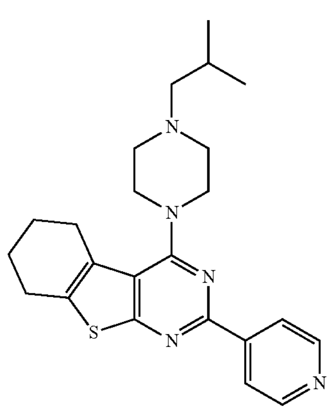 [SMILES: CC(C)CN1CCN(c2nc(-c3ccncc3)nc3sc4c(c23)CCCC4)CC1] | 4-(4-Isobutyl-piperazin-1-yl)-2-pyridin-4-yl-5,6,7,8-tetrahydro-benzo[4,5]thieno[2,3-d]pyrimidine |

| Ex | Activity | Structure | Name |
|---|---|---|---|
| 135 | C* | 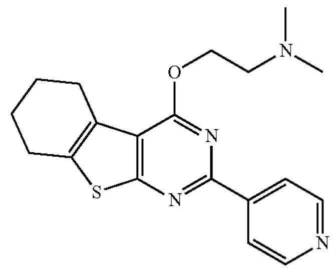 [SMILES: CN(C)CCOc1nc(-c2ccncc2)nc2sc3c(c12)CCCC3] | Dimethyl-[2-(2-pyridin-4-yl-5,6,7,8-tetrahydro-benzo[4,5]thieno[2,3-d]pyrimidin-4-yloxy)-ethyl]-amine |
| 136 | B* | 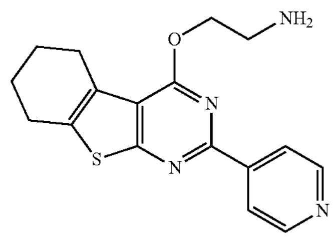 [SMILES: NCCOc1nc(-c2ccncc2)nc2sc3c(c12)CCCC3] | 2-(2-Pyridin-4-yl-5,6,7,8-tetrahydro-benzo[4,5]thieno[2,3-d]pyrimidin-4-yloxy)-ethylamine |
| 137 | C* | 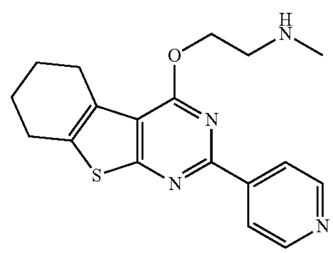 [SMILES: CNCCOc1nc(-c2ccncc2)nc2sc3c(c12)CCCC3] | Methyl-[2-(2-pyridin-4-yl-5,6,7,8-tetrahydro-benzo[4,5]thieno[2,3-d]pyrimidin-4-yloxy)-ethyl]-amine |
| 138 | C* | 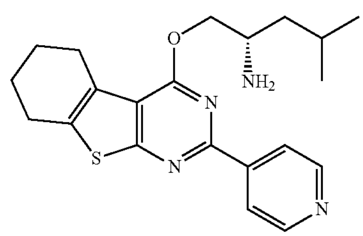 [SMILES: CC(C)C[C@H](N)COc1nc(-c2ccncc2)nc2sc3c(c12)CCCC3] | (S)-3-Methyl-1-(2-pyridin-4-yl-5,6,7,8-tetrahydro-benzo[4,5]thieno[2,3-d]pyrimidin-4-yloxymethyl)-butylamine |
| 139 | C | 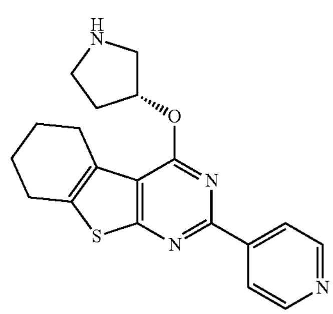 [SMILES: c1cc(-c2nc(O[C@@H]3CCNC3)c3c4c(sc3n2)CCCC4)ccn1] | 2-Pyridin-4-yl-4-((R)-pyrrolidin-3-yloxy)-5,6,7,8-tetrahydro-benzo[4,5]thieno[2,3-d]pyrimidine |
| 140 | C* | 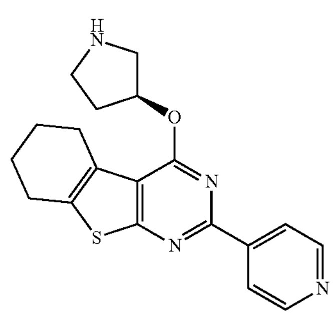 [SMILES: c1cc(-c2nc(O[C@H]3CCNC3)c3c4c(sc3n2)CCCC4)ccn1] | 2-Pyridin-4-yl-4-((S)-pyrrolidin-3-yloxy)-5,6,7,8-tetrahydro-benzo[4,5]thieno[2,3-d]pyrimidine |

| Ex | Activity | Structure | Name |
|---|---|---|---|
| 141 | C* | 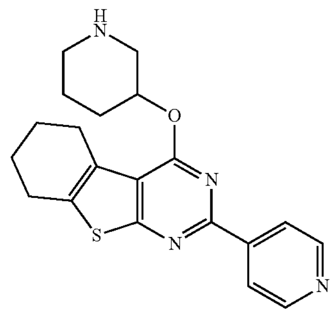 [SMILES: c1cc(-c2nc(OC3CCCNC3)c3c4c(sc3n2)CCCC4)ccn1] | 4-(Piperidin-3-yloxy)-2-pyridin-4-yl-5,6,7,8-tetrahydro-benzo[4,5]thieno[2,3-d]pyrimidine |
| 142 | D* | 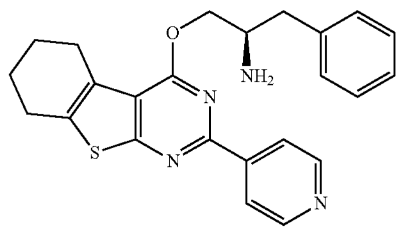 [SMILES: N[C@@H](COc1nc(-c2ccncc2)nc2sc3c(c12)CCCC3)Cc1ccccc1] | (R)-2-Phenyl-1-(2-pyridin-4-yl-5,6,7,8-tetrahydro-benzo[4,5]thieno[2,3-d]pyrimidin-4-yloxymethyl)-ethylamine |
| 143 | B* | 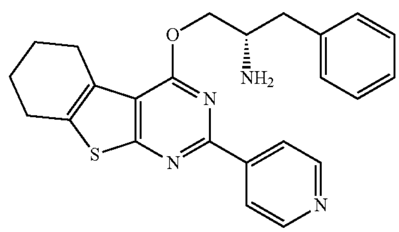 [SMILES: N[C@H](COc1nc(-c2ccncc2)nc2sc3c(c12)CCCC3)Cc1ccccc1] | (S)-2-Phenyl-1-(2-pyridin-4-yl-5,6,7,8-tetrahydro-benzo[4,5]thieno[2,3-d]pyrimidin-4-yloxymethyl)-ethylamine |
| 144 | B* | 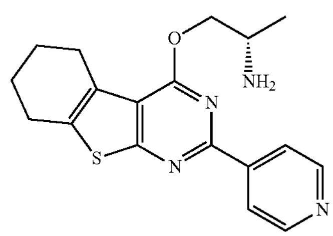 [SMILES: C[C@H](N)COc1nc(-c2ccncc2)nc2sc3c(c12)CCCC3] | (S)-1-Methyl-2-(2-pyridin-4-yl-5,6,7,8-tetrahydro-benzo[4,5]thieno[2,3-d]pyrimidin-4-yloxy)-ethylamine |
| 145 | C* | 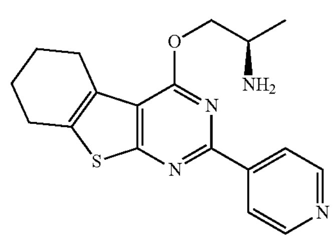 [SMILES: C[C@@H](N)COc1nc(-c2ccncc2)nc2sc3c(c12)CCCC3] | (R)-1-Methyl-2-(2-pyridin-4-yl-5,6,7,8-tetrahydro-benzo[4,5]thieno[2,3-d]pyrimidin-4-yloxy)-ethylamine |
| 146 | C* | 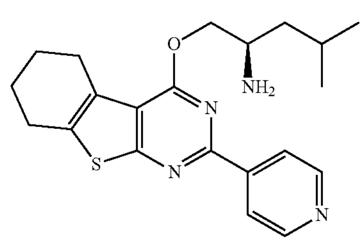 [SMILES: CC(C)C[C@@H](N)COc1nc(-c2ccncc2)nc2sc3c(c12)CCCC3] | (R)-3-Methyl-1-(2-pyridin-4-yl-5,6,7,8-tetrahydro-benzo[4,5]thieno[2,3-d]pyrimidin-4-yloxymethyl)-butylamine |

| Ex | Activity | Structure | Name |
|---|---|---|---|
| 147 | D* | 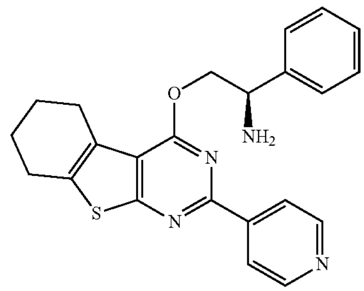 [SMILES: N[C@@H](COc1nc(-c2ccncc2)nc2sc3c(c12)CCCC3)c1ccccc1] | (R)-1-Phenyl-2-(2-pyridin-4-yl-5,6,7,8-tetrahydro-benzo[4,5]thieno[2,3-d]pyrimidin-4-yloxy)-ethylamine |
| 148 | D* | 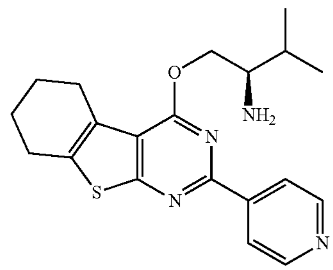 [SMILES: CC(C)[C@@H](N)COc1nc(-c2ccncc2)nc2sc3c(c12)CCCC3] | (R)-2-Methyl-1-(2-pyridin-4-yl-5,6,7,8-tetrahydro-benzo[4,5]thieno[2,3-d]pyrimidin-4-yloxymethyl)-propylamine |
| 149 | C* | 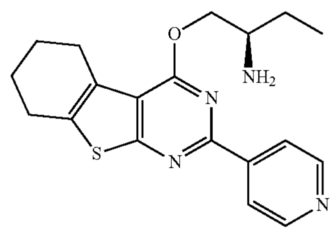 [SMILES: CC[C@@H](N)COc1nc(-c2ccncc2)nc2sc3c(c12)CCCC3] | (R)-1-(2-Pyridin-4-yl-5,6,7,8-tetrahydro-benzo[4,5]thieno[2,3-d]pyrimidin-4-yloxymethyl)-propylamine |
| 150 | C* | 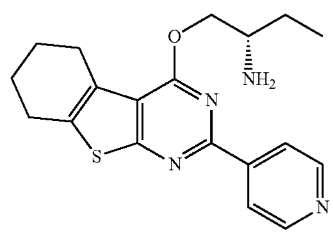 [SMILES: CC[C@H](N)COc1nc(-c2ccncc2)nc2sc3c(c12)CCCC3] | (S)-1-(2-Pyridin-4-yl-5,6,7,8-tetrahydro-benzo[4,5]thieno[2,3-d]pyrimidin-4-yloxymethyl)-propylamine |
| 151 | C* | 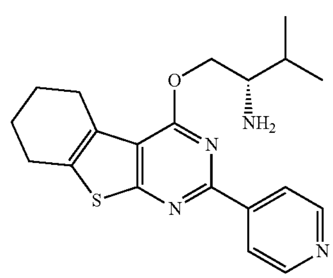 [SMILES: CC(C)[C@H](N)COc1nc(-c2ccncc2)nc2sc3c(c12)CCCC3] | (S)-2-Methyl-1-(2-pyridin-4-yl-5,6,7,8-tetrahydro-benzo[4,5]thieno[2,3-d]pyrimidin-4-yloxymethyl)-propylamine |
| 152 | C* | 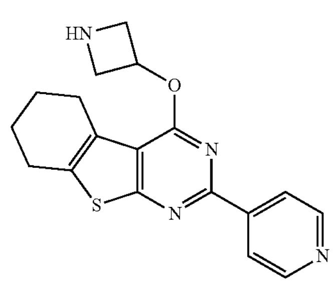 [SMILES: c1cc(-c2nc(OC3CNC3)c3c4c(sc3n2)CCCC4)ccn1] | 4-(Azetidin-3-yloxy)-2-pyridin-4-yl-5,6,7,8-tetrahydro-benzo[4,5]thieno[2,3-d]pyrimidine |

-continued

| Ex | Activity | Structure | Name |
|---|---|---|---|
| 153 | C* | 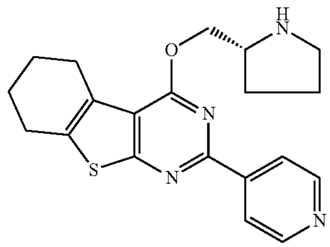 [SMILES: c1cc(-c2nc(OC[C@H]3CCCN3)c3c4c(sc3n2)CCCC4)ccn1] | 2-Pyridin-4-yl-4-((R)-1-pyrrolidin-2-ylmethoxy)-5,6,7,8-tetrahydro-benzo[4,5]thieno[2,3-d]pyrimidine |
| 154 | C* | 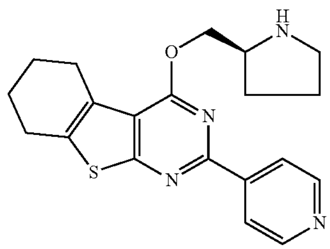 [SMILES: c1cc(-c2nc(OC[C@@H]3CCCN3)c3c4c(sc3n2)CCCC4)ccn1] | 2-Pyridin-4-yl-4-((S)-1-pyrrolidin-2-ylmethoxy)-5,6,7,8-tetrahydro-benzo[4,5]thieno[2,3-d]pyrimidine |
| 155 | C* | 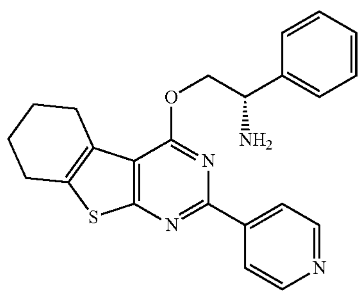 [SMILES: N[C@H](COc1nc(-c2ccncc2)nc2sc3c(c12)CCCC3)c1ccccc1] | (S)-1-Phenyl-2-(2-pyridin-4-yl-5,6,7,8-tetrahydro-benzo[4,5]thieno[2,3-d]pyrimidin-4-yloxy)-ethylamine |
| 156 | C* | 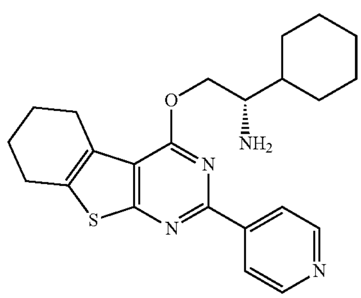 [SMILES: N[C@H](COc1nc(-c2ccncc2)nc2sc3c(c12)CCCC3)C1CCCCC1] | (S)-1-Cyclohexyl-2-(2-pyridin-4-yl-5,6,7,8-tetrahydro-benzo[4,5]thieno[2,3-d]pyrimidin-4-yloxy)-ethylamine |
| 157 | C* | 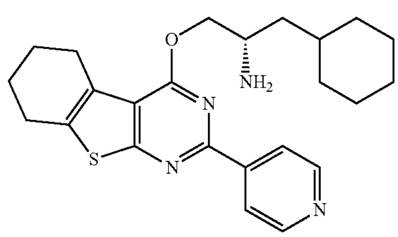 [SMILES: N[C@H](COc1nc(-c2ccncc2)nc2sc3c(c12)CCCC3)CC1CCCCC1] | (S)-2-Cyclohexyl-1-(2-pyridin-4-yl-5,6,7,8-tetrahydro-benzo[4,5]thieno[2,3-d]pyrimidin-4-yloxymethyl)-ethylamine |
| 158 | D* | 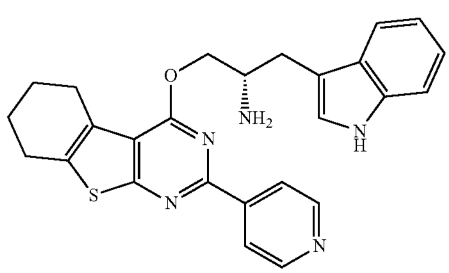 [SMILES: N[C@H](COc1nc(-c2ccncc2)nc2sc3c(c12)CCCC3)Cc1c[nH]c2ccccc12] | (S)-2-(1H-Indol-3-yl)-1-(2-pyridin-4-yl-5,6,7,8-tetrahydro-benzo[4,5]thieno[2,3-d]pyrimidin-4-yloxymethyl)-ethylamine |

-continued

| Ex | Activity | Structure | Name |
|---|---|---|---|
| 159 | C* | 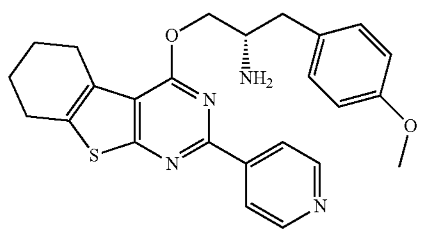 [SMILES: COc1ccc(C[C@H](N)COc2nc(-c3ccncc3)nc3sc4c(c23)CCCC4)cc1] | (S)-1-(4-Methoxy-benzyl)-2-(2-pyridin-4-yl-5,6,7,8-tetrahydro-benzo[4,5]thieno[2,3-d]pyrimidin-4-yloxy)-ethylamine |
| 160 | D* | 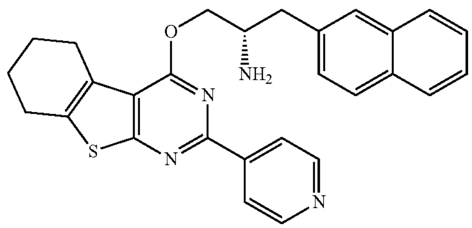 [SMILES: N[C@H](COc1nc(-c2ccncc2)nc2sc3c(c12)CCCC3)Cc1ccc2ccccc2c1] | (S)-1-Naphthalen-2-ylmethyl-2-(2-pyridin-4-yl-5,6,7,8-tetrahydro-benzo[4,5]thieno[2,3-d]pyrimidin-4-yloxy)-ethylamine |
| 161 | C* | 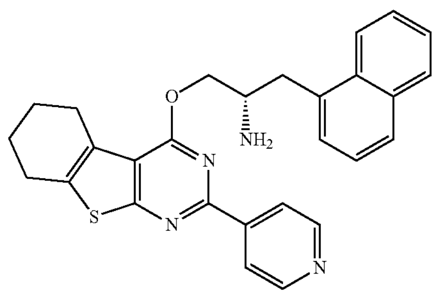 [SMILES: N[C@H](COc1nc(-c2ccncc2)nc2sc3c(c12)CCCC3)Cc1cccc2ccccc12] | (S)-1-Naphthalen-1-ylmethyl-2-(2-pyridin-4-yl-5,6,7,8-tetrahydro-benzo[4,5]thieno[2,3-d]pyrimidin-4-yloxy)-ethylamine |
| 162 | D* | 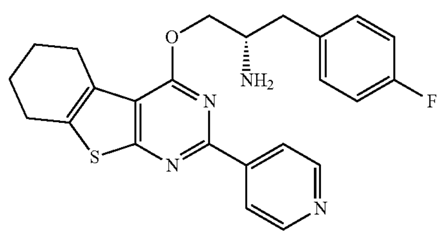 [SMILES: N[C@H](COc1nc(-c2ccncc2)nc2sc3c(c12)CCCC3)Cc1ccc(F)cc1] | (S)-1-(4-Fluoro-benzyl)-2-(2-pyridin-4-yl-5,6,7,8-tetrahydro-benzo[4,5]thieno[2,3-d]pyrimidin-4-yloxy)-ethylamine |
| 163 | C* | 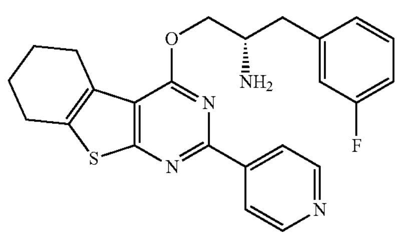 [SMILES: N[C@H](COc1nc(-c2ccncc2)nc2sc3c(c12)CCCC3)Cc1cccc(F)c1] | (S)-1-(3-Fluoro-benzyl)-2-(2-pyridin-4-yl-5,6,7,8-tetrahydro-benzo[4,5]thieno[2,3-d]pyrimidin-4-yloxy)-ethylamine |
| 164 | C* | 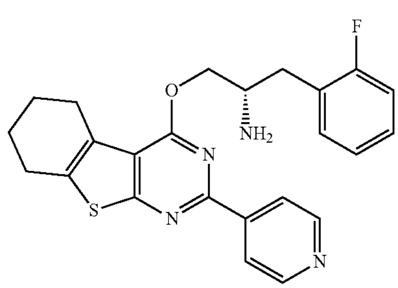 [SMILES: N[C@H](COc1nc(-c2ccncc2)nc2sc3c(c12)CCCC3)Cc1ccccc1F] | (S)-1-(2-Fluoro-benzyl)-2-(2-pyridin-4-yl-5,6,7,8-tetrahydro-benzo[4,5]thieno[2,3-d]pyrimidin-4-yloxy)-ethylamine |

-continued

| Ex | Activity | Structure | Name |
|---|---|---|---|
| 165 | C* | 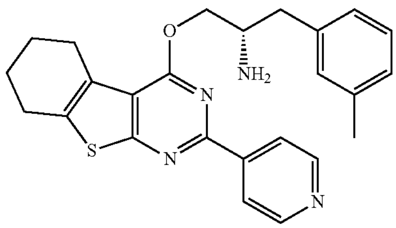 [SMILES: Cc1cccc(C[C@H](N)COc2nc(-c3ccncc3)nc3sc4c(c23)CCCC4)c1] | (S)-1-(3-Methyl-benzyl)-2-(2-pyridin-4-yl-5,6,7,8-tetrahydro-benzo[4,5]thieno[2,3-d]pyrimidin-4-yloxy)-ethylamine |
| 166 | C* | 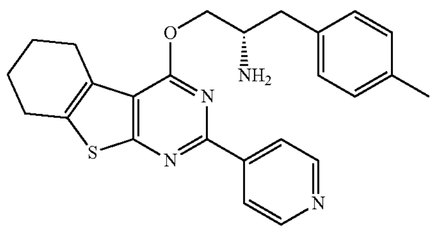 [SMILES: Cc1ccc(C[C@H](N)COc2nc(-c3ccncc3)nc3sc4c(c23)CCCC4)cc1] | (S)-1-(4-Methyl-benzyl)-2-(2-pyridin-4-yl-5,6,7,8-tetrahydro-benzo[4,5]thieno[2,3-d]pyrimidin-4-yloxy)-ethylamine |
| 167 | D* | 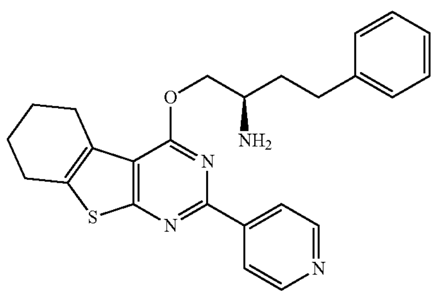 [SMILES: N[C@H](CCc1ccccc1)COc1nc(-c2ccncc2)nc2sc3c(c12)CCCC3] | (R)-3-Phenyl-1-(2-pyridin-4-yl-5,6,7,8-tetrahydro-benzo[4,5]thieno[2,3-d]pyrimidin-4-yloxymethyl)-propylamine |
| 168 | C* | 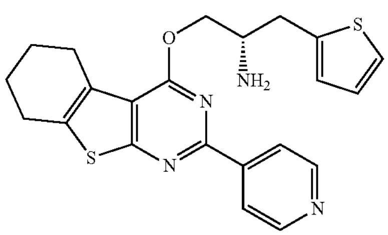 [SMILES: N[C@H](COc1nc(-c2ccncc2)nc2sc3c(c12)CCCC3)Cc1cccs1] | (S)-2-(2-Pyridin-4-yl-5,6,7,8-tetrahydro-benzo[4,5]thieno[2,3-d]pyrimidin-4-yloxy)-1-thiophen-2-ylmethyl-ethylamine |
| 169 | D* | 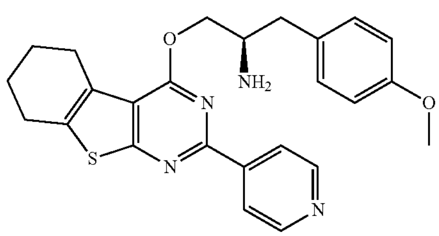 [SMILES: COc1ccc(C[C@@H](N)COc2nc(-c3ccncc3)nc3sc4c(c23)CCCC4)cc1] | (R)-1-(4-Methoxy-benzyl)-2-(2-pyridin-4-yl-5,6,7,8-tetrahydro-benzo[4,5]thieno[2,3-d]pyrimidin-4-yloxy)-ethylamine |
| 170 | D* | 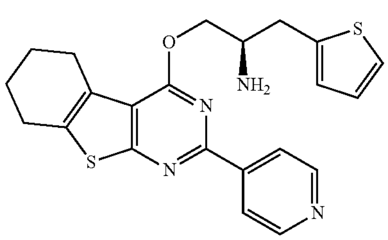 [SMILES: N[C@@H](COc1nc(-c2ccncc2)nc2sc3c(c12)CCCC3)Cc1cccs1] | (R)-2-(2-Pyridin-4-yl-5,6,7,8-tetrahydro-benzo[4,5]thieno[2,3-d]pyrimidin-4-yloxy)-1-thiophen-2-ylmethyl-ethylamine |

-continued

| Ex | Activity | Structure | Name |
|---|---|---|---|
| 171 | C* | 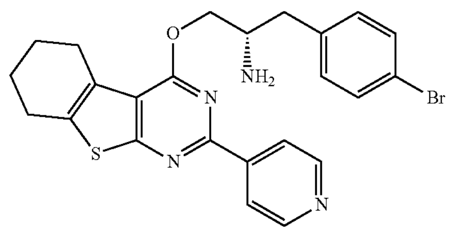 [SMILES: N[C@H](COc1nc(-c2ccncc2)nc2sc3c(c12)CCCC3)Cc1ccc(Br)cc1] | (S)-1-(4-Bromo-benzyl)-2-(2-pyridin-4-yl-5,6,7,8-tetrahydro-benzo[4,5]thieno[2,3-d]pyrimidin-4-yloxy)-ethylamine |
| 172 | D* | 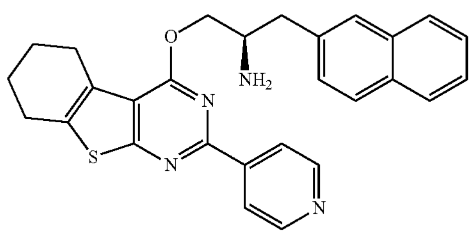 [SMILES: N[C@@H](COc1nc(-c2ccncc2)nc2sc3c(c12)CCCC3)Cc1ccc2ccccc2c1] | (R)-1-Naphthalen-2-ylmethyl-2-(2-pyridin-4-yl-5,6,7,8-tetrahydro-benzo[4,5]thieno[2,3-d]pyrimidin-4-yloxy)-ethylamine |
| 173 | C* | 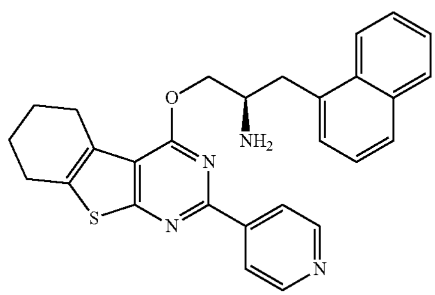 [SMILES: N[C@@H](COc1nc(-c2ccncc2)nc2sc3c(c12)CCCC3)Cc1cccc2ccccc12] | (R)-1-Naphthalen-1-ylmethyl-2-(2-pyridin-4-yl-5,6,7,8-tetrahydro-benzo[4,5]thieno[2,3-d]pyrimidin-4-yloxy)-ethylamine |
| 174 | C* | 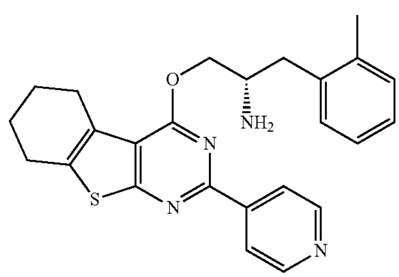 [SMILES: Cc1ccccc1C[C@H](N)COc1nc(-c2ccncc2)nc2sc3c(c12)CCCC3] | (S)-1-(2-Methyl-benzyl)-2-(2-pyridin-4-yl-5,6,7,8-tetrahydro-benzo[4,5]thieno[2,3-d]pyrimidin-4-yloxy)-ethylamine |
| 175 | D* | 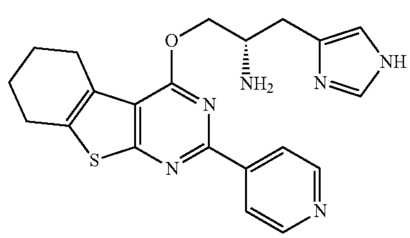 [SMILES: N[C@H](COc1nc(-c2ccncc2)nc2sc3c(c12)CCCC3)Cc1c[nH]cn1] | (S)-1-(1H-Imidazol-4-ylmethyl)-2-(2-pyridin-4-yl-5,6,7,8-tetrahydro-benzo[4,5]thieno[2,3-d]pyrimidin-4-yloxy)-ethylamine |
| 176 | D* | 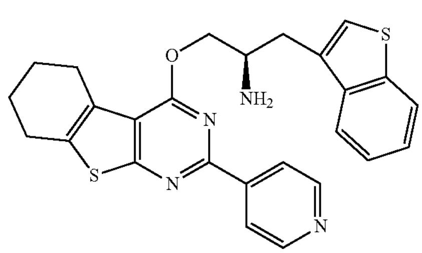 [SMILES: N[C@@H](COc1nc(-c2ccncc2)nc2sc3c(c12)CCCC3)Cc1csc2ccccc12] | (R)-1-Benzo[b]thiophen-3-ylmethyl-2-(2-pyridin-4-yl-5,6,7,8-tetrahydro-benzo[4,5]thieno[2,3-d]pyrimidin-4-yloxy)-ethylamine |

| Ex | Activity | Structure | Name |
|---|---|---|---|
| 177 | D* | 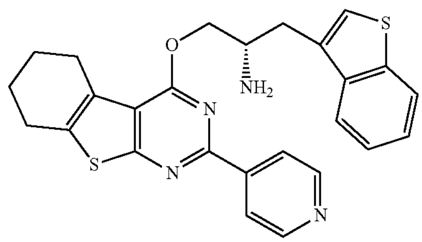 [SMILES: N[C@H](COc1nc(-c2ccncc2)nc2sc3c(c12)CCCC3)Cc1csc2ccccc12] | (S)-1-Benzo[b]thiophen-3-ylmethyl-2-(2-pyridin-4-yl-5,6,7,8-tetrahydro-benzo[4,5]thieno[2,3-d]pyrimidin-4-yloxy)-ethylamine |
| 178 | C* | 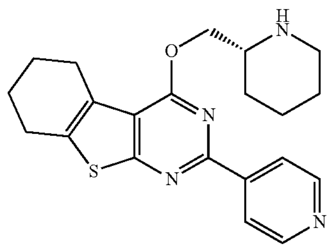 [SMILES: c1cc(-c2nc(OC[C@H]3CCCCN3)c3c4c(sc3n2)CCCC4)ccn1] | 4-((R)-1-Piperidin-2-ylmethoxy)-2-pyridin-4-yl-5,6,7,8-tetrahydro-benzo[4,5]thieno[2,3-d]pyrimidine |
| 179 | D* | 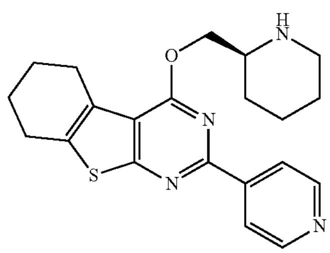 [SMILES: c1cc(-c2nc(OC[C@@H]3CCCCN3)c3c4c(sc3n2)CCCC4)ccn1] | 4-((S)-1-Piperidin-2-ylmethoxy)-2-pyridin-4-yl-5,6,7,8-tetrahydro-benzo[4,5]thieno[2,3-d]pyrimidine |
| 180 | C* | 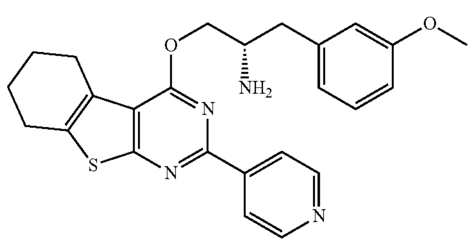 [SMILES: COc1cccc(C[C@H](N)COc2nc(-c3ccncc3)nc3sc4c(c23)CCCC4)c1] | (S)-1-(3-Methoxy-benzyl)-2-(2-pyridin-4-yl-5,6,7,8-tetrahydro-benzo[4,5]thieno[2,3-d]pyrimidin-4-yloxy)-ethylamine |
| 181 | B* | 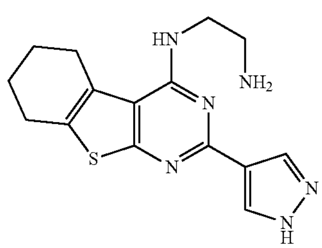 [SMILES: NCCNc1nc(-c2cn[nH]c2)nc2sc3c(c12)CCCC3] | N*1*-[2-(1H-Pyrazol-4-yl)-5,6,7,8-tetrahydro-benzo[4,5]thieno[2,3-d]pyrimidin-4-yl]-ethane-1,2-diamine |
| 182 | B* | 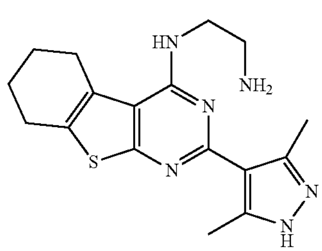 [SMILES: Cc1n[nH]c(C)c1-c1nc(NCCN)c2c3c(sc2n1)CCCC3] | N*1*-[2-(3,5-Dimethyl-1H-pyrazol-4-yl)-5,6,7,8-tetrahydro-benzo[4,5]thieno[2,3-d]pyrimidin-4-yl]-ethane-1,2-diamine |

| Ex | Activity | Structure | Name |
|---|---|---|---|
| 183 | B* | 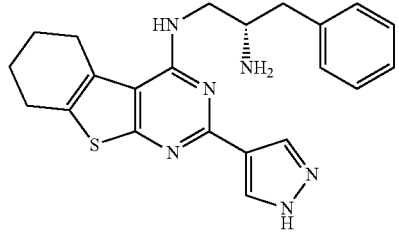 [SMILES: N[C@H](CNc1nc(-c2cn[nH]c2)nc2sc3c(c12)CCCC3)Cc1ccccc1] | (S)-3-Phenyl-N*1*-[2-(1H-pyrazol-4-yl)-5,6,7,8-tetrahydro-benzo[4,5]thieno[2,3-d]pyrimidin-4-yl]-propane-1,2-diamine |
| 184 | C* | 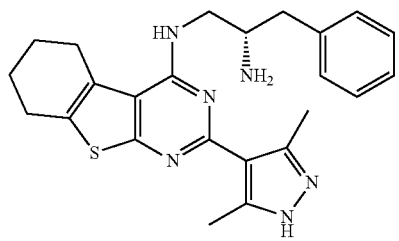 [SMILES: Cc1n[nH]c(C)c1-c1nc(NC[C@@H](N)Cc2ccccc2)c2c3c(sc2n1)CCCC3] | (S)-N*1*-[2-(3,5-Dimethyl-1H-pyrazol-4-yl)-5,6,7,8-tetrahydro-benzo[4,5]thieno[2,3-d]pyrimidin-4-yl]-3-phenyl-propane-1,2-diamine |
| 185 | B* | 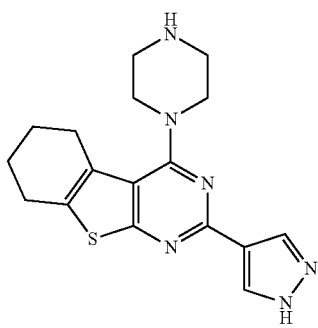 [SMILES: c1n[nH]cc1-c1nc(N2CCNCC2)c2c3c(sc2n1)CCCC3] | 4-Piperazin-1-yl-2-(1H-pyrazol-4-yl)-5,6,7,8-tetrahydro-benzo[4,5]thieno[2,3-d]pyrimidine |
| 186 | B* | 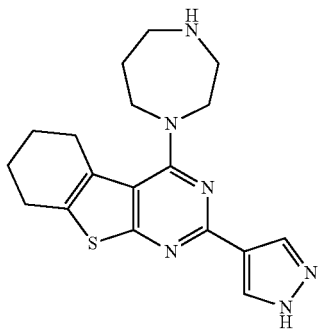 [SMILES: c1n[nH]cc1-c1nc(N2CCCNCC2)c2c3c(sc2n1)CCCC3] | 4-[1,4]Diazepan-1-yl-2-(1H-pyrazol-4-yl)-5,6,7,8-tetrahydro-benzo[4,5]thieno[2,3-d]pyrimidine |
| 187 | B* | 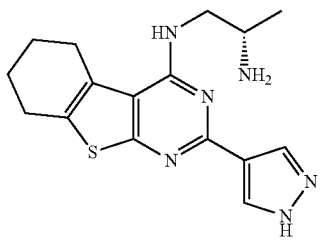 [SMILES: C[C@H](N)CNc1nc(-c2cn[nH]c2)nc2sc3c(c12)CCCC3] | (S)-N*1*-[2-(1H-Pyrazol-4-yl)-5,6,7,8-tetrahydro-benzo[4,5]thieno[2,3-d]pyrimidin-4-yl]-propane-1,2-diamine |

| Ex | Activity | Structure | Name |
|---|---|---|---|
| 188 | C* | 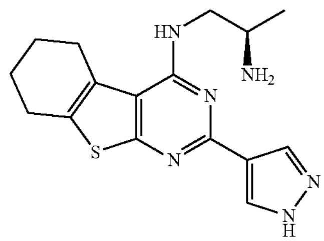 [SMILES: C[C@@H](N)CNc1nc(-c2cn[nH]c2)nc2sc3c(c12)CCCC3] | (R)-N*1*-[2-(1H-Pyrazol-4-yl)-5,6,7,8-tetrahydro-benzo[4,5]thieno[2,3-d]pyrimidin-4-yl]-propane-1,2-diamine |
| 189 | B* | 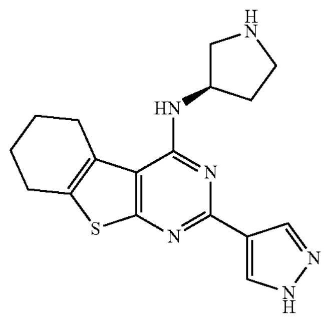 [SMILES: c1n[nH]cc1-c1nc(N[C@@H]2CCNC2)c2c3c(sc2n1)CCCC3] | [2-(1H-Pyrazol-4-yl)-5,6,7,8-tetrahydro-benzo[4,5]thieno[2,3-d]pyrimidin-4-yl]-(R)-pyrrolidin-3-yl-amine |
| 190 | B* | 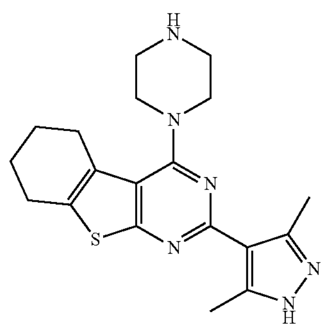 [SMILES: Cc1n[nH]c(C)c1-c1nc(N2CCNCC2)c2c3c(sc2n1)CCCC3] | 2-(3,5-Dimethyl-1H-pyrazol-4-yl)-4-piperazin-1-yl-5,6,7,8-tetrahydro-benzo[4,5]thieno[2,3-d]pyrimidine |
| 191 | B* | 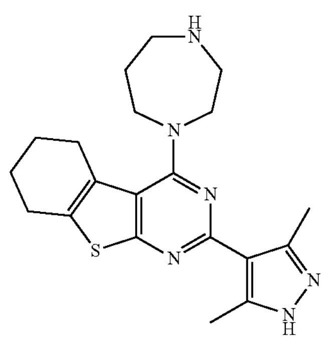 [SMILES: Cc1n[nH]c(C)c1-c1nc(N2CCCNCC2)c2c3c(sc2n1)CCCC3] | 4-[1,4]Diazepan-1-yl-2-(3,5-dimethyl-1H-pyrazol-4-yl)-5,6,7,8-tetrahydro-benzo[4,5]thieno[2,3-d]pyrimidine |
| 192 | C* | 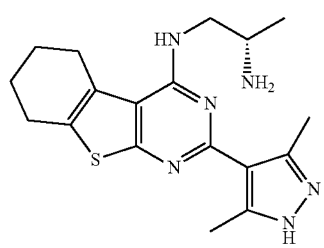 [SMILES: Cc1n[nH]c(C)c1-c1nc(NC[C@H](C)N)c2c3c(sc2n1)CCCC3] | (S)-N*1*-[2-(3,5-Dimethyl-1H-pyrazol-4-yl)-5,6,7,8-tetrahydro-benzo[4,5]thieno[2,3-d]pyrimidin-4-yl]-propane-1,2-diamine |

| Ex | Activity | Structure | Name |
|---|---|---|---|
| 193 | D* | 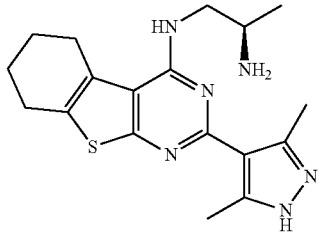 [SMILES: Cc1n[nH]c(C)c1-c1nc(NC[C@@H](C)N)c2c3c(sc2n1)CCCC3] | (R)-N*1*-[2-(3,5-Dimethyl-1H-pyrazol-4-yl)-5,6,7,8-tetrahydro-benzo[4,5]thieno[2,3-d]pyrimidin-4-yl]-propane-1,2-diamine |
| 194 | B* | 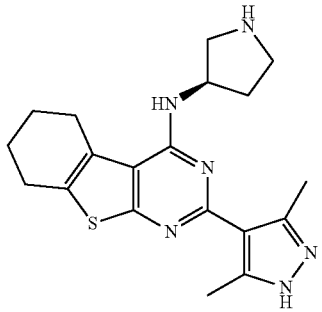 [SMILES: Cc1n[nH]c(C)c1-c1nc(N[C@@H]2CCNC2)c2c3c(sc2n1)CCCC3] | [2-(3,5-Dimethyl-1H-pyrazol-4-yl)-5,6,7,8-tetrahydro-benzo[4,5]thieno[2,3-d]pyrimidin-4-yl]-(R)-pyrrolidin-3-yl-amine |
| 195 | >60 μM | 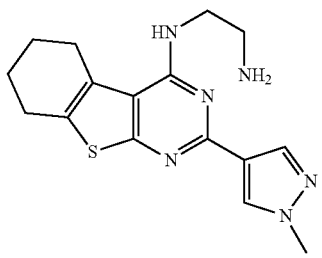 [SMILES: Cn1cc(-c2nc(NCCN)c3c4c(sc3n2)CCCC4)cn1] | N*1*-[2-(1-Methyl-1H-pyrazol-4-yl)-5,6,7,8-tetrahydro-benzo[4,5]thieno[2,3-d]pyrimidin-4-yl]-ethane-1,2-diamine |
| 196 | C | 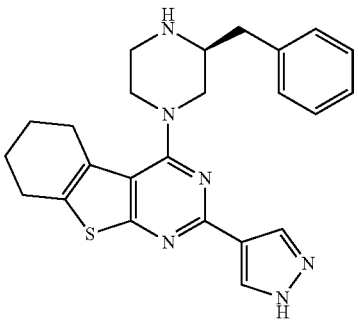 [SMILES: c1ccc(C[C@H]2CN(c3nc(-c4cn[nH]c4)nc4sc5c(c34)CCCC5)CCN2)cc1] | 4-((S)-3-Benzyl-piperazin-1-yl)-2-(1H-pyrazol-4-yl)-5,6,7,8-tetrahydro-benzo[4,5]thieno[2,3-d]pyrimidine |
| 300 | A | 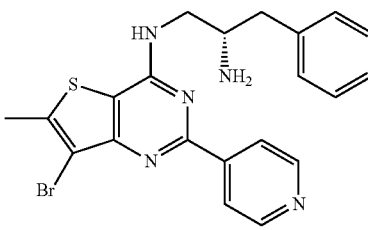 | (S)-N*1*-(7-Bromo-6-methyl-2-pyridin-4-yl-thieno[3,2-d]pyrimidin-4-yl)-3-phenyl-propane-1,2-diamine |

| Ex | Activity | Structure | Name |
|---|---|---|---|
| 301 | C* | 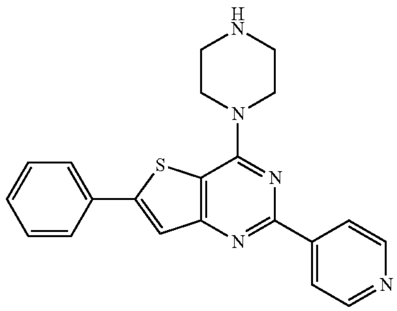 [SMILES: c1ccc(-c2cc3nc(-c4ccncc4)nc(N4CCNCC4)c3s2)cc1] | 6-Phenyl-4-piperazin-1-yl-2-pyridin-4-yl-thieno[3,2-d]pyrimidine |
| 302 | A* | 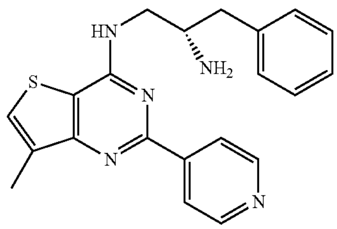 [SMILES: Cc1csc2c(NC[C@@H](N)Cc3ccccc3)nc(-c3ccncc3)nc12] | (S)-N*1*-(7-Methyl-2-pyridin-4-yl-thieno[3,2-d]pyrimidin-4-yl)-3-phenyl-propane-1,2-diamine |
| 303 | D | 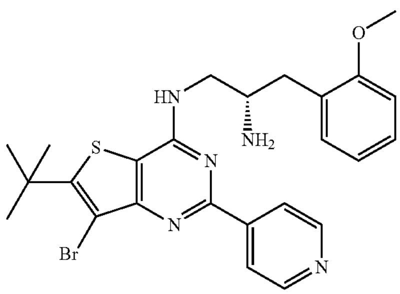 [SMILES: COc1ccccc1C[C@H](N)CNc1nc(-c2ccncc2)nc2c(Br)c(C(C)(C)C)sc12] | (S)-N*1*-(7-Bromo-6-tert-butyl-2-pyridin-4-yl-thieno[3,2-d]pyrimidin-4-yl)-3-(2-methoxy-phenyl)-propane-1,2-diamine |
| 304 | A | 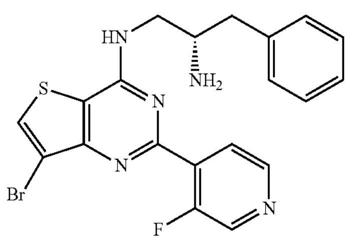 [SMILES: N[C@H](CNc1nc(-c2ccncc2F)nc2c(Br)csc12)Cc1ccccc1] | (S)-N*1*-[7-Bromo-2-(4-methyl-thiazol-5-yl)-thieno[3,2-d]pyrimidin-4-yl]-3-phenyl-propane-1,2-diamine |
| 305 | B | 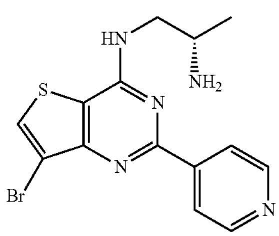 [SMILES: C[C@H](N)CNc1nc(-c2ccncc2)nc2c(Br)csc12] | (S)-N*1*-(7-Bromo-2-pyridin-4-yl-thieno[3,2-d]pyrimidin-4-yl)-propane-1,2-diamine |
| 306 | A | 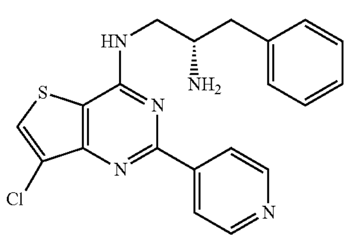 [SMILES: N[C@H](CNc1nc(-c2ccncc2)nc2c(Cl)csc12)Cc1ccccc1] | (S)-N*1*-(7-Chloro-2-pyridin-4-yl-thieno[3,2-d]pyrimidin-4-yl)-3-phenyl-propane-1,2-diamine |

| Ex | Activity | Structure | Name |
|---|---|---|---|
| 307 | D* | 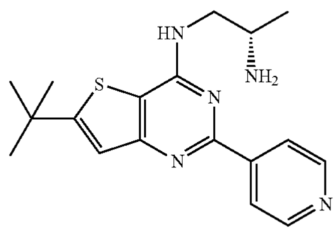 [SMILES: C[C@H](N)CNc1nc(-c2ccncc2)nc2cc(C(C)(C)C)sc12] | (S)-N*1*-(6-tert-Butyl-2-pyridin-4-yl-thieno[3,2-d]pyrimidin-4-yl)-propane-1,2-diamine |
| 308 | D* | 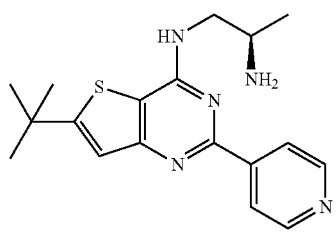 [SMILES: C[C@@H](N)CNc1nc(-c2ccncc2)nc2cc(C(C)(C)C)sc12] | (R)-N*1*-(6-tert-Butyl-2-pyridin-4-yl-thieno[3,2-d]pyrimidin-4-yl)-propane-1,2-diamine |
| 309 | C | 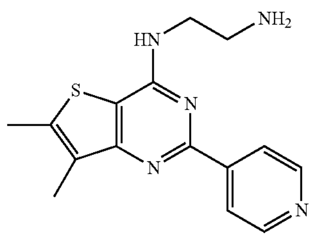 [SMILES: Cc1sc2c(NCCN)nc(-c3ccncc3)nc2c1C] | N*1*-(6,7-Dimethyl-2-pyridin-4-yl-thieno[3,2-d]pyrimidin-4-yl)-ethane-1,2-diamine |
| 310 | C | 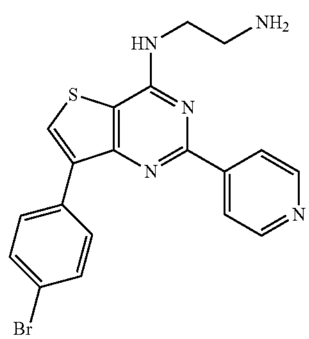 [SMILES: NCCNc1nc(-c2ccncc2)nc2c(-c3ccc(Br)cc3)csc12] | N*1*-[7-(4-Bromo-phenyl)-2-pyridin-4-yl-thieno[3,2-d]pyrimidin-4-yl]-ethane-1,2-diamine |
| 311 | D* | 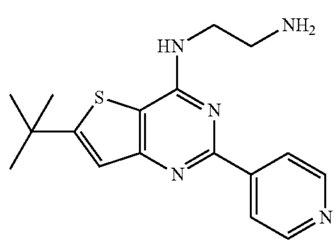 [SMILES: CC(C)(C)c1cc2nc(-c3ccncc3)nc(NCCN)c2s1] | N*1*-(6-tert-Butyl-2-pyridin-4-yl-thieno[3,2-d]pyrimidin-4-yl)-ethane-1,2-diamine |
| 312 | C* | 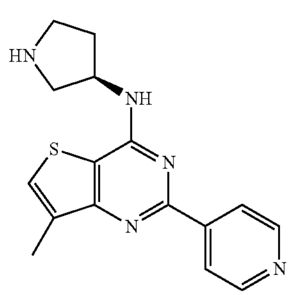 [SMILES: Cc1csc2c(N[C@@H]3CCNC3)nc(-c3ccncc3)nc12] | (7-Methyl-2-pyridin-4-yl-thieno[3,2-d]pyrimidin-4-yl)-(R)-pyrrolidin-3-yl-amine |

-continued

| Ex | Activity | Structure | Name |
|---|---|---|---|
| 313 | D* | 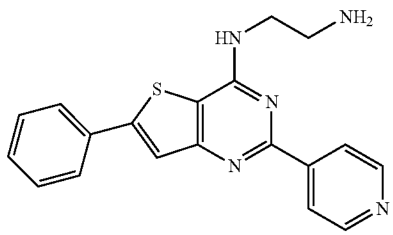 [SMILES: NCCNc1nc(-c2ccncc2)nc2cc(-c3ccccc3)sc12] | N*1*-(6-Phenyl-2-pyridin-4-yl-thieno[3,2-d]pyrimidin-4-yl)-ethane-1,2-diamine |
| 314 | B | 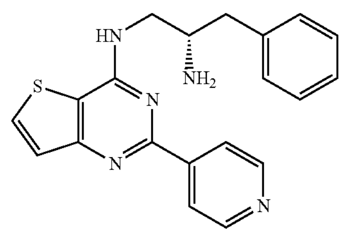 [SMILES: N[C@H](CNc1nc(-c2ccncc2)nc2ccsc12)Cc1ccccc1] | (S)-3-Phenyl-N*1*-(2-pyridin-4-yl-thieno[3,2-d]pyrimidin-4-yl)-propane-1,2-diamine |
| 315 | D | 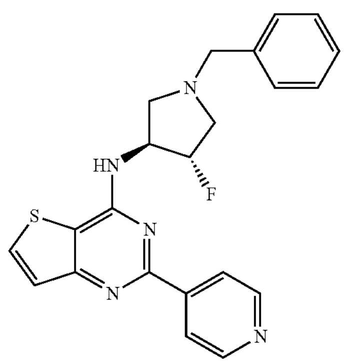 [SMILES: F[C@H]1CN(Cc2ccccc2)C[C@@H]1Nc1nc(-c2ccncc2)nc2ccsc12] | ((3S,4S)-1-Benzyl-4-fluoro-pyrrolidin-3-yl)-(2-pyridin-4-yl-thieno[3,2-d]pyrimidin-4-yl)-amine |
| 316 | C | 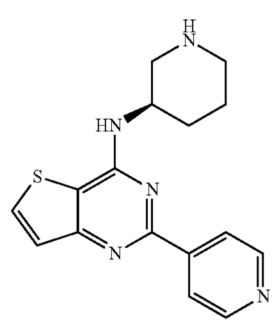 [SMILES: c1cc(-c2nc(N[C@@H]3CCCNC3)c3sccc3n2)ccn1] | (R)-Piperidin-3-yl-(2-pyridin-4-yl-thieno[3,2-d]pyrimidin-4-yl)-amine |
| 317 | C | 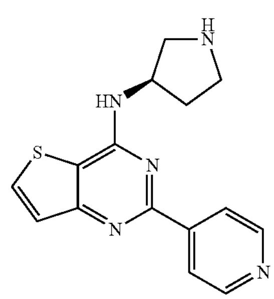 [SMILES: c1cc(-c2nc(N[C@@H]3CCNC3)c3sccc3n2)ccn1] | (2-Pyridin-4-yl-thieno[3,2-d]pyrimidin-4-yl)-(R)-pyrrolidin-3-yl-amine |

| Ex | Activity | Structure | Name |
|---|---|---|---|
| 318 | D | 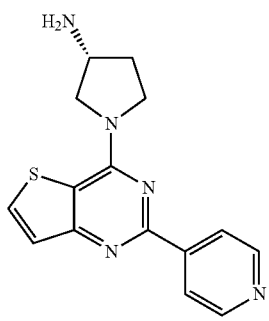 [SMILES: N[C@@H]1CCN(c2nc(-c3ccncc3)nc3ccsc23)C1] | (R)-1-(2-Pyridin-4-yl-thieno[3,2-d]pyrimidin-4-yl)-pyrrolidin-3-ylamine |
| 319 | C | 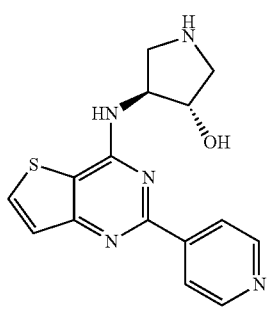 [SMILES: O[C@H]1CNC[C@@H]1Nc1nc(-c2ccncc2)nc2ccsc12] | (3S,4S)-4-(2-Pyridin-4-yl-thieno[3,2-d]pyrimidin-4-ylamino)-pyrrolidin-3-ol |
| 320 | D | 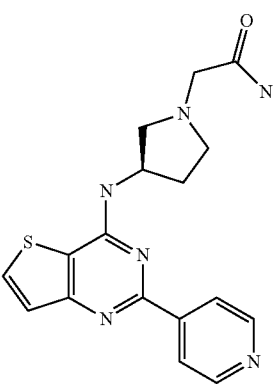 [SMILES: NC(=O)CN1CC[C@@H](Nc2nc(-c3ccncc3)nc3ccsc23)C1] | 2-[(R)-3-(2-Pyridin-4-yl-thieno[3,2-d]pyrimidin-4-ylamino)-pyrrolidin-1-yl]-acetamide |
| 321 | D | 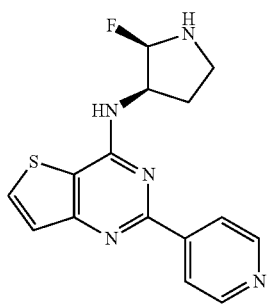 [SMILES: F[C@H]1NCC[C@H]1Nc1nc(-c2ccncc2)nc2ccsc12] | ((3S,4R)-4-Fluoro-pyrrolidin-3-yl)-(2-pyridin-4-yl-thieno[3,2-d]pyrimidin-4-yl)-amine |

-continued

| Ex | Activity | Structure | Name |
|---|---|---|---|
| 322 | C | 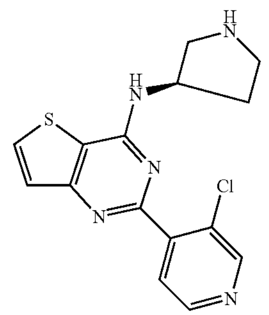 [SMILES: Clc1cnccc1-c1nc(N[C@@H]2CCNC2)c2sccc2n1] | [2-(3-Chloro-pyridin-4-yl)-thieno[3,2-d]pyrimidin-4-yl]-(R)-pyrrolidin-3-yl-amine |
| 323 | C | 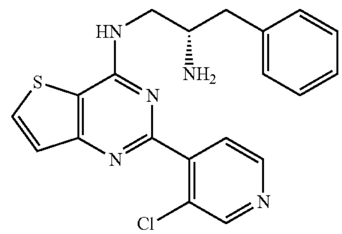 [SMILES: N[C@H](CNc1nc(-c2ccncc2Cl)nc2ccsc12)Cc1ccccc1] | (S)-N*1*-[2-(3-Chloro-pyridin-4-yl)-thieno[3,2-d]pyrimidin-4-yl]-3-phenyl-propane-1,2-diamine |
| 324 | D | 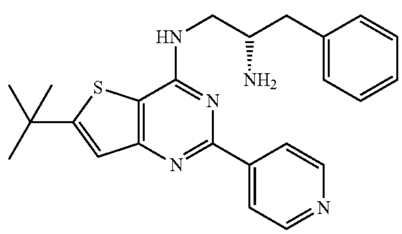 | (S)-N*1*-(6-tert-Butyl-2-pyridin-4-yl-thieno[3,2-d]pyrimidin-4-yl)-3-phenyl-propane-1,2-diamine |
| 325 | B | 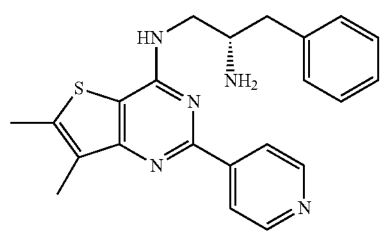 [SMILES: Cc1sc2c(NC[C@@H](N)Cc3ccccc3)nc(-c3ccncc3)nc2c1C] | (S)-N*1*-(6,7-Dimethyl-2-pyridin-4-yl-thieno[3,2-d]pyrimidin-4-yl)-3-phenyl-propane-1,2-diamine |
| 326 | C | 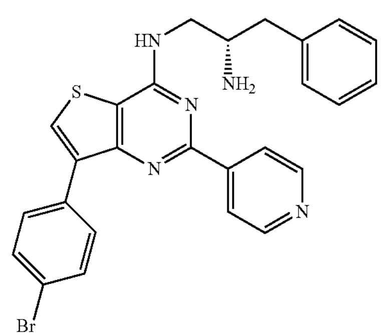 [SMILES: N[C@H](CNc1nc(-c2ccncc2)nc2c(-c3ccc(Br)cc3)csc12)Cc1ccccc1] | (S)-N*1*-[7-(4-Bromo-phenyl)-2-pyridin-4-yl-thieno[3,2-d]pyrimidin-4-yl]-3-phenyl-propane-1,2-diamine |

-continued

| Ex | Activity | Structure | Name |
|---|---|---|---|
| 327 | C | 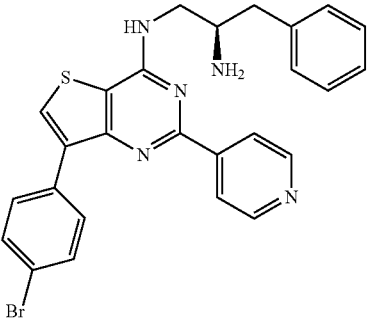 [SMILES: N[C@@H](CNc1nc(-c2ccncc2)nc2c(-c3ccc(Br)cc3)csc12)Cc1ccccc1] | (R)-N*1*-[7-(4-Bromo-phenyl)-2-pyridin-4-yl-thieno[3,2-d]pyrimidin-4-yl]-3-phenyl-propane-1,2-diamine |
| 328 | B | 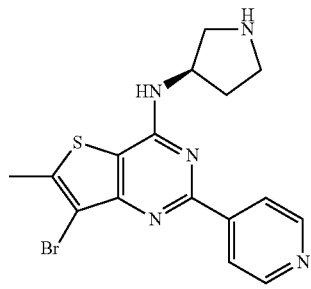 [SMILES: Cc1sc2c(N[C@@H]3CCNC3)nc(-c3ccncc3)nc2c1Br] | (7-Bromo-6-methyl-2-pyridin-4-yl-thieno[3,2-d]pyrimidin-4-yl)-(R)-pyrrolidin-3-yl-amine |
| 329 | C | 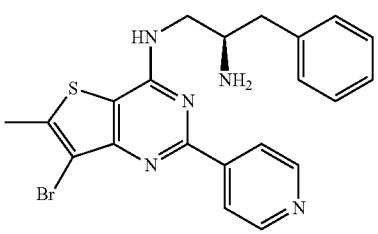 [SMILES: Cc1sc2c(NC[C@H](N)Cc3ccccc3)nc(-c3ccncc3)nc2c1Br] | (R)-N*1*-(7-Bromo-6-methyl-2-pyridin-4-yl-thieno[3,2-d]pyrimidin-4-yl)-3-phenyl-propane-1,2-diamine |
| 330 | C | 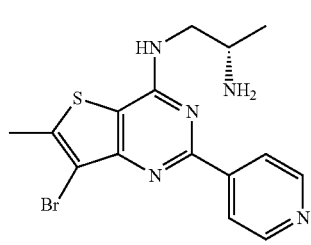 [SMILES: Cc1sc2c(NC[C@H](C)N)nc(-c3ccncc3)nc2c1Br] | (R)-N*1*-(7-Bromo-6-methyl-2-pyridin-4-yl-thieno[3,2-d]pyrimidin-4-yl)-propane-1,2-diamine |
| 331 | C | 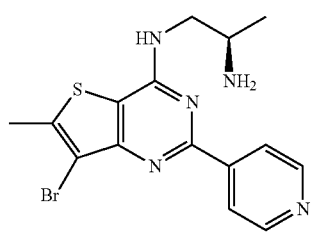 [SMILES: Cc1sc2c(NC[C@@H](C)N)nc(-c3ccncc3)nc2c1Br] | (S)-N*1*-(7-Bromo-6-methyl-2-pyridin-4-yl-thieno[3,2-d]pyrimidin-4-yl)-propane-1,2-diamine |
| 332 | C | 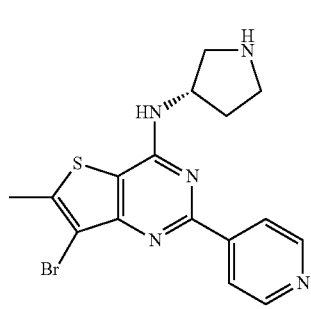 [SMILES: Cc1sc2c(N[C@H]3CCNC3)nc(-c3ccncc3)nc2c1Br] | (7-Bromo-6-methyl-2-pyridin-4-yl-thieno[3,2-d]pyrimidin-4-yl)-(S)-pyrrolidin-3-yl-amine |

| Ex | Activity | Structure | Name |
|---|---|---|---|
| 333 | D | 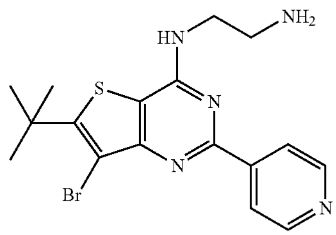 [SMILES: CC(C)(C)c1sc2c(NCCN)nc(-c3ccncc3)nc2c1Br] | N*1*-(7-Bromo-6-tert-butyl-2-pyridin-4-yl-thieno[3,2-d]pyrimidin-4-yl)-ethane-1,2-diamine |
| 334 | C | 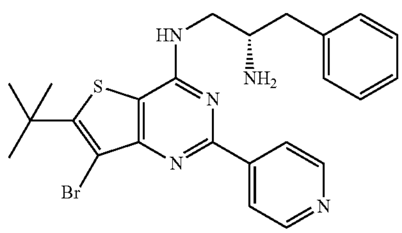 [SMILES: CC(C)(C)c1sc2c(NC[C@@H](N)Cc3ccccc3)nc(-c3ccncc3)nc2c1Br] | (S)-N*1*-(7-Bromo-6-tert-butyl-2-pyridin-4-yl-thieno[3,2-d]pyrimidin-4-yl)-3-phenyl-propane-1,2-diamine |
| 335 | D | 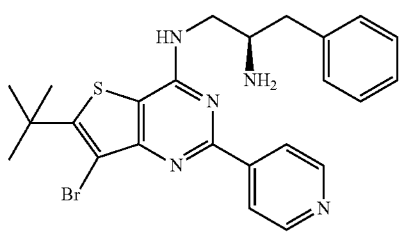 [SMILES: CC(C)(C)c1sc2c(NC[C@H](N)Cc3ccccc3)nc(-c3ccncc3)nc2c1Br] | (R)-N*1*-(7-Bromo-6-tert-butyl-2-pyridin-4-yl-thieno[3,2-d]pyrimidin-4-yl)-3-phenyl-propane-1,2-diamine |
| 336 | A | 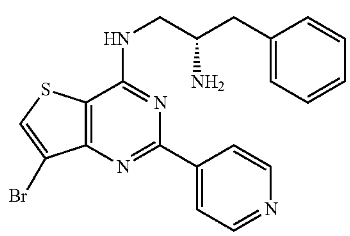 | (S)-N*1*-(7-Bromo-2-pyridin-4-yl-thieno[3,2-d]pyrimidin-4-yl)-3-phenyl-propane-1,2-diamine |
| 337 | B | 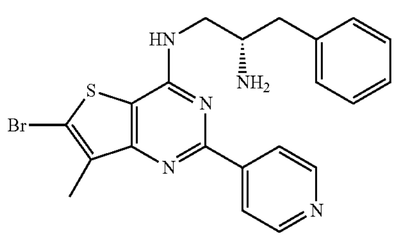 [SMILES: Cc1c(Br)sc2c(NC[C@@H](N)Cc3ccccc3)nc(-c3ccncc3)nc12] | (S)-N*1*-(6-Bromo-7-methyl-2-pyridin-4-yl-thieno[3,2-d]pyrimidin-4-yl)-3-phenyl-propane-1,2-diamine |
| 338 | D | 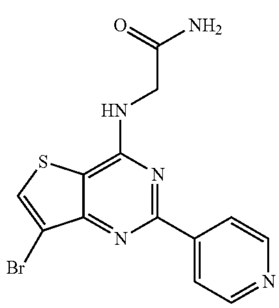 [SMILES: NC(=O)CNc1nc(-c2ccncc2)nc2c(Br)csc12] | 2-(7-Bromo-2-pyridin-4-yl-thieno[3,2-d]pyrimidin-4-ylamino)-acetamide |

| Ex | Activity | Structure | Name |
|---|---|---|---|
| 339 | D | 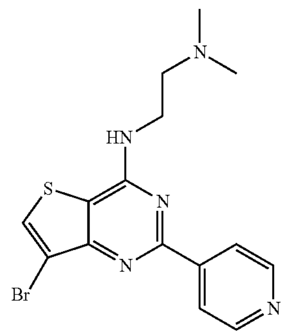 [SMILES: CN(C)CCNc1nc(-c2ccncc2)nc2c(Br)csc12] | N'-(7-Bromo-2-pyridin-4-yl-thieno[3,2-d]pyrimidin-4-yl)-N,N-dimethyl-ethane-1,2-diamine |
| 340 | B | 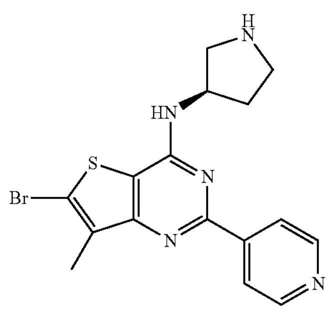 [SMILES: Cc1c(Br)sc2c(N[C@@H]3CCNC3)nc(-c3ccncc3)nc12] | (6-Bromo-7-methyl-2-pyridin-4-yl-thieno[3,2-d]pyrimidin-4-yl)-(R)-pyrrolidin-3-yl-amine |
| 341 | D | 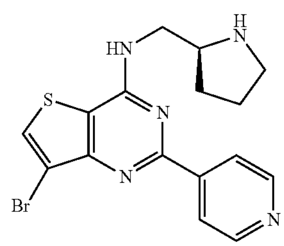 [SMILES: Brc1csc2c(NC[C@@H]3CCCN3)nc(-c3ccncc3)nc12] | (7-Bromo-2-pyridin-4-yl-thieno[3,2-d]pyrimidin-4-yl)-(S)-1-pyrrolidin-2-ylmethyl-amine |
| 342 | D | 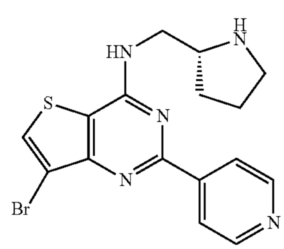 [SMILES: Brc1csc2c(NC[C@H]3CCCN3)nc(-c3ccncc3)nc12] | (7-Bromo-2-pyridin-4-yl-thieno[3,2-d]pyrimidin-4-yl)-(R)-1-pyrrolidin-2-ylmethyl-amine |
| 343 | B | 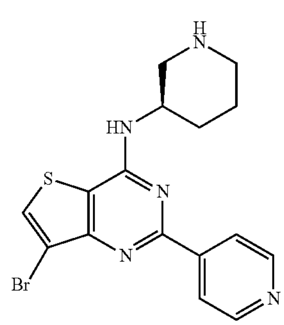 [SMILES: Brc1csc2c(N[C@@H]3CCCNC3)nc(-c3ccncc3)nc12] | (7-Bromo-2-pyridin-4-yl-thieno[3,2-d]pyrimidin-4-yl)-(R)-piperidin-3-yl-amine |

| Ex | Activity | Structure | Name |
|---|---|---|---|
| 344 | C | 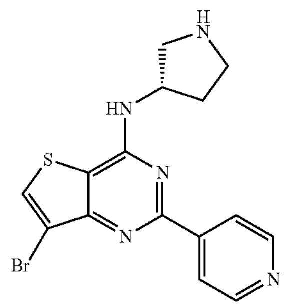 [SMILES: Brc1csc2c(N[C@H]3CCNC3)nc(-c3ccncc3)nc12] | (7-Bromo-2-pyridin-4-yl-thieno[3,2-d]pyrimidin-4-yl)-(S)-pyrrolidin-3-yl-amine |
| 345 | C | 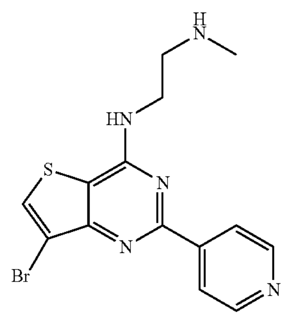 [SMILES: CNCCNc1nc(-c2ccncc2)nc2c(Br)csc12] | N-(7-Bromo-2-pyridin-4-yl-thieno[3,2-d]pyrimidin-4-yl)-N'-methyl-ethane-1,2-diamine |
| 346 | C | 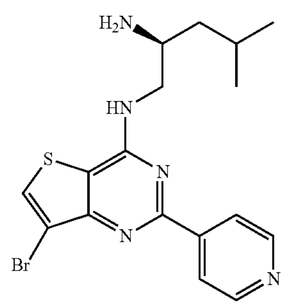 [SMILES: CC(C)C[C@H](N)CNc1nc(-c2ccncc2)nc2c(Br)csc12] | (S)-N*1*-(7-Bromo-2-pyridin-4-yl-thieno[3,2-d]pyrimidin-4-yl)-4-methyl-pentane-1,2-diamine |
| 347 | B | 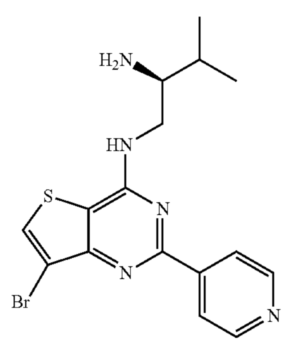 [SMILES: CC(C)[C@H](N)CNc1nc(-c2ccncc2)nc2c(Br)csc12] | (S)-N*1*-(7-Bromo-2-pyridin-4-yl-thieno[3,2-d]pyrimidin-4-yl)-3-methyl-butane-1,2-diamine |
| 348 | B | 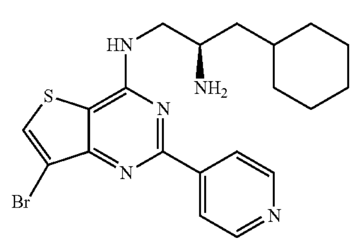 [SMILES: N[C@@H](CNc1nc(-c2ccncc2)nc2c(Br)csc12)CC1CCCCC1] | (S)-N*1*-(7-Bromo-2-pyridin-4-yl-thieno[3,2-d]pyrimidin-4-yl)-3-cyclohexyl-propane-1,2-diamine |

| Ex | Activity | Structure | Name |
|---|---|---|---|
| 349 | B | 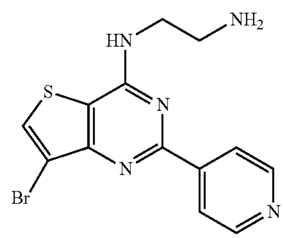 [SMILES: NCCNc1nc(-c2ccncc2)nc2c(Br)csc12] | N*1*-(7-Bromo-2-pyridin-4-yl-thieno[3,2-d]pyrimidin-4-yl)-ethane-1,2-diamine |
| 350 | B | 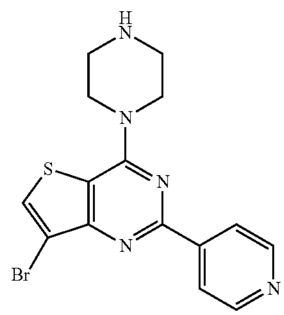 [SMILES: Brc1csc2c(N3CCNCC3)nc(-c3ccncc3)nc12] | 7-Bromo-4-piperazin-1-yl-2-pyridin-4-yl-thieno[3,2-d]pyrimidine |
| 351 | A | 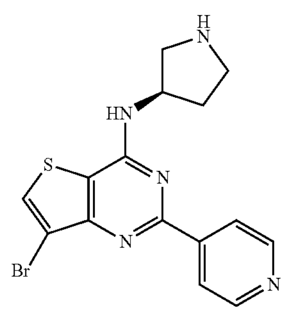 [SMILES: Brc1csc2c(N[C@@H]3CCNC3)nc(-c3ccncc3)nc12] | (7-Bromo-2-pyridin-4-yl-thieno[3,2-d]pyrimidin-4-yl)-(R)-pyrrolidin-3-yl-amine |
| 352 | C | 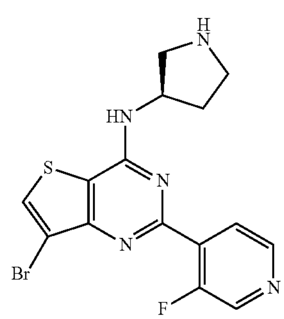 [SMILES: Fc1cnccc1-c1nc(N[C@@H]2CCNC2)c2scc(Br)c2n1] | [7-Bromo-2-(3-fluoro-pyridin-4-yl)-thieno[3,2-d]pyrimidin-4-yl]-(R)-pyrrolidin-3-yl-amine |
| 353 | D | 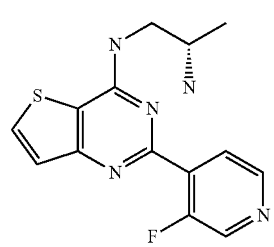 [SMILES: C[C@H](N)CNc1nc(-c2ccncc2F)nc2ccsc12] | (S)-N*1*-[2-(3-Fluoro-pyridin-4-yl)-thieno[3,2-d]pyrimidin-4-yl]-propane-1,2-diamine |

-continued

| Ex | Activity | Structure | Name |
|---|---|---|---|
| 354 | D | 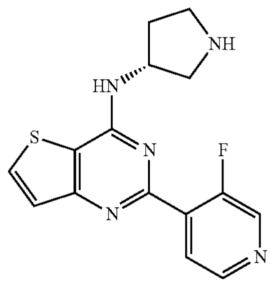 [SMILES: Fc1cnccc1-c1nc(N[C@@H]2CCNC2)c2sccc2n1] | [2-(3-Fluoro-pyridin-4-yl)-thieno[3,2-d]pyrimidin-4-yl]-(R)-pyrrolidin-3-yl-amine |
| 355 | C | 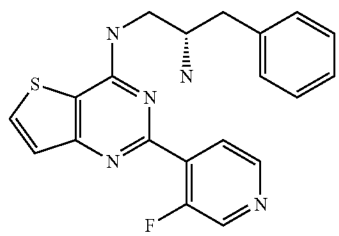 [SMILES: N[C@H](CNc1nc(-c2ccncc2F)nc2ccsc12)Cc1ccccc1] | (S)-N*1*-[2-(3-Fluoro-pyridin-4-yl)-thieno[3,2-d]pyrimidin-4-yl]-3-phenyl-propane-1,2-diamine |
| 356 | D* | 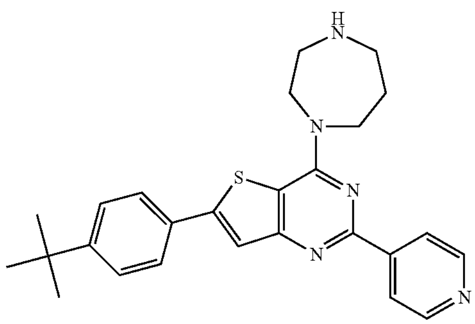 [SMILES: CC(C)(C)c1ccc(-c2cc3nc(-c4ccncc4)nc(N4CCCNCC4)c3s2)cc1] | 6-(4-tert-Butyl-phenyl)-4-[1,4]diazepan-1-yl-2-pyridin-4-yl-thieno[3,2-d]pyrimidine |
| 357 | D | 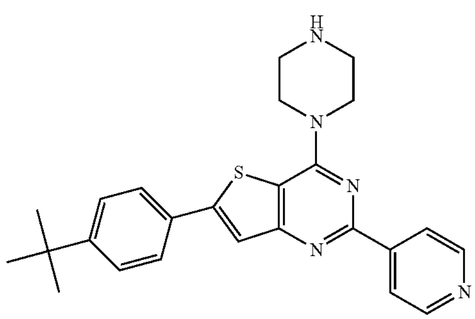 [SMILES: CC(C)(C)c1ccc(-c2cc3nc(-c4ccncc4)nc(N4CCNCC4)c3s2)cc1] | 6-(4-tert-Butyl-phenyl)-4-piperazin-1-yl-2-pyridin-4-yl-thieno[3,2-d]pyrimidine |
| 358 | D* | 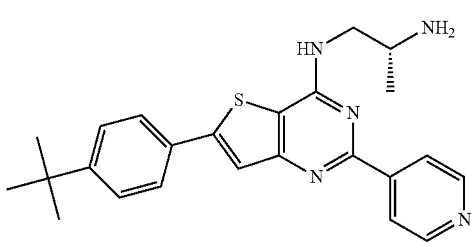 [SMILES: C[C@@H](N)CNc1nc(-c2ccncc2)nc2cc(-c3ccc(C(C)(C)C)cc3)sc12] | (R)-N*1*-[6-(4-tert-Butyl-phenyl)-2-pyridin-4-yl-thieno[3,2-d]pyrimidin-4-yl]-propane-1,2-diamine |

-continued

| Ex | Activity | Structure | Name |
|---|---|---|---|
| 359 | D* | 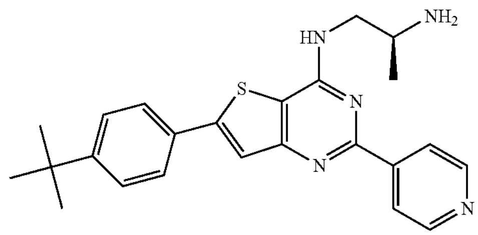 [SMILES: C[C@H](N)CNc1nc(-c2ccncc2)nc2cc(-c3ccc(C(C)(C)C)cc3)sc12] | (S)-N*1*-[6-(4-tert-Butyl-phenyl)-2-pyridin-4-yl-thieno[3,2-d]pyrimidin-4-yl]-propane-1,2-diamine |
| 360 | D* | 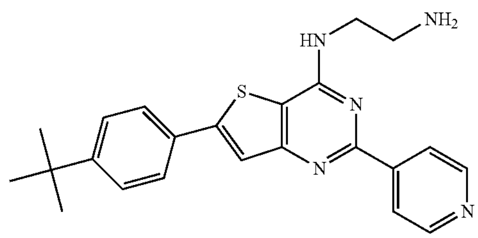 [SMILES: CC(C)(C)c1ccc(-c2cc3nc(-c4ccncc4)nc(NCCN)c3s2)cc1] | N*1*-[6-(4-tert-Butyl-phenyl)-2-pyridin-4-yl-thieno[3,2-d]pyrimidin-4-yl]-ethane-1,2-diamine |
| 361 | B* | 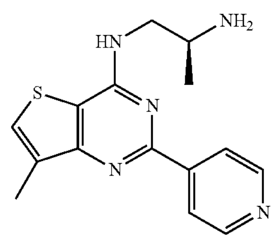 [SMILES: Cc1csc2c(NC[C@H](C)N)nc(-c3ccncc3)nc12] | (S)-N*1*-(7-Methyl-2-pyridin-4-yl-thieno[3,2-d]pyrimidin-4-yl)-propane-1,2-diamine |
| 362 | B* | 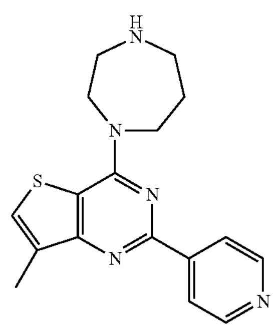 [SMILES: Cc1csc2c(N3CCCNCC3)nc(-c3ccncc3)nc12] | 4-[1,4]Diazepan-1-yl-7-methyl-2-pyridin-4-yl-thieno[3,2-d]pyrimidine |
| 363 | B* | 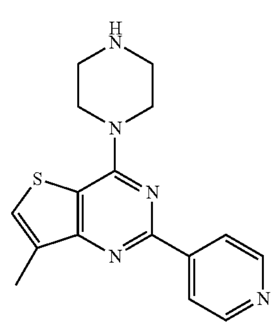 [SMILES: Cc1csc2c(N3CCNCC3)nc(-c3ccncc3)nc12] | 7-Methyl-4-piperazin-1-yl-2-pyridin-4-yl-thieno[3,2-d]pyrimidine |

-continued

| Ex | Activity | Structure | Name |
|---|---|---|---|
| 364 | C* | 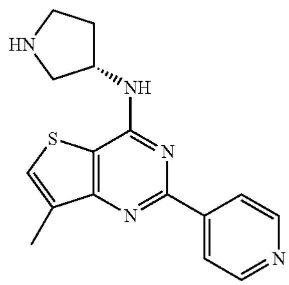 [SMILES: Cc1csc2c(N[C@H]3CCNC3)nc(-c3ccncc3)nc12] | (7-Methyl-2-pyridin-4-yl-thieno[3,2-d]pyrimidin-4-yl)-(S)-pyrrolidin-3-yl-amine |
| 365 | C* | 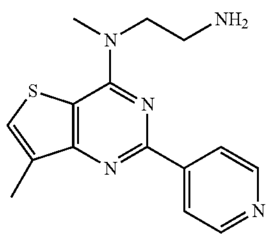 [SMILES: Cc1csc2c(N(C)CCN)nc(-c3ccncc3)nc12] | N*1*-Methyl-N*1*-(7-methyl-2-pyridin-4-yl-thieno[3,2-d]pyrimidin-4-yl)-ethane-1,2-diamine |
| 366 | D* | 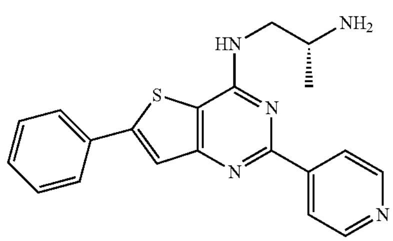 [SMILES: C[C@@H](N)CNc1nc(-c2ccncc2)nc2cc(-c3ccccc3)sc12] | (R)-N*1*-(6-Phenyl-2-pyridin-4-yl-thieno[3,2-d]pyrimidin-4-yl)-propane-1,2-diamine |
| 367 | D* | 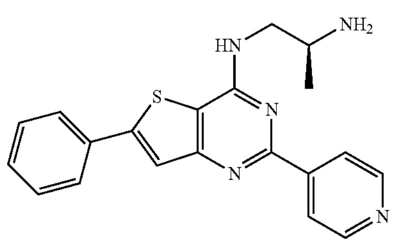 [SMILES: C[C@H](N)CNc1nc(-c2ccncc2)nc2cc(-c3ccccc3)sc12] | (S)-N*1*-(6-Phenyl-2-pyridin-4-yl-thieno[3,2-d]pyrimidin-4-yl)-propane-1,2-diamine |
| 368 | C* | 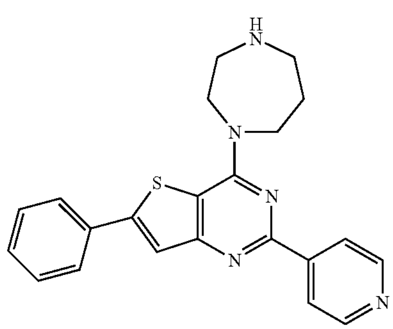 [SMILES: c1ccc(-c2cc3nc(-c4ccncc4)nc(N4CCCNCC4)c3s2)cc1] | 4-[1,4]Diazepan-1-yl-6-phenyl-2-pyridin-4-yl-thieno[3,2-d]pyrimidine |
| 369 | C* | 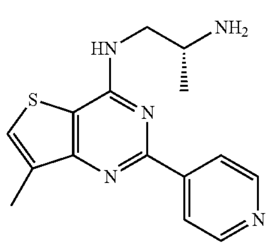 [SMILES: Cc1csc2c(NC[C@@H](C)N)nc(-c3ccncc3)nc12] | (R)-N*1*-(7-Methyl-2-pyridin-4-yl-thieno[3,2-d]pyrimidin-4-yl)-propane-1,2-diamine |

-continued

| Ex | Activity | Structure | Name |
|---|---|---|---|
| 370 | B* | 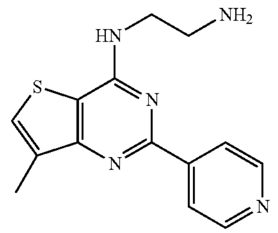 [SMILES: Cc1csc2c(NCCN)nc(-c3ccncc3)nc12] | N*1*-(7-Methyl-2-pyridin-4-yl-thieno[3,2-d]pyrimidin-4-yl)-ethane-1,2-diamine |
| 371 | B* | 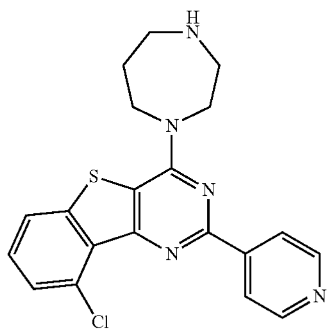 [SMILES: Clc1cccc2sc3c(N4CCCNCC4)nc(-c4ccncc4)nc3c12] | 9-Chloro-4-[1,4]diazepan-1-yl-2-pyridin-4-yl-benzo[4,5]thieno[3,2-d]pyrimidine |
| 372 | B* | 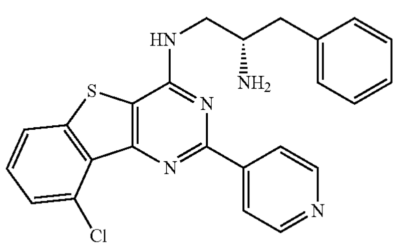 [SMILES: N[C@H](CNc1nc(-c2ccncc2)nc2c1sc1cccc(Cl)c12)Cc1ccccc1] | (S)-N*1*-(9-Chloro-2-pyridin-4-yl-benzo[4,5]thieno[3,2-d]pyrimidin-4-yl)-3-phenyl-propane-1,2-diamine |
| 373 | B* | 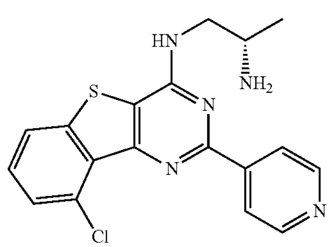 [SMILES: C[C@H](N)CNc1nc(-c2ccncc2)nc2c1sc1cccc(Cl)c12] | (S)-N*1*-(9-Chloro-2-pyridin-4-yl-benzo[4,5]thieno[3,2-d]pyrimidin-4-yl)-propane-1,2-diamine |
| 374 | B* | 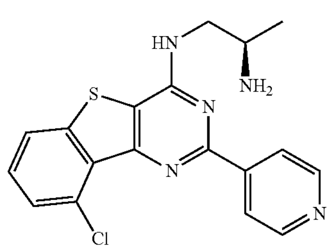 [SMILES: C[C@@H](N)CNc1nc(-c2ccncc2)nc2c1sc1cccc(Cl)c12] | (R)-N*1*-(9-Chloro-2-pyridin-4-yl-benzo[4,5]thieno[3,2-d]pyrimidin-4-yl)-propane-1,2-diamine |
| 375 | C* | 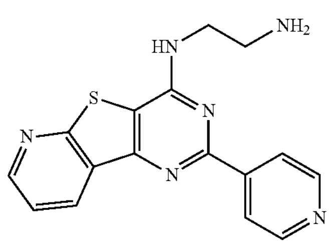 [SMILES: NCCNc1nc(-c2ccncc2)nc2c1sc1ncccc12] | N*1*-(2-Pyridin-4-yl-pyrido[3',2':4,5]thieno[3,2-d]pyrimidin-4-yl)-ethane-1,2-diamine |

| Ex | Activity | Structure | Name |
|---|---|---|---|
| 376 | D* | 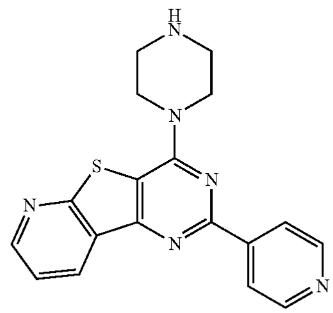 [SMILES: c1cnc2sc3c(N4CCNCC4)nc(-c4ccncc4)nc3c2c1] | 4-Piperazin-1-yl-2-pyridin-4-yl-pyrido[3',2':4,5]thieno[3,2-d]pyrimidine |
| 377 | C* | 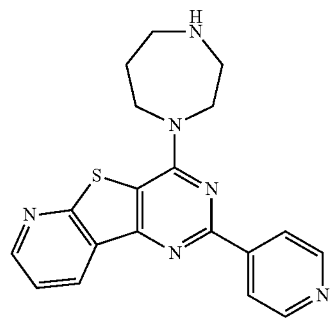 [SMILES: c1cnc2sc3c(N4CCCNCC4)nc(-c4ccncc4)nc3c2c1] | 4-[1,4]Diazepan-1-yl-2-pyridin-4-yl-pyrido[3',2':4,5]thieno[3,2-d]pyrimidine |
| 378 | C* | 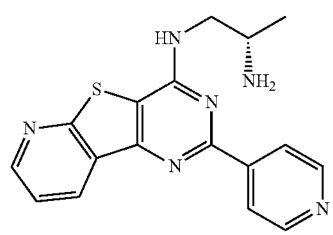 [SMILES: C[C@H](N)CNc1nc(-c2ccncc2)nc2c1sc1ncccc12] | (S)-N*1*-(2-Pyridin-4-yl-pyrido[3',2':4,5]thieno[3,2-d]pyrimidin-4-yl)-propane-1,2-diamine |
| 379 | D* | 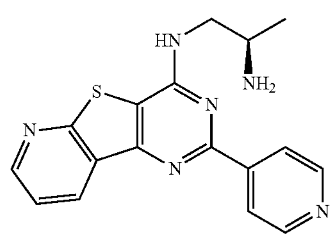 [SMILES: C[C@@H](N)CNc1nc(-c2ccncc2)nc2c1sc1ncccc12] | (R)-N*1*-(2-Pyridin-4-yl-pyrido[3',2':4,5]thieno[3,2-d]pyrimidin-4-yl)-propane-1,2-diamine |
| 380 | C* | 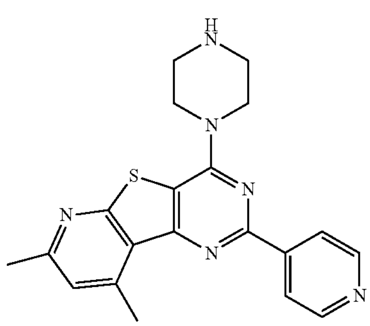 [SMILES: Cc1cc(C)c2c(n1)sc1c(N3CCNCC3)nc(-c3ccncc3)nc12] | 7,9-Dimethyl-4-piperazin-1-yl-2-pyridin-4-yl-pyrido[3',2':4,5]thieno[3,2-d]pyrimidine |

| Ex | Activity | Structure | Name |
|---|---|---|---|
| 381 | C* | 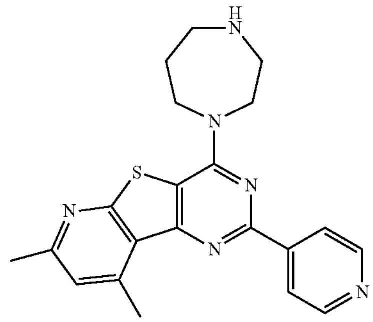 [SMILES: Cc1cc(C)c2c(n1)sc1c(N3CCCNCC3)nc(-c3ccncc3)nc12] | 4-[1,4]Diazepan-1-yl-7,9-dimethyl-2-pyridin-4-yl-pyrido[3',2':4,5]thieno[3,2-d]pyrimidine |
| 382 | B* | 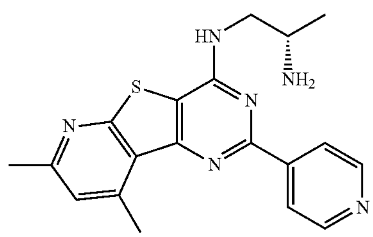 [SMILES: Cc1cc(C)c2c(n1)sc1c(NC[C@H](C)N)nc(-c3ccncc3)nc12] | (S)-N*1*-(7,9-Dimethyl-2-pyridin-4-yl-pyrido[3',2':4,5]thieno[3,2-d]pyrimidin-4-yl)-propane-1,2-diamine |
| 383 | C* | 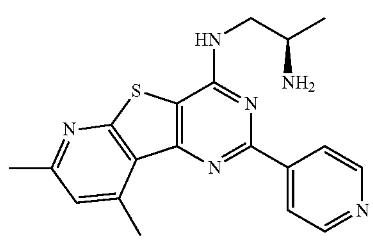 [SMILES: Cc1cc(C)c2c(n1)sc1c(NC[C@@H](C)N)nc(-c3ccncc3)nc12] | (R)-N*1*-(7,9-Dimethyl-2-pyridin-4-yl-pyrido[3',2':4,5]thieno[3,2-d]pyrimidin-4-yl)-propane-1,2-diamine |
| 384 | C* | 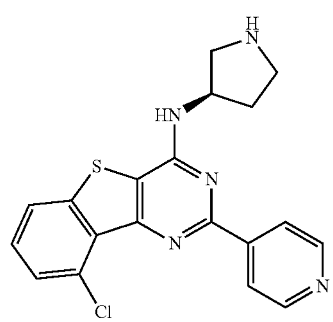 [SMILES: Clc1cccc2sc3c(N[C@@H]4CCNC4)nc(-c4ccncc4)nc3c12] | (9-Chloro-2-pyridin-4-yl-benzo[4,5]thieno[3,2-d]pyrimidin-4-yl)-(R)-pyrrolidin-3-yl-amine |
| 385 | C* | 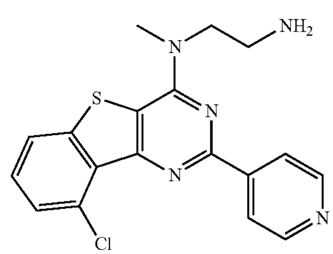 [SMILES: CN(CCN)c1nc(-c2ccncc2)nc2c1sc1cccc(Cl)c12] | N*1*-(9-Chloro-2-pyridin-4-yl-benzo[4,5]thieno[3,2-d]pyrimidin-4-yl)-N*1*-methyl-ethane-1,2-diamine |
| 386 | B* | 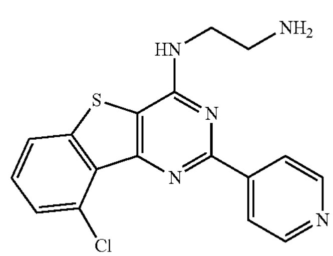 [SMILES: NCCNc1nc(-c2ccncc2)nc2c1sc1cccc(Cl)c12] | N*1*-(9-Chloro-2-pyridin-4-yl-benzo[4,5]thieno[3,2-d]pyrimidin-4-yl)-ethane-1,2-diamine |

-continued

| Ex | Activity | Structure | Name |
|---|---|---|---|
| 387 | B* | 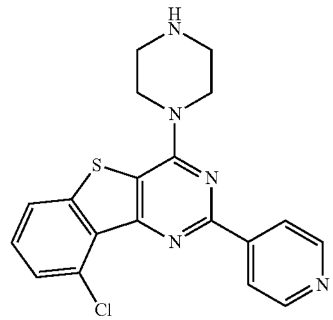 [SMILES: Clc1cccc2sc3c(N4CCNCC4)nc(-c4ccncc4)nc3c12] | 9-Chloro-4-piperazin-1-yl-2-pyridin-4-yl-benzo[4,5]thieno[3,2-d]pyrimidine |
| 388 | A | 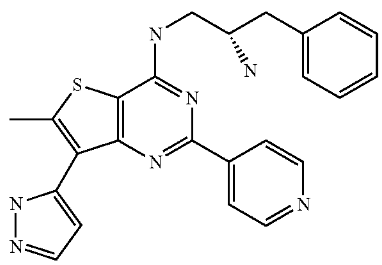 [SMILES: Cc1sc2c(NC[C@@H](N)Cc3ccccc3)nc(-c3ccncc3)nc2c1-c1ccn[nH]1] | (S)-N*1*-[6-Methyl-7-(2H-pyrazol-3-yl)-2-pyridin-4-yl-thieno[3,2-d]pyrimidin-4-yl]-3-phenyl-propane-1,2-diamine |
| 389 | C | 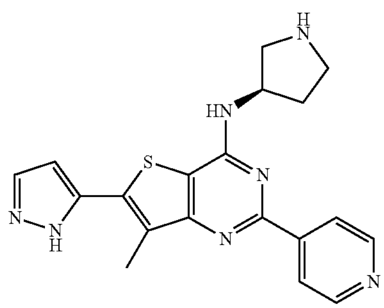 [SMILES: Cc1c(-c2ccn[nH]2)sc2c(N[C@@H]3CCNC3)nc(-c3ccncc3)nc12] | [7-Methyl-6-(2H-pyrazol-3-yl)-2-pyridin-4-yl-thieno[3,2-d]pyrimidin-4-yl]-(R)-pyrrolidin-3-yl-amine |
| 390 | A | 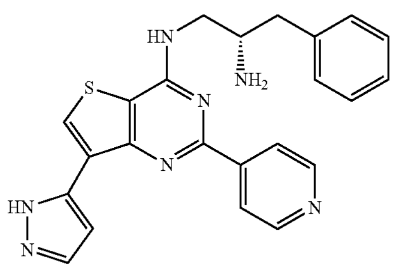 [SMILES: N[C@H](CNc1nc(-c2ccncc2)nc2c(-c3ccn[nH]3)csc12)Cc1ccccc1] | (S)-3-Phenyl-N*1*-[7-(2H-pyrazol-3-yl)-2-pyridin-4-yl-thieno[3,2-d]pyrimidin-4-yl]-propane-1,2-diamine |
| 391 | C | 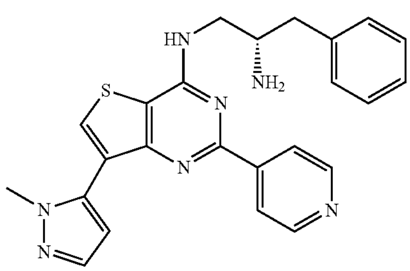 [SMILES: Cn1nccc1-c1csc2c(NC[C@@H](N)Cc3ccccc3)nc(-c3ccncc3)nc12] | (S)-N*1*-[7-(2-Methyl-2H-pyrazol-3-yl)-2-pyridin-4-yl-thieno[3,2-d]pyrimidin-4-yl]-3-phenyl-propane-1,2-diamine |

| Ex | Activity | Structure | Name |
|---|---|---|---|
| 392 | C | 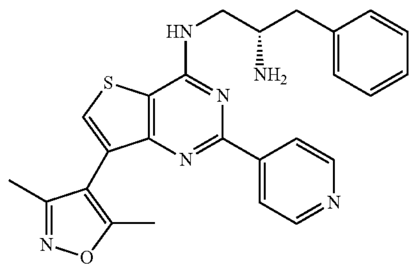 [SMILES: Cc1noc(C)c1-c1csc2c(NC[C@@H](N)Cc3ccccc3)nc(-c3ccncc3)nc12] | N*1*-[7-(3,5-Dimethyl-isoxazol-4-yl)-2-pyridin-4-yl-thieno[3,2-d]pyrimidin-4-yl]-3-phenyl-propane-1,2-diamine |
| 393 | B | 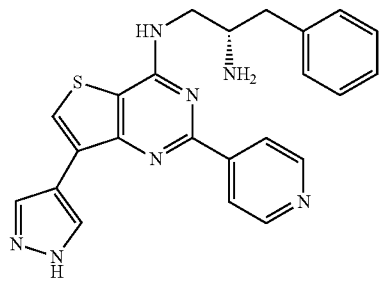 [SMILES: N[C@H](CNc1nc(-c2ccncc2)nc2c(-c3cn[nH]c3)csc12)Cc1ccccc1] | (S)-3-Phenyl-N*1*-[7-(1H-pyrazol-4-yl)-2-pyridin-4-yl-thieno[3,2-d]pyrimidin-4-yl]-propane-1,2-diamine |
| 394 | C | 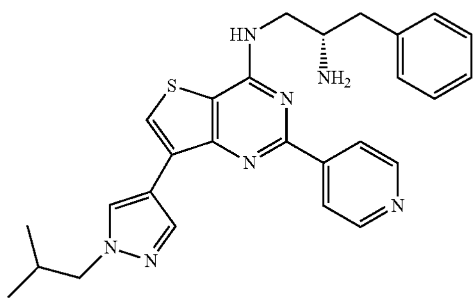 [SMILES: CC(C)Cn1cc(-c2csc3c(NC[C@@H](N)Cc4ccccc4)nc(-c4ccncc4)nc23)cn1] | (S)-N*1*-[7-(1-Isobutyl-1H-pyrazol-4-yl)-2-pyridin-4-yl-thieno[3,2-d]pyrimidin-4-yl]-3-phenyl-propane-1,2-diamine |
| 395 | C | 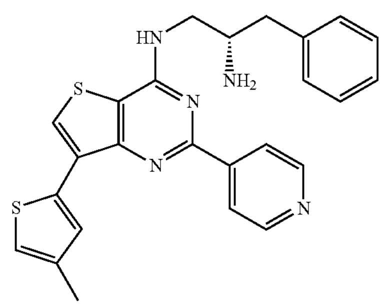 [SMILES: Cc1csc(-c2csc3c(NC[C@@H](N)Cc4ccccc4)nc(-c4ccncc4)nc23)c1] | (S)-N*1*-[7-(4-Methyl-thiophen-2-yl)-2-pyridin-4-yl-thieno[3,2-d]pyrimidin-4-yl]-3-phenyl-propane-1,2-diamine |
| 396 | B | 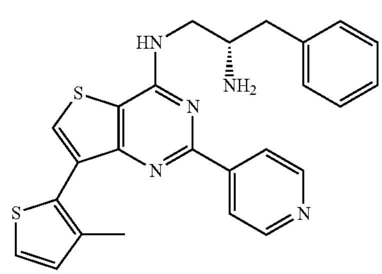 [SMILES: Cc1ccsc1-c1csc2c(NC[C@@H](N)Cc3ccccc3)nc(-c3ccncc3)nc12] | (S)-N*1*-[7-(3-Methyl-thiophen-2-yl)-2-pyridin-4-yl-thieno[3,2-d]pyrimidin-4-yl]-3-phenyl-propane-1,2-diamine |

| Ex | Activity | Structure | Name |
|---|---|---|---|
| 397 | B | 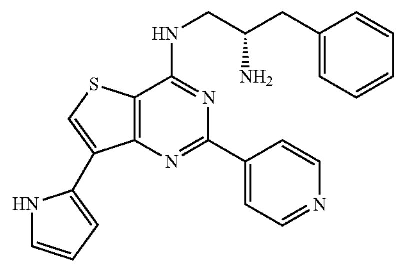 [SMILES: N[C@H](CNc1nc(-c2ccncc2)nc2c(-c3ccc[nH]3)csc12)Cc1ccccc1] | (S)-3-Phenyl-N*1*-[2-pyridin-4-yl-7-(1H-pyrrol-2-yl)-thieno[3,2-d]pyrimidin-4-yl]-propane-1,2-diamine |
| 398 | B | 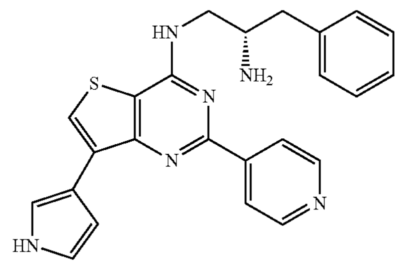 [SMILES: N[C@H](CNc1nc(-c2ccncc2)nc2c(-c3cc[nH]c3)csc12)Cc1ccccc1] | (S)-3-Phenyl-N*1*-[2-pyridin-4-yl-7-(1H-pyrrol-3-yl)-thieno[3,2-d]pyrimidin-4-yl]-propane-1,2-diamine |
| 399 | C | 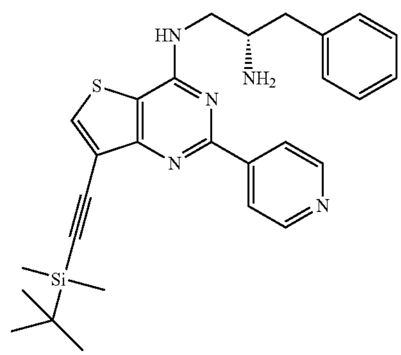 [SMILES: CC(C)(C)[Si](C)(C)C#Cc1csc2c(NC[C@@H](N)Cc3ccccc3)nc(-c3ccncc3)nc12] | (S)-N*1*-{7-[(tert-Butyl-dimethyl-silanyl)-ethynyl]-2-pyridin-4-yl-thieno[3,2-d]pyrimidin-4-yl}-3-phenyl-propane-1,2-diamine |
| 400 | A | 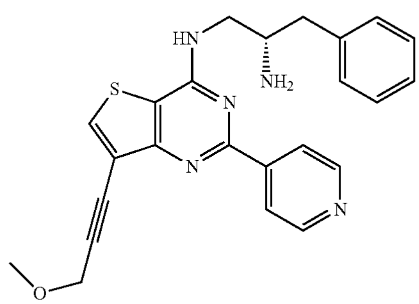 [SMILES: COCC#Cc1csc2c(NC[C@@H](N)Cc3ccccc3)nc(-c3ccncc3)nc12] | (S)-N*1*-[7-(3-Methoxy-prop-1-ynyl)-2-pyridin-4-yl-thieno[3,2-d]pyrimidin-4-yl]-3-phenyl-propane-1,2-diamine |
| 401 | B | 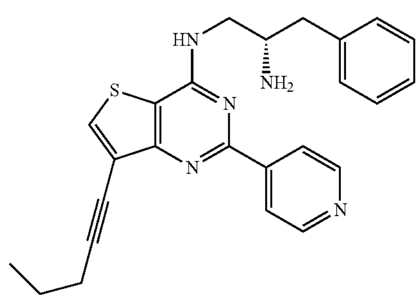 [SMILES: CCCC#Cc1csc2c(NC[C@@H](N)Cc3ccccc3)nc(-c3ccncc3)nc12] | (S)-N*1*-(7-Pent-1-ynyl-2-pyridin-4-yl-thieno[3,2-d]pyrimidin-4-yl)-3-phenyl-propane-1,2-diamine |

-continued

| Ex | Activity | Structure | Name |
|---|---|---|---|
| 402 | B | 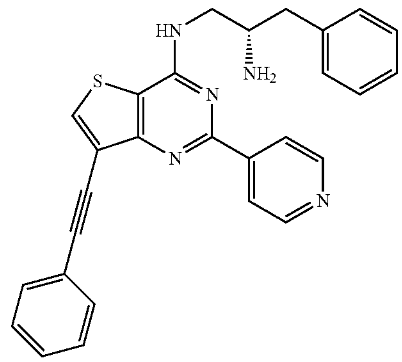 [SMILES: N[C@H](CNc1nc(-c2ccncc2)nc2c(C#Cc3ccccc3)csc12)Cc1ccccc1] | (S)-3-Phenyl-N*1*-(7-phenylethynyl-2-pyridin-4-yl-thieno[3,2-d]pyrimidin-4-yl)-propane-1,2-diamine |
| 403 | A | 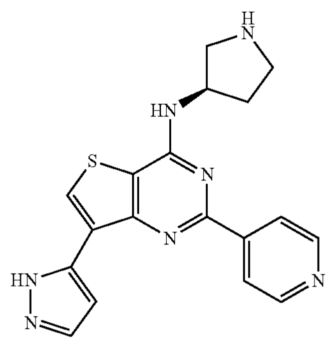 [SMILES: c1cc(-c2nc(N[C@@H]3CCNC3)c3scc(-c4ccn[nH]4)c3n2)ccn1] | [7-(2H-Pyrazol-3-yl)-2-pyridin-4-yl-thieno[3,2-d]pyrimidin-4-yl]-(R)-pyrrolidin-3-yl-amine |
| 404 | B | 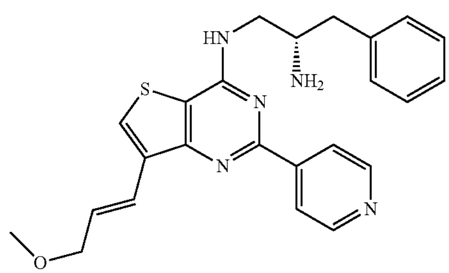 [SMILES: COC/C=C/c1csc2c(NC[C@@H](N)Cc3ccccc3)nc(-c3ccncc3)nc12] | (S)-N*1*-[7-((E)-3-Methoxy-propenyl)-2-pyridin-4-yl-thieno[3,2-d]pyrimidin-4-yl]-3-phenyl-propane-1,2-diamine |
| 405 | A | 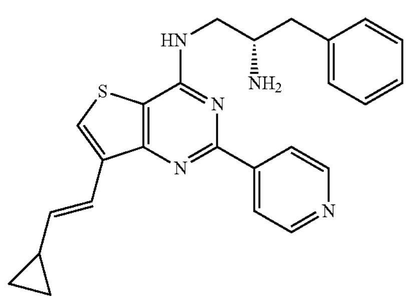 [SMILES: N[C@H](CNc1nc(-c2ccncc2)nc2c(/C=C/C3CC3)csc12)Cc1ccccc1] | (S)-N*1*-[7-((E)-2-Cyclopropyl-vinyl)-2-pyridin-4-yl-thieno[3,2-d]pyrimidin-4-yl]-3-phenyl-propane-1,2-diamine |
| 406 | C | 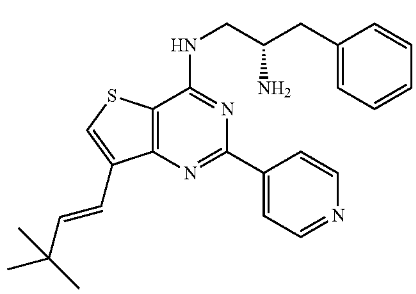 [SMILES: CC(C)(C)/C=C/c1csc2c(NC[C@@H](N)Cc3ccccc3)nc(-c3ccncc3)nc12] | (S)-N*1*-[7-((E)-3,3-Dimethyl-but-1-enyl)-2-pyridin-4-yl-thieno[3,2-d]pyrimidin-4-yl]-3-phenyl-propane-1,2-diamine |

| Ex | Activity | Structure | Name |
|---|---|---|---|
| 407 | A | 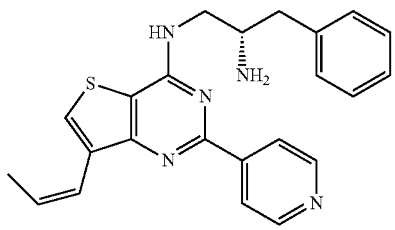 [SMILES: C/C=C\c1csc2c(NC[C@@H](N)Cc3ccccc3)nc(-c3ccncc3)nc12] | (S)-3-Phenyl-N*1*-[7-((Z)-propenyl)-2-pyridin-4-yl-thieno[3,2-d]pyrimidin-4-yl]-propane-1,2-diamine |
| 408 | A | 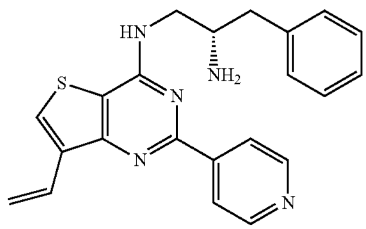 [SMILES: C=Cc1csc2c(NC[C@@H](N)Cc3ccccc3)nc(-c3ccncc3)nc12] | (S)-3-Phenyl-N*1*-(2-pyridin-4-yl-7-vinyl-thieno[3,2-d]pyrimidin-4-yl)-propane-1,2-diamine |
| 409 | B | 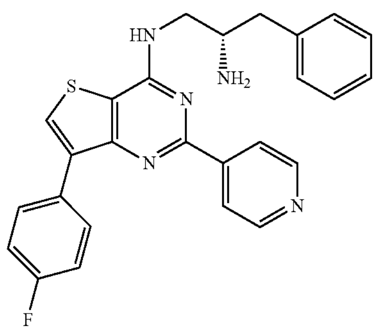 [SMILES: N[C@H](CNc1nc(-c2ccncc2)nc2c(-c3ccc(F)cc3)csc12)Cc1ccccc1] | (S)-N*1*-[7-(4-Fluoro-phenyl)-2-pyridin-4-yl-thieno[3,2-d]pyrimidin-4-yl]-3-phenyl-propane-1,2-diamine |
| 410 | C | 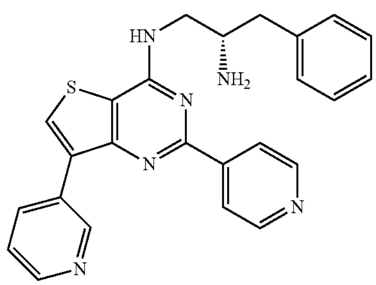 [SMILES: N[C@H](CNc1nc(-c2ccncc2)nc2c(-c3cccnc3)csc12)Cc1ccccc1] | (S)-3-Phenyl-N*1*-(2-pyridin-4-yl-7-pyridin-3-yl-thieno[3,2-d]pyrimidin-4-yl)-propane-1,2-diamine |
| 411 | C | 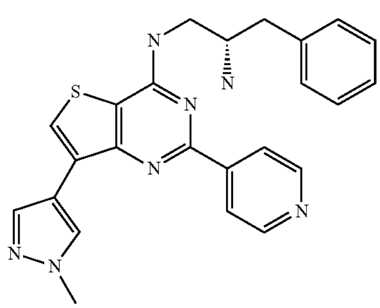 [SMILES: Cn1cc(-c2csc3c(NC[C@@H](N)Cc4ccccc4)nc(-c4ccncc4)nc23)cn1] | (S)-N*1*-[7-(1-Methyl-1H-pyrazol-4-yl)-2-pyridin-4-yl-thieno[3,2-d]pyrimidin-4-yl]-3-phenyl-propane-1,2-diamine |

-continued

| Ex | Activity | Structure | Name |
|---|---|---|---|
| 412 | C | 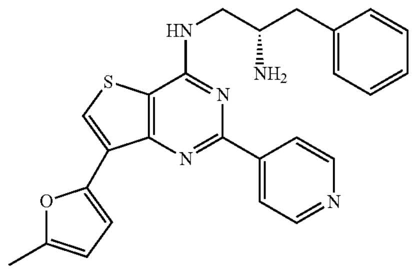 [SMILES: Cc1ccc(-c2csc3c(NC[C@@H](N)Cc4ccccc4)nc(-c4ccncc4)nc23)o1] | (S)-N*1*-[7-(5-Methyl-furan-2-yl)-2-pyridin-4-yl-thieno[3,2-d]pyrimidin-4-yl]-3-phenyl-propane-1,2-diamine |
| 413 | A | 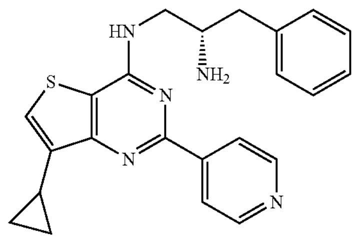 [SMILES: N[C@H](CNc1nc(-c2ccncc2)nc2c(C3CC3)csc12)Cc1ccccc1] | (S)-N*1*-(7-Cyclopropyl-2-pyridin-4-yl-thieno[3,2-d]pyrimidin-4-yl)-3-phenyl-propane-1,2-diamine |
| 414 | B | 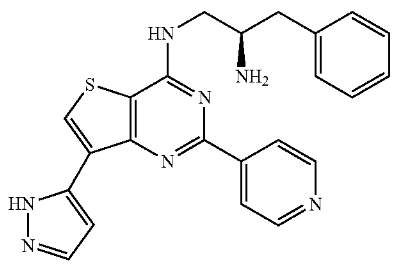 [SMILES: N[C@@H](CNc1nc(-c2ccncc2)nc2c(-c3ccn[nH]3)csc12)Cc1ccccc1] | (R)-3-Phenyl-N*1*-[7-(1H-pyrazol-3-yl)-2-pyridin-4-yl-thieno[3,2-d]pyrimidin-4-yl]-propane-1,2-diamine |
| 415 | C | 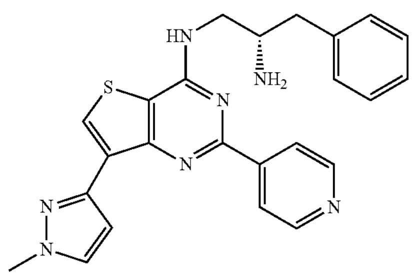 [SMILES: Cn1ccc(-c2csc3c(NC[C@@H](N)Cc4ccccc4)nc(-c4ccncc4)nc23)n1] | (S)-N*1*-[7-(1-Methyl-1H-pyrazol-3-yl)-2-pyridin-4-yl-thieno[3,2-d]pyrimidin-4-yl]-3-phenyl-propane-1,2-diamine |
| 416 | A | 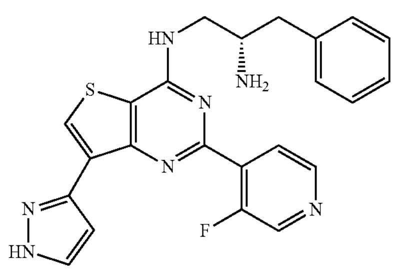 [SMILES: N[C@H](CNc1nc(-c2ccncc2F)nc2c(-c3cc[nH]n3)csc12)Cc1ccccc1] | (S)-N*1*-[2-(3-Fluoro-pyridin-4-yl)-7-(1H-pyrazol-3-yl)-thieno[3,2-d]pyrimidin-4-yl]-3-phenyl-propane-1,2-diamine |
| 417 | B | 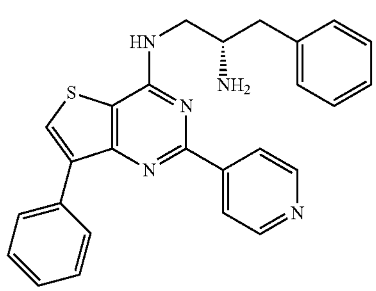 [SMILES: N[C@H](CNc1nc(-c2ccncc2)nc2c(-c3ccccc3)csc12)Cc1ccccc1] | (S)-3-Phenyl-N*1*-(7-phenyl-2-pyridin-4-yl-thieno[3,2-d]pyrimidin-4-yl)-propane-1,2-diamine |

-continued

| Ex | Activity | Structure | Name |
|---|---|---|---|
| 418 | B | 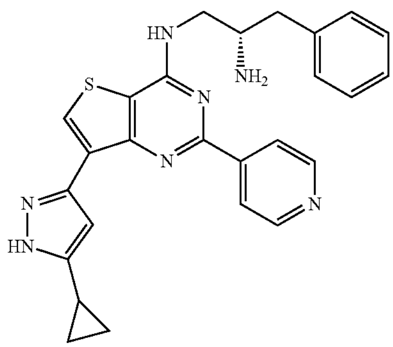 [SMILES: N[C@H](CNc1nc(-c2ccncc2)nc2c(-c3cc(C4CC4)[nH]n3)csc12)Cc1ccccc1] | (S)-N*1*-[7-(5-Cyclopropyl-1H-pyrazol-3-yl)-2-pyridin-4-yl-thieno[3,2-d]pyrimidin-4-yl]-3-phenyl-propane-1,2-diamine |
| 419 | B | 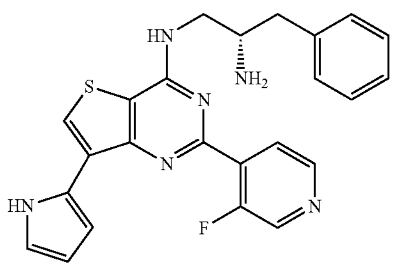 [SMILES: N[C@H](CNc1nc(-c2ccncc2F)nc2c(-c3ccc[nH]3)csc12)Cc1ccccc1] | (S)-N*1*-[2-(3-Fluoro-pyridin-4-yl)-7-(1H-pyrrol-2-yl)-thieno[3,2-d]pyrimidin-4-yl]-3-phenyl-propane-1,2-diamine |
| 420 | B | 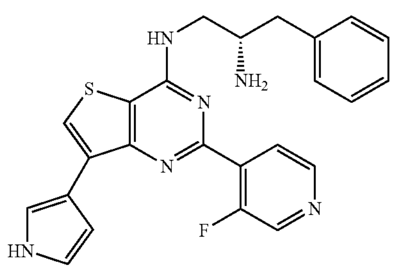 [SMILES: N[C@H](CNc1nc(-c2ccncc2F)nc2c(-c3cc[nH]c3)csc12)Cc1ccccc1] | (S)-N*1*-[2-(3-Fluoro-pyridin-4-yl)-7-(1H-pyrrol-3-yl)-thieno[3,2-d]pyrimidin-4-yl]-3-phenyl-propane-1,2-diamine |
| 421 | C | 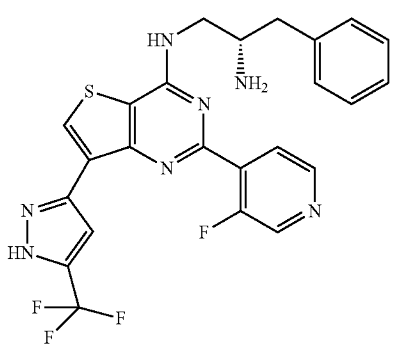 [SMILES: N[C@H](CNc1nc(-c2ccncc2F)nc2c(-c3cc(C(F)(F)F)[nH]n3)csc12)Cc1ccccc1] | (S)-N*1*-[2-(3-Fluoro-pyridin-4-yl)-7-(5-trifluoromethyl-2H-pyrazol-3-yl)-thieno[3,2-d]pyrimidin-4-yl]-3-phenyl-propane-1,2-diamine |
| 422 | C | 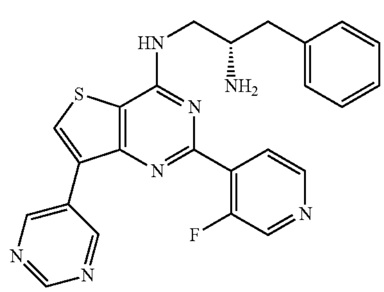 [SMILES: N[C@H](CNc1nc(-c2ccncc2F)nc2c(-c3cncnc3)csc12)Cc1ccccc1] | (R)-N*1*-[2-(3-Fluoro-pyridin-4-yl)-7-pyrimidin-5-yl-thieno[3,2-d]pyrimidin-4-yl]-3-phenyl-propane-1,2-diamine |

-continued

| Ex | Activity | Structure | Name |
|---|---|---|---|
| 423 | C | 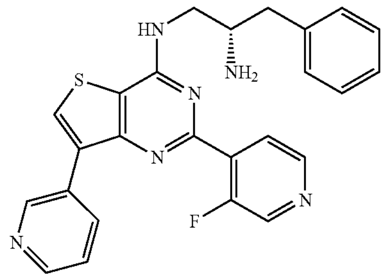 [SMILES: N[C@H](CNc1nc(-c2ccncc2F)nc2c(-c3cccnc3)csc12)Cc1ccccc1] | (R)-N*1*-[2-(3-Fluoro-pyridin-4-yl)-7-pyridin-3-yl-thieno[3,2-d]pyrimidin-4-yl]-3-phenyl-propane-1,2-diamine |
| 424 | C | 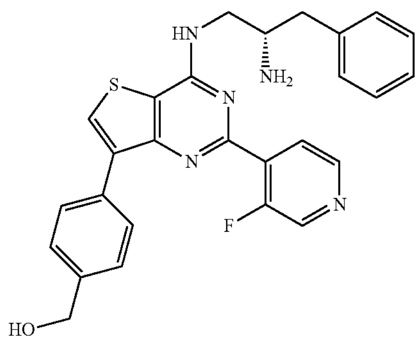 [SMILES: N[C@H](CNc1nc(-c2ccncc2F)nc2c(-c3ccc(CO)cc3)csc12)Cc1ccccc1] | {4-[4-((R)-2-Amino-3-phenyl-propylamino)-2-(3-fluoro-pyridin-4-yl)-thieno[3,2-d]pyrimidin-7-yl]-phenyl}-methanol |
| 425 | C | 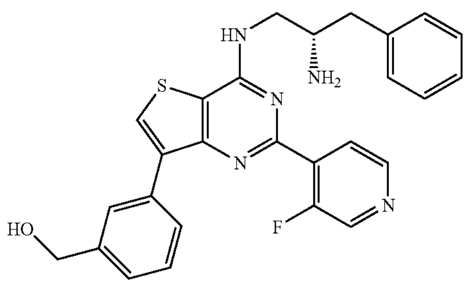 [SMILES: N[C@H](CNc1nc(-c2ccncc2F)nc2c(-c3cccc(CO)c3)csc12)Cc1ccccc1] | {3-[4-((R)-2-Amino-3-phenyl-propylamino)-2-(3-fluoro-pyridin-4-yl)-thieno[3,2-d]pyrimidin-7-yl]-phenyl}-methanol |
| 426 | B | 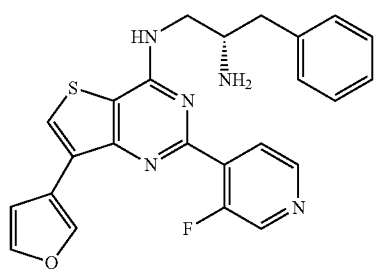 | (R)-N*1*-[2-(3-Fluoro-pyridin-4-yl)-7-furan-3-yl-thieno[3,2-d]pyrimidin-4-yl]-3-phenyl-propane-1,2-diamine |
| 427 | C | 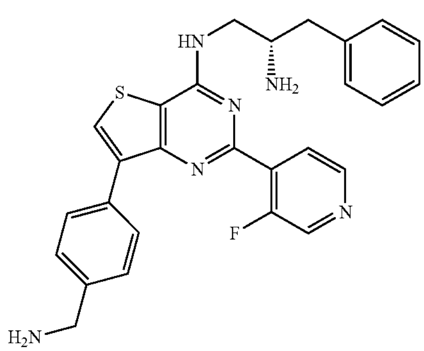 [SMILES: NCc1ccc(-c2csc3c(NC[C@@H](N)Cc4ccccc4)nc(-c4ccncc4F)nc23)cc1] | (R)-N*1*-[7-(4-Aminomethyl-phenyl)-2-(3-fluoro-pyridin-4-yl)-thieno[3,2-d]pyrimidin-4-yl]-3-phenyl-propane-1,2-diamine |

-continued

| Ex | Activity | Structure | Name |
|---|---|---|---|
| 428 | C | 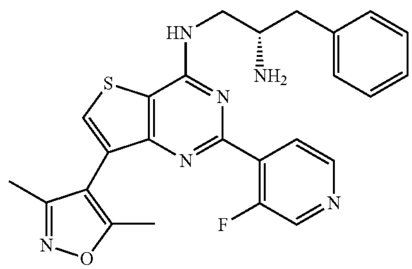 [SMILES: Cc1noc(C)c1-c1csc2c(NC[C@@H](N)Cc3ccccc3)nc(-c3ccncc3F)nc12] | (R)-N*1*-[7-(3,5-Dimethyl-isoxazol-4-yl)-2-(3-fluoro-pyridin-4-yl)-thieno[3,2-d]pyrimidin-4-yl]-3-phenyl-propane-1,2-diamine |
| 429 | C | 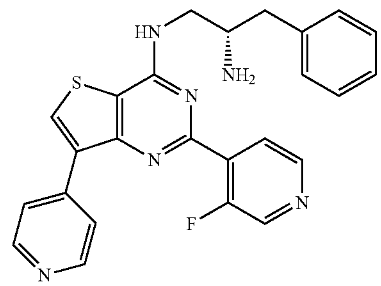 [SMILES: N[C@H](CNc1nc(-c2ccncc2F)nc2c(-c3ccncc3)csc12)Cc1ccccc1] | (R)-N*1*-[2-(3-Fluoro-pyridin-4-yl)-7-pyridin-4-yl-thieno[3,2-d]pyrimidin-4-yl]-3-phenyl-propane-1,2-diamine |
| 430 | C | 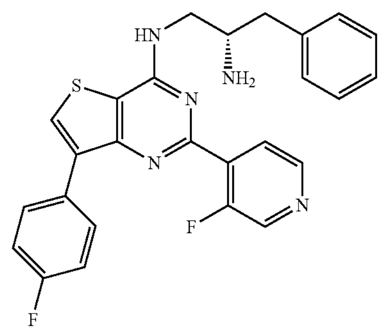 [SMILES: N[C@H](CNc1nc(-c2ccncc2F)nc2c(-c3ccc(F)cc3)csc12)Cc1ccccc1] | (R)-N*1*-[7-(4-Fluoro-phenyl)-2-(3-fluoro-pyridin-4-yl)-thieno[3,2-d]pyrimidin-4-yl]-3-phenyl-propane-1,2-diamine |
| 431 | C | 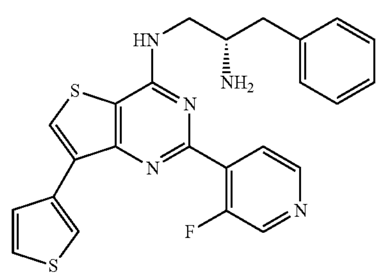 [SMILES: N[C@H](CNc1nc(-c2ccncc2F)nc2c(-c3ccsc3)csc12)Cc1ccccc1] | (R)-N*1*-[2-(3-Fluoro-pyridin-4-yl)-7-thiophen-3-yl-thieno[3,2-d]pyrimidin-4-yl]-3-phenyl-propane-1,2-diamine |
| 432 | B | 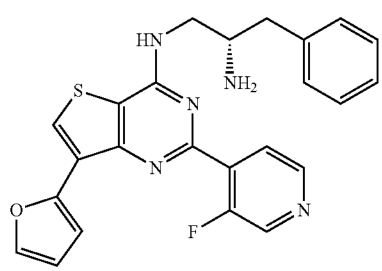 [SMILES: N[C@H](CNc1nc(-c2ccncc2F)nc2c(-c3ccco3)csc12)Cc1ccccc1] | (R)-N*1*-[2-(3-Fluoro-pyridin-4-yl)-7-furan-2-yl-thieno[3,2-d]pyrimidin-4-yl]-3-phenyl-propane-1,2-diamine |

| Ex | Activity | Name |
|---|---|---|
| 433 | C | (S)-N*1*-[2-(3-Fluoro-pyridin-4-yl)-7-o-tolyl-thieno[3,2-d]pyrimidin-4-yl]-3-phenyl-propane-1,2-diamine |
| 434 | C | (S)-N*1*-[2-(3-Fluoro-pyridin-4-yl)-7-phenyl-thieno[3,2-d]pyrimidin-4-yl]-3-phenyl-propane-1,2-diamine |
| 435 | C | S)-N*1*-[7-(4-Aminomethyl-furan-2-yl)-2-(3-fluoro-pyridin-4-yl)-thieno[3,2-d]pyrimidin-4-yl]-3-phenyl-propane-1,2-diamine |
| 436 | D | (S)-N*1*-[6-tert-Butyl-7-(3-fluoro-phenyl)-2-pyridin-4-yl-thieno[3,2-d]pyrimidin-4-yl]-3-phenyl-propane-1,2-diamine |
| 437 | C | (S)-N*1*-[6-tert-Butyl-7-(1H-pyrazol-4-yl)-2-pyridin-4-yl-thieno[3,2-d]pyrimidin-4-yl]-3-phenyl-propane-1,2-diamine |

-continued

| Ex | Activity | Structure | Name |
|---|---|---|---|
| 438 | C | 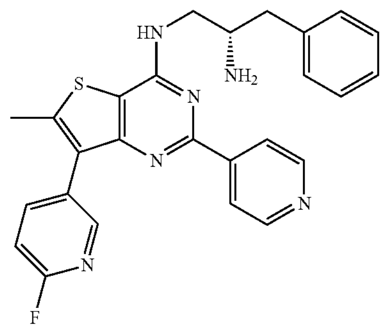 [SMILES: Cc1sc2c(NC[C@@H](N)Cc3ccccc3)nc(-c3ccncc3)nc2c1-c1ccc(F)nc1] | (S)-N*1*-[7-(6-Fluoro-pyridin-3-yl)-6-methyl-2-pyridin-4-yl-thieno[3,2-d]pyrimidin-4-yl]-3-phenyl-propane-1,2-diamine |
| 439 | D | 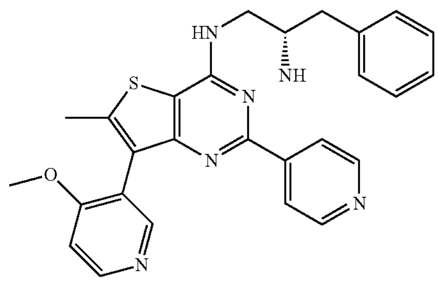 [SMILES: COc1ccncc1-c1c(C)sc2c(NC[C@@H](N)Cc3ccccc3)nc(-c3ccncc3)nc12] | (S)-N*1*-[7-(4-Methoxy-pyridin-3-yl)-6-methyl-2-pyridin-4-yl-thieno[3,2-d]pyrimidin-4-yl]-3-phenyl-propane-1,2-diamine |
| 440 | D | 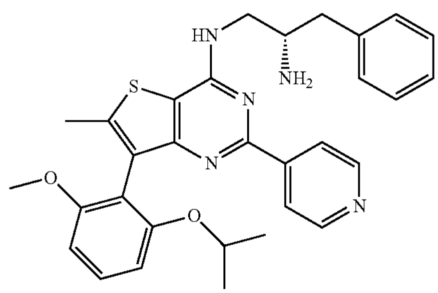 [SMILES: COc1cccc(OC(C)C)c1-c1c(C)sc2c(NC[C@@H](N)Cc3ccccc3)nc(-c3ccncc3)nc12] | (S)-N*1*-[7-(2-Isopropoxy-6-methoxy-phenyl)-6-methyl-2-pyridin-4-yl-thieno[3,2-d]pyrimidin-4-yl]-3-phenyl-propane-1,2-diamine |
| 441 | D | 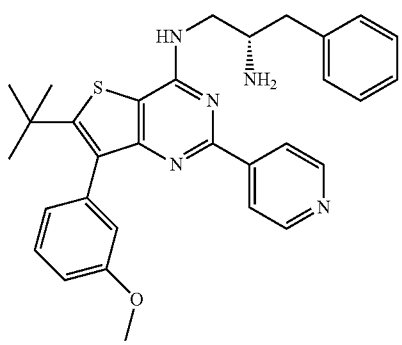 [SMILES: COc1cccc(-c2c(C(C)(C)C)sc3c(NC[C@@H](N)Cc4ccccc4)nc(-c4ccncc4)nc23)c1] | (S)-N*1*-[6-tert-Butyl-7-(3-methoxy-phenyl)-2-pyridin-4-yl-thieno[3,2-d]pyrimidin-4-yl]-3-phenyl-propane-1,2-diamine |
| 442 | D | 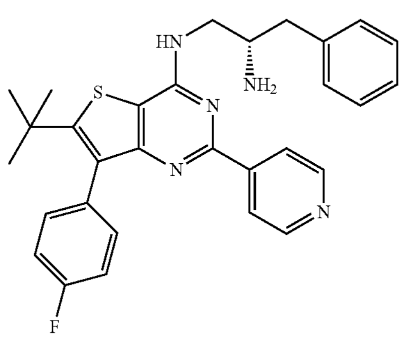 [SMILES: CC(C)(C)c1sc2c(NC[C@@H](N)Cc3ccccc3)nc(-c3ccncc3)nc2c1-c1ccc(F)cc1] | (S)-N*1*-[6-tert-Butyl-7-(4-fluoro-phenyl)-2-pyridin-4-yl-thieno[3,2-d]pyrimidin-4-yl]-3-phenyl-propane-1,2-diamine |

-continued

| Ex | Activity | Structure | Name |
|---|---|---|---|
| 443 | D | 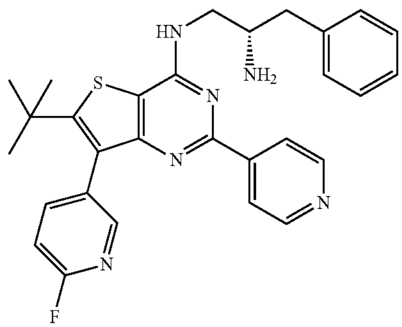 [SMILES: CC(C)(C)c1sc2c(NC[C@@H](N)Cc3ccccc3)nc(-c3ccncc3)nc2c1-c1ccc(F)nc1] | (S)-N*1*-[6-tert-Butyl-7-(6-fluoro-pyridin-3-yl)-2-pyridin-4-yl-thieno[3,2-d]pyrimidin-4-yl]-3-phenyl-propane-1,2-diamine |
| 444 | D | 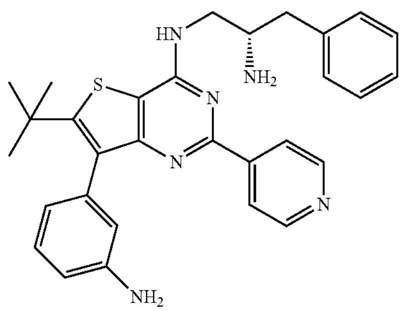 [SMILES: CC(C)(C)c1sc2c(NC[C@@H](N)Cc3ccccc3)nc(-c3ccncc3)nc2c1-c1cccc(N)c1] | (S)-N*1*-[7-(3-Amino-phenyl)-6-tert-butyl-2-pyridin-4-yl-thieno[3,2-d]pyrimidin-4-yl]-3-phenyl-propane-1,2-diamine |
| 445 | D | 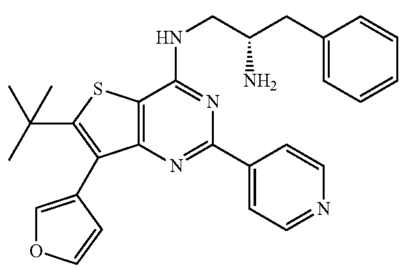 [SMILES: CC(C)(C)c1sc2c(NC[C@@H](N)Cc3ccccc3)nc(-c3ccncc3)nc2c1-c1ccoc1] | (S)-N*1*-(6-tert-Butyl-7-furan-3-yl-2-pyridin-4-yl-thieno[3,2-d]pyrimidin-4-yl)-3-phenyl-propane-1,2-diamine |
| 446 | D | 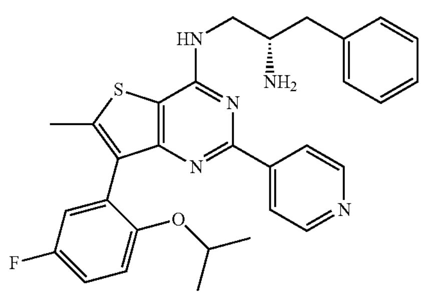 [SMILES: Cc1sc2c(NC[C@@H](N)Cc3ccccc3)nc(-c3ccncc3)nc2c1-c1cc(F)ccc1OC(C)C] | (S)-N*1*-[7-(5-Fluoro-2-isopropoxy-phenyl)-6-methyl-2-pyridin-4-yl-thieno[3,2-d]pyrimidin-4-yl]-3-phenyl-propane-1,2-diamine |
| 447 | C | 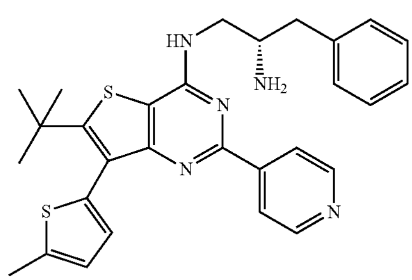 [SMILES: Cc1ccc(-c2c(C(C)(C)C)sc3c(NC[C@@H](N)Cc4ccccc4)nc(-c4ccncc4)nc23)s1] | (S)-N*1*-[6-tert-Butyl-7-(5-methyl-thiophen-2-yl)-2-pyridin-4-yl-thieno[3,2-d]pyrimidin-4-yl]-3-phenyl-propane-1,2-diamine |

| Ex | Activity | Structure | Name |
|---|---|---|---|
| 448 | C | 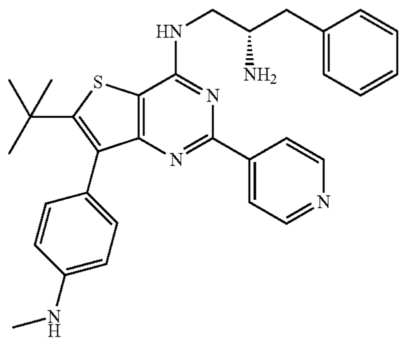 [SMILES: CNc1ccc(-c2c(C(C)(C)C)sc3c(NC[C@@H](N)Cc4ccccc4)nc(-c4ccncc4)nc23)cc1] | (S)-N*1*-[6-tert-Butyl-7-(4-methylamino-phenyl)-2-pyridin-4-yl-thieno[3,2-d]pyrimidin-4-yl]-3-phenyl-propane-1,2-diamine |
| 449 | C | 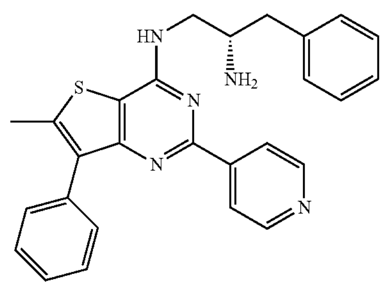 [SMILES: Cc1sc2c(NC[C@@H](N)Cc3ccccc3)nc(-c3ccncc3)nc2c1-c1ccccc1] | (S)-N*1*-(6-Methyl-7-phenyl-2-pyridin-4-yl-thieno[3,2-d]pyrimidin-4-yl)-3-phenyl-propane-1,2-diamine |
| 450 | D | 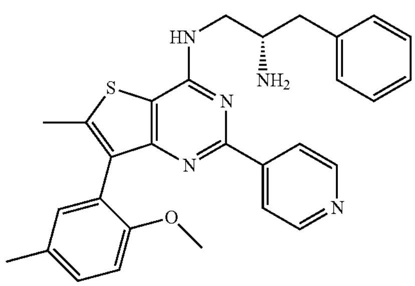 [SMILES: COc1ccc(C)cc1-c1c(C)sc2c(NC[C@@H](N)Cc3ccccc3)nc(-c3ccncc3)nc12] | (S)-N*1*-[7-(2-Methoxy-5-methyl-phenyl)-6-methyl-2-pyridin-4-yl-thieno[3,2-d]pyrimidin-4-yl]-3-phenyl-propane-1,2-diamine |
| 451 | D | 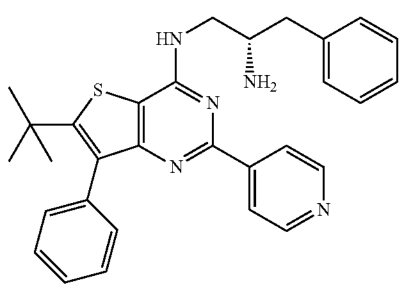 [SMILES: CC(C)(C)c1sc2c(NC[C@@H](N)Cc3ccccc3)nc(-c3ccncc3)nc2c1-c1ccccc1] | (S)-N*1*-(6-tert-Butyl-7-phenyl-2-pyridin-4-yl-thieno[3,2-d]pyrimidin-4-yl)-3-phenyl-propane-1,2-diamine |
| 452 | D | 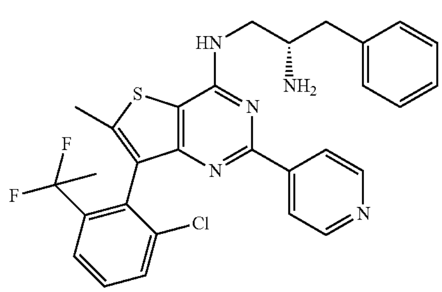 [SMILES: Cc1sc2c(NC[C@@H](N)Cc3ccccc3)nc(-c3ccncc3)nc2c1-c1c(Cl)cccc1C(C)(F)F] | (S)-N*1*-[7-(2-Chloro-6-trifluoromethyl-phenyl)-6-methyl-2-pyridin-4-yl-thieno[3,2-d]pyrimidin-4-yl]-3-phenyl-propane-1,2-diamine |

-continued

| Ex | Activity | Structure | Name |
|---|---|---|---|
| 453 | D | 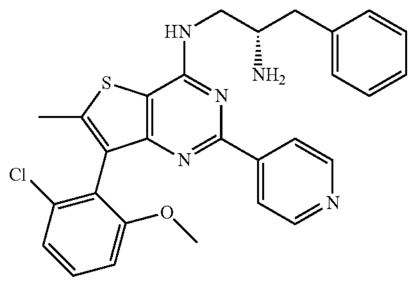 [SMILES: COc1cccc(Cl)c1-c1c(C)sc2c(NC[C@@H](N)Cc3ccccc3)nc(-c3ccncc3)nc12] | (S)-N*1*-[7-(2-Chloro-6-methoxy-phenyl)-6-methyl-2-pyridin-4-yl-thieno[3,2-d]pyrimidin-4-yl]-3-phenyl-propane-1,2-diamine |
| 454 | D | 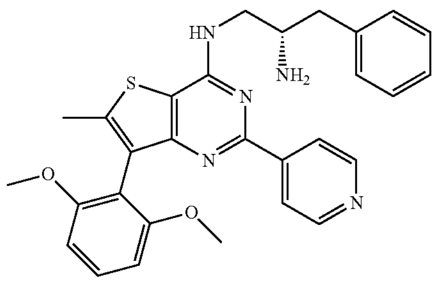 [SMILES: COc1cccc(OC)c1-c1c(C)sc2c(NC[C@@H](N)Cc3ccccc3)nc(-c3ccncc3)nc12] | (S)-N*1*-[7-(2,6-Dimethoxy-phenyl)-6-methyl-2-pyridin-4-yl-thieno[3,2-d]pyrimidin-4-yl]-3-phenyl-propane-1,2-diamine |
| 455 | D | 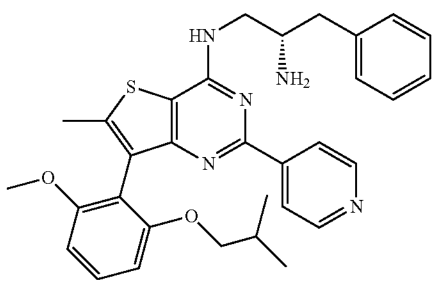 [SMILES: COc1cccc(OCC(C)C)c1-c1c(C)sc2c(NC[C@@H](N)Cc3ccccc3)nc(-c3ccncc3)nc12] | (S)-N*1*-[7-(2-Isobutoxy-6-methoxy-phenyl)-6-methyl-2-pyridin-4-yl-thieno[3,2-d]pyrimidin-4-yl]-3-phenyl-propane-1,2-diamine |
| 456 | D | 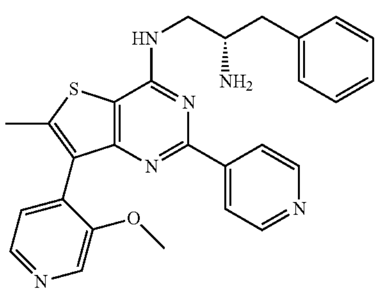 [SMILES: COc1cnccc1-c1c(C)sc2c(NC[C@@H](N)Cc3ccccc3)nc(-c3ccncc3)nc12] | (S)-N*1*-[7-(3-Methoxy-pyridin-4-yl)-6-methyl-2-pyridin-4-yl-thieno[3,2-d]pyrimidin-4-yl]-3-phenyl-propane-1,2-diamine |
| 457 | D | 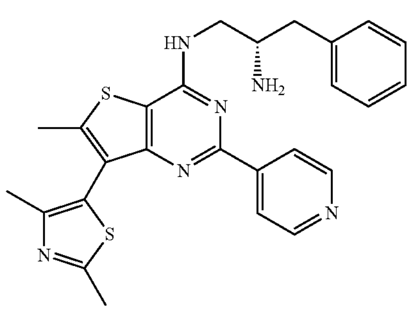 [SMILES: Cc1nc(C)c(-c2c(C)sc3c(NC[C@@H](N)Cc4ccccc4)nc(-c4ccncc4)nc23)s1] | (S)-N*1*-[7-(2,4-Dimethyl-thiazol-5-yl)-6-methyl-2-pyridin-4-yl-thieno[3,2-d]pyrimidin-4-yl]-3-phenyl-propane-1,2-diamine |

| Ex | Activity | Structure | Name |
|---|---|---|---|
| 458 | D | 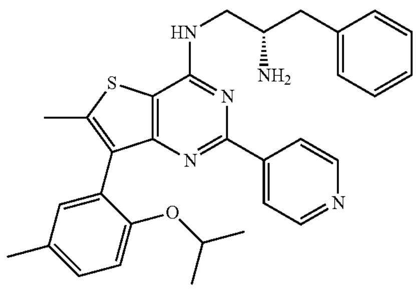 [SMILES: Cc1ccc(OC(C)C)c(-c2c(C)sc3c(NC[C@@H](N)Cc4ccccc4)nc(-c4ccncc4)nc23)c1] | (S)-N*1*-[7-(2-Isopropoxy-5-methyl-phenyl)-6-methyl-2-pyridin-4-yl-thieno[3,2-d]pyrimidin-4-yl]-3-phenyl-propane-1,2-diamine |
| 459 | D | 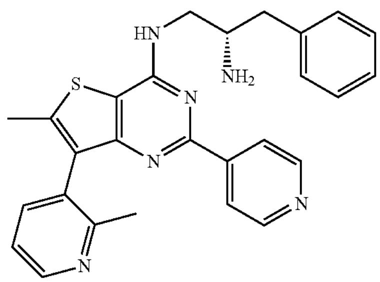 [SMILES: Cc1ncccc1-c1c(C)sc2c(NC[C@@H](N)Cc3ccccc3)nc(-c3ccncc3)nc12] | (S)-N*1*-[6-Methyl-7-(2-methyl-pyridin-3-yl)-2-pyridin-4-yl-thieno[3,2-d]pyrimidin-4-yl]-3-phenyl-propane-1,2-diamine |
| 460 | D | 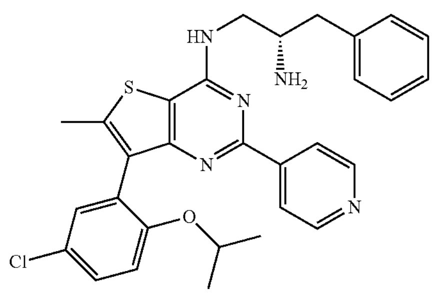 [SMILES: Cc1sc2c(NC[C@@H](N)Cc3ccccc3)nc(-c3ccncc3)nc2c1-c1cc(Cl)ccc1OC(C)C] | (S)-N*1*-[7-(5-Chloro-2-isopropoxy-phenyl)-6-methyl-2-pyridin-4-yl-thieno[3,2-d]pyrimidin-4-yl]-3-phenyl-propane-1,2-diamine |
| 461 | D | 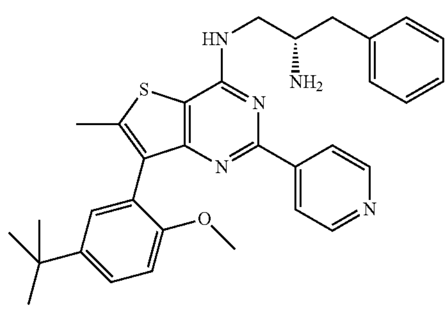 [SMILES: COc1ccc(C(C)(C)C)cc1-c1c(C)sc2c(NC[C@@H](N)Cc3ccccc3)nc(-c3ccncc3)nc12] | (S)-N*1*-[7-(5-tert-Butyl-2-methoxy-phenyl)-6-methyl-2-pyridin-4-yl-thieno[3,2-d]pyrimidin-4-yl]-3-phenyl-propane-1,2-diamine |
| 462 | D | 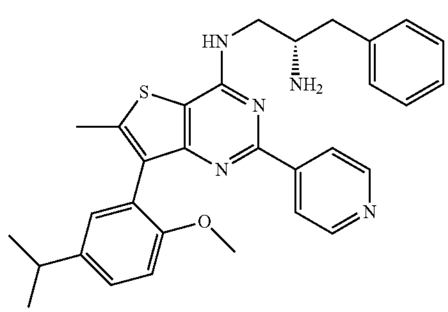 [SMILES: COc1ccc(C(C)C)cc1-c1c(C)sc2c(NC[C@@H](N)Cc3ccccc3)nc(-c3ccncc3)nc12] | (S)-N*1*-[7-(5-Isopropyl-2-methoxy-phenyl)-6-methyl-2-pyridin-4-yl-thieno[3,2-d]pyrimidin-4-yl]-3-phenyl-propane-1,2-diamine |

| Ex | Activity | Structure | Name |
|---|---|---|---|
| 463 | D | 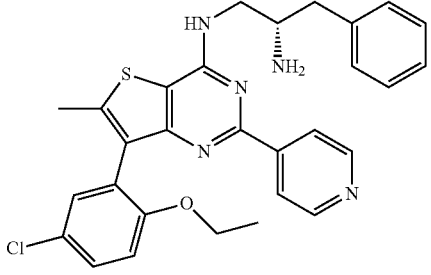 [SMILES: CCOc1ccc(Cl)cc1-c1c(C)sc2c(NC[C@@H](N)Cc3ccccc3)nc(-c3ccncc3)nc12] | (S)-N*1*-[7-(5-Chloro-2-ethoxy-phenyl)-6-methyl-2-pyridin-4-yl-thieno[3,2-d]pyrimidin-4-yl]-3-phenyl-propane-1,2-diamine |
| 464 | D | 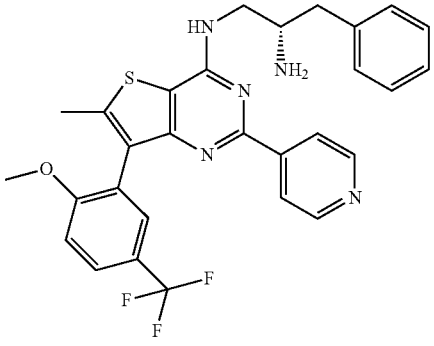 [SMILES: COc1ccc(C(F)(F)F)cc1-c1c(C)sc2c(NC[C@@H](N)Cc3ccccc3)nc(-c3ccncc3)nc12] | (S)-N*1*-[7-(2-Methoxy-5-trifluoromethyl-phenyl)-6-methyl-2-pyridin-4-yl-thieno[3,2-d]pyrimidin-4-yl]-3-phenyl-propane-1,2-diamine |
| 465 | D | 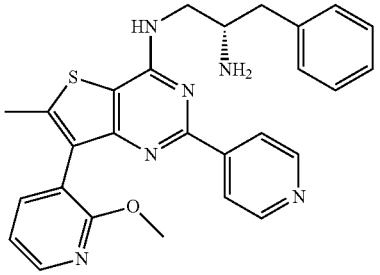 [SMILES: COc1ncccc1-c1c(C)sc2c(NC[C@@H](N)Cc3ccccc3)nc(-c3ccncc3)nc12] | (S)-N*1*-[7-(2-Methoxy-pyridin-3-yl)-6-methyl-2-pyridin-4-yl-thieno[3,2-d]pyrimidin-4-yl]-3-phenyl-propane-1,2-diamine |
| 466 | D | 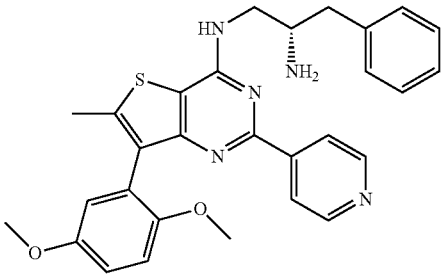 [SMILES: COc1ccc(OC)c(-c2c(C)sc3c(NC[C@@H](N)Cc4ccccc4)nc(-c4ccncc4)nc23)c1] | (S)-N*1*-[7-(2,5-Dimethoxy-phenyl)-6-methyl-2-pyridin-4-yl-thieno[3,2-d]pyrimidin-4-yl]-3-phenyl-propane-1,2-diamine |
| 467 | D | 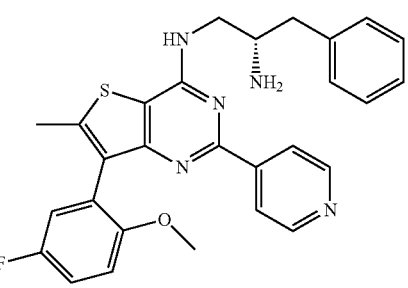 | (S)-N*1*-[7-(5-Fluoro-2-methoxy-phenyl)-6-methyl-2-pyridin-4-yl-thieno[3,2-d]pyrimidin-4-yl]-3-phenyl-propane-1,2-diamine |

-continued

| Ex | Activity | Structure | Name |
|---|---|---|---|
| 468 | C | 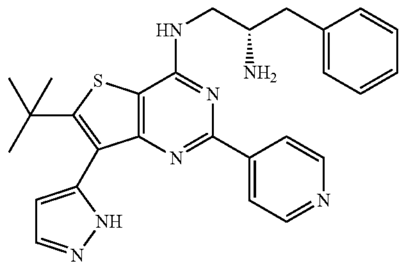 [SMILES: CC(C)(C)c1sc2c(NC[C@@H](N)Cc3ccccc3)nc(-c3ccncc3)nc2c1-c1ccn[nH]1] | (S)-N*1*-[6-tert-Butyl-7-(2H-pyrazol-3-yl)-2-pyridin-4-yl-thieno[3,2-d]pyrimidin-4-yl]-3-phenyl-propane-1,2-diamine |
| 469 | D | 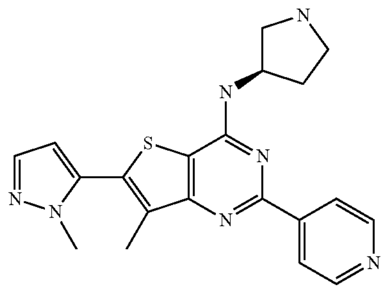 [SMILES: Cc1c(-c2ccnn2C)sc2c(N[C@@H]3CCNC3)nc(-c3ccncc3)nc12] | [7-Methyl-6-(2-methyl-2H-pyrazol-3-yl)-2-pyridin-4-yl-thieno[3,2-d]pyrimidin-4-l]-(R)-pyrrolidin-3-yl-amine |
| 470 | D | 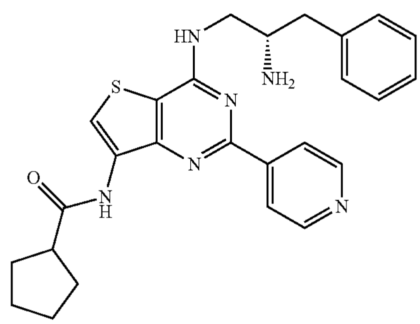 [SMILES: N[C@H](CNc1nc(-c2ccncc2)nc2c(NC(=O)C3CCCC3)csc12)Cc1ccccc1] | Cyclopentanecarboxylic acid [4-((S)-2-amino-3-phenyl-propylamino)-2-pyridin-4-yl-thieno[3,2-d]pyrimidin-7-yl]-amide |
| 471 | D | 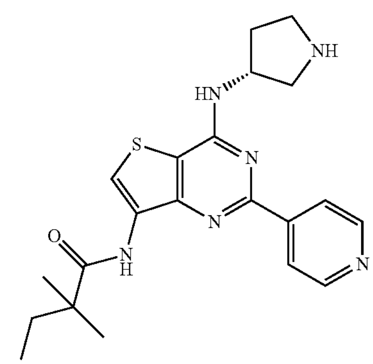 [SMILES: CCC(C)(C)C(=O)Nc1csc2c(N[C@@H]3CCNC3)nc(-c3ccncc3)nc12] | 2,2-Dimethyl-N-[2-pyridin-4-yl-4-((R)-pyrrolidin-3-ylamino)-thieno[3,2-d]pyrimidin-7-yl]-butyramide |
| 472 | D | 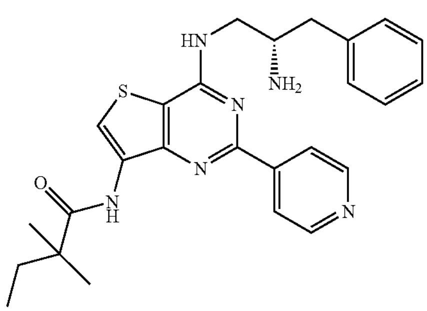 [SMILES: CCC(C)(C)C(=O)Nc1csc2c(NC[C@@H](N)Cc3ccccc3)nc(-c3ccncc3)nc12] | N-[4-((S)-2-Amino-3-phenyl-propylamino)-2-pyridin-4-yl-thieno[3,2-d]pyrimidin-7-yl]-2,2-dimethyl-butyramide |

-continued

| Ex | Activity | Structure | Name |
|---|---|---|---|
| 473 | D | 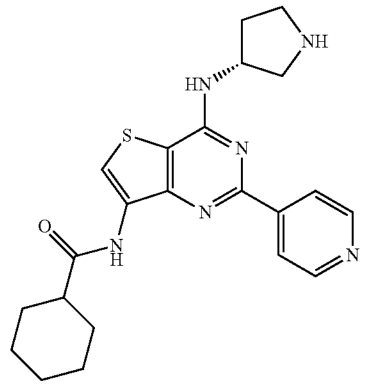 [SMILES: O=C(Nc1csc2c(N[C@@H]3CCNC3)nc(-c3ccncc3)nc12)C1CCCCC1] | Cyclohexanecarboxylic acid [2-pyridin-4-yl-4-((R)-pyrrolidin-3-ylamino)-thieno[3,2-d]pyrimidin-7-yl]-amide |
| 474 | D | 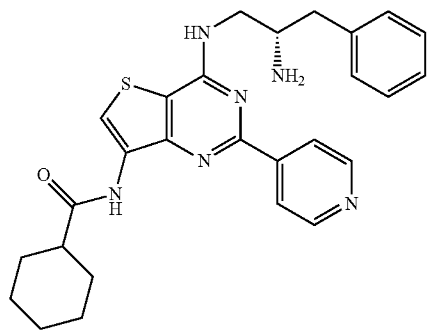 [SMILES: N[C@H](CNc1nc(-c2ccncc2)nc2c(NC(=O)C3CCCCC3)csc12)Cc1ccccc1] | Cyclohexanecarboxylic acid [4-((S)-2-amino-3-phenyl-propylamino)-2-pyridin-4-yl-thieno[3,2-d]pyrimidin-7-yl]-amide |
| 475 | D | 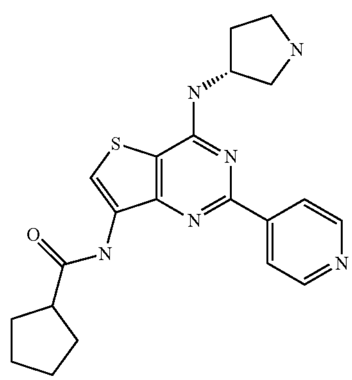 [SMILES: O=C(Nc1csc2c(N[C@@H]3CCNC3)nc(-c3ccncc3)nc12)C1CCCC1] | Cyclopentanecarboxylic acid [2-pyridin-4-yl-4-((R)-pyrrolidin-3-ylamino)-thieno[3,2-d]pyrimidin-7-yl]-amide |
| 476 | D* | 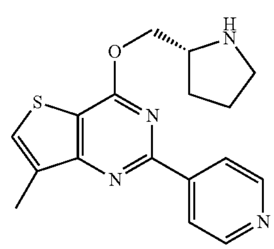 [SMILES: Cc1csc2c(OC[C@H]3CCCN3)nc(-c3ccncc3)nc12] | 7-Methyl-2-pyridin-4-yl-4-((R)-1-pyrrolidin-2-ylmethoxy)-thieno[3,2-d]pyrimidine |
| 477 | D* | 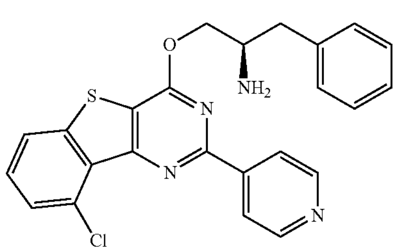 [SMILES: N[C@@H](COc1nc(-c2ccncc2)nc2c1sc1cccc(Cl)c12)Cc1ccccc1] | (R)-1-(9-Chloro-2-pyridin-4-yl-benzo[4,5]thieno[3,2-d]pyrimidin-4-yloxymethyl)-2-phenyl-ethylamine |

| Ex | Activity | Structure | Name |
|---|---|---|---|
| 478 | D* | 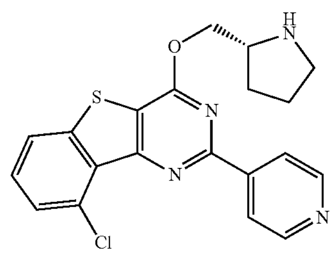 [SMILES: Clc1cccc2sc3c(OC[C@H]4CCCN4)nc(-c4ccncc4)nc3c12] | 9-Chloro-2-pyridin-4-yl-4-((R)-1-pyrrolidin-2-ylmethoxy)-benzo[4,5]thieno[3,2-d]pyrimidine |
| 479 | C* | 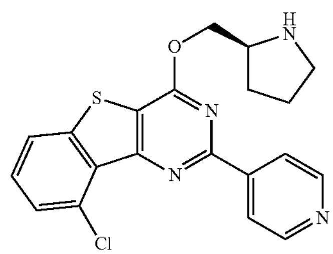 [SMILES: Clc1cccc2sc3c(OC[C@@H]4CCCN4)nc(-c4ccncc4)nc3c12] | 9-Chloro-2-pyridin-4-yl-4-((S)-1-pyrrolidin-2-ylmethoxy)-benzo[4,5]thieno[3,2-d]pyrimidine |
| 480 | D* | 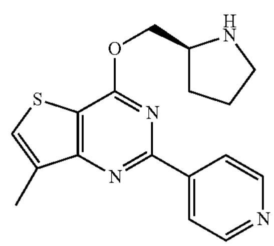 [SMILES: Cc1csc2c(OC[C@@H]3CCCN3)nc(-c3ccncc3)nc12] | 7-Methyl-2-pyridin-4-yl-4-((S)-1-pyrrolidin-2-ylmethoxy)-thieno[3,2-d]pyrimidine |
| 481 | D* | 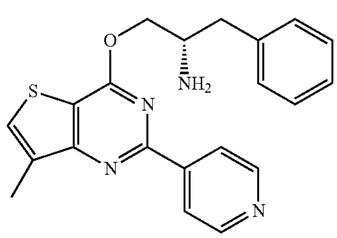 [SMILES: Cc1csc2c(OC[C@@H](N)Cc3ccccc3)nc(-c3ccncc3)nc12] | (S)-1-(7-Methyl-2-pyridin-4-yl-thieno[3,2-d]pyrimidin-4-yloxymethyl)-2-phenyl-ethylamine |
| 482 | D* | 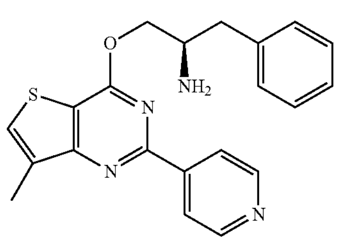 [SMILES: Cc1csc2c(OC[C@H](N)Cc3ccccc3)nc(-c3ccncc3)nc12] | (R)-1-(7-Methyl-2-pyridin-4-yl-thieno[3,2-d]pyrimidin-4-yloxymethyl)-2-phenyl-ethylamine |
| 483 | D* | 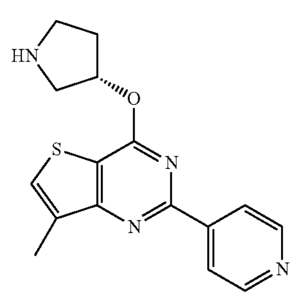 [SMILES: Cc1csc2c(O[C@H]3CCNC3)nc(-c3ccncc3)nc12] | 7-Methyl-2-pyridin-4-yl-4-((S)-pyrrolidin-3-yloxy)-thieno[3,2-d]pyrimidine |

| Ex | Activity | Structure | Name |
| --- | --- | --- | --- |
| 484 | C* | 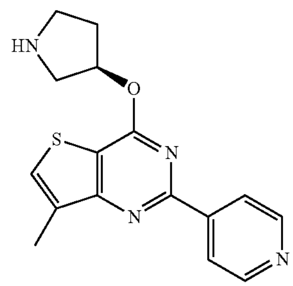 [SMILES: Cc1csc2c(O[C@@H]3CCNC3)nc(-c3ccncc3)nc12] | 7-Methyl-2-pyridin-4-yl-4-((R)-pyrrolidin-3-yloxy)-thieno[3,2-d]pyrimidine |
| 485 | B | 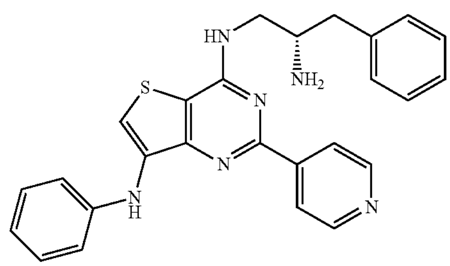 [SMILES: N[C@H](CNc1nc(-c2ccncc2)nc2c(Nc3ccccc3)csc12)Cc1ccccc1] | N*4*-((S)-2-Amino-3-phenyl-propyl)-N*7*-phenyl-2-pyridin-4-yl-thieno[3,2-d]pyrimidine-4,7-diamine |
| 486 | A | 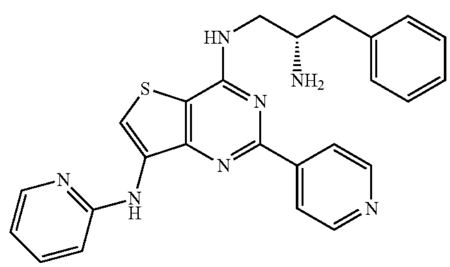 [SMILES: N[C@H](CNc1nc(-c2ccncc2)nc2c(Nc3ccccn3)csc12)Cc1ccccc1] | N*4*-((S)-2-Amino-3-phenyl-propyl)-2-pyridin-4-yl-N*7*-pyridin-2-yl-thieno[3,2-d]pyrimidine-4,7-diamine |
| 487 | C | 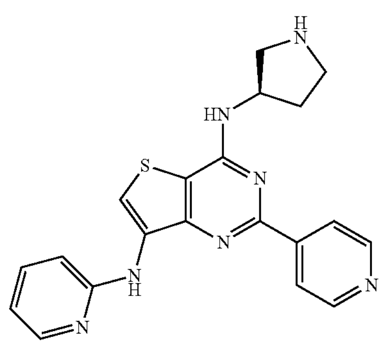 [SMILES: c1ccc(Nc2csc3c(N[C@@H]4CCNC4)nc(-c4ccncc4)nc23)nc1] | 2-Pyridin-4-yl-N*7*-pyridin-2-yl-N*4*-(R)-pyrrolidin-3-yl-thieno[3,2-d]pyrimidine-4,7-diamine |
| 488 | B | 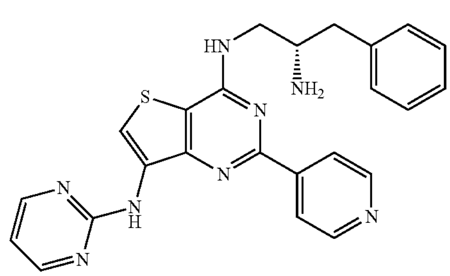 [SMILES: N[C@H](CNc1nc(-c2ccncc2)nc2c(Nc3ncccn3)csc12)Cc1ccccc1] | N*4*-((S)-2-Amino-3-phenyl-propyl)-2-pyridin-4-yl-N*7*-pyrimidin-2-yl-thieno[3,2-d]pyrimidine-4,7-diamine |

| Ex | Activity | Structure | Name |
|---|---|---|---|
| 489 | C | 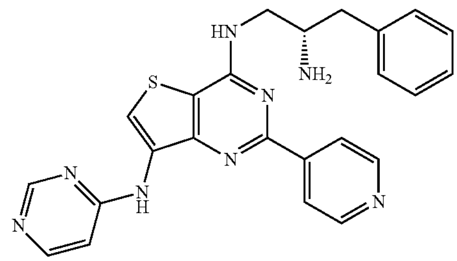 [SMILES: N[C@H](CNc1nc(-c2ccncc2)nc2c(Nc3ccncn3)csc12)Cc1ccccc1] | N*4*-((S)-2-Amino-3-phenyl-propyl)-2-pyridin-4-yl-N*7*-pyrimidin-4-yl-thieno[3,2-d]pyrimidine-4,7-diamine |
| 490 | A | 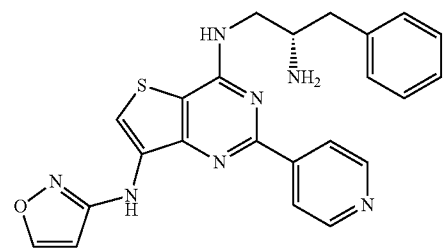 [SMILES: N[C@H](CNc1nc(-c2ccncc2)nc2c(Nc3ccon3)csc12)Cc1ccccc1] | N*4*-((S)-2-Amino-3-phenyl-propyl)-N*7*-(5-methyl-isoxazol-3-yl)-2-pyridin-4-yl-thieno[3,2-d]pyrimidine-4,7-diamine |
| 491 | C | 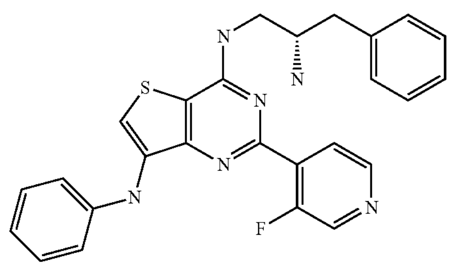 [SMILES: N[C@H](CNc1nc(-c2ccncc2F)nc2c(Nc3ccccc3)csc12)Cc1ccccc1] | N*4*-((S)-2-Amino-3-phenyl-propyl)-2-(3-fluoro-pyridin-4-yl)-N*7*-phenyl-thieno[3,2-d]pyrimidine-4,7-diamine |
| 492 | D | 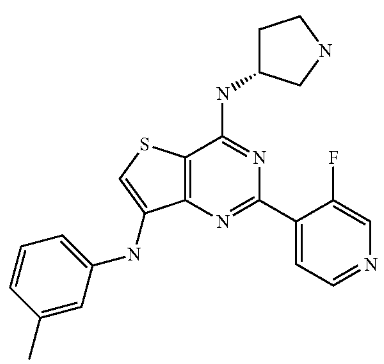 [SMILES: Cc1cccc(Nc2csc3c(N[C@@H]4CCNC4)nc(-c4ccncc4F)nc23)c1] | 2-(3-Fluoro-pyridin-4-yl)-N*4*-(R)-pyrrolidin-3-yl-N*7*-m-tolyl-thieno[3,2-d]pyrimidine-4,7-diamine |
| 493 | D | 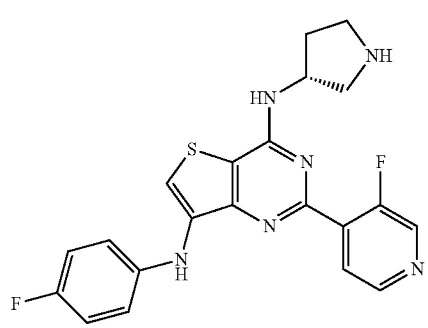 [SMILES: Fc1ccc(Nc2csc3c(N[C@@H]4CCNC4)nc(-c4ccncc4F)nc23)cc1] | N*7*-(4-Fluoro-phenyl)-2-(3-fluoro-pyridin-4-yl)-N*4*-(R)-pyrrolidin-3-yl-thieno[3,2-d]pyrimidine-4,7-diamine |

| Ex | Activity | Structure | Name |
|---|---|---|---|
| 494 | D | 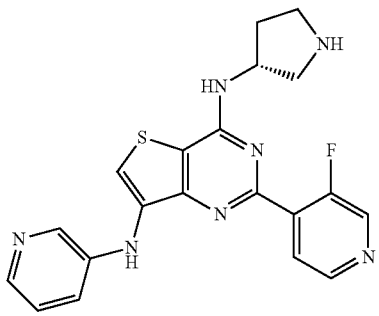 [SMILES: Fc1cnccc1-c1nc(N[C@@H]2CCNC2)c2scc(Nc3cccnc3)c2n1] | 2-(3-Fluoro-pyridin-4-yl)-N*7*-pyridin-3-yl-N*4*-(R)-pyrrolidin-3-yl-thieno[3,2-d]pyrimidine-4,7-diamine |
| 495 | D | 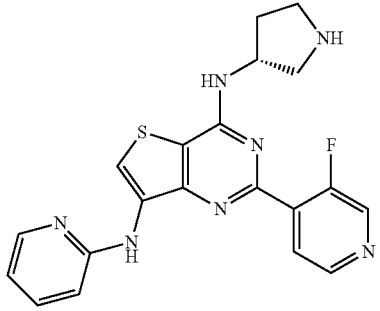 [SMILES: Fc1cnccc1-c1nc(N[C@@H]2CCNC2)c2scc(Nc3ccccn3)c2n1] | 2-(3-Fluoro-pyridin-4-yl)-N*7*-pyridin-2-yl-N*4*-(R)-pyrrolidin-3-yl-thieno[3,2-d]pyrimidine-4,7-diamine |
| 496 | D | 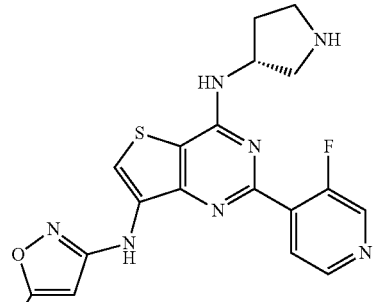 | 2-(3-Fluoro-pyridin-4-yl)-N*7*-(5-methyl-isoxazol-3-yl)-N*4*-(R)-pyrrolidin-3-yl-thieno[3,2-d]pyrimidine-4,7-diamine |
| 497 | D | 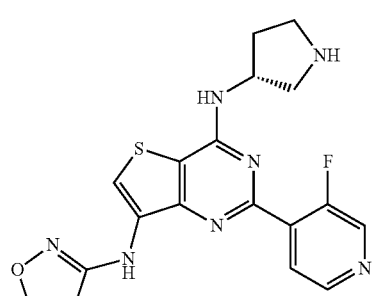 | 2-(3-Fluoro-pyridin-4-yl)-N*7*-isoxazol-3-yl-N*4*-(R)-pyrrolidin-3-yl-thieno[3,2-d]pyrimidine-4,7-diamine |
| 498 | C | 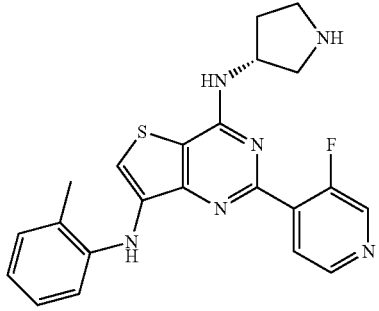 [SMILES: Cc1ccccc1Nc1csc2c(N[C@@H]3CCNC3)nc(-c3ccncc3F)nc12] | 2-(3-Fluoro-pyridin-4-yl)-N*4*-(R)-pyrrolidin-3-yl-N*7*-o-tolyl-thieno[3,2-d]pyrimidine-4,7-diamine |

-continued

| Ex | Activity | Structure | Name |
|---|---|---|---|
| 499 | C | 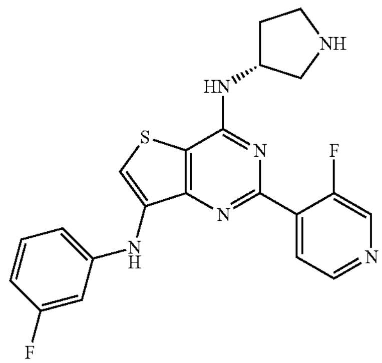 [SMILES: Fc1cccc(Nc2csc3c(N[C@@H]4CCNC4)nc(-c4ccncc4F)nc23)c1] | N*7*-(3-Fluoro-phenyl)-2-(3-fluoro-pyridin-4-yl)-N*4*-(R)-pyrrolidin-3-yl-thieno[3,2-d]pyrimidine-4,7-diamine |
| 500 | B | 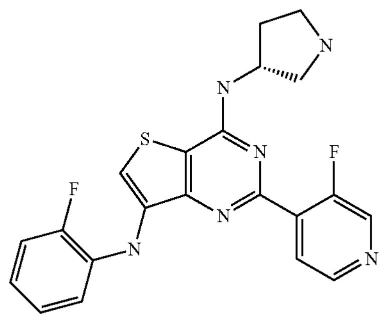 [SMILES: Fc1ccccc1Nc1csc2c(N[C@@H]3CCNC3)nc(-c3ccncc3F)nc12] | N*7*-(2-Fluoro-phenyl)-2-(3-fluoro-pyridin-4-yl)-N*4*-(R)-pyrrolidin-3-yl-thieno[3,2-d]pyrimidine-4,7-diamine |
| 501 | B | 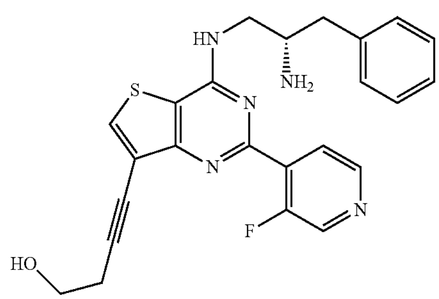 | 4-[4-((S)-2-Amino-3-phenyl-propylamino)-2-(3-fluoro-pyridin-4-yl)-thieno[3,2-d]pyrimidin-7-yl]-but-3-yn-1-ol |
| 502 | C | 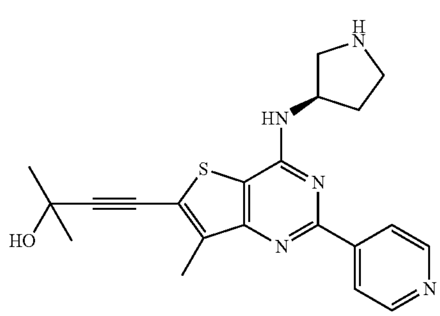 [SMILES: Cc1c(C#CC(C)(C)O)sc2c(N[C@@H]3CCNC3)nc(-c3ccncc3)nc12] | 2-Methyl-4-[7-methyl-2-pyridin-4-yl-4-((R)-pyrrolidin-3-ylamino)-thieno[3,2-d]pyrimidin-6-yl]-but-3-yn-2-ol |
| 503 | B | 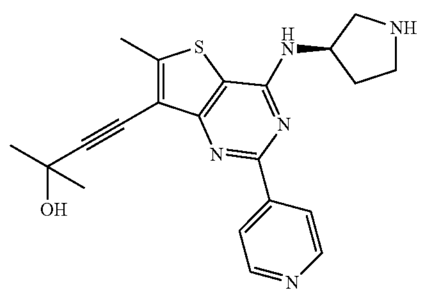 [SMILES: Cc1sc2c(N[C@@H]3CCNC3)nc(-c3ccncc3)nc2c1C#CC(C)(C)O] | 2-Methyl-4-[6-methyl-2-pyridin-4-yl-4-((R)-pyrrolidin-3-ylamino)-thieno[3,2-d]pyrimidin-7-yl]-but-3-yn-2-ol |

| Ex | Activity | Structure | Name |
|---|---|---|---|
| 504 | A | 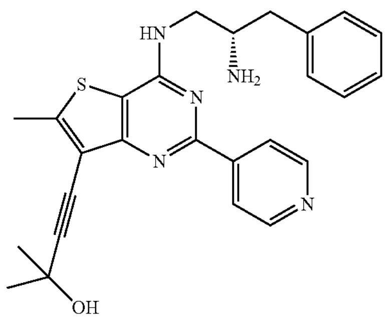 [SMILES: Cc1sc2c(NC[C@@H](N)Cc3ccccc3)nc(-c3ccncc3)nc2c1C#CC(C)(C)O] | 4-[4-((S)-2-Amino-3-phenyl-propylamino)-6-methyl-2-pyridin-4-yl-thieno[3,2-d]pyrimidin-7-yl]-2-methyl-but-3-yn-2-ol |
| 505 | C | 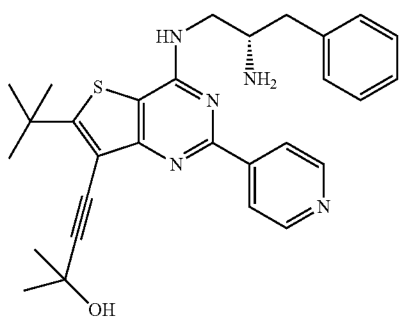 [SMILES: CC(C)(O)C#Cc1c(C(C)(C)C)sc2c(NC[C@@H](N)Cc3ccccc3)nc(-c3ccncc3)nc12] | 4-[4-((S)-2-Amino-3-phenyl-propylamino)-6-tert-butyl-2-pyridin-4-yl-thieno[3,2-d]pyrimidin-7-yl]-2-methyl-but-3-yn-2-ol |
| 506 | A | 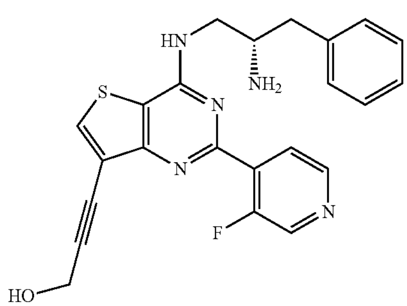 [SMILES: N[C@H](CNc1nc(-c2ccncc2F)nc2c(C#CCO)csc12)Cc1ccccc1] | 3-[4-((S)-2-Amino-3-phenyl-propylamino)-2-(3-fluoro-pyridin-4-yl)-thieno[3,2-d]pyrimidin-7-yl]-prop-2-yn-1-ol |
| 507 | B | 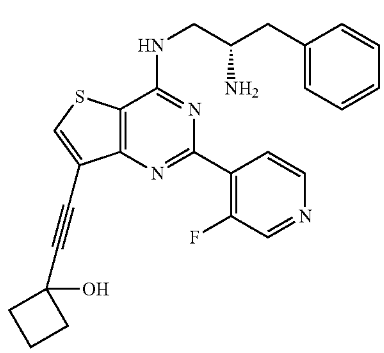 [SMILES: N[C@H](CNc1nc(-c2ccncc2F)nc2c(C#CC3(O)CCC3)csc12)Cc1ccccc1] | 1-[4-((S)-2-Amino-3-phenyl-propylamino)-2-(3-fluoro-pyridin-4-yl)-thieno[3,2-d]pyrimidin-7-ylethynyl]-cyclobutanol |

-continued

| Ex | Activity | Structure | Name |
|---|---|---|---|
| 508 | B | 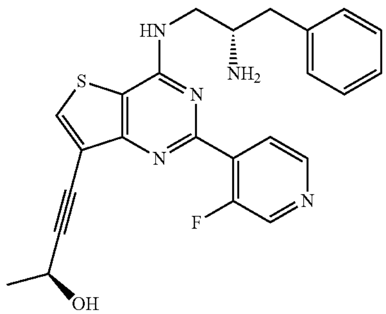 [SMILES: C[C@H](O)C#Cc1csc2c(NC[C@@H](N)Cc3ccccc3)nc(-c3ccncc3F)nc12] | (S)-4-[4-((S)-2-Amino-3-phenyl-propylamino)-2-(3-fluoro-pyridin-4-yl)-thieno[3,2-d]pyrimidin-7-yl]-but-3-yn-2-ol |
| 509 | B | 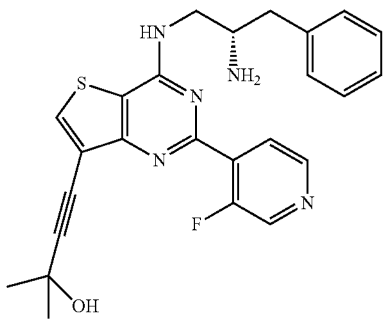 [SMILES: CC(C)(O)C#Cc1csc2c(NC[C@@H](N)Cc3ccccc3)nc(-c3ccncc3F)nc12] | 4-[4-((S)-2-Amino-3-phenyl-propylamino)-2-(3-fluoro-pyridin-4-yl)-thieno[3,2-d]pyrimidin-7-yl]-2-methyl-but-3-yn-2-ol |
| 510 | A | 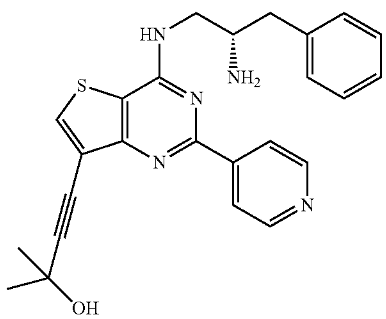 [SMILES: CC(C)(O)C#Cc1csc2c(NC[C@@H](N)Cc3ccccc3)nc(-c3ccncc3)nc12] | 4-[4-((S)-2-Amino-3-phenyl-propylamino)-2-pyridin-4-yl-thieno[3,2-d]pyrimidin-7-yl]-2-methyl-but-3-yn-2-ol |
| 511 | C | 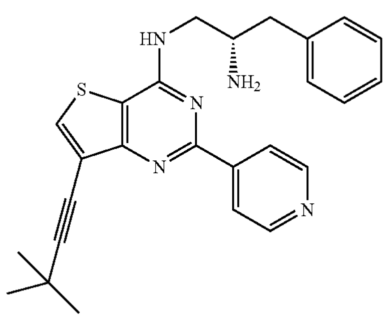 [SMILES: CC(C)(C)C#Cc1csc2c(NC[C@@H](N)Cc3ccccc3)nc(-c3ccncc3)nc12] | (S)-N*1*-[7-(3,3-Dimethyl-but-1-ynyl)-2-pyridin-4-yl-thieno[3,2-d]pyrimidin-4-yl]-3-phenyl-propane-1,2-diamine |
| 512 | A | 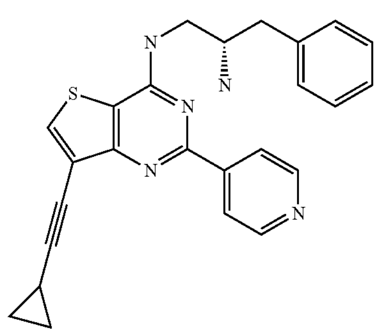 [SMILES: N[C@H](CNc1nc(-c2ccncc2)nc2c(C#CC3CC3)csc12)Cc1ccccc1] | (S)-N*1*-(7-Cyclopropylethynyl-2-pyridin-4-yl-thieno[3,2-d]pyrimidin-4-yl)-3-phenyl-propane-1,2-diamine |

| Ex | Activity | Structure | Name |
|---|---|---|---|
| 513 | A | 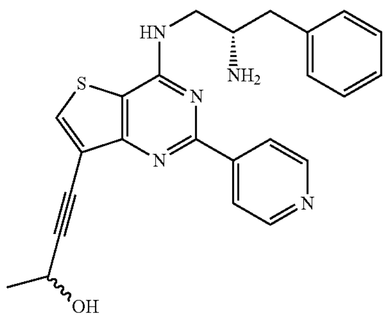 | 4-[4-((S)-2-Amino-3-phenyl-propylamino)-2-pyridin-4-yl-thieno[3,2-d]pyrimidin-7-yl]-but-3-yn-2-ol |
| 514 | B | 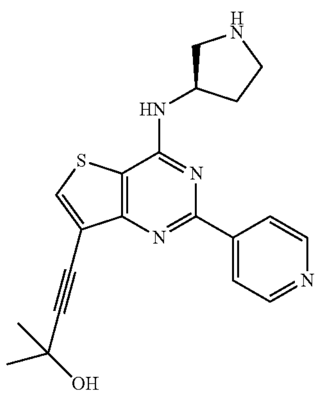 [SMILES: CC(C)(O)C#Cc1csc2c(N[C@@H]3CCNC3)nc(-c3ccncc3)nc12] | 2-Methyl-4-[2-pyridin-4-yl-4-((R)-pyrrolidin-3-ylamino)-thieno[3,2-d]pyrimidin-7-yl]-but-3-yn-2-ol |
| 515 | A | 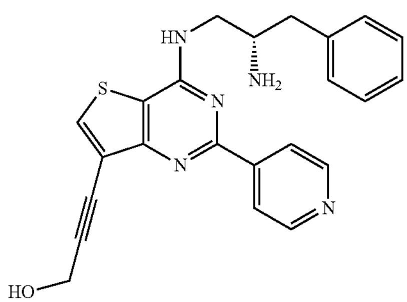 [SMILES: N[C@H](CNc1nc(-c2ccncc2)nc2c(C#CCO)csc12)Cc1ccccc1] | 3-[4-((S)-2-Amino-3-phenyl-propylamino)-2-pyridin-4-yl-thieno[3,2-d]pyrimidin-7-yl]-prop-2-yn-1-ol |
| 516 | C | 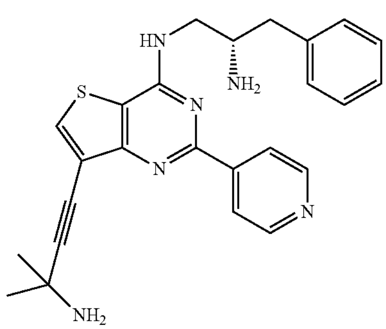 [SMILES: CC(C)(N)C#Cc1csc2c(NC[C@@H](N)Cc3ccccc3)nc(-c3ccncc3)nc12] | (S)-N*1*-[7-(3-Amino-3-methyl-but-1-ynyl)-2-pyridin-4-yl-thieno[3,2-d]pyrimidin-4-yl]-3-phenyl-propane-1,2-diamine |

-continued

| Ex | Activity | Structure | Name |
|---|---|---|---|
| 517 | A | 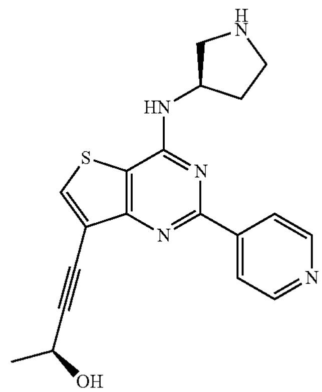 [SMILES: C[C@H](O)C#Cc1csc2c(N[C@@H]3CCNC3)nc(-c3ccncc3)nc12] | (S)-4-[2-Pyridin-4-yl-4-((R)-pyrrolidin-3-ylamino)-thieno[3,2-d]pyrimidin-7-yl]-but-3-yn-2-ol |
| 518 | B | 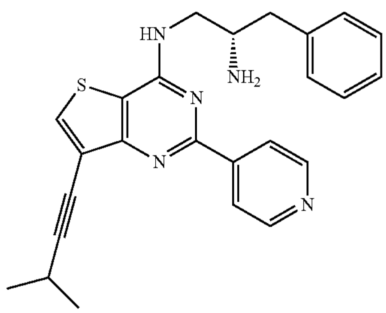 [SMILES: CC(C)C#Cc1csc2c(NC[C@@H](N)Cc3ccccc3)nc(-c3ccncc3)nc12] | (S)-N*1*-[7-(3-Methyl-but-1-ynyl)-2-pyridin-4-yl-thieno[3,2-d]pyrimidin-4-yl]-3-phenyl-propane-1,2-diamine |
| 519 | C | 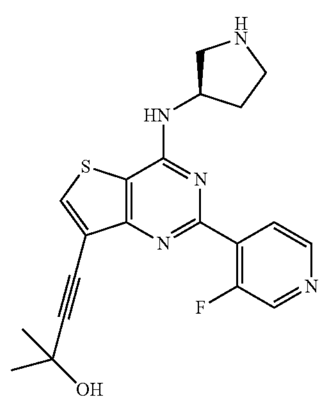 [SMILES: CC(C)(O)C#Cc1csc2c(N[C@@H]3CCNC3)nc(-c3ccncc3F)nc12] | 4-[2-(3-Fluoro-pyridin-4-yl)-4-((R)-pyrrolidin-3-ylamino)-thieno[3,2-d]pyrimidin-7-yl]-2-methyl-but-3-yn-2-ol |
| 520 | B | 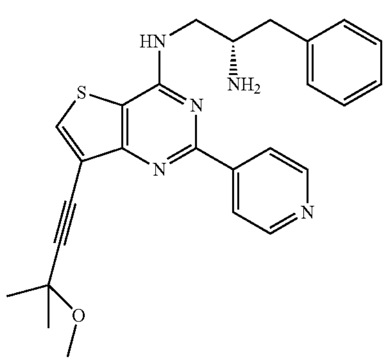 [SMILES: COC(C)(C)C#Cc1csc2c(NC[C@@H](N)Cc3ccccc3)nc(-c3ccncc3)nc12] | (S)-N*1*-[7-(3-Methoxy-3-methyl-but-1-ynyl)-2-pyridin-4-yl-thieno[3,2-d]pyrimidin-4-yl]-3-phenyl-propane-1,2-diamine |

-continued

| Ex | Activity | Structure | Name |
|---|---|---|---|
| 521 | A | 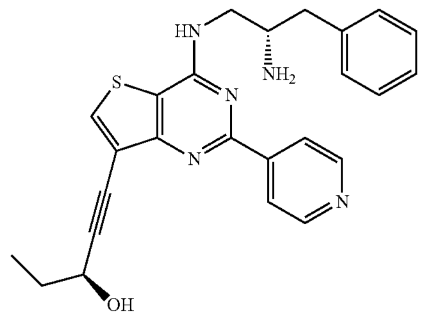 [SMILES: CC[C@H](O)C#Cc1csc2c(NC[C@@H](N)Cc3ccccc3)nc(-c3ccncc3)nc12] | S)-1-[4-((S)-2-Amino-3-phenyl-propylamino)-2-pyridin-4-yl-thieno[3,2-d]pyrimidin-7-yl]-pent-1-yn-3-ol |
| 522 | C | 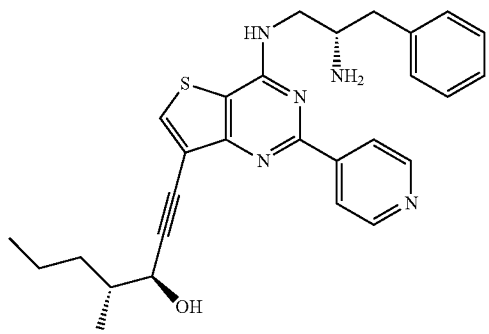 [SMILES: CCC[C@@H](C)[C@H](O)C#Cc1csc2c(NC[C@@H](N)Cc3ccccc3)nc(-c3ccncc3)nc12] | (S)-1-[4-((S)-2-Amino-3-phenyl-propylamino)-2-pyridin-4-yl-thieno[3,2-d]pyrimidin-7-yl]-4-methyl-hept-1-yn-3-ol |
| 523 | B | 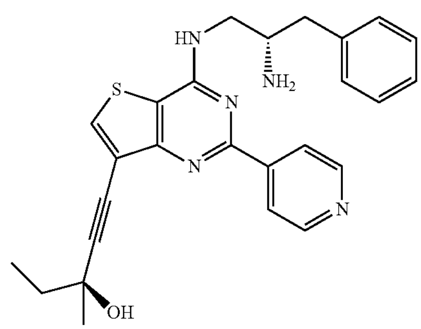 [SMILES: CC[C@](C)(O)C#Cc1csc2c(NC[C@@H](N)Cc3ccccc3)nc(-c3ccncc3)nc12] | (S)-1-[4-((S)-2-Amino-3-phenyl-propylamino)-2-pyridin-4-yl-thieno[3,2-d]pyrimidin-7-yl]-3-methyl-pent-1-yn-3-ol |
| 524 | C | 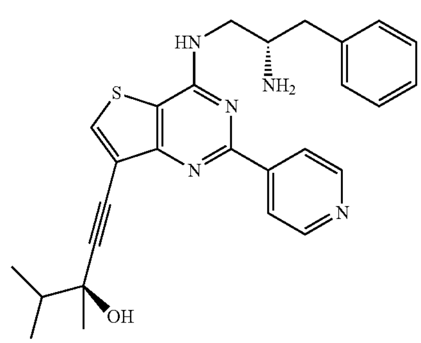 [SMILES: CC(C)[C@](C)(O)C#Cc1csc2c(NC[C@@H](N)Cc3ccccc3)nc(-c3ccncc3)nc12] | (S)-1-[4-((S)-2-Amino-3-phenyl-propylamino)-2-pyridin-4-yl-thieno[3,2-d]pyrimidin-7-yl]-3,4-dimethyl-pent-1-yn-3-ol |

| Ex | Activity | Structure | Name |
|---|---|---|---|
| 525 | C | 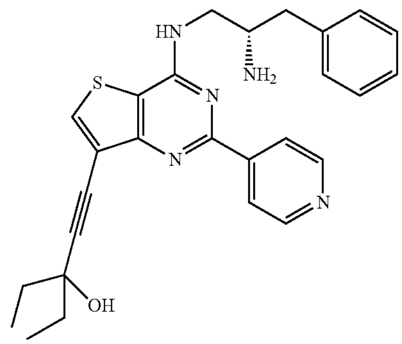 [SMILES: CCC(O)(C#Cc1csc2c(NC[C@@H](N)Cc3ccccc3)nc(-c3ccncc3)nc12)CC] | 1-[4-(2-Amino-3-phenyl-propylamino)-2-pyridin-4-yl-thieno[3,2-d]pyrimidin-7-yl]-3-ethyl-pent-1-yn-3-ol |
| 526 | B | 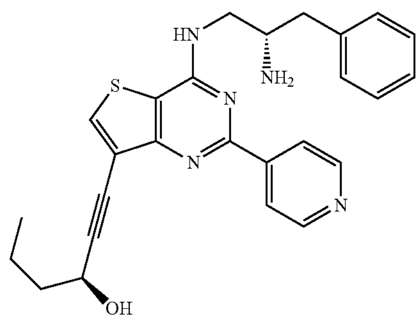 [SMILES: CCC[C@H](O)C#Cc1csc2c(NC[C@@H](N)Cc3ccccc3)nc(-c3ccncc3)nc12] | (S)-1-[4-((S)-2-Amino-3-phenyl-propylamino)-2-pyridin-4-yl-thieno[3,2-d]pyrimidin-7-yl]-hex-1-yn-3-ol |
| 527 | D | 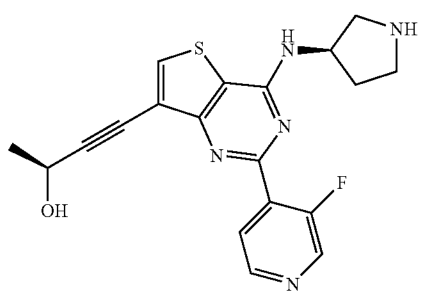 [SMILES: C[C@H](O)C#Cc1csc2c(N[C@@H]3CCNC3)nc(-c3ccncc3F)nc12] | (S)-4-[2-(3-Fluoro-pyridin-4-yl)-4-((R)-pyrrolidin-3-ylamino)-thieno[3,2-d]pyrimidin-7-yl]-but-3-yn-2-ol |
| 528 | A | 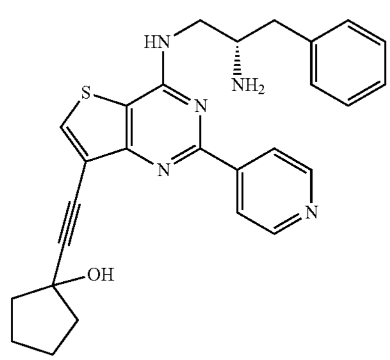 [SMILES: N[C@H](CNc1nc(-c2ccncc2)nc2c(C#CC3(O)CCCC3)csc12)Cc1ccccc1] | 2-[4-((S)-2-Amino-3-phenyl-propylamino)-2-pyridin-4-yl-thieno[3,2-d]pyrimidin-7-ylethynyl]-cyclopentanol |

-continued

| Ex | Activity | Structure | Name |
|---|---|---|---|
| 529 | B | 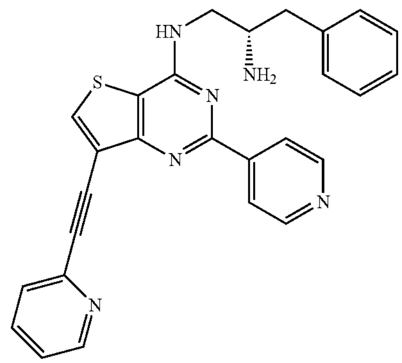 [SMILES: N[C@H](CNc1nc(-c2ccncc2)nc2c(C#Cc3ccccn3)csc12)Cc1ccccc1] | (S)-3-Phenyl-N*1*-(2-pyridin-4-yl-7-pyridin-2-ylethynyl-thieno[3,2-d]pyrimidin-4-yl)-propane-1,2-diamine |
| 530 | B | 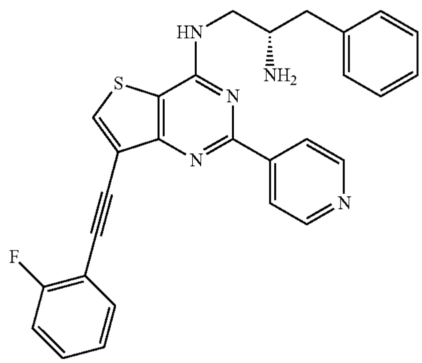 [SMILES: N[C@H](CNc1nc(-c2ccncc2)nc2c(C#Cc3ccccc3F)csc12)Cc1ccccc1] | (S)-N*1*-[7-(2-Fluoro-phenylethynyl)-2-pyridin-4-yl-thieno[3,2-d]pyrimidin-4-yl]-3-phenyl-propane-1,2-diamine |
| 531 | A | 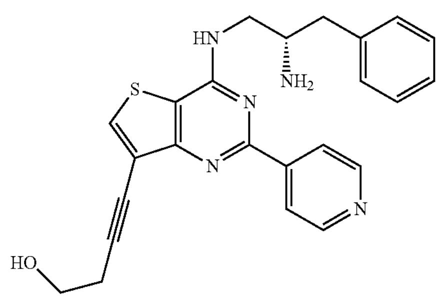 [SMILES: N[C@H](CNc1nc(-c2ccncc2)nc2c(C#CCCO)csc12)Cc1ccccc1] | 4-[4-((S)-2-Amino-3-phenyl-propylamino)-2-pyridin-4-yl-thieno[3,2-d]pyrimidin-7-yl]-but-3-yn-1-ol |
| 532 | A | 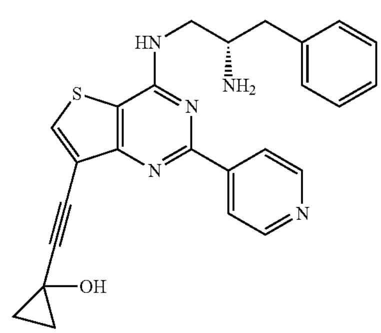 [SMILES: N[C@H](CNc1nc(-c2ccncc2)nc2c(C#CC3(O)CC3)csc12)Cc1ccccc1] | 1-[4-((S)-2-Amino-3-phenyl-propylamino)-2-pyridin-4-yl-thieno[3,2-d]pyrimidin-7-ylethynyl]-cyclopropanol |

-continued

| Ex | Activity | Structure | Name |
|---|---|---|---|
| 533 | A | 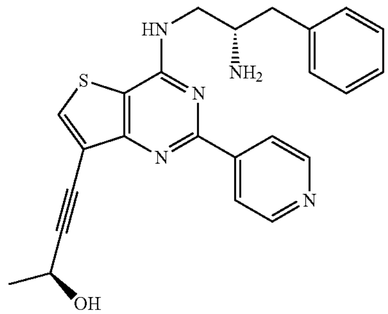 [SMILES: C[C@H](O)C#Cc1csc2c(NC[C@@H](N)Cc3ccccc3)nc(-c3ccncc3)nc12] | (S)-4-[4-((S)-2-Amino-3-phenyl-propylamino)-2-pyridin-4-yl-thieno[3,2-d]pyrimidin-7-yl]-but-3-yn-2-ol |
| 534 | A | 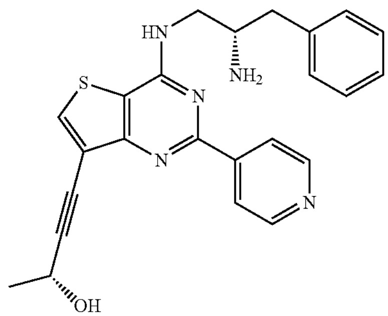 | (R)-4-[4-((S)-2-Amino-3-phenyl-propylamino)-2-pyridin-4-yl-thieno[3,2-d]pyrimidin-7-yl]-but-3-yn-2-ol |
| 535 | C | 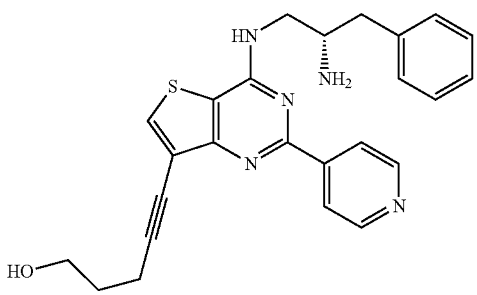 [SMILES: N[C@H](CNc1nc(-c2ccncc2)nc2c(C#CCCCO)csc12)Cc1ccccc1] | 5-[4-((S)-2-Amino-3-phenyl-propylamino)-2-pyridin-4-yl-thieno[3,2-d]pyrimidin-7-yl]-pent-4-yn-1-ol |
| 536 | A | 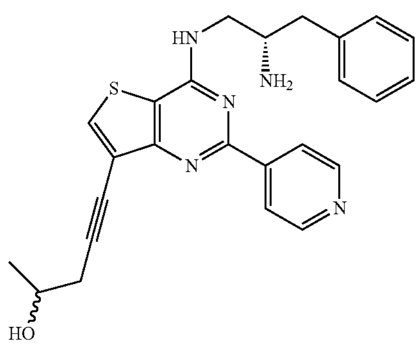 [SMILES: CC(O)CC#Cc1csc2c(NC[C@@H](N)Cc3ccccc3)nc(-c3ccncc3)nc12] | 5-[4-((S)-2-Amino-3-phenyl-propylamino)-2-pyridin-4-yl-thieno[3,2-d]pyrimidin-7-yl]-pent-4-yn-2-ol |
| 537 | B | 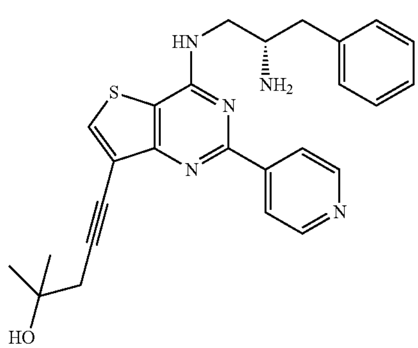 [SMILES: CC(C)(O)CC#Cc1csc2c(NC[C@@H](N)Cc3ccccc3)nc(-c3ccncc3)nc12] | 5-[4-((S)-2-Amino-3-phenyl-propylamino)-2-pyridin-4-yl-thieno[3,2-d]pyrimidin-7-yl]-2-methyl-pent-4-yn-2-ol |

-continued

| Ex | Activity | Structure | Name |
|---|---|---|---|
| 538 | B | 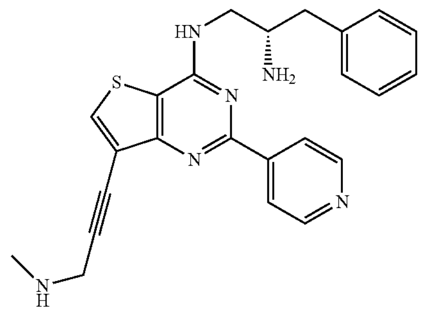 [SMILES: CNCC#Cc1csc2c(NC[C@@H](N)Cc3ccccc3)nc(-c3ccncc3)nc12] | (S)-N*1*-[7-(3-Methylamino-prop-1-ynyl)-2-pyridin-4-yl-thieno[3,2-d]pyrimidin-4-yl]-3-phenyl-propane-1,2-diamine |
| 539 | A | 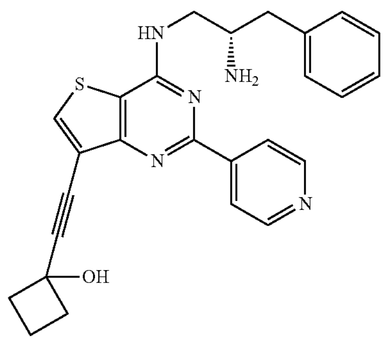 [SMILES: N[C@H](CNc1nc(-c2ccncc2)nc2c(C#CC3(O)CCC3)csc12)Cc1ccccc1] | 1-[4-((S)-2-Amino-3-phenyl-propylamino)-2-pyridin-4-yl-thieno[3,2-d]pyrimidin-7-ylethynyl]-cyclobutanol |
| 540 | B | 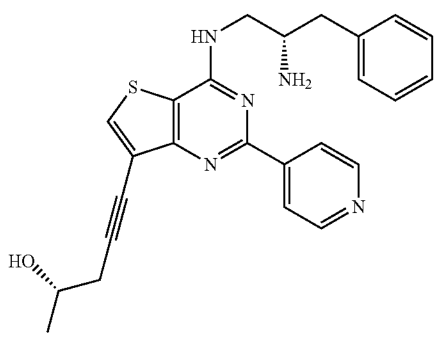 [SMILES: C[C@H](O)CC#Cc1csc2c(NC[C@@H](N)Cc3ccccc3)nc(-c3ccncc3)nc12] | (S)-5-[4-((S)-2-Amino-3-phenyl-propylamino)-2-pyridin-4-yl-thieno[3,2-d]pyrimidin-7-yl]-pent-4-yn-2-ol |
| 541 | A | 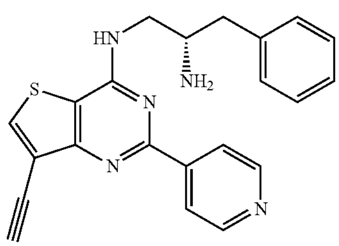 [SMILES: C#Cc1csc2c(NC[C@@H](N)Cc3ccccc3)nc(-c3ccncc3)nc12] | (S)-N*1*-(7-Ethynyl-2-pyridin-4-yl-thieno[3,2-d]pyrimidin-4-yl)-3-phenyl-propane-1,2-diamine |
| 542 | A | 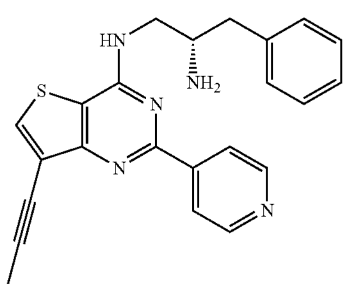 [SMILES: CC#Cc1csc2c(NC[C@@H](N)Cc3ccccc3)nc(-c3ccncc3)nc12] | (S)-3-Phenyl-N*1*-(7-prop-1-ynyl-2-pyridin-4-yl-thieno[3,2-d]pyrimidin-4-yl)-propane-1,2-diamine |

-continued

| Ex | Activity | Structure | Name |
|---|---|---|---|
| 543 | C | 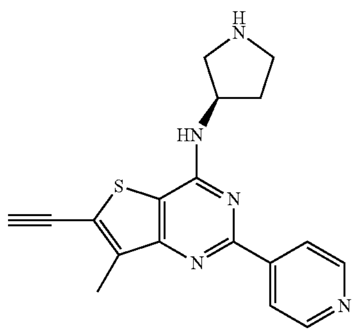 [SMILES: C#Cc1sc2c(N[C@@H]3CCNC3)nc(-c3ccncc3)nc2c1C] | (6-Ethynyl-7-methyl-2-pyridin-4-yl-thieno[3,2-d]pyrimidin-4-yl)-(R)-pyrrolidin-3-yl-amine |
| 544 | A | 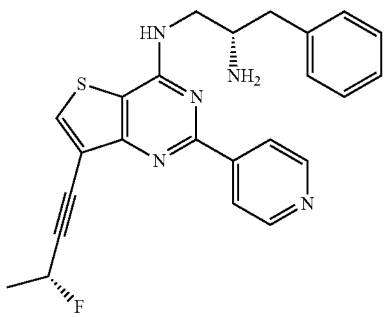 [SMILES: C[C@@H](F)C#Cc1csc2c(NC[C@@H](N)Cc3ccccc3)nc(-c3ccncc3)nc12] | (S)-N*1*-[7-((R)-3-Fluoro-but-1-ynyl)-2-pyridin-4-yl-thieno[3,2-d]pyrimidin-4-yl]-3-phenyl-propane-1,2-diamine |
| 545 | A | 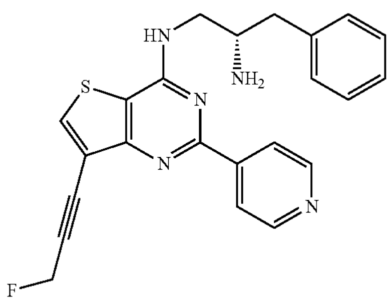 [SMILES: N[C@H](CNc1nc(-c2ccncc2)nc2c(C#CCF)csc12)Cc1ccccc1] | (S)-N*1*-[7-(3-Fluoro-prop-1-ynyl)-2-pyridin-4-yl-thieno[3,2-d]pyrimidin-4-yl]-3-phenyl-propane-1,2-diamine |
| 546 | B | 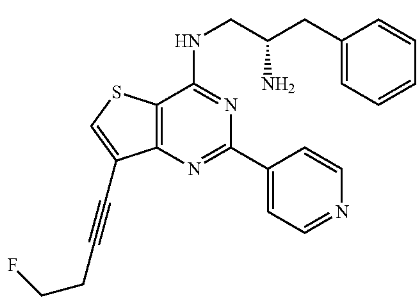 [SMILES: N[C@H](CNc1nc(-c2ccncc2)nc2c(C#CCCF)csc12)Cc1ccccc1] | (S)-N*1*-[7-(4-Fluoro-but-1-ynyl)-2-pyridin-4-yl-thieno[3,2-d]pyrimidine |
| 547 | A | 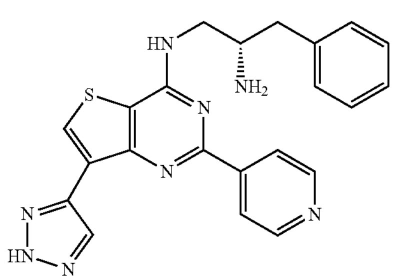 [SMILES: N[C@H](CNc1nc(-c2ccncc2)nc2c(-c3cn[nH]n3)csc12)Cc1ccccc1] | (S)-3-Phenyl-N*1*-[2-pyridin-4-yl-7-(2H-[1,2,3]triazol-4-yl)-thieno[3,2-d]pyrimidin-4-yl]-propane-1,2-diamine |

| Ex | Activity | Structure | Name |
|---|---|---|---|
| 548 | B | 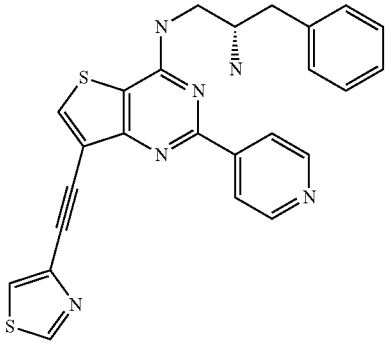 [SMILES: N[C@H](CNc1nc(-c2ccncc2)nc2c(C#Cc3cscn3)csc12)Cc1ccccc1] | (S)-3-Phenyl-N*1*-(2-pyridin-4-yl-7-thiazol-4-ylethynyl-thieno[3,2-d]pyrimidin-4-yl)-propane-1,2-diamine |
| 549 | A | 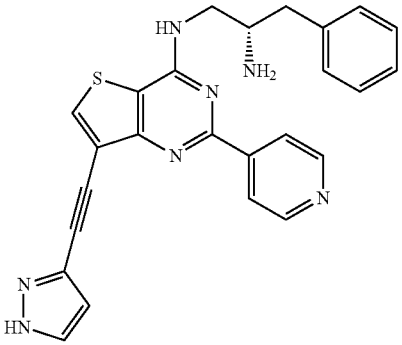 [SMILES: N[C@H](CNc1nc(-c2ccncc2)nc2c(C#Cc3cc[nH]n3)csc12)Cc1ccccc1] | (S)-3-Phenyl-N*1*-[7-(1H-pyrazol-3-ylethynyl)-2-pyridin-4-yl-thieno[3,2-d]pyrimidin-4-yl]-propane-1,2-diamine |
| 550 | C | 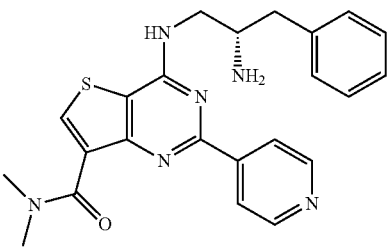 [SMILES: CN(C)C(=O)c1csc2c(NC[C@@H](N)Cc3ccccc3)nc(-c3ccncc3)nc12] | 4-((S)-2-Amino-3-phenyl-propylamino)-2-pyridin-4-yl-thieno[3,2-d]pyrimidine-7-carboxylic acid dimethylamide |
| 551 | B | 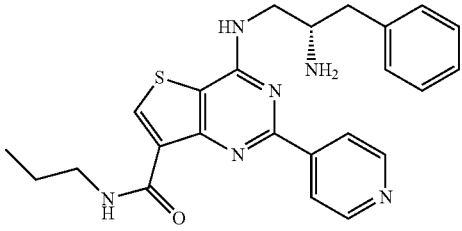 [SMILES: CCCNC(=O)c1csc2c(NC[C@@H](N)Cc3ccccc3)nc(-c3ccncc3)nc12] | 4-((S)-2-Amino-3-phenyl-propylamino)-2-pyridin-4-yl-thieno[3,2-d]pyrimidine-7-carboxylic acid propylamide |
| 552 | C | 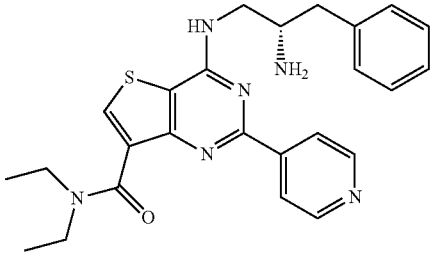 [SMILES: CCN(CC)C(=O)c1csc2c(NC[C@@H](N)Cc3ccccc3)nc(-c3ccncc3)nc12] | 4-((S)-2-Amino-3-phenyl-propylamino)-2-pyridin-4-yl-thieno[3,2-d]pyrimidine-7-carboxylic acid diethylamide |

| Ex | Activity | Structure | Name |
|---|---|---|---|
| 553 | A | 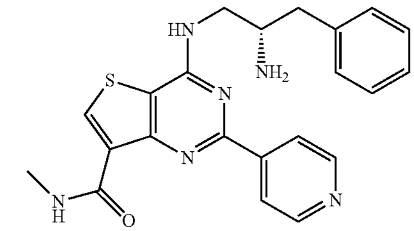 [SMILES: CNC(=O)c1csc2c(NC[C@@H](N)Cc3ccccc3)nc(-c3ccncc3)nc12] | 4-((S)-2-Amino-3-phenyl-propylamino)-2-pyridin-4-yl-thieno[3,2-d]pyrimidine-7-carboxylic acid methylamide |
| 554 | B | 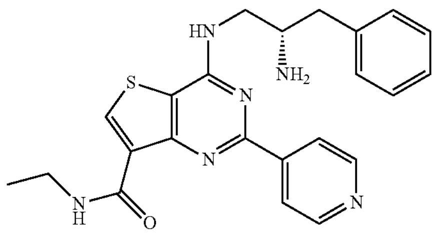 [SMILES: CCNC(=O)c1csc2c(NC[C@@H](N)Cc3ccccc3)nc(-c3ccncc3)nc12] | 4-((S)-2-Amino-3-phenyl-propylamino)-2-pyridin-4-yl-thieno[3,2-d]pyrimidine-7-carboxylic acid ethylamide |
| 555 | C | 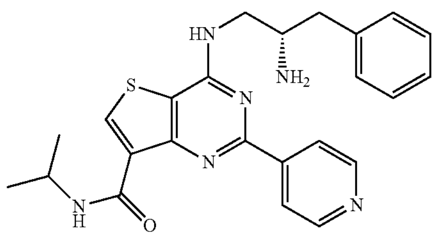 [SMILES: CC(C)NC(=O)c1csc2c(NC[C@@H](N)Cc3ccccc3)nc(-c3ccncc3)nc12] | 4-((S)-2-Amino-3-phenyl-propylamino)-2-pyridin-4-yl-thieno[3,2-d]pyrimidine-7-carboxylic acid isopropylamide |
| 556 | B | 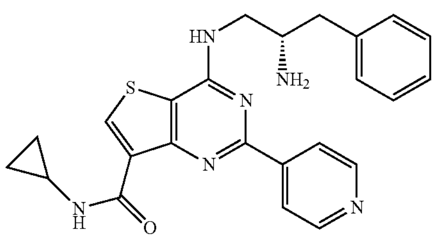 [SMILES: N[C@H](CNc1nc(-c2ccncc2)nc2c(C(=O)NC3CC3)csc12)Cc1ccccc1] | 4-((S)-2-Amino-3-phenyl-propylamino)-2-pyridin-4-yl-thieno[3,2-d]pyrimidine-7-carboxylic acid cyclopropylamide |
| 557 | C | 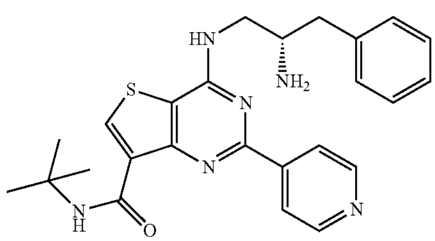 [SMILES: CC(C)(C)NC(=O)c1csc2c(NC[C@@H](N)Cc3ccccc3)nc(-c3ccncc3)nc12] | 4-((S)-2-Amino-3-phenyl-propylamino)-2-pyridin-4-yl-thieno[3,2-d]pyrimidine-7-carboxylic acid tert-butylamide |
| 558 | B | 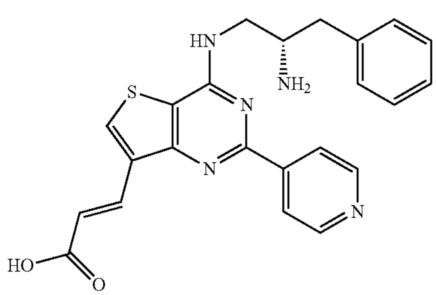 [SMILES: N[C@H](CNc1nc(-c2ccncc2)nc2c(/C=C/C(=O)O)csc12)Cc1ccccc1] | (E)-3-[4-((S)-2-Amino-3-phenyl-propylamino)-2-pyridin-4-yl-thieno[3,2-d]pyrimidin-7-yl]-acrylic acid |

-continued

| Ex | Activity | Structure | Name |
|---|---|---|---|
| 559 | B | 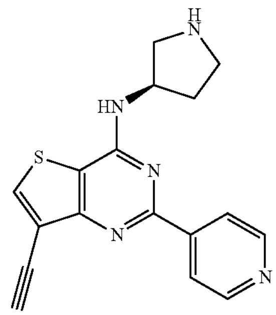 [SMILES: C#Cc1csc2c(N[C@@H]3CCNC3)nc(-c3ccncc3)nc12] | (7-Ethynyl-2-pyridin-4-yl-thieno[3,2-d]pyrimidin-4-yl)-(R)-pyrrolidin-3-yl-amine |
| 560 | A | 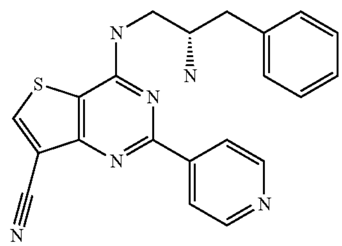 [SMILES: N#Cc1csc2c(NC[C@@H](N)Cc3ccccc3)nc(-c3ccncc3)nc12] | 4-((S)-2-Amino-3-phenyl-propylamino)-2-pyridin-4-yl-thieno[3,2-d]pyrimidine-7-carbonitrile |
| 561 | B | 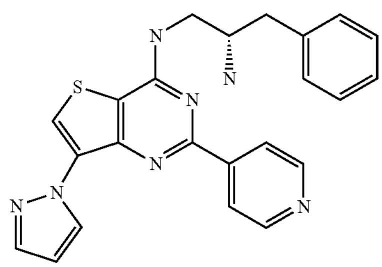 [SMILES: N[C@H](CNc1nc(-c2ccncc2)nc2c(-n3cccn3)csc12)Cc1ccccc1] | (S)-3-Phenyl-N*1*-(7-pyrazol-1-yl-2-pyridin-4-yl-thieno[3,2-d]pyrimidin-4-yl)-propane-1,2-diamine |
| 562 | B | 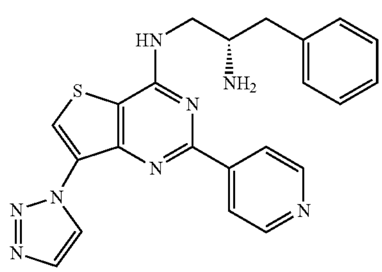 [SMILES: N[C@H](CNc1nc(-c2ccncc2)nc2c(-n3ccnn3)csc12)Cc1ccccc1] | (S)-3-Phenyl-N*1*-(2-pyridin-4-yl-7-[1,2,3]triazol-1-yl-thieno[3,2-d]pyrimidin-4-yl)-propane-1,2-diamine |
| 563 | C | 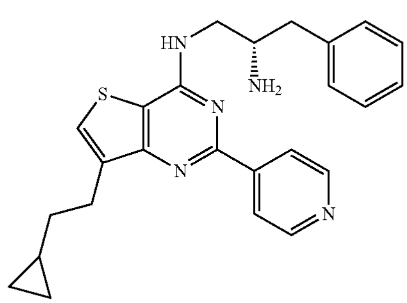 [SMILES: N[C@H](CNc1nc(-c2ccncc2)nc2c(CCC3CC3)csc12)Cc1ccccc1] | (S)-N*1*-[7-(2-Cyclopropyl-ethyl)-2-pyridin-4-yl-thieno[3,2-d]pyrimidin-4-yl]-3-phenyl-propane-1,2-diamine |

-continued

| Ex | Activity | Structure | Name |
|---|---|---|---|
| 564 | C | 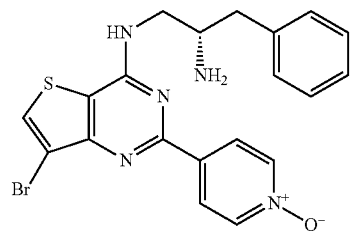 [SMILES: N[C@H](CNc1nc(-c2cc[n+]([O-])cc2)nc2c(Br)csc12)Cc1ccccc1] | S)-N*1*-[7-Bromo-2-(1-oxy-pyridin-4-yl)-thieno[3,2-d]pyrimidin-4-yl]-3-phenyl-propane-1,2-diamine |
| 565 | C | 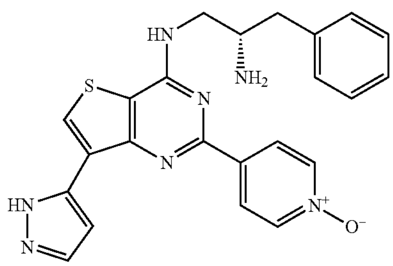 [SMILES: N[C@H](CNc1nc(-c2cc[n+]([O-])cc2)nc2c(-c3ccn[nH]3)csc12)Cc1ccccc1] | (S)-N*1*-[2-(1-Oxy-pyridin-4-yl)-7-(2H-pyrazol-3-yl)-thieno[3,2-d]pyrimidin-4-yl]-3-phenyl-propane-1,2-diamine |
| 566 | B | 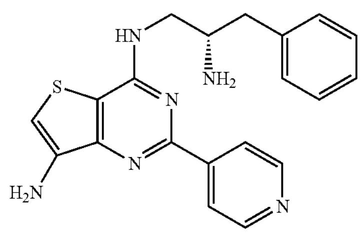 [SMILES: Nc1csc2c(NC[C@@H](N)Cc3ccccc3)nc(-c3ccncc3)nc12] | N*4*-((S)-2-Amino-3-phenyl-propyl)-2-pyridin-4-yl-thieno[3,2-d]pyrimidine-4,7-diamine |
| 567 | C | 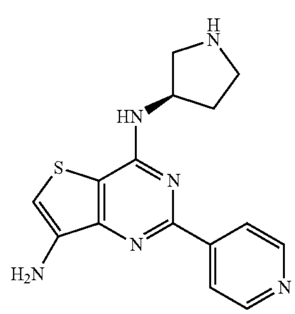 [SMILES: Nc1csc2c(N[C@@H]3CCNC3)nc(-c3ccncc3)nc12] | 2-Pyridin-4-yl-N*4*-(R)-pyrrolidin-3-yl-thieno[3,2-d]pyrimidine-4,7-diamine |
| 568 | B | 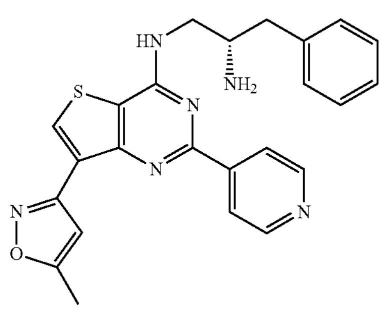 [SMILES: Cc1cc(-c2csc3c(NC[C@@H](N)Cc4ccccc4)nc(-c4ccncc4)nc23)no1] | (S)-N*1*-[7-(5-Methyl-isoxazol-3-yl)-2-pyridin-4-yl-thieno[3,2-d]pyrimidin-4-yl]-3-phenyl-propane-1,2-diamine |

-continued

| Ex | Activity | Structure | Name |
|---|---|---|---|
| 569 | A | 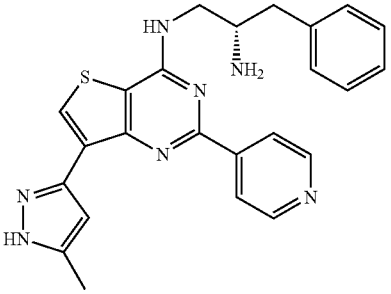 [SMILES: Cc1cc(-c2csc3c(NC[C@@H](N)Cc4ccccc4)nc(-c4ccncc4)nc23)n[nH]1] | (S)-N*1*-[7-(5-Methyl-1H-pyrazol-3-yl)-2-pyridin-4-yl-thieno[3,2-d]pyrimidin-4-yl]-3-phenyl-propane-1,2-diamine |
| 570 | C | 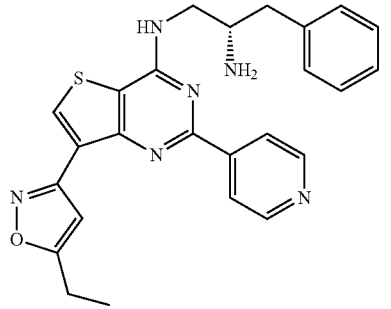 [SMILES: CCc1cc(-c2csc3c(NC[C@@H](N)Cc4ccccc4)nc(-c4ccncc4)nc23)no1] | (S)-N*1*-[7-(5-Ethyl-isoxazol-3-yl)-2-pyridin-4-yl-thieno[3,2-d]pyrimidin-4-yl]-3-phenyl-propane-1,2-diamine |
| 571 | A | 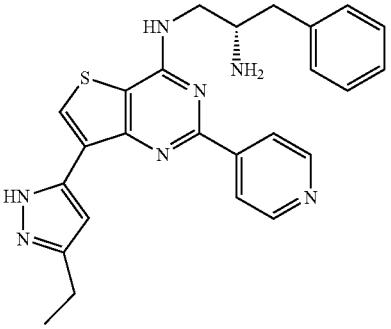 [SMILES: CCc1cc(-c2csc3c(NC[C@@H](N)Cc4ccccc4)nc(-c4ccncc4)nc23)[nH]n1] | (S)-N*1*-[7-(5-Ethyl-2H-pyrazol-3-yl)-2-pyridin-4-yl-thieno[3,2-d]pyrimidin-4-yl]-3-phenyl-propane-1,2-diamine |
| 572 | B | 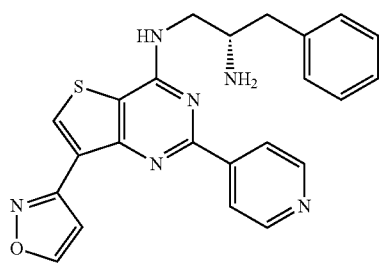 [SMILES: N[C@H](CNc1nc(-c2ccncc2)nc2c(-c3ccon3)csc12)Cc1ccccc1] | (S)-N*1*-(7-Isoxazol-3-yl-2-pyridin-4-yl-thieno[3,2-d]pyrimidin-4-yl)-3-phenyl-propane-1,2-diamine |
| 573 | C | 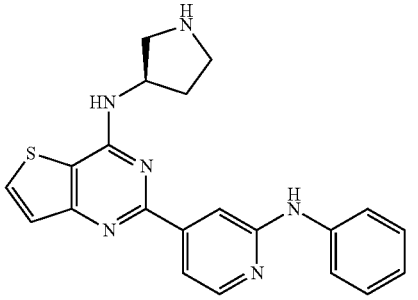 [SMILES: c1ccc(Nc2cc(-c3nc(N[C@@H]4CCNC4)c4sccc4n3)ccn2)cc1] | [2-(2-Phenylamino-pyridin-4-yl)-thieno[3,2-d]pyrimidin-4-yl]-(R)-pyrrolidin-3-yl-amine |

| Ex | Activity | Structure | Name |
|---|---|---|---|
| 574 | C | 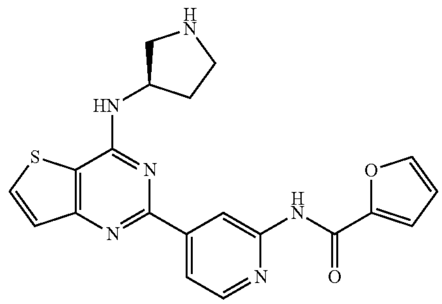 [SMILES: O=C(Nc1cc(-c2nc(N[C@@H]3CCNC3)c3sccc3n2)ccn1)c1ccco1] | Furan-2-carboxylic acid {4-[4-((R)-pyrrolidin-3-ylamino)-thieno[3,2-d]pyrimidin-2-yl]-pyridin-2-yl}-amide |
| 575 | B | 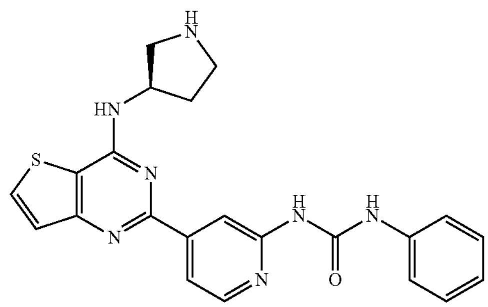 [SMILES: O=C(Nc1ccccc1)Nc1cc(-c2nc(N[C@@H]3CCNC3)c3sccc3n2)ccn1] | 1-Phenyl-3-{4-[4-((R)-pyrrolidin-3-ylamino)-thieno[3,2-d]pyrimidin-2-yl]-pyridin-2-yl}-urea |
| 576 | D | 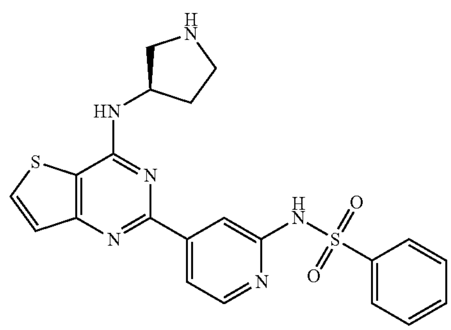 [SMILES: O=S(=O)(Nc1cc(-c2nc(N[C@@H]3CCNC3)c3sccc3n2)ccn1)c1ccccc1] | N-{4-[4-((R)-Pyrrolidin-3-ylamino)-thieno[3,2-d]pyrimidin-2-yl]-pyridin-2-yl}-benzenesulfonamide |
| 577 | B | 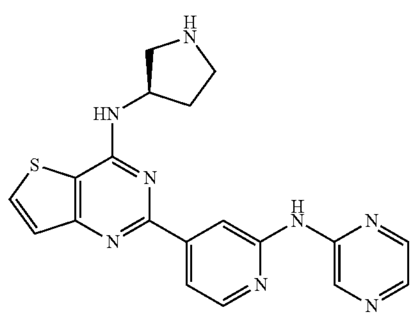 [SMILES: c1cnc(Nc2cc(-c3nc(N[C@@H]4CCNC4)c4sccc4n3)ccn2)cn1] | {2-[2-(Pyrazin-2-ylamino)-pyridin-4-yl]-thieno[3,2-d]pyrimidin-4-yl}-(R)-pyrrolidin-3-yl-amine |
| 578 | B | 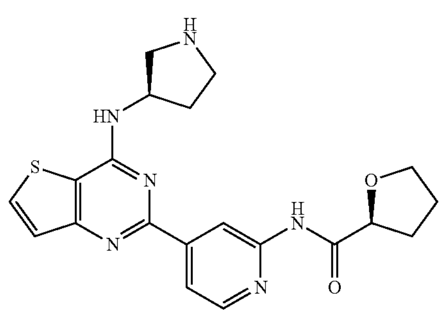 [SMILES: O=C(Nc1cc(-c2nc(N[C@@H]3CCNC3)c3sccc3n2)ccn1)[C@@H]1CCCO1] | (S)-Tetrahydro-furan-2-carboxylic acid {4-[4-((R)-pyrrolidin-3-ylamino)-thieno[3,2-d]pyrimidin-2-yl]-pyridin-2-yl}-amide |

-continued

| Ex | Activity | Structure | Name |
|---|---|---|---|
| 579 | C | 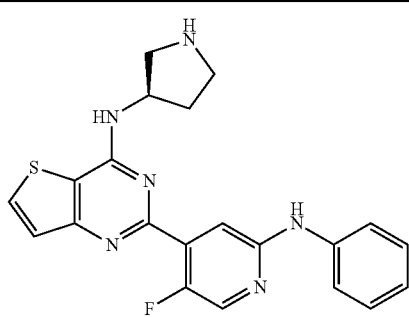 | [2-(5-Fluoro-2-phenylamino-pyridin-4-yl)-thieno[3,2-d]pyrimidin-4-yl]-(R)-pyrrolidin-3-yl-amine |
| 580 | B | 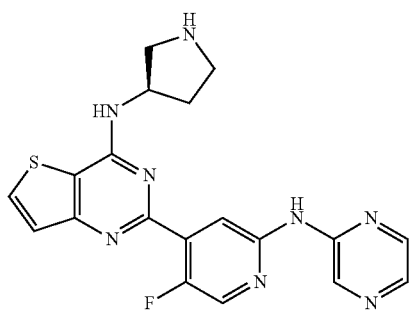 [SMILES: Fc1cnc(Nc2cnccn2)cc1-c1nc(N[C@@H]2CCNC2)c2sccc2n1] | {2-[5-Fluoro-2-(pyrazin-2-ylamino)-pyridin-4-yl]-thieno[3,2-d]pyrimidin-4-yl}-(R)-pyrrolidin-3-yl-amine |
| 581 | C | 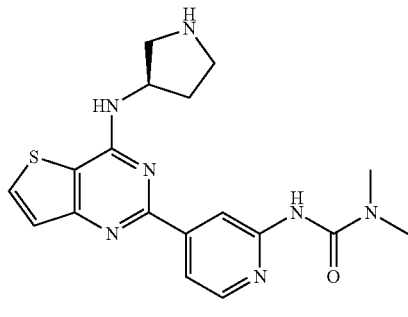 [SMILES: CN(C)C(=O)Nc1cc(-c2nc(N[C@@H]3CCNC3)c3sccc3n2)ccn1] | 1,1-Dimethyl-3-{4-[4-((R)-pyrrolidin-3-ylamino)-thieno[3,2-d]pyrimidin-2-yl]-pyridin-2-yl}-urea |
| 582 | C | 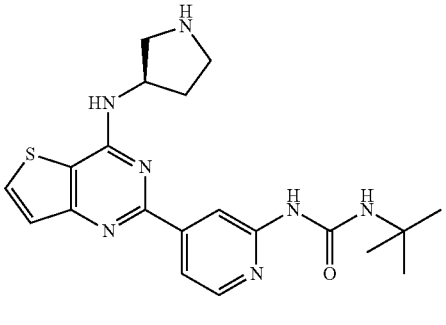 [SMILES: CC(C)(C)NC(=O)Nc1cc(-c2nc(N[C@@H]3CCNC3)c3sccc3n2)ccn1] | 1-tert-Butyl-3-{4-[4-((R)-pyrrolidin-3-ylamino)-thieno[3,2-d]pyrimidin-2-yl]-pyridin-2-yl}-urea |
| 583 | C | 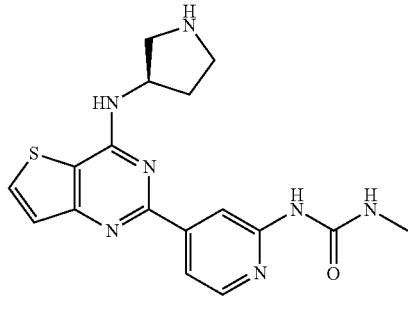 [SMILES: CNC(=O)Nc1cc(-c2nc(N[C@@H]3CCNC3)c3sccc3n2)ccn1] | 1-Methyl-3-{4-[4-((R)-pyrrolidin-3-ylamino)-thieno[3,2-d]pyrimidin-2-yl]-pyridin-2-yl}-urea |

| Ex | Activity | Structure | Name |
|---|---|---|---|
| 584 | C | 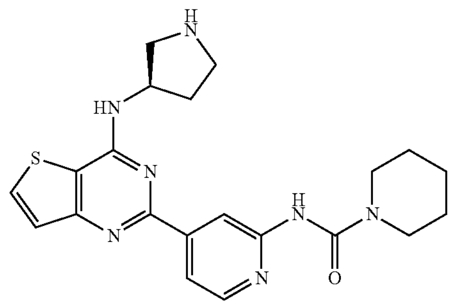 [SMILES: O=C(Nc1cc(-c2nc(N[C@@H]3CCNC3)c3sccc3n2)ccn1)N1CCCCC1] | Piperidine-1-carboxylic acid {4-[4-((R)-pyrrolidin-3-ylamino)-thieno[3,2-d]pyrimidin-2-yl]-pyridin-2-yl}-amide |
| 585 | C | 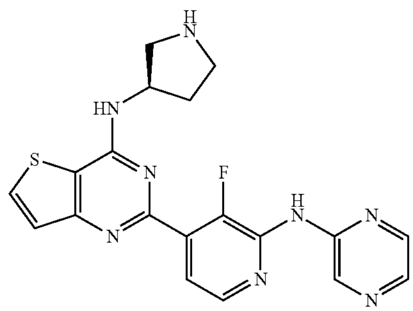 [SMILES: Fc1c(-c2nc(N[C@@H]3CCNC3)c3sccc3n2)ccnc1Nc1cnccn1] | {2-[3-Fluoro-2-(pyrazin-2-ylamino)-pyridin-4-yl]-thieno[3,2-d]pyrimidin-4-yl}-(R)-pyrrolidin-3-yl-amine |
| 586 | B | 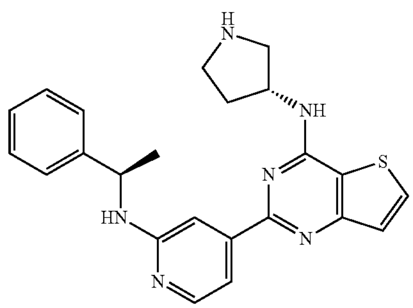 [SMILES: C[C@@H](Nc1cc(-c2nc(N[C@@H]3CCNC3)c3sccc3n2)ccn1)c1ccccc1] | {2-[2-((R)-1-Phenyl-ethylamino)-pyridin-4-yl]-thieno[3,2-d]pyrimidin-4-yl}-(R)-pyrrolidin-3-yl-amine |
| 587 | B | 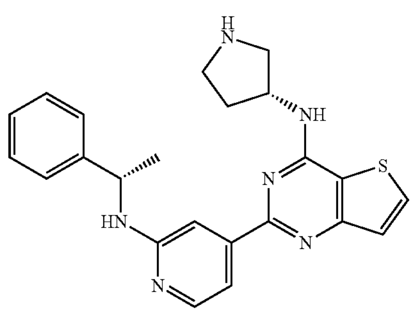 [SMILES: C[C@H](Nc1cc(-c2nc(N[C@@H]3CCNC3)c3sccc3n2)ccn1)c1ccccc1] | {2-[2-((S)-1-Phenyl-ethylamino)-pyridin-4-yl]-thieno[3,2-d]pyrimidin-4-yl}-(R)-pyrrolidin-3-yl-amine |
| 588 | B | 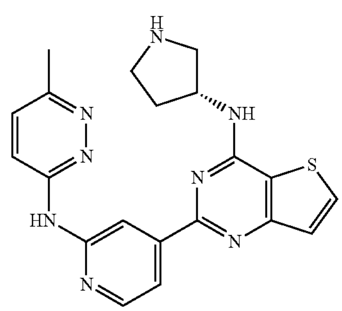 [SMILES: Cc1ccc(Nc2cc(-c3nc(N[C@@H]4CCNC4)c4sccc4n3)ccn2)nn1] | {2-[2-(6-Methyl-pyridazin-3-ylamino)-pyridin-4-yl]-thieno[3,2-d]pyrimidin-4-yl}-(R)-pyrrolidin-3-yl-amine |

| Ex | Activity | Structure | Name |
|---|---|---|---|
| 589 | C | 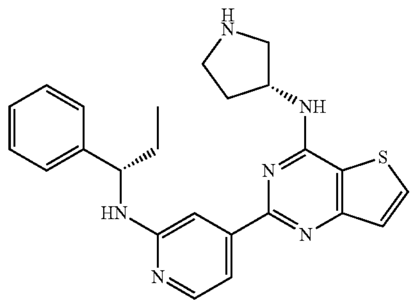 [SMILES: CC[C@H](Nc1cc(-c2nc(N[C@@H]3CCNC3)c3sccc3n2)ccn1)c1ccccc1] | {2-[2-((S)-1-Phenyl-propylamino)-pyridin-4-yl]-thieno[3,2-d]pyrimidin-4-yl}-(R)-pyrrolidin-3-yl-amine |
| 590 | C | 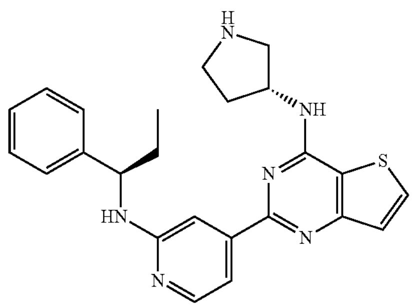 [SMILES: CC[C@@H](Nc1cc(-c2nc(N[C@@H]3CCNC3)c3sccc3n2)ccn1)c1ccccc1] | {2-[2-((R)-1-Phenyl-propylamino)-pyridin-4-yl]-thieno[3,2-d]pyrimidin-4-yl}-(R)-pyrrolidin-3-yl-amine |
| 591 | C | 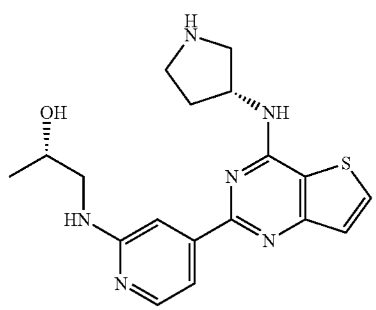 [SMILES: C[C@H](O)CNc1cc(-c2nc(N[C@@H]3CCNC3)c3sccc3n2)ccn1] | (S)-1-{4-[4-((R)-Pyrrolidin-3-ylamino)-thieno[3,2-d]pyrimidin-2-yl]-pyridin-2-ylamino}-propan-2-ol |
| 592 | C | 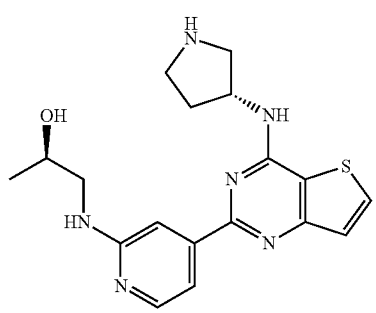 [SMILES: C[C@@H](O)CNc1cc(-c2nc(N[C@@H]3CCNC3)c3sccc3n2)ccn1] | (R)-1-{4-[4-((R)-Pyrrolidin-3-ylamino)-thieno[3,2-d]pyrimidin-2-yl]-pyridin-2-ylamino}-propan-2-ol |
| 593 | C | 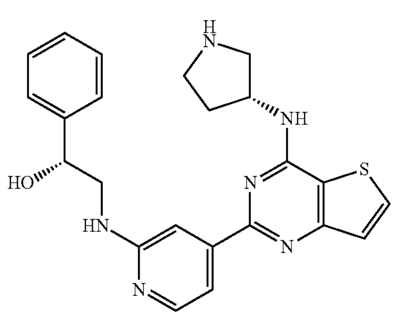 [SMILES: O[C@@H](CNc1cc(-c2nc(N[C@@H]3CCNC3)c3sccc3n2)ccn1)c1ccccc1] | (R)-1-Phenyl-2-{4-[4-((R)-pyrrolidin-3-ylamino)-thieno[3,2-d]pyrimidin-2-yl]-pyridin-2-ylamino}-ethanol |

| Ex | Activity | Structure | Name |
|---|---|---|---|
| 594 | C | 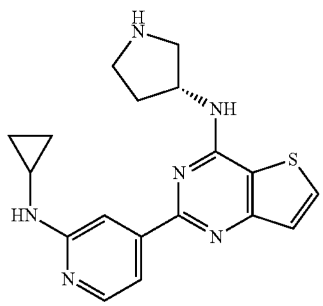 [SMILES: c1cc(-c2nc(N[C@@H]3CCNC3)c3sccc3n2)cc(NC2CC2)n1] | [2-(2-Cyclopropylamino-pyridin-4-yl)-thieno[3,2-d]pyrimidin-4-yl]-(R)-pyrrolidin-3-yl-amine |
| 595 | B | 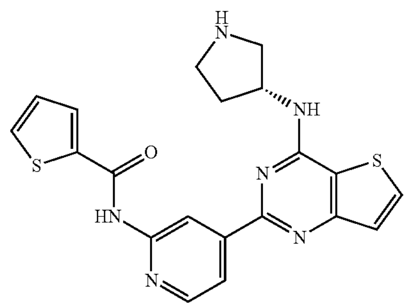 [SMILES: O=C(Nc1cc(-c2nc(N[C@@H]3CCNC3)c3sccc3n2)ccn1)c1cccs1] | Thiophene-2-carboxylic acid {4-[4-((R)-pyrrolidin-3-ylamino)-thieno[3,2-d]pyrimidin-2-yl]-pyridin-2-yl}-amide |
| 596 | B | 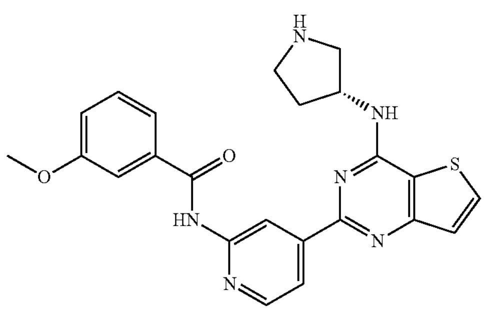 [SMILES: COc1cccc(C(=O)Nc2cc(-c3nc(N[C@@H]4CCNC4)c4sccc4n3)ccn2)c1] | 3-Methoxy-N-{4-[4-((R)-pyrrolidin-3-ylamino)-thieno[3,2-d]pyrimidin-2-yl]-pyridin-2-yl}-benzamide |
| 597 | C | 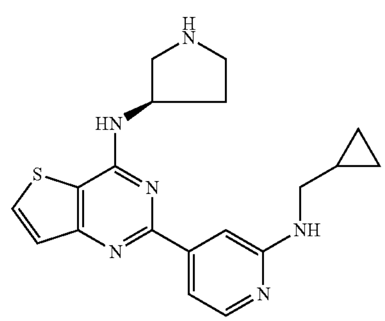 [SMILES: c1cc(-c2nc(N[C@@H]3CCNC3)c3sccc3n2)cc(NCC2CC2)n1] | {2-[2-(Cyclopropylmethyl-amino)-pyridin-4-yl]-thieno[3,2-d]pyrimidin-4-yl}-(R)-pyrrolidin-3-yl-amine |
| 598 | C | 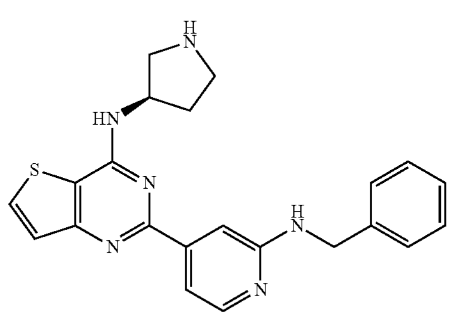 [SMILES: c1ccc(CNc2cc(-c3nc(N[C@@H]4CCNC4)c4sccc4n3)ccn2)cc1] | [2-(2-Benzylamino-pyridin-4-yl)-thieno[3,2-d]pyrimidin-4-yl]-(R)-pyrrolidin-3-yl-amine |

| Ex | Activity | Structure | Name |
|---|---|---|---|
| 599 | B | 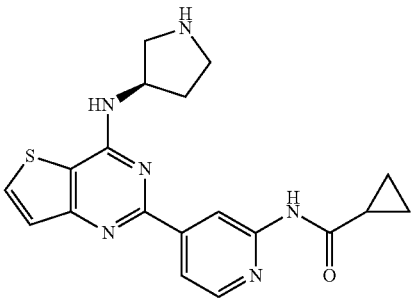 [SMILES: O=C(Nc1cc(-c2nc(N[C@@H]3CCNC3)c3sccc3n2)ccn1)C1CC1] | Cyclopropanecarboxylic acid {4-[4-((R)-pyrrolidin-3-ylamino)-thieno[3,2-d]pyrimidin-2-yl]-pyridin-2-yl}-amide |
| 600 | C | 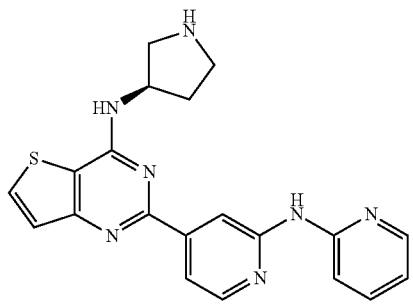 [SMILES: c1ccc(Nc2cc(-c3nc(N[C@@H]4CCNC4)c4sccc4n3)ccn2)nc1] | {2-[2-(Pyridin-2-ylamino)-pyridin-4-yl]-thieno[3,2-d]pyrimidin-4-yl}-(R)-pyrrolidin-3-yl-amine |
| 601 | B | 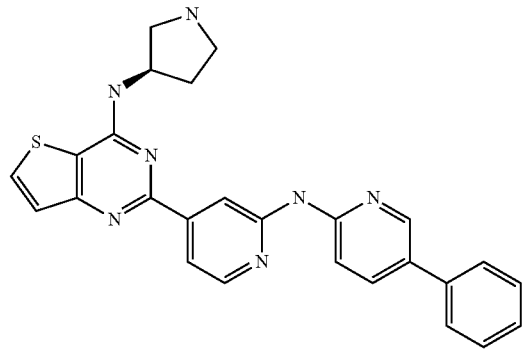 [SMILES: c1ccc(-c2ccc(Nc3cc(-c4nc(N[C@@H]5CCNC5)c5sccc5n4)ccn3)nc2)cc1] | {2-[2-(5-Phenyl-pyridin-2-ylamino)-pyridin-4-yl]-thieno[3,2-d]pyrimidin-4-yl}-(R)-pyrrolidin-3-yl-amine |
| 602 | B | 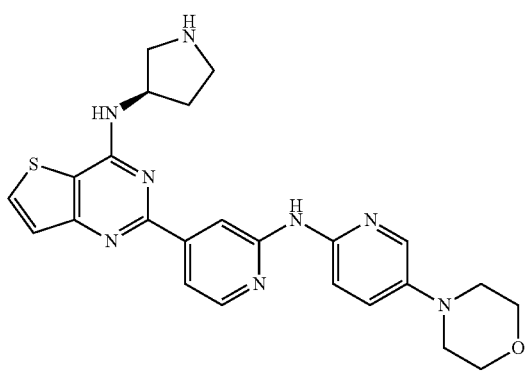 [SMILES: c1cc(-c2nc(N[C@@H]3CCNC3)c3sccc3n2)cc(Nc2ccc(N3CCOCC3)cn2)n1] | {2-[2-(5-Morpholin-4-yl-pyridin-2-ylamino)-pyridin-4-yl]-thieno[3,2-d]pyrimidin-4-yl}-(R)-pyrrolidin-3-yl-amine |

| Ex | Activity | Structure | Name |
|---|---|---|---|
| 603 | B | 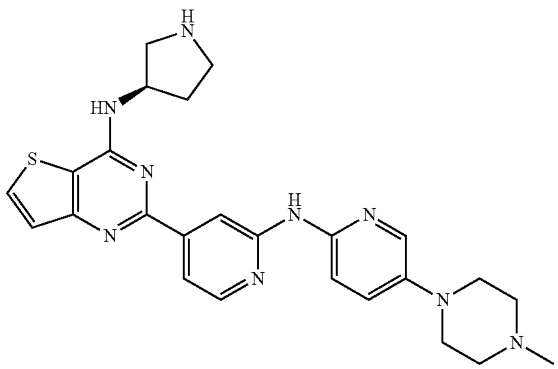 [SMILES: CN1CCN(c2ccc(Nc3cc(-c4nc(N[C@@H]5CCNC5)c5sccc5n4)ccn3)nc2)CC1] | (2-{2-[5-(4-Methyl-piperazin-1-yl)-pyridin-2-ylamino]-pyridin-4-yl}-thieno[3,2-d]pyrimidin-4-yl)-(R)-pyrrolidin-3-yl-amine |
| 604 | B | 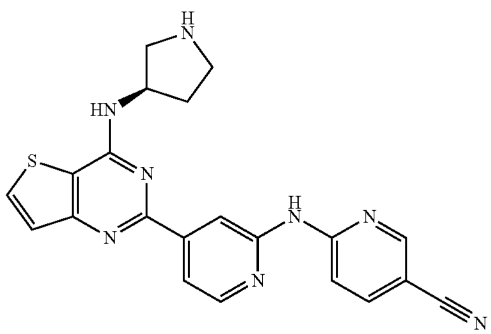 [SMILES: N#Cc1ccc(Nc2cc(-c3nc(N[C@@H]4CCNC4)c4sccc4n3)ccn2)nc1] | 6-{4-[4-((R)-Pyrrolidin-3-ylamino)-thieno[3,2-d]pyrimidin-2-yl]-pyridin-2-ylamino}-nicotinonitrile |
| 605 | B | 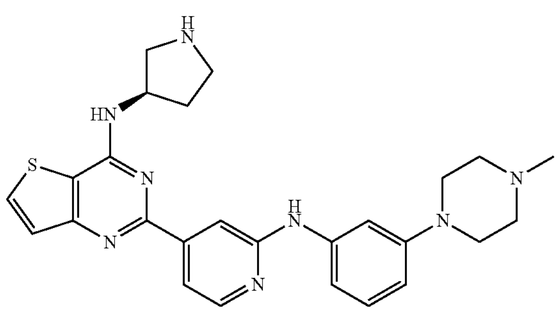 [SMILES: CN1CCN(c2cccc(Nc3cc(-c4nc(N[C@@H]5CCNC5)c5sccc5n4)ccn3)c2)CC1] | (2-{2-[3-(4-Methyl-piperazin-1-yl)-phenylamino]-pyridin-4-yl}-thieno[3,2-d]pyrimidin-4-yl)-(R)-pyrrolidin-3-yl-amine |
| 606 | C | 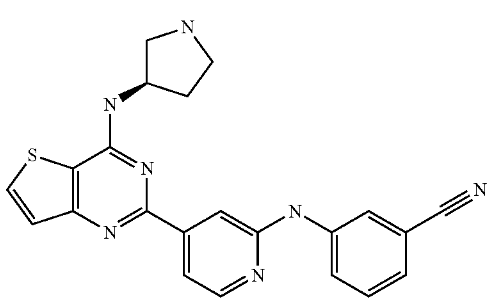 [SMILES: N#Cc1cccc(Nc2cc(-c3nc(N[C@@H]4CCNC4)c4sccc4n3)ccn2)c1] | 3-{4-[4-((R)-Pyrrolidin-3-ylamino)-thieno[3,2-d]pyrimidin-2-yl]-pyridin-2-ylamino}-benzonitrile |

| Ex | Activity | Structure | Name |
|---|---|---|---|
| 607 | C | 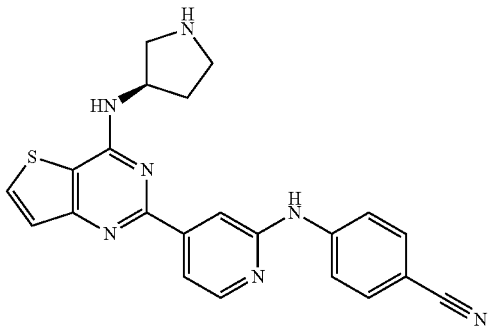 [SMILES: N#Cc1ccc(Nc2cc(-c3nc(N[C@@H]4CCNC4)c4sccc4n3)ccn2)cc1] | 4-{4-[4-((R)-Pyrrolidin-3-ylamino)-thieno[3,2-d]pyrimidin-2-yl]-pyridin-2-ylamino}-benzonitrile |
| 608 | B | 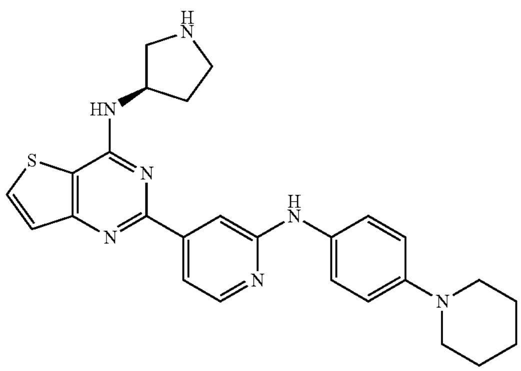 [SMILES: c1cc(-c2nc(N[C@@H]3CCNC3)c3sccc3n2)cc(Nc2ccc(N3CCCCC3)cc2)n1] | {2-[2-(4-Piperidin-1-yl-phenylamino)-pyridin-4-yl]-thieno[3,2-d]pyrimidin-4-yl}-(R)-pyrrolidin-3-yl-amine |
| 609 | B | 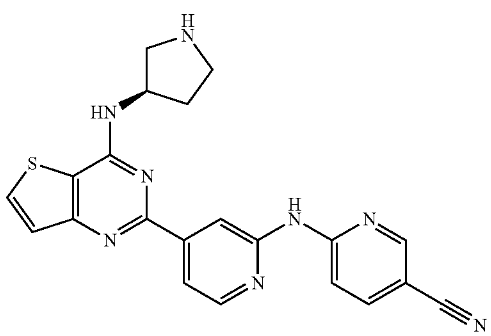 [SMILES: N#Cc1ccc(Nc2cc(-c3nc(N[C@@H]4CCNC4)c4sccc4n3)ccn2)nc1] | 6-{4-[4-((R)-Pyrrolidin-3-ylamino)-thieno[3,2-d]pyrimidin-2-yl]-pyridin-2-ylamino}-nicotinonitrile |
| 610 | C | 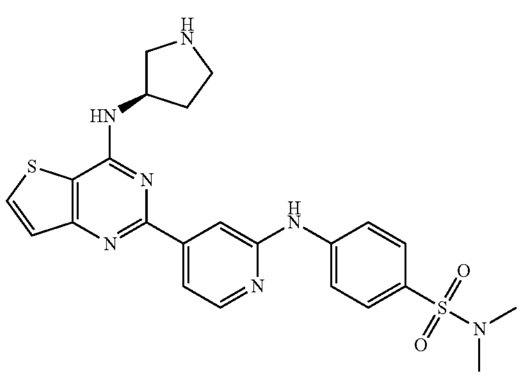 [SMILES: CN(C)S(=O)(=O)c1ccc(Nc2cc(-c3nc(N[C@@H]4CCNC4)c4sccc4n3)ccn2)cc1] | N,N-Dimethyl-4-{4-[4-((R)-pyrrolidin-3-ylamino)-thieno[3,2-d]pyrimidin-2-yl]-pyridin-2-ylamino}-benzenesulfonamide |

-continued

| Ex | Activity | Structure | Name |
|---|---|---|---|
| 611 | C | 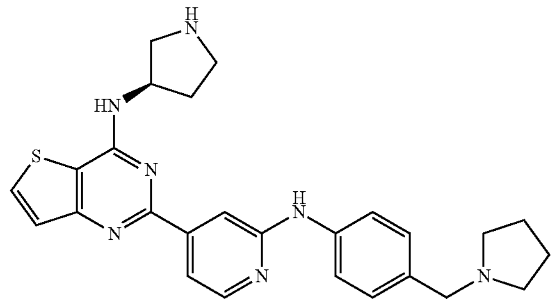 [SMILES: c1cc(-c2nc(N[C@@H]3CCNC3)c3sccc3n2)cc(Nc2ccc(CN3CCCC3)cc2)n1] | (R)-Pyrrolidin-3-yl-{2-[2-(4-pyrrolidin-1-ylmethyl-phenylamino)-pyridin-4-yl]-thieno[3,2-]pyrimidin-4-yl}-amine |
| 612 | C | 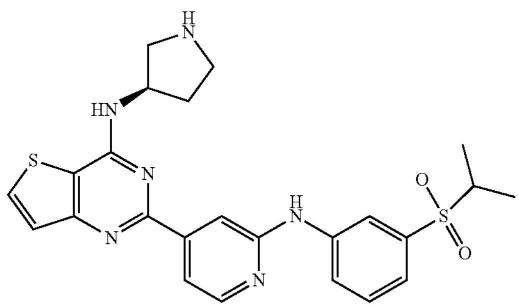 | (2-{2-[3-(Propane-2-sulfonyl)-phenylamino]-pyridin-4-yl}-thieno[3,2-d]pyrimidin-4-yl)-(R)-pyrrolidin-3-yl-amine |
| 613 | B | 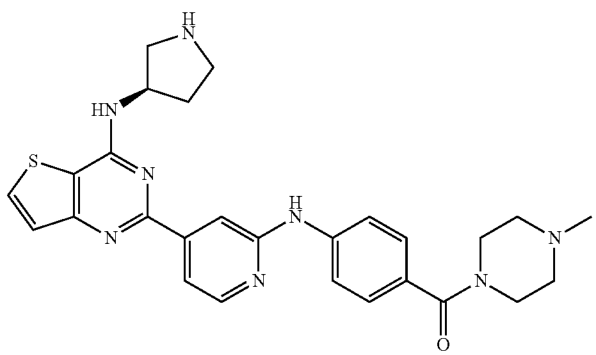 [SMILES: CN1CCN(C(=O)c2ccc(Nc3cc(-c4nc(N[C@@H]5CCNC5)c5sccc5n4)ccn3)cc2)CC1] | (4-Methyl-piperazin-1-yl)-(4-{4-[4-((R)-pyrrolidin-3-ylamino)-thieno[3,2-d]pyrimidin-2-yl]-pyridin-2-ylamino}-phenyl)-methanone |
| 614 | B | 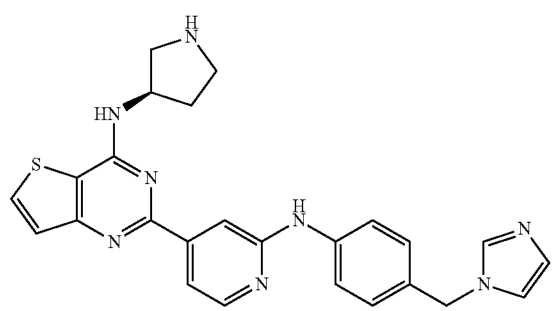 [SMILES: c1cn(Cc2ccc(Nc3cc(-c4nc(N[C@@H]5CCNC5)c5sccc5n4)ccn3)cc2)cn1] | {2-[2-(4-Imidazol-1-ylmethyl-phenylamino)-pyridin-4-yl]-thieno[3,2-d]pyrimidin-4-yl}-(R)-pyrrolidin-3-yl-amine |
| 615 | C | 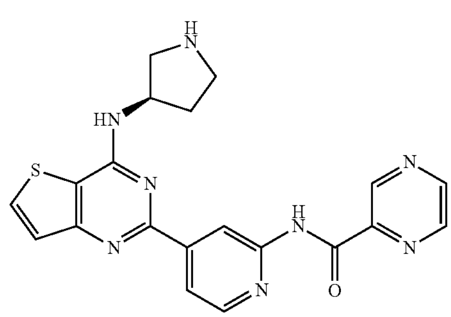 [SMILES: O=C(Nc1cc(-c2nc(N[C@@H]3CCNC3)c3sccc3n2)ccn1)c1cnccn1] | Pyrazine-2-carboxylic acid {4-[4-((R)-pyrrolidin-3-ylamino)-thieno[3,2-d]pyrimidin-2-yl]-pyridin-2-yl}-amide |

| Ex | Activity | Structure | Name |
|---|---|---|---|
| 616 | B | 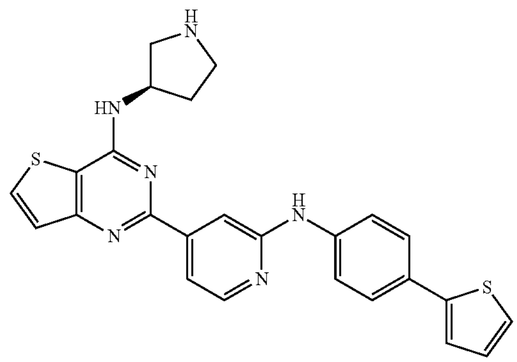 [SMILES: c1csc(-c2ccc(Nc3cc(-c4nc(N[C@@H]5CCNC5)c5sccc5n4)ccn3)cc2)c1] | (R)-Pyrrolidin-3-yl-{2-[2-(4-thiophen-2-yl-phenylamino)-pyridin-4-yl]-thieno[3,2-d]pyrimidin-4-yl}-amine |
| 617 | B | 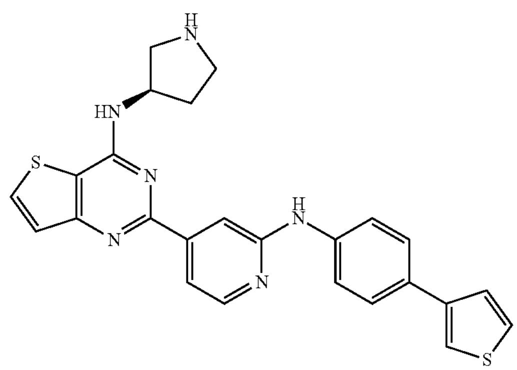 [SMILES: c1cc(-c2nc(N[C@@H]3CCNC3)c3sccc3n2)cc(Nc2ccc(-c3ccsc3)cc2)n1] | (R)-Pyrrolidin-3-yl-{2-[2-(4-thiophen-3-yl-phenylamino)-pyridin-4-yl]-thieno[3,2-d]pyrimidin-4-yl}-amine |
| 618 | B | 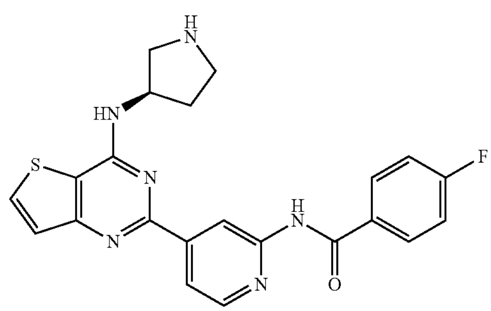 [SMILES: O=C(Nc1cc(-c2nc(N[C@@H]3CCNC3)c3sccc3n2)ccn1)c1ccc(F)cc1] | 4-Fluoro-N-{4-[4-((R)-pyrrolidin-3-ylamino)-thieno[3,2-d]pyrimidin-2-yl]-pyridin-2-yl}-benzamide |
| 619 | D | 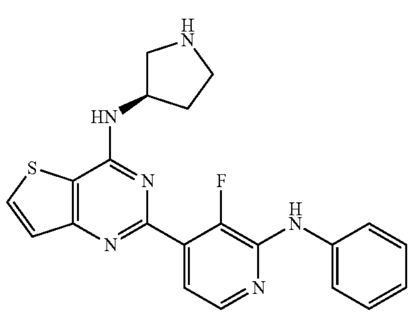 [SMILES: Fc1c(-c2nc(N[C@@H]3CCNC3)c3sccc3n2)ccnc1Nc1ccccc1] | [2-(3-Fluoro-2-phenylamino-pyridin-4-yl)-thieno[3,2-d]pyrimidin-4-yl]-(R)-pyrrolidin-3-yl-amine |

-continued

| Ex | Activity | Structure | Name |
|---|---|---|---|
| 620 | B | 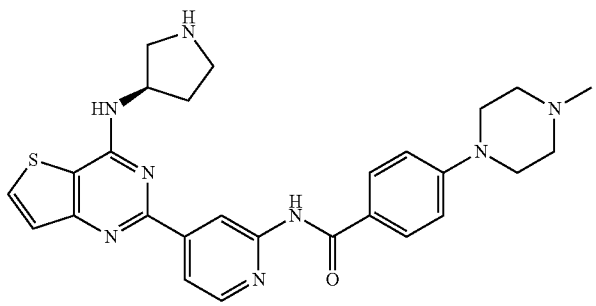 [SMILES: CN1CCN(c2ccc(C(=O)Nc3cc(-c4nc(N[C@@H]5CCNC5)c5sccc5n4)ccn3)cc2)CC1] | 4-(4-Methyl-piperazin-1-yl)-N-{4-[4-((R)-pyrrolidin-3-ylamino)-thieno[3,2-d]pyrimidin-2-yl]-pyridin-2-yl}-benzamide |
| 621 | B | 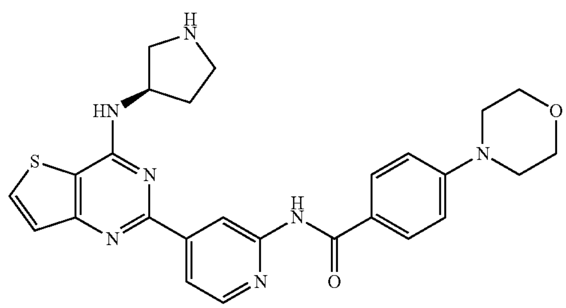 [SMILES: O=C(Nc1cc(-c2nc(N[C@@H]3CCNC3)c3sccc3n2)ccn1)c1ccc(N2CCOCC2)cc1] | 4-Morpholin-4-yl-N-{4-[4-((R)-pyrrolidin-3-ylamino)-thieno[3,2-d]pyrimidin-2-yl]-pyridin-2-yl}-benzamide |
| 622 | D | 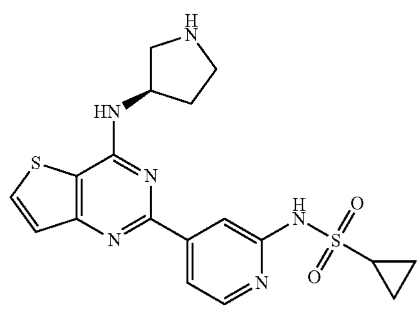 [SMILES: O=S(=O)(Nc1cc(-c2nc(N[C@@H]3CCNC3)c3sccc3n2)ccn1)C1CC1] | Cyclopropanesulfonic acid {4-[4-((R)-pyrrolidin-3-ylamino)-thieno[3,2-d]pyrimidin-2-yl]-pyridin-2-yl}-amide |
| 623 | D | 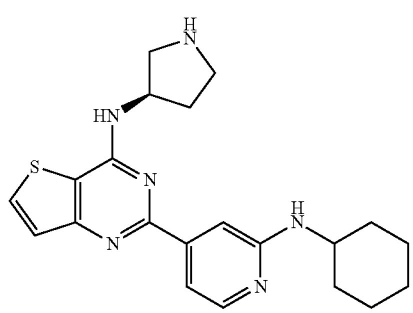 [SMILES: c1cc(-c2nc(N[C@@H]3CCNC3)c3sccc3n2)cc(NC2CCCCC2)n1] | [2-(2-Cyclohexylamino-pyridin-4-yl)-thieno[3,2-d]pyrimidin-4-yl]-(R)-pyrrolidin-3-yl-amine |
| 624 | D | 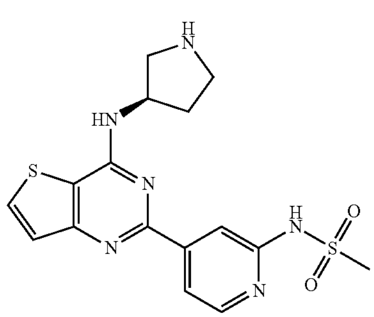 [SMILES: CS(=O)(=O)Nc1cc(-c2nc(N[C@@H]3CCNC3)c3sccc3n2)ccn1] | N-{4-[4-((R)-Pyrrolidin-3-ylamino)-thieno[3,2-d]pyrimidin-2-yl]-pyridin-2-yl}-methanesulfonamide |

| Ex | Activity | Structure | Name |
|---|---|---|---|
| 625 | D | 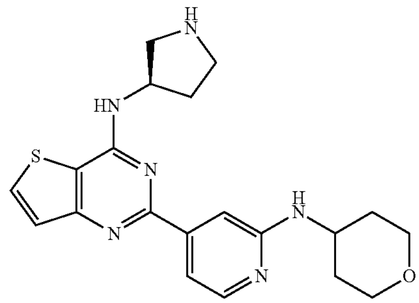 [SMILES: c1cc(-c2nc(N[C@@H]3CCNC3)c3sccc3n2)cc(NC2CCOCC2)n1] | (R)-Pyrrolidin-3-yl-{2-[2-(tetrahydro-pyran-4-ylamino)-pyridin-4-yl]-thieno[3,2-d]pyrimidin-4-yl}-amine |
| 626 | C | 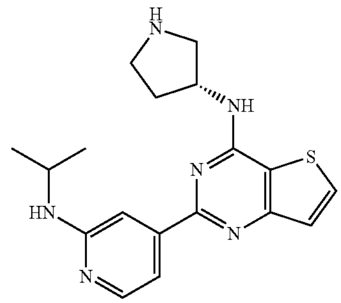 [SMILES: CC(C)Nc1cc(-c2nc(N[C@@H]3CCNC3)c3sccc3n2)ccn1] | [2-(2-Isopropylamino-pyridin-4-yl)-thieno[3,2-d]pyrimidin-4-yl]-(R)-pyrrolidin-3-yl-amine |
| 627 | C | 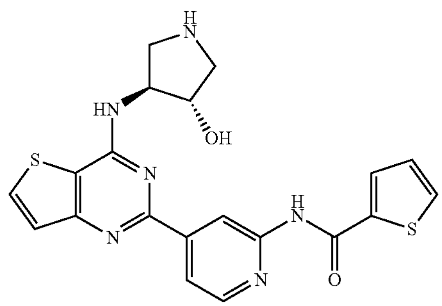 [SMILES: O=C(Nc1cc(-c2nc(N[C@H]3CNC[C@@H]3O)c3sccc3n2)ccn1)c1cccs1] | Thiophene-2-carboxylic acid {4-[4-((3S,4S)-4-hydroxy-pyrrolidin-3-ylamino)-thieno[3,2-d]pyrimidin-2-yl]-pyridin 2-yl}-amide |
| 628 | C | 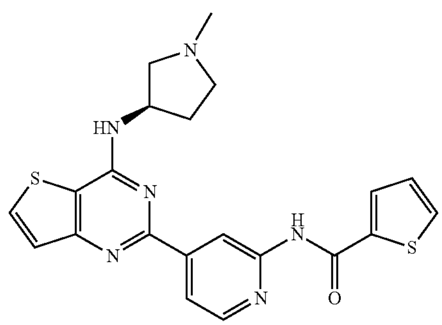 [SMILES: CN1CC[C@@H](Nc2nc(-c3ccnc(NC(=O)c4cccs4)c3)nc3ccsc23)C1] | Thiophene-2-carboxylic acid {4-[4-((R)-1-methyl-pyrrolidin-3-ylamino)-thieno[3,2-d]pyrimidin-2-yl]-pyridin-2-yl}-amide |
| 629 | C | 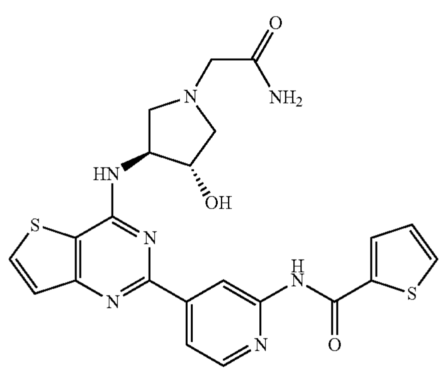 [SMILES: NC(=O)CN1C[C@H](Nc2nc(-c3ccnc(NC(=O)c4cccs4)c3)nc3ccsc23)[C@@H](O)C1] | Thiophene-2-carboxylic acid {4-[4-((3S,4S)-1-carbamoylmethyl-4-hydroxy-pyrrolidin-3-ylamino)-thieno[3,2-d]pyrimidin-2-yl]-pyridin-2-yl}-amide |

-continued

| Ex | Activity | Structure | Name |
|---|---|---|---|
| 630 | D | 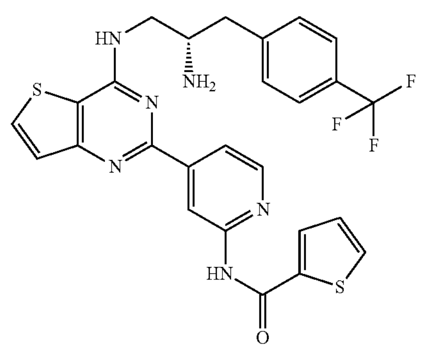 [SMILES: N[C@H](CNc1nc(-c2ccnc(NC(=O)c3cccs3)c2)nc2ccsc12)Cc1ccc(C(F)(F)F)cc1] | Thiophene-2-carboxylic acid (4-{4-[(S)-2-amino-3-(4-trifluoromethyl-phenyl)-propylamino]-thieno[3,2-d]pyrimidin-2-yl}-pyridin-2-yl)-amide |
| 631 | D | 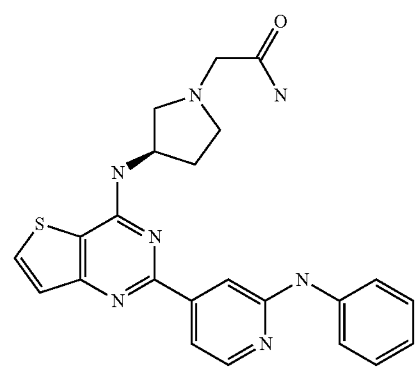 [SMILES: NC(=O)CN1CC[C@@H](Nc2nc(-c3ccnc(Nc4ccccc4)c3)nc3ccsc23)C1] | 2-{(R)-3-[2-(2-Phenylamino-pyridin-4-yl)-thieno[3,2-d]pyrimidin-4-ylamino]-pyrrolidin-1-yl}-acetamide |
| 632 | C | 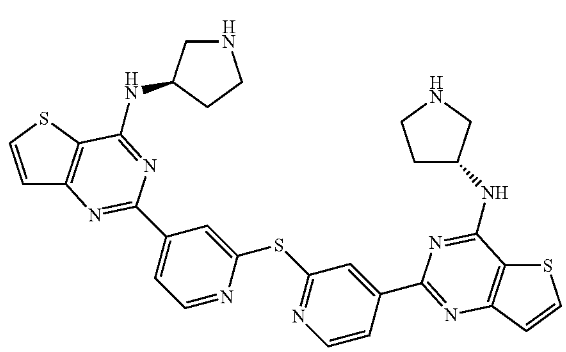 [SMILES: c1cc(-c2nc(N[C@@H]3CCNC3)c3sccc3n2)cc(Sc2cc(-c3nc(N[C@@H]4CCNC4)c4sccc4n3)ccn2)n1] | |

| Ex | Activity | Structure | Name |
|---|---|---|---|
| 633 | D | 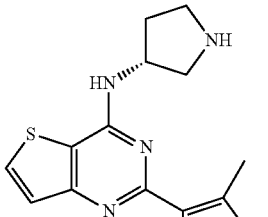 | [2-(5-Methyl-1H-pyrazol-4-yl)-thieno[3,2-d]pyrimidin-4-yl]-(R)-pyrrolidin-3-yl-amine |
| 634 | C | 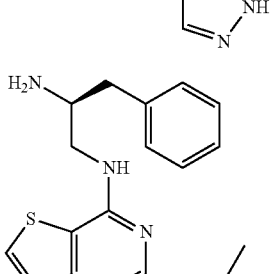 | (S)-N*1*-[2-(5-Methyl-1H-pyrazol-4-yl)-thieno[3,2-d]pyrimidin-4-yl]-3-phenyl-propane-1,2-diamine |

Preferably, a compound of the present invention (i.e., a compound of formula (I) or a salt thereof) has an $IC_{50}$ in an IMAP assay against full length PKCι at 150 μM ATP of <40 μM. In one embodiment, a compound of the present invention has an $IC_{50}$ in an IMAP assay against full length PKCι at 15 μM ATP of 40 μM-10 μM. More preferably, a compound of the present invention has an $IC_{50}$ in an IMAP assay against full length PKCι at 15 μM ATP of 10 μM-1 μM. In one embodiment, a compound of the present invention has an $IC_{50}$ in an IMAP assay against full length PKCι at 15 μM ATP of 1 μM-0.1 μM. More preferably, a compound of the present invention has an $IC_{50}$ in an IMAP assay against full length PKCι at 15 μM ATP of <0. μM.

Preferably, a compound of the present invention (i.e., a compound of formula (I) or a salt thereof) has an $IC_{50}$ in an IMAP assay against kinase domain PKCι at 25 μM ATP of <4 μM. In one embodiment, a compound of the present invention has an $IC_{50}$ in an IMAP assay against kinase domain PKCι at 25 μM ATP of 40 μM-10 μM. More preferably, a compound of the present invention has an $IC_{50}$ in an IMAP assay against kinase domain PKCι at 2 μM ATP of 10 μM-1 μM. In one embodiment, a compound of the present invention has an $IC_{50}$ in an IMAP assay against kinase domain PKCι at 2 μM ATP of 1 μM-0.1 μM. More preferably, a compound of the present invention has an $IC_{50}$ in an IMAP assay against kinase domain PKCι at 2 μM ATP of <0. μM.

As those skilled in the art will appreciate, numerous modifications and variations of the present invention are possible in light of the above teachings. It is therefore understood that within the scope of the appended claims, the invention may be practiced otherwise than as specifically described herein, and the scope of the invention is intended to encompass all such variations.

Each publication referenced herein is incorporated by reference in its entirety for all purposes.

Additional Preferred Embodiments of the present invention include:

1. A compound of formula (I)

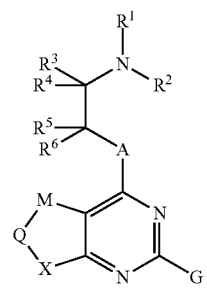

(I)

or a salt form thereof,
wherein
 A is $NR^{11}$, O, or S;
 M-Q-X is a group of formula

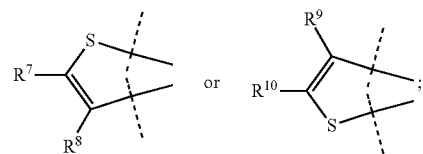

G is a group of formula

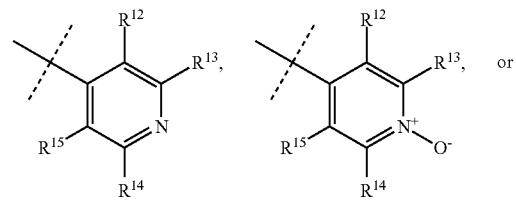

-continued

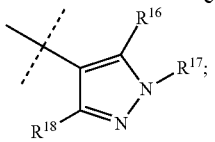

$R^1$, $R^2$, $R^{11}$, and $R^{17}$ are independently chosen from H, $C_{1-6}$alkyl optionally substituted by 1-13 $R^{19}$, $C_{2-6}$alkenyl optionally substituted by 1-11 $R^{19}$, $C_{2-6}$alkynyl optionally substituted by 1-9 $R^{19}$, $C_{6-11}$aryl optionally substituted by 1-11 $R^{19}$, $C_{7-16}$arylalkyl optionally substituted by 1-19 $R^{19}$, $C_{3-11}$cycloalkyl optionally substituted by 1-21 $R^{19}$, $C_{4-17}$cycloalkylalkyl optionally substituted by 1-32 $R^{19}$, 3-15 membered heterocycloalkyl optionally substituted by 1-28 $R^{19}$, 4-21 membered heterocycloalkylalkyl optionally substituted by 1-40 $R^{19}$, 5-15 membered heteroaryl optionally substituted by 1-15 $R^{19}$, 6-21 membered heteroarylalkyl optionally substituted by 1-27 $R^{19}$, and —$OR^{20}$ $R^3$, $R^4$, $R^5$, $R^6$, $R^7$, $R^8$, $R^9$, $R^{10}$, $R^{12}$, $R^{13}$, $R^{14}$, $R^{15}$, $R^{16}$, and $R^8$ are independently chosen from H, $C_{1-6}$alkyl optionally substituted by 1-13 $R^{19}$, $C_{2-6}$alkenyl optionally substituted by 1-11 $R^{19}$, $C_{2-6}$alkynyl optionally substituted by 1-9 $R^{19}$, $C_{6-11}$aryl optionally substituted by 1-11 $R^{19}$, $C_{7-16}$arylalkyl optionally substituted by 1-19 $R^{19}$, $C_{3-11}$cycloalkyl optionally substituted by 1-21 $R^{19}$, $C_{4-17}$cycloalkylalkyl optionally substituted by 1-32 $R^{19}$, 3-15 membered heterocycloalkyl optionally substituted by 1-28 $R^{19}$, 4-21 membered heterocycloalkylalkyl optionally substituted by 1-40 $R^{19}$, 5-15 membered heteroaryl optionally substituted by 1-15 $R^{19}$, 6-21 membered heteroarylalkyl optionally substituted by 1-27 $R^{19}$, halogen, —CN, —C(=O)$R^{20}$, —C(=O)O$R^{20}$, —C(=O)N$R^{22}R^{23}$, —C(=O)C(=O)$R^{20}$, —C(=N$R^{25}$)$R^{20}$, —C(=N$R^{25}$)N$R^{22}R^{23}$, —C(=NOH)N$R^{22}R^{23}$, —C(=NO$R^{26}$)$R^{20}$, —C(=NN$R^{22}R^{23}$)$R^{20}$, —C(=NN$R^{24}$C(=O)$R^{21}$)$R^{20}$, —C(=NN$R^{24}$C(=O)O$R^{21}$)$R^{20}$, —C(=S)N$R^{22}R^{23}$, —NC, —NO$_2$, —N$R^{22}R^{23}$, —N$R^{24}$N$R^{22}R^{23}$, —N=N$R^{24}$, —N$R^{24}$O$R^{26}$, —N$R^{24}$C(=O)$R^{20}$, —N$R^{24}$C(=O)C(=O)$R^{20}$, —N$R^{24}$C(=O)O$R^{21}$, —N$R^{24}$C(=O)C(=O)O$R^{21}$, —N$R^{24}$C(=O)N$R^{22}R^{23}$, —N$R^{24}$C(=O)N$R^{24}$C(=O)$R^{20}$, —N$R^{24}$C(=O)N$R^{24}$C(=O)O$R^{20}$, —N$R^{24}$C(=N$R^{25}$)N$R^{22}R^{23}$, —N$R^{24}$C(=O)C(=O)N$R^{22}R^{23}$, —N$R^{24}$C(=S)$R^{20}$, —N$R^{24}$C(=S)O$R^{20}$, —N$R^{24}$C(=S)N$R^{22}R^{23}$, —$R^{24}$S(=O)$_2R^{21}$, —N$R^{24}$S(=O)$_2$N$R^{22}R^{23}$, —N$R^{24}$P(=O)$R^{28}R^{28}$, —N$R^{24}$P(=O)(N$R^{22}R^{23}$)(N$R^{22}R^{23}$), —N$R^{24}$P(=O)(O$R^{20}$)(O$R^{20}$), —N$R^{24}$P(=O)(S$R^{20}$)(S$R^{20}$), —O$R^{20}$, —OCN, —OC(=O)$R^{20}$, —OC(=O)N$R^{22}R^{23}$, —OC(=O)O$R^{20}$, —OC(=N$R^{25}$)N$R^{22}R^{23}$, —OS(=O)$R^{20}$, —OS(=O)$_2R^{20}$, —OS(=O)$_2$O$R^{20}$, —OS(=O)$_2$N$R^{22}R^{23}$, —OP(=O)$R^{28}R^{28}$, —OP(=O)(N$R^{22}R^{23}$)(N$R^{22}R^{23}$), —OP(=O)(O$R^{20}$)(O$R^{20}$), —OP(=O)(S$R^{20}$)(S$R^{20}$), —Si($R^{24}$)$_3$, —SCN, —S(=O)$_nR^{20}$, —S(=O)$_2$O$R^{20}$, —SO$_3R^{27}$, —S(=O)$_2$N$R^{22}R^{23}$, —S(=O)N$R^{22}R^{23}$, —SP(=O)$R^{28}R^{28}R^{28}$, —SP(=O)(N$R^{22}R^{23}$)(N$R^{22}R^{23}$), —SP(=O)(O$R^{20}$)(O$R^{20}$), —SP(=O)(S$R^{20}$)(S$R^{20}$), —P(=O)$R^{28}R^{28}$, —P(=O)(N$R^{22}R^{23}$)(2$R^{22}R^{23}$), —P(=O)(O$R^{20}$)(O$R^{20}$), and —P(=O)(S$R^{20}$)(S$R^{20}$);

any of $R^1$ and $R^2$, $R^1$ and $R^3$, $R^1$ and $R^5$, $R^1$ and $R^{11}$, $R^4$ and $R^{11}$, $R^6$ and $R^{11}$, and $R^{16}$ and $R^{17}$ can, together with the atoms linking them, form a 3-15 membered heterocycloalkyl optionally substituted by 1-28 $R^{19}$ or a 5-15 membered heteroaryl optionally substituted by 1-15 $R^{19}$;

any of $R^3$ and $R^6$, $R^7$ and $R^8$, $R^9$ and $R^{10}$, $R^{12}$ and $R^{13}$, and $R^{14}$ and $R^{15}$ can, together with the atoms linking them, form a $C_{6-11}$aryl optionally substituted by 1-11 $R^{19}$, $C_{3-11}$cycloalkyl optionally substituted by 1-21 $R^{19}$, 3-15 membered heterocycloalkyl optionally substituted by 1-28 $R^{19}$ or a 5-15 membered heteroaryl optionally substituted by 1-15 $R^{19}$;

$R^3$ and $R^5$ or $R^4$ and $R^6$ can together form a double bond;

any of $R^3$ and $R^4$, and $R^5$ and $R^6$ can together form =O, =N$R^{20}$, =NO$R^{20}$, or =S;

$R^{19}$ at each occurrence is independently chosen from $C_{1-6}$alkyl optionally substituted by 1-13 $R^{39}$, $C_{2-6}$alkenyl optionally substituted by 1-11 $R^{39}$, $C_{2-6}$alkynyl optionally substituted by 1-9 $R^{39}$, $C_{6-11}$aryl optionally substituted by 1-11 $R^{39}$, $C_{7-16}$arylalkyl optionally substituted by 1-19 $R^{39}$, $C_{3-11}$cycloalkyl optionally substituted by 1-21 $R^{39}$, $C_{4-17}$cycloalkylalkyl optionally substituted by 1-32 $R^{39}$, 3-15 membered heterocycloalkyl optionally substituted by 1-28 $R^{39}$, 4-21 membered heterocycloalkylalkyl optionally substituted by 1-40 $R^{39}$, 5-15 membered heteroaryl optionally substituted by 1-15 $R^{39}$, 6-21 membered heteroarylalkyl optionally substituted by 1-27 $R^{39}$, halogen, —CN, —C(=O)$R^{30}$, —C(=O)O$R^{30}$, —C(=O)N$R^{32}R^{33}$, —C(=O)C(=O)$R^{30}$, —C(=N$R^{35}$)$R^{30}$, —C(=N$R^{35}$)N$R^{32}R^{33}$, —C(=NOH)N$R^{32}R^{33}$, —C(=NO$R^{36}$)$R^{30}$, —C(=NN$R^{32}R^{33}$)$R^{30}$, —C(=NN$R^{34}$C(=O)$R^{31}$)$R^{30}$, —C(=NN$R^{34}$C(=O)O$R^{31}$)$R^{30}$, —C(=S)N$R^{32}R^{33}$, —NC, —NO$_2$, —N$R^{32}R^{33}$, —N$R^{34}$N$R^{32}R^{33}$, —N=N$R^{34}$=N$R^{30}$, =NO$R^{30}$, —N$R^{34}R^{36}$, —N$R^{34}$C(=O)$R^{30}$, —N$R^{34}$C(=O)C(=O)$R^{30}$, —N$R^{34}$C(=O)O$R^{31}$, —N$R^{34}$C(=O)C(=O)O$R^{31}$, —N$R^{34}$C(=O)N$R^{32}R^{33}$, —N$R^{34}$C(=O)N$R^{34}$C(=O)$R^{30}$, —N$R^{34}$C(=O)N$R^{34}$C(=O)O$R^{30}$, —N$R^{34}$C(=N$R^{35}$)N$R^{32}R^{33}$, —N$R^{34}$C(=O)C(=O)N$R^{32}R^{33}$, —N$R^{34}$C(=S)$R^{30}$, —N$R^{34}$C(=S)O$R^{30}$, —N$R^{34}$C(=S)N$R^{32}R^{33}$, —N$R^{34}$S(=O)$_2R^{31}$, —N$R^{34}$S(=O)$_2$N$R^{32}R^{33}$, —N$R^{34}$P(=O)$R^{38}R^{38}$, —N$R^{34}$P(=O)(N$R^{32}R^{33}$)(N$R^{32}R^{33}$), —N$R^{34}$P(=O)(O$R^{30}$)(O$R^{30}$), —N$R^{34}$P(=O)(S$R^{30}$)(S$R^{30}$), —O$R^{30}$, =O, —OCN, —OC(=O)$R^{30}$, —OC(=O)N$R^{32}R^{33}$, —OC(=O)O$R^{30}$, —OC(=N$R^{35}$)N$R^{32}R^{33}$, —OS(=O)$R^{30}$, —OS(=O)$_2R^{30}$, —OS(=O)$_2$O$R^{30}$, —OS(=O)$_2$N$R^{32}R^{33}$, —OP(=O)$R^{38}R^{38}$, —OP(=O)(N$R^{32}R^{33}$)(N$R^{32}R^{33}$), —OP(=O)(O$R^{30}$)(O$R^{30}$), —OP(=O)(S$R^{30}$)(S$R^{30}$), —Si($R^{34}$)$_3$, —SCN, =S, —S(=O)$_nR^{30}$, —S(=O)$_2$O$R^{30}$, —SO$_3R^{37}$, —S(=O)$_2$N$R^{32}R^{33}$, —S(=O)N$R^{32}R^{33}$, —SP(=O)$R^{38}R^{38}$, —SP(=O)(N$R^{32}R^{33}$)(N$R^{32}R^{33}$), —SP(=O)(O$R^{30}$)(O$R^{30}$), —SP(=O)(S$R^{30}$)(S$R^{30}$), —P(=O)$R^{38}R^{38}$, —P(=O)(N$R^{32}R^{33}$)(N$R^{32}R^{33}$), —P(=O)(O$R^{30}$)(O$R^{30}$), and —P(=O)(S$R^{30}$)(S$R^{30}$);

$R^{20}$, $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H, $C_{1-6}$alkyl optionally substituted by 1-13 $R^{49}$, $C_{2-6}$alkenyl optionally substituted by 1-11 $R^{49}$, $C_{2-6}$alkynyl optionally substituted by 1-9 $R^{49}$, $C_{6-11}$aryl optionally substituted by 1-11 $R^{49}$, $C_{7-16}$arylalkyl optionally substituted by 1-19 $R^{49}$, $C_{3-11}$cycloalkyl optionally substituted by 1-21 $R^{49}$, $C_{4-17}$cycloalkylalkyl optionally substituted by 1-32 $R^{49}$, 3-15 membered heterocycloalkyl optionally substituted by 1-28 $R^{49}$, 4-21 membered heterocycloalkylalkyl optionally substituted by 1-40 $R^{49}$, 5-15 membered heteroaryl optionally substituted by 1-15 $R^{49}$, and 6-21 membered heteroarylalkyl optionally substituted by 1-27 $R^{49}$;

$R^{28}$ and $R^{38}$ at each occurrence is independently chosen from $C_{1-6}$alkyl optionally substituted by 1-13 $R^{49}$, $C_{2-6}$alkenyl optionally substituted by 1-11 $R^{49}$, $C_{2-6}$alkynyl optionally substituted by 1-9 $R^{49}$, $C_{6-11}$aryl optionally substituted by 1-11 $R^{49}$, $C_{7-16}$arylalkyl optionally substituted by 1-19 $R^{49}$, $C_{3-11}$cycloalkyl optionally substituted by 1-21 $R^{49}$, $C_{4-17}$cycloalkylalkyl optionally substituted by 1-32 $R^{49}$, 3-15 membered heterocycloalkyl optionally substituted by 1-28 $R^{49}$, 4-21 membered heterocycloalkylalkyl optionally substituted by 1-40 $R^{49}$, 5-15 membered heteroaryl optionally substituted by 1-15 $R^{49}$, and 6-21 membered heteroarylalkyl optionally substituted by 1-27 $R^{49}$;

$R^{22}$, $R^{23}$, $R^{32}$ and $R^{33}$ at each occurrence is independently chosen from H, $C_{1-6}$alkyl optionally substituted by 1-13 $R^{59}$, $C_{2-6}$alkenyl optionally substituted by 1-11 $R^{59}$, $C_{2-6}$alkynyl optionally substituted by 1-9 $R^{59}$, $C_{6-11}$aryl optionally substituted by 1-11 $R^{59}$, $C_{7-16}$arylalkyl optionally substituted by 1-19 $R^{59}$, $C_{3-11}$-cycloalkyl optionally substituted by 1-21 $R^{59}$, $C_{4-17}$cycloalkylalkyl optionally substituted by 1-32 $R^{59}$, 3-15 membered heterocycloalkyl optionally substituted by 1-28 $R^{59}$, 4-21 membered heterocycloalkylalkyl optionally substituted by 1-40 $R^{59}$, 5-15 membered heteroaryl optionally substituted by 1-15 $R^{59}$, and 6-21 membered heteroarylalkyl optionally substituted by 1-27 $R^{59}$;

or any $R^{22}$ and $R^{23}$ and/or $R^{32}$ and $R^{33}$ may form, together with the nitrogen atom to which they are attached, a 3-15 membered heterocycloalkyl optionally substituted by 1-28 $R^{69}$ or a 5-15 membered heteroaryl optionally substituted by 1-15 $R^{69}$ $R^{39}$, $R^{49}$, $R^{59}$ and $R^{69}$ at each occurrence is independently chosen from $C_{1-6}$ alkyl optionally substituted by 1-13 $R^{79}$, $C_{2-6}$alkenyl optionally substituted by 1-11 $R^{79}$, $C_{2-6}$alkynyl optionally substituted by 1-9 $R^{79}$, $C_{6-11}$aryl optionally substituted by 1-11 $R^{79}$, $C_{7-16}$arylalkyl optionally substituted by 1-19 $R^{79}$, $C_{3-11}$-cycloalkyl optionally substituted by 1-21 $R^{79}$, $C_{4-17}$cycloalkylalkyl optionally substituted by 1-32 $R^{79}$, 3-15 membered heterocycloalkyl optionally substituted by 1-28 $R^{79}$, 4-21 membered heterocycloalkylalkyl optionally substituted by 1-40 $R^{79}$, 5-15 membered heteroaryl optionally substituted by 1-15 $R^{79}$, 6-21 membered heteroarylalkyl optionally substituted by 1-27 $R^{79}$, halogen, —CN, —C(=O)$R^{70}$, —C(=O)O$R^{70}$, —C(=O)N$R^{72}R^{73}$, —C(=O)C(=O)$R^{70}$, —C(=N$R^{75}$)$R^{70}$, —C(=N$R^{75}$)N$R^{72}R^{73}$, —C(=NOH)N$R^{72}R^{73}$, —C(=NO$R^{76}$)$R^{70}$, —C(=NN$R^{72}R^{73}$)$R^{70}$, —C(=NN$R^{74}$C(=O)$R^{71}$)$R^{70}$, —C(=NN$R^{74}$C(=O)O$R^{71}$)$R^{70}$, —C(=S)N$R^{72}R^{73}$, —NC, —NO$_2$, —N$R^{72}R^{73}$, —N$R^{74}$N$R^{72}R^{73}$, —N=N$R^{74}$—N$R^{70}$, =NO$R^{70}$, —N$R^{74}$O$R^{76}$, —N$R^{74}$C(=O)$R^{70}$, —N$R^{74}$C(=O)C(=O)$R^{70}$, —$R^{74}$C(=O)O$R^{71}$, —N$R^{74}$C(=O)C(=O)OR, —N$R^{74}$C(=O)N$R^{72}R^{73}$, —N$R^{74}$C(=O)N$R^{74}$C(=O)$R^{70}$, —N$R^{74}$C(=O)N$R^{74}$C(=O)O$R^{70}$, —N$R^{74}$C(=N$R^{75}$)N$R^{72}R^{73}$, —N$R^{74}$C(=O)C(=O)N$R^{72}R^{73}$, —$R^{74}$C(=S)$R^{70}$, —N$R^{74}$C(=S)O$R^{70}$, —N$R^{74}$C(=S)N$R^{72}R^{73}$, —N$R^{74}$S(=O)$_2$$R^{71}$, —N$R^{74}$S(=O)$_2$N$R^{72}R^{73}$, —N$R^{74}$P(=O)$R^{78}R^{78}$, —N$R^{74}$P(=O)(N$R^{72}R^{73}$)(N$R^{72}R^{73}$), —N$R^{74}$P(=O)(O$R^{70}$)(O$R^{70}$), —N$R^{74}$P(=O)(S$R^{70}$)(S$R^{70}$), —O$R^{70}$, =O, —OCN, —OC(=O)$R^{70}$, —OC(=O)N$R^{72}R^{73}$, —OC(=O)O$R^{70}$, —OC(=N$R^{75}$)N$R^{72}R^{73}$, —OS(=O)$R^{70}$, —OS(=O)$_2$$R^{70}$, —OS(=O)$_2$O$R^{70}$, —OS(=O)$_2$N$R^{72}R^{73}$, —OP(=O)$R^{78}R^{78}$, —OP(=O)(N$R^{72}R^{73}$)(N$R^{72}R^{73}$), —OP(=O)(O$R^{70}$)(O$R^{70}$), —OP(=O)(S$R^{70}$)(S$R^{70}$), —Si($R^{74}$)$_3$, —SCN, =S, —S(=O)$_n$$R^{70}$, —S(=O)$_2$O$R^{70}$, —SO$_3$$R^{77}$, —S(=O)$_2$N$R^{72}R^{73}$, —S(=O)N$R^{72}R^{73}$, —SP(=O)$R^{78}R^{78}$, —SP(=O)(N$R^{72}R^{73}$)(N$R^{72}R^{73}$), —SP(=O)(O$R^{70}$)(O$R^{70}$), —SP(=O)(S$R^{70}$)(S$R^{70}$), —P(=O)$R^{78}R^{78}$, —P(=O)(N$R^{72}R^{73}$)(N$R^{72}R^{73}$), —P(=O)(O$R^{70}$)(O$R^{70}$), and —P(=O)(S$R^{70}$)(S$R^{70}$);

$R^{70}$, $R^{71}$, $R^{74}$, $R^{75}$, $R^{76}$ and $R^{77}$ at each occurrence is independently chosen from H, $C_{1-6}$alkyl optionally substituted by 1-13 $R^{89}$, $C_{2-6}$alkenyl optionally substituted by 1-11 $R^{89}$, $C_{2-6}$alkynyl optionally substituted by 1-9 $R^{89}$, $C_{6-11}$aryl optionally substituted by 1-11 $R^{89}$, $C_{7-16}$arylalkyl optionally substituted by 1-19 $R^{89}$, $C_{3-11}$cycloalkyl optionally substituted by 1-21 $R^{89}$, $C_{4-17}$cycloalkylalkyl optionally substituted by 1-32 $R^{89}$, 3-15 membered heterocycloalkyl optionally substituted by 1-28 $R^{89}$, 4-21 membered heterocycloalkylalkyl optionally substituted by 1-40 $R^{89}$, 5-15 membered heteroaryl optionally substituted by 1-15 $R^{89}$, and 6-21 membered heteroarylalkyl optionally substituted by 1-27 $R^{89}$;

$R^{72}$ and $R^{73}$ at each occurrence is independently chosen from H, $C_{1-6}$alkyl optionally substituted by 1-13 $R^{99}$, $C_{2-6}$alkenyl optionally substituted by 1-11 $R^{99}$, $C_{2-6}$alkynyl optionally substituted by 1-9 $R^{99}$, $C_{6-11}$aryl optionally substituted by 1-11 $R^{99}$, $C_{7-16}$arylalkyl optionally substituted by 1-19 $R^{99}$, $C_{3-11}$cycloalkyl optionally substituted by 1-21 $R^{99}$, $C_{4-17}$cycloalkylalkyl optionally substituted by 1-32 $R^{99}$, 3-15 membered heterocycloalkyl optionally substituted by 1-28 $R^{99}$, 4-21 membered heterocycloalkylalkyl optionally substituted by 1-40 $R^{99}$, 5-15 membered heteroaryl optionally substituted by 1-15 $R^{99}$, and 6-21 membered heteroarylalkyl optionally substituted by 1-27 $R^{99}$; or any $R^{72}$ and $R^{73}$ may form, together with the nitrogen atom to which they are attached, a 3-15 membered heterocycloalkyl optionally substituted by 1-28 $R^{109}$ or a 5-15 membered heteroaryl optionally substituted by 1-15 $R^{109}$;

$R^{78}$ at each occurrence is independently chosen from $C_{1-6}$alkyl optionally substituted by 1-13 $R^{89}$, $C_{2-6}$alkenyl optionally substituted by 1-11 $R^{89}$, $C_{2-6}$alkynyl optionally substituted by 1-9 $R^{89}$, $C_{6-11}$aryl optionally substituted by 1-11 $R^{89}$, $C_{7-16}$arylalkyl optionally substituted by 1-19 $R^{89}$, $C_{3-11}$cycloalkyl optionally substituted by 1-21 $R^{89}$, $C_{4-17}$cycloalkylalkyl optionally substituted by 1-32 $R^{89}$, 3-15 membered heterocycloalkyl optionally substituted by 1-28 $R^{89}$, 4-21 membered heterocycloalkylalkyl optionally substituted by 1-40 $R^{89}$, 5-15 membered heteroaryl optionally substituted by 1-15 $R^{89}$, and 6-21 membered heteroarylalkyl optionally substituted by 1-27 $R^{89}$;

$R^{79}$, $R^{89}$, $R^{99}$ and $R^{109}$ at each occurrence is independently chosen from $C_{1-6}$ alkyl optionally substituted by 1-13 halogen, $C_{2-6}$alkenyl, $C_{2-6}$alkynyl, $C_{6-11}$aryl, $C_{7-16}$arylalkyl, $C_{3-11}$cycloalkyl, $C_{4-17}$cycloalkylalkyl, 3-15 membered heterocycloalkyl, 4-21 membered heterocycloalkylalkyl, 5-15 membered heteroaryl, 6-21 membered heteroarylalkyl, halogen, —CN, —C(=O)$R^{110}$, —C(=O)O$R^{110}$, —C(=O)N$R^{110}R^{110}$, —C(=O)C(=O)$R^{110}$, —C(=N$R^{110}$)$R^{110}$, —C(=N$R^{110}$N$R^{110}R^{110}$, —C(=NOH)N$R^{110}R^{110}$, —C(=NO$R^{110}$)$R^{110}$, —C(=NN$R^{110}R^{110}$)$R^{10}$, —C(=NN$R^{110}$C(=O)$R^{110}$)$R^{110}$, —C(=NN$R^{110}$C(=O)O$R^{110}$)$R^{110}$, —C(=S)N$R^{110}R^{110}$, —NC, —NO$_2$, —NR$^{110}$R$^{110}$, —NR$^{110}$NR$^{110}$R$^{110}$, —N=NR$^{110}$, =NR$^{110}$, =NOR$^{110}$, —NR$^{110}$OR$^{110}$, —NR$^{110}$C(=O)R$^{110}$, —NR$^{110}$C(=O)C(=O)R$^{110}$, —NR$^{110}$C(=O)OR$^{110}$, —NR$^{110}$C(=O)C(=O)OR$^{110}$, —NR$^{110}$C(=O)NR$^{110}$R$^{110}$, —NR$^{110}$C(=O)NR$^{110}$C(=O)R$^{110}$, —NR$^{110}$C(=O)NR$^{110}$C(=O)OR$^{110}$, —NR$^{110}$C(=NR$^{110}$)NR$^{110}$R$^{110}$, —NR$^{110}$C(=O)C(=O)NR$^{110}$R$^{110}$, —NR$^{110}$C(=S)R$^{110}$, —NR$^{110}$C(=S)OR$^{110}$, —NR$^{110}$C(=S)NR$^{110}$R$^{110}$, —NR$^{110}$S(=O)$_2$R$^{110}$, —NR$^{110}$S(=O)$_2$NR$^{110}$R$^{110}$, —NR$^{110}$P(=O)R$^{111}$R$^{111}$, —NR$^{110}$P(=O)(NR$^{110}$R$^{110}$)(NR$^{110}$R$^{110}$), —NR$^{110}$P(=O)(OR$^{110}$)(OR$^{110}$), —NR$^{110}$P(=O)(SR$^{110}$)(SR$^{110}$), —OR$^{110}$, =, —OCN, —OC(=O)R$^{110}$, —OC(=O)NR$^{110}$R$^{110}$, —OC(=O)OR$^{110}$, —OC(=NR$^{110}$) NR$^{110}$R$^{110}$, —OS(=O)R$^{110}$, —OS(=O)$_2$R$^{110}$, —OS(=O)$_2$OR$^{110}$, —OS(=O)$_2$NR$^{110}$R$^{110}$, —OP(=O)R$^{111}$R$^{111}$, —OP(=O)(NR$^{110}$R$^{110}$)(NR$^{110}$R$^{110}$), —OP(=O)(OR$^{110}$)(OR$^{110}$), —OP(=O)(SR$^{110}$)(SR$^{110}$), —Si(R$^{110}$)$_3$, —SCN, =S, —S(=O)$_n$R$^{110}$, —S(=O)$_2$OR$^{110}$, —SO$_3$R$^{110}$, —S(=O)$_2$NR$^{110}$R$^{110}$, —S(=O)NR$^{110}$R$^{110}$, —SP(=O)R$^{111}$R$^{111}$, —SP(=O)(NR$^{110}$R$^{110}$)(NR$^{110}$R$^{110}$), —SP(=O)(OR$^{110}$)(OR$^{110}$), —SP(=O)(SR$^{110}$)(SR$^{110}$), —P(=O)R$^{111}$R$^{111}$, —P(=O)(NR$^{110}$R$^{110}$)(NR$^{110}$R$^{110}$), —P(=O)(OR$^{110}$)(OR$^{110}$), and —P(=O)(SR$^{110}$)(SR$^{110}$);

R$^{110}$ at each occurrence is independently chosen from H, C$_{1-6}$alkyl and C$_{1-6}$-haloalkyl;

R$^{111}$ at each occurrence is independently chosen from C$_{1-6}$alkyl and C$_{1-6}$-haloalkyl; and n at each occurrence is independently chosen from 0, 1, and 2.

2. A compound as defined in Preferred Embodiment 1, wherein A is NR$^{11}$.

3. A compound as defined in Preferred Embodiments 1 or 2, wherein G is a group of formula

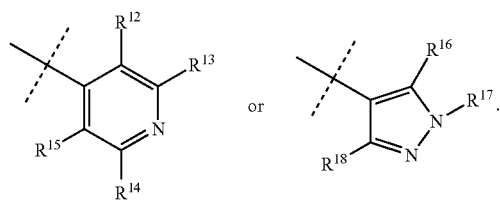

4. A compound as defined in Preferred Embodiment 3, wherein G is a group of formula

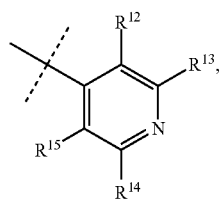

and the compound of formula (I) is a compound of formula (Ic)

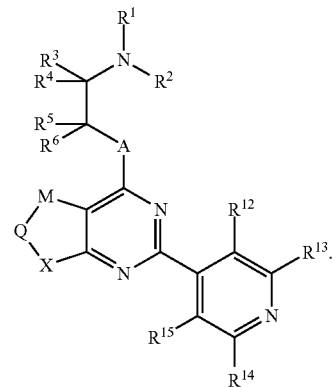

5. A compound as defined in any of Preferred Embodiments 1-4, wherein R$^1$, R$^2$, and R$^{11}$ are independently chosen from H and C$_{1-6}$alkyl optionally substituted by 1-3 R$^{19}$; R$^3$, R$^4$, R$^5$, and R$^6$ are independently chosen from H, C$_{1-6}$alkyl optionally substituted by 1-3 R$^{19}$, halogen, —CN, —C(=O)R$^{20}$, —C(=O)OR$^{20}$, —C(=O)NR$^{22}$R$^{23}$, —NO$_2$, —NR$^{22}$R$^{23}$, —NR$^{24}$C(=O)R$^{20}$, —NR$^{24}$S(=O)$_2$R$^{21}$, —OR$^{20}$, —OC(=O)R$^{20}$, —S(=O)$_n$R$^{20}$, and —S(=O)$_2$NR$^{22}$R$^{23}$; alternatively, R$^3$ and R$^6$ can, together with the atoms linking them, form a C$_{6-10}$aryl optionally substituted by 1-3 R$^{19}$, C$_{3-10}$cycloalkyl optionally substituted by 1-3 R$^{19}$, 3-10 membered heterocycloalkyl optionally substituted by 1-3 R$^{19}$ or a 5-10 membered heteroaryl optionally substituted by 1-3 R$^{19}$; alternatively R$^3$ and R$^5$ or R$^4$ and R$^6$ can together form a double bond; and alternatively any of R$^1$ and R$^2$, R$^1$ and R$^3$, R$^1$ and R$^5$, R$^1$ and R$^{11}$, R$^4$ and R$^{11}$, and R$^6$ and R$^{11}$ can, together with the atoms linking them, form a 5-15 membered heterocycloalkyl optionally substituted by 1-3 R$^{19}$ or a 5-15 membered heteroaryl optionally substituted by 1-3 R$^{19}$.

6. A compound as defined in any of Preferred Embodiments 1-4, wherein R$^1$, R$^2$, and R$^{11}$ are independently chosen from H and C$_{1-6}$alkyl optionally substituted by 1-3 R$^{19}$; R$^3$, R$^4$, R$^5$, and R$^6$ are independently chosen from H, C$_{1-6}$alkyl optionally substituted by 1-3 R$^{19}$, halogen, —CN, —C(=O)R$^{20}$, —C(=O)NR$^{22}$R$^{23}$, —NR$^{22}$R$^{23}$, —NR$^{24}$C(=O)R$^{20}$, —NR$^{24}$S(=O)$_2$R$^{21}$, —OR$^{20}$, —S(=O)$_n$R$^{20}$, and —S(=O)$_2$NR$^{22}$R$^{23}$; alternatively any of R$^1$ and R$^2$, R$^1$ and R$^3$, R$^1$ and R$^5$, R$^1$ and R$^{11}$, R$^4$ and R$^{11}$, and R$^6$ and R$^{11}$ can, together with the atoms linking them, form a 5-15 membered heterocycloalkyl optionally substituted by 1-3 R$^{19}$.

7. A compound as defined in any of Preferred Embodiments 1-4, wherein R$^1$, R$^4$, R$^5$, R$^6$, and R$^{11}$ are independently chosen from H and C$_{1-6}$alkyl optionally substituted by 1-13 R$^{19}$; R$^2$ is chosen from H, C$_{1-6}$alkyl optionally substituted by 1-13 R$^{19}$, C$_{7-16}$arylalkyl optionally substituted by 1-19 R$^{19}$, and 6-21 membered heteroarylalkyl optionally substituted by 1-27 R$^{19}$; R$^3$ is chosen from H, C$_{1-6}$alkyl optionally substituted by 1-13 R$^{19}$, C$_{7-16}$arylalkyl optionally substituted by 1-19 R$^{19}$, C$_{4-17}$cycloalkylalkyl optionally substituted by 1-32 R$^{19}$, and 6-21 membered heteroarylalkyl optionally substituted by 1-27 R$^{19}$; alternatively, R$^3$ and R$^6$ can, together with the atoms linking them, form a C$_{3-10}$cycloalkyl optionally substituted by 1-6 R$^{19}$; alternatively R$^3$ and R$^4$ can together form =O; and alternatively any of R and R$^2$, R and R$^3$, R and R$^5$, R and R$^{11}$, R$^4$ and R$^{11}$, and R$^6$ and R$^{11}$ can, together with the atoms linking them, form a 3-15 membered heterocycloalkyl optionally substituted by 1-22 R$^{19}$.

8. A compound as defined in any of Preferred Embodiments 1-4, wherein $R^1$, $R^4$, $R^5$, $R^6$, and $R^{11}$ are independently chosen from H and $C_{1-6}$alkyl optionally substituted by 1-3 $R^{19}$; $R^2$ is chosen from H, $C_{1-6}$alkyl optionally substituted by 1-3 $R^{19}$, $C_{7-11}$arylalkyl optionally substituted by 1-3 $R^{19}$, and 6-10 membered heteroarylalkyl optionally substituted by 1-3 $R^{19}$; $R^3$ is chosen from H, $C_{1-6}$alkyl optionally substituted by 1-3 $R^{19}$, $C_{7-11}$arylalkyl optionally substituted by 1-9 $R^{19}$, $C_{6-7}$cycloalkylalkyl optionally substituted by 1-6 $R^{19}$, and 6-11 membered heteroarylalkyl optionally substituted by 1-7 $R^{19}$; and alternatively any of $R^1$ and $R^2$, $R^1$ and $R^3$, $R^1$ and $R^5$, $R^1$ and $R^{11}$, and $R^4$ and $R^{11}$ can, together with the atoms linking them, form a 3-7 membered heterocycloalkyl optionally substituted by 1-3 $R^{19}$.

9. A compound as defined in any of Preferred Embodiments 1-8, wherein $R^7$, $R^8$, $R^9$, and $R^{10}$ are independently chosen from H, $C_{1-6}$alkyl optionally substituted by 1-3 $R^{19}$, $C_{2-6}$alkenyl optionally substituted by 1-3 $R^{19}$, $C_{2-6}$alkynyl optionally substituted by 1-3 $R^{19}$, $C_{6-10}$aryl optionally substituted by 1-3 $R^{19}$, $C_{7-11}$arylalkyl optionally substituted by 1-3 $R^{19}$, $C_{3-7}$cycloalkyl optionally substituted by 1-3 $R^{19}$, $C_{4-8}$cycloalkylalkyl optionally substituted by 1-3 $R^{19}$, 3-7 membered heterocycloalkyl optionally substituted by 1-3 $R^{19}$, 4-8 membered heterocycloalkylalkyl optionally substituted by 1-3 $R^{19}$, 5-6 membered heteroaryl optionally substituted by 1-3 $R^{19}$, 6-21 membered heteroarylalkyl optionally substituted by 1-3 $R^{19}$, halogen, —CN, —C(=O)$R^{20}$, —C(=O)O$R^{20}$, —C(=O)N$R^{22}R^{23}$, —NC, —NO$_2$, —N$R^{22}R^{23}$, —N$R^{24}$O$R^{26}$, —N$R^{24}$C(=O)$R^{20}$, —N$R^{24}$C(=O)O$R^{21}$, —N$R^{24}$C(=O)N$R^{22}R^{23}$, —N$R^{24}$S(=O)$_2R^{21}$, —N$R^{24}$S(=O)$_2$N$R^{22}R^{23}$, —O$R^{20}$, —OCN, —OC(=O)$R^{20}$, —OC(=O)N$R^{22}R^{23}$, —OC(=O)O$R^{20}$, —OS(=O)$_2R^{20}$, —OS(=O)$_2$O$R^{20}$, —OS(=O)$_2$N$R^{22}R^{23}$, —S(=O)$_nR^{20}$, and —S(=O)$_2$N$R^{22}R^{23}$; alternatively, either or both of $R^7$ and $R^8$, and/or $R^9$ and $R^{10}$, can, together with the atoms linking them, form a $C_{6-10}$aryl optionally substituted by 1-3 $R^{19}$, $C_{3-7}$cycloalkyl optionally substituted by 1-3 $R^{19}$, 3-7 membered heterocycloalkyl optionally substituted by 1-3 $R^{19}$ or a 5-6 membered heteroaryl optionally substituted by 1-3 $R^{19}$.

10. A compound as defined in any of Preferred Embodiments 1-8, wherein $R^7$, $R^8$, $R^9$, and $R^{10}$ are independently chosen from H, $C_{1-6}$alkyl optionally substituted by 1-3 $R^{19}$, $C_{2-6}$alkynyl optionally substituted by 1-3 $R^{19}$, $C_{6-10}$aryl optionally substituted by 1-3 $R^{19}$, $C_{3-7}$cycloalkyl optionally substituted by 1-3 $R^{19}$, 3-7 membered heterocycloalkyl optionally substituted by 1-3 $R^{19}$, 5-6 membered heteroaryl optionally substituted by 1-3 $R^{19}$, halogen, —CN, —C(=O)$R^{20}$, —C(=O)N$R^{22}R^{23}$, —NO$_2$, —N$R^{22}R^{23}$, —N$R^{24}$S(=O)$_2R^{21}$, —O$R^{20}$, —S(=O)$_nR^{20}$, and —S(=O)$_2$N$R^{22}R^{23}$; alternatively, either or both of $R^7$ and $R^8$, and/or $R^9$ and $R^{10}$, can, together with the atoms linking them, form a $C_{3-7}$cycloalkyl optionally substituted by 1-3 $R^{19}$, or a 3-7 membered heterocycloalkyl optionally substituted by 1-3 $R^{19}$.

11. A compound as defined in any of Preferred Embodiments 1-8, wherein $R^7$, $R^8$, $R^9$, and $R^{10}$ are independently chosen from H, $C_{1-6}$alkyl optionally substituted by 1-13 $R^{19}$, $C_{2-6}$alkenyl optionally substituted by 1-11 $R^{19}$, $C_{2-6}$alkynyl optionally substituted by 1-9 $R^{19}$, $C_{6-11}$aryl optionally substituted by 1-11 $R^{19}$, $C_{7-16}$arylalkyl optionally substituted by 1-19 $R^{19}$, $C_{3-11}$cycloalkyl optionally substituted by 1-21 $R^{19}$, 3-15 membered heterocycloalkyl optionally substituted by 1-28 $R^{19}$, 5-15 membered heteroaryl optionally substituted by 1-15 $R^{19}$, 6-21 membered heteroarylalkyl optionally substituted by 1-27 $R^{19}$, halogen, —CN, —C(=O)$R^{20}$, —C(=O)N$R^{22}R^{23}$, —N$R^{22}R^{23}$, —N$R^{24}$C(=O)$R^{20}$, and —O$R^{20}$; alternatively, either or both of $R^7$ and $R^8$, and/or $R^9$ and $R^{10}$, can, together with the atoms linking them, form a $C_{6-11}$aryl optionally substituted by 1-11 $R^{19}$, $C_{3-11}$cycloalkyl optionally substituted by 1-21 $R^{19}$, 3-15 membered heterocycloalkyl optionally substituted by 1-28 $R^{19}$ or a 5-15 membered heteroaryl optionally substituted by 1-15 $R^{19}$.

12. A compound as defined in any of Preferred Embodiments 1-8, wherein $R^7$ and $R^{10}$ are independently chosen from H, $C_{1-6}$alkyl optionally substituted by 1-3 $R^{19}$, $C_{2-6}$alkenyl optionally substituted by 1-3 $R^{19}$, $C_{2-6}$alkynyl optionally substituted by 1-3 $R^{19}$, $C_{6-11}$aryl optionally substituted by 1-3 $R^{19}$, $C_{7-16}$arylalkyl optionally substituted by 1-3 $R^{19}$, $C_{3-11}$cycloalkyl optionally substituted by 1-3 $R^{19}$, 3-15 membered heterocycloalkyl optionally substituted by 1-3 $R^{19}$, 5-15 membered heteroaryl optionally substituted by 1-3 $R^{19}$, 6-21 membered heteroarylalkyl optionally substituted by 1-3 $R^{19}$, halogen, —CN, —C(=O)$R^{20}$, —C(=O)N$R^{22}R^{23}$, —N$R^{22}R^{23}$, —N$R^{24}$C(=O)$R^{20}$, and —O$R^{20}$; R and $R^9$ are independently chosen from $C_{1-6}$alkyl optionally substituted by 1-3 $R^{19}$, $C_{2-6}$alkenyl optionally substituted by 1-3 $R^{19}$, $C_{2-6}$alkynyl optionally substituted by 1-3 $R^{19}$, $C_6$11aryl optionally substituted by 1-3 $R^{19}$, $C_{7-16}$arylalkyl optionally substituted by 1-3 $R^{19}$, $C_3$11cycloalkyl optionally substituted by 1-3 $R^{19}$, 3-15 membered heterocycloalkyl optionally substituted by 1-3 $R^{19}$, 5-15 membered heteroaryl optionally substituted by 1-3 $R^{19}$, 6-21 membered heteroarylalkyl optionally substituted by 1-3 $R^{19}$, halogen, —CN, —C(=O)$R^{20}$, —C(=O)N$R^{22}R^{23}$, —N$R^{22}R^{23}$, —N$R^{24}$C(=O)$R^{20}$, and —O$R^{20}$; alternatively, either or both of $R^7$ and $R^8$, and/or $R^9$ and $R^{10}$, can, together with the atoms linking them, form a $C_{6-11}$aryl optionally substituted by 1-3 $R^{19}$, $C_3$11cycloalkyl optionally substituted by 1-3 $R^{19}$, 3-15 membered heterocycloalkyl optionally substituted by 1-3 $R^{19}$ or a 5-15 membered heteroaryl optionally substituted by 1-3 $R^{19}$.

13. A compound as defined in any of Preferred Embodiments 1-8, wherein $R^7$, $R^8$, $R^9$, and $R^{10}$ are independently chosen from H, $C_{1-6}$alkyl optionally substituted by 1-3 $R^{19}$, $C_{2-6}$alkenyl optionally substituted by 1-3 $R^{19}$, $C_{2-6}$alkynyl optionally substituted by 1-3 $R^{19}$, $C_{6-10}$aryl optionally substituted by 1-3 $R^{19}$, $C_{7-11}$arylalkyl optionally substituted by 1-3 $R^{19}$, $C_{3-10}$cycloalkyl optionally substituted by 1-3 $R^{19}$, 3-10 membered heterocycloalkyl optionally substituted by 1-3 $R^{19}$, 5-10 membered heteroaryl optionally substituted by 1-3 $R^{19}$, 6-11 membered heteroarylalkyl optionally substituted by 1-3 $R^{19}$, halogen, —CN, —C(=O)$R^{20}$, —C(=O)N$R^{22}R^{23}$, —N$R^{22}R^{23}$, —N$R^{24}$C(=O)$R^{20}$, and —O$R^{20}$; alternatively, either or both of $R^7$ and $R^8$, and/or $R^9$ and $R^{10}$, can, together with the atoms linking them, form a $C_{6-10}$aryl optionally substituted by 1-3 $R^{19}$, $C_{3-10}$cycloalkyl optionally substituted by 1-3 $R^{19}$, 3-10 membered heterocycloalkyl optionally substituted by 1-3 $R^{19}$ or a 5-10 membered heteroaryl optionally substituted by 1-3 $R^{19}$.

14. A compound as defined in any of Preferred Embodiments 1-8, wherein $R^7$, $R^8$, $R^9$, and $R^{10}$ are independently chosen from H, $C_{1-6}$alkyl optionally substituted by 1-3 $R^{19}$, $C_{2-6}$alkenyl optionally substituted by 1-3 $R^{19}$, $C_{2-6}$alkynyl optionally substituted by 1-3 $R^{19}$, phenyl optionally substituted by 1-3 $R^{19}$, $C_{3-6}$cycloalkyl optionally substituted by 1-3 $R^{19}$, 3-6 membered heterocycloalkyl optionally substituted by 1-3 $R^{19}$, 5-6 membered heteroaryl optionally substituted by 1-3 $R^{19}$ halogen, —CN, —C(=O)$R^{20}$, —C(=O)N$R^{22}R^{23}$, —N$R^{22}R^{23}$, —N$R^{24}$C(=O)$R^{20}$, and —O$R^{20}$; alternatively, either or both of $R^7$ and $R^8$, and/or $R^9$ and $R^{10}$, can, together with the atoms linking them, form a phenyl optionally substituted by 1-3 $R^{19}$, $C_{3-6}$ cycloalkyl optionally substituted by 1-3 $R^{19}$, 3-6 membered heterocycloalkyl optionally substituted by 1-3 $R^{19}$ or a 5-6 membered heteroaryl optionally substituted by 1-3 $R^{19}$.

15. A compound as defined in any of Preferred Embodiments 1-14, wherein $R^{12}$, $R^{13}$, $R^{14}$, and $R^{15}$ are independently chosen from H, $C_{1-6}$alkyl optionally substituted by 1-3 $R^{19}$, $C_{2-6}$alkenyl optionally substituted by 1-3 $R^{19}$, $C_{2-6}$alkynyl optionally substituted by 1-3 $R^{19}$, $C_{6-10}$aryl optionally substituted by 1-3 $R^{19}$, $C_{3-7}$cycloalkyl optionally substituted by 1-3 $R^{19}$, 3-7 membered heterocycloalkyl optionally substituted by 1-3 $R^{19}$, 5-6 membered heteroaryl optionally substituted by 1-3 $R^{19}$, halogen, —CN, —C(=O)$R^{20}$, —C(=O)O$R^{20}$, —C(=O)N$R^{22}R^{23}$, —NO$_2$, —N$R^{22}R^{23}$, —$R^{24}$C(=O)$R^{20}$, —N$R^{24}$C(=O)O$R^{21}$, —N$R^{24}$C(=O)N$R^{22}R^{23}$, —N$R^{24}$S(=O)$_2R^{21}$, —N$R^{24}$S(=O)$_2$N$R^{22}R^{23}$, —O$R^{20}$, —OC(=O)$R^{20}$, —OC(=O)N$R^{22}R^{23}$, —OC(=O)O$R^{20}$, —S(=O)$_nR^{20}$, —S(=O)$_2OR^{20}$, —SO$_3R^{27}$, —S(=O)$_2$N$R^{22}R^{23}$, —S(=O)N$R^{22}R^{23}$, —P(=O)$R^{28}R^{28}$, —P(=O)(N$R^{22}R^{23}$)(N$R^{22}R^{23}$), and —P(=O)(O$R^{20}$)(O$R^{20}$); alternatively, either or both of $R^{12}$ and $R^{13}$, and/or $R^{14}$ and $R^{15}$, can, together with the atoms linking them, form a $C_{6-10}$aryl optionally substituted by 1-3 $R^{19}$, $C_{3-7}$cycloalkyl optionally substituted by 1-3 $R^{19}$, 3-7 membered heterocycloalkyl optionally substituted by 1-3 $R^{19}$ or a 5-6 membered heteroaryl optionally substituted by 1-3 $R^{19}$.

16. A compound as defined in any of Preferred Embodiments 1-14, wherein $R^{12}$, $R^{13}$, $R^{14}$, and $R^{15}$ are independently chosen from H, $C_{1-6}$alkyl optionally substituted by 1-3 $R^{19}$, $C_{2-6}$alkenyl optionally substituted by 1-3 $R^{19}$, $C_{2-6}$alkynyl optionally substituted by 1-3 $R^{19}$, $C_{6-10}$aryl optionally substituted by 1-3 $R^{19}$, $C_{3-7}$cycloalkyl optionally substituted by 1-3 $R^{19}$, 3-7 membered heterocycloalkyl optionally substituted by 1-3 $R^{19}$, 5-6 membered heteroaryl optionally substituted by 1-3 $R^{19}$, halogen, —CN, —C(=O)$R^{20}$, —C(=O)N$R^{22}R^{23}$, —NO$_2$, —N$R^{22}R^{23}$, —N$R^{24}$C(=O)$R^{20}$, —N$R^{24}$S(=O)$_2R^{21}$, —O$R^{20}$, —S(=O)$_nR^{20}$, and —S(=O)$_2$N$R^{22}R^{23}$; alternatively, either or both of $R^{12}$ and $R^{13}$, and/or $R^{14}$ and $R^{15}$, can, together with the atoms linking them, form a $C_{6-10}$aryl optionally substituted by 1-3 $R^{19}$, $C_{3-7}$cycloalkyl optionally substituted by 1-3 $R^{19}$, 3-7 membered heterocycloalkyl optionally substituted by 1-3 $R^{19}$ or a 5-6 membered heteroaryl optionally substituted by 1-3 $R^{19}$.

17. A compound as defined in any of Preferred Embodiments 1-14, wherein $R^{12}$, $R^{13}$, and $R^{14}$ are H; $R^{15}$ is chosen from H, $C_{1-6}$alkyl optionally substituted by 1-3 $R^{19}$, $C_{2-6}$alkenyl optionally substituted by 1-3 $R^{19}$, $C_{2-6}$alkynyl optionally substituted by 1-3 $R^{19}$, $C_{6-10}$aryl optionally substituted by 1-3 $R^{19}$, $C_{3-7}$cycloalkyl optionally substituted by 1-3 $R^{19}$, 3-7 membered heterocycloalkyl optionally substituted by 1-3 $R^{19}$, 5-6 membered heteroaryl optionally substituted by 1-3 $R^{19}$, halogen, —CN, —C(=O)$R^{20}$, —C(=O)N$R^{22}R^{23}$, —NO$_2$, —N$R^{22}R^{23}$, —N$R^{24}$C(=O)$R^{20}$, —N$R^{24}$S(=O)$_2R^{21}$, —O$R^{20}$, —S(=O)$_nR^{20}$, and —S(=O)$_2$N$R^{22}R^{23}$.

18. A compound as defined in any of Preferred Embodiments 1-14, wherein $R^{12}$, $R^{13}$, $R^{14}$, and $R^{15}$ are independently chosen from H, halogen, —N$R^{22}R^{23}$, —N$R^{24}$C(=O)$R^{20}$, —N$R^{24}$C(=O)N$R^{22}R^{23}$, —O$R^{20}$, and —S(=O)$_2$N$R^{22}R^{23}$.

19. A compound as defined in any of Preferred Embodiments 1-14, wherein $R^{12}$, $R^{13}$, and $R^{15}$ are H; $R^{14}$ is chosen from H, halogen, —N$R^{22}R^{23}$, —N$R^{24}$C(=O)$R^{20}$, —N$R^{24}$C(=O)N$R^{22}R^{23}$, —O$R^{20}$, and —S(=O)$_2$N$R^{22}R^{23}$.

20. A compound as defined in any of Preferred Embodiments 1-3 or 5-19, wherein $R^{17}$ is chosen from H and $C_{1-6}$alkyl; $R^{16}$ and $R^{18}$ are independently chosen from H, $C_{1-6}$alkyl optionally substituted by 1-3 $R^{19}$, $C_{6-10}$aryl optionally substituted by 1-3 $R^{19}$, $C_{7-11}$arylalkyl optionally substituted by 1-3 $R^{19}$, $C_{3-10}$cycloalkyl optionally substituted by 1-3 $R^{19}$, 3-10 membered heterocycloalkyl optionally substituted by 1-3 $R^{19}$, 5-10 membered heteroaryl optionally substituted by 1-3 $R^{19}$, halogen, —CN, —C(=O)$R^{20}$, —C(=O)O$R^{20}$, —C(=O)N$R^{22}R^{23}$, —NC, —NO$_2$, —N$R^{22}R^{23}$, —N$R^{24}$C(=O)$R^{20}$, —N$R^{24}$C(=O)O$R^{21}$, —N$R^{24}$C(=O)N$R^{22}R^{23}$, —N$R^{24}$S(=O)$_2R^{21}$, —O$R^{20}$, —OCN, —OC(=O)$R^{20}$, —OC(=O)N$R^{22}R^{23}$, —SCN, —S(=O)$_nR^{20}$, —S(=O)$_2OR^{20}$, —SO$_3R^{27}$, —S(=O)$_2$N$R^{22}R^{23}$, and —S(=O)N$R^{22}R^{23}$; alternatively, $R^{16}$ and $R^{17}$ can, together with the atoms linking them, form a 3-10 membered heterocycloalkyl optionally substituted by 1-3 $R^{19}$ or a 5-10 membered heteroaryl optionally substituted by 1-3 $R^{19}$.

21. A compound as defined in any of Preferred Embodiments 1-3 or 5-19, wherein $R^{17}$ is chosen from H and $C_{1-6}$alkyl; $R^{16}$ and $R^{18}$ are independently chosen from H, $C_{1-6}$alkyl optionally substituted by 1-3 $R^{19}$, $C_{6-10}$aryl optionally substituted by 1-3 $R^{19}$, $C_{7-11}$arylalkyl optionally substituted by 1-3 $R^{19}$, $C_{3-10}$cycloalkyl optionally substituted by 1-3 $R^{19}$, 3-10 membered heterocycloalkyl optionally substituted by 1-3 $R^{19}$, 5-10 membered heteroaryl optionally substituted by 1-3 $R^{19}$ halogen, —CN, —C(=O)$R^{20}$, —C(=O)N$R^{22}R^{23}$, —NO$_2$, —N$R^{22}R^{23}$, —N$R^{24}$C(=O)$R^{20}$, —N$R^{24}$S(=O)$_2R^{21}$, —O$R^{20}$, —S(=O)$_nR^{20}$, and —S(=O)$_2$N$R^{22}R^{23}$; alternatively, $R^{16}$ and $R^{17}$ can, together with the atoms linking them, form a 3-10 membered heterocycloalkyl optionally substituted by 1-3 $R^{19}$ or a 5-10 membered heteroaryl optionally substituted by 1-3 $R^{19}$.

22. A compound as defined in any of Preferred Embodiments 1-3 or 5-19, wherein $R^{17}$ is H; and $R^{16}$ and $R^{18}$ are independently chosen from H and $C_{1-6}$alkyl optionally substituted by 1-3 $R^{19}$.

23. A compound as defined in any of Preferred Embodiments 1-3 or 5-19, wherein $R^{17}$ is H; and $R^{16}$ and $R^{18}$ are independently chosen from H and $C_{1-6}$alkyl.

24. A compound as defined in any of Preferred Embodiments 1-23, wherein $R^{19}$ at each occurrence is independently chosen from $C_{1-6}$alkyl optionally substituted by 1-3 $R^{39}$, $C_{2-6}$alkenyl optionally substituted by 1-3 $R^{39}$, $C_{2-6}$alkynyl optionally substituted by 1-3 $R^{39}$, $C_{6-10}$aryl optionally substituted by 1-3 $R^{39}$, $C_{7-11}$arylalkyl optionally substituted by 1-3 $R^{39}$, $C_{3-10}$cycloalkyl optionally substituted by 1-3 $R^{39}$, 3-10 membered heterocycloalkyl optionally substituted by 1-3 $R^{39}$, 5-10 membered heteroaryl optionally substituted by 1-3 $R^{39}$, halogen, —CN, —C(=O)$R^{30}$, —C(=O)O$R^{30}$, —C(=O)N$R^{32}R^{33}$, —NO$_2$, —N$R^{32}R^{33}$, —N$R^{34}$C(=O)$R^{30}$, —N$R^{34}$C(=O)N$R^{32}R^{33}$, —$R^{34}$S(=O)$_2R^{31}$, —N$R^{34}$S(=O)$_2$N$R^{32}R^{33}$, —O$R^{30}$, =O, —OC(=O)$R^{30}$, —OC(=O)N$R^{32}R^{33}$, —Si($R^{34}$)$_3$, =S, —S(=O)$_nR^{30}$, and —S(=O)$_2$N$R^{32}R^{33}$.

25. A compound as defined in any of Preferred Embodiments 1-23, wherein $R^{19}$ at each occurrence is independently chosen from $C_{1-6}$alkyl optionally substituted by 1-3 $R^{39}$, $C_{6-10}$aryl optionally substituted by 1-3 $R^{39}$, $C_{7-11}$arylalkyl optionally substituted by 1-3 $R^{39}$, $C_{3-6}$cycloalkyl optionally substituted by 1-3 $R^{39}$, 3-6 membered heterocycloalkyl optionally substituted by 1-3 $R^{39}$, 5-6 membered heteroaryl optionally substituted by 1-3 $R^{39}$, halogen, —CN, —C(=O)$R^{30}$, —C(=O)N$R^{32}R^{33}$, —N$R^{32}R^{33}$, —N$R^{34}$C(=O)$R^{30}$, —N$R^{34}$S(=O)$_2R^{31}$, —O$R^{30}$, =O, —S(=O)$_nR^{30}$, and —S(=O)$_2$N$R^{32}R^{33}$.

26. A compound as defined in any of Preferred Embodiments 1-23, wherein $R^{19}$ at each occurrence is independently chosen from $C_{1-6}$alkyl optionally substituted by 1-3 $R^{39}$, $C_{6-10}$aryl optionally substituted by 1-3 $R^{39}$, $C_{3-6}$cycloalkyl optionally substituted by 1-3 $R^{39}$, 3-6 membered heterocycloalkyl optionally substituted by 1-3 $R^{39}$, 5-6 membered heteroaryl optionally substituted by 1-3 $R^{39}$, halogen, —C(=O)O$R^{30}$, —N$R^{32}R^{33}$, and —O$R^{30}$.

27. A compound as defined in any of Preferred Embodiments 1-23, wherein $R^{19}$ at each occurrence is independently chosen from $C_{1-6}$alkyl, phenyl optionally substituted by 1-3 $R^{39}$, $C_{3-6}$cycloalkyl, 3-6 membered heterocycloalkyl optionally substituted by 1-3 $R^{39}$, 5-6 membered heteroaryl, halogen, —C(=O)O$R^{30}$, —N$R^{32}R^{33}$ and —O$R^{30}$.

28. A compound as defined in any of Preferred Embodiments 1-27, wherein $R^{20}$, $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H, $C_{1-6}$alkyl optionally substituted by 1-6 $R^{49}$, $C_{2-6}$alkenyl optionally substituted by 1-6 $R^{49}$, $C_{2-6}$alkynyl optionally substituted by 1-6 $R^{49}$, $C_{6-10}$aryl optionally substituted by 1-6 $R^{49}$, $C_{7-11}$arylalkyl optionally substituted by 1-6 $R^{49}$, $C_{3-10}$cycloalkyl optionally substituted by 1-6 $R^{49}$, 3-10 membered heterocycloalkyl optionally substituted by 1-6 $R^{49}$, and 5-10 membered heteroaryl optionally substituted by 1-6 $R^{49}$.

29. A compound as defined in any of Preferred Embodiments 1-27, wherein $R^{20}$, $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H, $C_{1-6}$alkyl optionally substituted by 1-3 $R^{49}$, phenyl optionally substituted by 1-3 $R^{49}$, $C_{3-6}$ cycloalkyl optionally substituted by 1-3 $R^{49}$, 3-6 membered heterocycloalkyl optionally substituted by 1-3 $R^{49}$, and 5-6 membered heteroaryl optionally substituted by 1-3 $R^{49}$.

30. A compound as defined in any of Preferred Embodiments 1-27, wherein $R^{20}$, $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H, $C_{1-6}$alkyl optionally substituted by 1-3 $R^{49}$, $C_{6-10}$aryl optionally substituted by 1-3 $R^{49}$, $C_{3-6}$cycloalkyl optionally substituted by 1-3 $R^{49}$ 3-6 membered heterocycloalkyl optionally substituted by 1-3 $R^{49}$, and 5-6 membered heteroaryl optionally substituted by 1-3 $R^{49}$.

31. A compound as defined in any of Preferred Embodiments 1-27, wherein $R^{20}$, $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H, $C_{1-6}$alkyl optionally substituted by 1-3 $R^{49}$, phenyl optionally substituted by 1-3 $R^{49}$, $C_{3-6}$cycloalkyl optionally substituted by 1-3 $R^{49}$, 5-6 membered heterocycloalkyl optionally substituted by 1-3 $R^{49}$, and 5-6 membered heteroaryl optionally substituted by 1-3 $R^{49}$.

32. A compound as defined in any of Preferred Embodiments 1-27, wherein $R^{20}$ at each occurrence is independently chosen from H, $C_{1-6}$alkyl optionally substituted by 1-3 $R^{49}$, phenyl optionally substituted by 1-3 $R^{49}$, $C_{3-6}$cycloalkyl optionally substituted by 1-3 $R^{49}$, 5-6 membered heterocycloalkyl optionally substituted by 1-3 $R^{49}$, and 5-6 membered heteroaryl optionally substituted by 1-3 $R^{49}$; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H and $C_{1-6}$alkyl.

33. A compound as defined in any of Preferred Embodiments 1-32, wherein $R^{28}$ and $R^{38}$ at each occurrence is independently chosen from $C_{1-6}$alkyl optionally substituted by 1-3 $R^{49}$, $C_{2-6}$alkenyl optionally substituted by 1-3 $R^{49}$, $C_{2-6}$alkynyl optionally substituted by 1-3 $R^{49}$, $C_{6-10}$aryl optionally substituted by 1-3 $R^{49}$, $C_{7-11}$arylalkyl optionally substituted by 1-3 $R^{49}$, $C_{3-10}$cycloalkyl optionally substituted by 1-3 $R^{49}$, 3-10 membered heterocycloalkyl optionally substituted by 1-3 $R^{49}$, and 5-10 membered heteroaryl optionally substituted by 1-3 $R^{49}$.

34. A compound as defined in any of Preferred Embodiments 1-33, wherein $R^{22}$, $R^{23}$, $R^{32}$ and $R^{33}$ at each occurrence is independently chosen from H, $C_{1-6}$alkyl, $C_{6-10}$aryl, $C_{7-11}$arylalkyl, $C_{3-10}$cycloalkyl, 3-10 membered heterocycloalkyl, and 5-10 membered heteroaryl.

35. A compound as defined in any of Preferred Embodiments 1-33, wherein $R^{22}$ at each occurrence is independently chosen from H, $C_{1-6}$alkyl optionally substituted by 1-3 $R^{59}$, $C_{2-6}$alkenyl optionally substituted by 1-3 $R^{59}$, $C_{2-6}$alkynyl optionally substituted by 1-3 $R^{59}$, $C_{6-10}$aryl optionally substituted by 1-3 $R^{59}$, $C_{7-11}$arylalkyl optionally substituted by 1-3 $R^{59}$, $C_{3-10}$cycloalkyl optionally substituted by 1-3 $R^{59}$, 3-10 membered heterocycloalkyl optionally substituted by 1-3 $R^{59}$, and 5-10 membered heteroaryl optionally substituted by 1-3 $R^{59}$; $R^{23}$, $R^{32}$ and $R^{33}$ at each occurrence is independently chosen from H and $C_{1-6}$alkyl; alternatively, any $R^{22}$ and $R^{23}$ and/or $R^{32}$ and $R^{33}$ may form, together with the nitrogen atom to which they are attached, a 3-10 membered heterocycloalkyl optionally substituted by 1-3 $R^{69}$ or a 5-10 membered heteroaryl optionally substituted by 1-3 $R^{69}$.

36. A compound as defined in any of Preferred Embodiments 1-33, wherein $R^{22}$ at each occurrence is independently chosen from H, phenyl optionally substituted by 1 $R^{59}$, and 6 membered heteroaryl optionally substituted by 1 $R^{59}$; $R^{23}$, $R^{32}$ and $R^{33}$ at each occurrence is independently chosen from H and $C_{1-6}$alkyl.

37. A compound as defined in any of Preferred Embodiments 1-36, wherein $R^{39}$, $R^{49}$, $R^{59}$ and $R^{69}$ at each occurrence is independently chosen from $C_{1-6}$alkyl optionally substituted by 1-3 $R^{79}$, $C_{2-6}$alkenyl optionally substituted by 1-3 $R^{79}$, $C_{2-6}$alkynyl optionally substituted by 1-3 $R^{79}$, $C_{6-10}$aryl optionally substituted by 1-3 $R^{79}$, $C_{7-11}$arylalkyl optionally substituted by 1-3 $R^{79}$, $C_{3-10}$cycloalkyl optionally substituted by 1-3 $R^{79}$, 3-10 membered heterocycloalkyl optionally substituted by 1-3 $R^{79}$, 5-10 membered heteroaryl optionally substituted by 1-3 $R^{79}$, halogen, —CN, —C(=O)$R^{70}$, —C(=O)O$R^{70}$, —C(=O)N$R^{72}R^{73}$, —NO$_2$, —N$R^{72}R^{73}$, —N$R^{74}$C(=O)$R^{70}$, —N$R^{74}$C(=O)N$R^{72}R^{73}$, —N$R^{74}$S(=O)$_n R^{71}$, —O$R^{70}$, =O, —S(=O)$_n R^{70}$ and —S(=O)$_2$N$R^{72}R^{73}$.

38. A compound as defined in any of Preferred Embodiments 1-37, wherein $R^{39}$, $R^{49}$, $R^{59}$ and $R^{69}$ at each occurrence is independently chosen from $C_{1-6}$alkyl, phenyl, 5-6 membered heterocycloalkyl, 5-9 membered heteroaryl, —CN, and —C(=O)$R^{70}$.

39. A compound as defined in any of Preferred Embodiments 1-38, wherein $R^{70}$, $R^{71}$, $R^{74}$, $R^{75}$, $R^{76}$ and $R^{77}$ at each occurrence is independently chosen from H, $C_{1-6}$alkyl optionally substituted by 1-3 $R^{89}$, $C_{6-10}$aryl optionally substituted by 1-3 $R^{89}$, $C_{7-11}$arylalkyl optionally substituted by 1-3 $R^{89}$, $C_{3-10}$cycloalkyl optionally substituted by 1-3 $R^{89}$, 3-10 membered heterocycloalkyl optionally substituted by 1-3 $R^{89}$, and 5-10 membered heteroaryl optionally substituted by 1-3 $R^{89}$.

40. A compound as defined in any of Preferred Embodiments 1-38, wherein $R^{70}$, $R^{71}$, $R^{74}$, $R^{75}$, $R^{76}$ and $R^{77}$ at each occurrence is independently chosen from H, $C_{1-6}$alkyl, and 5-6 membered heterocycloalkyl.

41. A compound as defined in any of Preferred Embodiments 1-40, wherein $R^{72}$ and $R^{73}$ at each occurrence is independently chosen from H, $C_{1-6}$alkyl optionally substituted by 1-3 $R^{99}$, $C_{2-6}$alkenyl optionally substituted by 1-3 $R^{99}$, $C_{2-6}$alkynyl optionally substituted by 1-3 $R^{99}$, $C_{6-10}$aryl optionally substituted by 1-3 $R^{99}$, $C_{7-11}$arylalkyl optionally substituted by 1-3 $R^{99}$, $C_{3-10}$cycloalkyl optionally substituted by 1-3 $R^{99}$, 3-10 membered heterocycloalkyl optionally substituted by 1-3 $R^{99}$, and 5-10 membered heteroaryl optionally substituted by 1-3 $R^{99}$; alternatively, any $R^{72}$ and $R^{73}$ may form, together with the nitrogen atom to which they are attached, a 3-10 membered heterocycloalkyl optionally substituted by 1-3 $R^{109}$ or a 5-10 membered heteroaryl optionally substituted by 1-3 $R^{109}$.

42. A compound as defined in any of Preferred Embodiments 1-40, wherein $R^{72}$ and $R^{73}$ at each occurrence is independently chosen from H, $C_{1-6}$alkyl, phenyl, benzyl, $C_{5-6}$cycloalkyl, 5-6 membered heterocycloalkyl, and 5-6 membered heteroaryl; alternatively, any $R^{72}$ and $R^{73}$ may form, together with the nitrogen atom to which they are attached, a 5-6 membered heterocycloalkyl or a 5-6 membered heteroaryl.

43. A compound as defined in any of Preferred Embodiments 1-42, wherein $R^{78}$ at each occurrence is independently chosen from $C_{1-6}$alkyl optionally substituted by 1-3 $R^{89}$, $C_{2-6}$alkenyl optionally substituted by 1-3 $R^{89}$, $C_{2-6}$alkynyl optionally substituted by 1-3 $R^{89}$, $C_{6-10}$aryl optionally substituted by 1-3 $R^{89}$, $C_{7-11}$arylalkyl optionally substituted by 1-3 $R^{89}$, $C_{3-10}$cycloalkyl optionally substituted by 1-3 $R^{89}$, 3-10 membered heterocycloalkyl optionally substituted by 1-3 $R^{89}$, and 5-10 membered heteroaryl optionally substituted by 1-3 $R^{89}$.

44. A compound as defined in any of Preferred Embodiments 1-42, wherein $R^{78}$ at each occurrence is independently chosen from $C_{1-6}$alkyl, phenyl, benzyl, $C_{3-6}$ cycloalkyl, 3-6 membered heterocycloalkyl, and 5-6 membered heteroaryl.

45. A compound as defined in any of Preferred Embodiments 1-44, wherein $R^{79}$, $R^{89}$, $R^{99}$ and $R^{109}$ at each occurrence is independently chosen from $C_{1-6}$alkyl optionally substituted by 1-3 halogen, $C_{2-6}$alkenyl, $C_{2-6}$alkynyl, $C_{6-10}$aryl, $C_{7-11}$arylalkyl, $C_{3-10}$cycloalkyl, 3-10 membered heterocycloalkyl, 5-10 membered heteroaryl, halogen, —CN, —C(=O)R$^{110}$, —C(=O)OR$^{10}$, —C(=O)NR$^{110}$R$^{110}$, —NO$_2$, —NR$^{110}$R$^{110}$, —NR$^{110}$OR$^{110}$, —NR$^{110}$C(=O)R$^{110}$, —NR$^{110}$C(=O)NR$^{110}$R$^{110}$, —NR$^{110}$S(=O)$_2$R$^{110}$, —NR$^{110}$S(=O)$_2$NR$^{110}$R$^{110}$, —OR$^{110}$, =O, —OCN, —OC(=O)R$^{110}$, —S(=O)R$^{110}$, —S(=O)$_2$NR$^{110}$R$^{110}$, and —S(=O)NR$^{110}$R$^{110}$.

46. A compound as defined in any of Preferred Embodiments 1-45, wherein $R^{110}$ at each occurrence is independently chosen from H, $C_{1-6}$alkyl and $C_{1-6}$-haloalkyl.

47. A compound as defined in any of Preferred Embodiments 1-46, wherein $R^{11}$ at each occurrence is independently chosen from $C_{1-6}$alkyl and $C_{1-6}$-haloalkyl.

What is claimed is:

1. A compound, or a pharmaceutically acceptable salt thereof, of formula I:

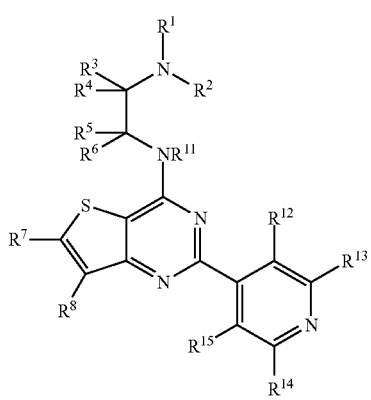

(I)

wherein, $R^1$, $R^2$, and $R^{11}$ are independently chosen from H and $C_{1-6}$alkyl optionally substituted by 1-13 $R^{19}$;

$R^3$ is chosen from H, $C_{1-6}$alkyl optionally substituted by 1-13 $R^{19}$, $C_{7-11}$ arylalkyl optionally substituted by 1-9 $R^{19}$, $C_{6-7}$cycloalkylalkyl optionally substituted by 1-6 $R^{19}$, and 6-11 membered heteroarylalkyl optionally substituted by 1-7 $R^{19}$;

$R^4$, $R^5$, and $R^6$ are H;

$R^7$ is selected from H and $C_{1-6}$alkyl optionally substituted by 1-3 $R^{19}$;

$R^8$ is selected from $C_{2-6}$alkynyl optionally substituted by 1-3 $R^{19}$;

$R^{12}$, $R^{13}$, $R^{14}$, and $R^{15}$ are independently chosen from H, $C_{1-6}$alkyl optionally substituted by 1-3 $R^{19}$, halogen, —NR$^{22}$R$^{23}$, —NR$^{24}$C(=O)R$^{20}$, —R$^{24}$C(=O)NR$^{22}$R$^{23}$, —OR$^{20}$, and —S(=O)$_2$NR$^{22}$R$^{23}$;

$R^{19}$ at each occurrence is independently chosen from $C_{1-6}$alkyl, phenyl, $C_{3-6}$cycloalkyl, 3-6 membered heterocycloalkyl, halogen, —C(=O)OR$^{30}$ and —OR$^{30}$; and $R^{20}$, $R^{22}$, $R^{23}$, $R^{24}$, and $R^{30}$ at each occurrence are independently chosen from H and $C_{1-6}$alkyl.

2. The compound, or pharmaceutically acceptable salt thereof, according to claim 1 wherein $R^1$ and $R^2$ are H.

3. The compound, or pharmaceutically acceptable salt thereof, according to claim 1 wherein $R^{11}$ is H.

4. The compound, or pharmaceutically acceptable salt thereof, according to claim 1 wherein $R^1$, $R^2$ and $R^{11}$ are H.

5. The compound, or pharmaceutically acceptable salt thereof, according to claim 1 wherein $R^3$ is selected from $C_{1-6}$alkyl optionally substituted by 1-13 $R^{19}$ and $C_{7-11}$arylalkyl optionally substituted by 1-9 $R^{19}$.

6. The compound, or pharmaceutically acceptable salt thereof, according to claim 1 wherein $R^7$ is H.

7. The compound, or pharmaceutically acceptable salt thereof, according to claim 1 wherein $R^{19}$ is selected from $C_{1-6}$alkyl, phenyl, $C_{3-6}$cycloalkyl, halogen and —OR$^{30}$.

8. The compound, or pharmaceutically acceptable salt thereof, according to claim 1 wherein $R^{12}$, $R^{13}$, $R^{14}$, and $R^{15}$ are independently chosen from H and halogen.

9. The compound, or a pharmaceutically acceptable salt thereof, selected from the group consisting of:

| Structure | Name |
|---|---|
| 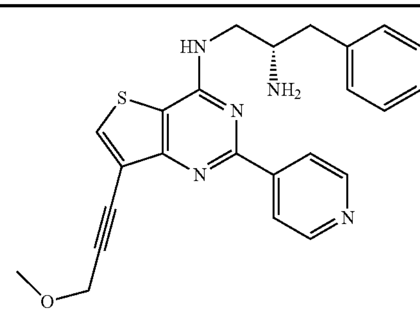 | (S)-N*1*-[7-(3-Methoxy-prop-1-ynyl)-2-pyridin-4-yl-thieno[3,2-d]pyrimidin-4-yl]-3-phenyl-propane-1,2-diamine |

| Structure | Name |
|---|---|
| 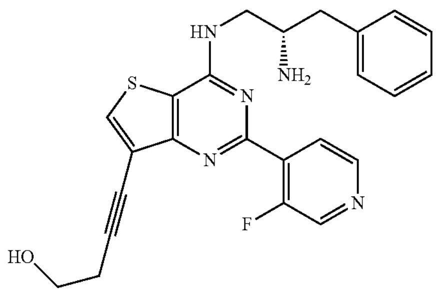 [SMILES: N[C@H](CNc1nc(-c2ccncc2F)nc2c(C#CCCO)csc12)Cc1ccccc1] | 4-[4-((S)-2-Amino-3-phenyl-propylamino)-2-(3-fluoro-pyridin-4-yl)-thieno[3,2-d]pyrimidin-7-yl]-but-3-yn-1-ol |
| 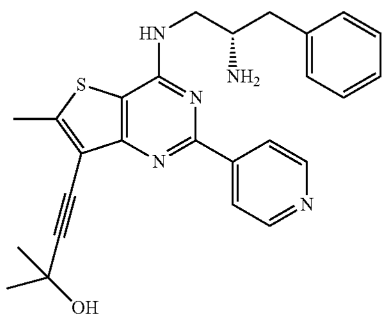 [SMILES: Cc1sc2c(NC[C@@H](N)Cc3ccccc3)nc(-c3ccncc3)nc2c1C#CC(C)(C)O] | 4-[4-((S)-2-Amino-3-phenyl-propylamino)-6-methyl-2-pyridin-4-yl-thieno[3,2-d]pyrimidin-7-yl]-2-methyl-but-3-yn-2-ol |
| 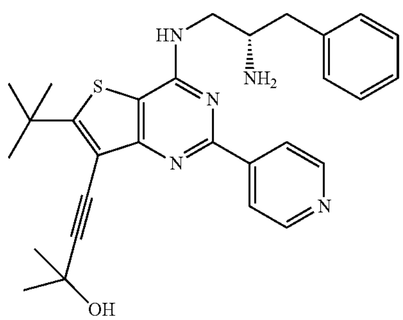 [SMILES: CC(C)(O)C#Cc1c(C(C)(C)C)sc2c(NC[C@@H](N)Cc3ccccc3)nc(-c3ccncc3)nc12] | 4-[4-((S)-2-Amino-3-phenyl-propylamino)-6-tert-butyl-2-pyridin-4-yl-thieno[3,2-d]pyrimidin-7-yl]-2-methyl-but-3-yn-2-ol |
| 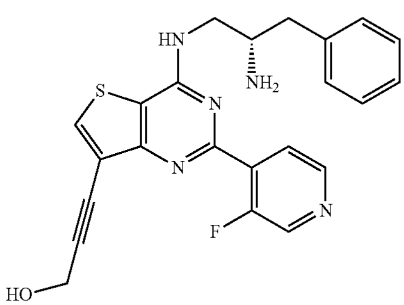 [SMILES: N[C@H](CNc1nc(-c2ccncc2F)nc2c(C#CCO)csc12)Cc1ccccc1] | 3-[4-((S)-2-Amino-3-phenyl-propylamino)-2-(3-fluoro-pyridin-4-yl)-thieno[3,2-d]pyrimidin-7-yl]-prop-2-yn-1-ol |
| 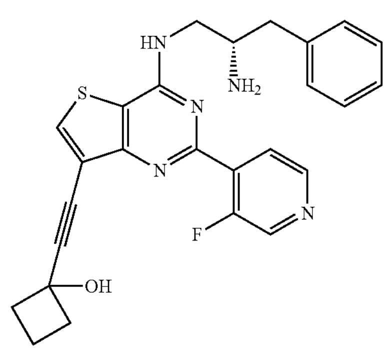 [SMILES: N[C@H](CNc1nc(-c2ccncc2F)nc2c(C#CC3(O)CCC3)csc12)Cc1ccccc1] | 1-[4-((S)-2-Amino-3-phenyl-propylamino)-2-(3-fluoro-pyridin-4-yl)-thieno[3,2-d]pyrimidin-7-ylethynyl]-cyclobutanol |

-continued

| Structure | Name |
|---|---|
| 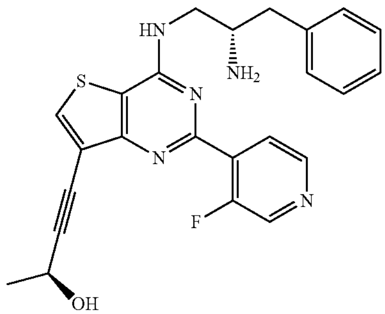 [SMILES: C[C@H](O)C#Cc1csc2c(NC[C@@H](N)Cc3ccccc3)nc(-c3ccncc3F)nc12] | (S)-4-[4-((S)-2-Amino-3-phenyl-propylamino)-2-(3-fluoro-pyridin-4-yl)-thieno[3,2-d]pyrimidin-7-yl]-but-3-yn-2-ol |
| 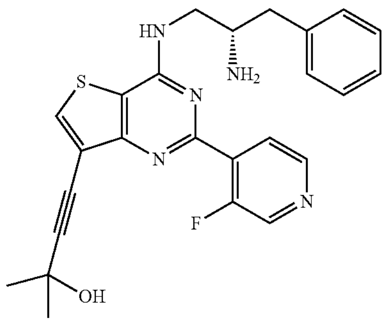 [SMILES: CC(C)(O)C#Cc1csc2c(NC[C@@H](N)Cc3ccccc3)nc(-c3ccncc3F)nc12] | 4-[4-((S)-2-Amino-3-phenyl-propylamino)-2-(3-fluoro-pyridin-4-yl)-thieno[3,2-d]pyrimidin-7-yl]-2-methyl-but-3-yn-2-ol |
| 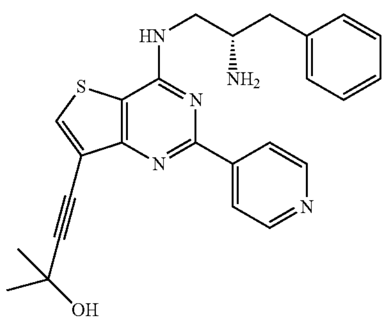 [SMILES: CC(C)(O)C#Cc1csc2c(NC[C@@H](N)Cc3ccccc3)nc(-c3ccncc3)nc12] | 4-[4-((S)-2-Amino-3-phenyl-propylamino)-2-pyridin-4-yl-thieno[3,2-d]pyrimidin-7-yl]-2-methyl-but-3-yn-2-ol |
| 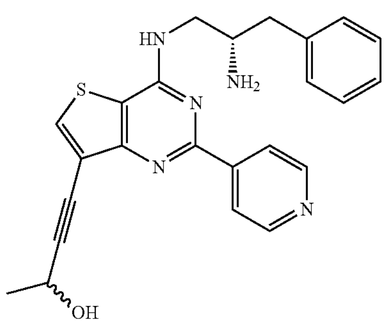 [SMILES: CC(O)C#Cc1csc2c(NC[C@@H](N)Cc3ccccc3)nc(-c3ccncc3)nc12] | 4-[4-((S)-2-Amino-3-phenyl-propylamino)-2-pyridin-4-yl-thieno[3,2-d]pyrimidin-7-yl]-but-3-yn-2-ol |
| 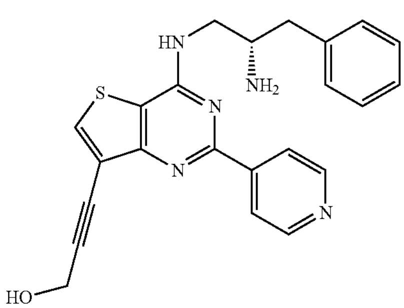 [SMILES: N[C@H](CNc1nc(-c2ccncc2)nc2c(C#CCO)csc12)Cc1ccccc1] | 3-[4-((S)-2-Amino-3-phenyl-propylamino)-2-pyridin-4-yl-thieno[3,2-d]pyrimidin-7-yl]-prop-2-yn-1-ol |

| Structure | Name |
|---|---|
| 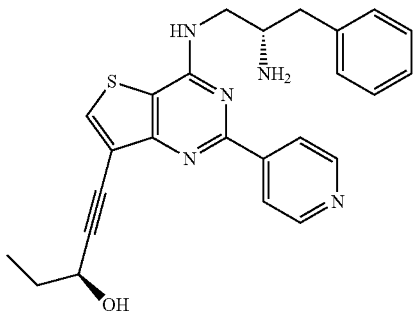 [SMILES: CC[C@H](O)C#Cc1csc2c(NC[C@@H](N)Cc3ccccc3)nc(-c3ccncc3)nc12] | S)-1-[4-((S)-2-Amino-3-phenyl-propylamino)-2-pyridin-4-yl-thieno[3,2-d]pyrimidin-7-yl]-pent-1-yn-3-ol |
| 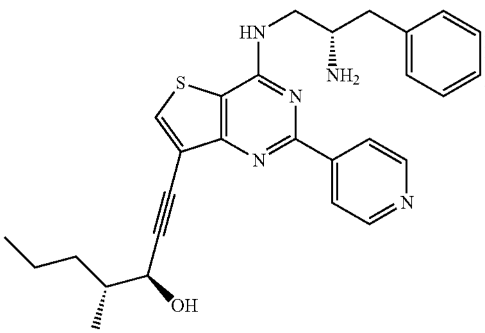 [SMILES: CCC[C@@H](C)[C@H](O)C#Cc1csc2c(NC[C@@H](N)Cc3ccccc3)nc(-c3ccncc3)nc12] | (S)-1-[4-((S)-2-Amino-3-phenyl-propylamino)-2-pyridin-4-yl-thieno[3,2-d]pyrimidin-7-yl]-4-methyl-hept-1-yn-3-ol |
| 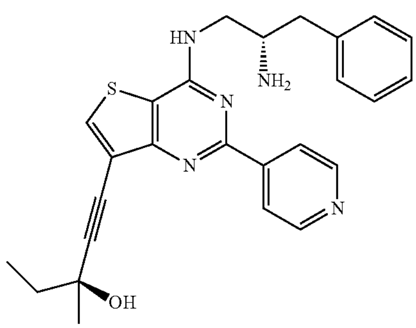 [SMILES: CC[C@](C)(O)C#Cc1csc2c(NC[C@@H](N)Cc3ccccc3)nc(-c3ccncc3)nc12] | (S)-1-[4-((S)-2-Amino-3-phenyl-propylamino)-2-pyridin-4-yl-thieno[3,2-d]pyrimidin-7-yl]-3-methyl-pent-1-yn-3-ol |
| 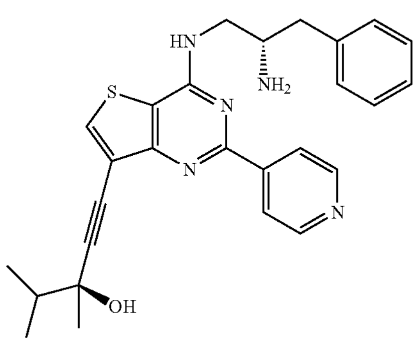 [SMILES: CC(C)[C@](C)(O)C#Cc1csc2c(NC[C@@H](N)Cc3ccccc3)nc(-c3ccncc3)nc12] | (S)-1-[4-((S)-2-Amino-3-phenyl-propylamino)-2-pyridin-4-yl-thieno[3,2-d]pyrimidin-7-yl]-3,4-dimethyl-pent-1-yn-3-ol |

-continued

| Structure | Name |
|---|---|
| 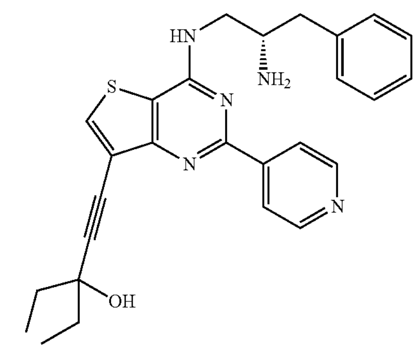 [SMILES: CCC(O)(C#Cc1csc2c(NC[C@@H](N)Cc3ccccc3)nc(-c3ccncc3)nc12)CC] | 1-[4-(2-Amino-3-phenyl-propylamino)-2-pyridin-4-yl-thieno[3,2-d]pyrimidin-7-yl]-3-ethyl-pent-1-yn-3-ol |
| 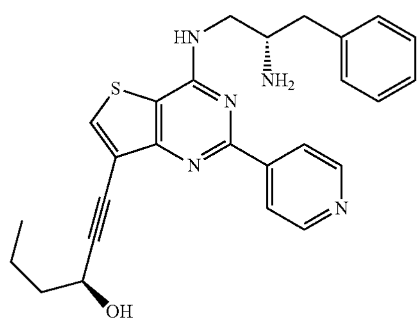 [SMILES: CCC[C@H](O)C#Cc1csc2c(NC[C@@H](N)Cc3ccccc3)nc(-c3ccncc3)nc12] | (S)-1-[4-((S)-2-Amino-3-phenyl-propylamino)-2-pyridin-4-yl-thieno[3,2-d]pyrimidin-7-yl]-hex-1-yn-3-ol |
| 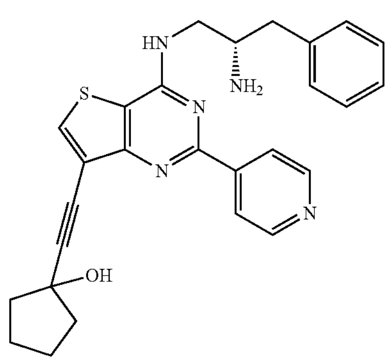 [SMILES: N[C@H](CNc1nc(-c2ccncc2)nc2c(C#CC3(O)CCCC3)csc12)Cc1ccccc1] | 1-[4-((S)-2-Amino-3-phenyl-propylamino)-2-pyridin-4-yl-thieno[3,2-d]pyrimidin-7-ylethynyl]-cyclopentanol |
| 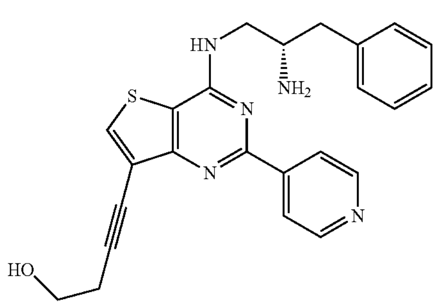 [SMILES: N[C@H](CNc1nc(-c2ccncc2)nc2c(C#CCCO)csc12)Cc1ccccc1] | 4-[4-((S)-2-Amino-3-phenyl-propylamino)-2-pyridin-4-yl-thieno[3,2-d]pyrimidin-7-yl]-but-3-yn-1-ol |

-continued

| Structure | Name |
|---|---|
| 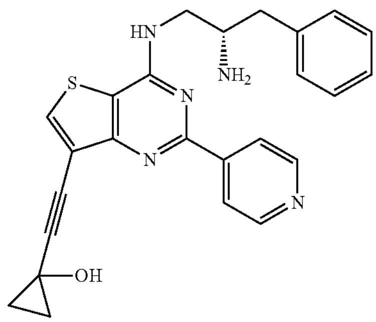 [SMILES: N[C@H](CNc1nc(-c2ccncc2)nc2c(C#CC3(O)CC3)csc12)Cc1ccccc1] | 1-[4-((S)-2-Amino-3-phenyl-propylamino)-2-pyridin-4-yl-thieno[3,2-d]pyrimidin-7-ylethynyl]-cyclopropanol |
| 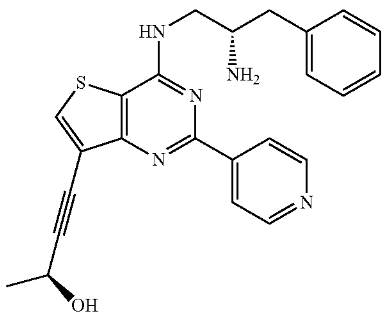 [SMILES: C[C@H](O)C#Cc1csc2c(NC[C@@H](N)Cc3ccccc3)nc(-c3ccncc3)nc12] | (S)-4-[4-((S)-2-Amino-3-phenyl-propylamino)-2-pyridin-4-yl-thieno[3,2-d]pyrimidin-7-yl]-but-3-yn-2-ol |
| 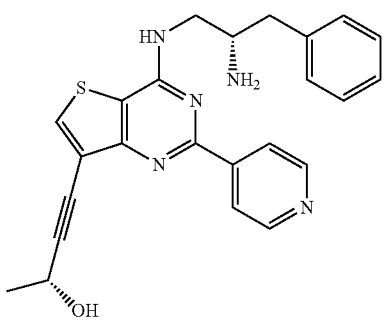 [SMILES: C[C@@H](O)C#Cc1csc2c(NC[C@@H](N)Cc3ccccc3)nc(-c3ccncc3)nc12] | (R)-4-[4-((S)-2-Amino-3-phenyl-propylamino)-2-pyridin-4-yl-thieno[3,2-d]pyrimidin-7-yl]-but-3-yn-2-ol |
| 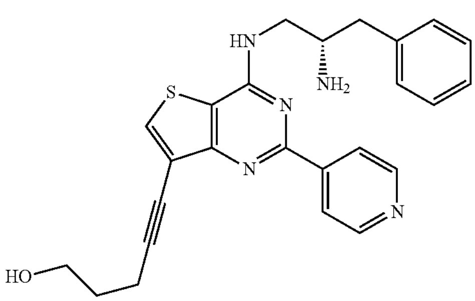 [SMILES: N[C@H](CNc1nc(-c2ccncc2)nc2c(C#CCCCO)csc12)Cc1ccccc1] | 5-[4-((S)-2-Amino-3-phenyl-propylamino)-2-pyridin-4-yl-thieno[3,2-d]pyrimidin-7-yl]-pent-4-yn-1-ol |
| 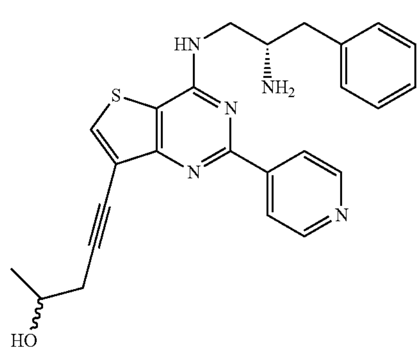 [SMILES: CC(O)CC#Cc1csc2c(NC[C@@H](N)Cc3ccccc3)nc(-c3ccncc3)nc12] | 5-[4-((S)-2-Amino-3-phenyl-propylamino)-2-pyridin-4-yl-thieno[3,2-d]pyrimidin-7-yl]-pent-4-yn-2-ol |

| Structure | Name |
|---|---|
| 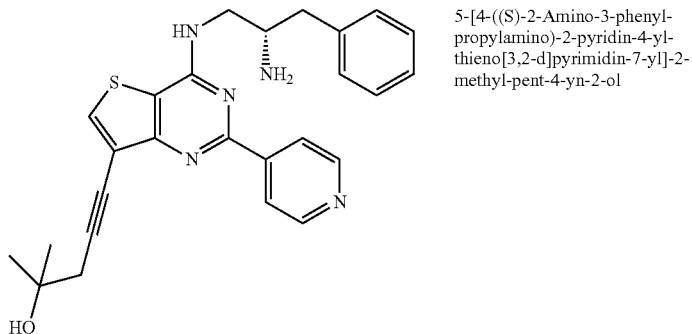 | 5-[4-((S)-2-Amino-3-phenyl-propylamino)-2-pyridin-4-yl-thieno[3,2-d]pyrimidin-7-yl]-2-methyl-pent-4-yn-2-ol |
| 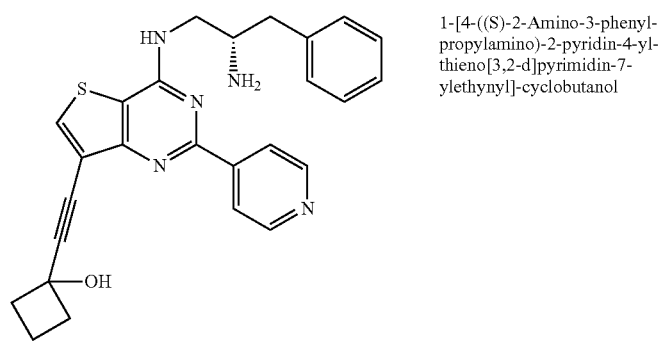 | 1-[4-((S)-2-Amino-3-phenyl-propylamino)-2-pyridin-4-yl-thieno[3,2-d]pyrimidin-7-ylethynyl]-cyclobutanol |
| 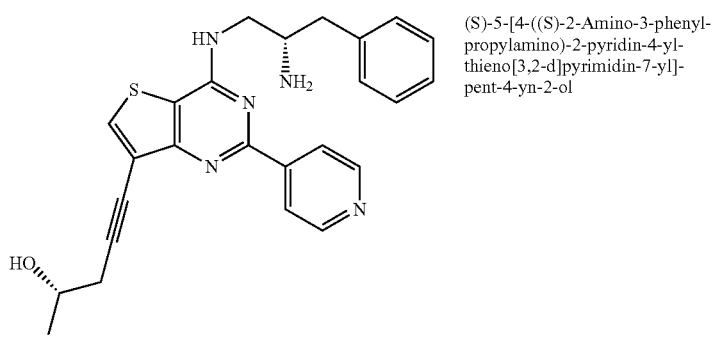 | (S)-5-[4-((S)-2-Amino-3-phenyl-propylamino)-2-pyridin-4-yl-thieno[3,2-d]pyrimidin-7-yl]-pent-4-yn-2-ol |
| 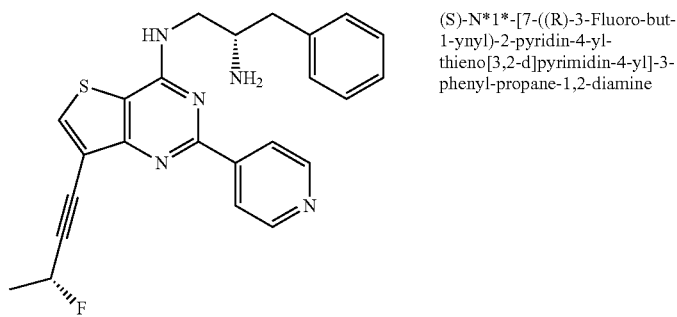 | (S)-N*1*-[7-((R)-3-Fluoro-but-1-ynyl)-2-pyridin-4-yl-thieno[3,2-d]pyrimidin-4-yl]-3-phenyl-propane-1,2-diamine |

| Structure | Name |
|---|---|
| 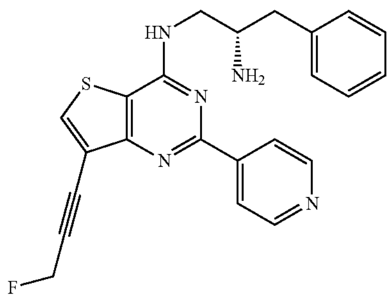 [SMILES: N[C@H](CNc1nc(-c2ccncc2)nc2c(C#CCF)csc12)Cc1ccccc1] | (S)-N*1*-[7-(3-Fluoro-prop-1-ynyl)-2-pyridin-4-yl-thieno[3,2-d]pyrimidin-4-yl]-3-phenyl-propane-1,2-diamine |
| 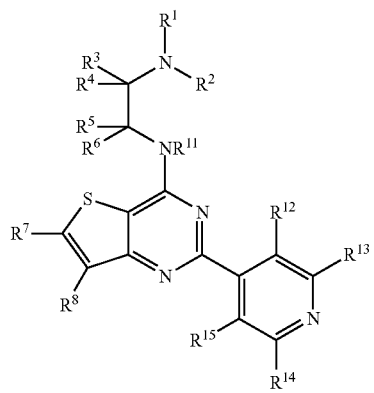 and | (S)-N*1*-[7-(4-Fluoro-but-1-ynyl)-2-pyridin-4-yl-thieno[3,2-d]pyrimidine. |

10. A pharmaceutical composition comprising a compound of Formula I, or a pharmaceutically acceptable salt thereof, and a pharmaceutically acceptable excipient, wherein Formula I is:

(I)

wherein, $R^1$, $R^2$, and $R^{11}$ are independently chosen from H and $C_{1-6}$alkyl optionally substituted by 1-13 $R^{19}$;

$R^3$ is chosen from H, $C_{1-6}$alkyl optionally substituted by 1-13 $R^{19}$, $C_{7-11}$arylalkyl optionally substituted by 1-9 $R^{19}$, $C_{6-7}$cycloalkylalkyl optionally substituted by 1-6 $R^{19}$, and 6-11 membered heteroarylalkyl optionally substituted by 1-7 $R^{19}$;

$R^4$, $R^5$, and $R^6$ are H;

$R^7$ is selected from H and $C_{1-6}$alkyl optionally substituted by 1-3 $R^{19}$;

$R^8$ is selected from $C_{2-6}$alkynyl optionally substituted by 1-3 $R^{19}$;

$R^{12}$, $R^{13}$, $R^{14}$, and $R^{15}$ are independently chosen from H, $C_{1-6}$alkyl optionally substituted by 1-3 $R^{19}$, halogen, —$NR^{22}R^{23}$, —$NR^{24}C(=O)R^{20}$, —$NR^{24}C(=O)NR^{22}R^{23}$, —$OR^{20}$, and —$S(=O)_2NR^{22}R^{23}$;

$R^{19}$ at each occurrence is independently chosen from $C_{1-6}$alkyl, phenyl, $C_{3-6}$cycloalkyl, 3-6 membered heterocycloalkyl, halogen, —$C(=O)OR^{30}$ and —$OR^{30}$; and $R^{20}$, $R^{22}$, $R^{23}$, $R^{24}$, and $R^{30}$ at each occurrence are independently chosen from H and $C_{1-6}$alkyl.

* * * * *